US012718954B2

(12) United States Patent
Robl et al.

(10) Patent No.: US 12,718,954 B2

(45) Date of Patent: Aug. 25, 2026

(54) UNSUPERVISED MACHINE LEARNING METHODS FOR CLASSIFYING A LUPUS DISEASE STATE OF A SUBJECT

(71) Applicant: AMPEL, LLC, Charlottesville, VA (US)

(72) Inventors: Robert Robl, Charlottesville, VA (US); Prathyusha Bachali, Charlottesville, VA (US); Amrie C. Grammer, Charlottesville, VA (US); Peter E. Lipsky, Charlottesville, VA (US)

(73) Assignee: AMPEL, LLC, Charlottesville, VA (US)

( * ) Notice: Subject to any disclaimer, the term of this patent is extended or adjusted under 35 U.S.C. 154(b) by 0 days.

(21) Appl. No.: 18/806,149

(22) Filed: Aug. 15, 2024

(65) Prior Publication Data

US 2025/0078957 A1 Mar. 6, 2025

Related U.S. Application Data

(63) Continuation of application No. PCT/US2023/013173, filed on Feb. 15, 2023.

(60) Provisional application No. 63/424,397, filed on Nov. 10, 2022, provisional application No. 63/407,591, filed on Sep. 16, 2022, provisional application No. 63/310,974, filed on Feb. 16, 2022.

(51) Int. Cl.

| | |
|---|---|
| ***G16H 50/30*** | (2018.01) |
| ***C12Q 1/68*** | (2018.01) |
| ***G16B 25/10*** | (2019.01) |
| ***G16B 40/30*** | (2019.01) |
| ***G16H 10/40*** | (2018.01) |
| ***G16H 10/60*** | (2018.01) |
| ***G16H 50/20*** | (2018.01) |
| ***G16H 50/70*** | (2018.01) |

(52) U.S. Cl.

CPC ............. *G16H 50/30* (2018.01); *G16B 25/10* (2019.02); *G16B 40/30* (2019.02); *G16H 10/40* (2018.01); *G16H 10/60* (2018.01); *G16H 50/20* (2018.01); *G16H 50/70* (2018.01); *C12Q 1/68* (2013.01); *C12Q 2600/106* (2013.01); *C12Q 2600/112* (2013.01); *C12Q 2600/118* (2013.01); *C12Q 2600/178* (2013.01)

(58) Field of Classification Search

None

See application file for complete search history.

(56) References Cited

U.S. PATENT DOCUMENTS

| | | | |
|---|---|---|---|
| 6,949,338 B2 | 9/2005 | Rheins | |
| 7,991,557 B2 | 8/2011 | Liew | |
| 8,148,067 B2 * | 4/2012 | Lal | C12Q 1/6809 435/6.1 |
| 8,504,343 B2 | 8/2013 | Chawla | |
| 9,340,830 B2 | 5/2016 | Lipson | |
| 9,822,400 B2 | 11/2017 | Dennis, Jr. | |
| 10,978,196 B2 | 4/2021 | Lefkofsky | |
| 11,037,685 B2 | 6/2021 | Lefkofsky | |
| 11,195,525 B2 | 12/2021 | Tahara | |
| 11,309,090 B2 | 4/2022 | Lefkofsky | |
| 2003/0154032 A1 | 8/2003 | Pittman | |
| 2006/0094056 A1 * | 5/2006 | Chappell | G01N 33/6863 435/7.1 |
| 2006/0257852 A1 | 11/2006 | Rappuoli | |
| 2007/0059717 A1 | 3/2007 | Pascual | |
| 2007/0231816 A1 | 10/2007 | Chaussabel | |
| 2007/0269804 A1 | 11/2007 | Liew | |
| 2008/0108058 A1 | 5/2008 | Behrens | |
| 2009/0298060 A1 | 12/2009 | Lal | |
| 2011/0118130 A1 | 5/2011 | Loring | |
| 2011/0238319 A1 | 9/2011 | Adamko | |
| 2011/0262485 A1 | 10/2011 | Barber | |
| 2013/0274134 A1 | 10/2013 | Lindstedt | |
| 2014/0135225 A1 | 5/2014 | Crow | |
| 2015/0218640 A1 | 8/2015 | Brandon | |
| 2015/0310163 A1 | 10/2015 | Kingsmore | |
| 2016/0109453 A1 | 4/2016 | Weinhausel | |
| 2016/0210403 A1 | 7/2016 | Zhang | |
| 2017/0342493 A1 | 11/2017 | Barril et al. | |
| 2017/0349950 A1 | 12/2017 | Regev | |
| 2018/0057859 A1 | 3/2018 | Nelson | |
| 2018/0096738 A1 | 4/2018 | Moturu | |
| 2018/0217141 A1 | 8/2018 | Sasso | |

(Continued)

FOREIGN PATENT DOCUMENTS

| | | |
|---|---|---|
| CN | 111041089 A | 4/2020 |
| EP | 2326731 B1 | 6/2011 |

(Continued)

OTHER PUBLICATIONS

Kegerreis et al. (Scientific Reports, 2019, vol. 9, Article No. 9617, pp. 1-12) (Year: 2019).*

(Continued)

*Primary Examiner* — Pablo S Whaley

(74) *Attorney, Agent, or Firm* — WILSON SONSINI GOODRICH & ROSATI

(57) ABSTRACT

The present disclosure provides systems and methods for classifying lupus disease state of a patient is disclosed. The method can include analyzing a patient data set comprising or derived from gene expression measurements data of at least 2 genes, from a biological sample obtained or derived from the patient, to classify the lupus disease state of the patient. The at least 2 genes can be selected from Tables 17-1 to 17-30, and/or Tables 24-1 to 24-30.

16 Claims, 105 Drawing Sheets

(56) References Cited

U.S. PATENT DOCUMENTS

| | | | |
|---|---|---|---|
| 2018/0305689 | A1 | 10/2018 | Sætrom |
| 2018/0364229 | A1 | 12/2018 | James |
| 2019/0065670 | A1 | 2/2019 | Yandell |
| 2019/0080051 | A1 | 3/2019 | Menche |
| 2019/0100795 | A1 | 4/2019 | Verhaegh |
| 2019/0108912 | A1 | 4/2019 | Spurlock, III |
| 2019/0127803 | A1 | 5/2019 | Hacohen |
| 2019/0131016 | A1 | 5/2019 | Cohen |
| 2019/0203298 | A1 | 7/2019 | Sandoval Del Amor |
| 2019/0287644 | A1 | 9/2019 | Karma |
| 2019/0292600 | A1 | 9/2019 | Spira |
| 2019/0313920 | A1 | 10/2019 | Banerjee |
| 2020/0069973 | A1 | 3/2020 | Lou |
| 2020/0090787 | A1 | 3/2020 | Lipsky et al. |
| 2020/0143278 | A1 | 5/2020 | Narain |
| 2020/0185063 | A1 | 6/2020 | Narain |
| 2020/0190589 | A1 | 6/2020 | Akmaev |
| 2020/0232046 | A1 | 7/2020 | Kennedy |
| 2020/0342958 | A1 | 10/2020 | McGovern |
| 2020/0402643 | A1 | 12/2020 | Trees |
| 2021/0071255 | A1 | 3/2021 | Regev |
| 2021/0090694 | A1 | 3/2021 | Colley et al. |
| 2021/0098082 | A1 | 4/2021 | Udyavar |
| 2021/0104321 | A1 | 4/2021 | Lipsky |
| 2021/0142910 | A1 | 5/2021 | Hafez |
| 2021/0225517 | A1 | 7/2021 | Baloglu |
| 2021/0232934 | A1 | 7/2021 | Lai et al. |
| 2021/0254056 | A1 | 8/2021 | Liu |
| 2022/0375609 | A1 | 11/2022 | Guo |
| 2023/0279097 | A1 | 9/2023 | Cesaroni et al. |
| 2024/0282449 | A1 | 8/2024 | Martinez et al. |
| 2024/0428948 | A1 | 12/2024 | Robl et al. |
| 2025/0022541 | A1 | 1/2025 | Robl et al. |
| 2025/0174366 | A1 | 5/2025 | Grammer et al. |

FOREIGN PATENT DOCUMENTS

| | | | |
|---|---|---|---|
| EP | 2389582 | A1 | 11/2011 |
| EP | 2389582 | B1 | 11/2011 |
| EP | 3052193 | B1 | 8/2016 |
| EP | 3465200 | A1 | 4/2019 |
| WO | 2002057414 | A2 | 7/2002 |
| WO | 2006074370 | A2 | 7/2006 |
| WO | 2008079374 | A2 | 7/2008 |
| WO | 2008091708 | A2 | 7/2008 |
| WO | 2010008543 | A2 | 1/2010 |
| WO | 2010065940 | A1 | 6/2010 |
| WO | 2010084312 | A1 | 7/2010 |
| WO | 2012118856 | A1 | 9/2012 |
| WO | 2012150276 | A1 | 11/2012 |
| WO | 2016057705 | A1 | 4/2016 |
| WO | WO-2016081701 | A2 | 5/2016 |
| WO | 2016141214 | A1 | 9/2016 |
| WO | 2017019918 | A1 | 2/2017 |
| WO | 2017093750 | A1 | 6/2017 |
| WO | 2017147196 | A1 | 8/2017 |
| WO | 2017164936 | A1 | 9/2017 |
| WO | 2017205823 | A1 | 11/2017 |
| WO | 2017214068 | A1 | 12/2017 |
| WO | 2018161052 | A1 | 9/2018 |
| WO | 2018191558 | A1 | 10/2018 |
| WO | 2019178546 | A1 | 9/2019 |
| WO | 2020014620 | A1 | 1/2020 |
| WO | WO-2020047453 | A1 | 3/2020 |
| WO | 2020081204 | A1 | 4/2020 |
| WO | 2020102043 | A1 | 5/2020 |
| WO | 2020102519 | A1 | 5/2020 |
| WO | 2020142551 | A1 | 7/2020 |
| WO | 2020264426 | A1 | 12/2020 |
| WO | 2021026097 | A1 | 2/2021 |
| WO | 2021034712 | A1 | 2/2021 |
| WO | 2021041726 | A1 | 3/2021 |
| WO | 2021055742 | A1 | 3/2021 |
| WO | 2021231713 | A2 | 11/2021 |
| WO | WO-2022246553 | A1 | 12/2022 |
| WO | WO-2023158713 | A1 | 8/2023 |
| WO | WO-2023215331 | A1 | 11/2023 |
| WO | WO-2023215618 | A2 | 11/2023 |
| WO | WO-2024015621 | A1 | 1/2024 |
| WO | WO-2024044500 | A1 | 2/2024 |
| WO | WO-2024102199 | A1 | 5/2024 |
| WO | WO-2024148050 | A2 | 7/2024 |
| WO | WO-2025064586 | A1 | 3/2025 |
| WO | WO-2025250602 | A1 | 12/2025 |

OTHER PUBLICATIONS

Agache I, Akdis CA. Precision medicine and phenotypes, endotypes, genotypes, regiotypes, and theratypes of allergic diseases. J Clin Invest. 2019, vol. 129, No. 4, p. 1493-503.

Andreoletti et al. Transcriptomic analysis of immune cells in a multi-ethnic cohort of systemic lupus erythematosus patients identifies ethnicity- and disease-specific expression signatures. Commun Biol 2021, vol. 4, No. 488, p. 1-13.

Bastian et al. Molecular Subtypes with Distinct Clinical Phenotypes and Actionable Targets in Adult B Cell Precursor ALL Treatment According to GMALL Protocols. Blood, 2020, vol. 136, Suppl, p. 1-4.

Battaglia et al. Introducing the Endotype Concept to Address the Challenge of Disease Heterogeneity in Type 1 Diabetes. Diabetes Care, 2020, vol. 43, p. 5-12.

Catalina et al. Patient ancestry significantly contributes to molecular heterogeneity of systemic lupus erythematosus. JCI Insight. 2020, vol. 5, No. 15, e140380, p. 1-20.

Chawla et al. SMOTE: Synthetic Minority Over-sampling Technique. J Artif Intell Res, 2002, vol. 16, p. 321-357.

Chiche, Modular transcriptional repertoire analyses of adults with systemic lupus erythematosus reveal distinct type I and type II interferon signatures, Arthritis Rheumatol. 2014, vol. 66, No. 6, p. 1-20.

Daamen et al. Comprehensive transcriptomic analysis of COVID-19 blood, lung, and airway. Sci Rep 2021, vol. 11, No. 7052, p. 1-19.

Diaz-Gallo et al. Four Systemic Lupus Erythematosus Subgroups, Defined by Autoantibodies Status, Differ Regarding HLA-DRB1 Genotype Associations and Immunological and Clinical Manifestations. ACR Open Rheumatol, 2022, vol. 4, No. 1, p. 27-39.

Dilokthanakul et al. Deep Unsupervised Clustering with Gaussian Mixture Variational Autoencoders. Under Review Conference Paper ICLR, 2016, p. 1-12.

Ding et al. Identification of a gene-expression predictor for diagnosis and personalized stratification of lupus patients. PLoS One, 2018, vol. 13, No. 7, e0198325, p. 1-16.

Dörner T, Farner NL, Lipsky PE. Ig λ and Heavy Chain Gene Usage in Early Untreated Systemic Lupus Erythematosus Suggests Intensive B Cell Stimulation. J Immunol. 1999, vol. 163, No. 2, p. 1027-1036.

Fanouriakis et al.. Update on the diagnosis and management of systemic lupus erythematosus. Ann Rheum Dis, 2021, vol. 18, p. 14-25.

Figgett et al. Machine learning applied to whole-blood RNA-sequencing data uncovers distinct subsets of patients with systemic lupus erythematosus. Clin Transl Immunology, 2019, e1093, p. 1-15.

Furie et al. Novel Evidence-Based Systemic Lupus Erythematosus Responder Index. Arthritis Rheum, 2009, vol. 61, No. 9, p. 1143-1151.

Garantziotis et al. Molecular Taxonomy of Systemic Lupus Erythematosus Through Data-Driven Patient Stratification: Molecular Endotypes and Cluster-Tailored Drugs. Front Immunol. 2022, vol. 13, Art 860726, p. 1-11.

Guthridge JM, Lu R, Tran LTH, et al. Adults with systemic lupus exhibit distinct molecular phenotypes in a cross-sectional study. EClinicalMedicine, 2020, vol. 20, p. 1-7.

Hoffman et al. Gene Expression and Pharmacodynamic Changes in 1,760 Systemic Lupus Erythematosus Patients From Two Phase III Trials of BAFF Blockade With Tabalumab. Arthritis Rheumatol, 2017, vol. 69, No. 3, p. 643-654.

(56) References Cited

OTHER PUBLICATIONS

Hothorn et al. Implementing a Class of Permutation Tests: The coin Package. J Stat Softw, 2008, vol. 28, No. 8, p. 1-23.
Hubbard et al. Analysis of gene expression from systemic lupus erythematosus synovium reveals myeloid cell-driven pathogenesis of lupus arthritis. Sci Rep, 2020, vol. 10, Art17361, p. 1-17.
Hubbard et al. Transcriptomics data: pointing the way to subclassification and personalized medicine in systemic lupus erythematosus. Curr Opin Rheumatol, Nov. 1, 2021, vol. 33, No. 6, p. 579-85.
Hunter JD. Matplotlib: A 2D graphics environment. Comput Sci Eng. 2007, vol. 9, No. 3, p. 90-95.
Kingsmore et al. Altered expression of genes controlling metabolism characterizes the tissue response to immune injury in lupus. Sci Rep, 2021, vol. 11, Art 14789, p. 1-18.
Kuhn, caret: Classification and Regression Training. R package version 6.0-92, 2023, downloaded Nov. 6, 2024.
Leung et al., Machine Learning in Genomic Medicine: A Review of Computational Problems and Data Sets, Proc. of the IEEE, 2016, vol. 104, No. 1, p. 176-197.
Lewis et al. The effect of ethnicity and genetic ancestry on the epidemiology, clinical features and outcome of systemic lupus erythematosus. Rheumatology, 2017, vol. 56, Issue 1, p. i67-i77.
Lopez-Dominguez et al. Transcription Factor Activity Inference in Systemic Lupus Erythematosus. Life, 2021, vol. 11, No. 299, p. 1-12.
Lundberg et al. A Unified Approach to Interpreting Model Predictions. Adv Neural Inf Process Syst, 2017, p. 1-10.
Martínez et al., Machine learning reveals distinct gene signature profiles in lesional and nonlesional regions of inflammatory skin diseases Sci Adv., 2022, vol. 8, p. 1-15.
Merrill et al. Efficacy and safety of subcutaneous tabalumab, a monoclonal antibody to B-cell activating factor, in patients with systemic lupus erythematosus: Results from ILLUMINATE-2, a 52-week, phase III, multicentre, randomised, double-blind, placebo-controlled study. Ann Rheum Dis, 2016, vol. 75, p. 332-340.
Nehar-Belaid et al. Mapping systemic lupus erythematosus heterogeneity at the single-cell level. Nat Immunol, 2020, vol. 21, p. 1094-1106.
Neumann et al. Molecular Subgroups of T Cell Acute Lymphoblastic Leukemia in Adults Treated According to GMALL Protocols. Blood, 2020, vol. 136, Supp 1, p. 1-4.
Pedregosa et al. Scikit-learn: Machine Learning in Python. J Mach Learn Res, 2011, downloaded Nov. 6, 2024.
Petrelli et al. Autoimmune Inflammation and Insulin Resistance: Hallmarks so Far and Yet so Close to Explain Diabetes Endotypes. Curr Diab Rep, 2021, vol. 21, No. 54, p. 1-10.
Petri et al. Classification and definition of major flares in SLE clinical trials. Lupus, 1999Jul2, vol. 8, p. 685-691.
Petri et al. Sub-setting systemic lupus erythematosus by combined molecular phenotypes defines divergent populations in two phase III randomized trials. Rheumatology, 221, vol. 60, p. 5390-5396.
R Core Team (2021). R: A language and environment for statistical computing. R Foundation for Statistical Computing, Vienna, Austria, downloaded Nov. 6, 2024.
Schrodi et al., Genetic-based prediction of disease traits: prediction is very difficult, especially about the future, Frontiers in Genetics, 2014, vol. 5, Art. 162, p. 1-18.
Shobha et al. Identification and stratification of systemic lupus erythematosus patients into two transcriptionally distinct clusters based on IFN-I signature. Lupus, 2021, vol. 30, No. 5, p. 762-74.
Tarn et al. In search of pathobiological endotypes: a systems approach to early rheumatoid arthritis. Expert Rev Clin Immunol, Jun. 2, 2020, vol. 16, No. 6, p. 621-630.
Toro-Domínguez et al. Stratification of Systemic Lupus Erythematosus Patients Into Three Groups of Disease Activity Progression According to Longitudinal Gene Expression. Arthritis Rheumatol, 2018, vol. 70, No. 12, p. 2025-2035.
Van Vollenhoven et al. Conceptual framework for defining disease modification in systemic lupus erythematosus: a call for formal criteria. Lupus Sci Med, 2022, vol. 9, e000634, p. 1-7.
Wild F (2022). Isa: Latent Semantic Analysis. R package version 0.73.3, downloaded Nov. 6, 2024.
Yones et al. Interpretable machine learning identifies paediatric Systemic Lupus Erythematosus subtypes based on gene expression data. Sci Rep, 2022, vol. 12, Art 7433, p. 1-10.
Sun et al., IER3IP1 deficiency leads to increased 13-cell death and decreased 13-cell proliferation, Oncotarget, 2017, vol. 8, No. 34, p. 56768-56779.
Szklarczyk et al. STRING v10: protein-protein interaction networks, integrated over the tree of life. Nucleic Acids Research 2015, vol. 43, D447-D452.
Taylor et al.: Risk alleles for systemic lupus erythematosus in a large case-control collection and associations with clinical subphenotypes. PLoS Genet., 2011, vol. 7, No. 2, e1001311, p. 1-11.
Tesser et al. Higher interferon score and normal complement levels may identify a distinct clinical subset in children with systemic lupus erythematosus. Arthritis Research & Therapy 2020, vol. 22, No. 91, p. 1-12.
Tilburg et al. A genetic polymorphism that is associated with mitochondrial energy metabolism increases risk of fibromyalgia. Pain 2020, vol. 161, p. 2860-2871.
Vaughn et al.: Lupus risk variants in the PXK locus alter B-cell receptor internalization. Front Genet, 2015, vol. 5, Art 450, p. 1-12.
Villanueva et al.: Netting neutrophils induced endothelial damage, infiltrate tissues, and expose immunostimulatory molecules in systemic lupus erythematosus. J Immunol., 2011, vol. 187, No. 1, p. 538-552.
Vollenhoven et al.: Efficacy and Safety of Ustekinumab, an IL-12 and IL-23 Inhibitor, in Patients with Active Systemic Lupus Erythematosus: Results of a Multicentre, Double-Blind, Phase 2, Randomised, Controlled Study. The Lancet, 2018, vol. 392, Issue 10155, p. 1330-1339.
Waddell et al.: Dissecting Interferon-Induced Transcriptional Programs in Human Peripheral Blood Cells. PLoS One, 2010, vol. 5, No. 3, e9753, 13 pages.
Wang et al., "Supramolecular Kandinsky circles with high antibacterial activity," Nature Communications, 2018, vol. 9, No. 1815, p. 1-9.
Wolfe et al. 2016 Revisions to the 2010/2011 fibromyalgia diagnostic criteria. Seminars in Arthritis and Rheumatism 2016, vol. 46. p. 319-329.
Wolfe et al. Fibromyalgia Criteria and Severity Scales for Clinical and Epidemiological Studies: A Modification of the ACR Preliminary Diagnostic Criteria for Fibromyalgia. The Journal of Rheumatology 2011, vol. 38, p. 1113-1122.
Wolfe et al. The American College of Rheumatology Preliminary Diagnostic Criteria for Fibromyalgia and Measurement of Symptom Severity. Arthritis Care & Research 2010, vol. 62, p. 600-610.
Wolfe et al. The Use of Polysymptomatic Distress Categories in the Evaluation of Fibromyalgia (FM) and FM Severity. The Journal of Rheumatology 2015, vol. 42, p. 1494-1501.
Wright et al.: Low-density granulocytes: functionally distinct, immature neutrophils in rheumatoid arthritis with altered properties and defective TNF signaling. J Leukoc Biol, 2017, vol. 101, No. , p. 599-611.
Wu et al. Mitochondrial dysfunction in neurodegenerative diseases and drug targets via apoptotic signaling. Mitochondrion 2019, vol. 49, p. 35-45.
Xiao et al.: Dynamic expression of microRNAs in M2b polarized macrophages associated with systemic lupus erythematosus. Gene, 2014, vol. 547, No. 2, p. 300-309.
Xu et al., "Identification of cell types from single-cell transcriptomes using a novel clustering method," Bioinformatics, 2015, vol. 31, No. 12, p. 1974-80.
Yang et al.: Oxidative stress and Treg and Th17 dysfunction in systemic lupus erythematosus. Oxid Med Cell Longev, 2016, p. 1-9.
Zheng et al., "Massively parallel digital transcriptional profiling of single cells," Nature Communications, 2017, vol. 4, p. 1-12.
Quinn et al., Prognostic Factors in a Large Cohort Patients with Early Undifferentiated Inflammatory Arthritis After Application of a Structured Management Protocol, Arthritis & Rheumatism, 2003, vol. 48, No. 11, p. 3039-3045.

(56) References Cited

OTHER PUBLICATIONS

Karrar et al.: Abnormal B-cell development in systemic supus erythematosus: what the genetics tell US. Arthritis Rheumatol, 2018, vol. 70, No. 4, p. 496-507.
Katsiari et al. The Pathophysiologic Role of Monocytes and Macrophages in Systemic Lupus Erythematosus: A Reappraisal. Seminars in Arthritis and Rheumatism 2010, vol. 39, p. 491-503.
Kegerreis et al.: A gene expression module that identifies low-density granulocytes in the blood of patients with systemic lupus erythematosus is associated with low complement, elevated anti-dsDNA titer and both the interferon and TNF signatures. J Immunol 200, 2018, Issue 1 Supplement, 45.4.
Kegerreis et al.: A novel approach to analyze single cell RNA-SEQ data from Lupus Nephritis samples. Lupus Sci Med., 2018, Issue 5(supp 2), 2 pages.
Kegerreis et al.: Machine learning approaches to predict lupus disease activity from gene expression data. Nature Communications. Scientific Reports, 2019, vol. 9, No. 9617, p. 1-12.
Kingsmore et al.: Transcriptomic Meta-analysis of Lupus Affected Tissues Reveals Shared Immune, Metabolic, and Biochemical Dysregulation [abstract]. Arthritis Rheumatol, 2019; 71 (suppl 10). https://acrabstracts.org/abstract/transcriptomic-meta-analysis-of-lupus-affected-tissues-reveals-shared-immune-metabolic-and-biochemical-dysregulation/. Accessed May 20, 2024. Abstract No. 2899.
Knopf and Sangole, "Scientific Data Visualization Using Three-dimensional Self-organizing Feature Maps," 2001 IEEE International Conference on Systems, Man and Cybernetics: e-Systems and e-Man for Cybernetics in Cyberspace, Cat. No. 01 CH37236, 2002, vol. 2, p. 759-764.
Koga et al.: T cells and IL-17 in lupus nephritis. Clin Immunol., 2017, vol. 185, p. 95-99.
Kousathanas, et al., "Whole genome sequencing reveals host factors underlying critical Covid-19," Nature, 2022, vol. 607, 31 pages.
Kuhn: Building predictive models in R using the caret package. J Stat Softw., 2008, vol. 28, No. 5, p. 1-26.
Labonte et al.: Analysis of Lupus Nephritis Gene Expression Reveals Dysregulation of Pathogenic Pathways Activated Within Infiltrating Cells [abstract]. Arthritis Rheumatol. 2019; 71 (suppl 10). https://acrabstracts.org/abstract/analysis-of-lupus-nephritis-gene-expression-reveals-dysregulation-of-pathogenic-pathways-activated-within-infiltrating-cells/. Accessed May 20, 2024. Abstract No. 1930.
Labonte et al.: Identification of alterations in macrophage activation associated with disease activity in systemic lupus erythematosus. PloS one, 2018, vol. 13, No. 12, e0208132, p. 1-23.
Langefeld et al.: Transancestral mapping and genetic load in systemic lupus erythematosus. Nature Communications, 2017, p. 1-18.
Langfelder et al. WGCNA: an R package for weighted correlation network analysis. BMC Bioinformatics, 2008, vol. 9, No. 559, p. 1-13.
Leek et al. The sva package for removing batch effects and other unwanted variation in high-throughput experiments. Bioinformatics 2012, vol. 28, p. 882-883.
Li et al.: TIPE2 alleviates systemic lupus erythematosus through regulating macrophage polarization. Cell Physiol Biochem, 2016, vol. 38, No. 1, p. 330-339.
Liaw et al. Classification and regression by randomForest. R News, 2002, vol. 2, No. 3, p. 18-22.
Lood et al.: Neutrophil extracellular traps enriched in oxidized mitochondrial DNA are interferogenic and contribute to lupus-like disease. Nat Med., 2016, vol. 22, No. 2, p. 146-153.
Love et al. Moderated estimation of fold change and dispersion for RNA-seq data with DESeq2. Genome Biology 2014, vol. 15-550, p. 1-21.
Lugar et al.: Molecular characterization of circulating plasma cells in patients with systemic lupus erythematosus. PLoS One, 2012, vol. 7, No. 9, e44362, p. 1-15.
Ma et al. The contribution of macrophages to systemic lupus erythematosus. Clinical Immunology 2019, vol. 207, p. 1-9.
MacDonald J. R package "affycoretools": Functions useful for those doing repetitive analyses with Affymetrix GeneChips. R package version 1680, 2020, p. 1-13, downloaded Aug. 13, 2024.
Martinez: Macrophage activation and polarization. Front Biosci., 2008, vol. 13, p. 453-461.
McKenzie et al. DGCA: A comprehensive R package for Differential Gene Correlation Analysis. BMC Systems Biology 2016, vol. 10, No. 106, p. 1-25.
Meeus et al. The role of mitochondrial dysfunctions due to oxidative and nitrosative stress in the chronic pain or chronic fatigue syndromes and fibromyalgia patients: peripheral and central mechanisms as therapeutic targets? Expert Opinion on Therapeutic Targets 2013, vol. 17, p. 1081-1089.
Moussa et al., Single cell RNA-seq data clustering using TF-IDF based methods. BMC Genomics, 2018, vol. 19, Suppl 6, p. 31-45.
Nickles et al.: Blood RNA profiling in a large cohort of multiple sclerosis patients and healthy controls. Human Molecular Genetics, 2013, vol. 22, No. 20, p. 4194-4205.
Owen et al.: BD-01 Big Data Analyses. E-Genes identified via transancestral SNP mapping and gene expression analysis reveal novel targeted therapies for African-American and European-American SLE patients. Lupus Sci Med, 2018, Issue 5, Suppl 2, 2 pages Abstract.
Petri et al. Association between changes in gene signatures expression and disease activity among patients with systemic lupus erythematosus. BMC Med Genomics 2019, vol. 12, No. 4, p. 1-9.
Petri et al. Derivation and validation of the Systemic Lupus International Collaborating Clinics classification criteria for systemic lupus erythematosus. Arthritis & Rheumatism 2012; vol. 64, p. 2677-2686.
Petri et al. Validity and reliability of lupus activity measures in the routine clinic setting. J Rheumatol 1992, vol. 19, No. 1, p. 53-9.
Picard et al.: International Union of Immunological Societies: 2017 Primary Immunodeficiency Diseases Committee Report on Inborn Errors of Immunity. J Clin Immunol., 2018, vol. 38, No. 1, p. 96-128.
Plaiser et al.: Rank-rank hypergeometric overlap: identification of statistically significant overlap between gene-expression signatures. Neucleic Acids Res, 2010, vol. 38, No. 17, e169, p. 1-17.
Plotly Technologies Inc. Plotly collaborative data science. https://plot.ly 2015, downloaded Aug. 13, 2024.
Postal et al. Clinical and serological manifestations associated with interferon-α levels in childhood-onset systemic lupus erythematosus. Clinics 2012, vol. 67, p. 157-162.
R package "corrplot": Visualization of a Correlation Matrix. Version 0.92. https://github.com/taiyun/corrplot 2021, downloaded Aug. 13, 2024.
Ritchie et al.: Limma powers differential expression analyses for RNA-sequencing and microarray studies. Nucleic Acids Res. 2015, vol. 43, No. 7, e47, p. 1-13.
Robin et al.: pROC: an open-source package for R and S+ to analyze and compare ROC curves. BMC Bioinformatics, 2011, vol. 12, No. 77, p. 1-8.
Rocha et al.: Type I interferon transcriptional signature in neutrophils and high frequency of low-density granulocytes are associated with tissue damage in malaria. Cell Rep., 2015, vol. 13, No. 12, p. 2829-2841.
Rogers et al., A novel approach to addressing fibromyalgia symptomatology in SLE. In: Abstracts. Lupus Foundation of America; 2019, 102, A77.
Rogers et al., Using Clinical Characteristics and Patient-Reported Outcome Measures to Categorize Systemic Lupus Erythematosus Subtypes. Arthritis Care & Research, 2021, vol. 73, p. 386-393.
Rother et al.: Disturbed T cell signaling and altered Th17 and regulatory T cell subsets in the pathogenesis of systemic lupus erythematosus. Frontiers in Immunology, 2015, vol. 6, Article 610, p. 1-10.
Russell et al. Persistent fatigue induced by interferon-alpha: a novel, inflammation-based, proxy model of chronic fatigue syndrome. Psychoneuroendocrinology 2019, vol. 100, p. 276-285.
Scapini et al.: Human neutrophils in the saga of cellular heterogeneity: insights and open questions. Immunol Rev., 2016, vol. 273, No. 1, p. 48-60.

(56) References Cited

OTHER PUBLICATIONS

Schmidt et al.: Autoimmunity and primary immunodeficiency: two sides of the same coin? Nat Rev Rheumatol., 2017, vol. 14, No. 1, p. 7-18.
Schut-Bakker et al., Cluster analysis of flow cytometric list mode data on a personal computer. Cytometry, 1993, vol. 14, No. 6, p. 649-659.
Shao et al. CellTalkDB: a manually curated database of ligand-receptor interactions in humans and mice. Briefings in Bioinformatics 2021, vol. 22, Issue 4, p. 1-10.
She et al.: Definition, conservation and epigenetics of housekeeping and tissue-enriched genes. BMC Genomics, 2009, vol. 10, No. 269, p. 1-12.
Song et al. Multiscale Embedded Gene Co-expression Network Analysis. PLOS Computational Biology 2015, vol. 11, p. 1-35.
Catalina. Gene Expression Analysis Delineates the Roles of Multiple Type1 Interferons in Systemic Lupus Erythematosus. FOCiS 2018 Abstract Supplement W.20. San Francisco, Jun. 20-23.
Chalmers et al.: Therapeutic targeting of macrophages in lupus nephritis. Discov Med, 2015, vol. 20, No. 108, p. 43-49.
Chiche et al.: Modular transcriptional repertoire analyses of adults with systemic lupus erythematosus reveal distinct type I and type II interferon signatures. Arthritis Rheumatol. 66(6):1583-1595 (2014).
Clancy, RM et al. "Identification of Candidate Loci at 6p21 and 21 q22 in a Genome-Wide Association Study of Cardiac Manifestations of Neonatal Lupus", Arthritis and Rheumatism. vol. 62, No. 11, 2010, p. 3415-3424.
Cloke et al.: Characterization of a novel populations of low-density granulocytes associated with disease severity in HIV-1 infection. PLoS One, 2012, vol. 7, No. 11, e48939.
Cohen: Statistical power analysis for the behavioral sciences. 2nd ed. Hillsdale, N.J.: Lawrence Erlbaum Associates (1988), p. 1-41.
Crow et al., Microarray analysis of gene expression in lupus, Oct. 2003, Arthritis Research & Therapy, 2003, vol. 5, No. 6, p. 279-287.
Daamen, AR et al. "Molecular mechanisms governing the progression of nephritis in lupus prone mice and human lupus patients" Frontiers in Immunology, 2023, vol. 14, 17 pages.
Deng et al., "Single-cell RNA-seq reveals dynamic, random monoallelic gene expression in mammalian cells," Science, vol. 343, Jan. 10, 2014, pp. 193-196.
Deng et al.: Low-density granulocytes are elevated in mycobacterial infection and associated with the severity of tuberculosis. PLoS One, 2016, vol. 11, No. 4, e0153567.
Deng et al.: Mesenchymal stem cells promote CD206 expression and phagocytic activity of macrophages through IL-6 in systemic lupus erythematosus. Clin Immunol, 2015, vol. 161, No. 2, p. 209-216.
Denny et al.: A distinct subset of proinflammatory neutrophils isolated from patients with systemic lupus erythematosus induces vascular damage and synthesizes type I Interferons. J Immunol, 2010, vol. 184, No. 6, p. 3284-3297.
Der E., et al., "Single cell RNA Sequencing to Dissect the Molecular Heterogeneity in Lupus Nephritis," JCI Insight, May 2017, vol. 2, No. 9, p. 1-12.
Deweerd et al.: Structural basis of a unique interferon-beta signaling axis mediated via the receptor IFNARI. Nat. Immunol., 2013, vol. 14, p. 901-907.
Durinck et al. BioMart and Bioconductor: a powerful link between biological databases and microarray data analysis. Bioinformatics 2005, vol. 21, p. 3439-3440.
Fairfax, BP et al. "Genetics of gene expression in primary immune cells identifies cell type-specific master regulators and roles of HLA alleles", Nature Genetics, 2012, vol. 44, No. 5, p. 502-510.
Feng et al. Association of increased interferon-inducible gene expression with disease activity and lupus nephritis in patients with systemic lupus erythematosus. Arthritis & Rheumatism 2006, vol. 54, p. 2951-2962.
Ferretti et al. Overview of the Pathogenesis of Systemic Lupus Erythematosus. In: Systemic Lupus Erythematosus. Elsevier; 2016, p. 55-62.
Friedman et al.: Regularization paths for generalized linear models via coordinate descent. J Stat Softw, 2010, vol. 33, No. 1, p. 1-22.
Gladman et al. Systemic lupus erythematosus disease activity index 2000. J Rheumatol 2002, vol. 29, p. 288-91.
Goebel et al. Passive transfer of fibromyalgia symptoms from patients to mice. Journal of Clinical Investigation 2021, vol. 131, No. 13, p. 1-16.
Grammer et al.: Drug repositioning in SLE: crowd-sourcing, literature-mining and Big Data analysis. Lupus, 2016, vol. 25, No. 10, p. 1150-1170.
Gu et al. Complex heatmaps reveal patterns and correlations in multidimensional genomic data. Bioinformatics 2016, vol. 32, p. 2847-2849.
Gupta et al. Distinct Functions of Autoantibodies Against Interferon in Systemic Lupus Erythematosus: A Comprehensive Analysis of Anticytokine Autoantibodies in Common Rheumatic Diseases. Arthritis & Rheumatology 2016, vol. 68, p. 1677-1687.
Hacbarth et al.: Low density neutrophils in patients with systemic lupus erythematosus, rheumatoid arthritis, and acute rheumatic fever. Arhritis Rheum, 1986, vol. 29, No. 11, p. 1334-1342.
Hanzelmann et al.: GSVA: gene set variation analysis for microarray and RNA-Seq data. BMC Bioinformatics, 2013, vol. 14, No. 7, p. 1-15.
Harris et al.: Analysis of Discoid Lupus Erythematosus (DLE) Gene Expression Reveals Dysregulation of Pathogenic Pathways Associated with Infiltrating Immune/Inflammatory Cells [abstract]. Arthritis Rheumatol. 2019; 71 (suppl 10). https://acrabstracts.org/abstracUanalysis-of-discoid-lupus-erythematosus-dle-gene-expression-reveals-dysregulation-of-pathogenic-pathways-associated-with-infiltrating-immune-inflammatory-cells/. Accessed May 20, 2024. Abstract No. 1939.
Healy et al.: Differential transcriptional response profiles in human myeloid cell populations. Clin Immunol, 2018, vol. 189, p. 63-74.
Hochberg MC. Updating the American college of rheumatology revised criteria for the classification of systemic lupus erythematosus. Arthritis & Rheumatism 1997, vol. 40, p. 1725.
Hoffman et al.: Gene Expression and Pharmacodynamic Changes in 1,760 Systemic Lupus Erythematosus Patients From Two Phase III Trials of BAFF Blockade With Tabalumab. Arthritis & Rheumatology, 2016, vol. 69, p. 643-654.
Hornik et al., "Spherical k-Means Clustering," Journal of Statistical Software, 2012, vol. 50, Issue 10, pp. 1-22.
Hubbard et al. Anti-RNP antibodies are associated with the interferon gene signature but not decreased complement levels in SLE. Annals of the Rheumatic Diseases 2022, vol. 81, No. 632, abstract.
Hubbard et al.: Analysis of Gene Expression from Systemic Lupus Erythematosus Synovium Reveals Unique Pathogenic Mechanisms [abstract]. Arthritis Rheumatol. 2019; 71 (suppl 10). https://acrabstracts.org/abstract/analysis-of-gene-expression-from-systemic-lupus-erythematosus-synovium-reveals-unique-pathogenic-mechanisms/. Accessed May 20, 2024. Abstract No. 2022.
International Search Report and Written Opinion for PCT/US2019/049129, mailed Dec. 16, 2019.
International Search Report and Written Opinion for PCT/US2019/060641, mailed Mar. 9, 2020.
International Search Report and Written Opinion for PCT/US2021/031535, mailed Sep. 17, 2021.
International Search Report and Written Opinion for PCT/US2021/032230, mailed Nov. 5, 2021.
International Search Report and Written Opinion for PCT/US2021/065348, mailed Mar. 24, 2022.
International Search Report and Written Opinion for PCT/US2022/035552, mailed Dec. 8, 2022.
International Search Report and Written Opinion for PCT/US2022/046337, mailed Mar. 10, 2023.
International Search Report and Written Opinion for PCT/US2023/013173, mailed Jun. 28, 2023.
International Search Report and Written Opinion for PCT/US2023/020752, mailed Jul. 17, 2023.
International Search Report and Written Opinion for PCT/US2023/021260, mailed Oct. 18, 2023.
International Search Report and Written Opinion for PCT/US2023/027847, mailed Nov. 30, 2023.

(56) References Cited

OTHER PUBLICATIONS

International Search Report and Written Opinion for PCT/US2023/032946, mailed Feb. 15, 2024.
International Search Report and Written Opinion for PCT/US2023/050281, mailed Mar. 29, 2023.
Jochems et al.: Antidepressant-like properties of novel HDAC6-selective inhibitors with improved brain bioavailability. Neuropsychopharmacology, 2014, vol. 39, No. 2, p. 389-400.
Jones et al. Genome-wide expression profiling in the peripheral blood of patients with fibromyalgia. Clin Exp Rheumatol 2016, vol. 34, S96, p. 89-98.
Jourde-Chiche et al.: Modular transcriptional repertoire analyses identify a blood neutrophil signature as a candidate biomarker for lupus nephritis. Rheumatology (Oxford). 2017, vol. 56, No. 3, p. 477-487.
Abrahamowicz et al.: Development and Validation of a Novel Evidence-Based Lupus Multivariable Outcome Score for Clinical Trials. Arthritis & Rheumatology, 2018, vol. 70, No. 9, p. 1450-1458.
Baechler et al. Interferon-inducible gene expression signature in peripheral blood cells of patients with severe lupus. Proceedings of the National Academy of Sciences 2003, vol. 100, p. 2610-2615.
Banchereau et al.: Personalized immunomonitoring uncovers molecular networks that stratify lupus patients. Cell, 2016, vol. 165, No. 6, p. 551-565.
Barraclough et al., Altered cognitive function in systemic lupus erythematosus and associations with inflammation and functional and structural brain changes. Annals of the Rheumatic Diseases 2019; vol. 78, p. 934-940.
Bax et al. Carnitine Palmitoyl Transferase Deficiency in a University Immunology Practice. Current Rheumatology Reports 2020, vol. 22, p. 1-8.
Bengtsson et al.: Role of interferons in SLE. Best Pract Res Clin Rheumatol, 2017, vol. 31, No. 3, p. 415-428.
Benjamini et al.: Controlling the false discovery rate: a practical and powerful approach to multiple testing. J R Stat Soc Series B Stat Methodol, 1995, vol. 57, No. 1, p. 289-300.
Bennett et al. Interferon and Granulopoiesis Signatures in Systemic Lupus Erythematosus Blood. Journal of Experimental Medicine 2003, vol. 197, p. 711-723.
Berthier et al.: Cross-Species Transcriptional Network Analysis Defines Shared Inflammatory Responses in Murine and Human Lupus Nephritis. J. Immunol, 2012, vol. 189, No. 2, p. 988-1001.
Beyer et al.: High-resolution transcriptome of human macrophages. PLoS One, 2012, vol. 7, No. 9, e45466.
Blair et al.: Belimumab: A Review in Systemic Lupus Erythematosus. Drugs, 2018, vol. 78, No. 3, p. 355-366.
Blighe K, Lun A. R package "PCAtools": Everything Principal Components Analysis. R package version 2.2.0. https:// github.com/kevinblighe/PCAtools 2020, downloaded Aug. 13, 2024.
Breiman et al.: Classification and regression trees. New York: CRC Press. (1999).
Caielli et al. Oxidized mitochondrial nucleoids released by neutrophils drive type I interferon production in human lupus. Journal of Experimental Medicine 2016, vol. 213, p. 697-713.
Carbon et al. The Gene Ontology resource: enriching a Gold mine. Nucleic Acids Research 2021, vol. 49, D325-D334.
Carlucci et al.: Neutrophil subsets and their gene signature associate with vascular inflammation and coronary atherosclerosis in lupus. JCI Insight, 2018, vol. 3, No. 8, e99276.
Catalina et al. Patient ancestry significantly contributes to molecular heterogeneity of systemic lupus erythematosus. JCI Insight 2020, vol. 5, No. 15, p. 1-20.
Catalina et al.: Gene expression analysis delineates the potential roles of multiple interferons in systemic lupus erythematosus. Communications Biology, 2019, vol. 2, No. 140, p. 1-13.
Catalina et al.: Gene expression analysis Demonstrates that Multiple Type 1 Interferons Are Involved in Lupus Pathogenesis [abstract]. Arthritis Rheumatol. 2017, Abstract No. 2818, access May 17, 2024.
Catalina. A Role for IFNB in Systemic Lupus Erythematosus (SLE) is Predicted by Analysis of Gene Expression Data Sets. Precision in Immunology FOCIS 2017 Abstract Supplement W.20. Chicago, Jun. 14-17.
Cover et al., Nearest Neighbor Pattern Classification, IEEE Transactions of Inforamtion Theory, Jan. 1967, vol. 13(1), pp. 21-27.
2019 ACR/ARP Annual Meeting Abstract Supplement. Arthritis and Rheumatology 71(Suppl_10):1-5420 (2019).
Adzhubei, I., Jordan, D. M. & Sunyaev, S. R. Predicting functional effect of human missense mutations using PolyPhen-2. Curr. Protoc. Hum. Genet., 2013, p. 1-52.
Adzhubei, Ivan et al. Predicting Functional Effect of Human Missense Mutations Using PolyPhen-2. Current protocols in Human Genetics Chapter 7:Unit7.20, 1-41 (2013).
Alarcon-Segovia, Donato et al. Familial aggregation of systemic lupus erythematosus, rheumatoid arthritis, and other autoimmune diseases in 1,177 lupus patients from the GLADEL cohort. Arthritis and Rheumatism 52(4):1138-1147 (2005).
Alenghat, Francis J. The prevalence of atherosclerosis in those with inflammatory connective tissue disease by race, age and traditional risk factors. Scientific Reports 6(1):20303, 1-9 (2016).
Alexander, Tobias et al. The proteasome inhibitior bortezomib depletes plasma cells and ameliorates clinical manifestations of refractory systemic lupus erythematosus. Annals of the Rheumatic Diseases 74(7):1474-1478 (2015).
Alperin, et al., Monogenic Lupus: A Developing Paradigm of Disease. Frontiers in immunology, 2018, v9, art2496, p. 1-11.
Aoki, Masayo et al. Sphingosine-1-phosphate signaling in immune cells and inflammation: roles and therapeutic potential. Mediators of Inflammation 2016(1):8606878, 1-11 (2016).
Aringer, M. et al. Current state of evidence on 'off-label' therapeutic options for systemic lupus erythematosus, including biological immunosuppressive agents, in Germany, Austria and Switzerland—a consensus report. Lupus 21(4):386-401 (2012).
Banchereau, Romain et al. Personalized immunomonitoring uncovers molecular networks that stratify lupus patients. Cell 165(3):551-565 (2016).
Barabasi, Albert-Laszlo, and Eric Bonabeau. Scale-free networks. Scientific American 288(5):60-69 (2003).
Barnado, April et al. Phenome-wide association study identifies marked increased in burden of comorbidities in African Americans with systemic lupus erythematosus. Arthritis Research & Therapy 20(1):69, 1-11 (2018).
Bentham, James et al. Genetic association analyses implicate aberrant regulation of innate and adaptive immunity genes in the pathogenesis of systemic lupus erythematosus. Nature Genetics 47(12):1457-1464 (2015).
Bernatsky, S. et al. Mortality in systemic lupus erythematosus. Arthritis & Rheumatism: Official Journal of the American College of Rheumatology 54(8):2550-2557 (2006).
Bjornadal, Lena et al. Cardiovascular disease a hazard despite improved prognosis in patients with systemic lupus erythematosus: results from a Swedish population based study 1964- 95. The Journal of rheumatology 31(4):713-719 (2004).
Bortezomib Injection. Chemo Care, 2025; [retrieved on 2026-01-06]. Available at URL: https://chemocare.com/druginfo/bortezomib pp. 1-4.
Brainarray. Version 24.0.0, ENSE. [retrieved on Jan. 8, 2026]. Available at URL: http://brainarray.mbni.med.umich.edu/Brainarray/Database/CustomCDF/24.0.0/ense.asp.
Bucciol, G. et al. Lessons learned from the study of human inborn errors of innate immunity. J. Allergy Clin. Immunol., 2019, v143, 507-527.
Buskiewicz, I. A. et al. Reactive oxygen species induce virus-independent MAVS oligomerization in systemic lupus erythematosus. Sci. Signal., 2016, v9, ra115 p. 1-38.
Caielli, S. et al. Erythroid mitochondrial retention triggers myeloid-dependent type I interferon in human SLE. Cell, 2021, v184, p. 4464-4479.
Cannon, Maren E. et al. Deciphering the emerging complexities of molecular mechanisms at GWAS loci. The American Journal of Human Genetics 103(5):637-653 (2018).

(56) References Cited

OTHER PUBLICATIONS

Cartier, Andreane et al. Sphingosine 1-phosphate: lipid signaling in pathology and therapy. Science 366(6463):ear5551, 1-14 (2019).
Caswell, Thomas A. et al. matplotlib/matplotlib: REL: v3.3.4. Zenodo (2021).
Catalina et al.: Ancestry Influences the Gene Expression Profile in Systemic Lupus Erythematosus and Contributes to Transcriptomic Heterogeneity in Lupus Patients. AMPEL BioSolutions and 2RILITE Research Institute (2019) Abstract.
Catalina, Michelle D. et al. The pathogenesis of systemic lupus erythematosus: harnessing big data to understand the molecular basis of lupus. Journal of autoimmunity 110:102359, 1-20 (2020). Published Online Dec. 2, 2019.
Choi, Yongwook et al. Predicting the functional effect of amino acid substitutions and indels. Nature Methods 7(10):e46688, 1-13 (2012).
Ciccacci, Cinzia. Discovering the genetic contribution to cardiovascular diseases in patients affected by autoimmune diseases. Annals of translational medicine 6(Suppl_1):S44, 1-3 (2018).
ClinicalTrials.gov Identifier: NCT01196091. A Study of LY2127399 in Participants With Systemic Lupus Erythematosus, Record created Jun. 11, 2018. pp. 1-24. [retrieved on Jan. 13, 2026] Available at URL: https://clinicaltrials.gov/study/NCT01196091?term=NCT01196091&rank=1.
ClinicalTrials.gov Identifier: NCT01205438. A Study of LY2127399 in Participants With Systemic Lupus Erythematosus, Record created Jun. 18, 2018. pp. 1-36. [retrieved on Jan. 13, 2026] Available at URL: https://clinicaltrials.gov/study/NCT01205438?term=NCT01205438&rank=1.
Clowse et al.: Biologic Differences Between Type 1 and 2 Lupus. Duke University Medical School. Poster.
Co-pending U.S. Appl. No. 19/199,677, inventors Davis; Haley et al., filed May 6, 2025.
Co-pending U.S. Appl. No. 19/259,293, inventors Shrotri; Sneha et al., filed Jul. 3, 2025.
Co-pending U.S. Appl. No. 19/267,957, inventors Owen; Katherine A. et al., filed Jul. 14, 2025.
Corradin, Olivia., and Peter C Scacheri. Enhancer variants: evaluating functions in common disease. Genome Medicine 6(10):85, 1-14 (2014).
Cortes, Adrian., and Matthew A Brown. Promise and pitfalls of the Immunochip. Arthritis Research & Therapy 13(1):101, 1-3 (2011).
Cruz, C. S. D. & Kang, M.-J. Mitochondrial dysfunction and damage associated molecular patterns (DAMPs) in chronic inflammatory diseases. Mitochondrion, 2018, v41, p. 37-44.
Cunninghame Graham, D. S. & Vyse, T. J. The candidate gene approach: Have murine models informed the study of human SLE? Clinical and Experimental Immunology, 2004, v137, p. 1-7.
Dai, Manhong et al. Evolving gene/transcript definitions significantly alter the interpretation of GeneChip data. Nucleic acids research 33(20):e175, 1-9 (2005).
Dai, R. & Ahmed, S. A. microRNA, a new paradigm for understanding immunoregulation, inflammation, and autoimmune diseases. Transl. Res., 2011, v157, p. 163-179.
Davis et al.: Genome Documentation of Molecular Pathways Driving the Autoimmune Disease Systemic Lupus Erythematosus by Cross Referencing Signaling Checkpoints in the Immune System Identified in Patients with Primary Immunodeficiency. Poster Ampel Bio Solutions LLC (Oct. 25, 2018).
De Leeuw, Wim C. et al. Salvaging Affymetrix probes after probe-level re-annotation. BMC research notes 1(1):66, 1-5 (2008).
Demirkaya, et al., New Horizons in the Genetic Etiology of Systemic Lupus Erythematosus and Lupus-Like Disease: Monogenic Lupus and Beyond. J. Clin. Med., 2020, v9, 712, p. 1-20.
Eckschlager, Tomas et al. Histone deacetylase inhibitors as anti-cancer drugs. International Journal of Molecular Sciences 18(7):1414, 1-25 (2017).
Emilsson, Valur et al. Genetics of gene expression and its effect on disease. Nature 452(7186):423-428 (2008).
Errante et al., Primary immunodeficiency association with systemic lupus erythematosus: Review of literature and lessons learned by the Rheumatology Division of a tertiary university hospital at Sao Paulo, Brazil. Revista Brasileira de Reumatologia, 2016, v56, p. 58-68.
Extended European Search Report for European Application No. 19884758.4, mailed Oct. 21, 2022, 15 Pages.
Faissner, Simon., and Ralf Gold. Progressive multiple sclerosis: latest therapeutic developments and future directions. Therapeutic Advances in Neurological Disorders 12:1756286419878323, 1-11 (2019).
Feldman, C. H. et al. Epidemiology and sociodemographics of systemic lupus erythematosus and lupus nephritis among US adults with Medicaid coverage, 2000-2004. Arthritis Rheum., 2013, v65, p. 753-763.
Fernandez, D., Bonilla, E., Mirza, N., Niland, B. & Perl, A. Rapamycin reduces disease activity and normalizes T cell activation-induced calcium fluxing in patients with systemic lupus erythematosus. Arthritis Rheum., 2006 v54, 2983-2988.
Fishilevich, Simon et al. GeneHancer: genome-wide integration of enhancers and target genes in GeneCards. Database 2017:bax028, 1-17 (2017).
Freedman, Barry I. et al. End-stage renal disease in African Americans with lupus nephritis is associated with APOL1. Arthritis and Rheumatology 66(2):390-396 (2014).
Furie, Richard et al. A phase III, randomized, placebo-controlled study of belimumab, a monoclonal antibody that inhibits B lymphocyte stimulator, in patients with systemic lupus erythematosus. Arthritis & Rheumatism 63(12):3918-3930 (2011).
Gajofatto, Alberto. Spotlight on siponimod and its potential in the treatment of secondary progressive multiple sclerosis: the evidence to date. Drug Design, Development and Therapy 11:3153-3157 (2017).
Gene Set Enrichment Analysis, Human MSigDB Collections. UCSanDiego: Broad institute, [retrieved on Jan. 9, 2026]. Available at URL:https://www.gsea-msigdb.org/gsea/msigdb/collections.jsp pp. 1-3.
Geneontology, The Gene Ontology Resource, [retrieved on 2026-01-09]. Available at URL:https://geneontology.org/ pp. 1-4.
Ghilardi et al.: Selective inhibition of NF-KB Inducing Kinase (NIK) is Therapeutically Efficacious in IFN-Accelerated Lupus Nephritis Prone Mice. FOCIS 2018 Abstract Supplement F. 28. San Francisco, Jun. 20-23.
Giles, B. M. & Boackle, S. A. Linking complement and anti-dsDNA antibodies in the pathogenesis of systemic lupus erythematosus. Immunol. Res, 2013, v55, p. 1-20.
Glur, Christoph et al. Data.tree: General Purpose Hierarchical Data Structure. R Package Version 1.0.0 :1-65 (2020).
Goulielmos, George N. et al. The genetics and molecular pathogenesis of systemic lupus erythematosus (SLE) in populations of different ancestry. Gene 668:59-72 (2018).
Graham, et al., Review of recent genome-wide association scans in lupus. in Journal of Internal Medicine, 2009, v265, p. 680-688.
Grammer, Amrie C, and Peter E. Lipsky. Drug repositioning strategies for the identification of novel therapies for rheumatic autoimmune inflammatory diseases. Rheumatic diseases clinics of North America 43(3):467-480 (2017).
Grayson et al. Metabolic pathways and immunometabolism in rare kidney diseases. Ann. Rheum. Dis., 2018, v77, p. 1227-1234.
Greenfest-Allen, Emily et al. iterativeWGCNA: iterative refinement to improve module detection from WGCNA co-expression networks. BioRxiv 234062 :1-24 (2017).
Griss, J. et al. B cells sustain inflammation and predict response to immune checkpoint blockade in human melanoma. Nat. Commun., 2019, v10, 4186, p. 1-14.
Harris et al.: Analysis of Discoid Lupus Erythematosus (DLE) Gene Expression Reveals Dysregulation of Pathogenic Pathways Associated with Infiltrating Immune/Inflammatory Cells. AMPEL BioSolutions and RILITE Research Institute. Poster Nov. 1, 2019.
Heberle, Henry et al. InteractiVenn: a web-based tool for the analysis of sets through Venn diagrams. BMC Bioinformatics 16(1):169, 1-7 (2015).
Hoffman, et al. Gene Expression and Pharmacodynamic Changes in 1,760 Systemic Lupus Erythematosus Patients From Two Phase III

(56) References Cited

OTHER PUBLICATIONS

Trials of BAFF Blockade With Tabalumab. Arthritis Rheumatol, vol. 69, No. 3, p. 643-654. (2017).
Hoffman, R W. et al. Series GSE88884, Gene expression changes in baseline SLE patients vs. healthy controls from two phase III trials (ILLUMINATE-1 and ILLUMINATE-2) of B cell activating factor blockade with tabalumab. Record created Oct. 18, 2016. pp. 1-2. [retrieved on Jan. 8, 2026] Available at URL:https://www.ncbi.nlm.nih.gov/geo/query/acc.cgi?acc=GSE88884.
Honarpisheh, M., Kohler, P., Rauchhaupt, E. Von & Lech, M. The involvement of microRNAs in modulation of innate and adaptive immunity in systemic lupus erythematosus and lupus nephritis. J. Immunol. Res. 2018, ArtID4126106, 15 pages.
Hubbard, Erika et al. Analysis of Lupus Synovitis Gene Expression Reveals Dysregulation of Pathogenic Pathways Activated within Infiltrating Immune Cells. Poster presented at ACR/ARHP Annual Meeting. p. 1 (2018).
Hubbard et al.: Analysis of Gene Expression from Systemic Lupus Erythematosus Synovium Reveals Unique Pathogenic Mechanisms [Abstract]. Annual Meeting of the American College of Rheumatology. Chicago, IL (Jun. 2019).
Hubbard et al.: Analysis of Lupus Synovitis Gene Expression Reveals Dysregulation of Pathogenic PathwaysActivated within Infiltrating Immune Cells. Arthritis Rheumatol., 2018, vol. 70, suppl 10, 2018, 2 pages.
IL283131 Office Action dated Oct. 30, 2025.
Jakes, R. W. et al. Systematic review of the epidemiology of systemic lupus erythematosus in the Asia-Pacific region: Prevalence, incidence, clinical features, and mortality. Arthritis Care Res., 2012, v64, 159-168.
Julia, A. et al. Genome-wide association study meta-analysis identifies five new loci for systemic lupus erythematosus. Arthritis Res. Ther., 2018, v20, 100, p. 1-10.
Kain, J. et al. Mendelian randomization and pathway analysis demonstrate shared genetic associations between lupus and coronary artery disease. Cell Rep. Med., 2022, v3, 100805, p. 1-18.
Kammer, G. M. et al. Deficient type I protein kinase A isozyme activity in systemic lupus erythematosus T lymphocytes. The Journal of Clinical Investigation 94(1):422-430 (1994).
Kammer, Gary M. Deficient protein kinase a in systemic lupus erythematosus: a disorder of T lymphocyte signal transduction. Annals of the New York Academy of Sciences 968(1):96-105 (2002).
Kanehisa, M., Furumichi, M., Sato, Y., Kawashima, M. & Ishiguro-Watanabe, M. Kegg for taxonomy-based analysis of pathways and genomes. Nucleic Acids Res., 2023, v51, D587-D592.
Kappos, Ludwig et al. Siponimod versus placebo in secondary progressive multiple sclerosis (EXPAND): a double-blind, randomised, phase 3 study. The Lancet 391(10127):1263-1273 (2018).
Kegerreis et al.: A novel approach to analyze single cell RNA-Seq data from lupus nephritis samples. Abstract. https://lupus.bmj.com/content/5/Suppl_2/A17.2.info (2018).
Kingsmore et al.: Transcriptomic meta-analysis of lupus affected tissues reveals shared immune, metabolic, and biochemical dysregulation. Ampel BioSolutions, LLC. (2019).
Kingsmore et al.: Transcriptomic meta-analysis of lupus affected tissues reveals shared immune, metabolic, and biochemical dysregulation. Ampel BioSolutions, LLC. Annual Meeting (2019).
Kolde, Raivo. pheatmap: Pretty Heatmaps. R package version 1.0.12 :1-8 (2019).
Labonte et al.: Analysis of Lupus Nephritis Gene Expression Reveals Dysregulation of Pathogenic Pathways Activated Within Infiltrating Cells. (2019).
Labonte et al.: Identification of Perturbations in Macrophage Polarization in Active Systemic Lupus Erythematosus. Ampel Bio Solutions LLC. AAI 2018 Abstract.
Labonte et al.: Identification of Perturbations in Macrophage Polarization in Active Systemic Lupus Erythematosus. Ampel Bio Solutions LLC. AAI 2018 Poster.
Lai, Z.-W. et al. N-Acetylcysteine reduces disease activity by blocking mammalian target of rapamycin in T cells from systemic lupus erythematosus patients: A randomized, double-blind, placebo-controlled trial. Arthritis Rheum., v64, 2937-2946.
Lam, Wing Y. et al. Metabolic links between plasma cell survival, secretion, and stress. Trends in Immunology 39(1):19-27 (2018). Published online Sep. 11, 2017.
Lamore III, Raymond et al. Belimumab (benlysta): a breakthrough therapy for systemic lupus erythematosus. Pharmacy and Therapeutics 37(4):212-214, 217, 226 (2012).
Lanata, C. M. et al. Genetic contributions to lupus nephritis in a multi-ethnic cohort of systemic lupus erythematous patients. PLoS ONE, 2018, v13, e0199003, p. 1-15.
Langfelder, P. et al. Defining clusters from a hierarchical cluster tree: the Dynamic Tree Cut package for R. Bioinformatics 24(5):719-720 (2008).
Lattanzi, B. et al. Measures of disease activity and damage in pediatric systemic lupus erythematosus: British Isles Lupus Assessment Group (BILAG), European Consensus Lupus Activity Measurement (ECLAM), Systemic Lupus Activity Measure (SLAM), Systemic Lupus Erythematosus Disease Activity Index (SLEDAI), Physician's Global Assessment of Disease Activity (MD Global), and Systemic Lupus International Collaborating. Arthritis Care Res., 2011, v63, Supp11, p. S112-117.
Leonard, Dag et al. Novel gene variants associated with cardiovascular disease in systemic lupus erythematosus and rheumatoid arthritis. Annals of the rheumatic diseases 77(7):1063-1069 (2018).
Lessard, et al. Identification of a Systemic Lupus Erythematosus Risk Locus Spanning ATG16L2, FCHSD2, and P2RY2 in Koreans. Arthritis Rheumatol. 2016, vol. 68(5), p. 1197-209.
Li, M. et al. Chinese SLE Treatment and Research group (CSTAR) registry: I. Major clinical characteristics of Chinese patients with systemic lupus erythematosus. Lupus, 2013, v22, 1192-1199.
Li, P. et al. Glutathione peroxidase 4-regulated neutrophil ferroptosis induces systemic autoimmunity. Nat. Immunol., 2021, v22, 1107-1117.
Lightfoot, Yaima L. et al. Metabolic abnormalities and oxidative stress in lupus. Current Opinion in Rheumatology 29(5):442-449 (2017).
Li,P.H. & Lau, C. S. Lupus in the far East: A modern epidemic. Int. J. Rheum. Dis., 2017, v20, 523-525.
Lipsky, P. E. SP0156 How big data help us understand new and old therapy targets. Speaker Presentations Genomic imprinting and post-translational modifications :38, p. 1 (2017).
Liu, D. & Zhang, W. Pioglitazone attenuates lupus nephritis symptoms in mice by modulating miR-21-5p/TIMP3 Axis: The key role of the activation of peroxisome proliferator-activated receptor-y. Inflammation, 2021, v44, 1416-1425.
Liu, Yudong, and Mariana J. Kaplan. Cardiovascular disease in systemic lupus erythematosus: an update. Current opinion in rheumatology 30(5):441-448 (2018).
Lonsdale, John et al. The genotype-tissue expression (GTEx) project. Nature genetics 45(6):580-585 (2013).
Marchiani, Anna et al. Curcumin and curcumin-like molecules: from spice to drugs. Current medicinal chemistry 21(2):204-222 (2014).
Mccusker, C. & Warrington, R. Primary immunodeficiency. Allergy, Asthma Clin. Immunol., 2011, v7, Suppl; p. 1-8.
Mckenzie, Andrew T. et al. Brain Cell Type Specific Gene Expression and Co-expression Network Architectures. Scientific reports 8(1):8868, 1-19 (2018).
Menard, Laurence C. et al. B cells from African American lupus patients exhibit an activated phenotype. JCI Insight 1(9):1-14 (2016).
Merrill, Joan T. et al. Efficacy and safety of rituximab in moderately-to-severely active systemic lupus erythematosus: the randomized, double-blind, phase II/III systemic lupus erythematosus evaluation of rituximab trial. Arthritis & Rheumatism 62(1):222-233 (2010).
Mi, Huaiyu et al. Panther version 11: expanded annotation data from Gene Ontology and Reactome pathways, and data analysis tool enhancements. Nucleic Acids Research 45(D1):D183-D189 (2017). Published online Nov. 29, 2016.
Mok, M. Y. & Li, W. L. Do Asian patients have worse lupus ?. Lupus, 2010, v19, 1384-1390.

(56) References Cited

OTHER PUBLICATIONS

Morley, Michael et al. Genetic analysis of genome-wide variation in human gene expression. Nature 430(7001):743-747 (2004).
Morris, David L. et al. Genome-wide association meta-analysis in Chinese and European individuals identifies ten new loci associated with systemic lupus erythematosus. Nature Genetics 48(8):940-946 (2016).
Namas, R., Renauer, P., Ognenovski, M., Tsou, P. S. & Sawalha, A. H. Histone H2AX phosphorylation as a measure of DNA double-strand breaks and a marker of environmental stress and disease activity in lupus. Lupus Sci. Med., 2016, v3, e000148, p. 1-6.
Nasonov, E. et al. Standard medical care of patients with systemic lupus erythematosus (SLE) in large specialised centres: data from the Russian Federation, Ukraine and Republic of Kazakhstan (ESSENCE). Lupus science & medicine 2(1):e000060, 1-8 (2015).
Navarra, Sandra V. et al. Efficacy and safety of belimumab in patients with active systemic lupus erythematosus: a randomised, placebo-controlled, phase 3 trial. The Lancet 377(9767):721-731 (2011).
Navid, Fatemeh., and Robert A. Colbert. Causes and consequences of endoplasmic reticulum stress in rheumatic disease. Nature Reviews Rheumatology 13(1):25-40 (2017). Published online Dec. 1, 2016.
Nossent, J. C., Becker-Merok, A., Rischmueller, M. & Lester, S. Susceptibility for lupus nephritis by low copy number of the FCGR3B gene is linked to increased levels of pathogenic autoantibodies. Autoimmune Dis. 2013, v2013, Art 750814, p1-6.
Owen, et al, Analysis of Trans-Ancestral SLE Risk Loci Identifies Unique Biologic Networks and Drug Targets in African and European Ancestries. Am J Hum Genet. 2021, vol. 107(5), p. 864-81.
Owen et al.: The Integration of Genetic Data, Molecular Pathway Analysis and Differential Expression to Delineate the Impact of Ancestral Differences on Lupus. Abstract (2019).
Owen et al.: The Integration of Genetic Data, Molecular Pathway Analysis and Differential Expression to Delineate the Impact of Ancestral Differences on Lupus. Poster (2019).
PCT/US2021/032230 International Preliminary Report on Patentability dated Nov. 24, 2022.
PCT/US2023/013173 International Preliminary Report on Patentability dated Aug. 29, 2024.
PCT/US2023/013173 Invitation to Pay Additional Fees dated Apr. 27, 2023.
PCT/US2023/021260 International Preliminary Report on Patentability dated Nov. 21, 2024.
PCT/US2023/021260 Invitation to Pay Additional Fees dated Jul. 5, 2023.
PCT/US2023/032946 International Preliminary Report on Patentability dated May 22, 2025.
PCT/US2023/032946 Invitation to Pay Additional Fees dated Nov. 6, 2023.
PCT/US2025/031147 International Search Report and Written Opinion dated Sep. 2, 2025.
Ratliff, B. B., Abdulmandi, W., Pawar R. & Wolin, M. S. Oxidant mechanisms in renal injury and disease. Antioxid. Redox Signal. 2016, v25, p. 119-146.
Ravasz, Erzsebet et al. Hierarchical organization of modularity in metabolic networks. Science 297(5586):1551-1555 (2002).
Ren, Jingjing et al. Selective histone deacetylase 6 inhibition normalizes B cell activation and germinal center formation in a model of systemic lupus erythematosus. Frontiers in Immunology 10:2512, 1-16 (2019).
Richman, I. B. et al. European genetic ancestry is associated with a decreased risk of lupus nephritis. Arthritis Rheum., 2012, v64, p. 1-16.
Riege, K. et al. Massive effect on LncRNAs in human monocytes during fungal and bacterial infections and in response to vitamins A and D. Sci. Rep., 2017, v7, 40598, p. 1-13.
Robinson, E. K., Coverrubias, S. & Carpenter, S. The how and why of IncRNA function: An innate immune perspective. Biochimica et Biophysica Acta Gene Regulat. Mech., 2020, v1863, 194419, p. 1-17.
Rovin, Brad H. et al. Efficacy and safety of rituximab in patients with active proliferative lupus nephritis: the Lupus Nephritis Assessment with Rituximab study. Arthritis & Rheumatism 64(4):1215-1226 (2012).
Rullo, Ornella Josephine et al. Recent insights into the genetic basis of systemic lupus erythematosus. Annals of the Rheumatic Diseases 72:ii56-ii61 (2013). Published online Dec. 19, 2012.
Sandling, J. K. et al. A candidate gene study of the type i interferon pathway implicates IKBKE and IL8 as risk loci for SLE. Eur. J. Hum. Genet., 2011, v19, p. 479-484.
Schadt, Eric E. et al. Genetics of gene expression surveyed in maize, mouse and man. Nature 422(6929):297-302 (2003).
Shah, D., Mahajan, N., Sah, S., Nath, S. K. & Paudyal, B. Oxidative stress and its biomarkers in systemic lupus erythematosus. J. Biomed. Sci., 2014, v21(23), p. 1-13.
Shannon, Paul et al. Cytoscape: a software environment for integrated models of biomolecular interaction networks. Genome Research 13(11):2498-2504 (2003).
Siddani, et al., Candidate Gene Identification for Systemic Lupus Erythematosus Using Network Centrality Measures and Gene Ontology. PLOS One, 2013, v8, iss12, e81766, p. 1-8.
Sim, Ngak-Leng et al. SIFT web server: predicting effects of amino acid substitutions on proteins. Nucleic Acids Research 40(W1):W452-W457 (2012).
Song, Won-Min and Bin Zhang. MEGENA: Multiscale Clustering of Geometrical Network. R package version 1.3.7 :1-24 (2018).
Stavast, Christiaan J. et al. The non-canonical aspects of microRNAs: many roads to gene regulation. Cells 8(11):1465, 1-20 (2019).
Stearrett, Nathaniel et al. Expression of Human Endogenous Retroviruses in Systemic Lupus Erythematosus: Multiomic Integration With Gene Expression. Frontiers in immunology 12:1485 (2021).
Stein, N. et al. IFNG-AS1 enhances interferon gamma production in human natural killer cells. iScience, 2019, v11, p. 466-473.
Stranger, Barbara E. et al. Patterns of cis regulatory variation in diverse human populations. PLoS genetics 8(4):e1002639, 1-13 (2012).
Sun, Celi et al. High-density genotyping of immune-related loci identifies new SLE risk variants in individuals with Asian ancestry. Nature genetics 48(3):323-330 (2016).
Systemic lupus erythematosus. MedlinePlus, Apr. 27, 2022; [retrieved on Jan. 6, 2026]. Available at URL:https://medlineplus.gov/genetics/condition/systemic-lupus- erythematosus/#definition pp. 1-7.
Tangye, S. G. et al. Human Inborn Errors of Immunity: 2019 Update on the Classification from the International Union of Immunological Societies Expert Committee. J. Clin. Immunol., 2020, v40, p. 24-64.
Thaventhiran, J. E. D. et al. Whole-genome sequencing of a sporadic primary immunodeficiency cohort. Nature, v583, p. 90-95.
The Protein Atlas, 2022. Available online at www.proteinatlas.org.
Tsai, C.-Y. et al. Aberrant non-coding RNA expression in patients with systemic lupus erythematosus: Consequences for immune dysfunctions and tissue damage. Biomolecules, 2020, v10, p. 1-24.
Tsai, C-Y. et al. Cross-talk between mitochondrial dysfunction-provoked oxidative stress and aberrant noncoding RNA expression in the pathogenesis and pathophysiology of SLE. Int. J. Mol. Sci., 2019, v20(5183), p. 1-18.
Tumminello, M. et al. A tool for filtering information in complex systems. Proceedings of the National Academy of Sciences 102(30):10421-10426 (2005).
U.S. Appl. No. 18/806,109 Office Action dated Jan. 6, 2026.
U.S. Appl. No. 18/806,109 Office Action dated Jun. 9, 2025.
U.S. Appl. No. 18/806,109 Office Action dated Nov. 27, 2024.
Van Der Harst, Pim, and Niek Verweij. Identification of 64 novel genetic loci provides an expanded view on the genetic architecture of coronary artery disease. Circulation research 122(3):433-443 (2018).
Vaser, Robert et al. SIFT missense predictions for genomes. Nature protocols 11(1):1-9 (2016).
Wang et al.: Glomerular and Tubular Transcriptional Profiles Reveal Gene Clusters Specific for Different Stages of Glomerulonephritis in NZM2328 mice. Poster/Abstract Oct. 16, 2018. 16 pages.
Wang, Jing et al. HACER: an atlas of human active enhancers to interpret regulatory variants. Nucleic acids research 47(D1):D106-D112 (2019).

(56) References Cited

OTHER PUBLICATIONS

Wang, X. et al. Long noncoding RNAs in the regulation of oxidative stress. Oxid. Med. Cell. Longev. 2019, vs2019 (1318795), p. 1-7.
Wang, Y-F. et al. Identification of 38 novel loci for systemic lupus erythematosus and genetic heterogeneity between ancestral groups. Nat. Commun., 2021, v12(772), p. 1-13.
Ward, Lucas D, and Manolis Kellis. HaploReg v4: systematic mining of putative causal variants, cell types, regulators and target genes for human complex traits and disease. Nucleic acids research 44(D1):D877-D881 (2016).
Wehbi, Vanessa L, and Kjetil Tasken. Molecular mechanisms for cAMP-mediated immunoregulation in T cells—role of anchored protein kinase a signaling units. Frontiers in immunology 7:222, 1-19 (2016).
Westra, Harm-Jan et al. Systematic identification of trans eQTLs as putative drivers of known disease associations. Nature genetics 45(10):1238-1243 (2013).
Wickham, Hadley, and Carson Sievert. ggplot2: elegant graphics for data analysis. New York: springer, 10:1-3 (2016).
Williams, Edith M. et al. I too, am America: a review of research on systemic lupus erythematosus in African-Americans. Lupus science & medicine 3(1):e000144, 1-22 (2016).
Wilson et al., Augmented glucose dependency of autoreactive B cells provides a treatment target for lupus. 2022, p. 1-65, downloaded May 7, 2025; bioRxiv preprint doi: https://doi.org/10.1101/2022.02.01.475510.
Xie, Z. et al. Gene set knowledge discovery with Enrichr. Curr. Protoc., 2021, v1, e90, p. 1-84.
Yang et al. Genome-wide association study in Asian populations identifies variants in ETS1 and WDFY4 associated with systemic lupus erythematosus. PLoS Genet. 2010, vol. 6(2): e1000841, p. 1-11.
Yap, D. Y. H. & Chan, T. M. Lupus nephritis in Asia: Clinical features and management. Kidney Dis., 2015, v1, p. 100109.
Yip, Andy M and Steve Horvath. Gene Network Interconnectedness and the Generalized Topological Overlap Measure. BMC bioinformatics 8(1):22, 1-14 (2007).
Yip, Terry Cheuk-Fung et al. Predictors of the start of declining eGFR in patients with systemic lupus erythematosus. Lupus 30(1):15-24 (2021). Published Online Oct. 28, 2020.
Zayat, A. S et al. Defining inflammatory musculoskeletal manifestations in systemic lupus erythematosus. Rheumatology, 2019, v58, p. 304-312.
Zeller, Carlos B, and Simone Appenzeller. Cardiovascular disease in systemic lupus erythematosus: the role of traditional and lupus related risk factors. Current cardiology reviews 4(2):116-122 (2008).
Zhang, C., Wang, H., Yin, L., Mao, Y. & Zhou, W. Immunometabolism in the pathogenesis of systemic lupus erythematosus. J. Transl. Autoimmun., 2020, v3(100046), p. 1-10.
Zhang, H. et al. Anti-dsDNA antibodies bind to TLR4 and activate NLRP3 inflammasome in lupus monocytes/ macrophages. J. Transl. Med., 2016, v14(156), p. 1-12.
Zhang, Xiaopei et al. Mechanisms and functions of long non-coding RNAs at multiple regulatory levels. International journal of molecular sciences 20(22):5573, 1-29 (2019).
Abdel-Naser, et al. Increased Activity and No. of Epidermal Melanocytes in Lesional Psoriatic Skin, Dermatology 232, 425-430 (2016).
Adams, et al. Global metabolic profiling of human osteoarthritic synovium. Osteoarthr. Cartil., vol. 20, p. 64-7 (2012).
Afshinnia, et al. Impaired B-oxidation and altered complex lipid fatty acid partitioning with advancing Ckd. J. Am. Soc. Nephrol. 29, 295-306 (2018).
Agostinelli, Robust stepwise regression. J. Appl. Stat. 29, 825-840 (2002).
Ahmed, et al. Transcriptional Profiling Suggests Extensive Metabolic Rewiring of Human and Mouse Macrophages during Early Interferon Alpha Responses. Mediators Inflamm., vol. 2018, Article 59608619, 15 pages (2018).
Ahmed, S. Ansar et al. Sex hormones, immune responses, and autoimmune diseases. Mechanisms of sex hormone action. American Journal of Pathology 121(3):531-551 (1985).
Ahmed, Sadia, and Jennifer H. Anolik. B cell biology and related therapies in SLE. Rheumatic Diseases Clinics of North America 36(1):109, 1-25 (2010).
Aitman, Timothy J. et al. Copy number polymorphism in Fcgr3 predisposes to glomerulonephritis in rats and humans. Nature 439(7078):851-855 (2006).
Ajeganova, et al Patients with SLE have higher risk of cardiovascular events and mortality in comparison with controls with the same levels of traditional risk factors and intima-media measures, which is related to accumulated disease damage and antiphospholipid syndrome: a case-control study over 10 years. Lupus Sci. Med. 2021, vol. 8, No. 1, e000454, p. 1-11.
Alarcón-Riquelme, et al. Genome-Wide Association Study in an Amerindian Ancestry Population Reveals Novel Systemic Lupus Erythematosus Risk Loci and the Role of European Admixture. Arthritis Rheumatol, 2016, vol. 68, No. 4, p. 932-943.
Alkady, M. Mannose binding lectin gene polymorphism and preclinical carotid atherosclerosis in patients with systemic lupus erythematosus. Egyptian Journal of Immunology 17(2):131-141 (2010).
Almaani, Salem et al. Rethinking lupus nephritis classification on a molecular level. Journal of Clinical Medicine 8(10):1524, 1-15 (2019).
Arazi, et al. The immune cell landscape in kidneys of patients with lupus nephritis. Nat. Immunol., vol. 20(7), p. 902-914 (2019).
Aringer M, et al. 2019 European League Against Rheumatism/ American College of Rheumatology Classification Criteria for Systemic Lupus Erythematosus. Arthritis and Rheumatology 71(9): 1400-1412 (2019). Published online Aug. 6, 2019.
Armstrong, et al., GWAS identifies novel SLE susceptibility genes and explains the association of the HLA region Genes Immun 2014, vol. 15, No. 6, p. 347-354.
Asano, Systemic sclerosis, J. Dermatol., v45, p. 128-138 (2018).
Ashley, et al. Genetics and cardiovascular disease a policy statement from the American Heart Association. Circulation, 2012, vol. 126, No. 1, p. 142-157.
Assassi, et al. Dissecting the heterogeneity of skin gene expression patterns in systemic sclerosis, Arthritis Rheumatol., vol. 67, p. 3016-3026 (2015).
Au Q, et al. Grouped feature importance and combined features effect plot. Data Min Knowl Discov 36: 1401-1450 (2022).
Badawi, Aysha I. Z. et al. Serum tumor necrosis factor-like weak inducer of apoptosis (TWEAK) and leptin as biomarkers of accelerated atherosclerosis. The Egyptian Rheumatologist 39(2):75-81 (2017).
Bagavant, et al. Pathogenesis of kidney disease in systemic lupus erythematosus. Current Opinion in Rheumatology vol. 21, p. 489-494 (2009).
Bagavant, Harini et al. Role for nephritogenic T cells in lupus glomerulonephritis: progression to renal failure is accompanied by T cell activation and expansion in regional lymph nodes. Journal of Immunology 177(11):8258-8265 (2006).
Bakshi, et al. Unmet Needs in the Pathogenesis and Treatment of Systemic Lupus Erythematosus. Clin. Rev. Allergy Immunol., 2018, vol. 55, No. 3, p. 352-367.
Ballermann, Glomerular endothelial cell differentiation. Kidney Int., v67, p. 1668-1671 (2005).
Banica LM, et al. Dysregulation of anergy-related factors involved in regulatory T cells defects in Systemic Lupus Erythematosus patients: Rapamycin and Vitamin D efficacy in restoring regulatory T cells. 19(12):1294-1303 (2014).
Banno, et al. Pathway-specific profiling identifies the NF-KB-dependent tumor necrosis factor a-regulated genes in epidermal keratinocytes, J. Biol. Chem., vol. 280, p. 18973-18980 (2005).
Barron, et al. Perivascular Adventitial Fibroblast Specialization Accompanies T Cell Retention in the Inflamed Human Dermis, J. Immunol., vol. 202, p. 56-68 (2019).
Berthier, et al. Molecular Profiling of Cutaneous Lupus Lesions Identifies Subgroups Distinct from Clinical Phenotypes, J. Clin. Med., vol. 8, No. 1244, p. 1-15 (2019).

(56) References Cited

OTHER PUBLICATIONS

Bethunaickan, R., et al. Identification of stage-specific genes associated with lupus nephritis and response to remission induction in (NZB x NZW)F1 and NZM2410 mice. Arthritis Rheumatol., v66, p. 2246-2258 (2014).
Bhalla, Manmeet et al. Extracellular adenosine signaling reverses the age-driven decline in the ability of neutrophils to kill *Streptococcus pneumonia*. Aging cell 19(10):e13218, 1-12 (2020).
Bhargava, et al. Mitochondrial energetics in the kidney. Nature Reviews Nephrology, vol. 13, p. 629-646 (2017).
Billi, Allison C. et al. Non-lesional and Lesional Lupus Skin Share Inflammatory Phenotypes that Drive Activation of CD16+ Dendritic Cells. BioRxiv, p. 1-35 (2021).
Billi, et al. The female-biased factor VGLL3 drives cutaneous and systemic autoimmunity, JCI Insight, vol. 4, p. 1-14 (2019).
Bilotta, et al., Liver X Receptors: Regulators of Cholesterol Metabolism, Inflammation, Autoimmunity, and Cancer Front Immunol. 2020, vol. 11, Art 584303, p. 1-10.
Biniecka, et al. Dysregulated bioenergetics: a key regulator of joint inflammation. Ann. Rheum. Dis., vol. 75, p. 2192-2200 (2016).
Bischl B, et al. mlr: Machine Learning in R. Journal of Machine Learning Research. 17: 1-5 (2016).
Blagus, et al. SMOTE for high-dimensional class-imbalanced data. BMC Bioinformatics, vol. 14, p. 1-16 (2013).
Blanchong, Carol A. et al. Deficiencies of human complement component C4a and C4b and heterozygosity in length variants of RP-C4-CYP21-TNX (Rccx) modules in Caucasians. The Journal of Experimental Medicine 191(12):2183-2196 (2000).
Blauvelt, A. et al. "The Immunologic Role of IL-17 in Psoriasis and Psoriatic Arthritis Pathogenesis," Clinical Reviews in Allergy & Immunology, vol. 55, pp. 379-390 (2018).
Blauvelt, et al. Certolizumab pegol for the treatment of patients with moderate-to-severe chronic plaque psoriasis: pooled analysis of week 16 data from three randomized controlled trials, J. Eur. Acad. Dermatology Venereol., vol. 33, p. 546-552 (2019).
Blume, Cornelia et al. Autoimmunity in CD73/Ecto-5'-nucleotidase deficient mice induces renal injury. PloS one 7(5): e37100, 1-14 (2012).
Bolger, et al. Trimmomatic: A flexible trimmer for Illumina sequence data, Bioinformatics, vol. 30, p. 2114-2120 (2014).
Bonventre, Joseph V. Kidney injury molecule-1 (KIM-1): a urinary biomarker and much more. Nephrology Dialysis Transplantation 24(11):3265-3268 (2009).
Bowden, Jack et al. Mendelian randomization with invalid instruments: effect estimation and bias detection through Egger regression. International Journal of Epidemiology 44(2):512-525 (2015).
Bradley SJ, et al. T cell transcriptomes describe patient subtypes in systemic lupus erythematosus. PLoS One. 10(11):e0141171: 1-19 (2015).
Breiman, Leo et al. Classification and Regression Trees. Chapter 6: Medical Diagnosis and Prognosis. Chapman & Hall/CRC: pp. 1-36 (1984).
Breiman, Leo. Random Forests. Machine Learning 45(1):5-32 (2001).
Broder, et al. Tubulointerstitial damage predicts end stage renal disease in lupus nephritis with preserved to moderately impaired renal function: A retrospective cohort study. Semin. Arthritis Rheum., vol. 47, p. 545-551 (2018).
Brodmerkel, et al. Modulation of inflammatory gene transcripts in psoriasis vulgaris: Differences between ustekinumab and etanercept, J. Allergy Clin. Immunol., vol. 143, p. 1965-1969 (2019).
Brunner, et al. The immunology of atopic dermatitis and its reversibility with broad-spectrum and targeted therapiesJ. Allergy Clin. Immunol., vol. 139, S65-S76 (2017).
Bult, Carol J. et al. Mouse genome database (MGD) 2019. Nucleic Acids Research 47(D1):D801-D806 (2019). Published online on Nov. 8, 2018.
Burgess, et al. Mendelian randomization with fine-mapped genetic data Choosing from large Nos. of correlated instrumental variables. Genet. Epidemiol. 2017, vol. 41, p. 714-725.
Calvo-Alen, et al., Lack of recording of systemic lupus erythematosus in the death certificates of lupus patients Rheumatology. 2005, vol. 44, Issue 9, p. 1186-1189.
Cantin, Greg et al. Analytical and Functional Similarity of the Biosimilar Candidate ABP 654 to Ustekinumab Reference Product. Drugs in R&D 23(4):421-438 (2023).
Cassano, et al. Case Report, Infliximab in Recalcitrant Severe Atopic Eczema Associated with Contact Allergy, Int'l Journal of Immunopathology and Pharmacology, vol. 19, No. 1, p. 237-240 (2006).
Castillo-Rodriguez, et al. Kidney Injury Marker 1 and Neutrophil Gelatinase-Associated Lipocalin in Chronic Kidney Disease. Nephron, vol. 136(4), p. 263-267 (2017).
Ceccarelli F, et al. Application of Machine Learning Models in Systemic Lupus Erythematosus. Int JMol Sci. 24(5):4514: 1-16 (2023).
Cheadle, et al. Analysis of Microarray Data Using Z Score Transformation, Journal of Molecular Diagnostics, vol. 5, No. 2, p. 73-81 (2003).
Chen, Anqun et al. Role of CD8+ T cells in crescentic glomerulonephritis. Nephrology Dialysis Transplantation 35(4):564-572 (2020).
Chen, et al.: Enrichr: interactive and collaborative HTML5 gene list enrichment analysis tool. BMC Bioinformatics. 14(128):1-14 (2013).
Chen, Ping-Min et al. Kidney tissue hypoxia dictates T cell-mediated injury in murine lupus nephritis. Science Translational Medicine 12(538):eaay1620, 1-13 (2020).
Cheng, et al. Profiling motility signal-specific genes in primary human keratinocytes, J. Invest. Dermatol., vol. 128, 1981-1990 (2008).
Chiricozzi, et al. Integrative responses to IL-17 and TNF-a in human keratinocytes account for key inflammatory pathogenic circuits in psoriasis, J. Invest. Dermatol., vol. 131, p. 677-687 (2011).
Chockalingam, et al. Microarray Data Processing Techniques for Genome-Scale Network Inference from Large Public Repositories. Microarrays, vol. 5, No. 23, p. 1-13 (2016).
Chong, et al. A subset of CD163+ macrophages displays mixed polarizations in discoid lupus skin. Arthritis Res. Ther., vol. 17, p. 1-10 (2015).
Chung, et al., Differential genetic associations for systemic lupus erythematosus based on anti-dsDNA autoantibody production. PLoS Genet. 2011, vol. 7, Iss3, e1001323, p. 1-11.
Cojocaru M, et al. Manifestations of Systemic Lupus Erythematosus. 6(4):330-336 (2011).
Couzi, Lionel et al. Predominance of CD8+ T lymphocytes among periglomerular infiltrating cells and link to the prognosis of class III and class IV lupus nephritis. Arthritis & Rheumatism 56(7):2362-2370 (2007).
Coxpres, db, Version 8.1; [retrieved on Feb. 16, 2026]. Available at URL:https://coxpresdb.jp/ p. 1.
CTV, Targeted Therapy Using Intradermal Injection of Etanercept for Remission Induction in Discoid Lupus Erythematosus (TARGET-DLE), U.S. Natl. Libr. Med. Clin. Trials, downloaded Jan. 23, 2025 (2019).
Cui, Mintian et al. Blood Genomics Identifies Three Subtypes of Systemic Lupus Erythematosus:"IFN-High,""NE-High," and "Mixed". Mediators of Inflammation 2021(1):6660164, 1-12 (2021).
Cutolo, Maurizio, and Ronald L. Wilder. Different roles for androgens and estrogens in the susceptibility to autoimmune rheumatic diseases. Rheumatic Disease Clinics of North America 26(4):825-839 (2000).
Cutolo, Maurizio et al. Androgens and estrogens modulate the immune and inflammatory responses in rheumatoid arthritis. Annals of the New York Academy of Sciences 966(1):131-142 (2002).
Dale, David C. et al. Comparison of agents producing a neutrophilic leukocytosis in man. Hydrocortisone, prednisone, endotoxin, and etiocholanolone. Journal of Clinical Investigation 56(4):808-813 (1975).
Davidson. What is damaging the kidney in lupus nephritis? Nat. Rev. Rheumatol., V12(3), p. 143-153 (2016).

(56) References Cited

OTHER PUBLICATIONS

Davies, et al., A genome-wide association study for coronary artery disease identifies a novel susceptibility locus in the major histocompatibility complex. Circ. Cardiovasc. Genet 2012, vol. 5(2), p. 217-25.
De Souza, et al. Autocrine IFN-I inhibits isocitrate dehydrogenase in the TCA cycle of LPS-stimulated macrophages. J. Clin. Invest., v129, p. 4239-4244 (2019).
Deleanu, et al. Biological therapies for atopic dermatitis: An update (review), Exp. Ther. Med., V17, p. 1061-1067 (2019).
Demirci, et al., Identification of a new susceptibility locus for systemic lupus erythematosus on chromosome 12 in individuals of European ancestry. Arthritis Rheumatol 2016 vol. 68(1), p. 174-83.
Deng, et al. Pathogenesis and targeted treatment of skin injury in SLE. Nat. Rev. Rheumatol., v11, p. 663-669 (2015).
Deng, Wei et al. Hypoxia inducible factor-1 alpha promotes mesangial cell proliferation in lupus nephritis. American Journal of Nephrology 40(6):507-515 (2015).
Der, et al. Tubular cell and keratinocyte single-cell transcriptomics applied to lupus nephritis reveal type I IFN and fibrosis relevant pathways. Nat. Immunol., v20(7), p. 915-927 (2019).
Dobin, Alexander et al. STAR: ultrafast universal RNA-seq aligner. Bioinformatics 29(1):15-21 (2013).
Domingo, et al. MicroRNAs in Several Cutaneous Autoimmune Diseases: Psoriasis, Cutaneous Lupus Erythematosus and Atopic Dermatitis. Cells, v9, p. 1-25 (2020).
D'Orazio, John et al. UV Radiation and the Skin. International Journal of Molecular Sciences 14(6):12222-12248 (2013).
Duhen, et al. Identification of a specific gene signature in human Th1/17 cells (BA13P.126), J. Immunol., v192, S177.12 (2014).
Eckardt, et al. Role of hypoxia in the pathogenesis of renal disease. Kidney International, v68, s99, S46-S51 (2005).
Eelen, et al. Endothelial cell metabolism in normal and diseased vasculature. Circ. Res., v116, p. 1231-1244 (2015).
Eisenberg, et al. Human housekeeping genes, revisited. Trends Genet, v29, p. 569-574 (2013).
Elkon, Keith B, and Vivian V. Stone. Type I interferon and systemic lupus erythematosus. Journal of Interferon & Cytokine Research 31(11):803-812 (2011).
EP19884758.4 Examination Report dated Nov. 5, 2025.
Esdaile, John M. et al. Traditional Framingham risk factors fail to fully account for accelerated atherosclerosis in systemic lupus erythematosus. Arthritis and Rheumatism 44(10):2331-2337 (2001).
Esteller, M. Non-coding RNAs in human disease. Nat Rev Genet 12(12):861-874 (Nov. 18, 2011).
Fagerberg, et al. Analysis of the human tissue-specific expression by genome-wide integration of transcriptomics and antibody-based proteomics. Mol. Cell. Proteomics, v13, p. 397-406 (2014).
Falasinnu, Titilola et al. Do death certificates underestimate the burden of rare diseases? The example of systemic lupus erythematosus mortality, Sweden, 2001-2013. Public Health Reports 133(4):481-488 (2018).
Falhammar, Henrik et al. Increased risk of autoimmune disorders in 21-hydroxylase deficiency: a Swedish population-based national cohort study. Journal of the Endocrine Society 3(5):1039-1052 (2019).
Fanouriakis A, et al. 2019 update of the EULAR recommendations for the management of systemic lupus erythematosus, Annals of the Rheumatic Diseases, 2019: 78(6):736-745.
Farrugia, Mark, and Byron Baron. The role of TNF-a in rheumatoid arthritis: a focus on regulatory T cells. Journal of clinical and translational research 2(3):84-90 (2016).
Fava, Andrea, and Michelle Petri. Systemic lupus erythematosus: diagnosis and clinical management. Journal of autoimmunity 96:1-13 (2019).
Feichtinger, et al. Mitochondrial dysfunction: A neglected component of skin diseases. Exp. Dermatol., v23, p. 607-614 (2014).
Feldner-Busztin, Dylan et al. Dealing with dimensionality: the application of machine learning to multi-omics data. Bioinformatics 39(2):btad021, 1-8 (2023).
Fine, Leon G. et al. Is there a common mechanism for the progression of different types of renal diseases other than proteinuria? Towards the unifying theme of chronic hypoxia. Kidney International 75:S22-S26 (2000).
Finucane, et al., Partitioning heritability by functional annotation using genome-wide association summary statistics. Nat Genet 2015, vol. 47(11), p. 1228-35.
Fortner, Karen A. et al. Targeting mitochondrial oxidative stress with MitoQ reduces NET formation and kidney disease in lupus-prone MRL-lpr mice. Lupus Science & Medicine 7(1):e000387, 1-9 (2020).
Frankenberger, et al. Expression of M-Ficolin in human monocytes and macrophages. Mol. Immunol., v45, p. 1424-1430 (2008).
Franz, et al. Low number of regulatory T cells in skin lesions of patients with cutaneous lupus erythematosus. Arthritis Rheum., v56, p. 1910-1920 (2007).
Franzen, Oscar et al. PanglaoDB: a web server for exploration of mouse and human single-cell RNA sequencing data. Database 2019:baz046, 1-9 (2019).
Fritsch, et al. Effects of interferons and viruses on metabolism. Frontiers in Immunology, vol. 7, art630, p. 1-13 (2016).
Fu, et al. Transcriptomic analysis uncovers novel synergistic mechanisms in combination therapy for lupus nephritis. Kidney Int., v93, p. 416-429 (2018).
Fu, Shu Man et al. Pathogenesis of proliferative lupus nephritis from a historical and personal perspective. Clinical Immunology 185:51-58, 1-18 (2017).
Fujita. The role of IL-22 and Th22 cells in human skin diseases. J. Dermatol. Sci., v7, Iss1, p. 3-8 (2013).
Fulco, Charles P. et al. Activity-by-Contact model of enhancer-promoter regulation from thousands of CRISPR perturbations. Nature Genetics 51(12):1664-1669 (2019).
Galvan, Daniel L. et al. The hallmarks of mitochondrial dysfunction in chronic kidney disease. Kidney international 92(5):1051-1057 (2017).
Gardet, et al. Pristane-Accelerated Autoimmune Disease in (SWR X NZB) F1 Mice Leads to Prominent Tubulointerstitial Inflammation and Human Lupus Nephritis-Like Fibrosis. PLoS One, v11, p. 1-19 (2016).
Gateva, et al., A large-scale replication study identifies TNIP1, PRDM1, JAZF1, UHRF1BP1 and IL 10 as risk loci for systemic lupus erythematosus. Nat Genet. 2009, vol. 41(11), p. 1228-33.
Gautier, Laurent et al. affy—analysis of Affymetrix GeneChip data at the probe level. Bioinformatics 20(3):307-315 (2004).
Gazel, et al. Transcriptional Profiling of Epidermal Keratinocytes: Comparison of Genes Expressed in Skin, Cultured Keratinocytes, and Reconstituted Epidermis, Using Large DNA Microarrays. J. Invest. Dermatol., v121, p. 1459-1468 (2003).
Ge, Yan et al. Cgnz1 allele confers kidney resistance to damage preventing progression of immune complex-mediated acute lupus glomerulonephritis. Journal of Experimental Medicine 210(11):2387-2401 (2013).
Ghorbaninezhad, Farid et al. Tumor necrosis factor-alpha in systemic lupus erythematosus: Structure, function and therapeutic implications. International Journal of Molecular Medicine 49(4):43, 1-13 (2022).
Gong, et al. The emerging role of interleukin-21 in allergic diseases (Review). Biomed. Reports, v1, p. 837-839 (2013).
Gottlieb, et al. Ustekinumab for psoriasis and psoriatic arthritis. J. Rheumatol., v39, p. 86-89 (2012).
Graham, et al., Genetic variants near TNFAIP3 on 6q23 are associated with systemic lupus erythematosus. Nat. Genet. 2008, vol. 40(9), p. 1059-61.
Graham, Jared H. et al. Estrogen receptor alpha signaling is responsible for the female sex bias in the loss of tolerance and immune cell activation induced by the lupus susceptibility locus Sle1b. Frontiers in Immunology 11:582214, 1-20 (2020).
Gualtierotti, R. et al. Updating on the pathogenesis of systemic lupus erythematosus. Autoimmunity Reviews 10(1):3-7 (2010).
Gubbels Bupp, Melanie R, and Trine N. Jorgensen. Androgen-induced immunosuppression. Frontiers in Immunology 9:794, 1-16 (2018).

(56) References Cited

OTHER PUBLICATIONS

Gupta, et al., Bite of the wolf innate immune responses propagate autoimmunity in lupus. J. Clin. Inves 2021, vol. 131 (3), e144918, p. 1-13.

Guttman-Yassky, et al. Dupilumab progressively improves systemic and cutaneous abnormalities in patients with atopic dermatitis. J. Allergy Clin. Immunol., v143, p. 155-172 (2019).

Habuka, et al. The kidney transcriptome and proteome defined by transcriptomics and antibody-based profiling. PLoS One, v9, p. 1-19 (2014).

Haladyj, Ewa, and Ricard Cervera. Do we still need renal biopsy in lupus nephritis ?. Reumatologia 54(2):61-66 (2016).

Hallan, et al. Metabolomics and Gene Expression Analysis Reveal Down-regulation of the Citric Acid (TCA) Cycle in Non-diabetic CKD Patients. EBioMedicine, v26, p. 68-77 (2017).

Han, et al. Genome-wide association study in a Chinese Han population identifies nine new susceptibility loci for systemic lupus erythematosus. Nat. Genet. 2009 vol. 41(11), p. 1234-7.

Han, Shizhong et al. Evaluation of imputation-based association in and around the integrin-α-M (ITGAM) gene and replication of robust association between a non-synonymous functional variant within ITGAM and systemic lupus erythematosus (SLE). Human molecular genetics 18(6):1171-1180 (2009).

Harley, et al Genome-wide association scan in women with systemic lupus erythematosus identifies susceptibility variants in ITGAM, PXK, KIAA1542 and other loci. Nat. Genet. 2008, vol. 40(2), p. 204-10.

Hartiala, et al., Genome-wide analysis identifies novel susceptibility lod for myocardial infarction. Eur Heart J. 2021, vol. 42(9), p. 919-33.

Hawkes, et al. Discovery of the IL-23/IL-17 Signaling Pathway and the Treatment of Psoriasis. J. Immunol., v201, p. 1605-1613 (2018).

Hedges. Distribution Theory for Glass's Estimator of Effect size and Related Estimators. J. Educ. Stat, v6, n2, p. 107-128 (1981).

Hemani, et al. The MR-Base platform supports systematic causal inference across the human phenome. Elife. 2008, vol. 7: e34408, p. 1-29.

Heng, et al. Immunological Genome Project Consortium: networks of gene expression in immune cells. Nat Immunol. 9(10):1091-1094 (2008).

Hirakawa, et al. Dual Oxidase 1 Induced by Th2 Cytokines Promotes STAT6 Phosphorylation via Oxidative Inactivation of Protein Tyrosine Phosphatase 18 in Human Epidermal Keratinocytes, J. Immunol., v186, p. 4762-4770 (2011).

Hollbacher, et al. Transcriptomic profiling of human effector and regulatory T cell subsets identifies predictive population signatures, Immunohorizons, v4, p. 585-596 (2021).

Hom, et al., Association of systemic lupus erythematosus with CBorf13-BLK and ITGAM-ITGAX N. Engl. J. Med. 2006, Val 358(9), p. 900-9.

Hong, Seokchan et al. The emerging role of renal tubular epithelial cells in the immunological pathophysiology of lupus nephritis. Frontiers in Immunology 11:578952, 1-8 (2020).

Howson, et al. Fifteen new risk loci for coronary artery disease highlight arterial-wall-specific mechanisms Nat. Genet. 2017, vol. 49(7), p. 1113-9.

Hrdlickova, Barbara et al. Genetic variation in the non-coding genome: involvement of micro-RNAs and long non-coding RNAs in disease. Biochimica et Biophysica Acta—Molecular Basis of Disease 1842(10):1910-1922 (2014).

Hsieh, Christine et al. Predicting outcomes of lupus nephritis with tubulointerstitial inflammation and scarring. Arthritis Care & Research 63(6):865-874 (2011).

Huang, Shujun et al. Applications of support vector machine (SVM) learning in cancer genomics. Cancer genomics & proteomics 15(1):41-51 (2018).

Idborg, Helena et al. TNF-alpha and plasma albumin as biomarkers of disease activity in systemic lupus erythematosus. Lupus Science and Medicine 5(1):e000260, 1-11 (2018).

Iwamoto, et al. Associations between type I interferon and antiphospholipid antibody status differ between ancestral backgrounds, Lupus Sci. Med., v5, p. 1-4 (2018).

Jabbari, et al. Dominant Th1 and minimal Th17 skewing in discoid lupus revealed by transcriptomic comparison with psoriasis, J. Invest. Dermatol., v134, p. 87-95 (2014).

Jacobi, et al. Infliximab in the treatment of moderate to severe atopic dermatitis., J. Am. Acad. Dermatol., v52, p. 522-526 (2005).

Janssen Pharmaceuticals, Janssen announces discontinuation of Phase 3 LOTUS study evaluating Ustekinumab in systemic lupus erythematosus, Janssen Pharm. Available at https://www.jnj.com/janssen-announces-discontinuation-of-phase-3-lotus-study-evaluating-ustekinumab-in-systemic-lupus-erythematosus (2020).

Jin, et al. IL-21R is essential for epicutaneous sensitization and allergic skin inflammation in humans and mice, J. Clin. Invest., v119, p. 47-60 (2009).

Kalinin, Alexandr A. et al. Deep learning in pharmacogenomics: from gene regulation to patient stratification. Pharmacogenomics 19(7):629-650 (2018).

Kalucka, et al. Quiescent Endothelial Cells Upregulate Fatty Acid B-Oxidation for Vasculoprotection via Redox Homeostasis. Cell Metab., v28, p. 881-894 (2018).

Kamat, et al., PhenoScanner V2: an expanded tool for searching human genotype-phenotype associations. Bioinformatics 2019, vol. 35(22), p. 4851-3.

Kang et al. Defective fatty acid oxidation in renal tubular epithelial cells plays a key role in kidney fibrosis development. Nat Med 21(1):37-46 (2015).

Katewa, et al. Btk-specific inhibition blocks pathogenic plasma cell signatures and myeloid cell- associated damage in IFNa-driven lupus nephritis. JCI insight, v2, e90111, p. 1-19 (2017).

Katz, et al. Systemic Lupus Erythematosus is Associated With Increased Prevalence of Atherosclerotic Cardiovascular Disease in Hospitalized Patients Mayo. Clin. Proc. 2019, vol. 94(8), p. 1436-1443.

Keenan, et al. The Library of Integrated Network-Based Cellular Signatures NIH Program: System-Level Cataloging of Human Cells Response to Perturbations Cell Syst. 2018, vol. 6, p. 13-24.

Kelly, et al. Metabolic reprogramming in macrophages and dendritic cells in innate immunity. Cell Res., v25, p. 771-784 (2015).

Kidani, et al. Lipids rule: resetting lipid metabolism restores T cell function in systemic lupus erythematosus. J. Clin. Invest., v124, p. 482-485 (2014).

Kim, Hye-Jung et al. CD8+ T regulatory cells express the Ly49 Class I Mhc receptor and are defective in autoimmune prone B6-Yaa mice. Proceedings of the National Academy of Sciences 108(5):2010-2015 (2011).

Kingsmore, et al. Metabolic dysregulation characterizes the tissue response to immune injury in systemic lupus erythematosus and inflammatory skin diseases. Lupus Science Medicine, v8, Supp2, 2 pages (2021).

Kirou, et al. Activation of the interferon-a pathway identifies a subgroup of systemic lupus erythematosus patients with distinct serologic features and active disease, Arthritis Rheum., v52, p. 1491-1503 (2005).

Kozyrev, et al., Functional variants in the B-cell gene BANK1 are associated with systemic lupus erythematosus. Nat Genet. 2008, vol. 40(2), p. 211-6.

Kramer, et al., Causal analysis approaches in ingenuity pathway analysis. Bioinformatics. 30(4):523-530 (2014).

Kramer, Judit et al. C4BQ0 allotype as risk factor for myocardial infarction. BMJ 309(6950):313-314 (1994).

Krzywinski, et al. Classification and regression trees. Nature Methods, vol. 14 p. 757-758 (2017).

Kuehne, et al. Acute Activation of Oxidative Pentose Phosphate Pathway as First-Line Response to Oxidative Stress in Human Skin Cells. Mol. Cell, v59, p. 359-371 (2015).

Kuhn, et al., STITCH 2: an interaction network database for small molecules and proteins. Nucleic Acids Res 2010, vol. 38, Database issue, p. D552-6.

Kuleshov, Maxim V. et al. Enrichr: a comprehensive gene set enrichment analysis web server 2016 update. Nucleic Acids Research 44(W1):W90-W97 (2016).

(56) References Cited

OTHER PUBLICATIONS

Kuriakose, Jeeba et al. Patrolling monocytes promote the pathogenesis of early lupus-like glomerulonephritis. Journal of Clinical Investigation 129(6):2251-2265 (2019).
Kutukculer, et al. CD4+CD25+Foxp3+ T regulatory cells, Th1 (CCR5, IL-2, IFN-y) and Th2 (CCR4, IL-4, Il-13) type chemokine receptors and intracellular cytokines in children with common variable immunodeficiency, Int. J. Immunopathol. Pharmacol., v29, p. 241-251 (2016).
Lahita, Robert G. The role of sex hormones in systemic lupus erythematosus. Current Opinion in Rheumatology 11(5):352-356 (1999).
Lang, Thomas J. et al. Increased severity of murine lupus in female mice is due to enhanced expansion of pathogenic T cells. Journal of Immunology 171(11):5795-5801 (2003).
Langrish, et al. IL-23 drives a pathogenic T cell population that induces autoimmune inflammation, J. Exp. Med., v201, p. 233-240 (2005).
Laporte, et al. Apoptosis in established and healing psoriasis, Dermatology, v200, p. 314-316 (2000).
Leatherwood, Cianna et al. Clinical characteristics and renal prognosis associated with interstitial fibrosis and tubular atrophy (IFTA) and vascular injury in lupus nephritis biopsies. Seminars in Arthritis and Rheumatism 49(3):396-404 (2019).
Lee, et al., Genome-wide pathway analysis of genome-wide association studies on systemic lupus erythematosus and rheumatoid arthritis. Mol. Biol. Rep. 2012, vol. 39, p. 10627-35.
Leonard, et al., Coronary heart disease in systemic lupus erythematosus is associated with interferon regulatory factor-8 gene variants. Circ. Cardiovasc. Genet. 2013, vol. 6(3), p. 255-63.
Leonard, et al. Novel gene variants associated with cardiovascular disease in systemic lupus erythematosus and rheumatoid arthritis. Ann. Rheum. Dis. 2018, vol. 77, p. 1063-9.
Levinson, et al., Coronary artery disease (CAD) risk factor analysis in an age-stratified hospital population with systemic lupus erythematosus (SLE). Int. J. Cardiol. Hypertens 2020, vol. 7:100056, p. 1-5.
Li, et al. Interferon signature gene expression is correlated with autoantibody profiles in patients with incomplete lupus syndromes, Clin. Exp. Immunol., v159, p. 281-291 (2010).
Li, et al. Metabolic Factors that Contribute to Lupus Pathogenesis. Crit. Rev. Immunol., v36, p. 75-98 (2016).
Li, et al. Transcriptome analysis of psoriasis in a large case-control sample: RNA-seq provides insights into disease mechanisms, J. Invest. Dermatol., v134, p. 1828-1838 (2014).
Li, et al. Type I interferon modulates Langerhans cell ADAM17 to promote photosensitivity in lupus, BioRxiv, 38 pages (2021).
Li, Ying et al. Discovery of biomarker genes from earthworm microarray data by discriminant analysis and clustering. 2009 International Joint Conference on Bioinformatics, Systems Biology and Intelligent Computing :23-29 (2009).
Liao, et al. FeatureCounts: An efficient general purpose program for assigning sequence reads to genomic features, Bioinformatics, v30, p. 923-930 (2014).
Liao, et al. The Subread aligner: Fast, accurate and scalable read mapping by seed-and-vote, Nucleic Acids Res., v41, n10, p. 1-17 (2013).
Liberzon, Arthur et al. Molecular Signatures Database (MSigDB) 3.0. Bioinformatics 27(12):1739-1740 (2011).
Liu, Bi-Cheng et al. Renal tubule injury: a driving force toward chronic kidney disease. Kidney International 93(3):568-579 (2018).
Liu, et al., Cardiovascular disease in systemic lupus erythematosus: An update. Curr Opin Rheumatol. 2018, vol. 30(5), p. 441-8.
Liu, et al. Enhanced Inflammasome Activity in Systemic Lupus Erythematosus Is Mediated via Type I Interferon-Induced Up-Regulation of Interferon Regulatory Factor 1, Arthritis Rheumatol., v69, p. 1840-1849 (2017).
Liu, et al., Proprotein convertase subtilisin kexin 9 is associated with disease activity and is implicated in immune activation in systemic lupus erythematosus. Lupus. 2020, vol. 29(8), p. 825-35.
Lopez, et al., Cardiovascular Disease. In StatPearls, 2021, editorial board, StatPearls Publishing, p. 1-12. (2021).
Lorenzo-Vizcaya, et al. The use of anti-TNF-alpha therapies for patients with systemic lupus erythematosus. Where are we now?, Expert Opin. Biol. Ther., v21, p. 639-647 (2021).
Lundstrom, Emeli et al. HLA-DRB104/13 alleles are associated with vascular disease and antiphospholipid antibodies in systemic lupus erythematosus. Annals of the Rheumatic Diseases 72(6):1018-1025 (2013).
Ma, R. et al. Intrarenal macrophage infiltration induced by T cells is associated with podocyte injury in lupus nephritis patients. Lupus 25(14):1577-1586 (2016).
Maciver, et al. Metabolic Regulation of T Lymphocytes. Annu. Rev. Immunol., v31, p. 259-283 (2013).
Magder, et al., Incidence of and Risk Factors for Adverse Cardiovascular Events Among Patients With Systemic Lupus Erythematosus. Am. J. Epidemiol. 2012, vol. 176(8), p. 708-719.
Maleki, Farhad et al. Gene Set Analysis: Challenges, Opportunities, and Future Research. Frontiers in genetics 11:654, 1-16 (2020).
Malik, et al. Multiancestry genome-wide association study of 520,000 subjects identifies 32 loci associated with stroke and stroke subtypes. Nat. Genet. 2018, vol. 50(4), p. 524-537.
Mande, et al. Fas ligand promotes an inducible TLR-dependent model of cutaneous lupus-like inflammation, J. Clin. Invest., v128, p. 2966-2978 (2018).
Mannik, Mart et al. Multiple autoantibodies form the glomerular immune deposits in patients with systemic lupus erythematosus. Journal of Rheumatology 30(7):1495-1504 (2003).
Mansourian, et al. The Global Error Assessment (GEA) model for the selection of differentially expressed genes in microarray data, Bioinformatics, v20, p. 2726-2737 (2004).
Marees, et al., A tutorial on conducting genome-wide association studies: Quality control and statistical analysis. International Journal of Methods in Psychiatric Research 27(2):e1608 [1-10] (2018).
Maria, Naomi I, and Anne Davidson. Protecting the kidney in systemic lupus erythematosus: from diagnosis to therapy. Nature Reviews Rheumatology 16(5):255-267 (2020).
Markowitz, G. S, and V. D. D'agati. The ISN/RPS 2003 classification of lupus nephritis: an assessment at 3 years. Kidney international 71(6):491-495 (2007).
Martin, M et al. Systemic lupus erythematosus and lymphopenia: Clinical and pathophysiological features. La Revue de Médecine Interne 38(9):603-613 (2017).
Martinez, et al. Comparative analysis of inflammatory skin diseases reveals shared and distinct gene signature profiles in lesional and nonlesional regions. #507 Society for Investigative Dermatology annual meeting May 18-21, 2022.
Maz, et al. Cutaneous and systemic connections in lupus, Curr. Opin. Rheumatol., v32, p. 583-589 (2020).
McLaren, William et al. The Ensembl Variant Effect Predictor. Genome Biology 17(1):122, 1-14 (2016).
McMahon, Maureen et al. Systemic lupus erythematosus and cardiovascular disease: prediction and potential for therapeutic intervention. Expert Review of Clinical Immunology 7(2):227-241 (2011).
Md Yusof, Md Yuzaiful, and Edward M Vital. Early intervention in systemic lupus erythematosus: time for action to improve outcomes and health-care utilization. Rheumatology advances in practice 6(1):rkab106, 1-2 (2021).
Mehta, et al. Targeting metabolism for lupus therapy. Sci. Transl. Med., v7, iss274, p. 1-2 (2015).
Menche, et al. Integrating personalized gene expression profiles into predictive disease-associated gene pools, npj Syst. Biol. Appl., v3, p. 1-10 (2017).
Menter, et al. Adalimumab therapy for moderate to severe psoriasis: A randomized, controlled phase III trial, J. Am. Acad. Dermatol., v58, n1, p. 106-115 (2008).
Menter, et al. Joint AAD-NPF guidelines of care for the management and treatment of psoriasis with biologics, J. Am. Acad. Dermatol., v80, p. 1029-1072 (2019).
Mimura, Imari, and Masaomi Nangaku. The suffocating kidney: tubulointerstitial hypoxia in end- stage renal disease. Nature Reviews Nephrology 6(11):667-678 (2010).

(56) References Cited

OTHER PUBLICATIONS

Miyachi, Kazusa et al. Relationship of systemic type I interferon activity with clinical phenotypes, disease activity, and damage accrual in systemic lupus erythematosus in treatment-naive patients: a retrospective longitudinal analysis. Arthritis Research and Therapy 25(1):26, 1-13 (2023).
Mobus, et al. Atopic dermatitis displays stable and dynamic skin transcriptome signatures, J. Allergy Clin. Immunol., v147, p. 213-223 (2021).
Moe, et al., Long-term outcome in systemic lupus erythematosus, knowledge from population- based cohorts. J. Clin. Med. 2021, vol. 10, Art 4306, p. 1-14.
Moghaddam, et al., All-cause and cause-specific mortality in systemic lupus erythematosus: a population-based study. Rheumatology 2022, vol. 61, p. 367-376.
Mohajer, Faeze Sadat et al. Structural, functional and molecular dynamics analysis of the native and mutated actin to study its effect on congenital myopathy. Journal of Biomolecular Structure and Dynamics 35(7):1608-1614 (2017). Published Online Jul. 22, 2016.
Moldovan, Camelia, and Radu Dogaru. Fast support vector classifier applied to microarray data. In Proceedings of the 2014 6th International Conference on Electronics, Computers and Artificial Intelligence (ECAI) :67-72 (2014).
Morand, et al. Trial of Anifrolumab in Active Systemic Lupus Erythematosus, N. Engl. J. Med., v382, p. 211-221 (2020).
Morel, Immunometabolism in systemic lupus erythematosus. Nat. Rev. Rheumatol, v13, p. 280-290 (2017).
Morris, et al., clusterMaker: a multi-algorithm clustering plugin for Cytoscape. BMC Bioinformatics, vol. 12, Art 436, p. 1-14 (2011).
Moschen, Alexander R. et al. Lipocalin-2: a master mediator of intestinal and metabolic inflammation. Trends in Endocrinology & Metabolism 28(5):388-397 (2017).
Moulton, Vaishali R. Sex hormones in acquired immunity and autoimmune disease. Frontiers in Immunology 9:2279, 1-21 (2018).
Mubarak, Muhammed, and Hamid Nasri. ISN/RPS 2003 classification of lupus nephritis: time to take a look on the achievements and limitations of the schema. Journal of Nephropathology 3(3):87-90 (2014).
Murdoch, W James. et al. Definitions, methods, and applications in interpretable machine learning. Proceedings of the National Academy of Sciences of the United States of America 116(44):22071-22080 (2019).
Nakagawa, et al. Abnormal angiogenesis in diabetic nephropathy. Diabetes, v58, p. 1471-1478 (2009).
Nangaku, Masaomi. Chronic hypoxia and tubulointerstitial injury: a final common pathway to end-stage renal failure. Journal of the American Society of Nephrology 17(1):17-25 (2006).
Nasser, Joseph et al. Genome-wide enhancer maps link risk variants to disease genes. Nature 593(7858):238-243 (2021).
NCT03517722, A Study of Ustekinumab in Participants With Active Systemic Lupus Erythematosus; https://clinicaltrials.gov/ct2/show/NCT03517722/ accessed Oct. 10, 2025 (2021).
NCT03866317, A Study to Assess the Safety and Efficacy of Secukinumab in Alleviating Symptoms of Discoid Lupus Erythematosus, U.S. Natl. Libr. Med. Clin. Trials, accessed Oct. 10, 2025; https://www.clinicaltrials.gov/study/NCT03866317 (2021).
Nielsen, Jonas B. et al. Biobank-driven genomic discovery yields new insight into atrial fibrillation biology. Nature Genetics 50(9):1234-1239 (2018).
Nikpay, et al. A comprehensive 1000 Genomes-based genome-wide association meta-analysis of coronary artery disease. Nat. Genet 2015, vol. 47(10), p. 1121-30.
Nograles, et al. Th17 cytokines interleukin (IL)-17 and IL-22 modulate distinct inflammatory and keratinocyte-response pathways, Br. J. Dermatol., v159, p. 1092-1102 (2008).
Northcott, Melissa et al. Glucocorticoid gene signatures in systemic lupus erythematosus and the effects of type I interferon: a cross-sectional and in-vitro study. The Lancet Rheumatology 3(5):e357-e370 (2021).
Ohlenschlaeger, Tommy et al. Mannose-binding lectin variant alleles and the risk of arterial thrombosis in systemic lupus erythematosus. New England Journal of Medicine 351(3):260-267 (2004).
Oishi, et al., A functional SNP in the NKX2.5-binding site of ITPR3 promoter is associated with susceptibility to systemic lupus erythematosus in Japanese population. J. Hum. Genet. 2008, vol. 53(2), p. 151-62.
Okada, et al. A genome-wide association study identified AFF1 as a susceptibility locus for systemic lupus eyrthematosus in Japanese. PLOS Genet 2012, vol. 8, les 1, e1002455, p. 1-10.
Ortega, L. M. et al. Lupus nephritis: pathologic features, epidemiology and a guide to therapeutic decisions. Lupus 19(5):557-574 (2010).
Panousis, Nikolaos I., et al. Combined genetic and transcriptome analysis of patients with SLE: distinct, targetable signatures for susceptibility and severity. Annals of the rheumatic diseases 78.8: 1079-1089. (2019).
Pantel, et al. Direct Type I IFN but Not MDA5/TLR3 Activation of Dendritic Cells Is Required for Maturation and Metabolic Shift to Glycolysis after Poly IC Stimulation. PLoS Biol., v12, e1001759, p. 1-11 (2014).
Pasquali, et al. The keratinocyte transcriptome in psoriasis: Pathways related to immune responses, cell cycle and keratinization, Acta Derm. Venereol., v99, p. 196-205 (2019).
Patel, Gene Expression Profiling to Understand the Alterations in the Monocyte Compartment of Pediatric Systemic Lupus Erythematosus [Dissertation), 2008, Baylor University, 24 pages.
PCT/US2023/020752 International Preliminary Report on Patentability dated Nov. 14, 2024.
PCT/US2023/027847 International Preliminary Report on Patentability dated Jan. 30, 2025.
PCT/US2023/027847 Invitation to Pay Additional Fees dated Sep. 25, 2023.
PCT/US2023/032947 International Preliminary Report on Patentability dated May 22, 2025.
PCT/US2023/032947 International Search Report and Written Opinion dated Feb. 6, 2024.
PCT/US2023/032947 Invitation to Pay Additional Fees dated Nov. 17, 2023.
PCT/US2024/010125 International Preliminary Report on Patentability dated Jul. 17, 2025.
PCT/US2024/010125 International Search Report and Written Opinion dated Jun. 28, 2024.
PCT/US2024/010125 Invitation to Pay Additional Fees dated Apr. 8, 2024.
PCT/US2024/047337 International Search Report and Written Opinion dated Dec. 23, 2024.
Peterson, Karin S. et al. Characterization of heterogeneity in the molecular pathogenesis of lupus nephritis from transcriptional profiles of laser-captured glomeruli. Journal of Clinical Investigation 113(12):1722-1733 (2004).
Petri, et al., Original research: Development of a systemic lupus erythematosus cardiovascular risk equation. Lupus Sci Med. 2019, vol. 6(1), 6000346, p. 1-8.
Petri, et al. Risk factors for coronary artery disease in patients with systemic lupus erythematosus. Am. J. Med. 1992 vol. 93(5), p. 513-9.
Piranavan, et al. Management of cardiovascular disease in patients with systemic lupus erythematosus. Expert. Opin Pharmacother. 2020, vol. 21(13), p. 1617-1628.
Portoles, Jose et al. Anemia in chronic kidney disease: from pathophysiology and current treatments, to future agents. Frontiers in Medicine 8:642296, 1-14 (2021).
Puscas, et al. Psoriasis: Association of interleukin-17 gene polymorphisms with severity and response to treatment (Review), Exp. Ther. Med., v18, p. 875-880 (2019).
Qiagen Ingenuity Pathway Analysis website (IPA Qiagen Redwood City; www.qiagen.com/ingenuity) (2013).
Quinn, et al. Expression and regulation of sterol 27-hydroxylase (CYP27A1) in human macrophages: a role for RXR and PPARgamma ligands. Biochem. 2005, vol. 385, p. 823-830.
Quintero-Gonzalez, Diana C. et al. Mitochondria as a key player in systemic lupus erythematosus. Autoimmunity 55(8):497-505 (2022).

(56) References Cited

OTHER PUBLICATIONS

Rai, Richa et al. RNA-seq Analysis Reveals Unique Transcriptome Signatures in Systemic Lupus Erythematosus Patients with Distinct Autoantibody Specificities. PloS one 11(11):e0166312, 1-35 (2016).
Raj, et al. Regulatory polymorphisms modulate the expression of HLA class II molecules and promote autoimmunity. Elife 2016, vol. 5: e12089, p. 1-52.
Ramirez, Genetics in systemic lupus erythematosus entering the borough of cardiovascular risk Ann. Transi. Med. 2018, vol. 6, Suppl 1, S14, p. 1-4.
Ramirez-Carrozzi, et al. IL-17C regulates the innate immune function of epithelial cells in an autocrine manner, Nat. Immunol., v12, n12, p. 1159-1166 (2011).
Reich, et al. Infliximab induction and maintenance therapy for moderate-to-severe psoriasis: A phase III, multicentre, double-blind trial, Lancet, v366, p. 1367-1374 (2005).
Reimand, Juri et al. g:Profiler—a web-based toolset for functional profiling of gene lists from large-scale experiments. Nucleic acids research 35(Web Server issue):W193-W200 (2007).
Reiss, Effects of inflammation on cholesterol metabolism: Impact on systemic lupus erythematosus. Curr. Rheumatol. Rep., v11, p. 255-260 (2009).
Reiss, et al. Plasma from systemic lupus patients compromises cholesterol homeostasis: a potential mechanism linking autoimmunity to atherosclerotic cardiovascular disease. Rheumatol. Int. 2010, vol. 30(5), p. 591-8.
Reynolds, John et al. Anti-CD8 monoclonal antibody therapy is effective in the prevention and treatment of experimental autoimmune glomerulonephritis. Journal of the American Society of Nephrology 13(2):359-369 (2002).
Rheumatoid arthritis. Mayoclinic, [Retrieved on Jan. 14, 2026]. Available at https://www.mayoclinic.org/diseases-conditions/rheumatoid-arthritis/diagnosis-treatment/drc-20353653 pp. 1-16.
Ribero, et al. The Cutaneous Spectrum of Lupus Erythematosus, Clin. Rev. Allergy Immunol., v53, p. 291-305 (2017).
Rider, Virginia et al. Molecular mechanisms involved in the estrogen-dependent regulation of calcineurin in systemic lupus erythematosus T cells. Clinical Immunology 95(2):124-134 (2000).
Robert, et al. Interleukin-17 and lupus: enough to be a target? for which patients?, Lupus, v29, p. 6-14 (2020).
Ronnblom, Lars, and Dag Leonard. Interferon pathway in SLE: one key to unlocking the mystery of the disease. Lupus science and medicine 6(1):e000270, 1-11 (2019).
Rovin, B. et al.. The kidney biopsy in lupus nephritis: is it still relevant?. Rheumatic diseases clinics of North America 40(3):537, 1-16 (2014).
Runjic, F. et al. Association of anticardiolipin antibodies, complement and leptin with the severity of coronary artery disease expressed as syntax score. Journal of Physiology and Pharmacology 71(3):383-388 (2020).
Sakhi, Hamza et al. Podocyte injury in lupus nephritis. Journal of Clinical Medicine 8(9):1340, 1-14 (2019).
Sappino, et al. Smooth muscle differentiation in scleroderma fibroblastic cells, Am. J. Pathol., v137, n3, p. 585-591 (1990).
Sargent, et al. A TGFB-responsive gene signature is associated with a subset of diffuse scleroderma with increased disease severity, J. Invest. Dermatol., v130, p. 694-705 (2010).
Sarkar, et al. Photosensitivity and type i IFN responses in cutaneous lupus are driven by epidermal-derived interferon kappa, Ann. Rheum. Dis., v77, p. 1653-1664 (2018).
Sawalha, et al. Genetic association of interleukin-21 polymorphisms with systemic lupus erythematosus, Ann. Rheum. Dis., v67, p. 458-461 (2008).
Schiffer, et al. Activated renal macrophages are markers of disease onset and disease remission in lupus nephritis.. J. Immunol, v180(3), p. 1938-1947 (2008).
Schunkert, et al. Large-scale association analysis identifies 13 new susceptibility loci for coronary artery disease. Nat. Genet. 2011, vol. 43(4), p. 333-338.
Schwartz, M. M. Irreproducibility of the activity and chronicity indices limits their utility in the management of lupus nephritis. Lupus Nephritis Collaborative Study Group. American Journal of Kidney Diseases 21(4):374-377 (1993).
Schwartzman-Morris, Julie, and Chaim Putterman. Gender differences in the pathogenesis and outcome of lupus and of lupus nephritis. Journal of Immunology Research 2012(1):604892, 1-9 (2012).
Sebastiani, Gian D. et al. The Importance of an Early Diagnosis in Systemic Lupus Erythematosus. The Israel Medical Association Journal 18(3-4):212-215 (2016).
Shah, Masaud et al. In silico mechanistic analysis of IRF3 inactivation and high-risk HPV E6 species-dependent drug response. Scientific Reports 5(1):13446, 1-14 (2015).
Sharabi, et al. T cell metabolism: new insights in systemic lupus erythematosus pathogenesis and therapy. Nat. Rev. Rheumatol., v16, p. 100-112 (2020).
Sharma, et al. Metabolomics Reveals Signature of Mitochondrial Dysfunction in Diabetic Kidney Disease. J. Am. Soc. Nephrol., v24, p. 1901-1912 (2013).
Shen, et al. Structure-function relationships in the IL-17 receptor: Implications for signal transduction and therapy. Cytokine, v41, p. 92-104 (2008).
Shim, Gil-Jin et al. Autoimmune glomerulonephritis with spontaneous formation of splenic germinal centers in mice lacking the estrogen receptor alpha gene. Proceedings of the National Academy of Sciences 101(6):1720-1724 (2004).
Shipman, et al. A protective Langerhans cell keratinocyte axis that is dysfunctional in photosensitivity, Sci. Transl. Med., v10, p. 1-11 (2018).
Shu, et al. Hypoxia and Hypoxia-Inducible Factors in Kidney Injury and Repair. Cells, v8, n207, p. 1-21 (2019).
Simon, et al. Alteration of fatty acid oxidation in tubular epithelial cells: From acute kidney injury to renal fibrogenesis. Front. Med., v2, art52, p. 1-8 (2015).
Skaug, et al. Global skin gene expression analysis of early diffuse cutaneous systemic sclerosis shows a prominent innate and adaptive inflammatory profile, Ann Rheum Dis, v79, p. 379-386 (2020).
Sneha, P, and C. George Priya Doss. Molecular dynamics: new frontier in personalized medicine. Advances in protein chemistry and structural biology 102:181-224 (2016). Published Online 2015.
Staley, et al. PhenoScanner a database of human genotype-phenotype associations. Bioinformatics, 2016, vol. 32(20), p. 3207-9.
Stratigou, Victoria et al. Altered expression of signalling lymphocyte activation molecule receptors in T-cells from lupus nephritis patients-a potential biomarker of disease activity. Rheumatology 56(7):1206-1216 (2017).
Suarez-Fueyo, A. et al. T cells in systemic lupus erythematosus. Current opinion in immunology 43:32-38 (2016).
Suarez-Fueyo, Abel et al. T cells and autoimmune kidney disease. Nature Reviews Nephrology 13(6):329-343 (2017).
Subramanian, Aravind et al. Gene Set Enrichment Analysis: a Knowledge-based Approach for Interpreting Genome-wide Expression Profiles. Proceedings of the National Academy of Sciences of the United States of America 102(43):15545-15550 (2005).
Sun, et al. Glomerular Endothelial Cell Injury and Damage Precedes That of Podocytes in Adriamycin-Induced Nephropathy. PLoS One, v8, iss1, e55027, p. 1-12 (2013).
Sung, Sun-sang J, and Shu Man Fu. Interactions among glomerulus infiltrating macrophages and intrinsic cells via cytokines in chronic lupus glomerulonephritis. Journal of Autoimmunity 106:102331, 1-13 (2020).
Sung, Sun-sang J. et al. Dependence of glomerulonephritis induction on novel intraglomerular alternatively activated bone marrow-derived macrophages and Mac-1 and PD-L1 in lupus-prone NZM2328 mice. Journal of Immunology 198(7):2589-2601 (2017).
Suárez-Fariñas, et al. Evaluation of the Psoriasis Transcriptome across Different Studies by Gene Set Enrichment Analysis (GSEA), PLos One, v5, iss4, e10247, p. 1-8 (2010).
Svenungsson, et al. A STAT4 risk allele is associated with ischaemic cerebrovascular events and anti-phospholipid antibodies in systemic lupus erythematosus. Ann. Rheum Dis. 2010, vol. 69, p. 834-40.

(56) References Cited

OTHER PUBLICATIONS

Swindell, et al. Dissecting the psoriasis transcriptome: Inflammatory- and cytokine-driven gene expression in lesions from 163 patients, BMC Genomics, v14, n527, p. 1-20 (2013).
Szklarczyk, et al. The STRING database in 2021: customizable protein-protein networks, and functional characterization of user-uploaded gene/measurement sets. Nucleic Acids Res. 2021, vol. 49, p. D605-0612.
Tarasov, et al. Sambamba: fast processing of NGS alignment formats, Bioinformatics, v31, p. 2032-2034 (2015).
Tebbe, et al. Epidemiology and socioeconomic impact of skin disease in lupus erythematosus, Lupus, v6, p. 96-104 (1997).
Teixeira, et al. Novel Insights in Systemic Lupus Erythematosus and Atherosclerosis. Front. Med. 2018, vol. 4, Art 262, p. 1-17.
The GTEx Consortium., The Genotype-Tissue Expression (GTEx) Project. Nature Genetics 45(6):580-585 (2013).
Thomas, et al. Mortality associated with systemic lupus erythematosus in France assessed by multiple-cause-of-death analysis. Arthritis Rheumatol. 2014, vol. 66(9), p. 2503-11.
Tian, et al. Meta-Analysis Derived (MAD) Transcriptome of Psoriasis Defines the "Core" Pathogenesis of Disease, PLoS One, v7, Iss 9, e44274, p. 1-15 (2012).
Tian, Yuexin et al. Nestin protects podocyte from injury in lupus nephritis by mitophagy and oxidative stress. Cell Death & Disease 11(5):319, 1-19 (2020).
Tilstra, J. S., et al. Kidney-infiltrating T cells in murine lupus nephritis are metabolically and functionally exhausted. J. Clin. Invest, v128, p. 4884-4897 (2018).
Tomalin, Lewis E, et al., Short-Term Transcriptional Response to IL-17 Receptor-a Antagonism in the Treatment of Psoriasis. The Journal of Allergy and Clinical Immunology 145(3):922-932 (2020).
Toro-Dominguez, Daniel et al. Shared signatures between rheumatoid arthritis, systemic lupus erythematosus and Sjogren's syndrome uncovered through gene expression meta-analysis. Arthritis research and therapy 16(6):489, 1-8 (2014).
Trautmann, et al. Role of apoptosis in atopic dermatitis, Int. Arch. Allergy Immunol., v124, p. 230-232 (2001).
Tripathy, Debu et al. Ribociclib (LEE011): Mechanism of Action and Clinical Impact of This Selective Cyclin-Dependent Kinase 4/6 Inhibitor in Various Solid Tumors. Clinical cancer research : an official journal of the American Association for Cancer Research 23(13): 3251-3262 (2017).
Trowsdale, et al. Major histocompatibility complex genomics and human disease Annu. Rev. Genomics Hum. Genet 2013, vol. 14, p. 301-23.
Tsoi, et al. Atopic Dermatitis Is an IL-13-Dominant Disease with Greater Molecular Heterogeneity Compared to Psoriasis, J. Invest. Dermatol., v139, p. 1480-1489 (2019).
Tsoi, et al. Cytokine responses in nonlesional psoriatic skin as clinical predictor to anti-TNF agents, J. Allergy Clin. Immunol., v149, n2, p. 640-649 (2022).
Tsoi, et al. Hypersensitive IFN Responses in Lupus Keratinocytes Reveal Key Mechanistic Determinants in Cutaneous Lupus, J. Immunol., v202, p. 2121-2130 (2019).
Tyring, et al. Etanercept and clinical outcomes, fatigue, and depression in psoriasis, double- blind placebo-controlled randomized phase III trial, Lancet, v367, p. 29-35 (2006).
U.S. Appl. No. 17/924,955 Office Action dated Sep. 29, 2024.
U.S. Appl. No. 19/199,682 Office Action dated Sep. 19, 2025.
Uhlen, Mathias et al. Tissue-based map of the human proteome. Science 347(6220):1260419, 1-11 (2015).
Ungar, et al. Phase 2 randomized, double-blind study of IL-17 targeting with secukinumab in atopic dermatitis, J. Allergy Clin. Immunol., v147, p. 394-397 (2021).
U.S. Appl. No. 16/679,109 Office Action dated Dec. 17, 2025.
U.S. Appl. No. 16/679,109 Office Action dated Feb. 27, 2025.
U.S. Appl. No. 16/679,109 Office Action dated Jan. 18, 2023.
U.S. Appl. No. 16/679,109 Office Action dated May 15, 2024.
U.S. Appl. No. 16/679,109 Office Action dated Sep. 19, 2023.
U.S. Appl. No. 17/924,955 Notice of Allowance dated Apr. 16, 2025.
U.S. Appl. No. 18/753,672 Office Action dated Apr. 9, 2025.
U.S. Appl. No. 18/753,672 Office Action dated Oct. 10, 2025.
U.S. Appl. No. 18/753,672 Office Action dated Sep. 16, 2024.
U.S. Appl. No. 19/259,293 Office Action dated Feb. 24, 2026.
Uva, et al. Cutaneous manifestations of systemic lupus erythematosus, Autoimmune Dis., v2012, art834291, 15 pages (2012).
Valdimarsson, et al. Immunopathogenic mechanisms in psoriasis, Clin Exp Immunol, v135, p. 1-8 (2004).
Vashisht, et al. Hearth-Holmes, Belimumab for the treatment of recalcitrant cutaneous lupus, Lupus, v26, p. 857-864 (2017).
Vazquez, et al. Immunological and clinical heterogeneity in cutaneous lupus erythematosus, Br. J. Dermatol., v185, p. 480-481 (2021).
Verbanck, Marie et al. Detection of widespread horizontal pleiotropy in causal relationships inferred from Mendelian randomization between complex traits and diseases. Nature Genetics 50(5):693-698 (2018).
Viau, A., et al. Lipocalin 2 is essential for chronic kidney disease progression in mice and humans. J. Clin. Invest., v120, p. 4065-4076 (2010).
Viikinkoski, Emma et al. Red blood cell transfusion induces abnormal HIF-1α response to cytokine storm after adult cardiac surgery. Scientific Reports 11(1):22230, 1-9 (2021).
Viola, et al. The metabolic signature of macrophage responses. Front Immunol., v10, art1462, p. 1-16 (2019).
Wanders, et al. Metabolic interplay between peroxisomes and other subcellular organelles including mitochondria and the endoplasmic reticulum. Front. Cell Dev. Biol., v3, art 83, p. 1-15 (2016).
Wang, Guan et al. Validation of whole-blood transcriptome signature during microdose recombinant human erythropoietin (rHuEpo) administration. BMC Genomics 18(Suppl 8):817, 1-14 (2017).
Wang, L. et al. Predicting diagnostic gene expression profiles associated with immune infiltration in patients with lupus nephritis. Frontiers in immunology 13:839197, 1-23 (2022).
Warren et al. Genome-wide association analysis identifies novel blood pressure loci and offers biological insights into cardiovascular risk. Nature Genetics 49(3):403-415 (2017).
Waters et al., Initial B cell activation induces metabolic reprogramming and mitochondrial remodeling. iScience 5:99-109 (2018).
Waters, Samuel T. et al. Breaking tolerance to double stranded DNA, nucleosome, and other nuclear antigens is not required for the pathogenesis of lupus glomerulonephritis. Journal of Experimental Medicine 199(2):255-264 (2004).
Waters, Samuel T. et al. NZM2328: a new mouse model of systemic lupus erythematosus with unique genetic susceptibility loci. Clinical Immunology 100(3):372-383 (2001).
Webb, et al. A polymorphism within interleukin-21 receptor (IL21R) confers risk for systemic lupus erythematosus, Arthritis Rheumatol., v60, p. 2402-2407 (2009).
Weening, J. J., et al. The classification of glomerulonephritis in systemic lupus erythematosus revisited. Kidney Int.., v65, p. 521-530 (2004).
Weening, Jan J. et al. The Classification of Glomerulonephritis in Systemic Lupus Erythematosus Revisited. Journal of the American Society of Nephrology 15(2):241-250 (2004).
Wenzel, Cutaneous lupus erythematosus: new insights into pathogenesis and therapeutic strategies, Nat. Rev Rheumatol., v15, p. 519-532 (2019).
Werth, et al., Brief Report: Pharmacodynamics, Safety, and Clinical Efficacy of AMG 811, a Human Anti-Interferon-y Antibody, in Patients With Discoid Lupus Erythematosus, Arthritis Rheumatol., s, v69, p. 1028-1034 (2017).
Wickersham, et al. Metabolic Stress Drives Keratinocyte Defenses against *Staphylococcus aureus* Infection. Cell Reports, v18, p. 2742-2751 (2017).
Wierenga, et al. HIF1/2-exerted control over glycolytic gene expression is not functionally relevant for glycolysis in human leukemic stem/progenitor cells, Cancer Metab., v7, p. 1-17 (2019).
Wing, et al. A distinct subpopulation of CD25-T-follicular regulatory cells localizes in the germinal centers, PNAS, v114, E6400-E6409 (2017).

(56) References Cited

OTHER PUBLICATIONS

Wolk, et al. IL-22 regulates the expression of genes responsible for antimicrobial defense, cellular differentiation, and mobility in keratinocytes: A potential role in psoriasis, Eur. J. Immunol., v36, p. 1309-1323 (2006).
Wu, et al. AMPK-mediated increase of glycolysis as an adaptive response to oxidative stress in human cells: Implication of the cell survival in mitochondrial diseases. Biochim. Biophys. Acta—Mol. Basis Dis., v1822, p. 233-247 (2012).
Wu, et al. Subclinical atherosclerosis in patients with systemic lupus erythematosus: A systemic review and meta analysis. Autoimmun. Rev. 2016, vol. 15, p. 22-37.
Wu, et al. Type 1 Interferons Induce Changes in Core Metabolism that Are Critical for Immune Function. Immunity. 2-16 v44, p. 1325-1336 (2016).
Wu, Tianzhi et al. Clusterprofiler 4.0: A Universal Enrichment Tool for Interpreting Omics Data. Innovation 2(3):100141, 1-10 (2021).
Xu, et al., Identification of prostate cancer modifier pathways using parental strain expression mapping, PNAS, v104, p. 17771-17776 (2007).
Xue, et al., Transcriptome landscape of myeloid cells in human skin reveals diversity, rare populations and putative DC progenitors. J. Dermatol. Sci., v97, p. 41-49 (2020).
Yang, et al. ELF1 is associated with systemic lupus erythematosus in Asian populations. Hum. Mol. Genet. 2011, vol. 20 (3), p. 601-7.
Yang, Wanling, et al., Meta-analysis followed by Replication Identifies loci in or near CDKN1B, TET3, CD80, DRAM1, and ARID5B as Associated with systemic Lupus Erythematosus in Asians, American Journal of Human Genetics, 92:41-51 (2013).
Yano, et al. Transcriptional responses of human epidermal keratinocytes to cytokine interleukin-1, J. Cell. Physiol., v214, p. 1-13 (2008).
Yao, et al. Immune responses against oxidized LDL as possible targets for prevention of atherosclerosis in systemic lupus erythematosus, Vascul Pharmacol. 2021, vol. 140, Art 106863, p. 1-13.
Yao, et al. Type I interferon: Potential therapeutic target for psoriasis?, PLoS One, v3, iss 7, e2737, p. 1-14 (2008).
Yazdany, et al., Original research: Systemic lupus erythematosus, stroke and myocardial infarction risk: a systematic review and meta-analysis. RMD Open 2020, vol. 6, e00124, p. 1-14.
Yen, et al., Brief Report: Lupus—An Unrecognized Leading Cause of Death in Young Females a Population-Based Study Using Nationwide Death Certificates, 2000-2015. Arthritis Rheumatol 2018, vol. 70(8), p. 1251-5.
Yin, Y., et al. Normalization of CD4+ T cell metabolism reverses lupus. Sci. Transl. Med., v7, n274, p. 1-20 (2015).
Yuzaiful, et al. Targeted Therapy Using Intradermal Injection of Etanercept for Remission Induction in Discoid Lupus Erythematosus (TARGET-DLE): Results From a Proof-Of-Concept Phase II Trial, Lupus Sci. Med., v6, A1-A227 (2019).
Zhao, Qingyuan et al. Statistical inference in two-sample summary-data Mendelian randomization using robust adjusted profile score. Annals of Statistics 48(3):1742-1769 (2020).
Zhao, Shanrong et al. Comparison of RNA-Seq and microarray in transcriptome profiling of activated T cells. PloS one 9(1):e78644, 1-13 (2014).
Zhao, X., et al. Metabolic regulation of dermal fibroblasts contributes to skin extracellular matrix homeostasis and fibrosis. Nat. Metab., v1, p. 147-157 (2019).
Zhong, Y. et al. Screening biomarkers for systemic lupus erythematosus based on machine learning and exploring their expression correlations with the ratios of various immune cells. Frontiers in immunology 13:873787, 1-12 (2022).
Zhou, Dong et al. Wnt/beta-catenin signaling in kidney injury and repair: a double-edged sword. Laboratory Investigation 96(2):156-167 (2016).
Zhou, Yuzhao et al. Comparison of kidney injury molecule-1 and other nephrotoxicity biomarkers in urine and kidney following acute exposure to gentamicin, mercury, and chromium. Toxicological Sciences 101(1):159-170 (2008).
Zhu, et al. Modular gene analysis reveals distinct molecular signatures for cutaneous lupus patient subsets, Br. J. Dermatol., v185, n3, p. 563-572 (2021).
Zhu, Xiao-Wei et al. Comprehensive Assessment of the Association between FCGR s polymorphisms and the risk of systemic lupus erythematosus: Evidence from a Meta-Analysis. Scientific reports 6(1):31617, 1-13 (2016).
Zimmerman, et al. Single-cell RNA sequencing identifies candidate renal resident macrophage gene expression signatures across species. J. Am. Soc. Nephrol.., v30, p. 767-781 (2019).
Panousis, Nikolaos I. et al. Combined genetic and transcriptome analysis of patients with SLE: distinct, targetable signatures for susceptibility and severity. Annals of the rheumatic diseases 78(8):1079-1089 with Supplementary Materials (2019).
U.S. Appl. No. 18/806,109 Office Action dated Mar. 25, 2026.
U.S. Appl. No. 19/267,957 Office Action dated Mar. 27, 2026.

* cited by examiner 4.16.64.204 (55) GO:cytoplasm,organonitrogen.compound.catabolic.process
4.16.64 (78) GO:cytoplasm,cofactor.metabolic.process
2.7.32.130 (30) GO:cell.cycle,cell.cycle.process
2.11.40 (52) Lug:B_Cell. GO:integral.component.of.membrane
2.11.40.143 (43) Lug:B_Cell. GO:plasma.membrane.part
3.13.47.149 (31) Anc:IFN. GO:response.to.virus
3.13.47 (117) Anc:IFN. GO:defense.response.to.other.organism
3.13.47.151 (23) GO:defense.response,innate.immune.response
3.13.48 (37) GO:response.to.virus,defense.response.to.virus
3.13 (231) Lug:Monocyte_Myeloid_Cell. GO:innate.immune.response
3.13.48.155 (21) GO:innate.immune.response,response.to.virus
3.13.50 (45) Tis:Monocyte/Myeloid.Cell. GO:immune.system.process
3.13.49.157 (20) GO:pos.reg.of.response.to.stimulus,reg.of.cytokine.production
3.13.49 (32) Anc:IFN. GO:reg.of.cytokine.production
2.6.29.125 (22) GO:prostate.gland.development,spinal.cord.development
2.5.21.95 (52) GO:cytosolic.ribosome,nuclear−transcribed.mRNA.catabolic,nonsense−mediated.decay
2.5.21.95.219 (37) GO:cytosolic.ribosome,ribosomal.subunit
2.5.21 (82) GO:ribosome,translational.initiation
2.5.26 (34) GO:cell−cell.junction,reg.of.keratinocyte.proliferation
2.5.21.94 (30) GO:translation,cytoplasmic.translation
2.5.23.103 (29) GO:RNA.metabolic.process,RNA.processing

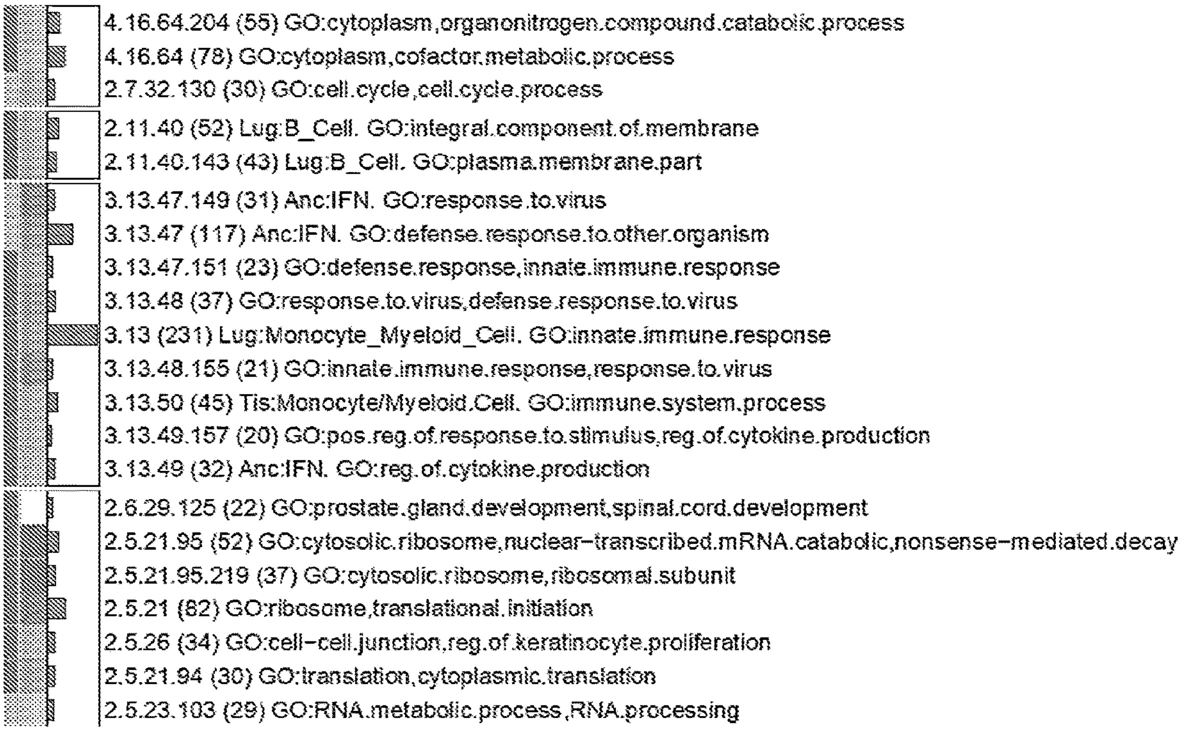

FIG. 4A-3

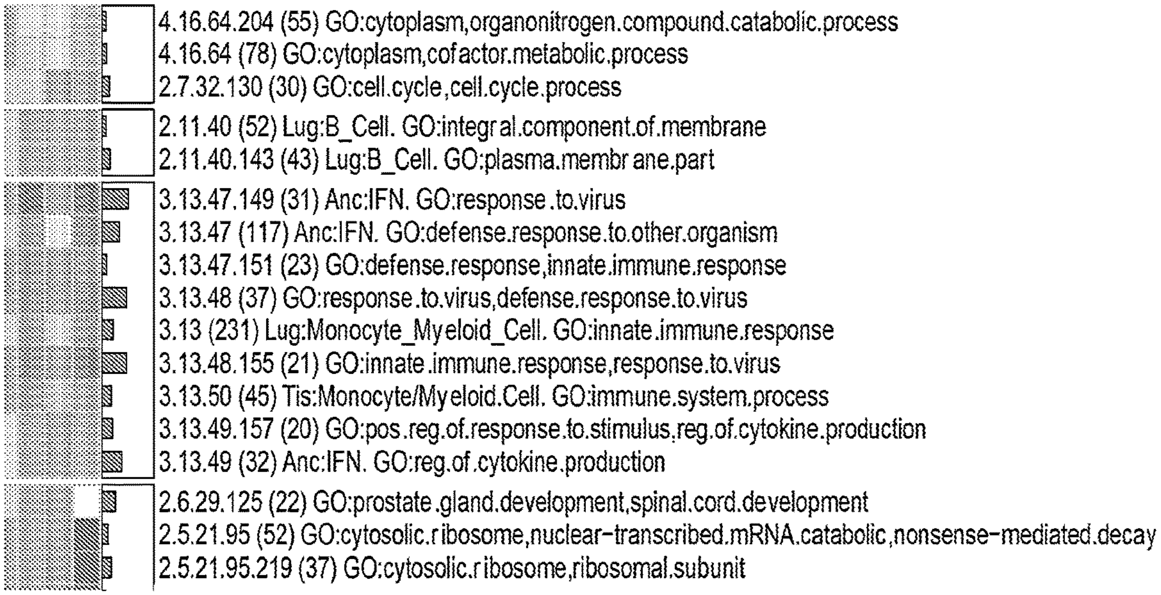

FIG. 4B-3

2.6.29.125 (22) GO:prostate.gland.development,spinal.cord.development
2.5.21.95 (52) GO:cytosolic.ribosome,nuclear-transcribed.mRNA.catabolic,nonsense-mediated.decay
2.5.21.95.219 (37) GO:cytosolic.ribosome,ribosomal.subunit
2.5.21 (82) GO:ribosome,translational.initiation
2.5.26 (34) GO:cell-cell.junction,reg.of.keratinocyte.proliferation
2.5.21.94 (30) GO:translation,cytoplasmic.translation
2.5.23.103 (29) GO:RNA.metabolic.process,RNA.processing
3.15 (125) GO:RNA.processing,RNA.metabolic.process
3.15.59 (61) GO:RNA.processing,RNA.metabolic.process
3.15.59.192 (25) GO:RNA.processing,RNA.metabolic.process
3.15.58 (64) GO:RNA.processing,RNA.metabolic.process
3.15.58.190 (39) GO:RNA.processing,nucleolus
3.15.59.193.303 (22) GO:nucleolus,RNA.processing
3.15.59.193 (36) GO:RNA.processing,nucleolus
3.15.58.191 (25) GO:RNA.processing,RNA.metabolic.process
2.6.30 (24) GO:transmembrane.signaling.receptor.activity,signaling.receptor.activity
3.14.51 (50) Lug:LDG_Blood_ONLY. GO:neutrophil.activation.involved.in.immune.response
3.14.57 (93) GO:spliceosomal.snRNP.complex,small.nuclear.ribonucleoprotein.complex
3.14.53.174 (22) GO:neg.reg.of.alpha-beta.T.cell.activation,reg.of.mast.cell.activation.involved.in.immune.response
2.7.31.126.248 (30) GO:cell.cycle,cell.cycle.process
2.7.31.126 (50) Anc:Cell.Cycle. GO:cell.cycle
2.7.31 (117) GO:chromosome.organization,chromosome
2.7 (153) GO:chromosome.organization,chromosome
2.7.31.127.250 (25) GO:nucleosome,DNA.packaging.complex
2.7.31.127 (38) GO:nucleosome,DNA.packaging.complex
2.5.19 (60) Anc:Unfolded.Protein. GO:endoplasmic.reticulum
m.up
down
pcnt
0 100 200
Size

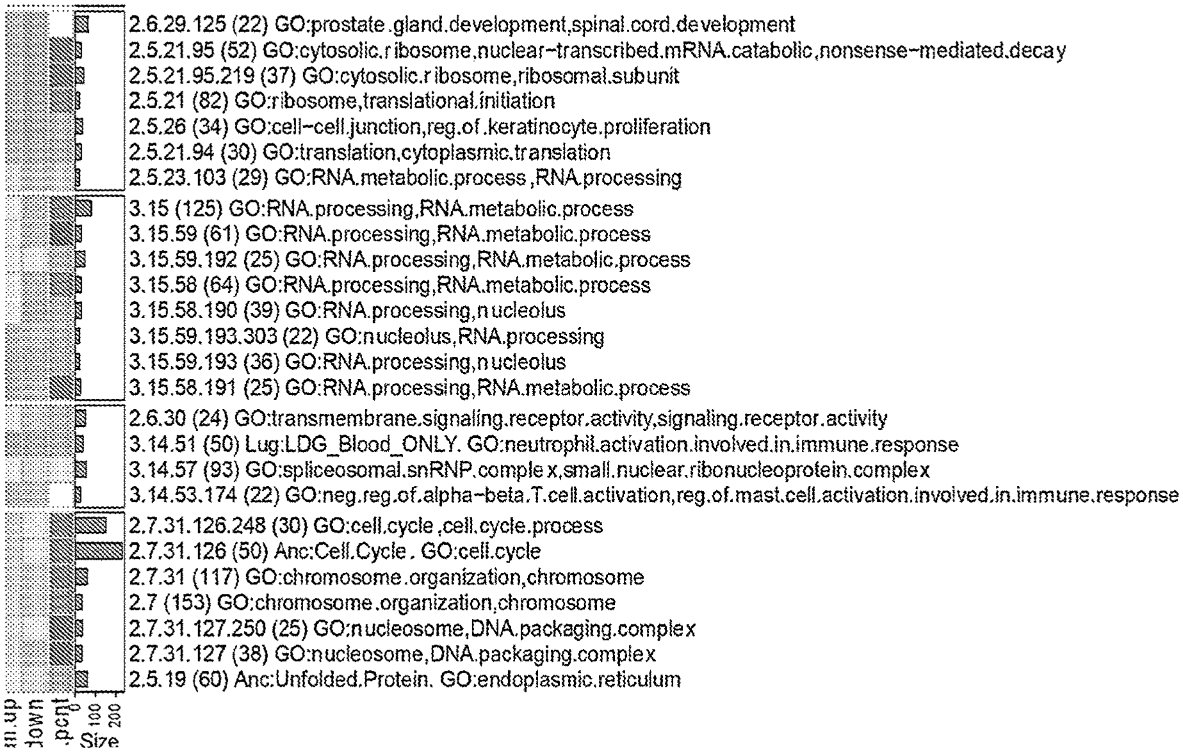

FIG. 4B-4

| Duke Patient Characteristics | | | | |
|---|---|---|---|---|
| Type.1 patients | 9 | | | |
| Type.2 patients | 9 | | | |
| Patient genders | 17 female, 1 male | | | |
| No. ancestral backgrounds | 3 (11 African ancestry: AA, 6 European ancestry: EA, 1 Hispanic ancestry: HA) | | | |
| Total no. sample attributes | 104 (see supplementary table) | | | |
| PC variance explained | PC1 | PC2 | PC3 | PC4 |
| | 20.9% | 16.9% | 15.3% | 13.2% |

3.15.175 (140): Lug:Neutrophil. GO:cell.activation.involved.in.immune.response
3.18.209 (53): GO:cell.diff,polymeric.cytoskeletal.fiber
6.35.228 (77): GO:protein−DNA.complex,chromatin
6.36.230 (160): Lug:Monocyte. GO:response.to.virus
6.36.234 (25): GO:extracellular.region,vesicle
6.36.235 (54): GO:transferase.activity,transferring.hexosyl.groups,protein.glycosylation
6.36.236 (21): GO:plasma.membrane.part,extrinsic.component.of.plasma.membrane
6.37.239 (32): GO:Rho.GTPase.binding,Rac.GTPase.binding
6.39.248 (57): Anc:IFN. GO:nucleic.acid.metabolic.process
6.42.256 (73): Anc:Cell.Cycle. GO:mitotic.cell.cycle 3.15.180 (37): GO:response.to.nitrogen.compound,reg.of.hormone.secretion
3.19.210 (55): GO:GTPase.regulator.activity,interleukin−18−mediated.signaling.pathway
3.19.211 (35): GO:small.molecule.biosynthetic.process,cellular.response.to.steroid.hormone
3.19.214 (21): GO:pos.reg.of.antimicrobial.peptide.production,reg.of.antimicrobial.humoral
6.37.240 (33): GO:neurotransmitter.metabolic.process,reg.of.Wnt.signaling.pathway 9.100.332 (39): GO:cytosolic.large.ribosomal.subunit,structural.constituent.of.ribosome
9.110.349 (29): GO:C−5.sterol.desaturase.activity,mannose.binding 3.15.176 (30): GO:G.protein−coupled.receptor.signaling.pathway,coupled.to.cyclic.nucleotid
3.20.216 (24): GO:muscle.structure.development,muscle.organ.development
6.40.252 (25): GO:inflammatory.response,L−type.voltage−gated.calcium.channel.complex
10.157.367 (32): GO:oxidative.phosphorylation,respiratory.chain 3.16.195 (20): GO:deaminating.activity,primary.amine.oxidase.activity
3.16.199 (21): GO:calcium.ion.binding,pos.reg.of.wound.healing
10.158.371 (28): GO:animal.organ.morphogenesis,reg.of.Wnt.signaling.pathway 5.22.218 (41): Anc:B.cells. GO:cytokinesis
5.23.222 (51): Anc:B.cells. GO:extracellular.matrix.organization 7.49.271 (70): GO:stem.cell.population.maintenance,maintenance.of.cell.number
7.49.272 (24): GO:cytosol,RNA.binding
7.49.273 (43): GO:neg.reg.of.extrinsic.apoptotic.signaling.pathway,porphyrin−containing.co
7.49.275 (36): GO:endosome,adult.locomotory.behavior

FIG. 27-1

A 3.15.176 (30) GO:G.protein~coupled.receptor.signaling.pathway,coupled.to.cyclic.nucleotide.second.messenger.
3.20.216 (24) GO:muscle.structure.development,muscle.organ.development
5.22.218 (41) Anc:B.cells. GO:cytokinesis
5.23.222 (51) Anc:B.cells. GO:extracellular.matrix.organization
6.40.252 (25) GO:inflammatory.response,L~type.voltage~gated.calcium.channel.complex
10.157.367 (32) GO:oxidative.phosphorylation,respiratory.chain
7.49.271 (70) GO:stem.cell.population.maintenance,maintenance.of.cell.number
7.49.272 (24) GO:cytosol,RNA.binding
7.49.273 (43) GO:neg.reg.of.extrinsic.apoptotic.signaling.pathway,porphyrin~containing.compound.biosynthetic.
7.49.275 (36) GO:endosome,adult.locomotory.behavior
3.15.175 (140) Lug:Neutrophil. GO:cell.activation.involved.in.immune.response
3.15.180 (37) GO:response.to.nitrogen.compound,reg.of.hormone.secretion
3.18.209 (53) GO:cell.diff,polymeric.cytoskeletal.fiber
3.19.210 (55) GO:GTPase.regulator.activity,interleukin~18~mediated.signaling.pathway
3.19.211 (35) GO:small.molecule.biosynthetic.process,cellular.response.to.steroid.hormone.stimulus
3.19.214 (21) GO:pos.reg.of.antimicrobial.peptide.production,reg.of.antimicrobial.humoral.response
6.37.240 (33) GO:neurotransmitter.metabolic.process,reg.of.Wnt.signaling.pathway
6.35.228 (77) GO:protein~DNA.complex,chromatin
6.36.230 (160) Lug:Monocyte. GO:response.to.virus
6.36.234 (25) GO:extracellular.region,vesicle
6.36.235 (54) GO:transferase.activity,transferring.hexosyl.groups,protein.glycosylation
6.36.236 (21) GO:plasma.membrane.part,extrinsic.component.of.plasma.membrane
6.37.239 (32) GO:Rho.GTPase.binding,Rac.GTPase.binding
6.39.248 (57) Anc:IFN. GO:nucleic.acid.metabolic.process
6.42.256 (73) Anc:Cell.Cycle. GO:mitotic.cell.cycle
3.16.195 (20) GO:deaminating.activity,primary.amine.oxidase.activity
3.16.199 (21) GO:calcium.ion.binding,pos.reg.of.wound.healing
9.100.332 (39) GO:cytosolic.large.ribosomal.subunit,structural.constituent.of.ribosome
9.110.349 (29) GO:C~5.sterol.desaturase.activity,mannose.binding
10.158.371 (28) GO:animal.organ.morphogenesis,reg.of.Wnt.signaling.pathway

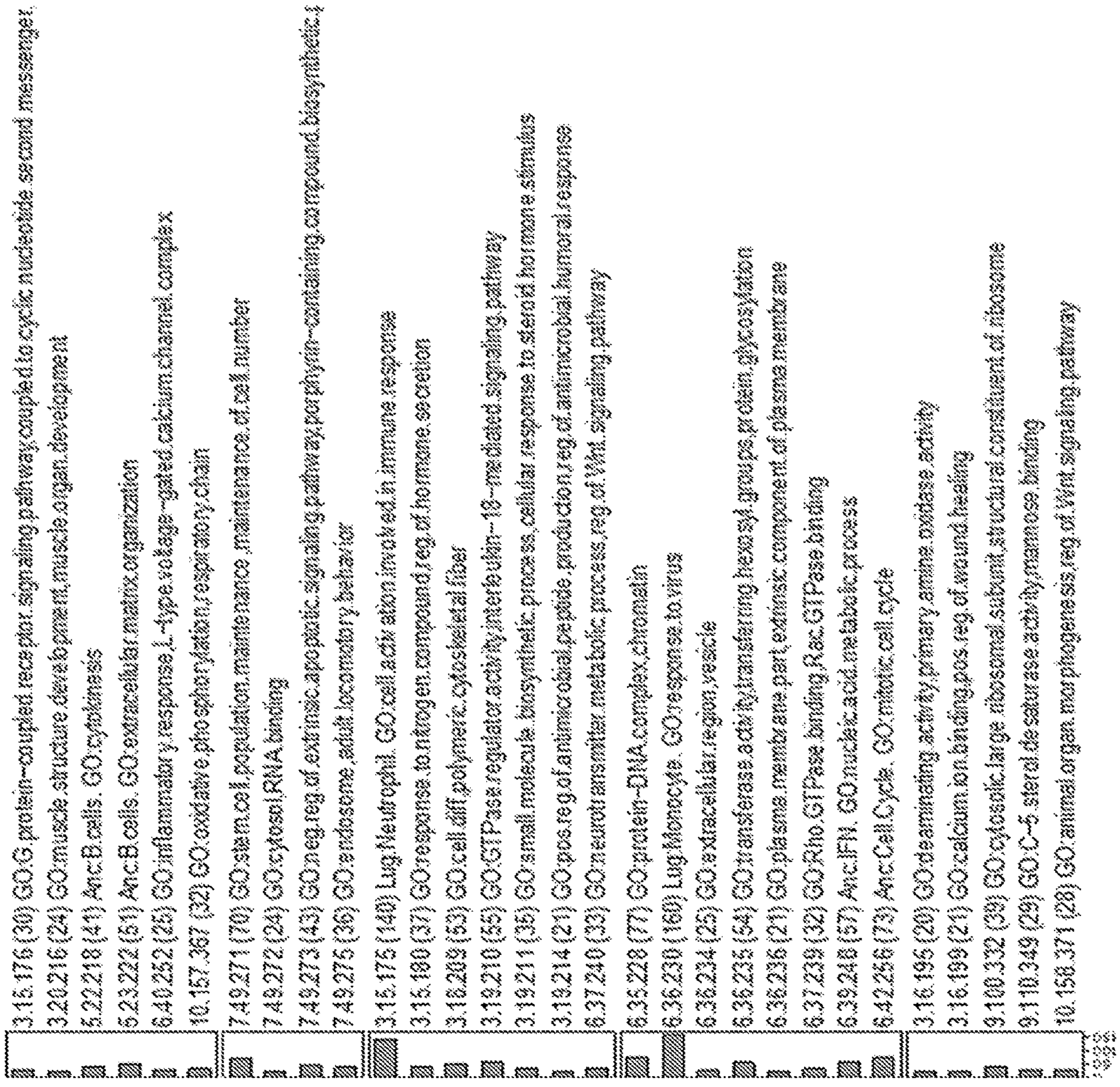

FIG. 29A-5

3.20 (Anc:Mono.Secreted. GO:synapse.pruning)
6.40 (GO:cation.transmembrane.transporter.activity,carnitine.shuttle)
9.98 (GO:reg.of.gene.expression,protein.localization.to.endoplasmic.reticulum)
9.110 (GO:spindle,C−5.sterol.desaturase.activity)
9.128 (GO:reg.of.axon.extension,axon.extension)
3.20.216 (GO:muscle.structure.development,muscle.organ.development)
6.40.252 (GO:inflammatory.response,L−type.voltage−gated.calcium.channel.complex)
9.110.349 (GO:C−5.sterol.desaturase.activity,mannose.binding)
9.110.349.510 (GO:C−5.sterol.desaturase.activity,protein.localization.to.paranode.region.of.axon)

10.157 (GO:oxidative.phosphorylation,respiratory.chain)
10.157.367 (GO:oxidative.phosphorylation,respiratory.chain)
7.49.271.472 (GO:cellular.response.to.endogenous.stimulus,metal.ion.transmembrane.transporter.activity
10.157.367.514 (GO:oxidative.phosphorylation,purine.nucleoside.triphosphate.metabolic.process)

6.36 (Lug:Monocyte. GO:response.to.virus)
6.36.230 (Lug:Monocyte. GO:response.to.virus)
6.36.230.438 (Anc:IFN. GO:response.to.virus)
6.36.230.439 (Anc:IFN. GO:reg.of.viral.life.cycle)

3.18 (Tis:T.cell. GO:reg.of.neuron.death)
6.37 (GO:cerebral.cortex.radial.glia.guided.migration,telencephalon.glial.cell.migration)
8.75 (GO:phospholipid.transporter.activity,phospholipid.transport)
3.18.209 (GO:cell.diff,polymeric.cytoskeletal.fiber)
3.19.214 (GO:pos.reg.of.antimicrobial.peptide.production,reg.of.antimicrobial.humoral.response)
6.36.234 (GO:extracellular.region,vesicle)
6.36.235 (GO:transferase.activity,transferring.hexosyl.groups,protein.glycosylation)
6.37.239 (GO:Rho.GTPase.binding,Rac.GTPase.binding)
6.37.240 (GO:neurotransmitter.metabolic.process,reg.of.Wnt.signaling.pathway)
3.18.209.408 (GO:reg.of.anatomical.structure.morphogenesis,forebrain.development)

6.42 (Anc:Cell.Cycle. GO:cell.cycle)
6.42.256 (Anc:Cell.Cycle. GO:mitotic.cell.cycle)
6.42.256.459 (Anc:Cell.Cycle. GO:cell.cycle)

FIG. 30A-2

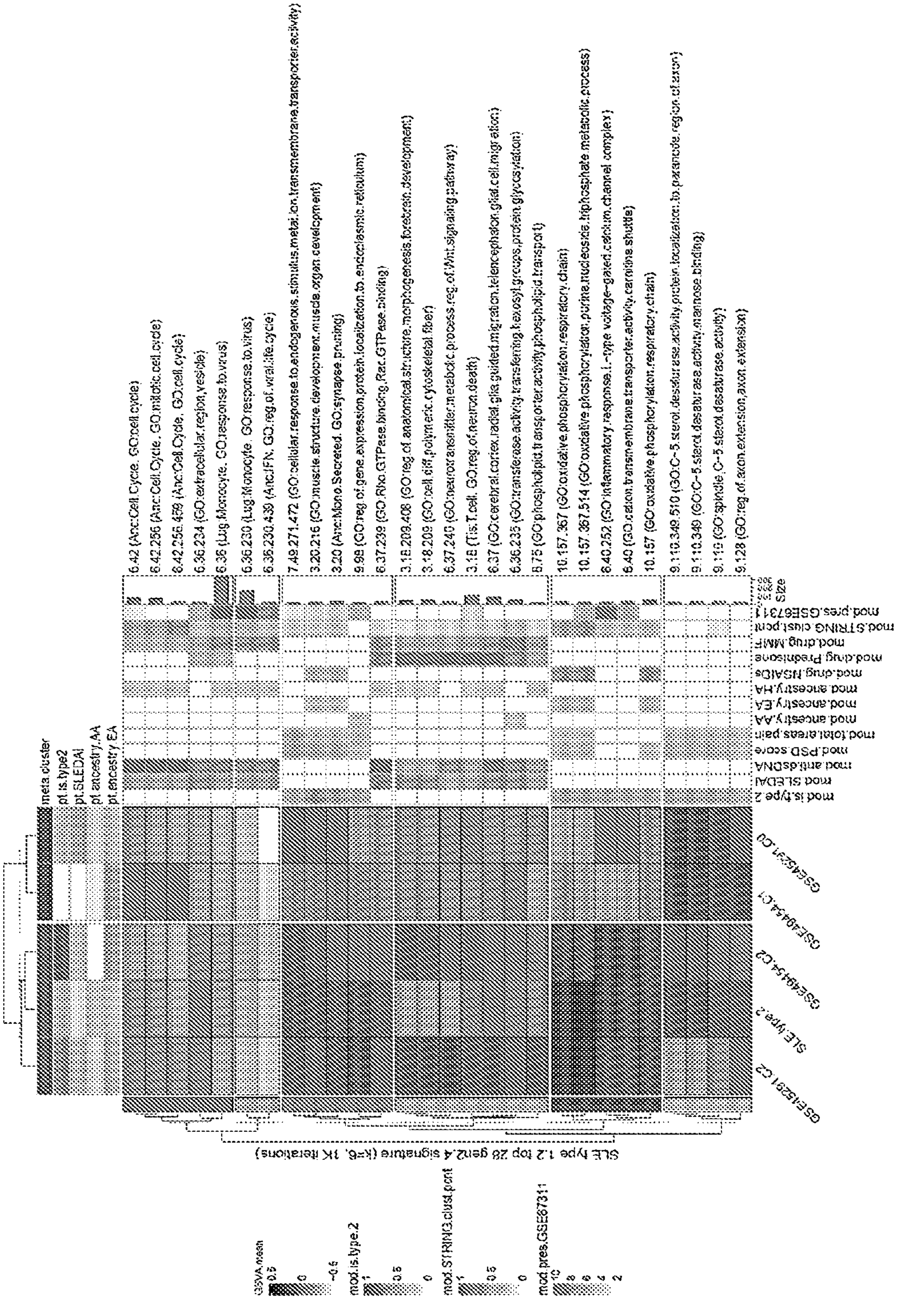

FIG. 34

SLE type 1,2 top 28 gen2.4 signature (k=6, 1K iterations)

meta.cluster
pt.is.type2
pt.SLEDAI
pt.ancestry.AA
pt.ancestry.EA 6.42 (Anc:Cell.Cycle, GO:cell.cycle)
6.42.256 (Anc:Cell.Cycle, GO:mitotic.cell.cycle)
6.42.256.459 (Anc:Cell.Cycle, GO:cell.cycle)
6.36.234 (GO:extracellular.region,vesicle)
6.36 (Lug:Monocyte, GO:response.to.virus)
6.36.230 (Lug:Monocyte, GO:response.to.virus)
6.36.230.439 (Anc:IFN, GO:reg.of.viral.life.cycle)
7.49.271.472 (GO:cellular.response.to.endogenous.stimulus,metal.ion.transmembrane.transporter.activity)
3.20.216 (GO:muscle.structure.development,muscle.organ.development)
3.20 (Anc:Mono.Secreted, GO:synapse.pruning)
9.98 (GO:reg.of.gene.expression,protein.localization.to.endoplasmic.reticulum)
6.37.239 (GO:Rho.GTPase.binding,Rac.GTPase.binding)
3.18.209.408 (GO:reg.of.anatomical.structure.morphogenesis,forebrain.development)
3.18.209 (GO:cell.diff,polymeric.cytoskeletal.fiber)
6.37.240 (GO:neurotransmitter.metabolic.process,reg.of.Wnt.signaling.pathway)
3.18 (Tis:T.cell, GO:reg.of.neuron.death)
6.37 (GO:cerebral.cortex.radial.glia.guided.migration,telencephalon.glial.cell.migration)
6.36.235 (GO:transferase.activity.transferring.hexosyl.groups,protein.glycosylation)
8.78 (GO:phospholipid.transporter.activity,phospholipid.transport)
10.157.367 (GO:oxidative.phosphorylation,respiratory.chain)
10.157.367.514 (GO:oxidative.phosphorylation,purine.nucleoside.triphosphate.metabolic.process)
6.40.252 (GO:inflammatory.response,L−type.voltage−gated.calcium.channel.complex)
6.40 (GO:cation.transmembrane.transporter.activity,carnitine.shuttle)
10.157 (GO:oxidative.phosphorylation,respiratory.chain)
9.110.349.510 (GO:C−5.sterol.desaturase.activity,protein.localization.to.paranode.region.of.axon)
9.110.349 (GO:C−5.sterol.desaturase.activity,mannose.binding)
9.110 (GO:spindle,C−5.sterol.desaturase.activity)
9.128 (GO:reg.of.axon.extension,axon.extension)

mod.is.type.2
mod.SLEDAI
mod.anti.dsDNA
mod.PSD.score
mod.total.areas.pain
mod.ancestry.AA
mod.ancestry.EA
mod.ancestry.HA
mod.drug.NSAIDs
mod.drug.Prednisone
mod.drug.MMF
mod.STRING.clust.pcnt
mod.pres.GSE67311
size GSE45291.C0
GSE49454.C1
GSE49454.C2
SLE.type.2
GSE45291.C2

GSVA.mean
0.5
0
−0.5
mod.is.type.2
1
0.5
0
mod.STRING.clust.pcnt
1
0.5
0
mod.pres.GSE67311
10
8
6
4
2

UNSUPERVISED MACHINE LEARNING METHODS FOR CLASSIFYING A LUPUS DISEASE STATE OF A SUBJECT

This application is a continuation of International PCT Application No. PCT/US2023/013173, filed Feb. 15, 2023, which claims priority to U.S. Provisional Patent Application No. 63/310,974, filed Feb. 16, 2022; U.S. Provisional Patent Application No. 63/407,591, filed Sep. 16, 2022; and U.S. Provisional Patent Application No. 63/424,397, filed Nov. 10, 2022, all of which are incorporated in full herein by reference.

BACKGROUND

Many diseases, for example systemic lupus erythematosus (SLE), are heterogeneous in nature, and have variable causation, course and responsiveness to therapy. Understanding molecular mechanisms of disease variation and sorting patients based on underlying molecular mechanisms can be useful in developing targeted personalized therapy.

SUMMARY

An aspect of the present disclosure is directed to a method for determining a gene set capable of classifying a disease state of a patient. The method can include any one of, any combination of or all of steps (a) to (d). Step (a) can include analyzing a data set to select N genes from an initial gene-set, said N genes are N variably expressed genes of a first gene-set, wherein the first gene-set is a subset of the initial gene-set, each gene of the first gene-set can be mapped to at least one known protein, and N is an integer number. Step (b) can include clustering the N genes into a plurality of gene clusters based at least on co-expression of the N genes in the plurality of reference samples. Step (c) can include correlating one or more gene clusters of the plurality of gene clusters with one or more sample traits of a plurality of reference subjects. Step (d) can include selecting a plurality of significant gene clusters based at least on strength of the correlation, wherein genes within the plurality of significant gene clusters form the gene set capable of classifying the disease state of a patient. The plurality of reference samples can be obtained from the plurality of reference subjects. The gene set obtained in step (d) is capable of classifying the disease state of a patient between endotypes of two or more endotypes of the disease state and/or not having the disease, and where each endotype of the two or more endotypes of the disease is present in at least some of the reference subjects. The data set can contain expression measurements of the genes of the initial gene-set, from the plurality of reference samples. In certain embodiments, the method includes obtaining the data set. In certain embodiments, wherein the data set comprises transcriptomic RNA sequencing data from each of the plurality of reference samples. In certain embodiments, the N genes are N most variably expressed genes. In certain embodiments, N is about 500 to about 10000. In certain embodiments, N is about 500 to about 10000 most variably expressed genes. In certain embodiments, N is about 5000. In certain embodiments, N is about 5000 most variably expressed genes. In certain embodiment, the N genes are clustered into the plurality of gene clusters of step (c) based at least on gene co-expression network analysis. In certain embodiments, the gene co-expression network analysis is performed using multiscale embedded gene co-expression network analysis (MEGENA), and/or weighted gene co-expression network analysis (WGCNA). In certain embodiments, the one or more gene clusters (e.g., in step (c)) comprises second, third and/or fourth generation gene clusters of the plurality of gene clusters. The second, third and/or fourth generation gene clusters of the plurality of gene clusters can be MEGENA second, third and/or fourth generation gene modules respectively. In certain embodiments, the one or more gene clusters (e.g., in step (c)) comprises third generation gene clusters of the plurality of gene clusters. The third generation gene clusters of the plurality of gene clusters can be MEGENA third generation gene modules respectively. In certain embodiments, the one or more gene clusters (e.g., in step (c)) comprises all gene clusters of the plurality of gene clusters. In certain embodiments, the third generation gene clusters are selected in step (d). In certain embodiments, the second, third, and/or fourth generation gene clusters are selected in step (d). The significant gene clusters can satisfy a threshold minimum size. In certain embodiments, each of the significant gene clusters satisfy a threshold minimum size. In certain embodiments, the threshold minimum size is about 15 to about 80 genes. In certain embodiments, the threshold minimum size is about 20 genes. In certain embodiments, the threshold minimum size is about 50 genes. In certain embodiments, the plurality of significant gene clusters selected in step (d) comprises 10 to 50 gene clusters. In certain embodiments, wherein the plurality of significant gene clusters selected in step (d) comprises 10 to 50 most strongly correlated gene cluster with the one or more sample traits.

In certain embodiments, the disease is lupus. In certain embodiments, the plurality of reference subjects comprises a first plurality of reference subjects having type 1 lupus, a second plurality of reference subjects having type 2 lupus, and a third plurality of reference subjects having type 1-2 lupus, and the gene set obtained in step (e) is capable of classifying whether a patient has type 1 lupus, type 2 lupus, or type 1-2 lupus. In certain embodiments, the one or more sample traits are selected from the sample traits listed in Table 10. In certain embodiments, the one or more sample traits comprise blood autoimmune antibody level, SLEDAI score, blood complement component 3 (C3) protein level, PSD score, age, ancestry, or any combination thereof. In certain embodiments, the one or more sample traits comprise blood autoimmune antibody level, age, Hispanic ancestry, Non-steroidal anti-inflammatory drugs usage, African ancestry, prednisone, amitriptyline usage, total areas of pain, or any combination thereof.

Certain aspects are directed to a method for classifying a lupus disease state of a patient. In certain embodiments, the method for classifying a lupus disease state of a patient comprises: analyzing a patient data set comprising or derived from gene expression measurements data of at least 2 genes selected from the genes listed within the gene set obtained in step (d) (e.g., as described herein), in a biological sample from the patient, to classify the lupus disease state of the patient as type 1 lupus, type 2 lupus, or type 1-2 lupus. In certain embodiments, the method for classifying a lupus disease state of a patient comprises: analyzing a patient data set comprising or derived from gene expression measurements data of at least 2 genes selected from the genes listed within the gene set obtained in step (d) (e.g., as described herein), in a biological sample from the patient, to classify the lupus disease state of the patient as type 1 lupus, or type 2 lupus. Genes within the gene set can be considered listed within the gene set. In certain embodiments, the patient data set comprises or is derived from gene expression measurements data of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 450, 500, 550, 600, 650, 700, 750, 850, 900, 950, 1000, 1050, 1100, 1150, 1200, 1250, 1300, 1350, 1400, 1450, 1500, 1550, 1600, 1700, 1800, 1900, 2000 or all genes, selected from the genes listed within the gene set. In certain embodiments, the patient data set comprises or is derived from gene expression measurements data of at least 2 to all, or any value or range there between, genes selected from the genes listed within each of one or more gene clusters selected from the significant gene clusters of the gene set, from the biological sample from the patient, wherein number of genes selected from the genes in each selected gene clusters may be different or same. In certain embodiments, the patient data set comprises or is derived from gene expression measurements data of an effective number of genes selected from the genes listed within each of the one or more gene clusters selected from significant gene clusters of the gene set, from the biological sample from the patient, wherein number of genes selected from the genes in each selected table may be different or same. As described herein, effective number of genes from a Table/gene cluster/gene module can include at least minimum number of genes selected from the Table/gene cluster/gene module to obtain the desired accuracy, sensitivity, specificity, positive predictive value and/or negative predictive value in disease state classification, such lupus disease state classification. In certain embodiments, the selected gene clusters comprise the significant gene clusters of the gene set. In certain embodiments, the patient data set is derived from the gene expression measurements data using gene set variation analysis (GSVA), gene set enrichment analysis (GSEA), enrichment algorithm, multiscale embedded gene co-expression network analysis (MEGENA), weighted gene co-expression network analysis (WGCNA), differential expression analysis, Z-score, log 2 expression analysis, or any combination thereof. In certain embodiments, the patient data set is derived from the gene expression measurements data using GSVA. In certain embodiments, the patient data set comprises one or more GSVA scores of the patient, wherein the one or more GSVA scores are generated based on one or more gene clusters selected from the significant gene clusters of the gene set, wherein for each selected cluster, at least one GSVA score of the patient is generated based on enrichment of expression of at least 2 genes listed within the selected gene cluster in the biological sample, and wherein the one or more GSVA scores comprise each generated GSVA score. In certain embodiments, the selected gene clusters comprise the significant gene clusters of the gene set. In certain embodiments, for each selected gene cluster, the at least one GSVA score of the patient is generated based on enrichment of expression of an effective number of genes selected from the genes listed in the respective selected gene cluster, in the biological sample, wherein number of genes selected from the genes in each selected gene cluster may be different or same. In certain embodiments, the analyzing the patient data set comprises providing the patient data set as an input to a machine-learning model trained to generate an inference of whether the patient data set is indicative of the patient having type 1 lupus, type 2 lupus, or type 1-2 lupus. In certain embodiments, the analyzing the patient data set comprises providing the patient data set as an input to a machine-learning model trained to generate an inference of whether the patient data set is indicative of the patient having type 1 lupus, or type 2 lupus. In certain embodiments, the patient data set comprises the one or more GSVA scores of the patient, and the machine-learning model generate the inference based at least on the one or more GSVA scores. In certain embodiments, the method further comprises receiving, as an output of the machine-learning model, the inference; and/or electronically outputting a report indicating the lupus disease state of the patient based on the inference. In certain embodiments, the machine-learning model is trained using linear regression, logistic regression, Ridge regression, Lasso regression, elastic net (EN) regression, support vector machine (SVM), gradient boosted machine (GBM), k nearest neighbors (kNN), generalized linear model (GLM), naïve Bayes (NB) classifier, neural network, Random Forest (RF), deep learning algorithm, linear discriminant analysis (LDA), decision tree learning (DTREE), adaptive boosting (ADB), Classification and Regression Tree (CART), hierarchical clustering, or any combination thereof. In certain embodiments, the patient is at elevated risk of having lupus. In certain embodiments, the patient is suspected of having lupus. In certain embodiments, the patient is asymptomatic for lupus. In certain embodiments, the patient has lupus. In certain embodiments, the patient is at elevated risk of having inactive lupus. In certain embodiments, the patient is suspected of having inactive lupus. In certain embodiments, the patient is asymptomatic for inactive lupus. In certain embodiments, the patient has inactive lupus. In certain embodiments, the patient is at elevated risk of having active lupus. In certain embodiments, the patient is suspected of having active lupus. In certain embodiments, the patient is asymptomatic for active lupus. In certain embodiments, the patient has active lupus. In certain embodiments, the patient is at elevated risk of having fibromyalgia. In certain embodiments, the patient is suspected of having fibromyalgia. In certain embodiments, the patient is asymptomatic for fibromyalgia. In certain embodiments, the patient has fibromyalgia. In certain embodiments, the patient is experiencing fatigue. In certain embodiments, the patient has or is suspected of having lupus and is experiencing fatigue. In certain embodiments, the significant gene clusters of the gene set are the gene clusters listed in Tables 17-1 to 17-30. Gene set listed within each of Tables 17-1 to 17-30 can form a significant gene cluster, and gene sets from different Tables (e.g., from Tables 17-1 to 17-30) can form different significant gene clusters. In certain embodiments, the significant gene clusters of the gene set are the gene clusters listed in Tables 24-1 to 24-30. Gene set listed within each of Tables 24-1 to 24-30 can form a significant gene cluster, and gene sets from different Tables (e.g., from Tables 24-1 to 24-30) can form different significant gene clusters. In certain embodiments, the method comprises selecting, recommending and/or administering a treatment to the patient based on the lupus disease state classification of the patient. In certain embodiments, the method comprises administering a treatment to the patient based on the lupus disease state classification of the patient. In certain embodiments, the treatment can be for type 1 lupus. In certain embodiments, the treatment can be for type 2 lupus. In certain embodiments, the treatment can be for type 1-2 lupus. The treatments for type 1, type 2 and type 1-2 lupus can be as described herein (e.g., in Detailed description, section II).

In certain embodiments, the method for classifying a lupus disease state of a patient comprises analyzing a patient data set comprising or derived from gene expression measurements data of at least 2 genes selected from the genes listed in Tables 17-1 to 17-30, from a biological sample obtained or derived from the patient, to classify the lupus disease state of the patient. In certain embodiments, classifying the lupus disease state of the patient can include classifying (e.g., determining) whether the patient has type 1, type 2, or type 1-2 lupus. In certain embodiments, classifying the lupus disease state of the patient can include classifying (e.g., determining) whether the patient has type 1, or type 2. In certain embodiments, the patient data set comprises or is derived from gene expression measurements data of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 450, 500, 550, 600, 650, 700, 750, 850, 900, 950, 1000, 1050, 1100, 1150, 1200, 1250, 1300, 1350, 1400, 1450, 1500, 1550, 1600, 1700, 1800, 1900, 2000 or all genes, selected from the genes listed in Tables 17-1 to 17-30, from the biological sample from the patient. In certain embodiments, the patient data set comprises or is derived from gene expression measurements data of at least 2 genes selected from the genes listed in each of one or more Tables selected from Tables 17-1 to 17-30, from the biological sample from the patient, wherein number of genes selected from different Tables may be different or the same. In certain embodiments, the patient data set comprises or is derived from gene expression measurements data of effective number of genes selected from the genes listed in each of one or more Tables selected from Tables 17-1 to 17-30, from the biological sample from the patient, wherein number of genes selected from different Tables may be different or the same. In certain embodiments, the patient data set comprises or is derived from gene expression measurements data of all genes listed in each of one or more Tables selected from Tables 17-1 to 17-30. In certain embodiments, the one or more Tables comprises at least 2, 3, 4, 5, 6, 7, 8, 9, 10, 11, 12, 13, 14, 15, 17, 18, 19, 20, 21, 22, 23, 24, 25, 27, 28, 29, or 30 Tables, e.g., the one or more Tables comprises at least 2, 3, 4, 5, 6, 7, 8, 9, 10, 11, 12, 13, 14, 15, 17, 18, 19, 20, 21, 22, 23, 24, 25, 27, 28, 29, or 30 Tables selected from Tables 17-1 to 17-30. In certain embodiments, Tables 17-1 to 17-30 are selected. In certain embodiments, the patient data set comprises module eigengenes (MEs), wherein the MEs can be of the gene modules formed based on the genes selected from each selected Table. For each selected Table (e.g., from Tables 17-1 to 17-30), genes selected from the Table (e.g., at least 2 genes, effective number of genes, or all the genes) can form a gene module, and the patient data set can contain ME of each gene modules formed, e.g., based on the Tables selected. In certain embodiments, the patient data set is derived from the gene expression measurements data using gene set variation analysis (GSVA), gene set enrichment analysis (GSEA), enrichment algorithm, multiscale embedded gene co-expression network analysis (MEGENA), weighted gene co-expression network analysis (WGCNA), differential expression analysis, Z-score, log 2 expression analysis, or any combination thereof. In certain embodiments, the patient data set is derived from the gene expression measurements data using GSVA. In certain embodiments, the patient data set is derived from the gene expression measurements data using GSVA, wherein the patient data set comprises one or more GSVA scores of the patient, wherein the one or more GSVA scores are generated based on the one or more Tables selected from Tables 17-1 to 17-30, wherein for each selected Table, at least one GSVA score of the patient is generated based on enrichment of expression of the genes selected from the selected Table, in the biological sample, and wherein the one or more GSVA scores comprise each generated GSVA score. In certain embodiments, for each selected Table, the at least one GSVA score of the patient is generated based on enrichment of expression of an effective number of genes selected from the genes listed in the selected Table, in the biological sample. In certain embodiments, analyzing the patient data set comprises providing the data set as an input to a machine-learning model trained to generate an inference of whether the patient data set is indicative of the patient having type 1 lupus, type 2 lupus, or type 1-2 lupus. In certain embodiments, analyzing the patient data set comprises providing the data set as an input to a machine-learning model trained to generate an inference of whether the patient data set is indicative of the patient having type 1 lupus, or type 2 lupus. In some embodiments, the inference can be, the patient data set is indicative of the patient having type 1 lupus, thereby the method classify that the patient has type 1 lupus. In some embodiments, the inference can be, the patient data set is indicative of the patient having type 2 lupus, thereby the method classify that the patient has type 2 lupus. In some embodiments, the inference can be, the patient data set is indicative of the patient having type 1-2 lupus, thereby the method classify that the patient has type 1-2 lupus. The method can classify lupus disease state of the patient based on the inference. In certain embodiments, the patient data set comprises the one or more GSVA scores of the patient, and the machine-learning model generate the inference based at least on the one or more GSVA scores. In certain embodiments, the patient data set comprises the MEs, and the machine-learning model generate the inference based at least on the MEs. In certain embodiments, the method further comprises receiving, as an output of the trained machine-learning model, the inference; and/or electronically outputting a report indicating the lupus disease state of the patient based on the inference. In certain embodiments, the machine-learning model is trained using linear regression, logistic regression, Ridge regression, Lasso regression, elastic net (EN) regression, support vector machine (SVM), gradient boosted machine (GBM), k nearest neighbors (kNN), generalized linear model (GLM), naïve Bayes (NB) classifier, neural network, Random Forest (RF), deep learning algorithm, linear discriminant analysis (LDA), decision tree learning (DTREE), adaptive boosting (ADB), Classification and Regression Tree (CART), hierarchical clustering, or any combination thereof. In certain embodiments, the machine learning model has a receiver operating characteristic (ROC) curve with an Area-Under-Curve (AUC) at least 0.85. In certain embodiments, analyzing the patient data set comprises generating a lupus disease risk score of the patient based on the patient data set, and classifying the whether the patient data set is indicative of the patient having type 1 lupus, or type 2 lupus based on the lupus disease risk score. The lupus disease risk score of the patient is generated based on the one or more GSVA scores of the patient. The method can classify the lupus disease state of the patient with an accuracy of at least 85%. The method can classify the lupus disease state of the patient with a sensitivity of at least 85%. The method can classify the lupus disease state of the patient with a specificity of at least 85%. The method can classify the lupus disease state of the patient with a positive predictive value of at least 85%. The method can classify the lupus disease state of the patient with a negative predictive value of at least 85%. In certain embodiments, the patient is at elevated risk of having lupus. In certain embodiments, the patient is suspected of having lupus. In certain embodiments, the patient is asymptomatic for lupus. In certain embodiments, the patient has lupus. In certain embodiments, the patient is at elevated risk of having inactive lupus. In certain embodiments, the patient is suspected of having inactive lupus. In certain embodiments, the patient is asymptomatic for inactive lupus. In certain embodiments, the patient has inactive lupus. In certain embodiments, the patient is at elevated risk of having active lupus. In certain embodiments, the patient is suspected of having active lupus. In certain embodiments, the patient is asymptomatic for active lupus. In certain embodiments, the patient has active lupus. In certain embodiments, the patient is at elevated risk of having fibromyalgia. In certain embodiments, the patient is suspected of having fibromyalgia. In certain embodiments, the patient is asymptomatic for fibromyalgia. In certain embodiments, the patient has fibromyalgia. In certain embodiments, the patient is experiencing fatigue. In certain embodiments, the patient has or is suspected of having lupus and is experiencing fatigue. In certain embodiments, the method further comprises selecting, recommending and/or administering a treatment based on the lupus disease state classification of the patient. In certain embodiments, the method further comprises administering a treatment based on the lupus disease state classification of the patient. In certain embodiments, the treatment can be for type 1 lupus. In certain embodiments, the treatment can be for type 2 lupus. In certain embodiments, the treatment can be for type 1-2 lupus. The treatments for type 1, type 2 and type 1-2 lupus can be as described herein (e.g., in Detailed description, section II).

In certain embodiments, the method for classifying a lupus disease state of a patient comprises analyzing a patient data set comprising or derived from gene expression measurements data of at least 2 genes selected from the genes listed in Tables 24-1 to 24-30, from a biological sample obtained or derived from the patient, to classify the lupus disease state of the patient. In certain embodiments, classifying the lupus disease state of the patient can include classifying (e.g., determining) whether the patient has type 1, type 2, or type 1-2 lupus. In certain embodiments, classifying the lupus disease state of the patient can include classifying (e.g., determining) whether the patient has type 1, or type 2. In certain embodiments, the patient data set comprises or is derived from gene expression measurements data of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 450, 500, 550, 600, 650, 700, 750, 850, 900, 950, 1000, 1050, 1100, 1150, 1200, 1250, 1300, 1350, 1400, 1450, 1500, 1550, 1600, 1700, 1800, 1900, 2000 or all genes, selected from the genes listed in Tables 17-1 to 17-30, from the biological sample from the patient. In certain embodiments, the patient data set comprises or is derived from gene expression measurements data of at least 2 genes selected from the genes listed in each of one or more Tables selected from Tables 24-1 to 24-30, from the biological sample from the patient, wherein number of genes selected from different Tables may be different or the same. In certain embodiments, the patient data set comprises or is derived from gene expression measurements data of effective number of genes selected from the genes listed in each of one or more Tables selected from Tables 24-1 to 24-30, from the biological sample from the patient, wherein number of genes selected from different Tables may be different or the same. In certain embodiments, the patient data set comprises or is derived from gene expression measurements data of all genes listed in each of one or more Tables selected from Tables 24-1 to 24-30. In certain embodiments, the one or more Tables comprises at least 2, 3, 4, 5, 6, 7, 8, 9, 10, 11, 12, 13, 14, 15, 17, 18, 19, 20, 21, 22, 23, 24, 25, 27, 28, 29, or 30 Tables, e.g., the one or more Tables comprises at least 2, 3, 4, 5, 6, 7, 8, 9, 10, 11, 12, 13, 14, 15, 17, 18, 19, 20, 21, 22, 23, 24, 25, 27, 28, 29, or 30 Tables selected from Tables 24-1 to 24-30. In certain embodiments, Tables 24-1 to 24-30 are selected. In certain embodiments, the patient data set comprises module eigengenes (MEs), wherein the MEs can be of the gene modules formed based on the genes selected from each selected Table. For each selected Table (e.g., from Tables 24-1 to 24-30), genes selected from the Table (e.g., at least 2 genes, effective number of genes, or all the genes) can form a gene module, and the patient data set can contain ME of each gene modules formed, e.g., based on the Tables selected. In certain embodiments, the patient data set is derived from the gene expression measurements data using gene set variation analysis (GSVA), gene set enrichment analysis (GSEA), enrichment algorithm, multiscale embedded gene co-expression network analysis (MEGENA), weighted gene co-expression network analysis (WGCNA), differential expression analysis, Z-score, log 2 expression analysis, or any combination thereof. In certain embodiments, the patient data set is derived from the gene expression measurements data using GSVA. In certain embodiments, the patient data set is derived from the gene expression measurements data using GSVA, wherein the patient data set comprises one or more GSVA scores of the patient, wherein the one or more GSVA scores are generated based on the one or more Tables selected from Tables 24-1 to 24-30, wherein for each selected Table, at least one GSVA score of the patient is generated based on enrichment of expression of the genes selected from the selected Table, in the biological sample, and wherein the one or more GSVA scores comprise each generated GSVA score. In certain embodiments, for each selected Table, the at least one GSVA score of the patient is generated based on enrichment of expression of an effective number of genes selected from the genes listed in the selected Table, in the biological sample. In certain embodiments, analyzing the patient data set comprises providing the data set as an input to a machine-learning model trained to generate an inference of whether the patient data set is indicative of the patient having type 1 lupus, type 2 lupus, or type 1-2 lupus. In certain embodiments, analyzing the patient data set comprises providing the data set as an input to a machine-learning model trained to generate an inference of whether the patient data set is indicative of the patient having type 1 lupus, or type 2 lupus. In some embodiments, the inference can be, the patient data set is indicative of the patient having type 1 lupus, thereby the method classify that the patient has type 1 lupus. In some embodiments, the inference can be, the patient data set is indicative of the patient having type 2 lupus, thereby the method classify that the patient has type 2 lupus. In some embodiments, the inference can be, the patient data set is indicative of the patient having type 1-2 lupus, thereby the method classify that the patient has type 1-2 lupus. The method can classify lupus disease state of the patient based on the inference. In certain embodiments, the patient data set comprises the one or more GSVA scores of the patient, and the machine-learning model generate the inference based at least on the one or more GSVA scores. In certain embodiments, the patient data set comprises the MEs, and the machine-learning model generate the inference based at least on the MEs. In certain embodiments, the method further comprises receiving, as an output of the trained machine-learning model, the inference; and/or electronically outputting a report indicating the lupus disease state of the patient based on the inference. In certain embodiments, the machine-learning model is trained using linear regression, logistic regression, Ridge regression, Lasso regression, elastic net (EN) regression, support vector machine (SVM), gradient boosted machine (GBM), k nearest neighbors (kNN), generalized linear model (GLM), naïve Bayes (NB) classifier, neural network, Random Forest (RF), deep learning algorithm, linear discriminant analysis (LDA), decision tree learning (DTREE), adaptive boosting (ADB), Classification and Regression Tree (CART), hierarchical clustering, or any combination thereof. In certain embodiments, the machine learning model has a receiver operating characteristic (ROC) curve with an Area-Under-Curve (AUC) at least 0.85. In certain embodiments, analyzing the patient data set comprises generating a lupus disease risk score of the patient based on the patient data set, and classifying the whether the patient data set is indicative of the patient having type 1 lupus, or type 2 lupus based on the lupus disease risk score. The lupus disease risk score of the patient is generated based on the one or more GSVA scores of the patient. The method can classify the lupus disease state of the patient with an accuracy of at least 85%. The method can classify the lupus disease state of the patient with a sensitivity of at least 85%. The method can classify the lupus disease state of the patient with a specificity of at least 85%. The method can classify the lupus disease state of the patient with a positive predictive value of at least 85%. The method can classify the lupus disease state of the patient with a negative predictive value of at least 85%. In certain embodiments, the patient is at elevated risk of having lupus. In certain embodiments, the patient is suspected of having lupus. In certain embodiments, the patient is asymptomatic for lupus. In certain embodiments, the patient has lupus. In certain embodiments, the patient is at elevated risk of having inactive lupus. In certain embodiments, the patient is suspected of having inactive lupus. In certain embodiments, the patient is asymptomatic for inactive lupus. In certain embodiments, the patient has inactive lupus. In certain embodiments, the patient is at elevated risk of having active lupus. In certain embodiments, the patient is suspected of having active lupus. In certain embodiments, the patient is asymptomatic for active lupus. In certain embodiments, the patient has active lupus. In certain embodiments, the patient is at elevated risk of having fibromyalgia. In certain embodiments, the patient is suspected of having fibromyalgia. In certain embodiments, the patient is asymptomatic for fibromyalgia. In certain embodiments, the patient has fibromyalgia. In certain embodiments, the patient is experiencing fatigue. In certain embodiments, the patient has or is suspected of having lupus and is experiencing fatigue. In certain embodiments, the method further comprises selecting, recommending and/or administering a treatment based on the lupus disease state classification of the patient. In certain embodiments, the method further comprises administering a treatment based on the lupus disease state classification of the patient. In certain embodiments, the treatment can be for type 1 lupus. In certain embodiments, the treatment can be for type 2 lupus. In certain embodiments, the treatment can be for type 1-2 lupus. The treatments for type 1, type 2 and type 1-2 lupus can be as described herein (e.g., in Detailed description, section II).

In an aspect, the present disclosure provides a method for developing a treatment model containing two or more treatment groups. The method can partition patients within a data set into the two or more treatment groups. The method can include any one of, any combination of, or all of steps (a) to (g). Step (a), can include obtaining a data set containing expression measurements of genes of an initial gene-set, from a plurality of patients. The data set can contain a plurality of individual data sets. The plurality of individual data sets can be obtained from the plurality of patients, where at least one individual data set is obtained from each of the patient. A respective individual data set can contain gene expression measurement data of a biological sample from a respective patient, of the genes of the initial gene-set. Step (b), can include, selecting N genes from the initial gene-set, where N is an integer number. In certain embodiments, the N genes are selected from a first gene-set, where the first gene-set is a subset of the initial gene-set. Each genes of the first gene-set can be mapped to at least one known protein. The first gene-set can be obtained from the initial gene-set, by removing genes that cannot be mapped to a known protein. In certain embodiments, the N genes are N variably expressed genes of the initial gene-set or the first gene-set or both. In certain embodiments, the N genes are N most variably expressed genes of the initial gene-set or the first gene-set or both. Step (c), can include clustering the N genes into a plurality of gene clusters based at least on co-expression of the N genes. Step (d), can include correlating the plurality of gene clusters with one or more sample traits, and selecting a plurality of significant gene clusters from the correlated gene clusters based at least on strength of the correlation of the plurality of gene clusters with the one or more sample traits. Step (e), can include overlapping one or more significant gene clusters with one or more gene function signature lists. Step (f), can include annotating the one or more significant gene clusters with one or more functional characterization based on the overlap. A gene function signature list can contain one or more functional characterization groups. A significant gene cluster can be annotated with a functional characterization if the significant gene cluster sufficiently overlaps with the respective functional characterization group. A significant cluster can sufficiently overlap with more than one functional characterization groups, and can be annotated with more than one functional characterizations, where the functional characterization groups can be from same or different gene function signature list. Every significant clusters may not sufficiently overlap, and all significant clusters may not be annotated. Step (g), can include partitioning the plurality of patients into two or more treatment groups.

In certain embodiments, N is about 500 to about 10,000. In certain embodiments, N is about 500 to about 10,000, most variably expressed genes of the initial gene-set or the first gene-set or both. Variable expression can be determined from the row variance, where genes with higher variable expression have higher row variance.

Correlation and strength of correlation the plurality of gene clusters with one or more sample traits can be measured by any suitable method, such as by Pearson's correlation and Pearson's correlation coefficient.

Sufficient overlap between a respective significant cluster and a respective functional characterization group, can satisfy overlap of a threshold minimum number of genes between the respective significant cluster and the respective functional characterization group. In certain embodiments, the threshold minimum number of genes are about 3 genes to about 12 genes. The overlap can be measured by any suitable technique. In certain embodiments, the overlap is measured using fisher's exact test. The sufficient overlap (e.g. for the threshold minimum number of genes) can have a threshold Fisher's adjusted p value. In certain particular embodiments, the threshold Fisher's adjusted p value for sufficient overlap can be about <0.3, about <0.2, or <0.1.

In certain embodiments, all patients in a treatment group are correlated with a set of significant gene clusters. In certain embodiments, i) all patients in a treatment group are correlated with a set of significant gene clusters, or ii) each significant cluster of the set of significant gene clusters is associated with the same gene functional characterization, or both. A patient can be correlated with a significant cluster based on patient's sample traits and/or gene expression in the biological sample from the patient. In certain embodiments, the plurality of patients are partitioned into the two or more treatment groups based at least on partitioning of the plurality significant gene clusters into the two or more treatment groups, where a respective patient gets partitioned into a treatment group based on partitioning of the significant gene cluster correlated to the respective patient. In some embodiments, each of the patients get partitioned into a treatment group based on partitioning of the significant gene cluster correlated to a respective patient. The plurality significant gene clusters can be partitioned into the two or more treatment groups based at least on partitioning of mean gene expression values of the plurality significant gene clusters. The mean gene expression values of the plurality significant gene clusters can be partitioned into the two or more treatment groups using any suitable method. In certain embodiments, the mean gene expression values of the significant clusters can be partitioned into the two or more treatment groups, using k-means clustering method.

In certain embodiments, the plurality of patients are partitioned into the two or more treatment groups based at least on gene set variation analysis (GSVA), for enrichment of at least 2 genes of the plurality of significant gene clusters. GSVA scores of the patients can be determined, and the patients can be partitioned into the two or more treatment groups based at least on the GSVA scores. For a respective patient, the GSVA score can be determined based at least on analyzing gene expression in the biological sample of the respective patient, for enrichment of at 2 least genes of the plurality significant gene clusters. The patients can be partitioned in the two or more treatment group based on the respective GSVA scores, using any suitable method. In certain embodiments, patients are partitioned in the two or more treatment group based on the respective GSVA scores, using k-means clustering method.

In certain embodiments, the plurality of patients are partitioned into the two or more treatment groups based at least on training a machine-learning model to infer a treatment group for a patient based on i) gene expressions of the patient of at least 2 genes of the plurality of significant gene clusters, and/or ii) the patient's one or more sample traits. In certain embodiments, the plurality of patients are partitioned into the two or more treatment groups based at least on training a machine-learning model to infer a treatment group for a patient based on gene expressions of the patient of at least 2 genes of the plurality of significant gene clusters. In certain embodiments, the plurality of patients are partitioned into the two or more treatment groups based at least on training a machine-learning model to infer a treatment group for a patient based on patient's one or more sample traits. In certain embodiments, the plurality of patients are partitioned into the two or more treatment groups based at least on training the machine-learning model to infer a treatment group for a patient based on i) gene expressions of the patient of at least 2 genes of the plurality of significant gene clusters, and ii) the patient's one or more sample traits. Gene expression measurement in a patient can be from the biological sample from the patient. In certain embodiments, the machine learning model is trained using linear regression, logistic regression (LOG), Ridge regression, Lasso regression, elastic net (EN) regression, support vector machine (SVM), gradient boosted machine (GBM), k nearest neighbors (kNN), generalized linear model (GLM), naïve Bayes (NB) classifier, neural network, Random Forest (RF), deep learning algorithm, linear discriminant analysis (LDA), decision tree learning (DTREE), or adaptive boosting (ADB), or any combination thereof. In certain embodiments, the machine learning model is trained using linear regression. In certain embodiments, the machine learning model is trained using logistic regression (LOG). In certain embodiments, the machine learning model is trained using Ridge regression. In certain embodiments, the machine learning model is trained using Lasso regression. In certain embodiments, the machine learning model is trained using elastic net (EN) regression. In certain embodiments, the machine learning model is trained using support vector machine (SVM). In certain embodiments, the machine learning model is trained using gradient boosted machine (GBM). In certain embodiments, the machine learning model is trained using k nearest neighbors (kNN). In certain embodiments, the machine learning model is trained using generalized linear model (GLM). In certain embodiments, the machine learning model is trained using naïve Bayes (NB) classifier. In certain embodiments, the machine learning model is trained using neural network. In certain embodiments, the machine learning model is trained using Random Forest (RF). In certain embodiments, the machine learning model is trained using deep learning algorithm, linear discriminant analysis (LDA). In certain embodiments, the machine learning model is trained using decision tree learning (DTREE). In certain embodiments, the machine learning model is trained using adaptive boosting (ADB). Certain aspects are directed to a method of training a machine-learning model according to the methods described herein.

In some embodiments, the trained machine learning model has an accuracy of at least about 90%, at least about 91%, at least about 92%, at least about 93%, at least about 94%, at least about 95%, at least about 96%, at least about 97%, at least about 98%, at least about 99%, at least about 99%, or more than about 99.5%. In some embodiments, the trained machine learning model has a sensitivity of at least about 90%, at least about 91%, at least about 92%, at least about 93%, at least about 94%, at least about 95%, at least about 96%, at least about 97%, at least about 98%, at least about 99%, or more than about 99%. In some embodiments, the trained machine learning model has a specificity of at least about 90%, at least about 91%, at least about 92%, at least about 93%, at least about 94%, at least about 95%, at least about 96%, at least about 97%, at least about 98%, at least about 99%, or more than about 99%. In some embodiments, the trained machine learning model has a positive predictive value of at least about 90%, at least about 91%, at least about 92%, at least about 93%, at least about 94%, at least about 95%, at least about 96%, at least about 97%, at least about 98%, at least about 99%, or more than about 99%. In some embodiments, the trained machine learning model has a negative predictive value of at least about 90%, at least about 91%, at least about 92%, at least about 93%, at least about 94%, at least about 95%, at least about 96%, at least about 97%, at least about 98%, at least about 99%, or more than about 99%. In some embodiments, the trained machine learning model has a receiver operating characteristic (ROC) curve with an Area-Under-Curve (AUC) at least about 0.90, at least about 0.91, at least about 0.92, at least about 0.93, at least about 0.94, at least about 0.95, at least about 0.96, at least about 0.97, at least about 0.98, at least about 0.99, or more than about 0.99.

The gene clusters of the plurality of gene clusters (e.g. obtained by clustering the N genes) can satisfy a threshold minimum size. In certain embodiments the minimum size can be 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, or 80 genes.

In certain embodiments, the plurality of significant gene clusters contains 10 to 80 gene clusters. In certain embodiments, the plurality of significant gene clusters contains about 10 gene clusters to about 80 gene clusters, that are most strongly correlated with the one or more sample traits.

In certain embodiments, the N genes are clustered into the plurality of gene clusters by, developing a planar filtered network (PFN) graph based on gene pair co-expression of the N genes, and extracting multiscale modules existing within the PFN graph to form the plurality of gene clusters. In certain embodiments, the PFN graph is generated by forming an adjacency matrix based on gene pair co-expression; ordering gene pairs according to strength of interaction and meeting a minimal false discovery rate; mapping gene pairs onto a sphere and add edges between them if and only if the resulting graph can still be embedded on a surface of a given genus g=k, where the edges are prohibited from crossing each other and the network wraps around on itself as the topological triangulations between cliques covering the sphere. In certain embodiments, the extracting multiscale modules existing within the PFN graph comprises iteratively extracting multiscale modules from topological cliques, wherein the iteration continues until a threshold a resolution parameter is met, and the module sizes decrease and approach the minimum threshold module size requirement. In certain embodiments, a second pass of statistical stringency can be performed to eliminate modules not meeting desired cluster requirements including minimal and maximum module size and significant gene cluster compactness. In certain embodiments, multiscale hub analysis (MHA) can be performed to identify module hub genes, defined as those genes with intramodular connections meeting a minimal significant hub degree.

In certain embodiments, the method can include determining treatment methods for the two or more treatment groups. For a respective treatment group a respective treatment method can be determined based at least on the functional annotation of the one or more significant gene clusters within the respective treatment group.

In certain embodiments, the one or more gene function signature lists contain AMPEL LuGENE, AMPEL Ancestry, AMPEL Endotype.32, Endotype.kidney, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof. In certain embodiments, the one or more gene function signature lists contain AMPEL LuGENE, AMPEL Ancestry, AMPEL tissues (Tis), Biologically Informed Gene Clustering (BIG-C) signature, Gene Ontology (GO) database, or any combination thereof. The gene function lists, the functional characterization groups (e.g. categories) within the list, and genes with the functional characterization groups for AMPEL Ancestry and BIG-C, are provided in Catalina, Michelle D., et al. "Patient ancestry significantly contributes to molecular heterogeneity of systemic lupus erythematosus." *JCI insight* 5.15 (2020); for GO is publicly available at geneontology.org; for BRETIGEA is provided in Mckenzie, Andrew T., et al. "Brain cell type specific gene expression and co-expression network architectures." *Scientific reports* 8.1 (2018): 1-19; for Hallmark gene sets, KEGG Pathway Database, Reactome signature is publicly available at gsea-msigdb.org/gsea/msigdb/collections.jsp.

In some embodiments, a first portion of the plurality of patients have lupus, and a second portion of the plurality of patients are healthy control. In certain embodiments, a first portion of the plurality of patients have lupus, and a second portion of the plurality of patients are healthy control; and the one or more sample traits include blood autoimmune antibody level, blood complement component 3 (C3) protein level, blood complement component 4 (C4) protein level, SLEDAI score, LuMOS score, drug usage, ancestral background, presence of leukopenia, presence of proteinuria, presence of vasculitis, or any combination thereof. Drug usage can be usage of drugs selected from corticosteroid, mycophenolate mofetil, methotrexate, and any combination thereof. In certain embodiments, a first portion of the plurality of patients have lupus, and a second portion of the plurality of patients are healthy control; the one or more sample traits include blood autoimmune antibody level, blood complement component 3 (C3) protein level, SLEDAI score, LuMOS score, corticosteroid usage, ancestral background, presence of leukopenia, presence of proteinuria, presence of vasculitis, or any combination thereof. In certain embodiments, a first portion of the plurality of patients have lupus, and a second portion of the plurality of patients are healthy control; and one or more gene function signature lists include AMPEL LuGENE, AMPEL Ancestry, AMPEL Endotype.32, Endotype.kidney, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof. In certain embodiments, a first portion of the plurality of patients have lupus, and a second portion of the plurality of patients are healthy control; the one or more sample traits include blood autoimmune antibody level, blood complement component 3 (C3) protein level, blood complement component 4 (C4) protein level, SLEDAI score, LuMOS score, drug usage, ancestral background, presence of leukopenia, presence of proteinuria, presence of vasculitis, or any combination thereof; and one or more gene function signature lists include AMPEL LuGENE, AMPEL Endotype.32, Endotype.kidney, AMPEL Ancestry, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof. In certain embodiments, a first portion of the plurality of patients have lupus, and a second portion of the plurality of patients are healthy control; the one or more sample traits includes blood autoimmune antibody level, blood complement component 3 (C3) protein level, SLEDAI score, corticosteroid usage, ancestral background, presence of leukopenia, presence of proteinuria, presence of vasculitis, or any combination thereof; and/or one or more gene function signature lists includes AMPEL LuGENE, AMPEL Ancestry, AMPEL tissues (Tis), Biologically Informed Gene Clustering (BIG-C) signature, Gene Ontology (GO) database, or any combination thereof.

In certain embodiments, wherein a first portion of the plurality of patients have SLE with active disease and without fibromyalgia, and a second portion of the plurality of patients have SLE without active disease, and with fibromyalgia. In certain embodiments, a first portion of the plurality of patients have SLE with active disease and without fibromyalgia, and a second portion of the plurality of patients have SLE without active disease, and with fibromyalgia; and the one or more sample traits include SLEDAI score, Fibromyalgia score, blood autoimmune antibody level, blood complement component 3 (C3) protein level, blood complement component 4 (C4) protein level, LuMOS score, immunotherapeutics usage, ancestral background, presence of leukopenia, presence of proteinuria, presence of vasculitis, or any combination thereof. Immunotherapeutics usage can be usage of immunotherapeutics selected from prednisone, mycophenolate mofetil, belimumab, duloxetine, and any combination thereof. In certain embodiments, a first portion of the plurality of patients have SLE with active disease and without fibromyalgia, and a second portion of the plurality of patients have SLE without active disease, and with fibromyalgia; and the one or more gene function signature lists include AMPEL LuGENE, AMPEL Ancestry, AMPEL Endotype.32, Endotype.kidney, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof. In certain embodiments, a first portion of the plurality of patients have SLE with active disease and without fibromyalgia, and a second portion of the plurality of patients have SLE without active disease, and with fibromyalgia; the one or more sample traits include SLEDAI score, Fibromyalgia score, blood autoimmune antibody level, blood complement component 3 (C3) protein level, blood complement component 4 (C4) protein level, LuMOS score, immunotherapeutics usage, ancestral background, presence of leukopenia, presence of proteinuria, presence of vasculitis, or any combination thereof; and the one or more gene function signature lists include AMPEL LuGENE, AMPEL Ancestry, AMPEL Endotype.32, Endotype.kidney, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof, or any combination thereof. In certain embodiments, a first portion of the plurality of patients have SLE with active disease and without fibromyalgia, and a second portion of the plurality of patients have SLE without active disease, and with fibromyalgia; the one or more sample traits include SLEDAI score, Fibromyalgia score, blood autoimmune antibody level, blood complement component 3 (C3) protein level, score, prednisone usage, mycophenolate mofetil usage, belimumab usage, duloxetine usage, ancestral background, or any combination thereof; and the one or more gene Biologically Informed Gene Clustering (BIG-C) signature, Gene Ontology (GO) database, or any combination thereof; or any combination thereof.

In certain embodiments, a first portion of the plurality of the patients have early inflammatory arthritis, and a second portion of the plurality of patients have advanced Rheumatoid arthritis. In certain embodiments, a first portion of the plurality of the patients have early inflammatory arthritis, and a second portion of the plurality of patients have advanced Rheumatoid arthritis; and the one or more sample traits include matrix metalloproteinase (MMP)-1 level in synovial biopsy sample, MMP-3 level in synovial biopsy sample, erythrocyte sedimentation rate, blood C-Reactive Protein level, age, sex, disease duration or any combination thereof. In certain embodiments, a first portion of the plurality of the patients have early inflammatory arthritis, and a second portion of the plurality of patients have advanced Rheumatoid arthritis; and the one or more gene function signature lists include AMPEL LuGENE, AMPEL Ancestry, AMPEL Endotype.32, Endotype.kidney, AMPEL tissues (Tis), Biologically Informed Gene Clustering (BIG-C) signature, Gene Ontology (GO) database, signature, or any combination thereof. In certain embodiments, a first portion of the plurality of the patients have early inflammatory arthritis, and a second portion of the plurality of patients have advanced Rheumatoid arthritis; the one or more sample traits include matrix metalloproteinase (MMP)-1 level in synovial biopsy sample, MMP-3 level in synovial biopsy sample, erythrocyte sedimentation rate, blood C-Reactive Protein level, age, sex, disease duration or any combination thereof; and the one or more gene function signature lists include AMPEL LuGENE, AMPEL Ancestry, AMPEL Endotype.32, Endotype.kidney, AMPEL tissues (Tis), Biologically Informed Gene Clustering (BIG-C) signature, Gene Ontology (GO) database, signature, or any combination thereof. In certain embodiments, a first portion of the plurality of the patients have early inflammatory arthritis, and a second portion of the plurality of patients have advanced Rheumatoid arthritis; the one or more sample traits include matrix metalloproteinase (MMP)-1 level in synovial biopsy sample, MMP-3 level in synovial biopsy sample, erythrocyte sedimentation rate, blood C-Reactive Protein level, age, sex, disease duration, or any combination thereof; and the one or more gene function signature lists include AMPEL LuGENE, AMPEL Ancestry, AMPEL tissues (Tis), Biologically Informed Gene Clustering (BIG-C) signature, Gene Ontology (GO) database, or any combination thereof.

In an aspect, the present disclosure provides a method for treating a patient. The method can include any one of, any combination of, or all of steps a', b', and c'. In step a', a test data set can be obtained. The test data set can contain gene expression measurement data of at least 2 genes of a biological sample from the patient, and/or measurement data of one or more sample traits of the patient. In some embodiments, the test data set can contain gene expression measurement data of at least 2 genes of the plurality of significant gene clusters of the biological sample from the patient, and/or measurement data of the one or more sample traits of the patient. Step b', can include classifying the patient into a treatment group of the two or more treatment groups. Step c', can include administering a treatment to the patient based on the treatment group of the patient.

In certain embodiments, the test data set can contain gene expression measurement data of at least 2 genes of the plurality of significant gene clusters of the biological sample from the patient. In certain embodiments, the test data set can contain measurement data of one or more sample traits of the patient. In certain embodiments, the test data set can contain gene expression measurement data of at least 2 genes of the plurality of significant gene clusters of a biological sample from the patient, and measurement data of one or more sample traits of the patient.

In certain embodiments, step b' includes comparing the test data set with the data set, and classifying the patient into a treatment group of the two or more treatment groups obtained from the data set. The data set can be a data set (e.g. of step a) described herein. The plurality of significant clusters can be a plurality of significant clusters described herein. The two or more treatment groups can be two or more treatment groups described herein. The plurality of significant clusters and the two or more treatment groups can be obtained from the data set according to the methods (e.g. of steps a, b, c, d, e, f, and/or g) described herein. In certain embodiments, the patient can be classified into a treatment group based on determining the significant gene cluster correlated to the patient, and classifying the patient into the treatment group of the correlated significant gene clusters. The significant cluster correlated to the patient can be determined based on the test data set (e.g. gene expression of the at least 2 genes of the plurality of significant gene clusters of the biological sample from the patient, and/or measurement data of one or more sample traits of the patient). In some embodiments, step b' includes using a trained machine learning model classify the patient into the treatment group. The trained machine learning model can be a trained machine learning model described herein. In certain embodiments, step b' includes classifying the patient into a treatment group based on GSVA. In certain embodiments, a GSVA score of the patient is calculated for enrichment of at least 2 genes of the plurality of significant gene clusters, and the patient is classified into the treatment group based on the GSVA score.

In an aspect, the present disclosure provides a method for determining fibromyalgia in a patient. The method can include any one of, any combination of, or all of steps a", b", and c". Step a" can include obtaining a test data set. The test data set can contain gene expression measurements in a biological sample from the patient. Step b" can include determining a GSVA score of the patient, from the test data set for enrichment of at least 2 genes listed in Table 4B. Step c" can include determining whether the patient has or does not have fibromyalgia based at least on the GSVA score of the patient. In certain embodiments, the method further includes administering a treatment to the patient. In certain embodiments, the method includes administering a treatment of fibromyalgia to the patient based at least on determination of fibromyalgia in the patient. In some embodiments, the GSVA score is determined with respect to a reference data set. In some embodiments, the reference data set can contain gene expression of at least 2 genes of the N genes from a plurality of patients. In some embodiments, the test data set can contain gene expression of one or more of at least 2 genes of the N genes of the patients. N genes can be the N genes described herein. The biological sample can be biological sample described herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 3-1. Magnified, top portion of the right vertical axis of FIG. 3. FIG. 3-2. Magnified, bottom portion of the right vertical axis of FIG. 3. FIG. 3-3. Magnified, left portion of the bottom horizontal axis of FIG. 3. FIG. 3-4. Magnified, right portion of the bottom horizontal axis of FIG. 3. FIG. 3-5. Magnified, left vertical axis of FIG. 3.

FIG. 4A-1. Magnified, top vertical axis of FIG. 4A. FIG. 4A-2. Magnified, left vertical axis of FIG. 4A. FIG. 4A-3. Magnified, top portion of the right vertical axis of FIG. 4A. FIG. 4A-4. Magnified, bottom portion of the right vertical axis of FIG. 4A. FIG. 4A-5. Magnified bottom horizontal axis of FIG. 4A.

FIG. 4B-1. Magnified, top vertical axis of FIG. 4B. FIG. 4B-2. Magnified, left vertical axis of FIG. 4B. FIG. 4B-3. Magnified, top portion of the right vertical axis of FIG. 4B. FIG. 4B-4. Magnified, bottom portion of the right vertical axis of FIG. 4B. FIG. 4B-5. Magnified, bottom horizontal axis of FIG. 4B.

FIG. 5A. African American (AA) ancestry. FIG. 5B. European American (EA) ancestry. FIG. 5C. Native American (NA) ancestry.

FIG. 6A. Corticosteroid (CS). FIG. 6B. Mycophenolate mofetil (MMF). FIG. 6C. Methotrexate (MTX).

FIG. 7A. Sunburst diagram showing ILLUM-1 top5K rowVar gene modules' eigengenes (ME) correlations to anti-dsDNA (yes=1 if assay>30 IU/mL else no=0).

FIG. 7B. Sunburst diagram showing significant overlap (Fisher's adj.p<0.05 and >=4 gene overlaps) of ILLUM-1top5K rowVar gene modules with LuGENE functional characterization groups.

FIG. 11A. Logistic Regression (LOG). FIG. 11B. Support Vector Machine (SVM). FIG. 11C. Random Forest (RF), for separating lupus patients into sub-clusters 0, 1, 2, 3, 4, and 5, based on gene expression measurement of the genes of the significant gene clusters (obtained from clustering ILLUM-1 top5k rowVar genes).

FIG. 12-1. Magnified, top portion of the right vertical axis of FIG. 12. FIG. 12-2. Magnified, bottom portion of the right vertical axis of FIG. 12. FIG. 12-3. Magnified, top portion of the left vertical axis of FIG. 12. FIG. 12-4. Magnified, bottom portion of the left vertical axis of FIG. 12.

FIG. 14-1. Magnified, top portion of the right vertical axis of FIG. 14. FIG. 14-2. Magnified, bottom portion of the right vertical axis of FIG. 14. FIG. 14-3. Magnified, left vertical axis of FIG. 14. FIG. 14-4. Magnified, bottom horizontal axis of FIG. 14.

FIG. 16A. Box-whiskers plot showing the abundance MMP-1 and MMP-3 transcripts between DMARD-naive (MMP-low, MMP-high) patients and advanced RA patients. Transcript abundance was determined by microarray chips. Data is presented as log 2 expression values and analyzed using Kruskal-Wallis test with a Dunn's post-hoc test. **P<0.0001, P<0.01, ns=non-significant. FIG. 16B. Box-whiskers plot showing mRNA expression of MMP-1 and MMP-3 between MMP-high and MMP-low groups. Data was generated using qPCR, presented as log 2 copy number and analyzed by Mann-Whitney test. P<0.01. FIG. 16C. Violin plot showing the transcript abundance of various MMPs in ERA patients FIG. 17A. Representative images showing immunohistochemical staining of MMP-1 (upper panel) and MMP-3 (lower panel) in the OCT-embedded tissue sections of MMP-low and MMP-high groups. FIG. 17B. Box-whiskers plot showing quantification of MMP-1 and MMP-3 IHC staining in the synovial lining and sublining of DMARD-naïve RA patients. Data was presented as IOD/area value indicating relative expression and analyzed by Mann-Whitney test. P<0.01, ns=non-significant. FIG. 17C. Box-whiskers plot showing quantification of MMP-1 and MMP-3 IHC staining in the synovial lining and sublining of MMP-low and MMP-high DMARD-naïve RA patients. Data was presented as IOD/area value indicating relative expression and analyzed by Mann-Whitney test. P<0.01, ns=non-significant. IOD=integrated optical density. FIG. 17D. Box-whiskers plot showing the expression of MMP-1 and MMP-3 in the serum of MMP-high and MMP-low ERA subjects. Data was analyzed by Mann-Whitney U test; ns=non-significant. FIG. 17E. Spearman rank correlation analysis between serum MMP-1 and MMP-3 levels in ERA patients (open circles=MMP-high; close circles=MMP-low). FIG. 17 F. Spearman rank correlation analysis between serum MMP-1 levels and hs-CRP in ERA patients (open circles=MMP-high; close circles=MMP-low). FIG. 17**G. Spearman rank correlation analysis between serum MMP-3 levels and hs-CRP in ERA patients.

FIG. 18A. Heatmap showing unsupervised hierarchical clustering of differentially expressed genes (DEGs) between MMP-high and MMP-low groups. Genes were clustered using Pearson correlation and complete linkage clustering algorithms. FIG. 18B. Heatmap showing 21/23 WGCNA modules with significant correlations to at least one clinical trait of the 17 EIA samples. Pearson correlation coefficients are colored according to the legend and values overlaid in their respective cells. FIG. 18C. Pearson correlation plot showing interactions between WGCNA modules and functional pathways. FIG. 18D. Hierarchical clustering plot showing Pearson correlation between MEGENA modules and clinical variables. FIG. 18E. Ingenuity pathway analysis (IPA) showing curated molecular interactions between DEGs in MMP-high cohort. Molecules highlighted in red (or shades of red) represent DEG that are elevated in MMP-high cohort.

FIGS. 19A and B. Box-whiskers plot showing DAS-CRP (19A) or hs-CRP (19B) levels (represented as mg/L) at baseline and short-term follow-up interval. Data was analyzed by Mann-Whitney test. ***P<0.001, *P<0.05. FIGS. 19C and D: Box-whiskers plot showing DAS-CRP (19C) or hs-CRP (19D) levels (represented as mg/L) at baseline and short-term follow-up interval in MMP-low and MMP-high groups. Data was analyzed by Mann-Whitney test. **P<0.01, ns=non-significant.

FIG. 20A. Box-whiskers plot showing mHAQAUC/year after 15 year follow-up between MMP-high and MMP-low groups. Data was analyzed by Mann-Whitney test; ns=non-significant. FIG. 20B. Pearson correlation plots showing the relationship between MMP-1 or MMP-3 levels at baseline and mHAQ AUC scores at 15 year follow-up.

FIG. 21A. 99/135 (73%) of calculable ILLUM-1 all genes, generations 2 through 5 modules were preserved (z.summ>2) in the ILLUM-1 top5k modules. FIG. 21B. 130/134 (97%) of the ILLUM-1 top5k calculable gen 2-5 mods were preserved in the ILLUM-1 all genes modules.

FIG. 27-1. Magnified, right vertical axis of FIG. 27. FIG. 27-2. Magnified, left vertical axis of FIG. 27. FIG. 27-3. Magnified, left portion of the bottom horizontal axis of FIG. 27. FIG. 27-4. Magnified, right portion of the bottom horizontal axis of FIG. 27.

FIG. 29A-1. Magnified, top vertical axis of FIG. 29A. FIG. 29A-2. Magnified, left vertical axis of FIG. 29A. FIG. 29A-3. Magnified, left portion of the bottom horizontal axis of FIG. 29A. FIG. 29A-4. Magnified, right portion of the bottom horizontal axis of FIG. 29A. FIG. 29A-5. Magnified, right vertical axis of FIG. 29A.

FIG. 30A-1. Magnified, left vertical axis of FIG. 30A. FIG. 30A-2. Magnified, right vertical axis of FIG. 30A. FIG. 30A-3. Magnified, top vertical axis of FIG. 30A. FIG. 30A-4. Magnified, left portion of the bottom horizontal axis of FIG. 30A. FIG. 30A-5. Magnified, right portion of the bottom horizontal axis of FIG. 30A.

FIG. 34: Type 1/2 SLE Modules identify a subset of patients with inactive SLE. GSVA analysis of patients with inactive SLE (SLEDAI<6) from GEO studies GSE45291 and GSE49454 using the top 30 cohort modules from Type 1/2 SLE as input gene sets. GSVA scores were clustered into four groups by k means clustering (1k iterations). Four test subsets having cosine similarity (r>+0.2) to the Type 2 SLE dataset (red arrow) were visualized. Column annotations include cosine similarities to the Type 2 SLE reference cluster and correlations to SLEDAI and ancestral background (AA and EA) within their respective studies. Module row annotations include only positive correlations to sample traits ranging from 0 to +1, percentage of module gene participation in predicted proteinprotein interactions (PPIs) per the STRING database, and z-summary module preservation scores in the GSE67311 fibromyalgia study where only modules at least minimally preserved (z.summ>2) are colored.

FIG. 44A: Correlations depicted amongst top clinical attributes of interest. FIG. 44B-C: Correlation of RLR to PSD score ($r=0.791$, $p<.0001$) including the confidence interval (FIG. 44B) and the same for correlation of RLR to SLEDAI ($r=-0.746$, $p<.0001$, FIG. 44C).

INCLUDED ASPECTS

Figure 1:
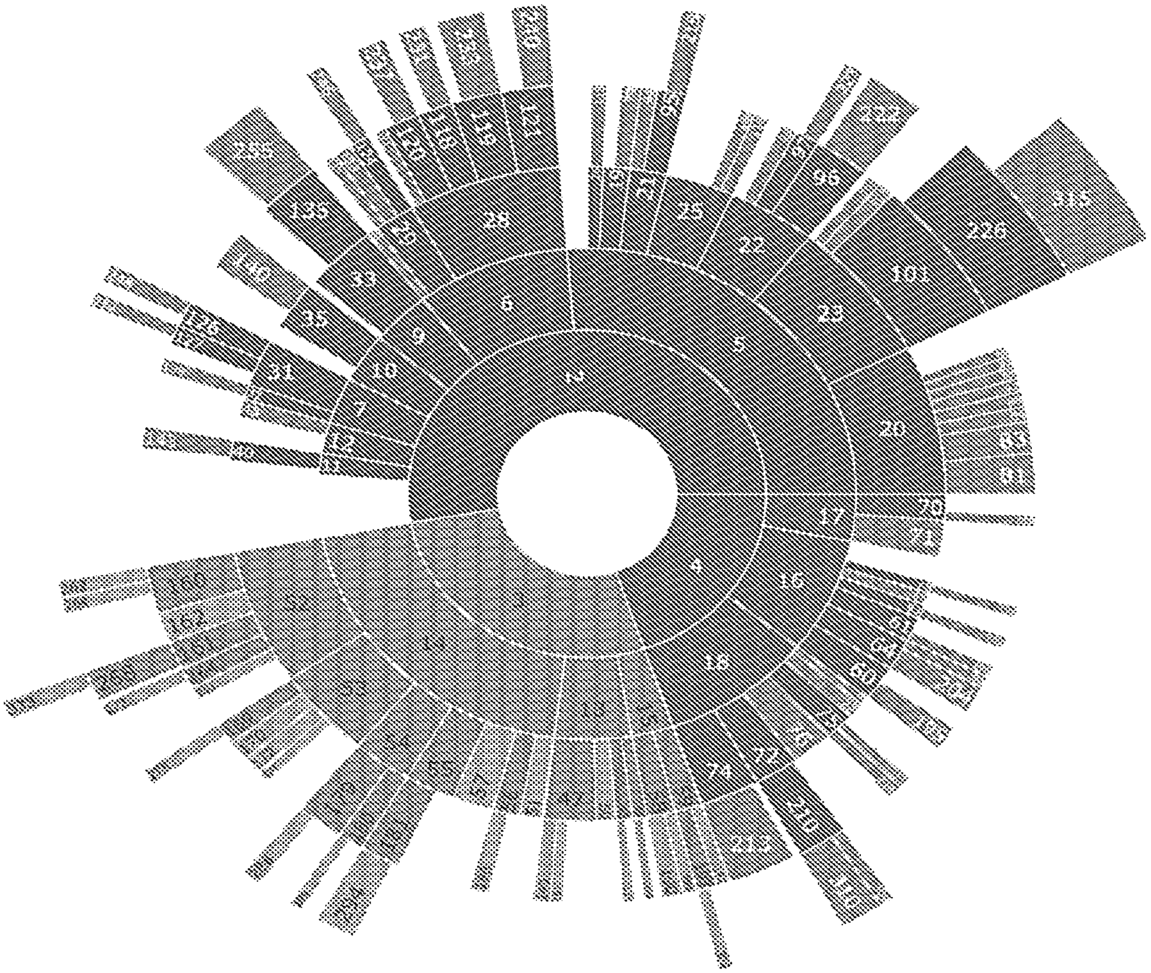
FIG. 1: Sunburst diagram showing ILLUM-1 top5k rowVar genes clustered by co-expression using CodeR-BP.

1. A method for developing a treatment model comprising two or more treatment groups, the method comprising:
   a) obtaining a data set comprising gene expression measurements of genes of an initial gene-set, from a plurality of patients;
   b) selecting N genes from the initial gene-set, said N genes are N variably expressed genes of a first gene-set, wherein the first gene-set is a subset of the initial gene-set, each gene of the first gene-set can be mapped to at least one known protein, and N is an integer number;
   c) clustering the N genes into a plurality of gene clusters based at least on co-expression of the N genes;
   d) correlating the plurality of gene clusters with one or more sample traits of the plurality of patients, and selecting a plurality of significant gene clusters based at least on strength of the correlation;
   e) overlapping one or more significant gene clusters with one or more gene function signature lists;
   f) annotating the one or more significant gene clusters with one or more functional characterizations based on sufficient overlap between the one or more significant gene clusters and the one or more gene function signature lists, wherein significant overlap satisfies overlap of a threshold minimum number of genes; and
   g) partitioning the plurality of patients into two or more treatment groups, wherein (i) all patients in a treatment group are associated with a set of significant gene clusters, or (ii) each significant cluster of the set of significant gene clusters is associated with the same functional characterization, or both.
2. The method of aspect 1, wherein the N genes are N most variably expressed genes.
3. The method of aspect 1 or 2, wherein N is about 500 to about 10000.
4. The method of any one of aspects 1 to 3, wherein N is about 5000.
5. The method of any one of aspects 1 to 4, wherein the plurality of patients is partitioned into the two or more treatment groups based at least on partitioning the significant gene clusters into the two or more treatment groups, wherein a patient gets partitioned into a treatment group based on partitioning of the significant gene cluster correlated to the patient.
6. The method of aspect 5, wherein the significant gene clusters are partitioned into the two or more treatment groups based at least on partitioning of mean gene expression values of the significant clusters.
7. The method of aspect 5 or 6, wherein the mean gene expression values are partitioned using k-means clustering method.
8. The method of any one of aspects 1 to 4, wherein the plurality of patients are partitioned into the two or more treatment groups based at least on gene set variation analysis (GSVA) of expressions of the genes of the plurality of significant gene clusters.
9. The method of aspect 8, wherein the plurality of patients are partitioned based at least on the GSVA analysis, using k-means clustering method.
10. The method of any one of aspects 1 to 4, wherein the plurality of patients are partitioned into the two or more treatment groups based at least on training a machine-learning model to infer a treatment group for a patient based on i) gene expressions of one or more genes of the plurality of significant gene clusters of the patient, and/or ii) the patient's one or more sample traits.
11. The method of aspect 10, wherein the machine learning model is trained using linear regression, logistic regression (LOG), Ridge regression, Lasso regression, elastic net (EN) regression, support vector machine (SVM), gradient boosted machine (GBM), k nearest neighbors (kNN), generalized linear model (GLM), naïve Bayes (NB) classifier, neural network, Random Forest (RF), deep learning algorithm, linear discriminant analysis (LDA), decision tree learning (DTREE), or adaptive boosting (ADB), or any combination thereof.
12. The method of aspect 10 or 11, wherein the trained machine learning model has an accuracy of at least about 90%, at least about 91%, at least about 92%, at least about 93%, at least about 94%, at least about 95%, at least about 96%, at least about 97%, at least about 98%, at least about 99%, or more than about 99%.
13. The method of any one of aspects 10 to 12, wherein the trained machine learning model has an sensitivity of at least about 90%, at least about 91%, at least about 92%, at least about 93%, at least about 94%, at least about 95%, at least about 96%, at least about 97%, at least about 98%, at least about 99%, or more than about 99%.

14. The method of any one of aspects 10 to 13, wherein the trained machine learning model has an specificity of at least about 90%, at least about 91%, at least about 92%, at least about 93%, at least about 94%, at least about 95%, at least about 96%, at least about 97%, at least about 98%, at least about 99%, or more than about 99%.
15. The method of any one of aspects 10 to 14, wherein the trained machine learning model has a positive predictive value of at least about 90%, at least about 91%, at least about 92%, at least about 93%, at least about 94%, at least about 95%, at least about 96%, at least about 97%, at least about 98%, at least about 99%, or more than about 99%.
16. The method of any one of aspects 10 to 15, wherein the trained machine learning model has a negative predictive value of at least about 90%, at least about 91%, at least about 92%, at least about 93%, at least about 94%, at least about 95%, at least about 96%, at least about 97%, at least about 98%, at least about 99%, or more than about 99%.
17. The method of any one of aspects 10 to 16, wherein the trained machine learning model has a receiver operating characteristic (ROC) curve with an Area-Under-Curve (AUC) at least about 0.90, at least about 0.91, at least about 0.92, at least about 0.93, at least about 0.94, at least about 0.95, at least about 0.96, at least about 0.97, at least about 0.98, at least about 0.99, or more than about 0.99.
18. The method of any one of aspects 1 to 17, further comprising determining treatment methods for the two or more treatment groups, wherein for a respective treatment group a respective treatment method is determined based at least on the functional annotation of one or more significant gene clusters associated with the respective treatment group.
19. The method of any one of aspects 1 to 18, wherein each of the significant gene clusters satisfy a threshold minimum size.
20. The method of aspect 19, wherein the threshold minimum size is about 15 to about 80 genes.
21. The method of aspect 20, wherein the threshold minimum size is about 20 genes.
22. The method of aspect 20, wherein the threshold minimum size is about 50 genes.
23. The method of any one of aspects 1 to 22, wherein the plurality of significant gene clusters comprises 10 to 50 gene clusters.
24. The method of any one of aspects 1 to 23, wherein the N genes are clustered into the plurality of gene clusters by a process comprising, developing a planar filtered network (PFN) graph based on gene pair co-expression of the N genes, and extracting multiscale modules existing within the PFN graph to form the plurality of gene clusters.
25. The method of any one of aspects 1 to 24, wherein the one or more gene function signature list comprises AMPEL LuGENE, AMPEL Ancestry, AMPEL Endotype.32, Endotype.kidney, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof, or any combination thereof.
26. The method of any one of aspects 1 to 25, wherein a first portion of the plurality of patients have Systemic lupus erythematosus (SLE), and a second portion of the plurality of patients are healthy control.
27. The method of aspect 26, wherein the one or more sample traits of the plurality of patients comprise blood autoimmune antibody level, blood complement component 3 (C3) protein level, blood complement component 4 (C4) protein level, SLEDAI score, LuMOS score, drug usage, ancestral history, presence of leukopenia, presence of proteinuria, presence of vasculitis, or any combination thereof.
28. The method of aspect 26 or 27, wherein the one or more gene function signature lists comprise AMPEL LuGENE, AMPEL Ancestry, AMPEL Endotype.32, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof.
29. The method of any one of aspects 1 to 25, wherein a first portion of the plurality of patients have SLE with active disease and with fibromyalgia, and a second portion of the plurality of patients have SLE without active disease, and without fibromyalgia.
30. The method of aspect 29, wherein the one or more sample traits of the plurality of patients comprise SLEDAI score, Fibromyalgia score, blood autoimmune antibody level, blood complement component 3 (C3) protein level, blood complement component 4 (C4) protein level, LuMOS score, immunotherapeutics usage, ancestral background, presence of leukopenia, presence of proteinuria, presence of vasculitis, or any combination thereof.
31. The method of aspect 29 or 30, wherein the one or more gene function signature list comprises AMPEL LuGENE, AMPEL Ancestry, AMPEL Endotype.32, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof.
32. The method of any one of aspects 1 to 25, wherein a first portion of the plurality of the patients have early inflammatory arthritis, and a second portion of the plurality of patients have advanced Rheumatoid arthritis.
33. The method of aspect 32, wherein the one or more sample traits of the plurality of patients comprise matrix metalloproteinase (MMP)-1 level in synovial biopsy sample, MMP-3 level in synovial biopsy sample, erythrocyte sedimentation rate, blood C-Reactive Protein level, or any combination thereof.
34. The method of aspect 32 or 33, wherein the one or more gene function signature list comprises Biologically Informed Gene Clustering (BIG-C) signature, Gene Ontology (GO) database, signature, Immune/Inflammation-Scope (I-Scope), Tissue-Scope (T-Scope), or any combination thereof.
35. A method for treating a patient, the method comprising:

obtaining a data set comprising gene expression measurements in a biological sample from the patient, of one or more genes of the plurality of significant gene clusters of aspect 1, or the one or more patient sample traits, or both;

classifying the patient into a treatment group of the two or more treatment groups of aspect 1, based on the gene expression measurements, or the one or more patient sample traits or both; and administering a treatment to the patient based on the treatment method of the treatment group of the patient, wherein the treatment method is determined according to aspect 18.

36. A method for determining a fibromyalgia in a patient, the method comprising:

obtaining a data set comprising gene expression measurements in a biological sample from the patient;

determining a GSVA score of the patient, from the data set for enrichment of at least 2 genes listed in Table 4B; and determining fibromyalgia in the patient based at least on the GSVA score of the patient.

37. The method of aspect 36, further comprising administering a treatment for fibromyalgia to the patient determined to have fibromyalgia.

38. A method for determining a gene set capable of classifying a disease state of a patient, the method comprising:

a) analyzing a data set to select N genes from an initial gene-set, said N genes are N variably expressed genes of a first gene-set, wherein the first gene-set is a subset of the initial gene-set, each gene of the first gene-set can be mapped to at least one known protein, and N is an integer number;

b) clustering the N genes into a plurality of gene clusters based at least on co-expression of the N genes in a plurality of reference samples;

c) correlating one or more gene clusters of the plurality of gene clusters with one or more sample traits of a plurality of reference subjects; and d) selecting a plurality of significant gene clusters based at least on strength of the correlation, wherein genes within the plurality of significant gene clusters form the gene set capable of classifying the disease state of a patient, wherein the gene set obtained in step (d) is capable of classifying the disease state of a patient between endotypes of two or more endotypes of the disease state and/or not having the disease, and wherein each endotype of the two or more endotypes of the disease is present in at least some of the reference subjects, and wherein the plurality of reference samples are obtained from the plurality of reference subjects.

39. The method of aspect 38, wherein the data set comprises transcriptomic RNA sequencing data from each of the plurality of reference samples.

40. The method of aspect 38 or 39, wherein the N genes are N most variably expressed genes.

41. The method of any one of aspects 38 to 40, wherein N is about 500 to about 10000.

42. The method of any one of aspects 38 to 41, wherein N is about 5000.

43. The method of any one of aspects 38 to 42, wherein the N genes are clustered into the plurality of gene clusters of step (b) based at least on gene co-expression network analysis.

44. The method of aspect 43, wherein the gene co-expression network analysis is performed using multiscale embedded gene co-expression network analysis (MEGENA), and/or weighted gene co-expression network analysis (WGCNA).

45. The method of any one of aspects 38 to 44, wherein each of the significant gene clusters satisfy a threshold minimum size.

46. The method of aspect 45, wherein the threshold minimum size is about 15 to about 80 genes.

47. The method of aspect 45, wherein the threshold minimum size is about 20 genes.

48. The method of aspect 46, wherein the threshold minimum size is about 50 genes.

49. The method of any one of aspect 38 to 48, wherein the plurality of significant gene clusters selected in step (d) comprises 10 to 50 gene clusters.

50. The method of any one of aspects 38 to 49, wherein the plurality of significant gene clusters selected in step (d) comprises 10 to 50 most strongly correlated gene clusters with the one or more sample traits.

51. The method of any one of aspects 38 to 50, wherein the disease is lupus.

52. The method of aspect 51, wherein the plurality of reference subjects comprises a first plurality of reference subjects having type 1 lupus, a second plurality of reference subjects having type 2 lupus, and a third plurality of reference subjects having type 1-2 lupus, and the gene set obtained in step (a) is capable of classifying whether a patient has type 1 lupus, type 2 lupus, or type 1-2 lupus.

53. The method of aspects 38 to 52, wherein the one or more sample traits are selected from the sample traits listed in Table 10.

54. The method of any one of aspects 38 to 53, wherein the one or more sample traits comprise blood autoimmune antibody level, SLEDAI score, blood complement component 3 (C3) protein level, PSD score, age, ancestry, or any combination thereof.

55. The method of any one of aspects 38 to 53, wherein the one or more sample traits comprise blood autoimmune antibody level, age, Hispanic ancestry, Nonsteroidal anti-inflammatory drugs usage, African ancestry, prednisone, amitriptyline usage, total areas of pain, or any combination thereof.

56. A method for classifying a lupus disease state of a patient, the method comprising: analyzing a patient data set comprising or derived from gene expression measurements data of at least 2 genes selected from the genes listed within the gene set of step (d) of any one of aspects 51 to 55 in a biological sample obtained or derived from the patient, to classify the lupus disease state of the patient as type 1 lupus, type 2 lupus, or type 1-2 lupus.

57. The method of aspect 56, wherein the patient data set comprises or is derived from gene expression measurements data of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 450, 500, 550, 600, 650, 700, 750, 850, 900, 950, 1000, 1050, 1100, 1150, 1200, 1250, 1300, 1350, 1400, 1450, 1500, 1550, 1600, 1700, 1800, 1900, 2000 or all genes, selected from the genes listed within the gene set of step (d) of any one of aspects 51 to 55, from the biological sample from the patient.

58. The method of aspect 56 or 57, wherein the patient data set comprises or is derived from gene expression measurements data of at least 2 to all, or any value or range there between, genes selected from the genes listed within each of one or more gene clusters selected from the significant gene clusters of any one of aspects 51 to 55, in the biological sample from the patient, wherein number of genes selected from the genes in each selected gene clusters may be different or the same.

59. The method of any one of aspects 58 to 59, wherein the patient data set comprises or is derived from gene expression measurements data of an effective number of genes selected from the genes listed within each of the one or more gene clusters selected from significant gene clusters of any one of aspects 51 to 55, from the biological sample from the patient, wherein number of genes selected from the genes in each selected table may be different or the same.

60. The method of aspect 58 or 59, wherein the selected gene clusters comprise the significant gene clusters of any one of aspects 51 to 55.

61. The method of any one of aspects 56 to 60, wherein the patient data set is derived from the gene expression measurements data using gene set variation analysis (GSVA), gene set enrichment analysis (GSEA), enrichment algorithm, multiscale embedded gene co-expression network analysis (MEGENA), weighted gene co-expression network analysis (WGCNA), differential expression analysis, Z-score, log 2 expression analysis, or any combination thereof.

62. The method of any one of aspects 56 to 61, wherein the patient data set is derived from the gene expression measurements data using GSVA.

63. The method of aspect 61, wherein the patient data set comprises one or more GSVA scores of the patient, wherein the one or more GSVA scores are generated based on one or more gene clusters selected from the significant gene clusters of any one of aspects 51 to 55, wherein for each selected cluster, at least one GSVA score of the patient is generated based on enrichment of expression of at least 2 genes listed within the selected gene cluster in the biological sample, and wherein the one or more GSVA scores comprise each generated GSVA score.

64. The method of aspect 63, wherein the selected gene clusters comprises the significant gene clusters of any one of aspects 51 to 61.

65. The method of aspect 63 or 64, wherein for each selected gene cluster, the at least one GSVA score of the patient is generated based on enrichment of expression of an effective number of genes selected from the genes listed in the respective selected gene cluster, in the biological sample, wherein number of genes selected from the genes in each selected gene cluster may be different or the same.

66. The method of any one of aspects 56 to 65, wherein the analyzing the patient data set comprises providing the data set as an input to a machine-learning model trained to generate an inference of whether the patient data set is indicative of the patient having type 1 lupus, type 2 lupus, or type 1-2 lupus.

67. The method of aspect 66, wherein the patient data set comprises the one or more GSVA scores of the patient, and the machine-learning model generate the inference based at least on the one or more GSVA scores.

68. The method of aspect 66 or 67, wherein the method further comprises receiving, as an output of the trained machine-learning model, the inference; and/or electronically outputting a report indicating the lupus disease state of the patient based on the inference.

69. The method of any one of aspects 66 to 68, wherein the machine-learning model is trained using linear regression, logistic regression, Ridge regression, Lasso regression, elastic net (EN) regression, support vector machine (SVM), gradient boosted machine (GBM), k nearest neighbors (kNN), generalized linear model (GLM), naïve Bayes (NB) classifier, neural network, Random Forest (RF), deep learning algorithm, linear discriminant analysis (LDA), decision tree learning (DTREE), adaptive boosting (ADB), Classification and Regression Tree (CART), hierarchical clustering, or any combination thereof.

70. The method of any one of aspects 56 to 69, wherein the patient is at elevated risk of having lupus.

71. The method of any one of aspects 56 to 69, wherein the patient is suspected of having lupus.

72. The method of any one of aspects 56 to 69, wherein the patient is asymptomatic for lupus.

73. The method of any one of aspects 56 to 69, wherein the patient has lupus.

74. The method of any one of aspects 56 to 69, wherein the patient is at elevated risk of having, is suspected of having, is asymptomatic for, and/or has inactive lupus.

75. The method of any one of aspects 56 to 74, wherein the patient is at elevated risk of having, is suspected of having, is asymptomatic for, and/or has fibromyalgia.

76. The method of any one of aspects 56 to 75, wherein the gene set of step (d), comprises the genes listed in the Tables 17-1 to 17-30.

77. The method of aspects 76, wherein the significant gene clusters of the gene set of (d) are the gene clusters listed in Tables 17-1 to 17-30.

78. The method of any one of aspects 56 to 77, further comprising administering a treatment based on the lupus disease state classification of the patient.

79. The method of aspects 78, wherein the treatment is for type 1 lupus, type 2 lupus, or type 1-2 lupus.

80. A method for classifying a lupus disease state of a patient, the method comprising: analyzing a patient data set comprising or derived from gene expression measurements data of at least 2 genes selected from the genes listed in Tables 17-1 to 17-30, from a biological sample obtained or derived from the patient, to classify the lupus disease state of the patient.

81. The method of aspect 81, wherein the patient data set comprises or is derived from gene expression measurements data of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 450, 500, 550, 600, 650, 700, 750, 850, 900, 950, 1000, 1050, 1100, 1150, 1200, 1250, 1300, 1350, 1400, 1450, 1500, 1550, 1600, 1700, 1800, 1900, 2000, or all, genes, selected from the genes listed in Tables 17-1 to 17-30, from the biological sample from the patient.

82. The method of aspect 80 or 81, wherein the patient data set comprises or is derived from gene expression measurements data of at least 2 genes selected from the genes listed in each of one or more Tables selected from Tables 17-1 to 17-30, from the biological sample from the patient, wherein number of genes selected from different Tables may be different or the same.

83. The method of aspect 80 or 81, wherein the patient data set comprises or is derived from gene expression measurements data of an effective number of genes selected from the genes listed in each of one or more Tables selected from Tables 17-1 to 17-30, from the biological sample from the patient, wherein number of genes selected from different Tables may be different or the same.

84. The method of aspect 80 or 81, wherein the patient data set comprises or is derived from gene expression measurements data of all genes listed in each of one or more Tables selected from Tables 17-1 to 17-30.

85. The method of any one of aspects 82 to 84, wherein the one or more selected Tables comprise at least 2, 3, 4, 5, 6, 7, 8, 9, 10, 11, 12, 13, 14, 15, 17, 18, 19, 20, 21, 22, 23, 24, 25, 27, 28, 29, or 30 Tables.

86. The method of any one of aspects 82 to 85, wherein Tables 17-1 to 17-30 are selected.

87. The method of any one of aspects 82 to 86, wherein the patient data set comprises module eigengenes (MEs), wherein the MEs are of the gene modules formed based on the genes selected from each selected Table.

88. The method of any one of aspects 82 or 86, wherein the patient data set is derived from the gene expression measurements data using gene set variation analysis (GSVA), gene set enrichment analysis (GSEA), enrichment algorithm, multiscale embedded gene co-expression network analysis (MEGENA), weighted gene co-expression network analysis (WGCNA), differential expression analysis, Z-score, log 2 expression analysis, or any combination thereof.

89. The method of any one of aspects 82 or 86, wherein the patient data set is derived from the gene expression measurements data using GSVA.

90. The method of aspect 89, wherein the patient data set comprises one or more GSVA scores of the patient, wherein the one or more GSVA scores are generated based on the one or more Tables selected from Tables 17-1 to 17-30, wherein for each selected Table, at least one GSVA score of the patient is generated based on enrichment of expression of the genes selected from the selected Table, in the biological sample, and wherein the one or more GSVA scores comprise each at least one generated patient GSVA score.

91. The method of aspect 90, wherein for each selected Table, the at least one GSVA score of the patient is generated based on enrichment of expression of an effective number of genes selected from the genes listed in the selected Table, in the biological sample.

92. The method of any one of aspects 80 to 91, wherein the analyzing the patient data set comprises providing the data set as an input to a machine-learning model trained to generate an inference of whether the patient data set is indicative of the patient having type 1 lupus, type 2 lupus, or type 1-2 lupus.

93. The method of aspect 92, wherein the patient data set comprises the one or more GSVA scores of the patient, and the machine-learning model generates the inference based at least on the one or more GSVA scores.

94. The method of aspect 92, wherein the patient data set comprises the MEs, and the machine-learning model generates the inference based at least on the MEs.

95. The method of any one of aspects 92 to 94, wherein the method further comprises receiving, as an output of the machine-learning model, the inference; and/or electronically outputting a report indicating the lupus disease state of the patient based on the inference.

96. The method of any one of aspects 92 to 95, wherein the machine-learning model is trained using linear regression, logistic regression, Ridge regression, Lasso regression, elastic net (EN) regression, support vector machine (SVM), gradient boosted machine (GBM), k nearest neighbors (kNN), generalized linear model (GLM), naïve Bayes (NB) classifier, neural network, Random Forest (RF), deep learning algorithm, linear discriminant analysis (LDA), decision tree learning (DTREE), adaptive boosting (ADB), Classification and Regression Tree (CART), hierarchical clustering, or any combination thereof.

97. The method of any one of aspects 92 to 96, wherein the machine learning model has a receiver operating characteristic (ROC) curve with an Area-Under-Curve (AUC) of at least 0.85.

98. The method of any one of aspects 80 to 91, wherein the analyzing the patient data set comprises generating a lupus disease risk score of the patient based on the patient data set, and classifying the whether the patient data set is indicative of the patient having type 1 lupus, or type 2 lupus based on the lupus disease risk score.

99. The method of aspect 98, wherein the lupus disease risk score of the patient is generated based on the one or more GSVA scores of the patient.

100. The method of any one of aspects 80 to 99, wherein the method classifies the lupus disease state of the patient with an accuracy of at least 85%, sensitivity of at least 85%, specificity of at least 85%, positive predictive value of at least 85%, negative predictive value of at least 85%, or any combination thereof.

101. The method of any one of aspects 80 to 100, wherein the patient is at elevated risk of having lupus.

102. The method of any one of aspects 80 to 100, wherein the patient is suspected of having lupus.

103. The method of any one of aspects 80 to 100, wherein the patient is asymptomatic for lupus.

104. The method of any one of aspects 80 to 100, wherein the patient has lupus.

105. The method of any one of aspects 80 to 100, wherein the patient is at elevated risk of having, is suspected of having, is asymptomatic for, and/or has inactive lupus.

106. The method of any one of aspects 80 to 100, wherein the patient is at elevated risk of having, is suspected of having, is asymptomatic for, and/or has fibromyalgia.

107. The method of any one of aspects 80 to 106, further comprising selecting, recommending and/or administering a treatment based on the lupus disease state classification of the patient.

108. The method of aspect 107, wherein the treatment is for type 1 lupus, type 2 lupus, or type 1-2 lupus.

109. A method for classifying a lupus disease state of a patient, the method comprising: analyzing a patient data set comprising or derived from gene expression measurements data of at least 2 genes selected from the genes listed in Tables 24-1 to 24-30, from a biological sample obtained or derived from the patient, to classify the lupus disease state of the patient.

110. The method of aspect 109, wherein the patient data set comprises or is derived from gene expression measurements data of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 450, 500, 550, 600, 650, 700, 750, 850, 900, 950, 1000, 1050, 1100, 1150, 1200, 1250, 1300, 1350, 1400, 1450, 1500, 1550, 1600, 1700, 1800, 1900, 2000, or all, genes, selected from the genes listed in Tables 24-1 to 24-30, from the biological sample from the patient.

111. The method of aspect 109 or 110, wherein the patient data set comprises or is derived from gene expression measurements data of at least 2 genes selected from the genes listed in each of one or more Tables selected from Tables 24-1 to 24-30, from the biological sample from the patient, wherein number of genes selected from different Tables may be different or the same.

112. The method of aspect 109 or 110, wherein the patient data set comprises or is derived from gene expression measurements data of an effective number of genes selected from the genes listed in each of one or more Tables selected from Tables 24-1 to 24-30, from the biological sample from the patient, wherein number of genes selected from different Tables may be different or the same.

113. The method of aspect 109 or 110, wherein the patient data set comprises or is derived from gene expression measurements data of all genes listed in each of one or more Tables selected from Tables 24-1 to 24-30.

114. The method of any one of aspects 111 to 113, wherein the one or more selected Tables comprise at least 2, 3, 4, 5, 6, 7, 8, 9, 10, 11, 12, 13, 14, 15, 17, 18, 19, 20, 21, 22, 23, 24, 25, 27, 28, 29, or 30 Tables.

115. The method of any one of aspects 111 to 114, wherein Tables 24-1 to 24-30 are selected.

116. The method of any one of aspects 111 to 115, wherein the patient data set comprises module eigengenes (MEs), wherein the MEs are of the gene modules formed based on the genes selected from each selected Table.

117. The method of any one of aspects 109 to 115, wherein the patient data set is derived from the gene expression measurements data using gene set variation analysis (GSVA), gene set enrichment analysis (GSEA), enrichment algorithm, multiscale embedded gene co-expression network analysis (MEGENA), weighted gene co-expression network analysis (WGCNA), differential expression analysis, Z-score, log 2 expression analysis, or any combination thereof.

118. The method of any one of aspects 109 to 115, wherein the patient data set is derived from the gene expression measurements data using GSVA.

119. The method of aspect 118, wherein the patient data set comprises one or more GSVA scores of the patient, wherein the one or more GSVA scores are generated based on the one or more Tables selected from Tables 24-1 to 24-30, wherein for each selected Table, at least one GSVA score of the patient is generated based on enrichment of expression of the genes selected from the selected Table, in the biological sample, and wherein the one or more GSVA scores comprise each at least one generated patient GSVA score.

120. The method of aspect 119, wherein for each selected Table, the at least one GSVA score of the patient is generated based on enrichment of expression of an effective number of genes selected from the genes listed in the selected Table, in the biological sample.

121. The method of any one of aspects 109 to 120, wherein the analyzing the patient data set comprises providing the data set as an input to a machine-learning model trained to generate an inference of whether the patient data set is indicative of the patient having type 1 lupus, type 2 lupus, or type 1-2 lupus.

122. The method of aspect 121, wherein the patient data set comprises the one or more GSVA scores of the patient, and the machine-learning model generates the inference based at least on the one or more GSVA scores.

123. The method of aspect 121, wherein the patient data set comprises the MEs, and the machine-learning model generates the inference based at least on the MEs.

124. The method of any one of aspects 121 to 123, wherein the method further comprises receiving, as an output of the trained machine-learning model, the inference; and/or electronically outputting a report indicating the lupus disease state of the patient based on the inference.

125. The method of any one of aspects 121 or 124, wherein the machine-learning model is trained using linear regression, logistic regression, Ridge regression, Lasso regression, elastic net (EN) regression, support vector machine (SVM), gradient boosted machine (GBM), k nearest neighbors (kNN), generalized linear model (GLM), naïve Bayes (NB) classifier, neural network, Random Forest (RF), deep learning algorithm, linear discriminant analysis (LDA), decision tree learning (DTREE), adaptive boosting (ADB), Classification and Regression Tree (CART), hierarchical clustering, or any combination thereof.

126. The method of any one of aspects 121 or 125, wherein the machine learning model has a receiver operating characteristic (ROC) curve with an Area-Under-Curve (AUC) of at least 0.85.

127. The method of any one of aspects 109 or 120, wherein the analyzing the patient data set comprises generating a lupus disease risk score of the patient based on the patient data set, and classifying the whether the patient data set is indicative of the patient having type 1 lupus, or type 2 lupus based on the lupus disease risk score.

128. The method of aspect 127, wherein the lupus disease risk score of the patient is generated based on the one or more GSVA scores of the patient.

129. The method of any one of aspects 109 or 128, wherein the method classifies the lupus disease state of the patient with an accuracy of at least 85%, sensitivity of at least 85%, specificity of at least 85%, positive predictive value of at least 85%, negative predictive value of at least 85%, or any combination thereof.

130. The method of any one of aspects 109 or 129, wherein the patient is at elevated risk of having lupus.

131. The method of any one of aspects 109 or 129, wherein the patient is suspected of having lupus.

132. The method of any one of aspects 109 or 129, wherein the patient is asymptomatic for lupus.
133. The method of any one of aspects 109 or 129, wherein the patient has lupus.
134. The method of any one of aspects 109 or 129, wherein the patient is at elevated risk of having, is suspected of having, is asymptomatic for, and/or has inactive lupus.
135. The method of any one of aspects 109 or 129, wherein the patient is at elevated risk of having, is suspected of having, is asymptomatic for, and/or has fibromyalgia.
136. The method of any one of aspects 109 or 135, further comprising selecting, recommending and/or administering a treatment based on the lupus disease state classification of the patient.
137. The method of aspect 136, wherein the treatment is for type 1 lupus, type 2 lupus, or type 1-2 lupus.

DETAILED DESCRIPTION

Certain aspects of the present disclosure are directed to methods and systems for unsupervised clustering of genes to elucidate gene modules that are capable of classifying a disease state of a patient. The gene modules can be used to classify, and/or treat a disease state of a patient. Classifying a disease state of a patient can include determining whether that patient has the disease and/or which endotype out of two or more endotypes of the disease the patient has. Methods can include identifying and/or providing targeted therapy for a patient based on the disease state classification of the patient. As shown in a non-limiting manner in example 5, a preprocessing step used in the clustering process, such as selecting certain number of most variably expressed genes for clustering, as an non-limiting example top 5000 rowVar genes as in example 5, can be useful in dimensionality reduction, obtaining relatively high quality data for gene clustering and subsequent analysis, reducing noise from the data, and improving speed of computer systems. As discussed in Example 5, several benefits may be realized through the selection and use of top 5000 rowVar gene filtration techniques, including but not limited to a significant reduction in dimensionality that significantly reduces the computational resources needed to train machine learning models, while still being characterized with high module preservation reduction in noise, that in one example, resulted in the identification of additional functional annotations that were not otherwise detected using the full ILLUM-1 baseline (e.g., family of down-regulated snoRNA (SNORD) genes which involved in SLE).

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description. Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3. As used herein, the singular forms "a," "an," and "the" include plural references unless the context clearly dictates otherwise. Any reference to "or" herein is intended to encompass "and/or" unless otherwise stated.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the term "about" refers to an amount that is near the stated amount by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The terms "subject", "test subject", "reference subject", "patient", "test patient" or "reference patient", as used herein, generally refer to a human, such as a human patient.

The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Reference in the specification to "embodiments," "certain embodiments," "preferred embodiments," "specific embodiments," "some embodiments," "an embodiment," "one embodiment" or "other embodiments" mean that a particular feature, structure, or characteristic described in connection with the embodiments is included in at least some embodiments, but not necessarily all embodiments, of the present disclosure.

The biological sample can comprise a blood sample, isolated peripheral blood mononuclear cells (PBMCs), a tissue biopsy sample, a synovial biopsy sample, a nasal fluid sample, a saliva sample, a urine sample, a stool sample, or any derivative thereof. In some embodiments, the biological sample comprises a blood sample, or any derivative thereof. In some embodiments, the biological sample comprises PBMCs, or any derivative thereof. In some embodiments, the biological sample comprises a tissue biopsy sample, or any derivative thereof. In some embodiments, the biological sample comprises a synovial biopsy sample, or any derivative thereof. In some embodiments, the biological sample comprises a skin biopsy sample, or any derivative thereof. In some embodiments, the biological sample comprises a nasal fluid sample, or any derivative thereof. In some embodiments, the biological sample comprises a saliva sample, or any derivative thereof. In some embodiments, the biological sample comprises a urine sample, or any derivative thereof. In some embodiments, the biological sample comprises a stool sample, or any derivative thereof. The reference biological samples can comprise blood samples, isolated peripheral blood mononuclear cells (PBMCs), tissue biopsy samples, synovial biopsy samples, nasal fluid, saliva, urine, stool, or any derivative thereof. In some embodiments, the reference biological samples comprise blood samples, or any derivative thereof. In some embodiments, the reference biological samples comprise PBMCs, or any derivative thereof. In some embodiments, the reference biological samples comprise tissue biopsy samples, or any derivative thereof. In some embodiments, the reference biological samples comprise synovial biopsy samples, or any derivative thereof. In some embodiments, the reference biological samples comprise skin biopsy samples, or any derivative thereof. In some embodiments, the reference biological samples comprise nasal fluid samples, or any derivative thereof. In some embodiments, the reference biological samples comprise saliva samples, or any derivative thereof. In some embodiments, the reference biological samples comprise urine samples, or any derivative thereof. In some embodiments, the reference biological samples comprise stool samples, or any derivative thereof. The blood sample can be a whole blood sample, blood cells, serum, plasma, or any combination thereof.

To obtain a blood sample, various techniques may be used, e.g., a syringe or other vacuum suction device. A blood sample can be optionally pre-treated or processed prior to use. A sample, such as a blood sample, may be analyzed under any of the methods and systems herein within 4 weeks, 2 weeks, 1 week, 6 days, 5 days, 4 days, 3 days, 2 days, 1 day, 12 hr, 6 hr, 3 hr, 2 hr, or 1 hr from the time the sample is obtained, or longer if frozen. When obtaining a sample from a subject (e.g., blood sample), the amount can vary depending upon subject size and the condition being screened. In some embodiments, at least 10 mL, 5 mL, 1 mL, 0.5 mL, 250, 200, 150, 100, 50, 40, 30, 20, 10, 9, 8, 7, 6, 5, 4, 3, 2, or 1 μL of a sample is obtained. In some embodiments, 1-50, 2-40, 3-30, or 4-20 μL of sample is obtained. In some embodiments, more than 5, 10, 15, 20, 25, 30, 35, 40, 45, 50, 55, 60, 65, 70, 75, 80, 85, 90, 95 or 100 μL of a sample is obtained.

I. Methods for Determining a Gene Set Capable of Classifying a Disease State of a Patient One aspect of the present disclosure is directed to a method for determining a gene set capable of classifying a disease state of a patient. The method can include, any one of, any combination of, or all of steps (a), (b), (c), and (d). Step (a) can include analyzing a data set to select N genes from an initial gene-set, where N is an integer number. The data set can comprise gene expression measurement data of genes of the initial gene-set, from a plurality of reference biological samples. The plurality of reference biological samples can be obtained or derived from a plurality of reference subjects. In certain embodiments, analyzing the dataset can include obtaining a first gene-set from the initial gene-set, and selecting the N genes from the first gene-set. The first gene-set can be a subset of the initial gene-set. Each genes of the first gene-set can be mapped to at least one known protein. The first gene-set can be obtained from the initial gene-set by removing genes that cannot be mapped to a known protein. In certain embodiments, the genes within the first gene-set are protein coding genes. In certain embodiments, the mapping is performed using the publicly available R BioMaRt package to query probes for any corresponding HGNC gene symbol mappings. The N genes can be selected from the initial gene-set or the first gene-set based on variation in the gene expression within the plurality of reference biological samples. In certain embodiments, the N genes are N variably expressed genes of the initial gene-set or the first gene-set or both. In certain embodiments, the N genes are N variably expressed genes of the initial gene-set. In certain embodiments, the N genes are N variably expressed genes of the first gene-set. In certain embodiments, the N genes are N most variably expressed genes of the initial gene-set or the first gene-set or both. In certain embodiments, the N genes are N most variably expressed genes of the initial gene-set. In certain embodiments, the N genes are N most variably expressed genes of the first gene-set. The variable expression can be based on gene expression in the plurality of reference biological samples. The genes selected in step (a), e.g., from the initial gene set, and/or the first gene set, may or may not contain any additional gene over the N genes. Step (b) can include clustering the N genes into a plurality of gene clusters. Step (c) can include correlating one or more gene clusters of the plurality of gene clusters with one or more sample traits of the plurality of reference subjects. Step (d) can include selecting a plurality of significant gene clusters from the gene clusters correlated in step (c), based at least on strength of the correlation. Genes within the plurality of significant gene clusters of step (d) form the gene set capable of classifying the disease state of the patient. Gene expression measurements data of the genes of the gene set obtained in step (d) in a biological sample from the patient is capable of classifying the disease state of the patient. Classifying the disease state of the patient can include determining whether that patient has the disease and/or which endotype out of two or more endotypes of the disease the patient has. In certain embodiments, the method includes obtaining the data set. The two or more endotypes of the disease, between which the gene set of (d) is capable of classifying a patient into, depends at least on the disease endotype distribution within the plurality of reference subjects, where each endotype of the two or more endotypes of the disease is present in at least a portion (e.g., some) of the reference subjects. In a non-limiting example, the plurality of reference subjects comprise a first plurality of reference subjects having a first endotype of the disease, a second plurality of reference subjects having a second endotype of the disease, and a third plurality of reference subjects having a third endotype of the disease, and the gene set obtained in step (d) is capable of classifying whether a patient has the first endotype of the disease, the second endotype of the disease, or the third endotype of the disease. The method can optionally include functionally annotating the plurality of significant gene clusters obtained in step (d). The plurality of significant gene clusters can be functionally annotated using the steps (e) and (f), as described in the section III of the detailed description. The two or more endotype may or may not include all endotypes of the disease. The reference subjects may or may not include healthy controls and/or known cohorts. The method can be performed and/or implemented in a computer.

The data set can contain a plurality of individual data sets. The plurality of individual data sets can be obtained from the plurality of reference subjects. In certain embodiments, from each reference subject of the plurality of reference subjects, an individual data set of the plurality of individual data sets is obtained. Different individual data sets can be obtained from different reference subjects. A respective individual data set can contain gene expression measurements from a reference biological sample from a respective reference subject, of the genes of the initial gene set. In some embodiments, each individual data set contains gene expression measurements from a reference biological sample from a reference subject of the plurality of reference subject, of the genes of the initial gene-set.

In certain embodiments, the genes in the initial gene set can be genes, protein coding genes, transcribed genes, or subsets thereof, in the plurality of reference biological samples. In certain embodiments, genes in the initial gene set can be the genes, protein coding genes, transcribed genes, or subsets thereof, for which gene expression measurements data from the plurality of reference biological samples are available, in the data set. In certain embodiments, genes in the initial gene set can be the genes, protein coding genes, transcribed genes, or subsets thereof, for which gene expression measurements data from each reference biological sample of the plurality of reference biological samples are available, in the data set. In certain embodiments, the subsets of genes, protein coding genes, or transcribed genes can be obtained by removing genes, protein coding genes, or transcribed genes respectively that one of skill in the art would want to remove, such as genes with low copy number etc.

In certain embodiments, the N genes are N most variably expressed genes of the initial gene set or first gene set or both, in the data set. Selecting N most variably expressed genes, e.g., from the initial gene set or first gene set or both, for clustering can be useful for dimensionality reduction, obtaining high quality data for gene clustering and subsequent analysis, reducing noise from the data, and improving speed of computer systems.

In certain embodiments, the N most variably expressed genes are selected using variable expression. Variable expression can be measured using row variance, where genes with higher variable expression within the plurality of reference biological samples, have higher row variance. Averaged (mean) row variance can be stored as a matrix where the averaged gene expressions of each gene (e.g., of the initial gene set or the first gene set) are rows, and samples (e.g., reference patients/reference biological samples) are columns. The matrix can be sorted by decreasing row averaged variance and the top N genes can be selected, to obtain N most variably expressed genes. Using row variance can allow obtaining clusters in an unsupervised and statistically non-biased manner based on statistically significant gene expression sample clustering. Such method can work with datasets having sufficient, relatively low, or without healthy controls.

In certain embodiments, N is about 500 to about 10,000. In certain embodiments, N is about 500 to about 10,000, most variably expressed genes of the initial gene-set or the first gene-set or both. In certain embodiments, N is about 500 to about 1,000, 500 to about 2,000, about 500 to about 3,000, about 500 to about 4,000, about 500 to about 4,500, about 500 to about 5,000, about 500 to about 5,500, about 500 to about 6,000, about 500 to about 7,000, about 500 to about 8,000, about 500 to about 9,000, about 500 to about 10,000, 1,000 to about 2,000, about 1,000 to about 3,000, about 1,000 to about 4,000, about 1,000 to about 4,500, about 1,000 to about 5,000, about 1,000 to about 5,500, about 1,000 to about 6,000, about 1,000 to about 7,000, about 1,000 to about 8,000, about 1,000 to about 9,000, about 1,000 to about 10,000, about 2,000 to about 3,000, about 2,000 to about 4,000, about 2,000 to about 4,500, about 2,000 to about 5,000, about 2,000 to about 5,500, about 2,000 to about 6,000, about 2,000 to about 7,000, about 2,000 to about 8,000, about 2,000 to about 9,000, about 2,000 to about 10,000, about 3,000 to about 4,000, about 3,000 to about 4,500, about 3,000 to about 5,000, about 3,000 to about 5,500, about 3,000 to about 6,000, about 3,000 to about 7,000, about 3,000 to about 8,000, about 3,000 to about 9,000, about 3,000 to about 10,000, about 4,000 to about 4,500, about 4,000 to about 5,000, about 4,000 to about 5,500, about 4,000 to about 6,000, about 4,000 to about 7,000, about 4,000 to about 8,000, about 4,000 to about 9,000, about 4,000 to about 10,000, about 4,500 to about 5,000, about 4,500 to about 5,500, about 4,500 to about 6,000, about 4,500 to about 7,000, about 4,500 to about 8,000, about 4,500 to about 9,000, about 4,500 to about 10,000, about 5,000 to about 5,500, about 5,000 to about 6,000, about 5,000 to about 7,000, about 5,000 to about 8,000, about 5,000 to about 9,000, about 5,000 to about 10,000, about 5,500 to about 6,000, about 5,500 to about 7,000, about 5,500 to about 8,000, about 5,500 to about 9,000, about 5,500 to about 10,000, about 6,000 to about 7,000, about 6,000 to about 8,000, about 6,000 to about 9,000, about 6,000 to about 10,000, about 7,000 to about 8,000, about 7,000 to about 9,000, about 7,000 to about 10,000, about 8,000 to about 9,000, about 8,000 to about 10,000, or about 9,000 to about 10,000. In certain embodiments, N is about 500 to about 1,000, 500 to about 2,000, about 500 to about 3,000, about 500 to about 4,000, about 500 to about 4,500, about 500 to about 5,000, about 500 to about 5,500, about 500 to about 6,000, about 500 to about 7,000, about 500 to about 8,000, about 500 to about 9,000, about 500 to about 10,000, 1,000 to about 2,000, about 1,000 to about 3,000, about 1,000 to about 4,000, about 1,000 to about 4,500, about 1,000 to about 5,000, about 1,000 to about 5,500, about 1,000 to about 6,000, about 1,000 to about 7,000, about 1,000 to about 8,000, about 1,000 to about 9,000, about 1,000 to about 10,000, about 2,000 to about 3,000, about 2,000 to about 4,000, about 2,000 to about 4,500, about 2,000 to about 5,000, about 2,000 to about 5,500, about 2,000 to about 6,000, about 2,000 to about 7,000, about 2,000 to about 8,000, about 2,000 to about 9,000, about 2,000 to about 10,000, about 3,000 to about 4,000, about 3,000 to about 4,500, about 3,000 to about 5,000, about 3,000 to about 5,500, about 3,000 to about 6,000, about 3,000 to about 7,000, about 3,000 to about 8,000, about 3,000 to about 9,000, about 3,000 to about 10,000, about 4,000 to about 4,500, about 4,000 to about 5,000, about 4,000 to about 5,500, about 4,000 to about 6,000, about 4,000 to about 7,000, about 4,000 to about 8,000, about 4,000 to about 9,000, about 4,000 to about 10,000, about 4,500 to about 5,000, about 4,500 to about 5,500, about 4,500 to about 6,000, about 4,500 to about 7,000, about 4,500 to about 8,000, about 4,500 to about 9,000, about 4,500 to about 10,000, about 5,000 to about 5,500, about 5,000 to about 6,000, about 5,000 to about 7,000, about 5,000 to about 8,000, about 5,000 to about 9,000, about 5,000 to about 10,000, about 5,500 to about 6,000, about 5,500 to about 7,000, about 5,500 to about 8,000, about 5,500 to about 9,000, about 5,500 to about 10,000, about 6,000 to about 7,000, about 6,000 to about 8,000, about 6,000 to about 9,000, about 6,000 to about 10,000, about 7,000 to about 8,000, about 7,000 to about 9,000, about 7,000 to about 10,000, about 8,000 to about 9,000, about 8,000 to about 10,000, or about 9,000 to about 10,000 most variably expressed genes of the initial gene-set or the first gene-set or both. In certain embodiments, N is about 500, about 1,000, about 2,000, about 3,000, about 4,000, about 4,500, about 5,000, about 5,500, about 6,000, about 7,000, about 8,000, about 9,000, or about 10,000. In certain embodiments, N is about 500, about 1,000, about 2,000, about 3,000, about 4,000, about 4,500, about 5,000, about 5,500, about 6,000, about 7,000, about 8,000, about 9,000, or about 10,000, most variably expressed genes of the initial gene-set or the first gene-set or both. In certain embodiments, N is at most about 1,000, about 2,000, about 3,000, about 4,000, about 4,500, about 5,000, about 5,500, about 6,000, about 7,000, about 8,000, about 9,000, or about 10,000. In certain embodiments, N is at most about 1,000, about 2,000, about 3,000, about 4,000, about 4,500, about 5,000, about 5,500, about 6,000, about 7,000, about 8,000, about 9,000, or about 10,000, most variably expressed genes of the initial gene-set or the first gene-set or both.

In certain embodiments, the N genes e.g., selected in step (a), can be clustered into the plurality of gene clusters of step (b) based at least on co-expression of the N genes, in the plurality of reference biological samples. Genes having similar expression in the plurality of reference biological samples can be clustered within a same cluster. Co-expression of the N genes, in the plurality of reference biological samples can be analyzed using gene co-expression network analysis. In certain embodiments, the N genes, can be clustered into the plurality of gene clusters of step (b) based on gene co-expression network analysis. In certain embodiments, the gene co-expression network analysis is performed using multiscale embedded gene co-expression network analysis (MEGENA), and/or weighted gene co-expression network analysis (WGCNA). In certain embodiments, the N genes, are clustered into the plurality of gene clusters of step (b) using MEGENA and/or WGCNA. In certain embodiments, the N genes, are clustered into the plurality of gene clusters of step (b) using MEGENA. In certain embodiments, the N genes, are clustered into the plurality of gene clusters of step (b) using WGCNA. MEGENA, and/or WGCNA can be performed using steps/methods as described herein, in the Examples, and/or as understood by one of skill in the art. In certain embodiments, the N genes are clustered into the plurality of gene clusters of step (b) by developing a planar filtered network (PFN) graph based on gene pair co-expression of the N genes in the plurality of reference biological samples, and extracting multiscale modules existing within the PFN graph to form the plurality of gene clusters of step (b). Amongst the N genes, the genes can be correlated to for their pair-wise co-expression similarities. Two genes having most similar in expression to any other gene can be paired as co-expressed genes. Gene pairwise expression comparisons can be assigned a global false discovery rate (FDR) calculation. Pairs below a given FDR p threshold can be discarded. FDR p threshold can be <0.35, <0.3, <0.25, <0.2, <0.1, <0.05, or <0.01. In certain embodiments, FDR p threshold is <0.2. Such removal of gene pairs can reduce risk of random choice affecting the correlation strengths. The remaining FDR significant pairs can be mapped onto a sphere, and edges can be created between them if and only if the resulting graph can still be embedded on a surface of a given genus. An "edge" in a co-expression network can be a line/connection created between two "nodes" (genes) and indicates similarity of gene expression between the two genes/nodes. An algorithm can place the pairs onto the virtual spherical surface, can and look back to examine other remaining unplaced pair. The most similar pair in expression to the last past placed pair onto the spherical surface can be joined by a new edge. All the while this placement scheme continues where edges aren't allowed to cross each other (meaning there are no exactly similar co-expression placements) and the network can inherently grow to occupy the sphere's surface. After the significant pairs by FDR are placed onto the sphere and edges are drawn between them, another pass of evaluation can be performed. "Triangulated" edges can be drawn between pair neighborhoods called "cliques". Triangles of edges are formed between highly co-expressed pair-pairs, and those neighborhoods of cliques that are together, as in highly related (clustered), are deemed as gene clusters and become the first "generation" of gene clusters. The algorithm continues by searching for further triangulations within the first generation (gen1) of clique clusters. Those genes that are most connected (given a compactness $\alpha$ parameter according to the algorithm) within cliques are inherited together as descendent modules (e.g. clusters), whereas the disconnected genes are discarded and not inherited. This process continues as gen1 cluster undergo the scrutiny of the algorithm and give way to second generation (gen2) and subsequent generations until no further meaningful triangulations are found within the terminal descendants, and/or minimum threshold cluster size requirement is reached. Thus a "multi-scale" network of modules (e.g. clusters) can be created. This translates as clusters of genes whose descendants become more and more densely connected by co-expression in the plurality of reference biological samples, with the implication the terminal descendants are most closely related by a shared biological regulatory network.

The gene clusters of the plurality of gene clusters (e.g. obtained in step (b)) can satisfy a threshold minimum size. In certain embodiments the minimum size is 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, or 80 genes. In certain embodiments the minimum size is 20 genes. In certain embodiments the minimum size of a gene cluster can be 10 genes to 80 genes. In certain embodiments the minimum size of a gene cluster can be 10 genes to 15 genes, 10 genes to 20 genes, 10 genes to 25 genes, 10 genes to 30 genes, 10 genes to 35 genes, 10 genes to 40 genes, 10 genes to 45 genes, 10 genes to 50 genes, 10 genes to 60 genes, 10 genes to 70 genes, 10 genes to 80 genes, 15 genes to 20 genes, 15 genes to 25 genes, 15 genes to 30 genes, 15 genes to 35 genes, 15 genes to 40 genes, 15 genes to 45 genes, 15 genes to 50 genes, 15 genes to 60 genes, 15 genes to 70 genes, 15 genes to 80 genes, 20 genes to 25 genes, 20 genes to 30 genes, 20 genes to 35 genes, 20 genes to 40 genes, 20 genes to 45 genes, 20 genes to 50 genes, 20 genes to 60 genes, 20 genes to 70 genes, 20 genes to 80 genes, 25 genes to 30 genes, 25 genes to 35 genes, 25 genes to 40 genes, 25 genes to 45 genes, 25 genes to 50 genes, 25 genes to 60 genes, 25 genes to 70 genes, 25 genes to 80 genes, 30 genes to 35 genes, 30 genes to 40 genes, 30 genes to 45 genes, 30 genes to 50 genes, 30 genes to 60 genes, 30 genes to 70 genes, 30 genes to 80 genes, 35 genes to 40 genes, 35 genes to 45 genes, 35 genes to 50 genes, 35 genes to 60 genes, 35 genes to 70 genes, 35 genes to 80 genes, 40 genes to 45 genes, 40 genes to 50 genes, 40 genes to 60 genes, 40 genes to 70 genes, 40 genes to 80 genes, 45 genes to 50 genes, 45 genes to 60 genes, 45 genes to 70 genes, 45 genes to 80 genes, 50 genes to 60 genes, 50 genes to 70 genes, 50 genes to 80 genes, 60 genes to 70 genes, 60 genes to 80 genes, or 70 genes to 80 genes. In certain embodiments the minimum size of a gene module can be 10 genes, 15 genes, 20 genes, 25 genes, 30 genes, 35 genes, 40 genes, 45 genes, 50 genes, 60 genes, 70 genes, or 80 genes. In certain embodiments the minimum size of a gene module can be at least 10 genes, 15 genes, 20 genes, 25 genes, 30 genes, 35 genes, 40 genes, 45 genes, 50 genes, 60 genes, or 70 genes. In certain embodiments the minimum size of a gene module can be at most 15 genes, 20 genes, 25 genes, 30 genes, 35 genes, 40 genes, 45 genes, 50 genes, 60 genes, 70 genes, or 80 genes.

The one or more sample traits can include clinical traits such as disease severity index, disease diagnostic parameter, etc.; biographical traits such as age, ancestry, gender, etc.; lifestyle traits such as certain drug usage, smoking habits, drinking habits, exercise habits, etc.; and/or the like, of the reference subjects. The one or more sample traits can depend on the disease, e.g., endotype of which the gene set obtained in step (d) is capable of classifying the patient into. A sample trait of the one or more sample traits of a reference subject can have subjective and/or objective value for the reference subject. Non-limiting example of the subjective sample traits can include disease level (such as SLE Disease Activity Index (SLEDAI), a clinical index in the case of lupus), areas of pain, ancestry, gender and other overt anecdotal features that are described by the patient or observed by a clinician but not objectively (quantifiably) measurable. For a subjective sample trait clinical ascertainments, objective laboratory assay results, and/or subject attributes can be retained as continuous numerical values, or encoded as discrete binary values (e.g., no=0 or yes=1). Non-limiting example of the objective sample traits can include blood autoimmune antibody level, blood complement component 3 (C3) protein level, age, drug usage, and the like, features that have quantifiable value.

Correlation and strength of correlation of the gene clusters of the plurality of gene clusters (e.g. obtained in step (b)) with the one or more sample traits can be measured by a suitable method. In certain embodiments, the one or more gene clusters (e.g., correlated in step (c)) comprises all the gene clusters of the plurality of gene clusters, e.g., all the gene clusters of the plurality of gene clusters are correlated with the one or more sample traits, in step (c). In certain embodiments, the one or more gene clusters (e.g., correlated in step (c)) comprises the third generation gene clusters of the plurality of gene clusters, e.g., the third generation gene clusters of the plurality of gene clusters are correlated with the one or more sample traits, in step (c). In certain embodiments, third generation gene clusters of the plurality of gene clusters are correlated with the one or more sample traits, in step (c), wherein the plurality of gene clusters are obtained in step (b) using MEGENA. The third generation gene clusters of the plurality of gene clusters can be MEGENA third generation gene modules. In certain embodiments, the one or more gene clusters (e.g., correlated in step (c)) comprises second, third and/or fourth generation gene clusters of the plurality of gene clusters, e.g., the second, third and/or fourth generation gene clusters of the plurality of gene clusters are correlated with the one or more sample traits, in step (c). In certain embodiments, second, third and/or fourth generation gene clusters of the plurality of gene clusters are correlated with the one or more sample traits, in step (c), wherein the plurality of gene clusters are obtained in step (b) using MEGENA. The second, third and/or fourth generation gene clusters of the plurality of gene clusters can be MEGENA second, third and/or fourth generation gene modules respectively. In certain embodiments, the correlation of the one or more gene clusters of the plurality of gene clusters with one or more sample traits can include correlating the module eigengenes (MEs) of the one or more gene clusters (e.g., of the gene clusters correlated in step (c)) with the one or more sample traits, and selecting the plurality of significant gene clusters based on the strength of correlation. In some embodiments, MEs for each of the gene cluster (e.g., that are correlated in step (c)) for each reference subjects are calculated. For the plurality of reference subjects and the gene clusters that are correlated in step (c), the gene cluster MEs can be correlated to the one or more sample traits, wherein gene cluster MEs of a respective reference subject can be correlated with one or more sample traits of the respective reference subject. A gene cluster can be considered as a gene module for calculating the MEs of the gene cluster. With regards to the cohort (plurality of reference subjects), sample trait correlation(s) that are not significant based on a threshold p value can be set to zero. For the plurality of reference subjects, absolute value of significant correlation to cohort can be ranked by row means, and gene clusters with desired highest significant absolute value of mean correlations are selected as the plurality of significant gene clusters. As a non-limiting example, 30 gene clusters were selected as the plurality of significant gene clusters, wherein gene clusters with 30 highest significant absolute value of mean correlations were selected. In some embodiments, the correlations is measured based on Pearson's correlation coefficient. The threshold p value can be 0.3, 0.25, 0.2, 0.1, 0.05, or 0.01. In certain embodiments, the threshold p value is 0.2. Accepting correlation with p-values<0.3, <0.25, <0.2, <0.1, <0.05, or <0.01, can capture known and validated correlations and biological processes while maintaining statistical integrity and reproducibility.

In certain embodiments, the plurality of significant gene clusters contain about 10 to about 80 gene clusters. In certain embodiments, the plurality of significant gene clusters contain about 10 gene clusters to about 80 gene clusters, that are most strongly correlated e.g., among the plurality of gene clusters, with the one or more sample traits. In certain embodiments, the plurality of significant gene clusters contain about 10 gene clusters to about 80 gene clusters, that are most strongly correlated e.g., among the gene clusters correlated in step (c), with the one or more sample traits. In certain embodiments, the plurality of significant gene clusters contain about 10 gene clusters to about 20 gene clusters, about 10 gene clusters to about 25 gene clusters, about 10 gene clusters to about 30 gene clusters, about 10 gene clusters to about 35 gene clusters, about 10 gene clusters to about 40 gene clusters, about 10 gene clusters to about 45 gene clusters, about 10 gene clusters to about 50 gene clusters, about 10 gene clusters to about 55 gene clusters, about 10 gene clusters to about 60 gene clusters, about 10 gene clusters to about 70 gene clusters, about 10 gene clusters to about 80 gene clusters, about 20 gene clusters to about 25 gene clusters, about 20 gene clusters to about 30 gene clusters, about 20 gene clusters to about 35 gene clusters, about 20 gene clusters to about 40 gene clusters, about 20 gene clusters to about 45 gene clusters, about 20 gene clusters to about 50 gene clusters, about 20 gene clusters to about 55 gene clusters, about 20 gene clusters to about 60 gene clusters, about 20 gene clusters to about 70 gene clusters, about 20 gene clusters to about 80 gene clusters, about 25 gene clusters to about 30 gene clusters, about 25 gene clusters to about 35 gene clusters, about 25 gene clusters to about 40 gene clusters, about 25 gene clusters to about 45 gene clusters, about 25 gene clusters to about 50 gene clusters, about 25 gene clusters to about 55 gene clusters, about 25 gene clusters to about 60 gene clusters, about 25 gene clusters to about 70 gene clusters, about 25 gene clusters to about 80 gene clusters, about 30 gene clusters to about 35 gene clusters, about 30 gene clusters to about 40 gene clusters, about 30 gene clusters to about 45 gene clusters, about 30 gene clusters to about 50 gene clusters, about 30 gene clusters to about 55 gene clusters, about 30 gene clusters to about 60 gene clusters, about 30 gene clusters to about 70 gene clusters, about 30 gene clusters to about 80 gene clusters, about 35 gene clusters to about 40 gene clusters, about 35 gene clusters to about 45 gene clusters, about 35 gene clusters to about 50 gene clusters, about 35 gene clusters to about 55 gene clusters, about 35 gene clusters to about 60 gene clusters, about 35 gene clusters to about 70 gene clusters, about 35 gene clusters to about 80 gene clusters, about 40 gene clusters to about 45 gene clusters, about 40 gene clusters to about 50 gene clusters, about 40 gene clusters to about 55 gene clusters, about 40 gene clusters to about 60 gene clusters, about 40 gene clusters to about 70 gene clusters, about 40 gene clusters to about 80 gene clusters, about 45 gene clusters to about 50 gene clusters, about 45 gene clusters to about 55 gene clusters, about 45 gene clusters to about 60 gene clusters, about 45 gene clusters to about 70 gene clusters, about 45 gene clusters to about 80 gene clusters, about 50 gene clusters to about 55 gene clusters, about 50 gene clusters to about 60 gene clusters, about 50 gene clusters to about 70 gene clusters, about 50 gene clusters to about 80 gene clusters, about 55 gene clusters to about 60 gene clusters, about 55 gene clusters to about 70 gene clusters, about 55 gene clusters to about 80 gene clusters, about 60 gene clusters to about 70 gene clusters, about 60 gene clusters to about 80 gene clusters, or about 70 gene clusters to about 80 gene clusters. In certain embodiments, the plurality of significant gene clusters contain about 10 gene clusters to about 20 gene clusters, about 10 gene clusters to about 25 gene clusters, about 10 gene clusters to about 30 gene clusters, about 10 gene clusters to about 35 gene clusters, about 10 gene clusters to about 40 gene clusters, about 10 gene clusters to about 45 gene clusters, about 10 gene clusters to about 50 gene clusters, about 10 gene clusters to about 55 gene clusters, about 10 gene clusters to about 60 gene clusters, about 10 gene clusters to about 70 gene clusters, about 10 gene clusters to about 80 gene clusters, about 20 gene clusters to about 25 gene clusters, about 20 gene clusters to about 30 gene clusters, about 20 gene clusters to about 35 gene clusters, about 20 gene clusters to about 40 gene clusters, about 20 gene clusters to about 45 gene clusters, about 20 gene clusters to about 50 gene clusters, about 20 gene clusters to about 55 gene clusters, about 20 gene clusters to about 60 gene clusters, about 20 gene clusters to about 70 gene clusters, about 20 gene clusters to about 80 gene clusters, about 25 gene clusters to about 30 gene clusters, about 25 gene clusters to about 35 gene clusters, about 25 gene clusters to about 40 gene clusters, about 25 gene clusters to about 45 gene clusters, about 25 gene clusters to about 50 gene clusters, about 25 gene clusters to about 55 gene clusters, about 25 gene clusters to about 60 gene clusters, about 25 gene clusters to about 70 gene clusters, about 25 gene clusters to about 80 gene clusters, about 30 gene clusters to about 35 gene clusters, about 30 gene clusters to about 40 gene clusters, about 30 gene clusters to about 45 gene clusters, about 30 gene clusters to about 50 gene clusters, about 30 gene clusters to about 55 gene clusters, about 30 gene clusters to about 60 gene clusters, about 30 gene clusters to about 70 gene clusters, about 30 gene clusters to about 80 gene clusters, about 35 gene clusters to about 40 gene clusters, about 35 gene clusters to about 45 gene clusters, about 35 gene clusters to about 50 gene clusters, about 35 gene clusters to about 55 gene clusters, about 35 gene clusters to about 60 gene clusters, about 35 gene clusters to about 70 gene clusters, about 35 gene clusters to about 80 gene clusters, about 40 gene clusters to about 45 gene clusters, about 40 gene clusters to about 50 gene clusters, about 40 gene clusters to about 55 gene clusters, about 40 gene clusters to about 60 gene clusters, about 40 gene clusters to about 70 gene clusters, about 40 gene clusters to about 80 gene clusters, about 45 gene clusters to about 50 gene clusters, about 45 gene clusters to about 55 gene clusters, about 45 gene clusters to about 60 gene clusters, about 45 gene clusters to about 70 gene clusters, about 45 gene clusters to about 80 gene clusters, about 50 gene clusters to about 55 gene clusters, about 50 gene clusters to about 60 gene clusters, about 50 gene clusters to about 70 gene clusters, about 50 gene clusters to about 80 gene clusters, about 55 gene clusters to about 60 gene clusters, about 55 gene clusters to about 70 gene clusters, about 55 gene clusters to about 80 gene clusters, about 60 gene clusters to about 70 gene clusters, about 60 gene clusters to about 80 gene clusters, or about 70 gene clusters to about 80 gene clusters, that are most strongly correlated, e.g., among the plurality of gene clusters, with the one or more sample traits. In certain embodiments, the plurality of significant gene clusters contain about 10 gene clusters to about 20 gene clusters, about 10 gene clusters to about 25 gene clusters, about 10 gene clusters to about 30 gene clusters, about 10 gene clusters to about 35 gene clusters, about 10 gene clusters to about 40 gene clusters, about 10 gene clusters to about 45 gene clusters, about 10 gene clusters to about 50 gene clusters, about 10 gene clusters to about 55 gene clusters, about 10 gene clusters to about 60 gene clusters, about 10 gene clusters to about 70 gene clusters, about 10 gene clusters to about 80 gene clusters, about 20 gene clusters to about 25 gene clusters, about 20 gene clusters to about 30 gene clusters, about 20 gene clusters to about 35 gene clusters, about 20 gene clusters to about 40 gene clusters, about 20 gene clusters to about 45 gene clusters, about 20 gene clusters to about 50 gene clusters, about 20 gene clusters to about 55 gene clusters, about 20 gene clusters to about 60 gene clusters, about 20 gene clusters to about 70 gene clusters, about 20 gene clusters to about 80 gene clusters, about 25 gene clusters to about 30 gene clusters, about 25 gene clusters to about 35 gene clusters, about 25 gene clusters to about 40 gene clusters, about 25 gene clusters to about 45 gene clusters, about 25 gene clusters to about 50 gene clusters, about 25 gene clusters to about 55 gene clusters, about 25 gene clusters to about 60 gene clusters, about 25 gene clusters to about 70 gene clusters, about 25 gene clusters to about 80 gene clusters, about 30 gene clusters to about 35 gene clusters, about 30 gene clusters to about 40 gene clusters, about 30 gene clusters to about 45 gene clusters, about 30 gene clusters to about 50 gene clusters, about 30 gene clusters to about 55 gene clusters, about 30 gene clusters to about 60 gene clusters, about 30 gene clusters to about 70 gene clusters, about 30 gene clusters to about 80 gene clusters, about 35 gene clusters to about 40 gene clusters, about 35 gene clusters to about 45 gene clusters, about 35 gene clusters to about 50 gene clusters, about 35 gene clusters to about 55 gene clusters, about 35 gene clusters to about 60 gene clusters, about 35 gene clusters to about 70 gene clusters, about 35 gene clusters to about 80 gene clusters, about 40 gene clusters to about 45 gene clusters, about 40 gene clusters to about 50 gene clusters, about 40 gene clusters to about 55 gene clusters, about 40 gene clusters to about 60 gene clusters, about 40 gene clusters to about 70 gene clusters, about 40 gene clusters to about 80 gene clusters, about 45 gene clusters to about 50 gene clusters, about 45 gene clusters to about 55 gene clusters, about 45 gene clusters to about 60 gene clusters, about 45 gene clusters to about 70 gene clusters, about 45 gene clusters to about 80 gene clusters, about 50 gene clusters to about 55 gene clusters, about 50 gene clusters to about 60 gene clusters, about 50 gene clusters to about 70 gene clusters, about 50 gene clusters to about 80 gene clusters, about 55 gene clusters to about 60 gene clusters, about 55 gene clusters to about 70 gene clusters, about 55 gene clusters to about 80 gene clusters, about 60 gene clusters to about 70 gene clusters, about 60 gene clusters to about 80 gene clusters, or about 70 gene clusters to about 80 gene clusters, that are most strongly correlated, e.g., among the gene clusters correlated in step (c), with the one or more sample traits. In certain embodiments, the plurality of significant gene clusters contain about 10 gene clusters, about 20 gene clusters, about 25 gene clusters, about 30 gene clusters, about 35 gene clusters, about 40 gene clusters, about 45 gene clusters, about 50 gene clusters, about 55 gene clusters, about 60 gene clusters, about 70 gene clusters, or about 80 gene clusters. In certain embodiments, the plurality of significant gene clusters contain about 10 gene clusters, about 20 gene clusters, about 25 gene clusters, about 30 gene clusters, about 35 gene clusters, about 40 gene clusters, about 45 gene clusters, about 50 gene clusters, about 55 gene clusters, about 60 gene clusters, about 70 gene clusters, or about 80 gene clusters, that are most strongly correlated with the one or more sample traits. In certain embodiments, the plurality of significant gene clusters contain about 10 gene clusters, about 20 gene clusters, about 25 gene clusters, about 30 gene clusters, about 35 gene clusters, about 40 gene clusters, about 45 gene clusters, about 50 gene clusters, about 55 gene clusters, about 60 gene clusters, about 70 gene clusters, or about 80 gene clusters, that are most strongly correlated, e.g., among the gene clusters correlated in step (c), with the one or more sample. In certain embodiments, the plurality of significant gene clusters contain at least about 10 gene clusters, about 20 gene clusters, about 25 gene clusters, about 30 gene clusters, about 35 gene clusters, about 40 gene clusters, about 45 gene clusters, about 50 gene clusters, about 55 gene clusters, about 60 gene clusters, or about 70 gene clusters. In certain embodiments, the plurality of significant gene clusters contain at most about 20 gene clusters, about 25 gene clusters, about 30 gene clusters, about 35 gene clusters, about 40 gene clusters, about 45 gene clusters, about 50 gene clusters, about 55 gene clusters, about 60 gene clusters, about 70 gene clusters, or about 80 gene clusters. In certain embodiments, the plurality of significant gene clusters contain at least about 10 gene clusters, about 20 gene clusters, about 25 gene clusters, about 30 gene clusters, about 35 gene clusters, about 40 gene clusters, about 45 gene clusters, about 50 gene clusters, about 55 gene clusters, about 60 gene clusters, or about 70 gene clusters, that are most strongly correlated with the one or more sample traits. In certain embodiments, the plurality of significant gene clusters contain at most about 20 gene clusters, about 25 gene clusters, about 30 gene clusters, about 35 gene clusters, about 40 gene clusters, about 45 gene clusters, about 50 gene clusters, about 55 gene clusters, about 60 gene clusters, about 70 gene clusters, or about 80 gene clusters, that are most strongly correlated with the one or more sample traits. In certain embodiments, the plurality of significant gene clusters contain at least about 10 gene clusters, about 20 gene clusters, about 25 gene clusters, about 30 gene clusters, about 35 gene clusters, about 40 gene clusters, about 45 gene clusters, about 50 gene clusters, about 55 gene clusters, about 60 gene clusters, or about 70 gene clusters, that are most strongly correlated, e.g., among the gene clusters correlated in step (c), with the one or more sample. In certain embodiments, the plurality of significant gene clusters contain at most about 20 gene clusters, about 25 gene clusters, about 30 gene clusters, about 35 gene clusters, about 40 gene clusters, about 45 gene clusters, about 50 gene clusters, about 55 gene clusters, about 60 gene clusters, about 70 gene clusters, or about 80 gene clusters, that are most strongly correlated, e.g., among the gene clusters correlated in step (c), with the one or more sample. In certain embodiments, in step (d) third generation gene clusters are selected. In certain embodiments, in step (d) second, third, and/or fourth generation gene clusters are selected. In certain embodiments, in step (d) third generation gene clusters are selected, wherein the plurality of significant gene clusters contain 10 to 80 most strongly correlated third generation gene clusters. In certain embodiments, in step (d) second, third and/or fourth generation gene clusters are selected, wherein the plurality of significant gene clusters contain 10 to 80 most strongly correlated second, third, and/or fourth generation gene clusters. In certain embodiments, in step (c) the second, third and/or fourth generation gene clusters of the plurality of gene clusters are correlated with the one or more sample traits, and the plurality of significant gene clusters selected in step (d) comprises second, third and/or fourth gene clusters, such as 20 to 50 second, third and/or fourth generation gene clusters that are most strongly correlated with the one or more sample traits, among the second, third and/or fourth generation gene clusters of the plurality of gene clusters. In certain embodiments, in step (c) the third generation gene clusters of the plurality of gene clusters are correlated with the one or more sample traits, and the plurality of significant gene clusters selected in step (d) comprises third generation gene clusters, such as 20 to 50 third generation gene clusters that are most strongly correlated with the one or more sample traits, among the third generation gene clusters of the plurality of gene clusters.

In certain embodiments, one or more redundant genes, such as redundant based on gene expression within the plurality of the reference biological samples can be excluded from the method (e.g., excluded before or after clustering of the genes). Redundant genes can have a correlation coefficients greater than a threshold value. The threshold value can be 0.6, 0.65, 0.7, 0.75, 0.8, 0.85, 0.9 or 0.95.

The disease can be arthritis, lupus, fibromyalgia, or any combination thereof. In certain embodiments, the disease is lupus. In certain embodiments, the disease is fibromyalgia. In certain embodiments, the disease is arthritis. Lupus can be any type of lupus including but not limited to systemic lupus erythematosus (SLE), cutaneous lupus erythematosus, drug-induced lupus, and neonatal lupus. In certain embodiments, the lupus is SLE. In certain embodiments, the arthritis is rheumatoid arthritis (RA), early inflammatory arthritis, or any combination thereof. In certain embodiments, the disease is SLE. In certain embodiments, the disease is RA.

In certain embodiments, the gene set obtained in step (d) is capable of classifying whether a patient has type 1 lupus, type 2 lupus, or type 1-2 lupus. In certain embodiments, the gene set obtained in step (d) is capable of classifying whether a patient has type 1 lupus, or type 2 lupus. In certain embodiments, the plurality of reference subjects comprises a first plurality of reference subjects having type 1 lupus, a second plurality of reference subjects having type 2 lupus, and a third plurality of reference subjects having type 1-2 lupus, and the gene set obtained in step (d) is capable of classifying whether a patient has type 1 lupus, type 2 lupus, or type 1-2 lupus. In certain embodiments, the plurality of reference subjects comprises a first plurality of reference subjects having type 1 lupus, a second plurality of reference subjects having type 2 lupus, and a third plurality of reference subjects having type 1-2 lupus, and the gene set obtained in step (d) is capable of classifying whether a patient has type 1 lupus, or type 2 lupus. In certain embodiments, the plurality of reference subjects comprises a first plurality of reference subjects having type 1 lupus, and a second plurality of reference subjects having type 2 lupus, and the gene set obtained in step (d) is capable of classifying whether a patient has type 1 lupus, or type 2 lupus. Type 1 lupus, type 2 lupus and type 1-2 lupus are endotypes of lupus.

In certain embodiments, i) the disease is lupus; ii) the plurality of reference subjects comprises a first plurality of reference subjects having type 1 lupus, a second plurality of reference subjects having type 2 lupus, and a third plurality of reference subjects having type 1-2 lupus; and iii) the gene set obtained in step (d) is capable of classifying whether a patient has type 1 lupus, type 2 lupus, or type 1-2 lupus. In certain embodiments, i) the disease is lupus; ii) the plurality of reference subjects comprises a first plurality of reference subjects having type 1 lupus, a second plurality of reference subjects having type 2 lupus, and a third plurality of reference subjects having type 1-2 lupus; and iii) the gene set obtained in step (d) is capable of classifying whether a patient has type 1 lupus, or type 2 lupus. In certain embodiments, i) the disease is lupus; ii) the plurality of reference subjects comprises a first plurality of reference subjects having type 1 lupus, and a second plurality of reference subjects having type 2 lupus; and iii) the gene set obtained in step (d) is capable of classifying whether a patient has type 1 lupus, or type 2 lupus.

In certain embodiments, the one or more sample traits are selected from the sample traits listed in Table 10. Sample traits listed in Table 10 are PSD score (PSD.score); SLEDAI; blood autoimmune antibody level (anti.dsDNA); blood complement component 3 (C3) protein level (complement_C3); Age; whether of African ancestry (AA) (ancestry_AA, yes=1, no=0); whether of European ancestry (EA) (ancestry_EA, yes=1, no=0); whether of hispanic ancestry (HA) (ancestry_HA, yes=1, no=0); whether a female (is_female yes=1, no=0); lu vas1 init (lu_vas1_init); lu vas2 init (lu_vas2_init); sledai arthritis (sledai_arthritis); sledai rash (sledai_rash); sledai ulcers (sledai_ulcers); sledai pleurisy (sledai_pleurisy); sledai leukopenia (sledai_leukopenia); sledai hematuria (sledai_hematuria); sledai pyuria (sledai_pyuria); sledai proteinuria (sledai_proteinuria); fatigue severity (fatigue_severity); cognitive; wake unrefresh (wake_unrefresh); headache symptom (headache_symptom); has cramps; has depression; total areas of pain (total_areas_of_pain); total symptom severity (Total_Symptom_Severity); totalpain; month flare (month_flare); week muscle (muscle_weak); muscle pain (muscle pain); swell joints (swell_joints); pain stiff joint (pain_stiff_joint); rash malar (rash_malar); rash sun (rash_sun); vasculitis; rash_oth; weight loss (wt_loss); fatigue; fever; swollen glands (swollen_glands); alopecia; dry eye mouth (dry_eye_mouth); sores_mouth_nose (sores_mouth_nose); Raynaud; short breath (short_breath); pain deep breath (pain_deep_breath); forget; feel depressed (feel_depressed); anxiety; headache; stroke; numb tingle (numb_tingle); belly pain (belly_pain); edema; hypertension; upc; urine foamy (urine_foamy); urine pain (urine_pain); rate lupus (rate_lupus); er visit (er_visit); little interest (little_interest); depressed; sleep trouble (sleep_trouble); tired; poor appetite (poor_appeti); disappoint; concentrate; slow fidget (slow_fidget); understand; follow direct (follow_direct); miss dose (miss_dose); when missed (when_missed); percent med (percent_med); hydroxychloroquine (HCQ) drug usage (drug.HCQ); Prednisone drug usage (drug.Prednisone); Cytoxan drug usage (drug.Cytoxan); Cellcept drug usage (drug.CellCept); mycophenolate mofetil (MMF) drug usage (drug.MMF); Azathioprine drug usage (drug.Azathioprine); Methotrexate drug usage (drug.Methotrexate); Benlysta drug usage (drug.Benlysta); Adalimumab drug usage (drug. Adalimumab); NSAIDs usage (drug.NSAIDs); Leflunomide drug usage (drug.Leflunomide); ACE drug usage (drug.ACE); ARB drug usage (drug.ARB); Aspirin drug usage (drug.Aspirin); Amlodipine drug usage (drug.Amlodipine); HCTZ drug usage (drug.HCTZ); Lasix drug usage (drug.Lasix); Metoprolol drug usage (drug.Metoprolol); Coreg drug usage (drug.Coreg); Chlorthalidone drug usage (drug.Chlorthalidone); Gabapentin drug usage (drug.Gabapentin); Lyrica drug usage (drug.Lyrica); Flexeril drug usage (drug.Flexeril); Elavil drug usage (drug.Elavil); Cymbalta drug usage (drug.Cymbalta); Effexor drug usage (drug.Effexor); Milnacipran drug usage (drug.Milnacipran); Wellbutrin drug usage (drug.Wellbutrin); and Tramadol drug usage (drug.Tramadol). In certain embodiments, the one or more sample traits include blood autoimmune antibody level, SLEDAI score, blood C3 protein level, PSD score, age, ancestry, Hispanic ancestry, African ancestry, Non-steroidal anti-inflammatory drugs usage, prednisone usage, amitriptyline usage, total areas of pain, or any combination thereof. In certain embodiments, the one or more sample traits include blood autoimmune antibody level, SLEDAI score, blood C3 protein level, PSD score, age, ancestry, or any combination thereof. In certain embodiments, the one or more sample traits include blood autoimmune antibody level, SLEDAI score, blood C3 protein level, PSD score, immunosuppressive drug usage, duloxetine usage, or any combination thereof. In certain embodiments, the one or more sample traits include blood autoimmune antibody level. In certain embodiments, the one or more sample traits include blood autoimmune antibody level, age, Hispanic ancestry, Non-steroidal anti-inflammatory drugs usage, African ancestry, prednisone usage, amitriptyline usage, total areas of pain, or any combination thereof. In certain embodiments, the one or more sample traits include blood autoimmune antibody level, SLEDAI score, blood C3 protein level, African ancestry, European ancestry, Hispanic ancestry, prednisone usage, CellCept usage, Benlysta usage, Cymbalta usage, or any combination thereof. In certain embodiments, the one or more sample traits include PSD score, SLEDAI score; blood autoimmune antibody level; blood complement C3 protein level; age; ancestry; African ancestry; European ancestry; Hispanic ancestry; lu vas2 init; sledai rash; sledai pleurisy; sledai leukopenia; sledai pyuria; sledai proteinuria; fatigue severity; wake unfresh; headache symptom; total areas of pain; total symptom severity; pain stiff joint; rash sun; vasculitis; wt. loss; fatigue; Raynaud; pain deep breath; forget; headache; stroke; upc; urine foamy; urine pain; tired; concentrate; follow direct; HCQ drug usage; is.type 2; Prednisone drug usage; Cellcept drug usage; Benlysta drug usage; NSAIDs usage; Coreg drug usage; Elavil drug usage; or any combination thereof.

In certain embodiments, the disease is lupus, and the one or more sample traits are selected from the sample traits listed in Table 10. In certain embodiments, the disease is lupus, and the one or more sample traits include blood autoimmune antibody level, SLEDAI score, blood C3 protein level, PSD score, age, ancestry, Hispanic ancestry, African ancestry, Non-steroidal anti-inflammatory drugs usage, prednisone usage, amitriptyline usage, total areas of pain, or any combination thereof. In certain embodiments, the disease is lupus, and the one or more sample traits include blood autoimmune antibody level, SLEDAI score, blood C3 protein level, PSD score, age, ancestry, or any combination thereof. In certain embodiments, the disease is lupus, and the one or more sample traits include blood autoimmune antibody level, SLEDAI score, blood C3 protein level, PSD score, immunosuppressive drug usage, duloxetine usage, or any combination thereof. In certain embodiments, the disease is lupus, and the one or more sample traits include blood autoimmune antibody level. In certain embodiments, the disease is lupus, and the one or more sample traits include blood autoimmune antibody level, age, Hispanic ancestry, Non-steroidal anti-inflammatory drugs usage, African ancestry, prednisone usage, amitriptyline usage, total areas of pain, or any combination thereof. In certain embodiments, the disease is lupus, and the one or more sample traits include blood autoimmune antibody level, SLEDAI score, blood C3 protein level, African ancestry, European ancestry, Hispanic ancestry, prednisone usage, CellCept usage, Benlysta usage, Cymbalta usage, or any combination thereof. In certain embodiments, the disease is lupus, and the one or more sample traits include PSD score, SLEDAI score; blood autoimmune antibody level; blood complement C3 protein level; age; ancestry; African ancestry; European ancestry; Hispanic ancestry; lu vas2 init; sledai rash; sledai pleurisy; sledai leukopenia; sledai pyuria; sledai proteinuria; fatigue severity; wake unfresh; headache symptom; total areas of pain; total symptom severity; pain stiff joint; rash sun; vasculitis; wt. loss; fatigue; Raynaud; pain deep breath; forget; headache; stroke; upc; urine foamy; urine pain; tired; concentrate; follow direct; HCQ drug usage; is.type 2; Prednisone drug usage; Cellcept drug usage; Benlysta drug usage; NSAIDs usage; Coreg drug usage; Elavil drug usage; or any combination thereof, or any combination thereof. In certain embodiments, i) the disease is lupus; ii) the plurality of reference subjects comprises a first plurality of reference subjects having type 1 lupus, a second plurality of reference subjects having type 2 lupus, and a third plurality of reference subjects having type 1-2 lupus; iii) the one or more sample traits are selected from the sample traits listed in Table 10; and iv) the gene set obtained in step (d) is capable of classifying whether a patient has type 1 lupus, type 2 lupus, or type 1-2 lupus. In certain embodiments, i) the disease is lupus; ii) the plurality of reference subjects comprises a first plurality of reference subjects having type 1 lupus, a second plurality of reference subjects having type 2 lupus, and a third plurality of reference subjects having type 1-2 lupus; iii) the one or more sample traits include blood autoimmune antibody level, SLEDAI score, blood C3 protein level, PSD score, age, ancestry, Hispanic ancestry, African ancestry, Non-steroidal anti-inflammatory drugs usage, prednisone usage, amitriptyline usage, total areas of pain, or any combination thereof; and iv) the gene set obtained in step (d) is capable of classifying whether a patient has type 1 lupus, type 2 lupus, or type 1-2 lupus. In certain embodiments, i) the disease is lupus; ii) the plurality of reference subjects comprises a first plurality of reference subjects having type 1 lupus, a second plurality of reference subjects having type 2 lupus, and a third plurality of reference subjects having type 1-2 lupus; iii) the one or more sample traits include blood autoimmune antibody level, SLEDAI score, blood C3 protein level, PSD score, age, ancestry, or any combination thereof; and iv) the gene set obtained in step (d) is capable of classifying whether a patient has type 1 lupus, type 2 lupus, or type 1-2 lupus. In certain embodiments, i) the disease is lupus; ii) the plurality of reference subjects comprises a first plurality of reference subjects having type 1 lupus, a second plurality of reference subjects having type 2 lupus, and a third plurality of reference subjects having type 1-2 lupus; iii) the one or more sample traits include blood autoimmune antibody level; and iv) the gene set obtained in step (d) is capable of classifying whether a patient has type 1 lupus, type 2 lupus, or type 1-2 lupus. In certain embodiments, i) the disease is lupus; ii) the plurality of reference subjects comprises a first plurality of reference subjects having type 1 lupus, a second plurality of reference subjects having type 2 lupus, and a third plurality of reference subjects having type 1-2 lupus; iii) the one or more sample traits include blood autoimmune antibody level, SLEDAI score, blood C3 protein level, PSD score, immunosuppressive drug usage, duloxetine usage, or any combination thereof; and iv) the gene set obtained in step (d) is capable of classifying whether a patient has type 1 lupus, type 2 lupus, or type 1-2 lupus. In certain embodiments, i) the disease is lupus; ii) the plurality of reference subjects comprises a first plurality of reference subjects having type 1 lupus, a second plurality of reference subjects having type 2 lupus, and a third plurality of reference subjects having type 1-2 lupus; iii) the one or more sample traits include blood autoimmune antibody level, age, Hispanic ancestry, Non-steroidal anti-inflammatory drugs usage, African ancestry, prednisone usage, amitriptyline usage, total areas of pain, or any combination thereof; and iv) the gene set obtained in step (d) is capable of classifying whether a patient has type 1 lupus, type 2 lupus, or type 1-2 lupus. In certain embodiments, i) the disease is lupus; ii) the plurality of reference subjects comprises a first plurality of reference subjects having type 1 lupus, a second plurality of reference subjects having type 2 lupus, and a third plurality of reference subjects having type 1-2 lupus; iii) the one or more sample traits include blood autoimmune antibody level, SLEDAI score, blood C3 protein level, African ancestry, European ancestry, Hispanic ancestry, prednisone usage, CellCept usage, Benlysta usage, Cymbalta usage, or any combination thereof; and iv) the gene set obtained in step (d) is capable of classifying whether a patient has type 1 lupus, type 2 lupus, or type 1-2 lupus. In certain embodiments, i) the disease is lupus; ii) the plurality of reference subjects comprises a first plurality of reference subjects having type 1 lupus, a second plurality of reference subjects having type 2 lupus, and a third plurality of reference subjects having type 1-2 lupus; iii) the one or more sample traits include PSD score, SLEDAI score; blood autoimmune antibody level; blood complement C3 protein level; age; ancestry; African ancestry; European ancestry; Hispanic ancestry; lu vas2 init; sledai rash; sledai pleurisy; sledai leukopenia; sledai pyuria; sledai proteinuria; fatigue severity; wake unfresh; headache symptom; total areas of pain; total symptom severity; pain stiff joint; rash sun; vasculitis; wt. loss; fatigue; Raynaud; pain deep breath; forget; headache; stroke; upc; urine foamy; urine pain; tired; concentrate; follow direct; HCQ drug usage; is.type 2; Prednisone drug usage; Cellcept drug usage; Benlysta drug usage; NSAIDs usage; Coreg drug usage; Elavil drug usage; or any combination thereof, or any combination thereof; and iv) the gene set obtained in step (d) is capable of classifying whether a patient has type 1 lupus, type 2 lupus, or type 1-2 lupus. In certain embodiments, i) the disease is lupus; ii) the plurality of reference subjects comprises a first plurality of reference subjects having type 1 lupus, and a second plurality of reference subjects having type 2 lupus; iii) the one or more sample traits are selected from the sample traits listed in Table 10; and iv) the gene set obtained in step (d) is capable of classifying whether a patient has type 1 lupus, or type 2 lupus. In certain embodiments, i) the disease is lupus; ii) the plurality of reference subjects comprises a first plurality of reference subjects having type 1 lupus, and a second plurality of reference subjects having type 2 lupus; iii) the one or more sample traits include blood autoimmune antibody level, SLEDAI score, blood C3 protein level, PSD score, age, ancestry, Hispanic ancestry, African ancestry, Non-steroidal anti-inflammatory drugs usage, prednisone usage, amitriptyline usage, total areas of pain, or any combination thereof; and iv) the gene set obtained in step (d) is capable of classifying whether a patient has type 1 lupus, or type 2 lupus. In certain embodiments, i) the disease is lupus; ii) the plurality of reference subjects comprises a first plurality of reference subjects having type 1 lupus, and a second plurality of reference subjects having type 2 lupus; iii) the one or more sample traits include blood autoimmune antibody level, SLEDAI score, blood C3 protein level, PSD score, age, ancestry, or any combination thereof; and iv) the gene set obtained in step (d) is capable of classifying whether a patient has type 1 lupus, or type 2 lupus. In certain embodiments, i) the disease is lupus; ii) the plurality of reference subjects comprises a first plurality of reference subjects having type 1 lupus, and a second plurality of reference subjects having type 2 lupus; iii) the one or more sample traits include blood autoimmune antibody level; and iv) the gene set obtained in step (d) is capable of classifying whether a patient has type 1 lupus, or type 2 lupus. In certain embodiments, i) the disease is lupus; ii) the plurality of reference subjects comprises a first plurality of reference subjects having type 1 lupus, and a second plurality of reference subjects having type 2 lupus; iii) the one or more sample traits include blood autoimmune antibody level, age, Hispanic ancestry, Non-steroidal anti-inflammatory drugs usage, African ancestry, prednisone usage, amitriptyline usage, total areas of pain, or any combination thereof; and iv) the gene set obtained in step (d) is capable of classifying whether a patient has type 1 lupus, or type 2 lupus. In certain embodiments, i) the disease is lupus; ii) the plurality of reference subjects comprises a first plurality of reference subjects having type 1 lupus, and a second plurality of reference subjects having type 2 lupus; iii) the one or more sample traits include blood autoimmune antibody level, SLEDAI score, blood C3 protein level, African ancestry, European ancestry, Hispanic ancestry, prednisone usage, CellCept usage, Benlysta usage, Cymbalta usage, or any combination thereof; and iv) the gene set obtained in step (d) is capable of classifying whether a patient has type 1 lupus, or type 2 lupus. In certain embodiments, i) the disease is lupus; ii) the plurality of reference subjects comprises a first plurality of reference subjects having type 1 lupus, and a second plurality of reference subjects having type 2 lupus; iii) the one or more sample traits include blood autoimmune antibody level, SLEDAI score, blood C3 protein level, PSD score, immunosuppressive drug usage, duloxetine usage, or any combination thereof; and iv) the gene set obtained in step (d) is capable of classifying whether a patient has type 1 lupus, or type 2 lupus. In certain embodiments, i) the disease is lupus; ii) the plurality of reference subjects comprises a first plurality of reference subjects having type 1 lupus, and a second plurality of reference subjects having type 2 lupus; iii) the one or more sample traits include PSD score, SLEDAI score; blood autoimmune antibody level; blood complement C3 protein level; age; ancestry; African ancestry; European ancestry; Hispanic ancestry; lu vas2 init; sledai rash; sledai pleurisy; sledai leukopenia; sledai pyuria; sledai proteinuria; fatigue severity; wake unfresh; headache symptom; total areas of pain; total symptom severity; pain stiff joint; rash sun; vasculitis; wt. loss; fatigue; Raynaud; pain deep breath; forget; headache; stroke; upc; urine foamy; urine pain; tired; concentrate; follow direct; HCQ drug usage; is.type 2; Prednisone drug usage; Cellcept drug usage; Benlysta drug usage; NSAIDs usage; Coreg drug usage; Elavil drug usage; or any combination thereof, or any combination thereof; and iv) the gene set obtained in step (d) is capable of classifying whether a patient has type 1 lupus, or type 2 lupus.

The reference biological samples can comprise tissue biopsy samples, blood samples, isolated peripheral blood mononuclear cells (PBMCs), or any derivative thereof. In certain embodiments, the reference biological samples comprise tissue biopsy samples, or any derivative thereof. In certain embodiments, the tissue biopsy samples comprise synovial biopsy samples or any derivative thereof. In certain embodiments, the tissue biopsy samples comprise skin biopsy samples or any derivative thereof. In certain embodiments, the reference biological samples comprise blood samples, or any derivative thereof. In certain embodiments, the reference biological samples comprise PBMCs, or any derivative thereof. The reference subjects can be human. The gene set (e.g., obtained in the step (d)) can be used for diagnosis and/or treatment of the disease in a patient.

II. Methods for Classifying a Lupus Disease State of a Patient, and/or Treating Lupus in a Patient Certain aspects are directed to a method for classifying a lupus disease state of a patient. The method can include analyzing a patient data set comprising or derived from gene expression measurements data of at least 2 genes, from a biological sample obtained and/or derived from the patient. In certain embodiments, the gene expression measurements data (e.g., of which the patient data set is comprised of or derived from) is analyzed to classify the lupus disease state of the patient. In certain embodiments, classifying the lupus disease state of a patient includes classifying (e.g., determining) whether the patient has type 1 lupus, type 2 lupus, or type 1-2 lupus. The at least 2 genes (e.g., gene expression measurements data of which the patient data set is comprised of or derived from) can be selected from a gene set capable of classifying the lupus disease state of the patient. In certain embodiments, the at least 2 genes (e.g., gene expression measurements data of which the patient data set is comprised of or derived from) is selected from a gene set capable of classifying whether a patient has type 1 lupus, type 2 lupus, or type 1-2 lupus. In certain embodiments, the gene set capable of classifying whether a patient has type 1 lupus, type 2 lupus, or type 1-2 lupus, is a gene set of step (d) as described herein (e.g., in Detailed description, Section I). In certain embodiments, the gene set capable of classifying whether a patient has type 1 lupus, type 2 lupus, or type 1-2 lupus, is a gene set determined and/or obtained using a method containing steps (a), (b), (c), and/or (d), as described herein (e.g., in Detailed description, Section I). In certain embodiments, classifying lupus disease state of a patient includes classifying (e.g., determining) whether the patient has type 1 lupus, or type 2 lupus. In certain embodiments, the at least 2 genes (e.g., gene expression measurements data of which the patient data set is comprised of or derived from) is selected from a gene set capable of classifying whether a patient has type 1 lupus, or type 2 lupus. In certain embodiments, the gene set capable of classifying whether a patient has type 1 lupus, or type 2 lupus is a gene set of step (d) as described herein (e.g., in Detailed description, Section I). In certain embodiments, the gene set capable of classifying whether a patient has type 1 lupus, or type 2 lupus, is a gene set determined and/or obtained using a method containing steps (a), (b), (c), and/or (d), as described herein (e.g., in Detailed description, Section I). The genes listed in Tables 17-1 to 17-30 can form the gene set capable of classifying the lupus disease state of the patient. In certain embodiments, the genes listed in Tables 17-1 to 17-30 form the gene set capable of classifying whether a patient has type 1 lupus, type 2 lupus, or type 1-2 lupus. In certain embodiments, the genes listed in Tables 17-1 to 17-30 form the gene set capable of classifying whether a patient has type 1 lupus, or type 2 lupus. In certain embodiments, a patient data set comprising or derived from gene expression measurements data of 2 or more genes selected from the genes listed in Tables 17-1 to 17-30 is analyzed to classify whether the patient has type 1 lupus, type 2 lupus, or type 1-2 lupus. In certain embodiments, a patient data set comprising or derived from gene expression measurements data of 2 or more genes selected from the genes listed in Tables 17-1 to 17-30 is analyzed to classify whether the patient has type 1 lupus, or type 2 lupus. Gene clusters listed in the Tables 17-1 to 17-30 can be the plurality of significant gene clusters obtained in step (d). Gene clusters listed in the Tables 17-1 to 17-30 can be the plurality of significant gene clusters obtained in step (d), wherein in step (d) second, third and fourth generation gene clusters are selected. Genes within separate significant gene clusters (e.g., obtained in step (d)) are listed within separate Tables in Tables 17-1 to 17-30. The patient data set may or may not comprise or be derived from gene expression measurements data of any gene that is not listed in Tables 17-1 to 17-30. In certain embodiment, the patient data set does not comprise or is derived from gene expression measurements data of any gene that is not listed in Tables 17-1 to 17-30. The genes listed in Tables 24-1 to 24-30 can form the gene set capable of classifying the lupus disease state of the patient. In certain embodiments, the genes listed in Tables 24-1 to 24-30 form the gene set capable of classifying whether a patient has type 1 lupus, type 2 lupus, or type 1-2 lupus. In certain embodiments, the genes listed in Tables 24-1 to 24-30 form the gene set capable of classifying whether a patient has type 1 lupus, or type 2 lupus. In certain embodiments, a patient data set comprising or derived from gene expression measurements data of 2 or more genes selected from the genes listed in Tables 24-1 to 24-30 is analyzed to classify whether the patient has type 1 lupus, type 2 lupus, or type 1-2 lupus. In certain embodiments, a patient data set comprising or derived from gene expression measurements data of 2 or more genes selected from the genes listed in Tables 24-1 to 24-30 is analyzed to classify whether the patient has type 1 lupus, or type 2 lupus. Gene clusters listed in the Tables 24-1 to 24-30 can be the plurality of significant gene clusters obtained in step (d). Gene clusters listed in the Tables 24-1 to 24-30 can be the plurality of significant gene clusters obtained in step (d), wherein in step (d) third generation gene clusters are selected. Genes within separate significant gene clusters (e.g., obtained in step (d)) are listed within separate Tables in Tables 24-1 to 24-30. The patient data set may or may not comprise or be derived from gene expression measurements data of any gene that is not listed in Tables 24-1 to 24-30. In certain embodiment, the patient data set does not comprise or is derived from gene expression measurements data of any gene that is not listed in Tables 24-1 to 24-30. Characteristics of type 1, type 2 and type 1-2 (mixed) lupus, and clinical features of patients with type 1, type 2 or type 1-2 (mixed) lupus is presented in Example 6 and Table 12.

In certain embodiments, the patient data set comprises or is derived from gene expression measurements data of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 450, 500, 550, 600, 650, 700, 750, 850, 900, 950, 1000, 1050, 1100, 1150, 1200, 1250, 1300, 1350, 1400, 1450, 1500, 1550, 1600, 1700, 1800, 1900, 2000 or all, or any range, or value genes selected from the genes listed within the gene set capable of classifying the lupus disease state of the patient. The genes within a gene set can be the genes listed within the gene set. In certain embodiments, the patient data set comprises or is derived from gene expression measurements data of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 450, 500, 550, 600, 650, 700, 750, 850, 900, 950, 1000, 1050, 1100, 1150, 1200, 1250, 1300, 1350, 1400, 1450, 1500, 1550, 1600, 1700, 1800, 1900, 2000 or all, or any range, or value genes selected from the genes listed in Tables 17-1 to 17-30. Genes listed in Tables 17-1 to 17-30 include all the genes listed in Tables 17-1 to 17-30. In certain embodiments, the patient data set comprises or is derived from gene expression measurements data of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 450, 500, 550, 600, 650, 700, 750, 850, 900, 950, 1000, 1050, 1100, 1150, 1200, 1250, 1300, 1350, 1400, 1450, 1500, 1550, 1600, 1700, 1800, 1900, 2000 or all, or any range, or value genes selected from the genes listed in Tables 24-1 to 24-30. Genes listed in Tables 24-1 to 24-30 include all the genes listed in Tables 24-1 to 24-30.

In certain embodiments, the patient data set comprises or is derived from gene expression measurements data of at least 2 to all, or any value or range there between, genes selected from the genes listed within each of one or more gene clusters selected from the significant gene clusters of the gene set (e.g., capable of classifying the lupus disease state of the patient), from the biological sample from the patient, wherein number of genes selected from different selected gene clusters can be different or the same. As a non-limiting illustrative example, two significant clusters are selected, the patient data set comprises or is derived from gene expression measurements data of at least 4 genes (at least 2 from the one selected significant gene cluster, and at least 2 from the other selected significant gene cluster) from the biological sample from the patient, considering no overlap of genes exists between the clusters e.g., genes listed in the two clusters are all different. In certain embodiments, the patient data set comprises or is derived from gene expression measurements data of all genes listed within each of one or more gene clusters selected from the significant gene clusters of the gene set, from the biological sample from the patient. In certain embodiments, the patient data set comprises or is derived from gene expression measurements data of an effective number of genes selected from the genes listed within each of one or more gene clusters selected from the significant gene clusters of the gene set, from the biological sample from the patient, wherein number of genes selected from different selected gene clusters may be different or the same. The significant gene clusters of the gene set can be the significant gene clusters of step (d) as described herein (e.g., in Detailed description, Section I). In certain embodiments, all the significant gene clusters of the gene set are selected. In certain embodiments, the patient data set comprises or is derived from gene expression measurements data of at least 2 to all, or any value or range there between, genes selected from the genes listed within each significant gene clusters of the gene set, from the biological sample from the patient, wherein number of genes selected from different significant gene clusters may be different or same. In certain embodiments, the patient data set comprises or is derived from gene expression measurements data of all genes selected from each significant gene clusters of the gene set, from the biological sample from the patient. In certain embodiments, the patient data set comprises or is derived from gene expression measurements data of an effective number of genes selected from the genes listed within each significant gene clusters of the gene set, from the biological sample from the patient, wherein number of genes selected from different significant gene clusters may be different or same. In certain embodiments, the patient data set comprises Module eigengenes (MEs). In certain embodiments, the MEs can be of the gene modules formed based on the genes selected from the each selected gene clusters. In certain embodiments, the MEs can be of the gene modules formed based on the effective number of genes selected from the each selected gene clusters. In certain embodiments, the effective number of genes selected from each selected gene cluster can form a gene module (i.e., the gene module contains the selected effective number of genes), effective number of genes selected from different selected gene clusters can form different gene modules, and the patient data set contains MEs of each gene module formed. In certain embodiments, MEs can be of gene modules formed based on the selected gene clusters, where each selected gene cluster forms a gene module (e.g., the gene module contains all the gene listed within the selected gene cluster), and different selected gene clusters form different gene modules, and the patient data set contains MEs of each gene module formed. In certain embodiments, the MEs can be analyzed to classify the lupus disease state of the patient. In certain embodiments, the MEs can be analyzed to classify whether the patient has type 1 lupus, type 2 lupus, or type 1-2 lupus. In certain embodiments, the MEs can be analyzed to classify whether the patient has type 1 lupus, or type 2 lupus. In certain embodiments, analyzing the patient data set includes analyzing enrichment of the gene modules formed based on the gene clusters selected from the significant gene clusters, (e.g., as described in this paragraph) in the biological sample, e.g., enrichment of the gene modules in the biological sample can be analyzed to classify the lupus disease state of the patient. In certain embodiments, the genes selected from each selected gene cluster can form a gene module (i.e., the gene module contains the selected genes), and genes selected from different selected gene clusters can form different gene modules. In certain embodiments, the effective number of genes selected from each selected gene cluster can form a gene module (i.e., the gene module contains the selected effective number of genes), and effective number of genes selected from different selected gene clusters can form different gene modules. Enrichment of the gene modules in the biological sample can be measured with respect to a reference data set, such as a reference data set described herein and/or in the Examples. Enrichment of the gene modules in the biological sample can be determined using any suitable method including but not limited to gene set variation analysis (GSVA), Z-score, gene set enrichment analysis (GSEA), enrichment algorithm, differential expression analysis, log 2 expression analysis, or any combination thereof.

In certain embodiments, the patient data set comprises or is derived from gene expression measurements data of at least 2 to all, or any value or range there between, genes selected from the genes listed in each of one or more Tables selected from Tables 17-1 to 17-30, from the biological sample from the patient, wherein number of genes selected from different selected Tables may be different or the same. In certain embodiments, the patient data set comprises or is derived from gene expression measurements data of all genes selected from the genes listed in each of one or more Tables selected from Tables 17-1 to 17-30. In certain embodiments, the patient data set comprises or is derived from gene expression measurements data of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, or all, or any value or range there between, genes selected from the genes listed in each of one or more Tables selected from Tables 17-1 to 17-30, from the biological sample from the patient, wherein number of genes selected from different selected Tables may be different or same. In certain embodiments, the patient data set comprises or is derived from gene expression measurements data of an effective number of genes selected from the genes listed in each of one or more Tables selected from Tables 17-1 to 17-30, from the biological sample from the patient, wherein number of genes selected from different selected Tables may be different or same. In certain embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or any range there between Tables from Tables 17-1 to 17-30 are selected. In certain embodiments, at least 1 Table is selected from Tables 17-1 to 17-30, e.g., the patient data set comprises or is derived from gene expression measurements data of at least 2, an effective number and/or all genes selected from the genes listed in at least one Table selected from Tables 17-1 to 17-30, from the biological sample from the patient. In certain embodiments, at least 2 Tables are selected from Tables 17-1 to 17-30. In certain embodiments, at least 3 Tables are selected from Tables 17-1 to 17-30. In certain embodiments, at least 4 Tables are selected from Tables 17-1 to 17-30. In certain embodiments, at least 5 Tables are selected from Tables 17-1 to 17-30. In certain embodiments, at least 6 Tables are selected from Tables 17-1 to 17-30. In certain embodiments, at least 7 Tables are selected from Tables 17-1 to 17-30. In certain embodiments, at least 8 Tables are selected from Tables 17-1 to 17-30. In certain embodiments, at least 9 Tables are selected from Tables 17-1 to 17-30. In certain embodiments, at least 10 Tables are selected from Tables 17-1 to 17-30. In certain embodiments, at least 11 Tables are selected from Tables 17-1 to 17-30. In certain embodiments, at least 12 Tables are selected from Tables 17-1 to 17-30. In certain embodiments, at least 13 Tables are selected from Tables 17-1 to 17-30. In certain embodiments, at least 14 Tables are selected from Tables 17-1 to 17-30. In certain embodiments, at least 15 Tables are selected from Tables 17-1 to 17-30. In certain embodiments, at least 16 Tables are selected from Tables 17-1 to 17-30. In certain embodiments, at least 17 Tables are selected from Tables 17-1 to 17-30. In certain embodiments, at least 18 Tables are selected from Tables 17-1 to 17-30. In certain embodiments, at least 19 Tables are selected from Tables 17-1 to 17-30. In certain embodiments, at least 20 Tables are selected from Tables 17-1 to 17-30. In certain embodiments, at least 21 Tables are selected from Tables 17-1 to 17-30. In certain embodiments, at least 22 Tables are selected from Tables 17-1 to 17-30. In certain embodiments, at least 23 Tables are selected from Tables 17-1 to 17-30. In certain embodiments, at least 24 Tables are selected from Tables 17-1 to 17-30. In certain embodiments, at least 25 Tables are selected from Tables 17-1 to 17-30. In certain embodiments, at least 26 Tables are selected from Tables 17-1 to 17-30. In certain embodiments, at least 27 Tables are selected from Tables 17-1 to 17-30. In certain embodiments, at least 28 Tables are selected from Tables 17-1 to 17-30. In certain embodiments, at least 29 Tables are selected from Tables 17-1 to 17-30. In certain embodiments, Tables 17-1 to 17-30 are selected. In certain embodiments, the one or more Tables are selected from Tables 17-1 to 17-30, based on contribution of the Table (e.g., of the genes selected from the Table) in the lupus disease state classification of the patient. Contribution of a Table (e.g., of the genes selected from the Table) in the lupus disease state classification can be calculated using a method as described below. In certain embodiments, at least minimum number of Tables are selected from Tables 17-1 to 17-30, and an effective number of genes from each selected Table are selected, such that the method classifies the lupus disease state of the patient with desired accuracy, sensitivity, specificity, positive predictive value and/or negative predictive value, such as at least 85% accuracy, at least 85% sensitivity, at least 85% specificity, at least 85% positive predictive value and/or at least 85% negative predictive value. In certain embodiments, for each selected Table from the Tables 17-1 to 17-30, the patient data set comprises or is derived from gene expression measurement data of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 or all genes selected from the genes listed in the selected Table, wherein the number of genes selected from different selected Tables can be the same or different. In certain embodiments, for each selected Table from the Tables 17-1 to 17-30, the patient data set comprises or is derived from gene expression measurement data of all the genes listed in the selected Table. In certain embodiments, for each selected Table from Tables 17-1 to 17-30, the patient data set comprises or is derived from gene expression measurement data of an effective number of genes selected from the genes listed in the selected Table, wherein the number of genes selected from different selected Tables can be the same or different. As non-limiting example, 3 Tables, such as Table 17-1, Table 17-2 and Table 17-3 are selected from Tables: 17-1 to 17-30, the patient data set comprises or is derived from gene expression measurement data of at least 2 genes, effective number of genes, and/or all genes selected from the genes listed in each of the selected Tables, e.g., at least 2 genes, effective number of genes, and/or all genes selected from the genes listed in Table 17-1; at least 2 genes, effective number of genes, and/or all genes selected from the genes listed in Table 17-2; and at least 2 genes, effective number of genes, and/or all genes of genes selected from the genes listed in Table 17-3, wherein the number of genes selected from Tables 17-1, 17-2, and 17-3 can be the same or different. In certain embodiments, the at least 2 genes (e.g., expression measurement data of which the patient data set is comprised of or derived from) may or may not include gene(s) that are not listed in Tables 17-1 to 17-30. In certain embodiments, the at least 2 genes do not include any gene that is not listed in Tables 17-1 to 17-30. In certain embodiments, the patient data set comprises or is derived from gene expression measurements data of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, or all, or any value or range there between, genes selected from the genes listed within each of Tables 17-1 to 17-30, from the biological sample from the patient, wherein number of genes selected from different Tables may be different or same, e.g., the patient data set comprises or is derived from gene expression measurements data of at least 2 genes from Table 17-1 (i.e., at least 2 genes are selected from the genes listed in Table 17-1), at least 2 genes from Table 17-2, at least 2 genes from Table 17-3, at least 2 genes from Table 17-4, at least 2 genes from Table 17-5, at least 2 genes from Table 17-6, at least 2 genes from Table 17-7, at least 2 genes from Table 17-8, at least 2 genes from Table 17-9, at least 2 genes from Table 17-10, at least 2 genes from Table 17-11, at least 2 genes from Table 17-12, at least 2 genes from Table 17-13, at least 2 genes from Table 17-14, at least 2 genes from Table 17-15, at least 2 genes from Table 17-16, at least 2 genes from Table 17-17, at least 2 genes from Table 17-18, at least 2 genes from Table 17-19, at least 2 genes from Table 17-20, at least 2 genes from Table 17-21, at least 2 genes from Table 17-22, at least 2 genes from Table 17-23, at least 2 genes from Table 17-24, at least 2 genes from Table 17-25, at least 2 genes from Table 17-26, at least 2 genes from Table 17-27, at least 2 genes from Table 17-28, at least 2 genes from Table 17-29, and at least 2 genes from Table 17-30. In certain embodiments, the patient data set comprises or is derived from gene expression measurements data of effective number of genes selected from the genes listed within each of Tables 17-1 to 17-30, from the biological sample from the patient, wherein number of genes selected from different Tables may be different or same. In certain embodiments, the patient data set comprises the MEs, wherein the MEs can be of gene modules formed based on (e.g., comprising) the genes selected (e.g., at least 2 genes, effective number of genes, and/or all genes) from each Table selected from Tables 17-1 to 17-30, wherein the genes selected from each selected Table forms a gene module. In certain embodiments, the patient data set comprises the MEs, wherein the MEs can be of gene modules formed based on the effective number of genes selected from each Table selected from Tables 17-1 to 17-30, wherein genes selected from each selected Table forms a gene module. As a non-limiting example Tables 17-1, 17-2 and 17-3, are selected from Tables 17-1 to 17-30, wherein an effective number of genes selected from Table 17-1 form a gene module (say gene module 1), an effective number of genes selected from Table 17-2 form another gene module (say gene module 2), and an effective number of genes selected from Table 17-3 form another gene module (say gene module 3), and the patient data set comprises ME of gene module 1, ME of gene module 2, and ME of gene module 3. In certain embodiments, analyzing the patient data set includes analyzing the MEs (e.g., of the gene modules formed based on the Tables selected from Tables 17-1 to 17-30) to classify the lupus disease state of the patient, e.g., the MEs can be analyzed to classify the lupus disease state of the patient. In certain embodiments, the MEs can be analyzed to classify whether the patient has type 1 lupus, type 2 lupus, or type 1-2 lupus. In certain embodiments, the MEs can be analyzed to classify whether the patient has type 1 lupus, or type 2 lupus. In certain embodiments, analyzing the patient data set includes analyzing enrichment of the gene modules formed based on the Tables selected from Tables 17-1 to 17-30, (e.g., as described in this paragraph) in the biological sample, e.g., enrichment of the gene modules in the biological sample can be analyzed to classify the lupus disease state of the patient. In certain embodiments, the genes selected from each selected Table can form a gene module (i.e., the gene module contains the selected genes). In certain embodiments, the effective number of genes selected from each selected Table can form a gene module (i.e., the gene module contains the selected effective number of genes). Enrichment of the gene modules in the biological sample can be measured with respect to a reference data set, such as a reference data set described herein and/or in the Examples. Enrichment of the gene modules in the biological sample can be determined using any suitable method including but not limited to gene set variation analysis (GSVA), Z-score, gene set enrichment analysis (GSEA), enrichment algorithm, differential expression analysis, log 2 expression analysis, or any combination thereof. As a non-limiting example, Tables 17-1, 17-2 and 17-3, are selected from Tables 17-1 to 17-30, wherein an effective number of genes selected from Table 17-1 form a gene module (say gene module 1), an effective number of genes selected from Table 17-2 form another gene module (say gene module 2), and an effective number of genes selected from Table 17-3 form another gene module (say gene module 3), and enrichment of gene module 1, gene module 2 and gene module 3 in the biological sample can be analyzed to classify the lupus disease state of the patient.

In certain embodiments, the patient data set comprises or is derived from gene expression measurements data of at least 2 to all, or any value or range there between, genes selected from the genes listed within each of one or more Tables selected from Tables 24-1 to 24-30, from the biological sample from the patient, wherein number of genes selected from different selected Tables may be different or the same. In certain embodiments, the patient data set comprises or is derived from gene expression measurements data of all genes selected from the genes listed within each of one or more Tables selected from Tables 24-1 to 24-30. In certain embodiments, the patient data set comprises or is derived from gene expression measurements data of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, or all, or any value or range there between, genes selected from the genes listed within each of one or more Tables selected from Tables 24-1 to 24-30, from the biological sample from the patient, wherein number of genes selected from different selected Tables may be different or same. In certain embodiments, the patient data set comprises or is derived from gene expression measurements data of an effective number of genes selected from the genes listed within each of one or more Tables selected from Tables 24-1 to 24-30, from the biological sample from the patient, wherein number of genes selected from different selected Tables may be different or same. In certain embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or any range there between Tables from Tables 24-1 to 24-30 are selected. In certain embodiments, at least 1 Table is selected from Tables 24-1 to 24-30, e.g., the patient data set comprises or is derived from gene expression measurements data of at least 2, an effective number and/or all, genes selected from the genes listed within at least one Table selected from Tables 24-1 to 24-30, from the biological sample from the patient. In certain embodiments, at least 2 Tables are selected from Tables 24-1 to 24-30. In certain embodiments, at least 3 Tables are selected from Tables 24-1 to 24-30. In certain embodiments, at least 4 Tables are selected from Tables 24-1 to 24-30. In certain embodiments, at least 5 Tables are selected from Tables 24-1 to 24-30. In certain embodiments, at least 6 Tables are selected from Tables 24-1 to 24-30. In certain embodiments, at least 7 Tables are selected from Tables 24-1 to 24-30. In certain embodiments, at least 8 Tables are selected from Tables 24-1 to 24-30. In certain embodiments, at least 9 Tables are selected from Tables 24-1 to 24-30. In certain embodiments, at least 10 Tables are selected from Tables 24-1 to 24-30. In certain embodiments, at least 11 Tables are selected from Tables 24-1 to 24-30. In certain embodiments, at least 12 Tables are selected from Tables 24-1 to 24-30. In certain embodiments, at least 13 Tables are selected from Tables 24-1 to 24-30. In certain embodiments, at least 14 Tables are selected from 24-1 to 24-30. In certain embodiments, at least 15 Tables are selected from Tables 24-1 to 24-30. In certain embodiments, at least 16 Tables are selected from Tables 24-1 to 24-30. In certain embodiments, at least 17 Tables are selected from Tables 24-1 to 24-30. In certain embodiments, at least 18 Tables are selected from Tables 24-1 to 24-30. In certain embodiments, at least 19 Tables are selected from Tables 24-1 to 24-30. In certain embodiments, at least 20 Tables are selected from Tables 24-1 to 24-30. In certain embodiments, at least 21 Tables are selected from Tables 24-1 to 24-30. In certain embodiments, at least 22 Tables are selected from Tables 24-1 to 24-30. In certain embodiments, at least 23 Tables are selected from Tables 24-1 to 24-30. In certain embodiments, at least 24 Tables are selected from Tables 24-1 to 24-30. In certain embodiments, at least 25 Tables are selected from Tables 24-1 to 24-30. In certain embodiments, at least 26 Tables are selected from Tables 24-1 to 24-30. In certain embodiments, at least 27 Tables are selected from Tables 24-1 to 24-30. In certain embodiments, at least 28 Tables are selected from Tables 24-1 to 24-30. In certain embodiments, at least 29 Tables are selected from Tables 24-1 to 24-30. In certain embodiments, Tables 24-1 to 24-30 are selected. In certain embodiments, the one or more Tables are selected from Tables 24-1 to 24-30, based on contribution of the Table/Module (e.g., of the genes selected from the Table) in the lupus disease state classification of the patient. In certain embodiments, the Tables are selected from Tables 24-1 to 24-30 based on absolute coefficient value of the module/Table, shown in FIG. 42 and Table 24-1 to 24-30, wherein the one or more Tables selected comprises Tables with X highest absolute coefficient values (modulus of coefficient values), where X is an integer from 1 to 30. In a non-limiting example, X is 3, i.e., the one or more Tables selected from Tables 24-1 to 24-30 comprise Tables with 3 highest absolute coefficient values. i.e., Table 24-15 (module 6.37.240), Table 24-14 (6.36.236), and Table 24-17 (6.42.256), are selected. The absolute coefficient value of a Table/Module can be a measure of the contribution of the Table/Module (e.g., of the genes selected from the Table) in the lupus disease state classification of the patient. In certain embodiments, X is 1. In certain embodiments, X is 2. In certain embodiments, X is 3. In certain embodiments, X is 4. In certain embodiments, X is 5. In certain embodiments, X is 6. In certain embodiments, X is 7. In certain embodiments, X is 8. In certain embodiments, X is 9. In certain embodiments, X is 10. In certain embodiments, X is 11. In certain embodiments, X is 12. In certain embodiments, X is 13. In certain embodiments, X is 14. In certain embodiments, X is 15. In certain embodiments, X is 16. In certain embodiments, X is 17. In certain embodiments, X is 18. In certain embodiments, X is 19. In certain embodiments, X is 20. In certain embodiments, X is 21. In certain embodiments, X is 22. In certain embodiments, X is 23. In certain embodiments, X is 24. In certain embodiments, X is 25. In certain embodiments, X is 26. In certain embodiments, X is 27. In certain embodiments, X is 28. In certain embodiments, X is 29. In certain embodiments, X is 30. In certain embodiments, at least minimum number of Tables are selected from Tables 24-1 to 24-30, and an effective number of genes from each selected Tables are selected, such that the method classifies the lupus disease state of the patient with desired accuracy, sensitivity, specificity, positive predictive value and/or negative predictive value, such as at least 85% accuracy, at least 85% sensitivity, at least 85% specificity, at least 85% positive predictive value and/or at least 85% negative predictive value. In certain embodiments, for each selected Table from the Tables 24-1 to 24-30, the patient data set comprises or is derived from gene expression measurement data of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 or all genes selected from the genes listed in the selected Table, wherein the number of genes selected from different selected Tables can be the same or different. In certain embodiments, for each selected Table from the Tables 24-1 to 24-30, the patient data set comprises or is derived from gene expression measurement data of all the genes listed in the selected Table. In certain embodiments, for each selected Table from Tables 24-1 to 24-30, the patient data set comprises or is derived from gene expression measurement data of an effective number of genes selected from the genes listed in the selected Table, wherein the number of genes selected from different selected Tables can be the same or different. As non-limiting example, 3 Tables, such as Table 24-1, Table 24-2 and Table 24-3 are selected from Tables: 24-1 to 24-30, the patient data set comprises or is derived from gene expression measurement data of at least 2 genes, effective number of genes, and/or all genes selected from the genes listed in each of the selected Tables, e.g., at least 2 genes, effective number of genes, and/or all genes selected from the genes listed in Table 24-1; at least 2 genes, effective number of genes, and/or all genes selected from the genes listed in Table 24-2; and at least 2 genes, effective number of genes, and/or all genes of genes selected from the genes listed in Table 24-3, wherein the number of genes selected from Tables 24-1, 24-2, and 24-3 can be the same or different. In certain embodiments, the at least 2 genes (e.g., expression measurement data of which the patient data set is comprised of or derived from) may or may not include gene(s) that are not listed in Tables 24-1 to 24-30. In certain embodiments, the at least 2 genes do not include any gene that is not listed in Tables 24-1 to 24-30. In certain embodiments, the patient data set comprises or is derived from gene expression measurements data of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, or all, or any value or range there between, genes selected from the genes listed within each of Tables 24-1 to 24-30, from the biological sample from the patient, wherein number of genes selected from different Tables may be different or same, e.g., the patient data set comprises or is derived from gene expression measurements data of at least 2 genes from Table 24-1 (i.e., at least 2 genes selected from the genes listed in Table 24-1), at least 2 genes from Table 24-2, at least 2 genes from Table 24-3, at least 2 genes from Table 24-4, at least 2 genes from Table 24-5, at least 2 genes from Table 24-6, at least 2 genes from Table 24-7, at least 2 genes from Table 24-8, at least 2 genes from Table 24-9, at least 2 genes from Table 24-10, at least 2 genes from Table 24-11, at least 2 genes from Table 24-12, at least 2 genes from Table 24-13, at least 2 genes from Table 24-14, at least 2 genes from Table 24-15, at least 2 genes from Table 24-16, at least 2 genes from Table 24-17, at least 2 genes from Table 24-18, at least 2 genes from Table 24-19, at least 2 genes from Table 24-20, at least 2 genes from Table 24-21, at least 2 genes from Table 24-22, at least 2 genes from Table 24-23, at least 2 genes from Table 24-24, at least 2 genes from Table 25-25, at least 2 genes from Table 24-26, at least 2 genes from Table 24-27, at least 2 genes from Table 24-28, at least 2 genes from Table 24-29, and at least 2 genes from Table 24-30. In certain embodiments, the patient data set comprises or is derived from gene expression measurements data of effective number of genes selected from the genes listed within each of Tables 24-1 to 24-30, from the biological sample from the patient, wherein number of genes selected from different Tables may be different or same. In certain embodiments, the patient data set comprises the MEs, wherein the MEs can be of gene modules formed based on (e.g., comprising) genes selected (e.g., at least 2 genes, effective number of genes, and/or all genes) from each Table selected from Tables 24-1 to 24-30, wherein the genes selected from each selected Table forms a gene module. In certain embodiments, the patient data set comprises the MEs, wherein the MEs can be of gene modules formed based on the effective number of genes selected from each Table selected from Tables 24-1 to 24-30, wherein genes selected from each selected Table forms a gene module. As a non-limiting example Tables 24-1, 24-2 and 24-3, are selected from Tables 24-1 to 24-30, wherein an effective number of genes selected from Table 24-1 form a gene module (say gene module 1), an effective number of genes selected from Table 24-2 form another gene module (say gene module 2), and an effective number of genes selected from Table 24-3 form another gene module (say gene module 3), and the patient data set comprises ME of gene module 1, ME of gene module 2, and ME of gene module 3. In certain embodiments, analyzing the patient data set includes analyzing the MEs (e.g., of the gene modules formed based on the Tables selected from Tables 24-1 to 24-30) to classify the lupus disease state of the patient, e.g., the MEs can be analyzed to classify the lupus disease state of the patient. In certain embodiments, the MEs can be analyzed to classify whether the patient has type 1 lupus, type 2 lupus, or type 1-2 lupus. In certain embodiments, the MEs can be analyzed to classify whether the patient has type 1 lupus, or type 2 lupus. In certain embodiments, analyzing the patient data set includes analyzing enrichment of the gene modules formed based on the Tables selected from Tables 24-1 to 24-30, (e.g., as described in this paragraph) in the biological sample, e.g., enrichment of the gene modules in the biological sample can be analyzed to classify the lupus disease state of the patient. Enrichment of the gene modules in the biological sample can be measured with respect to a reference data set, such as a reference data set described herein and/or in the Examples. Enrichment of the gene modules in the biological sample can be determined using any suitable method including but not limited to gene set variation analysis (GSVA), Z-score, gene set enrichment analysis (GSEA), enrichment algorithm, differential expression analysis, log 2 expression analysis, or any combination thereof. In certain embodiments, the genes selected from each selected Table can form a gene module (i.e., the gene module contains the selected genes). In certain embodiments, the effective number of genes selected from each selected Table can form a gene module (i.e., the gene module contains the selected effective number of genes). As a non-limiting example Tables 24-1, 24-2 and 24-3, are selected from Tables 24-1 to 24-30, wherein an effective number of genes selected from Table 24-1 form a gene module (say gene module 1), an effective number of genes selected from Table 24-2 form another gene module (say gene module 2), and an effective number of genes selected from Table 24-3 form another gene module (say gene module 3), and enrichment of gene module 1, gene module 2 and gene module 3 in the biological sample can be analyzed to classify the lupus disease state of the patient.

The patient data set can be generated from the biological sample obtained or derived from the patient. For example, nucleic acid molecules of the patient in the biological sample can be assessed to obtain the patient data set. In certain embodiments, the gene expression measurement from the biological sample of the selected genes can be performed using any suitable method known to those of skill in the art including but not limited to DNA sequencing, RNA sequencing, microarray, RNA-Seq, qPCR, northern blotting, fluorescent in situ hybridization, serial analysis of gene expression, tiling arrays or any combination thereof, to obtain the patient data set. In certain embodiments, the gene expression measurement from the biological sample of the selected genes can be performed using RNA-Seq. In certain embodiments, the gene expression measurement of the biological sample of the selected genes can be performed using microarray. In certain embodiments, the patient data set can be derived from the gene expression measurement data of the biological sample, wherein the gene expression measurement data is analyzed using a suitable data analysis tool including but not limited to a BIG-C™ big data analysis tool, an I-Scope™ big data analysis tool, a T-Scope™ big data analysis tool, a CellScan big data analysis tool, an MS (Molecular Signature) Scoring™ analysis tool, gene set variation analysis (GSVA), Z-score, gene set enrichment analysis (GSEA), enrichment algorithm, multiscale embedded gene co-expression network analysis (MEGENA), weighted gene co-expression network analysis (WGCNA), differential expression analysis, log 2 expression analysis, or any combination thereof, to obtain the patient dataset. In certain embodiments, the gene expression measurement data of the biological sample can be analyzed using GSVA, to obtain the patient data set. In certain embodiments, the method comprises obtaining and/or deriving the biological sample from the patient. In certain embodiments, the method comprises analyzing the biological sample to obtain the gene expression measurement data from the biological sample. In certain embodiments, the method comprises analyzing the gene expression measurements to obtain the patient dataset. In certain embodiments, the method comprises obtaining and/or deriving the biological sample from the patient, and/or analyzing the biological sample to obtain the gene expression measurement data from the biological sample. In certain embodiments, the method comprises obtaining and/or deriving the biological sample from the patient, analyzing the biological sample to obtain the gene expression measurements data from the biological sample, and/or analyzing the gene expression measurements data, to obtain the patient dataset.

In certain embodiments, the patient data set is derived from the gene expression measurements data using a suitable data analysis tool. In certain embodiments, the data analysis tool can comprise gene set variation analysis (GSVA), gene set enrichment analysis (GSEA), enrichment algorithm, multiscale embedded gene co-expression network analysis (MEGENA), weighted gene co-expression network analysis (WGCNA), differential expression analysis, Z-score, log 2 expression analysis, or any combination thereof. In certain embodiments, the patient data set is derived from the gene expression measurements data using GSVA. In certain embodiments, the patient dataset is derived from the gene expression measurements data using GSVA, and comprises one or more GSVA scores of the patient. In certain embodiments, analyzing the patient dataset includes analyzing the one or more GSVA scores of the patient. In certain embodiments, the one or more GSVA scores of the patient can be analyzed to classify the lupus disease state of the patient. In certain embodiments, the one or more GSVA scores of the patient can be analyzed to classify whether the patient has type 1 lupus, type 2 lupus, or type 1-2 lupus. In certain embodiments, the one or more GSVA scores of the patient can be analyzed to classify whether the patient has type 1 lupus, or type 2 lupus. In certain embodiments, the one or more GSVA scores are generated based on the one or more gene clusters selected from the significant gene clusters of the gene set (e.g., capable of classifying the lupus disease state of the patient), wherein for each selected gene cluster, at least one GSVA score of the patient is generated based on enrichment of expression of at least 2 genes selected from the genes listed within the selected gene cluster in the biological sample. The one or more GSVA scores comprise each generated at least one GSVA score. The at least 2 genes from a respective selected gene cluster, can form the input gene set for generating the at least one GSVA score based on the respective selected gene cluster, using GSVA. The at least 2 genes of the patient data set (e.g., gene expression measurements data of which the patient data set is comprised of or derived from) can comprise the at least 2 genes from each of the selected gene clusters. In certain embodiments, for each selected gene cluster, the at least one GSVA score of the patient based on the selected gene cluster, can be generated based on enrichment of expression of at least 2 to all, or any value or range there between, genes selected from the respective selected gene cluster, in the biological sample wherein number of genes selected from different selected gene clusters can be same or different. In certain embodiments, for each selected gene cluster, the at least one GSVA score of the patient based on the selected gene cluster, can be generated based on enrichment of expression of effective number of genes selected from the genes listed within the respective selected gene cluster in the biological sample, wherein number of genes selected from different selected gene clusters can be same or different. In certain embodiments, for each selected gene cluster, the at least one GSVA score of the patient based on the selected gene cluster, can be generated based on enrichment of expression of all the genes within the respective selected gene cluster in the biological sample. In certain embodiments, all the significant gene clusters of the gene set are selected. The genes selected from a respective selected gene cluster, can form the input gene set for generating the at least one GSVA score of the patient based on the respective selected gene cluster, using GSVA. In certain embodiments, one GSVA score is generated from each of the selected gene cluster. In certain embodiments, the one or more GSVA scores of the patient are generated based on the one or more Tables selected from Tables 17-1 to 17-30, wherein for each selected Table, at least one GSVA score of the patient is generated based on enrichment of expression of at least 2 genes selected from genes listed in the selected Table, in the biological sample. In certain embodiments, the one or more GSVA scores of the patient are generated based on the one or more Tables selected from Tables 24-1 to 24-30, wherein for each selected Table, at least one GSVA score of the patient is generated based on enrichment of expression of at least 2 genes selected from genes listed in the selected Table, in the biological sample. The one or more GSVA scores comprise the each generated at least one GSVA score. The at least 2 genes selected from a respective selected Table, can form the input gene set for generating the at least one GSVA score of the patient based on the respective selected Table, using GSVA. The at least 2 genes of the patient data set can comprise the at least 2 genes from each of the selected Table. In certain embodiments, for each selected Table, the at least one GSVA score of the patient based on the selected Table, can be generated based on enrichment of expression of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, or all, or any value or range there between, genes selected from the genes listed in the respective selected Table, in the biological sample, wherein number of genes selected from different selected Table can be same or different. In certain embodiments, for each selected Table, the at least one GSVA score of the patient based on the selected Table, can be generated based on enrichment of expression of effective number genes selected from the genes listed within the respective selected Table in the biological sample, wherein number of genes selected from different selected Tables can be same or different. In certain embodiments, for each selected Table, the at least one GSVA score of the patient based on the selected Table, can be generated based on enrichment of expression of all the genes listed within the respective selected Table, in the biological sample. The genes selected from a respective selected Table, can form the input gene set for generating the at least one GSVA score of the patient based on the respective selected Table, using GSVA. In certain embodiments, one GSVA score is generated based on each of the selected Table. In certain embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or any range or value therebetween Tables are selected from Tables 17-1 to 17-30. In certain embodiments, Tables 17-1 to 17-30 are selected. In certain embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or any range or value therebetween Tables are selected from Tables 24-1 to 24-30. In certain embodiments, Tables 24-1 to 24-30 are selected.

In certain embodiments, the patient data set comprises or is derived from gene expression measurements data of at least 2 to all, or any value or range there between, genes selected from the genes within the gene modules listed in Tables 20 to 23. The gene modules listed in Tables 20 to 23 can identified using DGCA.

In certain embodiments, analyzing the patient data set includes providing the patient data set as an input to a machine-learning model trained to generate an inference based on the patient data set. The method can classify the lupus disease state of the patient based on the inference. The patient data set can be a patient data set described herein. In certain embodiments, a patient data set comprising or is derived from gene expression measurement data of 2 or more genes selected from the genes listed in Tables 17-1 to 17-30 can be provided as an input to the machine learning model. In certain embodiments, a patient data set comprising or is derived from gene expression measurement data of 2 or more genes selected from the genes listed in Tables 24-1 to 24-30 can be provided as an input to the machine learning model. In certain embodiments, analyzing the patient data set includes providing the patient data set as an input to a machine-learning model trained to generate an inference of whether the patient data set is indicative of the patient having type 1 lupus, type 2 lupus, or type 1-2 lupus, and the method classify the lupus disease state of the patient based on the inference. In certain embodiments, analyzing the patient data set includes providing the patient data set as an input to a machine-learning model trained to generate an inference of whether the patient data set is indicative of the patient having type 1 lupus, type 2 lupus, or type 1-2 lupus, and the method classify the lupus disease state of the patient based on the inference, wherein the patient data set comprises or is derived from gene expression measurement data of 2 or more genes selected from the genes listed in Tables 17-1 to 17-30. In certain embodiments, analyzing the patient data set includes providing the patient data set as an input to a machine-learning model trained to generate an inference of whether the patient data set is indicative of the patient having type 1 lupus, type 2 lupus, or type 1-2 lupus, and the method classify the lupus disease state of the patient based on the inference, wherein the patient data set comprises or is derived from gene expression measurement data of 2 or more genes selected from the genes listed in Tables 24-1 to 24-30. In certain embodiments, analyzing the patient data set includes providing the patient data set as an input to a machine-learning model trained to generate an inference of whether the patient data set is indicative of the patient having type 1 lupus, or type 2 lupus. In certain embodiments, analyzing the patient data set includes providing the patient data set as an input to a machine-learning model trained to generate an inference of whether the patient data set is indicative of the patient having type 1 lupus, or type 2 lupus, wherein the patient data set comprises or is derived from gene expression measurement data of 2 or more genes selected from the genes listed in Tables 17-1 to 17-30. In certain embodiments, analyzing the patient data set includes providing the patient data set as an input to a machine-learning model trained to generate an inference of whether the patient data set is indicative of the patient having type 1 lupus, or type 2 lupus, wherein the patient data set comprises or is derived from gene expression measurement data of 2 or more genes selected from the genes listed in Tables 24-1 to 24-30. The machine-learning model generates the inference based at least on the patient dataset. The inference can be the patient data set is indicative of the patient having type 1 lupus, wherein the method classify that the patient has type 1 lupus. The inference can be the patient data set is indicative of the patient having type 2 lupus, wherein the method classify that the patient has type 2 lupus. The inference can be the patient data set is indicative of the patient having type 1-2 lupus, wherein the method classify that the patient has type 1-2 lupus. In certain embodiments, the patient data set comprises the MEs, and the machine learning model generate the inference based at least on the MEs. In certain embodiments, the machine learning model is trained (e.g., has been trained) to generate the inference of whether the patient data set comprising the MEs is indicative of the patient having type 1 lupus, type 2 lupus, or type 1-2 lupus. In certain embodiments, the machine learning model is trained (e.g., has been trained) to generate the inference of whether the patient data set comprising the MEs is indicative of the patient having type 1 lupus, or type 2 lupus. In certain embodiments, the patient data set comprises the one or more GSVA scores of the patient, and the machine learning model generate the inference based at least on the one or more GSVA scores. In certain embodiments, the machine learning model is trained (e.g., has been trained) to generate the inference of whether the patient data set comprising the one or more GSVA scores of patient is indicative of the patient having type 1 lupus, type 2 lupus, or type 1-2 lupus. In certain embodiments, the machine learning model is trained (e.g., has been trained) to generate the inference of whether the patient data set comprising the one or more GSVA scores of patient is indicative of the patient having type 1 lupus, or type 2 lupus.

The machine-learning model, can generate the inference, based on comparing the patient data set to a reference data set. The reference data set can comprise and/or be derived from gene expression measurements data from a plurality of reference biological samples. The plurality of reference biological samples can be obtained or derived from a plurality of reference subjects. In certain embodiments, the reference biological samples comprise i) a first plurality of reference biological samples obtained or derived from reference subjects having type 1 lupus, ii) a second plurality of reference biological samples obtained or derived from reference subjects having type 2 lupus, and/or iii) a third plurality of reference biological samples obtained or derived from reference subjects having type 1-2 lupus. In certain embodiments, the reference biological samples comprise i) a first plurality of reference biological samples obtained or derived from reference subjects having type 1 lupus, and ii) a second plurality of reference biological samples obtained or derived from reference subjects having type 2 lupus. In certain embodiments, the reference data set can be a data set described herein, and/or in the Examples. The genes, expression measurements of which the reference dataset is comprised of or derived from, and the genes, expression measurements of which the patient dataset is comprised of or derived from, are at least partially same. In certain embodiments, the genes, expression measurements of which the reference dataset is comprised of or derived from, and the genes, expression measurements of which the patient dataset is comprised of or derived from, are the same. The machine learning model can be trained (e.g., can be obtained by training) with the reference data set. In certain embodiments, the machine learning model can be trained using a method, and/or data set as described in the examples. The one or more GSVA scores of the patient can be generated based on comparing the patient data set to the reference data set, wherein enrichment of genes in the biological sample from the patient can be determined based on comparing the gene expression measurements data from the biological sample, with the gene expression measurements data from the plurality of reference biological samples.

The inference from the machine learning model can include a confidence value between 0 and 1, such as, 0, 0.1, 0.2, 0.3, 0.4, 0.5, 0.6, 0.7, 0.8, 0.9 or 1, or any value or ranges there between. Higher confidence values may be correlated with a higher likelihood. In certain embodiments, the inference from the machine learning model can include a confidence value between 0 and 1, such as, 0, 0.1, 0.2, 0.3, 0.4, 0.5, 0.6, 0.7, 0.8, 0.9 or 1, or any value or ranges there between that the patient has type 1 lupus. In certain embodiments, the inference from the machine learning model can include a confidence value between 0 and 1, such as, 0, 0.1, 0.2, 0.3, 0.4, 0.5, 0.6, 0.7, 0.8, 0.9 or 1, or any value or ranges there between that the patient has type 2 lupus. In certain embodiments, the inference from the machine learning model can include a confidence value between 0 and 1, such as, 0, 0.1, 0.2, 0.3, 0.4, 0.5, 0.6, 0.7, 0.8, 0.9 or 1, or any value or ranges there between that the patient has type 1-2 lupus.

In certain embodiments, the machine-learning model is trained (e.g., has been trained) using linear regression, logistic regression, Ridge regression, Lasso regression, elastic net (EN) regression, support vector machine (SVM), gradient boosted machine (GBM), k nearest neighbors (kNN), generalized linear model (GLM), naïve Bayes (NB) classifier, neural network, Random Forest (RF), deep learning algorithm, linear discriminant analysis (LDA), decision tree learning (DTREE), adaptive boosting (ADB), Classification and Regression Tree (CART), hierarchical clustering, or any combination thereof. The algorithm of the machine learning model can be the machine learning classifiers, e.g., mentioned in this paragraph. The machine learning classifiers (e.g., linear regression, LOG, Ridge regression, Lasso regression, EN regression, SVM, GBM, kNN, GLM, NB classifier, neural network, a RF, deep learning algorithm, LDA, DTREE, ADB, CART, and/or hierarchical clustering) can be trained to obtain the machine learning model. In certain embodiments, the machine learning model is trained using linear regression. In certain embodiments, the machine learning model is trained using logistic regression (LOG). In certain embodiments, the machine learning model is trained using Ridge regression. In certain embodiments, the machine learning model is trained using Lasso regression. In certain embodiments, the machine learning model is trained using elastic net (EN) regression. In certain embodiments, the machine learning model is trained using support vector machine (SVM). In certain embodiments, the machine learning model is trained using gradient boosted machine (GBM). In certain embodiments, the machine learning model is trained using k nearest neighbors (kNN). In certain embodiments, the machine learning model is trained using generalized linear model (GLM). In certain embodiments, the machine learning model is trained using naïve Bayes (NB) classifier. In certain embodiments, the machine learning model is trained using neural network. In certain embodiments, the machine learning model is trained using Random Forest (RF). In certain embodiments, the machine learning model is trained using deep learning algorithm, linear discriminant analysis (LDA). In certain embodiments, the machine learning model is trained using decision tree learning (DTREE). In certain embodiments, the machine learning model is trained using adaptive boosting (ADB). In certain embodiments, the machine learning model is trained using CART. In certain embodiments, the machine learning model is trained using hierarchical clustering.

In certain embodiments, the method further comprises receiving, as an output of the machine-learning model, the inference; and/or electronically outputting a report indicating the lupus disease state of the patient based on the inference.

In certain embodiments, the machine learning model has a Receiver operating characteristic (ROC) curve having an Area-Under-Curve (AUC) of at least about 0.80, at least about 0.85, at least about 0.90, at least about 0.91, at least about 0.92, at least about 0.93, at least about 0.94, at least about 0.95, at least about 0.96, at least about 0.97, at least about 0.98, at least about 0.99, or more than about 0.99.

In some embodiments, the machine learning model has a ROC curve with an AUC of about 0.85 to about 1. In some embodiments, the machine learning model has a ROC curve with an AUC of about 0.85 to about 0.9, about 0.85 to about 0.92, about 0.85 to about 0.94, about 0.85 to about 0.95, about 0.85 to about 0.96, about 0.85 to about 0.98, about 0.85 to about 0.99, about 0.85 to about 0.993, about 0.85 to about 0.995, about 0.85 to about 0.998, about 0.85 to about 1, about 0.9 to about 0.92, about 0.9 to about 0.94, about 0.9 to about 0.95, about 0.9 to about 0.96, about 0.9 to about 0.98, about 0.9 to about 0.99, about 0.9 to about 0.993, about 0.9 to about 0.995, about 0.9 to about 0.998, about 0.9 to about 1, about 0.92 to about 0.94, about 0.92 to about 0.95, about 0.92 to about 0.96, about 0.92 to about 0.98, about 0.92 to about 0.99, about 0.92 to about 0.993, about 0.92 to about 0.995, about 0.92 to about 0.998, about 0.92 to about 1, about 0.94 to about 0.95, about 0.94 to about 0.96, about 0.94 to about 0.98, about 0.94 to about 0.99, about 0.94 to about 0.993, about 0.94 to about 0.995, about 0.94 to about 0.998, about 0.94 to about 1, about 0.95 to about 0.96, about 0.95 to about 0.98, about 0.95 to about 0.99, about 0.95 to about 0.993, about 0.95 to about 0.995, about 0.95 to about 0.998, about 0.95 to about 1, about 0.96 to about 0.98, about 0.96 to about 0.99, about 0.96 to about 0.993, about 0.96 to about 0.995, about 0.96 to about 0.998, about 0.96 to about 1, about 0.98 to about 0.99, about 0.98 to about 0.993, about 0.98 to about 0.995, about 0.98 to about 0.998, about 0.98 to about 1, about 0.99 to about 0.993, about 0.99 to about 0.995, about 0.99 to about 0.998, about 0.99 to about 1, about 0.993 to about 0.995, about 0.993 to about 0.998, about 0.993 to about 1, about 0.995 to about 0.998, about 0.995 to about 1, or about 0.998 to about 1. In some embodiments, the machine learning model has a ROC curve with an AUC of about 0.85, about 0.9, about 0.92, about 0.94, about 0.95, about 0.96, about 0.98, about 0.99, about 0.993, about 0.995, about 0.998, or about 1. In some embodiments, the machine learning model has a ROC curve with an AUC of at least about 0.85, about 0.9, about 0.92, about 0.94, about 0.95, about 0.96, about 0.98, about 0.99, about 0.993, about 0.995, or about 0.998.

In certain embodiments, analyzing the patient data set comprises generating a lupus disease risk score of the patient based on the patient data set, wherein the lupus disease state of the patient is classified based on the lupus disease risk score. In certain embodiments, the method classify whether the patient has type 1 lupus or type 2 lupus based on the lupus disease risk score of the patient. The lupus disease risk score of the patient can be compared to a reference value to classify the lupus disease state of the patient. In certain embodiments, the method classify whether the patient has type 1 lupus or type 2 lupus, based on comparing the lupus disease risk score of the patient to a reference value, wherein lupus disease risk score at one side (e.g., higher or lower) of the reference value is indicative of the patient having type 1 lupus, and lupus disease risk score at the other side (e.g., lower or higher respectively) of the reference value is indicative of the patient having type 2 lupus. The lupus disease risk score of the patient can be generated based on the one or more GSVA scores of the patient. In certain embodiments, the lupus disease risk score of the patient is generated based on the one or more GSVA scores of the patient, wherein the one or more GSVA scores are generated based on the one or more Tables selected from Tables 24-1 to 24-30, and the method classify whether the patient has type 1 lupus or type 2 lupus, based on the lupus disease risk score. In certain embodiments, the lupus disease risk score of the patient is generated based on the one or more GSVA scores of the patient, wherein the one or more GSVA scores are generated based on the one or more Tables selected from Tables 17-1 to 17-30, and the method classify whether the patient has type 1 lupus or type 2 lupus, based on the lupus disease risk score. In certain embodiments, generating the disease risk score of the patient comprises developing one or more weighted GSVA scores of the patient from the one or more GSVA scores, and summing the one or more weighted GSVA scores to obtain the lupus disease risk score of the patient. For a respective GSVA score of the one or more GSVA scores, the weighted GSVA score is obtained by multiplying the respective GSVA score with its respective weight factor, wherein the respective weight factor is determined based on contribution of the set of genes from which the respective GSVA score is generated, on the classification of the lupus disease state of the patient. The set of genes from which the respective GSVA score is generated, are the genes, based on enrichment of expression of which in the biological sample, the respective GSVA score is generated. In certain particular embodiments, the one or more GSVA score of the patient is binarized, and the binarized GSVA scores are multiplied with the respective weight factors to obtain the weighted GSVA scores. In certain embodiments, binarizing the one or more GSVA scores includes replacing all GSVA scores (e.g., of the one or more GSVA scores) above a threshold value with a first value, and replacing all GSVA scores (e.g., of the one or more GSVA scores) equal to or below the threshold value with a second value. In certain particular embodiments, the threshold value is 0, the first value is 1, and the second value is 0. The one or more GSVA scores can be generated using a method as described above. In certain embodiments, the weight factors are calculated based on training a machine learning model, wherein the trained machine learning model can classify the lupus disease state of a patient based on the one or more GSVA scores of the patient. The gene sets from which the one or more GSVA scores are generated can be the input features of the machine learning model. The machine learning model can be trained using a reference data set, wherein the one or more GSVA scores of the reference patients of the reference data set, can be input feature values. The feature co-efficient of the features can be the weight factors. The weight factor for a respective GSVA score can the feature co-efficient of the gene set (e.g., a feature) from which the GSVA score is generated. The feature co-efficient, can be the average feature co-efficient of the iterations run. In certain embodiments, the machine learning model can be trained using Logistic regression with lasso or ridge penalty. In certain embodiments, the one or more GSVA scores are generated based on the Tables 24-1 to 24-30, and the weight factor for a respective GSVA score generated based on a respective Table is given in FIG. 42, and Table Tables 24-1 to 24-30. In certain embodiments, the one or more GSVA scores are generated based on the Tables 24-1 to 24-30, and the weight factor for a respective GSVA score generated based on a respective Table is given in FIG. 42 and Table Tables 24-1 to 24-30, wherein the lupus disease risk score of the type-1 lupus patients is <1, and the lupus disease risk score of the type-2 lupus patients is ≥1.

Selecting effective number of genes from a Table/cluster (e.g., a Table from Tables 17-1 to 17-30, or Tables 24-1 to 24-30) can include selecting at least minimum number of genes from the Table/cluster to obtain desired accuracy, sensitivity, specificity, positive predictive value, and/or negative predictive value in classification of the lupus disease state of the patient. Desired accuracy, sensitivity, specificity, positive predictive value, and/or negative predictive value, can be an accuracy, sensitivity, specificity, positive predictive value, and/or negative predictive value respectively described herein. In certain embodiments, the desired accuracy, sensitivity, specificity, positive predictive value, and/or negative predictive value, is at least 85%. In certain embodiments, the desired accuracy, sensitivity, specificity, positive predictive value, and/or negative predictive value, is at least 90%. In certain embodiments, the desired accuracy, sensitivity, specificity, positive predictive value, and/or negative predictive value, is at least 95%. Effective number of genes for a cluster/Table can be determined using adjusted rand index (ARI) method. For a respective Table/cluster determination of effective number of genes for the Table/cluster can be done by performing k-Means clustering on randomly selected gene subsets by standard interval based on the total number of genes of the respective Table/cluster. Similarity between two clustering can be measured by adjusted rand index (ARI). For example, the adjusted rand index (ARI) is calculated between K-Means cluster memberships from each randomly selected gene subset to the cluster memberships obtained using total number of genes of the respective Table/cluster. The higher the ARI, the similar the cluster memberships and lower the ARI the weaker the cluster memberships suggesting more genes are required. The ARI can calculated to determine the effective number of genes for each Table/cluster selected. In certain embodiments, selecting effective number of genes from a Table (e.g., a Table from Tables 17-1 to 17-30, or Tables 24-1 to 24-30) can include selecting at least 60%, 70%, 80%, 90%, or all genes from the Table. In certain embodiments, selecting effective number of genes from a Table (e.g., a Table from Tables 17-1 to 17-30, or Tables 24-1 to 24-30) can include selecting at least 60%, 70%, 80%, 90%, or all genes from the Table, where the Table contains 100 or more genes. In certain embodiments, selecting effective number of genes from a Table (e.g., a Table from Tables 17-1 to 17-30, or Tables 24-1 to 24-30) can include selecting at least 70%, genes from the Table, where the Table contains 100 or more genes. In certain embodiments, selecting effective number of genes from a Table (e.g., a Table from Tables 17-1 to 17-30, or Tables 24-1 to 24-30) can include selecting at least 80%, 90%, 95% or all genes from the Table, where the Table contains less than 100 genes. In certain embodiments, selecting effective number of genes from a Table (e.g., a Table from Tables 17-1 to 17-30, or Tables 24-1 to 24-30) can include selecting all genes from the Table, where the Table contains less than 100 genes. In certain embodiments, at least minimum number of Tables (e.g., from Tables 24-1 to 24-30, or 17-1 to 17-30, such as based on the absolute coefficient value of the Tables) and effective number of genes from each of the selected Tables are selected, such that the method classifies lupus disease state of the patient with desired accuracy, sensitivity, specificity, positive predictive value and/or negative predictive value, such as at least 85% accuracy, at least 85% sensitivity, at least 85% specificity, at least 85% positive predictive value and/or at least 85% negative predictive value.

In certain embodiment, the patient is at elevated risk of having lupus. In certain embodiment, the patient is suspected of having lupus. In certain embodiment, the patient is asymptomatic for lupus. In certain embodiment, the patient has lupus. In certain embodiment, the patient is at elevated risk of having of having inactive lupus. In certain embodiment, the patient is suspected of having inactive lupus. In certain embodiment, the patient is asymptomatic for inactive lupus. In certain embodiment, the patient has inactive lupus. In certain embodiment, the patient is at elevated risk of having of having active lupus. In certain embodiment, the patient is suspected of having active lupus. In certain embodiment, the patient is asymptomatic for active lupus. In certain embodiment, the patient has active lupus. Lupus can be any type of lupus including but not limited to systemic lupus erythematosus (SLE), cutaneous lupus erythematosus, drug-induced lupus, and neonatal lupus. In certain embodiments, the lupus is SLE. In certain embodiment, the patient is at elevated risk of having of having fibromyalgia. In certain embodiment, the patient is suspected of having fibromyalgia. In certain embodiment, the patient is asymptomatic for fibromyalgia. In certain embodiment, the patient has fibromyalgia. In certain embodiments, the patient has and/or experiencing fatigue.

In certain embodiments, the method classify the lupus disease state of the patient with an accuracy of at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%. In certain embodiments, the method classify the lupus disease state of the patient with a sensitivity of at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%. In certain embodiments, the method classify the lupus disease state of the patient with a specificity of at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%. In certain embodiments, the method classify the lupus disease state of the patient with a positive predictive value of at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%. In certain embodiments, the method classify the lupus disease state of the patient with a negative predictive value of at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the method classify the lupus disease state of the patient with an accuracy of about 85% to about 100%. In some embodiments, the method classify the lupus disease state of the patient with an accuracy of about 85% to about 90%, about 85% to about 92%, about 85% to about 94%, about 85% to about 95%, about 85% to about 96%, about 85% to about 98%, about 85% to about 99%, about 85% to about 99.3%, about 85% to about 99.5%, about 85% to about 99.8%, about 85% to about 100%, about 90% to about 92%, about 90% to about 94%, about 90% to about 95%, about 90% to about 96%, about 90% to about 98%, about 90% to about 99%, about 90% to about 99.3%, about 90% to about 99.5%, about 90% to about 99.8%, about 90% to about 100%, about 92% to about 94%, about 92% to about 95%, about 92% to about 96%, about 92% to about 98%, about 92% to about 99%, about 92% to about 99.3%, about 92% to about 99.5%, about 92% to about 99.8%, about 92% to about 100%, about 94% to about 95%, about 94% to about 96%, about 94% to about 98%, about 94% to about 99%, about 94% to about 99.3%, about 94% to about 99.5%, about 94% to about 99.8%, about 94% to about 100%, about 95% to about 96%, about 95% to about 98%, about 95% to about 99%, about 95% to about 99.3%, about 95% to about 99.5%, about 95% to about 99.8%, about 95% to about 100%, about 96% to about 98%, about 96% to about 99%, about 96% to about 99.3%, about 96% to about 99.5%, about 96% to about 99.8%, about 96% to about 100%, about 98% to about 99%, about 98% to about 99.3%, about 98% to about 99.5%, about 98% to about 99.8%, about 98% to about 100%, about 99% to about 99.3%, about 99% to about 99.5%, about 99% to about 99.8%, about 99% to about 100%, about 99.3% to about 99.5%, about 99.3% to about 99.8%, about 99.3% to about 100%, about 99.5% to about 99.8%, about 99.5% to about 100%, or about 99.8% to about 100%. In some embodiments, the method classify the lupus disease state of the patient with an accuracy of about 85%, about 90%, about 92%, about 94%, about 95%, about 96%, about 98%, about 99%, about 99.3%, about 99.5%, about 99.8%, or about 100%. In some embodiments, the method classify the lupus disease state of the patient with an accuracy of at least about 85%, about 90%, about 92%, about 94%, about 95%, about 96%, about 98%, about 99%, about 99.3%, about 99.5%, or about 99.8%.

In some embodiments, the method classify the lupus disease state of the patient with a sensitivity of about 85% to about 100%. In some embodiments, the method classify the lupus disease state of the patient with a sensitivity of about 85% to about 90%, about 85% to about 92%, about 85% to about 94%, about 85% to about 95%, about 85% to about 96%, about 85% to about 98%, about 85% to about 99%, about 85% to about 99.3%, about 85% to about 99.5%, about 85% to about 99.8%, about 85% to about 100%, about 90% to about 92%, about 90% to about 94%, about 90% to about 95%, about 90% to about 96%, about 90% to about 98%, about 90% to about 99%, about 90% to about 99.3%, about 90% to about 99.5%, about 90% to about 99.8%, about 90% to about 100%, about 92% to about 94%, about 92% to about 95%, about 92% to about 96%, about 92% to about 98%, about 92% to about 99%, about 92% to about 99.3%, about 92% to about 99.5%, about 92% to about 99.8%, about 92% to about 100%, about 94% to about 95%, about 94% to about 96%, about 94% to about 98%, about 94% to about 99%, about 94% to about 99.3%, about 94% to about 99.5%, about 94% to about 99.8%, about 94% to about 100%, about 95% to about 96%, about 95% to about 98%, about 95% to about 99%, about 95% to about 99.3%, about 95% to about 99.5%, about 95% to about 99.8%, about 95% to about 100%, about 96% to about 98%, about 96% to about 99%, about 96% to about 99.3%, about 96% to about 99.5%, about 96% to about 99.8%, about 96% to about 100%, about 98% to about 99%, about 98% to about 99.3%, about 98% to about 99.5%, about 98% to about 99.8%, about 98% to about 100%, about 99% to about 99.3%, about 99% to about 99.5%, about 99% to about 99.8%, about 99% to about 100%, about 99.3% to about 99.5%, about 99.3% to about 99.8%, about 99.3% to about 100%, about 99.5% to about 99.8%, about 99.5% to about 100%, or about 99.8% to about 100%. In some embodiments, the method classify the lupus disease state of the patient with a sensitivity of about 85%, about 90%, about 92%, about 94%, about 95%, about 96%, about 98%, about 99%, about 99.3%, about 99.5%, about 99.8%, or about 100%. In some embodiments, the method classify the lupus disease state of the patient with a sensitivity of at least about 85%, about 90%, about 92%, about 94%, about 95%, about 96%, about 98%, about 99%, about 99.3%, about 99.5%, or about 99.8%.

In some embodiments, the method classify the lupus disease state of the patient with a specificity of about 85% to about 100%. In some embodiments, the method classify the lupus disease state of the patient with a specificity of about 85% to about 90%, about 85% to about 92%, about 85% to about 94%, about 85% to about 95%, about 85% to about 96%, about 85% to about 98%, about 85% to about 99%, about 85% to about 99.3%, about 85% to about 99.5%, about 85% to about 99.8%, about 85% to about 100%, about 90% to about 92%, about 90% to about 94%, about 90% to about 95%, about 90% to about 96%, about 90% to about 98%, about 90% to about 99%, about 90% to about 99.3%, about 90% to about 99.5%, about 90% to about 99.8%, about 90% to about 100%, about 92% to about 94%, about 92% to about 95%, about 92% to about 96%, about 92% to about 98%, about 92% to about 99%, about 92% to about 99.3%, about 92% to about 99.5%, about 92% to about 99.8%, about 92% to about 100%, about 94% to about 95%, about 94% to about 96%, about 94% to about 98%, about 94% to about 99%, about 94% to about 99.3%, about 94% to about 99.5%, about 94% to about 99.8%, about 94% to about 100%, about 95% to about 96%, about 95% to about 98%, about 95% to about 99%, about 95% to about 99.3%, about 95% to about 99.5%, about 95% to about 99.8%, about 95% to about 100%, about 96% to about 98%, about 96% to about 99%, about 96% to about 99.3%, about 96% to about 99.5%, about 96% to about 99.8%, about 96% to about 100%, about 98% to about 99%, about 98% to about 99.3%, about 98% to about 99.5%, about 98% to about 99.8%, about 98% to about 100%, about 99% to about 99.3%, about 99% to about 99.5%, about 99% to about 99.8%, about 99% to about 100%, about 99.3% to about 99.5%, about 99.3% to about 99.8%, about 99.3% to about 100%, about 99.5% to about 99.8%, about 99.5% to about 100%, or about 99.8% to about 100%. In some embodiments, the method classify the lupus disease state of the patient with a specificity of about 85%, about 90%, about 92%, about 94%, about 95%, about 96%, about 98%, about 99%, about 99.3%, about 99.5%, about 99.8%, or about 100%. In some embodiments, the method classify the lupus disease state of the patient with a specificity of at least about 85%, about 90%, about 92%, about 94%, about 95%, about 96%, about 98%, about 99%, about 99.3%, about 99.5%, or about 99.8%.

In some embodiments, the method classify the lupus disease state of the patient with a positive predictive value of about 85% to about 100%. In some embodiments, the method classify the lupus disease state of the patient with a positive predictive value of about 85% to about 90%, about 85% to about 92%, about 85% to about 94%, about 85% to about 95%, about 85% to about 96%, about 85% to about 98%, about 85% to about 99%, about 85% to about 99.3%, about 85% to about 99.5%, about 85% to about 99.8%, about 85% to about 100%, about 90% to about 92%, about 90% to about 94%, about 90% to about 95%, about 90% to about 96%, about 90% to about 98%, about 90% to about 99%, about 90% to about 99.3%, about 90% to about 99.5%, about 90% to about 99.8%, about 90% to about 100%, about 92% to about 94%, about 92% to about 95%, about 92% to about 96%, about 92% to about 98%, about 92% to about 99%, about 92% to about 99.3%, about 92% to about 99.5%, about 92% to about 99.8%, about 92% to about 100%, about 94% to about 95%, about 94% to about 96%, about 94% to about 98%, about 94% to about 99%, about 94% to about 99.3%, about 94% to about 99.5%, about 94% to about 99.8%, about 94% to about 100%, about 95% to about 96%, about 95% to about 98%, about 95% to about 99%, about 95% to about 99.3%, about 95% to about 99.5%, about 95% to about 99.8%, about 95% to about 100%, about 96% to about 98%, about 96% to about 99%, about 96% to about 99.3%, about 96% to about 99.5%, about 96% to about 99.8%, about 96% to about 100%, about 98% to about 99%, about 98% to about 99.3%, about 98% to about 99.5%, about 98% to about 99.8%, about 98% to about 100%, about 99% to about 99.3%, about 99% to about 99.5%, about 99% to about 99.8%, about 99% to about 100%, about 99.3% to about 99.5%, about 99.3% to about 99.8%, about 99.3% to about 100%, about 99.5% to about 99.8%, about 99.5% to about 100%, or about 99.8% to about 100%. In some embodiments, the method classify the lupus disease state of the patient with a positive predictive value of about 85%, about 90%, about 92%, about 94%, about 95%, about 96%, about 98%, about 99%, about 99.3%, about 99.5%, about 99.8%, or about 100%. In some embodiments, the method classify the lupus disease state of the patient with a positive predictive value of at least about 85%, about 90%, about 92%, about 94%, about 95%, about 96%, about 98%, about 99%, about 99.3%, about 99.5%, or about 99.8%.

In some embodiments, the method classify the lupus disease state of the patient with a negative predictive value of about 85% to about 100%. In some embodiments, the method classify the lupus disease state of the patient with a negative predictive value of about 85% to about 90%, about 85% to about 92%, about 85% to about 94%, about 85% to about 95%, about 85% to about 96%, about 85% to about 98%, about 85% to about 99%, about 85% to about 99.3%, about 85% to about 99.5%, about 85% to about 99.8%, about 85% to about 100%, about 90% to about 92%, about 90% to about 94%, about 90% to about 95%, about 90% to about 96%, about 90% to about 98%, about 90% to about 99%, about 90% to about 99.3%, about 90% to about 99.5%, about 90% to about 99.8%, about 90% to about 100%, about 92% to about 94%, about 92% to about 95%, about 92% to about 96%, about 92% to about 98%, about 92% to about 99%, about 92% to about 99.3%, about 92% to about 99.5%, about 92% to about 99.8%, about 92% to about 100%, about 94% to about 95%, about 94% to about 96%, about 94% to about 98%, about 94% to about 99%, about 94% to about 99.3%, about 94% to about 99.5%, about 94% to about 99.8%, about 94% to about 100%, about 95% to about 96%, about 95% to about 98%, about 95% to about 99%, about 95% to about 99.3%, about 95% to about 99.5%, about 95% to about 99.8%, about 95% to about 100%, about 96% to about 98%, about 96% to about 99%, about 96% to about 99.3%, about 96% to about 99.5%, about 96% to about 99.8%, about 96% to about 100%, about 98% to about 99%, about 98% to about 99.3%, about 98% to about 99.5%, about 98% to about 99.8%, about 98% to about 100%, about 99% to about 99.3%, about 99% to about 99.5%, about 99% to about 99.8%, about 99% to about 100%, about 99.3% to about 99.5%, about 99.3% to about 99.8%, about 99.3% to about 100%, about 99.5% to about 99.8%, about 99.5% to about 100%, or about 99.8% to about 100%. In some embodiments, the method classify the lupus disease state of the patient with a negative predictive value of about 85%, about 90%, about 92%, about 94%, about 95%, about 96%, about 98%, about 99%, about 99.3%, about 99.5%, about 99.8%, or about 100%. In some embodiments, the method classify the lupus disease state of the patient with a negative predictive value of at least about 85%, about 90%, about 92%, about 94%, about 95%, about 96%, about 98%, about 99%, about 99.3%, about 99.5%, or about 99.8%.

The machine-learning model can have the accuracy, sensitivity, specificity, positive predictive value, and/or negative predictive value, described above, and the accuracy, sensitivity, specificity, positive predictive value, and/or negative predictive value of the method can be based on the classification parameters of the machine-learning model, as described herein and/or as understood by one of skill in the art.

In certain embodiments, the method comprises selecting, recommending and/or administering a treatment to the patient based at least in part on the classification of the lupus disease state of the patient. In certain embodiments, the method comprises administering a treatment to the patient based at least in part on the classification of the lupus disease state of the patient. In certain embodiments, the method comprises selecting a treatment for the patient based at least in part on the classification of the lupus disease state of the patient. In certain embodiments, the method comprises recommending a treatment to the patient based at least in part on the classification of the lupus disease state of the patient. The treatment for type 1 lupus can be configured to treat, reduce a severity of, and/or reduce a risk of having type 1 lupus. The treatment for type 2 lupus can be configured to treat, reduce a severity of, and/or reduce a risk of having type 2 lupus. The treatment for type 1-2 lupus can be configured to treat, reduce a severity of, and/or reduce a risk of having type 1-2 lupus. The treatment for type 1 lupus can comprise a drug targeting one or more genes in a significant gene cluster positively correlated with type 1 lupus. The treatment for type 2 lupus can comprise a drug targeting one or more genes in a significant gene cluster positively correlated with type 2 lupus. In certain embodiments, the treatment for type 1-2 lupus can comprise a drug targeting one or more genes in a significant gene cluster positively correlated with type 1-2 lupus. In certain embodiments, the treatment for 1-2 lupus can include one or more treatment for type 1 lupus and one or more treatment for type 2 lupus. In certain embodiments, the treatment a drug targeting one or more genes in a significant gene cluster (e.g., from Tables 17-1 to 17-30 or 24-1 to 24-30) enriched in the patient. The treatment can comprises pharmaceutical composition.

In certain embodiments, the treatment for type 1 lupus comprise a drug targeting one or more genes selected from FLT3, NTRK1, JAK2, NTRK2, NTRK3, CSF1, FLT1, FLT3, FLT4, KDR, KIT, PDGFRA, PDGFRB, RET, TEK, CSF1R, PLA2G2D, ANO1, CACNA1C, CACNA1D, CACNA1F, CACNA1G, CACNA1H, CACNA1I, CACNA1S, CACNB1, CACNB2, CACNB3, CACNB4, CATSPER1, CATSPER2, CATSPER3, CATSPER4, PDE5A, PDE2A, PDE3B, PDE3A, S1PR1, CACN*, TRPM3, NR112, KCNA5, KCNA1, GLRB, GLRA3, GLRA1, CALM1, CACNB2, CACNA2D1, CACNA1S, CACNA1H, CACNA1F, CACNA1D, CACNA1C, PTGS2, PTGS1, PLA2G2E, LTF, KCNN4, CACNG1, CACNB2, CACNA2D2, CACNA2D1, CACNA1S, CACNA1H, CACNA1D, CACNA1C, DRD2, MAOA, MAOB, MPO, SLC6A3, SLC6A2, KDR, PDGFRA, CCND1, S1PR1, S1PR5, CDK4, CDK6, CCND1, CCND3, FOXM1, E2F3, PDGFB, Vegf, VEGFA, PDGFA, VEGFR, FLT1, KDR, FLT4, PDGFRA, PDGFRB, KIT, FGFR3, CDK2, CDK5, CDK7, CDK4, CDK6, CCND1, CCNE1, CDK9, CDK1, CDK4, CDK6, CCND1, CCNE1, CDK2, CDK5, CSNK1G3, RPS6KA1, SRC, CDK1, KDR, CDK4, CDK6, CDK6, CDK1, CDK5, CDK2, CDK1, GATA3, ITGB2, HMGCR, S1PR1, S1PR5, FOXP3, MTOR, KDR, PDG-FRA, PDGFRB, RAF1, PDGFB, Vegf, VEGFA, BRAF, DDR2, FGFR1, FLT1, FLT3, FLT4, KIT, RET, VEGFR, ELANE, PDGFB, Vegf, VEGFA, PDGFA, FLT1, FLT3, FLT4, PDGFRA, PDGFRB, CSF1R, KDR, KIT, RET, VEGFR, PDGFRA, FKBP1A, PPP3R2, PPP3R1, PPP3CC, PPP3CB, PPP3CA, GATA3, ESR1, ESR2, GPER1, PRKCZ, PRKCA, XBP1, FOXM1, CCND1, ERBB2, CEBPB, SP1, CYP3A5, EBP, PRKCB, PRKCD, PRKCE, PRKCG, PRKCI, PRKCQ, FLT1, FLT4, KDR, PDE5A, PDE3A, SRC, EGF, EGFR, Vegf, VEGFA, ERBB2, KDR, BRK1, RET, TIE1, PDE4D, PDE4A, PDE3A, PRSS1, TPSAB1, IGHE, EWSR1, MS4A2, FCER1A, CTSB, CTSD, CTSL, REN, GRM8, GRM7, GRM6, GRM5, GRM4, GRM3, GRM2, GRM1, CSF1R, FLT1, FLT3, FLT4, KDR, KIT, PDGFRA, PDGFRB, AURKA, FLT3, KDR, PDGFRA, SRC, CSF1R, EPHA1, FGFR1, FGFR2, FGFR3, FLT4, KIT, PTK2, PPARD, PPARA, PPARG, CSF1, FLT1, FLT3, FLT4, KDR, KIT, PDGFRA, PDGFRB, RET, TEK, CSF1R, CSF1R, FLT3, KIT, PDGFRA, PDG-FRB, RET, CDK5, CDK2, CDK1, PPARG, CDK2, CDK5, CDK6, CDK1, AKRIC3, ALOX5, ASIC1, ASIC3, KCNQ2, KCNQ3, PLA2G2A, PPARG, PTGS1, PTGS2, SCN4A, PRKCA, PDGFA, PDGFB, FLT3, CDK4, CDK6, CCND1, CCND3, FOXM1, E2F3, TRPM3, TRPC5, FFAR1, ACSL4, PPARG, FOXP3, MTOR, KDR, PDGFRA, PDGFRB, RAF1, PDGFB, Vegf, VEGFA, BRAF, DDR2, FGFR1, FLT1, FLT3, FLT4, KIT, RET, VEGFR, PDGFB, Vegf, VEGFA, PDGFA, FLT1, FLT3, FLT4, PDGFRA, PDGFRB, CSF1R, KDR, KIT, RET, VEGFR, PDGFRA, FGF1, FGF2, Vegf, VEGFA, VEGFR, FLT1, KDR, FLT4, BCL2, CSF1R, KIT, FLT3, TRPM3, PPARG, FLT3, NTRK1, JAK2, NTRK2, NTRK3, CDK1, CDK2, CDK5, GSK3A, GSK3B, CDK1, FLT3, ACVR1, BMPR1A, BMPR1B, EPHA2, FKBP1A, FLT1, FLT3, KDR, LCK, MKNK1, PRKAA1, RPS6KA1, SRC, PPARD, PPARA, PPARG, CSF1R, FLT3, KIT, PDGFRB, PPARG, P2RY10, S1PR2, CDK4, CDK6, CCND1, CCNE1, CDK2, CDK5, CSNK1G3, RPS6KA1, SRC, CDK1, PPARG, ACSL4, ESRRA, ESRRG, SER-PINE1, SLC29A1, TRPM3, PPARG, MDM2, MDM2, CSF1, FLT1, FLT3, FLT4, KDR, KIT, PDGFRA, PDGFRB, RET, TEK, CSF1R, MDM2, MDM2, CSF1, FLT1, FLT4, KDR, PLK4, PDPK1, CA12, MT-CO2, SLC12A3, SLC12A1, CA7, CA4, CA14, CA12, CA1, CA7, CA4, CA14, CA12, CA1, TUBB, TUBB1, TUBA1A, TUBA1B, TUBA1C, TUBA3C, TUBA3D, TUBA3E, TUBA4A, TUBB2A, TUBB2B, TUBB3, TUBB4A, TUBB4B, TUBB6, TUBB8, TUBG1, BCL2, MAP2, MAP4, MAPT, NR112, PDGFB, PDGFA, ABL1, KIT, TUBA1A, TUBA1B, TUBA1C, TUBA3C, TUBA3D, TUBA3E, TUBA4A, TUBB, TUBB1, TUBB2A, TUBB2B, TUBB3, TUBB4A, TUBB4B, TUBB6, TUBB8, TUBG1, PDGFB, Vegf, VEGFA, PDGFA, FLT1, FLT3, FLT4, PDGFRA, PDGFRB, CSF1R, KDR, KIT, RET, VEGFR, PDGFRA, TUBA1A, TUBA1B, TUBA1C, TUBA3C, TUBA3D, TUBA3E, TUBA4A, TUBB, TUBB1, TUBB2A, TUBB2B, TUBB3, TUBB4A, TUBB4B, TUBB6, TUBB8, MDM2, GLI1, WNT1, GRM8, GRM7, GRM6, GRM5, GRM4, GRM3, GRM2, GRM1, CA12, MT-CO2, HDAC1, HDAC3, HDAC4, HDAC5, HDAC6, HDAC7, HDAC8, HDAC9, IL1B, ILIR2, IL6R, TNF, HDAC2, PDGFA, PDGFB, PDGFA, PDGFB, ABL1, SRC, PRKCA, PDGFA, PDGFB, FLT3, PDGFB, PDGFA, ABL1, KIT, PDGFB, Vegf, VEGFA, PDGFA, VEGFR, FLT1, KDR, FLT4, PDGFRA, PDGFRB, KIT, FGFR3, KDR, PDGFRA, PDGFRB, RAF1, PDGFB, Vegf, VEGFA, BRAF, DDR2, FGFR1, FLT1, FLT3, FLT4, KIT, RET, VEGFR, PDGFB, Vegf, VEGFA, PDGFA, FLT1, FLT3, FLT4, PDGFRA, PDGFRB, CSF1R, KDR, KIT, RET, VEGFR, PDGFRA, PDGFB, PDGFA, BCR, ABL1, KIT, SRC, EGF, EGFR, Vegf, VEGFA, ERBB2, KDR, BRK1, RET, TIE1, Vegf, VEGFA, KDR, FGF1, FGF2, Vegf, VEGFA, VEGFR, FLT1, KDR, FLT4, SLC1A1, SLC1A2, SLC1A3, SLC1A6, SLC1A7, ALDH2, DBH, ALDH2, ALDH2, ABCG2, NFKB1, STAT3, EGFR, ERBB2, TACR1, TACR2, TAC1, TACR2, FGFR1, FGFR2, FGFR3, FGFR4, FLT1, FLT4, KDR, PDGFRA, PDGFRB, FCGR2B, CD79B, FCGR2B, FCGR2B, CSF1R, DDR1, TAOK2, FGFR1, TAOK3, FGFR4, FGFR2, TAOK1, LCK, FGFR3, MAP3K3, MAPK7, EPHB6, MAP3K4, TIE1, CD19, FCGR2B, EIF2AK2, CYP11B2, ADRB1, CACNA1H, CACNA2D2, KCNA7, KCNH2, JAK1, JAK2, JAK3, NFKB1, STAT3, EGFR, ERBB2, HRH1, CACNA1C, CACNA1D, CACNA1F, CACNA1S, CACNA1G, CACNA1H, CACNA1I, DRD2, NCOA1, NR3C2, HSD11B1, JAK2, STAT3, JAK3, JAK1, CETP, NR3C1, NR3C2, SLC6A4, SLC6A2, SIGMAR1, RAC2, RAC1, PGRMC1, OPRM1, OPRK1, OPRD1, NCF4, NCF2, NCF1, GRIN3A, CYBB, CYBA, CHRNB4, CHRNB2, CHRNA7, CHRNA4, CHRNA3, CHRNA2, TP53, NR3C2, TNNC2, TNNC1, PDE1B, PDE1A, NR3C2, CFTR, CALM1, CACNB2, CACNA2D2, CACNA2D1, CACNA1S, CACNA1H, CACNA1F, CACNA1D, CACNA1C, JAK1, JAK2, JAK3, HRH1, CALM1, CACNA1I, CACNA1H, CACNA1G, NR3C1, NR3C2, LTK, STK10, ABL1, NR3C1, NR3C2, ANO1, CACNA1C, CACNA1D, CACNA1F, CACNA1G, CACNA1H, CACNA1I, CACNA1S, CACNB1, CACNB2, CACNB3, CACNB4, CATSPER1, CATSPER2, CATSPER3, CAT-SPER4, KCNN4, CACNG1, CACNB2, CACNA2D2, CACNA2D1, CACNA1S, CACNA1H, CACNA1D, CACNA1C, PARP1, PARP9, PARP2, PARP3, ACO1, CHRNB2, CHRNA2, NR3C1, NR3C2, SERPINA6, PGR, ESR1, CCR2, CCL7, CCL8, CCL11, CCL13, CCL16, CCL2, CCR2, CCL7, CCL8, CCL11, CCL13, CCL16, CCL2, STAT1, JAK1, JAK3, JAK2, JAK1, JAK2, JAK3, TYK2, CHRNB2, CHRNA4, CHRNA3, JAK1, JAK3, JAK2, SLC6A4, SLC29A4, SCN5A, NALCN, KCNJ11, KCNH2, KCNA7, KCNA10, CYP3A4, CACNB4, CACNB3, CACNB2, CACNB1, CACNA1S, CACNA1I, CACNA1G, CACNA1F, CACNA1D, CACNA1C, CACNA1B, CACNA1A, EPHA3, ABL2, BRAF, CSF1R, DDR1, DDR2, EPHA2, EPHA4, EPHA5, EPHA8, EPHB2, EPHB3, EPHB4, FRK, KIT, MAPK11, MAPK14, PDG- FRA, PDGFRB, SRC, DDR2, DDR1, EPHB2, CTSB, CTSD, CTSL, REN, ANPEP, LAP3, NPEPPS, BAG1, PTGER4, PTGER3, PTGER1, EPHA3, ABL2, BRAF, CSF1R, DDR1, DDR2, EPHA2, EPHA4, EPHA5, EPHA8, EPHB2, EPHB3, EPHB4, FRK, KIT, MAPK11, MAPK14, PDGFRA, PDGFRB, SRC, CSF1, FLT1, FLT4, KDR, PLK4, CSF1R, FLT1, FLT3, FLT4, KDR, KIT, PDGFRA, PDGFRB, PPP3R2, PPIA, AURKA, FLT3, KDR, PDGFRA, SRC, CSF1R, EPHA1, FGFR1, FGFR2, FGFR3, FLT4, KIT, PTK2, CSF1R, FLT3, KIT, PDGFRB, PDGFB, PDGFA, BCR, ABL1, KIT, FGF1, FGF2, Vegf, VEGFA, VEGFR, FLT1, KDR, FLT4, CSF1, FLT1, FLT3, FLT4, KDR, KIT, PDGFRA, PDGFRB, RET, TEK, CSF1R, CACNA1A, CALM1, ORPD1, ORPK1, ORPM1, POMC, FLT4, FLT1, FLT4, KDR, KIT, PDGFB, PDGFA, ABL1, KIT, IGHE, EWSR1, MS4A2, FCER1A, PDGFB, Vegf, VEGFA, PDGFA, VEGFR, FLT1, KDR, FLT4, PDGFRA, PDGFRB, KIT, FGFR3, FGFR1, FGFR2, FGFR3, FGFR4, FLT1, FLT4, KDR, PDGFRA, PDGFRB, CSF1R, KIT, FLT3, CSF1R, FLT3, KIT, PDGFRA, PDGFRB, RET, FGFR1, FLT1, KDR, KIT, PDGFRA, PDGFRB, RET, KDR, PDGFRA, PDGFRB, RAF1, PDGFB, Vegf, VEGFA, BRAF, DDR2, FGFR1, FLT1, FLT3, FLT4, KIT, RET, VEGFR, PDGFB, Vegf, VEGFA, PDGFA, FLT1, FLT3, FLT4, PDGFRA, PDGFRB, CSF1R, KDR, KIT, RET, VEGFR, PDGFRA, FLT1, FLT4, KDR, SLC6A4, SLC29A4, SCN5A, NALCN, KCNJ11, KCNH2, KCNA7, KCNA10, CYP3A4, CACNB4, CACNB3, CACNB2, CACNB1, CACNA1S, CACNA1I, CACNA1G, CACNA1F, CACNA1D, CACNA1C, CACNA1B, CACNA1A, VEGFR, EGFR, FLT1, FLT4, KDR, BAG1, PTGER4, PTGER3, PTGER1, IL2RA, IL2RB, IL2RG, LCK, PTGFR, PTGFR, PTGDR, PTGER1, PTGER2, PTGER3, PTGER4, PTGFR, PTG1R, TBXA2R, LCK, CDK7, PDGFRB, PIK3CG, TAOK1, PTGFR, IL2RA, IL2RB, IL2RG, IL2RA, IL2RB, IL2RG, GNG5, ARFIP2, CXCR4, CXCL12, SRC, LCK, IL2RA, IL2RB, IL2RG, FOXP3, MTOR, PTGFR, NFKB1, STAT3, EGFR, ERBB2, SLC12A3, SLC12A1, CA7, CA4, CA14, CA12, CA1, ABCB1, ABCC1, ALB, CYP1A1, CYP3A4, GSTA1, GSTP1, TOP2A, MAOA, MAOB, MAOA, MAOB, CYP11B2, CYP1A1, CYP1A2, CYP3A13, CYP2A6, CYP3A4, MAOA, MAOB, DRD2, MAOA, MAOB, MPO, SLC6A3, SLC6A2, IGHE, EWSR1, MS4A2, FCER1A, MAOB, MAOA, ABAT, AOC3, GAD2, GPT, GPT2, MAOA, MAOB, SLC6A2, SLC6A3, SLC6A4, SLC12A1, SLC12A2, MAOA, PSMB2, PSMB8, PSMB9, PSMB10, PSMB1, PSMB5, ABCB1, ABCC1, ALB, CYP1A1, CYP3A4, GSTA1, GSTP1, TOP2A, PSMB9, PSMB8, PSMB9, PSMB10, PSMB8, PSMB10, PSMB9, SSTR4, SSTR1, SSTR2, SSTR3, SSTR5, PRKDC, ABCB1, ATP5F1E, ABCB1, OPRD1, OPRM1, SSTR1, SSTR2, SSTR3, SSTR4, SSTR5, ABCB1, CDK1, CDK2, CDK5, GSK3A, GSK3B, CDK4, CDK6, BCL2, BIRC5, CCNT1, CDK1, CDK5, CDK7, CDK8, CDK9, EGFR, MCL1, PYGM, XIAP, CDK2, CDK2, CDK5, CDK6, CDK1, TOP2B, TOP2A, KCNH2, TOP2A, CDK4, CDK6, CDK1, CDK5, CDK9, CDK2, CDK5, CDK1, CDK1, CDK5, CDK4, CDK2, CDK7, CDK9, ADRA1B, ADRA1D, ADRA2A, ADRA2B, ADRA2C, CALM1, CHRM1, CHRM3, DRD1, DRD2, DRD3, DRD4, DRD5, HRH1, HRH4, HTR1A, HTR2A, HTR2B, HTR2C, HTR6, HTR7, KCNH2, KIF11, ORM1, ORM2, SMPD1, TRPC5, CD38, TOP2B, TOP2A, CDK2, CDK9, CDK1, CDK5, CFLAR, TOP2A, TOP2B, TOP2A, CYP2E1, CYP3A5, TOP2B, TOP2A, ABCB1, ABCC1, ALB, CYP1A1, CYP3A4, GSTA1, GSTP1, TOP2A, TOP2A, GSK3B, CDK1, CDK5, CD38, KIF11, CDK1, CDK2, CDK3, CDK4, CDK6, AURKA, AURKB, CDK1, GSK3B, CDK1, CDK2, CDK5, MKI67, CYP19A1, EGFR, CCNA2, DLGAP5, CENPA, FANCI, KIF20A, PDGFA, TOP2A, TOP2B, TOP2A, CDC25A, CDC25B, CDC25C, CDK1, CDK2, CDK5, TOP2A, CDK1, CDK2, CDK5, CDK7, CDK2, CDK5, CDK7, CDK4, CDK6, CCND1, CCNE1, CDK9, CDK1, TOP2A, CDK4, CDK6, CCND1, CCNE1, CDK2, CDK5, CSNK1G3, RPS6KA1, SRC, CDK1, CDK2, CDK5, CCNE1, CCNA2, CDK5R1, TOP2A, TOP2B, KCNK10, KCNK2, KCNK4, KCNN4, SCN10A, SCN11A, SCN1A, SCN2A, SCN3A, SCN4A, SCN5A, SCN7A, SCN8A, SCN9A, SLC7A11, CDK1, CDK5, CDK2, CDK1, CD38, CYP3A5, TOP2A, LINC01934, CCDC167, ALPK2, CRMP1, SLC24A4, SLC40A1, MAP6, NUGGC, EDARADD, NPDC1, SH3RF2, MIR34AHG, TMEM18, NFASC, HEBP2, CD70, PLEKHA5, DACT1, DNAH6, TTC9, IKZF2, PHLDA1, BHLHE40-AS1, HSPG2, LINC01871, FDXR, PTK7, EGLN3, DEFA1, DEFA3, LTF, DEFA1B, DEFA4, LCN2, CAMP, BPI, MMP8, LINC02009, OLR1, ELANE, CRISP3, AZU1, PDE3A, LINC01579, LINC00671, ERG, TCN1, JDP2, ABCA13, ATP8B4, FGD4, ORM1, ENO2, PCOLCE2, TRAV8-4, IL18R1, DRC1, CHIT1, TXNL4B, MS4A3, OLFM4, CLTCL1, HTRA3, ASGR2, S1PR1, CITED4, CLDN18, SERPINB10, DOC2B, PGLYRP1, TUSC8, STOX2, CRISP2, VEGFA, CACNA1H, PRTN3, PLA2G2D, FCRL3, GUCY2C, PLBD1, CTSG, FKBP9, GATA3, MPO, MIR223HG, METTL7B, PRRT4, RNF144B, COL17A1, RNASE3, PCSK9, ARGI, PASK, ADCY6, NTRK1, HLA-DPB1, AFF2, H1-0, RTN4R, INHBA, ZC3H12D, TMEM252-DT, TMEM52B, THAP7-AS1, ATP2C2, IRF4, KCNE1B, GLOD5, DUOXA1, SEMA3C, LINC01529, TFF3, TRNP1, CCND1, COL4A1, SORCS2, BEX1, ATOH8, SLC5A9, TSPAN7, ASPG, CD163L1, RPL10P19, ST14, CSHL1, ANTXRL, TEKT2, PGM5, CABP1, COPDA1, KLHL8, TSKS, FBN1, TRPM2, ANO5, BAHCC1, HMGN3-AS1, ORM2, FOXC1, PHC1P1, OR6N1, CSGALNACT2, DEFA8P, SLAMF1, PXYLP1, MCEMP1, PARP4P2, MGST1, NLRC4, TUBA5P, NXF3, STOM, SEMA4C, SAMSN1, XKR7, TRBV7-4, RNU6-1176P, ACOX1, RAB44, ANLN, GRK1, JPH3, DIP2C, DDN-AS1, TCTEX1D1, ACVRL1, LRRC2, ARNT2, TRIM51BP, HDC, GRM3, GATA2, FKBP9P1, PRRG3, MTDHP1, WFDC5, KNDC1, LPAR3, TRIM51EP, LINC02474, RPS23P9, NRN1, MSANTD3-TMEFF1, MS4A2, ZNF273, LINC00958, MUC12, HIPK1-AS1, PTX4, SIGLEC10, AKAP12, CILP2, OGDHL, PRSS1, CA10, CTSD, ERI1, FBLIM1, KCNE1, ZBTB16, FKBP5, PFKFB2, FLT3, ECHDC3, CCND3, RELL1, SMAP2, MTARC1, KCNB1, TSC22D3, IRAK3, ENHO, IRS2, P2RY10, URAD, LOXL4, PPARG, UACA, SYT15, ITGA11, MY07A, LAMB2, DUSP5, PLGLB1, TRAV19, MYB, ERLIN1, TRAV39, NEK11, GAS2L3, H2AC12, SERPINB2, AKR7L, RASAL1, HSPB1, SEMA3G, SPSB1, HSF4, TMIGD2, IGHV1-69-2, MSC-AS1, KIF26A, MMRN1, GTSF1L, JSRP1, ASAP3, CD93, IFNLR1, MIR3142HG, PVT1, RPS23P3, USP46, THBD, SMOC2, TMEM44, CASTOR1, HCG27, ADAMTSL4-AS2, ADAMTSL4-AS1, FAR2, DNAH17, BTN1A1, TUBA1C, GLI1, FAAHP1, LINC02656, LINC01093, ZDHHC19, IFITM3P2, TMEM119, MIR24-2, SEMA3B, ALDH1A2, RBM47, BNIPL, CSF1, NEFL, CAPN13, TMEM221, KRT7, ENAH, PCP4L1, SMPDL3B, TEK, SPACA6, IGHD3-10, KLK1, KCTD15, LINC01791, MY06, KRT74, PRSS16, GRM2, PLXNA4, MIR3648-2, WNT1, MDM2, CNIH2, TULP2, SLC52A3, FGGY, RPS3AP18, ANK3-DT, CA12, H4C6, TAFA1, NANOS3, ARHGAP22, CNTF, VCX3B, DAAM2, ILIR2, ADIG, GSTT2B, PDGFB, TMIGD3, TRAV8-1, TPST1, EPCAM-DT, OLAH, SCRG1, ARHGAP24, SETD9, VCX3A, GUCY2D, SLC1A3, COL9A2, ARMC12, VSIG4, VCX, NIPAL2, SRGAP1, CCNA1, ST6GALNAC3, BSND, TBC1D8, GSTT2, FSD1, MAMSTR, TRAJ3, LAMB3, NT5DC4, ITGAD, FLTIP1, IL18RAP, PTPN3, MED6P1, ZNF667, CPLX1, SH3BP4, CASKIN1, HCG14, TAC3, FAM24B, HGD, TRBV10-1, TSHZ2, TRAV2, RN7SL251P, PTPDC1, CCDC181, PTG-FRN, STK19B, CYP2S1, ALOX15B, ADAMTS2, PER1, CPM, SAP30, GLDN, CD163, MARVELD1, KLF9, DDIT4, SIGLEC16, LINC00482, SH3PXD2B, VCAN, FHDC1, MIR181A1HG, MYO10, LINC01127, A4GALT, MS4A6A, IQGAP3, ALDH2, LINC01736, LRMDA, FHL2, LYZ, TRGJP, SPTLC2, ENPP3, ASB2, MARCHF1, BCAT1, ALDH1A1, NBPF2P, LINC02087, IQCD, LMX1B, ABCC11, CEACAM22P, LINC01629, LINC02288, SCN2B, NYAP1, KLRC1, GSTM2, OR7E66P, ELAPOR1, GGT8P, DNM1, PRRT1B, CDH22, COL6A5, PGC, TRBD1, F12, PSCA, H2AC18, SP110, TMEM191B, CASP1, NTNG2, LINC02213, ADCY4, H2BC6, CIB3, AIM2, LINC02212, TRIM25, APOBEC3A, H2BC18, H4C4, ADAMTSL4, CFAP58-DT, H4C8, ZNF396, ANKRD20A5P, MAPILC3B2, PDE9A, FCGR2B, SCART1, GSG1L, OR52K1, PPL, SMCHD1, TRAV16, JUP, FAM174B, H1-12P, SPATC1, RGL3, PAQR6, LGALSL, TMEM191C, LINC00173, LLCFC1, PI4KAP1, CDHR1, HSPA7, KCND1, VSIG10L, SLC16A8, OVOL1, ESCO2, C17orf97, HCG18, TACR2, SLC35F3, GRASLND, GPRASP2, CRHR2, TMEM244, CD300LD, TPBGL, NOVA1, LRRC77P, FCRLB, PMP22, H2AC19, CIR1, DDAH2, IL27, PSTK, NOXRED1, MYBPC3, PRRG4, KCNK7, TMEM132D, TMEM200B, CFAP99, FCGR2C, PDIA2, FGFR4, RNF112, IFI44L, SPATS2L, RSAD2, IFI44, DDX60, EIF2AK2, USP18, DDX58, CMPK2, HERC5, IFIT5, IFIH1, IFI6, EPSTI1, MX1, PLSCR1, PNPT1, FAM247A, ISG15, ZCCHC2, IFI27, SAMD9L, SMTNL1, CHMP5, STAT2, HERC6, PARP9, PHF11, SIGLEC1, OAS1, USP41, LY6E, MIR4477B, SAMD9, CCDC194, PARP12, IFI16, RSPH9, DDX60L, TUBA8, EPB41L5, TMEM123, ACO1, CETP, HES4, TRIM5, PARP14, HESX1, KLHDC7B, LIPA, KIAA1958, ACOT9, LAMP3, NRIR, LGALS3BP, FRG1HP, XAF1, LINC00487, TIMM10, ZNF684, EDAR, TDRD7, LINC02785, DOCK4, PLSCR2, MIR4477A, DTX3L, CHRNB2, KANK3, CMTR1, TSPOAP1, CCR5AS, GRAMD1B, RHAG, GPD2, FEZ1, CCRL2, NKD1, IGHV5-10-1, OR52K2, LTK, PRR5L, FAM230E, HIC1, OTOF, FAM131B, CCR12P, ANTXRLP1, APOBEC3B-AS1, SPON1, HLA-G, CACNA2D2, RASGRF2, LINC02574, TSPAN15, GDF7, LPAL2, AXL, HLA-F-AS1, ITGA9-AS1, LINC00638, CACNA1I, CCL8, PIMREG, COL5A1, MT1DP, ZNF600, EMP1, GPM6A, EBF4, IGHV3-64D, LINC00243, SLC26A5, LINC02068, HCG9, SLC8A3, RUFY4, S100A7, HEY2, SCARB2, CYP21A1P, P3H3, KIAA1841, FAM247B, AGRN, SP100, RNF213, REC8, FRG1KP, ANXA10, GNB4, MILR1, FRMD3, DNAJA1, PGAP1, SAMD4A, PRAL, DLG5, UNC93B4, LHFPL2, VSIG1, PMEL, SLITRK5, NR3C2, ALS2CL, IL17RE, FKBP10, USP13, BTN2A3P, TRAJ25, RPS2P7, JPH4, PPP1R27, RNF213-AS1, CAMK2N1, Clorf127, ZNF835, CSPG4P11, CA8, SYNDIG1L, KRT72, EPHB2, KRT73, LAP3, MS4A4A, LDLRAD3, KRT73-AS1, TCN2, C3AR1, LILRB4, BLVRA, CD300E, SSC4D, NID1, FBLN2, CTSL, HID1, MYOF, AK5, LINC01504, MIR503HG, CYP46A1, RARRES2, FAM170B-AS1, LINC01307, ODF3B, TYMP, LY6E-DT, FBXO39, SCO2, UNC93B3, IFITM3P4, UNC93B5, PPMIK-DT, UNC93B7, ITGA10, ENTPD1-AS1, OSBPL6, FLT4, FITM1, CAPN5, LRRC71, TRBV6-2, LINC02446, ISM1, KIT, CACNA1A, IGHE, SLC7A8, CHN1, LINC02754, SLPI, ACBD7, ERFE, LRRC36, FOLR3, TEKT1, FUT2, MID2, RGPD2, ULBP2, IL15, LINC01918, LINC01344, FAM178B, ISLR2, ADAMTS10, GALNT12, PPFIBP1, MTHFD1L, ZNF514, EPHB3, DNAJC15, MAFA, LRP12, TRBV7-1, ITGA7, LSP1P4, RETREG1, NEXN, TENT5A, GPRC5C, UTS2B, IL2RB, NCR3, RGL1, FCN1, PTGFR, CD300C, ADPRH, GPRC5D-AS1, TMEM255A, CD14, PLPP2, LINC01163, GNG5, GRIK4, KYNU, CDH24, ZNF208, CSAG3, RNF175, FCER1A, TLR2, PTGDR2, LINC02458, SLC12A1, DISC1, MAOA, UPB1, CC2D2A, OLFML2A, C1QTNF7-AS1, LGALSL-DT, SLC4A3, SRGAP2D, CCDC162P, LINC02568, WARS1, SEPTIN9-DT, GRB10, ZNF727, ASPH, C1QTNF7, CSAG2, OR52B4, EXT1, MROCK1, LINC02042, LINC00398, CYP1A1, PODXL2, LHFPL3-AS2, BATF2, IRF7, IFI35, LGALS9, OASL, DHX58, UBE2L6, HELZ2, PML, RTP4, SHISA5, KLHDC7B-DT, MT2A, RMI2, KPTN, ETV7, PARP10, BST2, UNC93B8, DRAP1, UNC93B1, DUX4L50, TTC21A, HSH2D, DUX4L37, TRIM69, TOR1B, MOV10, SSTR3, COLQ, ABCB1, UBE2Q2P2, TRGV9, SLC4A10, ANKRD22, LGALS9DP, RORC, LINC01531, NEURL3, SYT3, PXT1, MYBL1, FBX06, ISG20, RBCK1, NAPA, PSMB9, NAGK, MDK, ZNF496, KIAA0895L, MT2P1, FZD8, AANAT, EPOP, LINC01671, RAB40A, EPN2, MKI67, CCNA2, TPX2, BUB1, BIRC5, TOP2A, GTSE1, CDC20, CIT, PKMYT1, ESPL1, ASPM, ADAM23, HJURP, KIF18B, KIFC1, TROAP, NCAPG, MIXL1, CDK1, CDC25A, CDC45, CDKN3, ZC2HC1C, INAVA, OR13A1, HMGB3, IGHV1-3, NUF2, KIF4A, DLGAP5, MCM10, RNA5SP315, HMMR, GRAPL, NCAPH, CDT1, ATP5MGP1, CPAMD8, RFPL4A, ICA1, LINC00683, CNGB1, TWIST2, FIGNL2, CIDP5, CDCA3, PACSIN1, MTND4P24, KLHL33, FPGT-TNNI3K, CCNB2, KIF11, INSL6, NDC80, VPS33B-DT, LINC00475, DNM1P31, TSPAN3, SLC7A11, SLC9C1, CD38, GSDME, SKA1, TEDDM1, MYRFL, MTCL1, WBP1LP2, BMP8B, PDGFC, SNHG5, LINC02610, and TOP2B.

In certain embodiments, the treatment for type 1 lupus comprise AG-879, Aloisine, Alvocidib, Aminopurvalanol A, Amiodarone, Amiselimod, Amrinone, Arachidonyltrifluoromethane, Arcyriaflavin A, Arsenic Trioxide, AT-7519, Atorvastatin, Axitinib, Batimastat, Bisindolylmaleimide, Bortezomib, Briciclib, Cabozantinib, Cediranib, Cenerimod, Chlorpromazine, Cinnarizine, Cyclosporin A, Doxycycline, Entrectinib, Felodipine, Fingolimod, Flunarizine, GW-441756, HNHA, Ibudilast, Ilomastat, Lavendustin A, Lenvatinib, Lestaurtinib, Linifanib, Mepacrine, Mibefradil, Milrinone, Mocravimod, Nifedipine, Nimesulide, Nitrendipine, Nomifensine, Oxindole-I, Ozanimod, Palbociclib, Pazopanib, PHA-793887, Purvalanol A, Ramucirumab, Ribociclib, RO-3306, Roscovitine, Simvastatin, Siponimod, Sirolimus, Sorafenib, SSR-69071, Sunitinib, Tacrolimus, Tamoxifen, Tivozanib, Trequinsin, Vandetanib, Zardaverine, Gabexate, Omalizumab, Pepstatin, PHCCC, Cediranib, ENMD-2076, GW-501516, Linifanib, Quizartinib, Roscovitine, Acetyl-Farnesyl-Cysteine, Aminopurvalanol A, Diclofenac, Midostaurin, Palbociclib, Rosiglitazone, Sirolimus, Sorafenib, Sunitinib, Lenvatinib, Venetoclax, Pexidartinib, Pioglitazone, Lestaurtinib, Aloisine, RO-3306, TCS-359, Dorsomorphin, GSK-0660, GTP-14564, GW-1929, JTE-013, Purvalanol A, T-0070907, Troglitazone, HLI-373, JNJ-26854165, Linifanib, NUTLIN-3, Serdemetan, Axitinib, Celecoxib, Chlortalidone, Diclofenamide, Docetaxel, Nilotinib, Paclitaxel, Sunitinib, Vinorelbine, MDM2 Inhibitor, GANT-58, IWR-1-Endo, PHCCC, Valdecoxib, Givinostat, Pegpleranib, Dasatinib, Midostaurin, Nilotinib, Pazopanib, Sorafenib, Sunitinib, Imatinib, Vandetanib, Cabozantinib, Lenvatinib, DL-TBOA, Alda-1, Disulfiram, Prunetin, Butein, FK-888, GR-159897, PD-173074, PRV-3279, SM201, Valziflocept, WZ-7043, XmAb5871, 2-Aminopurine, Amiodarone, Baricitinib, Butein, Cinnarizine, Corticosterone, Cucurbitacin 1, Dalcetrapib, Dexamethasone, Dextromethorphan, Ellipticine, Eplerenone, Felodipine, Filgotinib, Flunarizine, Fluticasone, HG-5-113-01, Hydrocortisone, Mibefradil, Nitrendipine, Olaparib, Oxalomalic Acid, PG-9, Prednisolone, Progesterone, RS-102895, RS-504393, Sinensetin, Solcitinib, Tofacitinib, UB-165, Upadacitinib, Verapamil, ALW-II-38-3, ALW-II-49-7, Pepstatin, Tosedostat, 16,16-Dimethylprostaglandin E2, ALW-II-38-3, Axitinib, Cediranib, Cyclosporine, ENMD-2076, GTP-14564, Imatinib, Lenvatinib, Linifanib, Loperamide, MAZ-51, Motesanib, Nilotinib, Omalizumab, Pazopanib, PD-173074, Pexidartinib, Quizartinib, Semaxanib, Sorafenib, Sunitinib, Tivozanib, Verapamil, ZM-306416, 16,16-Dimethylprostaglandin E2, AMG-592, Aminogenistein, AZD1091, Cloprostenol, Fluprostenol, Iloprost, JW-7-24-1, Latanoprost, Low-dose IL-2, LY3471851, NSC-23766, PP-2, RG7835, Sirolimus, Travoprost, Butein, Chlortalidone, Hypericin, Indatraline, Isocarboxazid, Methoxsalen, Nialamide, Nomifensine, Omalizumab, Pargyline, Phenelzine, Piretanide, Tetrindole, Carfilzomib, Hypericin, Ixazomib, KZR-616, KZR-616 CONFIDENTIAL, L-803087, NU-7441, Oligomycin-C, Somatostatin, Zosuquidar, Aloisine, Alvocidib, Aminopurvalanol A, Amonafide, Amsacrine, AT-7519, BRD-K71726959, CGP-60474, Chlorpromazine, Daratumumab, Daunorubicin, Dinaciclib, Doxorubicin, Enrofloxacin, Etoposide, Hypericin, Idarubicin, Indirubin, Isatuximab, Ispinesib, JNJ-7706621, JW-67, Kenpaullone, Letrozole, Malonoben, Mitomycin C, Mitoxantrone, NSC-663284, NSC-693868, Ofloxacin, Olomoucine, PHA-793887, Pirarubicin, Purvalanol A, Purvalanol B, Razoxane, Riluzole, RO-3306, Roscovitine, TAK-079, Teniposide, or any combination thereof. In certain embodiments, the treatment for type 1 lupus comprise an IFN inhibitor, a neutrophil function inhibitor, a monocyte inhibitor, an IL-1 inhibitor, an TNF inhibitor, T cell inhibitor, a cell cycle inhibitor, a neurotransmitter uptake inhibitor, or any combination thereof. Non-limiting examples of IFN inhibitors include anifrolumab, and deucravacitinib. Non-limiting examples of TNF inhibitor include adalimumab, certolizumab pegol, etanercept, golimumab, and infliximab. Non-limiting examples of cell cycle inhibitor include palbociclib, ribociclib, and abemaciclib. Non-limiting examples of IL-1 inhibitors include Anakinra and Canakinumab. Non-limiting examples of neutrophil function inhibitors include Dasatinib, Apremilast, and Roflumilast. In certain embodiments, the treatment for type 1 lupus comprises Anifrolumab, Deucravacitinib, Adalimumab, Certolizumab pegol, Etanercept, Golimumab, Infliximab, Palbociclib, Ribociclib, Abemaciclib, Anakinra, Canakinumab, Dasatinib, Apremilast, Roflumilast, or any combination thereof. In certain embodiments, the treatment for type 1 lupus comprises Prednisone, Hydroxychloroquine, NSAIDS, Methotrexate (MTX), Cyclophosphamide (CTX), Mycophenolate mofetil (MMF), Azathioprine (AZA), Belimumab, Anifrolumab, Voclosporin, or any combination thereof. In certain embodiments, the treatment for type 1 lupus comprises Anifrolumab, Deucravacitinib, Adalimumab, Certolizumab pegol, Etanercept, Golimumab, Inflximab, Palbociclib, Ribociclib, Abemaciclib, Anakinra, Canakinumab, Dasatinib, Apremilast, Roflumilast, Prednisone, Hydroxychloroquine, NSAIDS, Methotrexate (MTX), Cyclophosphamide (CTX), Mycophenolate mofetil (MMF), Azathioprine (AZA), Belimumab, Anifrolumab, Voclosporin, or any combination thereof.

In certain embodiments, the treatment for type 2 lupus comprise a drug targeting one or more genes selected from BLM, RECQL, MAPT, HTT, ACE, ABAT, AOC3, GAD2, GPT, GPT2, MAOA, MAOB, SLC6A2, SLC6A3, SLC6A4, ATP1A1, ATP1A2, ATP1A3, ATP1A4, ATP1B1, ATP1B2, ATP1B3, FXYD2, CD40, CD40LG, CD4LG, NFKB (complex), ACY1, TNFRSF13C, TRPV1, FAAH, CNR2, CNR1, PTGS2, PTGS1, SCN11A, SCN10A, SCN9A, SCN8A, SCN7A, SCN5A, SCN4A, SCN3A, SCN2A, SCN1A, AKRIC3, ALOX5, ASIC1, ASIC3, KCNQ2, KCNQ3, PLA2G2A, PPARG, PTGS1, PTGS2, SCN4A, SLC6A4, SLC6A3, SLC6A2, HTR7, HTR1A, DRD5, DRD4, DRD3, DRD2, DRD1, DBH, SCN10A, SCN11A, SCN1A, SCN2A, SCN3A, SCN4A, SCN5A, SCN7A, SCN8A, SCN9A, BTLA, PLAU, SCN4A, SCN5A, SCN11A, SCN10A, SCN9A, SCN8A, SCN7A, SCN5A, SCN4A, SCN3A, SCN2A, SCN1A, CD79B, FCGR2B, CD79B, KCNK10, KCNK2, KCNK4, KCNN4, SCN10A, SCN11A, SCN1A, SCN2A, SCN3A, SCN4A, SCN5A, SCN7A, SCN8A, SCN9A, SLC7A11, DBH, ALDH2, CNR2, SLC6A4, SLC6A3, SLC6A2, HTR7, HTR1A, DRD5, DRD4, DRD3, DRD2, DRD1, EPHA3, ABL2, BRAF, CSF1R, DDR1, DDR2, EPHA2, EPHA4, EPHA5, EPHA8, EPHB2, EPHB3, EPHB4, FRK, KIT, MAPK11, MAPK14, PDGFRA, PDGFRB, SRC, ADRA1A, ADRA1B, ADRA1D, ADRA2A, ADRA2B, ADRA2C, CHRM1, CHRM2, CHRM3, CHRM4, CHRM5, DRD1, DRD2, DRD3, DRD4, DRD5, GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, HRH1, HRH4, HTR1A, HTR1B, HTR2A, HTR2B, HTR2C, HTR3A, HTR6, HTR7, SLC6A2, SLC6A3, SLC6A4, ADRA1B, ADRA1D, ADRA2A, ADRA2B, ADRA2C, CALM1, CHRM1, CHRM3, DRD1, DRD2, DRD3, DRD4, DRD5, HRH1, HRH4, HTR1A, HTR2A, HTR2B, HTR2C, HTR6, HTR7, KCNH2, KIF11, ORM1, ORM2, SMPD1, TRPC5, HRH4, HRH3, HRH2, HRH1, ADRA1A, ADRA1B, ADRA1D, ADRA2A, ADRA2B, ADRA2C, CALY, CHRM1, CHRM2, CHRM3, CHRM4, CHRM5, DRD1, DRD2, DRD3, DRD4, DRD5, HRH1, HRH4, HTR1A, HTR1B, HTR1D, HTR1E, HTR1F, HTR2A, HTR2B, HTR2C, HTR3A, HTR5A, HTR6, HTR7, CACNA1C, SLC29A1, ACVR1, BMPR1A, BMPR1B, EPHA2, FKBP1A, FLT1, FLT3, KDR, LCK, MKNK1, PRKAA1, RPS6KA1, SRC, HRH4, HRH3, SLC6A4, SLC6A3, SLC6A2, HTR*, HRH4, HRH3, HRH2, HRH1, DRD5, DRD4, DRD3, DRD2, DRD1, CHRM5, CHRM4, CHRM3, CHRM2, CHRM1, ADRB1, ADRA2C, ADRA2B, ADRA2A, ADRA1D, ADRA1B, ADRA1A, ADORA1, ADORA2A, ADORA2B, ADORA3, SLC29A1, ACSL4, ESRRA, ESRRG, SERPINE1, SLC29A1, TRPM3, PPARG, CSF2RB, IL5RA, PRDM1, TAL1, RELA, HNF1A, SP1, HDAC1, HDAC2, HDAC3, HDAC4, HDAC5, HDAC6, HDAC7, HDAC8, HDAC9, HDAC10, HDAC11, KCNMA1, ATP1A1, CA1, CA2, KCNJ11, KCNJ8, KCNMA1, SLC12A3, AURKA, FLT3, KDR, PDGFRA, SRC, CSF1R, EPHA1, FGFR1, FGFR2, FGFR3, FLT4, KIT, PTK2, KCNMA1, PRDM1, TAL1, RELA, HNF1A, SP1, HDAC2, HDAC3, HDAC4, HDAC6, HDAC7, HDAC8, HDAC9, HDAC1, HDAC5, EPAS1, NR5A1, DRD2, DRD3, CA2, CA3, EPAS1, BLVRB, GAP43, PRDM1, TAL1, RELA, HNF1A, SP1, HDAC10, HDAC11, HDAC2, HDAC3, HDAC5, HDAC6, HDAC8, HDAC9, HDAC1, BCL2L1, TOP1, BCL2L1, ATM, TGM2, BCL2L1, BCL2, BCL2, BCL2L1, BCL2L2, ATM, PRKDC, TGM2, BCL2L1, BCL2L2, BCL2, BCL2L1, MCL1, BCL2, S1PR3, S1PR1, OGDH, ALDH5A1, ACADSB, ABAT, SCNN*, SCN*, HDAC9, HDAC2, HDAC1, GUCY1A2, CSF1, FLT1, FLT3, FLT4, KDR, KIT, PDGFRA, PDGFRB, RET, TEK, CSF1R, GUCY1A2, GUCY1A3, GUCY1B3, CSF1R, FLT3, KIT, PDGFRA, PDGFRB, RET, FGFR1, FLT1, KDR, KIT, PDGFRA, PDGFRB, RET, RAF1, PDGFB, Vegf, VEGFA, BRAF, DDR2, FGFR1, FLT1, FLT3, FLT4, KIT, RET, VEGFR, PDGFB, Vegf, VEGFA, PDGFA, FLT1, FLT3, FLT4, PDGFRA, PDGFRB, CSF1R, KDR, KIT, RET, VEGFR, PDGFRA, SRC, EGF, EGFR, Vegf, VEGFA, ERBB2, KDR, BRK1, RET, MT-ATP6, MT-ND4, MT-ND2, MT-ND4L, MT-ATP8, MT-CO3, MT-CYB, MT-ND5, MT-CO2, MT-ND3, MT-ND1, FN1, MT-ND6, VIPR2, SPOCD1, SLC22A23, APOA1-AS, HSD17B7P2, BLM, MTMR9LP, SNPH, MT-TE, MEX3B, MT-CO1, SLC39A4, DGKH, LINC02745, NPAPIL, NETO2, BNIP3P1, RTN4RL1, PELATON, AOC3, RFX8, CADM1, EHF, GPR25, ACE, PTPRN, LRIG3, GPC2, SDC2, LINC00426, LINC00511, MROH9, CCL25, GLB1L3, AOC2, CCR7, RYR1, MOGAT1, BTNL10, NOG, SLC22A17, SPEG, CNN3, C1QA, LGALS1, GOLGA6L9, NT5E, KIR3DX1, GSTA6P, PATL2, KRT5, ATP1A4, AMPD2, EVC, SOX8, ANXA2P2, MDS2, ATP2B2, EPS8L1, CASQ1, PARP11-AS1, TSPAN6, E2F2, PAX5, LINC00926, LARGE2, HLA-DOA, BLNK, SYNPO, TNFRSF13C, FCRL2, CD40, BCL11A, LINC01342, STRBP, KCNH8, DNMT3L, CR2, COBLL1, CEP55, MIR4538, MIR5195, CELSR1, PRAMENP, SCGB3A1, FCMR, LINC01907, PCDH9, HRK, PKIG, LINC01413, DCLK2, H3C13, COLCA1, VWA7, E2F5, NUSAP1, SLC44A5, MICAL3, SPRY1, EPB41L2, RPS2P17, CENPV, TLCD2, NIBAN3, FCRL1, SNX22, AFF3, TCL1A, FCER2, CD79B, CORO2B, IGHM, COL19A1, SNX29P1, MIR4539, VPREB3, PMEPA1, ABCB4, SPIB, FADS3, SCN4A, BACH2, MMP11, CD200, STAP1, MYBPC2, NXPH4, KHDRBS2, MIR4537, AUTS2, TLE1, AEBP1, LIX1-AS1, TBC1D16, CNR2, HS3ST1, HLA-DQA2, DNAH11, AK8, HIP1R, RAB30, NEIL1, BTLA, PLD4, SLCO4C1, CIITA, LAMC1, LAMB4, FAM81A, COL9A1, DLGAP3, GPS2P1, LRRK2-DT, CNTNAP2, SRGAP2B, FAM225A, SRGAP2C, SRGAP2, RNASE2, ANKRD35, WNT7A, FAM225B, ROBO3, RETN, ZNF595, TARM1, DBH, TAF11L2, TLE2, DEPDC1, LINC01238, UCKL1-AS1, SLC45A3, LMO7, ESPNP, TRAJ20, NPTXR, GSDMC, SLC16A11, ACSM3, FMNL2, PLEKHB1, LINC02287, PNMT, FOXRED2, TRAJ32, ADGRE4P, PRSS33, SIGLEC8, ALOX15, HRH4, CACNG6, COL26A1, CACNG8, IL5RA, CLC, DNASE1L3, PTMS, RHOXF1P1, COL11A2, SLC4A9, SMPD3, IL34, LINC01226, ADAMTS7P1, SPNS3, EPHA2, ENPP7P8, RPL35AP26, SLC29A1, TFEC, YBX1P1, UBB, SLC25A39, YBX1, HBB, RNF10, FAM210B, DMTN, IGF2BP2, SLC6A8, UBBP4, ADIPOR1, MFSD2B, A2ML1-AS1, MPP1, FAXDC2, BNIP3L, PBX1, HPS1, AHSP, CHPT1, ISCA1P1, HAGH, GFUS, TAL1, SFRP2, EIF1B, RAB3IL1, KLC3, SHISA7, EMC3, FBX07, PPMIA, BCAM, TRIM10, PAGE2B, YBX1P10, LINC01036, SGIP1, CA2, SLC25A37, AQP1, KEL, PAGE2, RGS10, PINK1, EPHA1, CPNE7, SNX3, SLC6A19, KDM7A-DT, KCNMA1, LOXHD1, UBBP1, BLVRB, TMEM63B, TPGS2, BBOF1, FUNDC2P1, LRRC75A, Clorf116, KLHDC8A, Clorf198, POU5F1, BEND3P1, NCOA4, LEFTY1, TMEM121B, TRAJ39, CRB3, NUDT4P2, TRIM58, DCAF12, ANK1, MKRN1, NUDT4B, OSBP2, GMPR, GSPT1, DNAJC6, STRADBP1, RANBP10, RBM38, HBD, LTBP2, LINC01781, EPPK1, ARHGEF12, NUDT4, SOX6, FBX09, ANKRD9, ISCA1P6, ALDH6A1, TNS1, SLC4A1, SELENBP1, EPB42, NFIX, BCL2L1, GLRX5, ALAS2, SPTB, FECH, TENT5C, YBX3, SIAH2, SLC6A9, KRT1, TGM2, MARCHF8, STRADB, LGALS3, KLF1, CTNNAL1, SLC14A1, GLRX5P1, MT1L, RAP1GAP, MTDHP3, MKRN9P, TSPAN5, CREG1, ZNF429, CYBRD1, GSTA7P, SRRD, OR2W3, YBX3P1, TFDP1, MICAL2, CA3 -AS1, FKBP1B, ARHGEF37, IGHV3-35, PAQR9, CMBL, TMOD1, MXI1, SNCA, SLC6A10P, LINC00570, PLVAP, HEMGN, ABCC13, ALDH5A1, ISCA1, FAM83A, ABCA7, TLCD4, RNF11, NEDD4L, PLEK2, BAIAP3, PRPH2, CYP4F25P, CTSE, S1PR3, DNAJA4, CYP4F60P, CA15P1, FAM104A, CLN8, TTC25, GID4, MEIS3P1, C9orf78, EZR-AS1, RBP5, GASK1B, FZD5, MYCBPAP, ZDHHC2, RPL26P19, RPL34, ZNF785, UQCRB, RPS24P8, RARRES2P2, RPS8P10, SNRPE, PFDN4, RPL26P6, RPL31, TPT1P4, RPS3AP25, RASGRF2-AS1, NCK1-DT, LINC01284, EID2, RPL21P11, ARHGAP28, LINC01765, GRPEL2, RPL31P12, CBX3P2, LINC01424, AQP7, HLF, RLN3, HLA-DPA3, CCDC59, RARRES2P4, RPS18P9, RFPL3S, LINC02298, DMRTC1B, RET, LINC02884, TMEM132A, GUCY1A2, RPL7P19, SC5D, KBTBD8, PRELID3B, C12orf29, UGT8, IGIP, RLN2, CFAP54, UFL1, LRRC3, NAP1L3, UTP15, ZNF404, PTPN13, SMIM10L2A, CD207, ANKRD12, LINC00698, LVRN, ZNF471, LINC02575, HLTF, MYCT1, SPAG8, EXD2, LINC00402, XIRP1, CPNE4, ITPR1-DT, and TIE1.

In certain embodiments, the treatment for type 2 lupus comprises Heliomycin, Enalapril, Perindopril, Phenelzine, Digitoxin, BI 655064, Bleselumab, Dapirolizumab Pegol, FFP104, Iscalimab, N-Acetyl Cysteine, VAY736, AM-281, AM-404, Amylocaine, Arachidonamide, Diclofenac, Dopamine, GW-405833, JBT-101, JTE-907, JWH-015, Lamotrigine, LY3361237, Mexiletine, Oxcarbazepine, Polatuzumab Vedotin, PRV-3279, Riluzole, Disulfiram, Dopamine, Fusaric Acid, ALW-II-38-3, Amoxapine, Chlorpromazine, Clobenpropit, Clozapine, Dilazep, Dorsomorphin, Immepip, Iodophenpropit, Loxapine, N6-Cyclopentyladenosine, Troglitazone, YM-90709, Belinostat, BMS-191011, Creatine, Diazoxide, ENMD-2076, NS-1619, Panobinostat, PT-2385, SID-7969543, Sulpiride, TC-S-7009, U-74389F, Vorinostat, 2,3-DCPE, Bisbenzimide, CP-466722, GK921, Gossypol, HA-14-1, KU-55933, LDN-27219, Navitoclax, TW-37, Fingolimod, Valproic Acid, CFM-1571, Linifanib, ODQ, Quizartinib, Semaxanib, Sorafenib, Sunitinib, Vandetanib, or any combination thereof. In certain embodiments, the treatment for type 2 lupus comprises a B cell inhibitor, a plasma cell inhibitor, an Ig chains inhibitor, neuromuscular pathways inhibitor, or any combination thereof. Non-limiting examples of B cells inhibitors include Rituximab, Obinutuzmab, Ineilizumab, Ocrelizumab, and Ofatumumab. Non-limiting examples of plasma cell inhibitors include Bortezomib, Carfilzomib, Ixazomib, Daratumumab, Isatuximab, and Elotuzumab. In certain embodiments, the treatment for type 2 lupus comprise Rituximab, Obinutuzmab, Ineilizumab, Ocrelizumab, Ofatumumab, Bortezomib, Carfilzomib, Ixazomib, Daratumumab, Isatuximab, Elotuzumab, or any combination thereof. In certain embodiments, the treatment for type 2 lupus comprises duloxetine, gabapentin, milnacipran, pregabalin, or any combination thereof. In certain embodiments, the treatment for type 2 lupus comprises Rituximab, Obinutuzmab, Ineilizumab, Ocrelizumab, Ofatumumab, Bortezomib, Carfilzomib, Ixazomib, Daratumumab, Isatuximab, Elotuzumab, duloxetine, gabapentin, milnacipran, pregabalin, or any combination thereof. In certain embodiments, the treatment for type 2 lupus comprises physical therapy, occupational therapy, psychological counseling, mindfulness and/or other forms of meditation training, alcohol intake reduction, sleep hygiene training, dietary changes including observance of a keto plan (reductions of carbohydrate intake), or any combination thereof.

In certain embodiments, the treatment for type 1-2 lupus comprise an IFN inhibitor, a neutrophil function inhibitor, a monocyte inhibitor, an IL-1 inhibitor, an TNF inhibitor, a cell cycle inhibitor, a neurotransmitter uptake inhibitor, B cell inhibitor, a plasma cell inhibitor, an Ig chains inhibitor, neuromuscular pathways inhibitor, or any combination thereof. In certain embodiments, the treatment for type 1-2 lupus comprise anifrolumab, deucravacitinib, adalimumab, certolizumab pegol, etanercept, golimumab, inflximab. palbociclib, ribociclib, abemaciclib, Anakinra, Canakinumab, Dasatinib, Apremilast, Roflumilast, belimumab, rituximab, obinutuzmab, ineilizumab, ocrelizumab, ofatumumab, Mycophenolate, Bortezomib, Carfilzomib, Ixazomib, Daratumumab, Isatuximab, Elotuzumab, or any combination thereof.

In certain embodiments, one or more genes selected from the genes listed in Table 17-12 is enriched in the biological sample, and the treatment comprises IFN inhibitor. In certain embodiments, one or more genes selected from the genes listed in Table 17-13 is enriched in the biological sample, and the treatment comprises IFN inhibitor. In certain embodiments, one or more genes selected from the genes listed in Table 17-21 is enriched in the biological sample, and the treatment comprises cell cycle inhibitor. In certain embodiments, one or more genes selected from the genes listed in Table 17-22 is enriched in the biological sample, and the treatment comprises cell cycle inhibitor. In certain embodiments, one or more genes selected from the genes listed in Table 17-23 is enriched in the biological sample, and the treatment comprises cell cycle inhibitor.

The biological sample comprises a tissue biopsy sample, a blood sample, isolated peripheral blood mononuclear cells (PBMCs), or any derivative thereof. In certain embodiments, the biological sample comprises a tissue biopsy sample, or any derivative thereof. In certain embodiments, the tissue biopsy sample comprises a skin biopsy sample. In certain embodiments, the tissue biopsy sample comprises a synovial biopsy sample. In certain embodiments, the biological sample comprises a blood sample, or any derivative thereof. In certain embodiments, the biological sample comprises PBMCs, or any derivative thereof. The patient can be a human.

In certain embodiments, the method further comprises monitoring the lupus disease state of the patient, wherein the monitoring comprises assessing the lupus disease state of the patient at a plurality of different time points. A difference in the assessment of the lupus disease state of the patient among the plurality of time points can be indicative of one or more clinical indications selected from the group consisting of: (i) a classification of the lupus disease state of the patient, (ii) a prognosis of the lupus disease state of the patient, and (iii) an efficacy or non-efficacy of a course of treatment for treating the lupus disease state of the patient. In certain embodiments, the patient has been administered a treatment, and the method can assess an efficacy or non-efficacy of the treatment, for treating the lupus disease state of the patient. In certain embodiments, the patient has been administered a treatment, and the method can assess an efficacy or non-efficacy of the treatment, for treating type 1 lupus of the patient. In certain embodiments, the patient has been administered a treatment, and the method can assess an efficacy or non-efficacy of the treatment, for treating type 2 lupus of the patient. In certain embodiments, the patient has been administered a treatment, and the method can assess an efficacy or non-efficacy of the treatment, for treating type 1-2 lupus of the patient.

III. Methods for Developing a Treatment Model Containing Two or More Treatment Groups In an aspect, the present disclosure provides a method for developing a treatment model containing two or more treatment groups. The method can partition patients within a data set into the two or more treatment groups. The method can include any one of, any combination of, or all of steps (a) to (g). Step (a)-(d) can be as discussed above (as in section I of detailed description). Step (e), can include optionally overlapping one or more significant gene clusters with one or more gene function signature lists. Step (f), can include optionally annotating the one or more significant gene clusters with one or more functional characterization based on the overlap. A gene function signature list can contain one or more functional characterization groups. A significant gene cluster can be annotated with a functional characterization if the significant gene cluster sufficiently overlaps with the respective functional characterization group. As shown in a non-limiting manner in Example 1 and FIG. 3, the significant module 3.13.47.151 overlaps with functional characterization group “defense response” and “innate immune response” of the gene function signature list GO, and is annotated as defense.response,innate.immune.response. A significant cluster can sufficiently overlap with more than one functional characterization groups, and can be annotated with more than one functional characterizations, where the functional characterization groups can be from same or different gene function signature list. Every significant clusters may not sufficiently overlap, and all significant clusters may not be annotated. Step (g), can include partitioning the plurality of the reference subjects into two or more treatment groups. The reference subjects can i) include subjects with a disease, and ii) may or may not include healthy controls and/or known cohorts.

The plurality of significant gene clusters can be functionally annotated. Functional annotation can be based on overlapping of the significant gene clusters to the one or more gene function signature lists, e.g. curated signatures of cell types and/or biological functions. A gene function signature lists can contain of a collection of genes (represented as gene symbols) that have been statistically demonstrated using various metrics to be representative of a cell type and/or function, and genes in gene function signature lists, based on the a cell type and/or function can be grouped in to one or more functional characterization groups. The overlap can be include categorical comparison of gene symbols in a given cluster to gene symbols in a given functional characterization group, and can include findings of gene symbols in a cluster, within gene symbols in a given gene functional characterization group. Categorical comparisons can be conducted using any suitable technique. In some embodiments, categorical comparisons is conducted using the Fisher's exact test. As the number of comparisons increase so too does the possibility of random chance influence the overlap results, thus the Fisher's test has an associated p-value measurement of overlaps occurring by random chance alone. The sufficient overlap between, e.g. between a respective significant gene clusters and a respective functional characterization group, can have a threshold Fisher's adjusted p value. In certain embodiments, the threshold Fisher's adjusted p value for sufficient overlap is, <0.01, <0.05, <0.1, <0.15, <0.2, <0.25, <0.3, <0.35, <0.4, <0.45, or <0.5. In certain particular embodiments, the threshold Fisher's adjusted p value for sufficient overlap can be <0.3. In certain particular embodiments, the threshold Fisher's adjusted p value for sufficient overlap can be <0.2. The p value used can account for biological variability. Sufficient overlap, between a respective significant cluster and a respective functional characterization group, can also satisfy overlap of a threshold minimum number of genes between the respective significant cluster and the respective functional characterization group. Overlap of a threshold minimum number of genes can help in mitigate the risks in statistical threshold relaxation. In certain embodiments, the threshold minimum number of genes are about 3 genes to about 12 genes. In certain embodiments, the threshold minimum number of genes are about 3 genes to about 4 genes, about 3 genes to about 5 genes, about 3 genes to about 6 genes, about 3 genes to about 7 genes, about 3 genes to about 8 genes, about 3 genes to about 9 genes, about 3 genes to about 10 genes, about 3 genes to about 11 genes, about 3 genes to about 12 genes, about 4 genes to about 5 genes, about 4 genes to about 6 genes, about 4 genes to about 7 genes, about 4 genes to about 8 genes, about 4 genes to about 9 genes, about 4 genes to about 10 genes, about 4 genes to about 11 genes, about 4 genes to about 12 genes, about 5 genes to about 6 genes, about 5 genes to about 7 genes, about 5 genes to about 8 genes, about 5 genes to about 9 genes, about 5 genes to about 10 genes, about 5 genes to about 11 genes, about 5 genes to about 12 genes, about 6 genes to about 7 genes, about 6 genes to about 8 genes, about 6 genes to about 9 genes, about 6 genes to about 10 genes, about 6 genes to about 11 genes, about 6 genes to about 12 genes, about 7 genes to about 8 genes, about 7 genes to about 9 genes, about 7 genes to about 10 genes, about 7 genes to about 11 genes, about 7 genes to about 12 genes, about 8 genes to about 9 genes, about 8 genes to about 10 genes, about 8 genes to about 11 genes, about 8 genes to about 12 genes, about 9 genes to about 10 genes, about 9 genes to about 11 genes, about 9 genes to about 12 genes, about 10 genes to about 11 genes, about 10 genes to about 12 genes, or about 11 genes to about 12 genes. In certain embodiments, the threshold minimum number of genes are about 3 genes, about 4 genes, about 5 genes, about 6 genes, about 7 genes, about 8 genes, about 9 genes, about 10 genes, about 11 genes, or about 12 genes. Once identified, significant overlaps can be functionally annotated based on the overlapping one or more functional characterization groups. In certain embodiments, the method includes steps e and f. In certain embodiments, the method excludes steps e and f.

In certain embodiments, all the reference subjects in a treatment group are correlated with a set of significant gene clusters. In certain embodiments, i) all the reference subjects in a treatment group are correlated with a set of significant gene clusters, or ii) each significant cluster of the set of significant gene clusters is associated with the same gene functional characterization, or both. A reference subject can be correlated with a significant cluster based on the reference subject's sample traits and/or gene expression in the reference biological sample from the reference subjects.

In certain embodiments, the plurality of reference subjects are partitioned into the two or more treatment groups based at least on gene set variation analysis (GSVA). GSVA for enrichment of at least 2 to all, or any range or values there between, genes of the plurality of significant gene clusters, in the reference biological samples can be performed. In certain embodiments, for the plurality of reference subjects, GSVA scores can be generated using the plurality of significant gene clusters as input gene sets for GSVA. Different significant gene clusters can form different input gene sets for GSVA. Enrichment of the significant gene clusters, in a reference biological sample from a respective reference subject can be measured with respect to the cohort (e.g., plurality of reference samples/subjects) using GSVA to obtain the GSVA scores of the respective reference subject. In certain embodiments, GSVA scores for each reference subjects are generated. GSVA scores can be generated as described in the Examples, and/or as understood by one of ordinary skill in the art. The plurality of reference subjects can be partitioned into the two or more treatment groups based on the GSVA scores of the plurality of reference subjects. In certain embodiments, the plurality of reference subjects are partitioned into the two or more treatment groups based on the GSVA scores of the plurality of reference subjects based on k-means clustering method.

In certain embodiments, the plurality of reference subjects are partitioned into the two or more treatment groups based at module eigengenes (MEs) of the plurality of significant gene clusters. In certain embodiments, for each respective subjects, MEs of each of the plurality of significant gene clusters are calculated. In certain embodiments, the plurality of the reference subjects based on the MEs of the plurality of significant gene clusters are partitioned into the two or more treatment groups based on k-means clustering method.

In certain embodiments, the plurality of reference subjects are partitioned into the two or more treatment groups based at least on training a machine-learning model to infer a treatment group for a reference subject. The machine-learning model can be trained to infer a treatment group for a reference subject based on i) gene expressions of at least 2 genes of the plurality of significant gene clusters, in a reference biological sample from the reference subject, and/or ii) the reference subject's one or more sample traits. In certain embodiments, the machine-learning model is trained to infer a treatment group for a reference subject based on GSVA scores of the reference subject. In certain embodiments, the machine-learning model is trained to infer a treatment group for a reference subject based on MEs of the reference subject. The GSVA scores and/or MEs of a reference subject can be calculated as described herein. In certain embodiments, the machine-learning model is trained to infer a treatment group for a reference subject based on i) gene expressions of at least 2 genes of the plurality of significant gene clusters, in a reference biological sample from the reference subject, and ii) the reference subject's one or more sample traits. In certain embodiments, the machine-learning model is trained to infer a treatment group for a reference subject based on i) gene expressions of at least 2 genes of the plurality of significant gene clusters, in a reference biological sample from the reference subject. In certain embodiments, the plurality of reference subjects are partitioned into the two or more treatment groups based at least on training the machine-learning model to infer a treatment group for a reference subject based on i) gene expressions of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 550, 600, 650, 700, 750, 800, 850, 900, 950, 1000, 1100, 1200, 1300, 1400, 1500, 1600, 1700, 1800, 1900, or 2000, or any value or range there between, genes of the plurality of significant gene clusters, in a reference biological sample from the reference subject, and/or ii) the reference subject's at least 1, 2, 3, 4, 5, 6, 7, 8, 9, or 10, or any value or range there between, sample traits. In certain embodiments, the machine learning model is trained using linear regression, logistic regression (LOG), Ridge regression, Lasso regression, elastic net (EN) regression, support vector machine (SVM), gradient boosted machine (GBM), k nearest neighbors (kNN), generalized linear model (GLM), naïve Bayes (NB) classifier, neural network, Random Forest (RF), deep learning algorithm, linear discriminant analysis (LDA), decision tree learning (DTREE), or adaptive boosting (ADB), or any combination thereof. In certain embodiments, the machine learning model is trained using linear regression. In certain embodiments, the machine learning model is trained using logistic regression (LOG). In certain embodiments, the machine learning model is trained using Ridge regression. In certain embodiments, the machine learning model is trained using Lasso regression. In certain embodiments, the machine learning model is trained using elastic net (EN) regression. In certain embodiments, the machine learning model is trained using support vector machine (SVM). In certain embodiments, the machine learning model is trained using gradient boosted machine (GBM). In certain embodiments, the machine learning model is trained using k nearest neighbors (kNN). In certain embodiments, the machine learning model is trained using generalized linear model (GLM). In certain embodiments, the machine learning model is trained using naïve Bayes (NB) classifier. In certain embodiments, the machine learning model is trained using neural network. In certain embodiments, the machine learning model is trained using Random Forest (RF). In certain embodiments, the machine learning model is trained using deep learning algorithm, linear discriminant analysis (LDA). In certain embodiments, the machine learning model is trained using decision tree learning (DTREE). In certain embodiments, the machine learning model is trained using adaptive boosting (ADB). Certain aspects, are directed to a method of training a machine-learning model according to the methods described herein. The reference subjects in different treatment group can have different endotypes of a disease, such as different endotypes of the two or more endotypes of a disease, between which the gene set of (d) is capable of classifying a patient into.

In certain embodiments, the method includes steps e and f. In certain embodiments, the method excludes steps e and f.

In some embodiments, the trained machine learning model has an accuracy of at least about 90%, at least about 91%, at least about 92%, at least about 93%, at least about 94%, at least about 95%, at least about 96%, at least about 97%, at least about 98%, at least about 99%, at least about 99%, or more than about 99.5%. In some embodiments, the trained machine learning model has a sensitivity of at least about 90%, at least about 91%, at least about 92%, at least about 93%, at least about 94%, at least about 95%, at least about 96%, at least about 97%, at least about 98%, at least about 99%, or more than about 99%. In some embodiments, the trained machine learning model has a specificity of at least about 90%, at least about 91%, at least about 92%, at least about 93%, at least about 94%, at least about 95%, at least about 96%, at least about 97%, at least about 98%, at least about 99%, or more than about 99%. In some embodiments, the trained machine learning model has a positive predictive value of at least about 90%, at least about 91%, at least about 92%, at least about 93%, at least about 94%, at least about 95%, at least about 96%, at least about 97%, at least about 98%, at least about 99%, or more than about 99%. In some embodiments, the trained machine learning model has a negative predictive value of at least about 90%, at least about 91%, at least about 92%, at least about 93%, at least about 94%, at least about 95%, at least about 96%, at least about 97%, at least about 98%, at least about 99%, or more than about 99%. In some embodiments, the trained machine learning model has a receiver operating characteristic (ROC) curve with an Area-Under-Curve (AUC) at least about 0.90, at least about 0.91, at least about 0.92, at least about 0.93, at least about 0.94, at least about 0.95, at least about 0.96, at least about 0.97, at least about 0.98, at least about 0.99, or more than about 0.99.

In some embodiments, the trained machine learning model has a ROC curve with an AUC of about 0.85 to about 1. In some embodiments, the trained machine learning model has a ROC curve with an AUC of about 0.85 to about 0.9, about 0.85 to about 0.92, about 0.85 to about 0.94, about 0.85 to about 0.95, about 0.85 to about 0.96, about 0.85 to about 0.98, about 0.85 to about 0.99, about 0.85 to about 0.993, about 0.85 to about 0.995, about 0.85 to about 0.998, about 0.85 to about 1, about 0.9 to about 0.92, about 0.9 to about 0.94, about 0.9 to about 0.95, about 0.9 to about 0.96, about 0.9 to about 0.98, about 0.9 to about 0.99, about 0.9 to about 0.993, about 0.9 to about 0.995, about 0.9 to about 0.998, about 0.9 to about 1, about 0.92 to about 0.94, about 0.92 to about 0.95, about 0.92 to about 0.96, about 0.92 to about 0.98, about 0.92 to about 0.99, about 0.92 to about 0.993, about 0.92 to about 0.995, about 0.92 to about 0.998, about 0.92 to about 1, about 0.94 to about 0.95, about 0.94 to about 0.96, about 0.94 to about 0.98, about 0.94 to about 0.99, about 0.94 to about 0.993, about 0.94 to about 0.995, about 0.94 to about 0.998, about 0.94 to about 1, about 0.95 to about 0.96, about 0.95 to about 0.98, about 0.95 to about 0.99, about 0.95 to about 0.993, about 0.95 to about 0.995, about 0.95 to about 0.998, about 0.95 to about 1, about 0.96 to about 0.98, about 0.96 to about 0.99, about 0.96 to about 0.993, about 0.96 to about 0.995, about 0.96 to about 0.998, about 0.96 to about 1, about 0.98 to about 0.99, about 0.98 to about 0.993, about 0.98 to about 0.995, about 0.98 to about 0.998, about 0.98 to about 1, about 0.99 to about 0.993, about 0.99 to about 0.995, about 0.99 to about 0.998, about 0.99 to about 1, about 0.993 to about 0.995, about 0.993 to about 0.998, about 0.993 to about 1, about 0.995 to about 0.998, about 0.995 to about 1, or about 0.998 to about 1. In some embodiments, the trained machine learning model has a ROC curve with an AUC of about 0.85, about 0.9, about 0.92, about 0.94, about 0.95, about 0.96, about 0.98, about 0.99, about 0.993, about 0.995, about 0.998, or about 1. In some embodiments, the trained machine learning model has a ROC curve with an AUC of at least about 0.85, about 0.9, about 0.92, about 0.94, about 0.95, about 0.96, about 0.98, about 0.99, about 0.993, about 0.995, or about 0.998. In some embodiments, the trained machine learning model has a ROC curve with an AUC of at most about 0.9, about 0.92, about 0.94, about 0.95, about 0.96, about 0.98, about 0.99, about 0.993, about 0.995, about 0.998, or about 1.

In some embodiments, the trained machine learning model has an accuracy of about 85% to about 100%. In some embodiments, the trained machine learning model has an accuracy of about 85% to about 90%, about 85% to about 92%, about 85% to about 94%, about 85% to about 95%, about 85% to about 96%, about 85% to about 98%, about 85% to about 99%, about 85% to about 99.3%, about 85% to about 99.5%, about 85% to about 99.8%, about 85% to about 100%, about 90% to about 92%, about 90% to about 94%, about 90% to about 95%, about 90% to about 96%, about 90% to about 98%, about 90% to about 99%, about 90% to about 99.3%, about 90% to about 99.5%, about 90% to about 99.8%, about 90% to about 100%, about 92% to about 94%, about 92% to about 95%, about 92% to about 96%, about 92% to about 98%, about 92% to about 99%, about 92% to about 99.3%, about 92% to about 99.5%, about 92% to about 99.8%, about 92% to about 100%, about 94% to about 95%, about 94% to about 96%, about 94% to about 98%, about 94% to about 99%, about 94% to about 99.3%, about 94% to about 99.5%, about 94% to about 99.8%, about 94% to about 100%, about 95% to about 96%, about 95% to about 98%, about 95% to about 99%, about 95% to about 99.3%, about 95% to about 99.5%, about 95% to about 99.8%, about 95% to about 100%, about 96% to about 98%, about 96% to about 99%, about 96% to about 99.3%, about 96% to about 99.5%, about 96% to about 99.8%, about 96% to about 100%, about 98% to about 99%, about 98% to about 99.3%, about 98% to about 99.5%, about 98% to about 99.8%, about 98% to about 100%, about 99% to about 99.3%, about 99% to about 99.5%, about 99% to about 99.8%, about 99% to about 100%, about 99.3% to about 99.5%, about 99.3% to about 99.8%, about 99.3% to about 100%, about 99.5% to about 99.8%, about 99.5% to about 100%, or about 99.8% to about 100%. In some embodiments, the trained machine learning model has an accuracy of about 85%, about 90%, about 92%, about 94%, about 95%, about 96%, about 98%, about 99%, about 99.3%, about 99.5%, about 99.8%, or about 100%. In some embodiments, the trained machine learning model has an accuracy of at least about 85%, about 90%, about 92%, about 94%, about 95%, about 96%, about 98%, about 99%, about 99.3%, about 99.5%, or about 99.8%. In some embodiments, the trained machine learning model has an accuracy of at most about 90%, about 92%, about 94%, about 95%, about 96%, about 98%, about 99%, about 99.3%, about 99.5%, about 99.8%, or about 100%.

In some embodiments, the trained machine learning model has a sensitivity of about 85% to about 100%. In some embodiments, the trained machine learning model has a sensitivity of about 85% to about 90%, about 85% to about 92%, about 85% to about 94%, about 85% to about 95%, about 85% to about 96%, about 85% to about 98%, about 85% to about 99%, about 85% to about 99.3%, about 85% to about 99.5%, about 85% to about 99.8%, about 85% to about 100%, about 90% to about 92%, about 90% to about 94%, about 90% to about 95%, about 90% to about 96%, about 90% to about 98%, about 90% to about 99%, about 90% to about 99.3%, about 90% to about 99.5%, about 90% to about 99.8%, about 90% to about 100%, about 92% to about 94%, about 92% to about 95%, about 92% to about 96%, about 92% to about 98%, about 92% to about 99%, about 92% to about 99.3%, about 92% to about 99.5%, about 92% to about 99.8%, about 92% to about 100%, about 94% to about 95%, about 94% to about 96%, about 94% to about 98%, about 94% to about 99%, about 94% to about 99.3%, about 94% to about 99.5%, about 94% to about 99.8%, about 94% to about 100%, about 95% to about 96%, about 95% to about 98%, about 95% to about 99%, about 95% to about 99.3%, about 95% to about 99.5%, about 95% to about 99.8%, about 95% to about 100%, about 96% to about 98%, about 96% to about 99%, about 96% to about 99.3%, about 96% to about 99.5%, about 96% to about 99.8%, about 96% to about 100%, about 98% to about 99%, about 98% to about 99.3%, about 98% to about 99.5%, about 98% to about 99.8%, about 98% to about 100%, about 99% to about 99.3%, about 99% to about 99.5%, about 99% to about 99.8%, about 99% to about 100%, about 99.3% to about 99.5%, about 99.3% to about 99.8%, about 99.3% to about 100%, about 99.5% to about 99.8%, about 99.5% to about 100%, or about 99.8% to about 100%. In some embodiments, the trained machine learning model has a sensitivity of about 85%, about 90%, about 92%, about 94%, about 95%, about 96%, about 98%, about 99%, about 99.3%, about 99.5%, about 99.8%, or about 100%. In some embodiments, the trained machine learning model has a sensitivity of at least about 85%, about 90%, about 92%, about 94%, about 95%, about 96%, about 98%, about 99%, about 99.3%, about 99.5%, or about 99.8%. In some embodiments, the trained machine learning model has a sensitivity of at most about 90%, about 92%, about 94%, about 95%, about 96%, about 98%, about 99%, about 99.3%, about 99.5%, about 99.8%, or about 100%.

In some embodiments, the trained machine learning model has a specificity of about 85% to about 100%. In some embodiments, the trained machine learning model has a specificity of about 85% to about 90%, about 85% to about 92%, about 85% to about 94%, about 85% to about 95%, about 85% to about 96%, about 85% to about 98%, about 85% to about 99%, about 85% to about 99.3%, about 85% to about 99.5%, about 85% to about 99.8%, about 85% to about 100%, about 90% to about 92%, about 90% to about 94%, about 90% to about 95%, about 90% to about 96%, about 90% to about 98%, about 90% to about 99%, about 90% to about 99.3%, about 90% to about 99.5%, about 90% to about 99.8%, about 90% to about 100%, about 92% to about 94%, about 92% to about 95%, about 92% to about 96%, about 92% to about 98%, about 92% to about 99%, about 92% to about 99.3%, about 92% to about 99.5%, about 92% to about 99.8%, about 92% to about 100%, about 94% to about 95%, about 94% to about 96%, about 94% to about 98%, about 94% to about 99%, about 94% to about 99.3%, about 94% to about 99.5%, about 94% to about 99.8%, about 94% to about 100%, about 95% to about 96%, about 95% to about 98%, about 95% to about 99%, about 95% to about 99.3%, about 95% to about 99.5%, about 95% to about 99.8%, about 95% to about 100%, about 96% to about 98%, about 96% to about 99%, about 96% to about 99.3%, about 96% to about 99.5%, about 96% to about 99.8%, about 96% to about 100%, about 98% to about 99%, about 98% to about 99.3%, about 98% to about 99.5%, about 98% to about 99.8%, about 98% to about 100%, about 99% to about 99.3%, about 99% to about 99.5%, about 99% to about 99.8%, about 99% to about 100%, about 99.3% to about 99.5%, about 99.3% to about 99.8%, about 99.3% to about 100%, about 99.5% to about 99.8%, about 99.5% to about 100%, or about 99.8% to about 100%. In some embodiments, the trained machine learning model has a specificity of about 85%, about 90%, about 92%, about 94%, about 95%, about 96%, about 98%, about 99%, about 99.3%, about 99.5%, about 99.8%, or about 100%. In some embodiments, the trained machine learning model has a specificity of at least about 85%, about 90%, about 92%, about 94%, about 95%, about 96%, about 98%, about 99%, about 99.3%, about 99.5%, or about 99.8%. In some embodiments, the trained machine learning model has a specificity of at most about 90%, about 92%, about 94%, about 95%, about 96%, about 98%, about 99%, about 99.3%, about 99.5%, about 99.8%, or about 100%.

In some embodiments, the trained machine learning model has a positive predictive value of about 85% to about 100%. In some embodiments, the trained machine learning model has a positive predictive value of about 85% to about 90%, about 85% to about 92%, about 85% to about 94%, about 85% to about 95%, about 85% to about 96%, about 85% to about 98%, about 85% to about 99%, about 85% to about 99.3%, about 85% to about 99.5%, about 85% to about 99.8%, about 85% to about 100%, about 90% to about 92%, about 90% to about 94%, about 90% to about 95%, about 90% to about 96%, about 90% to about 98%, about 90% to about 99%, about 90% to about 99.3%, about 90% to about 99.5%, about 90% to about 99.8%, about 90% to about 100%, about 92% to about 94%, about 92% to about 95%, about 92% to about 96%, about 92% to about 98%, about 92% to about 99%, about 92% to about 99.3%, about 92% to about 99.5%, about 92% to about 99.8%, about 92% to about 100%, about 94% to about 95%, about 94% to about 96%, about 94% to about 98%, about 94% to about 99%, about 94% to about 99.3%, about 94% to about 99.5%, about 94% to about 99.8%, about 94% to about 100%, about 95% to about 96%, about 95% to about 98%, about 95% to about 99%, about 95% to about 99.3%, about 95% to about 99.5%, about 95% to about 99.8%, about 95% to about 100%, about 96% to about 98%, about 96% to about 99%, about 96% to about 99.3%, about 96% to about 99.5%, about 96% to about 99.8%, about 96% to about 100%, about 98% to about 99%, about 98% to about 99.3%, about 98% to about 99.5%, about 98% to about 99.8%, about 98% to about 100%, about 99% to about 99.3%, about 99% to about 99.5%, about 99% to about 99.8%, about 99% to about 100%, about 99.3% to about 99.5%, about 99.3% to about 99.8%, about 99.3% to about 100%, about 99.5% to about 99.8%, about 99.5% to about 100%, or about 99.8% to about 100%. In some embodiments, the trained machine learning model has a positive predictive value of about 85%, about 90%, about 92%, about 94%, about 95%, about 96%, about 98%, about 99%, about 99.3%, about 99.5%, about 99.8%, or about 100%. In some embodiments, the trained machine learning model has a positive predictive value of at least about 85%, about 90%, about 92%, about 94%, about 95%, about 96%, about 98%, about 99%, about 99.3%, about 99.5%, or about 99.8%. In some embodiments, the trained machine learning model has a positive predictive value of at most about 90%, about 92%, about 94%, about 95%, about 96%, about 98%, about 99%, about 99.3%, about 99.5%, about 99.8%, or about 100%.

In some embodiments, the trained machine learning model has a negative predictive value of about 85% to about 100%. In some embodiments, the trained machine learning model has a negative predictive value of about 85% to about 90%, about 85% to about 92%, about 85% to about 94%, about 85% to about 95%, about 85% to about 96%, about 85% to about 98%, about 85% to about 99%, about 85% to about 99.3%, about 85% to about 99.5%, about 85% to about 99.8%, about 85% to about 100%, about 90% to about 92%, about 90% to about 94%, about 90% to about 95%, about 90% to about 96%, about 90% to about 98%, about 90% to about 99%, about 90% to about 99.3%, about 90% to about 99.5%, about 90% to about 99.8%, about 90% to about 100%, about 92% to about 94%, about 92% to about 95%, about 92% to about 96%, about 92% to about 98%, about 92% to about 99%, about 92% to about 99.3%, about 92% to about 99.5%, about 92% to about 99.8%, about 92% to about 100%, about 94% to about 95%, about 94% to about 96%, about 94% to about 98%, about 94% to about 99%, about 94% to about 99.3%, about 94% to about 99.5%, about 94% to about 99.8%, about 94% to about 100%, about 95% to about 96%, about 95% to about 98%, about 95% to about 99%, about 95% to about 99.3%, about 95% to about 99.5%, about 95% to about 99.8%, about 95% to about 100%, about 96% to about 98%, about 96% to about 99%, about 96% to about 99.3%, about 96% to about 99.5%, about 96% to about 99.8%, about 96% to about 100%, about 98% to about 99%, about 98% to about 99.3%, about 98% to about 99.5%, about 98% to about 99.8%, about 98% to about 100%, about 99% to about 99.3%, about 99% to about 99.5%, about 99% to about 99.8%, about 99% to about 100%, about 99.3% to about 99.5%, about 99.3% to about 99.8%, about 99.3% to about 100%, about 99.5% to about 99.8%, about 99.5% to about 100%, or about 99.8% to about 100%. In some embodiments, the trained machine learning model has a negative predictive value of about 85%, about 90%, about 92%, about 94%, about 95%, about 96%, about 98%, about 99%, about 99.3%, about 99.5%, about 99.8%, or about 100%. In some embodiments, the trained machine learning model has a negative predictive value of at least about 85%, about 90%, about 92%, about 94%, about 95%, about 96%, about 98%, about 99%, about 99.3%, about 99.5%, or about 99.8%. In some embodiments, the trained machine learning model has a negative predictive value of at most about 90%, about 92%, about 94%, about 95%, about 96%, about 98%, about 99%, about 99.3%, about 99.5%, about 99.8%, or about 100%.

In certain embodiments, the method can include determining treatment methods for the two or more treatment groups. For a respective treatment group a respective treatment method can be determined based at least on the functional annotation of the one or more significant gene clusters within the respective treatment group.

In certain embodiments, the one or more gene function signature lists contain AMPEL LuGENE, AMPEL Ancestry (Anc), AMPEL Endotype.32 (Endo.32), Endotype.kidney, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof. In certain embodiments, the one or more gene function signature lists contain AMPEL LuGENE, AMPEL Ancestry (Anc), AMPEL tissues (Tis), Biologically Informed Gene Clustering (BIG-C) signature, Gene Ontology (GO) database, or any combination thereof. The gene function signature lists, the functional characterization groups (e.g. categories) within the list, and genes within the functional characterization groups for AMPEL Endotype.32 (Endo.32), AMPEL Ancestry (Anc), AMPEL tissues (Tis), and Biologically Informed Gene Clustering (BIG-C), are provided in Catalina, Michelle D., et al. "Patient ancestry significantly contributes to molecular heterogeneity of systemic lupus erythematosus." *JCI insight* 5.15 (2020); for GO is publicly available at geneontology.org; for BRETIGEA is provided in Mckenzie, Andrew T., et al. "Brain cell type specific gene expression and co-expression network architectures." *Scientific reports* 8.1 (2018): 1-19; for Hallmark gene sets, KEGG Pathway Database, Reactome signature is publicly available at gsea-msigdb.org/gsea/msigdb/collections.jsp.

In some embodiments, a first portion of the plurality of patients have lupus, and a second portion of the plurality of patients are healthy control. In certain embodiments, a first portion of the plurality of patients have lupus, and a second portion of the plurality of patients are healthy control; and the one or more sample traits include blood autoimmune antibody level, blood complement component 3 (C3) protein level, blood complement component 4 (C4) protein level, SLEDAI score, LuMOS score, drug usage, ancestral background, presence of leukopenia, presence of proteinuria, presence of vasculitis, or any combination thereof. Drug usage can be usage of drugs selected from corticosteroid, mycophenolate mofetil, methotrexate, and any combination thereof. In certain embodiments, a first portion of the plurality of patients have lupus, and a second portion of the plurality of patients are healthy control; the one or more sample traits include blood autoimmune antibody level, blood complement component 3 (C3) protein level, SLEDAI score, LuMOS score, corticosteroid usage, ancestral background, presence of leukopenia, presence of proteinuria, presence of vasculitis, or any combination thereof. In certain embodiments, a first portion of the plurality of patients have lupus, and a second portion of the plurality of patients are healthy control; and one or more gene function signature lists include AMPEL LuGENE, AMPEL Ancestry, AMPEL Endotype.32, Endotype.kidney, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof. In certain embodiments, a first portion of the plurality of patients have lupus, and a second portion of the plurality of patients are healthy control; the one or more sample traits include blood autoimmune antibody level, blood complement component 3 (C3) protein level, blood complement component 4 (C4) protein level, SLEDAI score, LuMOS score, drug usage, ancestral background, presence of leukopenia, presence of proteinuria, presence of vasculitis, or any combination thereof; and one or more gene function signature lists include AMPEL LuGENE, AMPEL Ancestry, AMPEL Endotype.32, Endotype.kidney, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof. In certain embodiments, a first portion of the plurality of patients have lupus, and a second portion of the plurality of patients are healthy control; the one or more sample traits includes blood autoimmune antibody level, blood complement component 3 (C3) protein level, SLEDAI score, LuMOS score, corticosteroid usage, ancestral background, presence of leukopenia, presence of proteinuria, presence of vasculitis, or any combination thereof; and/or one or more gene function signature lists includes AMPEL LuGENE, AMPEL Ancestry, AMPEL tissues (Tis), Biologically Informed Gene Clustering (BIG-C) signature, Gene Ontology (GO) database, or any combination thereof.

In certain embodiments, wherein a first portion of the plurality of patients have SLE with active disease and without fibromyalgia, and a second portion of the plurality of patients have SLE without active disease, and with fibromyalgia. In certain embodiments, a first portion of the plurality of patients have SLE with active disease and without fibromyalgia, and a second portion of the plurality of patients have SLE without active disease, and with fibromyalgia; and the one or more sample traits include SLEDAI score, Fibromyalgia score, blood autoimmune antibody level, blood complement component 3 (C3) protein level, blood complement component 4 (C4) protein level, LuMOS score, immunotherapeutics usage, ancestral background, presence of leukopenia, presence of proteinuria, presence of vasculitis, or any combination thereof. Immunotherapeutics usage can be usage of immunotherapeutics selected from prednisone, mycophenolate mofetil, belimumab, duloxetine, and any combination thereof. In certain embodiments, a first portion of the plurality of patients have SLE with active disease and without fibromyalgia, and a second portion of the plurality of patients have SLE without active disease, and with fibromyalgia; and the one or more gene function signature lists include AMPEL LuGENE, AMPEL Ancestry, AMPEL Endotype.32, Endotype.kidney, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof. In certain embodiments, a first portion of the plurality of patients have SLE with active disease and without fibromyalgia, and a second portion of the plurality of patients have SLE without active disease, and with fibromyalgia; the one or more sample traits include SLEDAI score, Fibromyalgia score, blood autoimmune antibody level, blood complement component 3 (C3) protein level, blood complement component 4 (C4) protein level, LuMOS score, immunotherapeutics usage, ancestral background, presence of leukopenia, presence of proteinuria, presence of vasculitis, or any combination thereof; and the one or more gene function signature lists include AMPEL LuGENE, AMPEL Ancestry, AMPEL Endotype.32, Endotype.kidney, AMPEL tissues (Tis), Biologically Informed Gene Clustering (BIG-C) signature, Gene Ontology (GO) database, Hallmark gene sets, KEGG Pathway Database, Reactome signature, BRETIGEA signature, or any combination thereof, or any combination thereof. In certain embodiments, a first portion of the plurality of patients have SLE with active disease and without fibromyalgia, and a second portion of the plurality of patients have SLE without active disease, and with fibromyalgia; the one or more sample traits include SLEDAI score, Fibromyalgia score, blood autoimmune antibody level, blood complement component 3 (C3) protein level, score, prednisone usage, mycophenolate mofetil usage, belimumab usage, duloxetine usage, ancestral background, or any combination thereof; and the one or more gene Biologically Informed Gene Clustering (BIG-C) signature, Gene Ontology (GO) database, or any combination thereof; or any combination thereof.

In certain embodiments, a first portion of the plurality of the patients have early inflammatory arthritis, and a second portion of the plurality of patients have advanced Rheumatoid arthritis. In certain embodiments, a first portion of the plurality of the patients have early inflammatory arthritis, and a second portion of the plurality of patients have advanced Rheumatoid arthritis; and the one or more sample traits include matrix metalloproteinase (MMP)-1 level in synovial biopsy sample, MMP-3 level in synovial biopsy sample, erythrocyte sedimentation rate, blood C-Reactive Protein level, age, sex, disease duration or any combination thereof. In certain embodiments, a first portion of the plurality of the patients have early inflammatory arthritis, and a second portion of the plurality of patients have advanced Rheumatoid arthritis; and the one or more gene function signature lists include AMPEL LuGENE, AMPEL Ancestry, AMPEL Endotype.32, Endotype.kidney, AMPEL tissues (Tis), Biologically Informed Gene Clustering (BIG-C) signature, Gene Ontology (GO) database, signature, Immune/Inflammation-Scope (I-Scope), Tissue-Scope (T-Scope), or any combination thereof. In certain embodiments, a first portion of the plurality of the patients have early inflammatory arthritis, and a second portion of the plurality of patients have advanced Rheumatoid arthritis; the one or more sample traits include matrix metalloproteinase (MMP)-1 level in synovial biopsy sample, MMP-3 level in synovial biopsy sample, erythrocyte sedimentation rate, blood C-Reactive Protein level, age, sex, disease duration, or any combination thereof; and the one or more gene function signature lists include AMPEL LuGENE, AMPEL Ancestry, AMPEL tissues (Tis), Biologically Informed Gene Clustering (BIG-C) signature, Gene Ontology (GO) database, or any combination thereof.

In an aspect, the present disclosure provides a method for treating a patient. The method can include any one of, any combination of, or all of steps a', b', and c'. In step a', a test data set can be obtained. The test data set can contain gene expression measurement data of at least 2 genes of a biological sample from the patient, and/or measurement data of one or more sample traits of the patient. In some embodiments, the test data set can contain gene expression measurement data of at least 2 genes of the plurality of significant gene clusters of the biological sample from the patient, and/or measurement data of the one or more sample traits of the patient. Step b', can include classifying the patient into a treatment group of the two or more treatment groups. Step c', can include administering a treatment to the patient based on the treatment group of the patient.

In certain embodiments, the test data set can contain gene expression measurement data of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 550, 600, 650, 700, 750, 800, 850, 900, 950, 1000, 1100, 1200, 1300, 1400, 1500, 1600, 1700, 1800, 1900, or 2000, or any value or range there between, genes of the plurality of significant gene clusters of the biological sample from the patient. In certain embodiments, the test data set can contain measurement data of at least 1, 2, 3, 4, 5, 6, 7, 8, 9, 10, 11, 12, 13, 14, 15, 16, 17, 18, 19, or 20, or range there between, sample traits of the patient. In certain embodiments, the test data set can contain gene expression measurement data of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 550, 600, 650, 700, 750, 800, 850, 900, 950, 1000, 1100, 1200, 1300, 1400, 1500, 1600, 1700, 1800, 1900, or 2000, or any value or range there between, genes of the plurality of significant gene clusters of a biological sample from the patient, and measurement data of at least 1, 2, 3, 4, 5, 6, 7, 8, 9, 10, 11, 12, 13, 14, 15, 16, 17, 18, 19, or 20, or range there between, sample traits of the patient.

In certain embodiments, step b' includes comparing the test data set with the data set, and classifying the patient into a treatment group of the two or more treatment groups obtained from the data set. The data set can be a data set (e.g. of step a) described herein. The plurality of significant clusters, can be a plurality of significant clusters described herein. The two or more treatment groups, can be two or more treatment groups described herein. The plurality of significant clusters and the two or more treatment groups can be obtained from the data set according to the methods (e.g. of steps a, b, c, d, e, f, and/or g) described herein. In certain embodiments, the patient can be classified into a treatment group based on determining the significant gene cluster correlated to the patient, and classifying the patient into the treatment group of the correlated significant gene clusters. The significant cluster correlated to the patient can be determined based on the test data set (e.g. gene expression of the at least 2 genes of the plurality of significant gene clusters of the biological sample from the patient, and/or measurement data of one or more sample traits of the patient). In some embodiments, step b' includes using a trained machine learning model classify the patient into the treatment group. The trained machine learning model can be a trained machine learning model described herein. In certain embodiments, step b' includes classifying the patient into a treatment group based on GSVA. In certain embodiments, a GSVA score of the patient is calculated for enrichment of at least 2 genes of the plurality of significant gene clusters, and the patient is classified into the treatment group based on the GSVA score. In certain embodiments, the GSVA score of the patient is calculated for enrichment of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 550, 600, 650, 700, 750, 800, 850, 900, 950, 1000, 1100, 1200, 1300, 1400, 1500, 1600, 1700, 1800, 1900, or 2000, or any value or range there between, genes of the plurality of significant gene clusters, and the patient is classified into the treatment group based on the GSVA score.

In an aspect, the present disclosure provides a method for determining fibromyalgia in a patient. The method can include any one of, any combination of, or all of steps a", b", and c". Step a" can include obtaining a test data set. The test data set can contain gene expression measurements in a biological sample from the patient. Step b" can include determining a GSVA score of the patient, from the test data set for enrichment of at least 2 genes listed in Table 4B. In certain embodiments, in step b" the GSVA score of the patient is determined, from the test data set for enrichment of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 550, 600, 650, 700, 750, 800, 850, 900, 950, 1000, 1100, 1200, 1300, 1400, 1500, 1600, 1700, 1800, 1900, or 2000, or any value or range there between, genes listed in Table 4B. Step c" can include determining whether the patient has or does not have fibromyalgia based at least on the GSVA score of the patient. In certain embodiments, the method further includes administering a treatment to the patient. In certain embodiments, the method includes administering a treatment of fibromyalgia to the patient based at least on determination of fibromyalgia in the patient. In some embodiments, the GSVA score is determined with respect to a reference data set. In some embodiments, the reference data set can contain gene expression of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 550, 600, 650, 700, 750, 800, 850, 900, 950, 1000, 1100, 1200, 1300, 1400, 1500, 1600, 1700, 1800, 1900, 2000, 3000, 4000, 5000, 6000, 7000, 8000, 9000, 10000, 11000, or 12000, or any value or range there between, genes of the N genes from a plurality of patients. In some embodiments, the test data set can contain gene expression of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 550, 600, 650, 700, 750, 800, 850, 900, 950, 1000, 1100, 1200, 1300, 1400, 1500, 1600, 1700, 1800, 1900, 2000, 3000, 4000, 5000, 6000, 7000, 8000, 9000, 10000, 11000, or 12000 or any value or range there between, genes of the N genes of the patients. N genes can be the N genes described herein. The biological sample can be biological sample described herein.

For example, ranges of subject data (e.g., gene expression data and/or sample trait data) may be expressed as a plurality of disjoint continuous ranges of continuous measurement values, and categories of subject data (e.g., gene expression data and/or sample trait data) may be expressed as a plurality of disjoint sets of measurement values (e.g., {"high", "low"}, {"high", "normal"}, {"low", "normal"}, {"high", "borderline high", "normal", "low"}, {"Yes", "No"}, {"Present", "Absent"} etc.). Sample traits may also include clinical labels indicating the subject's health history, such as a diagnosis of a disease or disorder, a previous administering of a clinical treatment (e.g., a drug, a surgical treatment, chemotherapy, radiotherapy, immunotherapy, etc.), physical traits (age, sex, ancestry, etc.), behavioral factors, or other health status (e.g., hypertension or high blood pressure, hyperglycemia or high blood glucose, hypercholesterolemia or high blood cholesterol, history of allergic reaction or other adverse reaction, etc.).

Figure 24:
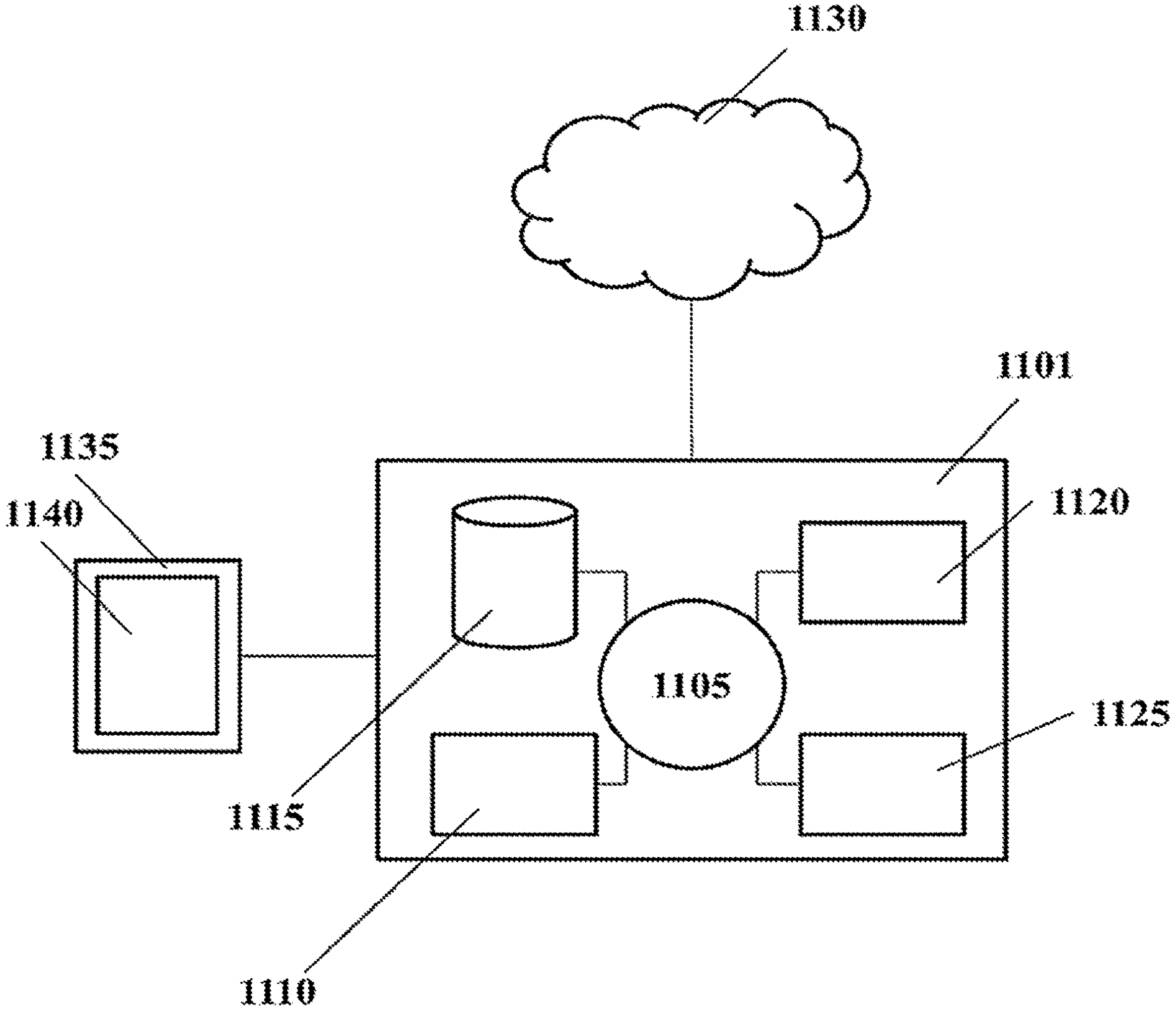
FIG. 24: An example of a computer system 1101 that is programmed or otherwise configured to implement methods provided herein.

The present disclosure provides computer systems that are programmed to implement methods of the disclosure. FIG. 24 shows a computer system 1101 that is programmed or otherwise configured to implement methods provided herein.

The computer system 1101 can be an electronic device of a user or a computer system that is remotely located with respect to the electronic device. The electronic device can be a mobile electronic device.

The computer system 1101 includes a central processing unit (CPU, also "processor" and "computer processor" herein) 1105, which can be a single core or multi core processor, or a plurality of processors for parallel processing. The computer system 1101 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1125, such as cache, other memory, data storage and/or electronic display adapters. The memory 1110, storage unit 1115, interface 1120 and peripheral devices 1125 are in communication with the CPU 1105 through a communication bus (solid lines), such as a motherboard. The storage unit 1115 can be a data storage unit (or data repository) for storing data. The computer system 1101 can be operatively coupled to a computer network ("network") 1130 with the aid of the communication interface 1120. The network 1130 can be the Internet, an internet and/or extranet, or an intranet and/or extranet that is in communication with the Internet.

The network 1130 in some cases is a telecommunication and/or data network. The network 1130 can include one or more computer servers, which can enable distributed computing, such as cloud computing. For example, one or more computer servers may enable cloud computing over the network 1130 ("the cloud") to perform various aspects of analysis, calculation, and generation of the present disclosure, such as, for example, obtaining a data set containing gene expression measurements of genes of an initial gene-set, from a plurality of patients; selecting N genes from the initial gene-set, said N genes are N variably expressed genes of a first gene-set, wherein the first gene-set is a subset of the initial gene-set, each gene of the first gene-set can be mapped to at least one known protein, and N is an integer number; clustering the N genes into a plurality of gene clusters based at least on co-expression of the N genes; correlating the plurality of gene clusters with one or more sample traits, and selecting a plurality of significant gene clusters based at least on strength of the correlation; overlapping one or more significant gene clusters with one or more gene function signature lists; annotating the one or more significant gene clusters with one or more functional characterizations based on sufficient overlap between one or more significant gene clusters and the one or more gene function signature lists, wherein significant overlap satisfies overlap of a threshold minimum number of genes; and partitioning the plurality of patients into two or more treatment groups, wherein (i) all patients in a treatment group are associated with a set of significant gene clusters, or (ii) each significant cluster of the set of significant gene clusters is associated with the same functional characterization, or both. Such cloud computing may be provided by cloud computing platforms such as, for example, Amazon Web Services (AWS), Microsoft Azure, Google Cloud Platform, and IBM cloud. The network 1130, in some cases with the aid of the computer system 1101, can implement a peer-to-peer network, which may enable devices coupled to the computer system 1101 to behave as a client or a server.

The CPU 1105 can execute a sequence of machine-readable instructions, which can be embodied in a program or software. The instructions may be stored in a memory location, such as the memory 1110. The instructions can be directed to the CPU 1105, which can subsequently program or otherwise configure the CPU 1105 to implement methods of the present disclosure. Examples of operations performed by the CPU 1105 can include fetch, decode, execute, and writeback.

The CPU 1105 can be part of a circuit, such as an integrated circuit. One or more other components of the system 1101 can be included in the circuit. In some cases, the circuit is an application specific integrated circuit (ASIC).

The storage unit 1115 can store files, such as drivers, libraries and saved programs. The storage unit 1115 can store user data, e.g., user preferences and user programs. The computer system 1101 in some cases can include one or more additional data storage units that are external to the computer system 1101, such as located on a remote server that is in communication with the computer system 1101 through an intranet or the Internet.

The computer system 1101 can communicate with one or more remote computer systems through the network 1130. For instance, the computer system 1101 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system 1101 via the network 1130.

Methods as described herein can be implemented by way of machine (e.g., computer processor) executable code stored on an electronic storage location of the computer system 1101, such as, for example, on the memory 1110 or electronic storage unit 1115. The machine executable or machine readable code can be provided in the form of software. During use, the code can be executed by the processor 1105. In some cases, the code can be retrieved from the storage unit 1115 and stored on the memory 1110 for ready access by the processor 1105. In some situations, the electronic storage unit 1115 can be precluded, and machine-executable instructions are stored on memory 1110.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1101 can include or be in communication with an electronic display 1135 that comprises a user interface (UI) 1140. Examples of user interfaces (UIs) include, without limitation, a graphical user interface (GUI) and web-based user interface. For example, the computer system can include a graphical user interface (GUI) configured to display, for example, subject data, identification of a lung nodule of the subject as a malignant lung nodule or a benign lung nodule, and/or predictions or assessments generated from subject data data.

Methods and systems of the present disclosure can be implemented by way of one or more algorithms. An algorithm can be implemented by way of software upon execution by the central processing unit 1105. The algorithm can, for example, obtain or asses a data set containing gene expression measurements of genes of an initial gene-set, from a plurality of patients; select N genes from the initial gene-set, said N genes are N variably expressed genes of a first gene-set, wherein the first gene-set is a subset of the initial gene-set, each gene of the first gene-set can be mapped to at least one known protein, and N is an integer number; cluster the N genes into a plurality of gene clusters based at least on co-expression of the N genes; correlate the plurality of gene clusters with one or more sample traits, and selecting a plurality of significant gene clusters based at least on strength of the correlation; overlap one or more significant gene clusters with one or more gene function signature lists; annotate the one or more significant gene clusters with one or more functional characterizations based on sufficient overlap between one or more significant gene clusters and the one or more gene function signature lists, wherein significant overlap satisfies overlap of a threshold minimum number of genes; and partition the plurality of patients into two or more treatment groups, wherein (i) all patients in a treatment group are associated with a set of significant gene clusters, or (ii) each significant cluster of the set of significant gene clusters is associated with the same functional characterization, or both.

EXAMPLES

Example 1: Unsupervised Clustering of Genes to Identify Subgroups of SLE Patients Gene expression analysis of whole blood samples from baseline SLE patients and healthy controls were studied in GEO GSE88887 ILLUMINATE-1 (ILLUM-1) study. The study included 813 patients and 10 healthy controls from 15 clinical site countries throughout North and South America and Europe (Table 1A). This diverse collection also includes 3 major ancestral backgrounds; African ancestry (AA), European American ancestry (EA), and Native American (NA).

TABLE 1A

ILLUM-1 study characteristics.
ILLUM-1 Study

| | | | | |
|---|---|---|---|---|
| No. patients | 813 | | | |
| No. controls | 10 | | | |
| No. site countries | 15 | | | |
| No. site continents | 3 (North & South America, Europe) | | | |
| No. ancestral backgrounds | 3 (African American: AA, European American: EA, Native American: NA) | | | |
| Total no. sample attributes | 86 | | | |
| PC variance explained | PC1 26.3% | PC2 11.4% | PC3 8% | PC4 4.9% |

This patient heterogeneity along with the paucity of controls presents many inherent challenges to traditional gene expression analysis. Co-Expression Based DeConvolution and Reconstruction of Biologic Pathways (CodeR-BP) technique was used to elucidate gene module enrichment patterns, regulatory networks, differentially expressed gene pairs within and between modules unique to each ancestral background, and identify specific subsets of patients, relationships with specific clinical or laboratory traits, from the ILLUM-1 study. Genes were annotated using the publicly available R bioMart package. Gene not mapped to any known proteins and genes having expression rows with an average standard deviation of zero were removed. Averaged gene expression rows were sorted by descending row variance, and the top 5,000 row variance (ILLUM-1 top5k rowVar) genes were selected for further analysis. This initial approach was useful for obtaining high quality data for gene clustering and subsequent analysis, reducing noise from the data, and improving speed of computer systems. PCA analysis was performed using the publicly available R prcomp package, and visualized including scree plots, biplots, eigen correlation plots, and loading genes contributing to the top 10 principal components. Sample traits are correlated to these top 10 PCs and the absolute values of the correlations sorted by descending contribution to variance. The top 20 sample traits contributing to each of the first 4 PCs were visualized. Clinical traits are correlated to these top 10 PCs and sorted by descending contribution to variance. The ILLUM-1 top5k rowVar genes were clustered based on Gene Co-Expression Network (GCN) generation and multi-scale module formation. Planar filtered network (PFN) was generated requiring a correlation false discovery rate (FDR)<0.2, and ensuing multi-scale gene modules were generated using the public R MEGENA package. Minimum module size was 20 genes. A formal tree object was created to establish module lineage and assign module lineage names. Gene modules were assigned "lineage" names based on their multi-scale dependency from the root module. For example, module 52 derived from module 14 derived from module 3 was named per lineage as M3.14.52. Module eigengenes (MEs) were calculated as the first principle component of the gene expression values within each modules. 40 modules with MEs significantly correlated to the presence of anti-dsDNA antibody (anti.dsDNA) within a patient's blood draw (yes/no, adjusted p.val<0.001) were identified. This 40 significant gene clusters were subsequently overlapped with various gene function signature lists selected from AMPEL LuGENE, Endotype.32, Endotype.kidney, and BIG-C, and the public Gene Ontology (GO) and BRETIGEA brain function lists. The modules were annotated according to the top overlapping functional category with the most significant p-value and a minimum of 4 overlapping genes. Sunburst diagrams showing module size and descendence were generated using the publicly available R plotly. The module lineage sunburst illustrating module ME significant correlations (p<0.05) to AA, EA, and NA ancestral backgrounds were generated. Sunburst correlations, illustrating significant correlations (p<0.05) of module ME to AA, EA, and NA ancestral backgrounds; patient's usage (yes/no) of the drugs corticosteroids (CS), mycophenolate mofetil (MMF), and methotrexate (MTX); presence (yes/no) of anti.dsDNA, and indicating majority LuGENE significant overlaps was included (p<0.05 with a minimum of 4 gene symbol overlaps), were generated.

Detailed Methods and Materials

Gene expression data and probe filtering Gene expression data from GSE88884 (1) was used for analysis. Data were generated with the Affymetrix Human Transcriptome Array 2.0 (HTA-2.0) chipset. We remapped the HTA-2.0 chipset definition file (CDF) probes to BrainArray v.24 GPL17586 HTA-2.0 probes (1), using the most recent human reference genome (1). Of the 67,528 original Affy probes, 32,500 probes were remapped and retained. The R package gcrma (1) was used to adjust for gene probe background noise and strengthen significant probe signal. Probes were further annotated using the R biomaRt (2) library and those missing mappings to known proteins were discarded. Duplicate gene symbols were removed using the collapseRows function in the R WGCNA package (3). Finally, the top 5,000 row variance (top5k rowVar) genes per standard deviation (top5k rowVar genes) were retained for further analysis.

All of the study's original 813 patients and 10 healthy controls from 15 clinical sites across 3 continents were retained. We restricted the sample attributes to 86, including clinical indices and laboratory measurements (Table 1A).

Principal component analysis (PCA) & mixed model patient clustering. The core R prcomp function and PCAtools package (1) were used to conduct exploratory PCA on the top5k rowVar genes. The first four principal components (PCs) were correlated using R Im linear regression to the 86 sample attributes and the top 20 traits contributing to PC variance identified and visualized using R ComplexHeatmap (1). PC1 and PC2 were specifically correlated to patient ancestral backgrounds including African ancestry (AA), European ancestry (EA), and Native American ancestry (NA) and visualized using PCAtools, including tinted concentration ellipses. The R Daisy dissimilarity matrix calculation algorithm within the cluster package (1) was used to carry out mixed module agglomerative clustering per PC1 through PC4 on their respective top 20 variance-contributing clinical traits. Within-cluster sum of squares and average silhouette widths were evaluated per Daisy PC for an appropriate Gower distance k-means split of patients into final Daisy PC clusters. All four PC clusters were cut into 6 respective patient groups which offered an acceptable balance of silhouette distance and consistency between the 4 groups. Sample traits were scaled between −1 and +1 and the top 20 per Daisy PC per patient cluster visualized using Complex Heatmap.

Weighted Gene Coexpression Network Analysis (WGCNA). WGCNA was run on a matrix [$S_i$, $G_i$] of the top 5,000 rowVar genes of row $S_i$ samples and column $G_i$ genes to generate a gene coexpression network (GCN) that was optimized towards a scale-free topology (SFT). Pearson correlations of c[$G_i$, $G_j$] were calculated to generate a square similarity/correlation matrix and converted to a distance matrix using 1−[corr matrix]. This was exponentiated to soft thresholding powers (STP) β of 1 through 30 in order to amplify disparities between weak and strong correlations and approach SFT, i.e. an adjacency of $0.8^4=0.4096$ vs. an adjacency of $0.2^4=0.0016$, and 0.8/0.2 being a 4-fold difference vs. 0.4096/0.0016 which is a 256-fold difference. Each of the 30 exponentiated matrices were measured for classic network fit indices including $r^2$ of SFT, mean network connectivity/density, centralization, and heterogeneity. An optimal STP of 30 was selected after comparison of the fit indices, and an ensuing signed topological overlay matrix (TOM) generated by weighting gene nodes based on their interconnectedness, or their similarity in terms of the commonality of nodes to which they connect (2, 3).

The WGCNA dynamic tree cutting algorithm using a deep split parameter of 4 (DS4) was used to split TOM genes into modules. The minimum module size was set to 50 genes, module detection cut height set to 1, and merge cut height set to 0.2. A secondary PAM stage with respect to the dendrogram was carried out after initial gene-to-module assignment, and genes reassigned to a closer centroid in an adjacent module as needed. The deep split algorithm is an adapted version of hierarchical clustering termed within WGCNA as dynamic tree cutting after complete-linkage metrics (2). DS4 and related settings led to formation of 14 modules which were semi-arbitrarily assigned color names for ease of reference. WGCNA color assignments were selected from the R color palette and are based on decreasing module size, beginning with turquoise followed by blue, brown, yellow, black, and so on.

The 86 clinical traits were numerically encoded either as numeric continuous variables or binary identifiers in order to be used for correlations. The WGCNA function plotDendroAndColors was utilized to depict a dendrogram of the Euclidean distance-clustered top5K rowVar gene expressions and the mean gene row expression correlations to the 86 sample traits.

R prcomp was used to calculate the first principal component of gene expression within each module as the module eigengene (ME), as well as strength of a gene's mean membership expression in each module (kME) and the sum of a gene's intramodular connections (kIM). Genes with both high kME and kIM values were designated as hub genes (2).

The MEs of individual modules per sample were correlated to the 86 numerically encoded and scaled sample traits per sample, and the top 40 significant correlations ($p<0.2$) visualized using ComplexHeatmap. To explore module functional enrichments, MEs were correlated to previously described cell and function defining gene sets and Gene Ontology (GO) signatures using Fisher's exact tests. Overlaps were considered significant if there was a minimum of 4 overlapping gene symbols and a p.val<0.05. Correlations were also calculated to Hallmark pathways, KEGG, and Reactome enrichments in a similar manner and visualized using bubble plots.

Basic R plots were generated per module to visualize probe correlation of select sample traits vs. kME and those vs. KIM. These were visually inspected to further gauge overall module performance and intramodular network density.

The TOM was converted to a list of gene pairs, and the edges between them assigned their TOM overlap scores. Cytoscape (7) was used to visualize this graph list where genes were colored by WGCNA module color assignment.

Iterative WGCNA. The R iterativeWGCNA package (7) was utilized to reduce WGCNA's greedy hierarchical gene-to-module assignments by enforcing a minimum kME for every gene. The algorithm performs multiple passes of module formation and evaluation of the gene kMEs within them. Any genes not meeting the minimum kME requirement are removed from modules generated during that pass. Module detection is then performed on those poorly fitting residual genes and the gene kMEs reevaluated. The process is repeated again until most genes are either properly fitted to satisfy the minimum kME, or given no recourse are placed into a discard grey module, and no new modules are generated. At the end of iteration all modules are examined and converged if they meet a similarity metric. We submitted the same WGCNA inputs to iterativeWGCNA through multiple experiments, with various combinations of minimum kME and minimum module size. Iterative outputs were coerced to follow WGCNA output structure for further analyses. Histograms of each combination were generated of the final kMEs, along with dendrogram/clinical traits figures to compare to the corresponding WGCNA figure.

CoCena2 Coexpression Analysis. The R CoCena2 package (2) was utilized for coexpression network analysis of the top 5,000 rowVar genes. The package identified the Louvain clustering method with a correlation cut-off of 0.702 as an optimal approach and formed 12 modules which were arbitrarily assigned color names. Cytoscape visualized the pattern of the top5,000 rowVar genes colored by their CoCena2 color assignments. Daisy Gower clustering was carried out as previously described, and PC1 through PC4 groups cut into 6 patient clusters each. These were correlated to the top 40 significantly correlated clinical traits, followed by pathway analysis using the various approaches described above.

Multiscale Embedded Gene Co-expression Network Analysis (MEGENA). The MEGENA (2) R package was used to generate a planar filtered network (PFN) based on connectedness weightings of gene expression after inputting the same top5,000 rowVar genes used for WGCNA, iterative WGCNA, and CoCena2. PFN creation was accomplished using a computationally optimized version of Planar Maximally Filtered Graphing (2), resulting in the mapping gene of pairs onto a topological sphere per the Myrvold-Boyer algorithm. PFN false discovery rate was restricted to $p<0.2$ Pairs most similar in correlation to other pairs were connected to one another resulting in the formation of triangles of coexpression connectivity. The resulting PFN was a network of gene nodes where edge weights were the strength of the correlation between the nodes. The PFN was submitted to MEGENA multi-scale clustering analysis (MCA) for the identification of lineages of gene modules, followed by performance of MEGENA multi-scale hub analysis (MHA) to identify densely intraconnected hub genes. A second pass of statistical stringency was performed to eliminate modules not meeting various cluster requirements. Summary module output required a minimum module size of 20 genes, no maximum module size, a module compactness p.val of 0.5, and a hub degree p.val of 0.5. 342 modules were initially detected across 11 scales with a resolutions ranging from 0.01 to 2.23, and 197 major hub genes. 149 significant summary modules were retained across six scales/generations with a resolutions ranging from 0.01 to 0.86. The resulting family hierarchy of summary modules was translated into a formal tree object. The R data. tree package (2) was used after reinserting any insignificant parents of orphaned modules as placeholder entries to allow for generation of a family tree without gaps. Modules were assigned "lineage" names based on their multiscale pedigree from the root MEGENA module, ergo module 52 derived from module 14 derived from module 3 being renamed per lineage as M3.14.52. We hereafter also refer to modules by their home generation/scale, here M3.14.52 being a third-generation (gen3) module.

We utilized the prcomp package to perform singular value decomposition and calculate MEGENA module eigengenes. MEGENA MEs were correlated to various binary-encoded sample traits. Modules were subsequently overlapped with AMPEL LuGENEC and BIG-CC, Hallmark, KEGG, and Reactome signatures.

The PFN of the top5k rowVar genes was imported into Cytoscape along with many gene node annotations including functional enrichments, hub node identification, differential expression log FC per cohort, and all generation/scale levels a gene was inherited into. The resulting base 5,000 member gene figure included any hub node labels sized according to their scaled degree of intramodular connectedness and was subsequently colored and annotated from varying perspectives.

A basic network node and edges graph was plotted of the summary modules and modules of interest annotated with majority functional overlap. A sunburst plot was generated using the R plotly (2) package as an alternative method to better visualize the module family tree and underlying multiscale relationships unique to the MEGENA paradigm. The sunburst modules were arbitrarily colored to indicate gen1 lineages. They were then recolored by the WGCNA module colors they would have been assigned to if 50% of a MEGENA module's genes overlapped with a given WGCNA module, which we term "WGCNA majority module assignment". Subsequent sunburst recolorations were generated to illustrate MEGENA ME significant correlations ($p<0.05$) to AA, EA, and NA ancestral backgrounds. These were followed by correlations to a patient's yes/no usage of the drugs corticosteroids (CS), mycophenolate mofetil (MMF), and methotrexate (MTX), yes/no presence of anti.dsDNA, and majority LuGENEC significant signature overlaps ($p<0.05$ with a minimum of 4 gene symbol overlaps).

Cytoscape was further utilized to graph PFN coexpression relationships specifically within two MEGENA modules M3.13 and M3.15, selected for their immunological interest. M3.13 gene nodes were again color filled with top significant LuGENEC enrichment. Nodes were outlined by any M3.13 gen4 gene inheritance, serving to illustrate the results of a resolution and potential biological rationale to descendant module placement. Any gene names that were part of the interferon gene family were colored red as part of a separate investigation. Labels and nodes were sized based on their degree of interconnectedness. M3.15 nodes were also outlined by any gen4 descendant module placement, but this time filled by significant differential expression log FC ($p<0.2$) per cohort.

As a complement to the M3.13 Cytoscape network, an M3.13 gene expression heatmap was generated using the R pheatmap package (2). Gene rows were grouped and labeled by either a M.13 gen4 placement, or if they were uninherited. Sample columns were arbitrarily clustered by Euclidean distances into k=8 clusters. The figure was visually inspected for differences in gene expression possibly corresponding to descendant module placement rationale.

Differential Gene Co-Expression Analysis (DGCA)

The R DGCA (2) software package was utilized to identify differentially expressed gene pairs across multiple distinct biological conditions. The top5,000 rowVar genes were submitted to the DGCA platform resulting in identification of 1,445,203 significant DGCA pairs (p.val difference between pairs<0.05). The 9 DGCA pair class patterns were totaled and visualized as bar charts for exploratory analysis.

Significant DGCA pairs were queried against the CellTalk (2) repository of 3,398 human ligands and receptors to further explore any biological evidence within the statistically implicated pairings. DGCA pairs were considered as overlaps if either member of a significant DGCA pair was found in the CellTalk list. Overlap pairs were annotated with any generation of MEGENA module they were found in, with specific annotation of the 37 modules with ME's significantly correlated to anti.dsDNA (p.val<0.0001).

The top 100,000 significant DGCA pairs were subset for continued investigation. The 9 pair class patterns were again totaled, visualized, and compared to the 9 pair patterns amongst all 1,445,203 significant DGCA pairs. The top 100,000 pairs were queried amongst the 149 summary MEGENA module genes as intramodular or intermodular and annotated as such. Class pair types were totaled per module and visualized with bar charts.

The plotly package was utilized to generate a sunburst of the totaled DGCA intermodular pairs between the top 12 interconnected gen3 modules, and the modules labeled with their top functional annotation determined earlier. A bar chart was generated using ggplot2 (2) of totaled M3.13.47 (IGS) DGCA intermodular connections to all other gen3 modules, excluding those made to modules orphaned by significance testing during early MEGENA summary module formation. Modules were functionally annotated as before, and bars colored by gen2 peerage. A similar bar chart was generated for M.3.14.51 (LDG).

Graph input files were prepared by combining intramodular connections/edges found between various pairings of gen3 MEGENA modules, with edge weights calculated as the MEGENA correlation strengths between gene nodes as scaled (1-pValDiff). All gene pairs were programmatically queried against the STRING-DB and those found within known PPIs annotated as such. Modified graph input files were submitted to Cytoscape for visualization. Network graphs were initially organized using Compound Spring Embedder (CoSE) before manual layout manipulation.

Gene Set Variation Analysis (GSVA). The GSVA (16) (V1.25.0) R software package was used as a non-parametric, unsupervised method for estimating the variation of predefined gene sets over all gen3 MEGENA log 2 gene expression values. GSVA input genes were evaluated if the interquartile range (IQR) of their expression across the samples was greater than 0. Enrichment scores (GSVA scores) were calculated non-parametrically using a Kolmogorov Smirnoff (KS)-like random walk statistic and a negative value for a particular sample and gene set, meaning that the gene set had a lower expression than the same gene set with a positive value. The enrichment scores (ES) were the largest positive and negative random walk deviations from zero, respectively, for a particular sample amongst the gen3 gene set. The GSVA scores underwent unsupervised k-means clustering, and six different disease phenotypes or clusters named clusters zero through five were used as labels.

Machine Learning (ML) Analysis. Removal of uninformative and redundant features (genes) was performed to reduce computational time and improve ML model performance. We assessed feature redundancy by computing the Pearson correlations between each feature and every other feature using the cor function within the Python ML package scikit learn (16), and features with correlation coefficients>0.9 removed from analysis. The dataset was split into 70% training and 30% validation, and class balancing strategies were applied on the training dataset. A OnevsRest strategy from scikit was implemented and nine different ML classifiers employed including Logistic Regression (LR), K-Nearest Neighbor (KNN), Naïve Bayes (NB), Support Vector Machines (SVM), Random Forest (RF), and Gradient Boosting (GB). Each was evaluated for sensitivity, specificity, Cohen kappa score, f-1 score, and accuracy including the usage of Receiver Operating Characteristic (ROC) curves plotted using the matplotlib Python library. Higher areas under the ROC curves represented a low false-positive rate and high true-positive rates. Gini impurity scores and confusion matrices were also evaluated. Gene expressions of the top 20% rowVar genes were averaged for each of the 6 ML clusters and chartered in PC1 vs PC2 space, and heatmaps prepared of select gen3 module gene expressions with column groupings by ML patient cluster.

Figure 2:
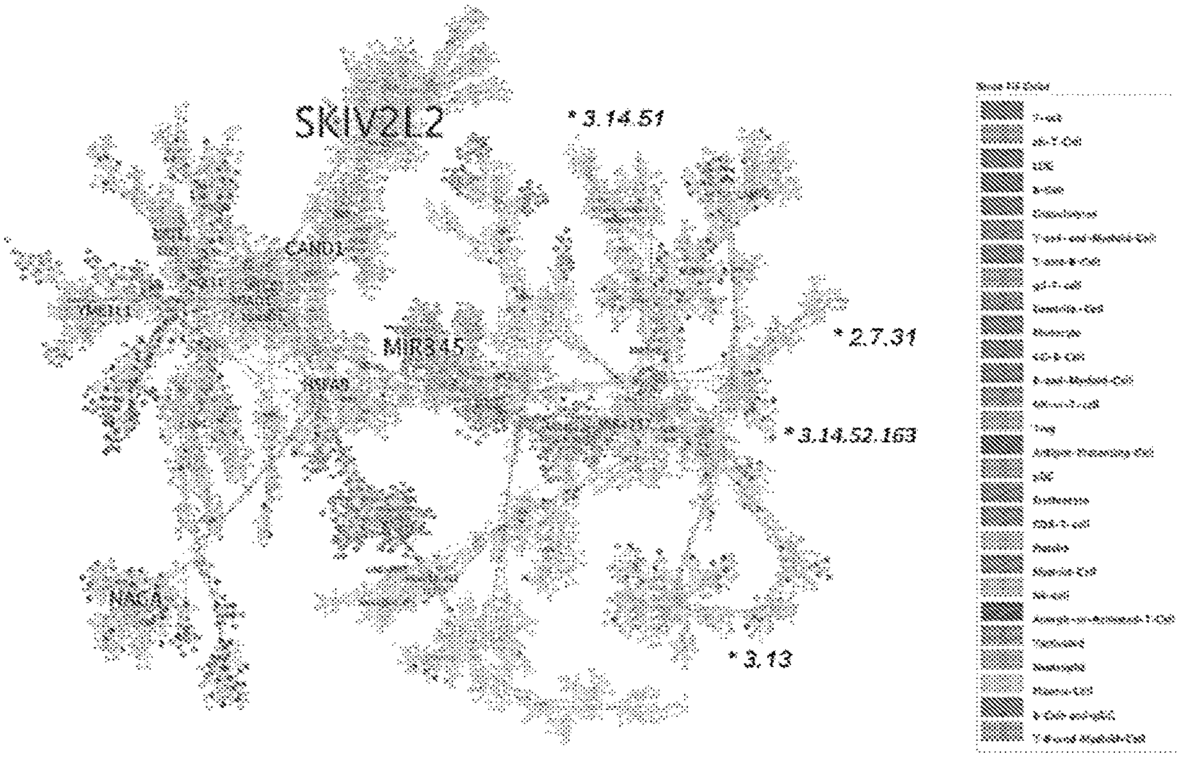
FIG. 2: Overlap of third generation modules (obtained from clustering ILLUM-1 top5k rowVar genes) with Ampel LuGENE gene function signature list.
Figure 3:
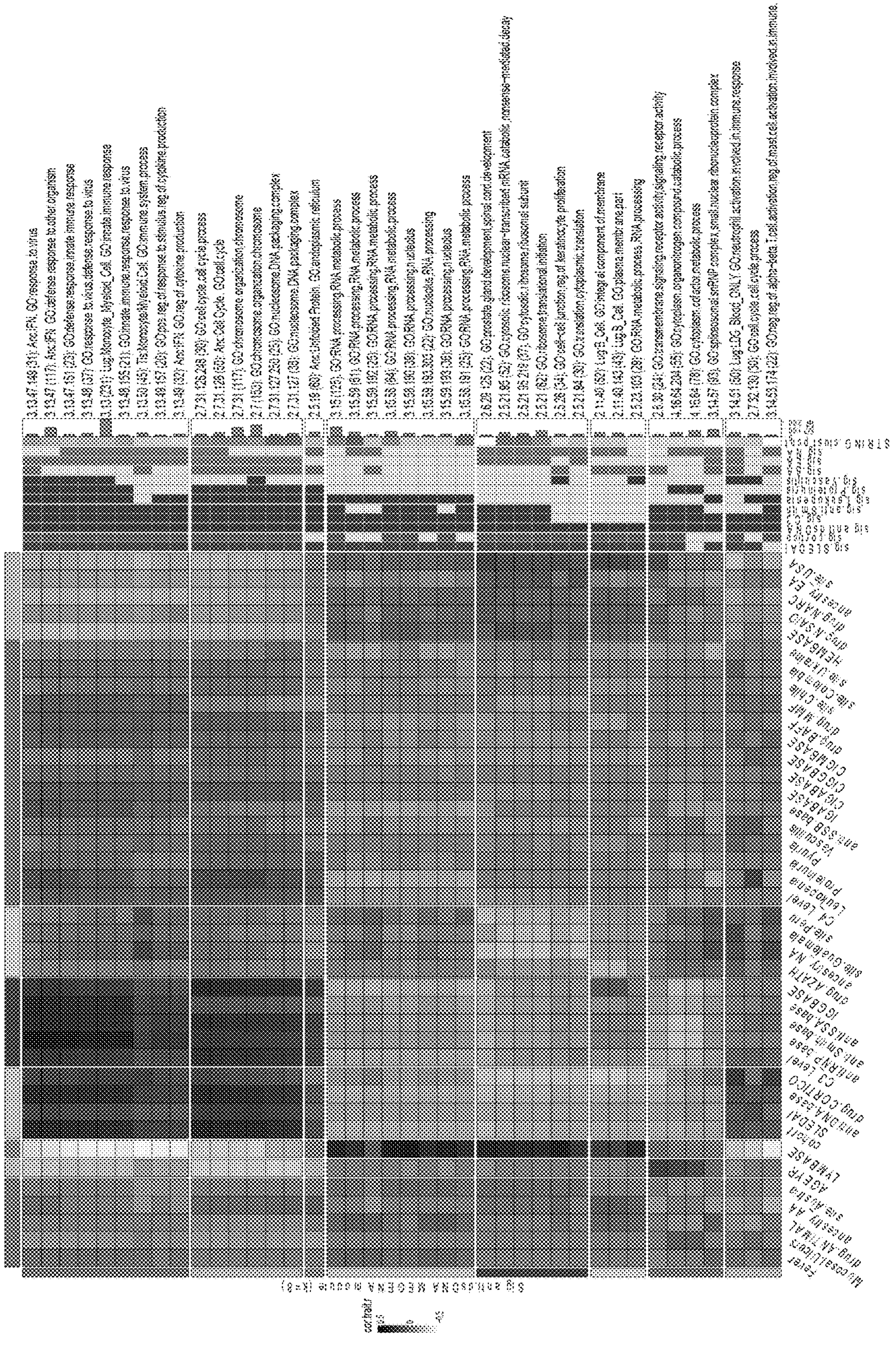
FIG. 3: ILLUM-1 top 5,000 row variance (top5k rowVar) genes MEGENA top 40 module eigengenes (MEs) significantly ($p<0.001$) correlated (sig corr) to anti.dsDNA and significantly ($p<0.2$) correlated to top 40 sig sample traits.
Figures 1, 3:
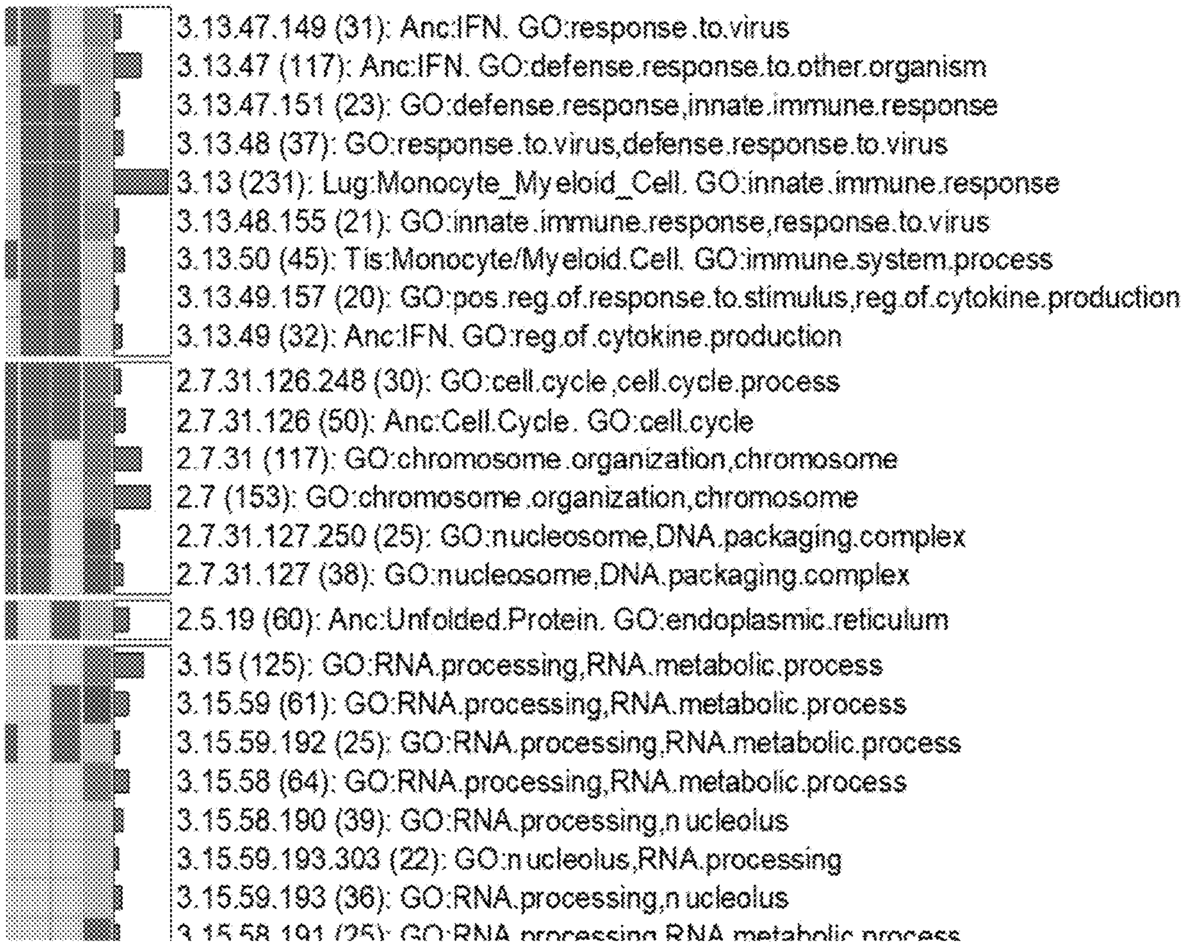
Figures 2, 3:
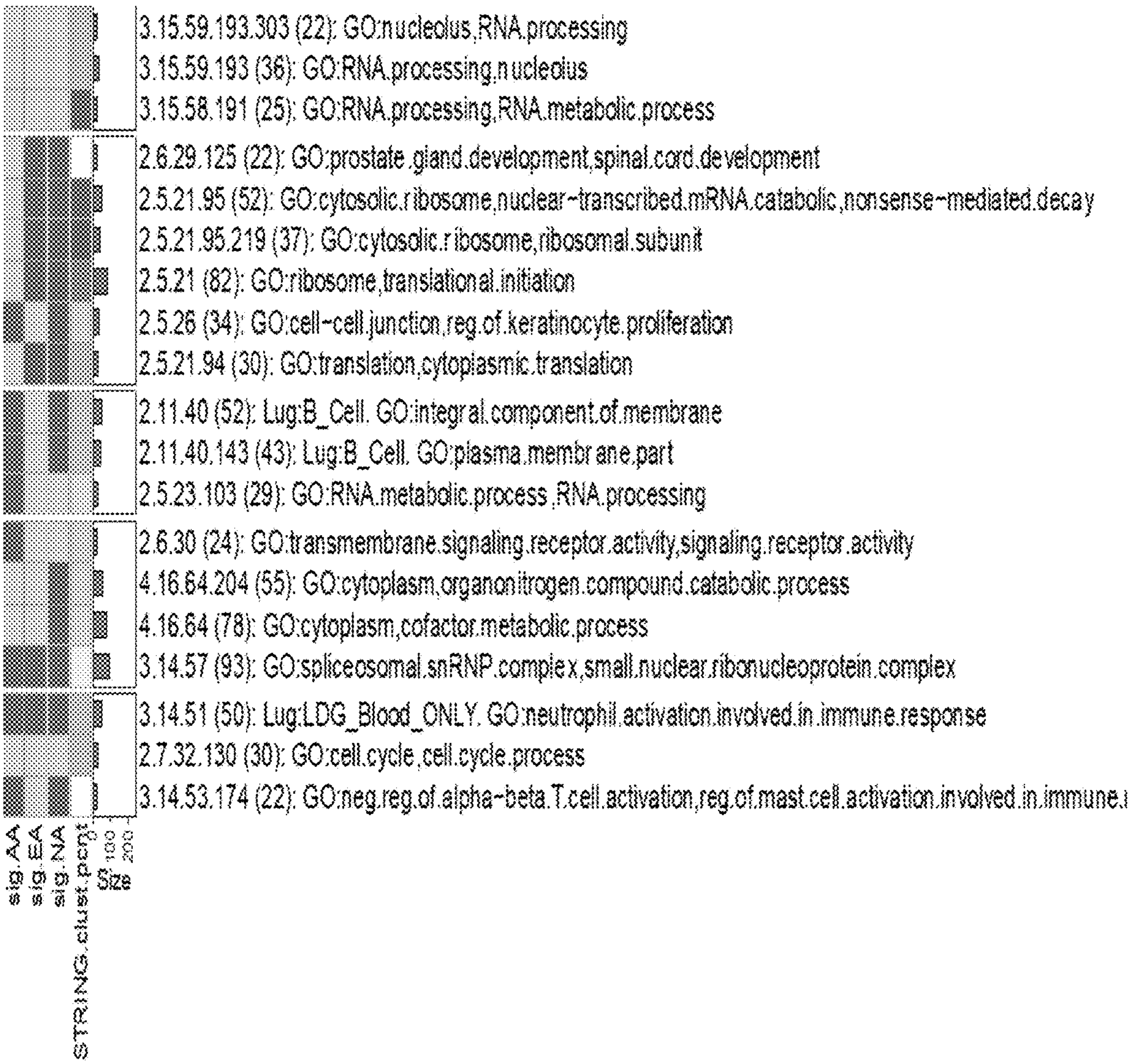
Figure 3:
Figures 3, 4:
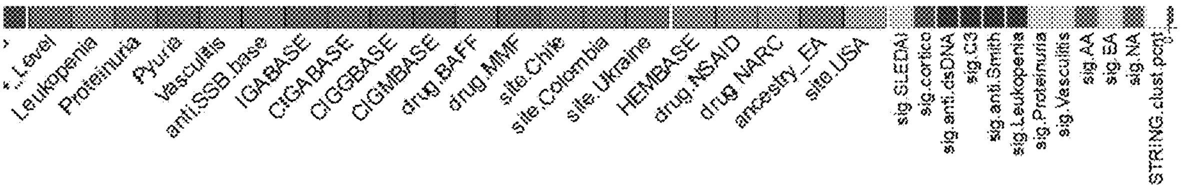
Figures 3, 4, 5:
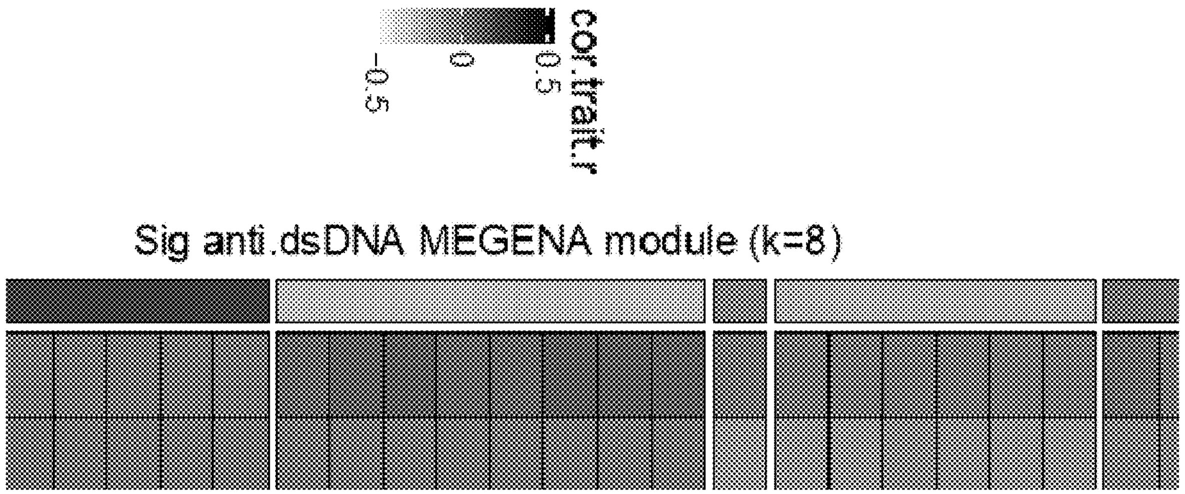

FIG. 1 shows a sunburst diagram of multiscale modules of ILLUM-1 top5k rowVar genes aggregated by co-expression. The inner most ring is made of the three founder second generation (gen2) modules, 2, 3, and 4. The second ring from center indicates immediate progeny of gen2, the third generation (gen3) modules and so on until all descendants are represented. Sunburst wedge size indicates the number of genes in the module. Modules become smaller as progeny modules lose genes given from their parents and they iterate towards higher module compactness. FIG. 2 shows overlap of planar filtered network (PFN) third generation modules & LuGENE. ILLUM-1 top5k rowVar gene coexpression PFN visualized using Cytoscape. Gene nodes were color filled by top significant LuGENE symbols overlap (minimum module overlap of 4 gene symbols, Fisher's overlap p.val<0.2), and color outlined by third generation module assignment. Gene hub node labels were sized by connectedness and labeled with gene symbol. Modules significant to anti.dsDNA (*) were labeled with their lineage name. FIG. 3 shows ILLUM-1 top 5,000 row variance (top5k rowVar) genes MEGENA top 40 module eigengenes (MEs) significantly (p<0.001) correlated (sig corr) to anti.dsDNA and significantly (p<0.2) correlated to top 40 sig sample traits. Top sample traits were identified by sorting the absolute values of row means of each sample trait correlation in descending order and selecting the top 40. Row (module) annotations recapitulate select columns in the heatmap and indicate if an ME had a significant positive or negative correlation to sample numeric SLEDAI score, yes/no corticosteroid usage, elevated anti.dsDNA autoantibodies, depleted complement C3 levels, elevated anti. Smith autoantibodies, leukopenia, proteinuria, vasculitis, ancestral background of African ancestry (AA), European ancestry (EA), or Native American ancestry (NA). STRING.clust.pont is the calculated local network clustering coefficient generated by programmatically querying the STRING database for the percentage of genes within a module predicted to have known protein-protein interactions (PPI), ranging from 0 to 100%. Size indicates the number of genes in a given module. Module names are functionally annotated by significant overlaps (enrichments) of gene symbols in a given module with various gene signature lists including AMPEL LuGENE (Lug), Ancestry (Anc), Tissues (Tis) signatures, and other AMPEL signatures specific to other applications, and the publicly available gene ontology (GO) signatures. Annotations from AMPEL lists are considered significant if there are at least 4 overlapping gene symbols between the module gene symbols and annotation signature gene symbols, and the Fisher's p value statistic of an overlap is p<0.2. Where there are multiple overlaps within a given AMPEL signature list, the most significant overlap is assigned. For selection of a given GO annotation, all GO annotations significant by p<0.2 per the GO enrichment algorithm are ranked in order of decreasing module coverage, meaning the percentage of a module's genes the GO enrichment describes. For these ILLUM-1 final figure annotations, the first top significant overlap within the AMPEL LuGENE signatures is assigned. If there is no significant LuGENE enrichment, an Ancestry enrichment is assigned, and barring that a Tissues enrichment. One of the three preferentially assigned AMPEL enrichments is then combined with the top significant GO coverage enrichment. Where are no AMPEL enrichments, the top two significant GO coverage enrichments are assigned to the module. Module enrichment annotations remain identical for all subsequent figures. Overlap calculations using other AMPEL signatures including Endotype-.kidney and BIG-C, as well as the publicly available BRETIGEA brain cell types were performed but not used for these annotations and are available as supplementary information.

Table 1B, lists the significant gene clusters (e.g. significantly correlated modules to anti.dsDNA) shown in FIG. 3, size (e.g. number of genes within the modules) of the clusters, functional characterization groups (e.g. categories) from LuGENE, AMPEL Ancestry, AMPEL Tissue, BIG-C and GO that overlaps with the clusters and respective p values, and functional annotation of the clusters. Table 1C lists the genes in the significant gene clusters of Table 1B.

TABLE 1B

The significant gene clusters as shown in FIG. 3

| lineage | mod.size | annot.luGENE | annot.luGENE.overlaps | annot.ancestry | annot.ancestry.overlaps | annot.tissue | annot.tissue.overlaps |
|---|---|---|---|---|---|---|---|
| 2.11.40 | 52 | B_Cell | 12 | | | | |
| 2.11.40.143 | 43 | B_Cell | 11 | | | | |
| 2.5.19 | 60 | | | Unfolded Protein | 11 | | |
| 2.5.21 | 82 | | | | | | |
| 2.5.21.94 | 30 | | | | | | |
| 2.5.21.95 | 52 | | | | | | |
| 2.5.21.95.219 | 37 | | | | | | |
| 2.5.23.103 | 29 | | | | | | |
| 2.5.26 | 34 | | | | | | |
| 2.6.29.125 | 22 | | | | | | |
| 2.6.30 | 24 | | | | | | |
| 2.7 | 153 | | | | | | |
| 2.7.31 | 117 | | | | | | |
| 2.7.31.126 | 50 | | | Cell Cycle | 6 | | |
| 2.7.31.126.248 | 30 | | | | | | |
| 2.7.31.127 | 38 | | | | | | |
| 2.7.31.127.250 | 25 | | | | | | |
| 2.7.32.130 | 30 | | | | | | |
| 3.13 | 231 | Monocyte_Myeloid_Cell | 9 | | | | |
| 3.13.47 | 117 | | | IFN | 30 | | |
| 3.13.47.149 | 31 | | | IFN | 16 | | |
| 3.13.47.151 | 23 | | | | | | |
| 3.13.48 | 37 | | | | | | |
| 3.13.48.155 | 21 | | | | | | |
| 3.13.49 | 32 | | | IFN | 4 | | |
| 3.13.49.157 | 20 | | | | | | |
| 3.13.50 | 45 | | | | | Monocyte/Myeloid Cell | 4 |
| 3.14.51 | 50 | LDG_Blood_ONLY | 10 | | | | |
| 3.14.53.174 | 22 | | | | | | |
| 3.14.57 | 93 | | | | | | |
| 3.15 | 125 | | | | | | |
| 3.15.58 | 64 | | | | | | |
| 3.15.58.190 | 39 | | | | | | |
| 3.15.58.191 | 25 | | | | | | |
| 3.15.59 | 61 | | | | | | |
| 3.15.59.192 | 25 | | | | | | |
| 3.15.59.193 | 36 | | | | | | |
| 3.15.59.193.303 | 22 | | | | | | |
| 4.16.64 | 78 | | | | | | |
| 4.16.64.204 | 55 | | | | | | |

| lineage | annot.BIG.C | annot.BIG.C.overlaps | annot.GO.1 | annot.GO.1.coverage | annot.GO.2 |
|---|---|---|---|---|---|
| 2.11.40 | | | integral component of membrane | 0.519 | integral component of plasma membrane |
| 2.11.40.143 | | | plasma membrane part | 0.372 | integral component of plasma membrane |
| 2.5.19 | | | endoplasmic reticulum | 0.583 | endoplasmic reticulum part |
| 2.5.21 | mRNA-Processing | 44 | ribosome | 0.5 | translational initiation |
| 2.5.21.94 | mRNA-Processing | 11 | translation | 0.433 | cytoplasmic translation |
| 2.5.21.95 | mRNA-Processing | 33 | cytosolic ribosome | 0.635 | nuclear-transcribed mRNA catabolic process, nonsense-mediated decay |

TABLE 1B-continued

| The significant gene clusters as shown in FIG. 3 | | | | | |
|---|---|---|---|---|---|
| 2.5.21.95.219 | mRNA-Processing | 21 | cytosolic ribosome | 0.568 | ribosomal subunit |
| 2.5.23.103 | Transcription-Factors | 4 | RNA metabolic process | 0.586 | RNA processing |
| 2.5.26 | Immune-Signaling | 4 | cell-cell junction | 0.118 | regulation of keratin ocyte prolife ration |
| 2.6.29.125 | General-Cell-Surface | 4 | prostate gland development | 0.091 | spinal cord development |
| 2.6.30 | Immune-Cell-Surface | 7 | transmembrane signaling receptor activity | 0.5 | signaling receptor activity |
| 2.7 | Pro-Cell-Cycle | 40 | chromosome organization | 0.516 | chromosome |
| 2.7.31 | Chromatin-Remodeling | 41 | chromosome organization | 0.598 | chromosome |
| 2.7.31.126 | | | cell cycle | 0.72 | cell cycle process |
| 2.7.31.126.248 | Pro-Cell-Cycle | 13 | cell cycle | 0.633 | cell cycle process |
| 2.7.31.127 | Chromatin-Remodeling | 37 | nucleosome | 0.947 | DNA packaging complex |
| 2.7.31.127.250 | | | nucleosome | 0.96 | DNA packaging complex |
| 2.7.32.130 | DNA-Repair | 7 | cell cycle | 0.5 | cell cycle process |
| 3.13 | | | innate immune response | 0.312 | response to virus |
| 3.13.47 | | | defense response to other organism | 0.248 | response to virus |
| 3.13.47.149 | | | response to virus | 0.516 | defense response to virus |
| 3.13.47.151 | | | defense response | 0.435 | innate immune response |
| 3.13.48 | Pattern-Recognition-Receptors | 9 | response to virus | 0.405 | defense response to virus |
| 3.13.48.155 | Interferon-Stimulated-Genes | 5 | innate immune response | 0.667 | response to virus |
| 3.13.49 | | | regulation of cytokine production | 0.312 | cytokine production |
| 3.13.49.157 | Intracellular-Signaling | 5 | positive regulation of response to stimulus | 0.55 | regulation of cytokine production |
| 3.13.50 | | | immune system process | 0.533 | immune response |
| 3.14.51 | | | neutrophil activation involved in immune response | 0.54 | neutrophil degranulation |
| 3.14.53.174 | | | negative regulation of alpha-beta T cell activation | 0.091 | regulation of mast cell activation involved in immune response |

TABLE 1B-continued

| The significant gene clusters as shown in FIG. 3 | | | | | |
|---|---|---|---|---|---|
| 3.14.57 | Unknown | 11 | spliceosomal snRNP complex | 0.108 | small nuclear ribonucleoprotein complex |
| 3.15 | | | RNA processing | 0.952 | RNA metabolic process |
| 3.15.58 | | | RNA processing | 0.906 | RNA metabolic process |
| 3.15.58.190 | | | RNA processing | 0.872 | nucleolus |
| 3.15.58.191 | | | RNA processing | 0.96 | RNA metabolic process |
| 3.15.59 | | | RNA processing | 1 | RNA metabolic process |
| 3.15.59.192 | | | RNA processing | 1 | RNA metabolic process |
| 3.15.59.193 | | | RNA processing | 1 | nucleolus |
| 3.15.59.193.303 | | | nucleolus | 1 | RNA processing |
| 4.16.64 | Ubiquitylation-and-Sumoylation | 4 | cytoplasm | 0.782 | cofactor metabolic process |
| 4.16.64.204 | | | cytoplasm | 0.836 | organo nitrogen compound catabolic process |

| lineage | annot.GO.2.coverage | annot.FIGURES |
|---|---|---|
| 2.11.40 | 0.288 | Lug: B_Cell. GO: integral.component.of.membrane |
| 2.11.40.143 | 0.279 | Lug: B_Cell. GO: plasma.membrane.part |
| 2.5.19 | 0.533 | Anc: Unfolded.Protein. GO: endoplasmic.reticulum |
| 2.5.21 | 0.488 | GO: ribosome, translational.initiation |
| 2.5.21.94 | 0.3 | GO: translation, cytoplasmic.translation |
| 2.5.21.95 | 0.596 | GO: cytosolic.ribosome, nuclear-transcribed.mRNA.catabolic, nonsense-mediated.decay |
| 2.5.21.95.219 | 0.568 | GO: cytosolic.ribosome, ribosomal.subunit |
| 2.5.23.103 | 0.379 | GO: RNA.metabolic.process, RNA.processing |
| 2.5.26 | 0.059 | GO: cell-cell.junction, reg.of.keratinocyte.proliferation |
| 2.6.29.125 | 0.091 | GO: prostate.gland.development, spinal.cord.development |
| 2.6.30 | 0.5 | GO: transmembrane.signaling.receptor.activity, signaling.receptor.activity |
| 2.7 | 0.503 | GO: chromosome.organization, chromosome |
| 2.7.31 | 0.59 | GO: chromosome.organization, chromosome |
| 2.7.31.126 | 0.64 | Anc: Cell.Cycle. GO: cell.cycle |
| 2.7.31.126.248 | 0.6 | GO: cell.cycle, cell.cycle.process |
| 2.7.31.127 | 0.947 | GO: nucleosome, DNA.packaging.complex |
| 2.7.31.127.250 | 0.96 | GO: nucleosome, DNA.packaging.complex |
| 2.7.32.130 | 0.433 | GO: cell.cycle, cell.cycle.process |
| 3.13 | 0.203 | Lug: Monocyte_Myeloid_Cell. GO: innate.immune.response |

TABLE 1B-continued

| The significant gene clusters as shown in FIG. 3 | | |
|---|---|---|
| 3.13.47 | 0.231 | Anc: IFN. GO: defense.response.to.other.organism |
| 3.13.47.149 | 0.484 | Anc: IFN. GO: response.to.virus |
| 3.13.47.151 | 0.348 | GO: defense.response, innate.immune.response |
| 3.13.48 | 0.378 | GO: response.to.virus, defense.response.to.virus |
| 3.13.48.155 | 0.571 | GO: innate.immune.response, response.to.virus |
| 3.13.49 | 0.312 | Anc: IFN. GO: reg.of.cytokine.production |
| 3.13.49.157 | 0.4 | GO: pos.reg.of.response.to.stimulus, reg.of.cytokine.production |
| 3.13.50 | 0.422 | Tis: Monocyte/Myeloid.Cell. GO: immune.system.process |
| 3.14.51 | 0.54 | Lug: LDG__Blood__ONLY. GO: neutrophil.activation.involved.in.immune.response |
| 3.14.53.174 | 0.091 | GO: neg.reg.of.alpha-beta.T.cell.activation, reg.of.mast.cell.activation.involved.in.immune.response |
| 3.14.57 | 0.108 | GO: spliceosomal.snRNP.complex, small.nuclear.ribonucleoprotein.complex |
| 3.15 | 0.952 | GO: RNA.processing, RNA.metabolic.process |
| 3.15.58 | 0.906 | GO: RNA.processing, RNA.metabolic.process |
| 3.15.58.190 | 0.872 | GO: RNA.processing, nucleolus |
| 3.15.58.191 | 0.96 | GO: RNA.processing, RNA.metabolic.process |
| 3.15.59 | 1 | GO: RNA.processing, RNA.metabolic.process |
| 3.15.59.192 | 1 | GO: RNA.processing, RNA.metabolic.process |
| 3.15.59.193 | 1 | GO: RNA.processing, nucleolus |
| 3.15.59.193.303 | 1 | GO: nucleolus, RNA.processing |
| 4.16.64 | 0.141 | GO: cytoplasm, cofactormetabolic.process |
| 4.16.64.204 | 0.2 | GO: cytoplasm, organonitrogen.compound.catabolic.process |

TABLE 1C

The genes within the significant gene clusters, listed in Table 1B. (2160 Genes Listed by: Gene Symbol | Module | Gene Description | Chromosome Number | Row Variance) ||)

ABCB4 | 2.11.40 | ATP binding cassette subfamily B member 4 | 7 | 0.068937993 || ADAM28 | 2.11.40 | ADAM metallopeptidase domain 28 | 8 | 0.197666459 || AFF3 | 2.11.40 | AF4/FMR2 family member 3 | 2 | 0.240000552 || BANK1 | 2.11.40 | B-cell scaffold protein with ankyrin repeats 1 | 4 | 0.53994287 || BCL11A | 2.11.40 | B-cell CLL/lymphoma 11A | 2 | 0.097061735 || BLK | 2.11.40 | BLK proto-oncogene, Src family tyrosine kinase | 8 | 0.121487225 || BTLA | 2.11.40 | B and T lymphocyte associated | 3 | 0.350510492 || CCR6 | 2.11.40 | chemokine (C-C motif) receptor 6 | 6 | 0.144021827 || CD200 | 2.11.40 | CD200 molecule | 3 | 0.068007852 || CD22 | 2.11.40 | CD22 molecule | 19 | 0.674809398 || CD72 | 2.11.40 | CD72 molecule | 9 | 0.190629509 || CD79A | 2.11.40 | CD79a molecule | 19 | 0.572912751 || CD79B | 2.11.40 | CD79b molecule | 17 | 0.136126694 || CDCA7L | 2.11.40 | cell division cycle associated 7 like | 7 | 0.239052625 || CIITA | 2.11.40 | class II, major histocompatibility complex, transactivator | 16 | 0.10324015 || CLEC17A | 2.11.40 | C-type lectin domain family 17 member A | 19 | 0.097147137 || CLECL1 | 2.11.40 | C-type lectin like 1 | 12 | 0.066236092 || CNR2 | 2.11.40 | cannabinoid receptor 2 | 1 | 0.075675274 || CR2 | 2.11.40 | complement component 3d receptor 2 | 1 | 0.222810084 || CXCR5 | 2.11.40 | chemokine (C-X-C motif) receptor 5 | 11 | 0.090317048 || DSP | 2.11.40 | desmoplakin | 6 | 0.154907089 || EBF1 | 2.11.40 | early B-cell factor 1 | 5 | 0.21593477 || FAM129C | 2.11.40 | family with sequence similarity 129 member C | 19 | 0.108938106 || FAM177B | 2.11.40 | family with sequence similarity 177 member B | 1 | 0.127877042 || FCER2 | 2.11.40 | Fc fragment of IgE receptor II | 19 | 0.295713738 || FCRL1 2.11.40 | Fc receptor like 1 | 1 | 0.571872347 || FCRL2 | 2.11.40 | Fc receptor like 2 | 1 | 0.280381556 || FCRLA | 2.11.40 | Fc receptor like A | 1 | 0.262489969 || LINC00926 | 2.11.40 | long intergenic non-protein coding RNA 926 | 15 | 0.07750836 || LOC102724714 | 2.11.40 | uncharacterized LOC102724714 | 2 | 0.087279461 || MGAT5 | 2.11.40 | mannosyl (alpha-1,6-)-

TABLE 1C-continued

The genes within the significant gene clusters, listed in Table 1B. (2160 Genes Listed by: Gene Symbol | Module | Gene Description | Chromosome Number | Row Variance) ||)

glycoprotein beta-1,6-N-acetyl-glucosaminyltransferase | 2 | 0.069468502 || MS4A1 | 2.11.40 | membrane spanning 4-domains A1 | 11 | 0.883228166 || OR11H2 | 2.11.40 | olfactory receptor family 11 subfamily H member 2 | 14 | 0.149188532 || OSBPL10 | 2.11.40 | oxysterol binding protein like 10 | 3 | 0.095815902 || P2RX5 | 2.11.40 | purinergic receptor P2X 5 | 17 | 0.224936924 || P2RX5-TAX1BP3 | 2.11.40 | P2RX5-TAXIBP3 readthrough (NMD candidate) | 17 | 0.080448604 || PAX5 | 2.11.40 | paired box 5 | 9 | 0.231758824 || PLEKHG1 | 2.11.40 | pleckstrin homology and RhoGEF domain containing G1 | 6 | 0.177042445 || PLPP5 | 2.11.40 | phospholipid phosphatase 5 | 8 | 0.143067342 || RALGPS2 | 2.11.40 | Ral GEF with PH domain and SH3 binding motif 2 | 1 | 0.325728061 || SCN3A | 2.11.40 | sodium voltage-gated channel alpha subunit 3 | 2 | 0.11668824 || SLC38A11 | 2.11.40 | solute carrier family 38 member 11 | 2 | 0.090014784 || SLC9A7 | 2.11.40 | solute carrier family 9 member A7 | X | 0.130018145 || SNORA70E | 2.11.40 | small nucleolar RNA, H/ACA box 70E | 11 | 0.136435541 || SPIB 2.11.40 | Spi-B transcription factor | 19 | 0.06669751 || STRBP | 2.11.40 | spermatid perinuclear RNA binding protein | 9 | 0.135890146 || TCL1A | 2.11.40 | T-cell leukemia/lymphoma 1A | 14 | 0.515447854 || TCL6 | 2.11.40 | T-cell leukemia/lymphoma 6 (non-protein coding) | 14 | 0.061855277 || TLR10 | 2.11.40 | toll like receptor 10 | 4 | 0.152433425 || TSPAN13 | 2.11.40 | tetraspanin 13 | 7 | 0.209456188 || VPREB3 | 2.11.40 | pre-B lymphocyte 3 | 22 | 0.129761505 || ZNF860 | 2.11.40 | zinc finger protein 860 | 3 | 0.119513709 || ABCB4 | 2.11.40.143 | ATP binding cassette subfamily B member 4 | 7 | 0.068937993 || AFF3 | 2.11.40.143 | AF4/FMR2 family member 3 | 2 | 0.240000552 || BANK1 | 2.11.40.143 | B-cell scaffold protein with ankyrin repeats 1 | 4 | 0.53994287 || BCL11A | 2.11.40.143 | B-cell CLL/lymphoma 11A | 2 | 0.097061735 || BLK | 2.11.40.143 | BLK proto-oncogene, Src family tyrosine kinase | 8 | 0.121487225 || CD200 | 2.11.40.143 | CD200 molecule | 3 | 0.068007852 || CD22 | 2.11.40.143 | CD22 molecule | 19 | 0.674809398 || CD72 | 2.11.40.143 | CD72 molecule | 9 | 0.190629509 || CD79A | 2.11.40.143 | CD79a molecule | 19 | 0.572912751 || CD79B | 2.11.40.143 | CD79b molecule | 17 | 0.136126694 || CDCA7L | 2.11.40.143 | cell division cycle associated 7 like | 7 | 0.239052625 || CLEC17A | 2.11.40.143 | C-type lectin domain family 17 member A | 19 | 0.097147137 || CLECL1 | 2.11.40.143 | C-type lectin like 1 | 12 | 0.066236092 || CNR2 | 2.11.40.143 | cannabinoid receptor 2 | 1 | 0.075675274 || CXCR5 | 2.11.40.143 | chemokine (C-X-C motif) receptor 5 | 11 | 0.090317048 || DSP | 2.11.40.143 | desmoplakin | 6 | 0.154907089 || EBF1 | 2.11.40.143 | early B-cell factor 1 | 5 | 0.21593477 || FAM129C | 2.11.40.143 | family with sequence similarity 129 member C | 19 | 0.108938106 || FAM177B | 2.11.40.143 | family with sequence similarity 177 member B | 1 | 0.127877042 || FCER2 | 2.11.40.143 | Fc fragment of IgE receptor II | 19 | 0.295713738 || FCRL1 | 2.11.40.143 | Fc receptor like 1 | 1 | 0.571872347 || FCRL2 | 2.11.40.143 | Fc receptor like 2 | 1 | 0.280381556 || FCRLA | 2.11.40.143 | Fc receptor like A | 1 | 0.262489969 || LINC00926 | 2.11.40.143 | long intergenic non-protein coding RNA 926 | 15 | 0.07750836 || LOC102724714 | 2.11.40.143 | uncharacterized LOC102724714 | 2 | 0.087279461 || MS4A1 | 2.11.40.143 | membrane spanning 4-domains Al | 11 | 0.883228166 || OR11H2 | 2.11.40.143 | olfactory receptor family 11 subfamily H member 2 | 14 | 0.149188532 || OSBPL10 | 2.11.40.143 | oxysterol binding protein like 10 | 3 | 0.095815902 || P2RX5 | 2.11.40.143 | purinergic receptor P2X 5 | 17 | 0.224936924 || P2RX5-TAX1BP3 | 2.11.40.143 | P2RX5-TAXIBP3 readthrough (NMD candidate) | 17 | 0.080448604 || PAX5 | 2.11.40.143 | paired box 5 | 9 | 0.231758824 || PLEKHG1 | 2.11.40.143 | pleckstrin homology and RhoGEF domain containing G1 | 6 | 0.177042445 || RALGPS2 | 2.11.40.143 | Ral GEF with PH domain and SH3 binding motif 2 | 1 | 0.325728061 || SCN3A | 2.11.40.143 | sodium voltage-gated channel alpha subunit 3 | 2 | 0.11668824 || SLC38A11 | 2.11.40.143 | solute carrier family 38 member 11 | 2 | 0.090014784 || SNORA70E | 2.11.40.143 | small nucleolar RNA, H/ACA box 70E | 11 | 0.136435541 || SPIB | 2.11.40.143 | Spi-B transcription factor | 19 | 0.06669751 || TCLIA | 2.11.40.143 | T-cell leukemia/lymphoma 1A | 14 | 0.515447854 || TCL6 | 2.11.40.143 | T-cell leukemia/lymphoma 6 (non-protein coding) | 14 | 0.061855277 || TLR10 | 2.11.40.143 | toll like receptor 10 | 4 | 0.152433425 || TSPAN13 | 2.11.40.143 | tetraspanin 13 | 7 | 0.209456188 || VPREB3 | 2.11.40.143 | pre-B lymphocyte 3 | 22 | 0.129761505 || ZNF860 | 2.11.40.143 | zinc finger protein 860 | 3 | 0.119513709 || AARS | 2.5.19 | alany1-tRNA synthetase | 16 | 0.095643338 || ALG3 | 2.5.19 | ALG3, alpha-1,3-mannosyltransferase | 3 | 0.065652613 || ATP2A2 | 2.5.19 | ATPase sarcoplasmic/endoplasmic reticulum Ca2+ transporting 2 | 12 | 0.083966298 || CALR | 2.5.19 | calreticulin | 19 | 0.140287657 || CALU | 2.5.19 | calumenin | 7 | 0.080405461 || CANX | 2.5.19 | calnexin | 5 | 0.101378832 || DCPS | 2.5.19 | decapping enzyme, scavenger | 11 | 0.07186834 || DDOST | 2.5.19 | dolichyl-diphosphooligosaccharide--protein glycosyltransferase non-catalytic subunit | 1 | 0.075630242 || DNAJB11 | 2.5.19 | DnaJ heat shock protein family (Hsp40) member B11 | 3 | 0.116552155 || EDEM1 | 2.5.19 | ER degradation enhancer, mannosidase alpha-like 1 | 3 | 0.071020785 || EHD4 | 2.5.19 | EH domain containing 4 | 15 | 0.06756623 || ENO1 | 2.5.19 | enolase 1, (alpha) | 1 | 0.079611834 || ERLEC1 | 2.5.19 | endoplasmic reticulum lectin 1 | 2 | 0.135258236 || F8A1 | 2.5.19 | coagulation factor VIII-associated 1 | X | 0.089454361 || FKBP11 | 2.5.19 | FK506 binding protein 11 | 12 | 0.112759074 || GLDC | 2.5.19 | glycine dehydrogenase (decarboxylating) | 9 | 0.229441541 || GPRC5D | 2.5.19 | G protein-coupled receptor class C group 5 member D | 12 | 0.219448068 || HERPUD1 | 2.5.19 | homocysteine-inducible, endoplasmic reticulum stress-inducible, ubiquitin-like domain member 1 | 16 | 0.084478583 || HRASLS2 | 2.5.19 | HRAS like suppressor 2 | 11 | 0.071870842 || HSP90B1 | 2.5.19 | heat shock protein 90 kDa beta family member 1 | 12 | 0.231787458 || HSP90B2P | 2.5.19 | heat shock protein 90 kDa beta family member 2, pseudogene | 15 | 0.269187385 || HSPA13 | 2.5.19 | heat shock protein family A (Hsp70) member 13 | 21 | 0.099440123 || HSPA5 | 2.5.19 | heat shock protein family A (Hsp70) member 5 | 9 | 0.114805555 || INTS7 | 2.5.19 | integrator complex subunit 7 | 1 | 0.120835669 || IRF4 | 2.5.19 | interferon regulatory factor 4 | 6 | 0.176431836 || ITM2C | 2.5.19 | integral membrane protein 2C | 2 | 0.147658377 || JCHAIN | 2.5.19 | joining chain of multimeric IgA and IgM | 4 | 1.576640708 || LGMN | 2.5.19 | legumain | 14 | 0.062351431 || LMAN1 | 2.5.19 | lectin, mannose binding 1 | 18 | 0.285518219 || MANEA | 2.5.19 | mannosidase endo-alpha | 6 | 0.229828031 | MIR550A3 |

TABLE 1C-continued

The genes within the significant gene clusters, listed in Table 1B. (2160 Genes Listed by: Gene Symbol | Module | Gene Description | Chromosome Number | Row Variance) ||)

2.5.19 | microRNA 550a-3 | 7 | 0.116895368 || MIR650 | 2.5.19 | microRNA 650 | | 0.899150223 || MLEC | 2.5.19 | malectin | 12 | 0.080974018 || MYDGF | 2.5.19 | myeloid-derived growth factor | 19 | 0.061961595 || MZB1 | 2.5.19 | marginal zone B and B1 cell specific protein | 5 | 0.351291588 || NCOA3 | 2.5.19 | nuclear receptor coactivator 3 | 20 | 0.067356037 || NME1 | 2.5.19 | NME/NM23 nucleoside diphosphate kinase 1 | 17 | 0.124297123 || NOMO2 | 2.5.19 | NODAL modulator 2 | 16 | 0.131651075 || NXPE3 | 2.5.19 | neurexophilin and PC-esterase domain family member 3 | 3 | 0.060382069 || P4HB | 2.5.19 | prolyl 4-hydroxylase subunit beta | 17 | 0.137044449 || PARM1 | 2.5.19 | prostate androgen-regulated mucin-like protein 1 | 4 | 0.103611889 || PDIA4 | 2.5.19 | protein disulfide isomerase family A member 4 | 7 | 0.151253329 || PDIA6 | 2.5.19 | protein disulfide isomerase family A member 6 | 2 | 0.075134753 || PPIB | 2.5.19 | peptidylprolyl isomerase B | 15 | 0.123993341 || PRDX4 | 2.5.19 | peroxiredoxin 4 | X | 0.063254322 || RPN1 | 2.5.19 | ribophorin I | 3 | 0.078964973 || RPN2 | 2.5.19 | ribophorin II | 20 | 0.132221573 || SEC11C | 2.5.19 | SEC11 homolog C, signal peptidase complex subunit | 18 | 0.206526286 || SEC24A | 2.5.19 | SEC24 homolog A, COPII coat complex component | 5 | 0.109782503 || SEC61A1 | 2.5.19 | Sec61 translocon alpha 1 subunit | 3 | 0.08245024 || SLC35B1 | 2.5.19 | solute carrier family 35 member B1 | 17 | 0.063837603 || SRM | 2.5.19 | spermidine synthase | 1 | 0.135685677 || SSR3 | 2.5.19 | signal sequence receptor, gamma (translocon-associated protein gamma) | 3 | 0.10945977 || STT3A | 2.5.19 | STT3A, catalytic subunit of the oligosaccharyltransferase complex | 11 | 0.150482375 || TNFRSF17 | 2.5.19 | tumor necrosis factor receptor superfamily member 17 | 16 | 0.260785959 || TRAM2 | 2.5.19 | translocation associated membrane protein 2 | 6 | 0.121830932 || TXNDC11 | 2.5.19 | thioredoxin domain containing 11 | 16 | 0.161347926 || UAP1 | 2.5.19 | UDP-N-acetylglucosamine pyrophosphorylase 1 | 1 | 0.090127097 || XBP1 | 2.5.19 | X-box binding protein 1 | 22 | 0.181340263 || YARS | 2.5.19 | tyrosyl-tRNA synthetase | 1 | 0.093981031 || C12orf57 | 2.5.21 | chromosome 12 open reading frame 57 | 12 | 0.076312548 || CD48 | 2.5.21 | CD48 molecule | 1 | 0.106957822 || CD52 | 2.5.21 | CD52 molecule | 1 | 0.182237052 || CNIH1 | 2.5.21 | cornichon family AMPA receptor auxiliary protein 1 | 14 | 0.075927179 || COX4I1 | 2.5.21 | cytochrome c oxidase subunit 4I1 | 16 | 0.065113972 || COX7C | 2.5.21 | cytochrome c oxidase subunit 7C | 5 | 0.122466216 || EEF2 | 2.5.21 | eukaryotic translation elongation factor 2 | 19 | 0.089768211 || EIF2A | 2.5.21 | eukaryotic translation initiation factor 2A | 3 | 0.11202727 || EIF2S3 | 2.5.21 | eukaryotic translation initiation factor 2 subunit gamma | X | 0.110062878 || EIF3E | 2.5.21 | eukaryotic translation initiation factor 3 subunit E | 8 | 0.185375085 || EIF3F | 2.5.21 | eukaryotic translation initiation factor 3 subunit F | 11 | 0.130312317 || EIF3H | 2.5.21 | eukaryotic translation initiation factor 3 subunit H | 8 | 0.126221252 || EIF3L | 2.5.21 | eukaryotic translation initiation factor 3 subunit L | 22 | 0.1903491 || EIF4B | 2.5.21 | eukaryotic translation initiation factor 4B | 12 | 0.093183967 || FAM117B | 2.5.21 | family with sequence similarity 117 member B | 2 | 0.146355543 || FAU | 2.5.21 | Finkel-Biskis-Reilly murine sarcoma virus (FBR-MuSV) ubiquitously expressed | 11 | 0.081721323 || GAS5 | 2.5.21 | growth arrest specific 5 (non-protein coding) | 1 | 0.260967548 || GLTSCR2 | 2.5.21 | glioma tumor suppressor candidate region gene 2 | 19 | 0.130046996 || HIBADH | 2.5.21 | 3-hydroxyisobutyrate dehydrogenase | 7 | 0.062671162 || HINT1 | 2.5.21 | histidine triad nucleotide binding protein 1 | 5 | 0.072725346 || HNRNPA1P10 | 2.5.21 | heterogeneous nuclear ribonucleoprotein A1 pseudogene 10 | 16 | 0.189310158 || IMPDH2 | 2.5.21 | IMP (inosine 5'-monophosphate) dehydrogenase 2 | 3 | 0.077562605 || LEPROTL1 | 2.5.21 | leptin receptor overlapping transcript-like 1 | 8 | 0.094315142 || LOC440311 | 2.5.21 | glioma tumor suppressor candidate region gene 2 pseudogene | | 0.134648089 || MRPL53 | 2.5.21 | mitochondrial ribosomal protein L53 | 2 | 0.086935926 || NACA2 | 2.5.21 | nascent polypeptide-associated complex alpha subunit 2 | 17 | 0.079478922 || NDFIP1 | 2.5.21 | Nedd4 family interacting protein 1 | 5 | 0.076106651 || NPM1P5 | 2.5.21 | nucleophosmin 1 (nucleolar phosphoprotein B23, numatrin) pseudogene 5 | 15 | 0.093548704 || NSA2 | 2.5.21 | NSA2, ribosome biogenesis homolog | 5 | 0.096765436 || PCYOX1 | 2.5.21 | prenylcysteine oxidase 1 | 2 | 0.166452006 || PITPNA-AS1 | 2.5.21 | PITPNA antisense RNA 1 | 17 | 0.060726564 || RACK1 | 2.5.21 | receptor for activated C kinase 1 | 5 | 0.115394599 || RPL10A | 2.5.21 | ribosomal protein L10a | 6 | 0.072702986 || RPL11 | 2.5.21 | ribosomal protein L11 | 1 | 0.120824538 || RPL12 | 2.5.21 | ribosomal protein L12 | 9 | 0.115748108 || RPL13A | 2.5.21 | ribosomal protein L13a | 19 | 0.132795073 || RPL13AP20 | 2.5.21 | ribosomal protein L13a pseudogene 20 | 12 | 0.161347314 || RPL13AP6 | 2.5.21 | ribosomal protein L13a pseudogene 6 | 10 | 0.129850143 || RPL15 | 2.5.21 | ribosomal protein L15 | 3 | 0.06704344 || RPL17 | 2.5.21 | ribosomal protein L17 | 18 | 0.069751008 || RPL18 | 2.5.21 | ribosomal protein L18 | 19 | 0.119302683 || RPL22L1 | 2.5.21 | ribosomal protein L22 like 1 | 3 | 0.065432456 || RPL23 | 2.5.21 | ribosomal protein L23 | 17 | 0.136978409 || RPL24 | 2.5.21 | ribosomal protein L24 | 3 | 0.161851242 || RPL27 | 2.5.21 | ribosomal protein L27 | 17 | 0.111993882 || RPL3 | 2.5.21 | ribosomal protein L3 | 22 | 0.084887753 || RPL30 | 2.5.21 | ribosomal protein L30 | 8 | 0.089497163 || RPL35A | 2.5.21 | ribosomal protein L35a | 3 | 0.069852489 || RPL36AL | 2.5.21 | ribosomal protein L36a like | 14 | 0.065116321 || RPL37 | 2.5.21 | ribosomal protein L37 | 5 | 0.076799422 || RPL38 | 2.5.21 | ribosomal protein L38 | 17 | 0.080575897 || RPL4 | 2.5.21 | ribosomal protein L4 | 15 | 0.153559114 || RPL5 | 2.5.21 | ribosomal protein L5 | 1 | 0.173078953 || RPL8 | 2.5.21 | ribosomal protein L8 | 8 | 0.099844191 || RPLP1 | 2.5.21 | ribosomal protein lateral stalk subunit P1 | 15 | 0.127554093 || RPLP2 | 2.5.21 | ribosomal protein lateral stalk subunit P2 | 11 | 0.071238007 || RPS13 | 2.5.21 | ribosomal protein S13 | 11 | 0.227351465 || RPS15 | 2.5.21 | ribosomal protein S15 | 19 | 0.061829932 || RPS16 | 2.5.21 | ribosomal protein S16 | 19 | 0.138540778 || RPS19 | 2.5.21 | ribosomal protein S19 | 19 | 0.13074389 || RPS20 | 2.5.21 | ribosomal protein S20 | 8 | 0.105401606 || RPS21 | 2.5.21 | ribosomal protein S21 | 20 | 0.091936887 || RPS23 | 2.5.21 | ribosomal protein S23 | 5 | 0.411190488 || RPS29 | 2.5.21 | ribosomal protein S29 | 14 | 0.093223307 || RPS3 | 2.5.21 | ribosomal protein S3 | 11 | 0.086053301 || RPS4X | 2.5.21 | ribosomal protein S4, X-linked | X | 0.102418804 || RPS4XP21 | 2.5.21 | ribosomal protein S4X pseudogene 21 | 19 | 0.076030546 || RPS5 | 2.5.21 | ribosomal protein S5 | 19 | 0.182851472 || RPS6 | 2.5.21 | ribosomal protein S6 |

TABLE 1C-continued

The genes within the significant gene clusters, listed in Table 1B. (2160 Genes Listed by: Gene Symbol | Module | Gene Description | Chromosome Number | Row Variance) ||)

9 | 0.109890296 || RPS8 | 2.5.21 | ribosomal protein S8 | 1 | 0.196574067 || RSLID1 | 2.5.21 | ribosomal LI domain containing 1 | 16 | 0.169517764 || RSL24D1 | 2.5.21 | ribosomal L24 domain containing 1 | 15 | 0.131499719 || SARAF | 2.5.21 | store-operated calcium entry-associated regulatory factor | 8 | 0.064286076 || SLC25A6 | 2.5.21 | solute carrier family 25 member 6 | X | 0.116914055 || SNHG16 | 2.5.21 | small nucleolar RNA host gene 16 | 17 | 0.077369616 || SNHG5 | 2.5.21 | small nucleolar RNA host gene 5 | 6 | 0.178139499 || TMEM14C | 2.5.21 | transmembrane protein 14C | 6 | 0.072948056 || TMEM256 | 2.5.21 | transmembrane protein 256 | 17 | 0.102056992 || TOMM20 | 2.5.21 | translocase of outer mitochondrial membrane 20 | 1 | 0.065027716 || TOMM6 | 2.5.21 | translocase of outer mitochondrial membrane 6 | 6 | 0.07366474 || TOMM7 | 2.5.21 | translocase of outer mitochondrial membrane 7 | 7 | 0.157037318 || UXT | 2.5.21 | ubiquitously expressed prefoldin like chaperone | X | 0.089518174 || CNIH1 | 2.5.21.94 | cornichon family AMPA receptor auxiliary protein 1 | 14 | 0.075927179 || COX7C | 2.5.21.94 | cytochrome c oxidase subunit 7C | 5 | 0.122466216 || EEF2 | 2.5.21.94 | eukaryotic translation elongation factor 2 | 19 | 0.089768211 || EIF2A | 2.5.21.94 | eukaryotic translation initiation factor 2A | 3 | 0.11202727 || EIF2S3 | 2.5.21.94 | eukaryotic translation initiation factor 2 subunit gamma | X | 0.110062878 || EIF3E | 2.5.21.94 | eukaryotic translation initiation factor 3 subunit E | 8 | 0.185375085 || EIF3F 2.5.21.94 | eukaryotic translation initiation factor 3 subunit F | 11 | 0.130312317 || EIF3H | 2.5.21.94 | eukaryotic translation initiation factor 3 subunit H | 8 | 0.126221252 || EIF3L | 2.5.21.94 | eukaryotic translation initiation factor 3 subunit L | 22 | 0.1903491 || EIF4B | 2.5.21.94 | eukaryotic translation initiation factor 4B | 12 | 0.093183967 || FAM117B | 2.5.21.94 | family with sequence similarity 117 member B | 2 | 0.146355543 || HIBADH | 2.5.21.94 | 3-hydroxyisobutyrate dehydrogenase | 7 | 0.062671162 || HNRNPA1P10 | 2.5.21.94 | heterogeneous nuclear ribonucleoprotein A1 pseudogene 10 | 16 | 0.189310158 || IMPDH2 | 2.5.21.94 | IMP (inosine 5'-monophosphate) dehydrogenase 2 | 3 | 0.077562605 || LEPROTL1 | 2.5.21.94 | leptin receptor overlapping transcript-like 1 | 8 | 0.094315142 || MRPL53 | 2.5.21.94 | mitochondrial ribosomal protein L53 | 2 | 0.086935926 || NDFIP1 | 2.5.21.94 | Nedd4 family interacting protein 1 | 5 | 0.076106651 || NPMIP5 | 2.5.21.94 | nucleophosmin 1 (nucleolar phosphoprotein B23, numatrin) pseudogene 5 | 15 | 0.093548704 || NSA2 | 2.5.21.94 | NSA2, ribosome biogenesis homolog | 5 | 0.096765436 || PCYOX1 | 2.5.21.94 | prenylcysteine oxidase 1 | 2 | 0.166452006 || RPL15 | 2.5.21.94 | ribosomal protein L15 | 3 | 0.06704344 || RPL36AL | 2.5.21.94 | ribosomal protein L36a like | 14 | 0.065116321 || RPS23 | 2.5.21.94 | ribosomal protein S23 | 5 | 0.411190488 || RSL1D1 | 2.5.21.94 | ribosomal LI domain containing 1 | 16 | 0.169517764 || RSL24D1 | 2.5.21.94 | ribosomal L24 domain containing 1 | 15 | 0.131499719 || SARAF | 2.5.21.94 | store-operated calcium entry-associated regulatory factor | 8 | 0.064286076 || SLC25A6 | 2.5.21.94 | solute carrier family 25 member 6 | X | 0.116914055 || SNHG16 | 2.5.21.94 | small nucleolar RNA host gene 16 | 17 | 0.077369616 || TOMM20 | 2.5.21.94 | translocase of outer mitochondrial membrane 20 | 1 | 0.065027716 || TOMM6 | 2.5.21.94 | translocase of outer mitochondrial membrane 6 | 6 | 0.07366474 || C12orf57 | 2.5.21.95 | chromosome 12 open reading frame 57 | 12 | 0.076312548 || CD48 | 2.5.21.95 | CD48 molecule | 1 | 0.106957822 | CD52 | 2.5.21.95 | CD52 molecule | 1 | 0.182237052 || COX411 | 2.5.21.95 | cytochrome c oxidase subunit 411 | 16 | 0.065113972 || FAU | 2.5.21.95 | Finkel-Biskis-Reilly murine sarcoma virus (FBR-MuSV) ubiquitously expressed | 11 | 0.081721323 || GAS5 | 2.5.21.95 | growth arrest specific 5 (non-protein coding) | 1 | 0.260967548 || GLTSCR2 | 2.5.21.95 | glioma tumor suppressor candidate region gene 2 | 19 | 0.130046996 || HINT1 | 2.5.21.95 | histidine triad nucleotide binding protein 1 | 5 | 0.072725346 || LOC440311 | 2.5.21.95 | glioma tumor suppressor candidate region gene 2 pseudogene | | 0.134648089 || NACA2 | 2.5.21.95 | nascent polypeptide-associated complex alpha subunit 2 | 17 | 0.079478922 || PITPNA-AS1 | 2.5.21.95 | PITPNA antisense RNA 1 | 17 | 0.060726564 || RACK1 | 2.5.21.95 | receptor for activated C kinase 1 | 5 | 0.115394599 || RPL10A | 2.5.21.95 | ribosomal protein L10a | 6 | 0.072702986 || RPL11 | 2.5.21.95 | ribosomal protein L11 | 1 | 0.120824538 || RPL12 | 2.5.21.95 | ribosomal protein L12 | 9 | 0.115748108 || RPL13A | 2.5.21.95 | ribosomal protein L13a | 19 | 0.132795073 || RPL13AP20 | 2.5.21.95 | ribosomal protein L13a pseudogene 20 | 12 | 0.161347314 || RPL13AP6 | 2.5.21.95 | ribosomal protein L13a pseudogene 6 | 10 | 0.129850143 || RPL17 | 2.5.21.95 | ribosomal protein L17 | 18 | 0.069751008 || RPL18 | 2.5.21.95 | ribosomal protein L18 | 19 | 0.119302683 || RPL22L1 | 2.5.21.95 | ribosomal protein L22 like 1 | 3 | 0.065432456 || RPL23 | 2.5.21.95 | ribosomal protein L23 | 17 | 0.136978409 || RPL24 | 2.5.21.95 | ribosomal protein L24 | 3 | 0.161851242 || RPL27 | 2.5.21.95 | ribosomal protein L27 | 17 | 0.111993882 || RPL3 | 2.5.21.95 | ribosomal protein L3 | 22 | 0.084887753 || RPL30 | 2.5.21.95 | ribosomal protein L30 | 8 | 0.089497163 || RPL35A | 2.5.21.95 | ribosomal protein L35a | 3 | 0.069852489 || RPL37 | 2.5.21.95 | ribosomal protein L37 | 5 | 0.076799422 || RPL38 | 2.5.21.95 | ribosomal protein L38 | 17 | 0.080575897 || RPL4 | 2.5.21.95 | ribosomal protein L4 | 15 | 0.153559114 || RPL5 | 2.5.21.95 | ribosomal protein L5 | 1 | 0.173078953 || RPL8 | 2.5.21.95 | ribosomal protein L8 | 8 | 0.099844191 || RPLP1 | 2.5.21.95 | ribosomal protein lateral stalk subunit P1 | 15 | 0.127554093 || RPLP2 | 2.5.21.95 | ribosomal protein lateral stalk subunit P2 | 11 | 0.071238007 || RPS13 | 2.5.21.95 | ribosomal protein S13 | 11 | 0.227351465 || RPS15 | 2.5.21.95 | ribosomal protein S15 | 19 | 0.061829932 || RPS16 | 2.5.21.95 | ribosomal protein S16 | 19 | 0.138540778 || RPS19 | 2.5.21.95 | ribosomal protein S19 | 19 | 0.13074389 || RPS20 | 2.5.21.95 | ribosomal protein S20 | 8 | 0.105401606 || RPS21 | 2.5.21.95 | ribosomal protein S21 | 20 | 0.091936887 || RPS29 | 2.5.21.95 | ribosomal protein S29 | 14 | 0.093223307 || RPS3 | 2.5.21.95 | ribosomal protein S3 | 11 | 0.086053301 || RPS4X | 2.5.21.95 | ribosomal protein S4, X-linked | X | 0.102418804 || RPS4XP21 | 2.5.21.95 | ribosomal protein S4X pseudogene 21 | 19 | 0.076030546 || RPS5 | 2.5.21.95 | ribosomal protein S5 | 19 | 0.182851472 || RPS6 | 2.5.21.95 | ribosomal protein S6 | 9 | 0.109890296 || RPS8 | 2.5.21.95 | ribosomal protein S8 | 1 | 0.196574067 | SNHG5 | 2.5.21.95 | small nucleolar RNA host gene 5 | 6 | 0.178139499 || TMEM14C | 2.5.21.95 | transmembrane protein 14C | 6 | 0.072948056 || TMEM256 | 2.5.21.95 | transmembrane protein 256 | 17 | 0.102056992 || TOMM7 | 2.5.21.95 | translocase of outer TABLE 1C-continued The genes within the significant gene clusters, listed in Table 1B. (2160 Genes Listed by: Gene Symbol | Module | Gene Description | Chromosome Number | Row Variance) ||)

mitochondrial membrane 7 | 7 | 0.157037318 || UXT | 2.5.21.95 | ubiquitously expressed prefoldin like chaperone | X | 0.089518174 || CD48 | 2.5.21.95.219 | CD48 molecule | 1 | 0.106957822 || CD52 | 2.5.21.95.219 | CD52 molecule | 1 | 0.182237052 || COX411 | 2.5.21.95.219 | cytochrome c oxidase subunit 4I1 | 16 | 0.065113972 || FAU | 2.5.21.95.219 | Finkel-Biskis-Reilly murine sarcoma virus (FBR-MuSV) ubiquitously expressed | 11 | 0.081721323 || GLTSCR2 | 2.5.21.95.219 | glioma tumor suppressor candidate region gene 2 | 19 | 0.130046996 || HINT1 | 2.5.21.95.219 | histidine triad nucleotide binding protein 1 | 5 | 0.072725346 || LOC440311 | 2.5.21.95.219 | glioma tumor suppressor candidate region gene 2 pseudogene | | 0.134648089 || NACA2 | 2.5.21.95.219 | nascent polypeptide-associated complex alpha subunit 2 | 17 | 0.079478922 || RACK1 | 2.5.21.95.219 | receptor for activated C kinase 1 5 | 0.115394599 || RPL11 | 2.5.21.95.219 | ribosomal protein L11 | 1 | 0.120824538 || RPL12 | 2.5.21.95.219 | ribosomal protein L12 | 9 | 0.115748108 || RPL13A | 2.5.21.95.219 | ribosomal protein L13a | 19 | 0.132795073 || RPL13AP20 | 2.5.21.95.219 | ribosomal protein L13a pseudogene 20 | 12 | 0.161347314 || RPL13AP6 | 2.5.21.95.219 | ribosomal protein L13a pseudogene 6 | 10 | 0.129850143 || RPL17 | 2.5.21.95.219 | ribosomal protein L17 | 18 | 0.069751008 || RPL18 | 2.5.21.95.219 | ribosomal protein L18 | 19 | 0.119302683 || RPL23 | 2.5.21.95.219 | ribosomal protein L23 | 17 | 0.136978409 || RPL24 | 2.5.21.95.219 | ribosomal protein L24 | 3 | 0.161851242 || RPL3 | 2.5.21.95.219 | ribosomal protein L3 | 22 | 0.084887753 || RPL30 | 2.5.21.95.219 | ribosomal protein L30 | 8 | 0.089497163 || RPL35A | 2.5.21.95.219 | ribosomal protein L35a | 3 | 0.069852489 || RPL38 | 2.5.21.95.219 | ribosomal protein L38 | 17 | 0.080575897 || RPL4 | 2.5.21.95.219 | ribosomal protein L4 | 15 | 0.153559114 || RPL8 | 2.5.21.95.219 | ribosomal protein L8 | 8 | 0.099844191 || RPLP1 | 2.5.21.95.219 | ribosomal protein lateral stalk subunit P1 | 15 | 0.127554093 || RPLP2 | 2.5.21.95.219 | ribosomal protein lateral stalk subunit P2 | 11 | 0.071238007 || RPS13 | 2.5.21.95.219 | ribosomal protein S13 | 11 | 0.227351465 || RPS15 | 2.5.21.95.219 | ribosomal protein S15 | 19 | 0.061829932 || RPS19 | 2.5.21.95.219 | ribosomal protein S19 | 19 | 0.13074389 || RPS4X | 2.5.21.95.219 | ribosomal protein S4, X-linked | X | 0.102418804 || RPS4XP21 | 2.5.21.95.219 | ribosomal protein S4X pseudogene 21 | 19 | 0.076030546 || RPS5 | 2.5.21.95.219 | ribosomal protein S5 | 19 | 0.182851472 || SNHG5 | 2.5.21.95.219 | small nucleolar RNA host gene 5 | 6 | 0.178139499 || TMEM14C | 2.5.21.95.219 | transmembrane protein 14C | 6 | 0.072948056 || TMEM256 | 2.5.21.95.219 | transmembrane protein 256 | 17 | 0.102056992 || TOMM7 | 2.5.21.95.219 | translocase of outer mitochondrial membrane 7 | 7 | 0.157037318 || UXT | 2.5.21.95.219 | ubiquitously expressed prefoldin like chaperone | X | 0.089518174 || CARF | 2.5.23.103 | calcium responsive transcription factor | 2 | 0.064446501 | CENPC | 2.5.23.103 | centromere protein C | 4 | 0.069683663 || CEP95 | 2.5.23.103 | centrosomal protein 95 kDa | 17 | 0.068936626 || COX11 | 2.5.23.103 | COX11 cytochrome c oxidase copper chaperone | 17 | 0.068948373 || CWF19L2 | 2.5.23.103 | CWF19-like 2, cell cycle control (*S. pombe*) | 11 | 0.080048075 || GAS5-AS1 | 2.5.23.103 | GAS5 antisense RNA 1 | 1 | 0.060663353 || LINS1 | 2.5.23.103 | lines homolog 1 | 15 | 0.099507064 || LOC100996579 | 2.5.23.103 | uncharacterized LOC100996579 | 2 | 0.135089513 || NR2C1 | 2.5.23.103 | nuclear receptor subfamily 2 group C member 1 | 12 | 0.066253637 || ODF2L | 2.5.23.103 | outer dense fiber of sperm tails 2 like | 1 | 0.081441868 || OFD1 | 2.5.23.103 | oral-facial-digital syndrome 1 | X | 0.066195227 || PIBF1 | 2.5.23.103 | progesterone immunomodulatory binding factor 1 | 13 | 0.081859387 || PLBD1-AS1 | 2.5.23.103 | PLBD1 antisense RNA 1 | 12 | 0.090065416 || PPWD1 | 2.5.23.103 | peptidylprolyl isomerase domain and WD repeat containing 1 | 5 | 0.080440961 || PRPF39 | 2.5.23.103 | pre-mRNA processing factor 39 | 14 | 0.091941986 || RBM45 | 2.5.23.103 | RNA binding motif protein 45 | 2 | 0.068148591 || RFXAP | 2.5.23.103 | regulatory factor X associated protein | 13 | 0.076832794 || SNHG1 | 2.5.23.103 | small nucleolar RNA host gene 1 | 11 | 0.163749533 || SNORD101 | 2.5.23.103 | small nucleolar RNA, C/D box 101 | 6 | 0.116622854 || SNORD19 | 2.5.23.103 | small nucleolar RNA, C/D box 19 | 3 | 0.06469283 || SNORD19B | 2.5.23.103 | small nucleolar RNA, C/D box 19B | 3 | 0.175591831 || SNORD45C | 2.5.23.103 | small nucleolar RNA, C/D box 45C | 1 | 0.110586371 || SNORD49A | 2.5.23.103 | small nucleolar RNA, C/D box 49A | 17 | 0.225593262 || SRSF7 | 2.5.23.103 | serine/arginine-rich splicing factor 7 | 2 | 0.091422344 || TNRC6C-AS1 | 2.5.23.103 | TNRC6C antisense RNA 1 | | 0.098479521 || TRMT13 | 2.5.23.103 | tRNA methyltransferase 13 homolog (*S. cerevisiae*) | 1 | 0.09431452 || TTC21B | 2.5.23.103 | tetratricopeptide repeat domain 21B | 2 | 0.067214492 || ZNF382 | 2.5.23.103 | zinc finger protein 382 | 19 | 0.139176778 || ZNF567 | 2.5.23.103 | zinc finger protein 567 | 19 | 0.071996581 || ANK3 | 2.5.26 | ankyrin 3, node of Ranvier (ankyrin G) | 10 | 0.189879912 || AP3M2 | 2.5.26 | adaptor related protein complex 3 mu 2 subunit | 8 | 0.074914935 || ATP8B2 | 2.5.26 | ATPase phospholipid transporting 8B2 | 1 | 0.138487798 || BCL11B | 2.5.26 | B-cell CLL/lymphoma 11B | 14 | 0.139378645 || BNIP3 | 2.5.26 | BCL2/adenovirus E1B 19 kDa interacting protein 3 | 10 | 0.101090192 || CASK | 2.5.26 | calcium/calmodulin-dependent serine protein kinase (MAGUK family) | X | 0.085455383 || CD40LG | 2.5.26 | CD40 ligand | X | 0.279193259 || CDC14A | 2.5.26 | cell division cycle 14A | 1 | 0.07163913 || DGKE | 2.5.26 | diacylglycerol kinase epsilon | 17 | 0.070645173 || DOCK9 | 2.5.26 | dedicator of cytokinesis 9 | 13 | 0.195476978 || FAAH2 | 2.5.26 | fatty acid amide hydrolase 2 | X | 0.140566466 || FAM169A | 2.5.26 | family with sequence similarity 169 member A | 5 | 0.076046943 || GCSAM | 2.5.26 | germinal center-associated, signaling and motility | 3 | 0.199665167 || GIMAP1 | 2.5.26 | GTPase, IMAP family member 1 | 7 | 0.107629864 || GIMAP5 | 2.5.26 | GTPase, IMAP family member 5 | 7 | 0.060810538 || GOLGA8EP | 2.5.26 | golgin A8 family member E, pseudogene | 15 | 0.294351429 || INPP4B | 2.5.26 | inositol polyphosphate-4-phosphatase type II B | 4 | 0.213345254 || KIAA1324L | 2.5.26 | KIAA1324-like | 7 | 0.074980132 || LRIG1 | 2.5.26 | leucine-rich repeats and immunoglobulin-like domains 1 | 3 | 0.068792915 || LY9 | 2.5.26 | lymphocyte antigen 9 | 1 | 0.093151976 || MDN1 | 2.5.26 | midasin AAA ATPase 1 | 6 | 0.088512767 || MIR1204 | 2.5.26 | microRNA 1204 | | 0.207142449 || MTR | 2.5.26 | 5-methyltetrahydrofolate-homocysteine methyltransferase | 1 | 0.089356761 || NMT2 | 2.5.26 | N-myristoyltransferase 2 | 10 |

TABLE 1C-continued

The genes within the significant gene clusters, listed in Table 1B. (2160 Genes Listed by: Gene Symbol | Module | Gene Description | Chromosome Number | Row Variance) ||)

0.135794772 || PATJ | 2.5.26 | PATJ, crumbs cell polarity complex component | 1 | 0.149496233 || PCNX2 | 2.5.26 | pecanex homolog 2 (*Drosophila*) | 1 | 0.082248858 || PKI55 | 2.5.26 | DKFZp434H1419 | 2 | 0.06126972 || PLCG1 | 2.5.26 | phospholipase C gamma 1 | 20 | 0.11240163 || PWAR5 | 2.5.26 | Prader Willi/Angelman region RNA 5 | 15 | 0.313808193 || SPOCK2 | 2.5.26 | sparc/osteonectin, cwcv and kazal-like domains proteoglycan (testican) 2 | 10 | 0.126970163 || UBASH3A | 2.5.26 | ubiquitin associated and SH3 domain containing A | 21 | 0.1376158 || ZBTB25 | 2.5.26 | zinc finger and BTB domain containing 25 | 14 | 0.072252515 || ZNF483 | 2.5.26 | zinc finger protein 483 | 9 | 0.099815947 || ZXDB | 2.5.26 | zinc finger, X-linked, duplicated B | X | 0.067192434 || AK5 | 2.6.29.125 | adenylate kinase 5 | 1 | 0.151451397 || CAMK2N1 | 2.6.29.125 | calcium/calmodulin-dependent protein kinase II inhibitor 1 | 1 | 0.06792661 || DSC1 | 2.6.29.125 | desmocollin 1 | 18 | 0.284786892 || EPHX2 | 2.6.29.125 | epoxide hydrolase 2 | 8 | 0.121319502 || FAM153A | 2.6.29.125 | family with sequence similarity 153 member A | 5 | 0.120667621 || FHIT | 2.6.29.125 | fragile histidine triad | 3 | 0.17833208 || GPRASP1 | 2.6.29.125 | G protein-coupled receptor associated sorting protein 1 | X | 0.07315188 || GSTM3 | 2.6.29.125 | glutathione S-transferase mu 3 (brain) | 1 | 0.176970379 || HOOK1 | 2.6.29.125 | hook microtubule-tethering protein 1 | 1 | 0.140447995 || KRT73 | 2.6.29.125 | keratin 73 | 12 | 0.099458916 || LEF1-AS1 | 2.6.29.125 | LEF1 antisense RNA 1 | 4 | 0.123565445 || LMO7 | 2.6.29.125 | LIM domain 7 | 13 | 0.068766528 || MID2 | 2.6.29.125 | midline 2 | X | 0.131591365 || NEO1 | 2.6.29.125 | neogenin 1 | 15 | 0.084219121 || NOG | 2.6.29.125 | noggin | 17 | 0.297630837 || PLAG1 | 2.6.29.125 | PLAG1 zinc finger | 8 | 0.110935487 || PLCL1 | 2.6.29.125 | phospholipase C like 1 | 2 | 0.086190232 || PLXDC1 | 2.6.29.125 | plexin domain containing 1 | 17 | 0.06329215 || RASGRF2 | 2.6.29.125 | Ras protein specific guanine nucleotide releasing factor 2 | 5 | 0.189025685 || SAMD12 | 2.6.29.125 | sterile alpha motif domain containing 12 | 8 | 0.068791058 || SLC16A10 | 2.6.29.125 | solute carrier family 16 member 10 | 6 | 0.096488668 || TSHZ2 | 2.6.29.125 | teashirt zinc finger homeobox 2 | 20 | 0.149706513 || ADGRE1 | 2.6.30 | adhesion G protein-coupled receptor E1 | 19 | 0.292244689 || ADGRE4P | 2.6.30 | adhesion G protein-coupled receptor E4, pseudogene | 19 | 0.515903261 || ALOX15 | 2.6.30 | arachidonate 15-lipoxygenase | 17 | 0.279705657 || CAT | 2.6.30 | catalase | 11 | 0.125093995 || CCR3 | 2.6.30 | chemokine (C-C motif) receptor 3 | 3 | 0.4904498 || CLC | 2.6.30 | Charcot-Leyden crystal galectin | 19 | 0.810928568 || CPA3 | 2.6.30 | carboxypeptidase A3 | 3 | 0.241919102 || CYSLTR2 | 2.6.30 | cysteinyl leukotriene receptor 2 | 13 | 0.241952032 || FRRS1 | 2.6.30 | ferric chelate reductase 1 | 1 | 0.097940303 || GPR34 | 2.6.30 | G protein-coupled receptor 34 | X | 0.158582573 || GPR82 | 2.6.30 | G protein-coupled receptor 82 | X | 0.162834919 || HDC | 2.6.30 | histidine decarboxylase | 15 | 0.067743346 || HRH4 | 2.6.30 | histamine receptor H4 | 18 | 0.257534247 || IDO1 | 2.6.30 | indoleamine 2,3-dioxygenase 1 | 8 | 0.506430991 || IL1RL1 | 2.6.30 | interleukin 1 receptor like 1 | 2 | 0.268456002 || IL3RA | 2.6.30 | interleukin 3 receptor subunit alpha | X | 0.131477593 || IL5RA | 2.6.30 | interleukin 5 receptor subunit alpha | 3 | 0.506845476 || LOC728084 | 2.6.30 | uncharacterized LOC728084 | 12 | 0.081241831 || MS4A2 | 2.6.30 | membrane spanning 4-domains A2 | 11 | 0.336683773 || P2RY14 | 2.6.30 | purinergic receptor P2Y14 | 3 | 0.52270094 || PTGDR2 | 2.6.30 | prostaglandin D2 receptor 2 | 11 | 0.06597408 || RHOXF1P1 | 2.6.30 | Rhox homeobox family member 1 pseudogene 1 | X | 0.115475394 || SIGLEC8 | 2.6.30 | sialic acid binding Ig like lectin 8 | 19 | 0.098315576 || UGT2B11 | 2.6.30 | UDP glucuronosyltransferase family 2 member B11 | 4 | 0.238793628 || ANKRD36BP2 | 2.7 | ankyrin repeat domain 36B pseudogene 2 | 2 | 0.185529086 || ANLN | 2.7 | anillin actin binding protein | 7 | 0.13282053 || APOBEC3B | 2.7 | apolipoprotein B mRNA editing enzyme catalytic subunit 3B | 22 | 0.131526145 || ARHGAP42 | 2.7 | Rho GTPase activating protein 42 | 11 | 0.157650751 || ASPM | 2.7 | abnormal spindle microtubule assembly | 1 | 0.157056475 || ATAD2 | 2.7 | ATPase family, AAA domain containing 2 | 8 | 0.069067933 || ATAD5 | 2.7 | ATPase family, AAA domain containing 5 | 17 | 0.100481705 || BARD1 | 2.7 | BRCA1 associated RING domain 1 | 2 | 0.073041571 || BMP2K | 2.7 | BMP2 inducible kinase | 4 | 0.068641559 || BRCA1 | 2.7 | breast cancer 1 | 17 | 0.062003742 || BRCA2 | 2.7 | breast cancer 2 | 13 | 0.09276469 || BRIP1 | 2.7 | BRCA1 interacting protein C-terminal helicase 1 | 17 | 0.094153579 || BUB1 | 2.7 | BUB1 mitotic checkpoint serine/threonine kinase | 2 | 0.243665407 || BUB1B | 2.7 | BUB1 mitotic checkpoint serine/threonine kinase B | 15 | 0.105612418 || CASC5 | 2.7 | cancer susceptibility candidate 5 | 15 | 0.089560364 || CCDC18 | 2.7 | coiled-coil domain containing 18 | 1 | 0.148587749 || CCNA2 | 2.7 | cyclin A2 | 4 | 0.318798027 || CCNB2 | 2.7 | cyclin B2 | 15 | 0.114978823 || CCNE2 | 2.7 | cyclin E2 | 8 | 0.073776768 || CD38 | 2.7 | CD38 molecule | 4 | 0.458499747 || CDC20 | 2.7 | cell division cycle 20 | 1 | 0.097168091 || CDC6 | 2.7 | cell division cycle 6 | 17 | 0.111618795 | CDK1 | 2.7 | cyclin-dependent kinase 1 | 10 | 0.073653595 || CDKN3 | 2.7 | cyclin-dependent kinase inhibitor 3 | 14 | 0.070093354 || CENPE | 2.7 | centromere protein E | 4 | 0.141358284 || CENPF | 2.7 | centromere protein F | 1 | 0.103689479 || CEP55 | 2.7 | centrosomal protein 55 kDa | 10 | 0.185732018 || CKAP2 | 2.7 | cytoskeleton associated protein 2 | 13 | 0.060443462 || CKAP2L | 2.7 | cytoskeleton associated protein 2 like | 2 | 0.070101198 || CLSPN | 2.7 | claspin | 1 | 0.094259192 || CNTLN | 2.7 | centlein | 9 | 0.088162835 || DIAPH3 | 2.7 | diaphanous related formin 3 | 13 | 0.061155395 || DLGAP5 | 2.7 | discs large homolog associated protein 5 | 14 | 0.150644317 || DMC1 | 2.7 | DNA meiotic recombinase 1 | 22 | 0.067368045 || DNA2 | 2.7 | DNA replication helicase/nuclease 2 | 10 | 0.074215098 || DTL | 2.7 | denticleless E3 ubiquitin protein ligase homolog | 1 | 0.271753443 || E2F8 | 2.7 | E2F transcription factor 8 | 11 | 0.075519117 || ELL2 | 2.7 | elongation factor for RNA polymerase II 2 | 5 | 0.138384569 || EPB41L4A | 2.7 | erythrocyte membrane protein band 4.1 like 4A | 5 | 0.126122953 || ESCO2 | 2.7 | establishment of sister chromatid cohesion N-acetyltransferase 2 | 8 | 0.237826227 || EXO1 | 2.7 | exonuclease 1 | 1 | 0.064620013 || FAM72A | 2.7 | family with sequence similarity 72 member A | 1 | 0.129731061 || FAM72B | 2.7 | family with sequence similarity 72 member B | 1 | 0.089919882 || FANCB | 2.7 | Fanconi anemia complementation group B | X | 0.089424045 || FANCI | 2.7 | Fanconi anemia complementation group I | 15 | 0.077340962 || FANCL | 2.7 | Fanconi anemia complementation group L | 2 |

TABLE 1C-continued

The genes within the significant gene clusters, listed in Table 1B. (2160 Genes Listed by: Gene Symbol | Module | Gene Description | Chromosome Number | Row Variance) ||)

0.074875621 || FCHO2 | 2.7 | FCH domain only 2 | 5 | 0.102811741 || GAB1 | 2.7 | GRB2 associated binding protein 1 | 4 | 0.068066433 || GKAP1 | 2.7 | G kinase anchoring protein 1 | 9 | 0.093193128 || HIST1H1B | 2.7 | histone cluster 1, H1b | 6 | 0.388150174 || HIST1H1C | 2.7 | histone cluster 1, Hlc | 6 | 0.121640485 || HIST1H1E | 2.7 | histone cluster 1, H1e | 6 | 0.177652782 || HIST1H2AB | 2.7 | histone cluster 1, H2ab | 6 | 0.228890255 || HIST1H2AE | 2.7 | histone cluster 1, H2ae | 6 | 0.206894371 || HIST1H2AG | 2.7 | histone cluster 1, H2ag | 6 | 0.217353578 || HIST1H2AH | 2.7 | histone cluster 1, H2ah | 6 | 0.1090121 || HIST1H2AI | 2.7 histone cluster 1, H2ai | 6 | 0.178083069 || HIST1H2AJ | 2.7 | histone cluster 1, H2aj | 6 | 0.652307519 || HIST1H2AK | 2.7 | histone cluster 1, H2ak | 6 | 0.077617746 || HIST1H2AL | 2.7 | histone cluster 1, H2al | 6 | 0.322160894 || HIST1H2AM | 2.7 | histone cluster 1, H2am | 6 | 0.177311123 || HIST1H2BB | 2.7 | histone cluster 1, H2bb | 6 | 0.093731129 || HIST1H2BD | 2.7 | histone cluster 1, H2bd | 6 | 0.138729526 || HIST1H2BE | 2.7 | histone cluster 1, H2be | 6 | 0.110153978 || HIST1H2BF | 2.7 | histone cluster 1, H2bf | 6 | 0.17258106 || HIST1H2BG | 2.7 histone cluster 1, H2bg | 6 | 0.124112845 || HIST1H2BH | 2.7 | histone cluster 1, H2bh | 6 | 0.17443153 || HIST1H2BI | 2.7 | histone cluster 1, H2bi | 6 | 0.203895637 || HIST1H2BJ | 2.7 | histone cluster 1, H2bj | 6 | 0.085252138 || HIST1H2BL | 2.7 | histone cluster 1, H2bl | 6 | 0.098464817 || HIST1H2BM | 2.7 | histone cluster 1, H2bm | 6 | 0.499738228 || HIST1H2BN | 2.7 | histone cluster 1, H2bn | 6 | 0.076659591 || HIST1H2BO | 2.7 | histone cluster 1, H2bo | 6 | 0.120787021 || HIST1H3B | 2.7 | histone cluster 1, H3b | | 0.446511858 || HIST1H3C | 2.7 | histone cluster 1, H3c | | 0.186392164 || HIST1H3F | 2.7 | histone cluster 1, H3f | 6 | 0.25010626 || HIST1H3G | 2.7 | histone cluster 1, H3g | 6 | 0.277815634 || HIST1H3H | 2.7 | histone cluster 1, H3h | 6 | 0.136755704 || HIST1H31 | 2.7 | histone cluster 1, H3i | 6 | 0.232625266 || HIST1H3J | 2.7 | histone cluster 1, H3j | 6 | 0.162444111 || HIST1H4A | 2.7 | histone cluster 1, H4a | 6 | 0.07018871 || HIST1H4B | 2.7 | histone cluster 1, H4b | 6 | 0.182287232 || HIST1H4C | 2.7 | histone cluster 1, H4c | 6 | 0.258960438 || HIST1H4F | 2.7 | histone cluster 1, H4f | 6 | 0.107124007 || HIST1H4H | 2.7 | histone cluster 1, H4h | 6 | 0.139872251 || HIST1H41 | 2.7 | histone cluster 1, H4i | 6 | 0.07019443 || HIST1H4L | 2.7 | histone cluster 1, H41 | 6 | 0.091164989 || HIST2H2AB | 2.7 | histone cluster 2, H2ab | 1 | 0.138036163 || HMMR | 2.7 | hyaluronan mediated motility receptor | 5 | 0.103506786 || ISPD | 2.7 | isoprenoid synthase domain containing | 7 | 0.089885343 || KIAA0101 | 2.7 | KIAA0101 | 15 | 0.125362695 || KIAA1524 | 2.7 | KIAA1524 | 3 | 0.077687655 || KIF11 | 2.7 | kinesin family member 11 | 10 | 0.199728421 || KIF14 | 2.7 | kinesin family member 14 | 1 | 0.162483039 || KIF18A | 2.7 | kinesin family member 18A | 11 | 0.084925337 || KIF20A | 2.7 | kinesin family member 20A | 5 | 0.068008851 || KIF20B | 2.7 | kinesin family member 20B | 10 | 0.111606003 || KIF23 | 2.7 | kinesin family member 23 | 15 | 0.086273992 || KIF2C | 2.7 | kinesin family member 2C | 1 | 0.069319369 || LINC01036 | 2.7 | long intergenic non-protein coding RNA 1036 | | 0.351926017 || LOC101927708 | 2.7 | uncharacterized LOC101927708 | 11 | 0.683267266 || LRRCC1 | 2.7 | leucine rich repeat and coiled-coil centrosomal protein 1 | 8 | 0.092080532 || MAN1A1 | 2.7 | mannosidase alpha class 1A member 1 | 6 | 0.116262795 || MASTL | 2.7 | microtubule associated serine/threonine kinase like | 10 | 0.088797212 || MCM10 | 2.7 | minichromosome maintenance 10 replication initiation factor | 10 | 0.075753313 || MCM4 | 2.7 | minichromosome maintenance complex component 4 | 8 | 0.08367917 || MCM6 | 2.7 | minichromosome maintenance complex component 6 | 2 | 0.131861005 || MCM8 | 2.7 | minichromosome maintenance 8 homologous recombination repair factor | 20 | 0.076561508 || MELK | 2.7 | maternal embryonic leucine zipper kinase | 9 | 0.069235134 || MIR516A2 | 2.7 | microRNA 516a-2 | 19 | 0.393471906 || MIR548AS | 2.7 | microRNA 548as | 13 | 0.083762078 || MIR670 | 2.7 | microRNA 670 | 11 | 0.067416816 || MKI67 | 2.7 | marker of proliferation Ki-67 | 10 | 0.298647817 || MYBL2 | 2.7 | MYB proto-oncogene like 2 | 20 | 0.083163929 || MYO1D | 2.7 | myosin ID | 17 | 0.083510744 || NCAPG | 2.7 | non-SMC condensin I complex subunit G | 4 | 0.127762858 || NCAPG2 | 2.7 | non-SMC condensin II complex subunit G2 | 7 | 0.073296471 || NDC80 | 2.7 | NDC80 kinetochore complex component | 18 | 0.158254963 || NEIL3 | 2.7 | nei like DNA glycosylase 3 | 4 | 0.061202894 || NUF2 | 2.7 | NUF2, NDC80 kinetochore complex component | 1 | 0.111921653 || NUP62CL | 2.7 | nucleoporin 62 kDa C-terminal like | X | 0.07167816 || NUSAP1 | 2.7 | nucleolar and spindle associated protein 1 | 15 | 0.102350377 || PCNA | 2.7 | proliferating cell nuclear antigen | 20 | 0.129755209 || PLK1 | 2.7 | polo like kinase 1 | 16 | 0.122096663 || POLE2 | 2.7 | polymerase (DNA) epsilon 2, accessory subunit | 14 | 0.069821069 || POLQ | 2.7 | polymerase (DNA) theta | 3 | 0.061470329 || PRR11 | 2.7 | proline rich 11 | 17 | 0.085926976 || PSAT1 | 2.7 | phosphoserine aminotransferase 1 | 9 | 0.078321273 || RAD51C | 2.7 | RAD51 paralog C | 17 | 0.090430302 || RBBP8 | 2.7 | retinoblastoma binding protein 8 | 18 | 0.061751956 || RRM2 | 2.7 | ribonucleotide reductase regulatory subunit M2 | 2 | 0.444770415 || RSRC1 | 2.7 | arginine/serine-rich coiled-coil 1 | 3 | 0.104738044 || SASS6 | 2.7 | SAS-6 centriolar assembly protein | 1 | 0.060255069 || SCLT1 | 2.7 | sodium channel and clathrin linker 1 | 4 | 0.071258633 || SHCBP1 | 2.7 | SHC SH2-domain binding protein 1 | 16 | 0.11911544 || SKA3 | 2.7 | spindle and kinetochore associated complex subunit 3 | 13 | 0.095409125 || SLC27A2 | 2.7 | solute carrier family 27 member 2 | 15 | 0.16989371 || SMC4 | 2.7 | structural maintenance of chromosomes 4 | 3 | 0.077307644 || SNORD3C | 2.7 | small nucleolar RNA, C/D box 3C | 17 | 1.570602905 || STIL | 2.7 | SCL/TAL1 interrupting locus | 1 | 0.157090776 || STMN1 | 2.7 | stathmin 1 | 1 | 0.092507435 || TBC1D31 | 2.7 | TBC1 domain family member 31 | 8 | 0.075416519 || TEX9 | 2.7 | testis expressed 9 | 15 | 0.06880906 || THEGL | 2.7 | theg spermatid protein-like | 4 | 0.18456694 || TOP2A | 2.7 | topoisomerase (DNA) II alpha | 17 | 0.263443136 || TPX2 | 2.7 | TPX2, microtubule-associated | 20 | 0.183698442 || TTK | 2.7 | TTK protein kinase | 6 | 0.064291541 || TYMS | 2.7 | thymidylate synthetase | 18 | 0.183671634 || UBE2F-SCLY | 2.7 | UBE2F-SCLY readthrough (NMD candidate) | 2 | 0.116031702 || VRK1 | 2.7 | vaccinia related kinase 1 | 14 | 0.140430476 || WDHD1 | 2.7 | WD repeat and HMG-box DNA binding protein 1 | 14 | 0.06850525 || XRCC2 | 2.7 | X-ray repair complementing defective repair in Chinese hamster cells 2 | 7 | 0.062051848 || ZWILCH | 2.7 | zwilch kinetochore protein | 15 | 0.060708866 || ANLN | 2.7.31 | anillin actin binding protein | 7 | 0.13282053 || APOBEC3B |

TABLE 1C-continued

The genes within the significant gene clusters, listed in Table 1B. (2160 Genes Listed by: Gene Symbol | Module | Gene Description | Chromosome Number | Row Variance) ||)

2.7.31 | apolipoprotein B mRNA editing enzyme catalytic subunit 3B | 22 | 0.131526145 || ASPM | 2.7.31 | abnormal spindle microtubule assembly | 1 | 0.157056475 || ATAD2 | 2.7.31 | ATPase family, AAA domain containing 2 | 8 | 0.069067933 || BRCA1 | 2.7.31 | breast cancer 1 | 17 | 0.062003742 || BRCA2 | 2.7.31 | breast cancer 2 | 13 | 0.09276469 || BUB1 | 2.7.31 | BUB1 mitotic checkpoint serine/threonine kinase | 2 | 0.243665407 || BUB1B | 2.7.31 | BUB1 mitotic checkpoint serine/threonine kinase B | 15 | 0.105612418 || CCNA2 | 2.7.31 | cyclin A2 | 4 | 0.318798027 || CCNB2 | 2.7.31 | cyclin B2 | 15 | 0.114978823 || CCNE2 | 2.7.31 | cyclin E2 | 8 | 0.073776768 || CD38 | 2.7.31 | CD38 molecule | 4 | 0.458499747 || CDC20 | 2.7.31 | cell division cycle 20 | 1 | 0.097168091 || CDC6 | 2.7.31 | cell division cycle 6 | 17 | 0.111618795 || CDK1 | 2.7.31 | cyclin-dependent kinase 1 | 10 | 0.073653595 || CDKN3 | 2.7.31 | cyclin-dependent kinase inhibitor 3 | 14 | 0.070093354 || CENPF | 2.7.31 | centromere protein F | 1 | 0.103689479 || CEP55 | 2.7.31 | centrosomal protein 55 kDa | 10 | 0.185732018 || CKAP2 | 2.7.31 | cytoskeleton associated protein 2 | 13 | 0.060443462 || CKAP2L | 2.7.31 | cytoskeleton associated protein 2 like | 2 | 0.070101198 || CLSPN | 2.7.31 | claspin | 1 | 0.094259192 || DLGAP5 | 2.7.31 | discs large homolog associated protein 5 | 14 | 0.150644317 || DTL | 2.7.31 | denticleless E3 ubiquitin protein ligase homolog | 1 | 0.271753443 || E2F8 | 2.7.31 | E2F transcription factor 8 | 11 | 0.075519117 || ELL2 | 2.7.31 | elongation factor for RNA polymerase II 2 | 5 | 0.138384569 || ESCO2 | 2.7.31 | establishment of sister chromatid cohesion N-acetyltransferase 2 | 8 | 0.237826227 || EXO1 | 2.7.31 | exonuclease 1 | 1 | 0.064620013 || FAM72A | 2.7.31 | family with sequence similarity 72 member A | 1 | 0.129731061 || FAM72B | 2.7.31 | family with sequence similarity 72 member B | 1 | 0.089919882 || FANCI | 2.7.31 | Fanconi anemia complementation group I | 15 | 0.077340962 || HIST1H1B | 2.7.31 | histone cluster 1, H1b | 6 | 0.388150174 || HIST1H1C | 2.7.31 | histone cluster 1, H1c | 6 | 0.121640485 || HIST1H1E | 2.7.31 | histone cluster 1, H1e | 6 | 0.177652782 || HIST1H2AB | 2.7.31 | histone cluster 1, H2ab | 6 | 0.228890255 || HIST1H2AE | 2.7.31 | histone cluster 1, H2ae | 6 | 0.206894371 || HIST1H2AG | 2.7.31 | histone cluster 1, H2ag | 6 | 0.217353578 || HIST1H2AH | 2.7.31 | histone cluster 1, H2ah | 6 | 0.1090121 || HIST1H2AI | 2.7.31 | histone cluster 1, H2ai | 6 | 0.178083069 || HIST1H2AJ | 2.7.31 | histone cluster 1, H2aj | 6 | 0.652307519 || HIST1H2AK | 2.7.31 | histone cluster 1, H2ak | 6 | 0.077617746 || HIST1H2AL | 2.7.31 | histone cluster 1, H2al | 6 | 0.322160894 || HIST1H2AM | 2.7.31 | histone cluster 1, H2am | 6 | 0.177311123 || HIST1H2BB | 2.7.31 | histone cluster 1, H2bb | 6 | 0.093731129 || HIST1H2BD | 2.7.31 | histone cluster 1, H2bd | 6 | 0.138729526 || HIST1H2BE | 2.7.31 | histone cluster 1, H2be | 6 | 0.110153978 || HIST1H2BF | 2.7.31 | histone cluster 1, H2bf | 6 | 0.17258106 || HIST1H2BG | 2.7.31 | histone cluster 1, H2bg | 6 | 0.124112845 || HIST1H2BH | 2.7.31 | histone cluster 1, H2bh | 6 | 0.17443153 || HIST1H2BI | 2.7.31 | histone cluster 1, H2bi | 6 | 0.203895637 || HIST1H2BJ | 2.7.31 | histone cluster 1, H2bj | 6 | 0.085252138 || HIST1H2BL | 2.7.31 | histone cluster 1, H2bl | 6 | 0.098464817 || HIST1H2BM | 2.7.31 | histone cluster 1, H2bm | 6 | 0.499738228 || HIST1H2BN | 2.7.31 | histone cluster 1, H2bn | 6 | 0.076659591 || HIST1H2BO | 2.7.31 | histone cluster 1, H2bo | 6 | 0.120787021 || HIST1H3B | 2.7.31 | histone cluster 1, H3b | | 0.446511858 || HIST1H3C | 2.7.31 | histone cluster 1, H3c | | 0.186392164 || HIST1H3F | 2.7.31 | histone cluster 1, H3f | 6 | 0.25010626 || HIST1H3G | 2.7.31 | histone cluster 1, H3g | 6 | 0.277815634 || HIST1H3H | 2.7.31 | histone cluster 1, H3h | 6 | 0.136755704 || HIST1H3I | 2.7.31 | histone cluster 1, H3i | 6 | 0.232625266 || HIST1H3J | 2.7.31 | histone cluster 1, H3j | 6 | 0.162444111 || HIST1H4A | 2.7.31 | histone cluster 1, H4a | 6 | 0.07018871 || HIST1H4B | 2.7.31 | histone cluster 1, H4b | 6 | 0.182287232 || HIST1H4C | 2.7.31 | histone cluster 1, H4c | 6 | 0.258960438 || HIST1H4F | 2.7.31 | histone cluster 1, H4f | 6 | 0.107124007 || HIST1H4H | 2.7.31 | histone cluster 1, H4h | 6 | 0.139872251 || HIST1H4I | 2.7.31 | histone cluster 1, H4i | 6 | 0.07019443 || HIST1H4L | 2.7.31 | histone cluster 1, H41 | 6 | 0.091164989 || HIST2H2AB | 2.7.31 | histone cluster 2, H2ab | 1 | 0.138036163 || HMMR | 2.7.31 | hyaluronan mediated motility receptor | 5 | 0.103506786 || KIAA0101 | 2.7.31 | KIAA0101 | 15 | 0.125362695 || KIAA1524 | 2.7.31 | KIAA1524 | 3 | 0.077687655 || KIF11 | 2.7.31 | kinesin family member 11 | 10 | 0.199728421 || KIF20A | 2.7.31 | kinesin family member 20A | 5 | 0.068008851 || KIF20B | 2.7.31 | kinesin family member 20B | 10 | 0.111606003 || KIF23 | 2.7.31 | kinesin family member 23 | 15 | 0.086273992 | KIF2C | 2.7.31 | kinesin family member 2C | 1 | 0.069319369 || MANIA1 | 2.7.31 | mannosidase alpha class 1A member 1 | 6 | 0.116262795 || MASTL | 2.7.31 | microtubule associated serine/threonine kinase like | 10 | 0.088797212 || MCM10 | 2.7.31 | minichromosome maintenance 10 replication initiation factor | 10 | 0.075753313 || MCM4 | 2.7.31 | minichromosome maintenance complex component 4 | 8 | 0.08367917 || MCM6 | 2.7.31 | minichromosome maintenance complex component 6 | 2 | 0.131861005 || MCM8 | 2.7.31 | minichromosome maintenance 8 homologous recombination repair factor | 20 | 0.076561508 || MELK | 2.7.31 | maternal embryonic leucine zipper kinase | 9 | 0.069235134 || MIR516A2 2.7.31 | microRNA 516a-2 | 19 | 0.393471906 || MIR548AS | 2.7.31 | microRNA 548as | 13 | 0.083762078 || MIR670 | 2.7.31 | microRNA 670 | 11 | 0.067416816 || MKI67 | 2.7.31 | marker of proliferation Ki-67 | 10 | 0.298647817 || MYBL2 | 2.7.31 | MYB proto-oncogene like 2 | 20 | 0.083163929 || MYO1D | 2.7.31 | myosin ID | 17 | 0.083510744 || NCAPG | 2.7.31 | non-SMC condensin I complex subunit G | 4 | 0.127762858 || NCAPG2 | 2.7.31 | non-SMC condensin II complex subunit G2 | 7 | 0.073296471 || NDC80 | 2.7.31 | NDC80 kinetochore complex component | 18 | 0.158254963 || NUF2 | 2.7.31 | NUF2, NDC80 kinetochore complex component | 1 | 0.111921653 || NUSAP1 | 2.7.31 | nucleolar and spindle associated protein 1 | 15 | 0.102350377 || PCNA | 2.7.31 | proliferating cell nuclear antigen | 20 | 0.129755209 || PLK1 | 2.7.31 | polo like kinase 1 | 16 | 0.122096663 || POLQ | 2.7.31 | polymerase (DNA) theta | 3 | 0.061470329 || PRR11 | 2.7.31 | proline rich 11 | 17 | 0.085926976 || PSAT1 | 2.7.31 | phosphoserine aminotransferase 1 | 9 | 0.078321273 || RAD51C | 2.7.31 | RAD51 paralog C | 17 | 0.090430302 || RBBP8 | 2.7.31 | retinoblastoma binding protein 8 | 18 | 0.061751956 || RRM2 2.7.31 | ribonucleotide reductase regulatory subunit M2 | 2 | 0.444770415 || SASS6 | 2.7.31 | SAS-6 centriolar assembly protein | 1 | 0.060255069 || SHCBP1 | 2.7.31 | SHC SH2-domain binding protein 1 | 16 | 0.11911544 || SLC27A2 | 2.7.31 | solute carrier family 27 member 2 | 15 |

TABLE 1C-continued

| The genes within the significant gene clusters, listed in Table 1B. (2160 Genes Listed by: Gene Symbol ǀ Module ǀ Gene Description ǀ Chromosome Number ǀ Row Variance) ǀǀ) |
|---|
| 0.16989371 ǀǀ SMC4 ǀ 2.7.31 ǀ structural maintenance of chromosomes 4 ǀ 3 ǀ 0.077307644 ǀǀ SNORD3C ǀ 2.7.31 ǀ small nucleolar RNA, C/D box 3C ǀ 17 ǀ 1.570602905 ǀǀ STMN1 ǀ 2.7.31 ǀ stathmin 1 ǀ 1 ǀ 0.092507435 ǀǀ TOP2A ǀ 2.7.31 ǀ topoisomerase (DNA) II alpha ǀ 17 ǀ 0.263443136 ǀǀ TPX2 ǀ 2.7.31 ǀ TPX2, microtubule-associated ǀ 20 ǀ 0.183698442 ǀǀ TTK ǀ 2.7.31 ǀ TTK protein kinase ǀ 6 ǀ 0.064291541 ǀǀ TYMS ǀ 2.7.31 ǀ thymidylate synthetase ǀ 18 ǀ 0.183671634 ǀǀ UBE2F-SCLY ǀ 2.7.31 ǀ UBE2F-SCLY readthrough (NMD candidate) ǀ 2 ǀ 0.116031702 ǀǀ WDHD1 ǀ 2.7.31 ǀ WD repeat and HMG-box DNA binding protein 1 ǀ 14 ǀ 0.06850525 ǀǀ XRCC2 ǀ 2.7.31 ǀ X-ray repair complementing defective repair in Chinese hamster cells 2 ǀ 7 ǀ 0.062051848 ǀǀ ZWILCH ǀ 2.7.31 ǀ zwilch kinetochore protein ǀ 15 ǀ 0.060708866 ǀǀ APOBEC3B ǀ 2.7.31.126 ǀ apolipoprotein B mRNA editing enzyme catalytic subunit 3B ǀ 22 ǀ 0.131526145 ǀǀ ATAD2 ǀ 2.7.31.126 ǀ ATPase family, AAA domain containing 2 ǀ 8 ǀ 0.069067933 ǀǀ BUB1 ǀ 2.7.31.126 ǀ BUB1 mitotic checkpoint serine/threonine kinase ǀ 2 ǀ 0.243665407 ǀǀ CCNA2 ǀ 2.7.31.126 ǀ cyclin A2 ǀ 4 ǀ 0.318798027 ǀǀ CCNB2 ǀ 2.7.31.126 ǀ cyclin B2 ǀ 15 ǀ 0.114978823 ǀǀ CCNE2 ǀ 2.7.31.126 ǀ cyclin E2 ǀ 8 ǀ 0.073776768 ǀǀ CD38 ǀ 2.7.31.126 ǀ CD38 molecule ǀ 4 ǀ 0.458499747 ǀǀ CDC20 ǀ 2.7.31.126 ǀ cell division cycle 20 ǀ 1 ǀ 0.097168091 ǀǀ CDC6 ǀ 2.7.31.126 ǀ cell division cycle 6 ǀ 17 ǀ 0.111618795 ǀǀ CDK1 ǀ 2.7.31.126 ǀ cyclin-dependent kinase 1 ǀ 10 ǀ 0.073653595 ǀǀ CEP55 ǀ 2.7.31.126 ǀ centrosomal protein 55 kDa ǀ 10 ǀ 0.185732018 ǀǀ DTL ǀ 2.7.31.126 ǀ denticleless E3 ubiquitin protein ligase homolog ǀ 1 ǀ 0.271753443 ǀǀ E2F8 ǀ 2.7.31.126 ǀ E2F transcription factor 8 ǀ 11 ǀ 0.075519117 ǀǀ ELL2 ǀ 2.7.31.126 ǀ elongation factor for RNA polymerase II 2 ǀ 5 ǀ 0.138384569 ǀǀ ESCO2 ǀ 2.7.31.126 ǀ establishment of sister chromatid cohesion N-acetyltransferase 2 ǀ 8 ǀ 0.237826227 ǀǀ EXO1 ǀ 2.7.31.126 ǀ exonuclease 1 ǀ 1 ǀ 0.064620013 ǀǀ FAM72A ǀ 2.7.31.126 ǀ family with sequence similarity 72 member A ǀ 1 ǀ 0.129731061 ǀǀ FAM72B ǀ 2.7.31.126 ǀ family with sequence similarity 72 member B ǀ 1 ǀ 0.089919882 ǀǀ FANCI ǀ 2.7.31.126 ǀ Fanconi anemia complementation group I ǀ 15 ǀ 0.077340962 ǀǀ HIST1H2AI ǀ 2.7.31.126 ǀ histone cluster 1, H2ai ǀ 6 ǀ 0.178083069 ǀǀ HIST1H2AK ǀ 2.7.31.126 ǀ histone cluster 1, H2ak ǀ 6 ǀ 0.077617746 ǀǀ KIAA0101 ǀ 2.7.31.126 ǀ KIAA0101 ǀǀ 15 ǀ 0.125362695 ǀ KIAA1524 ǀ 2.7.31.126 ǀ KIAA1524 ǀ 3 ǀ 0.077687655 ǀǀ KIF11 ǀ 2.7.31.126 ǀ kinesin family member 11 ǀ 10 ǀ 0.199728421 ǀǀ KIF20A ǀ 2.7.31.126 ǀ kinesin family member 20A ǀ 5 ǀ 0.068008851 ǀǀ KIF2C ǀ 2.7.31.126 ǀ kinesin family member 2C ǀ 1 ǀ 0.069319369 ǀǀ MAN1A1 ǀ 2.7.31.126 ǀ mannosidase alpha class 1A member 1 ǀ 6 ǀ 0.116262795 ǀǀ MCM4 ǀ 2.7.31.126 ǀ minichromosome maintenance complex component 4 ǀ 8 ǀ 0.08367917 ǀǀ MCM6 ǀ 2.7.31.126 ǀ minichromosome maintenance complex component 6 ǀ 2 ǀ 0.131861005 ǀǀ MKI67 ǀ 2.7.31.126 ǀ marker of proliferation Ki-67 ǀ 10 ǀ 0.298647817 ǀǀ MYBL2 ǀ 2.7.31.126 ǀ MYB proto-oncogene like 2 ǀ 20 ǀ 0.083163929 ǀǀ MYO1D ǀ 2.7.31.126 ǀ myosin ID ǀ 17 ǀ 0.083510744 ǀǀ NCAPG ǀ 2.7.31.126 ǀ non-SMC condensin I complex subunit G ǀ 4 ǀ 0.127762858 ǀǀ NCAPG2 ǀ 2.7.31.126 ǀ non-SMC condensin II complex subunit G2 ǀ 7 ǀ 0.073296471 ǀǀ NUF2 ǀ 2.7.31.126 ǀ NUF2, NDC80 kinetochore complex component ǀ 1 ǀ 0.111921653 ǀǀ PCNA ǀ 2.7.31.126 ǀ proliferating cell nuclear antigen ǀ 20 ǀ 0.129755209 ǀǀ PLK1 ǀ 2.7.31.126 ǀ polo like kinase 1 ǀ 16 ǀ 0.122096663 ǀǀ PRR11 ǀ 2.7.31.126 ǀ proline rich 11 ǀ 17 ǀ 0.085926976 ǀǀ PSAT1 ǀ 2.7.31.126 ǀ phosphoserine aminotransferase 1 ǀ 9 ǀ 0.078321273 ǀǀ RBBP8 ǀ 2.7.31.126 ǀ retinoblastoma binding protein 8 ǀ 18 ǀ 0.061751956 ǀǀ RRM2 ǀ 2.7.31.126 ǀ ribonucleotide reductase regulatory subunit M2 ǀ 2 ǀ 0.444770415 ǀǀ SHCBP1 ǀ 2.7.31.126 ǀ SHC SH2-domain binding protein 1 ǀ 16 ǀ 0.11911544 ǀǀ SLC27A2 ǀ 2.7.31.126 ǀ solute carrier family 27 member 2 ǀ 15 ǀ 0.16989371 ǀǀ STMN1 ǀ 2.7.31.126 ǀ stathmin 1 ǀ 1 ǀ 0.092507435 ǀ TOP2A ǀ 2.7.31.126 ǀ topoisomerase (DNA) II alpha ǀ 17 ǀ 0.263443136 ǀǀ TPX2 ǀ 2.7.31.126 ǀ TPX2, microtubule-associated ǀ 20 ǀ 0.183698442 ǀǀ TTK ǀ 2.7.31.126 ǀ TTK protein kinase ǀ 6 ǀ 0.064291541 ǀǀ TYMS ǀ 2.7.31.126 ǀ thymidylate synthetase ǀ 18 ǀ 0.183671634 ǀǀ WDHD1 ǀ 2.7.31.126 ǀ WD repeat and HMG-box DNA binding protein 1 ǀ 14 ǀ 0.06850525 ǀǀ XRCC2 2.7.31.126 ǀ X-ray repair complementing defective repair in Chinese hamster cells 2 ǀ 7 ǀ 0.062051848 ǀǀ APOBEC3B ǀ 2.7.31.126.248 ǀ apolipoprotein B mRNA editing enzyme catalytic subunit 3B ǀ 22 ǀ 0.131526145 ǀǀ BUB1 ǀ 2.7.31.126.248 ǀ BUB1 mitotic checkpoint serine/threonine kinase ǀ 2 ǀ 0.243665407 ǀǀ CCNA2 ǀ 2.7.31.126.248 ǀ cyclin A2 ǀ 4 ǀ 0.318798027 ǀǀ CCNE2 ǀ 2.7.31.126.248 ǀ cyclin E2 ǀ 8 ǀ 0.073776768 ǀǀ CD38 ǀ 2.7.31.126.248 ǀ CD38 molecule ǀ 4 ǀ 0.458499747 ǀǀ CDC6 ǀ 2.7.31.126.248 ǀ cell division cycle 6 ǀ 17 ǀ 0.111618795 ǀǀ CDK1 ǀ 2.7.31.126.248 ǀ cyclin-dependent kinase 1 ǀ 10 ǀ 0.073653595 ǀǀ CEP55 ǀ 2.7.31.126.248 ǀ centrosomal protein 55 kDa ǀ 10 ǀ 0.185732018 ǀǀ DTL ǀ 2.7.31.126.248 ǀ denticleless E3 ubiquitin protein ligase homolog ǀ 1 ǀ 0.271753443 ǀǀ ESCO2 ǀ 2.7.31.126.248 ǀ establishment of sister chromatid cohesion N-acetyltransferase 2 ǀ 8 ǀ 0.237826227 ǀǀ EXO1 ǀ 2.7.31.126.248 ǀ exonuclease 1 ǀ 1 ǀ 0.064620013 ǀǀ FAM72A ǀ 2.7.31.126.248 ǀ family with sequence similarity 72 member A ǀ 1 ǀ 0.129731061 ǀǀ FAM72B ǀ 2.7.31.126.248 ǀ family with sequence similarity 72 member B ǀ 1 ǀ 0.089919882 ǀǀ HIST1H2AI ǀ 2.7.31.126.248 ǀ histone cluster 1, H2ai ǀ 6 ǀ 0.178083069 ǀǀ HIST1H2AK ǀ 2.7.31.126.248 ǀ histone cluster 1, H2ak ǀ 6 ǀ 0.077617746 ǀǀ KIAA0101 ǀ 2.7.31.126.248 ǀ KIAA0101 ǀ 15 ǀ 0.125362695 ǀǀ MAN1A1 ǀ 2.7.31.126.248 ǀ mannosidase alpha class 1A member 1 ǀ 6 ǀ 0.116262795 ǀǀ MCM4 ǀ 2.7.31.126.248 ǀ minichromosome maintenance complex component 4 ǀ 8 ǀ 0.08367917 ǀǀ MCM6 ǀ 2.7.31.126.248 ǀ minichromosome maintenance complex component 6 ǀ 2 ǀ 0.131861005 ǀǀ MKI67 ǀ 2.7.31.126.248 ǀ marker of proliferation Ki-67 ǀ 10 ǀ 0.298647817 ǀǀ MYO1D ǀ 2.7.31.126.248 ǀ myosin ID ǀ 17 ǀ 0.083510744 ǀǀ PCNA ǀ 2.7.31.126.248 ǀ proliferating cell nuclear antigen ǀ 20 ǀ 0.129755209 ǀǀ PSAT1 ǀ 2.7.31.126.248 ǀ phosphoserine aminotransferase 1 ǀ 9 ǀ 0.078321273 ǀǀ RRM2 ǀ 2.7.31.126.248 ǀ ribonucleotide reductase regulatory subunit M2 ǀ 2 ǀ 0.444770415 ǀǀ SHCBP1 ǀ 2.7.31.126.248 ǀ SHC SH2-domain binding protein 1 ǀ 16 ǀ 0.11911544 ǀǀ SLC27A2 ǀ 2.7.31.126.248 ǀ solute carrier family 27 member 2 ǀ 15 ǀ 0.16989371 ǀǀ STMN1 ǀ 2.7.31.126.248 ǀ stathmin 1 ǀ 1 ǀ 0.092507435 ǀǀ TOP2A ǀ 2.7.31.126.248 ǀ topoisomerase (DNA) II alpha ǀ 17 ǀ 0.263443136 ǀǀ TPX2 ǀ 2.7.31.126.248 ǀ TPX2, microtubule-associated ǀ 20 ǀ 0.183698442 ǀǀ TYMS ǀ 2.7.31.126.248 ǀ thymidylate synthetase ǀ 18 ǀ 0.183671634 ǀǀ HIST1H1B ǀ 2.7.31.127 ǀ histone cluster 1, H1b ǀ 6 ǀ 0.388150174 ǀǀ HIST1H1C ǀ 2.7.31.127 ǀ histone cluster 1, Hlc ǀ 6 ǀ 0.121640485 ǀǀ HIST1H1E ǀ 2.7.31.127 ǀ histone cluster 1, H1e ǀ 6 ǀ 0.177652782 ǀǀ |

TABLE 1C-continued

The genes within the significant gene clusters, listed in Table 1B. (2160 Genes Listed by: Gene Symbol | Module | Gene Description | Chromosome Number | Row Variance) ||)

HIST1H2AB | 2.7.31.127 | histone cluster 1, H2ab | 6 | 0.228890255 || HIST1H2AE | 2.7.31.127 | histone cluster 1, H2ae | 6 | 0.206894371 || HIST1H2AG | 2.7.31.127 | histone cluster 1, H2ag | 6 | 0.217353578 || HIST1H2AH | 2.7.31.127 | histone cluster 1, H2ah | 6 | 0.1090121 || HIST1H2AJ | 2.7.31.127 | histone cluster 1, H2aj | 6 | 0.652307519 || HIST1H2AL | 2.7.31.127 | histone cluster 1, H2al | 6 | 0.322160894 || HIST1H2AM | 2.7.31.127 | histone cluster 1, H2am | 6 | 0.177311123 || HIST1H2BB | 2.7.31.127 | histone cluster 1, H2bb | 6 | 0.093731129 || HIST1H2BD | 2.7.31.127 | histone cluster 1, H2bd | 6 | 0.138729526 || HIST1H2BE | 2.7.31.127 | histone cluster 1, H2be | 6 | 0.110153978 || HIST1H2BF | 2.7.31.127 | histone cluster 1, H2bf | 6 | 0.17258106 || HIST1H2BG | 2.7.31.127 | histone cluster 1, H2bg | 6 | 0.124112845 || HIST1H2BH | 2.7.31.127 | histone cluster 1, H2bh | 6 | 0.17443153 || HIST1H2BI | 2.7.31.127 | histone cluster 1, H2bi | 6 | 0.203895637 || HIST1H2BJ | 2.7.31.127 | histone cluster 1, H2bj | 6 | 0.085252138 || HIST1H2BL | 2.7.31.127 | histone cluster 1, H2bl | 6 | 0.098464817 || HIST1H2BM | 2.7.31.127 | histone cluster 1, H2bm | 6 | 0.499738228 || HIST1H2BN | 2.7.31.127 | histone cluster 1, H2bn | 6 | 0.076659591 || HIST1H2BO | 2.7.31.127 | histone cluster 1, H2bo | 6 | 0.120787021 || HIST1H3B | 2.7.31.127 | histone cluster 1, H3b | | 0.446511858 || HIST1H3C | 2.7.31.127 | histone cluster 1, H3c | | 0.186392164 || HIST1H3F | 2.7.31.127 | histone cluster 1, H3f | 6 | 0.25010626 || HIST1H3G | 2.7.31.127 | histone cluster 1, H3g | 6 | 0.277815634 || HIST1H3H | 2.7.31.127 | histone cluster 1, H3h | 6 | 0.136755704 || HIST1H3I | 2.7.31.127 | histone cluster 1, H3i | 6 | 0.232625266 || HIST1H3J | 2.7.31.127 | histone cluster 1, H3j | 6 | 0.162444111 || HIST1H4A | 2.7.31.127 | histone cluster 1, H4a | 6 | 0.07018871 || HIST1H4B | 2.7.31.127 | histone cluster 1, H4b | 6 | 0.182287232 || HIST1H4C | 2.7.31.127 | histone cluster 1, H4c | 6 | 0.258960438 || HIST1H4F | 2.7.31.127 | histone cluster 1, H4f | 6 | 0.107124007 || HIST1H4H | 2.7.31.127 | histone cluster 1, H4h | 6 | 0.139872251 || HIST1H4I | 2.7.31.127 | histone cluster 1, H4i | 6 | 0.07019443 || HIST1H4L | 2.7.31.127 | histone cluster 1, H41 | 6 | 0.091164989 || HIST2H2AB | 2.7.31.127 | histone cluster 2, H2ab | 1 | 0.138036163 || SNORD3C | 2.7.31.127 | small nucleolar RNA, C/D box 3C | 17 | 1.570602905 || HIST1H1B | 2.7.31.127.250 | histone cluster 1, H1b | 6 | 0.388150174 || HIST1H2AB | 2.7.31.127.250 | histone cluster 1, H2ab | 6 | 0.228890255 || HIST1H2AE | 2.7.31.127.250 | histone cluster 1, H2ae | 6 | 0.206894371 || HIST1H2AG | 2.7.31.127.250 | histone cluster 1, H2ag | 6 | 0.217353578 || HIST1H2AH | 2.7.31.127.250 | histone cluster 1, H2ah | 6 | 0.1090121 || HIST1H2AJ | 2.7.31.127.250 | histone cluster 1, H2aj | 6 | 0.652307519 || HIST1H2AL | 2.7.31.127.250 | histone cluster 1, H2al | 6 | 0.322160894 || HIST1H2AM | 2.7.31.127.250 | histone cluster 1, H2am | 6 | 0.177311123 || HIST1H2BB | 2.7.31.127.250 | histone cluster 1, H2bb | 6 | 0.093731129 || HIST1H2BE | 2.7.31.127.250 | histone cluster 1, H2be | 6 | 0.110153978 || HIST1H2BF | 2.7.31.127.250 | histone cluster 1, H2bf | 6 | 0.17258106 || HIST1H2BI | 2.7.31.127.250 | histone cluster 1, H2bi | 6 | 0.203895637 || HIST1H2BL | 2.7.31.127.250 | histone cluster 1, H2bl | 6 | 0.098464817 || HIST1H2BM | 2.7.31.127.250 | histone cluster 1, H2bm | 6 | 0.499738228 || HIST1H2BN | 2.7.31.127.250 | histone cluster 1, H2bn | 6 | 0.076659591 || HIST1H3B | 2.7.31.127.250 | histone cluster 1, H3b | | 0.446511858 || HIST1H3C | 2.7.31.127.250 | histone cluster 1, H3c | | 0.186392164 || HIST1H3F | 2.7.31.127.250 | histone cluster 1, H3f | 6 | 0.25010626 || HIST1H3G | 2.7.31.127.250 | histone cluster 1, H3g | 6 | 0.277815634 || HIST1H3I | 2.7.31.127.250 | histone cluster 1, H3i | 6 | 0.232625266 || HIST1H3J | 2.7.31.127.250 | histone cluster 1, H3j | 6 | 0.162444111 || HIST1H4A | 2.7.31.127.250 | histone cluster 1, H4a | 6 | 0.07018871 || HIST1H4I | 2.7.31.127.250 | histone cluster 1, H4i | 6 | 0.07019443 || HIST1H4L | 2.7.31.127.250 | histone cluster 1, H41 | 6 | 0.091164989 || HIST2H2AB | 2.7.31.127.250 | histone cluster 2, H2ab | 1 | 0.138036163 || ANKRD36BP2 | 2.7.32.130 | ankyrin repeat domain 36B pseudogene 2 | 2 | 0.185529086 || ARHGAP42 | 2.7.32.130 | Rho GTPase activating protein 42 | 11 | 0.157650751 || ATAD5 | 2.7.32.130 | ATPase family, AAA domain containing 5 | 17 | 0.100481705 || BARD1 | 2.7.32.130 | BRCA1 associated RING domain 1 | 2 | 0.073041571 || BRIP1 | 2.7.32.130 | BRCA1 interacting protein C-terminal helicase 1 | 17 | 0.094153579 || CASC5 | 2.7.32.130 | cancer susceptibility candidate 5 | 15 | 0.089560364 || CENPE | 2.7.32.130 | centromere protein E | 4 | 0.141358284 || CNTLN | 2.7.32.130 | centlein | 9 | 0.088162835 || DIAPH3 | 2.7.32.130 | diaphanous related formin 3 | 13 | 0.061155395 || DMC1 | 2.7.32.130 | DNA meiotic recombinase 1 | 22 | 0.067368045 || DNA2 | 2.7.32.130 | DNA replication helicase/nuclease 2 | 10 | 0.074215098 || EPB41L4A | 2.7.32.130 | erythrocyte membrane protein band 4.1 like 4A | 5 | 0.126122953 || FANCB | 2.7.32.130 | Fanconi anemia complementation group B | X | 0.089424045 || FANCL | 2.7.32.130 | Fanconi anemia complementation group L | 2 | 0.074875621 || GAB1 | 2.7.32.130 | GRB2 associated binding protein 1 | 4 | 0.068066433 || GKAP1 | 2.7.32.130 | G kinase anchoring protein 1 | 9 | 0.093193128 || ISPD | 2.7.32.130 | isoprenoid synthase domain containing | 7 | 0.089885343 || KIF14 | 2.7.32.130 | kinesin family member 14 | 1 | 0.162483039 || KIF18A | 2.7.32.130 | kinesin family member 18A | 11 | 0.084925337 || LINC01036 | 2.7.32.130 | long intergenic non-protein coding RNA 1036 | | 0.351926017 || LOC101927708 | 2.7.32.130 | uncharacterized LOC101927708 | 11 | 0.683267266 || LRRCC1 | 2.7.32.130 | leucine rich repeat and coiled-coil centrosomal protein 1 | 8 | 0.092080532 || NEIL3 | 2.7.32.130 | nei like DNA glycosylase 3 | 4 | 0.061202894 || NUP62CL | 2.7.32.130 | nucleoporin 62 kDa C-terminal like | X | 0.07167816 || POLE2 | 2.7.32.130 | polymerase (DNA) epsilon 2, accessory subunit | 14 | 0.069821069 || SKA3 | 2.7.32.130 | spindle and kinetochore associated complex subunit 3 | 13 | 0.095409125 || STIL | 2.7.32.130 | SCL/TAL1 interrupting locus | 1 | 0.157090776 || TBC1D31 | 2.7.32.130 | TBC1 domain family member 31 | 8 | 0.075416519 || THEGL | 2.7.32.130 | theg spermatid protein-like | 4 | 0.18456694 || VRK1 | 2.7.32.130 | vaccinia related kinase 1 | 14 | 0.140430476 || ABCA1 | 3.13 | ATP binding cassette subfamily A member 1 | 9 | 0.280787966 || ABCG1 | 3.13 | ATP binding cassette subfamily G member 1 | 21 | 0.096418286 || ACOT9 | 3.13 | acyl-CoA thioesterase 9 | X | 0.130926287 || ADAR | 3.13 | adenosine deaminase, RNA-specific | 1 | 0.094800923 || AIM2 | 3.13 | absent in melanoma 2 | 1 | 0.332556929 || ALMS1P1 | 3.13 | ALMS1, centrosome and basal body associated protein pseudogene 1 | 2 | 0.092603349 ||

TABLE 1C-continued

The genes within the significant gene clusters, listed in Table 1B. (2160 Genes Listed by: Gene Symbol | Module | Gene Description | Chromosome Number | Row Variance) ||)

ANKFY1 | 3.13 | ankyrin repeat and FYVE domain containing 1 | 17 | 0.075291697 || ANKRD22 | 3.13 | ankyrin repeat domain 22 | 10 | 0.544288476 || ANKRD45 | 3.13 | ankyrin repeat domain 45 | 1 | 0.082634457 || APOL1 | 3.13 | apolipoprotein L1 | 22 | 0.131377313 || APOL2 | 3.13 | apolipoprotein L2 | 22 | 0.110787938 || APOL6 | 3.13 | apolipoprotein L6 | 22 | 0.143917583 || BATF2 | 3.13 | basic leucine zipper ATF-like transcription factor 2 | 11 | 0.066517445 || BISPR | 3.13 | BST2 interferon stimulated positive regulator (non-protein coding) | 19 | 0.199514412 || BLZF1 | 3.13 | basic leucine zipper nuclear factor 1 | 1 | 0.09034512 || BST2 | 3.13 | bone marrow stromal cell antigen 2 | 19 | 0.249135668 || BTN3A1 | 3.13 | butyrophilin subfamily 3 member A1 | 6 | 0.088770763 || BTN3A2 | 3.13 | butyrophilin subfamily 3 member A2 | 6 | 0.167615858 || BTN3A3 | 3.13 | butyrophilin subfamily 3 member A3 | 6 | 0.097165764 || C1GALT1 | 3.13 | core 1 synthase, glycoprotein-N-acetylgalactosamine 3-beta-galactosyltransferase 1 | 7 | 0.077899596 || C4orf33 | 3.13 | chromosome 4 open reading frame 33 | 4 | 0.065930067 || CARD16 | 3.13 | caspase recruitment domain family member 16 | 11 | 0.169897426 || CARD17 | 3.13 | caspase recruitment domain family member 17 | 11 | 0.642161107 || CARD6 | 3.13 | caspase recruitment domain family member 6 | 5 | 0.093827632 || CASP1 | 3.13 | caspase 1 | 11 | 0.136091591 || CASP10 | 3.13 | caspase 10 | 2 | 0.069452079 || CCDC146 | 3.13 | coiled-coil domain containing 146 | 7 | 0.181343816 || CCL2 | 3.13 | C-C motif chemokine ligand 2 | 17 | 0.504836333 || CCR1 | 3.13 | chemokine (C-C motif) receptor 1 | 3 | 0.386068575 || CD163 | 3.13 | CD163 molecule | 12 | 0.302524106 || CD274 | 3.13 | CD274 molecule | 9 | 0.48761392 || CEACAM1 | 3.13 | carcinoembryonic antigen related cell adhesion molecule 1 | 19 | 0.442833978 || CHMP5 | 3.13 | charged multivesicular body protein 5 | 9 | 0.142760433 || CLEC4A | 3.13 | C-type lectin domain family 4 member A | 12 | 0.137977448 || CMPK2 | 3.13 | cytidine/uridine monophosphate kinase 2 | 2 | 0.824835238 || CMTR1 | 3.13 | cap methyltransferase 1 | 6 | 0.143646768 || CNIH4 | 3.13 | cornichon family AMPA receptor auxiliary protein 4 | 1 | 0.071102476 || CPM | 3.13 | carboxypeptidase M | 12 | 0.142736862 || CXorf21 | 3.13 | chromosome X open reading frame 21 | X | 0.120124444 || CYSLTR1 | 3.13 | cysteinyl leukotriene receptor 1 | X | 0.181630807 || DAPP1 | 3.13 | dual adaptor of phosphotyrosine and 3-phosphoinositides | 4 | 0.101139222 || DDX58 | 3.13 | DEXD/H-box helicase 58 | 9 | 0.432370376 || DDX60 | 3.13 | DEXD/H-box helicase 60 | 4 | 0.982184993 || DDX60L | 3.13 | DEAD-box helicase 60-like | 4 | 0.374118058 || DHRS9 | 3.13 | dehydrogenase/reductase (SDR family) member 9 | 2 | 0.398312062 || DHX58 | 3.13 | DEXH-box helicase 58 | 17 | 0.206189554 || DRAM1 | 3.13 | DNA damage regulated autophagy modulator 1 | 12 | 0.095352545 || DRAP1 | 3.13 | DR1 associated protein 1 | 11 | 0.064515951 || DTX3L | 3.13 | deltex 3 like, E3 ubiquitin ligase | 3 | 0.183624016 || DYNLT1 | 3.13 | dynein light chain Tctex-type 1 | 6 | 0.088989236 || EIF2AK2 | 3.13 | eukaryotic translation initiation factor 2 alpha kinase 2 | 2 | 0.535347673 || EPSTI1 | 3.13 | epithelial stromal interaction 1 (breast) | 13 | 1.14046733 || ETV7 | 3.13 | ETS variant 7 | 6 | 0.264390153 || FAM46A | 3.13 | family with sequence similarity 46 member A | 6 | 0.072603053 || FAM8A1 | 3.13 | family with sequence similarity 8 member A1 | 6 | 0.098112763 || FAS | 3.13 | Fas cell surface death receptor | 10 | 0.092372163 || FBXO39 | 3.13 | F-box protein 39 | 17 | 0.072093178 || FCGR1A | 3.13 | Fc fragment of IgG receptor Ia | 1 | 0.693994982 || FCGRIB | 3.13 | Fc fragment of IgG receptor Ib | 1 | 0.376228514 || FCGR1CP | 3.13 | Fc fragment of IgG receptor Ic, pseudogene | 1 | 0.365954727 || FCGR2B | 3.13 | Fc fragment of IgG receptor IIb | 1 | 0.220151261 || FMNL2 | 3.13 | formin like 2 | 2 | 0.091899758 || FRMD3 | 3.13 | FERM domain containing 3 | 9 | 0.218337435 || GADD45B | 3.13 | growth arrest and DNA damage inducible beta | 19 | 0.082827584 || GALM | 3.13 | galactose mutarotase (aldose 1-epimerase) | 2 | 0.192283376 || GAPT | 3.13 | GRB2-binding adaptor protein, transmembrane | 5 | 0.152724923 || GBP1 | 3.13 | guanylate binding protein 1 | 1 | 0.411270752 || GBP1P1 | 3.13 | guanylate binding protein 1 pseudogene 1 | 1 | 0.252083945 || GBP2 | 3.13 | guanylate binding protein 2 | 1 | 0.142121847 || GBP3 | 3.13 | guanylate binding protein 3 | 1 | 0.310123296 || GBP4 | 3.13 | guanylate binding protein 4 | 1 | 0.32351413 || GBP5 | 3.13 | guanylate binding protein 5 | 1 | 0.347517017 || GBP6 | 3.13 | guanylate binding protein family member 6 | 1 | 0.172146871 || GLRX | 3.13 | glutaredoxin | 5 | 0.084109584 | GNB4 | 3.13 | G protein subunit beta 4 | 3 | 0.085977348 || GPD2 | 3.13 | glycerol-3-phosphate dehydrogenase 2 | 2 | 0.078830696 || GRAMD1B | 3.13 | GRAM domain containing 1B | 11 | 0.066086159 || GTPBP2 | 3.13 | GTP binding protein 2 | 6 | 0.074537978 || HELZ2 | 3.13 | helicase with zinc finger 2, transcriptional coactivator | 20 | 0.061804017 || HERC5 | 3.13 | HECT and RLD domain containing E3 ubiquitin protein ligase 5 | 4 | 1.514107421 || HESX1 | 3.13 | HESX homeobox 1 | 3 | 0.063992896 || HIST1H2AD | 3.13 | histone cluster 1, H2ad | 6 | 0.076644285 || HIST1H3D | 3.13 | histone cluster 1, H3d | 6 | 0.211857909 || HIST1H4D | 3.13 | histone cluster 1, H4d | 6 | 0.178916334 || HIST1H4K | 3.13 | histone cluster 1, H4k | 6 | 0.150572729 || HIST2H2BE | 3.13 | histone cluster 2, H2be | 1 | 0.207293801 || HNRNPLL | 3.13 | heterogeneous nuclear ribonucleoprotein L like | 2 | 0.063429633 || HSH2D | 3.13 | hematopoietic SH2 domain containing | 19 | 0.10941954 || IFI16 | 3.13 | interferon, gamma-inducible protein 16 | 1 | 0.152819724 || IFI35 | 3.13 | interferon induced protein 35 | 17 | 0.278146724 || IFI44 | 3.13 | interferon induced protein 44 | 1 | 2.08752131 || IFI44L | 3.13 | interferon induced protein 44 like | 1 | 3.33128148 || IFI6 | 3.13 | interferon, alpha-inducible protein 6 | 1 | 1.021254113 || IFIH1 | 3.13 | interferon induced, with helicase C domain 1 | 2 | 0.556663679 || IFIT1 | 3.13 | interferon induced protein with tetratricopeptide repeats 1 | 10 | 2.221831622 || IFIT2 | 3.13 | interferon induced protein with tetratricopeptide repeats 2 | 10 | 0.584812453 || IFIT3 | 3.13 | interferon induced protein with tetratricopeptide repeats 3 | 10 | 1.022684807 || IFIT5 | 3.13 | interferon induced protein with tetratricopeptide repeats 5 | 10 | 0.525041166 || IFITM1 | 3.13 | interferon induced transmembrane protein 1 | 11 | 0.168864948 || IFITM3 | 3.13 | interferon induced transmembrane protein 3 | 11 | 0.260199866 || IL1RN | 3.13 | interleukin 1 receptor antagonist | 2 | 0.198753741 || IRF1 | 3.13 | interferon regulatory factor 1 | 5 | 0.085758497 || IRF9 | 3.13 | interferon regulatory factor 9 | 14 | 0.096743797 || ISG15 | 3.13 | ISG15 ubiquitin-like modifier | 1 | 0.394697557 || ITGA1 | 3.13 | integrin subunit alpha 1 | 5 | 0.231947269 || JAK2 | 3.13 | Janus TABLE 1C-continued The genes within the significant gene clusters, listed in Table 1B. (2160 Genes Listed by: Gene Symbol | Module | Gene Description | Chromosome Number | Row Variance) ||)

kinase 2 | 9 | 0.099621131 || JPX | 3.13 | JPX transcript, XIST activator (non-protein coding) | X | 0.060446091 || JUP | 3.13 | junction plakoglobin | 17 | 0.189705459 || KIAA1958 | 3.13 | KIAA1958 | 9 | 0.089306884 || KLHDC7B | 3.13 | kelch domain containing 7B | 22 | 0.133737632 || LAMP3 | 3.13 | lysosomal associated membrane protein 3 | 3 | 0.387852736 || LAP3 | 3.13 | leucine aminopeptidase 3 | 4 | 0.462740011 || LGALS3BP | 3.13 | lectin, galactoside-binding, soluble, 3 binding protein | 17 | 0.301744028 || LGALS9 | 3.13 | lectin, galactoside-binding, soluble, 9 | 17 | 0.152901042 || LHFPL2 | 3.13 | lipoma HMGIC fusion partner-like 2 | 5 | 0.085246533 || LINC00152 | 3.13 | long intergenic non-protein coding RNA 152 | 2 | 0.10477045 || LINC00189 | 3.13 | long intergenic non-protein coding RNA 189 | 21 | 0.84175164 || LINC00487 | 3.13 | long intergenic non-protein coding RNA 487 | 2 | 0.257986055 || LINC01410 | 3.13 | long intergenic non-protein coding RNA 1410 | 9 | 0.357527205 || LOC101927027 | 3.13 | uncharacterized LOC101927027 | 2 | 0.159489632 || LOC101928227 | 3.13 | uncharacterized LOC101928227 | 15 | 0.081641209| | LOC105373098 | 3.13 | uncharacterized LOC105373098 | 22 | 0.411587667 || LOC729083 | 3.13 | uncharacterized LOC729083 | 3 | 0.062867231 || MARCKS | 3.13 | myristoylated alanine rich protein kinase C substrate | 6 | 0.112396821 || MILR1 | 3.13 | mast cell immunoglobulin-like receptor 1 | 17 | 0.209368701 || MIR1303 | 3.13 | microRNA 1303 | 5 | 0.15252495 || MIR4308 | 3.13 | microRNA 4308 | 14 | 0.083320614 || MOV10 | 3.13 | Mov10 RISC complex RNA helicase | 1 | 0.112182563 || MTIF | 3.13 | metallothionein 1F | 16 | 0.178664891 || MT1G | 3.13 | metallothionein 1G | 16 | 0.060784695 || MT1H | 3.13 | metallothionein 1H | 16 | 0.102404175 || MT1JP | 3.13 | metallothionein 1J, pseudogene | 16 | 0.256464075 || MT1X | 3.13 | metallothionein 1X | 16 | 0.185195038 || MT2A | 3.13 | metallothionein 2A | 16 | 0.328753513 || MX1 | 3.13 | MX dynamin like GTPase 1 | 21 | 1.071562251 || MX2 | 3.13 | MX dynamin like GTPase 2 | 21 | 0.25750327 || MYD88 | 3.13 | myeloid differentiation primary response 88 | 3 | 0.066309453 || NBN | 3.13 | nibrin | 8 | 0.112474837 || NMI | 3.13 | N-myc and STAT interactor | 2 | 0.148301216 || NT5C3A | 3.13 | 5'-nucleotidase, cytosolic IIIA | 7 | 0.167934707 || NUB1 | 3.13 | negative regulator of ubiquitin-like proteins 1 | 7 | 0.067576918 || OAS1 | 3.13 | 2'-5'-oligoadenylate synthetase 1 | 12 | 0.915871445 || OAS2 | 3.13 | 2'-5'-oligoadenylate synthetase 2 | 12 | 0.913005255 || OAS3 | 3.13 | 2'-5'-oligoadenylate synthetase 3 | 12 | 1.290342716 || OASL | 3.13 | 2'-5'-oligoadenylate synthetase like | 12 | 0.799654603 || OR52H1 | 3.13 | olfactory receptor family 52 subfamily H member 1 | 11 | 0.078483677 || OR52K1 | 3.13 | olfactory receptor family 52 subfamily K member 1 | 11 | 0.22937738 || OR52K2 | 3.13 | olfactory receptor family 52 subfamily K member 2 | 11 | 0.265437909 || OR52N4 | 3.13 | olfactory receptor family 52 subfamily N member 4 (gene/pseudogene) | 11 | 0.104972999 || OR56B1 | 3.13 | olfactory receptor family 56 subfamily B member 1 | 11 | 0.097773382 || OTOF | 3.13 | otoferlin | 2 | 0.16791902 || PARP11 | 3.13 | poly(ADP-ribose) polymerase family member 11 | 12 | 0.129115102 || PARP12 | 3.13 | poly(ADP-ribose) polymerase family member 12 | 7 | 0.369058306 || PARP14 | 3.13 | poly(ADP-ribose) polymerase family member 14 | 3 | 0.339596295 || PARP9 | 3.13 | poly(ADP-ribose) polymerase family member 9 | 3 | 0.276675907 || PATL1 | 3.13 | protein associated with topoisomerase II homolog 1 (yeast) | 11 | 0.06765744 || PDCD1LG2 | 3.13 | programmed cell death 1 ligand 2 | 9 | 0.192749507 || PGAP1 | 3.13 | post-GPI attachment to proteins 1 | 2 | 0.220884701 || PIK3AP1 | 3.13 | phosphoinositide-3-kinase adaptor protein 1 | 10 | 0.114421116 || PLSCR1 | 3.13 | phospholipid scramblase 1 | 3 | 0.516505035 || PMAIP1 | 3.13 | phorbol-12-myristate-13-acetate-induced protein 1 | 18 | 0.115237627 || PML | 3.13 | promyelocytic leukemia | 15 | 0.072759722 || PNPT1 | 3.13 | polyribonucleotide nucleotidyltransferase 1 | 2 | 0.316223651 | POLB | 3.13 | polymerase (DNA) beta | 8 | 0.098072401 || PPMIK | 3.13 | protein phosphatase, Mg2+/Mn2+ dependent 1K | 4 | 0.171529358 || PRRG4 | 3.13 | proline rich Gla (G-carboxyglutamic acid) 4 (transmembrane) | 11 | 0.290888317 || PSTPIP2 | 3.13 | proline-serine-threonine phosphatase interacting protein 2 | 18 | 0.193440456 || PTP4A1 | 3.13 | protein tyrosine phosphatase type IVA, member 1 | 6 | 0.103383806 | RBM43 | 3.13 | RNA binding motif protein 43 | 2 | 0.100154697 || RLN1 | 3.13 | relaxin 1 | 9 | 0.07247648 || RNF213 | 3.13 | ring finger protein 213 | 17 | 0.169813818 || RSAD2 | 3.13 | radical S-adenosyl methionine domain containing 2 | 2 | 2.541036973 || RTP4 | 3.13 | receptor (chemosensory) transporter protein 4 | 3 | 0.799089791 || SAMD9 | 3.13 | sterile alpha motif domain containing 9 | 7 | 0.227554962 || SAMD9L | 3.13 | sterile alpha motif domain containing 9-like | 7 | 0.413716083 || SAT1 | 3.13 | spermidine/spermine N1-acetyltransferase 1 | X | 0.153450967 || SECTM1 | 3.13 | secreted and transmembrane 1 | 17 | 0.087561354 || SERPING1 | 3.13 | serpin peptidase inhibitor, clade G (C1 inhibitor), member 1 | 11 | 0.892846417 || SESTD1 | 3.13 | SEC14 and spectrin domain containing 1 | 2 | 0.087439183 || SGMS2 | 3.13 | sphingomyelin synthase 2 | 4 | 0.13042374 || SHISA5 | 3.13 | shisa family member 5 | 3 | 0.090404805 || SIGLEC1 | 3.13 | sialic acid binding Ig like lectin 1 | 20 | 0.496544404 || SLFN12 | 3.13 | schlafen family member 12 | 17 | 0.187808839 || SORT1 | 3.13 | sortilin 1 | 1 | 0.141151129 || SP100 | 3.13 | SP100 nuclear antigen | 2 | 0.110446175 || SP140 | 3.13 | SP140 nuclear body protein | 2 | 0.181747485 || SPATS2L | 3.13 | spermatogenesis associated serine rich 2 like | 2 | 0.66682159 || SPIC | 3.13 | Spi-C transcription factor | 12 | 0.089210647 || SPTLC2 | 3.13 | serine palmitoyltransferase long chain base subunit 2 | 14 | 0.135070975 || SQRDL | 3.13 | sulfide quinone reductase-like (yeast) | 15 | 0.086035698 || SRGAP2 | 3.13 | SLIT-ROBO Rho GTPase activating protein 2 | 1 | 0.097253006 || STAT1 | 3.13 | signal transducer and activator of transcription 1 | 2 | 0.215234511 || STAT2 | 3.13 | signal transducer and activator of transcription 2 | 12 | 0.275295047 || STX11 | 3.13 | syntaxin 11 | 6 | 0.115327192 || TBC1D8 | 3.13 | TBC1 domain family member 8 | 2 | 0.079746068 || TDRD7 | 3.13 | tudor domain containing 7 | 9 | 0.205042782 || TIFA | 3.13 | TRAF interacting protein with forkhead associated domain | 4 | 0.123147729 || TIMM10 | 3.13 | translocase of inner mitochondrial membrane 10 homolog (yeast) | 11 | 0.146886027 || TMEM123 | 3.13 | transmembrane protein 123 | 11 | 0.165562023 || TMEM140 | 3.13 | transmembrane protein 140 | 7 | 0.1516408 || TMEM255A | 3.13 | transmembrane protein 255A | X | 0.09741285 || TMEM62 | 3.13 | transmembrane protein 62 | 15 | 0.094418297 || TMOD2 | 3.13 | tropomodulin 2 | 15 |

TABLE 1C-continued

| The genes within the significant gene clusters, listed in Table 1B. (2160 Genes Listed by: Gene Symbol \| Module \| Gene Description \| Chromosome Number \| Row Variance) \|\|) |
|---|
| 0.101086032 \|\| TNFAIP6 \| 3.13 \| TNF alpha induced protein 6 \| 2 \| 0.699075024 \|\| TNFSF10 \| 3.13 \| tumor necrosis factor superfamily member 10 \| 3 \| 0.133526449 \|\| TNFSF13B \| 3.13 \| tumor necrosis factor superfamily member 13b \| 13 \| 0.225821577 \|\| TOR1A \| 3.13 \| torsin family 1 member A \| 9 \| 0.077312382 \|\| TOR1B \| 3.13 \| torsin family 1 member B \| 9 \| 0.188175646 \|\| TRAFD1 \| 3.13 \| TRAF-type zinc finger domain containing 1 \| 12 \| 0.124837438 \|\| TRANK1 \| 3.13 \| tetratricopeptide repeat and ankyrin repeat containing 1 \| 3 \| 0.098079262 \|\| TRIM14 \| 3.13 \| tripartite motif containing 14 \| 9 \| 0.108579071 \|\| TRIM21 \| 3.13 \| tripartite motif containing 21 \| 11 \| 0.097575871 \|\| TRIM22 \| 3.13 \| tripartite motif containing 22 \| 11 \| 0.288648851 \|\| TRIM38 \| 3.13 \| tripartite motif containing 38 \| 6 \| 0.110180625 \|\| TRIM5 \| 3.13 \| tripartite motif containing 5 \| 11 \| 0.207718288 \|\| TRIM6 \| 3.13 \| tripartite motif containing 6 \| 11 \| 0.35451014 \|\| TTC26 \| 3.13 \| tetratricopeptide repeat domain 26 \| 7 \| 0.184919169 \|\| UBE2L6 \| 3.13 \| ubiquitin conjugating enzyme E2L 6 \| 11 \| 0.184224897 \|\| UBQLNL \| 3.13 \| ubiquilin-like \| 11 \| 0.068580785 \|\| UNC93B1 \| 3.13 \| unc-93 homolog B1 (*C. elegans*) \| 11 \| 0.079143058 \|\| USP17L15 \| 3.13 \| ubiquitin specific peptidase 17-like family member 15 \| 4 \| 0.08230898 \|\| USP18 \| 3.13 \| ubiquitin specific peptidase 18 \| 22 \| 0.980232149 \|\| USP25 \| 3.13 \| ubiquitin specific peptidase 25 \| 21 \| 0.060588743 \|\| XAF1 \| 3.13 \| XIAP associated factor 1 \| 17 \| 0.77655475 \|\| XRN1 \| 3.13 \| 5'-3' exoribonuclease 1 \| 3 \| 0.068397432 \|\| XXYLT1-AS2 \| 3.13 \| XXYLT1 antisense RNA 2 \| 3 \| 0.065520644 \|\| ZBP1 \| 3.13 \| Z-DNA binding protein 1 \| 20 \| 0.280313422 \|\| ZC3HAV1 \| 3.13 \| zinc finger CCCH-type containing, antiviral 1 \| 7 \| 0.083683811 \|\| ZCCHC2 \| 3.13 \| zinc finger CCHC-type containing 2 \| 18 \| 0.399452565 \|\| ZNF684 \| 3.13 \| zinc finger protein 684 \| 1 \| 0.161677841 \|\| ZNFX1 \| 3.13 \| zinc finger, NFX1-type containing 1 \| 20 \| 0.079215166 \|\| ALMS1P1 \| 3.13.47 \| ALMS1, centrosome and basal body associated protein pseudogene 1 \| 2 \| 0.092603349 \|\| ANKFY1 \| 3.13.47 \| ankyrin repeat and FYVE domain containing 1 \| 17 \| 0.075291697 \|\| ANKRD22 \| 3.13.47 \| ankyrin repeat domain 22 \| 10 \| 0.544288476 \|\| ANKRD45 \| 3.13.47 \| ankyrin repeat domain 45 \| 1 \| 0.082634457 \|\| APOL6 \| 3.13.47 \| apolipoprotein L6 \| 22 \| 0.143917583 \|\| BATF2 \| 3.13.47 \| basic leucine zipper ATF-like transcription factor 2 \| 11 \| 0.066517445 \| BISPR \| 3.13.47 \| BST2 interferon stimulated positive regulator (non-protein coding) \| 19 \| 0.199514412 \|\| BST2 \| 3.13.47 \| bone marrow stromal cell antigen 2 \| 19 \| 0.249135668 \|\| BTN3A1 \| 3.13.47 \| butyrophilin subfamily 3 member A1 \| 6 \| 0.088770763 \|\| BTN3A2 \| 3.13.47 \| butyrophilin subfamily 3 member A2 \| 6 \| 0.167615858 \|\| BTN3A3 \| 3.13.47 \| butyrophilin subfamily 3 member A3 \| 6 \| 0.097165764 \|\| C4orf33 \| 3.13.47 \| chromosome 4 open reading frame 33 \| 4 \| 0.065930067 \|\| CASP10 \| 3.13.47 \| caspase 10 \| 2 \| 0.069452079 \|\| CCL2 \| 3.13.47 \| C-C motif chemokine ligand 2 \| 17 \| 0.504836333 \|\| CCR1 \| 3.13.47 \| chemokine (C-C motif) receptor 1 \| 3 \| 0.386068575 \|\| CD163 \| 3.13.47 \| CD163 molecule \| 12 \| 0.302524106 \|\| CMPK2 \| 3.13.47 \| cytidine/uridine monophosphate kinase 2 \| 2 \| 0.824835238 \|\| CMTR1 \| 3.13.47 \| cap methyltransferase 1 \| 6 \| 0.143646768 \|\| CPM \| 3.13.47 \| carboxypeptidase M \| 12 \| 0.142736862 \|\| DDX60 \| 3.13.47 \| DEXD/H-box helicase 60 \| 4 \| 0.982184993 \|\| DHX58 \| 3.13.47 \| DEXH-box helicase 58 \| 17 \| 0.206189554 \|\| DRAP1 \| 3.13.47 \| DRI associated protein 1 \| 11 \| 0.064515951 \|\| DTX3L \| 3.13.47 \| deltex 3 like, E3 ubiquitin ligase \| 3 \| 0.183624016 \|\| EIF2AK2 \| 3.13.47 \| eukaryotic translation initiation factor 2 alpha kinase 2 \| 2 \| 0.535347673 \|\| EPSTI1 \| 3.13.47 \| epithelial stromal interaction 1 (breast) \| 13 \| 1.14046733 \|\| ETV7 \| 3.13.47 \| ETS variant 7 \| 6 \| 0.264390153 \|\| FAM46A \| 3.13.47 \| family with sequence similarity 46 member A \| 6 \| 0.072603053 \|\| FBXO39 \| 3.13.47 \| F-box protein 39 \| 17 \| 0.072093178 \|\| FMNL2 \| 3.13.47 \| formin like 2 \| 2 \| 0.091899758 \|\| GALM \| 3.13.47 \| galactose mutarotase (aldose 1-epimerase) \| 2 \| 0.192283376 \|\| GBP1 \| 3.13.47 \| guanylate binding protein 1 \| 1 \| 0.411270752 \|\| GBP1P1 \| 3.13.47 \| guanylate binding protein 1 pseudogene 1 \| 1 \| 0.252083945 \|\| GBP3 \| 3.13.47 \| guanylate binding protein 3 \| 1 \| 0.310123296 \|\| GBP4 \| 3.13.47 \| guanylate binding protein 4 \| 1 \| 0.32351413 \|\| GBP5 \| 3.13.47 \| guanylate binding protein 5 \| 1 \| 0.347517017 \|\| GBP6 \| 3.13.47 \| guanylate binding protein family member 6 \| 1 \| 0.172146871 \|\| GRAMD1B \| 3.13.47 \| GRAM domain containing 1B \| 11 \| 0.066086159 \|\| HELZ2 \| 3.13.47 \| helicase with zinc finger 2, transcriptional coactivator \| 20 \| 0.061804017 \|\| HERC5 \| 3.13.47 \| HECT and RLD domain containing E3 ubiquitin protein ligase 5 \| 4 \| 1.514107421 \|\| HESX1 \| 3.13.47 \| HESX homeobox 1 \| 3 \| 0.063992896 \|\| HNRNPLL \| 3.13.47 \| heterogeneous nuclear ribonucleoprotein L like \| 2 \| 0.063429633 \|\| IFI35 \| 3.13.47 \| interferon induced protein 35 \| 17 \| 0.278146724 \|\| IFI44 \| 3.13.47 \| interferon induced protein 44 \| 1 \| 2.08752131 \|\| IFI44L \| 3.13.47 \| interferon induced protein 44 like \| 1 \| 3.33128148 \|\| IFI6 \| 3.13.47 \| interferon, alpha-inducible protein 6 \| 1 \| 1.021254113 \|\| IFIH1 \| 3.13.47 \| interferon induced, with helicase C domain 1 \| 2 \| 0.556663679 \|\| IFIT1 \| 3.13.47 \| interferon induced protein with tetratricopeptide repeats 1 \| 10 \| 2.221831622 \|\| IFIT5 \| 3.13.47 \| interferon induced protein with tetratricopeptide repeats 5 \| 10 \| 0.525041166 \|\| IFITM3 \| 3.13.47 \| interferon induced transmembrane protein 3 \| 11 \| 0.260199866 \|\| ISG15 \| 3.13.47 \| ISG15 ubiquitin-like modifier \| 1 \| 0.394697557 \|\| JPX \| 3.13.47 \| JPX transcript, XIST activator (non-protein coding) \| X \| 0.060446091 \|\| JUP \| 3.13.47 \| junction plakoglobin \| 17 \| 0.189705459 \|\| KIAA1958 \| 3.13.47 \| KIAA1958 \| 9 \| 0.089306884 \|\| KLHDC7B \| 3.13.47 \| kelch domain containing 7B \| 22 \| 0.133737632 \|\| LAMP3 \| 3.13.47 \| lysosomal associated membrane protein 3 \| 3 \| 0.387852736 \|\| LGALS3BP \| 3.13.47 \| lectin, galactoside-binding, soluble, 3 binding protein \| 17 \| 0.301744028 \|\| LINC00487 \| 3.13.47 \| long intergenic non-protein coding RNA 487 \| 2 \| 0.257986055 \|\| LOC101927027 \| 3.13.47 \| uncharacterized LOC101927027 \| 2 \| 0.159489632 \|\| LOC101928227 \| 3.13.47 \| uncharacterized LOC101928227 \| 15 \| 0.081641209 \|\| LOC105373098 \| 3.13.47 \| uncharacterized LOC105373098 \| 22 \| 0.411587667 \|\| LOC729083 \| 3.13.47 \| uncharacterized LOC729083 \| 3 \| 0.062867231 \|\| MIR4308 \| 3.13.47 \| microRNA 4308 \| 14 \| 0.083320614 \|\| MOV10 \| 3.13.47 \| Mov10 RISC complex RNA helicase \| 1 \| 0.112182563 \|\| MT1F \| 3.13.47 \| metallothionein 1F \| 16 \| 0.178664891 \|\| MT1G \| 3.13.47 \| metallothionein 1G \| 16 \| 0.060784695 \|\| MT1H \| 3.13.47 \| metallothionein 1H \| 16 \| 0.102404175 \|\| MT1JP \| 3.13.47 \| metallothionein 1J, pseudogene \| 16 \| 0.256464075 \|\| MT1X \| 3.13.47 \| metallothionein 1X \| 16 \| 0.185195038 \|\| MT2A \| 3.13.47 \| metallothionein 2A \| 16 \| 0.328753513 \|\| MX1 \| 3.13.47 \| MX dynamin like GTPase 1 \| 21 \| 1.071562251 \|\| NUB1 \| 3.13.47 \| negative regulator of ubiquitin- |

TABLE 1C-continued

The genes within the significant gene clusters, listed in Table 1B. (2160 Genes Listed by: Gene Symbol | Module | Gene Description | Chromosome Number | Row Variance) ||)

like proteins 1 | 7 | 0.067576918 || OAS1 | 3.13.47 | 2'-5'-oligoadenylate synthetase 1 | 12 | 0.915871445 || OAS2 | 3.13.47 | 2'-5'-oligoadenylate synthetase 2 | 12 | 0.913005255 || OAS3 | 3.13.47 | 2'-5'-oligoadenylate synthetase 3 | 12 | 1.290342716 || OASL | 3.13.47 | 2'-5'-oligoadenylate synthetase like | 12 | 0.799654603 || OR52H1 | 3.13.47 | olfactory receptor family 52 subfamily H member 1 | 11 | 0.078483677 || OR52N4 | 3.13.47 | olfactory receptor family 52 subfamily N member 4 (gene/pseudogene) | 11 | 0.104972999 || OR56B1 | 3.13.47 | olfactory receptor family 56 subfamily B member 1 | 11 | 0.097773382 || OTOF | 3.13.47 | otoferlin | 2 | 0.16791902 || PARP11 | 3.13.47 | poly(ADP-ribose) polymerase family member 11 | 12 | 0.129115102 || PARP12 | 3.13.47 | poly(ADP-ribose) polymerase family member 12 | 7 | 0.369058306 || PGAP1 | 3.13.47 | post-GPI attachment to proteins 1 | 2 | 0.220884701 || PML | 3.13.47 | promyelocytic leukemia | 15 | 0.072759722 || PNPT1 | 3.13.47 | polyribonucleotide nucleotidyltransferase 1 | 2 | 0.316223651 || PPM1K | 3.13.47 | protein phosphatase, Mg2+/Mn2+ dependent 1K | 4 | 0.171529358| | PSTPIP2 | 3.13.47 | proline-serine-threonine phosphatase interacting protein 2 | 18 | 0.193440456 || RBM43 | 3.13.47 | RNA binding motif protein 43 | 2 | 0.100154697 || RNF213 | 3.13.47 | ring finger protein 213 | 17 | 0.169813818 || RSAD2 | 3.13.47 | radical S-adenosyl methionine domain containing 2 | 2 | 2.541036973 || RTP4 | 3.13.47 | receptor (chemosensory) transporter protein 4 | 3 | 0.799089791 || SAMD9 | 3.13.47 | sterile alpha motif domain containing 9 | 7 | 0.227554962 || SERPING1 | 3.13.47 | serpin peptidase inhibitor, clade G (C1 inhibitor), member 1 | 11 | 0.892846417 || SGMS2 | 3.13.47 | sphingomyelin synthase 2 | 4 | 0.13042374 || SIGLEC1 | 3.13.47 | sialic acid binding Ig like lectin 1 | 20 | 0.496544404 || SLFN12 | 3.13.47 | schlafen family member 12 | 17 | 0.187808839 || SP100 | 3.13.47 | SP100 nuclear antigen | 2 | 0.110446175 || SP140 | 3.13.47 | SP140 nuclear body protein | 2 | 0.181747485 || SPATS2L | 3.13.47 | spermatogenesis associated serine rich 2 like | 2 | 0.66682159 || SPIC | 3.13.47 | Spi-C transcription factor | 12 | 0.089210647 || SPTLC2 | 3.13.47 | serine palmitoyltransferase long chain base subunit 2 | 14 | 0.135070975 || SRGAP2 | 3.13.47 | SLIT-ROBO Rho GTPase activating protein 2 | 1 | 0.097253006 || STAT1 | 3.13.47 | signal transducer and activator of transcription 1 | 2 | 0.215234511 || TIMM10 | 3.13.47 | translocase of inner mitochondrial membrane 10 homolog (yeast) | 11 | 0.146886027 || TMEM123 | 3.13.47 | transmembrane protein 123 | 11 | 0.165562023 || TMEM255A | 3.13.47 | transmembrane protein 255A | X | 0.09741285 || TMEM62 | 3.13.47 | transmembrane protein 62 | 15 | 0.094418297 || TRIM14 | 3.13.47 | tripartite motif containing 14 | 9 | 0.108579071 || TRIM38 | 3.13.47 | tripartite motif containing 38 | 6 | 0.110180625 || TRIM5 | 3.13.47 | tripartite motif containing 5 | 11 | 0.207718288 || UBE2L6 | 3.13.47 | ubiquitin conjugating enzyme E2L 6 | 11 | 0.184224897 || UBQLNL | 3.13.47 | ubiquilin-like | 11 | 0.068580785 | USP17L15 | 3.13.47 | ubiquitin specific peptidase 17-like family member 15 | 4 | 0.08230898 || USP18 | 3.13.47 | ubiquitin specific peptidase 18 | 22 | 0.980232149 || XAF1 | 3.13.47 | XIAP associated factor 1 | 17 | 0.77655475 || XRN1 | 3.13.47 | 5'-3' exoribonuclease 1 | 3 | 0.068397432 || XXYLT1-AS2 | 3.13.47 | XXYLT1 antisense RNA 2 | 3 | 0.065520644 || ZCCHC2 | 3.13.47 | zinc finger CCHC-type containing 2 | 18 | 0.399452565 || BST2 | 3.13.47.149 | bone marrow stromal cell antigen 2 | 19 | 0.249135668 || CASP10 | 3.13.47.149 | caspase 10 | 2 | 0.069452079 || CMPK2 | 3.13.47.149 | cytidine/uridine monophosphate kinase 2 | 2 | 0.824835238 || DDX60 | 3.13.47.149 | DEXD/H-box helicase 60 | 4 | 0.982184993 || DRAP1 | 3.13.47.149 | DR1 associated protein 1 | 11 | 0.064515951 || EIF2AK2 | 3.13.47.149 | eukaryotic translation initiation factor 2 alpha kinase 2 | 2 | 0.535347673 || EPSTI1 | 3.13.47.149 | epithelial stromal interaction 1 (breast) | 13 | 1.14046733 || HERC5 | 3.13.47.149 | HECT and RLD domain containing E3 ubiquitin protein ligase 5 | 4 | 1.514107421 || IFI44 | 3.13.47.149 | interferon induced protein 44 | 1 | 2.08752131 || IFI44L | 3.13.47.149 | interferon induced protein 44 like | 1 | 3.33128148 || IFI6 | 3.13.47.149 | interferon, alpha-inducible protein 6 | 1 | 1.021254113 || IFIT1 | 3.13.47.149 | interferon induced protein with tetratricopeptide repeats 1 | 10 | 2.221831622 || IFIT5 | 3.13.47.149 | interferon induced protein with tetratricopeptide repeats 5 | 10 | 0.525041166 || IFITM3 | 3.13.47.149 | interferon induced transmembrane protein 3 | 11 | 0.260199866 || LINC00487 | 3.13.47.149 | long intergenic non-protein coding RNA 487 | 2 | 0.257986055 || LOC101927027 | 3.13.47.149 | uncharacterized LOC101927027 | 2 | 0.159489632 || MT1F | 3.13.47.149 | metallothionein 1F | 16 | 0.178664891 || MX1 | 3.13.47.149 | MX dynamin like GTPase 1 | 21 | 1.071562251 || OAS1 | 3.13.47.149 | 2'-5'-oligoadenylate synthetase 1 | 12 | 0.915871445 || OAS2 | 3.13.47.149 | 2'-5'-oligoadenylate synthetase 2 | 12 | 0.913005255 || OAS3 | 3.13.47.149 | 2'-5'-oligoadenylate synthetase 3 | 12 | 1.290342716 | OASL | 3.13.47.149 | 2'-5'-oligoadenylate synthetase like | 12 | 0.799654603 || PARP12 | 3.13.47.149 | poly(ADP-ribose) polymerase family member 12 | 7 | 0.369058306 || PPM1K | 3.13.47.149 | protein phosphatase, Mg2+/Mn2+ dependent 1K | 4 | 0.171529358 || RBM43 | 3.13.47.149 | RNA binding motif protein 43 | 2 | 0.100154697 || RNF213 | 3.13.47.149 | ring finger protein 213 | 17 | 0.169813818 || RSAD2 | 3.13.47.149 | radical S-adenosyl methionine domain containing 2 | 2 | 2.541036973 || SAMD9 | 3.13.47.149 | sterile alpha motif domain containing 9 | 7 | 0.227554962 || TMEM123 | 3.13.47.149 | transmembrane protein 123 | 11 | 0.165562023 || XAF1 | 3.13.47.149 | XIAP associated factor 1 | 17 | 0.77655475 || ZCCHC2 | 3.13.47.149 | zinc finger CCHC-type containing 2 | 18 | 0.399452565 || BISPR | 3.13.47.151 | BST2 interferon stimulated positive regulator (non-protein coding) | 19 | 0.199514412 || C4orf33 | 3.13.47.151 | chromosome 4 open reading frame 33 | 4 | 0.065930067 || CCR1 | 3.13.47.151 | chemokine (C-C motif) receptor 1 | 3 | 0.386068575 || DTX3L | 3.13.47.151 | deltex 3 like, E3 ubiquitin ligase | 3 | 0.183624016 || ETV7 | 3.13.47.151 | ETS variant 7 | 6 | 0.264390153 || GALM | 3.13.47.151 | galactose mutarotase (aldose 1-epimerase) | 2 | 0.192283376 || HNRNPLL | 3.13.47.151 | heterogeneous nuclear ribonucleoprotein L like | 2 | 0.063429633 || IFI35 | 3.13.47.151 | interferon induced protein 35 | 17 | 0.278146724 || IFIH1 | 3.13.47.151 | interferon induced, with helicase C domain 1 | 2 | 0.556663679 || JPX | 3.13.47.151 | JPX transcript, XIST activator (non-protein coding) | X | 0.060446091 || LOC105373098 | 3.13.47.151 | uncharacterized LOC105373098 | 22 | 0.411587667 || MOV10 | 3.13.47.151 | Mov10 RISC complex RNA helicase | 1 | 0.112182563 || MT1H | 3.13.47.151 | metallothionein 1H | 16 |

TABLE 1C-continued

The genes within the significant gene clusters, listed in Table 1B. (2160 Genes Listed by: Gene Symbol | Module | Gene Description | Chromosome Number | Row Variance) ||)

0.102404175 || MT1JP | 3.13.47.151 | metallothionein 1J, pseudogene | 16 | 0.256464075 || MT2A | 3.13.47.151 | metallothionein 2A | 16 | 0.328753513 || RTP4 | 3.13.47.151 | receptor (chemosensory) transporter protein 4 | 3 | 0.799089791 || SERPING1 | 3.13.47.151 | serpin peptidase inhibitor, clade G (C1 inhibitor), member 1 | 11 | 0.892846417 || SLFN12 | 3.13.47.151 | schlafen family member 12 | 17 | 0.187808839 || SP100 | 3.13.47.151 | SP100 nuclear antigen | 2 | 0.110446175 || STAT1 | 3.13.47.151 | signal transducer and activator of transcription 1 | 2 | 0.215234511 || TIMM10 | 3.13.47.151 | translocase of inner mitochondrial membrane 10 homolog (yeast) | 11 | 0.146886027 || TRIM38 | 3.13.47.151 | tripartite motif containing 38 | 6 | 0.110180625 || UBE2L6 | 3.13.47.151 | ubiquitin conjugating enzyme E2L 6 | 11 | 0.184224897 || ABCA1 | 3.13.48 | ATP binding cassette subfamily A member 1 | 9 | 0.280787966 || ABCG1 | 3.13.48 | ATP binding cassette subfamily G member 1 | 21 | 0.096418286 || ADAR | 3.13.48 | adenosine deaminase, RNA-specific | 1 | 0.094800923 || CHMP5 | 3.13.48 | charged multivesicular body protein 5 | 9 | 0.142760433 || DDX58 | 3.13.48 | DEXD/H-box helicase 58 | 9 | 0.432370376 || DDX60L | 3.13.48 | DEAD-box helicase 60-like | 4 | 0.374118058 || GPD2 | 3.13.48 | glycerol-3-phosphate dehydrogenase 2 | 2 | 0.078830696 || GTPBP2 | 3.13.48 | GTP binding protein 2 | 6 | 0.074537978 || HSH2D | 3.13.48 | hematopoietic SH2 domain containing | 19 | 0.10941954 || IFIT2 | 3.13.48 | interferon induced protein with tetratricopeptide repeats 2 | 10 | 0.584812453 || IFIT3 | 3.13.48 | interferon induced protein with tetratricopeptide repeats 3 | 10 | 1.022684807 || IFITM1 | 3.13.48 | interferon induced transmembrane protein 1 | 11 | 0.168864948 || IRF9 | 3.13.48 | interferon regulatory factor 9 | 14 | 0.096743797 || LAP3 | 3.13.48 | leucine aminopeptidase 3 | 4 | 0.462740011 || LGALS9 | 3.13.48 | lectin, galactoside-binding, soluble, 9 | 17 | 0.152901042 || MX2 | 3.13.48 | MX dynamin like GTPase 2 | 21 | 0.25750327 || OR52K1 | 3.13.48 | olfactory receptor family 52 subfamily K member 1 | 11 | 0.22937738 || OR52K2 | 3.13.48 | olfactory receptor family 52 subfamily K member 2 | 11 | 0.265437909 || PARP14 | 3.13.48 | poly(ADP-ribose) polymerase family member 14 | 3 | 0.339596295 || PARP9 | 3.13.48 | poly(ADP-ribose) polymerase family member 9 | 3 | 0.276675907 || PATL1 | 3.13.48 | protein associated with topoisomerase II homolog 1 (yeast) | 11 | 0.06765744 || PLSCR1 | 3.13.48 | phospholipid scramblase 1 | 3 | 0.516505035 || SAMD9L | 3.13.48 | sterile alpha motif domain containing 9-like | 7 | 0.413716083 || SHISA5 | 3.13.48 | shisa family member 5 | 3 | 0.090404805 || STAT2 | 3.13.48 | signal transducer and activator of transcription 2 | 12 | 0.275295047 || TDRD7 | 3.13.48 | tudor domain containing 7 | 9 | 0.205042782 || TOR1A | 3.13.48 | torsin family 1 member A | 9 | 0.077312382 || TOR1B | 3.13.48 | torsin family 1 member B | 9 | 0.188175646 || TRANK1 | 3.13.48 | tetratricopeptide repeat and ankyrin repeat containing 1 | 3 | 0.098079262 || TRIM22 | 3.13.48 | tripartite motif containing 22 | 11 | 0.288648851 || TRIM6 | 3.13.48 | tripartite motif containing 6 | 11 | 0.35451014 || TTC26 | 3.13.48 | tetratricopeptide repeat domain 26 | 7 | 0.184919169 || UNC93B1 | 3.13.48 | unc-93 homolog B1 (*C. elegans*) | 11 | 0.079143058 || ZBP1 | 3.13.48 | Z-DNA binding protein 1 | 20 | 0.280313422 || ZC3HAV1 | 3.13.48 | zinc finger CCCH-type containing, antiviral 1 | 7 | 0.083683811 || ZNF684 | 3.13.48 | zinc finger protein 684 | 1 | 0.161677841 || ZNFX1 | 3.13.48 | zinc finger, NFX1-type containing 1 | 20 | 0.079215166 || DDX58 | 3.13.48.155 | DEXD/H-box helicase 58 | 9 | 0.432370376 || DDX60L | 3.13.48.155 | DEAD-box helicase 60-like | 4 | 0.374118058 || HSH2D | 3.13.48.155 | hematopoietic SH2 domain containing | 19 | 0.10941954 || IFIT2 | 3.13.48.155 | interferon induced protein with tetratricopeptide repeats 2 | 10 | 0.584812453 || IFIT3 | 3.13.48.155 | interferon induced protein with tetratricopeptide repeats 3 | 10 | 1.022684807 || IFITM1 | 3.13.48.155 | interferon induced transmembrane protein 1 | 11 | 0.168864948 || IRF9 | 3.13.48.155 | interferon regulatory factor 9 | 14 | 0.096743797 || LAP3 | 3.13.48.155 | leucine aminopeptidase 3 | 4 | 0.462740011 || LGALS9 | 3.13.48.155 | lectin, galactoside-binding, soluble, 9 | 17 | 0.152901042 || MX2 | 3.13.48.155 | MX dynamin like GTPase 2 | 21 | 0.25750327 || OR52K1 | 3.13.48.155 | olfactory receptor family 52 subfamily K member 1 | 11 | 0.22937738 || OR52K2 | 3.13.48.155 | olfactory receptor family 52 subfamily K member 2 | 11 | 0.265437909 || PARP14 | 3.13.48.155 | poly(ADP-ribose) polymerase family member 14 | 3 | 0.339596295 || PARP9 | 3.13.48.155 | poly(ADP-ribose) polymerase family member 9 | 3 | 0.276675907 || PLSCR1 | 3.13.48.155 | phospholipid scramblase 1 | 3 | 0.516505035 || SAMD9L | 3.13.48.155 | sterile alpha motif domain containing 9-like | 7 | 0.413716083 || STAT2 | 3.13.48.155 | signal transducer and activator of transcription 2 | 12 | 0.275295047 || TRANK1 | 3.13.48.155 | tetratricopeptide repeat and ankyrin repeat containing 1 | 3 | 0.098079262 || TRIM22 | 3.13.48.155 | tripartite motif containing 22 | 11 | 0.288648851 || UNC93B1 | 3.13.48.155 | unc-93 homolog B1 (*C. elegans*) | 11 | 0.079143058 || ZBP1 | 3.13.48.155 | Z-DNA binding protein 1 | 20 | 0.280313422 || BLZF1 | 3.13.49 | basic leucine zipper nuclear factor 1 | 1 | 0.09034512 || C1GALT1 | 3.13.49 | core 1 synthase, glycoprotein-N-acetylgalactosamine 3-beta-galactosyltransferase 1 | 7 | 0.077899596 || CARD16 | 3.13.49 | caspase recruitment domain family member 16 | 11 | 0.169897426 || CARD17 | 3.13.49 | caspase recruitment domain family member 17 | 11 | 0.642161107 || CASP1 | 3.13.49 | caspase 1 | 11 | 0.136091591 || CLEC4A | 3.13.49 | C-type lectin domain family 4 member A | 12 | 0.137977448 || CXorf21 | 3.13.49 | chromosome X open reading frame 21 | X | 0.120124444 || CYSLTR1 | 3.13.49 | cysteinyl leukotriene receptor 1 | X | 0.181630807 || DAPP1 | 3.13.49 | dual adaptor of phosphotyrosine and 3-phosphoinositides | 4 | 0.101139222 || FCGR2B | 3.13.49 | Fc fragment of IgG receptor IIb | 1 | 0.220151261 || GADD45B | 3.13.49 | growth arrest and DNA damage inducible beta | 19 | 0.082827584 || GAPT | 3.13.49 | GRB2-binding adaptor protein, transmembrane | 5 | 0.152724923 || GLRX | 3.13.49 | glutaredoxin | 5 | 0.084109584 | IFI16 | 3.13.49 | interferon, gamma-inducible protein 16 | 1 | 0.152819724 || IL1RN | 3.13.49 | interleukin 1 receptor antagonist | 2 | 0.198753741 || JAK2 | 3.13.49 | Janus kinase 2 | 9 | 0.099621131 || LINC00189 | 3.13.49 | long intergenic non-protein coding RNA 189 | 21 | 0.84175164 || LINC01410 | 3.13.49 | long intergenic non-protein coding RNA 1410 | 9 | 0.357527205 || MARCKS | 3.13.49 | myristoylated alanine rich protein kinase C substrate | 6 | 0.112396821 || MIR1303 | 3.13.49 | microRNA 1303 | 5 | 0.15252495 || MYD88 | 3.13.49 | myeloid differentiation primary response 88 | 3 | 0.066309453 || NBN | 3.13.49 | nibrin | 8 |

TABLE 1C-continued

| The genes within the significant gene clusters, listed in Table 1B. (2160 Genes Listed by: Gene Symbol \| Module \| Gene Description \| Chromosome Number \| Row Variance) \|\|) |
|---|
| 0.112474837 \|\| NMI \| 3.13.49 \| N-myc and STAT interactor \| 2 \| 0.148301216 \|\| NT5C3A \| 3.13.49 \| 5'-nucleotidase, cytosolic IIIA \| 7 \| 0.167934707 \|\| PMAIP1 \| 3.13.49 \| phorbol-12-myristate-13-acetate-induced protein 1 \| 18 \| 0.115237627 \|\| PTP4A1 \| 3.13.49 \| protein tyrosine phosphatase type IVA, member 1 \| 6 \| 0.103383806 \|\| SAT1 \| 3.13.49 \| spermidine/spermine N1-acetyltransferase 1 \| X \| 0.153450967 \|\| SESTD1 \| 3.13.49 \| SEC14 and spectrin domain containing 1 \| 2 \| 0.087439183 \|\| TMOD2 \| 3.13.49 \| tropomodulin 2 \| 15 \| 0.101086032 \|\| TNFSF10 \| 3.13.49 \| tumor necrosis factor superfamily member 10 \| 3 \| 0.133526449 \|\| TNFSF13B \| 3.13.49 \| tumor necrosis factor superfamily member 13b \| 13 \| 0.225821577 \|\| USP25 \| 3.13.49 \| ubiquitin specific peptidase 25 \| 21 \| 0.060588743 \|\| C1GALT1 \| 3.13.49.157 \| core 1 synthase, glycoprotein-N-acetylgalactosamine 3-beta-galactosyltransferase 1 \| 7 \| 0.077899596 \|\| CASP1 \| 3.13.49.157 \| caspase 1 \| 11 \| 0.136091591 \|\| CLEC4A \| 3.13.49.157 \| C-type lectin domain family 4 member A \| 12 \| 0.137977448 \|\| CXorf21 \| 3.13.49.157 \| chromosome X open reading frame 21 \| X \| 0.120124444 \|\| FCGR2B \| 3.13.49.157 \| Fc fragment of IgG receptor IIb \| 1 \| 0.220151261 \|\| GADD45B \| 3.13.49.157 \| growth arrest and DNA damage inducible beta \| 19 \| 0.082827584 \|\| IFI16 \| 3.13.49.157 \| interferon, gamma-inducible protein 16 \| 1 \| 0.152819724 \|\| ILIRN \| 3.13.49.157 \| interleukin 1 receptor antagonist \| 2 \| 0.198753741 \|\| JAK2 \| 3.13.49.157 \| Janus kinase 2 \| 9 \| 0.099621131 \|\| MARCKS \| 3.13.49.157 \| myristoylated alanine rich protein kinase C substrate \| 6 \| 0.112396821 \|\| MIR1303 \| 3.13.49.157 \| microRNA 1303 \| 5 \| 0.15252495 \|\| MYD88 \| 3.13.49.157 \| myeloid differentiation primary response 88 \| 3 \| 0.066309453 \|\| NMI \| 3.13.49.157 \| N-myc and STAT interactor \| 2 \| 0.148301216 \|\| NT5C3A \| 3.13.49.157 \| 5'-nucleotidase, cytosolic IIIA \| 7 \| 0.167934707 \|\| PTP4A1 \| 3.13.49.157 \| protein tyrosine phosphatase type IVA, member 1 \| 6 \| 0.103383806 \|\| SESTD1 \| 3.13.49.157 \| SEC14 and spectrin domain containing 1 \| 2 \| 0.087439183 \|\| TMOD2 \| 3.13.49.157 \| tropomodulin 2 \| 15 \| 0.101086032 \|\| TNFSF10 \| 3.13.49.157 \| tumor necrosis factor superfamily member 10 \| 3 \| 0.133526449 \|\| TNFSF13B \| 3.13.49.157 \| tumor necrosis factor superfamily member 13b \| 13 \| 0.225821577 \|\| USP25 \| 3.13.49.157 \| ubiquitin specific peptidase 25 \| 21 \| 0.060588743 \|\| ACOT9 \| 3.13.50 \| acyl-CoA thioesterase 9 \| X \| 0.130926287 \|\| AIM2 \| 3.13.50 \| absent in melanoma 2 \| 1 \| 0.332556929 \|\| APOL1 \| 3.13.50 \| apolipoprotein L1 \| 22 \| 0.131377313 \|\| APOL2 \| 3.13.50 \| apolipoprotein L2 \| 22 \| 0.110787938 \|\| CARD6 \| 3.13.50 \| caspase recruitment domain family member 6 \| 5 \| 0.093827632 \|\| CCDC146 \| 3.13.50 \| coiled-coil domain containing 146 \| 7 \| 0.181343816 \|\| CD274 \| 3.13.50 \| CD274 molecule \| 9 \| 0.48761392 \|\| CEACAMI \| 3.13.50 \| carcinoembryonic antigen related cell adhesion molecule 1 \| 19 \| 0.442833978 \|\| CNIH4 \| 3.13.50 \| cornichon family AMPA receptor auxiliary protein 4 \| 1 \| 0.071102476 \|\| DHRS9 \| 3.13.50 \| dehydrogenase/reductase (SDR family) member 9 \| 2 \| 0.398312062 \|\| DRAM1 \| 3.13.50 \| DNA damage regulated autophagy modulator 1 \| 12 \| 0.095352545 \|\| DYNLT1 \| 3.13.50 \| dynein light chain Tctex-type 1 \| 6 \| 0.088989236 \|\| FAM8A1 \| 3.13.50 \| family with sequence similarity 8 member A1 \| 6 \| 0.098112763 \|\| FAS \| 3.13.50 \| Fas cell surface death receptor \| 10 \| 0.092372163 \|\| FCGR1A \| 3.13.50 \| Fc fragment of IgG receptor Ia \| 1 \| 0.693994982 \|\| FCGR1B \| 3.13.50 \| Fc fragment of IgG receptor Ib \| 1 \| 0.376228514 \|\| FCGR1CP \| 3.13.50 \| Fc fragment of IgG receptor Ic, pseudogene \| 1 \| 0.365954727 \|\| FRMD3 \| 3.13.50 \| FERM domain containing 3 \| 9 \| 0.218337435 \|\| GBP2 \| 3.13.50 \| guanylate binding protein 2 \| 1 \| 0.142121847 \|\| GNB4 \| 3.13.50 \| G protein subunit beta 4 \| 3 \| 0.085977348 \|\| HIST1H2AD \| 3.13.50 \| histone cluster 1, H2ad \| 6 \| 0.076644285 \|\| HIST1H3D \| 3.13.50 \| histone cluster 1, H3d \| 6 \| 0.211857909 \|\| HIST1H4D \| 3.13.50 \| histone cluster 1, H4d \| 6 \| 0.178916334 \|\| HIST1H4K \| 3.13.50 \| histone cluster 1, H4k \| 6 \| 0.150572729 \|\| HIST2H2BE \| 3.13.50 \| histone cluster 2, H2be \| 1 \| 0.207293801 \|\| IRF1 \| 3.13.50 \| interferon regulatory factor 1 \| 5 \| 0.085758497 \|\| ITGA1 \| 3.13.50 \| integrin subunit alpha 1 \| 5 \| 0.231947269 \|\| LHFPL2 \| 3.13.50 \| lipoma HMGIC fusion partner-like 2 \| 5 \| 0.085246533 \|\| LINC00152 \| 3.13.50 \| long intergenic non-protein coding RNA 152 \| 2 \| 0.10477045 \|\| MILR1 \| 3.13.50 \| mast cell immunoglobulin-like receptor 1 \| 17 \| 0.209368701 \|\| PDCD1LG2 \| 3.13.50 \| programmed cell death 1 ligand 2 \| 9 \| 0.192749507 \|\| PIK3AP1 \| 3.13.50 \| phosphoinositide-3-kinase adaptor protein 1 \| 10 \| 0.114421116 \|\| POLB \| 3.13.50 \| polymerase (DNA) beta \| 8 \| 0.098072401 \|\| PRRG4 \| 3.13.50 \| proline rich Gla (G-carboxyglutamic acid) 4 (transmembrane) \| 11 \| 0.290888317 \|\| RLN1 \| 3.13.50 \| relaxin 1 \| 9 \| 0.07247648 \|\| SECTM1 \| 3.13.50 \| secreted and transmembrane 1 \| 17 \| 0.087561354 \|\| SORT1 \| 3.13.50 \| sortilin 1 \| 1 \| 0.141151129 \|\| SQRDL \| 3.13.50 \| sulfide quinone reductase-like (yeast) \| 15 \| 0.086035698 \|\| STX11 \| 3.13.50 \| syntaxin 11 \| 6 \| 0.115327192 \|\| TBC1D8 \| 3.13.50 \| TBC1 domain family member 8 \| 2 \| 0.079746068 \|\| TIFA \| 3.13.50 \| TRAF interacting protein with forkhead associated domain \| 4 \| 0.123147729 \|\| TMEM140 \| 3.13.50 \| transmembrane protein 140 \| 7 \| 0.1516408 \|\| TNFAIP6 \| 3.13.50 \| TNF alpha induced protein 6 \| 2 \| 0.699075024 \|\| TRAFD1 \| 3.13.50 \| TRAF-type zinc finger domain containing 1 \| 12 \| 0.124837438 \|\| TRIM21 \| 3.13.50 \| tripartite motif containing 21 \| 11 \| 0.097575871 \|\| ABCA13 \| 3.14.51 \| ATP binding cassette subfamily A member 13 \| 7 \| 0.803027202 \|\| AFF2 \| 3.14.51 \| AF4/FMR2 family member 2 \| X \| 0.097636907 \|\| ANKRD18A \| 3.14.51 \| ankyrin repeat domain 18A \| 9 \| 0.084715742 \|\| ATP8B4 \| 3.14.51 \| ATPase phospholipid transporting 8B4 (putative) \| 15 \| 0.23755396 \|\| BCL2L15 \| 3.14.51 \| BCL2 like 15 \| 1 \| 0.275210299 \|\| BPI \| 3.14.51 \| bactericidal/permeability-increasing protein \| 20 \| 1.331122227 \|\| C15orf65 \| 3.14.51 \| chromosome 15 open reading frame 65 \| 15 \| 0.064697416 \|\| CAMP \| 3.14.51 \| cathelicidin antimicrobial peptide \| 3 \| 0.548629162 \|\| CEACAM6 \| 3.14.51 \| carcinoembryonic antigen related cell adhesion molecule 6 \| 19 \| 0.53774798 \|\| CEACAM8 \| 3.14.51 \| carcinoembryonic antigen related cell adhesion molecule 8 \| 19 \| 2.112047574 \|\| CHIT1 \| 3.14.51 \| chitinase 1 \| 1 \| 0.109898082 \|\| CLEC5A \| 3.14.51 \| C-type lectin domain family 5 member A \| 7 \| 0.243859067 \|\| CPNE2 \| 3.14.51 \| copine 2 \| 16 \| 0.082499911 \|\| CRISP2 \| 3.14.51 \| cysteine rich secretory protein 2 \| 6 \| 0.060903729 \|\| CRISP3 \| 3.14.51 \| cysteine rich secretory protein 3 \| 6 \| 1.284808354 \|\| CTSG \| 3.14.51 \| cathepsin G \| 14 \| 0.197950857 \|\| DACH1 \| 3.14.51 \| dachshund family transcription factor 1 \| 13 \| 0.086362921 \|\| DEFA4 \| 3.14.51 \| defensin alpha 4 \| 8 \| 1.190364805 \|\| ERG \| 3.14.51 \| v-ets avian erythroblastosis virus E26 oncogene homolog \| 21 \| 0.090262958 \|\| GADD45A \| 3.14.51 \| growth arrest and DNA damage |

TABLE 1C-continued

The genes within the significant gene clusters, listed in Table 1B. (2160 Genes Listed by: Gene Symbol | Module | Gene Description | Chromosome Number | Row Variance) ||)

inducible alpha | 1 | 0.1223582 || GPR84 | 3.14.51 | G protein-coupled receptor 84 | 12 | 0.263899425 || HP | 3.14.51 | haptoglobin | 16 | 0.581383667 || HPR | 3.14.51 | haptoglobin-related protein | 16 | 0.079041071 || INHBA | 3.14.51 | inhibin beta A | 7 | 0.084741889 || KLF5 | 3.14.51 | Kruppel-like factor 5 (intestinal) | 13 | 0.071326452 || LCN2 | 3.14.51 | lipocalin 2 | 9 | 0.818936423 || LINC01268 | 3.14.51 | long intergenic non-protein coding RNA 1268 | 6 | 0.086484349 || LTF | 3.14.51 | lactotransferrin | 3 | 1.471607971 || MFN2 | 3.14.51 | mitofusin 2 | 1 | 0.068108719 || MIR4668 | 3.14.51 | microRNA 4668 | 9 | 0.137624139 || MIR4718 | 3.14.51 | microRNA 4718 | 16 | 0.124842591 || MMP8 | 3.14.51 | matrix metallopeptidase 8 | 11 | 2.421111052 || MPO | 3.14.51 | myeloperoxidase | 17 | 0.615765815 || MS4A3 | 3.14.51 | membrane spanning 4-domains A3 | 11 | 0.889639487 || MYB | 3.14.51 | MYB proto-oncogene, transcription factor | 6 | 0.08838385 || OLFM4 | 3.14.51 | olfactomedin 4 | 13 | 1.913928383 || OLR1 | 3.14.51 | oxidized low density lipoprotein receptor 1 | 12 | 0.856204515 || OR6N2 | 3.14.51 | olfactory receptor family 6 subfamily N member 2 | 1 | 0.127833473 || PGLYRP1 | 3.14.51 | peptidoglycan recognition protein 1 | 19 | 0.248486122 || PIWIL4 | 3.14.51 | piwi-like RNA-mediated gene silencing 4 | 11 | 0.112370452 || RETN | 3.14.51 | resistin | 19 | 0.123530799 || RNASE2 | 3.14.51 | ribonuclease A family member 2 | 14 | 0.564844938 || RNASE3 | 3.14.51 | ribonuclease A family member 3 | 14 | 0.628634238 || SCD | 3.14.51 | stearoyl-CoA desaturase (delta-9-desaturase) | 10 | 0.080399472 || SERPINB10 | 3.14.51 | serpin peptidase inhibitor, clade B (ovalbumin), member 10 | 18 | 0.664252129 || SLC2A5 | 3.14.51 | solute carrier family 2 member 5 | 1 | 0.063413634 || TCN1 | 3.14.51 | transcobalamin 1 | 11 | 0.74656629 || UGCG | 3.14.51 | UDP-glucose ceramide glucosyltransferase | 9 | 0.116554797 || WIPI1 | 3.14.51 | WD repeat domain, phosphoinositide interacting 1 | 17 | 0.111000565 || ZNF788 | 3.14.51 | zinc finger family member 788 | 19 | 0.060381132 || ANKRD34B | 3.14.53.174 | ankyrin repeat domain 34B | 5 | 0.068858145 || AP5B1 | 3.14.53.174 | adaptor related protein complex 5 beta 1 subunit | 11 | 0.086371426 || CD300A | 3.14.53.174 | CD300a molecule | 17 | 0.076379429 || ECE1 | 3.14.53.174 | endothelin converting enzyme 1 | 1 | 0.061687884 || GAB2 | 3.14.53.174 | GRB2 associated binding protein 2 | 11 | 0.131696371 || GABARAPL1 | 3.14.53.174 | GABA(A) receptor-associated protein like 1 | 12 | 0.09356559 || HIST1H1T | 3.14.53.174 | histone cluster 1, H1t | 6 | 0.149948639 || HLX | 3.14.53.174 | H2.0-like homeobox | 1 | 0.08014155 || ITPRIP | 3.14.53.174 | inositol 1,4,5-trisphosphate receptor interacting protein | 10 | 0.073707647 || LOC101928067 | 3.14.53.174 | uncharacterized LOC101928067 | 2 | 0.060796624 || LOC339874 | 3.14.53.174 | uncharacterized LOC339874 | 3 | 0.108776447 || LTB4R | 3.14.53.174 | leukotriene B4 receptor | 14 | 0.085772078 || MTMR3 | 3.14.53.174 | myotubularin related protein 3 | 22 | 0.079625368 || NOV | 3.14.53.174 | nephroblastoma overexpressed | 8 | 0.11817201 || NTNG2 | 3.14.53.174 | netrin G2 | 9 | 0.117742546 || OR2B6 | 3.14.53.174 | olfactory receptor family 2 subfamily B member 6 | 6 | 0.117588483 || PFKFB4 | 3.14.53.174 | 6-phosphofructo-2-kinase/fructose-2,6-biphosphatase 4 | 3 | 0.100822685 || RPH3A | 3.14.53.174 | rabphilin 3A | 12 | 0.069330912 || SLC22A15 | 3.14.53.174 | solute carrier family 22 member 15 | 1 | 0.178771706 || TMCC3 | 3.14.53.174 | transmembrane and coiled-coil domain family 3 | 12 | 0.16101712 || UBN1 | 3.14.53.174 | ubinuclein 1 | 16 | 0.094173506 || UCP2 | 3.14.53.174 | uncoupling protein 2 (mitochondrial, proton carrier) | 11 | 0.06776175 || ADCY10P1 | 3.14.57 | adenylate cyclase 10 (soluble) pseudogene 1 | 6 | 0.089003743 || ANKRD44-IT1 | 3.14.57 | ANKRD44 intronic transcript 1 | 2 | 0.141357063 || ASAP1-IT2 | 3.14.57 | ASAP1 intronic transcript 2 | 8 | 0.131351713 || C6orf163 | 3.14.57 | chromosome 6 open reading frame 163 | 6 | 0.075096655 || C6orf229 | 3.14.57 | chromosome 6 open reading frame 229 | 6 | 0.197848662 || CCNL1 | 3.14.57 | cyclin L1 | 3 | 0.081754224 || CLHC1 | 3.14.57 | clathrin heavy chain linker domain containing 1 | 2 | 0.12320083 || CLK4 | 3.14.57 | CDC like kinase 4 | 5 | 0.098566196 || CRIPAK | 3.14.57 | cysteine rich PAK1 inhibitor | 0.088489861 || CXorf65 | 3.14.57 | chromosome X open reading frame 65 | X | 0.082869575 || EBLN2 | 3.14.57 | endogenous Bornavirus-like nucleoprotein 2 | 3 | 0.104117182 || FAM13A-AS1 | 3.14.57 | FAM13A antisense RNA 1 | 4 | 0.138782991 || FAM21EP | 3.14.57 | family with sequence similarity 21, member A pseudogene | 10 | 0.0608402 || FAM74A1 | 3.14.57 | family with sequence similarity 74 member A1 | 9 | 0.159651669 || GPR52 | 3.14.57 | G protein-coupled receptor 52 | 1 | 0.082162276 || HERC3 | 3.14.57 | HECT and RLD domain containing E3 ubiquitin protein ligase 3 | 4 | 0.060446876 || LINC-PINT | 3.14.57 | long intergenic non-protein coding RNA, p53 induced transcript | 7 | 0.121828681 || LINC00243 | 3.14.57 | long intergenic non-protein coding RNA 243 | 6 | 0.061499473 || LINC00641 | 3.14.57 | long intergenic non-protein coding RNA 641 | 14 | 0.118753208 || LINC01138 | 3.14.57 | long intergenic non-protein coding RNA 1138 | 1 | 0.105902703 || LOC100132686 | 3.14.57 | uncharacterized LOC100132686 | 11 | 0.102554956 || LOC100506142 | 3.14.57 | uncharacterized LOC100506142 | 2 | 0.062250618 || MIR1200 | 3.14.57 | microRNA 1200 | 7 | 0.129543113 || MIR1254-1 | 3.14.57 | microRNA 1254-1 | 10 | 0.127187763 || MIR1271 | 3.14.57 | microRNA 1271 | 5 | 0.072694468 || MIR1273A | 3.14.57 | microRNA 1273a | 8 | 0.252230455 || MIR1284 | 3.14.57 | microRNA 1284 | 3 | 0.133104573 || MIR1285-1 | 3.14.57 | microRNA 1285-1 | 7 | 0.066366449 || MIR1285-2 | 3.14.57 | microRNA 1285-2 | 2 | 0.079958112 || MIR1537 | 3.14.57 | microRNA 1537 | 1 | 0.142571196 || MIR15A | 3.14.57 | microRNA 15a | | 0.214264656 || MIR16-1 | 3.14.57 | microRNA 16-1 | 13 | 0.198532765 || MIR29B1 | 3.14.57 | microRNA 29b-1 | | 0.178821153 || MIR30E | 3.14.57 | microRNA 30e | 1 | 0.097947336 || MIR3136 | 3.14.57 | microRNA 3136 | 3 | 0.072166684 || MIR3198-1 | 3.14.57 | microRNA 3198-1 | 22 | 0.106607604 || MIR3916 | 3.14.57 | microRNA 3916 | | 0.078419517 || MIR4295 | 3.14.57 | microRNA 4295 | 10 | 0.165094271 || MIR4480 | 3.14.57 | microRNA 4480 | 10 | 0.095741807 || MIR4482 | 3.14.57 | microRNA 4482 | 10 | 0.085107375 || MIR544A | 3.14.57 | microRNA 544a | 14 | 0.081366615 || MIR548A2 | 3.14.57 | microRNA 548a-2 | 6 | 0.1478763 || MIR548B | 3.14.57 | microRNA 548b | 6 | 0.070107407 || MIR548D1 | 3.14.57 | microRNA 548d-1 | 8 | 0.07909121 || MIR548J | 3.14.57 | microRNA 548j | 22 | 0.081267386 || MIR548L | 3.14.57 | microRNA 5481 | 11 | 0.159420176 || MIR555 | 3.14.57 | microRNA 555 | | 0.206637646 || MIR579 | 3.14.57 | microRNA 579 | 5 | 0.087226173 ||

TABLE 1C-continued

The genes within the significant gene clusters, listed in Table 1B. (2160 Genes Listed by: Gene Symbol | Module | Gene Description | Chromosome Number | Row Variance) ||)

MIR581 | 3.14.57 | microRNA 581 | 5 | 0.104668275 || MIR591 | 3.14.57 | microRNA 591 | 7 | 0.063222869 || MIR616 | 3.14.57 | microRNA 616 | 12 | 0.115386008 || MIR645 | 3.14.57 | microRNA 645 | 20 | 0.08293807 || MIR7-1 | 3.14.57 | microRNA 7-1 | | 0.151530339 || NLRP1 | 3.14.57 | NLR family, pyrin domain containing 1 | 17 | 0.065763606 || NUTM2B-AS1 | 3.14.57 | NUTM2B antisense RNA 1 | 10 | 0.133410015 || PILRB | 3.14.57 | paired immunoglobin-like type 2 receptor beta | 7 | 0.226102713 || PSMD6-AS2 | 3.14.57 | PSMD6 antisense RNA 2 | 3 | 0.16424075 || RBM5-AS1 | 3.14.57 | RBM5 antisense RNA 1 | 3 | 0.070834773 || RNU4-1 | 3.14.57 | RNA, U4 small nuclear 1 | 12 | 0.250743507 || RNU4-2 | 3.14.57 | RNA, U4 small nuclear 2 | 12 | 0.277476825 || RNU5B-1 | 3.14.57 | RNA, U5B small nuclear 1 | 15 | 0.079061867 || RNVU1-1 | 3.14.57 | RNA, variant U1 small nuclear 1 | 1 | 0.145063445 || RNVU1-14 | 3.14.57 | RNA, variant U1 small nuclear 14 | 1 | 0.129427097 || RNVU1-17 | 3.14.57 | RNA, variant U1 small nuclear 17 | 1 | 0.162797196 || RNVU1-19 | 3.14.57 | RNA, variant U1 small nuclear 19 | 1 | 0.185999462 || RNVU1-3 | 3.14.57 | RNA, variant U1 small nuclear 3 | 1 | 0.105910357 || RNVU1-4 | 3.14.57 | RNA, variant U1 small nuclear 4 | 1 | 0.24672702 || RNVU1-6 | 3.14.57 | RNA, variant U1 small nuclear 6 | 1 | 0.112649811 || RNY1 | 3.14.57 | RNA, Ro-associated Y1 | 7 | 0.454422816 || RSRP1 | 3.14.57 | arginine/serine-rich protein 1 | 1 | 0.106759097 || SEC61A2 | 3.14.57 | Sec61 translocon alpha 2 subunit | 10 | 0.076685721 || SND1-IT1 | 3.14.57 | SND1 intronic transcript 1 | 7 | 0.079900206 || SNORA1 | 3.14.57 | small nucleolar RNA, H/ACA box 1 | 11 | 0.195401158 || SNORA16B | 3.14.57 | small nucleolar RNA, H/ACA box 16B | 1 | 0.199437905 || SNORA25 | 3.14.57 | small nucleolar RNA, H/ACA box 25 | 11 | 0.120961895 || SNORA2B | 3.14.57 | small nucleolar RNA, H/ACA box 2B | 12 | 0.06268578 || SNORA32 | 3.14.57 | small nucleolar RNA, H/ACA box 32 | 11 | 0.286860768 || SNORA36B | 3.14.57 | small nucleolar RNA, H/ACA box 36B | 1 | 0.116725379 || SNORA46 | 3.14.57 | small nucleolar RNA, H/ACA box 46 | 16 | 0.073365375 || SNORA69 | 3.14.57 | small nucleolar RNA, H/ACA box 69 | X | 0.080465194 || SNORA70B | 3.14.57 | small nucleolar RNA, H/ACA box 70B | 2 | 0.106747913 || SNORD116-28 | 3.14.57 | small nucleolar RNA, C/D box 116-28 | 15 | 0.115734895 || SNORD12 | 3.14.57 | small nucleolar RNA, C/D box 12 | 20 | 0.251551343 || SNORD12B | 3.14.57 | small nucleolar RNA, C/D box 12B | 20 | 0.226502642 || SNORD12C | 3.14.57 | small nucleolar RNA, C/D box 12C | 20 | 0.359302136 || SNORD1A | 3.14.57 | small nucleolar RNA, C/D box 1A | 17 | 0.117850102 || SNORD1B | 3.14.57 | small nucleolar RNA, C/D box 1B | 17 | 0.096829405 || SNORD56B | 3.14.57 | small nucleolar RNA, C/D box 56B | 14 | 0.342799003 || SNORD6 | 3.14.57 | small nucleolar RNA, C/D box 6 | 11 | 0.09758294 || SPDYE6 | 3.14.57 | speedy/RINGO cell cycle regulator family member E6 | 7 | 0.074522549 || SUMO4 | 3.14.57 | small ubiquitin-like modifier 4 | 6 | 0.086801016 || TIAF1 | 3.14.57 | TGFB1-induced anti-apoptotic factor 1 | 17 | 0.070491633 || VAMP1 | 3.14.57 | vesicle associated membrane protein 1 | 12 | 0.065090049 || MIR3134 | 3.15 | microRNA 3134 | 3 | 0.262357295 || MIR4273 | 3.15 | microRNA 4273 | 3 | 0.082023607 || MIR4461 | 3.15 | microRNA 4461 | 5 | 0.384785516 || MIR548W | 3.15 | microRNA 548w | 16 | 0.081448894 || PRB2 | 3.15 | proline-rich protein BstNI subfamily 2 | 12 | 0.062937945 || RNU4ATAC | 3.15 | RNA, U4atac small nuclear (U12-dependent splicing) | 2 | 0.229964652 || RNU5A-1 | 3.15 | RNA, U5A small nuclear 1 | 15 | 0.19332283 || SCARNA10 | 3.15 | small Cajal body-specific RNA 10 | 12 | 0.199095056 || SCARNA12 | 3.15 | small Cajal body-specific RNA 12 | 12 | 0.083317521 || SCARNA18 | 3.15 | small Cajal body-specific RNA 18 | 5 | 0.063705844 || SCARNA7 | 3.15 | small Cajal body-specific RNA 7 | 3 | 0.098966615 || SNORA11 | 3.15 | small nucleolar RNA, H/ACA box 11 | X | 0.116578206 || SNORA12 | 3.15 | small nucleolar RNA, H/ACA box 12 | 10 | 0.150748956 || SNORA13 | 3.15 | small nucleolar RNA, H/ACA box 13 | 5 | 0.104843327 || SNORA18 | 3.15 | small nucleolar RNA, H/ACA box 18 | 11 | 0.113176731 || SNORA20 | 3.15 | small nucleolar RNA, H/ACA box 20 | 6 | 0.310703114 || SNORA21 | 3.15 | small nucleolar RNA, H/ACA box 21 | 17 | 0.102667124 || SNORA22 | 3.15 | small nucleolar RNA, H/ACA box 22 | 7 | 0.264474715 || SNORA23 | 3.15 | small nucleolar RNA, H/ACA box 23 | 11 | 0.187669714 || SNORA24 | 3.15 | small nucleolar RNA, H/ACA box 24 | 4 | 0.102786235 || SNORA27 | 3.15 | small nucleolar RNA, H/ACA box 27 | 13 | 0.145080189 || SNORA28 | 3.15 | small nucleolar RNA, H/ACA box 28 | 14 | 0.110257219 || SNORA2A | 3.15 | small nucleolar RNA, H/ACA box 2A | 12 | 0.131848147 || SNORA2C | 3.15 | small nucleolar RNA, H/ACA box 2C | 12 | 0.135620965 || SNORA37 | 3.15 | small nucleolar RNA, H/ACA box 37 | 18 | 0.09937653 || SNORA38B | 3.15 | small nucleolar RNA, H/ACA box 38B | 17 | 0.123013113 || SNORA3A | 3.15 | small nucleolar RNA, H/ACA box 3A | 11 | 0.082940861 || SNORA3B | 3.15 | small nucleolar RNA, H/ACA box 3B | 11 | 0.065974394 || SNORA48 | 3.15 | small nucleolar RNA, H/ACA box 48 | 17 | 0.06503531 || SNORA49 | 3.15 | small nucleolar RNA, H/ACA box 49 | 12 | 0.094544745 || SNORA5A | 3.15 | small nucleolar RNA, H/ACA box 5A | 7 | 0.090952373 || SNORA62 | 3.15 | small nucleolar RNA, H/ACA box 62 | 3 | 0.196367276 || SNORA63 | 3.15 | small nucleolar RNA, H/ACA box 63 | 3 | 0.144000651 || SNORA64 | 3.15 | small nucleolar RNA, H/ACA box 64 | 16 | 0.090968174 || SNORA67 | 3.15 | small nucleolar RNA, H/ACA box 67 | 17 | 0.101248263 || SNORA68 | 3.15 | small nucleolar RNA, H/ACA box 68 | 19 | 0.12343153 || SNORA70C | 3.15 | small nucleolar RNA, H/ACA box 70C | 9 | 0.074910506 || SNORA71A | 3.15 | small nucleolar RNA, H/ACA box 71A | 20 | 0.117083003 || SNORA72 | 3.15 | small nucleolar RNA, H/ACA box 72 | 8 | 0.085924561 || SNORA73A | 3.15 | small nucleolar RNA, H/ACA box 73A | 1 | 0.09549443 || SNORA75 | 3.15 | small nucleolar RNA, H/ACA box 75 | 2 | 0.146338956 || SNORA7B | 3.15 | small nucleolar RNA, H/ACA box 7B | 3 | 0.128402481 || SNORA8 | 3.15 | small nucleolar RNA, H/ACA box 8 | 11 | 0.130210095 || SNORA9 | 3.15 | small nucleolar RNA, H/ACA box 9 | 7 | 0.149636803 || SNORD10 | 3.15 | small nucleolar RNA, C/D box 10 | 17 | 0.107047657 || SNORD100 | 3.15 | small nucleolar RNA, C/D box 100 | 6 | 0.377858398 || SNORD104 | 3.15 | small nucleolar RNA, C/D box 104 | 17 | 0.156609439 || SNORD105 | 3.15 | small nucleolar RNA, C/D box 105 | 19 | 0.073232886 || SNORD105B | 3.15 | small nucleolar RNA, C/D box 105B | 19 | 0.08319195 || SNORD11 | 3.15 | small nucleolar RNA, C/D box 11 | 2 | 0.197442685 || SNORD110 | 3.15 | small nucleolar RNA, C/D box 110 | 20 | 0.111009068 ||

TABLE 1C-continued

The genes within the significant gene clusters, listed in Table 1B. (2160 Genes Listed by: Gene Symbol | Module | Gene Description | Chromosome Number | Row Variance) ||)

SNORD115-7 | 3.15 | small nucleolar RNA, C/D box 115-7 | 15 | 0.075703688 || SNORD116-1 | 3.15 | small nucleolar RNA, C/D box 116-1 | 15 | 0.18989632 || SNORD116-12 | 3.15 | small nucleolar RNA, C/D box 116-12 | 15 | 0.06439302 || SNORD116-14 | 3.15 | small nucleolar RNA, C/D box 116-14 | 15 | 0.503356867 || SNORD116-15 | 3.15 | small nucleolar RNA, C/D box 116-15 | 15 | 0.428067636 || SNORD116-20 | 3.15 | small nucleolar RNA, C/D box 116-20 | 15 | 0.477329822 || SNORD116-23 | 3.15 | small nucleolar RNA, C/D box 116-23 | 15 | 0.13717486 || SNORD116-24 | 3.15 | small nucleolar RNA, C/D box 116-24 | 15 | 0.189680087 || SNORD116-26 | 3.15 | small nucleolar RNA, C/D box 116-26 | 15 | 0.129645369 || SNORD116-27 | 3.15 | small nucleolar RNA, C/D box 116-27 | 15 | 0.098275053 || SNORD116-29 | 3.15 | small nucleolar RNA, C/D box 116-29 | 15 | 0.140693023 | SNORD116-30 | 3.15 | small nucleolar RNA, C/D box 116-30 | 15 | 0.071441182 || SNORD116-4 | 3.15 | small nucleolar RNA, C/D box 116-4 | 15 | 0.282792051 || SNORD116-6 | 3.15 | small nucleolar RNA, C/D box 116-6 | 15 | 0.224621856 || SNORD116-8 | 3.15 | small nucleolar RNA, C/D box 116-8 | 15 | 0.235098666 || SNORD11B | 3.15 | small nucleolar RNA, C/D box 11B | 2 | 0.098079685 || SNORD121A | 3.15 | small nucleolar RNA, C/D box 121A | 9 | 0.081038817 || SNORD14A | 3.15 | small nucleolar RNA, C/D box 14A | 11 | 0.191364401 || SNORD14B | 3.15 | small nucleolar RNA, C/D box 14B | 11 | 0.143167187 || SNORD14C | 3.15 | small nucleolar RNA, C/D box 14C | 11 | 0.138714949 || SNORD14D | 3.15 | small nucleolar RNA, C/D box 14D | 11 | 1.116987602 || SNORD15A | 3.15 | small nucleolar RNA, C/D box 15A | 11 | 0.09954858 || SNORD15B | 3.15 | small nucleolar RNA, C/D box 15B | 11 | 0.118263347 || SNORD16 | 3.15 | small nucleolar RNA, C/D box 16 | 15 | 0.15251029 || SNORD17 | 3.15 | small nucleolar RNA, C/D box 17 | 20 | 0.080678301 || SNORD18A | 3.15 | small nucleolar RNA, C/D box 18A | 15 | 0.21083031 || SNORD1C | 3.15 | small nucleolar RNA, C/D box 1C | 17 | 0.096193961 || SNORD20 | 3.15 | small nucleolar RNA, C/D box 20 | 2 | 0.118912085 || SNORD22 | 3.15 | small nucleolar RNA, C/D box 22 | 11 | 0.173900806 || SNORD26 | 3.15 | small nucleolar RNA, C/D box 26 | 11 | 0.111250466 || SNORD27 | 3.15 | small nucleolar RNA, C/D box 27 | 11 | 0.285067464 || SNORD28 | 3.15 | small nucleolar RNA, C/D box 28 | 11 | 0.123511241 || SNORD30 | 3.15 | small nucleolar RNA, C/D box 30 | 11 | 0.171283763 || SNORD32A | 3.15 | small nucleolar RNA, C/D box 32A | 19 | 0.074029418 || SNORD34 | 3.15 | small nucleolar RNA, C/D box 34 | 19 | 0.149162269 || SNORD35A | 3.15 | small nucleolar RNA, C/D box 35A | 19 | 0.218012279 || SNORD36B | 3.15 | small nucleolar RNA, C/D box 36B | 9 | 0.261771279 || SNORD37 | 3.15 | small nucleolar RNA, C/D box 37 | 19 | 0.090849105 || SNORD38A | 3.15 | small nucleolar RNA, C/D box 38A | 1 | 0.195326681 || SNORD41 | 3.15 | small nucleolar RNA, C/D box 41 | 19 | 0.14443984 || SNORD42A | 3.15 | small nucleolar RNA, C/D box 42A | 17 | 0.163607197 || SNORD42B | 3.15 | small nucleolar RNA, C/D box 42B | 17 | 0.171351276 || SNORD45A | 3.15 | small nucleolar RNA, C/D box 45A | 1 | 0.220168302 || SNORD45B | 3.15 | small nucleolar RNA, C/D box 45B | 1 | 0.533601408 || SNORD46 | 3.15 | small nucleolar RNA, C/D box 46 | 1 | 0.12464111 || SNORD5 | 3.15 | small nucleolar RNA, C/D box 5 | 11 | 0.131110205 || SNORD50A | 3.15 | small nucleolar RNA, C/D box 50A | | 0.220173158 || SNORD51 | 3.15 | small nucleolar RNA, C/D box 51 | 2 | 0.080966294 || SNORD54 | 3.15 | small nucleolar RNA, C/D box 54 | 8 | 0.287039531 || SNORD55 | 3.15 | small nucleolar RNA, C/D box 55 | 1 | 0.140951409 || SNORD56 | 3.15 | small nucleolar RNA, C/D box 56 | 20 | 0.229186942 || SNORD57 | 3.15 | small nucleolar RNA, C/D box 57 | 20 | 0.108648299 || SNORD58A | 3.15 | small nucleolar RNA, C/D box 58A | 18 | 0.159550464 || SNORD59A | 3.15 | small nucleolar RNA, C/D box 59A | 12 | 0.215999704 || SNORD61 | 3.15 | small nucleolar RNA, C/D box 61 | X | 0.180099007 || SNORD63 | 3.15 | small nucleolar RNA, C/D box 63 | 5 | 0.287701625 || SNORD65 | 3.15 | small nucleolar RNA, C/D box 65 | 17 | 0.250623848 || SNORD69 | 3.15 | small nucleolar RNA, C/D box 69 | 3 | 0.116108218 || SNORD70 | 3.15 | small nucleolar RNA, C/D box 70 | 2 | 0.169741416 || SNORD71 | 3.15 | small nucleolar RNA, C/D box 71 | 16 | 0.159439686 || SNORD8 | 3.15 | small nucleolar RNA, C/D box 8 | 14 | 0.118625632 || SNORD82 | 3.15 | small nucleolar RNA, C/D box 82 | 2 | 0.498417514 || SNORD83B | 3.15 | small nucleolar RNA, C/D box 83B | 22 | 0.070643199 || SNORD87 | 3.15 | small nucleolar RNA, C/D box 87 | 8 | 0.106329374 || SNORD9 | 3.15 | small nucleolar RNA, C/D box 9 | 14 | 0.13643635 || SNORD90 | 3.15 | small nucleolar RNA, C/D box 90 | 9 | 0.155986698 || SNORD91B | 3.15 | small nucleolar RNA, C/D box 91B | 17 | 0.156502577 || SNORD92 | 3.15 | small nucleolar RNA, C/D box 92 | 2 | 0.111422554 || SNORD93 | 3.15 | small nucleolar RNA, C/D box 93 | 7 | 0.152827474 || SNORD94 | 3.15 | small nucleolar RNA, C/D box 94 | 2 | 0.085512128 || SNORD95 | 3.15 | small nucleolar RNA, C/D box 95 | 5 | 0.084310725 || SNORD96A | 3.15 | small nucleolar RNA, C/D box 96A | 5 | 0.075729715 || SNORD97 | 3.15 | small nucleolar RNA, C/D box 97 | 11 | 0.14871429 || SNORD99 | 3.15 | small nucleolar RNA, C/D box 99 | 1 | 0.093344814 || MIR3134 | 3.15.58 | microRNA 3134 | 3 | 0.262357295 || MIR4273 | 3.15.58 | microRNA 4273 | 3 | 0.082023607 || MIR4461 | 3.15.58 | microRNA 4461 | 5 | 0.384785516 || MIR548W | 3.15.58 | microRNA 548w | 16 | 0.081448894 || PRB2 | 3.15.58 | proline-rich protein BstNI subfamily 2 | 12 | 0.062937945 || RNU4ATAC | 3.15.58 | RNA, U4atac small nuclear (U12-dependent splicing) | 2 | 0.229964652 || SCARNA10 | 3.15.58 | small Cajal body-specific RNA 10 | 12 | 0.199095056 || SCARNA12 | 3.15.58 | small Cajal body-specific RNA 12 | 12 | 0.083317521 || SNORA20 | 3.15.58 | small nucleolar RNA, H/ACA box 20 | 6 | 0.310703114 || SNORA62 | 3.15.58 | small nucleolar RNA, H/ACA box 62 | 3 | 0.196367276 || SNORA63 | 3.15.58 | small nucleolar RNA, H/ACA box 63 | 3 | 0.144000651 || || SNORA68 | 3.15.58 | small nucleolar RNA, H/ACA box 68 | 19 | 0.12343153 | SNORA75 | 3.15.58 | small nucleolar RNA, H/ACA box 75 | 2 | 0.146338956 || SNORD10 | 3.15.58 | small nucleolar RNA, C/D box 10 | 17 | 0.107047657 || SNORD105 | 3.15.58 | small nucleolar RNA, C/D box 105 | 19 | 0.073232886 || SNORD105B | 3.15.58 | small nucleolar RNA, C/D box 105B | 19 | 0.08319195 || SNORD115-7 | 3.15.58 | small nucleolar RNA, C/D box 115-7 | 15 | 0.075703688 || SNORD116-1 | 3.15.58 | small nucleolar RNA, C/D box 116-1 | 15 | 0.18989632 || SNORD116-12 | 3.15.58 | small nucleolar RNA, C/D box 116-12 | 15 | 0.06439302 || SNORD116-14 | 3.15.58 | small nucleolar RNA, C/D box 116-14 | 15 | 0.503356867 ||

TABLE 1C-continued

The genes within the significant gene clusters, listed in Table 1B. (2160 Genes Listed by: Gene Symbol | Module | Gene Description | Chromosome Number | Row Variance) ||)

SNORD116-15 | 3.15.58 | small nucleolar RNA, C/D box 116-15 | 15 | 0.428067636 || SNORD116-20 | 3.15.58 | small nucleolar RNA, C/D box 116-20 | 15 | 0.477329822 || SNORD116-23 | 3.15.58 | small nucleolar RNA, C/D box 116-23 | 15 | 0.13717486 || SNORD116-24 | 3.15.58 | small nucleolar RNA, C/D box 116-24 | 15 | 0.189680087 || SNORD116-26 | 3.15.58 | small nucleolar RNA, C/D box 116-26 | 15 | 0.129645369 || SNORD116-27 | 3.15.58 | small nucleolar RNA, C/D box 116-27 | 15 | 0.098275053 || SNORD116-29 | 3.15.58 | small nucleolar RNA, C/D box 116-29 | 15 | 0.140693023 || SNORD116-30 | 3.15.58 | small nucleolar RNA, C/D box 116-30 | 15 | 0.071441182 || SNORD116-4 | 3.15.58 | small nucleolar RNA, C/D box 116-4 | 15 | 0.282792051 || SNORD116-6 | 3.15.58 | small nucleolar RNA, C/D box 116-6 | 15 | 0.224621856 || SNORD116-8 | 3.15.58 | small nucleolar RNA, C/D box 116-8 | 15 | 0.235098666 || SNORD11B | 3.15.58 | small nucleolar RNA, C/D box 11B | 2 | 0.098079685 || SNORD121A | 3.15.58 | small nucleolar RNA, C/D box 121A | 9 | 0.081038817 || SNORD15A | 3.15.58 | small nucleolar RNA, C/D box 15A | 11 | 0.09954858 || SNORD15B | 3.15.58 | small nucleolar RNA, C/D box 15B | 11 | 0.118263347 || SNORD16 | 3.15.58 | small nucleolar RNA, C/D box 16 | 15 | 0.15251029 || SNORD20 | 3.15.58 | small nucleolar RNA, C/D box 20 | 2 | 0.118912085 || SNORD26 | 3.15.58 | small nucleolar RNA, C/D box 26 | 11 | 0.111250466 || SNORD27 | 3.15.58 | small nucleolar RNA, C/D box 27 | 11 | 0.285067464 || SNORD28 | 3.15.58 | small nucleolar RNA, C/D box 28 | 11 | 0.123511241 || SNORD30 | 3.15.58 | small nucleolar RNA, C/D box 30 | 11 | 0.171283763 || SNORD32A | 3.15.58 | small nucleolar RNA, C/D box 32A | 19 | 0.074029418 || SNORD36B | 3.15.58 | small nucleolar RNA, C/D box 36B | 9 | 0.261771279 || SNORD37 | 3.15.58 | small nucleolar RNA, C/D box 37 | 19 | 0.090849105 || SNORD42A | 3.15.58 | small nucleolar RNA, C/D box 42A | 17 | 0.163607197 || SNORD42B | 3.15.58 | small nucleolar RNA, C/D box 42B | 17 | 0.171351276 || SNORD45B | 3.15.58 | small nucleolar RNA, C/D box 45B | 1 | 0.533601408 || SNORD46 | 3.15.58 | small nucleolar RNA, C/D box 46 | 1 | 0.12464111 || SNORD5 | 3.15.58 | small nucleolar RNA, C/D box 5 | 11 | 0.131110205 || SNORD51 | 3.15.58 | small nucleolar RNA, C/D box 51 | 2 | 0.080966294 || SNORD54 | 3.15.58 | small nucleolar RNA, C/D box 54 8 | 0.287039531 || SNORD56 | 3.15.58 | small nucleolar RNA, C/D box 56 | 20 | 0.229186942 || SNORD58A | 3.15.58 | small nucleolar RNA, C/D box 58A | 18 | 0.159550464 || SNORD59A | 3.15.58 | small nucleolar RNA, C/D box 59A | 12 | 0.215999704 || SNORD61 | 3.15.58 | small nucleolar RNA, C/D box 61 | X | 0.180099007 || SNORD63 | 3.15.58 | small nucleolar RNA, C/D box 63 | 5 | 0.287701625 || SNORD65 | 3.15.58 | small nucleolar RNA, C/D box 65 | 17 | 0.250623848 || SNORD69 | 3.15.58 | small nucleolar RNA, C/D box 69 | 3 | 0.116108218 || SNORD70 | 3.15.58 | small nucleolar RNA, C/D box 70 | 2 | 0.169741416 || SNORD82 | 3.15.58 | small nucleolar RNA, C/D box 82 | 2 | 0.498417514 || SNORD87 | 3.15.58 | small nucleolar RNA, C/D box 87 | 8 | 0.106329374 || SNORD90 | 3.15.58 | small nucleolar RNA, C/D box 90 | 9 | 0.155986698 || SNORD96A | 3.15.58 | small nucleolar RNA, C/D box 96A | 5 | 0.075729715 || SNORD99 | 3.15.58 | small nucleolar RNA, C/D box 99 | 1 | 0.093344814 || MIR3134 | 3.15.58.190 | microRNA 3134 | 3 | 0.262357295 || MIR4273 | 3.15.58.190 || microRNA 4273 | 3 | 0.082023607 || MIR4461 | 3.15.58.190 | microRNA 4461 | 5 | 0.384785516 || MIR548W | 3.15.58.190 | microRNA 548w | 16 | 0.081448894 || PRB2 | 3.15.58.190 | proline-rich protein BstNI subfamily 2 | 12 | 0.062937945 || SNORD105 | 3.15.58.190 | small nucleolar RNA, C/D box 105 | 19 | 0.073232886 || SNORD105B | 3.15.58.190 | small nucleolar RNA, C/D box 105B | 19 | 0.08319195 || SNORD115-7 | 3.15.58.190 | small nucleolar RNA, C/D box 115-7 | 15 | 0.075703688 || SNORD116-1 | 3.15.58.190 | small nucleolar RNA, C/D box 116-1 | 15 | 0.18989632 || SNORD116-12 | 3.15.58.190 | small nucleolar RNA, C/D box 116-12 | 15 | 0.06439302 || SNORD116-14 | 3.15.58.190 | small nucleolar RNA, C/D box 116-14 | 15 | 0.503356867 || SNORD116-15 | 3.15.58.190 | small nucleolar RNA, C/D box 116-15 | 15 | 0.428067636 || SNORD116-20 | 3.15.58.190 | small nucleolar RNA, C/D box 116-20 | 15 | 0.477329822 || SNORD116-23 | 3.15.58.190 | small nucleolar RNA, C/D box 116-23 | 15 | 0.13717486 || SNORD116-24 | 3.15.58.190 | small nucleolar RNA, C/D box 116-24 | 15 | 0.189680087 || SNORD116-26 | 3.15.58.190 | small nucleolar RNA, C/D box 116-26 | 15 | 0.129645369 || SNORD116-27 | 3.15.58.190 | small nucleolar RNA, C/D box 116-27 | 15 | 0.098275053 || SNORD116-29 | 3.15.58.190 | small nucleolar RNA, C/D box 116-29 | 15 | 0.140693023 || SNORD116-30 | 3.15.58.190 | small nucleolar RNA, C/D box 116-30 | 15 | 0.071441182 || SNORD116-4 | 3.15.58.190 | small nucleolar RNA, C/D box 116-4 | 15 | 0.282792051 || SNORD116-6 | 3.15.58.190 | small nucleolar RNA, C/D box 116-6 | 15 | 0.224621856 || SNORD116-8 | 3.15.58.190 | small nucleolar RNA, C/D box 116-8 | 15 | 0.235098666 || SNORD20 | 3.15.58.190 | small nucleolar RNA, C/D box 20 | 2 | 0.118912085 || SNORD26 | 3.15.58.190 | small nucleolar RNA, C/D box 26 | 11 | 0.111250466 || SNORD28 | 3.15.58.190 | small nucleolar RNA, C/D box 28 | 11 | 0.123511241 || SNORD32A | 3.15.58.190 | small nucleolar RNA, C/D box 32A | 19 | 0.074029418 || SNORD37 | 3.15.58.190 | small nucleolar RNA, C/D box 37 | 19 | 0.090849105 || SNORD42A | 3.15.58.190 | small nucleolar RNA, C/D box 42A | 17 | 0.163607197 || SNORD42B | 3.15.58.190 | small nucleolar RNA, C/D box 42B | 17 | 0.171351276 || SNORD45B | 3.15.58.190 | small nucleolar RNA, C/D box 45B | 1 | 0.533601408 || SNORD5 | 3.15.58.190 | small nucleolar RNA, C/D box 5 | 11 | 0.131110205 || SNORD54 | 3.15.58.190 | small nucleolar RNA, C/D box 54 | 8 | 0.287039531 || SNORD58A | 3.15.58.190 | small nucleolar RNA, C/D box 58A | 18 | 0.159550464 || SNORD59A | 3.15.58.190 | small nucleolar RNA, C/D box 59A | 12 | 0.215999704 || SNORD61 | 3.15.58.190 | small nucleolar RNA, C/D box 61 | X | 0.180099007 || SNORD63 | 3.15.58.190 | small nucleolar RNA, C/D box 63 | 5 | 0.287701625 || SNORD70 | 3.15.58.190 | small nucleolar RNA, C/D box 70 | 2 | 0.169741416 || SNORD87 | 3.15.58.190 | small nucleolar RNA, C/D box 87 | 8 | 0.106329374 || SNORD99 | 3.15.58.190 | small nucleolar RNA, C/D box 99 | 1 | 0.093344814 || RNU4ATAC | 3.15.58.191 | RNA, U4atac small nuclear (U12-dependent splicing) | 2 | 0.229964652 || SCARNA10 | 3.15.58.191 | small Cajal body-specific RNA 10 | 12 | 0.199095056 || SCARNA12 | 3.15.58.191 | small Cajal body-specific RNA 12 | 12 | 0.083317521 || SNORA20 | 3.15.58.191 | small nucleolar RNA, H/ACA box 20 | 6 | 0.310703114 || SNORA62 |

TABLE 1C-continued

| The genes within the significant gene clusters, listed in Table 1B. (2160 Genes Listed by: Gene Symbol \| Module \| Gene Description \| Chromosome Number \| Row Variance) \|\|) |
|---|
| 3.15.58.191 \| small nucleolar RNA, H/ACA box 62 \| 3 \| 0.196367276 \|\| SNORA63 \| 3.15.58.191 \| small nucleolar RNA, H/ACA box 63 \| 3 \| 0.144000651 \|\| SNORA68 \| 3.15.58.191 \| small nucleolar RNA, H/ACA box 68 \| 19 \| 0.12343153 \|\| SNORA75 \| 3.15.58.191 \| small nucleolar RNA, H/ACA box 75 \| 2 \| 0.146338956 \|\| SNORD10 \| 3.15.58.191 \| small nucleolar RNA, C/D box 10 \| 17 \| 0.107047657 \|\| SNORD11B \| 3.15.58.191 \| small nucleolar RNA, C/D box 11B \| 2 \| 0.098079685 \|\| SNORD121A \| 3.15.58.191 \| small nucleolar RNA, C/D box 121A \| 9 \| 0.081038817 \|\| SNORD15A \| 3.15.58.191 \| small nucleolar RNA, C/D box 15A \| 11 \| 0.09954858 \|\| SNORD15B \| 3.15.58.191 \| small nucleolar RNA, C/D box 15B \| 11 \| 0.118263347 \|\| SNORD16 \| 3.15.58.191 \| small nucleolar RNA, C/D box 16 \| 15 \| 0.15251029 \|\| SNORD27 \| 3.15.58.191 \| small nucleolar RNA, C/D box 27 \| 11 \| 0.285067464 \|\| SNORD30 \| 3.15.58.191 \| small nucleolar RNA, C/D box 30 \| 11 \| 0.171283763 \|\| SNORD36B \| 3.15.58.191 \| small nucleolar RNA, C/D box 36B \| 9 \| 0.261771279 \|\| SNORD46 \| 3.15.58.191 \| small nucleolar RNA, C/D box 46 \| 1 \| 0.12464111 \|\| SNORD51 \| 3.15.58.191 \| small nucleolar RNA, C/D box 51 \| 2 \| 0.080966294 \|\| SNORD56 \| 3.15.58.191 \| small nucleolar RNA, C/D box 56 \| 20 \| 0.229186942 \|\| SNORD65 \| 3.15.58.191 \| small nucleolar RNA, C/D box 65 \| 17 \| 0.250623848 \|\| SNORD69 \| 3.15.58.191 \| small nucleolar RNA, C/D box 69 \| 3 \| 0.116108218 \|\| SNORD82 \| 3.15.58.191 \| small nucleolar RNA, C/D box 82 \| 2 \| 0.498417514 \|\| SNORD90 \| 3.15.58.191 \| small nucleolar RNA, C/D box 90 \| 9 \| 0.155986698 \|\| SNORD96A \| 3.15.58.191 \| small nucleolar RNA, C/D box 96A \| 5 \| 0.075729715 \|\| RNU5A-1 \| 3.15.59 \| RNA, U5A small nuclear 1 \| 15 \| 0.19332283 \|\| SCARNA18 \| 3.15.59 \| small Cajal body-specific RNA 18 \| 5 \| 0.063705844 \|\| SCARNA7 \| 3.15.59 \| small Cajal body-specific RNA 7 \| 3 \| 0.098966615 \|\| SNORA11 \| 3.15.59 \| small nucleolar RNA, H/ACA box 11 \| X \| 0.116578206 \|\| SNORA12 \| 3.15.59 \| small nucleolar RNA, H/ACA box 12 \| 10 \| 0.150748956 \|\| SNORA13 \| 3.15.59 \| small nucleolar RNA, H/ACA box 13 \| 5 \| 0.104843327 \|\| SNORA18 \| 3.15.59 \| small nucleolar RNA, H/ACA box 18 \| 11 \| 0.113176731 \|\| SNORA21 \| 3.15.59 \| small nucleolar RNA, H/ACA box 21 \| 17 \| 0.102667124 \|\| SNORA22 \| 3.15.59 \| small nucleolar RNA, H/ACA box 22 \| 7 \| 0.264474715 \|\| SNORA23 \| 3.15.59 \| small nucleolar RNA, H/ACA box 23 \| 11 \| 0.187669714 \|\| SNORA24 \| 3.15.59 \| small nucleolar RNA, H/ACA box 24 \| 4 \| 0.102786235 \|\| SNORA27 \| 3.15.59 \| small nucleolar RNA, H/ACA box 27 \| 13 \| 0.145080189 \|\| SNORA28 \| 3.15.59 \| small nucleolar RNA, H/ACA box 28 \| 14 \| 0.110257219 \|\| SNORA2A \| 3.15.59 \| small nucleolar RNA, H/ACA box 2A \| 12 \| 0.131848147 \|\| SNORA2C \| 3.15.59 \| small nucleolar RNA, H/ACA box 2C \| 12 \| 0.135620965 \|\| SNORA37 \| 3.15.59 \| small nucleolar RNA, H/ACA box 37 \| 18 \| 0.09937653 \|\| SNORA38B \| 3.15.59 \| small nucleolar RNA, H/ACA box 38B \| 17 \| 0.123013113 \|\| SNORA3A \| 3.15.59 \| small nucleolar RNA, H/ACA box 3A \| 11 \| 0.082940861 \|\| SNORA3B \| 3.15.59 \| small nucleolar RNA, H/ACA box 3B \| 11 \| 0.065974394 \|\| SNORA48 \| 3.15.59 \| small nucleolar RNA, H/ACA box 48 \| 17 \| 0.06503531 \|\| SNORA49 \| 3.15.59 \| small nucleolar RNA, H/ACA box 49 \| 12 \| 0.094544745 \|\| SNORA5A \| 3.15.59 \| small nucleolar RNA, H/ACA box 5A \| 7 \| 0.090952373 \|\| SNORA64 \| 3.15.59 \| small nucleolar RNA, H/ACA box 64 \| 16 \| 0.090968174 \|\| SNORA67 \| 3.15.59 \| small nucleolar RNA, H/ACA box 67 \| 17 \| 0.101248263 \|\| SNORA70C \| 3.15.59 \| small nucleolar RNA, H/ACA box 70C \| 9 \| 0.074910506 \|\| SNORA71A \| 3.15.59 \| small nucleolar RNA, H/ACA box 71A \| 20 \| 0.117083003 \|\| SNORA72 \| 3.15.59 \| small nucleolar RNA, H/ACA box 72 \| 8 \| 0.085924561 \|\| SNORA73A \| 3.15.59 \| small nucleolar RNA, H/ACA box 73A \| 1 \| 0.09549443 \|\| SNORA7B \| 3.15.59 \| small nucleolar RNA, H/ACA box 7B \| 3 \| 0.128402481 \|\| SNORA8 \| 3.15.59 \| small nucleolar RNA, H/ACA box 8 \| 11 \| 0.130210095 \|\| SNORA9 \| 3.15.59 \| small nucleolar RNA, H/ACA box 9 \| 7 \| 0.149636803 \|\| SNORD100 \| 3.15.59 \| small nucleolar RNA, C/D box 100 \| 6 \| 0.377858398 \|\| SNORD104 \| 3.15.59 \| small nucleolar RNA, C/D box 104 \| 17 \| 0.156609439 \|\| SNORD11 \| 3.15.59 \| small nucleolar RNA, C/D box 11 \| 2 \| 0.197442685 \|\| SNORD110 \| 3.15.59 \| small nucleolar RNA, C/D box 110 \| 20 \| 0.111009068 \|\| SNORD14A \| 3.15.59 \| small nucleolar RNA, C/D box 14A \| 11 \| 0.191364401 \|\| SNORD14B \| 3.15.59 \| small nucleolar RNA, C/D box 14B \| 11 \| 0.143167187 \|\| SNORD14C \| 3.15.59 \| small nucleolar RNA, C/D box 14C \| 11 \| 0.138714949 \|\| SNORD14D \| 3.15.59 \| small nucleolar RNA, C/D box 14D \| 11 \| 1.116987602 \|\| SNORD17 \| 3.15.59 \| small nucleolar RNA, C/D box 17 \| 20 \| 0.080678301 \|\| SNORD18A \| 3.15.59 \| small nucleolar RNA, C/D box 18A \| 15 \| 0.21083031 \|\| SNORD1C \| 3.15.59 \| small nucleolar RNA, C/D box 1C \| 17 \| 0.096193961 \|\| SNORD22 \| 3.15.59 \| small nucleolar RNA, C/D box 22 \| 11 \| 0.173900806 \|\| SNORD34 \| 3.15.59 \| small nucleolar RNA, C/D box 34 \| 19 \| 0.149162269 \|\| SNORD35A \| 3.15.59 \| small nucleolar RNA, C/D box 35A \| 19 \| 0.218012279 \|\| SNORD38A \| 3.15.59 \| small nucleolar RNA, C/D box 38A \| 1 \| 0.195326681 \|\| SNORD41 \| 3.15.59 \| small nucleolar RNA, C/D box 41 \| 19 \| 0.14443984 \|\| SNORD45A \| 3.15.59 \| small nucleolar RNA, C/D box 45A \| 1 \| 0.220168302 \|\| SNORD50A \| 3.15.59 \| small nucleolar RNA, C/D box 50A \| \| 0.220173158 \|\| SNORD55 \| 3.15.59 \| small nucleolar RNA, C/D box 55 \| 1 \| 0.140951409 \|\| SNORD57 \| 3.15.59 \| small nucleolar RNA, C/D box 57 \| 20 \| 0.108648299 \|\| SNORD71 \| 3.15.59 \| small nucleolar RNA, C/D box 71 \| 16 \| 0.159439686 \|\| SNORD8 \| 3.15.59 \| small nucleolar RNA, C/D box 8 \| 14 \| 0.118625632 \|\| SNORD83B \| 3.15.59 \| small nucleolar RNA, C/D box 83B \| 22 \| 0.070643199 \|\| SNORD9 \| 3.15.59 \| small nucleolar RNA, C/D box 9 \| 14 \| 0.13643635 \|\| SNORD91B \| 3.15.59 \| small nucleolar RNA, C/D box 91B \| 17 \| 0.156502577 \|\| SNORD92 \| 3.15.59 \| small nucleolar RNA, C/D box 92 \| 2 \| 0.111422554 \|\| SNORD93 \| 3.15.59 \| small nucleolar RNA, C/D box 93 \| 7 \| 0.152827474 \|\| SNORD94 \| 3.15.59 \| small nucleolar RNA, C/D box 94 \| 2 \| 0.085512128 \|\| SNORD95 \| 3.15.59 \| small nucleolar RNA, C/D box 95 \| 5 \| 0.084310725 \|\| SNORD97 \| 3.15.59 \| small nucleolar RNA, C/D box 97 \| 11 \| 0.14871429 \|\| RNU5A-1 \| 3.15.59.192 \| RNA, U5A small nuclear 1 \| 15 \| 0.19332283 \|\| SCARNA18 \| 3.15.59.192 \| small Cajal body-specific RNA 18 \| 5 \| 0.063705844 \|\| SCARNA7 \| 3.15.59.192 \| small Cajal body-specific RNA 7 \| 3 \| 0.098966615 \|\| SNORA12 \| 3.15.59.192 \| small nucleolar RNA, H/ACA box 12 \| 10 \| 0.150748956 \|\| SNORA13 \| 3.15.59.192 \| small nucleolar RNA, H/ACA box 13 \| 5 \| 0.104843327 \|\| SNORA18 \| 3.15.59.192 \| small nucleolar RNA, H/ACA box 18 \| 11 \| 0.113176731 \|\| SNORA21 \| 3.15.59.192 \| small nucleolar RNA, H/ACA box 21 \| 17 \| 0.102667124 \|\| SNORA22 \| 3.15.59.192 \| small nucleolar RNA, H/ACA box 22 \| 7 \| |

TABLE 1C-continued

The genes within the significant gene clusters, listed in Table 1B. (2160 Genes Listed by: Gene Symbol | Module | Gene Description | Chromosome Number | Row Variance) ||)

0.264474715 || SNORA23 | 3.15.59.192 | small nucleolar RNA, H/ACA box 23 | 11 | 0.187669714 || SNORA24 | 3.15.59.192 | small nucleolar RNA, H/ACA box 24 | 4 | 0.102786235 || SNORA27 | 3.15.59.192 | small nucleolar RNA, H/ACA box 27 | 13 | 0.145080189 || SNORA28 | 3.15.59.192 | small nucleolar RNA, H/ACA box 28 | 14 | 0.110257219 || SNORA2A | 3.15.59.192 | small nucleolar RNA, H/ACA box 2A | 12 | 0.131848147 || SNORA2C | 3.15.59.192 | small nucleolar RNA, H/ACA box 2C | 12 | 0.135620965 || SNORA37 | 3.15.59.192 | small nucleolar RNA, H/ACA box 37 | 18 | 0.09937653 || SNORA3A | 3.15.59.192 | small nucleolar RNA, H/ACA box 3A | 11 | 0.082940861 || SNORA3B | 3.15.59.192 | small nucleolar RNA, H/ACA box 3B | 11 | 0.065974394 || SNORA48 | 3.15.59.192 | small nucleolar RNA, H/ACA box 48 | 17 | 0.06503531 || SNORA49 | 3.15.59.192 | small nucleolar RNA, H/ACA box 49 | 12 | 0.094544745 || SNORA67 | 3.15.59.192 | small nucleolar RNA, H/ACA box 67 | 17 | 0.101248263 || SNORA70C | 3.15.59.192 | small nucleolar RNA, H/ACA box 70C | 9 | 0.074910506 || SNORA71A | 3.15.59.192 | small nucleolar RNA, H/ACA box 71A | 20 | 0.117083003 || SNORA72 | 3.15.59.192 | small nucleolar RNA, H/ACA box 72 | 8 | 0.085924561 || SNORA73A | 3.15.59.192 | small nucleolar RNA, H/ACA box 73A | 1 | 0.09549443 || SNORA9 | 3.15.59.192 | small nucleolar RNA, H/ACA box 9 | 7 | 0.149636803 || SNORA11 | 3.15.59.193 | small nucleolar RNA, H/ACA box 11 | X | 0.116578206 || SNORA38B | 3.15.59.193 | small nucleolar RNA, H/ACA box 38B | 17 | 0.123013113 || SNORA5A | 3.15.59.193 | small nucleolar RNA, H/ACA box 5A | 7 | 0.090952373 || SNORA64 | 3.15.59.193 | small nucleolar RNA, H/ACA box 64 | 16 | 0.090968174 || SNORA7B | 3.15.59.193 | small nucleolar RNA, H/ACA box 7B | 3 | 0.128402481 || SNORA8 | 3.15.59.193 | small nucleolar RNA, H/ACA box 8 | 11 | 0.130210095 || SNORD100 | 3.15.59.193 | small nucleolar RNA, C/D box 100 | 6 | 0.377858398 || SNORD104 | 3.15.59.193 | small nucleolar RNA, C/D box 104 | 17 | 0.156609439 || SNORD11 | 3.15.59.193 | small nucleolar RNA, C/D box 11 | 2 | 0.197442685 || SNORD110 | 3.15.59.193 | small nucleolar RNA, C/D box 110 | 20 | 0.111009068 || SNORD14A | 3.15.59.193 | small nucleolar RNA, C/D box 14A | 11 | 0.191364401 || SNORD14B | 3.15.59.193 | small nucleolar RNA, C/D box 14B | 11 | 0.143167187 || SNORD14C | 3.15.59.193 | small nucleolar RNA, C/D box 14C | 11 | 0.138714949 || SNORD14D | 3.15.59.193 | small nucleolar RNA, C/D box 14D | 11 | 1.116987602 || SNORD17 | 3.15.59.193 | small nucleolar RNA, C/D box 17 | 20 | 0.080678301 || SNORD18A | 3.15.59.193 | small nucleolar RNA, C/D box 18A | 15 | 0.21083031 || SNORD1C | 3.15.59.193 | small nucleolar RNA, C/D box 1C | 17 | 0.096193961 || SNORD22 | 3.15.59.193 | small nucleolar RNA, C/D box 22 | 11 | 0.173900806 || SNORD34 | 3.15.59.193 | small nucleolar RNA, C/D box 34 | 19 | 0.149162269 || SNORD35A | 3.15.59.193 | small nucleolar RNA, C/D box 35A | 19 | 0.218012279 || SNORD38A | 3.15.59.193 | small nucleolar RNA, C/D box 38A | 1 | 0.195326681 || SNORD41 | 3.15.59.193 | small nucleolar RNA, C/D box 41 | 19 | 0.14443984 || SNORD45A | 3.15.59.193 | small nucleolar RNA, C/D box 45A | 1 | 0.220168302 || SNORD50A | 3.15.59.193 | small nucleolar RNA, C/D box 50A | | 0.220173158 || SNORD55 | 3.15.59.193 | small nucleolar RNA, C/D box 55 | 1 | 0.140951409 || SNORD57 | 3.15.59.193 | small nucleolar RNA, C/D box 57 | 20 | 0.108648299 || SNORD71 | 3.15.59.193 | small nucleolar RNA, C/D box 71 | 16 | 0.159439686 || SNORD8 | 3.15.59.193 | small nucleolar RNA, C/D box 8 | 14 | 0.118625632 || SNORD83B | 3.15.59.193 | small nucleolar RNA, C/D box 83B | 22 | 0.070643199 | SNORD9 | 3.15.59.193 | small nucleolar RNA, C/D box 9 | 14 | 0.13643635 || SNORD91B | 3.15.59.193 | small nucleolar RNA, C/D box 91B | 17 | 0.156502577 || SNORD92 | 3.15.59.193 | small nucleolar RNA, C/D box 92 | 2 | 0.111422554 || SNORD93 | 3.15.59.193 | small nucleolar RNA, C/D box 93 | 7 | 0.152827474 || SNORD94 | 3.15.59.193 | small nucleolar RNA, C/D box 94 | 2 | 0.085512128 || SNORD95 | 3.15.59.193 | small nucleolar RNA, C/D box 95 | 5 | 0.084310725 || SNORD97 | 3.15.59.193 | small nucleolar RNA, C/D box 97 | 11 | 0.14871429 || SNORA11 | 3.15.59.193.303 | small nucleolar RNA, H/ACA box 11 | X | 0.116578206 || SNORA38B | 3.15.59.193.303 | small nucleolar RNA, H/ACA box 38B | 17 | 0.123013113 || SNORA5A | 3.15.59.193.303 | small nucleolar RNA, H/ACA box 5A | 7 | 0.090952373 || SNORA64 | 3.15.59.193.303 | small nucleolar RNA, H/ACA box 64 | 16 | 0.090968174 || SNORA7B | 3.15.59.193.303 | small nucleolar RNA, H/ACA box 7B | 3 | 0.128402481 || SNORA8 | 3.15.59.193.303 | small nucleolar RNA, H/ACA box 8 | 11 | 0.130210095 || SNORD104 | 3.15.59.193.303 | small nucleolar RNA, C/D box 104 | 17 | 0.156609439 || SNORD110 | 3.15.59.193.303 | small nucleolar RNA, C/D box 110 | 20 | 0.111009068 || SNORD17 | 3.15.59.193.303 | small nucleolar RNA, C/D box 17 | 20 | 0.080678301 || SNORDIC | 3.15.59.193.303 | small nucleolar RNA, C/D box 1C | 17 | 0.096193961 || SNORD22 | 3.15.59.193.303 | small nucleolar RNA, C/D box 22 | 11 | 0.173900806 || SNORD34 | 3.15.59.193.303 | small nucleolar RNA, C/D box 34 | 19 | 0.149162269 || SNORD35A | 3.15.59.193.303 | small nucleolar RNA, C/D box 35A | 19 | 0.218012279 || SNORD38A | 3.15.59.193.303 | small nucleolar RNA, C/D box 38A | 1 | 0.195326681 || SNORD55 | 3.15.59.193.303 | small nucleolar RNA, C/D box 55 | 1 | 0.140951409 || SNORD71 | 3.15.59.193.303 | small nucleolar RNA, C/D box 71 | 16 | 0.159439686 || SNORD8 | 3.15.59.193.303 | small nucleolar RNA, C/D box 8 | 14 | 0.118625632 || SNORD83B | 3.15.59.193.303 | small nucleolar RNA, C/D box 83B | 22 | 0.070643199 || SNORD9 | 3.15.59.193.303 | small nucleolar RNA, C/D box 9 | 14 | 0.13643635 || SNORD93 | 3.15.59.193.303 | small nucleolar RNA, C/D box 93 | 7 | 0.152827474 || SNORD94 | 3.15.59.193.303 | small nucleolar RNA, C/D box 94 | 2 | 0.085512128 || SNORD97 3.15.59.193.303 | small nucleolar RNA, C/D box 97 | 11 | 0.14871429 || AHSP | 4.16.64 | alpha hemoglobin stabilizing protein | 16 | 0.894004081 || ASCC2 | 4.16.64 | activating signal cointegrator 1 complex subunit 2 | 22 | 0.242878762 || ATP5EP2 | 4.16.64 | ATP synthase, H+ transporting, mitochondrial F1 complex, epsilon subunit pseudogene 2 | 13 | 0.076523715 || BAG1 | 4.16.64 | BCL2 associated athanogene 1 | 9 | 0.204947086 || BBOF1 | 4.16.64 | basal body orientation factor 1 | 14 | 0.312818533 || BLVRB | 4.16.64 | biliverdin reductase B | 19 | 0.327391803 || BNIP3L | 4.16.64 | BCL2/adenovirus E1B 19 kDa interacting protein 3-like | 8 |

TABLE 1C-continued

The genes within the significant gene clusters, listed in Table 1B. (2160 Genes Listed by: Gene Symbol | Module | Gene Description | Chromosome Number | Row Variance) ||)

0.069630864 || BPGM | 4.16.64 | bisphosphoglycerate mutase | 7 | 0.229127526 || BSG | 4.16.64 | basigin (Ok blood group) | 19 | 0.198760089 || C7orf73 | 4.16.64 | chromosome 7 open reading frame 73 | 7 | 0.231454358 || C9orf153 | 4.16.64 | chromosome 9 open reading frame 153 | 9 | 0.063530563 || CA1 | 4.16.64 | carbonic anhydrase I | 8 | 0.555039886 || CCNDBP1 | 4.16.64 | cyclin D-type binding-protein 1 | 15 | 0.097192224 || CLIC2 | 4.16.64 | chloride intracellular channel 2 | X | 0.349363751 || CREG1 | 4.16.64 | cellular repressor of E1A stimulated genes 1 | 1 | 0.170737969 || CTSB | 4.16.64 | cathepsin B | 8 | 0.061292921 || DNAJB4 | 4.16.64 | DnaJ heat shock protein family (Hsp40) member B4 | 1 | 0.066471251 || DPCD | 4.16.64 | deleted in primary ciliary dyskinesia homolog (mouse) | 10 | 0.075200999 || EIF1B | 4.16.64 | eukaryotic translation initiation factor 1B | 3 | 0.182563437 || EIF2AK1 | 4.16.64 | eukaryotic translation initiation factor 2 alpha kinase 1 | 7 | 0.184697328 || ELOF1 | 4.16.64 | elongation factor 1 homolog | 19 | 0.125683441 || EMC3 | 4.16.64 | ER membrane protein complex subunit 3 | 3 | 0.130847743 || EPB41 | 4.16.64 | erythrocyte membrane protein band 4.1 | 1 | 0.130488955 || EPB42 | 4.16.64 | erythrocyte membrane protein band 4.2 | 15 | 0.668648475 || ERMAP | 4.16.64 | erythroblast membrane associated protein (Scianna blood group) | 1 | 0.174899593 || FAM104A | 4.16.64 | family with sequence similarity 104 member A | 17 | 0.216340181 || FAXDC2 | 4.16.64 | fatty acid hydroxylase domain containing 2 | 5 | 0.342240423 || FBX07 | 4.16.64 | F-box protein 7 | 22 | 0.071662128 || GABARAPL2 | 4.16.64 | GABA(A) receptor-associated protein like 2 | 16 | 0.213993393 || GDE1 | 4.16.64 | glycerophosphodiester phosphodiesterase 1 | 16 | 0.094014239 || GLRX5 | 4.16.64 | glutaredoxin 5 | 14 | 0.31204368 || GSPT1 | 4.16.64 | G1 to S phase transition 1 | 16 | 0.197027949 || GYPB | 4.16.64 | glycophorin B (MNS blood group) | 4 | 0.566098872 || HBD | 4.16.64 | hemoglobin subunit delta | 11 | 0.25593714 || HMBS | 4.16.64 | hydroxymethylbilane synthase | 11 | 0.106998127 || ISCA1 | 4.16.64 | iron-sulfur cluster assembly 1 | 9 | 0.249322509 || ITLN1 | 4.16.64 | intelectin 1 | 1 | 0.262731332 || KRT1 | 4.16.64 | keratin 1 | 12 | 0.207636121 || LGALS3 | 4.16.64 | lectin, galactoside-binding, soluble, 3 | 14 | 0.186735688 || LINC00570 | 4.16.64 | long intergenic non-protein coding RNA 570 | 2 | 0.232653962 || MOSPD1 | 4.16.64 | motile sperm domain containing 1 | X | 0.183193685 || MPP1 | 4.16.64 | membrane protein, palmitoylated 1 | X | 0.313716645 || NCOA4 | 4.16.64 | nuclear receptor coactivator 4 | 10 | 0.08229211 || NINJ2 | 4.16.64 | ninjurin 2 | 12 | 0.124557077 || OSBP2 | 4.16.64 | oxysterol binding protein 2 | 22 | 0.286954255 || PDZK1IP1 | 4.16.64 | PDZK1 interacting protein 1 | 1 | 0.418814923 || PITHD1 | 4.16.64 | PITH (C-terminal proteasome-interacting domain of thioredoxin-like) domain containing 1 | 1 | 0.474178089 || POLR1D | 4.16.64 | polymerase (RNA) I subunit D | 13 | 0.094415873 || PRDX6 | 4.16.64 | peroxiredoxin 6 | 1 | 0.241135346 || PSMF1 | 4.16.64 | proteasome inhibitor subunit 1 | 20 | 0.167097503 || RAB2B | 4.16.64 | RAB2B, member RAS oncogene family | 14 | 0.325730169 || RAB3IP | 4.16.64 | RAB3A interacting protein | 12 | 0.077269312 || RALBP1 | 4.16.64 | ralA binding protein 1 | 18 | 0.083748151 || RIOK3 | 4.16.64 | RIO kinase 3 | 18 | 0.320585689 || RPIA | 4.16.64 | ribose 5-phosphate isomerase A | 2 | 0.34195701 || SELENBP1 | 4.16.64 | selenium binding protein 1 | 1 | 0.74756733 || SELK | 4.16.64 | selenoprotein K | 3 | 0.110857362 || SESN3 | 4.16.64 | sestrin 3 | 11 | 0.137750937 || SLC14A1 | 4.16.64 | solute carrier family 14 member 1 (Kidd blood group) | 18 | 0.622940769 || SLC18B1 | 4.16.64 | solute carrier family 18 member B1 | 6 | 0.10424155 || SLC25A39 | 4.16.64 | solute carrier family 25 member 39 | 17 | 0.2138409 || SNCA | 4.16.64 | synuclein alpha | 4 | 0.164142929 || SNX3 | 4.16.64 | sorting nexin 3 | 6 | 0.141495105 || SPATA31D4 | 4.16.64 | SPATA31 subfamily D, member 4 | 9 | 0.152963823 || SRRD | 4.16.64 | SRR1 domain containing | 22 | 0.174557913 || SRSF8 | 4.16.64 | serine/arginine-rich splicing factor 8 | 11 | 0.063648116 || TBPL1 | 4.16.64 | TATA-box binding protein like 1 | 6 | 0.062035924 || TCP11L2 | 4.16.64 | t-complex 11, testis-specific-like 2 | 12 | 0.279053721 || TNS1 | 4.16.64 | tensin 1 | 2 | 0.215020894 || TRAK2 | 4.16.64 | trafficking protein, kinesin binding 2 | 2 | 0.209345299 || TRIM23 | 4.16.64 | tripartite motif containing 23 | 5 | 0.133156568 || TSPAN5 | 4.16.64 | tetraspanin 5 | 4 | 0.337122122 || TTC25 | 4.16.64 | tetratricopeptide repeat domain 25 | 17 | 0.081039868 || UBB | 4.16.64 | ubiquitin B | 17 | 0.084591988 || UBE2H | 4.16.64 | ubiquitin conjugating enzyme E2H | 7 | 0.10825541 || USP12 4.16.64 | ubiquitin specific peptidase 12 | 13 | 0.265769105 || WBP2 | 4.16.64 | WW domain binding protein 2 | 17 | 0.096833871 || ZRANB1 | 4.16.64 | zinc finger RANBP2-type containing 1 | 10 | 0.114136919 || ATP5EP2 | 4.16.64.204 | ATP synthase, H+ transporting, mitochondrial F1 complex, epsilon subunit pseudogene 2 | 13 | 0.076523715 || BAG1 | 4.16.64.204 | BCL2 associated athanogene 1 | 9 | 0.204947086 || BBOF1 | 4.16.64.204 | basal body orientation factor 1 | 14 | 0.312818533 || BLVRB | 4.16.64.204 | biliverdin reductase B | 19 | 0.327391803 || BNIP3L | 4.16.64.204 | BCL2/adenovirus E1B 19 kDa interacting protein 3-like | 8 | 0.069630864 || BPGM | 4.16.64.204 | bisphosphoglycerate mutase | 7 | 0.229127526 || C7orf73 | 4.16.64.204 | chromosome 7 open reading frame 73 | 7 | 0.231454358 || C9orf153 | 4.16.64.204 | chromosome 9 open reading frame 153 | 9 | 0.063530563 || CCNDBP1 | 4.16.64.204 | cyclin D-type binding-protein 1 | 15 | 0.097192224 || CLIC2 | 4.16.64.204 | chloride intracellular channel 2 | X | 0.349363751 || CREG1 | 4.16.64.204 | cellular repressor of E1A stimulated genes 1 | 1 | 0.170737969 || CTSB | 4.16.64.204 | cathepsin B | 8 | 0.061292921 || DNAJB4 | 4.16.64.204 | DnaJ heat shock protein family (Hsp40) member B4 | 1 | 0.066471251 || EIF1B | 4.16.64.204 | eukaryotic translation initiation factor 1B | 3 | 0.182563437 || EIF2AK1 | 4.16.64.204 | eukaryotic translation initiation factor 2 alpha kinase 1 | 7 | 0.184697328 || EMC3 | 4.16.64.204 | ER membrane protein complex subunit 3 | 3 | 0.130847743 || EPB41 | 4.16.64.204 | erythrocyte membrane protein band 4.1 | 1 | 0.130488955 || FAXDC2 | 4.16.64.204 | fatty acid hydroxylase domain containing 2 | 5 | 0.342240423 || FBX07 | 4.16.64.204 | F-box protein 7 | 22 | 0.071662128 || GABARAPL2 | 4.16.64.204 | GABA(A) receptor-associated protein like 2 | 16 | 0.213993393 || GDE1 | 4.16.64.204 | glycerophosphodiester phosphodiesterase 1 | 16 | 0.094014239 || GLRX5 | 4.16.64.204 | glutaredoxin 5 | 14 | 0.31204368 || GSPT1 | 4.16.64.204 | Gl to S phase transition 1 | 16 | 0.197027949 || ISCA1 | 4.16.64.204 | iron-sulfur cluster assembly 1 | 9 | 0.249322509 || LGALS3 | 4.16.64.204 | lectin, galactoside-binding, soluble, 3 | 14 | 0.186735688 || LINC00570 | 4.16.64.204 | long intergenic non-protein coding RNA 570 | 2 |

TABLE 1C-continued

| The genes within the significant gene clusters, listed in Table 1B. (2160 Genes Listed by: Gene Symbol \| Module \| Gene Description \| Chromosome Number \| Row Variance) \|\|) |
|---|
| 0.232653962 \|\| MOSPD1 \| 4.16.64.204 \| motile sperm domain containing 1 \| X \| 0.183193685 \|\| MPP1 \| 4.16.64.204 \| membrane protein, palmitoylated 1 \| X \| 0.313716645 \|\| NCOA4 \| 4.16.64.204 \| nuclear receptor coactivator 4 \| 10 \| 0.08229211 \|\| NINJ2 \| 4.16.64.204 \| ninjurin 2 \| 12 \| 0.124557077 \|\| PDZK1IP1 \| 4.16.64.204 \| PDZK1 interacting protein 1 \| 1 \| 0.418814923 \|\| PITHD1 \| 4.16.64.204 \| PITH (C-terminal proteasome-interacting domain of thioredoxin-like) domain containing 1 \| 1 \| 0.474178089 \|\| POLR1D \| 4.16.64.204 \| polymerase (RNA) I subunit D \| 13 \| 0.094415873 \|\| PRDX6 \| 4.16.64.204 \| peroxiredoxin 6 \| 1 \| 0.241135346 \|\| PSMF1 \| 4.16.64.204 \| proteasome inhibitor subunit 1 \| 20 \| 0.167097503 \|\| RAB2B \| 4.16.64.204 \| RAB2B, member RAS oncogene family \| 14 \| 0.325730169 \|\| RAB3IP \| 4.16.64.204 \| RAB3A interacting protein \| 12 \| 0.077269312 \|\| RALBP1 \| 4.16.64.204 \| ralA binding protein 1 \| 18 \| 0.083748151 \|\| RIOK3 \| 4.16.64.204 \| RIO kinase 3 \| 18 \| 0.320585689 \|\| RPIA \| 4.16.64.204 \| ribose 5-phosphate isomerase A \| 2 \| 0.34195701 \|\| SELK \| 4.16.64.204 \| selenoprotein K \| 3 \| 0.110857362 \|\| SESN3 \| 4.16.64.204 \| sestrin 3 \| 11 \| 0.137750937 \|\| SLC18B1 \| 4.16.64.204 \| solute carrier family 18 member B1 \| 6 \| 0.10424155 \|\| SNCA \| 4.16.64.204 \| synuclein alpha \| 4 \| 0.164142929 \|\| SNX3 \| 4.16.64.204 \| sorting nexin 3 \| 6 \| 0.141495105 \|\| SRRD \| 4.16.64.204 \| SRR1 domain containing \| 22 \| 0.174557913 \|\| SRSF8 \| 4.16.64.204 \| serine/arginine-rich splicing factor 8 \| 11 \| 0.063648116 \|\| TBPL1 \| 4.16.64.204 \| TATA-box binding protein like 1 \| 6 \| 0.062035924 \|\| TCP11L2 \| 4.16.64.204 \| t-complex 11, testis-specific-like 2 \| 12 \| 0.279053721 \|\| TRIM23 \| 4.16.64.204 \| tripartite motif containing 23 \| 5 \| 0.133156568 \|\| TSPAN5 \| 4.16.64.204 \| tetraspanin 5 \| 4 \| 0.337122122 \|\| UBE2H \| 4.16.64.204 \| ubiquitin conjugating enzyme E2H \| 7 \| 0.10825541 \|\| USP12 \| 4.16.64.204 \| ubiquitin specific peptidase 12 \| 13 \| 0.265769105 \|\| WBP2 \| 4.16.64.204 \| WW domain binding protein 2 \| 17 \| 0.096833871 \|\| ZRANB1 \| 4.16.64.204 \| zinc finger RANBP2-type containing 1 \| 10 \| 0.114136919 |

Figure 4A:
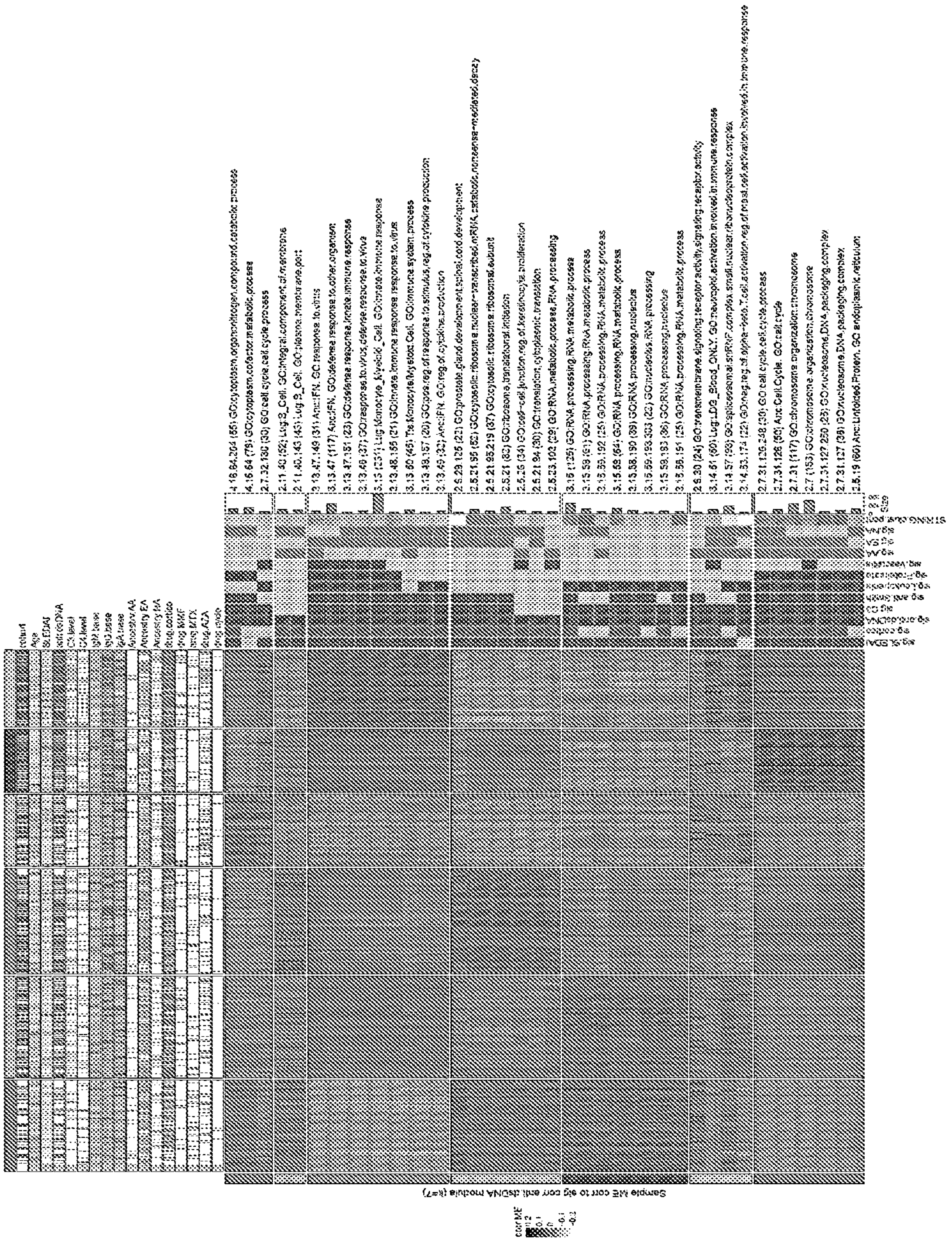
FIG. 4A: Estimated GSVA scores per sample of all ILLUM-1 top5k rowVar genes tested against the self top 40 MEs sig ($p<0.001$) corr to anti.dsDNA as GSVA signatures.
Figures 1, 4A:
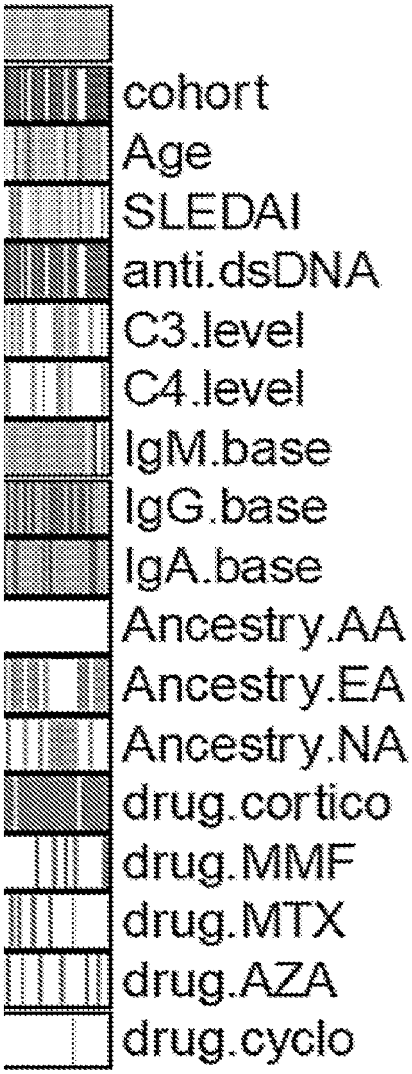
Figures 2, 4A:
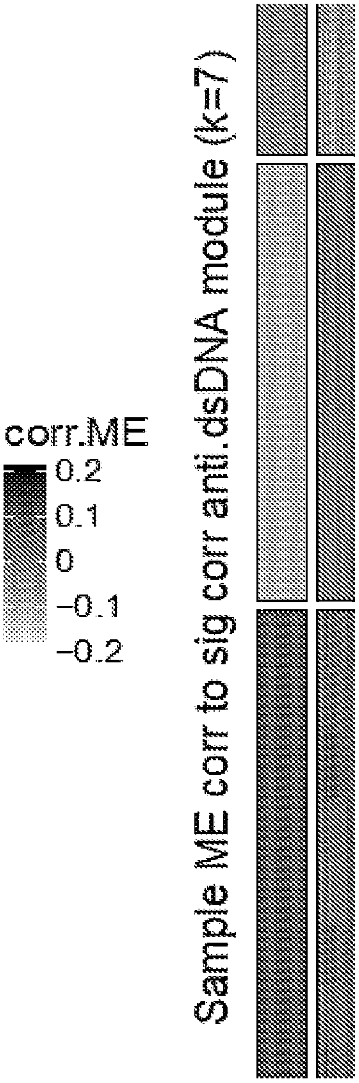
Figures 4, 4A:
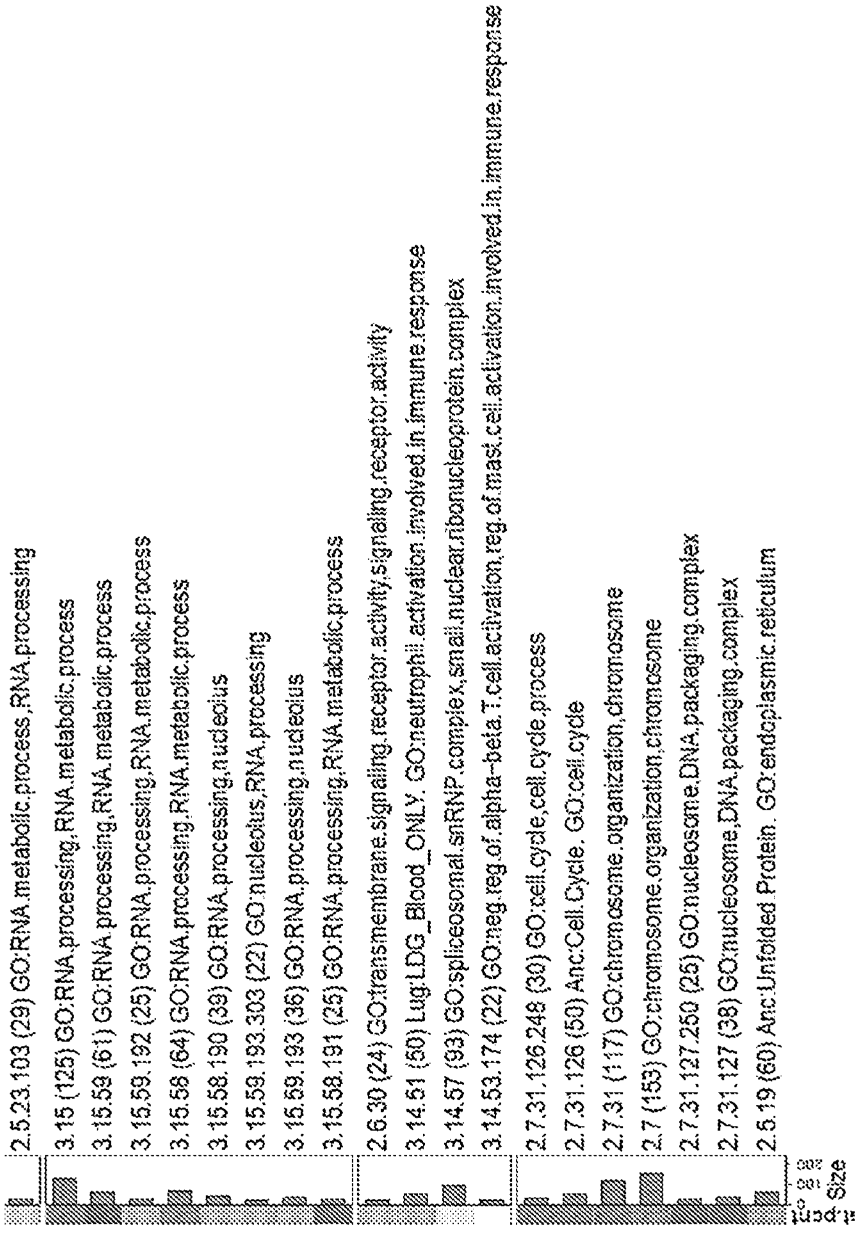
Figures 4, 4A, 5:

FIG. 4A shows estimated GSVA scores per sample of all ILLUM-1 top5k rowVar genes tested against the self top 40 MEs sig (p<0.001) corr to anti.dsDNA as GSVA signatures. Columns of samples are optimally clustered (1K iterations) on k=6 sample clusters. Rows of top 40 self GSVA module signatures are optimally clustered (1K iterations) on k=7 iterations. Per column (sample) annotations: ME.pt.clusts indicate how samples would have been clustered by correlating mean gene expression per sample to the top 40 MEs (ME correlations heatmap available as a supplementary figure). Also shown per sample column are numeric age of subject, numeric clinically assigned SLEDAI score, yes/no elevated anti.dsDNA, depleted C3 and C4, IgM, IgG, or IGA elevated above baseline, yes/no ancestral background of African ancestry (AA), European ancestry (EA), or Native American ancestry (NA), and yes/no usage of immunotherapeutic drugs including corticosteroids, mycophenolate mofetil (MMA), methotrexate (MTX), azathioprine (AZA), or cyclophosphamide (cyclo). Row (module) annotations are identical to FIG. 3 sample traits correlations to MEs heatmap. Additionally they include the z.summary (z.summ) statistic of the module preservation degree of these ILLUM-1 MEGENA top5k rowVar modules amongst all calculable MEGENA modules generated using all 12,534 genes mapping to known protein symbols given in the original ILLUM-1 study. Only preservations greater than a z.summ of 2 (the accepted minimal preservation threshold) are colored. [Where is z.summ shown in FIG. 4A]

Figure 4B:
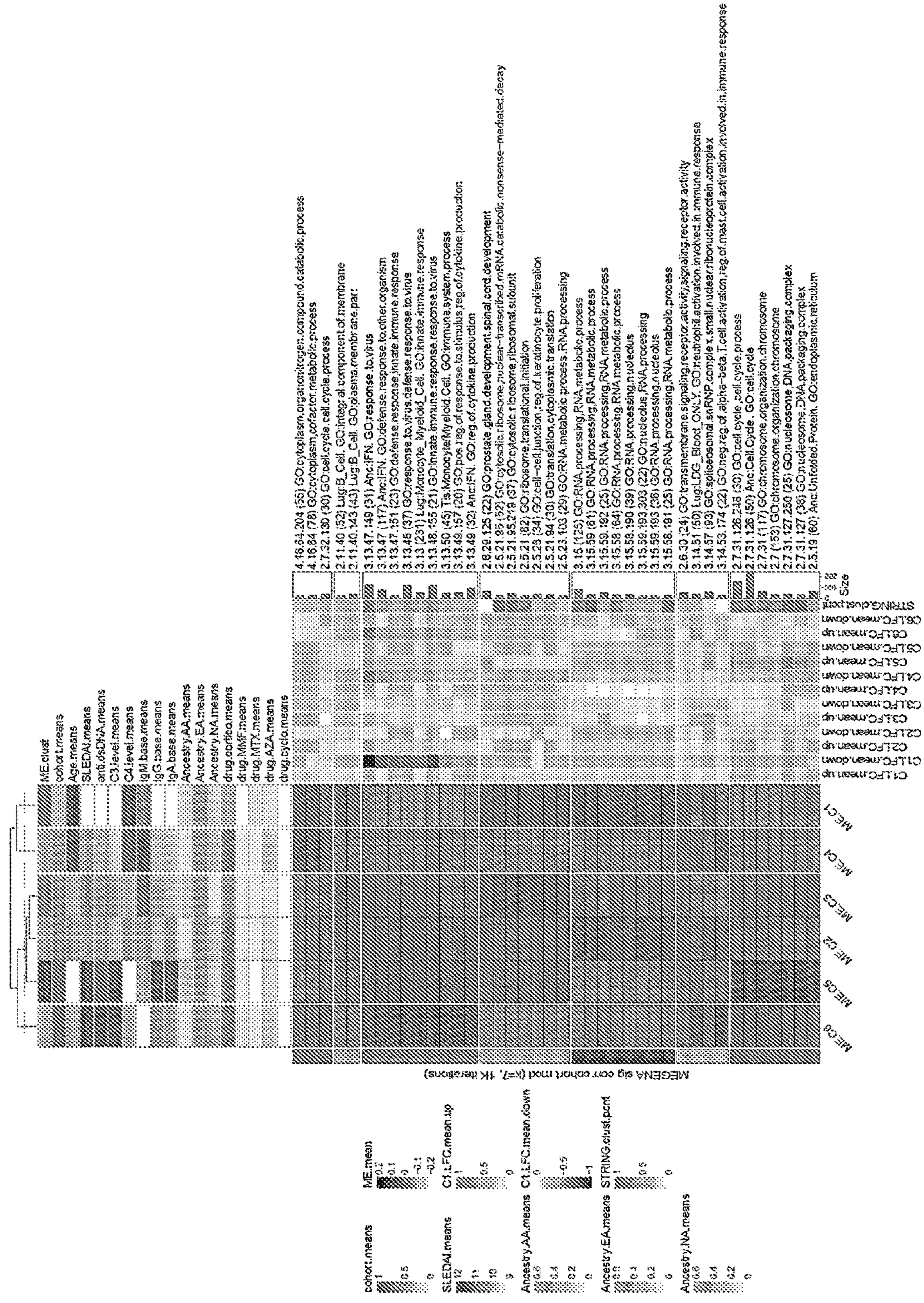
FIG. 4B: Row means of self GSVA scores of top 40 sig anti.dsDNA MEs per k=6 sample cluster.
Figures 1, 4B:
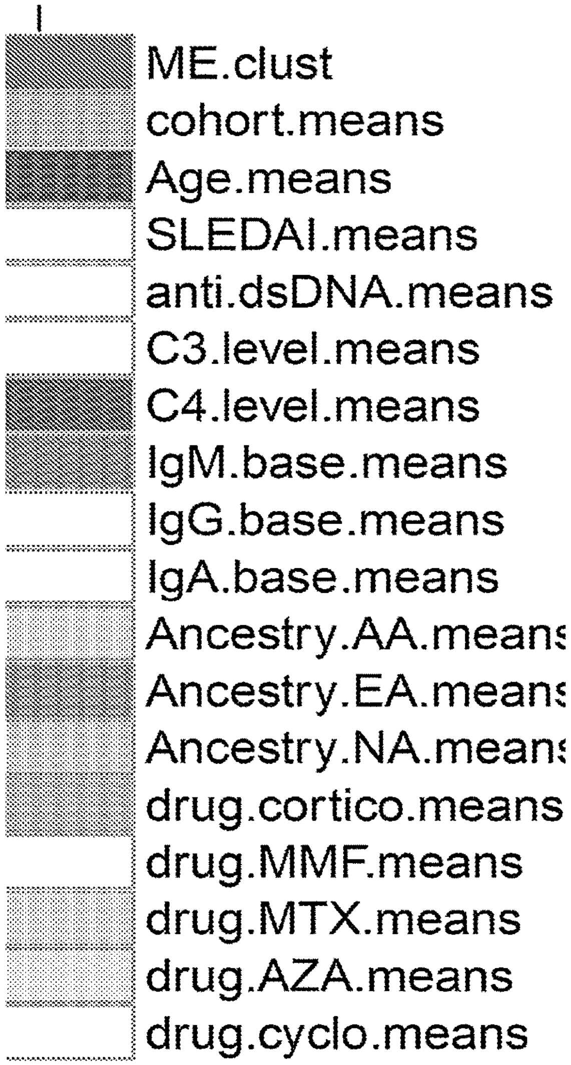
Figures 2, 4B:
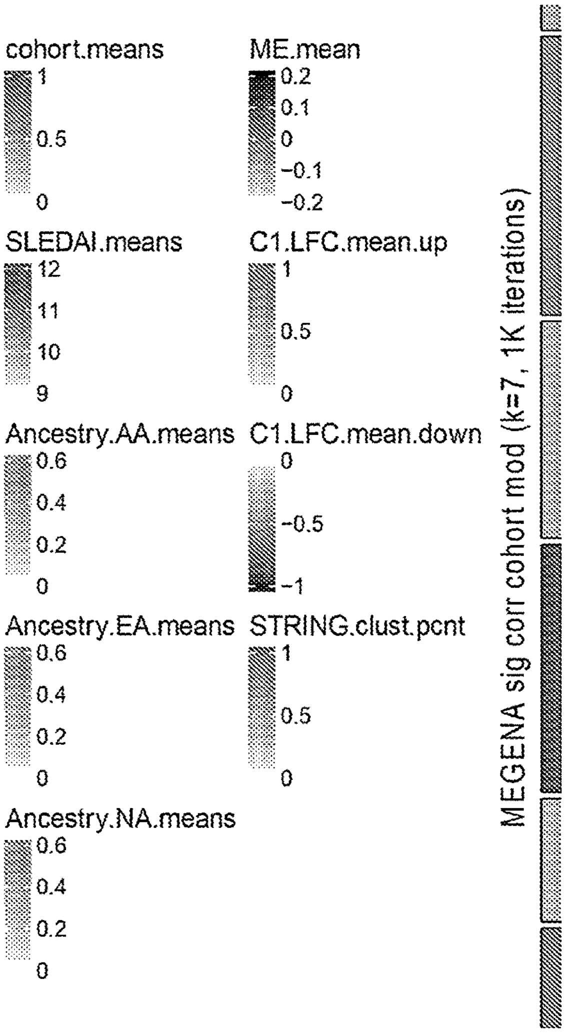
Figures 4, 4B, 5:
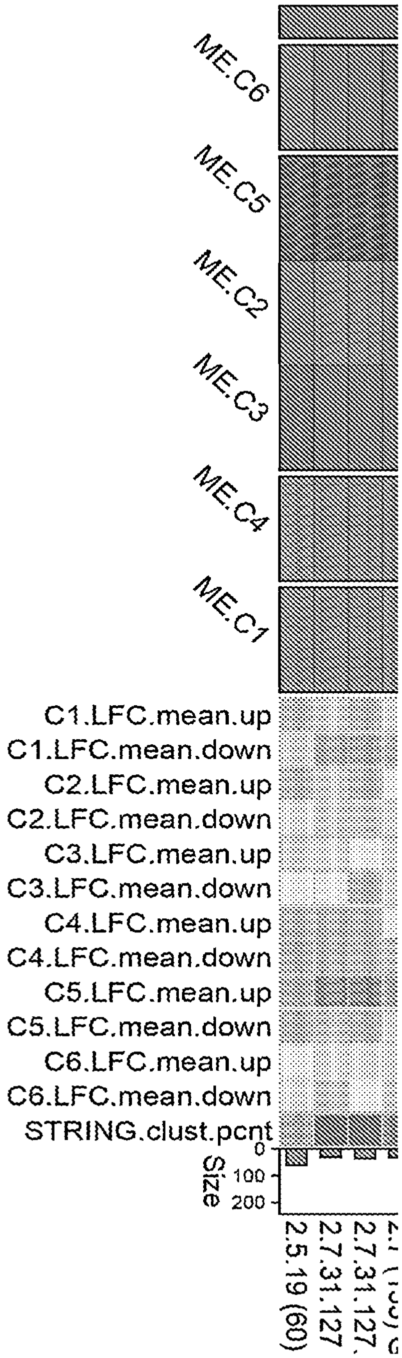

FIG. 4B shows row means of self GSVA scores of top 40 sig anti.dsDNA MEs per k=6 sample cluster. Column annotations of sample clusters are similar to the unaveraged GSVA scores figure, but here are also averaged per patient cluster. GSVA.clust indicates the color assigned to a sample cluster in the unaveraged GSVA figure and are accordingly labeled at the bottom of the columns. Row (module) annotations also include top5k averaged gene expression limma Bayesian-adjusted log fold changes (LFCs) per each sample cluster, where gene expressions in a given cluster are a reference group tested against gene expressions amongst all other sample clusters pooled together as a test group. Mean LFCs per each patient cluster are indicated as overexpressed LFCs ("up" meaning mean LFCs>0) and underexpressed LFCs ("down" meaning mean LFCs<0). Mean LFCs are colored grey where they are statistically insignificant, having an adjusted p.value>=0.2.

Figure 5A:
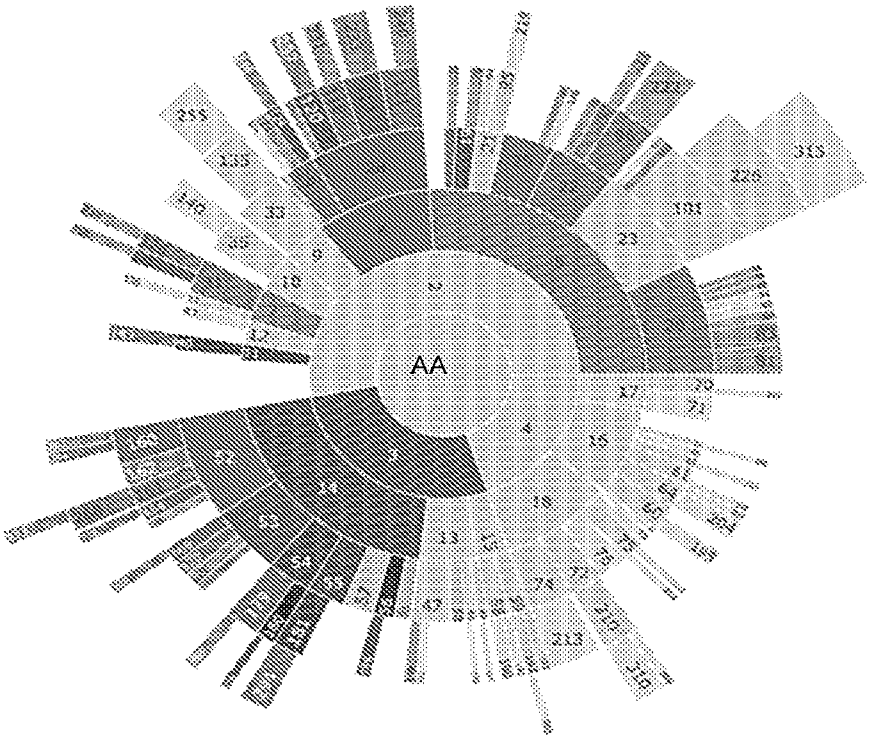
FIGS. 5A-5C: Sunburst diagram showing top5K rowVar gene module eigengene (ME) correlations ($p<0.2$) to patient's ancestry.
Figure 5B:
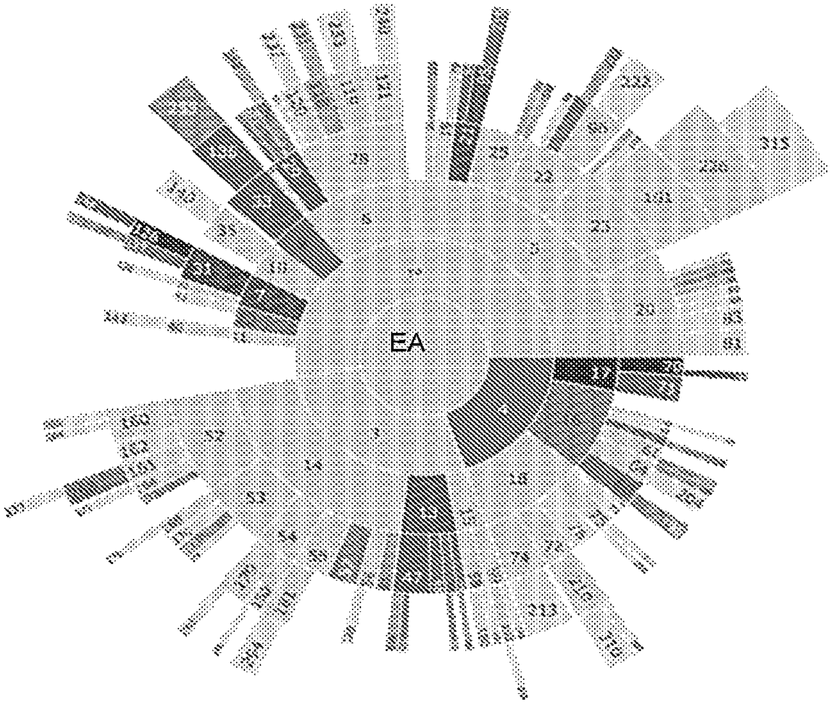
Figure 5C:
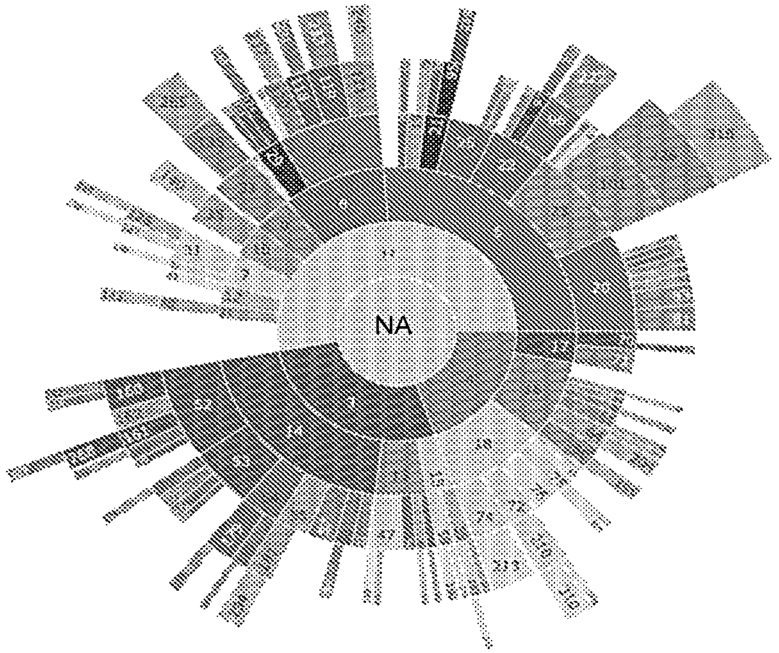

FIG. 5A-5C present sunburst diagrams showing ILLUM-1 top5K rowVar gene module eigengene (ME) correlations (p<0.2) to AA, African American ancestry (5A) EA, European American ancestry (5B) and NA, Native American ancestry (5C). Visual comparison demonstrates enrichment patterns unique to each ancestral background and implies differing molecular regulatory mechanisms in the lupus pathology. The sunbursts also demonstrate enrichment signatures that persist through gene inheritance by descendant modules as terminal generations are reached in the outermost concentric rings.

Figure 6A:
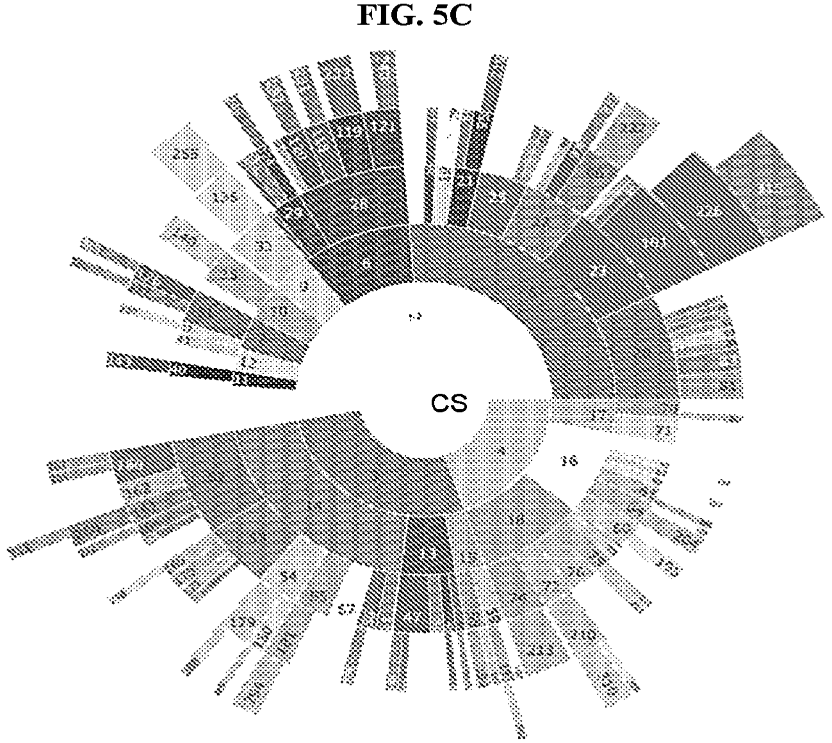
FIGS. 6A-6C: Sunburst diagrams showing ILLUM-1 top5K rowVar gene modules' eigengenes (ME) correlation to patient baseline drug usage.
Figure 6B:
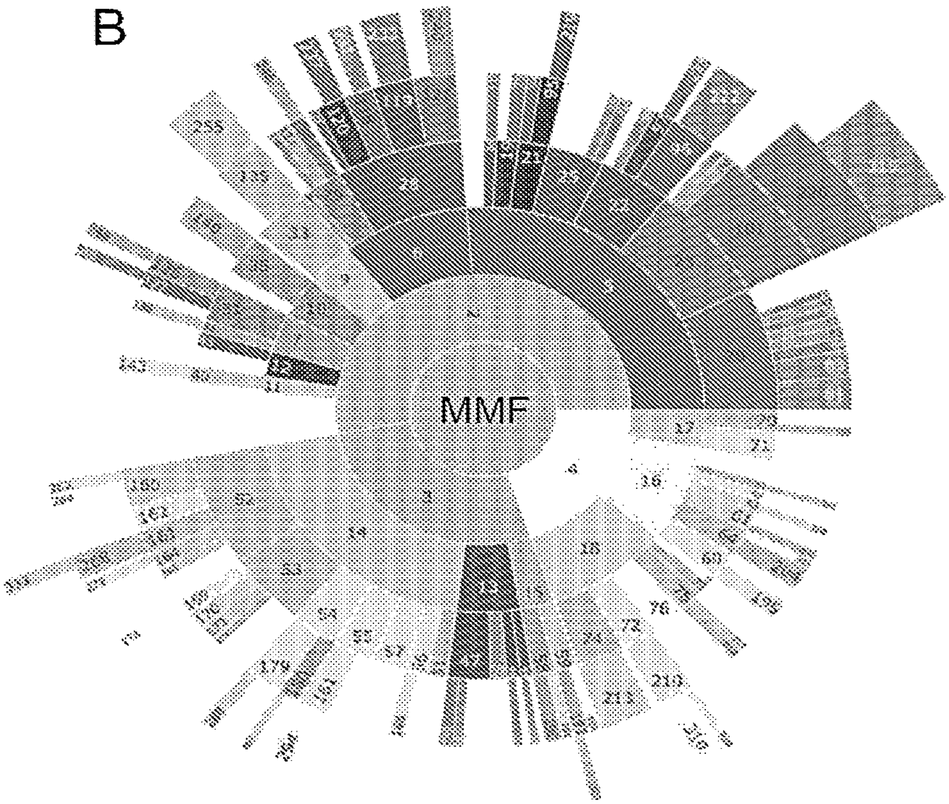
Figure 6C:
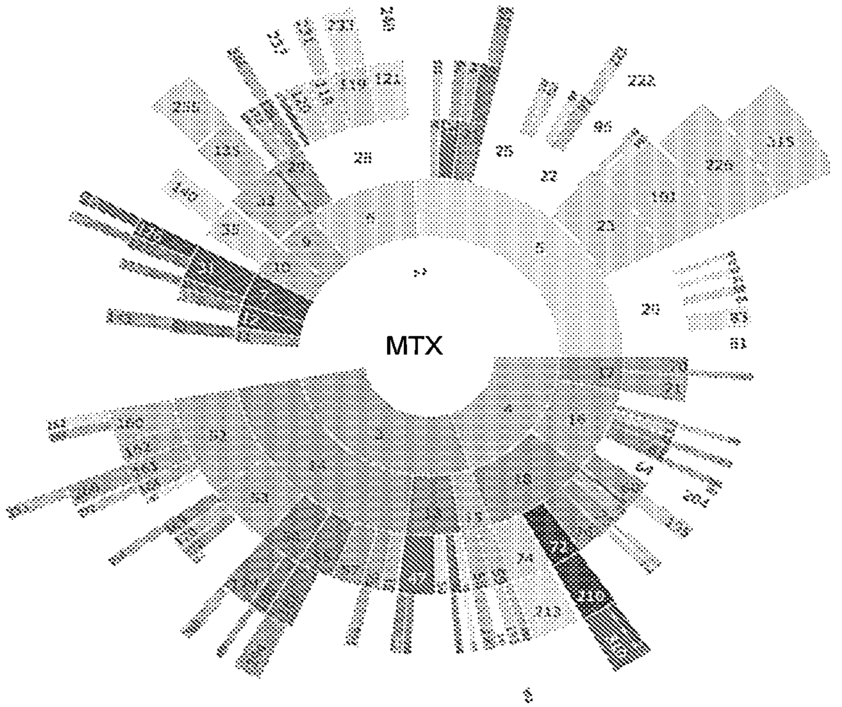

FIGS. 6A-6C present sunburst diagrams showing top5K rowVar gene module eigengene (ME) correlations (p<0.2) to patient baseline drug usage (yes=1, no=0): CS corticosteroid (6A) MMF mycophenolate mofetil (6B) and MTX methotrexate (6C). Similar to the ancestral background sunbursts, these demonstrate correlation patterns unique to each pharmacotherapeutic.

Figure 7A:
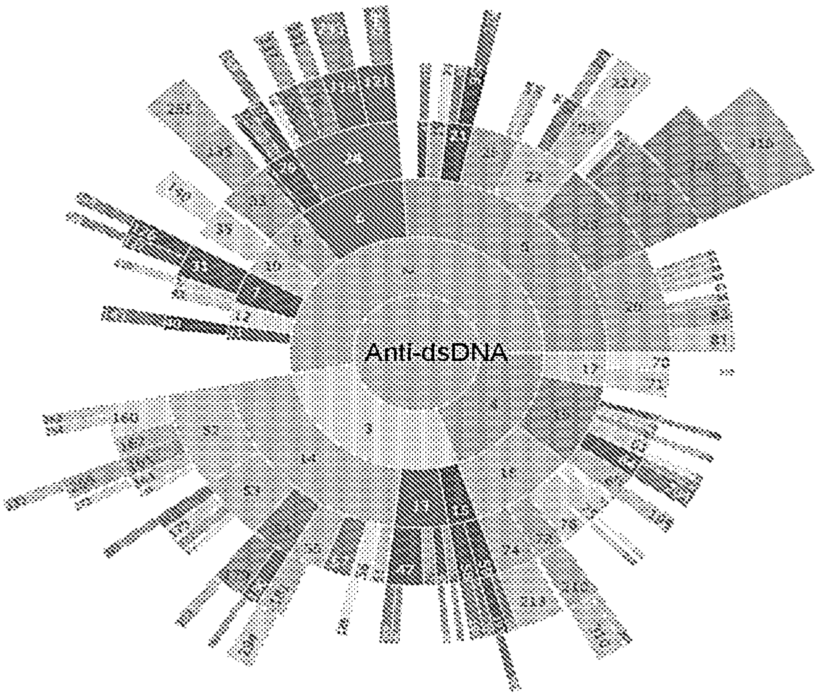
FIGS. 7A-7B.
Figure 7B:
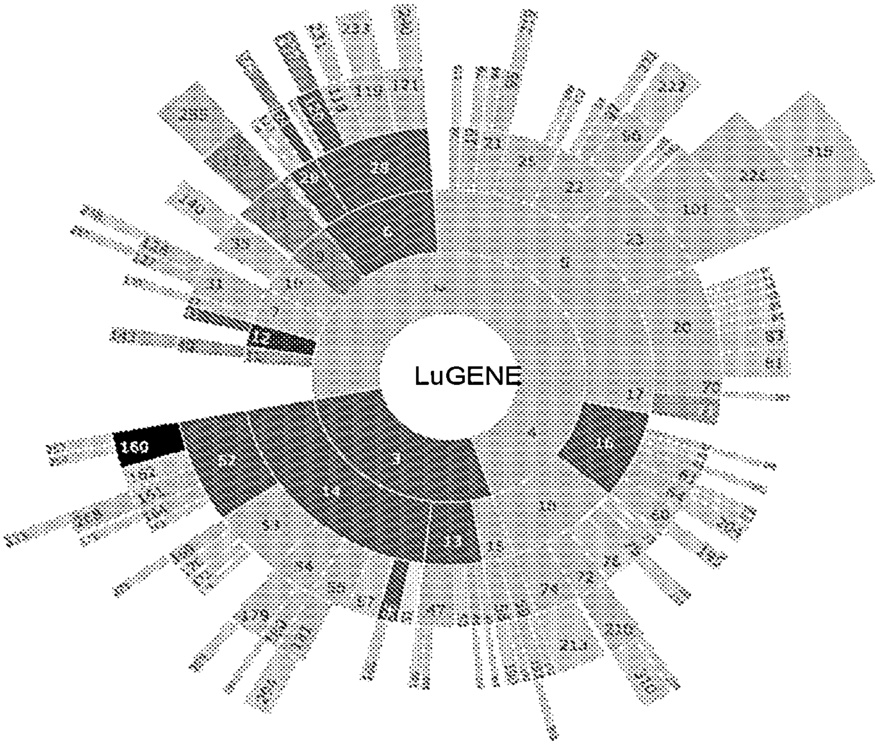

FIG. 7A presents a sunburst diagram showing ILLUM-1 top5K rowVar gene modules ME correlations to anti-dsDNA (yes=1 if assay>30 IU/mL else no=0). FIG. 7B presents a sunburst diagram showing ILLUM-1 top5K rowVar gene modules significant overlap (Fisher's adj.p<0.05 and >=4 gene overlaps) with LuGENE signatures. Module lineages that uniquely contain LuGENE signatures were B cells (M2.11), cytotoxic T cells (M2.12), monocytes (M2.9), T cells (M2.6), plasma cells (2.5), platelets (M2.17.71), erythrocytes (M4.16), myeloid cells (M3.13, M3.14), and a neutrophil module (M3.14.52.160). The ability to segregate members of the immune cell repertoire is an advancement from previous gene module formation approaches.

Figure 8:
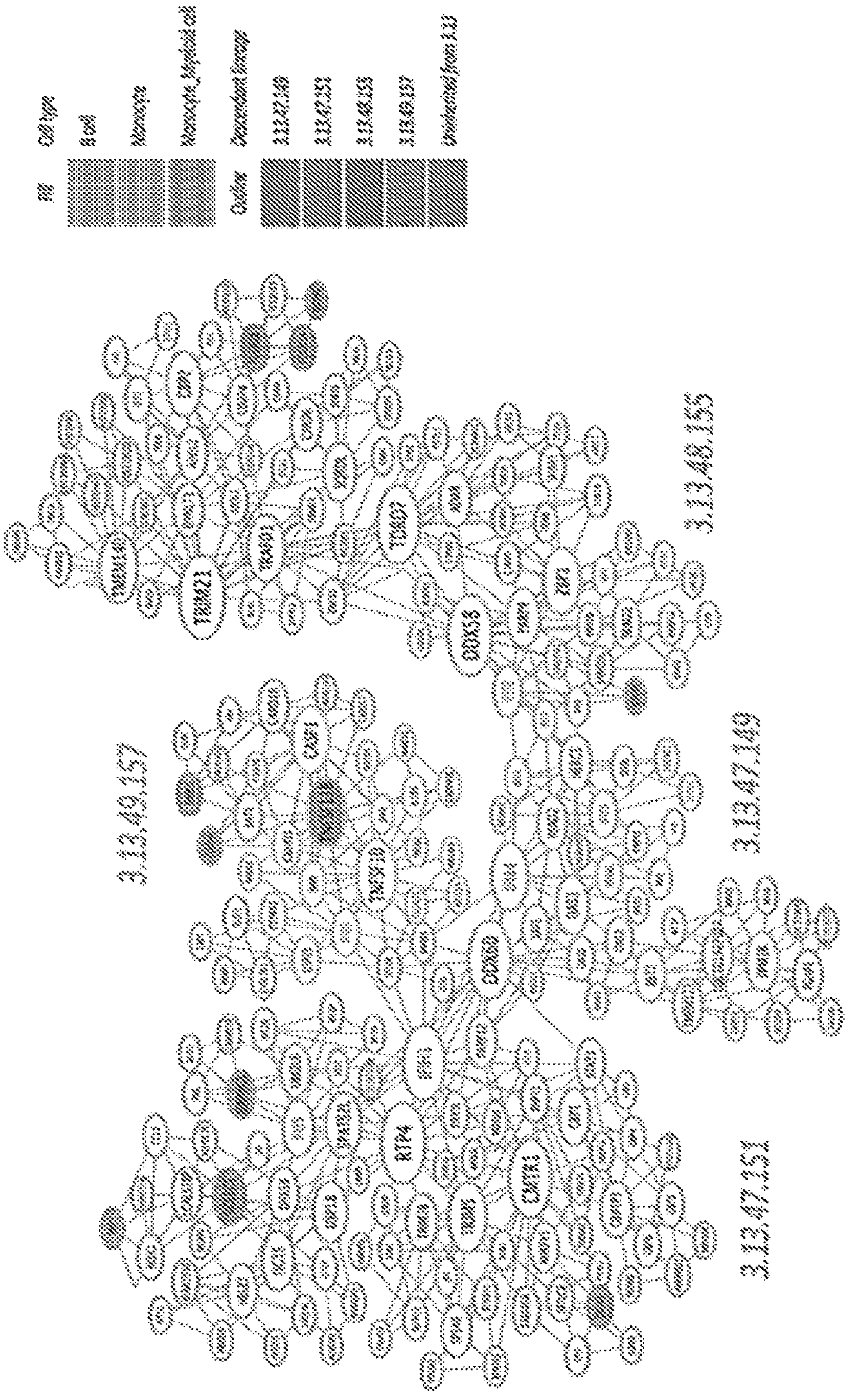
FIG. 8: Cytoscape visualization of co-expression networks within gene modules M3.13.47.149, M3.13.48.155, M3.13.47.151, and M3.13.49.157, obtained from clustering ILLUM-1 top5k rowVar genes.

FIG. 8 presents cytoscape visualization of coexpression networks within overexpressed and underexpressed gene modules of interest. Gene module M3.13 fourth generation descendants including M3.13.47.149, M3.13.48.155, M3.13.47.151, and M3.13.49.157 implicate succinct IFN regulatory networks within M3.31. Gene nodes were filled per significant LuGENE enrichment (Fisher's adj.p<0.05 and minimum overlaps >=4 gene), outlined according to M3.13 generation descendant module placement, and sized according to degree of interconnectedness/co-expression with neighboring genes. Uninherited genes (gray outlines) are those that remained within M3.13 and weren't duplicated in a descendant module. IFN genes were labeled red.

Figure 9:
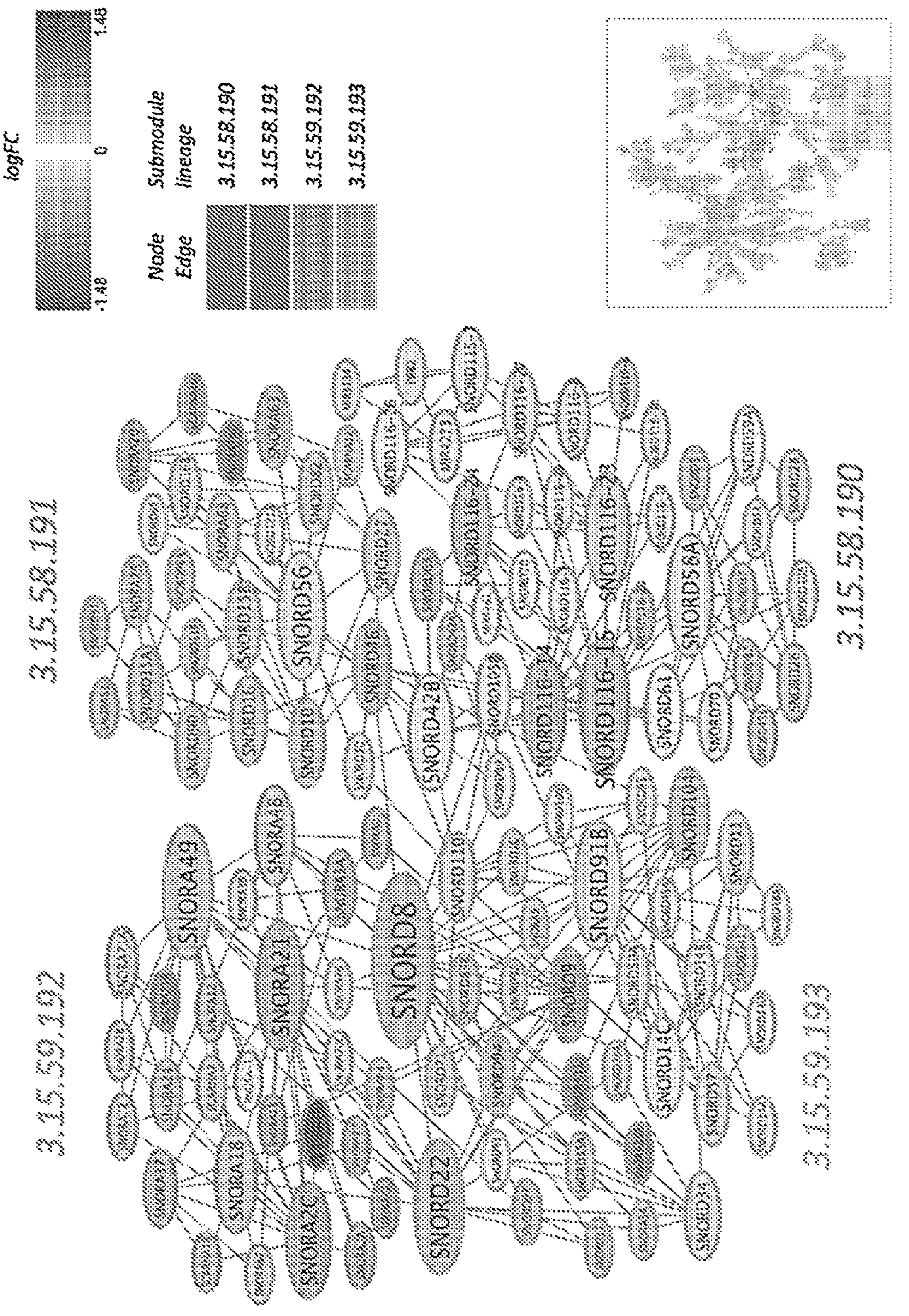
FIG. 9: Cytoscape visualization of M3.15 fourth generation (gen4) descendants—3.15.58.190, 3.15.58.191, 3.15.59.192, and 3.15.59.193, obtained from clustering ILLUM-1 top5k rowVar genes.

FIG. 9 presents cytoscape visualization of M3.15 fourth generation (gen4) descendants-3.15.58.190, 3.15.58.191, 3.15.59.192, and 3.15.59.193. Gene nodes are filled per significant log FC vs. healthy controls (adj.p<0.05), outlined according to M3.15 descendant gen4 module placement, and sized according to degree of interconnectedness/co-expression with neighboring genes. Unlike M3.13, all M3.15 genes persisted through inheritance to terminal gen4 module descendants. Also, all genes are significantly downregulated and part of the SnoRNA (small nucleolar RNA) class, related to RNA processing and implicated in the literature as being features of autoimmune pathogenesis.

Figure 10:
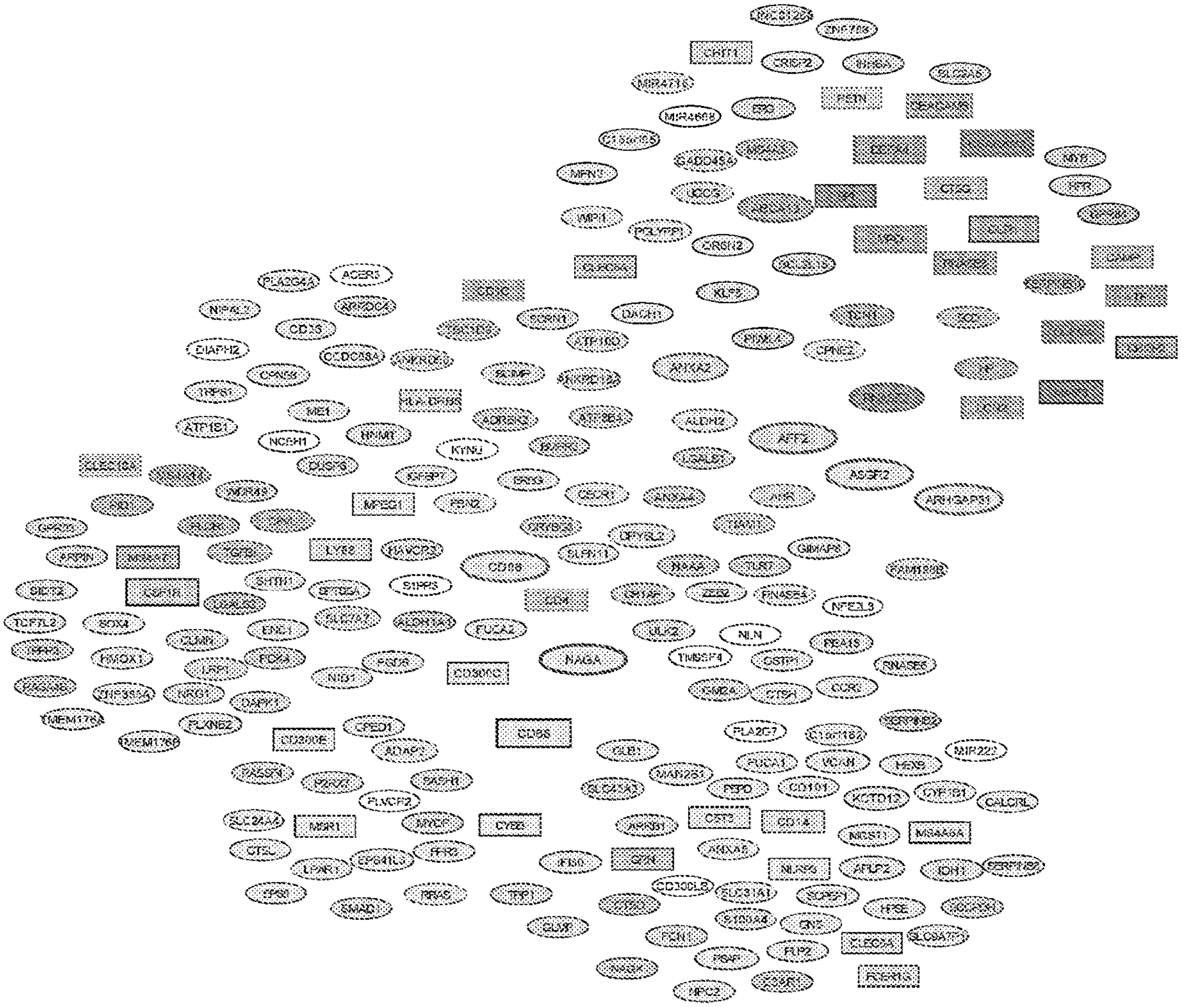
FIG. 10: Cytoscape visualization of intramodular correlation & intermodular differential gene correlation analysis (DGCA) pair significance between modules M2.9.33 (Monocytes) and M3.14.51 (LDG) modules (obtained from clustering ILLUM-1 top5k rowVar genes).

FIG. 10 presents cytoscape visualization of intramodular correlation & intermodular differential gene correlation analysis (DGCA) pair significance between M2.9.33 (Monocytes) and M3.14.51 (LDG) modules. Nodes were outlined as follows: red if the gene is entirely intramodular to M2.9.33, blue if the gene is entirely intramodular to M3.14.51, or green if the gene has at least one intermodular connection. Edges were colored as follows: red between intramodular M2.9.33 genes, blue between intramodular M3.14.51 genes, or green between DGCA intermodular genes. The DGCA condition was the presence of anti.dsDNA in a sample (yes=1, no=0). Edge line type indicates gene pair class where M2.9.33 monocyte intramodular pair connections are solid red, M3.14.51 LDG intramodulars are solid blue, DGCA +/+ pair classes are solid green, DGCA +/− or −/+ are dashed green, and DGCA −/− are dotted green. Thick edges indicate gene pairs that were programmatically queried against STRING-DB and found within known PPIs. Node and label size were based on the total number of edges (connectedness of the node) to other genes. Nodes were filled if there is a top sig module annotation (min overlaps >4, Fisher's p.val<0.05).

Figure 11A:
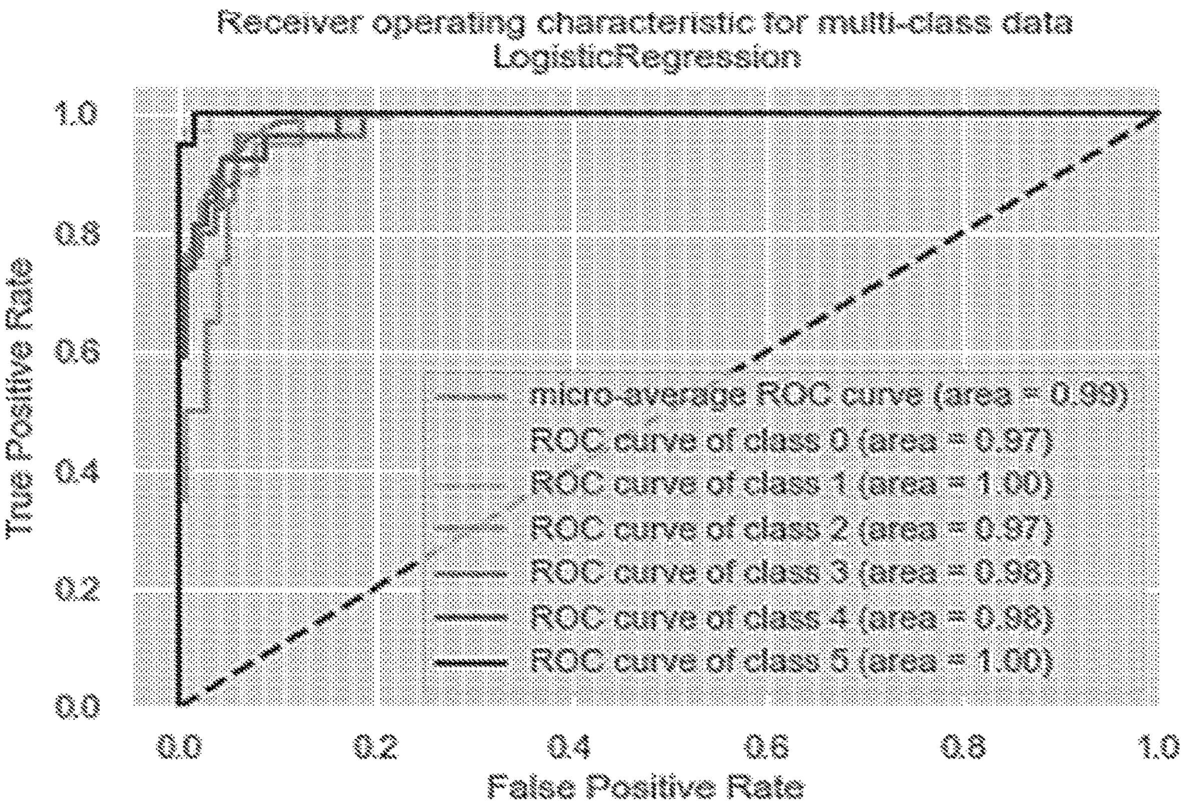
FIGS. 11A-11C: ROC curve for machine learning classifiers, for separating lupus patients into sub-clusters 0, 1, 2, 3, 4, and 5, based on gene expression measurement of the genes of the significant gene clusters (obtained from clustering ILLUM-1 top5k rowVar genes.
Figure 11B:
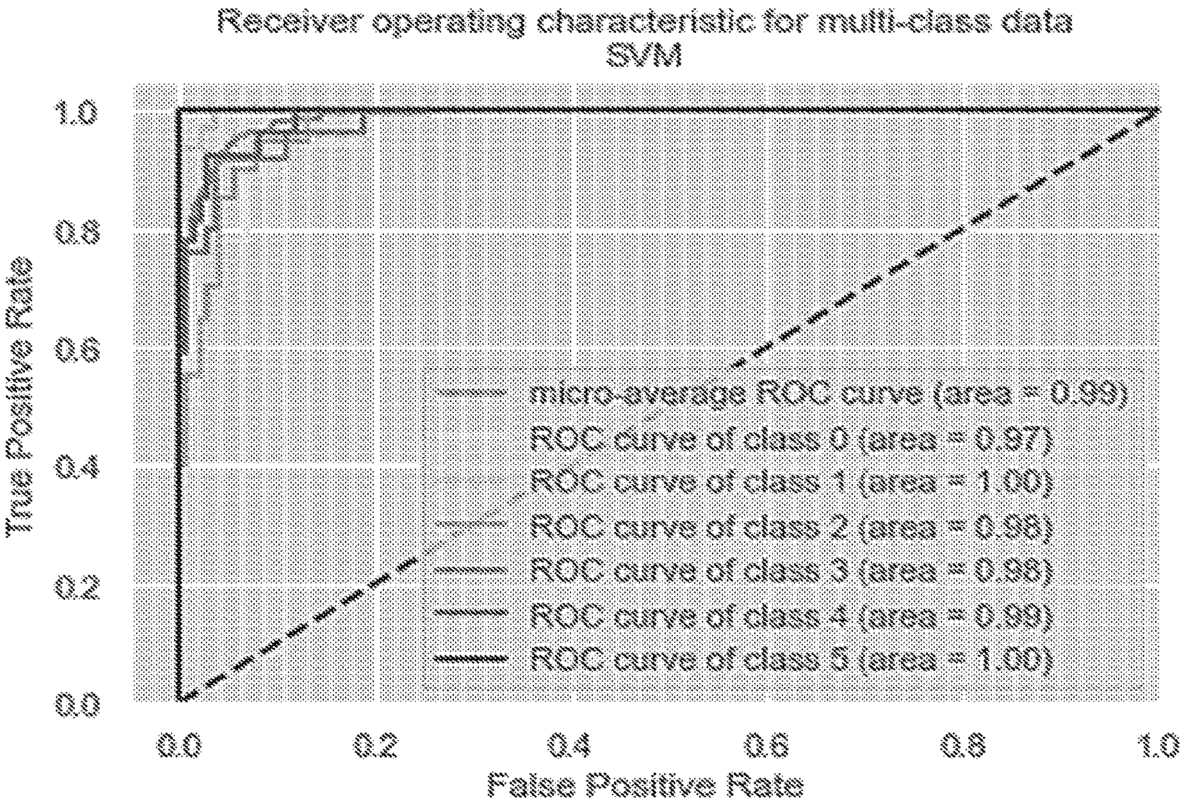
Figure 11C:
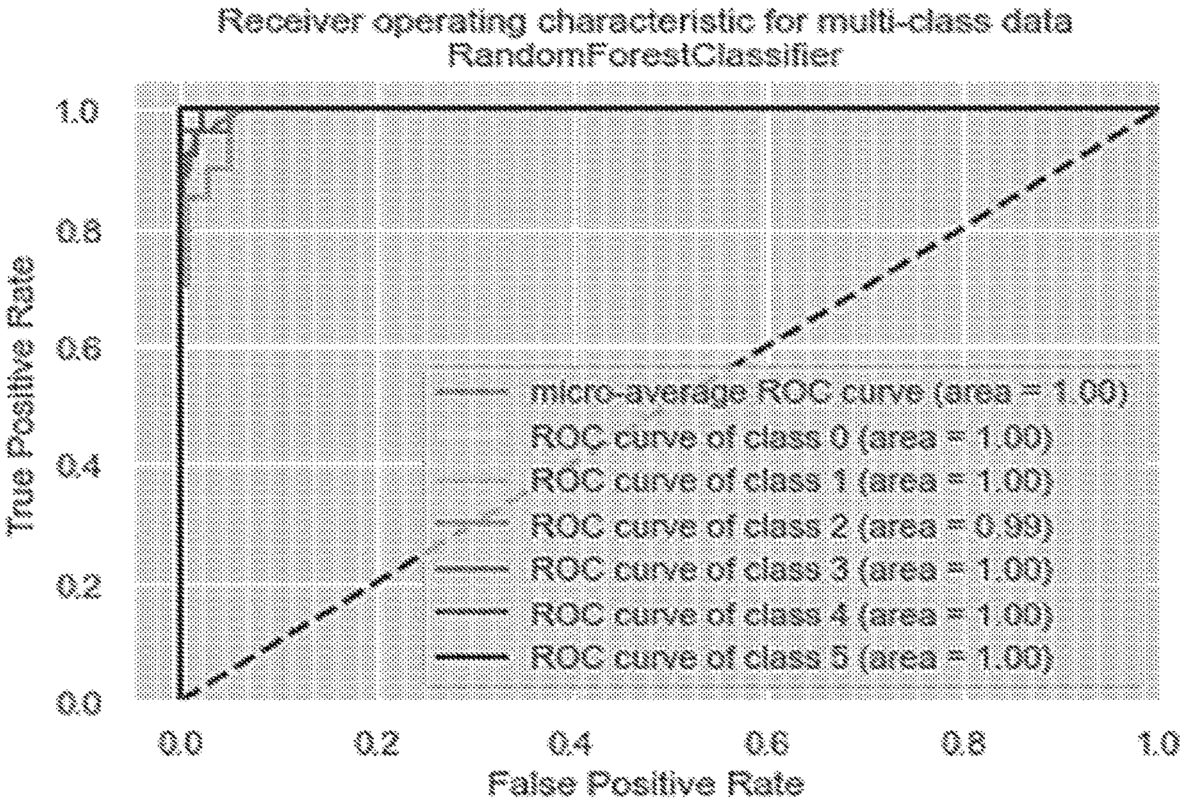

The Patients were clustered by machine learning (ML) into 6 subgroups using all genes found within the top 30 third generation gene modules most significantly correlated to the yes/no presence of anti.dsDNA as inputs into ML. FIGS. 11A-C shows the ROC curve for separating lupus samples into sub-clusters using 3 algorithms, e.g. Logistic Regression (LOG), Support Vector Machine (SVM), and Random Forest (RF). Classification metrics including sensitivity, specificity, precision, accuracy, and f1-score on 20% validation set are shown in Table 2A) LOG, Table 2B) SVM, and Table 2C) RF.

TABLE 2A

Classification metrics for separating lupus patients into 6 sub-clusters using LOG.

| Cluster | Sensitivity | Specificity | Precision | Accuracy | f1-score |
|---|---|---|---|---|---|
| 0 | 0.89 | 0.99 | 0.89 | 0.98 | 0.89 |
| 1 | 0.94 | 1 | 1 | 0.99 | 0.969072 |
| 2 | 0.85 | 1 | 1 | 0.98 | 0.918919 |
| 3 | 0.92 | 0.99 | 0.96 | 0.98 | 0.939574 |
| 4 | 1 | 0.96 | 0.82 | 0.96 | 0.901099 |
| 5 | 1 | 1 | 1 | 1 | 1 |

TABLE 2B

Classification metrics for separating lupus patients into 6 sub-clusters using

| Cluster | Sensitivity | Specificity | Precision | Accuracy | f1-score |
|---|---|---|---|---|---|
| 0 | 0.94 | 0.97 | 0.81 | 0.97 | 0.870171 |
| 1 | 0.88 | 1 | 1 | 0.98 | 0.93617 |
| 2 | 0.85 | 0.99 | 0.94 | 0.98 | 0.892737 |
| 3 | 0.84 | 0.99 | 0.95 | 0.97 | 0.89162 |
| 4 | 1 | 0.96 | 0.82 | 0.96 | 0.901099 |
| 5 | 1 | 1 | 1 | 1 | 1 |

TABLE 2C

Classification metrics for separating lupus patients into 6 sub-clusters using RF.

| Cluster | Sensitivity | Specificity | Precision 1 | Accuracy | f1-score |
|---|---|---|---|---|---|
| 0 | 0.89 | 0.99 | 0.89 | 0.98 | 0.89 |
| 1 | 0.88 | 1 | 1 | 0.98 | 0.93617 |
| 2 | 0.85 | 0.99 | 0.94 | 0.98 | 0.892737 |
| 3 | 0.92 | 0.99 | 0.96 | 0.98 | 0.939574 |
| 4 | 1 | 0.96 | 0.82 | 0.96 | 0.901099 |
| 5 | 1 | 0.99 | 0.98 | 0.99 | 0.989899 |

REFERENCES 1. ncbi.nlm.nih.gov/geo/query/acc.cgi?acc-GSE88884
2. brainarray.mbni.med.umich.edu/Brainarray/Database/CustomCDF/24.0.0/ense.asp
3. de Leeuw, Wim C et al. "Salvaging Affymetrix probes after probe-level re-annotation." *BMC research notes vol.* 1 66. 19 Aug. 2008, doi:10.1186/1756-0500-1-66
4. Jean Wu and Rafael Irizarry with contributions from James MacDonald Jeff Gentry (2020). germa: Background Adjustment Using Sequence Information. R package version 2.62.0.
5. BioMart and Bioconductor: a powerful link between biological databases and microarray data analysis. Steffen Durinck, Yves Moreau, Arek Kasprzyk, Sean Davis, Bart De Moor, Alvis Brazma and Wolfgang Huber, Bioinformatics 21, 3439-3440 (2005)
6. Langfelder P and Horvath S, WGCNA: an R package for weighted correlation network analysis. BMC Bioinformatics 2008, 9:559 doi:10.1186/1471-2105-9-559
7. Kevin Blighe and Aaron Lun (2020). PCAtools: PCAtools: Everything Principal Components Analysis. R package version 2.2.0. github.com/kevinblighe/PCAtools
8. Gu, Z. (2016) Complex heatmaps reveal patterns and correlations in multidimensional genomic data. Bioinformatics.
9. Maechler, M., Rousseeuw, P., Struyf, A., Hubert, M., Hornik, K. (2021). cluster: Cluster Analysis Basics and Extensions. R package version 2.1.1.
10. Barabasí, Albert-László, Bonabeau, Eric. "Scale-Free Networks." *Scientific American*, vol. 288, no. 5, Scientific American, a division of Nature America, Inc., 2003, pp. 60-69, jstor.org/stable/26060284.
11. Ravasz, E. (2002). Hierarchical Organization of Modularity in Metabolic Networks. Science, 297 (5586), 1551-1555. doi:10.1126/science. 1073374
12. Yip, A. M., Horvath, S. Gene network interconnectedness and the generalized topological overlap measure. *BMC Bioinformatics* 8, 22 (2007). doi.org/10.1186/1471-2105-8-22

14. Peter Langfelder, Bin Zhang, Steve Horvath, Defining clusters from a hierarchical cluster tree: the Dynamic Tree Cut package for R, *Bioinformatics*, Volume 24, Issue 5, 1 Mar. 2008, Pages 719-720, doi.org/10.1093/bioinformatics/btm563
15. Shannon P, Markiel A, Ozier O, Baliga N S, Wang J T, Ramage D, Amin N, Schwikowski B, Ideker T. Cytoscape: a software environment for integrated models of biomolecular interaction networks. Genome Research 2003 November; 13(11):2498-504
16. Emily Greenfest-Allen, Jean-Philippe Cartailler, Mark A. Magnuson, Christian J. Stoeckert Jr. iterativeWGCNA: iterative refinement to improve module detection from WGCNA co-expression networks. bioRxiv 234062; doi: doi.org/10.1101/234062
17. github-wiki-see.page/m/schultzelab/useful_chunks/wiki/CoCena-pipeline
18. Won-Min Song and Bin Zhang (2018). MEGENA: Multiscale Clustering of Geometrical Network. R package version 1.3.7. CRAN.R-project.org/package=MEGENA
19. Tumminello, M., Aste, T., Di Matteo, T., & Mantegna, R. N. (2005). *A tool for filtering information in complex systems*. Proceedings of the National Academy of Sciences of the United States of America, 102(30), 10421-10426.
20. Christoph Glur (2020). data.tree: General Purpose Hierarchical Data Structure. R package version 1.0.0. CRAN.R-project.org/package=data.tree
21. Plotly Technologies Inc. Title: Collaborative data science Publisher: Plotly Technologies Inc. Place of publication: Montréal, QC Date of publication: 2015 URL: plot.ly
22. Raivo Kolde (2019). pheatmap: Pretty Heatmaps. R package version 1.0.12. CRAN.R project.org/package=pheatmap
23. Mckenzie, A. T., Katsyv, I., Song, W M. et al. DGCA: A comprehensive R package for Differential Gene Correlation Analysis. *BMC Syst Biol* 10, 106 (2016). doi.org/10.1186/s12918-016-0349-1
24. Xin Shao, Jie Liao, Chengyu Li, Xiaoyan Lu, Junyun Cheng, Xiaohui Fan, CellTalkDB: a manually curated database of ligand-receptor interactions in humans and mice, *Briefings in Bioinformatics*, Volume 22, Issue 4, July 2021, bbaa269, doi.org/10.1093/bib/bbaa269
25. H. Wickham. ggplot2: Elegant Graphics for Data Analysis. Springer-Verlag New York, 2016.
26. Hänzelmann, S., Castelo, R. and Guinney, A. GSVA: gene set variation analysis for microarray and RNA-seq data. BMC Bioinformatics, 14:7, 2013.
27. Scikit-learn: Machine Learning in Python, Pedregosa et al., JMLR 12, pp. 2825-2830, 2011.
28. Thomas A Caswell, Michael Droettboom, Antony Lee, Elliott Sales de Andrade, John Hunter, Eric Firing, Tim Hoffmann, Jody Klymak, David Stansby, Nelle Varoquaux, Jens Hedegaard Nielsen, Benjamin Root, Ryan May, Phil Elson, Jouni K. Seppänen, Darren Dale, Jae-Joon Lee, Damon McDougall, Andrew Straw, Paul Ivanov. (2021). matplotlib/matplotlib: REL: v3.3.4 (v3.3.4). Zenodo. doi.org/10.5281/zenodo.4475376.

Example 2: Unsupervised Clustering of Genes to Identify Subgroups of Inflammatory Arthritis Patients Gene expression in fine-needle synovial biopsy samples from patients with early inflammatory arthritis was analyzed. Microarray data from the synovium of patients with early inflammatory arthritis underwent background correction and GCRMA normalization resulting in log 2 intensity values compiled into an expression set object (e-set). Three samples were removed for lack of patient metadata. As the ILLUM-1 analysis (Example 1), probes not mapping to a known HGNC protein were discarded. Averaged gene expression rows were sorted by absolute value of descending row variance and the top 5,000 row variance (inflammatory arthritis-top5k rowVar) genes among the remaining 17 early inflammatory arthritis samples were selected for further analysis. CodeR-BP technique was used to elucidate gene module enrichment patterns, regulatory networks, differentially expressed gene pairs within and between modules unique to each ancestral background, and identify specific subsets of patients, relationships with specific clinical or laboratory traits, from the study. The inflammatory arthritis top5k rowVar genes were clustered based on Gene Co-Expression Network (GCN) generation and multi-scale module formation. Planar filtered network (PFN) generated requiring a correlation false discovery rate (FDR)<0.2, and ensuing multi-scale gene modules were generated using the public R MEGENA package. Minimum module size was 20 genes. A formal tree object was created to establish module lineage and assign module lineage names. Gene modules were assigned "lineage" names based on their multi-scale dependency from the root module. Module eigengenes (MEs) were calculated as the first principle component of the gene expression values within each module. Modules with MEs significantly correlated with MMP2 cohort (more inflammatory arthritis) as well as with serologic numerical assay measurements of inflammation including erythrocyte sedimentation rate (ESR), blood C-Reactive Protein level (CRP) were identified. The significant gene clusters which were subsequently overlapped with various gene function signature lists selected from Immune/Inflammation-Scope (I-Scope), Tissue-Scope (T-Scope) and Biologically Informed Gene Clustering (BIG-C). I-Scope, T-Scope and BIG-C are functional aggregation tools for characterizing immune cells by type, tissue cells by type, and biologically classifying large groupings of genes, respectively. I-Scope categorizes gene transcripts into a possible 28 hematopoietic cell categories based on matching transcripts known to mark various types of immune/inflammatory cells. T-Scope is an additional aggregation tool to characterize cell types found in specific tissues. BIG-C sorts genes into 53 different groups based on their most probable biological function and/or cellular or subcellular localization. These transcriptomic signatures, along with others derived from literature [Catalina et al. 2020, Owen et al. 2020, Kingsmore et al. 2021, Daamen et al. 2021, & Culemann et al. 2019] and gene ontology (GO) terms, were utilized to calculate enrichment statistics among gene co-expression modules. Odds ratios and overlap p-values were calculated using Fisher's Exact test in R using the fisher.test( ) function. Statistical significance was obtained using an adjusted p-value≤0.2. Co-expression modules were annotated according to the top overlapping functional category with the most significant p-value and a minimum of 4 overlapping genes. In the absence of significant overlaps, "unknown" was the assigned annotation.

Figure 12:
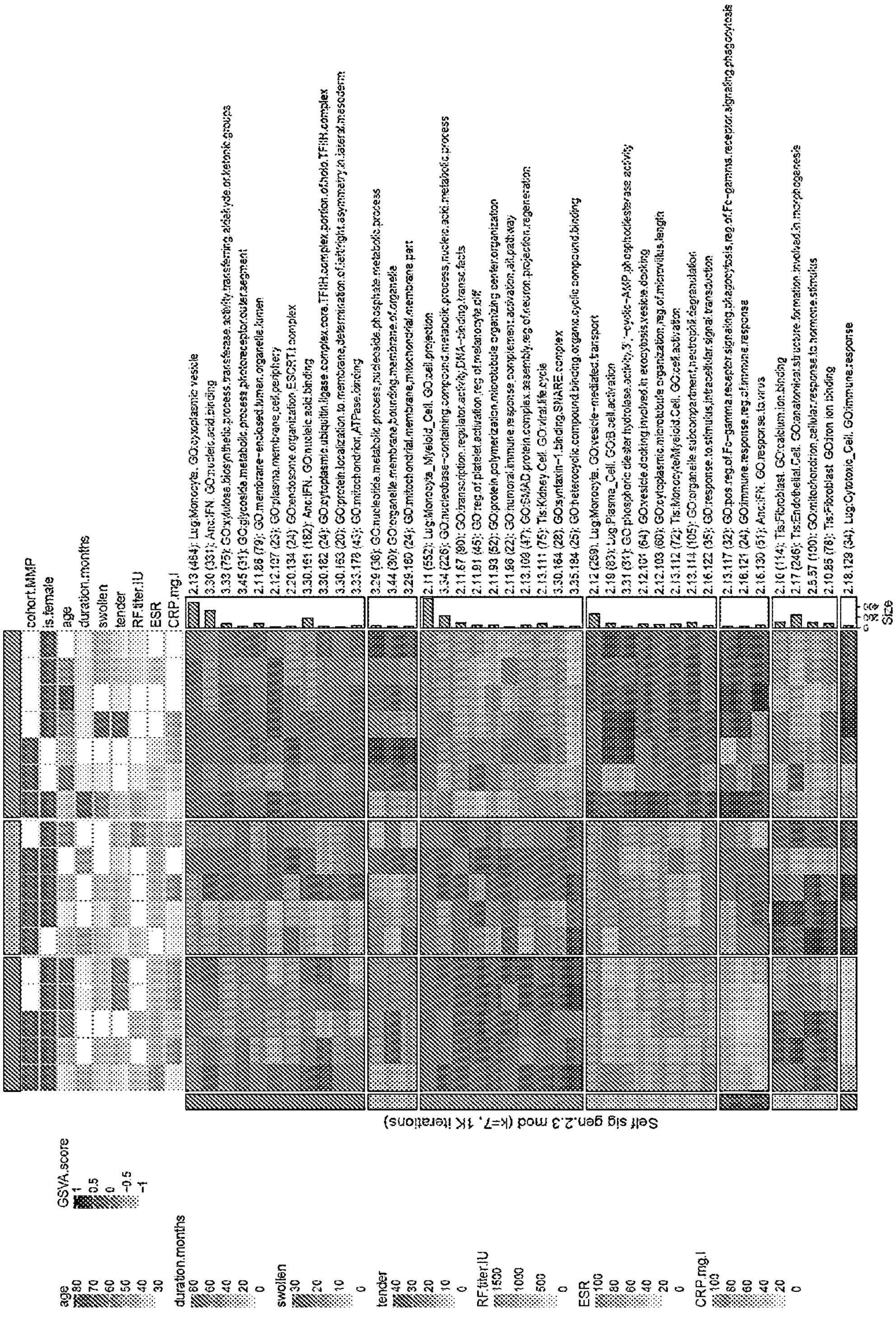
FIG. 12: Correlation of the significant genes modules (obtained from clustering inflammatory arthritis-top5k rowVar genes) with cohort (more inflammatory arthritis) and serologic features of inflammation including erythrocyte sedimentation rate (ESR) and C-Reactive Protein level (CRP).
Figures 1, 12:
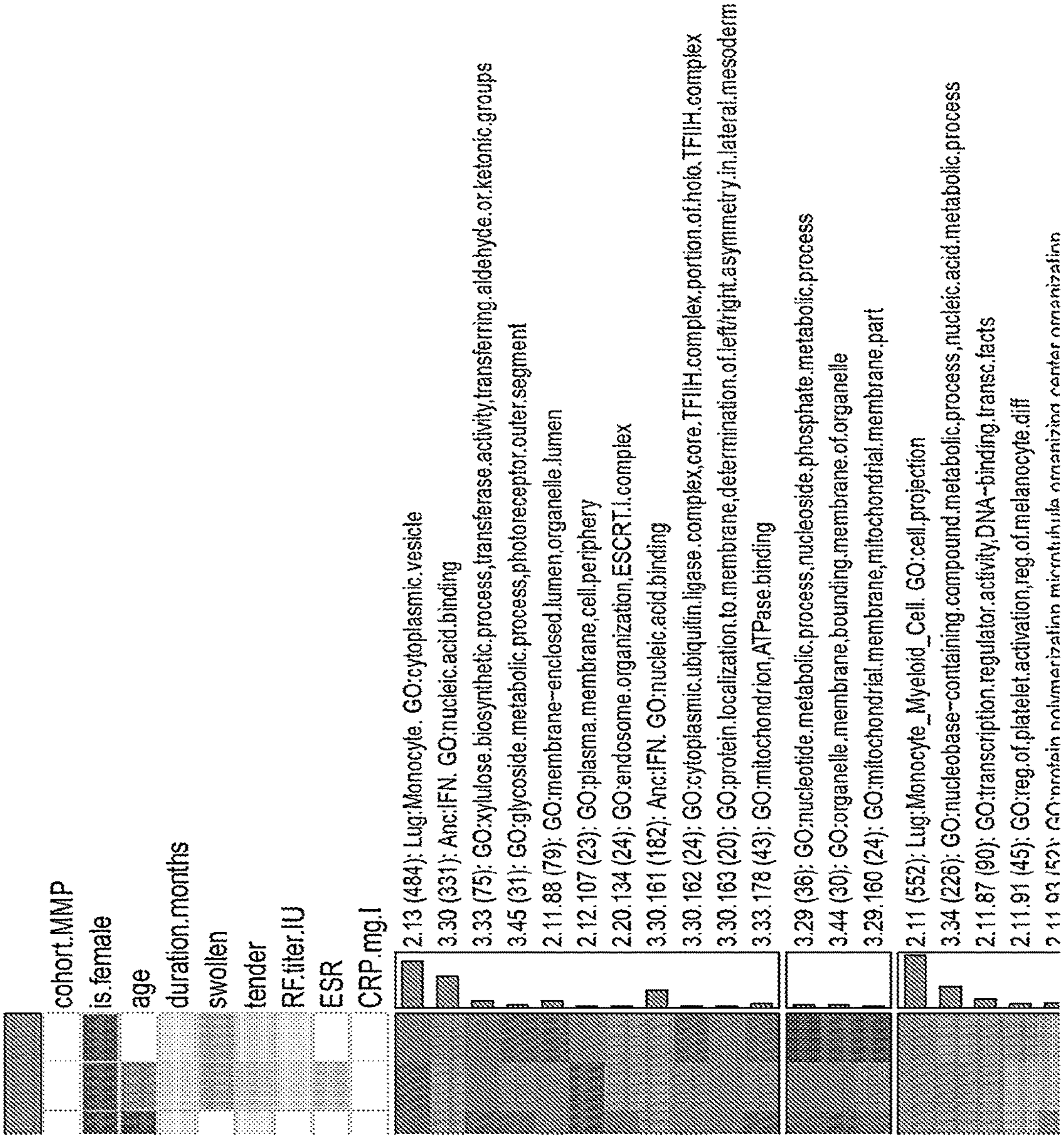
Figures 2, 12:
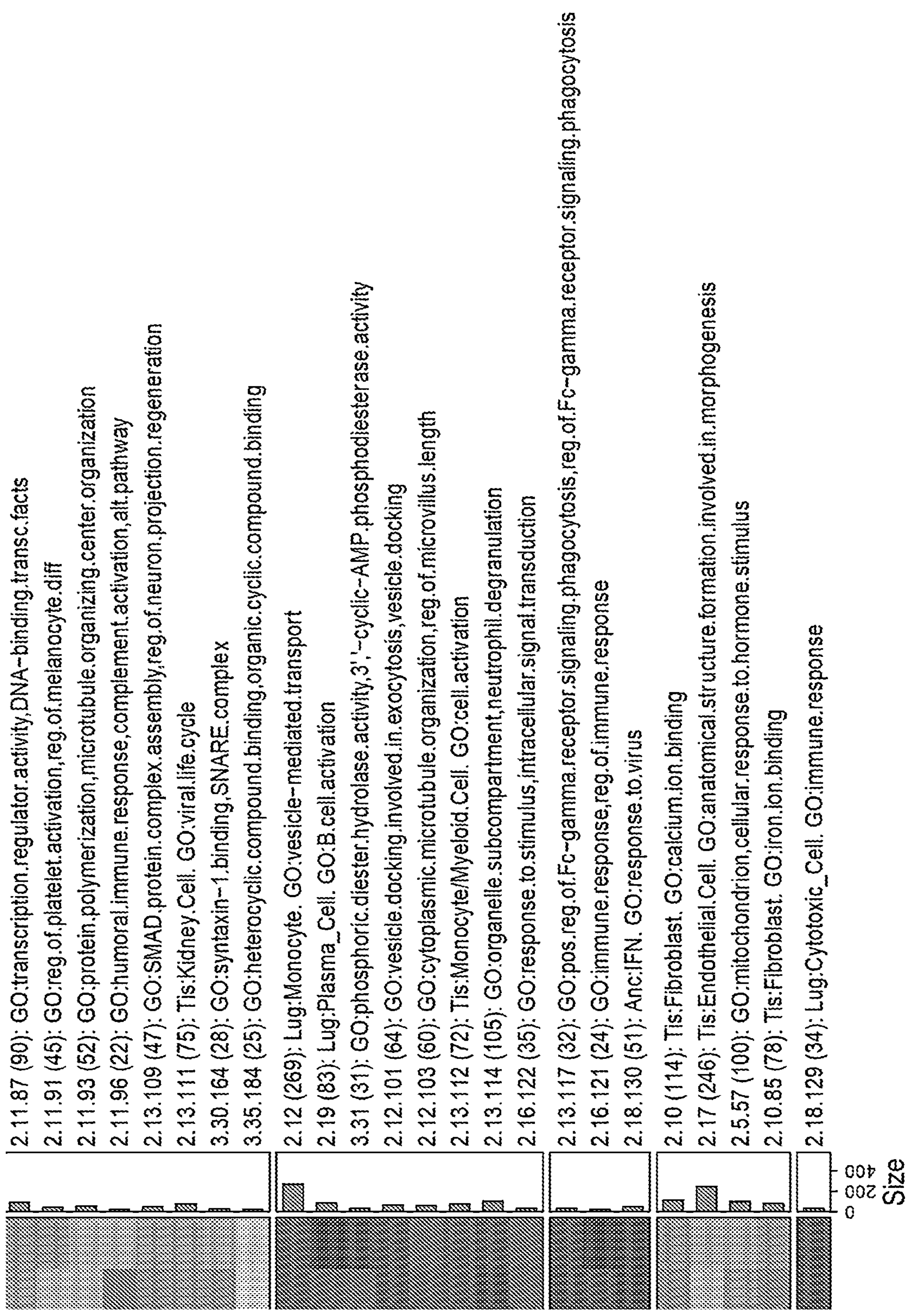
Figures 3, 12:
Figures 4, 12:
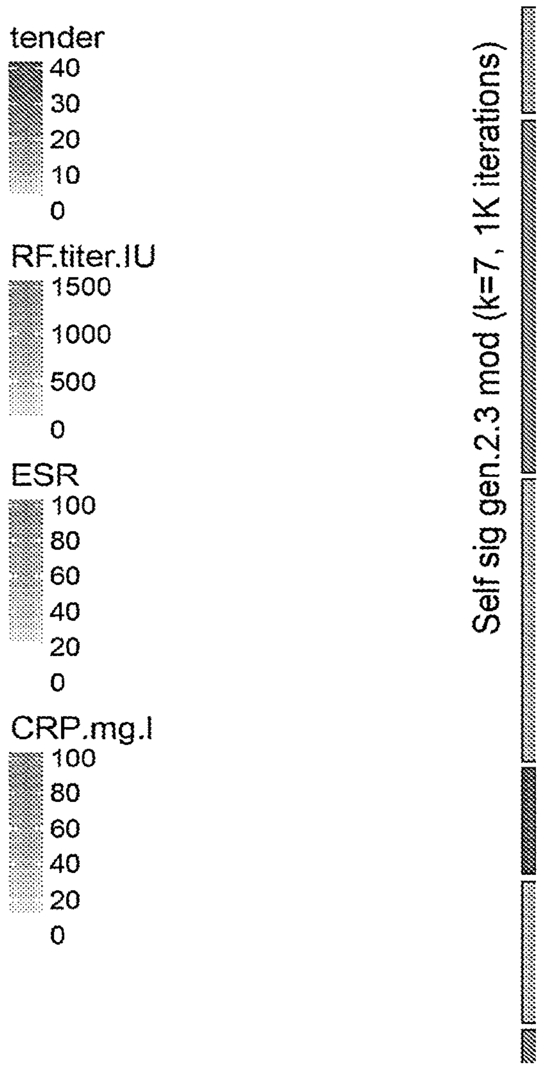

FIG. 12 shows correlation of the significant gene clusters with cohort (more inflammatory arthritis) as well as with serologic features of inflammation including ESR and CRP. Numbers in each box indicate significant correlation coefficients (p.val<0.2). Column labels indicate clinical features.

Rows were labeled by gene module names indicating lineage name, module size (number of genes, in parenthesis), followed by top significant cell type or functional annotations (e.g. functional characterization) selected from LuGENE, AMPEL Ancestry, AMPEL Tissue, BIG-C and GO (signature overlap >=4 gene symbols, Fisher's p.val<0.2). Table 3A, lists the significant gene clusters (e.g. significantly correlated modules to anti.dsDNA) shown in FIG. 12, size (e.g. number of genes within the modules) of the clusters, functional characterization groups (e.g. categories) from LuGENE, AMPEL Ancestry, AMPEL Tissue, BIG-C and GO that overlaps with the clusters and respective p values, and functional annotation of the clusters. Table 3B lists the genes in the significant gene clusters of Table 3A.

TABLE 3A

The significant gene clusters as shown in FIG. 12.

| lineage | mod.size | annot.luGENE | annot.luGENE.overlaps | annot.ancestry | annot.ancestry.overlaps | annot.tissue | annot.tissue.overlaps |
|---|---|---|---|---|---|---|---|
| 2.10 | 114 | | | | | Fibroblast | 8 |
| 2.10.85 | 78 | | | | | Fibroblast | 5 |
| 2.11 | 552 | Monocyte__Myeloid__Cell | 9 | | | | |
| 2.11.87 | 90 | | | | | | |
| 2.11.88 | 79 | | | | | | |
| 2.11.91 | 45 | | | | | | |
| 2.11.93 | 52 | | | | | | |
| 2.11.96 | 22 | | | | | | |
| 2.12 | 269 | Monocyte | 4 | | | | |
| 2.12.101 | 64 | | | | | | |
| 2.12.103 | 60 | | | | | | |
| 2.12.107 | 23 | | | | | | |
| 2.13 | 484 | Monocyte | 5 | | | | |
| 2.13.109 | 47 | | | | | | |
| 2.13.111 | 75 | | | | | Kidney Cell | 4 |
| 2.13.112 | 72 | | | | | Monocyte/ Myeloid Cell | 5 |
| 2.13.114 | 105 | | | | | | |
| 2.13.117 | 32 | | | | | | |
| 2.16.121 | 24 | | | | | | |
| 2.16.122 | 35 | | | | | | |
| 2.17 | 246 | | | | | Endothelial Cell | 6 |
| 2.18.129 | 34 | Cytotoxic__Cell | 8 | | | | |
| 2.18.130 | 51 | | | IFN | 19 | | |
| 2.19 | 83 | Plasma__Cell | 6 | | | | |
| 2.20.134 | 24 | | | | | | |
| 2.5.57 | 100 | | | | | | |
| 3.29 | 36 | | | | | | |
| 3.29.160 | 24 | | | | | | |
| 3.30 | 331 | | | IFN | 5 | | |
| 3.30.161 | 182 | | | IFN | 4 | | |
| 3.30.162 | 24 | | | | | | |
| 3.30.163 | 20 | | | | | | |
| 3.30.164 | 28 | | | | | | |
| 3.31 | 31 | | | | | | |
| 3.33 | 75 | | | | | | |
| 3.33.178 | 43 | | | | | | |
| 3.34 | 226 | | | | | | |
| 3.35.184 | 25 | | | | | | |
| 3.44 | 30 | | | | | | |
| 3.45 | 31 | | | | | | |

| Lineage | annot.BIG.C | annot.BIG.C.overlaps | annot.GO.1 | annot.GO.1.coverage |
|---|---|---|---|---|
| 2.10 | | | calciumion binding | 0.123 |
| 2.10.85 | | | iron ion binding | 0.064 |
| 2.11 | | | cell projection | 0.174 |
| 2.11.87 | Cytoskeleton | 12 | transcription regulator activity | 0.222 |
| 2.11.88 | mRNA-Processing | 5 | membrane-enclosed lumen | 0.506 |
| 2.11.91 | Transcription-Factors | 7 | regulation of platelet activation | 0.067 |
| 2.11.93 | Transporters | 4 | protein polymerization | 0.115 |
| 2.11.96 | | | humoral immune response | 0.136 |
| 2.12 | | | vesicle-mediated transport | 0.23 |
| 2.12.101 | Cytoskeleton | 7 | vesicle docking involved in exocytosis | 0.047 |
| 2.12.103 | Mitochondria-General | 4 | cytoplasmic microtubule organization | 0.05 |
| 2.12.107 | Immune-Cell-Surface | 4 | plasma membrane | 0.739 |
| 2.13 | | | cytoplasmic vesicle | 0.231 |
| 2.13.109 | | | SMAD protein complex assembly | 0.043 |

TABLE 3A-continued

| The significant gene clusters as shown in FIG. 12. | | | | |
|---|---|---|---|---|
| 2.13.111 | | | viral life cycle | 0.093 |
| 2.13.112 | | | cell activation | 0.319 |
| 2.13.114 | Lysosome | 7 | organelle subcompartment | 0.238 |
| 2.13.117 | | | positive regulation of Fc-gamma receptor signaling pathway involved in phagocytosis | 0.062 |
| 2.16.121 | Immune-Cell-Surface | 6 | immune response | 0.542 |
| 2.16.122 | General-Cell-Surface | 7 | response to stimulus | 0.829 |
| 2.17 | | | anatomical structure formation involved in morphogenesis | 0.22 |
| 2.18.129 | | | immune response | 0.588 |
| 2.18.130 | | | response to virus | 0.412 |
| 2.19 | | | B cell activation | 0.108 |
| 2.20.134 | | | endosome organization | 0.083 |
| 2.5.57 | Mitochondria-General | 10 | mitochondrion | 0.23 |
| 3.29 | Secreted-and-ECM | 4 | nucleotide metabolic process | 0.222 |
| 3.29.160 | | | mitochondrial membrane | 0.292 |
| 3.30 | | | nucleic acid binding | 0.266 |
| 3.30.161 | | | nucleic acid binding | 0.308 |
| 3.30.162 | | | cytoplasmic ubiquitin ligase complex | 0.042 |
| 3.30.163 | Unknown | 4 | protein localization to membrane | 0.2 |
| 3.30.164 | Transcription-Factors | 4 | syntaxin-1 binding | 0.071 |
| 3.31 | Unknown | 4 | phosphoric diester hydrolase activity | 0.097 |
| 3.33 | Ubiquitylation-and-Sumoylation | 5 | xylulose biosynthetic process | 0.027 |
| 3.33.178 | Unknown | 7 | mitochondrion | 0.302 |
| 3.34 | Unknown | 39 | nucleobase-containing compound metabolic process | 0.403 |
| 3.35.184 | Transcription-Factors | 4 | heterocyclic compound binding | 0.56 |
| 3.44 | Golgi | 5 | organelle membrane | 0.4 |
| 3.45 | | | glycoside metabolic process | 0.065 |

| Lineage | annot.GO.2 | annot.GO.2.coverage | annot.figures |
|---|---|---|---|
| 2.10 | positive regulation of megakaryocyte differentiation | 0.026 | Tis: Fibroblast. GO: calcium.ion.binding |
| 2.10.85 | endothelial cell development | 0.051 | Tis: Fibroblast. GO: iron.ion.binding |
| 2.11 | cytoplasmic region | 0.054 | Lug: Monocyte__Myeloid__Cell. GO: cell.projection |
| 2.11.87 | DNA-binding transcription factor activity | 0.189 | GO: transcription.regulator.activity, DNA-binding.transc.facts |
| 2.11.88 | organelle lumen | 0.506 | GO: membrane-enclosed.lumen, organelle.lumen |
| 2.11.91 | regulation of melanocyte differentiation | 0.044 | GO: reg.of.platelet.activation, reg.of.melanocyte.diff |
| 2.11.93 | microtubule organizing center organization | 0.077 | GO: protein.polymerization, microtubule.organizing.center.organization |
| 2.11.96 | complement activation, alternative pathway | 0.091 | GO: humoral.immune.response, complement.activation, alt. pathway |
| 2.12 | leukocyte activation involved in immune response | 0.119 | Lug: Monocyte. GO: vesicle-mediated.transport |
| 2.12.101 | vesicle docking | 0.047 | GO: vesicle.docking.involved.in.exocytosis, vesicle.docking |
| 2.12.103 | regulation of microvillus length | 0.033 | GO: cytoplasmic.microtubule.organization, reg.of.microvillus.length |
| 2.12.107 | cell periphery | 0.739 | GO: plasma.membrane, cell.periphery |
| 2.13 | leukocyte mediated immunity | 0.118 | Lug: Monocyte. GO: cytoplasmic.vesicle |

TABLE 3A-continued

| The significant gene clusters as shown in FIG. 12. | | | |
|---|---|---|---|
| 2.13.109 | regulation of neuron projection regeneration | 0.043 | GO: SMAD.protein.complex.assembly, reg.of.neuron.projection.regeneration |
| 2.13.111 | establishment of vesicle localization | 0.08 | Tis: Kidney.Cell. GO: viral.life.cycle |
| 2.13.112 | leukocyte mediated immunity | 0.25 | Tis: Monocyte/Myeloid.Cell. GO: cell.activation |
| 2.13.114 | neutrophil degranulation | 0.143 | GO: organelle.subcompartment, neutrophil.degranulation |
| 2.13.117 | regulation of Fc-gamma receptor signaling pathway involved in phagocytosis | 0.062 | GO: pos.reg.of.Fc-gamma.receptor.signaling.phagocytosis, reg.of.Fc-gamma.receptor.signaling.phagocytosis |
| 2.16.121 | regulation of immune response | 0.375 | GO: immune.response, reg.of.immune.response |
| 2.16.122 | intracellular signal transduction | 0.486 | GO: response.to.stimulus, intracellular.signal.transduction |
| 2.17 | vasculature development | 0.187 | Tis: Endothelial.Cell. GO: anatomical.structureformation.in-volved.in.morphogenesis |
| 2.18.129 | lymphocyte activation | 0.382 | Lug: Cytotoxic__Cell. GO: immune.response |
| 2.18.130 | defense response to virus | 0.392 | Anc: IFN. GO: response.to.virus |
| 2.19 | adaptive immune response | 0.108 | Lug: Plasma__Cell. GO: B.cell.activation |
| 2.20.134 | ESCRTI complex | 0.042 | GO: endosome.organization, ESCRT.I.complex |
| 2.5.57 | cellular response to hormone stimulus | 0.16 | GO: mitochondrion, cellular.response.to.hormone.stimulus |
| 3.29 | nucleoside phosphate metabolic process | 0.222 | GO: nucleotide.metabolic.process, nucleoside.phosphate.metabolic.process |
| 3.29.160 | mitochondrial membrane part | 0.208 | GO: mitochondrial.membrane, mitochondrial.membrane.part |
| 3.30 | RNA processing | 0.082 | Anc: IFN. GO: nucleic acid.binding |
| 3.30.161 | catalytic complex | 0.143 | Anc: IFN. GO: nucleic.acid.binding |
| 3.30.162 | core TFIIH complex portion of holo TFIIH complex | 0.042 | GO: cytoplasmic.ubiquitin.ligase.complex, core.TFIIH.complex.portion.of.holo.TFIIH.complex |
| 3.30.163 | determination of left/right asymmetry in lateral mesoderm | 0.05 | GO: protein.localization.to.membrane, determination.of.left/ right.asymmetry.in.lateral.mesoderm |
| 3.30.164 | SNARE complex | 0.071 | GO: syntaxin-1.binding, SNARE.complex |
| 3.31 | 3',5'-cyclic-AMP phosphodiesterase activity | 0.065 | GO: phosphoric.diester.hydrolase.activity, 3',-cyclic-AMP.phosphodiesterase.activity |
| 3.33 | transferase activity, transferring aldehyde or ketonic groups | 0.027 | GO: xylulose.biosynthetic.process, transferase.activity, transferring.aldehyde.or.ketonic.groups |
| 3.33.178 | ATPase binding | 0.07 | GO: mitochondrion, ATPase.binding |
| 3.34 | nucleic acid metabolic process | 0.376 | GO: nucleobase-containing.compound.metabolic.process, nucleic.acid.metabolic.process |
| 3.35.184 | organic cyclic compound binding | 0.56 | GO: heterocyclic.compound.binding, organic.cyclic.compound.binding |
| 3.44 | bounding membrane of organelle | 0.333 | GO: organelle.membrane, bounding.membrane.of.organelle |
| 3.45 | photoreceptor outer segment | 0.065 | GO: glycoside.metabolic.process, photoreceptor.outer.segment |

TABLE 3B

The genes within the significant gene clusters, listed in Table 3A. (3966 Genes Listed by: Gene Symbol | Gen 2 Module | Gene Description | RowVariance | Gen 3 Module ||)

ABLIM3 | 2.10 | actin binding LIM protein family member 3 | 0.918107416 | 2.10.85 || ACTG2 | 2.10 | actin, gamma 2, smooth muscle, enteric | 2.681393002 | 2.10.86 || ADAMTS9-AS2 | 2.10 | ADAMTS9 antisense RNA 2 | 0.354316084 | 2.10.86 || ADGRL3 | 2.10 | adhesion G protein-coupled receptor L3 | 0.321441803 | 2.10.85 || AIF1L | 2.10 | allograft inflammatory factor 1-like | 1.238551409 | 2.10.85 || AOC1 | 2.10 | amine oxidase, copper containing 1 | 0.472162092 | 2.10.86 || ATP8A1 | 2.10 | ATPase phospholipid transporting 8A1 | 1.060010383 | 2.10.85 || B4GAT1 | 2.10 | beta-1,4-glucuronyltransferase 1 | 0.373823148 | 2.10.86 || BCAM | 2.10 | basal cell adhesion molecule (Lutheran blood group) | 0.512976091 | 2.10.86 || BEND7 | 2.10 | BEN domain containing 7 | 0.563042785 | 2.10.86 || BMP2K | 2.10 | BMP2 inducible kinase | 0.426726609 | 2.10.85 || BMX | 2.10 | BMX non-receptor tyrosine kinase | 0.561782814 | 2.10.86 || C10orf128 | 2.10 | chromosome 10 open reading frame 128 | 0.544142073 | 2.10.85 || C1QTNF2 | 2.10 | C1q and tumor necrosis factor related protein 2 | 1.27557369 | 2.10.85 || C1QTNF3 | 2.10 | C1q and tumor necrosis factor related protein 3 | 1.779854009 | 2.10.85 || C2orf88 | 2.10 | chromosome 2 open reading frame 88 | 0.553845983 | 2.10.86 || CCDC146 | 2.10 | coiled-coil domain containing 146 | 1.196073898 | 2.10.85 || CEP70 | 2.10 | centrosomal protein 70 kDa | 0.341250967 | 2.10.85 || CHL1 | 2.10 | cell adhesion molecule L1 like | 0.568801659 | 2.10.85 || CKB | 2.10 | creatine kinase, brain | 0.340419667 | 2.10.85 || CLDN5 | 2.10 | claudin 5 | 0.67316544 | 2.10.85 || CNKSR3 | 2.10 | CNKSR family member 3 | 1.087384668 | 2.10.85 || CNN1 | 2.10 | calponin 1 | 1.226206206 | 2.10.86 || CRABP2 | 2.10 | cellular retinoic acid binding protein 2 | 1.179542489 | 2.10.85 || CSN1S1 | 2.10 | casein alpha s1 | 11.00008899 | 2.10.85 || CSRP2 | 2.10 | cysteine and glycine rich protein 2 | 0.847806183 | 2.10.85 || CX3CL1 | 2.10 | C-X3-C motif chemokine ligand 1 | 0.583778583 | 2.10.86 || CYP39A1 | 2.10 | cytochrome P450 family 39 subfamily A member 1 | 0.22957737 | 2.10.85 || CYP4X1 | 2.10 | cytochrome P450 family 4 subfamily X member 1 | 1.492758688 | 2.10.85 || DMTN | 2.10 | dematin actin binding protein | 1.067084419 | 2.10.85 || DPY19L2 | 2.10 | dpy-19 like 2 (*C. elegans*) | 0.522178905 | 2.10.85 || EFHD1 | 2.10 | EF-hand domain family member D1 | 0.868032029 | 2.10.85 || EFNA1 | 2.10 | ephrin-A1 | 0.595345339 | 2.10.85 || EGFL6 | 2.10 | EGF like domain multiple 6 | 2.909166402 | 2.10.85 || ELOVL7 | 2.10 | ELOVL fatty acid elongase 7 | 1.099867015 | 2.10.85 || EMX2 | 2.10 | empty spiracles homeobox 2 | 0.368974286 | 2.10.86 || FAM118A | 2.10 | family with sequence similarity 118 member A | 0.533069348 | 2.10.86 || FAM69A | 2.10 | family with sequence similarity 69 member A | 0.75771855 | 2.10.85 || FASN | 2.10 | fatty acid synthase | 2.156334083 | 2.10.85 || FBLN2 | 2.10 | fibulin 2 | 1.910088947 | 2.10.85 || FBN1 | 2.10 | fibrillin 1 | 0.329511475 | 2.10.85 || FCGR1B | 2.10 | Fc fragment of IgG receptor Ib | 1.963637721 | 2.10.86 || GALNT15 | 2.10 | polypeptide N-acetylgalactosaminyltransferase 15 | 1.404681672 | 2.10.85 || GDF10 | 2.10 | growth differentiation factor 10 | 1.037748667 | 2.10.86 || GFOD1 | 2.10 | glucose-fructose oxidoreductase domain containing 1 | 0.244455616 | 2.10.85 || GLIPR1 | 2.10 | GLI pathogenesis related 1 | 0.579992726 | 2.10.86 || GPC4 | 2.10 | glypican 4 | 0.574899 | 2.10.86 || GPER1 | 2.10 | G protein-coupled estrogen receptor 1 | 0.251087757 | 2.10.86 || GPR146 | 2.10 | G protein-coupled receptor 146 | 0.269563856 | 2.10.85 || GPRC5B | 2.10 | G protein-coupled receptor class C group 5 member B | 1.059447382 | 2.10.85 || GYPC | 2.10 | glycophorin C (Gerbich blood group) | 0.231357572 | 2.10.85 || HEY2 | 2.10 | hes related family bHLH transcription factor with YRPW motif 2 | 0.853286389 | 2.10.86 || IMMP2L | 2.10 | inner mitochondrial membrane peptidase subunit 2 | 0.303389131 | 2.10.85 || ITGA8 | 2.10 | integrin subunit alpha 8 | 0.490647066 | 2.10.86 || KCNK6 | 2.10 | potassium two pore domain channel subfamily K member 6 | 0.280116384 | 2.10.85 || KL | 2.10 | klotho | 0.456734788 | 2.10.85 || KNSTRN | 2.10 | kinetochore-localized astrin/SPAG5 binding protein | 0.475362014 | 2.10.86 || LGI4 | 2.10 | leucine-rich repeat LGI family member 4 | 0.420987386 | 2.10.85 || LMOD1 | 2.10 | leiomodin 1 | 1.765563041 | 2.10.86 || LRRK2 | 2.10 | leucine-rich repeat kinase 2 | 0.38013275 | 2.10.86 || MGST2 | 2.10 | microsomal glutathione S-transferase 2 | 0.302643467 | 2.10.85 || MS4A7 | 2.10 | membrane spanning 4-domains A7 | 0.299950563 | 2.10.85 || MTMR11 | 2.10 | myotubularin related protein 11 | 0.216755965 | 2.10.86 || MYO5C | 2.10 | myosin VC | 1.284655035 | 2.10.85 || NAA30 | 2.10 | N(alpha)-acetyltransferase 30, NatC catalytic subunit | 0.220156535 | 2.10.85 || NHSL1 | 2.10 | NHS like 1 | 1.237192591 | 2.10.85 || NPNT | 2.10 | nephronectin | 0.946837793 | 2.10.85 || NPR1 | 2.10 | natriuretic peptide receptor 1 | 0.469798282 | 2.10.85 || NPY1R | 2.10 | neuropeptide Y receptor Y1 | 2.188509459 | 2.10.85 || NR3C2 | 2.10 | nuclear receptor subfamily 3 group C member 2 | 1.259023048 | 2.10.86 || NTM | 2.10 | neurotrimin | 0.724804606 | 2.10.85 || OSR1 | 2.10 | odd-skipped related transciption factor 1 | 1.020581264 | 2.10.86 || P4HA3 | 2.10 | prolyl 4-hydroxylase subunit alpha 3 | 0.547012038 | 2.10.85 || PAMR1 | 2.10 | peptidase domain containing associated with muscle regeneration 1 | 0.659003856 | 2.10.85 || PARD3B | 2.10 | par-3 family cell polarity regulator beta | 0.254279079 | 2.10.85 || PCDH19 | 2.10 | protocadherin 19 | 0.320377378 | 2.10.86 || PDE2A | 2.10 | phosphodiesterase 2A | 0.717288025 | 2.10.85 || PECAM1 | 2.10 | platelet/endothelial cell adhesion molecule 1 | 0.378678836 | 2.10.85 || PLCB4 | 2.10 | phospholipase C beta 4 | 1.608628586 | 2.10.85 || PLP1 | 2.10 | proteolipid protein 1 | 1.048854407 | 2.10.85 || PPP1R12B | 2.10 | protein phosphatase 1 regulatory subunit 12B | 0.990958928 | 2.10.86 || PPP1R14A | 2.10 | protein phosphatase 1 regulatory inhibitor subunit 14A | 0.810386166 | 2.10.85 || PPP2R5A | 2.10 | protein phosphatase 2 regulatory subunit B', alpha | 0.363039828 | 2.10.85 || PRR5 | 2.10 | proline rich 5 | 0.404725987 | 2.10.85 || PRRG3 | 2.10 | proline rich Gla (G-carboxyglutamic acid) 3 (transmembrane) | 0.45436329 | 2.10.86 || PXMP2 | 2.10 | peroxisomal membrane protein 2 | 0.295405095 | 2.10.85 || RAB7B | 2.10 | RAB7B, member RAS oncogene family | 0.244838109 | 2.10.86 || RBPMS2 | 2.10 | RNA binding protein with multiple splicing 2 | 0.22140223 | 2.10.86 || RPIA | 2.10 | ribose 5-phosphate isomerase A | 0.327943173 | 2.10.85 || SAMSN1 | 2.10 | SAM domain, SH3 domain and nuclear localization signals 1 | 0.373414953 | 2.10.85 || SCAI | 2.10 | suppressor of cancer cell invasion | 0.34960713 | 2.10.85 || SCAPER | 2.10 | S-phase cyclin A-associated protein in the ER | 0.233490435 | 2.10.86 || SCD | 2.10 | stearoyl-CoA desaturase (delta-9-desaturase) | 2.135434836 | 2.10.85 || SCIN | 2.10 | scinderin | 0.608164379 | 2.10.85 || SERPINI1 | 2.10 | serpin peptidase inhibitor, clade I (neuroserpin), member 1 | 0.827771811 | 2.10.86 || SH3BGRL2 | 2.10 | SH3 domain binding glutamate rich protein like 2 | 1.247498167 | 2.10.85 || SLC38A6 | 2.10 | solute carrier family 38 member 6 | 0.264391916 | 2.10.85 || SNCG | 2.10 | synuclein gamma | 0.847912157 | 2.10.85 || STAT5B | 2.10 | signal transducer and activator of transcription 5B | 0.260382058 | 2.10.85 || STK39 | 2.10 | serine/threonine kinase 39 | 0.92253157 | 2.10.85 || STRADB | 2.10 | STE20-related kinase adaptor beta | 0.463501365 | 2.10.85 || TACR1 | 2.10 | tachykinin receptor 1 | 0.927781846 | 2.10.85 ||

TABLE 3B-continued

The genes within the significant gene clusters, listed in Table 3A. (3966 Genes Listed by: Gene Symbol | Gen 2 Module | Gene Description | RowVariance | Gen 3 Module ||)

TBC1D8 | 2.10 | TBC1 domain family member 8 | 0.420615476 | 2.10.85 || TCEAL7 | 2.10 | transcription elongation factor A like 7 | 0.89570466 | 2.10.85 || TESC | 2.10 | tescalcin | 0.222983729 | 2.10.86 || TF | 2.10 | transferrin | 3.804873105 | 2.10.85 || TIMD4 | 2.10 | T-cell immunoglobulin and mucin domain containing 4 | 4.181045228 | 2.10.85 || TLE1 | 2.10 | transducin like enhancer of split 1 | 0.29581844 | 2.10.85 || TNFSF8 | 2.10 | tumor necrosis factor superfamily member 8 | 0.537943722 | 2.10.85 || TUB | 2.10 | tubby bipartite transcription factor | 0.596297969 | 2.10.86 || VRK3 | 2.10 | vaccinia related kinase 3 | 0.224945685 | 2.10.85 || WFS1 | 2.10 | wolframin ER transmembrane glycoprotein | 0.423762466 | 2.10.85 || WTIP | 2.10 | Wilms tumor 1 interacting protein | 0.250272167 | 2.10.86 || ZFPM2 | 2.10 | zinc finger protein, FOG family member 2 | 1.097936248 | 2.10.86 || ABLIM3 | 2.10.85 | actin binding LIM protein family member 3 | 0.918107416 | 2.10.85 || ADGRL3 | 2.10.85 | adhesion G protein-coupled receptor L3 | 0.321441803 | 2.10.85 || AIF1L | 2.10.85 | allograft inflammatory factor 1-like | 1.238551409 | 2.10.85 || ATP8A1 | 2.10.85 | ATPase phospholipid transporting 8A1 | 1.060010383 | 2.10.85 || BMP2K | 2.10.85 | BMP2 inducible kinase | 0.426726609 | 2.10.85 || C10orf128 | 2.10.85 | chromosome 10 open reading frame 128 | 0.544142073 | 2.10.85 || C1QTNF2 | 2.10.85 | C1q and tumor necrosis factor related protein 2 | 1.27557369 | 2.10.85 || C1QTNF3 | 2.10.85 | C1q and tumor necrosis factor related protein 3 | 1.779854009 | 2.10.85 || CCDC146 | 2.10.85 | coiled-coil domain containing 146 | 1.196073898 | 2.10.85 || CEP70 | 2.10.85 | centrosomal protein 70 kDa | 0.341250967 | 2.10.85 || CHL1 | 2.10.85 | cell adhesion molecule L1 like | 0.568801659 | 2.10.85 || CKB | 2.10.85 | creatine kinase, brain | 0.340419667 | 2.10.85 || CLDN5 | 2.10.85 | claudin 5 | 0.67316544 | 2.10.85 || CNKSR3 | 2.10.85 | CNKSR family member 3 | 1.087384668 | 2.10.85 || CRABP2 | 2.10.85 | cellular retinoic acid binding protein 2 | 1.179542489 | 2.10.85 || CSN1S1 | 2.10.85 | casein alpha s1 | 11.00008899 | 2.10.85 || CSRP2 | 2.10.85 | cysteine and glycine rich protein 2 | 0.847806183 | 2.10.85 || CYP39A1 | 2.10.85 | cytochrome P450 family 39 subfamily A member 1 | 0.22957737 | 2.10.85 || CYP4X1 | 2.10.85 | cytochrome P450 family 4 subfamily X member 1 | 1.492758688 | 2.10.85 || DMTN | 2.10.85 | dematin actin binding protein | 1.067084419 | 2.10.85 || DPY19L2 | 2.10.85 | dpy-19 like 2 (*C. elegans*) | 0.522178905 | 2.10.85 || EFHD1 | 2.10.85 | EF-hand domain family member D1 | 0.868032029 | 2.10.85 || EFNA1 | 2.10.85 | ephrin-A1 | 0.595345339 | 2.10.85 || EGFL6 | 2.10.85 | EGF like domain multiple 6 | 2.909166402 | 2.10.85 || ELOVL7 | 2.10.85 | ELOVL fatty acid elongase 7 | 1.099867015 | 2.10.85 || FAM69A | 2.10.85 | family with sequence similarity 69 member A | 0.75771855 | 2.10.85 || FASN | 2.10.85 | fatty acid synthase | 2.156334083 | 2.10.85 || FBLN2 | 2.10.85 | fibulin 2 | 1.910088947 | 2.10.85 || FBN1 | 2.10.85 | fibrillin 1 | 0.329511475 | 2.10.85 || GALNT15 | 2.10.85 | polypeptide N-acetylgalactosaminyltransferase 15 | 1.404681672 | 2.10.85 || GFOD1 | 2.10.85 | glucose-fructose oxidoreductase domain containing 1 | 0.244455616 | 2.10.85 || GPR146 | 2.10.85 | G protein-coupled receptor 146 | 0.269563856 | 2.10.85 || GPRC5B | 2.10.85 | G protein-coupled receptor class C group 5 member B | 1.059447382 | 2.10.85 || GYPC | 2.10.85 | glycophorin C (Gerbich blood group) | 0.231357572 | 2.10.85 || IMMP2L | 2.10.85 | inner mitochondrial membrane peptidase subunit 2 | 0.303389131 | 2.10.85 || KCNK6 | 2.10.85 | potassium two pore domain channel subfamily K member 6 | 0.280116384 | 2.10.85 || KL | 2.10.85 | klotho | 0.456734788 | 2.10.85 || LGI4 | 2.10.85 | leucine-rich repeat LGI family member 4 | 0.420987386 | 2.10.85 || MGST2 | 2.10.85 | microsomal glutathione S-transferase 2 | 0.302643467 | 2.10.85 || MS4A7 | 2.10.85 | membrane spanning 4-domains A7 | 0.299950563 | 2.10.85 || MYO5C | 2.10.85 | myosin VC | 1.284655035 | 2.10.85 || NAA30 | 2.10.85 | N(alpha)-acetyltransferase 30, NatC catalytic subunit | 0.220156535 | 2.10.85 || NHSL1 | 2.10.85 | NHS like 1 | 1.237192591 | 2.10.85 || NPNT | 2.10.85 | nephronectin | 0.946837793 | 2.10.85 || NPR1 | 2.10.85 | natriuretic peptide receptor 1 | 0.469798282 | 2.10.85 || NPY1R | 2.10.85 | neuropeptide Y receptor Y1 | 2.188509459 | 2.10.85 || NTM | 2.10.85 | neurotrimin | 0.724804606 | 2.10.85 || P4HA3 | 2.10.85 | prolyl 4-hydroxylase subunit alpha 3 | 0.547012038 | 2.10.85 || PAMR1 | 2.10.85 | peptidase domain containing associated with muscle regeneration 1 | 0.659003856 | 2.10.85 || PARD3B | 2.10.85 | par-3 family cell polarity regulator beta | 0.254279079 | 2.10.85 || PDE2A | 2.10.85 | phosphodiesterase 2A | 0.717288025 | 2.10.85 || PECAM1 | 2.10.85 | platelet/endothelial cell adhesion molecule 1 | 0.378678836 | 2.10.85 || PLCB4 | 2.10.85 | phospholipase C beta 4 | 1.608628586 | 2.10.85 || PLP1 | 2.10.85 | proteolipid protein 1 | 1.048854407 | 2.10.85 || PPP1R14A | 2.10.85 | protein phosphatase 1 regulatory inhibitor subunit 14A | 0.810386166 | 2.10.85 || PPP2R5A | 2.10.85 | protein phosphatase 2 regulatory subunit B', alpha | 0.363039828 | 2.10.85 || PRR5 | 2.10.85 | proline rich 5 | 0.404725987 | 2.10.85 || PXMP2 | 2.10.85 | peroxisomal membrane protein 2 | 0.295405095 | 2.10.85 || RPIA | 2.10.85 | ribose 5-phosphate isomerase A | 0.327943173 | 2.10.85 || SAMSN1 | 2.10.85 | SAM domain, SH3 domain and nuclear localization signals 1 | 0.373414953 | 2.10.85 || SCAI | 2.10.85 | suppressor of cancer cell invasion | 0.34960713 | 2.10.85 || SCD | 2.10.85 | stearoyl-CoA desaturase (delta-9-desaturase) | 2.135434836 | 2.10.85 || SCIN | 2.10.85 | scinderin | 0.608164379 | 2.10.85 || SH3BGRL2 | 2.10.85 | SH3 domain binding glutamate rich protein like 2 | 1.247498167 | 2.10.85 || SLC38A6 | 2.10.85 | solute carrier family 38 member 6 | 0.264391916 | 2.10.85 || SNCG | 2.10.85 | synuclein gamma | 0.847912157 | 2.10.85 || STAT5B | 2.10.85 | signal transducer and activator of transcription 5B | 0.260382058 | 2.10.85 || STK39 | 2.10.85 | serine/threonine kinase 39 | 0.92253157 | 2.10.85 || STRADB | 2.10.85 | STE20-related kinase adaptor beta | 0.463501365 | 2.10.85 || TACR1 | 2.10.85 | tachykinin receptor 1 | 0.927781846 | 2.10.85 || TBC1D8 | 2.10.85 | TBC1 domain family member 8 | 0.420615476 | 2.10.85 || TCEAL7 | 2.10.85 | transcription elongation factor A like 7 | 0.89570466 | 2.10.85 || TF | 2.10.85 | transferrin | 3.804873105 | 2.10.85 || TIMD4 | 2.10.85 | T-cell immunoglobulin and mucin domain containing 4 | 4.181045228 | 2.10.85 || TLE1 | 2.10.85 | transducin like enhancer of split 1 | 0.29581844 | 2.10.85 || TNFSF8 | 2.10.85 | tumor necrosis factor superfamily member 8 | 0.537943722 | 2.10.85 || VRK3 | 2.10.85 | vaccinia related kinase 3 | 0.224945685 | 2.10.85 || WFS1 | 2.10.85 | wolframin ER transmembrane glycoprotein | 0.423762466 | 2.10.85 || AASDH | 2.11 | aminoadipate-semialdehyde dehydrogenase | 0.460028186 | — || ABAT | 2.11 | 4-aminobutyrate aminotransferase | 0.459696688 | 2.11.91 || ABCD3 | 2.11 | ATP binding cassette subfamily D member 3 | 0.303894131 | 2.11.88 || ABI2 | 2.11 | abl-interactor 2 | 0.750557435 | 2.11.93 || ABI3BP | 2.11 | ABI family member 3 binding protein | 0.380939275 | 2.11.93 || ACADSB | 2.11 | acyl-CoA dehydrogenase, short/branched chain | 0.448305681 | 2.11.87 || ACOT7 | 2.11 | acyl-CoA thioesterase 7 | 1.191420448 | 2.11.88 || ACOX2 | 2.11 | acyl-CoA oxidase 2, branched chain | 0.589616328 | 2.11.87 || ADAM28 | 2.11 | ADAM metallopeptidase domain 28 | 4.175760629 | 2.11.94 ||

TABLE 3B-continued

The genes within the significant gene clusters, listed in Table 3A. (3966 Genes Listed by: Gene Symbol | Gen 2 Module | Gene Description | RowVariance | Gen 3 Module ||)

ADAMTS15 | 2.11 | ADAM metallopeptidase with thrombospondin type 1 motif 15 | 0.961050341 | 2.11.94 || ADAMTS5 | 2.11 | ADAM metallopeptidase with thrombospondin type 1 motif 5 | 0.787279475 | 2.11.91 || ADCY3 | 2.11 | adenylate cyclase 3 | 0.370864487 | 2.11.94 || ADCY9 | 2.11 | adenylate cyclase 9 | 0.329183235 | 2.11.94 || ADD3 | 2.11 | adducin 3 | 0.607985917 | 2.11.87 || AIG1 | 2.11 | androgen-induced 1 | 1.007814018 | 2.11.95 || AKR1A1 | 2.11 | aldo-keto reductase family 1, member A1 (aldehyde reductase) | 0.266734234 | 2.11.88 || ALDH18A1 | 2.11 | aldehyde dehydrogenase 18 family member A1 | 0.317919461 | 2.11.90 || ALDH3A2 | 2.11 | aldehyde dehydrogenase 3 family member A2 | 0.47984049 | 2.11.95 || AMIGO2 | 2.11 | adhesion molecule with Ig-like domain 2 | 0.814772914 | 2.11.87 || AMOTL1 | 2.11 | angiomotin like 1 | 0.402363786 | 2.11.95 || ANKRD36B | 2.11 | ankyrin repeat domain 36B | 0.705201592 | 2.11.88 || AOX1 | 2.11 | aldehyde oxidase 1 | 1.679142604 | 2.11.94 || AQP1 | 2.11 | aquaporin 1 (Colton blood group) | 0.523004709 | — || ARHGAP25 | 2.11 | Rho GTPase activating protein 25 | 0.653693319 | 2.11.94 || ARHGEF12 | 2.11 | Rho guanine nucleotide exchange factor 12 | 0.253338823 | 2.11.91 || ARNTL2 | 2.11 | aryl hydrocarbon receptor nuclear translocator like 2 | 0.494590322 | 2.11.96 || ARSK | 2.11 | arylsulfatase family member K | 0.245695698 | 2.11.94 || ATE1 | 2.11 | arginyltransferase 1 | 0.515901455 | — || ATL1 | 2.11 | atlastin GTPase 1 | 0.398278492 | 2.11.90 || ATOH8 | 2.11 | atonal bHLH transcription factor 8 | 0.342741943 | 2.11.92 || ATP2A3 | 2.11 | ATPase sarcoplasmic/endoplasmic reticulum Ca2+ transporting 3 | 0.539887479 | — || B3GNT5 | 2.11 | UDP-GlcNAc:betaGal beta-1,3-N-acetylglucosaminyltransferase 5 | 0.496099263 | 2.11.94 || BAX | 2.11 | BCL2-associated X protein | 0.286362311 | 2.11.88 || BBS10 | 2.11 | Bardet-Biedl syndrome 10 | 0.259991801 | 2.11.92 || BBX | 2.11 | bobby sox homolog (*Drosophila*) | 0.309003234 | — || BIRC7 | 2.11 | baculoviral IAP repeat containing 7 | 0.364114946 | 2.11.89 || BMP4 | 2.11 | bone morphogenetic protein 4 | 1.275566837 | 2.11.94 || BMPR1A | 2.11 | bone morphogenetic protein receptor type 1A | 0.613503708 | 2.11.87 || BNC2 | 2.11 | basonuclin 2 | 0.902943933 | 2.11.91 || BRAP | 2.11 | BRCA1 associated protein | 0.223831083 | — || BTN2A2 | 2.11 | butyrophilin subfamily 2 member A2 | 0.475629665 | 2.11.94 || C11orf96 | 2.11 | chromosome 11 open reading frame 96 | 1.09996502 | 2.11.95 || C12orf29 | 2.11 | chromosome 12 open reading frame 29 | 0.311949406 | 2.11.95 || C15orf48 | 2.11 | chromosome 15 open reading frame 48 | 9.470344982 | 2.11.94 || C17orf80 | 2.11 | chromosome 17 open reading frame 80 | 0.268113993 | 2.11.95 || C19orf68 | 2.11 | chromosome 19 open reading frame 68 | 0.454827829 | 2.11.88 || C22orf39 | 2.11 | chromosome 22 open reading frame 39 | 0.215432391 | 2.11.91 || C7 | 2.11 | complement component 7 | 5.235794833 | 2.11.96 || C7orf50 | 2.11 | chromosome 7 open reading frame 50 | 0.563034422 | 2.11.89 || C7orf55 | 2.11 | chromosome 7 open reading frame 55 | 0.668742837 | 2.11.87 || CADPS2 | 2.11 | Ca2+ dependent secretion activator 2 | 0.573610167 | 2.11.90 || CALD1 | 2.11 | caldesmon 1 | 0.418718877 | 2.11.91 || CAMLG | 2.11 | calcium modulating ligand | 0.285590664 | 2.11.96 || CASP6 | 2.11 | caspase 6 | 0.798729681 | 2.11.88 || CASR 2.11 | calcium sensing receptor | 0.229062214 | 2.11.89 || CAV1 | 2.11 | caveolin 1 | 0.398398443 | 2.11.95 || CBR1 | 2.11 | carbonyl reductase 1 | 0.34570911 | 2.11.88 || CCAR1 | 2.11 | cell division cycle and apoptosis regulator 1 | 0.31308275 | 2.11.88 || CCDC3 | 2.11 | coiled-coil domain containing 3 | 1.522689954 | 2.11.95 || CCSAP | 2.11 | centriole, cilia and spindle associated protein | 0.263171876 | 2.11.95 || CD248 | 2.11 | CD248 molecule | 0.68823608 | 2.11.91 || CD37 | 2.11 | CD37 molecule | 1.133372643 | 2.11.94 || CD38 | 2.11 | CD38 molecule | 2.150406121 | 2.11.88 || CD53 | 2.11 | CD53 molecule | 0.50285979 | 2.11.94 || CDC14B | 2.11 | cell division cycle 14B | 0.606848097 | 2.11.95 || CDC37L1 | 2.11 | cell division cycle 37-like 1 | 0.231469743 | 2.11.87 || CDC42BPA | 2.11 | CDC42 binding protein kinase alpha | 0.998600128 | 2.11.95 || CDKN3 | 2.11 | cyclin-dependent kinase inhibitor 3 | 0.895603292 | 2.11.90 || CDO1 | 2.11 | cysteine dioxygenase type 1 | 0.759959385 | 2.11.95 || CEBPA-AS1 | 2.11 | CEBPA antisense RNA 1 (head to head) | 0.219803491 | 2.11.88 || CEMP1 | 2.11 | cementum protein 1 | 0.327109293 | 2.11.88 || CEP126 | 2.11 | centrosomal protein 126 kDa | 1.892868245 | 2.11.88 || CEP164 | 2.11 | centrosomal protein 164 kDa | 0.955611752 | 2.11.88 || CEP290 | 2.11 | centrosomal protein 290 kDa | 0.263768045 | 2.11.87 || CEP57 | 2.11 | centrosomal protein 57 kDa | 0.366056851 | 2.11.91 || CEP85 | 2.11 | centrosomal protein 85 kDa | 0.383549817 | 2.11.93 || CFH | 2.11 | complement factor H | 0.713023953 | 2.11.96 || CILP | 2.11 | cartilage intermediate layer protein | 4.923465697 | 2.11.92 || CLASP1 | 2.11 | cytoplasmic linker associated protein 1 | 0.271094193 | 2.11.93 || CLOCK | 2.11 | clock circadian regulator | 0.293393216 | 2.11.87 || CMTM4 | 2.11 | CKLF like MARVEL transmembrane domain containing 4 | 0.314085805 | 2.11.94 || COG6 | 2.11 | component of oligomeric golgi complex 6 | 0.286369934 | 2.11.90 || COL27A1 | 2.11 | collagen type XXVII alpha 1 | 0.892869302 | 2.11.87 || COL7A1 | 2.11 | collagen type VII alpha 1 | 0.368213732 | 2.11.88 || CPA3 | 2.11 | carboxypeptidase A3 | 1.668080728 | 2.11.90 || CPE | 2.11 | carboxypeptidase E | 1.901786183 | 2.11.96 || CPVL | 2.11 | carboxypeptidase, vitellogenic like | 0.287188234 | 2.11.94 || CPXM2 | 2.11 | carboxypeptidase X (M14 family), member 2 | 0.709943449 | — || CSF2RA | 2.11 | colony stimulating factor 2 receptor alpha subunit | 0.606462659 | 2.11.95 || CTGF | 2.11 | connective tissue growth factor | 0.827377472 | 2.11.92 || CTSH | 2.11 | cathepsin H | 0.62741109 | 2.11.94 || CTSV | 2.11 | cathepsin V | 0.291857737 | 2.11.95 || CTU2 | 2.11 | cytosolic thiouridylase subunit 2 homolog (*S. pombe*) | 0.382667246 | 2.11.95 || CWC27 | 2.11 | CWC27 spliceosome associated protein homolog | 0.243405515 | 2.11.87 || CX3CR1 | 2.11 | chemokine (C-X3-C motif) receptor 1 | 1.892071056 | — || CXCR4 | 2.11 | chemokine (C-X-C motif) receptor 4 | 1.269143152 | 2.11.94 || CYB5R4 | 2.11 | cytochrome b5 reductase 4 | 0.392472681 | 2.11.94 || CYP26B1 | 2.11 | cytochrome P450 family 26 subfamily B member 1 | 2.559696531 | 2.11.92 || CYR61 | 2.11 | cysteine rich angiogenic inducer 61 | 2.036162468 | 2.11.95 || CYTH4 | 2.11 | cytohesin 4 | 0.614764481 | 2.11.94 || DAAM1 | 2.11 | dishevelled associated activator of morphogenesis 1 | 0.471280572 | 2.11.87 || DAB2 | 2.11 | Dab, mitogen-responsive phosphoprotein, homolog 2 (*Drosophila*) | 0.438747419 | 2.11.93 || DCBLD1 | 2.11 | discoidin, CUB and LCCL domain containing 1 | 0.229067276 | 2.11.92 || DCBLD2 | 2.11 | discoidin, CUB and LCCL domain containing 2 | 0.444713707 | 2.11.93 || DCLK2 | 2.11 | doublecortin like kinase 2 | 0.511160655 | 2.11.87 || DDR2 | 2.11 | discoidin domain receptor tyrosine kinase 2 | 0.942052657 | 2.11.87 || DDX10 | 2.11 | DEAD-box helicase 10 | 0.233683198 | 2.11.92 || DDX54 | 2.11 | DEAD-box helicase 54 | 0.613719873 | 2.11.88 || DESI1 | 2.11 | desumoylating isopeptidase 1 | 0.404636144 | 2.11.96 || DHRS4-AS1 | 2.11 | DHRS4 antisense RNA 1 | 0.23517016 | 2.11.95 || DHX33 | 2.11 | DEAH-box helicase 33 | 0.378118657 | 2.11.88 || DIAPH2 | 2.11 | diaphanous related formin 2 | 0.275314812 | 2.11.91 || DIO2 | 2.11 | deiodinase, iodothyronine, type II | 3.958061425 | 2.11.90 || DIP2C | 2.11 | disco interacting TABLE 3B-continued The genes within the significant gene clusters, listed in Table 3A. (3966 Genes Listed by: Gene Symbol | Gen 2 Module | Gene Description | RowVariance | Gen 3 Module ||)

protein 2 homolog C | 0.519361999 | 2.11.91 || DIXDC1 | 2.11 | DIX domain containing 1 | 0.759440001 | 2.11.87 || DLC1 | 2.11 | DLC1 Rho GTPase activating protein | 1.330005516 | 2.11.95 || DMXL2 | 2.11 | Dmx like 2 | 0.392168413 | 2.11.95 || DNAJB9 | 2.11 | DnaJ heat shock protein family (Hsp40) member B9 | 0.375758976 | 2.11.88 || DOHH | 2.11 | deoxyhypusine hydroxylase/monooxygenase | 0.423163335 | 2.11.94 || DPP4 | 2.11 | dipeptidyl peptidase 4 | 1.0578736 | 2.11.88 || DPY19L3 | 2.11 | dpy-19 like 3 (*C. elegans*) | 0.596164066 | 2.11.93 || DPY19L4 | 2.11 | dpy-19 like 4 (*C. elegans*) | 0.543100176 | 2.11.93 || DSPP | 2.11 | dentin sialophosphoprotein | 0.260053984 | 2.11.93 || DYNC2H1 | 2.11 | dynein cytoplasmic 2 heavy chain 1 | 0.277564418 | 2.11.90 || DYNC2LI1 | 2.11 | dynein cytoplasmic 2 light intermediate chain 1 | 0.626974122 | 2.11.87 || DZIP1L | 2.11 | DAZ interacting zinc finger protein 1 like | 0.475805534 | 2.11.94 || EBF1 | 2.11 | early B-cell factor 1 | 0.937984168 | 2.11.87 || EBF2 | 2.11 | early B-cell factor 2 | 3.351821547 | 2.11.87 || EBPL | 2.11 | emopamil binding protein like | 0.556331861 | 2.11.91 || EDEM2 | 2.11 | ER degradation enhancer, mannosidase alpha-like 2 | 0.286374549 | 2.11.88 || EDN1 | 2.11 | endothelin 1 | 0.394131287 | 2.11.94 || EFCAB7 | 2.11 | EF-hand calcium binding domain 7 | 0.460111073 | 2.11.93 || EFS | 2.11 | embryonal Fyn-associated substrate | 0.591158755 | 2.11.87 || EIF5A | 2.11 | eukaryotic translation initiation factor 5A | 5.16344018 | 2.11.95 || EIF5B | 2.11 | eukaryotic translation initiation factor 5B | 0.310760685 | 2.11.89 || EMSY | 2.11 | EMSY, BRCA2 interacting transcriptional repressor | 0.363617224 | 2.11.89 || EMX2OS | 2.11 | EMX2 opposite strand/antisense RNA | 0.226374468 | 2.11.94 || EPB41L2 | 2.11 | erythrocyte membrane protein band 4.1-like 2 | 0.261723475 | 2.11.92 || EPHA4 | 2.11 | EPH receptor A4 | 0.51724409 | 2.11.94 || EPS8 | 2.11 | epidermal growth factor receptor pathway substrate 8 | 0.248989987 | — || ERAP2 | 2.11 | endoplasmic reticulum aminopeptidase 2 | 5.584573823 | 2.11.95 || ERGIC1 | 2.11 | endoplasmic reticulum-golgi intermediate compartment 1 | 0.22486897 | 2.11.94 || ETNK1 | 2.11 | ethanolamine kinase 1 | 0.226392511 | — || EVA1C | 2.11 | eva-1 homolog C (*C. elegans*) | 1.030366337 | 2.11.96 || EVI2A | 2.11 | ecotropic viral integration site 2A | 0.468198362 | 2.11.94 || EXT1 | 2.11 | exostosin glycosyltransferase 1 | 0.376437861 | 2.11.93 || EYA4 | 2.11 | EYA transcriptional coactivator and phosphatase 4 | 0.759943865 | 2.11.87 || FAM107A | 2.11 | family with sequence similarity 107 member A | 1.51719541 | 2.11.94 || FAM122B | 2.11 | family with sequence similarity 122B | 0.290955827 | — || FAM179B | 2.11 | family with sequence similarity 179 member B | 0.306610698 | 2.11.93 || FAM210B | 2.11 | family with sequence similarity 210 member B | 0.277177641 | 2.11.87 || FAM228B | 2.11 | family with sequence similarity 228 member B | 0.349991862 | 2.11.96 || FAM92A1 | 2.11 | family with sequence similarity 92 member A1 | 0.634098775 | 2.11.91 || FANCL | 2.11 | Fanconi anemia complementation group L | 0.259473729 | 2.11.93 || FBLN5 | 2.11 | fibulin 5 | 1.139777302 | 2.11.96 || FBXL17 | 2.11 | F-box and leucine-rich repeat protein 17 | 0.321221777 | 2.11.87 || FBXO31 | 2.11 | F-box protein 31 | 0.378024398 | — || FCGR2A | 2.11 | Fc fragment of IgG receptor IIa | 0.53215917 | 2.11.94 || FCGR2C | 2.11 | Fc fragment of IgG receptor IIc (gene/pseudogene) | 1.154315254 | 2.11.94 || FERMT3 | 2.11 | fermitin family member 3 | 0.485470904 | 2.11.94 || FEZ1 | 2.11 | fasciculation and elongation protein zeta 1 | 1.316610022 | 2.11.94 || FGF13 | 2.11 | fibroblast growth factor 13 | 0.987877209 | 2.11.87 || FGF18 | 2.11 | fibroblast growth factor 18 | 0.690756108 | 2.11.94 || FIGN | 2.11 | fidgetin | 1.045218876 | 2.11.88 || FKBP7 | 2.11 | FK506 binding protein 7 | 0.484285465 | 2.11.90 || FKBP9 | 2.11 | FK506 binding protein 9 | 0.41759953 | — || FLJ20021 | 2.11 | uncharacterized LOC90024 | 0.284145227 | 2.11.93 || FLVCR2 | 2.11 | feline leukemia virus subgroup C cellular receptor family member 2 | 0.587439889 | 2.11.94 || FNDC3B | 2.11 | fibronectin type III domain containing 3B | 0.227687911 | 2.11.93 || FNDC4 | 2.11 | fibronectin type III domain containing 4 | 0.4953917 | 2.11.87 || FOCAD | 2.11 | focadhesin | 0.268845132 | 2.11.95 || FPR1 | 2.11 | formyl peptide receptor 1 | 0.886015891 | 2.11.93 || FUT5 | 2.11 | fucosyltransferase 5 | 0.385385121 | 2.11.93 || FYN | 2.11 | FYN proto-oncogene, Src family tyrosine kinase | 0.285535416 | 2.11.87 || GABRB2 | 2.11 | gamma-aminobutyric acid type A receptor beta2 subunit | 5.135305883 | 2.11.94 || GALNT1 | 2.11 | polypeptide N-acetylgalactosaminyltransferase 1 | 0.256250248 | 2.11.90 || GAREM1 | 2.11 | GRB2 associated regulator of MAPK1 subtype 1 | 1.00034877 | 2.11.93 || GEM | 2.11 | GTP binding protein overexpressed in skeletal muscle | 0.619526415 | 2.11.95 || GLDN | 2.11 | gliomedin | 2.746948959 | 2.11.92 || GLP1R | 2.11 | glucagon like peptide 1 receptor | 0.286795346 | 2.11.87 || GLT8D2 | 2.11 | glycosyltransferase 8 domain containing 2 | 0.75143036 | 2.11.90 || GMFG | 2.11 | glia maturation factor gamma | 0.45780896 | 2.11.93 || GMIP | 2.11 | GEM interacting protein | 0.715174351 | 2.11.94 || GNA11 | 2.11 | G protein subunit alpha 11 | 0.295970179 | 2.11.91 || GNA15 | 2.11 | G protein subunit alpha 15 | 0.448280239 | 2.11.95 || GNG12 | 2.11 | G protein subunit gamma 12 | 0.309818361 | 2.11.91 || GOLGA2 | 2.11 | golgin A2 | 0.458222426 | 2.11.93 || GOLIM4 | 2.11 | golgi integral membrane protein 4 | 0.322114154 | 2.11.93 || GPATCH1 | 2.11 | G-patch domain containing 1 | 0.219040373 | 2.11.96 || GPATCH4 | 2.11 | G-patch domain containing 4 | 0.31136234 | 2.11.89 || GPHN | 2.11 | gephyrin | 0.379120059 | 2.11.87 || GPR183 | 2.11 | G protein-coupled receptor 183 | 1.160733904 | 2.11.94 || GPR65 | 2.11 | G protein-coupled receptor 65 | 0.526628376 | 2.11.87 || GPSM2 | 2.11 | G-protein signaling modulator 2 | 0.564926901 | 2.11.91 || GPX8 | 2.11 | glutathione peroxidase 8 (putative) | 0.84832034 | 2.11.90 || GSAP | 2.11 | gamma-secretase activating protein | 0.663756338 | 2.11.94 || GSTT1 | 2.11 | glutathione S-transferase theta 1 | 1.747692966 | 2.11.91 || GTPBP2 | 2.11 | GTP binding protein 2 | 1.042769987 | 2.11.88 || GXYLT2 | 2.11 | glucoside xylosyltransferase 2 | 0.737361809 | 2.11.94 || HAMP | 2.11 | hepcidin antimicrobial peptide | 0.284354134 | 2.11.91 || HAUS6 | 2.11 | HAUS augmin like complex subunit 6 | 0.560054086 | 2.11.93 || HCLS1 | 2.11 | hematopoietic cell-specific Lyn substrate 1 | 0.522189768 | 2.11.94 || HDAC9 | 2.11 | histone deacetylase 9 | 0.408359818 | 2.11.94 || HEATR5A | 2.11 | HEAT repeat containing 5A | 0.352183612 | — || HES1 | 2.11 | hes family bHLH transcription factor 1 | 0.693985311 | 2.11.87 || HEY1 | 2.11 | hes related family bHLH transcription factor with YRPW motif 1 | 0.458956865 | 2.11.94 || HLA-DRB6 | 2.11 | major histocompatibility complex, class II, DR beta 6 (pseudogene) | 0.63924165 | 2.11.94 || HMGA1 | 2.11 | high mobility group AT-hook 1 | 0.760994377 | 2.11.95 || HOXA5 | 2.11 | homeobox A5 | 0.886096098 | 2.11.93 || HOXD8 | 2.11 | homeobox D8 | 0.399510556 | 2.11.94 || HS2ST1 | 2.11 | heparan sulfate 2-O-sulfotransferase 1 | 0.314728488 | — || HSPA5 | 2.11 | heat shock protein family A (Hsp70) member 5 | 0.255106633 | 2.11.95 || IBSP | 2.11 | integrin binding sialoprotein | 0.255171768 | 2.11.87 || ICAM3 | 2.11 | intercellular adhesion molecule 3 | 1.221039619 | — || IFT80 | 2.11 | intraflagellar transport 80 | 0.411958681 | 2.11.93 || IGDCC4 | 2.11 | immunoglobulin superfamily, DCC subclass, member 4 |

TABLE 3B-continued

The genes within the significant gene clusters, listed in Table 3A. (3966 Genes Listed by: Gene Symbol | Gen 2 Module | Gene Description | RowVariance | Gen 3 Module ||)

1.34717997 | 2.11.91 || IL18BP | 2.11 | interleukin 18 binding protein | 1.786824388 | 2.11.94 || IMPACT | 2.11 | impact RWD domain protein | 0.473801861 | — || INSR | 2.11 | insulin receptor | 1.130743908 | 2.11.88 || INTS2 | 2.11 | integrator complex subunit 2 | 0.310307903 | 2.11.88 || IRAK1BP1 | 2.11 | interleukin 1 receptor associated kinase 1 binding protein 1 | 0.384567859 | 2.11.88 || IRS1 | 2.11 | insulin receptor substrate 1 | 1.206137104 | 2.11.94 || ISYNA1 | 2.11 | inositol-3-phosphate synthase 1 | 0.467806734 | 2.11.88 || ITPR2 | 2.11 | inositol 1,4,5-trisphosphate receptor type 2 | 0.577070542 | 2.11.88 || IVNS1ABP | 2.11 | influenza virus NS1A binding protein | 0.302793942 | 2.11.88 || JPX | 2.11 | JPX transcript, XIST activator (non-protein coding) | 0.780111483 | 2.11.87 || KBTBD6 | 2.11 | kelch repeat and BTB domain containing 6 | 0.412701021 | 2.11.94 || KCNF1 | 2.11 | potassium voltage-gated channel modifier subfamily F member 1 | 0.22645375 | 2.11.89 || KCNJ2 | 2.11 | potassium voltage-gated channel subfamily J member 2 | 0.732493091 | 2.11.93 || KCNT2 | 2.11 | potassium sodium-activated channel subfamily T member 2 | 1.179764931 | 2.11.87 || KCTD1 | 2.11 | potassium channel tetramerization domain containing 1 | 0.4321372 | 2.11.94 || KCTD3 | 2.11 | potassium channel tetramerization domain containing 3 | 0.745709664 | 2.11.87 || KDELC2 | 2.11 | KDEL motif containing 2 | 0.344744974 | 2.11.91 || KIRREL | 2.11 | kin of IRRE like (*Drosophila*) | 0.51901249 | — || KITLG | 2.11 | KIT ligand | 1.097244876 | 2.11.91 || KIZ | 2.11 | kizuna centrosomal protein | 0.311161849 | 2.11.95 || KLHL20 | 2.11 | kelch like family member 20 | 0.472326564 | 2.11.88 || KLHL42 | 2.11 | kelch like family member 42 | 0.353682523 | 2.11.95 || KLHL6 | 2.11 | kelch like family member 6 | 1.730773716 | 2.11.94 || KLHL8 | 2.11 | kelch like family member 8 | 0.377497362 | 2.11.88 || KLK15 | 2.11 | kallikrein related peptidase 15 | 0.583177926 | 2.11.88 || KMT5A | 2.11 | lysine methyltransferase 5A | 0.451503802 | 2.11.87 || KPNA5 | 2.11 | karyopherin subunit alpha 5 | 0.471170469 | 2.11.88 || LACTB | 2.11 | lactamase beta | 0.523962336 | 2.11.94 || LAMP2 | 2.11 | lysosomal associated membrane protein 2 | 0.317829107 | 2.11.88 || LAMTOR4 | 2.11 | late endosomal/lysosomal adaptor, MAPK and MTOR activator 4 | 0.21450644 | 2.11.88 || LAPTM4B | 2.11 | lysosomal protein transmembrane 4 beta | 0.602776882 | 2.11.91 || LARP6 | 2.11 | La ribonucleoprotein domain family member 6 | 0.800145084 | 2.11.95 || LDOC1 | 2.11 | leucine zipper, down-regulated in cancer 1 | 0.429951968 | 2.11.95 || LEPROTL1 | 2.11 | leptin receptor overlapping transcript-like 1 | 0.369399864 | 2.11.87 || LGALS9 | 2.11 | lectin, galactoside-binding, soluble, 9 | 0.513488433 | 2.11.94 || LIMA1 | 2.11 | LIM domain and actin binding 1 | 0.25014224 | 2.11.95 || LIMCH1 | 2.11 | LIM and calponin homology domains 1 | 1.258866277 | 2.11.87 || LINC01139 | 2.11 | long intergenic non-protein coding RNA 1139 | 0.581493857 | 2.11.96 || LIPT1 | 2.11 | lipoyltransferase 1 | 0.344910038 | 2.11.91 || LOC101927027 | 2.11 | uncharacterized LOC101927027 | 0.275757716 | 2.11.87 || LOC146880 | 2.11 | Rho GTPase activating protein 27 pseudogene | 0.51948776 | 2.11.88 || LOC400043 | 2.11 | uncharacterized LOC400043 | 0.328282968 | 2.11.93 || LPAR1 | 2.11 | lysophosphatidic acid receptor 1 | 0.310764182 | 2.11.95 || LPXN | 2.11 | leupaxin | 0.914802675 | 2.11.94 || LYN | 2.11 | LYN proto-oncogene, Src family tyrosine kinase | 0.356572728 | 2.11.95 || LYRM5 | 2.11 | LYR motif containing 5 | 0.276852304 | 2.11.87 || LYRM7 | 2.11 | LYR motif containing 7 | 0.547635505 | 2.11.88 || LYZ | 2.11 | lysozyme | 0.298216054 | 2.11.87 || MAB21L2 | 2.11 | mab-21-like 2 (*C. elegans*) | 4.062089165 | 2.11.96 || MAGEH1 | 2.11 | MAGE family member H1 | 0.217957682 | 2.11.91 || MAN1C1 | 2.11 | mannosidase alpha class 1C member 1 | 0.702672171 | 2.11.95 || MAOB | 2.11 | monoamine oxidase B | 1.976978543 | 2.11.95 || MAP2K1 | 2.11 | mitogen-activated protein kinase kinase 1 | 0.243976669 | 2.11.90 || MAP9 | 2.11 | microtubule associated protein 9 | 1.228570929 | 2.11.87 || MAPKBP1 | 2.11 | mitogen-activated protein kinase binding protein 1 | 0.389266249 | 2.11.95 || MATK | 2.11 | megakaryocyte-associated tyrosine kinase | 1.377160924 | 2.11.87 || MBP | 2.11 | myelin basic protein | 0.578176871 | 2.11.96 || ME3 | 2.11 | malic enzyme 3, NADP(+)-dependent, mitochondrial | 0.307783143 | 2.11.92 || MED13 | 2.11 | mediator complex subunit 13 | 0.222155278 | 2.11.88 || METTL6 | 2.11 | methyltransferase like 6 | 0.254287019 | 2.11.87 || MKLN1 | 2.11 | muskelin 1 | 0.25163679 | 2.11.88 || MLLT3 | 2.11 | myeloid/lymphoid or mixed-lineage leukemia; translocated to, 3 | 0.364863776 | 2.11.93 || MMAA | 2.11 | methylmalonic aciduria (cobalamin deficiency) cblA type | 0.354714539 | 2.11.88 || MMP25 | 2.11 | matrix metallopeptidase 25 | 0.259601703 | 2.11.88 || MOCS2 | 2.11 | molybdenum cofactor synthesis 2 | 0.610107611 | 2.11.94 || MORC4 | 2.11 | MORC family CW-type zinc finger 4 | 1.154152263 | 2.11.92 || MPND | 2.11 | MPN domain containing | 0.254515893 | 2.11.88 || MR1 | 2.11 | major histocompatibility complex, class I-related | 0.267692959 | 2.11.88 || MRPL23 | 2.11 | mitochondrial ribosomal protein L23 | 0.305797447 | 2.11.88 || MRPS7 | 2.11 | mitochondrial ribosomal protein S7 | 0.380177879 | 2.11.88 || MRS2 | 2.11 | MRS2, magnesium transporter | 0.374654346 | 2.11.87 || MSRB3 | 2.11 | methionine sulfoxide reductase B3 | 0.992582706 | 2.11.95 || MTFP1 | 2.11 | mitochondrial fission process 1 | 0.298762142 | 2.11.87 || MTUS1 | 2.11 | microtubule associated tumor suppressor 1 | 0.566893205 | — || MUC3A | 2.11 | mucin 3A, cell surface associated | 0.86970088 | 2.11.89 || MYLK | 2.11 | myosin light chain kinase | 1.49867473 | 2.11.87 || MYO10 | 2.11 | myosin X | 0.814300842 | 2.11.95 || MYO1B | 2.11 | myosin IB | 0.476073037 | — || MYO6 | 2.11 | myosin VI | 0.6419066 | 2.11.91 || MYRF | 2.11 | myelin regulatory factor | 0.554442417 | 2.11.89 || NAA16 | 2.11 | N(alpha)-acetyltransferase 16, NatA auxiliary subunit | 0.423375126 | — || NAALADL1 | 2.11 | N-acetylated alpha-linked acidic dipeptidase-like 1 | 0.245776186 | 2.11.88 || NACC1 | 2.11 | nucleus accumbens associated 1 | 0.237676889 | 2.11.89 || NADK2 | 2.11 | NAD kinase 2, mitochondrial | 0.239248157 | 2.11.87 || NCKAP1 | 2.11 | NCK associated protein 1 | 0.271919447 | 2.11.95 || NDFIP2 | 2.11 | Nedd4 family interacting protein 2 | 0.4471862 | 2.11.94 || NECAP2 | 2.11 | NECAP endocytosis associated 2 | 0.218385326 | 2.11.94 || NEDD4 | 2.11 | neural precursor cell expressed, developmentally down-regulated 4, E3 ubiquitin protein ligase | 0.808755476 | 2.11.91 || NEK1 | 2.11 | NIMA related kinase 1 | 0.734884915 | 2.11.88 || NEK6 | 2.11 | NIMA related kinase 6 | 0.448948841 | 2.11.94 || NFKBIE | 2.11 | NFKB inhibitor epsilon | 0.526990652 | 2.11.94 || NLK | 2.11 | nemo-like kinase | 0.21872192 | 2.11.94 || NLRC4 | 2.11 | NLR family, CARD domain containing 4 | 0.578897082 | 2.11.87 || NOD2 | 2.11 | nucleotide binding oligomerization domain containing 2 | 1.301056187 | 2.11.95 || NOL12 | 2.11 | nucleolar protein 12 | 0.284900775 | 2.11.93 || NOX4 | 2.11 | NADPH oxidase 4 | 1.108116391 | 2.11.92 || NR2C1 | 2.11 | nuclear receptor subfamily 2 group C member 1 | 0.454975321 | 2.11.87 || NRG1 | 2.11 | neuregulin 1 | 0.368595639 | 2.11.89 || NT5C3B | 2.11 | 5'-nucleotidase, cytosolic IIIB | 0.244925717 | 2.11.95 || NUCKS1 | 2.11 | nuclear casein kinase and cyclin-dependent kinase substrate 1 | 0.898450913 | 2.11.88 || NUDT16 | 2.11 | nudix hydrolase 16 | 0.326143374 | 2.11.94 || NUDT6 | 2.11 | nudix hydrolase 6 |

TABLE 3B-continued

The genes within the significant gene clusters, listed in Table 3A. (3966 Genes Listed by: Gene Symbol | Gen 2 Module | Gene Description | RowVariance | Gen 3 Module ||)

0.484537329 | 2.11.87 || NUP133 | 2.11 | nucleoporin 133 kDa | 0.592055283 | — || ODC1 | 2.11 | ornithine decarboxylase 1 | 0.569456629 | — || OLFM1 | 2.11 | olfactomedin 1 | 1.358666772 | 2.11.95 || OLFML1 | 2.11 | olfactomedin like 1 | 0.689591651 | 2.11.95 || OSBPL5 | 2.11 | oxysterol binding protein like 5 | 0.273643339 | 2.11.89 || OSMR | 2.11 | oncostatin M receptor | 1.503278899 | 2.11.93 || PALD1 | 2.11 | phosphatase domain containing, paladin 1 | 0.555556096 | 2.11.95 || PARM1 | 2.11 | prostate androgen-regulated mucin-like protein 1 | 1.023653832 | 2.11.91 || PARVA | 2.11 | parvin alpha | 0.468790584 | 2.11.95 || PARVG | 2.11 | parvin gamma | 0.537607892 | 2.11.94 || PCDHB14 | 2.11 | protocadherin beta 14 | 1.252426102 | 2.11.93 || PDE10A | 2.11 | phosphodiesterase 10A | 0.593443067 | 2.11.93 || PDGFA | 2.11 | platelet derived growth factor subunit A | 0.773068746 | 2.11.94 || PDGFRA | 2.11 | platelet derived growth factor receptor alpha | 0.736213488 | 2.11.90 || PDZD8 | 2.11 | PDZ domain containing 8 | 0.372559184 | 2.11.94 || PHACTR2 | 2.11 | phosphatase and actin regulator 2 | 0.37221586 | 2.11.87 || PID1 | 2.11 | phosphotyrosine interaction domain containing 1 | 0.433982727 | 2.11.96 || PIGX | 2.11 | phosphatidylinositol glycan anchor biosynthesis class X | 0.294978944 | 2.11.88 || PIK3AP1 | 2.11 | phosphoinositide-3-kinase adaptor protein 1 | 0.385622164 | 2.11.94 || PLA2G12A | 2.11 | phospholipase A2 group XIIA | 0.445961327 | 2.11.87 || PLA2R1 | 2.11 | phospholipase A2 receptor 1 | 0.644370683 | 2.11.89 || PLAC9 | 2.11 | placenta specific 9 | 0.857845635 | 2.11.95 || PLCG2 | 2.11 | phospholipase C gamma 2 | 0.220766749 | — || PLEK | 2.11 | pleckstrin | 0.551911738 | 2.11.87 || PLEKHG4 | 2.11 | pleckstrin homology and RhoGEF domain containing G4 | 0.325898829 | 2.11.92 || PLEKHO1 | 2.11 | pleckstrin homology domain containing O1 | 0.614364413 | 2.11.94 || PLS3 | 2.11 | plastin 3 | 0.294103102 | 2.11.91 || PMP22 | 2.11 | peripheral myelin protein 22 | 0.313324977 | 2.11.92 || PNKD | 2.11 | paroxysmal nonkinesigenic dyskinesia | 0.245392908 | 2.11.95 || PPIC | 2.11 | peptidylprolyl isomerase C | 0.357138142 | 2.11.90 || PPM1H | 2.11 | protein phosphatase, Mg2+/Mn2+ dependent 1H | 0.613125859 | 2.11.89 || PPP1R37 | 2.11 | protein phosphatase 1 regulatory subunit 37 | 0.227052078 | 2.11.88 || PRDX1 | 2.11 | peroxiredoxin 1 | 0.316156677 | 2.11.88 || PRELP | 2.11 | proline/arginine-rich end leucine-rich repeat protein | 1.601044294 | 2.11.92 || PRICKLE2 | 2.11 | prickle planar cell polarity protein 2 | 0.782184554 | 2.11.96 || PRKG1 | 2.11 | protein kinase, cGMP-dependent, type I | 0.774538466 | 2.11.91 || PRMT6 | 2.11 | protein arginine methyltransferase 6 | 0.318595128 | 2.11.91 || PRRX2 | 2.11 | paired related homeobox 2 | 1.039433208 | 2.11.90 || PTBP2 | 2.11 | polypyrimidine tract binding protein 2 | 0.219911518 | 2.11.95 || PTGER3 | 2.11 | prostaglandin E receptor 3 | 1.554612837 | 2.11.89 || PTGES2 | 2.11 | prostaglandin E synthase 2 | 0.430878063 | 2.11.88 || PTPN14 | 2.11 | protein tyrosine phosphatase, non-receptor type 14 | 0.630354757 | 2.11.87 || PTPN7 | 2.11 | protein tyrosine phosphatase, non-receptor type 7 | 0.261209531 | 2.11.91 || PTPRG | 2.11 | protein tyrosine phosphatase, receptor type G | 0.965505574 | 2.11.91 || PTRF | 2.11 | polymerase I and transcript release factor | 0.401843121 | 2.11.95 || PURA | 2.11 | purine-rich element binding protein A | 0.261900751 | 2.11.87 || PUS3 | 2.11 | pseudouridylate synthase 3 | 0.42898479 | 2.11.94 || PYCARD | 2.11 | PYD and CARD domain containing | 0.25248098 | 2.11.94 || QSER1 | 2.11 | glutamine and serine rich 1 | 0.232034763 | 2.11.88 || RAB11FIP2 | 2.11 | RAB11 family interacting protein 2 (class I) | 0.371953995 | 2.11.88 || RAB23 | 2.11 | RAB23, member RAS oncogene family | 0.547504018 | 2.11.87 || RAB40B | 2.11 | RAB40B, member RAS oncogene family | 0.691557143 | 2.11.95 || RAI2 | 2.11 | retinoic acid induced 2 | 0.548407973 | 2.11.87 || RALBP1 | 2.11 | ralA binding protein 1 | 0.422724086 | 2.11.88 || RALGPS2 | 2.11 | Ral GEF with PH domain and SH3 binding motif 2 | 0.646081783 | — || RAMP2 | 2.11 | receptor (G protein-coupled) activity modifying protein 2 | 0.817071625 | — || RASAL3 | 2.11 | RAS protein activator like 3 | 0.536053481 | — || RASGRP2 | 2.11 | RAS guanyl releasing protein 2 | 0.253098453 | 2.11.91 || RASL10B | 2.11 | RAS like family 10 member B | 0.225353115 | 2.11.88 || RASSF4 | 2.11 | Ras association domain family member 4 | 0.577137313 | 2.11.95 || RBAK | 2.11 | RB associated KRAB zinc finger | 0.234868336 | 2.11.88 || RBM38 | 2.11 | RNA binding motif protein 38 | 0.649239844 | — || RBM43 | 2.11 | RNA binding motif protein 43 | 0.800925923 | — || RELL1 | 2.11 | RELT like 1 | 0.293016625 | 2.11.95 || RERGL | 2.11 | RERG like | 2.458315954 | 2.11.94 || REV3L | 2.11 | REV3 like, DNA directed polymerase zeta catalytic subunit | 0.376334466 | 2.11.92 || RFC4 | 2.11 | replication factor C subunit 4 | 0.345789189 | — || RGMB | 2.11 | repulsive guidance molecule family member b | 0.496642884 | 2.11.95 || RIN1 | 2.11 | Ras and Rab interactor 1 | 0.339814741 | 2.11.89 || RNASE6 | 2.11 | ribonuclease A family member k6 | 0.443789107 | — || RNASET2 | 2.11 | ribonuclease T2 | 0.455239506 | 2.11.94 || RND3 | 2.11 | Rho family GTPase 3 | 0.428249245 | 2.11.95 || RNF144B | 2.11 | ring finger protein 144B | 0.35329375 | 2.11.87 || RNF180 | 2.11 | ring finger protein 180 | 0.349359912 | 2.11.94 || ROBO1 | 2.11 | roundabout guidance receptor 1 | 0.513564066 | 2.11.95 || ROR1 | 2.11 | receptor tyrosine kinase-like orphan receptor 1 | 0.546233645 | — || RORA | 2.11 | RAR related orphan receptor A | 0.401012354 | 2.11.87 || RRAS2 | 2.11 | related RAS viral (r-ras) oncogene homolog 2 | 2.046008627 | 2.11.94 || RUNXIT1 | 2.11 | runt related transcription factor 1; translocated to, 1 (cyclin D related) | 1.548689058 | 2.11.87 || SACS | 2.11 | sacsin molecular chaperone | 0.485582191 | 2.11.93 || SAMD4A | 2.11 | sterile alpha motif domain containing 4A | 0.447671749 | 2.11.87 || SAP30 | 2.11 | Sin3A associated protein 30 kDa | 0.605909372 | 2.11.94 || SASH1 | 2.11 | SAM and SH3 domain containing 1 | 0.619338966 | 2.11.91 || SCNN1A | 2.11 | sodium channel epithelial 1 alpha subunit | 0.337628112 | 2.11.89 || SCO2 | 2.11 | SCO2 cytochrome c oxidase assembly protein | 0.762355096 | 2.11.94 || SDF2L1 | 2.11 | stromal cell derived factor 2 like 1 | 0.349428243 | 2.11.88 || SEC16B | 2.11 | SEC16 homolog B, endoplasmic reticulum export factor | 0.340832577 | 2.11.91 || SELP | 2.11 | selectin P | 1.790362768 | 2.11.91 || SEMA4A | 2.11 | semaphorin 4A | 0.365692765 | 2.11.87 || SEMA7A | 2.11 | semaphorin 7A (John Milton Hagen blood group) | 0.302560808 | 2.11.88 || SEPT8 | 2.11 | septin 8 | 0.267651618 | 2.11.93 || SERPINB1 | 2.11 | serpin peptidase inhibitor, clade B (ovalbumin), member 1 | 0.252267199 | 2.11.95 || SFN | 2.11 | stratifin | 0.467860274 | 2.11.94 || SFRP1 | 2.11 | secreted frizzled-related protein 1 | 2.692419347 | 2.11.94 || SFSWAP | 2.11 | splicing factor, suppressor of white-apricot homolog | 0.375126962 | 2.11.88 || SH3PXD2A | 2.11 | SH3 and PX domains 2A | 0.386457248 | 2.11.93 || SHOX2 | 2.11 | short stature homeobox 2 | 1.268819877 | 2.11.87 || SIGLEC10 | 2.11 | sialic acid binding Ig like lectin 10 | 1.113832539 | 2.11.87 || SIGLEC9 | 2.11 | sialic acid binding Ig like lectin 9 | 0.430433642 | 2.11.96 || SIKE1 | 2.11 | suppressor of IKBKE 1 | 0.386816426 | — || SIVA1 | 2.11 | SIVA1 apoptosis inducing factor | 0.295265925 | 2.11.88 || SKA2 | 2.11 | spindle and kinetochore associated complex subunit 2 | 0.243261777 | 2.11.95 || SLA | 2.11 | Src-like-adaptor | 0.247621608 | 2.11.94 || SLAMF8 | 2.11 | SLAM family member 8 | 5.562850311 | 2.11.94 || SLC16A14 | 2.11 | solute carrier family 16

TABLE 3B-continued

The genes within the significant gene clusters, listed in Table 3A. (3966 Genes Listed by: Gene Symbol | Gen 2 Module | Gene Description | RowVariance | Gen 3 Module ||)

member 14 | 0.51291194 | 2.11.95 || SLC16A6 | 2.11 | solute carrier family 16 member 6 | 1.372102975 | 2.11.93 || SLC17A9 | 2.11 | solute carrier family 17 member 9 | 1.29964194 | 2.11.87 || SLC22A7 | 2.11 | solute carrier family 22 member 7 | 0.320622105 | 2.11.87 || SLC2A10 | 2.11 | solute carrier family 2 member 10 | 1.284795292 | 2.11.90 || SLC2A5 | 2.11 | solute carrier family 2 member 5 | 0.855621559 | 2.11.96 || SLC5A3 | 2.11 | solute carrier family 5 member 3 | 1.125767521 | 2.11.93 || SLCO2A1 | 2.11 | solute carrier organic anion transporter family member 2A1 | 0.595840495 | 2.11.93 || SLIT2 | 2.11 | slit guidance ligand 2 | 1.534824777 | 2.11.93 || SLPI | 2.11 | secretory leukocyte peptidase inhibitor | 0.985296136 | 2.11.94 || SMAP2 | 2.11 | small ArfGAP2 | 0.587418747 | 2.11.94 || SMARCA1 | 2.11 | SWI/SNF related, matrix associated, actin dependent regulator of chromatin, subfamily a, member 1 | 0.518225364 | 2.11.91 || SMCO4 | 2.11 | single-pass membrane protein with coiled-coil domains 4 | 0.567333671 | 2.11.94 || SNRNP48 | 2.11 | small nuclear ribonucleoprotein U11/U12 subunit 48 | 0.385402187 | 2.11.88 || SNX21 | 2.11 | sorting nexin family member 21 | 1.248192959 | 2.11.87 || SOBP | 2.11 | sine oculis binding protein homolog | 1.928931461 | 2.11.87 || SPA17 | 2.11 | sperm autoantigenic protein 17 | 0.285280326 | 2.11.89 || SPAG16 | 2.11 | sperm associated antigen 16 | 0.915477114 | 2.11.87 || SPATA7 | 2.11 | spermatogenesis associated 7 | 1.368215056 | 2.11.87 || SPIN4 | 2.11 | spindlin family member 4 | 0.770418964 | — || SPOCK1 | 2.11 | sparc/osteonectin, cwcv and kazal-like domains proteoglycan (testican) 1 | 1.725208877 | 2.11.91 || SRGAP2C | 2.11 | SLIT-ROBO Rho GTPase activating protein 2C | 0.480654427 | 2.11.88 || SSC4D | 2.11 | scavenger receptor cysteine rich family, 4 domains | 0.291927929 | 2.11.88 || STARD13 | 2.11 | StAR related lipid transfer domain containing 13 | 0.294783875 | 2.11.95 || SYBU | 2.11 | syntabulin | 0.87407809 | 2.11.92 || SYNGR2 | 2.11 | synaptogyrin 2 | 0.571686213 | 2.11.94 || SYNPO | 2.11 | synaptopodin | 0.295647298 | 2.11.87 || SYTL2 | 2.11 | synaptotagmin like 2 | 1.265626995 | 2.11.87 || TAPBPL | 2.11 | TAP binding protein like | 1.128158128 | 2.11.94 || TBC1D12 | 2.11 | TBC1 domain family member 12 | 0.22746469 | 2.11.92 || TBC1D16 | 2.11 | TBC1 domain family member 16 | 0.617692994 | 2.11.92 || TBC1D8B | 2.11 | TBC1 domain family member 8B | 0.93406443 | 2.11.93 || TBL1X | 2.11 | transducin (beta)-like 1X-linked | 0.489219089 | 2.11.88 || TBL3 | 2.11 | transducin (beta)-like 3 | 0.279280529 | 2.11.88 || TCEAL8 | 2.11 | transcription elongation factor A like 8 | 0.244030796 | 2.11.90 || TCEAL9 | 2.11 | transcription elongation factor A like 9 | 0.322005675 | 2.11.90 || TCF4 | 2.11 | transcription factor 4 | 0.458828535 | 2.11.87 || TFDP2 | 2.11 | transcription factor Dp-2 (E2F dimerization partner 2) | 0.736516249 | 2.11.91 || TFPI | 2.11 | tissue factor pathway inhibitor | 0.566235882 | 2.11.87 || TGFB1I1 | 2.11 | transforming growth factor beta 1 induced transcript 1 | 0.507765297 | — || TGFBR3 | 2.11 | transforming growth factor beta receptor III | 1.507257805 | 2.11.92 || THAP3 | 2.11 | THAP domain containing, apoptosis associated protein 3 | 0.568537294 | 2.11.87 || THAP5 | 2.11 | THAP domain containing 5 | 0.263448751 | — || TIMM44 | 2.11 | translocase of inner mitochondrial membrane 44 | 0.255360129 | 2.11.88 || TLR2 | 2.11 | toll like receptor 2 | 1.299433362 | 2.11.94 || TMA16 | 2.11 | translation machinery associated 16 homolog | 0.604362157 | 2.11.88 || TMEFF2 | 2.11 | transmembrane protein with EGF like and two follistatin like domains 2 | 0.709341931 | 2.11.91 || TMEM108 | 2.11 | transmembrane protein 108 | 2.284817953 | 2.11.87 || TMEM136 | 2.11 | transmembrane protein 136 | 0.50399416 | 2.11.93 || TMEM163 | 2.11 | transmembrane protein 163 | 0.269732545 | 2.11.87 || TMEM192 | 2.11 | transmembrane protein 192 | 0.550107757 | 2.11.88 || TMEM208 | 2.11 | transmembrane protein 208 | 0.483224276 | 2.11.88 || TMEM237 | 2.11 | transmembrane protein 237 | 0.280687141 | 2.11.87 || TMEM51 | 2.11 | transmembrane protein 51 | 0.770185115 | 2.11.95 || TMOD2 | 2.11 | tropomodulin 2 | 0.309966241 | — || TMTC3 | 2.11 | transmembrane and tetratricopeptide repeat containing 3 | 0.501999476 | — || TNFAIP8L3 | 2.11 | TNF alpha induced protein 8 like 3 | 0.256780873 | 2.11.89 || TNFRSF11A | 2.11 | tumor necrosis factor receptor superfamily member 11a | 1.490932349 | 2.11.95 || TNFRSF21 | 2.11 | tumor necrosis factor receptor superfamily member 21 | 0.542314989 | 2.11.96 || TNS2 | 2.11 | tensin 2 | 0.425631795 | 2.11.92 || TRERF1 | 2.11 | transcriptional regulating factor 1 | 0.700646116 | 2.11.93 || TRIB1 | 2.11 | tribbles pseudokinase 1 | 0.406969487 | 2.11.93 || TRIM13 | 2.11 | tripartite motif containing 13 | 0.67103634 | 2.11.93 || TRIM56 | 2.11 | tripartite motif containing 56 | 0.83888073 | — || TRIP11 | 2.11 | thyroid hormone receptor interactor 11 | 0.306304647 | 2.11.87 || TRNT1 | 2.11 | tRNA nucleotidyl transferase, CCA-adding, 1 | 0.442827291 | 2.11.93 || TRPV2 | 2.11 | transient receptor potential cation channel subfamily V member 2 | 0.317197105 | 2.11.88 || TSC22D1 | 2.11 | TSC22 domain family member 1 | 0.371148126 | 2.11.95 || TSPAN15 | 2.11 | tetraspanin 15 | 0.512575205 | 2.11.93 || TTC25 | 2.11 | tetratricopeptide repeat domain 25 | 0.219233441 | 2.11.87 || TTC28 | 2.11 | tetratricopeptide repeat domain 28 | 1.083496716 | 2.11.93 || TTC37 | 2.11 | tetratricopeptide repeat domain 37 | 0.304527669 | — || TTC6 | 2.11 | tetratricopeptide repeat domain 6 | 0.666114507 | 2.11.94 || TTC8 | 2.11 | tetratricopeptide repeat domain 8 | 0.856140725 | 2.11.93 || TTLL9 | 2.11 | tubulin tyrosine ligase like 9 | 0.393028309 | 2.11.89 || TUBA4A | 2.11 | tubulin alpha 4a | 0.631849282 | — || TWIST1 | 2.11 | twist family bHLH transcription factor 1 | 0.835937996 | 2.11.95 || TWISTNB | 2.11 | TWIST neighbor | 3.257124484 | 2.11.90 || TXNDC11 | 2.11 | thioredoxin domain containing 11 | 0.579050214 | 2.11.88 || TYMP | 2.11 | thymidine phosphorylase | 0.947070876 | 2.11.94 || UBN1 | 2.11 | ubinuclein 1 | 0.333970619 | 2.11.88 || UBTD2 | 2.11 | ubiquitin domain containing 2 | 0.353079528 | 2.11.87 || UCP2 | 2.11 | uncoupling protein 2 (mitochondrial, proton carrier) | 0.322404283 | 2.11.90 || UNKL | 2.11 | unkempt family like zinc finger | 0.228147833 | — || VCAN | 2.11 | versican | 0.446645843 | — || VGLL3 | 2.11 | vestigial like family member 3 | 1.251616228 | 2.11.91 || VMO1 | 2.11 | vitelline membrane outer layer 1 homolog (chicken) | 0.340727067 | — || WARS2 | 2.11 | tryptophanyl tRNA synthetase 2, mitochondrial | 0.70446101 | 2.11.96 || WLS | 2.11 | wntless Wnt ligand secretion mediator | 1.31650603 | 2.11.96 || WNT5A | 2.11 | wingless-type MMTV integration site family member 5A | 0.412515726 | 2.11.94 || WRN | 2.11 | Werner syndrome RecQ like helicase | 0.247501696 | 2.11.89 || YAP1 | 2.11 | Yes associated protein 1 | 0.605460411 | 2.11.95 || YES1 | 2.11 | YES proto-oncogene 1, Src family tyrosine kinase | 0.625134871 | 2.11.87 || ZBED3 | 2.11 | zinc finger BED-type containing 3 | 0.289258338 | 2.11.87 || ZBED6 | 2.11 | zinc finger BED-type containing 6 | 0.965378396 | 2.11.87 || ZBTB37 | 2.11 | zinc finger and BTB domain containing 37 | 0.423861555 | — || ZBTB44 | 2.11 | zinc finger and BTB domain containing 44 | 0.66153182 | 2.11.88 || ZBTB8A | 2.11 | zinc finger and BTB domain containing 8A | 0.843068611 | 2.11.87 || ZC3H14 | 2.11 | zinc finger CCCH-type containing 14 | 0.431930295 | 2.11.88 || ZCCHC24 | 2.11 | zinc finger CCHC-type containing 24 | 0.958574416 | 2.11.87 || ZDHHC9 | 2.11 | zinc finger DHHC-type containing 9 |

TABLE 3B-continued

The genes within the significant gene clusters, listed in Table 3A. (3966 Genes Listed by: Gene Symbol | Gen 2 Module | Gene Description | RowVariance | Gen 3 Module ||)

0.360693978 | 2.11.94 || ZEB1 | 2.11 | zinc finger E-box binding homeobox 1 | 0.734907942 | 2.11.91 || ZFAS1 | 2.11 | ZNFX1 antisense RNA 1 | 0.216926924 | 2.11.88 || ZFHX4 | 2.11 | zinc finger homeobox 4 | 1.487261107 | 2.11.96 || ZFP1 | 2.11 | ZFP1 zinc finger protein | 0.656534532 | 2.11.94 || ZFP90 | 2.11 | ZFP90 zinc finger protein | 1.647601439 | 2.11.88 || ZHX1 | 2.11 | zinc fingers and homeoboxes 1 | 0.399846336 | 2.11.88 || ZMYM3 | 2.11 | zinc finger MYM-type containing 3 | 0.228678583 | 2.11.89 || ZNF112 | 2.11 | zinc finger protein 112 | 0.263784849 | 2.11.87 || ZNF213 | 2.11 | zinc finger protein 213 | 0.279066572 | 2.11.95 || ZNF264 | 2.11 | zinc finger protein 264 | 0.659488215 | — || ZNF268 | 2.11 | zinc finger protein 268 | 0.89780186 | 2.11.93 || ZNF271P | 2.11 | zinc finger protein 271, pseudogene | 0.750163201 | 2.11.87 || ZNF329 | 2.11 | zinc finger protein 329 | 0.232425809 | 2.11.93 || ZNF426 | 2.11 | zinc finger protein 426 | 1.54676683 | 2.11.88 || ZNF432 | 2.11 | zinc finger protein 432 | 0.249140608 | — || ZNF443 | 2.11 | zinc finger protein 443 | 0.241857926 | 2.11.88 || ZNF45 | 2.11 | zinc finger protein 45 | 0.255425089 | 2.11.91 || ZNF462 | 2.11 | zinc finger protein 462 | 1.060098814 | 2.11.94 || ZNF503 | 2.11 | zinc finger protein 503 | 0.935714707 | 2.11.93 || ZNF507 | 2.11 | zinc finger protein 507 | 0.334228087 | 2.11.96 || ZNF512B | 2.11 | zinc finger protein 512B | 0.500698568 | 2.11.93 || ZNF567 | 2.11 | zinc finger protein 567 | 1.122144387 | 2.11.87 || ZNF600 | 2.11 | zinc finger protein 600 | 0.255226768 | 2.11.91 || ZNF608 | 2.11 | zinc finger protein 608 | 1.201445355 | 2.11.91 || ZNF618 | 2.11 | zinc finger protein 618 | 1.07071906 | 2.11.93 || ZNF703 | 2.11 | zinc finger protein 703 | 0.549888949 | 2.11.94 || ZNF823 | 2.11 | zinc finger protein 823 | 0.508288076 | 2.11.87 || ZNF827 | 2.11 | zinc finger protein 827 | 0.939881938 | 2.11.91 || ZNF83 | 2.11 | zinc finger protein 83 | 0.311507378 | 2.11.87 || ACADSB | 2.11.87 | acyl-CoA dehydrogenase, short/branched chain | 0.448305681 | 2.11.87 || ACOX2 | 2.11.87 | acyl-CoA oxidase 2, branched chain | 0.589616328 | 2.11.87 || ADD3 | 2.11.87 | adducin 3 | 0.607985917 | 2.11.87 || AMIGO2 | 2.11.87 | adhesion molecule with Ig-like domain 2 | 0.814772914 | 2.11.87 || BMPR1A | 2.11.87 | bone morphogenetic protein receptor type 1A | 0.613503708 | 2.11.87 || C7orf55 | 2.11.87 | chromosome 7 open reading frame 55 | 0.668742837 | 2.11.87 || CDC37L1 | 2.11.87 | cell division cycle 37-like 1 | 0.231469743 | 2.11.87 || CEP290 | 2.11.87 | centrosomal protein 290 kDa | 0.263768045 | 2.11.87 || CLOCK | 2.11.87 | clock circadian regulator | 0.293393216 | 2.11.87 || COL27A1 | 2.11.87 | collagen type XXVII alpha 1 | 0.892869302 | 2.11.87 || CWC27 | 2.11.87 | CWC27 spliceosome associated protein homolog | 0.243405515 | 2.11.87 || DAAM1 | 2.11.87 | dishevelled associated activator of morphogenesis 1 | 0.471280572 | 2.11.87 || DCLK2 | 2.11.87 | doublecortin like kinase 2 | 0.511160655 | 2.11.87 || DDR2 | 2.11.87 | discoidin domain receptor tyrosine kinase 2 | 0.942052657 | 2.11.87 || DIXDC1 | 2.11.87 | DIX domain containing 1 | 0.759440001 | 2.11.87 || DYNC2LI1 | 2.11.87 | dynein cytoplasmic 2 light intermediate chain 1 | 0.626974122 | 2.11.87 || EBF1 | 2.11.87 | early B-cell factor 1 | 0.937984168 | 2.11.87 || EBF2 | 2.11.87 | early B-cell factor 2 | 3.351821547 | 2.11.87 || EFS | 2.11.87 | embryonal Fyn-associated substrate | 0.591158755 | 2.11.87 || EYA4 | 2.11.87 | EYA transcriptional coactivator and phosphatase 4 | 0.759943865 | 2.11.87 || FAM210B | 2.11.87 | family with sequence similarity 210 member B | 0.277177641 | 2.11.87 || FBXL17 | 2.11.87 | F-box and leucine-rich repeat protein 17 | 0.321221777 | 2.11.87 || FGF13 | 2.11.87 | fibroblast growth factor 13 | 0.987877209 | 2.11.87 || FNDC4 | 2.11.87 | fibronectin type III domain containing 4 | 0.4953917 | 2.11.87 || FYN | 2.11.87 | FYN proto-oncogene, Src family tyrosine kinase | 0.285535416 | 2.11.87 || GLP1R | 2.11.87 | glucagon like peptide 1 receptor | 0.286795346 | 2.11.87 || GPHN | 2.11.87 | gephyrin | 0.379120059 | 2.11.87 || GPR65 | 2.11.87 | G protein-coupled receptor 65 | 0.526628376 | 2.11.87 || HES1 | 2.11.87 | hes family bHLH transcription factor 1 | 0.693985311 | 2.11.87 || IBSP | 2.11.87 | integrin binding sialoprotein | 0.255171768 | 2.11.87 || JPX | 2.11.87 | JPX transcript, XIST activator (non-protein coding) | 0.780111483 | 2.11.87 || KCNT2 | 2.11.87 | potassium sodium-activated channel subfamily T member 2 | 1.179764931 | 2.11.87 || KCTD3 | 2.11.87 | potassium channel tetramerization domain containing 3 | 0.745709664 | 2.11.87 || KMT5A | 2.11.87 | lysine methyltransferase 5A | 0.451503802 | 2.11.87 || LEPROTL1 | 2.11.87 | leptin receptor overlapping transcript-like 1 | 0.369399864 | 2.11.87 || LIMCH1 | 2.11.87 | LIM and calponin homology domains 1 | 1.258866277 | 2.11.87 || LOC101927027 | 2.11.87 | uncharacterized LOC101927027 | 0.275757716 | 2.11.87 || LYRM5 | 2.11.87 | LYR motif containing 5 | 0.276852304 | 2.11.87 || LYZ | 2.11.87 | lysozyme | 0.298216054 | 2.11.87 || MAP9 | 2.11.87 | microtubule associated protein 9 | 1.228570929 | 2.11.87 || MATK | 2.11.87 | megakaryocyte-associated tyrosine kinase | 1.377160924 | 2.11.87 || METTL6 | 2.11.87 | methyltransferase like 6 | 0.254287019 | 2.11.87 || MRS2 | 2.11.87 | MRS2, magnesium transporter | 0.374654346 | 2.11.87 || MTFP1 | 2.11.87 | mitochondrial fission process 1 | 0.298762142 | 2.11.87 || MYLK | 2.11.87 | myosin light chain kinase | 1.49867473 | 2.11.87 || NADK2 | 2.11.87 | NAD kinase 2, mitochondrial | 0.239248157 | 2.11.87 || NLRC4 | 2.11.87 | NLR family, CARD domain containing 4 | 0.578897082 | 2.11.87 || NR2C1 | 2.11.87 | nuclear receptor subfamily 2 group C member 1 | 0.454975321 | 2.11.87 || NUDT6 | 2.11.87 | nudix hydrolase 6 | 0.484537329 | 2.11.87 || PHACTR2 | 2.11.87 | phosphatase and actin regulator 2 | 0.37221586 | 2.11.87 || PLA2G12A | 2.11.87 | phospholipase A2 group XIIA | 0.445961327 | 2.11.87 || PLEK | 2.11.87 | pleckstrin | 0.551911738 | 2.11.87 || PTPN14 | 2.11.87 | protein tyrosine phosphatase, non-receptor type 14 | 0.630354757 | 2.11.87 || PURA | 2.11.87 | purine-rich element binding protein A | 0.261900751 | 2.11.87 || RAB23 | 2.11.87 | RAB23, member RAS oncogene family | 0.547504018 | 2.11.87 || RAI2 | 2.11.87 | retinoic acid induced 2 | 0.548407973 | 2.11.87 || RNF144B | 2.11.87 | ring finger protein 144B | 0.35329375 | 2.11.87 || RORA | 2.11.87 | RAR related orphan receptor A | 0.401012354 | 2.11.87 || RUNX1T1 | 2.11.87 | runt related transcription factor 1; translocated to, 1 (cyclin D related) | 1.548689058 | 2.11.87 || SAMD4A | 2.11.87 | sterile alpha motif domain containing 4A | 0.447671749 | 2.11.87 || SEMA4A | 2.11.87 | semaphorin 4A | 0.365692765 | 2.11.87 || SHOX2 | 2.11.87 | short stature homeobox 2 | 1.268819877 | 2.11.87 || SIGLEC10 | 2.11.87 | sialic acid binding Ig like lectin 10 | 1.113832539 | 2.11.87 || SLC17A9 | 2.11.87 | solute carrier family 17 member 9 | 1.29964194 | 2.11.87 || SLC22A7 | 2.11.87 | solute carrier family 22 member 7 | 0.320622105 | 2.11.87 || SNX21 | 2.11.87 | sorting nexin family member 21 | 1.248192959 | 2.11.87 || SOBP | 2.11.87 | sine oculis binding protein homolog | 1.928931461 | 2.11.87 || SPAG16 | 2.11.87 | sperm associated antigen 16 | 0.915477114 | 2.11.87 || SPATA7 | 2.11.87 | spermatogenesis associated 7 | 1.368215056 | 2.11.87 || SYNPO | 2.11.87 | synaptopodin | 0.295647298 | 2.11.87 || SYTL2 | 2.11.87 | synaptotagmin like 2 | 1.265626995 | 2.11.87 || TCF4 | 2.11.87 | transcription factor 4 | 0.458828535 | 2.11.87 || TFPI | 2.11.87 | tissue factor pathway inhibitor | 0.566235882 | 2.11.87 || THAP3 | 2.11.87 | THAP domain containing, apoptosis associated protein 3 |

TABLE 3B-continued

The genes within the significant gene clusters, listed in Table 3A. (3966 Genes Listed by: Gene Symbol | Gen 2 Module | Gene Description | RowVariance | Gen 3 Module ||)

0.568537294 | 2.11.87 || TMEM108 | 2.11.87 | transmembrane protein 108 | 2.284817953 | 2.11.87 || TMEM163 | 2.11.87 | transmembrane protein 163 | 0.269732545 | 2.11.87 || TMEM237 | 2.11.87 | transmembrane protein 237 | 0.280687141 | 2.11.87 || TRIP11 | 2.11.87 | thyroid hormone receptor interactor 11 | 0.306304647 | 2.11.87 || TTC25 | 2.11.87 | tetratricopeptide repeat domain 25 | 0.219233441 | 2.11.87 || UBTD2 | 2.11.87 | ubiquitin domain containing 2 | 0.353079528 | 2.11.87 || YES1 | 2.11.87 | YES proto-oncogene 1, Src family tyrosine kinase | 0.625134871 | 2.11.87 || ZBED3 | 2.11.87 | zinc finger BED-type containing 3 | 0.289258338 | 2.11.87 || ZBED6 | 2.11.87 || zinc finger BED-type containing 6 | 0.965378396 | 2.11.87 || ZBTB8A | 2.11.87 | zinc finger and BTB domain containing 8A | 0.843068611 | 2.11.87 || ZCCHC24 | 2.11.87 | zinc finger CCHC-type containing 24 | 0.958574416 | 2.11.87 || ZNF112 | 2.11.87 | zinc finger protein 112 | 0.263784849 | 2.11.87 || ZNF271P | 2.11.87 | zinc finger protein 271, pseudogene | 0.750163201 | 2.11.87 || ZNF567 | 2.11.87 | zinc finger protein 567 | 1.122144387 | 2.11.87 || ZNF823 | 2.11.87 | zinc finger protein 823 | 0.508288076 | 2.11.87 || ZNF83 | 2.11.87 | zinc finger protein 83 | 0.311507378 | 2.11.87 || ABCD3 | 2.11.88 | ATP binding cassette subfamily D member 3 | 0.303894131 | 2.11.88 || ACOT7 | 2.11.88 | acyl-CoA thioesterase 7 | 1.191420448 | 2.11.88 || AKR1A1 | 2.11.88 | aldo-keto reductase family 1, member A1 (aldehyde reductase) | 0.266734234 | 2.11.88 || ANKRD36B | 2.11.88 | ankyrin repeat domain 36B | 0.705201592 | 2.11.88 || BAX | 2.11.88 | BCL2-associated X protein | 0.286362311 | 2.11.88 || C19orf68 | 2.11.88 | chromosome 19 open reading frame 68 | 0.454827829 | 2.11.88 || CASP6 | 2.11.88 | caspase 6 | 0.798729681 | 2.11.88 || CBR1 | 2.11.88 | carbonyl reductase 1 | 0.34570911 | 2.11.88 || CCAR1 | 2.11.88 | cell division cycle and apoptosis regulator 1 | 0.31308275 | 2.11.88 || CD38 | 2.11.88 | CD38 molecule | 2.150406121 | 2.11.88 || CEBPA-AS1 | 2.11.88 | CEBPA antisense RNA 1 (head to head) | 0.219803491 | 2.11.88 || CEMP1 | 2.11.88 | cementum protein 1 | 0.327109293 | 2.11.88 || CEP126 | 2.11.88 | centrosomal protein 126 kDa | 1.892868245 | 2.11.88 || CEP164 | 2.11.88 | centrosomal protein 164 kDa | 0.955611752 | 2.11.88 || COL7A1 | 2.11.88 | collagen type VII alpha 1 | 0.368213732 | 2.11.88 || DDX54 | 2.11.88 | DEAD-box helicase 54 | 0.613719873 | 2.11.88 || DHX33 | 2.11.88 | DEAH-box helicase 33 | 0.378118657 | 2.11.88 || DNAJB9 | 2.11.88 | DnaJ heat shock protein family (Hsp40) member B9 | 0.375758976 | 2.11.88 || DPP4 | 2.11.88 | dipeptidyl peptidase 4 | 1.0578736 | 2.11.88 || EDEM2 | 2.11.88 | ER degradation enhancer, mannosidase alpha-like 2 | 0.286374549 | 2.11.88 || FIGN | 2.11.88 | fidgetin | 1.045218876 | 2.11.88 || GTPBP2 | 2.11.88 | GTP binding protein 2 | 1.042769987 | 2.11.88 || INSR | 2.11.88 | insulin receptor | 1.130743908 | 2.11.88 || INTS2 | 2.11.88 | integrator complex subunit 2 | 0.310307903 | 2.11.88 || IRAK1BP1 | 2.11.88 | interleukin 1 receptor associated kinase 1 binding protein 1 | 0.384567859 | 2.11.88 || ISYNA1 | 2.11.88 | inositol-3-phosphate synthase 1 | 0.467806734 | 2.11.88 || ITPR2 | 2.11.88 | inositol 1,4,5-trisphosphate receptor type 2 | 0.577070542 | 2.11.88 || IVNS1ABP | 2.11.88 | influenza virus NS1A binding protein | 0.302793942 | 2.11.88 || KLHL20 | 2.11.88 | kelch like family member 20 | 0.472326564 | 2.11.88 || KLHL8 | 2.11.88 | kelch like family member 8 | 0.377497362 | 2.11.88 || KLK15 | 2.11.88 | kallikrein related peptidase 15 | 0.583177926 | 2.11.88 || KPNA5 | 2.11.88 | karyopherin subunit alpha 5 | 0.471170469 | 2.11.88 || LAMP2 | 2.11.88 | lysosomal associated membrane protein 2 | 0.317829107 | 2.11.88 || LAMTOR4 | 2.11.88 | late endosomal/lysosomal adaptor, MAPK and MTOR activator 4 | 0.21450644 | 2.11.88 || LOC146880 | 2.11.88 | Rho GTPase activating protein 27 pseudogene | 0.51948776 | 2.11.88 || LYRM7 | 2.11.88 | LYR motif containing 7 | 0.547635505 | 2.11.88 || MED13 | 2.11.88 | mediator complex subunit 13 | 0.222155278 | 2.11.88 || MKLN1 | 2.11.88 | muskelin 1 | 0.25163679 | 2.11.88 || MMAA | 2.11.88 | methylmalonic aciduria (cobalamin deficiency) cblA type | 0.354714539 | 2.11.88 || MMP25 | 2.11.88 | matrix metallopeptidase 25 | 0.259601703 | 2.11.88 || MPND | 2.11.88 | MPN domain containing | 0.254515893 | 2.11.88 || MR1 | 2.11.88 | major histocompatibility complex, class I-related | 0.267692959 | 2.11.88 || MRPL23 | 2.11.88 | mitochondrial ribosomal protein L23 | 0.305797447 | 2.11.88 || MRPS7 | 2.11.88 | mitochondrial ribosomal protein S7 | 0.380177879 | 2.11.88 || NAALADL1 | 2.11.88 | N-acetylated alpha-linked acidic dipeptidase-like 1 | 0.245776186 | 2.11.88 || NEK1 | 2.11.88 | NIMA related kinase 1 | 0.734884915 | 2.11.88 || NUCKS1 | 2.11.88 | nuclear casein kinase and cyclin-dependent kinase substrate 1 | 0.898450913 | 2.11.88 || PIGX | 2.11.88 | phosphatidylinositol glycan anchor biosynthesis class X | 0.294978944 | 2.11.88 || PPP1R37 | 2.11.88 | protein phosphatase 1 regulatory subunit 37 | 0.227052078 | 2.11.88 || PRDX1 | 2.11.88 | peroxiredoxin 1 | 0.316156677 | 2.11.88 || PTGES2 | 2.11.88 | prostaglandin E synthase 2 | 0.430878063 | 2.11.88 || QSER1 | 2.11.88 | glutamine and serine rich 1 | 0.232034763 | 2.11.88 || RAB11FIP2 | 2.11.88 | RAB11 family interacting protein 2 (class I) | 0.371953995 | 2.11.88 || RALBP1 | 2.11.88 | ralA binding protein 1 | 0.422724086 | 2.11.88 || RASL10B | 2.11.88 | RAS like family 10 member B | 0.225353115 | 2.11.88 || RBAK | 2.11.88 | RB associated KRAB zinc finger | 0.234868336 | 2.11.88 || SDF2L1 | 2.11.88 | stromal cell derived factor 2 like 1 | 0.349428243 | 2.11.88 || SEMA7A | 2.11.88 | semaphorin 7A (John Milton Hagen blood group) | 0.302560808 | 2.11.88 || SFSWAP | 2.11.88 | splicing factor, suppressor of white-apricot homolog | 0.375126962 | 2.11.88 || SIVA1 | 2.11.88 | SIVA1 apoptosis inducing factor | 0.295265925 | 2.11.88 || SNRNP48 | 2.11.88 | small nuclear ribonucleoprotein U11/U12 subunit 48 | 0.385402187 | 2.11.88 || SRGAP2C | 2.11.88 | SLIT-ROBO Rho GTPase activating protein 2C | 0.480654427 | 2.11.88 || SSC4D | 2.11.88 | scavenger receptor cysteine rich family, 4 domains | 0.291927929 | 2.11.88 || TBL1X | 2.11.88 | transducin (beta)-like 1X-linked | 0.489219089 | 2.11.88 || TBL3 | 2.11.88 | transducin (beta)-like 3 | 0.279280529 | 2.11.88 || TIMM44 | 2.11.88 | translocase of inner mitochondrial membrane 44 | 0.255360129 | 2.11.88 || TMA16 | 2.11.88 | translation machinery associated 16 homolog | 0.604362157 | 2.11.88 || TMEM192 | 2.11.88 | transmembrane protein 192 | 0.550107757 | 2.11.88 || TMEM208 | 2.11.88 | transmembrane protein 208 | 0.483224276 | 2.11.88 || TRPV2 | 2.11.88 | transient receptor potential cation channel subfamily V member 2 | 0.317197105 | 2.11.88 || TXNDC11 | 2.11.88 | thioredoxin domain containing 11 | 0.579050214 | 2.11.88 || UBN1 | 2.11.88 | ubinuclein 1 | 0.333970619 | 2.11.88 || ZBTB44 | 2.11.88 | zinc finger and BTB domain containing 44 | 0.66153182 | 2.11.88 || ZC3H14 | 2.11.88 | zinc finger CCCH-type containing 14 | 0.431930295 | 2.11.88 || ZFAS1 | 2.11.88 | ZNFX1 antisense RNA 1 | 0.216926924 | 2.11.88 || ZFP90 | 2.11.88 | ZFP90 zinc finger protein | 1.647601439 | 2.11.88 || ZHX1 | 2.11.88 | zinc fingers and homeoboxes 1 | 0.399846336 | 2.11.88 || ZNF426 | 2.11.88 | zinc finger protein 426 | 1.54676683 | 2.11.88 || ZNF443 | 2.11.88 | zinc finger protein 443 | 0.241857926 | 2.11.88 || ABAT | 2.11.91 | 4-aminobutyrate aminotransferase | 0.459696688 | 2.11.91 || ADAMTS5 | 2.11.91 | ADAM metallopeptidase with thrombospondin type 1 motif 5 |

TABLE 3B-continued

The genes within the significant gene clusters, listed in Table 3A. (3966 Genes Listed by: Gene Symbol | Gen 2 Module | Gene Description | RowVariance | Gen 3 Module ||)

0.787279475 | 2.11.91 || ARHGEF12 | 2.11.91 | Rho guanine nucleotide exchange factor 12 | 0.253338823 | 2.11.91 || BNC2 | 2.11.91 | basonuclin 2 | 0.902943933 | 2.11.91 || C22orf39 | 2.11.91 | chromosome 22 open reading frame 39 | 0.215432391 | 2.11.91 || CALD1 | 2.11.91 | caldesmon 1 | 0.418718877 | 2.11.91 || CD248 | 2.11.91 | CD248 molecule | 0.68823608 | 2.11.91 || CEP57 | 2.11.91 | centrosomal protein 57 kDa | 0.366056851 | 2.11.91 || DIAPH2 | 2.11.91 | diaphanous related formin 2 | 0.275314812 | 2.11.91 || DIP2C | 2.11.91 | disco interacting protein 2 homolog C | 0.519361999 | 2.11.91 || EBPL | 2.11.91 | emopamil binding protein like | 0.556331861 | 2.11.91 || FAM92A1 | 2.11.91 | family with sequence similarity 92 member A1 | 0.634098775 | 2.11.91 || GNA11 | 2.11.91 | G protein subunit alpha 11 | 0.295970179 | 2.11.91 || GNG12 | 2.11.91 | G protein subunit gamma 12 | 0.309818361 | 2.11.91 || GPSM2 | 2.11.91 | G-protein signaling modulator 2 | 0.564926901 | 2.11.91 || GSTT1 | 2.11.91 | glutathione S-transferase theta 1 | 1.747692966 | 2.11.91 || HAMP | 2.11.91 | hepcidin antimicrobial peptide | 0.284354134 | 2.11.91 || IGDCC4 | 2.11.91 | immunoglobulin superfamily, DCC subclass, member 4 | 1.34717997 | 2.11.91 || KDELC2 | 2.11.91 | KDEL motif containing 2 | 0.344744974 | 2.11.91 || KITLG | 2.11.91 | KIT ligand | 1.097244876 | 2.11.91 || LAPTM4B | 2.11.91 | lysosomal protein transmembrane 4 beta | 0.602776882 | 2.11.91 || LIPT1 | 2.11.91 | lipoyltransferase 1 | 0.344910038 | 2.11.91 || MAGEH1 | 2.11.91 | MAGE family member H1 | 0.217957682 | 2.11.91 || MYO6 | 2.11.91 | myosin VI | 0.6419066 | 2.11.91 || NEDD4 | 2.11.91 | neural precursor cell expressed, developmentally down-regulated 4, E3 ubiquitin protein ligase | 0.808755476 | 2.11.91 || PARM1 | 2.11.91 | prostate androgen-regulated mucin-like protein 1 | 1.023653832 | 2.11.91 || PLS3 | 2.11.91 | plastin 3 | 0.294103102 | 2.11.91 || PRKG1 | 2.11.91 | protein kinase, cGMP-dependent, type I | 0.774538466 | 2.11.91 || PRMT6 | 2.11.91 | protein arginine methyltransferase 6 | 0.318595128 | 2.11.91 || PTPN7 | 2.11.91 | protein tyrosine phosphatase, non-receptor type 7 | 0.261209531 | 2.11.91 || PTPRG | 2.11.91 | protein tyrosine phosphatase, receptor type G | 0.965505574 | 2.11.91 || RASGRP2 | 2.11.91 | RAS guanyl releasing protein 2 | 0.253098453 | 2.11.91 || SASH1 | 2.11.91 | SAM and SH3 domain containing 1 | 0.619338966 | 2.11.91 || SEC16B | 2.11.91 | SEC16 homolog B, endoplasmic reticulum export factor | 0.340832577 | 2.11.91 || SELP | 2.11.91 | selectin P | 1.790362768 | 2.11.91 || SMARCA1 | 2.11.91 | SWI/SNF related, matrix associated, actin dependent regulator of chromatin, subfamily a, member 1 | 0.518225364 | 2.11.91 || SPOCK1 | 2.11.91 | sparc/osteonectin, cwcv and kazal-like domains proteoglycan (testican) 1 | 1.725208877 | 2.11.91 || TFDP2 | 2.11.91 | transcription factor Dp-2 (E2F dimerization partner 2) | 0.736516249 | 2.11.91 || TMEFF2 | 2.11.91 | transmembrane protein with EGF like and two follistatin like domains 2 | 0.709341931 | 2.11.91 || VGLL3 | 2.11.91 | vestigial like family member 3 | 1.251616228 | 2.11.91 || ZEB1 | 2.11.91 | zinc finger E-box binding homeobox 1 | 0.734907942 | 2.11.91 || ZNF45 | 2.11.91 | zinc finger protein 45 | 0.255425089 | 2.11.91 || ZNF600 | 2.11.91 | zinc finger protein 600 | 0.255226768 | 2.11.91 || ZNF608 | 2.11.91 | zinc finger protein 608 | 1.201445355 | 2.11.91 || ZNF827 | 2.11.91 | zinc finger protein 827 | 0.939881938 | 2.11.91 || ABI2 | 2.11.93 | abl-interactor 2 | 0.750557435 | 2.11.93 || ABI3BP | 2.11.93 | ABI family member 3 binding protein | 0.380939275 | 2.11.93 || CEP85 | 2.11.93 | centrosomal protein 85 kDa | 0.383549817 | 2.11.93 || CLASP1 | 2.11.93 | cytoplasmic linker associated protein 1 | 0.271094193 | 2.11.93 || DAB2 | 2.11.93 | Dab, mitogen-responsive phosphoprotein, homolog 2 (*Drosophila*) | 0.438747419 | 2.11.93 || DCBLD2 | 2.11.93 | discoidin, CUB and LCCL domain containing 2 | 0.444713707 | 2.11.93 || DPY19L3 | 2.11.93 | dpy-19 like 3 (*C. elegans*) | 0.596164066 | 2.11.93 || DPY19L4 | 2.11.93 | dpy-19 like 4 (*C. elegans*) | 0.543100176 | 2.11.93 || DSPP | 2.11.93 | dentin sialophosphoprotein | 0.260053984 | 2.11.93 || EFCAB7 | 2.11.93 | EF-hand calcium binding domain 7 | 0.460111073 | 2.11.93 || EXT1 | 2.11.93 | exostosin glycosyltransferase 1 | 0.376437861 | 2.11.93 || FAM179B | 2.11.93 | family with sequence similarity 179 member B | 0.306610698 | 2.11.93 || FANCL | 2.11.93 | Fanconi anemia complementation group L | 0.259473729 | 2.11.93 || FLJ20021 | 2.11.93 | uncharacterized LOC90024 | 0.284145227 | 2.11.93 || FNDC3B | 2.11.93 | fibronectin type III domain containing 3B | 0.227687911 | 2.11.93 || FPR1 | 2.11.93 | formyl peptide receptor 1 | 0.886015891 | 2.11.93 || FUT5 | 2.11.93 | fucosyltransferase 5 | 0.385385121 | 2.11.93 || GAREM1 | 2.11.93 | GRB2 associated regulator of MAPK1 subtype 1 | 1.00034877 | 2.11.93 || GMFG | 2.11.93 | glia maturation factor gamma | 0.45780896 | 2.11.93 || GOLGA2 | 2.11.93 | golgin A2 | 0.458222426 | 2.11.93 || GOLIM4 | 2.11.93 | golgi integral membrane protein 4 | 0.322114154 | 2.11.93 || HAUS6 | 2.11.93 | HAUS augmin like complex subunit 6 | 0.560054086 | 2.11.93 || HOXA5 | 2.11.93 | homeobox A5 | 0.886096098 | 2.11.93 || IFT80 | 2.11.93 | intraflagellar transport 80 | 0.411958681 | 2.11.93 || KCNJ2 | 2.11.93 | potassium voltage-gated channel subfamily J member 2 | 0.732493091 | 2.11.93 || LOC400043 | 2.11.93 | uncharacterized LOC400043 | 0.328282968 | 2.11.93 || MLLT3 | 2.11.93 | myeloid/lymphoid or mixed-lineage leukemia; translocated to, 3 | 0.364863776 | 2.11.93 || NOL12 | 2.11.93 | nucleolar protein 12 | 0.284900775 | 2.11.93 || OSMR | 2.11.93 | oncostatin M receptor | 1.503278899 | 2.11.93 || PCDHB14 | 2.11.93 | protocadherin beta 14 | 1.252426102 | 2.11.93 || PDE10A | 2.11.93 | phosphodiesterase 10A | 0.593443067 | 2.11.93 || SACS | 2.11.93 | sacsin molecular chaperone | 0.485582191 | 2.11.93 || SEPT8 | 2.11.93 | septin 8 | 0.267651618 | 2.11.93 || SH3PXD2A | 2.11.93 | SH3 and PX domains 2A | 0.386457248 | 2.11.93 || SLC16A6 | 2.11.93 | solute carrier family 16 member 6 | 1.372102975 | 2.11.93 || SLC5A3 | 2.11.93 | solute carrier family 5 member 3 | 1.125767521 | 2.11.93 || SLCO2A1 | 2.11.93 | solute carrier organic anion transporter family member 2A1 | 0.595840495 | 2.11.93 || SLIT2 | 2.11.93 | slit guidance ligand 2 | 1.534824777 | 2.11.93 || TBC1D8B | 2.11.93 | TBC1 domain family member 8B | 0.93406443 | 2.11.93 || TMEM136 | 2.11.93 | transmembrane protein 136 | 0.50399416 | 2.11.93 || TRERF1 | 2.11.93 | transcriptional regulating factor 1 | 0.700646116 | 2.11.93 || TRIB1 | 2.11.93 | tribbles pseudokinase 1 | 0.406969487 | 2.11.93 || TRIM13 | 2.11.93 | tripartite motif containing 13 | 0.67103634 | 2.11.93 || TRNT1 | 2.11.93 | tRNA nucleotidyl transferase, CCA-adding, 1 | 0.442827291 | 2.11.93 || TSPAN15 | 2.11.93 | tetraspanin 15 | 0.512575205 | 2.11.93 || TTC28 | 2.11.93 | tetratricopeptide repeat domain 28 | 1.083496716 | 2.11.93 || TTC8 | 2.11.93 | tetratricopeptide repeat domain 8 | 0.856140725 | 2.11.93 || ZNF268 | 2.11.93 | zinc finger protein 268 | 0.89780186 | 2.11.93 || ZNF329 | 2.11.93 | zinc finger protein 329 | 0.232425809 | 2.11.93 || ZNF503 | 2.11.93 | zinc finger protein 503 | 0.935714707 | 2.11.93 || ZNF512B | 2.11.93 | zinc finger protein 512B | 0.500698568 | 2.11.93 || ZNF618 | 2.11.93 | zinc finger protein 618 | 1.07071906 | 2.11.93 || ARNTL2 | 2.11.96 | aryl hydrocarbon receptor nuclear translocator like 2 | 0.494590322 | 2.11.96 || C7 | 2.11.96 | complement component 7 | 5.235794833 | 2.11.96 || CAMLG | 2.11.96 | calcium modulating ligand | 0.285590664 | 2.11.96 || CFH | 2.11.96 | complement factor H | 0.713023953 | 2.11.96 || CPE |

TABLE 3B-continued

The genes within the significant gene clusters, listed in Table 3A. (3966 Genes Listed by: Gene Symbol | Gen 2 Module | Gene Description | RowVariance | Gen 3 Module ||)

2.11.96 | carboxypeptidase E | 1.901786183 | 2.11.96 || DESI1 | 2.11.96 | desumoylating isopeptidase 1 | 0.404636144 | 2.11.96 || EVA1C | 2.11.96 | eva-1 homolog C (*C. elegans*) | 1.030366337 | 2.11.96 || FAM228B | 2.11.96 | family with sequence similarity 228 member B | 0.349991862 | 2.11.96 || FBLN5 | 2.11.96 | fibulin 5 | 1.139777302 | 2.11.96 || GPATCH1 | 2.11.96 | G-patch domain containing 1 | 0.219040373 | 2.11.96 || LINC01139 | 2.11.96 | long intergenic non-protein coding RNA 1139 | 0.581493857 | 2.11.96 || MAB21L2 | 2.11.96 | mab-21-like 2 (*C. elegans*) | 4.062089165 | 2.11.96 || MBP | 2.11.96 | myelin basic protein | 0.578176871 | 2.11.96 || PID1 | 2.11.96 | phosphotyrosine interaction domain containing 1 | 0.433982727 | 2.11.96 || PRICKLE2 | 2.11.96 | prickle planar cell polarity protein 2 | 0.782184554 | 2.11.96 || SIGLEC9 | 2.11.96 | sialic acid binding Ig like lectin 9 | 0.430433642 | 2.11.96 || SLC2A5 | 2.11.96 | solute carrier family 2 member 5 | 0.855621559 | 2.11.96 || TNFRSF21 | 2.11.96 | tumor necrosis factor receptor superfamily member 21 | 0.542314989 | 2.11.96 || WARS2 | 2.11.96 | tryptophanyl tRNA synthetase 2, mitochondrial | 0.70446101 | 2.11.96 || WLS | 2.11.96 | wntless Wnt ligand secretion mediator | 1.31650603 | 2.11.96 || ZFHX4 | 2.11.96 | zinc finger homeobox 4 | 1.487261107 | 2.11.96 || ZNF507 | 2.11.96 | zinc finger protein 507 | 0.334228087 | 2.11.96 || ABCA6 | 2.12 | ATP binding cassette subfamily A member 6 | 2.446980416 | 2.12.103 || ACE | 2.12 | angiotensin I converting enzyme | 0.822173231 | 2.12.101 || ADAP1 | 2.12 | ArfGAP with dual PH domains 1 | 0.227749312 | 2.12.101 || ADGRE5 | 2.12 | adhesion G protein-coupled receptor E5 | 0.576993351 | 2.12.101 || AGPAT3 | 2.12 | 1-acylglycerol-3-phosphate O-acyltransferase 3 | 0.326055015 | 2.12.101 || ALCAM | 2.12 | activated leukocyte cell adhesion molecule | 0.749551732 | 2.12.104 || ALDH5A1 | 2.12 | aldehyde dehydrogenase 5 family member A1 | 0.281576773 | 2.12.103 || ALDH7A1 | 2.12 | aldehyde dehydrogenase 7 family member A1 | 0.234976944 | — || ALDOC | 2.12 | aldolase, fructose-bisphosphate C | 0.943730749 | 2.12.103 || ANGPT1 | 2.12 | angiopoietin 1 | 3.008389668 | 2.12.101 || ANKRD46 | 2.12 | ankyrin repeat domain 46 | 0.780596259 | 2.12.103 || ANPEP | 2.12 | alanyl aminopeptidase, membrane | 1.337916135 | 2.12.103 || ANXA1 | 2.12 | annexin A1 | 0.256970367 | 2.12.106 || APEX2 | 2.12 | apurinic/apyrimidinic endodeoxyribonuclease 2 | 0.218435554 | 2.12.101 || APOLD1 | 2.12 | apolipoprotein L domain containing 1 | 1.16275303 | 2.12.107 || ARHGEF10L | 2.12 | Rho guanine nucleotide exchange factor 10 like | 0.229452534 | 2.12.101 || ARRDC4 | 2.12 | arrestin domain containing 4 | 0.332199587 | 2.12.103 || ASPN | 2.12 | asporin | 0.761715506 | 2.12.106 || ATG4B | 2.12 | autophagy related 4B cysteine peptidase | 0.256069183 | 2.12.103 || ATP1B1 | 2.12 | ATPase Na+/K+ transporting subunit beta 1 | 0.607829393 | 2.12.105 || B4GALT1 | 2.12 | UDP-Gal:betaGlcNAc beta 1,4-galactosyltransferase, polypeptide 1 | 0.544686323 | 2.12.104 || BAG3 | 2.12 | BCL2 associated athanogene 3 | 0.229697872 | 2.12.105 || BAHD1 | 2.12 | bromo adjacent homology domain containing 1 | 0.266102832 | 2.12.106 || BBIP1 | 2.12 | BBSome interacting protein 1 | 0.216472744 | 2.12.103 || BBOF1 | 2.12 | basal body orientation factor 1 | 0.324475326 | 2.12.104 || BCAR3 | 2.12 | breast cancer anti-estrogen resistance 3 | 0.297371169 | 2.12.103 || BIN2 | 2.12 | bridging integrator 2 | 0.251622852 | 2.12.101 || C1GALT1 | 2.12 | core 1 synthase, glycoprotein-N-acetylgalactosamine 3-beta-galactosyltransferase 1 | 1.306472927 | 2.12.104 || CACNA2D1 | 2.12 | calcium voltage-gated channel auxiliary subunit alpha2delta 1 | 1.548364794 | — || CARD19 | 2.12 | caspase recruitment domain family member 19 | 0.234570383 | 2.12.101 || CCDC88A | 2.12 | coiled-coil domain containing 88A | 0.223034609 | 2.12.104 || CCL19 | 2.12 | C-C motif chemokine ligand 19 | 2.41316504 | 2.12.106 || CCND3 | 2.12 | cyclin D3 | 0.366729564 | 2.12.101 || CCNG1 | 2.12 | cyclin G1 | 0.239865274 | — || CCR1 | 2.12 | chemokine (C-C motif) receptor 1 | 0.715344552 | 2.12.104 || CCR5 | 2.12 | chemokine (C-C motif) receptor 5 (gene/pseudogene) | 1.540711162 | 2.12.104 || CD14 | 2.12 | CD14 molecule | 0.476939467 | 2.12.104 || CD300C | 2.12 | CD300c molecule | 1.120289507 | 2.12.101 || CD4 | 2.12 | CD4 molecule | 0.222176835 | 2.12.104 || CD44 | 2.12 | CD44 molecule (Indian blood group) | 0.250184608 | 2.12.101 || CD86 | 2.12 | CD86 molecule | 0.874437231 | 2.12.107 || CDC34 | 2.12 | cell division cycle 34 | 0.227013035 | 2.12.106 || CECR1 | 2.12 | cat eye syndrome chromosome region, candidate 1 | 1.519960814 | 2.12.104 || CHFR | 2.12 | checkpoint with forkhead and ring finger domains, E3 ubiquitin protein ligase | 0.376419996 | 2.12.101 || CIITA | 2.12 | class II, major histocompatibility complex, transactivator | 0.408325037 | 2.12.107 || CISD1 | 2.12 | CDGSH iron sulfur domain 1 | 0.581864792 | 2.12.104 || CLEC1A | 2.12 | C-type lectin domain family 1 member A | 0.292741233 | 2.12.104 || CLEC4E | 2.12 | C-type lectin domain family 4 member E | 1.282428339 | 2.12.101 || CLEC7A | 2.12 | C-type lectin domain family 7 member A | 0.765737967 | 2.12.107 || CMTM7 | 2.12 | CKLF like MARVEL transmembrane domain containing 7 | 0.229634714 | 2.12.103 || CNDP2 | 2.12 | CNDP dipeptidase 2 (metallopeptidase M20 family) | 0.314323478 | 2.12.107 || CNN3 | 2.12 | calponin 3 | 1.57669861 | 2.12.101 || CRIP2 | 2.12 | cysteine rich protein 2 | 1.358696907 | 2.12.106 || CRTAM | 2.12 | cytotoxic and regulatory T-cell molecule | 0.492695708 | 2.12.107 || CSF1R | 2.12 | colony stimulating factor 1 receptor | 0.521530062 | 2.12.104 || CSK | 2.12 | c-src tyrosine kinase | 0.421471419 | 2.12.101 || CSTB | 2.12 | cystatin B | 0.662075204 | 2.12.103 || CTSA | 2.12 | cathepsin A | 0.410870922 | 2.12.106 || CTSS | 2.12 | cathepsin S | 0.293650137 | 2.12.107 || CXCL16 | 2.12 | C-X-C motif chemokine ligand 16 | 0.961606521 | 2.12.104 || CYP27A1 | 2.12 | cytochrome P450 family 27 subfamily A member 1 | 0.575476 | 2.12.103 || CYTH1 | 2.12 | cytohesin 1 | 0.281087033 | 2.12.104 || DBN1 | 2.12 | drebrin 1 | 0.359697531 | 2.12.107 || DCUN1D1 | 2.12 | defective in cullin neddylation 1 domain containing 1 | 0.27787274 | 2.12.101 || DDIT4 | 2.12 | DNA damage inducible transcript 4 | 1.002173711 | 2.12.105 || DEF6 | 2.12 | DEF6, guanine nucleotide exchange factor | 0.256345421 | 2.12.104 || DENND5A | 2.12 | DENN domain containing 5A | 0.238081052 | 2.12.101 || DENND5B | 2.12 | DENN domain containing 5B | 0.686236457 | 2.12.104 || DHRS9 | 2.12 | dehydrogenase/reductase (SDR family) member 9 | 1.280820142 | 2.12.104 || DMD | 2.12 | dystrophin | 3.102263099 | 2.12.103 || DNAJB4 | 2.12 | DnaJ heat shock protein family (Hsp40) member B4 | 0.328615897 | 2.12.107 || DPEP2 | 2.12 | dipeptidase 2 | 1.720455863 | 2.12.104 || DSC2 | 2.12 | desmocollin 2 | 0.25527513 | 2.12.107 || DUXAP10 | 2.12 | double homeobox A pseudogene 10 | 2.713198962 | 2.12.101 || ECM1 | 2.12 | extracellular matrix protein 1 | 0.928792043 | 2.12.103 || EFNA5 | 2.12 | ephrin-A5 | 0.949534783 | 2.12.104 || EMILIN2 | 2.12 | elastin microfibril interfacer 2 | 0.846147238 | — || ENO2 | 2.12 | enolase 2 (gamma, neuronal) | 1.925091902 | 2.12.101 || ESF1 | 2.12 | ESF1 nucleolar pre-rRNA processing protein homolog | 0.694909511 | 2.12.101 || EVI2B | 2.12 | ecotropic viral integration site 2B | 0.442802766 | 2.12.104 || EZR | 2.12 | ezrin | 0.35464123 | 2.12.103 || FAM217B | 2.12 | family with sequence similarity 217

TABLE 3B-continued

The genes within the significant gene clusters, listed in Table 3A. (3966 Genes Listed by: Gene Symbol | Gen 2 Module | Gene Description | RowVariance | Gen 3 Module ||)

member B | 0.408663559 | 2.12.105 || FAM76B | 2.12 | family with sequence similarity 76 member B | 0.241659847 | 2.12.103 || FAR2 | 2.12 | fatty acyl-CoA reductase 2 | 0.977900947 | 2.12.101 || FBXL4 | 2.12 | F-box and leucine-rich repeat protein 4 | 0.529242019 | 2.12.104 || FBXO3 | 2.12 | F-box protein 3 | 0.568917163 | 2.12.105 || FGF7 | 2.12 | fibroblast growth factor 7 | 1.359856902 | 2.12.101 || FGR | 2.12 | FGR proto-oncogene, Src family tyrosine kinase | 2.300021414 | 2.12.104 || FILIP1 | 2.12 | filamin A interacting protein 1 | 2.150542453 | 2.12.105 || FOXP4 | 2.12 | forkhead box P4 | 0.361538465 | 2.12.106 || FRAT1 | 2.12 | frequently rearranged in advanced T-cell lymphomas 1 | 0.506487654 | 2.12.101 || FXYD1 | 2.12 | FXYD domain containing ion transport regulator 1 | 0.938165093 | — || FXYD2 | 2.12 | FXYD domain containing ion transport regulator 2 | 0.440705488 | 2.12.101 || FYCO1 | 2.12 | FYVE and coiled-coil domain containing 1 | 0.569072965 | — || GABRB1 | 2.12 | gamma-aminobutyric acid type A receptor beta1 subunit | 2.96219369 | 2.12.104 || GALNT12 | 2.12 | polypeptide N-acetylgalactosaminyltransferase 12 | 1.09110838 | 2.12.101 || GALNT6 | 2.12 | polypeptide N-acetylgalactosaminyltransferase 6 | 0.588788908 | 2.12.107 || GAS2L1 | 2.12 | growth arrest specific 2 like 1 | 0.602767108 | 2.12.106 || GGCX | 2.12 | gamma-glutamyl carboxylase | 0.273747239 | 2.12.103 || GLMP | 2.12 | glycosylated lysosomal membrane protein | 0.243880069 | 2.12.103 || GPCPD1 | 2.12 | glycerophosphocholine phosphodiesterase 1 | 0.576944971 | 2.12.103 || GPR137B | 2.12 | G protein-coupled receptor 137B | 0.253109168 | 2.12.103 || GRB2 | 2.12 | growth factor receptor bound protein 2 | 0.331028902 | 2.12.107 || GRINA | 2.12 | glutamate ionotropic receptor NMDA type subunit associated protein 1 | 0.350327141 | 2.12.104 || GTPBP8 | 2.12 | GTP-binding protein 8 (putative) | 0.475705316 | 2.12.101 || H1F0 | 2.12 | H1 histone family member 0 | 0.364999083 | 2.12.106 || H2AFY | 2.12 | H2A histone family member Y | 0.440754871 | 2.12.104 || HAS2 | 2.12 | hyaluronan synthase 2 | 1.207932395 | 2.12.104 || HIBCH | 2.12 | 3-hydroxyisobutyryl-CoA hydrolase | 0.488970484 | 2.12.103 || HLA-J | 2.12 | major histocompatibility complex, class I, J (pseudogene) | 0.504591289 | 2.12.101 || HMHA1 | 2.12 | histocompatibility (minor) HA-1 | 0.596715737 | 2.12.104 || HPCAL1 | 2.12 | hippocalcin like 1 | 0.496071858 | 2.12.101 || HRH1 | 2.12 | histamine receptor H1 | 0.48659057 | 2.12.104 || HSPA2 | 2.12 | heat shock protein family A (Hsp70) member 2 | 1.229622178 | — || HSPB2 | 2.12 | heat shock protein family B (small) member 2 | 0.699781793 | — || HSPB8 | 2.12 | heat shock protein family B (small) member 8 | 1.289429847 | — || IFT140 | 2.12 | intraflagellar transport 140 | 0.229390913 | 2.12.104 || IFT88 | 2.12 | intraflagellar transport 88 | 0.330102919 | 2.12.105 || IGFBP3 | 2.12 | insulin like growth factor binding protein 3 | 0.691039618 | — || IL10RA | 2.12 | interleukin 10 receptor subunit alpha | 0.57834018 | 2.12.104 || ILK | 2.12 | integrin linked kinase | 0.246792144 | 2.12.106 || IMMP1L | 2.12 | inner mitochondrial membrane peptidase subunit 1 | 0.406962095 | 2.12.105 || INHBC | 2.12 | inhibin beta C | 0.264875814 | — || ITGB2 | 2.12 | integrin subunit beta 2 | 1.491347188 | 2.12.104 || JUP | 2.12 | junction plakoglobin | 0.73926426 | 2.12.101 || KCNAB2 | 2.12 | potassium voltage-gated channel subfamily A regulatory beta subunit 2 | 1.204761556 | 2.12.104 || KCNMB1 | 2.12 | potassium calcium-activated channel subfamily M regulatory beta subunit 1 | 0.62959806 | — || KDM1B | 2.12 | lysine demethylase 1B | 0.571725926 | — || KDM3A | 2.12 | lysine demethylase 3A | 0.534088404 | 2.12.101 || KIAA0513 | 2.12 | KIAA0513 | 0.307126608 | 2.12.101 || KIF1B | 2.12 | kinesin family member 1B | 0.413102517 | 2.12.105 || KIF9 | 2.12 | kinesin family member 9 | 0.226814631 | 2.12.105 || LBX2-AS1 | 2.12 | LBX2 antisense RNA 1 | 0.246214046 | 2.12.101 || LGALSL | 2.12 | lectin, galactoside-binding-like | 0.698144253 | 2.12.105 || LHFPL2 | 2.12 | lipoma HMGIC fusion partner-like 2 | 0.49592026 | 2.12.103 || LINC00894 | 2.12 | long intergenic non-protein coding RNA 894 | 0.481509831 | 2.12.104 || LOC154761 | 2.12 | family with sequence similarity 115, member C pseudogene | 1.412367117 | 2.12.103 || LOC374443 | 2.12 | C-type lectin domain family 2 member D pseudogene | 0.441781327 | 2.12.101 || LONP1 | 2.12 | lon peptidase 1, mitochondrial | 0.243949601 | 2.12.101 || LPCAT2 | 2.12 | lysophosphatidylcholine acyltransferase 2 | 0.728406381 | 2.12.106 || LRP5 | 2.12 | LDL receptor related protein 5 | 0.324201869 | 2.12.107 || LZTFL1 | 2.12 | leucine zipper transcription factor like 1 | 0.306767959 | 2.12.105 || MANBA | 2.12 | mannosidase beta | 0.265479243 | 2.12.103 || MAP7D1 | 2.12 | MAP7 domain containing 1 | 0.21489017 | 2.12.101 || MARCH1 | 2.12 | membrane associated ring-CH-type finger 1 | 0.664350399 | 2.12.107 || MEIS2 | 2.12 | Meis homeobox 2 | 1.453497642 | 2.12.101 || MERTK | 2.12 | MER proto-oncogene, tyrosine kinase | 1.090440676 | 2.12.103 || MGA | 2.12 | MGA, MAX dimerization protein | 0.345347405 | 2.12.104 || MID1 | 2.12 | midline 1 | 1.014800351 | 2.12.103 || MIDN | 2.12 | midnolin | 0.397682982 | — || MIR146A | 2.12 | microRNA 146a | 0.290852577 | 2.12.103 || MPP1 | 2.12 | membrane protein, palmitoylated 1 | 0.288529638 | 2.12.101 || MPP5 | 2.12 | membrane protein, palmitoylated 5 | 0.241556347 | 2.12.105 || MREG | 2.12 | melanoregulin | 1.498263672 | 2.12.107 || MRPL19 | 2.12 | mitochondrial ribosomal protein L19 | 0.247269123 | 2.12.104 || MYADM | 2.12 | myeloid-associated differentiation marker | 0.667791803 | 2.12.106 || MYC | 2.12 | v-myc avian myelocytomatosis viral oncogene homolog | 0.346971875 | 2.12.107 || MYD88 | 2.12 | myeloid differentiation primary response 88 | 0.599349644 | 2.12.101 || MYO1E | 2.12 | myosin IE | 0.260241201 | 2.12.101 || MYOF | 2.12 | myoferlin | 0.285690144 | 2.12.106 || NAA15 | 2.12 | N(alpha)-acetyltransferase 15, NatA auxiliary subunit | 0.390736172 | 2.12.101 || NANOS1 | 2.12 | nanos homolog 1 (*Drosophila*) | 0.54898783 | 2.12.103 || NCF2 | 2.12 | neutrophil cytosolic factor 2 | 1.048558482 | 2.12.101 || NCKIPSD | 2.12 | NCK interacting protein with SH3 domain | 0.344097509 | 2.12.106 || NDRG1 | 2.12 | N-myc downstream regulated 1 | 0.439750954 | 2.12.103 || NECTIN3 | 2.12 | nectin cell adhesion molecule 3 | 0.41568067 | 2.12.105 || NFKBIZ | 2.12 | NFKB inhibitor zeta | 0.371426958 | — || NOP9 | 2.12 | NOP9 nucleolar protein | 0.322998316 | 2.12.104 || OSBPL3 | 2.12 | oxysterol binding protein like 3 | 0.292025729 | 2.12.107 || OTUD1 | 2.12 | OTU deubiquitinase 1 | 0.432181994 | 2.12.103 || P2RX7 | 2.12 | purinergic receptor P2X 7 | 1.410038537 | 2.12.107 || PAPSS2 | 2.12 | 3'-phosphoadenosine 5'-phosphosulfate synthase 2 | 0.356985586 | 2.12.103 || PATL1 | 2.12 | protein associated with topoisomerase II homolog 1 (yeast) | 0.451781219 | 2.12.101 || PAWR | 2.12 | pro-apoptotic WT1 regulator | 1.674403695 | 2.12.103 || PEG3 | 2.12 | paternally expressed 3 | 0.62981622 | 2.12.107 || PELI1 | 2.12 | pellino E3 ubiquitin protein ligase 1 | 0.348654689 | 2.12.104 || PFKP | 2.12 | phosphofructokinase, platelet | 0.702107291 | 2.12.106 || PGD | 2.12 | phosphogluconate dehydrogenase | 0.53732397 | 2.12.101 || PIK3C2B | 2.12 | phosphatidylinositol-4-phosphate 3-kinase catalytic subunit type 2 beta | 0.63483958 | 2.12.103 || PLK3 | 2.12 | polo like kinase 3 | 0.406159757 | 2.12.103 || PNMA2 | 2.12 | paraneoplastic Ma antigen 2 | 0.863778695 | 2.12.104 || PNO1 | 2.12 | partner of NOB1 homolog | 0.369837084 | 2.12.101 ||

TABLE 3B-continued

The genes within the significant gene clusters, listed in Table 3A. (3966 Genes Listed by: Gene Symbol | Gen 2 Module | Gene Description | RowVariance | Gen 3 Module ||)

PNPLA6 | 2.12 | patatin like phospholipase domain containing 6 | 0.461952597 | — || POGK | 2.12 | pogo transposable element with KRAB domain | 0.225286897 | 2.12.101 || PPM1M | 2.12 | protein phosphatase, Mg2+/Mn2+ dependent 1M | 1.091444897 | 2.12.106 || PTCH1 | 2.12 | patched 1 | 0.699706032 | 2.12.107 || PTGFR | 2.12 | prostaglandin F receptor | 2.888425389 | 2.12.101 || PTK2B | 2.12 | protein tyrosine kinase 2 beta | 1.103557067 | 2.12.104 || PTPN6 | 2.12 | protein tyrosine phosphatase, non-receptor type 6 | 0.589655517 | 2.12.104 || QPCT | 2.12 | glutaminyl-peptide cyclotransferase | 1.625708384 | 2.12.101 || RAB11B | 2.12 | RAB11B, member RAS oncogene family | 0.45922951 | 2.12.101 || RAB28 | 2.12 | RAB28, member RAS oncogene family | 0.271338912 | 2.12.105 || RAB31 | 2.12 | RAB31, member RAS oncogene family | 0.215426784 | 2.12.107 || RAB8A | 2.12 | RAB8A, member RAS oncogene family | 0.230331134 | 2.12.101 || RAPGEF4 | 2.12 | Rap guanine nucleotide exchange factor 4 | 0.966494078 | — || RARRES1 | 2.12 | retinoic acid receptor responder (tazarotene induced) 1 | 2.495773677 | 2.12.101 || RCSD1 | 2.12 | RCSD domain containing 1 | 0.560084528 | 2.12.104 || RHBDF2 | 2.12 | rhomboid 5 homolog 2 (*Drosophila*) | 0.712330442 | 2.12.104 || RHOBTB1 | 2.12 | Rho related BTB domain containing 1 | 0.310172604 | — || RIN3 | 2.12 | Ras and Rab interactor 3 | 0.471907039 | 2.12.103 || RNF187 | 2.12 | ring finger protein 187 | 0.369042429 | 2.12.106 || RNF219 | 2.12 | ring finger protein 219 | 0.253617613 | 2.12.103 || RPRD1A | 2.12 | regulation of nuclear pre-mRNA domain containing 1A | 0.367871682 | 2.12.103 || RUNDC3B | 2.12 | RUN domain containing 3B | 0.455915526 | — || S100A10 | 2.12 | S100 calcium binding protein A10 | 0.221750942 | 2.12.101 || S100A11 | 2.12 | S100 calcium binding protein A11 | 0.313350115 | 2.12.103 || SCFD2 | 2.12 | sec1 family domain containing 2 | 0.269780851 | 2.12.101 || SELPLG | 2.12 | selectin P ligand | 0.446154855 | 2.12.104 || SGCB | 2.12 | sarcoglycan beta | 0.519046643 | 2.12.105 || SGK1 | 2.12 | serum/glucocorticoid regulated kinase 1 | 0.671092889 | 2.12.103 || SGMS2 | 2.12 | sphingomyelin synthase 2 | 0.568789822 | 2.12.103 || SIRPB1 | 2.12 | signal regulatory protein beta 1 | 0.780891036 | 2.12.103 || SIRT7 | 2.12 | sirtuin 7 | 0.233507051 | 2.12.103 || SIX1 | 2.12 | SIX homeobox 1 | 1.031010244 | 2.12.105 || SLC22A15 | 2.12 | solute carrier family 22 member 15 | 0.414116218 | 2.12.103 || SLC31A2 | 2.12 | solute carrier family 31 member 2 | 1.086103798 | 2.12.104 || SLC43A3 | 2.12 | solute carrier family 43 member 3 | 0.404004154 | 2.12.104 || SLC6A8 | 2.12 | solute carrier family 6 member 8 | 1.164768002 | 2.12.101 || SLC8A1 | 2.12 | solute carrier family 8 member A1 | 0.382467359 | 2.12.107 || SLC8B1 | 2.12 | solute carrier family 8 member B1 | 0.215308981 | 2.12.103 || SP4 | 2.12 | Sp4 transcription factor | 0.363196732 | 2.12.103 || SPINT1 | 2.12 | serine peptidase inhibitor, Kunitz type 1 | 0.409337336 | 2.12.103 || SPP1 | 2.12 | secreted phosphoprotein 1 | 4.314548464 | 2.12.105 || SPRY1 | 2.12 | sprouty RTK signaling antagonist 1 | 1.075125941 | 2.12.107 || SPTLC2 | 2.12 | serine palmitoyltransferase long chain base subunit 2 | 0.461048192 | 2.12.101 || SRC | 2.12 | SRC proto-oncogene, non-receptor tyrosine kinase | 0.703451349 | 2.12.106 || SRXN1 | 2.12 | sulfiredoxin 1 | 0.245431157 | 2.12.106 || ST14 | 2.12 | suppression of tumorigenicity 14 | 0.668616128 | 2.12.105 || ST3GAL1 | 2.12 | ST3 beta-galactoside alpha-2,3-sialyltransferase 1 | 0.378196061 | 2.12.101 || STAB1 | 2.12 | stabilin 1 | 0.273598284 | 2.12.103 || STEAP3 | 2.12 | STEAP3 metalloreductase | 0.884953473 | 2.12.103 || STXBP2 | 2.12 | syntaxin binding protein 2 | 0.847787556 | 2.12.101 || SULF2 | 2.12 | sulfatase 2 | 0.426220136 | 2.12.101 || SUSD6 | 2.12 | sushi domain containing 6 | 0.380056742 | 2.12.104 || SVIL | 2.12 | supervillin | 0.812893235 | — || SVIP | 2.12 | small VCP/p97-interacting protein | 0.748015774 | 2.12.103 || SYK | 2.12 | spleen tyrosine kinase | 0.499574814 | 2.12.104 || TACC2 | 2.12 | transforming acidic coiled-coil containing protein 2 | 0.266123476 | — || TAGLN2 | 2.12 | transgelin 2 | 0.412705258 | 2.12.106 || TBC1D4 | 2.12 | TBC1 domain family member 4 | 0.40550098 | 2.12.103 || TBCK | 2.12 | TBC1 domain containing kinase | 0.29938482 | 2.12.101 || TCF7 | 2.12 | transcription factor 7 (T-cell specific, HMG-box) | 0.503769999 | 2.12.103 || TCIRG1 | 2.12 | T-cell immune regulator 1, ATPase H+ transporting V0 subunit a3 | 0.594879156 | 2.12.103 || TCN2 | 2.12 | transcobalamin 2 | 0.391362798 | 2.12.104 || TGFBI | 2.12 | transforming growth factor beta induced | 0.614476288 | 2.12.103 || THEMIS2 | 2.12 | thymocyte selection associated family member 2 | 0.893339303 | 2.12.101 || TMCC3 | 2.12 | transmembrane and coiled-coil domain family 3 | 0.975389749 | 2.12.103 || TMEM43 | 2.12 | transmembrane protein 43 | 0.309809559 | 2.12.106 || TREM1 | 2.12 | triggering receptor expressed on myeloid cells 1 | 3.022587711 | 2.12.103 || TSPAN17 | 2.12 | tetraspanin 17 | 0.241860003 | 2.12.101 || TUBB3 | 2.12 | tubulin beta 3 class III | 0.223478301 | 2.12.106 || TUBGCP2 | 2.12 | tubulin gamma complex associated protein 2 | 0.396993298 | 2.12.103 || TWF2 | 2.12 | twinfilin actin binding protein 2 | 0.30778344 | 2.12.103 || UNC5B | 2.12 | unc-5 netrin receptor B | 1.104647732 | 2.12.104 || USP46 | 2.12 | ubiquitin specific peptidase 46 | 0.842920331 | 2.12.104 || UTS2 | 2.12 | urotensin 2 | 0.355683143 | — || VAC14 | 2.12 | Vac14 homolog (*S. cerevisiae*) | 0.308091951 | 2.12.106 || WDFY3-AS2 | 2.12 | WDFY3 antisense RNA 2 | 0.448186957 | 2.12.105 || YBX3 | 2.12 | Y-box binding protein 3 | 0.416102805 | 2.12.105 || YIF1B | 2.12 | Yip1 interacting factor homolog B, membrane trafficking protein | 0.376639455 | 2.12.103 || ZAK | 2.12 | sterile alpha motif and leucine zipper containing kinase AZK | 0.638478903 | — || ZHX2 | 2.12 | zinc fingers and homeoboxes 2 | 0.512369898 | 2.12.105 || ZMYM5 | 2.12 | zinc finger MYM-type containing 5 | 0.664464766 | 2.12.101 || ZNF124 | 2.12 | zinc finger protein 124 | 0.715444937 | 2.12.101 || ZNF304 | 2.12 | zinc finger protein 304 | 0.226046247 | 2.12.103 || ZNF385A | 2.12 | zinc finger protein 385A | 0.765763932 | 2.12.104 || ZNF616 | 2.12 | zinc finger protein 616 | 0.267943177 | — || ZNF687 | 2.12 | zinc finger protein 687 | 0.305127493 | 2.12.101 || ZNF91 | 2.12 | zinc finger protein 91 | 0.856868546 | 2.12.103 || ACE | 2.12.101 | angiotensin I converting enzyme | 0.822173231 | 2.12.101 || ADAP1 | 2.12.101 | ArfGAP with dual PH domains 1 | 0.227749312 | 2.12.101 || ADGRE5 | 2.12.101 | adhesion G protein-coupled receptor E5 | 0.576993351 | 2.12.101 || AGPAT3 | 2.12.101 | 1-acylglycerol-3-phosphate O-acyltransferase 3 | 0.326055015 | 2.12.101 || ANGPT1 | 2.12.101 | angiopoietin 1 | 3.008389668 | 2.12.101 || APEX2 | 2.12.101 | apurinic/apyrimidinic endodeoxyribonuclease 2 | 0.218435554 | 2.12.101 || ARHGEF10L | 2.12.101 | Rho guanine nucleotide exchange factor 10 like | 0.229452534 | 2.12.101 || BIN2 | 2.12.101 | bridging integrator 2 | 0.251622852 | 2.12.101 || CARD19 | 2.12.101 | caspase recruitment domain family member 19 | 0.234570383 | 2.12.101 || CCND3 | 2.12.101 | cyclin D3 | 0.366729564 | 2.12.101 || CD300C | 2.12.101 | CD300c molecule | 1.120289507 | 2.12.101 || CD44 | 2.12.101 | CD44 molecule (Indian blood group) | 0.250184608 | 2.12.101 || CHFR | 2.12.101 | checkpoint with forkhead and ring finger domains, E3 ubiquitin protein ligase | 0.376419996 | 2.12.101 || CLEC4E | 2.12.101 | C-type lectin domain family 4 member E | 1.282428339 | 2.12.101 || CNN3 | 2.12.101 | calponin 3 | 1.57669861 | 2.12.101 || CSK |

TABLE 3B-continued

The genes within the significant gene clusters, listed in Table 3A. (3966 Genes Listed by: Gene Symbol | Gen 2 Module | Gene Description | RowVariance | Gen 3 Module ||)

2.12.101 | c-src tyrosine kinase | 0.421471419 | 2.12.101 || DCUN1D1 | 2.12.101 | defective in cullin neddylation 1 domain containing 1 | 0.27787274 | 2.12.101 || DENND5A | 2.12.101 | DENN domain containing 5A | 0.238081052 | 2.12.101 || DUXAP10 | 2.12.101 | double homeobox A pseudogene 10 | 2.713198962 | 2.12.101 || ENO2 | 2.12.101 | enolase 2 (gamma, neuronal) | 1.925091902 | 2.12.101 || ESF1 | 2.12.101 | ESF1 nucleolar pre-rRNA processing protein homolog | 0.694909511 | 2.12.101 || FAR2 | 2.12.101 | fatty acyl-CoA reductase 2 | 0.977900947 | 2.12.101 || FGF7 | 2.12.101 | fibroblast growth factor 7 | 1.359856902 | 2.12.101 || FRAT1 | 2.12.101 | frequently rearranged in advanced T-cell lymphomas 1 | 0.506487654 | 2.12.101 || FXYD2 | 2.12.101 | FXYD domain containing ion transport regulator 2 | 0.440705488 | 2.12.101 || GALNT12 | 2.12.101 | polypeptide N-acetylgalactosaminyltransferase 12 | 1.09110838 | 2.12.101 || GTPBP8 | 2.12.101 | GTP-binding protein 8 (putative) | 0.475705316 | 2.12.101 || HLA-J | 2.12.101 | major histocompatibility complex, class I, J (pseudogene) | 0.504591289 | 2.12.101 || HPCAL1 | 2.12.101 | hippocalcin like 1 | 0.496071858 | 2.12.101 || JUP | 2.12.101 | junction plakoglobin | 0.73926426 | 2.12.101 || KDM3A | 2.12.101 | lysine demethylase 3A | 0.534088404 | 2.12.101 || KIAA0513 | 2.12.101 | KIAA0513 | 0.307126608 | 2.12.101 || LBX2-AS1 | 2.12.101 | LBX2 antisense RNA 1 | 0.246214046 | 2.12.101 || LOC374443 | 2.12.101 | C-type lectin domain family 2 member D pseudogene | 0.441781327 | 2.12.101 || LONP1 | 2.12.101 | lon peptidase 1, mitochondrial | 0.243949601 | 2.12.101 || MAP7D1 | 2.12.101 | MAP7 domain containing 1 | 0.21489017 | 2.12.101 || MEIS2 | 2.12.101 | Meis homeobox 2 | 1.453497642 | 2.12.101 || MPP1 | 2.12.101 | membrane protein, palmitoylated 1 | 0.288529638 | 2.12.101 || MYD88 | 2.12.101 | myeloid differentiation primary response 88 | 0.599349644 | 2.12.101 || MYO1E | 2.12.101 | myosin IE | 0.260241201 | 2.12.101 || NAA15 | 2.12.101 | N(alpha)-acetyltransferase 15, NatA auxiliary subunit | 0.390736172 | 2.12.101 || NCF2 | 2.12.101 | neutrophil cytosolic factor 2 | 1.048558482 | 2.12.101 || PATL1 | 2.12.101 | protein associated with topoisomerase II homolog 1 (yeast) | 0.451781219 | 2.12.101 || PGD | 2.12.101 | phosphogluconate dehydrogenase | 0.53732397 | 2.12.101 || PNO1 | 2.12.101 | partner of NOB1 homolog | 0.369837084 | 2.12.101 || POGK | 2.12.101 | pogo transposable element with KRAB domain | 0.225286897 | 2.12.101 || PTGFR | 2.12.101 | prostaglandin F receptor | 2.888425389 | 2.12.101 || QPCT | 2.12.101 | glutaminyl-peptide cyclotransferase | 1.625708384 | 2.12.101 || RAB11B | 2.12.101 | RAB11B, member RAS oncogene family | 0.45922951 | 2.12.101 || RAB8A | 2.12.101 | RAB8A, member RAS oncogene family | 0.230331134 | 2.12.101 || RARRES1 | 2.12.101 | retinoic acid receptor responder (tazarotene induced) 1 | 2.495773677 | 2.12.101 || S100A10 | 2.12.101 | S100 calcium binding protein A10 | 0.221750942 | 2.12.101 || SCFD2 | 2.12.101 | sec1 family domain containing 2 | 0.269780851 | 2.12.101 || SLC6A8 | 2.12.101 | solute carrier family 6 member 8 | 1.164768002 | 2.12.101 || SPTLC2 | 2.12.101 | serine palmitoyltransferase long chain base subunit 2 | 0.461048192 | 2.12.101 || ST3GAL1 | 2.12.101 | ST3 beta-galactoside alpha-2,3-sialyltransferase 1 | 0.378196061 | 2.12.101 || STXBP2 | 2.12.101 | syntaxin binding protein 2 | 0.847787556 | 2.12.101 || SULF2 | 2.12.101 | sulfatase 2 | 0.426220136 | 2.12.101 || TBCK | 2.12.101 | TBC1 domain containing kinase | 0.29938482 | 2.12.101 || THEMIS2 | 2.12.101 | thymocyte selection associated family member 2 | 0.893339303 | 2.12.101 || TSPAN17 | 2.12.101 | tetraspanin 17 | 0.241860003 | 2.12.101 || ZMYM5 | 2.12.101 | zinc finger MYM-type containing 5 | 0.664464766 | 2.12.101 || ZNF124 | 2.12.101 | zinc finger protein 124 | 0.715444937 | 2.12.101 || ZNF687 | 2.12.101 | zinc finger protein 687 | 0.305127493 | 2.12.101 || ABCA6 | 2.12.103 | ATP binding cassette subfamily A member 6 | 2.446980416 | 2.12.103 || ALDH5A1 | 2.12.103 | aldehyde dehydrogenase 5 family member A1 | 0.281576773 | 2.12.103 || ALDOC | 2.12.103 | aldolase, fructose-bisphosphate C | 0.943730749 | 2.12.103 || ANKRD46 | 2.12.103 | ankyrin repeat domain 46 | 0.780596259 | 2.12.103 || ANPEP | 2.12.103 | alanyl aminopeptidase, membrane | 1.337916135 | 2.12.103 || ARRDC4 | 2.12.103 | arrestin domain containing 4 | 0.332199587 | 2.12.103 || ATG4B | 2.12.103 | autophagy related 4B cysteine peptidase | 0.256069183 | 2.12.103 || BBIP1 | 2.12.103 | BBSome interacting protein 1 | 0.216472744 | 2.12.103 || BCAR3 | 2.12.103 | breast cancer anti-estrogen resistance 3 | 0.297371169 | 2.12.103 || CMTM7 | 2.12.103 | CKLF like MARVEL transmembrane domain containing 7 | 0.229634714 | 2.12.103 || CSTB | 2.12.103 | cystatin B | 0.662075204 | 2.12.103 || CYP27A1 | 2.12.103 | cytochrome P450 family 27 subfamily A member 1 | 0.575476 | 2.12.103 || DMD | 2.12.103 | dystrophin | 3.102263099 | 2.12.103 || ECM1 | 2.12.103 | extracellular matrix protein 1 | 0.928792043 | 2.12.103 || EZR | 2.12.103 | ezrin | 0.35464123 | 2.12.103 || FAM76B | 2.12.103 | family with sequence similarity 76 member B | 0.241659847 | 2.12.103 || GGCX | 2.12.103 | gamma-glutamyl carboxylase | 0.273747239 | 2.12.103 || GLMP | 2.12.103 | glycosylated lysosomal membrane protein | 0.243880069 | 2.12.103 || GPCPD1 | 2.12.103 | glycerophosphocholine phosphodiesterase 1 | 0.576944971 | 2.12.103 || GPR137B | 2.12.103 | G protein-coupled receptor 137B | 0.253109168 | 2.12.103 || HIBCH | 2.12.103 | 3-hydroxyisobutyryl-CoA hydrolase | 0.488970484 | 2.12.103 || LHFPL2 | 2.12.103 | lipoma HMGIC fusion partner-like 2 | 0.49592026 | 2.12.103 || LOC154761 | 2.12.103 | family with sequence similarity 115, member C pseudogene | 1.412367117 | 2.12.103 || MANBA | 2.12.103 | mannosidase beta | 0.265479243 | 2.12.103 || MERTK | 2.12.103 | MER proto-oncogene, tyrosine kinase | 1.090440676 | 2.12.103 || MID1 | 2.12.103 | midline 1 | 1.014800351 | 2.12.103 || MIR146A | 2.12.103 | microRNA 146a | 0.290852577 | 2.12.103 || NANOS1 | 2.12.103 | nanos homolog 1 (*Drosophila*) | 0.54898783 | 2.12.103 || NDRG1 | 2.12.103 | N-myc downstream regulated 1 | 0.439750954 | 2.12.103 || OTUD1 | 2.12.103 | OTU deubiquitinase 1 | 0.432181994 | 2.12.103 || PAPSS2 | 2.12.103 | 3'-phosphoadenosine 5'-phosphosulfate synthase 2 | 0.356985586 | 2.12.103 || PAWR | 2.12.103 | pro-apoptotic WT1 regulator | 1.674403695 | 2.12.103 || PIK3C2B | 2.12.103 | phosphatidylinositol-4-phosphate 3-kinase catalytic subunit type 2 beta | 0.63483958 | 2.12.103 || PLK3 | 2.12.103 | polo like kinase 3 | 0.406159757 | 2.12.103 || RIN3 | 2.12.103 | Ras and Rab interactor 3 | 0.471907039 | 2.12.103 || RNF219 | 2.12.103 | ring finger protein 219 | 0.253617613 | 2.12.103 || RPRD1A | 2.12.103 | regulation of nuclear pre-mRNA domain containing 1A | 0.367871682 | 2.12.103 || S100A11 | 2.12.103 | S100 calcium binding protein A11 | 0.313350115 | 2.12.103 || SGK1 | 2.12.103 | serum/glucocorticoid regulated kinase 1 | 0.671092889 | 2.12.103 || SGMS2 | 2.12.103 | sphingomyelin synthase 2 | 0.568789822 | 2.12.103 || SIRPB1 | 2.12.103 | signal regulatory protein beta 1 | 0.780891036 | 2.12.103 || SIRT7 | 2.12.103 | sirtuin 7 | 0.233507051 | 2.12.103 || SLC22A15 | 2.12.103 | solute carrier family 22 member 15 | 0.414116218 | 2.12.103 || SLC8B1 | 2.12.103 | solute carrier family 8 member B1 | 0.215308981 | 2.12.103 || SP4 | 2.12.103 | Sp4 transcription factor | 0.363196732 | 2.12.103 || SPINT1 | 2.12.103 | serine peptidase inhibitor, Kunitz type 1 | 0.409337336 |

TABLE 3B-continued

The genes within the significant gene clusters, listed in Table 3A. (3966 Genes Listed by: Gene Symbol | Gen 2 Module | Gene Description | RowVariance | Gen 3 Module ||)

2.12.103 || STAB1 | 2.12.103 | stabilin 1 | 0.273598284 | 2.12.103 || STEAP3 | 2.12.103 | STEAP3 metalloreductase | 0.884953473 | 2.12.103 || SVIP | 2.12.103 | small VCP/p97-interacting protein | 0.748015774 | 2.12.103 || TBC1D4 | 2.12.103 | TBC1 domain family member 4 | 0.40550098 | 2.12.103 || TCF7 | 2.12.103 | transcription factor 7 (T-cell specific, HMG-box) | 0.503769999 | 2.12.103 || TCIRG1 | 2.12.103 | T-cell immune regulator 1, ATPase H+ transporting V0 subunit a3 | 0.594879156 | 2.12.103 || TGFBI | 2.12.103 | transforming growth factor beta induced | 0.614476288 | 2.12.103 || TMCC3 | 2.12.103 | transmembrane and coiled-coil domain family 3 | 0.975389749 | 2.12.103 || TREM1 | 2.12.103 | triggering receptor expressed on myeloid cells 1 | 3.022587711 | 2.12.103 || TUBGCP2 | 2.12.103 | tubulin gamma complex associated protein 2 | 0.396993298 | 2.12.103 || TWF2 | 2.12.103 | twinfilin actin binding protein 2 | 0.30778344 | 2.12.103 || YIF1B | 2.12.103 | Yip1 interacting factor homolog B, membrane trafficking protein | 0.376639455 | 2.12.103 || ZNF304 | 2.12.103 | zinc finger protein 304 | 0.226046247 | 2.12.103 || ZNF91 | 2.12.103 | zinc finger protein 91 | 0.856868546 | 2.12.103 || APOLD1 | 2.12.107 | apolipoprotein L domain containing 1 | 1.16275303 | 2.12.107 || CD86 | 2.12.107 | CD86 molecule | 0.874437231 | 2.12.107 || CIITA | 2.12.107 | class II, major histocompatibility complex, transactivator | 0.408325037 | 2.12.107 || CLEC7A | 2.12.107 | C-type lectin domain family 7 member A | 0.765737967 | 2.12.107 || CNDP2 | 2.12.107 | CNDP dipeptidase 2 (metallopeptidase M20 family) | 0.314323478 | 2.12.107 || CRTAM | 2.12.107 | cytotoxic and regulatory T-cell molecule | 0.492695708 | 2.12.107 || CTSS | 2.12.107 | cathepsin S | 0.293650137 | 2.12.107 || DBN1 | 2.12.107 | drebrin 1 | 0.359697531 | 2.12.107 || DNAJB4 | 2.12.107 | DnaJ heat shock protein family (Hsp40) member B4 | 0.328615897 | 2.12.107 || DSC2 | 2.12.107 | desmocollin 2 | 0.25527513 | 2.12.107 || GALNT6 | 2.12.107 | polypeptide N-acetylgalactosaminyltransferase 6 | 0.588788908 | 2.12.107 || GRB2 | 2.12.107 | growth factor receptor bound protein 2 | 0.331028902 | 2.12.107 || LRP5 | 2.12.107 | LDL receptor related protein 5 | 0.324201869 | 2.12.107 || MARCH1 | 2.12.107 | membrane associated ring-CH-type finger 1 | 0.664350399 | 2.12.107 || MREG | 2.12.107 | melanoregulin | 1.498263672 | 2.12.107 || MYC | 2.12.107 | v-myc avian myelocytomatosis viral oncogene homolog | 0.346971875 | 2.12.107 || OSBPL3 | 2.12.107 | oxysterol binding protein like 3 | 0.292025729 | 2.12.107 || P2RX7 | 2.12.107 | purinergic receptor P2X 7 | 1.410038537 | 2.12.107 || PEG3 | 2.12.107 | paternally expressed 3 | 0.62981622 | 2.12.107 || PTCH1 | 2.12.107 | patched 1 | 0.699706032 | 2.12.107 || RAB31 | 2.12.107 | RAB31, member RAS oncogene family | 0.215426784 | 2.12.107 || SLC8A1 | 2.12.107 | solute carrier family 8 member A1 | 0.382467359 | 2.12.107 || SPRY1 | 2.12.107 | sprouty RTK signaling antagonist 1 | 1.075125941 | 2.12.107 || ABCA7 | 2.13 | ATP binding cassette subfamily A member 7 | 0.242566393 | 2.13.114 || ABCC3 | 2.13 | ATP binding cassette subfamily C member 3 | 0.812744141 | — || ABCD1 | 2.13 | ATP binding cassette subfamily D member 1 | 0.3229188 | 2.13.114 || ABHD12 | 2.13 | abhydrolase domain containing 12 | 0.39543476 | 2.13.114 || ACP2 | 2.13 | acid phosphatase 2, lysosomal | 0.664126978 | 2.13.112 || ACP5 | 2.13 | acid phosphatase 5, tartrate resistant | 1.260127755 | 2.13.115 || ACSL4 | 2.13 | acyl-CoA synthetase long-chain family member 4 | 0.363441248 | — || ACSM5 | 2.13 | acyl-CoA synthetase medium-chain family member 5 | 0.683890782 | 2.13.111 || ADPGK | 2.13 | ADP-dependent glucokinase | 0.292056261 | 2.13.114 || ADRBK1 | 2.13 | adrenergic, beta, receptor kinase 1 | 0.557067614 | 2.13.111 || AEBP2 | 2.13 | AE binding protein 2 | 0.324321466 | 2.13.111 || AGMAT | 2.13 | agmatinase | 0.606004319 | 2.13.111 || AGTR1 | 2.13 | angiotensin II receptor type 1 | 1.435580979 | 2.13.115 || AGTRAP | 2.13 | angiotensin II receptor associated protein | 0.31645459 | 2.13.114 || AHNAK2 | 2.13 | AHNAK nucleoprotein 2 | 1.156764235 | 2.13.109 || AMOTL2 | 2.13 | angiomotin like 2 | 0.690294426 | 2.13.115 || ANK2 | 2.13 | ankyrin 2, neuronal | 0.853893541 | 2.13.115 || ANKIB1 | 2.13 | ankyrin repeat and IBR domain containing 1 | 0.251107709 | 2.13.111 || ANKRD13B | 2.13 | ankyrin repeat domain 13B | 0.249764536 | — || ANKRD44 | 2.13 | ankyrin repeat domain 44 | 0.419715692 | 2.13.117 || AP1B1 | 2.13 | adaptor related protein complex 1 beta 1 subunit | 0.313746684 | 2.13.114 || AQP9 | 2.13 | aquaporin 9 | 3.36202372 | 2.13.109 || ARAP1 | 2.13 | ArfGAP with RhoGAP domain, ankyrin repeat and PH domain 1 | 0.270031263 | 2.13.114 || ARFRP1 | 2.13 | ADP ribosylation factor related protein 1 | 0.314641078 | 2.13.109 || ARHGAP12 | 2.13 | Rho GTPase activating protein 12 | 0.233692783 | 2.13.112 || ARHGAP20 | 2.13 | Rho GTPase activating protein 20 | 3.587873186 | 2.13.116 || ARHGAP30 | 2.13 | Rho GTPase activating protein 30 | 0.553082233 | 2.13.117 || ARHGAP5 | 2.13 | Rho GTPase activating protein 5 | 0.262890248 | 2.13.116 || ARHGDIA | 2.13 | Rho GDP dissociation inhibitor (GDI) alpha | 0.344731536 | 2.13.114 || ARHGEF28 | 2.13 | Rho guanine nucleotide exchange factor 28 | 0.276366556 | 2.13.114 || ARL13B | 2.13 | ADP ribosylation factor like GTPase 13B | 0.42198126 | 2.13.116 || ARMC7 | 2.13 | armadillo repeat containing 7 | 0.335938816 | 2.13.109 || ARPC4 | 2.13 | actin related protein 2/3 complex subunit 4 | 0.338889024 | 2.13.114 || ARRB2 | 2.13 | arrestin, beta 2 | 0.667353075 | 2.13.112 || ARSA | 2.13 | arylsulfatase A | 0.750160235 | 2.13.111 || ATP13A1 | 2.13 | ATPase 13A1 | 0.271731484 | 2.13.109 || ATP1A1 | 2.13 | ATPase Na+/K+ transporting subunit alpha 1 | 0.256338538 | 2.13.114 || ATP2A2 | 2.13 | ATPase sarcoplasmic/endoplasmic reticulum Ca2+ transporting 2 | 0.227494642 | 2.13.109 || ATP6AP1 | 2.13 | ATPase H+ transporting accessory protein 1 | 0.385387572 | 2.13.114 || ATP6V0B | 2.13 | ATPase H+ transporting V0 subunit b | 0.285343938 | 2.13.115 || ATP6V0C | 2.13 | ATPase H+ transporting V0 subunit c | 0.258838881 | 2.13.114 || ATP6V1B2 | 2.13 | ATPase H+ transporting V1 subunit B2 | 0.372650633 | 2.13.117 || B3GALNT1 | 2.13 | beta-1,3-N-acetylgalactosaminyltransferase 1 (globoside blood group) | 0.780057 | 2.13.111 || BCL9L | 2.13 | B-cell CLL/lymphoma 9-like | 0.423412072 | — || BICC1 | 2.13 | BicC family RNA binding protein 1 | 0.668961195 | 2.13.116 || BLNK | 2.13 | B-cell linker | 0.435714403 | 2.13.112 || BMF | 2.13 | Bcl2 modifying factor | 0.408173976 | 2.13.114 || BOC | 2.13 | BOC cell adhesion associated, oncogene regulated | 0.517281217 | 2.13.116 || BRI3 | 2.13 | brain protein I3 | 0.276505057 | 2.13.114 || BTK | 2.13 | Bruton tyrosine kinase | 0.249249202 | — || BTN2A1 | 2.13 | butyrophilin subfamily 2 member A1 | 0.298190254 | — || C10orf10 | 2.13 | chromosome 10 open reading frame 10 | 1.450562961 | 2.13.112 || C11orf74 | 2.13 | chromosome 11 open reading frame 74 | 0.356840888 | 2.13.114 || C11orf95 | 2.13 | chromosome 11 open reading frame 95 | 0.548649164 | 2.13.116 || C15orf40 | 2.13 | chromosome 15 open reading frame 40 | 0.352275868 | 2.13.116 || C1QA | 2.13 | complement component 1, q subcomponent, A chain | 0.421878129 | — || C1QB | 2.13 | complement component 1, q subcomponent, B chain | 0.572935654 | — || C1QC | 2.13 | complement component 1, q subcomponent, C chain | 0.217455591 | — || C2orf76 | 2.13 | chromosome 2 open reading frame 76 | 0.779841415 | 2.13.117 ||

TABLE 3B-continued

The genes within the significant gene clusters, listed in Table 3A. (3966 Genes Listed by: Gene Symbol | Gen 2 Module | Gene Description | RowVariance | Gen 3 Module ||)

C3AR1 | 2.13 | complement component 3a receptor 1 | 0.844804571 | — || C3orf38 | 2.13 | chromosome 3 open reading frame 38 | 0.507900912 | 2.13.111 || C5AR1 | 2.13 | complement component 5a receptor 1 | 0.611938719 | 2.13.111 || C6orf203 | 2.13 | chromosome 6 open reading frame 203 | 0.273248312 | 2.13.116 || C9orf40 | 2.13 | chromosome 9 open reading frame 40 | 0.436229202 | 2.13.112 || CAPG | 2.13 | capping actin protein, gelsolin like | 1.250053934 | 2.13.115 || CBLB | 2.13 | Cbl proto-oncogene B, E3 ubiquitin protein ligase | 0.6990346 | 2.13.114 || CCDC34 | 2.13 | coiled-coil domain containing 34 | 0.271448568 | 2.13.109 || CCDC71L | 2.13 | coiled-coil domain containing 71-like | 0.447881502 | 2.13.114 || CD163 | 2.13 | CD163 molecule | 0.82788387 | — || CD33 | 2.13 | CD33 molecule | 0.458006501 | 2.13.114 || CD58 | 2.13 | CD58 molecule | 0.222572712 | 2.13.112 || CD74 | 2.13 | CD74 molecule | 0.237274973 | 2.13.112 || CD84 | 2.13 | CD84 molecule | 0.687760285 | 2.13.115 || CD99P1 | 2.13 | CD99 molecule pseudogene 1 | 0.975712846 | 2.13.114 || CDC25B | 2.13 | cell division cycle 25B | 0.234935615 | 2.13.117 || CDC42 | 2.13 | cell division cycle 42 | 0.249055075 | 2.13.114 || CDH23 | 2.13 | cadherin-related 23 | 0.235240172 | 2.13.111 || CDK2 | 2.13 | cyclin-dependent kinase 2 | 0.378352115 | 2.13.111 || CDK6 | 2.13 | cyclin-dependent kinase 6 | 0.313501183 | 2.13.114 || CEBPD | 2.13 | CCAAT/enhancer binding protein delta | 0.311601959 | 2.13.114 || CEP68 | 2.13 | centrosomal protein 68 kDa | 0.797869674 | 2.13.115 || CHKA | 2.13 | choline kinase alpha | 0.242642167 | 2.13.114 || CHST11 | 2.13 | carbohydrate (chondroitin 4) sulfotransferase 11 | 0.741694504 | 2.13.117 || CHSY3 | 2.13 | chondroitin sulfate synthase 3 | 0.50778913 | 2.13.114 || CKS1B | 2.13 | CDC28 protein kinase regulatory subunit 1B | 0.45252261 | 2.13.115 || CKS2 | 2.13 | CDC28 protein kinase regulatory subunit 2 | 1.100558823 | 2.13.114 || CLDN11 | 2.13 | claudin 11 | 1.352899095 | 2.13.112 || CMTM8 | 2.13 | CKLF like MARVEL transmembrane domain containing 8 | 0.247960622 | — || COMT | 2.13 | catechol-O-methyltransferase | 0.240369811 | 2.13.114 || COTL1 | 2.13 | coactosin-like F-actin binding protein 1 | 0.419338939 | 2.13.112 || CPNE1 | 2.13 | copine 1 | 0.306504255 | 2.13.112 || CROCC | 2.13 | ciliary rootlet coiled-coil, rootletin | 0.554760445 | 2.13.115 || CROT | 2.13 | carnitine O-octanoyltransferase | 0.275350575 | 2.13.109 || CSPP1 | 2.13 | centrosome and spindle pole associated protein 1 | 0.298382526 | 2.13.112 || CTBP2 | 2.13 | C-terminal binding protein 2 | 0.221798346 | 2.13.111 || CTNNAL1 | 2.13 | catenin alpha-like 1 | 0.941381818 | 2.13.114 || CTSB | 2.13 | cathepsin B | 0.444678736 | 2.13.112 || CTSD | 2.13 | cathepsin D | 0.598024566 | 2.13.115 || CTSL | 2.13 | cathepsin L | 0.791556213 | 2.13.111 || DAGLB | 2.13 | diacylglycerol lipase beta | 0.412141118 | 2.13.114 || DAPK1 | 2.13 | death-associated protein kinase 1 | 0.355467029 | 2.13.112 || DCLK1 | 2.13 | doublecortin like kinase 1 | 1.823815254 | 2.13.115 || DDAH1 | 2.13 | dimethylarginine dimethylaminohydrolase 1 | 1.054038883 | 2.13.115 || DGKA | 2.13 | diacylglycerol kinase alpha | 0.235711422 | 2.13.109 || DHRS7 | 2.13 | dehydrogenase/reductase (SDR family) member 7 | 0.227646413 | 2.13.114 || DMPK | 2.13 | dystrophia myotonica protein kinase | 0.644506824 | — || DNM2 | 2.13 | dynamin 2 | 0.307178926 | 2.13.111 || DOCK2 | 2.13 | dedicator of cytokinesis 2 | 0.396958644 | 2.13.116 || DOCK9 | 2.13 | dedicator of cytokinesis 9 | 0.994743112 | 2.13.115 || DOK2 | 2.13 | docking protein 2 | 0.406246015 | 2.13.112 || DOK3 | 2.13 | docking protein 3 | 1.407402243 | 2.13.117 || DTD2 | 2.13 | D-tyrosyl-tRNA deacylase 2 (putative) | 0.414817763 | 2.13.111 || DUBR | 2.13 | DPPA2 upstream binding RNA | 0.550940468 | 2.13.109 || ECT2 | 2.13 | epithelial cell transforming 2 | 0.34471067 | 2.13.114 || EFNB2 | 2.13 | ephrin-B2 | 1.356697214 | 2.13.116 || EGR1 | 2.13 | early growth response 1 | 2.184401604 | 2.13.111 || EGR3 | 2.13 | early growth response 3 | 0.802268668 | 2.13.114 || EID2 | 2.13 | EP300 interacting inhibitor of differentiation 2 | 0.334727204 | 2.13.109 || ENPP4 | 2.13 | ectonucleotide pyrophosphatase/phosphodiesterase 4 (putative) | 0.459210345 | 2.13.114 || ERLIN2 | 2.13 | ER lipid raft associated 2 | 0.388337469 | 2.13.116 || ESR1 | 2.13 | estrogen receptor 1 | 0.758299814 | 2.13.116 || ETS1 | 2.13 | ETS proto-oncogene 1, transcription factor | 0.385794104 | 2.13.115 || EVL | 2.13 | Enah/Vasp-like | 0.51540568 | 2.13.117 || F8 | 2.13 | coagulation factor VIII | 0.969874965 | 2.13.111 || FAM105A | 2.13 | family with sequence similarity 105 member A | 0.379660874 | 2.13.112 || FAM109A | 2.13 | family with sequence similarity 109 member A | 0.277290623 | 2.13.114 || FAM129B | 2.13 | family with sequence similarity 129 member B | 0.558431272 | 2.13.114 || FAM13C | 2.13 | family with sequence similarity 13 member C | 0.978243254 | 2.13.116 || FAM171A1 | 2.13 | family with sequence similarity 171 member A1 | 0.822847258 | 2.13.116 || FAM172A | 2.13 | family with sequence similarity 172 member A | 0.765955214 | 2.13.111 || FAM229B | 2.13 | family with sequence similarity 229 member B | 0.620487724 | 2.13.117 || FAM53B | 2.13 | family with sequence similarity 53 member B | 0.220473279 | 2.13.114 || FAM78A | 2.13 | family with sequence similarity 78 member A | 0.293370287 | 2.13.116 || FAM96A | 2.13 | family with sequence similarity 96 member A | 0.240033343 | 2.13.112 || FAT4 | 2.13 | FAT atypical cadherin 4 | 1.070560014 | 2.13.116 || FBP1 | 2.13 | fructose-bisphosphatase 1 | 4.173658928 | 2.13.115 || FCER1G | 2.13 | Fc fragment of IgE receptor Ig | 0.777975804 | 2.13.112 || FCGR2B | 2.13 | Fc fragment of IgG receptor IIb | 0.953106891 | 2.13.116 || FHL5 | 2.13 | four and a half LIM domains 5 | 1.775450295 | 2.13.112 || FKBP10 | 2.13 | FK506 binding protein 10 | 1.497576934 | 2.13.114 || FMNL1 | 2.13 | formin like 1 | 0.645099805 | 2.13.112 || FOXO4 | 2.13 | forkhead box O4 | 0.358715734 | 2.13.114 || FPR3 | 2.13 | formyl peptide receptor 3 | 0.974917252 | 2.13.115 || FTH1 | 2.13 | ferritin, heavy polypeptide 1 | 0.235701696 | 2.13.112 || FUS | 2.13 | FUS RNA binding protein | 0.255595073 | — || GAA | 2.13 | glucosidase, alpha; acid | 0.86547707 | 2.13.114 || GALNT11 | 2.13 | polypeptide N-acetylgalactosaminyltransferase 11 | 0.248601142 | 2.13.109 || GBGT1 | 2.13 | globoside alpha-1,3-N-acetylgalactosaminyltransferase 1 | 0.247002466 | 2.13.115 || GDAP1 | 2.13 | ganglioside induced differentiation associated protein 1 | 0.357898066 | 2.13.109 || GFRA1 | 2.13 | GDNF family receptor alpha 1 | 1.117068893 | 2.13.116 || GHDC | 2.13 | GH3 domain containing | 0.254119438 | 2.13.112 || GIMAP7 | 2.13 | GTPase, IMAP family member 7 | 0.329129516 | 2.13.115 || GLIDR | 2.13 | glioblastoma down-regulated RNA | 1.137115929 | 2.13.109 || GM2A | 2.13 | GM2 ganglioside activator | 0.355757498 | 2.13.114 || GMPR2 | 2.13 | guanosine monophosphate reductase 2 | 0.237416458 | — || GPNMB | 2.13 | glycoprotein nmb | 0.466321045 | 2.13.114 || GPR1 | 2.13 | G protein-coupled receptor 1 | 1.220139673 | 2.13.109 || GRAMD3 | 2.13 | GRAM domain containing 3 | 0.446615819 | 2.13.109 || GRIPAP1 | 2.13 | GRIP1 associated protein 1 | 0.272956233 | — || GRN | 2.13 | granulin | 0.447978794 | 2.13.114 || GSPT2 | 2.13 | G1 to S phase transition 2 | 0.359818944 | 2.13.116 || GSTO1 | 2.13 | glutathione S-transferase omega 1 | 0.265590052 | 2.13.115 || HACD3 | 2.13 | 3-

TABLE 3B-continued

The genes within the significant gene clusters, listed in Table 3A. (3966 Genes Listed by: Gene Symbol | Gen 2 Module | Gene Description | RowVariance | Gen 3 Module ||)

hydroxyacyl-CoA dehydratase 3 | 0.366670218 | 2.13.112 || HAPLN3 | 2.13 | hyaluronan and proteoglycan link protein 3 | 0.256133193 | — || HAVCR2 | 2.13 | hepatitis A virus cellular receptor 2 | 0.809067425 | 2.13.115 || HCK | 2.13 | HCK proto-oncogene, Src family tyrosine kinase | 0.591574122 | 2.13.111 || HDGFRP3 | 2.13 | hepatoma-derived growth factor, related protein 3 | 0.355894211 | 2.13.116 || HECW2 | 2.13 | HECT, C2 and WW domain containing E3 ubiquitin protein ligase 2 | 1.386960007 | 2.13.112 || HEXB | 2.13 | hexosaminidase subunit beta | 0.571878974 | 2.13.114 || HGF | 2.13 | hepatocyte growth factor | 0.882763197 | 2.13.109 || HK3 | 2.13 | hexokinase 3 | 1.301991786 | 2.13.112 || HMG20A | 2.13 | high mobility group 20A | 0.215790117 | 2.13.116 || HMOX1 | 2.13 | heme oxygenase 1 | 1.262125375 | 2.13.115 || HOXA10 | 2.13 | homeobox A10 | 1.078769313 | 2.13.116 || HOXA3 | 2.13 | homeobox A3 | 0.456875599 | 2.13.111 || HOXB6 | 2.13 | homeobox B6 | 0.668773405 | 2.13.114 || HOXC10 | 2.13 | homeobox C10 | 1.897134168 | 2.13.109 || HPS5 | 2.13 | HPS5, biogenesis of lysosomal organelles complex 2 subunit 2 | 0.415991705 | 2.13.116 || HSPA12A | 2.13 | heat shock protein family A (Hsp70) member 12A | 0.473957291 | 2.13.111 || HTR2A | 2.13 | 5-hydroxytryptamine receptor 2A | 0.430489177 | 2.13.111 || HVCN1 | 2.13 | hydrogen voltage gated channel 1 | 0.395585015 | 2.13.114 || IDH2 | 2.13 | isocitrate dehydrogenase 2 (NADP+), mitochondrial | 0.630488179 | 2.13.111 || IGF2BP2 | 2.13 | insulin like growth factor 2 mRNA binding protein 2 | 0.954990871 | 2.13.111 || IGIP | 2.13 | IgA-inducing protein | 0.701594348 | 2.13.116 || IGSF10 | 2.13 | immunoglobulin superfamily member 10 | 0.878588832 | 2.13.111 || IKZF4 | 2.13 | IKAROS family zinc finger 4 | 0.325366992 | 2.13.109 || IL13RA2 | 2.13 | interleukin 13 receptor subunit alpha 2 | 2.550295806 | 2.13.112 || IL15 | 2.13 | interleukin 15 | 0.814306198 | 2.13.117 || IL17RA | 2.13 | interleukin 17 receptor A | 0.455702783 | 2.13.117 || INO80D | 2.13 | INO80 complex subunit D | 0.971483252 | 2.13.111 || INPP4B | 2.13 | inositol polyphosphate-4-phosphatase type II B | 1.917873318 | 2.13.112 || IQCK | 2.13 | IQ motif containing K | 0.322032485 | 2.13.115 || IRF8 | 2.13 | interferon regulatory factor 8 | 0.516252625 | 2.13.117 || ITGA6 | 2.13 | integrin subunit alpha 6 | 0.400699663 | 2.13.115 || ITGB3 | 2.13 | integrin subunit beta 3 | 1.493493017 | 2.13.115 || KBTBD7 | 2.13 | kelch repeat and BTB domain containing 7 | 0.6206987 | 2.13.111 || KCNN4 | 2.13 | potassium calcium-activated channel subfamily N member 4 | 1.262571821 | 2.13.115 || KCTD5 | 2.13 | potassium channel tetramerization domain containing 5 | 0.459915482 | 2.13.109 || KHDRBS3 | 2.13 | KH domain containing, RNA binding, signal transduction associated 3 | 1.029569179 | 2.13.115 || KIAA1468 | 2.13 | KIAA1468 | 0.253685207 | 2.13.117 || KIAA1671 | 2.13 | KIAA1671 | 0.844416438 | 2.13.116 || KIF1C | 2.13 | kinesin family member 1C | 0.499234725 | 2.13.111 || KLF3-AS1 | 2.13 | KLF3 antisense RNA 1 | 2.13451177 | 2.13.116 || KLF9 | 2.13 | Kruppel-like factor 9 | 0.553886869 | 2.13.114 || KLHDC1 | 2.13 | kelch domain containing 1 | 0.353289329 | 2.13.109 || LAPTM5 | 2.13 | lysosomal protein transmembrane 5 | 0.463046131 | 2.13.112 || LAT2 | 2.13 | linker for activation of T-cells family member 2 | 0.574086734 | 2.13.111 || LDLRAD4 | 2.13 | low density lipoprotein receptor class A domain containing 4 | 0.671584873 | 2.13.109 || LHFP | 2.13 | lipoma HMGIC fusion partner | 0.625315112 | 2.13.115 || LIFR | 2.13 | leukemia inhibitory factor receptor alpha | 2.429454608 | 2.13.112 || LINC00304 | 2.13 | long intergenic non-protein coding RNA 304 | 0.393501478 | 2.13.114 || LINC00632 | 2.13 | long intergenic non-protein coding RNA 632 | 1.047050423 | 2.13.109 || LINC00936 | 2.13 | long intergenic non-protein coding RNA 936 | 0.700387452 | 2.13.109 || LPAR4 | 2.13 | lysophosphatidic acid receptor 4 | 0.218232239 | 2.13.116 || LRIF1 | 2.13 | ligand dependent nuclear receptor interacting factor 1 | 0.503312043 | 2.13.117 || LRIG3 | 2.13 | leucine-rich repeats and immunoglobulin like domains 3 | 0.499218829 | 2.13.116 || LRRC16A | 2.13 | leucine rich repeat containing 16A | 0.908080901 | 2.13.112 || LRRC4C | 2.13 | leucine rich repeat containing 4C | 0.69611547 | 2.13.116 || LTA4H | 2.13 | leukotriene A4 hydrolase | 0.72641255 | 2.13.112 || LYST | 2.13 | lysosomal trafficking regulator | 0.651096213 | — || MAD2L1 | 2.13 | MAD2 mitotic arrest deficient-like 1 (yeast) | 1.100419452 | 2.13.114 || MAGI2 | 2.13 | membrane associated guanylate kinase, WW and PDZ domain containing 2 | 1.075266587 | 2.13.116 || MAL | 2.13 | mal T-cell differentiation protein | 0.394359158 | 2.13.109 || MAN2B1 | 2.13 | mannosidase alpha class 2B member 1 | 0.467641762 | 2.13.112 || MAP1B | 2.13 | microtubule associated protein 1B | 1.701090816 | 2.13.112 || MAP1S | 2.13 | microtubule associated protein 1S | 0.566819557 | — || MAPKAP1 | 2.13 | mitogen-activated protein kinase associated protein 1 | 0.334436347 | 2.13.111 || MARCO | 2.13 | macrophage receptor with collagenous structure | 2.002377443 | 2.13.115 || MATN2 | 2.13 | matrilin 2 | 2.369189186 | 2.13.115 || MBOAT1 | 2.13 | membrane bound O-acyltransferase domain containing 1 | 0.357216125 | 2.13.114 || MCC | 2.13 | mutated in colorectal cancers | 1.2531783 | 2.13.116 || MCTP1 | 2.13 | multiple C2 and transmembrane domain containing 1 | 0.988495346 | 2.13.114 || ME1 | 2.13 | malic enzyme 1, NADP(+)-dependent, cytosolic | 0.278326942 | 2.13.114 || MEF2A | 2.13 | myocyte enhancer factor 2A | 0.350986547 | 2.13.117 || METTL18 | 2.13 | methyltransferase like 18 | 0.601436544 | 2.13.115 || MFSD1 | 2.13 | major facilitator superfamily domain containing 1 | 0.240993841 | 2.13.112 || MGAT1 | 2.13 | mannosyl (alpha-1,3-)-glycoprotein beta-1,2-N-acetylglucosaminyltransferase | 0.350451991 | 2.13.114 || MGME1 | 2.13 | mitochondrial genome maintenance exonuclease 1 | 0.220814438 | 2.13.117 || MICU3 | 2.13 | mitochondrial calcium uptake family member 3 | 1.463454331 | 2.13.116 || MINA | 2.13 | MYC induced nuclear antigen | 0.283548651 | 2.13.114 || MIR99AHG | 2.13 | mir-99a-let-7c cluster host gene | 4.859450805 | 2.13.111 || MKL2 | 2.13 | MKL/myocardin-like 2 | 0.633333227 | 2.13.115 || MOV10 | 2.13 | Mov10 RISC complex RNA helicase | 0.377095973 | — || MPZL2 | 2.13 | myelin protein zero like 2 | 0.894110176 | 2.13.111 || MRPS30 | 2.13 | mitochondrial ribosomal protein S30 | 0.249330581 | 2.13.111 || MRVI1 | 2.13 | murine retrovirus integration site 1 homolog | 0.233691875 | 2.13.115 || MS4A14 | 2.13 | membrane spanning 4-domains A14 | 0.900422952 | 2.13.114 || MS4A2 | 2.13 | membrane spanning 4-domains A2 | 1.073406565 | 2.13.116 || MS4A4A | 2.13 | membrane spanning 4-domains A4A | 0.516479686 | — || MS4A6A | 2.13 | membrane spanning 4-domains A6A | 0.363578436 | 2.13.111 || MSH2 | 2.13 | mutS homolog 2 | 0.505425044 | 2.13.112 || MSR1 | 2.13 | macrophage scavenger receptor 1 | 0.903071728 | — || MTSS1 | 2.13 | metastasis suppressor 1 | 0.257173936 | — || MVP | 2.13 | major vault protein | 0.242014911 | 2.13.114 || MYRIP | 2.13 | myosin VIIA and Rab interacting protein | 2.974821829 | 2.13.111 || NAGA | 2.13 | N-acetylgalactosaminidase, alpha- | 0.418428557 | 2.13.112 || NAGPA | 2.13 | N-acetylglucosamine-1-phosphodiester alpha-N-acetylglucosaminidase | 0.325417838 | 2.13.114 || NAP1L3 | 2.13 | nucleosome assembly protein 1 like 3 | 1.765809462 | 2.13.111 || NAV1 | 2.13 | neuron navigator 1 | 0.606213548 | 2.13.109 || NAV2 | 2.13 | neuron navigator 2 | 0.735707401 | 2.13.109 || NCEH1 | 2.13 | neutral cholesterol ester hydrolase 1 |

TABLE 3B-continued

| The genes within the significant gene clusters, listed in Table 3A. (3966 Genes Listed by: Gene Symbol ∣ Gen 2 Module ∣ Gene Description ∣ RowVariance ∣ Gen 3 Module ‖) |
| --- |
| 0.642700746 ∣ — ‖ NEDD4L ∣ 2.13 ∣ neural precursor cell expressed, developmentally down-regulated 4-like, E3 ubiquitin protein ligase ∣ 0.812970685 ∣ 2.13.111 ‖ NEGR1 ∣ 2.13 ∣ neuronal growth regulator 1 ∣ 4.682478671 ∣ 2.13.111 ‖ NET1 ∣ 2.13 ∣ neuroepithelial cell transforming 1 ∣ 0.867597081 ∣ 2.13.112 ‖ NEURL2 ∣ 2.13 ∣ neuralized E3 ubiquitin protein ligase 2 ∣ 0.990915265 ∣ — ‖ NFAM1 ∣ 2.13 ∣ NFAT activating protein with ITAM motif 1 ∣ 0.393442758 ∣ 2.13.116 ‖ NFE2L3 ∣ 2.13 ∣ nuclear factor, erythroid 2 like 3 ∣ 1.400239678 ∣ 2.13.116 ‖ NFIA ∣ 2.13 ∣ nuclear factor I/A ∣ 1.269390224 ∣ 2.13.111 ‖ NFIB ∣ 2.13 ∣ nuclear factor I/B ∣ 1.594047921 ∣ 2.13.111 ‖ NINL ∣ 2.13 ∣ ninein like ∣ 0.38619854 ∣ 2.13.116 ‖ NOVA1 ∣ 2.13 ∣ neuro-oncological ventral antigen 1 ∣ 2.94232798 ∣ 2.13.111 ‖ NPC1 ∣ 2.13 ∣ Niemann-Pick disease, type C1 ∣ 0.659163398 ∣ 2.13.117 ‖ NR1H3 ∣ 2.13 ∣ nuclear receptor subfamily 1 group H member 3 ∣ 0.772364085 ∣ 2.13.112 ‖ NR5A2 ∣ 2.13 ∣ nuclear receptor subfamily 5 group A member 2 ∣ 0.259931 ∣ — ‖ NSUN6 ∣ 2.13 ∣ NOP2/Sun RNA methyltransferase family member 6 ∣ 0.682024825 ∣ 2.13.116 ‖ NTRK2 ∣ 2.13 ∣ neurotrophic tyrosine kinase, receptor, type 2 ∣ 4.633944435 ∣ 2.13.111 ‖ NUP62 ∣ 2.13 ∣ nucleoporin 62 kDa ∣ 0.385630702 ∣ 2.13.117 ‖ ODF2L ∣ 2.13 ∣ outer dense fiber of sperm tails 2 like ∣ 0.289734932 ∣ 2.13.112 ‖ OMA1 ∣ 2.13 ∣ OMA1 zinc metallopeptidase ∣ 0.277222184 ∣ 2.13.111 ‖ OSBPL10 ∣ 2.13 ∣ oxysterol binding protein like 10 ∣ 0.502131041 ∣ 2.13.115 ‖ OSGEPL1 ∣ 2.13 ∣ O-sialoglycoprotein endopeptidase-like 1 ∣ 0.601682073 ∣ 2.13.112 ‖ OSGIN2 ∣ 2.13 ∣ oxidative stress induced growth inhibitor family member 2 ∣ 0.485072903 ∣ 2.13.117 ‖ P2RX4 ∣ 2.13 ∣ purinergic receptor P2X 4 ∣ 0.778628666 ∣ 2.13.112 ‖ P4HB ∣ 2.13 ∣ prolyl 4-hydroxylase subunit beta ∣ 0.342471626 ∣ 2.13.114 ‖ PARP10 ∣ 2.13 ∣ poly(ADP-ribose) polymerase family member 10 ∣ 0.543773678 ∣ 2.13.111 ‖ PARP3 ∣ 2.13 ∣ poly(ADP-ribose) polymerase family member 3 ∣ 0.264796188 ∣ 2.13.112 ‖ PARP6 ∣ 2.13 ∣ poly(ADP-ribose) polymerase family member 6 ∣ 0.25692068 ∣ 2.13.114 ‖ PARVB ∣ 2.13 ∣ parvin beta ∣ 0.70562519 ∣ 2.13.114 ‖ PBX1 ∣ 2.13 ∣ pre-B-cell leukemia homeobox 1 ∣ 0.688052051 ∣ 2.13.111 ‖ PCDH18 ∣ 2.13 ∣ protocadherin 18 ∣ 1.056745674 ∣ 2.13.115 ‖ PCDH9 ∣ 2.13 ∣ protocadherin 9 ∣ 1.739731223 ∣ 2.13.116 ‖ PCDHB16 ∣ 2.13 ∣ protocadherin beta 16 ∣ 2.67915659 ∣ 2.13.109 ‖ PCK2 ∣ 2.13 ∣ phosphoenolpyruvate carboxykinase 2, mitochondrial ∣ 0.278442824 ∣ 2.13.115 ‖ PCSK5 ∣ 2.13 ∣ proprotein convertase subtilisin/kexin type 5 ∣ 0.734443093 ∣ 2.13.111 ‖ PCYOX1L ∣ 2.13 ∣ prenylcysteine oxidase 1 like ∣ 0.284605579 ∣ 2.13.111 ‖ PDAP1 ∣ 2.13 ∣ PDGFA associated protein 1 ∣ 0.402836026 ∣ 2.13.114 ‖ PDIA4 ∣ 2.13 ∣ protein disulfide isomerase family A member 4 ∣ 0.215029764 ∣ — ‖ PDK4 ∣ 2.13 ∣ pyruvate dehydrogenase kinase 4 ∣ 5.958649538 ∣ — ‖ PEX12 ∣ 2.13 ∣ peroxisomal biogenesis factor 12 ∣ 0.563432071 ∣ 2.13.112 ‖ PIK3IP1 ∣ 2.13 ∣ phosphoinositide-3-kinase interacting protein 1 ∣ 0.330308467 ∣ 2.13.114 ‖ PIK3R5 ∣ 2.13 ∣ phosphoinositide-3-kinase regulatory subunit 5 ∣ 0.676437862 ∣ 2.13.114 ‖ PILRA ∣ 2.13 ∣ paired immunoglobin-like type 2 receptor alpha ∣ 0.994717293 ∣ 2.13.112 ‖ PKM ∣ 2.13 ∣ pyruvate kinase, muscle ∣ 0.485963464 ∣ 2.13.114 ‖ PKN2 ∣ 2.13 ∣ protein kinase N2 ∣ 0.366914792 ∣ 2.13.114 ‖ PLA2G15 ∣ 2.13 ∣ phospholipase A2 group XV ∣ 0.308512115 ∣ 2.13.115 ‖ PLAUR ∣ 2.13 ∣ plasminogen activator, urokinase receptor ∣ 1.130963658 ∣ — ‖ PLBD1 ∣ 2.13 ∣ phospholipase B domain containing 1 ∣ 0.798153641 ∣ 2.13.114 ‖ PLCB1 ∣ 2.13 ∣ phospholipase C beta 1 ∣ 1.300908665 ∣ 2.13.116 ‖ PLD3 ∣ 2.13 ∣ phospholipase D family member 3 ∣ 0.447032144 ∣ 2.13.114 ‖ PLEKHH2 ∣ 2.13 ∣ pleckstrin homology, MyTH4 and FERM domain containing H2 ∣ 1.691812098 ∣ 2.13.115 ‖ PLP2 ∣ 2.13 ∣ proteolipid protein 2 (colonic epithelium-enriched) ∣ 0.241328907 ∣ 2.13.114 ‖ PLSCR4 ∣ 2.13 ∣ phospholipid scramblase 4 ∣ 0.947501888 ∣ 2.13.111 ‖ PLTP ∣ 2.13 ∣ phospholipid transfer protein ∣ 0.303211382 ∣ — ‖ POLR3K ∣ 2.13 ∣ polymerase (RNA) III subunit K ∣ 0.233338628 ∣ 2.13.114 ‖ PON2 ∣ 2.13 ∣ paraoxonase 2 ∣ 0.237306537 ∣ 2.13.114 ‖ PPDPF ∣ 2.13 ∣ pancreatic progenitor cell differentiation and proliferation factor ∣ 0.310586024 ∣ 2.13.114 ‖ PPL ∣ 2.13 ∣ periplakin ∣ 2.509024142 ∣ 2.13.111 ‖ PPP1R2 ∣ 2.13 ∣ protein phosphatase 1 regulatory inhibitor subunit 2 ∣ 0.219633925 ∣ 2.13.109 ‖ PREX1 ∣ 2.13 ∣ phosphatidylinositol-3,4,5-trisphosphate-dependent Rac exchange factor 1 ∣ 0.250217617 ∣ 2.13.117 ‖ PRICKLE1 ∣ 2.13 ∣ prickle planar cell polarity protein 1 ∣ 0.522802685 ∣ 2.13.111 ‖ PRRG1 ∣ 2.13 ∣ proline rich Gla (G-carboxyglutamic acid) 1 ∣ 0.653723801 ∣ 2.13.114 ‖ PRRT2 ∣ 2.13 ∣ proline rich transmembrane protein 2 ∣ 0.234783992 ∣ 2.13.116 ‖ PRTFDC1 ∣ 2.13 ∣ phosphoribosyl transferase domain containing 1 ∣ 1.210007463 ∣ 2.13.116 ‖ PTAFR ∣ 2.13 ∣ platelet activating factor receptor ∣ 0.478181238 ∣ 2.13.114 ‖ PTGER2 ∣ 2.13 ∣ prostaglandin E receptor 2 ∣ 0.628419606 ∣ 2.13.112 ‖ PTPN13 ∣ 2.13 ∣ protein tyrosine phosphatase, non-receptor type 13 ∣ 0.881444917 ∣ 2.13.112 ‖ PTPRB ∣ 2.13 ∣ protein tyrosine phosphatase, receptor type B ∣ 1.346443092 ∣ 2.13.115 ‖ PTPRJ ∣ 2.13 ∣ protein tyrosine phosphatase, receptor type J ∣ 0.758561814 ∣ 2.13.117 ‖ PTPRS ∣ 2.13 ∣ protein tyrosine phosphatase, receptor type S ∣ 1.499861491 ∣ 2.13.109 ‖ PUS7 ∣ 2.13 ∣ pseudouridylate synthase 7 (putative) ∣ 0.302191589 ∣ 2.13.112 ‖ PVR ∣ 2.13 ∣ poliovirus receptor ∣ 0.219811576 ∣ 2.13.116 ‖ QRSL1 ∣ 2.13 ∣ glutaminyl-tRNA synthase (glutamine-hydrolyzing)-like 1 ∣ 0.410479951 ∣ 2.13.115 ‖ QSOX1 ∣ 2.13 ∣ quiescin sulfhydryl oxidase 1 ∣ 0.368927339 ∣ 2.13.114 ‖ RAB30 ∣ 2.13 ∣ RAB30, member RAS oncogene family ∣ 1.077446891 ∣ 2.13.112 ‖ RAPGEF1 ∣ 2.13 ∣ Rap guanine nucleotide exchange factor 1 ∣ 0.572073564 ∣ 2.13.117 ‖ RBM47 ∣ 2.13 ∣ RNA binding motif protein 47 ∣ 0.486946946 ∣ 2.13.117 ‖ RBMS3 ∣ 2.13 ∣ RNA binding motif, single stranded interacting protein 3 ∣ 2.229894728 ∣ 2.13.111 ‖ RCAN2 ∣ 2.13 ∣ regulator of calcineurin 2 ∣ 1.848732911 ∣ 2.13.116 ‖ RFX7 ∣ 2.13 ∣ regulatory factor X7 ∣ 0.222841625 ∣ 2.13.111 ‖ RFXAP ∣ 2.13 ∣ regulatory factor X associated protein ∣ 0.316740682 ∣ 2.13.116 ‖ RGCC ∣ 2.13 ∣ regulator of cell cycle ∣ 0.714836677 ∣ 2.13.112 ‖ RGS14 ∣ 2.13 ∣ regulator of G-protein signaling 14 ∣ 0.262440781 ∣ 2.13.111 ‖ RGS19 ∣ 2.13 ∣ regulator of G-protein signaling 19 ∣ 0.373091892 ∣ 2.13.111 ‖ RHOBTB3 ∣ 2.13 ∣ Rho related BTB domain containing 3 ∣ 0.984989625 ∣ — ‖ RHOQ ∣ 2.13 ∣ ras homolog family member Q ∣ 0.241573272 ∣ 2.13.114 ‖ RMND1 ∣ 2.13 ∣ required for meiotic nuclear division 1 homolog ∣ 0.27153658 ∣ 2.13.109 ‖ RNF130 ∣ 2.13 ∣ ring finger protein 130 ∣ 0.3114708 ∣ 2.13.114 ‖ RNF149 ∣ 2.13 ∣ ring finger protein 149 ∣ 0.242885372 ∣ 2.13.109 ‖ RNF166 ∣ 2.13 ∣ ring finger protein 166 ∣ 0.238032034 ∣ 2.13.112 ‖ RNF19B ∣ 2.13 ∣ ring finger protein 19B ∣ 0.527534608 ∣ — ‖ RNF220 ∣ 2.13 ∣ ring finger protein 220 ∣ 0.446547478 ∣ — ‖ RNPC3 ∣ 2.13 ∣ RNA binding region (RNP1, RRM) containing 3 ∣ 0.431345942 ∣ 2.13.111 ‖ RNPEP ∣ 2.13 ∣ arginyl aminopeptidase ∣ 0.214773118 ∣ 2.13.112 ‖ RTN1 ∣ 2.13 ∣ reticulon 1 ∣ 1.017538562 ∣ 2.13.111 ‖ RUNX3 ∣ 2.13 ∣ runt related transcription factor 3 ∣ 1.275263144 ∣ 2.13.117 ‖ S100A9 ∣ 2.13 ∣ S100 calcium binding protein A9 ∣ 1.27256495 ∣ 2.13.109 ‖ SCRN3 ∣ 2.13 ∣ secernin 3 ∣ 0.248950373 ∣ 2.13.114 ‖ SDC3 ∣ 2.13 ∣ syndecan 3 ∣ 0.223505318 ∣ 2.13.117 ‖ SEC22B ∣ 2.13 ∣ SEC22 homolog B, vesicle trafficking protein (gene/pseudogene) ∣ 0.2457394 ∣ 2.13.114 ‖ SEMA3E ∣ 2.13 ∣ semaphorin 3E ∣ 3.704350922 ∣ 2.13.109 ‖ SEMA6A ∣ 2.13 ∣ semaphorin 6A |

TABLE 3B-continued

The genes within the significant gene clusters, listed in Table 3A. (3966 Genes Listed by: Gene Symbol | Gen 2 Module | Gene Description | RowVariance | Gen 3 Module ||)

| 1.425697763 | 2.13.112 || SENP7 | 2.13 | SUMO1/sentrin specific peptidase 7 | 0.340935043 | 2.13.112 || SEPT6 | 2.13 | septin 6 | 0.311496997 | 2.13.117 || SESN1 | 2.13 | sestrin 1 | 0.400746385 | — || SETBP1 | 2.13 | SET binding protein 1 | 1.268880786 | 2.13.109 || SETD9 | 2.13 | SET domain containing 9 | 0.43506454 | 2.13.112 || SFRP2 | 2.13 | secreted frizzled-related protein 2 | 4.809938046 | 2.13.117 || SGOL2 | 2.13 | shugoshin-like 2 (*S. pombe*) | 0.677440331 | 2.13.114 || SH3BGRL3 | 2.13 | SH3 domain binding glutamate rich protein like 3 | 0.332563528 | 2.13.114 || SH3TC1 | 2.13 | SH3 domain and tetratricopeptide repeats 1 | 0.63890962 | — || SHTN1 | 2.13 | shootin 1 | 0.220706261 | — || SIAH2 | 2.13 | siah E3 ubiquitin protein ligase 2 | 0.273356021 | 2.13.109 || SIGLEC1 | 2.13 | sialic acid binding Ig like lectin 1 | 0.544833518 | 2.13.114 || SIRPA | 2.13 | signal regulatory protein alpha | 0.518829285 | 2.13.114 || SLC11A2 | 2.13 | solute carrier family 11 member 2 | 0.215419556 | 2.13.115 || SLC15A3 | 2.13 | solute carrier family 15 member 3 | 0.867682008 | 2.13.112 || SLC16A7 | 2.13 | solute carrier family 16 member 7 | 1.623659067 | 2.13.114 || SLC25A19 | 2.13 | solute carrier family 25 member 19 | 1.556127813 | 2.13.112 || SLC25A37 | 2.13 | solute carrier family 25 member 37 | 0.814925352 | 2.13.111 || SLC25A45 | 2.13 | solute carrier family 25 member 45 | 0.265283041 | 2.13.111 || SLC29A3 | 2.13 | solute carrier family 29 member 3 | 0.289963854 | — || SLC36A1 | 2.13 | solute carrier family 36 member 1 | 0.763146391 | 2.13.109 || SLC37A2 | 2.13 | solute carrier family 37 member 2 | 0.490969374 | 2.13.115 || SLC44A2 | 2.13 | solute carrier family 44 member 2 | 0.405020492 | 2.13.115 || SLC4A4 | 2.13 | solute carrier family 4 member 4 | 0.349407919 | 2.13.111 || SLC7A7 | 2.13 | solute carrier family 7 member 7 | 0.812936831 | 2.13.115 || SLC9A6 | 2.13 | solute carrier family 9 member A6 | 0.221078859 | 2.13.114 || SLCO2B1 | 2.13 | solute carrier organic anion transporter family member 2B1 | 0.464845675 | 2.13.112 || SMAD6 | 2.13 | SMAD family member 6 | 0.547174726 | 2.13.116 || SMAD9 | 2.13 | SMAD family member 9 | 2.670235747 | 2.13.116 || SMPDL3A | 2.13 | sphingomyelin phosphodiesterase acid like 3A | 0.31952755 | 2.13.114 || SNX16 | 2.13 | sorting nexin 16 | 0.407255662 | 2.13.115 || SOCS5 | 2.13 | suppressor of cytokine signaling 5 | 0.274385882 | 2.13.111 || SOWAHC | 2.13 | sosondowah ankyrin repeat domain family member C | 0.471996181 | 2.13.111 || SP140L | 2.13 | SP140 nuclear body protein like | 0.290145129 | 2.13.117 || SPI1 | 2.13 | Spi-1 proto-oncogene | 1.01704837 | 2.13.112 || SPPL2A | 2.13 | signal peptide peptidase like 2A | 0.293854081 | 2.13.111 || SRPX | 2.13 | sushi repeat containing protein, X-linked | 1.127971398 | 2.13.115 || SSPN | 2.13 | sarcospan | 0.631170689 | 2.13.109 || STARD8 | 2.13 | StAR related lipid transfer domain containing 8 | 0.362554692 | 2.13.109 || STK3 | 2.13 | serine/threonine kinase 3 | 0.325402616 | 2.13.111 || STON1 | 2.13 | stonin 1 | 1.356403913 | 2.13.111 || SUSD2 | 2.13 | sushi domain containing 2 | 1.705192024 | 2.13.115 || SYNJ2 | 2.13 | synaptojanin 2 | 1.185253446 | 2.13.111 || SYNPO2 | 2.13 | synaptopodin 2 | 3.221199695 | 2.13.112 || TAB1 | 2.13 | TGF-beta activated kinase 1/MAP3K7 binding protein 1 | 0.241853879 | 2.13.112 || TBXAS1 | 2.13 | thromboxane A synthase 1 | 0.708020188 | 2.13.115 || TCF7L2 | 2.13 | transcription factor 7 like 2 | 0.638065185 | 2.13.115 || TCFL5 | 2.13 | transcription factor-like 5 (basic helix-loop-helix) | 0.516830521 | 2.13.116 || TFEC | 2.13 | transcription factor EC | 1.194345762 | 2.13.112 || THAP8 | 2.13 | THAP domain containing 8 | 0.216626417 | 2.13.114 || THRB | 2.13 | thyroid hormone receptor beta | 0.935485167 | 2.13.116 || TM6SF1 | 2.13 | transmembrane 6 superfamily member 1 | 0.240612663 | 2.13.112 || TMEM129 | 2.13 | transmembrane protein 129 | 0.263432145 | 2.13.114 || TMEM133 | 2.13 | transmembrane protein 133 | 1.017890961 | 2.13.115 || TMEM176A | 2.13 | transmembrane protein 176A | 0.282487188 | 2.13.114 || TMEM176B | 2.13 | transmembrane protein 176B | 0.316009486 | 2.13.114 || TMEM198B | 2.13 | transmembrane protein 198B (pseudogene) | 0.333031752 | 2.13.114 || TMEM259 | 2.13 | transmembrane protein 259 | 0.455797342 | 2.13.114 || TMEM64 | 2.13 | transmembrane protein 64 | 0.598506919 | 2.13.114 || TMEM70 | 2.13 | transmembrane protein 70 | 0.342005197 | 2.13.109 || TMTC2 | 2.13 | transmembrane and tetratricopeptide repeat containing 2 | 0.978419575 | 2.13.114 || TNFAIP2 | 2.13 | TNF alpha induced protein 2 | 0.51361715 | 2.13.112 || TNFSF13 | 2.13 | tumor necrosis factor superfamily member 13 | 0.45299741 | 2.13.112 || TNK2 | 2.13 | tyrosine kinase, non-receptor, 2 | 0.227917443 | 2.13.114 || TNS3 | 2.13 | tensin 3 | 0.31387926 | 2.13.117 || TPP1 | 2.13 | tripeptidyl peptidase I | 0.279185597 | 2.13.114 || TREM2 | 2.13 | triggering receptor expressed on myeloid cells 2 | 2.389008842 | 2.13.115 || TRHDE-AS1 | 2.13 | TRHDE antisense RNA 1 | 0.962822387 | 2.13.111 || TRIM2 | 2.13 | tripartite motif containing 2 | 2.395669817 | 2.13.111 || TRMT6 | 2.13 | tRNA methyltransferase 6 | 0.674126391 | 2.13.114 || TRPC1 | 2.13 | transient receptor potential cation channel subfamily C member 1 | 0.787398783 | 2.13.116 || TSC22D3 | 2.13 | TSC22 domain family member 3 | 0.831241773 | 2.13.114 || TSC22D4 | 2.13 | TSC22 domain family member 4 | 0.32029484 | 2.13.109 || TSHZ2 | 2.13 | teashirt zinc finger homeobox 2 | 1.052241312 | 2.13.111 || TSHZ3 | 2.13 | teashirt zinc finger homeobox 3 | 0.887191214 | 2.13.111 || TSPAN4 | 2.13 | tetraspanin 4 | 0.248755326 | 2.13.114 || TSPAN7 | 2.13 | tetraspanin 7 | 2.212393459 | 2.13.115 || TSPO | 2.13 | translocator protein | 0.237547491 | 2.13.114 || TSPYL4 | 2.13 | TSPY-like 4 | 0.279529651 | 2.13.116 || TTC38 | 2.13 | tetratricopeptide repeat domain 38 | 0.297274267 | 2.13.114 || TTC7A | 2.13 | tetratricopeptide repeat domain 7A | 0.370564594 | 2.13.114 || TUBB2A | 2.13 | tubulin beta 2A class IIa | 0.325023776 | 2.13.117 || TULP3 | 2.13 | tubby like protein 3 | 0.97655164 | 2.13.111 || TYROBP | 2.13 | TYRO protein tyrosine kinase binding protein | 0.395515118 | 2.13.112 || UBE2D1 | 2.13 | ubiquitin conjugating enzyme E2D 1 | 0.308882488 | 2.13.114 || UBXN11 | 2.13 | UBX domain protein 11 | 0.290569158 | 2.13.115 || UNC93B1 | 2.13 | unc-93 homolog B1 (*C. elegans*) | 0.897472824 | 2.13.112 || USB1 | 2.13 | U6 snRNA biogenesis 1 | 0.252964287 | 2.13.111 || USP30 | 2.13 | ubiquitin specific peptidase 30 | 0.230007773 | 2.13.116 || USP31 | 2.13 | ubiquitin specific peptidase 31 | 0.873679346 | 2.13.115 || UST | 2.13 | uronyl-2-sulfotransferase | 1.849184976 | 2.13.109 || VAMP8 | 2.13 | vesicle associated membrane protein 8 | 0.447244737 | 2.13.112 || VAV1 | 2.13 | vav guanine nucleotide exchange factor 1 | 0.540446216 | — || VDAC1 | 2.13 | voltage dependent anion channel 1 | 0.256143418 | 2.13.115 || VPS9D1 | 2.13 | VPS9 domain containing 1 | 0.442328486 | 2.13.112 || VSIG4 | 2.13 | V-set and immunoglobulin domain containing 4 | 0.824504065 | — || WASF3 | 2.13 | WAS protein family member 3 | 1.618709402 | 2.13.111 || WDFY4 | 2.13 | WDFY family member 4 | 0.310390837 | 2.13.117 || WIPI1 | 2.13 | WD repeat domain, phosphoinositide interacting 1 | 0.308108308 | 2.13.111 || WRAP73 | 2.13 | WD repeat containing, antisense to TP73 | 0.273668604 | 2.13.112 || WWOX | 2.13 | WW domain containing oxidoreductase | 0.689727208 | 2.13.116 || WWTR1 | 2.13 | WW domain containing transcription regulator 1 | 0.729080311 | 2.13.116 || XG | 2.13 | Xg blood group | 1.753857649 | 2.13.111 || YWHAH |

TABLE 3B-continued

The genes within the significant gene clusters, listed in Table 3A. (3966 Genes Listed by: Gene Symbol | Gen 2 Module | Gene Description | RowVariance | Gen 3 Module ||)

2.13 | tyrosine 3-monooxygenase/tryptophan 5-monooxygenase activation protein eta | 0.33826808 | 2.13.112 || ZBTB10 | 2.13 | zinc finger and BTB domain containing 10 | 0.855741505 | 2.13.111 || ZBTB16 | 2.13 | zinc finger and BTB domain containing 16 | 3.507241815 | 2.13.114 || ZBTB20 | 2.13 | zinc finger and BTB domain containing 20 | 0.518239496 | 2.13.109 || ZC2HC1A | 2.13 | zinc finger C2HC-type containing 1A | 0.324258645 | 2.13.112 || ZC3H12D | 2.13 | zinc finger CCCH-type containing 12D | 0.684374131 | 2.13.117 || ZDHHC7 | 2.13 | zinc finger DHHC-type containing 7 | 0.267367989 | 2.13.114 || ZMYND15 | 2.13 | zinc finger MYND-type containing 15 | 0.466281515 | 2.13.114 || ZNF138 | 2.13 | zinc finger protein 138 | 0.308645533 | 2.13.114 || ZNF260 | 2.13 | zinc finger protein 260 | 0.224175965 | 2.13.112 || ZNF496 | 2.13 | zinc finger protein 496 | 0.220785982 | 2.13.116 || ZNF521 | 2.13 | zinc finger protein 521 | 1.320710484 | 2.13.116 || ZNF542P | 2.13 | zinc finger protein 542, pseudogene | 0.215619471 | 2.13.109 || ZNF559 | 2.13 | zinc finger protein 559 | 0.388113122 | 2.13.116 || ZNF652 | 2.13 | zinc finger protein 652 | 1.650701242 | — || ZNF677 | 2.13 | zinc finger protein 677 | 0.652095407 | 2.13.116 || ZNF70 | 2.13 | zinc finger protein 70 | 0.68226777 | 2.13.109 || ZNF844 | 2.13 | zinc finger protein 844 | 0.521160528 | 2.13.109 || ZNF880 | 2.13 | zinc finger protein 880 | 0.77964843 | 2.13.109 || ZSCAN26 | 2.13 | zinc finger and SCAN domain containing 26 | 0.35784647 | 2.13.116 || AHNAK2 | 2.13.109 | AHNAK nucleoprotein 2 | 1.156764235 | 2.13.109 || AQP9 | 2.13.109 | aquaporin 9 | 3.36202372 | 2.13.109 || ARFRP1 | 2.13.109 | ADP ribosylation factor related protein 1 | 0.314641078 | 2.13.109 || ARMC7 | 2.13.109 | armadillo repeat containing 7 | 0.335938816 | 2.13.109 || ATP13A1 | 2.13.109 | ATPase 13A1 | 0.271731484 | 2.13.109 || ATP2A2 | 2.13.109 | ATPase sarcoplasmic/endoplasmic reticulum Ca2+ transporting 2 | 0.227494642 | 2.13.109 || CCDC34 | 2.13.109 | coiled-coil domain containing 34 | 0.271448568 | 2.13.109 || CROT | 2.13.109 | carnitine O-octanoyltransferase | 0.275350575 | 2.13.109 || DGKA | 2.13.109 | diacylglycerol kinase alpha | 0.235711422 | 2.13.109 || DUBR | 2.13.109 | DPPA2 upstream binding RNA | 0.550940468 | 2.13.109 || EID2 | 2.13.109 | EP300 interacting inhibitor of differentiation 2 | 0.334727204 | 2.13.109 || GALNT11 | 2.13.109 | polypeptide N-acetylgalactosaminyltransferase 11 | 0.248601142 | 2.13.109 || GDAP1 | 2.13.109 | ganglioside induced differentiation associated protein 1 | 0.357898066 | 2.13.109 || GLIDR | 2.13.109 | glioblastoma down-regulated RNA | 1.137115929 | 2.13.109 || GPR1 | 2.13.109 | G protein-coupled receptor 1 | 1.220139673 | 2.13.109 || GRAMD3 | 2.13.109 | GRAM domain containing 3 | 0.446615819 | 2.13.109 || HGF | 2.13.109 | hepatocyte growth factor | 0.882763197 | 2.13.109 || HOXC10 | 2.13.109 | homeobox C10 | 1.897134168 | 2.13.109 || IKZF4 | 2.13.109 | IKAROS family zinc finger 4 | 0.325366992 | 2.13.109 || KCTD5 | 2.13.109 | potassium channel tetramerization domain containing 5 | 0.459915482 | 2.13.109 || KLHDC1 | 2.13.109 | kelch domain containing 1 | 0.353289329 | 2.13.109 || LDLRAD4 | 2.13.109 | low density lipoprotein receptor class A domain containing 4 | 0.671584873 | 2.13.109 || LINC00632 | 2.13.109 | long intergenic non-protein coding RNA 632 | 1.047050423 | 2.13.109 || LINC00936 | 2.13.109 | long intergenic non-protein coding RNA 936 | 0.700387452 | 2.13.109 || MAL | 2.13.109 | mal T-cell differentiation protein | 0.394359158 | 2.13.109 || NAV1 | 2.13.109 | neuron navigator 1 | 0.606213548 | 2.13.109 || NAV2 | 2.13.109 | neuron navigator 2 | 0.735707401 | 2.13.109 || PCDHB16 | 2.13.109 | protocadherin beta 16 | 2.67915659 | 2.13.109 || PPP1R2 | 2.13.109 | protein phosphatase 1 regulatory inhibitor subunit 2 | 0.219633925 | 2.13.109 || PTPRS | 2.13.109 | protein tyrosine phosphatase, receptor type S | 1.499861491 | 2.13.109 || RMND1 | 2.13.109 | required for meiotic nuclear division 1 homolog | 0.27153658 | 2.13.109 || RNF149 | 2.13.109 | ring finger protein 149 | 0.242885372 | 2.13.109 || S100A9 | 2.13.109 | S100 calcium binding protein A9 | 1.27256495 | 2.13.109 || SEMA3E | 2.13.109 | semaphorin 3E | 3.704350922 | 2.13.109 || SETBP1 | 2.13.109 | SET binding protein 1 | 1.268880786 | 2.13.109 || SIAH2 | 2.13.109 | siah E3 ubiquitin protein ligase 2 | 0.273356021 | 2.13.109 || SLC36A1 | 2.13.109 | solute carrier family 36 member 1 | 0.763146391 | 2.13.109 || SSPN | 2.13.109 | sarcospan | 0.631170689 | 2.13.109 || STARD8 | 2.13.109 | StAR related lipid transfer domain containing 8 | 0.362554692 | 2.13.109 || TMEM70 | 2.13.109 | transmembrane protein 70 | 0.342005197 | 2.13.109 || TSC22D4 | 2.13.109 | TSC22 domain family member 4 | 0.32029484 | 2.13.109 || UST | 2.13.109 | uronyl-2-sulfotransferase | 1.849184976 | 2.13.109 || ZBTB20 | 2.13.109 | zinc finger and BTB domain containing 20 | 0.518239496 | 2.13.109 || ZNF542P | 2.13.109 | zinc finger protein 542, pseudogene | 0.215619471 | 2.13.109 || ZNF70 | 2.13.109 | zinc finger protein 70 | 0.68226777 | 2.13.109 || ZNF844 | 2.13.109 | zinc finger protein 844 | 0.521160528 | 2.13.109 || ZNF880 | 2.13.109 | zinc finger protein 880 | 0.77964843 | 2.13.109 || ACSM5 | 2.13.111 | acyl-CoA synthetase medium-chain family member 5 | 0.683890782 | 2.13.111 || ADRBK1 | 2.13.111 | adrenergic, beta, receptor kinase 1 | 0.557067614 | 2.13.111 || AEBP2 | 2.13.111 | AE binding protein 2 | 0.324321466 | 2.13.111 || AGMAT | 2.13.111 | agmatinase | 0.606004319 | 2.13.111 || ANKIB1 | 2.13.111 | ankyrin repeat and IBR domain containing 1 | 0.251107709 | 2.13.111 || ARSA | 2.13.111 | arylsulfatase A | 0.750160235 | 2.13.111 || B3GALNT1 | 2.13.111 | beta-1,3-N-acetylgalactosaminyltransferase 1 (globoside blood group) | 0.780057 | 2.13.111 || C3orf38 | 2.13.111 | chromosome 3 open reading frame 38 | 0.507900912 | 2.13.111 || C5AR1 | 2.13.111 | complement component 5a receptor 1 | 0.611938719 | 2.13.111 || CDH23 | 2.13.111 | cadherin-related 23 | 0.235240172 | 2.13.111 || CDK2 | 2.13.111 | cyclin-dependent kinase 2 | 0.378352115 | 2.13.111 || CTBP2 | 2.13.111 | C-terminal binding protein 2 | 0.221798346 | 2.13.111 || CTSL | 2.13.111 | cathepsin L | 0.791556213 | 2.13.111 || DNM2 | 2.13.111 | dynamin 2 | 0.307178926 | 2.13.111 || DTD2 | 2.13.111 | D-tyrosyl-tRNA deacylase 2 (putative) | 0.414817763 | 2.13.111 || EGR1 | 2.13.111 | early growth response 1 | 2.184401604 | 2.13.111 || F8 | 2.13.111 | coagulation factor VIII | 0.969874965 | 2.13.111 || FAM172A | 2.13.111 | family with sequence similarity 172 member A | 0.765955214 | 2.13.111 || HCK | 2.13.111 | HCK proto-oncogene, Src family tyrosine kinase | 0.591574122 | 2.13.111 || HOXA3 | 2.13.111 | homeobox A3 | 0.456875599 | 2.13.111 || HSPA12A | 2.13.111 | heat shock protein family A (Hsp70) member 12A | 0.473957291 | 2.13.111 || HTR2A | 2.13.111 | 5-hydroxytryptamine receptor 2A | 0.430489177 | 2.13.111 || IDH2 | 2.13.111 | isocitrate dehydrogenase 2 (NADP+), mitochondrial | 0.630488179 | 2.13.111 || IGF2BP2 | 2.13.111 | insulin like growth factor 2 mRNA binding protein 2 | 0.954990871 | 2.13.111 || IGSF10 | 2.13.111 | immunoglobulin superfamily member 10 | 0.878588832 | 2.13.111 || INO80D | 2.13.111 | INO80 complex subunit D | 0.971483252 | 2.13.111 || KBTBD7 | 2.13.111 | kelch repeat and BTB domain containing 7 | 0.6206987 | 2.13.111 || KIF1C | 2.13.111 | kinesin family member 1C | 0.499234725 | 2.13.111 || LAT2 | 2.13.111 | linker for activation of T-cells family member 2 | 0.574086734 | 2.13.111 || MAPKAP1 | 2.13.111 | mitogen-activated protein kinase TABLE 3B-continued The genes within the significant gene clusters, listed in Table 3A. (3966 Genes Listed by: Gene Symbol | Gen 2 Module | Gene Description | RowVariance | Gen 3 Module ||)

associated protein 1 | 0.334436347 | 2.13.111 || MIR99AHG | 2.13.111 | mir-99a-let-7c cluster host gene | 4.859450805 | 2.13.111 || MPZL2 | 2.13.111 | myelin protein zero like 2 | 0.894110176 | 2.13.111 || MRPS30 | 2.13.111 | mitochondrial ribosomal protein S30 | 0.249330581 | 2.13.111 || MS4A6A | 2.13.111 | membrane spanning 4-domains A6A | 0.363578436 | 2.13.111 || MYRIP | 2.13.111 | myosin VIIA and Rab interacting protein | 2.974821829 | 2.13.111 || NAP1L3 | 2.13.111 | nucleosome assembly protein 1 like 3 | 1.765809462 | 2.13.111 || NEDD4L | 2.13.111 | neural precursor cell expressed, developmentally down-regulated 4-like, E3 ubiquitin protein ligase | 0.812970685 | 2.13.111 || NEGR1 | 2.13.111 | neuronal growth regulator 1 | 4.682478671 | 2.13.111 || NFIA | 2.13.111 | nuclear factor I/A | 1.269390224 | 2.13.111 || NFIB | 2.13.111 | nuclear factor I/B | 1.594047921 | 2.13.111 || NOVA1 | 2.13.111 | neuro-oncological ventral antigen 1 | 2.94232798 | 2.13.111 || NTRK2 | 2.13.111 | neurotrophic tyrosine kinase, receptor, type 2 | 4.633944435 | 2.13.111 || OMA1 | 2.13.111 | OMA1 zinc metallopeptidase | 0.277222184 | 2.13.111 || PARP10 | 2.13.111 | poly(ADP-ribose) polymerase family member 10 | 0.543773678 | 2.13.111 || PBX1 | 2.13.111 | pre-B-cell leukemia homeobox 1 | 0.688052051 | 2.13.111 || PCSK5 | 2.13.111 | proprotein convertase subtilisin/kexin type 5 | 0.734443093 | 2.13.111 || PCYOX1L | 2.13.111 | prenylcysteine oxidase 1 like | 0.284605579 | 2.13.111 || PLSCR4 | 2.13.111 | phospholipid scramblase 4 | 0.947501888 | 2.13.111 || PPL | 2.13.111 | periplakin | 2.509024142 | 2.13.111 || PRICKLE1 | 2.13.111 | prickle planar cell polarity protein 1 | 0.522802685 | 2.13.111 || RBMS3 | 2.13.111 | RNA binding motif, single stranded interacting protein 3 | 2.229894728 | 2.13.111 || RFX7 | 2.13.111 | regulatory factor X7 | 0.222841625 | 2.13.111 || RGS14 | 2.13.111 | regulator of G-protein signaling 14 | 0.262440781 | 2.13.111 || RGS19 | 2.13.111 | regulator of G-protein signaling 19 | 0.373091892 | 2.13.111 || RNPC3 | 2.13.111 | RNA binding region (RNP1, RRM) containing 3 | 0.431345942 | 2.13.111 | RTN1 | 2.13.111 | reticulon 1 | 1.017538562 | 2.13.111 || SLC25A37 | 2.13.111 | solute carrier family 25 member 37 | 0.814925352 | 2.13.111 || SLC25A45 | 2.13.111 | solute carrier family 25 member 45 | 0.265283041 | 2.13.111 || SLC4A4 | 2.13.111 | solute carrier family 4 member 4 | 0.349407919 | 2.13.111 || SOCS5 | 2.13.111 | suppressor of cytokine signaling 5 | 0.274385882 | 2.13.111 || SOWAHC | 2.13.111 | sosondowah ankyrin repeat domain family member C | 0.471996181 | 2.13.111 || SPPL2A | 2.13.111 | signal peptide peptidase like 2A | 0.293854081 | 2.13.111 || STK3 | 2.13.111 | serine/threonine kinase 3 | 0.325402616 | 2.13.111 || STON1 | 2.13.111 | stonin 1 | 1.356403913 | 2.13.111 || SYNJ2 | 2.13.111 | synaptojanin 2 | 1.185253446 | 2.13.111 || TRHDE-AS1 | 2.13.111 | TRHDE antisense RNA 1 | 0.962822387 | 2.13.111 || TRIM2 | 2.13.111 | tripartite motif containing 2 | 2.395669817 | 2.13.111 || TSHZ2 | 2.13.111 | teashirt zinc finger homeobox 2 | 1.052241312 | 2.13.111 || TSHZ3 | 2.13.111 | teashirt zinc finger homeobox 3 | 0.887191214 | 2.13.111 || TULP3 | 2.13.111 | tubby like protein 3 | 0.97655164 | 2.13.111 || USB1 | 2.13.111 | U6 snRNA biogenesis 1 | 0.252964287 | 2.13.111 || WASF3 | 2.13.111 | WAS protein family member 3 | 1.618709402 | 2.13.111 || WIPI1 | 2.13.111 | WD repeat domain, phosphoinositide interacting 1 | 0.308108308 | 2.13.111 || XG | 2.13.111 | Xg blood group | 1.753857649 | 2.13.111 || ZBTB10 | 2.13.111 | zinc finger and BTB domain containing 10 | 0.855741505 | 2.13.111 || ACP2 | 2.13.112 | acid phosphatase 2, lysosomal | 0.664126978 | 2.13.112 || ARHGAP12 | 2.13.112 | Rho GTPase activating protein 12 | 0.233692783 | 2.13.112 || ARRB2 | 2.13.112 | arrestin, beta 2 | 0.667353075 | 2.13.112 || BLNK | 2.13.112 | B-cell linker | 0.435714403 | 2.13.112 || C10orf10 | 2.13.112 | chromosome 10 open reading frame 10 | 1.450562961 | 2.13.112 || C9orf40 | 2.13.112 | chromosome 9 open reading frame 40 | 0.436229202 | 2.13.112 || CD58 | 2.13.112 | CD58 molecule | 0.222572712 | 2.13.112 || CD74 | 2.13.112 | CD74 molecule | 0.237274973 | 2.13.112 || CLDN11 | 2.13.112 | claudin 11 | 1.352899095 | 2.13.112 || COTL1 | 2.13.112 | coactosin-like F-actin binding protein 1 | 0.419338939 | 2.13.112 || CPNE1 | 2.13.112 | copine 1 | 0.306504255 | 2.13.112 || CSPP1 | 2.13.112 | centrosome and spindle pole associated protein 1 | 0.298382526 | 2.13.112 || CTSB | 2.13.112 | cathepsin B | 0.444678736 | 2.13.112 || DAPK1 | 2.13.112 | death-associated protein kinase 1 | 0.355467029 | 2.13.112 || DOK2 | 2.13.112 | docking protein 2 | 0.406246015 | 2.13.112 || FAM105A | 2.13.112 | family with sequence similarity 105 member A | 0.379660874 | 2.13.112 || FAM96A | 2.13.112 | family with sequence similarity 96 member A | 0.240033343 | 2.13.112 || FCER1G | 2.13.112 | Fc fragment of IgE receptor Ig | 0.777975804 | 2.13.112 || FHL5 | 2.13.112 | four and a half LIM domains 5 | 1.775450295 | 2.13.112 || FMNL1 | 2.13.112 | formin like 1 | 0.645099805 | 2.13.112 || FTH1 | 2.13.112 | ferritin, heavy polypeptide 1 | 0.235701696 | 2.13.112 || GHDC | 2.13.112 | GH3 domain containing | 0.254119438 | 2.13.112 || HACD3 | 2.13.112 | 3-hydroxyacyl-CoA dehydratase 3 | 0.366670218 | 2.13.112 || HECW2 | 2.13.112 | HECT, C2 and WW domain containing E3 ubiquitin protein ligase 2 | 1.386960007 | 2.13.112 || HK3 | 2.13.112 | hexokinase 3 | 1.301991786 | 2.13.112 || IL13RA2 | 2.13.112 | interleukin 13 receptor subunit alpha 2 | 2.550295806 | 2.13.112 || INPP4B | 2.13.112 | inositol polyphosphate-4-phosphatase type II B | 1.917873318 | 2.13.112 || LAPTM5 | 2.13.112 | lysosomal protein transmembrane 5 | 0.463046131 | 2.13.112 || LIFR | 2.13.112 | leukemia inhibitory factor receptor alpha | 2.429454608 | 2.13.112 || LRRC16A | 2.13.112 | leucine rich repeat containing 16A | 0.908080901 | 2.13.112 | LTA4H | 2.13.112 | leukotriene A4 hydrolase | 0.72641255 | 2.13.112 || MAN2B1 | 2.13.112 | mannosidase alpha class 2B member 1 | 0.467641762 | 2.13.112 || MAP1B | 2.13.112 | microtubule associated protein 1B | 1.701090816 | 2.13.112 || MFSD1 | 2.13.112 | major facilitator superfamily domain containing 1 | 0.240993841 | 2.13.112 || MSH2 | 2.13.112 | mutS homolog 2 | 0.505425044 | 2.13.112 || NAGA | 2.13.112 | N-acetylgalactosaminidase, alpha- | 0.418428557 | 2.13.112 || NET1 | 2.13.112 | neuroepithelial cell transforming 1 | 0.867597081 | 2.13.112 || NR1H3 | 2.13.112 | nuclear receptor subfamily 1 group H member 3 | 0.772364085 | 2.13.112 || ODF2L | 2.13.112 | outer dense fiber of sperm tails 2 like | 0.289734932 | 2.13.112 || OSGEPL1 | 2.13.112 | O-sialoglycoprotein endopeptidase-like 1 | 0.601682073 | 2.13.112 || P2RX4 | 2.13.112 | purinergic receptor P2X 4 | 0.778628666 | 2.13.112 || PARP3 | 2.13.112 | poly(ADP-ribose) polymerase family member 3 | 0.264796188 | 2.13.112 || PEX12 | 2.13.112 | peroxisomal biogenesis factor 12 | 0.563432071 | 2.13.112 || PILRA | 2.13.112 | paired immunoglobin-like type 2 receptor alpha | 0.994717293 | 2.13.112 || PTGER2 | 2.13.112 | prostaglandin E receptor 2 | 0.628419606 | 2.13.112 || PTPN13 | 2.13.112 | protein tyrosine phosphatase, non-receptor type 13 | 0.881444917 | 2.13.112 || PUS7 | 2.13.112 | pseudouridylate synthase 7 (putative) | 0.302191589 | 2.13.112 || RAB30 | 2.13.112 | RAB30, member RAS oncogene family | 1.077446891 | 2.13.112 || RGCC | 2.13.112 | regulator of cell cycle | 0.714836677 | 2.13.112 || RNF166 | 2.13.112 | ring finger protein 166 | 0.238032034 | 2.13.112 ||

TABLE 3B-continued

The genes within the significant gene clusters, listed in Table 3A. (3966 Genes Listed by: Gene Symbol | Gen 2 Module | Gene Description | RowVariance | Gen 3 Module ||)

RNPEP | 2.13.112 | arginyl aminopeptidase | 0.214773118 | 2.13.112 || SEMA6A | 2.13.112 | semaphorin 6A | 1.425697763 | 2.13.112 || SENP7 | 2.13.112 | SUMO1/sentrin specific peptidase 7 | 0.340935043 | 2.13.112 || SETD9 | 2.13.112 | SET domain containing 9 | 0.43506454 | 2.13.112 || SLC15A3 | 2.13.112 | solute carrier family 15 member 3 | 0.867682008 | 2.13.112 || SLC25A19 | 2.13.112 | solute carrier family 25 member 19 | 1.556127813 | 2.13.112 || SLCO2B1 | 2.13.112 | solute carrier organic anion transporter family member 2B1 | 0.464845675 | 2.13.112 || SPI1 | 2.13.112 | Spi-1 proto-oncogene | 1.01704837 | 2.13.112 || SYNPO2 | 2.13.112 | synaptopodin 2 | 3.221199695 | 2.13.112 || TAB1 | 2.13.112 | TGF-beta activated kinase 1/MAP3K7 binding protein 1 | 0.241853879 | 2.13.112 || TFEC | 2.13.112 | transcription factor EC | 1.194345762 | 2.13.112 || TM6SF1 | 2.13.112 | transmembrane 6 superfamily member 1 | 0.240612663 | 2.13.112 || TNFAIP2 | 2.13.112 | TNF alpha induced protein 2 | 0.51361715 | 2.13.112 || TNFSF13 | 2.13.112 | tumor necrosis factor superfamily member 13 | 0.45299741 | 2.13.112 || TYROBP | 2.13.112 | TYRO protein tyrosine kinase binding protein | 0.395515118 | 2.13.112 || UNC93B1 | 2.13.112 | unc-93 homolog B1 (*C. elegans*) | 0.897472824 | 2.13.112 || VAMP8 | 2.13.112 | vesicle associated membrane protein 8 | 0.447244737 | 2.13.112 || VPS9D1 | 2.13.112 | VPS9 domain containing 1 | 0.442328486 | 2.13.112 || WRAP73 | 2.13.112 | WD repeat containing, antisense to TP73 | 0.273668604 | 2.13.112 || YWHAH | 2.13.112 | tyrosine 3-monooxygenase/tryptophan 5-monooxygenase activation protein eta | 0.33826808 | 2.13.112 || ZC2HC1A | 2.13.112 | zinc finger C2HC-type containing 1A | 0.324258645 | 2.13.112 || ZNF260 | 2.13.112 | zinc finger protein 260 | 0.224175965 | 2.13.112 || ABCA7 | 2.13.114 | ATP binding cassette subfamily A member 7 | 0.242566393 | 2.13.114 || ABCD1 | 2.13.114 | ATP binding cassette subfamily D member 1 | 0.3229188 | 2.13.114 || ABHD12 | 2.13.114 | abhydrolase domain containing 12 | 0.39543476 | 2.13.114 || ADPGK | 2.13.114 | ADP-dependent glucokinase | 0.292056261 | 2.13.114 || AGTRAP | 2.13.114 | angiotensin II receptor associated protein | 0.31645459 | 2.13.114 || AP1B1 | 2.13.114 | adaptor related protein complex 1 beta 1 subunit | 0.313746684 | 2.13.114 || ARAP1 | 2.13.114 | ArfGAP with RhoGAP domain, ankyrin repeat and PH domain 1 | 0.270031263 | 2.13.114 || ARHGDIA | 2.13.114 | Rho GDP dissociation inhibitor (GDI) alpha | 0.344731536 | 2.13.114 || ARHGEF28 | 2.13.114 | Rho guanine nucleotide exchange factor 28 | 0.276366556 | 2.13.114 || ARPC4 | 2.13.114 | actin related protein 2/3 complex subunit 4 | 0.338889024 | 2.13.114 || ATP1A1 | 2.13.114 | ATPase Na+/K+ transporting subunit alpha 1 | 0.256338538 | 2.13.114 || ATP6AP1 | 2.13.114 | ATPase H+ transporting accessory protein 1 | 0.385387572 | 2.13.114 || ATP6V0C | 2.13.114 | ATPase H+ transporting V0 subunit c | 0.258838881 | 2.13.114 || BMF | 2.13.114 | Bcl2 modifying factor | 0.408173976 | 2.13.114 || BRI3 | 2.13.114 | brain protein I3 | 0.276505057 | 2.13.114 || C11orf74 | 2.13.114 | chromosome 11 open reading frame 74 | 0.356840888 | 2.13.114 || CBLB | 2.13.114 | Cbl proto-oncogene B, E3 ubiquitin protein ligase | 0.6990346 | 2.13.114 || CCDC71L | 2.13.114 | coiled-coil domain containing 71-like | 0.447881502 | 2.13.114 || CD33 | 2.13.114 | CD33 molecule | 0.458006501 | 2.13.114 || CD99P1 | 2.13.114 | CD99 molecule pseudogene 1 | 0.975712846 | 2.13.114 || CDC42 | 2.13.114 | cell division cycle 42 | 0.249055075 | 2.13.114 || CDK6 | 2.13.114 | cyclin-dependent kinase 6 | 0.313501183 | 2.13.114 || CEBPD | 2.13.114 | CCAAT/enhancer binding protein delta | 0.311601959 | 2.13.114 || CHKA | 2.13.114 | choline kinase alpha | 0.242642167 | 2.13.114 || CHSY3 | 2.13.114 | chondroitin sulfate synthase 3 | 0.50778913 | 2.13.114 || CKS2 | 2.13.114 | CDC28 protein kinase regulatory subunit 2 | 1.100558823 | 2.13.114 || COMT | 2.13.114 | catechol-O-methyltransferase | 0.240369811 | 2.13.114 || CTNNAL1 | 2.13.114 | catenin alpha-like 1 | 0.941381818 | 2.13.114 || DAGLB | 2.13.114 | diacylglycerol lipase beta | 0.412141118 | 2.13.114 || DHRS7 | 2.13.114 | dehydrogenase/reductase (SDR family) member 7 | 0.227646413 | 2.13.114 || ECT2 | 2.13.114 | epithelial cell transforming 2 | 0.34471067 | 2.13.114 || EGR3 | 2.13.114 | early growth response 3 | 0.802268668 | 2.13.114 || ENPP4 | 2.13.114 | ectonucleotide pyrophosphatase/phosphodiesterase 4 (putative) | 0.459210345 | 2.13.114 || FAM109A | 2.13.114 | family with sequence similarity 109 member A | 0.277290623 | 2.13.114 || FAM129B | 2.13.114 | family with sequence similarity 129 member B | 0.558431272 | 2.13.114 || FAM53B | 2.13.114 | family with sequence similarity 53 member B | 0.220473279 | 2.13.114 || FKBP10 | 2.13.114 | FK506 binding protein 10 | 1.497576934 | 2.13.114 || FOXO4 | 2.13.114 | forkhead box O4 | 0.358715734 | 2.13.114 || GAA | 2.13.114 | glucosidase, alpha; acid | 0.86547707 | 2.13.114 || GM2A | 2.13.114 | GM2 ganglioside activator | 0.355757498 | 2.13.114 || GPNMB | 2.13.114 | glycoprotein nmb | 0.466321045 | 2.13.114 || GRN | 2.13.114 | granulin | 0.447978794 | 2.13.114 || HEXB | 2.13.114 | hexosaminidase subunit beta | 0.571878974 | 2.13.114 || HOXB6 | 2.13.114 | homeobox B6 | 0.668773405 | 2.13.114 || HVCN1 | 2.13.114 | hydrogen voltage gated channel 1 | 0.395585015 | 2.13.114 || KLF9 | 2.13.114 | Kruppel-like factor 9 | 0.553886869 | 2.13.114 || LINC00304 | 2.13.114 | long intergenic non-protein coding RNA 304 | 0.393501478 | 2.13.114 || MAD2L1 | 2.13.114 | MAD2 mitotic arrest deficient-like 1 (yeast) | 1.100419452 | 2.13.114 || MBOAT1 | 2.13.114 | membrane bound O-acyltransferase domain containing 1 | 0.357216125 | 2.13.114 || MCTP1 | 2.13.114 | multiple C2 and transmembrane domain containing 1 | 0.988495346 | 2.13.114 || ME1 | 2.13.114 | malic enzyme 1, NADP(+)-dependent, cytosolic | 0.278326942 | 2.13.114 || MGAT1 | 2.13.114 | mannosyl (alpha-1,3-)-glycoprotein beta-1,2-N-acetylglucosaminyltransferase | 0.350451991 | 2.13.114 || MINA | 2.13.114 | MYC induced nuclear antigen | 0.283548651 | 2.13.114 || MS4A14 | 2.13.114 | membrane spanning 4-domains A14 | 0.900422952 | 2.13.114 || MVP | 2.13.114 | major vault protein | 0.242014911 | 2.13.114 || NAGPA | 2.13.114 | N-acetylglucosamine-1-phosphodiester alpha-N-acetylglucosaminidase | 0.325417838 | 2.13.114 || P4HB | 2.13.114 | prolyl 4-hydroxylase subunit beta 0.342471626 | 2.13.114 || PARP6 | 2.13.114 | poly(ADP-ribose) polymerase family member 6 | 0.25692068 | 2.13.114 || PARVB | 2.13.114 | parvin beta | 0.70562519 | 2.13.114 || PDAP1 | 2.13.114 | PDGFA associated protein 1 | 0.402836026 | 2.13.114 || PIK3IP1 | 2.13.114 | phosphoinositide-3-kinase interacting protein 1 | 0.330308467 | 2.13.114 || PIK3R5 | 2.13.114 | phosphoinositide-3-kinase regulatory subunit 5 | 0.676437862 | 2.13.114 || PKM | 2.13.114 | pyruvate kinase, muscle | 0.485963464 | 2.13.114 || PKN2 | 2.13.114 | protein kinase N2 | 0.366914792 | 2.13.114 || PLBD1 | 2.13.114 | phospholipase B domain containing 1 | 0.798153641 | 2.13.114 || PLD3 | 2.13.114 | phospholipase D family member 3 | 0.447032144 | 2.13.114 || PLP2 | 2.13.114 | proteolipid protein 2 (colonic epithelium-enriched) | 0.241328907 | 2.13.114 || POLR3K | 2.13.114 | polymerase (RNA) III subunit K | 0.233338628 | 2.13.114 || PON2 | 2.13.114 | paraoxonase 2 | 0.237306537 | 2.13.114 || PPDPF | 2.13.114 | pancreatic progenitor cell differentiation and proliferation factor | 0.310586024 | 2.13.114 || PRRG1 |

TABLE 3B-continued

The genes within the significant gene clusters, listed in Table 3A. (3966 Genes Listed by: Gene Symbol | Gen 2 Module | Gene Description | RowVariance | Gen 3 Module ||)

2.13.114 | proline rich Gla (G-carboxyglutamic acid) 1 | 0.653723801 | 2.13.114 || PTAFR | 2.13.114 | platelet activating factor receptor | 0.478181238 | 2.13.114 || QSOX1 | 2.13.114 | quiescin sulfhydryl oxidase 1 | 0.368927339 | 2.13.114 || RHOQ | 2.13.114 | ras homolog family member Q | 0.241573272 | 2.13.114 || RNF130 | 2.13.114 | ring finger protein 130 | 0.3114708 | 2.13.114 || SCRN3 | 2.13.114 | secernin 3 | 0.248950373 | 2.13.114 || SEC22B | 2.13.114 | SEC22 homolog B, vesicle trafficking protein (gene/pseudogene) | 0.2457394 | 2.13.114 || SGOL2 | 2.13.114 | shugoshin-like 2 (*S. pombe*) | 0.677440331 | 2.13.114 || SH3BGRL3 | 2.13.114 | SH3 domain binding glutamate rich protein like 3 | 0.332563528 | 2.13.114 || SIGLEC1 | 2.13.114 | sialic acid binding Ig like lectin 1 | 0.544833518 | 2.13.114 || SIRPA | 2.13.114 | signal regulatory protein alpha | 0.518829285 | 2.13.114 || SLC16A7 | 2.13.114 | solute carrier family 16 member 7 | 1.623659067 | 2.13.114 || SLC9A6 | 2.13.114 | solute carrier family 9 member A6 | 0.221078859 | 2.13.114 || SMPDL3A | 2.13.114 | sphingomyelin phosphodiesterase acid like 3A | 0.31952755 | 2.13.114 || THAP8 | 2.13.114 | THAP domain containing 8 | 0.216626417 | 2.13.114 || TMEM129 | 2.13.114 | transmembrane protein 129 | 0.263432145 | 2.13.114 || TMEM176A | 2.13.114 | transmembrane protein 176A | 0.282487188 | 2.13.114 || TMEM176B | 2.13.114 | transmembrane protein 176B | 0.316009486 | 2.13.114 || TMEM198B | 2.13.114 | transmembrane protein 198B (pseudogene) | 0.333031752 | 2.13.114 || TMEM259 | 2.13.114 | transmembrane protein 259 | 0.455797342 | 2.13.114 || TMEM64 | 2.13.114 | transmembrane protein 64 | 0.598506919 | 2.13.114 || TMTC2 | 2.13.114 | transmembrane and tetratricopeptide repeat containing 2 | 0.978419575 | 2.13.114 || TNK2 | 2.13.114 | tyrosine kinase, non-receptor, 2 | 0.227917443 | 2.13.114 || TPP1 | 2.13.114 | tripeptidyl peptidase I | 0.279185597 | 2.13.114 || TRMT6 | 2.13.114 | tRNA methyltransferase 6 | 0.674126391 | 2.13.114 || TSC22D3 | 2.13.114 | TSC22 domain family member 3 | 0.831241773 | 2.13.114 || TSPAN4 | 2.13.114 | tetraspanin 4 | 0.248755326 | 2.13.114 || TSPO | 2.13.114 | translocator protein | 0.237547491 | 2.13.114 || TTC38 | 2.13.114 | tetratricopeptide repeat domain 38 | 0.297274267 | 2.13.114 || TTC7A | 2.13.114 | tetratricopeptide repeat domain 7A | 0.370564594 | 2.13.114 || UBE2D1 | 2.13.114 | ubiquitin conjugating enzyme E2D 1 | 0.308882488 | 2.13.114 || ZBTB16 | 2.13.114 | zinc finger and BTB domain containing 16 | 3.507241815 | 2.13.114 || ZDHHC7 | 2.13.114 | zinc finger DHHC-type containing 7 | 0.267367989 | 2.13.114 || ZMYND15 | 2.13.114 | zinc finger MYND-type containing 15 | 0.466281515 | 2.13.114 || ZNF138 | 2.13.114 | zinc finger protein 138 | 0.308645533 | 2.13.114 || ANKRD44 | 2.13.117 | ankyrin repeat domain 44 | 0.419715692 | 2.13.117 || ARHGAP30 | 2.13.117 | Rho GTPase activating protein 30 | 0.553082233 | 2.13.117 || ATP6V1B2 | 2.13.117 | ATPase H+ transporting V1 subunit B2 | 0.372650633 | 2.13.117 || C2orf76 | 2.13.117 | chromosome 2 open reading frame 76 | 0.779841415 | 2.13.117 || CDC25B | 2.13.117 | cell division cycle 25B | 0.234935615 | 2.13.117 || CHST11 | 2.13.117 | carbohydrate (chondroitin 4) sulfotransferase 11 | 0.741694504 | 2.13.117 || DOK3 | 2.13.117 | docking protein 3 | 1.407402243 | 2.13.117 || EVL | 2.13.117 | Enah/Vasp-like | 0.51540568 | 2.13.117 || FAM229B | 2.13.117 | family with sequence similarity 229 member B | 0.620487724 | 2.13.117 || IL15 | 2.13.117 | interleukin 15 | 0.814306198 | 2.13.117 || IL17RA | 2.13.117 | interleukin 17 receptor A | 0.455702783 | 2.13.117 || IRF8 | 2.13.117 | interferon regulatory factor 8 | 0.516252625 | 2.13.117 || KIAA1468 | 2.13.117 | KIAA1468 | 0.253685207 | 2.13.117 || LRIF1 | 2.13.117 | ligand dependent nuclear receptor interacting factor 1 | 0.503312043 | 2.13.117 || MEF2A | 2.13.117 | myocyte enhancer factor 2A | 0.350986547 | 2.13.117 || MGME1 | 2.13.117 | mitochondrial genome maintenance exonuclease 1 | 0.220814438 | 2.13.117 || NPC1 | 2.13.117 | Niemann-Pick disease, type C1 | 0.659163398 | 2.13.117 || NUP62 | 2.13.117 | nucleoporin 62 kDa | 0.385630702 | 2.13.117 || OSGIN2 | 2.13.117 | oxidative stress induced growth inhibitor family member 2 | 0.485072903 | 2.13.117 || PREX1 | 2.13.117 | phosphatidylinositol-3,4,5-trisphosphate-dependent Rac exchange factor 1 | 0.250217617 | 2.13.117 || PTPRJ | 2.13.117 | protein tyrosine phosphatase, receptor type J | 0.758561814 | 2.13.117 || RAPGEF1 | 2.13.117 | Rap guanine nucleotide exchange factor 1 | 0.572073564 | 2.13.117 || RBM47 | 2.13.117 | RNA binding motif protein 47 | 0.486946946 | 2.13.117 || RUNX3 | 2.13.117 | runt related transcription factor 3 | 1.275263144 | 2.13.117 || SDC3 | 2.13.117 | syndecan 3 | 0.223505318 | 2.13.117 || SEPT6 | 2.13.117 | septin 6 | 0.311496997 | 2.13.117 || SFRP2 | 2.13.117 | secreted frizzled-related protein 2 | 4.809938046 | 2.13.117 || SP140L | 2.13.117 | SP140 nuclear body protein like | 0.290145129 | 2.13.117 || TNS3 | 2.13.117 | tensin 3 | 0.31387926 | 2.13.117 || TUBB2A | 2.13.117 | tubulin beta 2A class IIa | 0.325023776 | 2.13.117 || WDFY4 | 2.13.117 | WDFY family member 4 | 0.310390837 | 2.13.117 || ZC3H12D | 2.13.117 | zinc finger CCCH-type containing 12D | 0.684374131 | 2.13.117 || ARHGAP9 | 2.16.121 | Rho GTPase activating protein 9 | 0.518721369 | 2.16.121 || CCR2 | 2.16.121 | chemokine (C-C motif) receptor 2 | 2.238090097 | 2.16.121 || CD48 | 2.16.121 | CD48 molecule | 1.237135937 | 2.16.121 || CD52 | 2.16.121 | CD52 molecule | 1.862049647 | 2.16.121 || CDC42SE2 | 2.16.121 | CDC42 small effector 2 | 0.306215443 | 2.16.121 || CORO1A | 2.16.121 | coronin 1A | 1.034299612 | 2.16.121 || DSTYK | 2.16.121 | dual serine/threonine and tyrosine protein kinase | 0.335087459 | 2.16.121 || F5 | 2.16.121 | coagulation factor V | 2.475642818 | 2.16.121 || FCN1 | 2.16.121 | ficolin 1 | 3.497920465 | 2.16.121 || FGD3 | 2.16.121 | FYVE, RhoGEF and PH domain containing 3 | 0.806294346 | 2.16.121 || IKZF1 | 2.16.121 | IKAROS family zinc finger 1 | 0.384997667 | 2.16.121 || IL2RG | 2.16.121 | interleukin 2 receptor subunit gamma | 0.937783702 | 2.16.121 || ITGAL | 2.16.121 | integrin subunit alpha L | 1.473962494 | 2.16.121 || LRCH4 | 2.16.121 | leucine-rich repeats and calponin homology (CH) domain containing 4 | 0.27162551 | 2.16.121 || MLKL | 2.16.121 | mixed lineage kinase domain-like | 0.234233086 | 2.16.121 || NAP1L5 | 2.16.121 | nucleosome assembly protein 1 like 5 | 0.807252711 | 2.16.121 || PRKCB | 2.16.121 | protein kinase C beta | 1.957382364 | 2.16.121 || RAC2 | 2.16.121 | ras-related C3 botulinum toxin substrate 2 (rho family, small GTP binding protein Rac2) | 1.353567681 | 2.16.121 || RASSF5 | 2.16.121 | Ras association domain family member 5 | 0.766637803 | 2.16.121 || SASH3 | 2.16.121 | SAM and SH3 domain containing 3 | 0.817474107 | 2.16.121 || SEMA4D | 2.16.121 | semaphorin 4D | 1.778919845 | 2.16.121 || SLAMF7 | 2.16.121 | SLAM family member 7 | 1.569509011 | 2.16.121 || TMC8 | 2.16.121 | transmembrane channel like 8 | 0.597734204 | 2.16.121 || TRIM6 | 2.16.121 | tripartite motif containing 6 | 0.524072509 | 2.16.121 || BCR | 2.16.122 | breakpoint cluster region | 0.415560216 | 2.16.122 || C17orf62 | 2.16.122 | chromosome 17 open reading frame 62 | 0.255637923 | 2.16.122 || CSF2RB | 2.16.122 | colony stimulating factor 2 receptor beta common subunit | 0.818078341 | 2.16.122 || DNASE1L3 | 2.16.122 | deoxyribonuclease I-like 3 | 2.214070063 | 2.16.122 || DOCK8 | 2.16.122 | dedicator of cytokinesis 8 | 0.42091134 | 2.16.122 || FOXP2 | 2.16.122 |

TABLE 3B-continued

The genes within the significant gene clusters, listed in Table 3A. (3966 Genes Listed by: Gene Symbol | Gen 2 Module | Gene Description | RowVariance | Gen 3 Module ||)

forkhead box P2 | 2.156829532 | 2.16.122 || GPR160 | 2.16.122 | G protein-coupled receptor 160 | 1.441278593 | 2.16.122 || GPRASP1 | 2.16.122 | G protein-coupled receptor associated sorting protein 1 | 1.115161134 | 2.16.122 || HCST | 2.16.122 | hematopoietic cell signal transducer | 1.151591744 | 2.16.122 || HTR2B | 2.16.122 | 5-hydroxytryptamine receptor 2B | 1.496781013 | 2.16.122 || IER5 | 2.16.122 | immediate early response 5 | 0.358472406 | 2.16.122 || IGF1 | 2.16.122 | insulin like growth factor 1 | 1.754852301 | 2.16.122 || ITGB2-AS1 | 2.16.122 | ITGB2 antisense RNA 1 | 1.721017218 | 2.16.122 || KAZN | 2.16.122 | kazrin, periplakin interacting protein | 0.929325905 | 2.16.122 || LCP1 | 2.16.122 | lymphocyte cytosolic protein 1 (L-plastin) | 1.068888034 | 2.16.122 || MYO1F | 2.16.122 | myosin IF | 0.503103547 | 2.16.122 || NBEAL2 | 2.16.122 | neurobeachin like 2 | 0.410898235 | 2.16.122 || NPR3 | 2.16.122 | natriuretic peptide receptor 3 | 1.737416682 | 2.16.122 || RASSF2 | 2.16.122 | Ras association domain family member 2 | 0.41778909 | 2.16.122 || RCAN3 | 2.16.122 | RCAN family member 3 | 0.307824209 | 2.16.122 || RFX5 | 2.16.122 | regulatory factor X5 | 0.305684472 | 2.16.122 || RGMA | 2.16.122 | repulsive guidance molecule family member a | 2.014608159 | 2.16.122 || S1PR3 | 2.16.122 | sphingosine-1-phosphate receptor 3 | 1.798519463 | 2.16.122 || SECTM1 | 2.16.122 | secreted and transmembrane 1 | 0.981491923 | 2.16.122 || SH3RF1 | 2.16.122 | SH3 domain containing ring finger 1 | 0.910632771 | 2.16.122 || SOX9 | 2.16.122 | SRY-box 9 | 0.952326647 | 2.16.122 || SPON1 | 2.16.122 | spondin 1 | 2.599595358 | 2.16.122 || SRGN | 2.16.122 | serglycin | 0.356178993 | 2.16.122 || STK10 | 2.16.122 | serine/threonine kinase 10 | 0.302351805 | 2.16.122 || STK38 | 2.16.122 | serine/threonine kinase 38 | 0.233097472 | 2.16.122 || TAGAP | 2.16.122 | T-cell activation RhoGTPase activating protein | 0.84233511 | 2.16.122 || TERT | 2.16.122 | telomerase reverse transcriptase | 0.293475695 | 2.16.122 || TIGD1 | 2.16.122 | tigger transposable element derived 1 | 0.229965831 | 2.16.122 || TLR8 | 2.16.122 | toll like receptor 8 | 0.706115783 | 2.16.122 || TUBB2B | 2.16.122 | tubulin beta 2B class IIb | 2.431655015 | 2.16.122 || ACKR1 | 2.17 | atypical chemokine receptor 1 (Duffy blood group) | 1.453950152 | 2.17.125 || ACVRL1 | 2.17 | activin A receptor like type 1 | 0.457941698 | 2.17.126 || ADAMTS16 | 2.17 | ADAM metallopeptidase with thrombospondin type 1 motif 16 | 0.594432283 | 2.17.124 || ADAMTS9 | 2.17 | ADAM metallopeptidase with thrombospondin type 1 motif 9 | 0.600967661 | 2.17.126 || ADCY1 | 2.17 | adenylate cyclase 1 (brain) | 1.589641497 | 2.17.124 || ADGRF5 | 2.17 | adhesion G protein-coupled receptor F5 | 1.04552692 | 2.17.125 || ADGRG1 | 2.17 | adhesion G protein-coupled receptor G1 | 0.847277013 | 2.17.126 || ADGRL2 | 2.17 | adhesion G protein-coupled receptor L2 | 1.122101436 | 2.17.125 | ADGRL4 | 2.17 | adhesion G protein-coupled receptor L4 | 1.352331518 | 2.17.125 || AKR7A2 | 2.17 | aldo-keto reductase family 7, member A2 | 0.214630329 | 2.17.124 || ANKRD29 | 2.17 | ankyrin repeat domain 29 | 1.095693821 | 2.17.125 || ANKRD50 | 2.17 | ankyrin repeat domain 50 | 0.978119219 | 2.17.127 || APBB1IP | 2.17 | amyloid beta precursor protein binding family B member 1 interacting protein | 0.237345876 | 2.17.124 || ARHGAP29 | 2.17 | Rho GTPase activating protein 29 | 1.21795146 | 2.17.125 || ARL15 | 2.17 | ADP ribosylation factor like GTPase 15 | 0.322412003 | 2.17.124 || AVPR1A | 2.17 | arginine vasopressin receptor 1A | 1.752850075 | 2.17.124 || BACE2 | 2.17 | beta-site APP-cleaving enzyme 2 | 0.51524745 | 2.17.124 || BASP1 | 2.17 | brain abundant membrane attached signal protein 1 | 0.427576478 | — || C11orf45 | 2.17 | chromosome 11 open reading frame 45 | 0.471956294 | 2.17.124 || C1orf115 | 2.17 | chromosome 1 open reading frame 115 | 2.391779001 | 2.17.125 || C1orf162 | 2.17 | chromosome 1 open reading frame 162 | 0.804747996 | 2.17.124 || C21orf91 | 2.17 | chromosome 21 open reading frame 91 | 0.419842289 | 2.17.124 || C3orf70 | 2.17 | chromosome 3 open reading frame 70 | 0.586569523 | 2.17.124 || C8orf4 | 2.17 | chromosome 8 open reading frame 4 | 2.034107668 | 2.17.124 || CALCRL | 2.17 | calcitonin receptor like receptor | 1.054186733 | 2.17.125 || CC2D1A | 2.17 | coiled-coil and C2 domain containing 1A | 0.221733565 | 2.17.124 || CCNG2 | 2.17 | cyclin G2 | 0.220557952 | 2.17.125 || CD200 | 2.17 | CD200 molecule | 1.652979997 | — || CD24 | 2.17 | CD24 molecule | 0.894409745 | 2.17.125 || CD34 | 2.17 | CD34 molecule | 1.288607951 | 2.17.125 || CDH13 | 2.17 | cadherin 13 | 0.579778488 | 2.17.127 || CEP112 | 2.17 | centrosomal protein 112 kDa | 1.319818315 | 2.17.124 || CHML | 2.17 | choroideremia-like (Rab escort protein 2) | 0.519521543 | 2.17.125 || CHN1 | 2.17 | chimerin 1 | 0.808407772 | — || CLIP4 | 2.17 | CAP-Gly domain containing linker protein family member 4 | 0.494595917 | — || COBLL1 | 2.17 | cordon-bleu WH2 repeat protein like 1 | 0.974430835 | 2.17.124 || COL15A1 | 2.17 | collagen type XV alpha 1 | 0.844352503 | 2.17.126 || COL21A1 | 2.17 | collagen type XXI alpha 1 | 1.421131949 | 2.17.124 || COL4A1 | 2.17 | collagen type IV alpha 1 | 0.491598467 | 2.17.126 || COL4A2 | 2.17 | collagen type IV alpha 2 | 0.537549227 | 2.17.126 || COQ2 | 2.17 | coenzyme Q2 4-hydroxybenzoate polyprenyltransferase | 0.389520277 | 2.17.124 || CPNE2 | 2.17 | copine 2 | 0.312011555 | 2.17.126 || CTDSPL | 2.17 | CTD small phosphatase like | 0.216582787 | 2.17.125 || CYBA | 2.17 | cytochrome b-245, alpha polypeptide | 0.273760957 | 2.17.124 || CYGB | 2.17 | cytoglobin | 0.278587725 | 2.17.124 || CYYR1 | 2.17 | cysteine/tyrosine-rich 1 | 1.907969486 | 2.17.124 || DDX6 | 2.17 | DEAD-box helicase 6 | 0.235178602 | 2.17.127 || DNAJC12 | 2.17 | DnaJ heat shock protein family (Hsp40) member C12 | 0.416158071 | 2.17.126 || DOCK6 | 2.17 | dedicator of cytokinesis 6 | 0.352211575 | 2.17.126 || EBF3 | 2.17 | early B-cell factor 3 | 0.821326334 | 2.17.124 || ECM2 | 2.17 | extracellular matrix protein 2, female organ and adipocyte specific | 0.48635108 | 2.17.125 || EDNRA | 2.17 | endothelin receptor type A | 0.941379977 | 2.17.127 || EIF2B4 | 2.17 | eukaryotic translation initiation factor 2B subunit delta | 0.244574254 | 2.17.125 || EIF2D | 2.17 | eukaryotic translation initiation factor 2D | 0.227236737 | 2.17.124 || EMCN | 2.17 | endomucin | 1.495883234 | 2.17.124 || EMP3 | 2.17 | epithelial membrane protein 3 | 0.409891746 | 2.17.125 || ENPEP | 2.17 | glutamyl aminopeptidase | 0.883521596 | 2.17.126 || ENPP2 | 2.17 | ectonucleotide pyrophosphatase/phosphodiesterase 2 | 1.098641394 | 2.17.124 || EPAS1 | 2.17 | endothelial PAS domain protein 1 | 0.453120964 | 2.17.125 || EPB41L4A | 2.17 | erythrocyte membrane protein band 4.1 like 4A | 0.404663911 | 2.17.125 || ETS2 | 2.17 | ETS proto-oncogene 2, transcription factor | 0.239877709 | 2.17.125 || F2R | 2.17 | coagulation factor II thrombin receptor | 1.688783268 | 2.17.125 || FAM129A | 2.17 | family with sequence similarity 129 member A | 0.346193165 | 2.17.126 || FAM160B1 | 2.17 | family with sequence similarity 160 member B1 | 0.320470916 | 2.17.125 || FAM162B | 2.17 | family with sequence similarity 162 member B | 0.577189799 | 2.17.125 || FAM171B | 2.17 | family with sequence similarity 171 member B | 1.119407096 | 2.17.124 || FAM200A | 2.17 | family with sequence similarity 200 member A | 0.224937704 | 2.17.124 || FAM43A | 2.17 | family with sequence similarity 43 member A | 1.677486112 | 2.17.125 || FAM84B | 2.17 | family with sequence TABLE 3B-continued The genes within the significant gene clusters, listed in Table 3A. (3966 Genes Listed by: Gene Symbol | Gen 2 Module | Gene Description | RowVariance | Gen 3 Module ||)

similarity 84 member B | 1.449202678 | 2.17.125 || FBLIM1 | 2.17 | filamin binding LIM protein 1 | 0.41760694 | — || FGD6 | 2.17 | FYVE, RhoGEF and PH domain containing 6 | 0.358933985 | — || FHL2 | 2.17 | four and a half LIM domains 2 | 0.997569729 | 2.17.124 || FILIP1L | 2.17 | filamin A interacting protein 1-like | 0.564700768 | 2.17.126 || FKBP5 | 2.17 | FK506 binding protein 5 | 1.68023215 | 2.17.127 || FNBP1L | 2.17 | formin binding protein 1 like | 1.739539906 | 2.17.124 || FRMD6 | 2.17 | FERM domain containing 6 | 0.813775409 | 2.17.127 || FRS2 | 2.17 | fibroblast growth factor receptor substrate 2 | 0.497605461 | 2.17.125 | FRY | 2.17 | FRY microtubule binding protein | 1.374563277 | 2.17.124 || FZD6 | 2.17 | frizzled class receptor 6 | 2.143549057 | 2.17.124 || GAB1 | 2.17 | GRB2 associated binding protein 1 | 0.894078708 | 2.17.125 || GABPA | 2.17 | GA binding protein transcription factor alpha subunit | 0.252598746 | 2.17.124 || GCNT1 | 2.17 | glucosaminyl (N-acetyl) transferase 1, core 2 | 0.256167146 | 2.17.125 || GJA1 | 2.17 | gap junction protein alpha 1 | 0.608554029 | 2.17.127 || GJA5 | 2.17 | gap junction protein alpha 5 | 0.291113658 | 2.17.125 || GJC1 | 2.17 | gap junction protein gamma 1 | 1.409491655 | 2.17.126 || GLUL | 2.17 | glutamate-ammonia ligase | 0.274341822 | 2.17.127 || GNG11 | 2.17 | G protein subunit gamma 11 | 0.647739649 | 2.17.125 || GPM6B | 2.17 | glycoprotein M6B | 1.430720582 | 2.17.127 || GUCY1A3 | 2.17 | guanylate cyclase 1, soluble, alpha 3 | 1.97743888 | 2.17.124 || GUCY1B3 | 2.17 | guanylate cyclase 1, soluble, beta 3 | 0.787217465 | 2.17.125 || HACE1 | 2.17 | HECT domain and ankyrin repeat containing E3 ubiquitin protein ligase 1 | 1.264601713 | 2.17.124 || HEPH | 2.17 | hephaestin | 0.811394897 | 2.17.125 || HHEX | 2.17 | hematopoietically expressed homeobox | 0.554651618 | 2.17.126 || HOXB3 | 2.17 | homeobox B3 | 0.361887424 | 2.17.125 || HS3ST1 | 2.17 | heparan sulfate-glucosamine 3-sulfotransferase 1 | 1.093853563 | 2.17.124 || HTRA3 | 2.17 | HtrA serine peptidase 3 | 0.393260739 | 2.17.125 || ICA1L | 2.17 | islet cell autoantigen 1 like | 0.29295291 | 2.17.125 || ID1 | 2.17 | inhibitor of DNA binding 1, HLH protein | 1.134172555 | 2.17.124 || IER5L | 2.17 | immediate early response 5-like | 0.315954629 | 2.17.127 || IFI6 | 2.17 | interferon, alpha-inducible protein 6 | 1.122576884 | 2.17.124 || IKBIP | 2.17 | IKBKB interacting protein | 0.460792882 | 2.17.127 || IL17RD | 2.17 | interleukin 17 receptor D | 2.247920877 | 2.17.124 || IL33 | 2.17 | interleukin 33 | 3.774111262 | 2.17.124 || INPP5F | 2.17 | inositol polyphosphate-5-phosphatase F | 0.28349311 | 2.17.124 || ITGA1 | 2.17 | integrin subunit alpha 1 | 0.896671188 | 2.17.124 || ITGAM | 2.17 | integrin subunit alpha M | 0.815666746 | 2.17.124 || ITGB1BP1 | 2.17 | integrin subunit beta 1 binding protein 1 | 0.297177921 | 2.17.125 || JAG1 | 2.17 | jagged 1 | 0.713930058 | 2.17.124 || JAG2 | 2.17 | jagged 2 | 0.510481438 | 2.17.126 || JAM2 | 2.17 | junctional adhesion molecule 2 | 1.376858038 | 2.17.124 || JAZF1 | 2.17 | JAZF zinc finger 1 | 0.225918822 | 2.17.125 || KATNAL1 | 2.17 | katanin p60 subunit A like 1 | 0.60518728 | 2.17.125 || KCNJ8 | 2.17 | potassium voltage-gated channel subfamily J member 8 | 0.817309587 | 2.17.125 || KCTD15 | 2.17 | potassium channel tetramerization domain containing 15 | 1.396051842 | 2.17.125 || KCTD9 | 2.17 | potassium channel tetramerization domain containing 9 | 0.263593011 | 2.17.124 || KDELC1 | 2.17 | KDEL motif containing 1 | 0.683934832 | 2.17.127 || KDR | 2.17 | kinase insert domain receptor | 1.052951732 | 2.17.124 || KLHL7 | 2.17 | kelch like family member 7 | 0.265123513 | 2.17.125 || LAMA4 | 2.17 | laminin subunit alpha 4 | 0.70683101 | 2.17.124 || LAMC1 | 2.17 | laminin subunit gamma 1 | 0.292868302 | 2.17.125 || LARS2 | 2.17 | leucyl-tRNA synthetase 2 | 0.344724682 | 2.17.125 || LATS1 | 2.17 | large tumor suppressor kinase 1 | 0.294057251 | 2.17.124 || LBH | 2.17 | limb bud and heart development | 0.484850762 | 2.17.127 || LDB2 | 2.17 | LIM domain binding 2 | 1.683616689 | 2.17.125 || LEF1 | 2.17 | lymphoid enhancer binding factor 1 | 1.169334617 | — || LHX6 | 2.17 | LIM homeobox 6 | 1.178086198 | 2.17.125 || LOC730102 | 2.17 | quinone oxidoreductase-like protein 2 pseudogene | 0.356612157 | 2.17.125 || LRRC32 | 2.17 | leucine rich repeat containing 32 | 0.706824339 | 2.17.124 || LRRN3 | 2.17 | leucine rich repeat neuronal 3 | 1.626717762 | 2.17.125 || LY86 | 2.17 | lymphocyte antigen 86 | 0.440570375 | 2.17.125 || MALL | 2.17 | mal, T-cell differentiation protein-like | 0.585499746 | 2.17.127 || MAP3K11 | 2.17 | mitogen-activated protein kinase kinase kinase 11 | 0.239659423 | 2.17.126 || MAP4K4 | 2.17 | mitogen-activated protein kinase kinase kinase kinase 4 | 0.599566721 | 2.17.125 || MBTD1 | 2.17 | mbt domain containing 1 | 0.216931757 | 2.17.125 || MECOM | 2.17 | MDS1 and EVI1 complex locus | 1.723154479 | 2.17.124 || MEGF9 | 2.17 | multiple EGF like domains 9 | 0.281345659 | 2.17.126 || MMRN2 | 2.17 | multimerin 2 | 0.723845587 | 2.17.125 || MPDZ | 2.17 | multiple PDZ domain crumbs cell polarity complex component | 0.834525641 | 2.17.124 || MRPL1 | 2.17 | mitochondrial ribosomal protein L1 | 0.416587495 | 2.17.124 || MUC1 | 2.17 | mucin 1, cell surface associated | 0.315899817 | 2.17.124 || MYCT1 | 2.17 | myc target 1 | 0.725785281 | 2.17.125 || MYH10 | 2.17 | myosin, heavy chain 10, non-muscle | 1.164370368 | 2.17.125 || MYH9 | 2.17 | myosin, heavy chain 9, non-muscle | 0.319845011 | 2.17.126 || MYL9 | 2.17 | myosin light chain 9 | 0.775610304 | 2.17.125 || MYO9A | 2.17 | myosin IXA | 0.427453096 | 2.17.125 || NAB1 | 2.17 | NGFI-A binding protein 1 | 0.226484788 | 2.17.124 || NEURL1B | 2.17 | neuralized E3 ubiquitin protein ligase 1B | 0.887200485 | 2.17.125 || NID1 | 2.17 | nidogen 1 | 1.492436869 | 2.17.124 || NID2 | 2.17 | nidogen 2 | 0.760702668 | 2.17.127 || NOV | 2.17 | nephroblastoma overexpressed | 2.844005169 | 2.17.124 || NR2F2 | 2.17 | nuclear receptor subfamily 2 group F member 2 | 0.742757478 | 2.17.124 || NRN1 | 2.17 | neuritin 1 | 2.075579212 | 2.17.124 || NUAK1 | 2.17 | NUAK family kinase 1 | 0.93337636 | 2.17.125 || NUDT7 | 2.17 | nudix hydrolase 7 | 0.501954265 | 2.17.125 || NUP35 | 2.17 | nucleoporin 35 kDa | 0.267511533 | 2.17.124 || ODF2 | 2.17 | outer dense fiber of sperm tails 2 | 0.241298677 | 2.17.124 || OLFML2A | 2.17 | olfactomedin like 2A | 1.226393628 | 2.17.125 || PDE5A | 2.17 | phosphodiesterase 5A | 1.833210985 | 2.17.124 || PI15 | 2.17 | peptidase inhibitor 15 | 0.982996573 | 2.17.124 || PIBF1 | 2.17 | progesterone immunomodulatory binding factor 1 | 0.32317475 | 2.17.124 || PKDCC | 2.17 | protein kinase domain containing, cytoplasmic | 1.548070767 | 2.17.125 || PKP4 | 2.17 | plakophilin 4 | 1.099430083 | 2.17.124 || PLA2G7 | 2.17 | phospholipase A2 group VII | 0.382480958 | 2.17.126 || PLAU | 2.17 | plasminogen activator, urokinase | 0.404867694 | 2.17.127 || PLCL1 | 2.17 | phospholipase C like 1 | 0.308847875 | 2.17.126 || PLEK2 | 2.17 | pleckstrin 2 | 0.345893639 | 2.17.126 || PLPPR4 | 2.17 | phospholipid phosphatase related 4 | 1.825862147 | 2.17.125 || PLVAP | 2.17 | plasmalemma vesicle associated protein | 0.570043008 | 2.17.126 || PODN | 2.17 | podocan | 0.58543331 | 2.17.125 || PRDX2 | 2.17 | peroxiredoxin 2 | 0.263026189 | 2.17.124 || PREX2 | 2.17 | phosphatidylinositol-3,4,5-trisphosphate-dependent Rac exchange factor 2 | 1.973934179 | 2.17.124 || PRKAG2 | 2.17 | protein kinase AMP-activated non-catalytic subunit gamma 2 | 0.229869396 | — || PRKCDBP | 2.17 | protein kinase C delta binding protein | 0.691940304 | 2.17.127 || PRKD1 | 2.17 | protein kinase D1 |

TABLE 3B-continued

The genes within the significant gene clusters, listed in Table 3A. (3966 Genes Listed by: Gene Symbol | Gen 2 Module | Gene Description | RowVariance | Gen 3 Module ||)

0.659899578 | 2.17.125 || PTGR1 | 2.17 | prostaglandin reductase 1 | 0.280966942 | 2.17.124 || PTK2 | 2.17 | protein tyrosine kinase 2 | 0.261036342 | 2.17.125 || PTPN21 | 2.17 | protein tyrosine phosphatase, non-receptor type 21 | 0.928169001 | 2.17.125 || PTPRM | 2.17 | protein tyrosine phosphatase, receptor type M | 0.255088825 | 2.17.125 || PWWP2A | 2.17 | PWWP domain containing 2A | 0.28773633 | 2.17.124 || PXN | 2.17 | paxillin | 0.249626232 | 2.17.126 || RAMP3 | 2.17 | receptor (G protein-coupled) activity modifying protein 3 | 0.84866751 | 2.17.124 || RARA | 2.17 | retinoic acid receptor alpha | 6.344036067 | 2.17.125 || RASL12 | 2.17 | RAS like family 12 | 0.470244108 | 2.17.125 || RASSF3 | 2.17 | Ras association domain family member 3 | 0.255685815 | 2.17.126 || RFTN1 | 2.17 | raftlin, lipid raft linker 1 | 0.541508935 | 2.17.126 || RHOJ | 2.17 | ras homolog family member J | 2.003469568 | 2.17.124 || RNF123 | 2.17 | ring finger protein 123 | 0.241512255 | 2.17.124 || RNF144A | 2.17 | ring finger protein 144A | 0.709145952 | 2.17.124 || ROBO4 | 2.17 | roundabout guidance receptor 4 | 0.718387723 | 2.17.125 || ROCK2 | 2.17 | Rho associated coiled-coil containing protein kinase 2 | 0.714350491 | 2.17.125 || S100A16 | 2.17 | S100 calcium binding protein A16 | 0.390001119 | 2.17.124 || S1PR1 | 2.17 | sphingosine-1-phosphate receptor 1 | 0.332036442 | 2.17.125 || SCN4B | 2.17 | sodium voltage-gated channel beta subunit 4 | 1.674532567 | 2.17.125 || SDPR | 2.17 | serum deprivation response | 3.070893994 | 2.17.125 || SERPINH1 | 2.17 | serpin peptidase inhibitor, clade H (heat shock protein 47), member 1, (collagen binding protein 1) | 0.622630995 | — || SFRP4 | 2.17 | secreted frizzled-related protein 4 | 3.262301646 | 2.17.124 || SH2D3C | 2.17 | SH2 domain containing 3C | 0.404744321 | 2.17.126 || SH3BP4 | 2.17 | SH3-domain binding protein 4 | 0.656715251 | 2.17.125 || SHANK3 | 2.17 | SH3 and multiple ankyrin repeat domains 3 | 1.371147921 | 2.17.125 || SHE | 2.17 | Src homology 2 domain containing E | 0.522594512 | 2.17.125 || SIDT2 | 2.17 | SID1 transmembrane family member 2 | 0.290703187 | — || SKP2 | 2.17 | S-phase kinase-associated protein 2, E3 ubiquitin protein ligase | 0.505014297 | 2.17.125 || SLC12A2 | 2.17 | solute carrier family 12 member 2 | 0.614484188 | 2.17.124 || SLC1A3 | 2.17 | solute carrier family 1 member 3 | 1.689860068 | 2.17.127 || SLC30A4 | 2.17 | solute carrier family 30 member 4 | 0.215053029 | 2.17.124 || SLC39A10 | 2.17 | solute carrier family 39 member 10 | 0.266715622 | 2.17.124 || SLIT3 | 2.17 | slit guidance ligand 3 | 0.70833372 | 2.17.125 || SMAD1 | 2.17 | SMAD family member 1 | 1.235149314 | 2.17.124 || SMIM3 | 2.17 | small integral membrane protein 3 | 0.330690153 | 2.17.127 || SMU1 | 2.17 | smu-1 suppressor of mec-8 and unc-52 homolog (*C. elegans*) | 0.22452513 | — || SNAI2 | 2.17 | snail family zinc finger 2 | 0.818480827 | — || SNCAIP | 2.17 | synuclein alpha interacting protein | 0.588192354 | 2.17.124 || SNRK | 2.17 | SNF related kinase | 0.286185619 | 2.17.125 || SOCS2 | 2.17 | suppressor of cytokine signaling 2 | 0.913068369 | 2.17.124 || SOX4 | 2.17 | SRY-box 4 | 0.936367705 | 2.17.127 || SOX7 | 2.17 | SRY-box 7 | 1.873947217 | 2.17.125 || SPATS2 | 2.17 | spermatogenesis associated serine rich 2 | 0.275087211 | — || SPNS2 | 2.17 | spinster homolog 2 (*Drosophila*) | 0.36332731 | 2.17.125 || STARD9 | 2.17 | StAR related lipid transfer domain containing 9 | 0.67986022 | 2.17.125 || STON2 | 2.17 | stonin 2 | 0.851091766 | 2.17.124 || SYNE2 | 2.17 | spectrin repeat containing, nuclear envelope 2 | 1.976751419 | 2.17.126 || TAF12 | 2.17 | TATA-box binding protein associated factor 12 | 0.22949498 | 2.17.124 || TAGLN | 2.17 | transgelin | 1.219161942 | 2.17.124 || TANC1 | 2.17 | tetratricopeptide repeat, ankyrin repeat and coiled-coil containing 1 | 1.727561303 | 2.17.124 || TEK | 2.17 | TEK receptor tyrosine kinase | 1.433203869 | 2.17.124 || TGFB3 | 2.17 | transforming growth factor beta 3 | 0.504305292 | 2.17.127 || THSD7A | 2.17 | thrombospondin type 1 domain containing 7A | 2.484067083 | 2.17.125 || THY1 | 2.17 | Thy-1 cell surface antigen | 0.688637056 | — || TM4SF1 | 2.17 | transmembrane 4 L six family member 1 | 0.79382655 | 2.17.124 || TM4SF18 | 2.17 | transmembrane 4 L six family member 18 | 2.53876737 | 2.17.124 || TMEM204 | 2.17 | transmembrane protein 204 | 0.484166564 | 2.17.125 || TMEM47 | 2.17 | transmembrane protein 47 | 0.970410186 | 2.17.124 || TPM1 | 2.17 | tropomyosin 1 (alpha) | 0.498805397 | 2.17.124 || TSPAN12 | 2.17 | tetraspanin 12 | 2.208235108 | 2.17.124 || TUSC3 | 2.17 | tumor suppressor candidate 3 | 0.861076537 | 2.17.127 || TWSG1 | 2.17 | twisted gastrulation BMP signaling modulator 1 | 0.258197131 | 2.17.127 || VWA5A | 2.17 | von Willebrand factor A domain containing 5A | 0.491093621 | 2.17.127 || XRCC2 | 2.17 | X-ray repair complementing defective repair in Chinese hamster cells 2 | 0.34576168 | 2.17.126 || ZBTB46 | 2.17 | zinc finger and BTB domain containing 46 | 0.267531395 | 2.17.125 || ZCCHC2 | 2.17 | zinc finger CCHC-type containing 2 | 2.080932972 | 2.17.127 || ZMYM4 | 2.17 | zinc finger MYM-type containing 4 | 0.227299065 | 2.17.125 || ZNF227 | 2.17 | zinc finger protein 227 | 0.286384307 | 2.17.125 || ZNF529 | 2.17 | zinc finger protein 529 | 0.358239722 | 2.17.124 || ZNF614 | 2.17 | zinc finger protein 614 | 0.266891515 | 2.17.124 || ZNF808 | 2.17 | zinc finger protein 808 | 0.312485463 | 2.17.127 || ZNHIT6 | 2.17 | zinc finger HIT-type containing 6 | 0.291553481 | 2.17.124 || AKNA | 2.18.129 | AT-hook transcription factor | 0.464370735 | 2.18.129 || BIRC3 | 2.18.129 | baculoviral IAP repeat containing 3 | 0.665883746 | 2.18.129 || CD2 | 2.18.129 | CD2 molecule | 1.920481085 | 2.18.129 || CD3D | 2.18.129 | CD3d molecule | 2.267328959 | 2.18.129 | CD3G | 2.18.129 | CD3g molecule | 1.1898177 | 2.18.129 || CD8A | 2.18.129 | CD8a molecule | 1.502794773 | 2.18.129 || CST7 | 2.18.129 | cystatin F | 0.257916524 | 2.18.129 || CTSW | 2.18.129 | cathepsin W | 0.668527574 | 2.18.129 || CXCL13 | 2.18.129 | C-X-C motif chemokine ligand 13 | 7.675943343 | 2.18.129 || DENND2D | 2.18.129 | DENN domain containing 2D | 0.410314385 | 2.18.129 || EOMES | 2.18.129 | eomesodermin | 1.215836207 | 2.18.129 || GCLC | 2.18.129 | glutamate-cysteine ligase catalytic subunit | 0.232367024 | 2.18.129 || GZMA | 2.18.129 | granzyme A | 4.131331048 | 2.18.129 || GZMH | 2.18.129 | granzyme H | 1.344984481 | 2.18.129 || GZMK | 2.18.129 | granzyme K | 4.225613474 | 2.18.129 || IL32 | 2.18.129 | interleukin 32 | 1.777840703 | 2.18.129 || ITK | 2.18.129 | IL2 inducible T-cell kinase | 1.353024592 | 2.18.129 || KIAA1551 | 2.18.129 | KIAA1551 | 0.365408529 | 2.18.129 || KLRB1 | 2.18.129 | killer cell lectin like receptor B1 | 0.751935713 | 2.18.129 || LCK | 2.18.129 | LCK proto-oncogene, Src family tyrosine kinase | 2.104403831 | 2.18.129 || NKG7 | 2.18.129 | natural killer cell granule protein 7 | 1.708688625 | 2.18.129 || NLRC3 | 2.18.129 | NLR family, CARD domain containing 3 | 0.216441871 | 2.18.129 || PDCD4 | 2.18.129 | programmed cell death 4 (neoplastic transformation inhibitor) | 0.325133438 | 2.18.129 || PRF1 | 2.18.129 | perforin 1 | 1.331921421 | 2.18.129 || PTPRCAP | 2.18.129 | protein tyrosine phosphatase, receptor type C associated protein | 0.611743348 | 2.18.129 || RASGRP1 | 2.18.129 | RAS guanyl releasing protein 1 | 1.931153541 | 2.18.129 || SH2D1A | 2.18.129 | SH2 domain containing 1A | 0.653395578 | 2.18.129 || STAMBPL1 | 2.18.129 | STAM binding protein like 1 | 0.356935406 | 2.18.129 || TOX | 2.18.129 | thymocyte selection associated high mobility group box | 0.245434058 | 2.18.129 || TRAF3IP3 |

TABLE 3B-continued

| The genes within the significant gene clusters, listed in Table 3A. (3966 Genes Listed by: Gene Symbol ∣ Gen 2 Module ∣ Gene Description ∣ RowVariance ∣ Gen 3 Module ‖) |
| --- |
| 2.18.129 ∣ TRAF3 interacting protein 3 ∣ 0.769992424 ∣ 2.18.129 ‖ TRAT1 ∣ 2.18.129 ∣ T cell receptor associated transmembrane adaptor 1 ∣ 0.894694549 ∣ 2.18.129 ‖ TSPAN13 ∣ 2.18.129 ∣ tetraspanin 13 ∣ 0.782661139 ∣ 2.18.129 ‖ VNN1 ∣ 2.18.129 ∣ vanin 1 ∣ 1.310387591 ∣ 2.18.129 ‖ XCL1 ∣ 2.18.129 ∣ X-C motif chemokine ligand 1 ∣ 0.455387609 ∣ 2.18.129 ‖ ADAR ∣ 2.18.130 ∣ adenosine deaminase, RNA-specific ∣ 0.225307616 ∣ 2.18.130 ‖ APOE ∣ 2.18.130 ∣ apolipoprotein E ∣ 0.991942596 ∣ 2.18.130 ‖ APOL1 ∣ 2.18.130 ∣ apolipoprotein L1 ∣ 0.647504829 ∣ 2.18.130 ‖ C1orf53 ∣ 2.18.130 ∣ chromosome 1 open reading frame 53 ∣ 0.526630676 ∣ 2.18.130 ‖ CD6 ∣ 2.18.130 ∣ CD6 molecule ∣ 0.374716271 ∣ 2.18.130 ‖ CLEC4A ∣ 2.18.130 ∣ C-type lectin domain family 4 member A ∣ 0.502901431 ∣ 2.18.130 ‖ CMPK2 ∣ 2.18.130 ∣ cytidine/uridine monophosphate kinase 2 ∣ 1.85702603 ∣ 2.18.130 ‖ CTDSPL2 ∣ 2.18.130 ∣ CTD small phosphatase like 2 ∣ 0.268585085 ∣ 2.18.130 ‖ DDX60 ∣ 2.18.130 ∣ DEXD/H-box helicase 60 ∣ 0.346977964 ∣ 2.18.130 ‖ EIF2AK2 ∣ 2.18.130 ∣ eukaryotic translation initiation factor 2 alpha kinase 2 ∣ 0.318282855 ∣ 2.18.130 ‖ FCGR3B ∣ 2.18.130 ∣ Fc fragment of IgG receptor IIIb ∣ 0.9155816 ∣ 2.18.130 ‖ FGL2 ∣ 2.18.130 ∣ fibrinogen like 2 ∣ 0.584297365 ∣ 2.18.130 ‖ FMO3 ∣ 2.18.130 ∣ flavin containing monooxygenase 3 ∣ 1.156549149 ∣ 2.18.130 ‖ FST ∣ 2.18.130 ∣ follistatin ∣ 0.540062872 ∣ 2.18.130 ‖ HPSE ∣ 2.18.130 ∣ heparanase ∣ 1.247455214 ∣ 2.18.130 ‖ IFI35 ∣ 2.18.130 ∣ interferon induced protein 35 ∣ 0.850518409 ∣ 2.18.130 ‖ IFI44 ∣ 2.18.130 ∣ interferon induced protein 44 ∣ 0.813721828 ∣ 2.18.130 ‖ IFI44L ∣ 2.18.130 ∣ interferon induced protein 44 like ∣ 1.821139894 ∣ 2.18.130 ‖ IFIH1 ∣ 2.18.130 ∣ interferon induced, with helicase C domain 1 ∣ 0.554506761 ∣ 2.18.130 ‖ IFIT1 ∣ 2.18.130 ∣ interferon induced protein with tetratricopeptide repeats 1 ∣ 0.916194528 ∣ 2.18.130 ‖ IFIT2 ∣ 2.18.130 ∣ interferon induced protein with tetratricopeptide repeats 2 ∣ 0.79521356 ∣ 2.18.130 ‖ IFIT3 ∣ 2.18.130 ∣ interferon induced protein with tetratricopeptide repeats 3 ∣ 0.789995391 ∣ 2.18.130 ‖ INSIG1 ∣ 2.18.130 ∣ insulin induced gene 1 ∣ 0.28016302 ∣ 2.18.130 ‖ IRF9 ∣ 2.18.130 ∣ interferon regulatory factor 9 ∣ 0.254031035 ∣ 2.18.130 ‖ ISG15 ∣ 2.18.130 ∣ ISG15 ubiquitin-like modifier ∣ 0.999772267 ∣ 2.18.130 ‖ LGALS3BP ∣ 2.18.130 ∣ lectin, galactoside-binding, soluble, 3 binding protein ∣ 0.386352906 ∣ 2.18.130 ‖ LXN ∣ 2.18.130 ∣ latexin ∣ 0.798649782 ∣ 2.18.130 ‖ LYSMD2 ∣ 2.18.130 ∣ LysM domain containing 2 ∣ 0.318579984 ∣ 2.18.130 ‖ MICAL1 ∣ 2.18.130 ∣ microtubule associated monooxygenase, calponin and LIM domain containing 1 ∣ 0.31709165 ∣ 2.18.130 ‖ MX1 ∣ 2.18.130 ∣ MX dynamin like GTPase 1 ∣ 1.356763919 ∣ 2.18.130 ‖ MX2 ∣ 2.18.130 ∣ MX dynamin like GTPase 2 ∣ 1.279741767 ∣ 2.18.130 ‖ NMI ∣ 2.18.130 ∣ N-myc and STAT interactor ∣ 0.445756082 ∣ 2.18.130 ‖ OAS1 ∣ 2.18.130 ∣ 2'-5'-oligoadenylate synthetase 1 ∣ 1.295257967 ∣ 2.18.130 ‖ OAS2 ∣ 2.18.130 ∣ 2'-5'-oligoadenylate synthetase 2 ∣ 1.52539947 ∣ 2.18.130 ‖ OAS3 ∣ 2.18.130 ∣ 2'-5'-oligoadenylate synthetase 3 ∣ 1.089135973 ∣ 2.18.130 ‖ OASL ∣ 2.18.130 ∣ 2'-5'-oligoadenylate synthetase like ∣ 0.562245942 ∣ 2.18.130 ‖ PARP12 ∣ 2.18.130 ∣ poly(ADP-ribose) polymerase family member 12 ∣ 0.748927974 ∣ 2.18.130 ‖ PARP14 ∣ 2.18.130 ∣ poly(ADP-ribose) polymerase family member 14 ∣ 0.580266692 ∣ 2.18.130 ‖ PARP9 ∣ 2.18.130 ∣ poly(ADP-ribose) polymerase family member 9 ∣ 0.3652565 ∣ 2.18.130 ‖ PRRG4 ∣ 2.18.130 ∣ proline rich Gla (G-carboxyglutamic acid) 4 (transmembrane) ∣ 0.35055221 ∣ 2.18.130 ‖ RSAD2 ∣ 2.18.130 ∣ radical S-adenosyl methionine domain containing 2 ∣ 1.617422099 ∣ 2.18.130 ‖ S100A8 ∣ 2.18.130 ∣ S100 calcium binding protein A8 ∣ 1.214556196 ∣ 2.18.130 ‖ SAMD9L ∣ 2.18.130 ∣ sterile alpha motif domain containing 9-like ∣ 0.545082576 ∣ 2.18.130 ‖ SDC4 ∣ 2.18.130 ∣ syndecan 4 ∣ 0.483005798 ∣ 2.18.130 ‖ STAT2 ∣ 2.18.130 ∣ signal transducer and activator of transcription 2 ∣ 0.219550065 ∣ 2.18.130 ‖ STOX2 ∣ 2.18.130 ∣ storkhead box 2 ∣ 0.371157973 ∣ 2.18.130 ‖ SUN2 ∣ 2.18.130 ∣ Sad1 and UNC84 domain containing 2 ∣ 0.300036584 ∣ 2.18.130 ‖ TRDMT1 ∣ 2.18.130 ∣ tRNA aspartic acid methyltransferase 1 ∣ 0.285733098 ∣ 2.18.130 ‖ VAMP5 ∣ 2.18.130 ∣ vesicle associated membrane protein 5 ∣ 0.480879097 ∣ 2.18.130 ‖ VRK2 ∣ 2.18.130 ∣ vaccinia related kinase 2 ∣ 0.219343149 ∣ 2.18.130 ‖ XAF1 ∣ 2.18.130 ∣ XIAP associated factor 1 ∣ 0.528186189 ∣ 2.18.130 ‖ AMER1 ∣ 2.19 ∣ APC membrane recruitment protein 1 ∣ 0.50274814 ∣ 2.19.133 ‖ ANKRD36BP2 ∣ 2.19 ∣ ankyrin repeat domain 36B pseudogene 2 ∣ 0.525829363 ∣ 2.19.133 ‖ ANOS1 ∣ 2.19 ∣ anosmin 1 ∣ 0.980796077 ∣ 2.19.132 ‖ APCDD1L ∣ 2.19 ∣ adenomatosis polyposis coli down-regulated 1-like ∣ 0.222203679 ∣ 2.19.132 ‖ BHLHE22 ∣ 2.19 ∣ basic helix-loop-helix family member e22 ∣ 0.278392269 ∣ 2.19.132 ‖ BMS1P20 ∣ 2.19 ∣ BMS1, ribosome biogenesis factor pseudogene 20 ∣ 5.907840779 ∣ 2.19.133 ‖ BTG2 ∣ 2.19 ∣ BTG family member 2 ∣ 0.403392154 ∣ 2.19.133 ‖ C18orf54 ∣ 2.19 ∣ chromosome 18 open reading frame 54 ∣ 0.46889736 ∣ 2.19.133 ‖ CD27 ∣ 2.19 ∣ CD27 molecule ∣ 1.56949754 ∣ 2.19.133 ‖ CD79A ∣ 2.19 ∣ CD79a molecule ∣ 2.879891667 ∣ 2.19.133 ‖ CD79B ∣ 2.19 ∣ CD79b molecule ∣ 0.759518551 ∣ 2.19.133 ‖ CHRNG ∣ 2.19 ∣ cholinergic receptor nicotinic gamma subunit ∣ 0.308008286 ∣ 2.19.133 ‖ COL11A1 ∣ 2.19 ∣ collagen type XI alpha 1 ∣ 4.086943037 ∣ 2.19.132 ‖ COL25A1 ∣ 2.19 ∣ collagen type XXV alpha 1 ∣ 0.226206641 ∣ 2.19.133 ‖ CPNE5 ∣ 2.19 ∣ copine 5 ∣ 1.28299047 ∣ 2.19.133 ‖ CRELD2 ∣ 2.19 ∣ cysteine rich with EGF like domains 2 ∣ 0.249185191 ∣ 2.19.133 ‖ EAF2 ∣ 2.19 ∣ ELL associated factor 2 ∣ 1.119908659 ∣ 2.19.133 ‖ EPB41 ∣ 2.19 ∣ erythrocyte membrane protein band 4.1 ∣ 0.250479543 ∣ 2.19.132 ‖ ERAP1 ∣ 2.19 ∣ endoplasmic reticulum aminopeptidase 1 ∣ 0.839914071 ∣ 2.19.132 ‖ ERMP1 ∣ 2.19 ∣ endoplasmic reticulum metallopeptidase 1 ∣ 0.260101199 ∣ 2.19.132 ‖ FAM46C ∣ 2.19 ∣ family with sequence similarity 46 member C ∣ 2.638930709 ∣ 2.19.133 ‖ FCMR ∣ 2.19 ∣ Fc fragment of IgM receptor ∣ 2.283307814 ∣ 2.19.132 ‖ FCRL5 ∣ 2.19 ∣ Fc receptor like 5 ∣ 3.627434799 ∣ 2.19.132 ‖ FKBP11 ∣ 2.19 ∣ FK506 binding protein 11 ∣ 0.633428957 ∣ 2.19.132 ‖ FRMD4B ∣ 2.19 ∣ FERM domain containing 4B ∣ 0.216226296 ∣ 2.19.133 ‖ GCLM ∣ 2.19 ∣ glutamate-cysteine ligase modifier subunit ∣ 0.266062766 ∣ 2.19.133 ‖ GPR26 ∣ 2.19 ∣ G protein-coupled receptor 26 ∣ 0.214475114 ∣ 2.19.133 ‖ GUSBP11 ∣ 2.19 ∣ glucuronidase, beta pseudogene 11 ∣ 3.13291442 ∣ 2.19.132 ‖ HERPUD1 ∣ 2.19 ∣ homocysteine-inducible, endoplasmic reticulum stress-inducible, ubiquitin-like domain member 1 ∣ 0.282531445 ∣ 2.19.133 ‖ IKZF3 ∣ 2.19 ∣ IKAROS family zinc finger 3 ∣ 0.301579275 ∣ 2.19.133 ‖ ING2 ∣ 2.19 ∣ inhibitor of growth family member 2 ∣ 0.317272413 ∣ 2.19.133 ‖ ISG20 ∣ 2.19 ∣ interferon stimulated exonuclease gene 20 kDa ∣ 2.041973791 ∣ 2.19.133 ‖ ITM2C ∣ 2.19 ∣ integral membrane protein 2C ∣ 1.126536183 ∣ 2.19.133 ‖ JCHAIN ∣ 2.19 ∣ joining chain of multimeric IgA and IgM ∣ 5.896710789 ∣ 2.19.132 ‖ KNTC1 ∣ 2.19 ∣ kinetochore associated 1 ∣ 0.358488124 ∣ 2.19.133 ‖ KRT222 ∣ 2.19 ∣ keratin 222 ∣ 1.07253478 ∣ 2.19.132 ‖ LACC1 ∣ 2.19 ∣ laccase domain containing 1 ∣ 0.374901618 ∣ 2.19.133 ‖ LAX1 ∣ 2.19 ∣ lymphocyte transmembrane adaptor 1 ∣ 0.782768797 ∣ 2.19.132 ‖ LGALS8 ∣ 2.19 ∣ lectin, galactoside-binding, soluble, 8 ∣ 0.338306562 ∣ 2.19.133 ‖ LGMN ∣ 2.19 ∣ legumain ∣ 0.233818531 ∣ 2.19.132 ‖ MEI1 ∣ 2.19 ∣ meiotic double-stranded break formation protein 1 ∣ 0.80281807 ∣ 2.19.133 ‖ MFHAS1 ∣ 2.19 ∣ malignant fibrous histiocytoma amplified sequence 1 ∣ 0.261979953 ∣ 2.19.133 ‖ MIAT |

TABLE 3B-continued

The genes within the significant gene clusters, listed in Table 3A. (3966 Genes Listed by: Gene Symbol | Gen 2 Module | Gene Description | RowVariance | Gen 3 Module ||)

| 2.19 | myocardial infarction associated transcript (non-protein coding) | 0.295785352 | 2.19.133 || MS4A1 | 2.19 | membrane spanning 4-domains A1 | 5.929678189 | 2.19.132 || MZB1 | 2.19 | marginal zone B and B1 cell specific protein | 5.087395139 | 2.19.132 || NABP2 | 2.19 | nucleic acid binding protein 2 | 0.236296146 | 2.19.133 || NELL2 | 2.19 | neural EGFL like 2 | 0.387771765 | 2.19.132 || NRP2 | 2.19 | neuropilin 2 | 0.418605035 | 2.19.133 || NTN1 | 2.19 | netrin 1 | 0.977358167 | 2.19.132 || OMD | 2.19 | osteomodulin | 2.010523976 | 2.19.132 || P2RX5 | 2.19 | purinergic receptor P2X 5 | 0.800455048 | 2.19.133 || PDCD1LG2 | 2.19 | programmed cell death 1 ligand 2 | 0.225415117 | 2.19.133 || PDK1 | 2.19 | pyruvate dehydrogenase kinase 1 | 1.265409784 | 2.19.133 || PIM2 | 2.19 | Pim-2 proto-oncogene, serine/threonine kinase | 2.54261936 | 2.19.132 || PLPP5 | 2.19 | phospholipid phosphatase 5 | 0.306185429 | 2.19.132 || POU2AF1 | 2.19 | POU class 2 associating factor 1 | 6.127952622 | 2.19.132 || PRDM1 | 2.19 | PR domain 1 | 1.057510938 | 2.19.132 || PRDX4 | 2.19 | peroxiredoxin 4 | 0.301002066 | 2.19.132 || RNF141 | 2.19 | ring finger protein 141 | 0.233401383 | 2.19.132 || SDC1 | 2.19 | syndecan 1 | 2.630474379 | 2.19.133 || SEC11C | 2.19 | SEC11 homolog C, signal peptidase complex subunit | 0.90082139 | 2.19.133 || SERPINE2 | 2.19 | serpin peptidase inhibitor, clade E (nexin, plasminogen activator inhibitor type 1), member 2 | 1.567647357 | 2.19.132 || SHROOM1 | 2.19 | shroom family member 1 | 0.278403439 | 2.19.133 || SLC25A43 | 2.19 | solute carrier family 25 member 43 | 0.369260817 | 2.19.133 || SLC38A1 | 2.19 | solute carrier family 38 member 1 | 1.024186126 | 2.19.132 || SLC7A5 | 2.19 | solute carrier family 7 member 5 | 0.827271478 | 2.19.133 || SNX25 | 2.19 | sorting nexin 25 | 0.263921575 | 2.19.132 || SPAG4 | 2.19 | sperm associated antigen 4 | 2.366853485 | 2.19.133 || SPOCK2 | 2.19 | sparc/osteonectin, cwcv and kazal-like domains proteoglycan (testican) 2 | 0.341752292 | 2.19.133 || SSR4 | 2.19 | signal sequence receptor, delta | 0.458774358 | 2.19.133 || ST6GAL1 | 2.19 | ST6 beta-galactosamide alpha-2,6-sialyltranferase 1 | 0.582754683 | 2.19.133 || SYTL1 | 2.19 | synaptotagmin like 1 | 0.921967393 | 2.19.133 || TDRD3 | 2.19 | tudor domain containing 3 | 0.459567248 | 2.19.133 || TIFA | 2.19 | TRAF interacting protein with forkhead associated domain | 0.487811773 | 2.19.132 || TNFRSF17 | 2.19 | tumor necrosis factor receptor superfamily member 17 | 3.462596721 | 2.19.133 || TP53INP1 | 2.19 | tumor protein p53 inducible nuclear protein 1 | 0.308472309 | 2.19.132 || TPD52 | 2.19 | tumor protein D52 | 2.035248091 | 2.19.132 || TTC7B | 2.19 | tetratricopeptide repeat domain 7B | 0.361215418 | 2.19.133 || TXNDC15 | 2.19 | thioredoxin domain containing 15 | 0.254461953 | 2.19.133 || UHRF1BP1 | 2.19 | UHRF1 binding protein 1 | 0.402231232 | 2.19.132 || XBP1 | 2.19 | X-box binding protein 1 | 0.763304853 | 2.19.132 || XRRA1 | 2.19 | X-ray radiation resistance associated 1 | 0.793846928 | 2.19.133 || ZFP64 | 2.19 | ZFP64 zinc finger protein | 0.236269082 | 2.19.133 || CPSF2 | 2.20.134 | cleavage and polyadenylation specific factor 2 | 0.312514552 | 2.20.134 || CTNNBIP1 | 2.20.134 | catenin beta interacting protein 1 | 0.364519822 | 2.20.134 || CYP1A2 | 2.20.134 | cytochrome P450 family 1 subfamily A member 2 | 0.309345787 | 2.20.134 || FAM109B | 2.20.134 | family with sequence similarity 109 member B | 0.580511341 | 2.20.134 || GMEB1 | 2.20.134 | glucocorticoid modulatory element binding protein 1 | 0.356125841 | 2.20.134 || HMG20B | 2.20.134 | high mobility group 20B | 0.295005592 | 2.20.134 || IRF5 | 2.20.134 | interferon regulatory factor 5 | 1.044864182 | 2.20.134 || ITGB3BP | 2.20.134 | integrin subunit beta 3 binding protein | 0.719615236 | 2.20.134 || LOC441666 | 2.20.134 | zinc finger protein 91 pseudogene | 1.441786817 | 2.20.134 || OPHN1 | 2.20.134 | oligophrenin 1 | 0.333288257 | 2.20.134 || PANX1 | 2.20.134 | pannexin 1 | 0.279004738 | 2.20.134 || RASEF | 2.20.134 | RAS and EF-hand domain containing | 0.39832375 | 2.20.134 || RECK | 2.20.134 | reversion inducing cysteine rich protein with kazal motifs | 0.252057572 | 2.20.134 || SCD5 | 2.20.134 | stearoyl-CoA desaturase 5 | 0.748681998 | 2.20.134 || SH3GL3 | 2.20.134 | SH3-domain GRB2-like 3 | 1.108918296 | 2.20.134 || SLC20A1 | 2.20.134 | solute carrier family 20 member 1 | 0.31769957 | 2.20.134 || TIMM8A | 2.20.134 | translocase of inner mitochondrial membrane 8 homolog A (yeast) | 0.263195296 | 2.20.134 || TMEM241 | 2.20.134 | transmembrane protein 241 | 0.411636957 | 2.20.134 || TRIB2 | 2.20.134 | tribbles pseudokinase 2 | 0.281368198 | 2.20.134 || TRIM4 | 2.20.134 | tripartite motif containing 4 | 0.530234587 | 2.20.134 || TRIM47 | 2.20.134 | tripartite motif containing 47 | 0.328967302 | 2.20.134 || VPS37B | 2.20.134 | VPS37B, ESCRT-I subunit | 0.293588562 | 2.20.134 || YPEL3 | 2.20.134 | yippee like 3 | 0.3094805 | 2.20.134 || ZNF595 | 2.20.134 | zinc finger protein 595 | 4.945063628 | 2.20.134 || ACSS3 | 2.5.57 | acyl-CoA synthetase short-chain family member 3 | 1.256611482 | 2.5.57 || ADIRF | 2.5.57 | adipogenesis regulatory factor | 2.358053196 | 2.5.57 || ADRA2A | 2.5.57 | adrenoceptor alpha 2A | 4.385344968 | 2.5.57 || AKR1C1 | 2.5.57 | aldo-keto reductase family 1, member C1 | 1.57756812 | 2.5.57 || AKR1C2 | 2.5.57 | aldo-keto reductase family 1, member C2 | 1.899316279 | 2.5.57 || ALDH6A1 | 2.5.57 | aldehyde dehydrogenase 6 family member A1 | 0.503721404 | 2.5.57 || AR | 2.5.57 | androgen receptor | 1.230295387 | 2.5.57 || ARHGAP42 | 2.5.57 | Rho GTPase activating protein 42 | 0.510328956 | 2.5.57 || ATP2B4 | 2.5.57 | ATPase plasma membrane Ca2+ transporting 4 | 0.312991447 | 2.5.57 || ATP9A | 2.5.57 | ATPase phospholipid transporting 9A (putative) | 1.483950078 | 2.5.57 || BDKRB2 | 2.5.57 | bradykinin receptor B2 | 0.566291259 | 2.5.57 || BOK | 2.5.57 | BCL2-related ovarian killer | 1.599041866 | 2.5.57 || C19orf12 | 2.5.57 | chromosome 19 open reading frame 12 | 0.378582294 | 2.5.57 || C1orf198 | 2.5.57 | chromosome 1 open reading frame 198 | 0.320478948 | 2.5.57 || C1orf21 | 2.5.57 | chromosome 1 open reading frame 21 | 0.612533147 | 2.5.57 || CCDC69 | 2.5.57 | coiled-coil domain containing 69 | 0.585257644 | 2.5.57 || CD300LG | 2.5.57 | CD300 molecule like family member g | 2.343699976 | 2.5.57 || CDC42EP4 | 2.5.57 | CDC42 effector protein 4 | 0.490169413 | 2.5.57 || CHRDL1 | 2.5.57 | chordin-like 1 | 6.246501097 | 2.5.57 || CLMP | 2.5.57 | CXADR-like membrane protein | 0.852551641 | 2.5.57 || CYB5A | 2.5.57 | cytochrome b5 type A (microsomal) | 0.738641051 | 2.5.57 || DTX4 | 2.5.57 | deltex 4, E3 ubiquitin ligase | 0.39616286 | 2.5.57 || EHBP1 | 2.5.57 | EH domain binding protein 1 | 0.938640122 | 2.5.57 || EHD2 | 2.5.57 | EH domain containing 2 | 0.65223393 | 2.5.57 || F11R | 2.5.57 | F11 receptor | 0.449768336 | 2.5.57 || FABP4 | 2.5.57 | fatty acid binding protein 4 | 9.948984309 | 2.5.57 || FAHD2A | 2.5.57 | fumarylacetoacetate hydrolase domain containing 2A | 0.397171336 | 2.5.57 || FAM213A | 2.5.57 | family with sequence similarity 213 member A | 2.244678642 | 2.5.57 || FERMT2 | 2.5.57 | fermitin family member 2 | 0.514762935 | 2.5.57 || FGFBP2 | 2.5.57 | fibroblast growth factor binding protein 2 | 5.210037915 | 2.5.57 || FZD4 | 2.5.57 | frizzled class receptor 4 | 1.516536159 | 2.5.57 || GHR | 2.5.57 | growth hormone receptor | 5.216950489 | 2.5.57 || GNAI1 | 2.5.57 | G protein subunit alpha i1 | 3.712385374 | 2.5.57 || GPATCH11 | 2.5.57 | G-patch domain containing 11 | 0.248577992 | 2.5.57 || HADH | 2.5.57 | hydroxyacyl-CoA dehydrogenase |

TABLE 3B-continued

The genes within the significant gene clusters, listed in Table 3A. (3966 Genes Listed by: Gene Symbol | Gen 2 Module | Gene Description | RowVariance | Gen 3 Module ||)

0.973225336 | 2.5.57 || HSDL2 | 2.5.57 | hydroxysteroid dehydrogenase like 2 | 1.035299237 | 2.5.57 || IGFBP6 | 2.5.57 | insulin like growth factor binding protein 6 | 1.144522243 | 2.5.57 || IGSF21 | 2.5.57 | immunoglobin superfamily member 21 | 0.817858137 | 2.5.57 || INHBB | 2.5.57 | inhibin beta B | 1.565653343 | 2.5.57 || ITGA7 | 2.5.57 | integrin subunit alpha 7 | 1.731401261 | 2.5.57 || ITIH5 | 2.5.57 | inter-alpha-trypsin inhibitor heavy chain family member 5 | 3.462851228 | 2.5.57 || JADE1 | 2.5.57 | jade family PHD finger 1 | 0.796229967 | 2.5.57 || KAT2B | 2.5.57 | lysine acetyltransferase 2B | 0.246457883 | 2.5.57 || KLF15 | 2.5.57 | Kruppel-like factor 15 | 0.404555382 | 2.5.57 || KYNU | 2.5.57 | kynureninase | 1.07034307 | 2.5.57 || LGALS12 | 2.5.57 | lectin, galactoside-binding, soluble, 12 | 1.350671351 | 2.5.57 || LGR4 | 2.5.57 | leucine-rich repeat containing G protein-coupled receptor 4 | 1.311926721 | 2.5.57 || LIN7A | 2.5.57 | lin-7 homolog A, crumbs cell polarity complex component | 0.713127587 | 2.5.57 || LINC01003 | 2.5.57 | long intergenic non-protein coding RNA 1003 | 0.611201414 | 2.5.57 || LYRM1 | 2.5.57 | LYR motif containing 1 | 0.641753021 | 2.5.57 || MARC2 | 2.5.57 | mitochondrial amidoxime reducing component 2 | 0.539094609 | 2.5.57 || MAST4 | 2.5.57 | microtubule associated serine/threonine kinase family member 4 | 1.119455151 | 2.5.57 || MCCC1 | 2.5.57 | methylcrotonoyl-CoA carboxylase 1 | 0.432055636 | 2.5.57 || MEST | 2.5.57 | mesoderm specific transcript | 5.725357017 | 2.5.57 || MFAP5 | 2.5.57 | microfibrillar associated protein 5 | 4.485133533 | 2.5.57 || MGAT4A | 2.5.57 | mannosyl (alpha-1,3-)-glycoprotein beta-1,4-N-acetylglucosaminyltransferase, isozyme A | 0.371351088 | 2.5.57 || MGLL | 2.5.57 | monoglyceride lipase | 0.819650779 | 2.5.57 || MGST1 | 2.5.57 | microsomal glutathione S-transferase 1 | 3.86837584 | 2.5.57 || MME | 2.5.57 | membrane metallo-endopeptidase | 0.721228403 | 2.5.57 || MTURN | 2.5.57 | maturin, neural progenitor differentiation regulator homolog (Xenopus) | 2.881061114 | 2.5.57 || MUT | 2.5.57 | methylmalonyl-CoA mutase | 0.26506776 | 2.5.57 || NCOA1 | 2.5.57 | nuclear receptor coactivator 1 | 0.249938333 | 2.5.57 || NNAT | 2.5.57 | neuronatin | 0.723923091 | 2.5.57 || PALMD | 2.5.57 | palmdelphin | 1.312827119 | 2.5.57 || PCCA | 2.5.57 | propionyl-CoA carboxylase alpha subunit | 0.290492087 | 2.5.57 || PCK1 | 2.5.57 | phosphoenolpyruvate carboxykinase 1 | 9.173211642 | 2.5.57 || PDHX | 2.5.57 | pyruvate dehydrogenase complex component X | 0.540566351 | 2.5.57 || PERP | 2.5.57 | PERP, TP53 apoptosis effector | 1.534320177 | 2.5.57 || PET117 | 2.5.57 | PET117 homolog | 0.304053751 | 2.5.57 || PEX11A | 2.5.57 | peroxisomal biogenesis factor 11 alpha | 0.707187052 | 2.5.57 || PHLDB2 | 2.5.57 | pleckstrin homology like domain family B member 2 | 0.629724474 | 2.5.57 || PIR | 2.5.57 | pirin | 0.962374479 | 2.5.57 || PJA1 | 2.5.57 | praja ring finger ubiquitin ligase 1 | 0.265450662 | 2.5.57 || PLA2G16 | 2.5.57 | phospholipase A2 group XVI | 2.039006238 | 2.5.57 || PLIN5 | 2.5.57 | perilipin 5 | 0.517786657 | 2.5.57 || PLXDC2 | 2.5.57 | plexin domain containing 2 | 0.412229253 | 2.5.57 || POLI | 2.5.57 | polymerase (DNA) iota | 0.924882514 | 2.5.57 || PPARG | 2.5.57 | peroxisome proliferator activated receptor gamma | 1.453567624 | 2.5.57 || PPP2R1B | 2.5.57 | protein phosphatase 2 regulatory subunit A, beta | 1.505337477 | 2.5.57 || RALGAPA2 | 2.5.57 | Ral GTPase activating protein catalytic alpha subunit 2 | 0.738386312 | 2.5.57 || RBP4 | 2.5.57 | retinol binding protein 4 | 3.619055585 | 2.5.57 || RBPMS | 2.5.57 | RNA binding protein with multiple splicing | 0.886181558 | 2.5.57 || SELENBP1 | 2.5.57 | selenium binding protein 1 | 1.409902949 | 2.5.57 || SEMA3G | 2.5.57 | semaphorin 3G | 1.798415431 | 2.5.57 || SESTD1 | 2.5.57 | SEC14 and spectrin domain containing 1 | 0.453768368 | 2.5.57 || SGCE | 2.5.57 | sarcoglycan epsilon | 1.422041389 | 2.5.57 || SH3D19 | 2.5.57 | SH3 domain containing 19 | 0.590620952 | 2.5.57 || SIK2 | 2.5.57 | salt inducible kinase 2 | 1.100510344 | 2.5.57 || SLC25A20 | 2.5.57 | solute carrier family 25 member 20 | 0.287242627 | 2.5.57 || SLC25A33 | 2.5.57 | solute carrier family 25 member 33 | 0.756888187 | 2.5.57 || SLC9A1 | 2.5.57 | solute carrier family 9 member A1 | 0.22427177 | 2.5.57 || SORL1 | 2.5.57 | sortilin-related receptor, L(DLR class) A repeats containing | 0.929365898 | 2.5.57 || SPTBN1 | 2.5.57 | spectrin beta, non-erythrocytic 1 | 0.961247885 | 2.5.57 || TAPT1 | 2.5.57 | transmembrane anterior posterior transformation 1 | 0.346661131 | 2.5.57 || TBC1D2 | 2.5.57 | TBC1 domain family member 2 | 0.609191709 | 2.5.57 || TEAD1 | 2.5.57 | TEA domain transcription factor 1 | 0.797688257 | 2.5.57 || TMEM135 | 2.5.57 | transmembrane protein 135 | 1.023373064 | 2.5.57 || TOB1 | 2.5.57 | transducer of ERBB2, 1 | 0.279597861 | 2.5.57 || TSKU | 2.5.57 | tsukushi, small leucine rich proteoglycan | 0.828512375 | 2.5.57 || USF3 | 2.5.57 | upstream transcription factor family member 3 | 0.342030412 | 2.5.57 || ACOT13 | 3.29 | acyl-CoA thioesterase 13 | 0.370379542 | 3.29.160 || ARID3A | 3.29 | AT-rich interaction domain 3A | 0.38604131 | 3.29.160 || DANCR | 3.29 | differentiation antagonizing non-protein coding RNA | 0.492106201 | — || DEXI | 3.29 | Dexi homolog (mouse) | 0.358144674 | — || DNAJC7 | 3.29 | DnaJ heat shock protein family (Hsp40) member C7 | 0.236518842 | — || DOCK5 | 3.29 | dedicator of cytokinesis 5 | 0.818765291 | — || EP300 | 3.29 | E1A binding protein p300 | 0.380938161 | 3.29.160 || FIS1 | 3.29 | fission, mitochondrial 1 | 0.288441357 | 3.29.160 || GCNT7 | 3.29 | glucosaminyl (N-acetyl) transferase family member 7 | 0.238017495 | 3.29.160 || GPX7 | 3.29 | glutathione peroxidase 7 | 0.750372703 | 3.29.160 || LARP4B | 3.29 | La ribonucleoprotein domain family member 4B | 0.351785718 | 3.29.160 || MCEE | 3.29 | methylmalonyl-CoA epimerase | 0.376691829 | 3.29.160 || MILR1 | 3.29 | mast cell immunoglobulin-like receptor 1 | 0.533631543 | — || MRPL48 | 3.29 | mitochondrial ribosomal protein L48 | 0.337494272 | 3.29.160 || N4BP2L2 | 3.29 | NEDD4 binding protein 2-like 2 | 0.300221207 | 3.29.160 || NAA38 | 3.29 | N(alpha)-acetyltransferase 38, NatC auxiliary subunit | 0.259988906 | 3.29.160 || NAXE | 3.29 | NAD(P)HX epimerase | 0.240081124 | — || NDUFA13 | 3.29 | NADH:ubiquinone oxidoreductase subunit A13 | 0.226874413 | 3.29.160 || NME1 | 3.29 | NME/NM23 nucleoside diphosphate kinase 1 | 0.466163737 | 3.29.160 || PEPD | 3.29 | peptidase D | 0.235898545 | — || PINK1 | 3.29 | PTEN induced putative kinase 1 | 0.282007013 | 3.29.160 || PLGRKT | 3.29 | plasminogen receptor, C-terminal lysine transmembrane protein | 0.405399761 | 3.29.160 || POP5 | 3.29 | POP5 homolog, ribonuclease P/MRP subunit | 0.259027764 | 3.29.160 || PRPS1 | 3.29 | phosphoribosyl pyrophosphate synthetase 1 | 0.233745789 | — || PTRHD1 | 3.29 | peptidyl-tRNA hydrolase domain containing 1 | 0.279295428 | 3.29.160 || RNASEH2C | 3.29 | ribonuclease H2 subunit C | 0.341173901 | 3.29.160 || RPA3 | 3.29 | replication protein A3 | 0.267876142 | 3.29.160 || SMIM19 | 3.29 | small integral membrane protein 19 | 0.266262055 | 3.29.160 || SMYD3 | 3.29 | SET and MYND domain containing 3 | 0.228881457 | — || TBRG1 | 3.29 | transforming growth factor beta regulator 1 | 0.253776071 | 3.29.160 || TMEM261 | 3.29 | transmembrane protein 261 | 0.27175084 | 3.29.160 || TPSAB1 | 3.29 | tryptase alpha/beta 1 | 1.158017906 | — || TPSB2 | 3.29 | tryptase beta 2 (gene/pseudogene) | 1.616666898 | — || UQCRQ | 3.29 | ubiquinol-cytochrome c reductase complex III TABLE 3B-continued The genes within the significant gene clusters, listed in Table 3A. (3966 Genes Listed by: Gene Symbol | Gen 2 Module | Gene Description | RowVariance | Gen 3 Module ||)

subunit VII | 0.221191949 | 3.29.160 || WDR6 | 3.29 | WD repeat domain 6 | 0.253672531 | — || ZNF32 | 3.29 | zinc finger protein 32 | 0.241519498 | 3.29.160 || ACOT13 | 3.29.160 | acyl-CoA thioesterase 13 | 0.370379542 | 3.29.160 || ARID3A | 3.29.160 | AT-rich interaction domain 3A | 0.38604131 | 3.29.160 || EP300 | 3.29.160 | E1A binding protein p300 | 0.380938161 | 3.29.160 || FIS1 | 3.29.160 | fission, mitochondrial 1 | 0.288441357 | 3.29.160 || GCNT7 | 3.29.160 | glucosaminyl (N-acetyl) transferase family member 7 | 0.238017495 | 3.29.160 || GPX7 | 3.29.160 | glutathione peroxidase 7 | 0.750372703 | 3.29.160 || LARP4B | 3.29.160 | La ribonucleoprotein domain family member 4B | 0.351785718 | 3.29.160 || MCEE | 3.29.160 | methylmalonyl-CoA epimerase | 0.376691829 | 3.29.160 || MRPL48 | 3.29.160 | mitochondrial ribosomal protein L48 | 0.337494272 | 3.29.160 || N4BP2L2 | 3.29.160 || NEDD4 binding protein 2-like 2 | 0.300221207 | 3.29.160 || NAA38 | 3.29.160 | N(alpha)-acetyltransferase 38, NatC auxiliary subunit | 0.259988906 | 3.29.160 || NDUFA13 | 3.29.160 | NADH:ubiquinone oxidoreductase subunit A13 | 0.226874413 | 3.29.160 || NME1 | 3.29.160 | NME/NM23 nucleoside diphosphate kinase 1 | 0.466163737 | 3.29.160 || PINK1 | 3.29.160 | PTEN induced putative kinase 1 | 0.282007013 | 3.29.160 || PLGRKT | 3.29.160 | plasminogen receptor, C-terminal lysine transmembrane protein | 0.405399761 | 3.29.160 || POP5 | 3.29.160 | POP5 homolog, ribonuclease P/MRP subunit | 0.259027764 | 3.29.160 || PTRHD1 | 3.29.160 | peptidyl-tRNA hydrolase domain containing 1 | 0.279295428 | 3.29.160 || RNASEH2C | 3.29.160 | ribonuclease H2 subunit C | 0.341173901 | 3.29.160 || RPA3 | 3.29.160 | replication protein A3 | 0.267876142 | 3.29.160 || SMIM19 | 3.29.160 | small integral membrane protein 19 | 0.266262055 | 3.29.160 || TBRG1 | 3.29.160 | transforming growth factor beta regulator 1 | 0.253776071 | 3.29.160 || TMEM261 | 3.29.160 | transmembrane protein 261 | 0.27175084 | 3.29.160 || UQCRQ | 3.29.160 | ubiquinol-cytochrome c reductase complex III subunit VII | 0.221191949 | 3.29.160 || ZNF32 | 3.29.160 | zinc finger protein 32 | 0.241519498 | 3.29.160 || AAAS | 3.30 | aladin WD repeat nucleoporin | 0.352373522 | 3.30.161 || AAK1 | 3.30 | AP2 associated kinase 1 | 0.358812961 | 3.30.163 || AASS | 3.30 | aminoadipate-semialdehyde synthase | 1.282105419 | 3.30.164 || ABCF2 | 3.30 | ATP binding cassette subfamily F member 2 | 0.22823075 | 3.30.163 || ACO2 | 3.30 | aconitase 2 | 0.295624058 | 3.30.161 || ADAM15 | 3.30 | ADAM metallopeptidase domain 15 | 0.346230317 | 3.30.161 || ADAM17 | 3.30 | ADAM metallopeptidase domain 17 | 0.31099106 | — || ADAM33 | 3.30 | ADAM metallopeptidase domain 33 | 0.254840952 | 3.30.161 || ADAT1 | 3.30 | adenosine deaminase, tRNA-specific 1 | 0.52589383 | 3.30.161 || AGA | 3.30 | aspartylglucosaminidase | 0.233971109 | 3.30.162 || AGBL5 | 3.30 | ATP/GTP binding protein-like 5 | 0.350600851 | 3.30.161 || AGTPBP1 | 3.30 | ATP/GTP binding protein 1 | 0.408045446 | — || ALDH1B1 | 3.30 | aldehyde dehydrogenase 1 family member B1 | 0.307312348 | 3.30.161 || ALMS1 | 3.30 | ALMS1, centrosome and basal body associated protein | 0.317654559 | 3.30.161 || ALPK1 | 3.30 | alpha kinase 1 | 0.335151621 | 3.30.161 || ANKHD1 | 3.30 | ankyrin repeat and KH domain containing 1 | 0.729834743 | — || ANKLE2 | 3.30 | ankyrin repeat and LEM domain containing 2 | 0.456517817 | 3.30.161 || ANKRD12 | 3.30 | ankyrin repeat domain 12 | 0.318898415 | — || AP1AR | 3.30 | adaptor related protein complex 1 associated regulatory protein | 0.673226766 | 3.30.161 || APOPT1 | 3.30 | apoptogenic 1, mitochondrial | 0.268376405 | 3.30.161 || ARID2 | 3.30 | AT-rich interaction domain 2 | 0.330695084 | 3.30.161 || ARIH2 | 3.30 | ariadne RBR E3 ubiquitin protein ligase 2 | 0.368630654 | 3.30.164 || ARMC9 | 3.30 | armadillo repeat containing 9 | 0.396598752 | — || ASXL1 | 3.30 | additional sex combs like 1, transcriptional regulator | 0.715793671 | 3.30.161 || ATAD3B | 3.30 | ATPase family, AAA domain containing 3B | 0.271465067 | 3.30.161 || ATF4 | 3.30 | activating transcription factor 4 | 0.216035027 | 3.30.161 || ATP8B1 | 3.30 | ATPase phospholipid transporting 8B1 | 0.43453393 | 3.30.161 || ATXN7L1 | 3.30 | ataxin 7 like 1 | 0.249254691 | — || AZI2 | 3.30 | 5-azacytidine induced 2 | 0.364985673 | 3.30.161 || B4GALT3 | 3.30 | UDP-Gal:betaGlcNAc beta 1,4-galactosyltransferase, polypeptide 3 | 0.262314081 | — || BCL2L1 | 3.30 | BCL2 like 1 | 0.47724347 | 3.30.161 || BLOC1S3 | 3.30 | biogenesis of lysosomal organelles complex 1 subunit 3 | 0.239303652 | 3.30.161 || BLZF1 | 3.30 | basic leucine zipper nuclear factor 1 | 0.358699956 | — || BMP7 | 3.30 | bone morphogenetic protein 7 | 0.245166177 | 3.30.161 || BMS1P5 | 3.30 | BMS1, ribosome biogenesis factor pseudogene 5 | 0.681368074 | 3.30.162 || BORCS6 | 3.30 | BLOC-1 related complex subunit 6 | 0.253484607 | 3.30.164 || BPTF | 3.30 | bromodomain PHD finger transcription factor | 0.305189338 | 3.30.161 || BSG | 3.30 | basigin (Ok blood group) | 0.316299297 | 3.30.163 || C12orf43 | 3.30 | chromosome 12 open reading frame 43 | 0.606791983 | 3.30.164 || C19orf60 | 3.30 | chromosome 19 open reading frame 60 | 0.247303532 | 3.30.161 || C20orf194 | 3.30 | chromosome 20 open reading frame 194 | 0.496257029 | 3.30.164 || C2orf68 | 3.30 | chromosome 2 open reading frame 68 | 1.19619938 | 3.30.161 || C9orf64 | 3.30 | chromosome 9 open reading frame 64 | 0.343659592 | 3.30.161 || CAMKMT | 3.30 | calmodulin-lysine N-methyltransferase | 0.265474786 | — || CAPS2 | 3.30 | calcyphosine 2 | 0.871079797 | — || CASP10 | 3.30 | caspase 10 | 0.592607805 | 3.30.161 || CCDC152 | 3.30 | coiled-coil domain containing 152 | 0.294292919 | 3.30.161 || CCM2 | 3.30 | CCM2 scaffolding protein | 0.317281828 | 3.30.163 || CCZ1B | 3.30 | CCZ1 homolog B, vacuolar protein trafficking and biogenesis associated | 0.349017772 | 3.30.163 || CDK13 | 3.30 | cyclin-dependent kinase 13 | 0.576340437 | 3.30.161 || CDK2AP2 | 3.30 | cyclin-dependent kinase 2 associated protein 2 | 0.430001629 | 3.30.161 || CDK5RAP1 | 3.30 | CDK5 regulatory subunit associated protein 1 | 0.360318468 | — || CENPBD1 | 3.30 | CENPB DNA-binding domain containing 1 | 0.374199987 | 3.30.161 || CEP152 | 3.30 | centrosomal protein 152 kDa | 0.260393368 | 3.30.162 || CEP76 | 3.30 | centrosomal protein 76 kDa | 0.267774115 | — || CEP89 | 3.30 | centrosomal protein 89 kDa | 0.746193621 | 3.30.162 || CIB1 | 3.30 | calcium and integrin binding 1 | 0.330967419 | — || CLEC12A | 3.30 | C-type lectin domain family 12 member A | 4.275025327 | — || CNPY3 | 3.30 | canopy FGF signaling regulator 3 | 0.274351945 | 3.30.161 || CNTLN | 3.30 | centlein | 1.530856311 | 3.30.161 || CRIPT | 3.30 | CXXC repeat containing interactor of PDZ3 domain | 0.421443808 | 3.30.163 || CRYBB2P1 | 3.30 | crystallin beta B2 pseudogene 1 | 0.261306653 | 3.30.161 || CUTC | 3.30 | cutC copper transporter | 0.486947462 | — || CXorf21 | 3.30 | chromosome X open reading frame 21 | 0.331323197 | 3.30.162 || CYB5R1 | 3.30 | cytochrome b5 reductase 1 | 0.421170473 | — || CYC1 | 3.30 | cytochrome c1 | 0.223575465 | 3.30.161 || DAPP1 | 3.30 | dual adaptor of phosphotyrosine and 3-phosphoinositides | 0.35628854 | 3.30.161 || DBT | 3.30 | dihydrolipoamide branched chain transacylase E2 | 0.310379857 | 3.30.161 || DDB2 | 3.30 | damage specific DNA binding protein 2 | 0.241096702 | 3.30.161 || DEFB1 | 3.30 | defensin beta 1 | 4.132062917 | — || DHFRL1 | 3.30 | dihydrofolate reductase like 1 | 0.243966395 | 3.30.161 || DHPS |

TABLE 3B-continued

The genes within the significant gene clusters, listed in Table 3A. (3966 Genes Listed by: Gene Symbol | Gen 2 Module | Gene Description | RowVariance | Gen 3 Module ||)

3.30 | deoxyhypusine synthase | 0.253298759 | 3.30.161 || DHRSX | 3.30 | dehydrogenase/reductase (SDR family) X-linked | 0.477668615 | — || DIP2A | 3.30 | disco interacting protein 2 homolog A | 0.622451462 | 3.30.161 || DLGAP4 | 3.30 | discs large homolog associated protein 4 | 0.512951009 | 3.30.161 || DNAJC27 | 3.30 | DnaJ heat shock protein family (Hsp40) member C27 | 0.310844827 | 3.30.161 || E2F3 | 3.30 | E2F transcription factor 3 | 0.259237654 | — || EBLN3 | 3.30 | endogenous Bornavirus-like nucleoprotein 3 | 0.259890806 | 3.30.163 || EIF3C | 3.30 | eukaryotic translation initiation factor 3 subunit C | 1.718522589 | — || ELAVL3 | 3.30 | ELAV like neuron-specific RNA binding protein 3 | 0.538596786 | 3.30.164 || EPHB4 | 3.30 | EPH receptor B4 | 0.526923635 | 3.30.161 || ETHE1 | 3.30 | ethylmalonic encephalopathy 1 | 0.447625879 | 3.30.162 || EXOSC2 | 3.30 | exosome component 2 | 0.285655288 | 3.30.161 || FAM155A | 3.30 | family with sequence similarity 155 member A | 0.845409308 | — || FAM161B | 3.30 | family with sequence similarity 161 member B | 0.351430932 | 3.30.161 || FAM173B | 3.30 | family with sequence similarity 173 member B | 0.778665319 | — || FAM185A | 3.30 | family with sequence similarity 185 member A | 0.409938388 | 3.30.161 || FAM50A | 3.30 | family with sequence similarity 50 member A | 0.275008177 | 3.30.161 || FAM63A | 3.30 | family with sequence similarity 63 member A | 0.309692891 | 3.30.161 || FARSA | 3.30 | phenylalanyl-tRNA synthetase alpha subunit | 0.243472131 | 3.30.161 || FBXL14 | 3.30 | F-box and leucine-rich repeat protein 14 | 0.24496978 | 3.30.164 || FBXW12 | 3.30 | F-box and WD repeat domain containing 12 | 0.215501759 | 3.30.161 || FCF1 | 3.30 | FCF1 rRNA-processing protein | 1.564275516 | 3.30.161 || FJX1 | 3.30 | four jointed box 1 | 0.393358658 | — || FLJ35934 | 3.30 | FLJ35934 | 1.465558321 | 3.30.161 || FMO4 | 3.30 | flavin containing monooxygenase 4 | 0.279914387 | — || FOLR2 | 3.30 | folate receptor 2 (fetal) | 0.224800243 | — || FOXC2 | 3.30 | forkhead box C2 | 0.494783451 | 3.30.161 || FTX | 3.30 | FTX transcript, XIST regulator (non-protein coding) | 0.367138006 | 3.30.161 || FUCA1 | 3.30 | fucosidase, alpha-L-1, tissue | 0.351798571 | — || GAS2L3 | 3.30 | growth arrest specific 2 like 3 | 0.457955472 | — || GDAP2 | 3.30 | ganglioside induced differentiation associated protein 2 | 0.245697891 | 3.30.161 || GLUD2 | 3.30 | glutamate dehydrogenase 2 | 0.515300288 | 3.30.161 || GPATCH2L | 3.30 | G-patch domain containing 2 like | 1.960179904 | 3.30.163 || GPR180 | 3.30 | G protein-coupled receptor 180 | 0.700540683 | 3.30.161 || GPX1 | 3.30 | glutathione peroxidase 1 | 0.217753186 | — || GRSF1 | 3.30 | G-rich RNA sequence binding factor 1 | 0.2286843 | 3.30.161 || GTF2H3 | 3.30 | general transcription factor IIH subunit 3 | 0.466118302 | 3.30.162 || GUCD1 | 3.30 | guanylyl cyclase domain containing 1 | 0.236375233 | 3.30.161 || H6PD | 3.30 | hexose-6-phosphate dehydrogenase (glucose 1-dehydrogenase) | 0.420292436 | 3.30.163 || HACD4 | 3.30 | 3-hydroxyacyl-CoA dehydratase 4 | 0.219712177 | 3.30.161 || HIC2 | 3.30 | hypermethylated in cancer 2 | 0.648115152 | — || HOMER3 | 3.30 | homer scaffolding protein 3 | 0.432097501 | 3.30.162 || HOXC9 | 3.30 | homeobox C9 | 0.439238775 | 3.30.164 || HSCB | 3.30 | HscB mitochondrial iron-sulfur cluster co-chaperone | 0.401953843 | 3.30.161 || ISG20L2 | 3.30 | interferon stimulated exonuclease gene 20 kDa like 2 | 0.577257953 | 3.30.161 || KANSL1L | 3.30 | KAT8 regulatory NSL complex subunit 1 like | 0.58843994 | 3.30.161 || KATNB1 | 3.30 | katanin p80 (WD repeat containing) subunit B 1 | 0.282564914 | 3.30.161 || KIFC3 | 3.30 | kinesin family member C3 | 0.683956714 | — || KLF8 | 3.30 | Kruppel-like factor 8 | 0.94019415 | 3.30.161 || KXD1 | 3.30 | KxDL motif containing 1 | 0.255973442 | 3.30.161 || LARS | 3.30 | leucyl-tRNA synthetase | 0.269634877 | 3.30.161 || LIME1 | 3.30 | Lck interacting transmembrane adaptor 1 | 0.219325616 | 3.30.161 || LINS1 | 3.30 | lines homolog 1 | 1.661817972 | — || LMAN2 | 3.30 | lectin, mannose binding 2 | 0.27351954 | 3.30.161 || LOC100506282 | 3.30 | uncharacterized LOC100506282 | 0.967848883 | 3.30.162 || LOC388692 | 3.30 | uncharacterized LOC388692 | 0.247042414 | 3.30.161 || LSM10 | 3.30 | LSM10, U7 small nuclear RNA associated | 0.372634322 | — || LSM4 | 3.30 | LSM4 homolog, U6 small nuclear RNA and mRNA degradation associated | 0.295416034 | 3.30.161 || MAP3K2 | 3.30 | mitogen-activated protein kinase kinase kinase 2 | 0.239860097 | — || MAPRE3 | 3.30 | microtubule associated protein RP/EB family member 3 | 0.357711959 | 3.30.164 || MBIP | 3.30 | MAP3K12 binding inhibitory protein 1 | 0.707044418 | 3.30.164 || MCM5 | 3.30 | minichromosome maintenance complex component 5 | 0.311663026 | 3.30.161 || MED1 | 3.30 | mediator complex subunit 1 | 0.437689844 | 3.30.161 || MED10 | 3.30 | mediator complex subunit 10 | 0.318993623 | 3.30.161 || MED25 | 3.30 | mediator complex subunit 25 | 0.283174309 | 3.30.161 || MFNG | 3.30 | MFNG O-fucosylpeptide 3-beta-N-acetylglucosaminyltransferase | 0.281534973 | 3.30.161 || MFSD4B | 3.30 | major facilitator superfamily domain containing 4B | 0.426375024 | 3.30.162 || MIB1 | 3.30 | mindbomb E3 ubiquitin protein ligase 1 | 0.36953511 | 3.30.161 || MOB3B | 3.30 | MOB kinase activator 3B | 0.411911627 | — || MRPL42 | 3.30 | mitochondrial ribosomal protein L42 | 0.352435304 | — || MRPS25 | 3.30 | mitochondrial ribosomal protein S25 | 0.346073909 | 3.30.161 || MRPS34 | 3.30 | mitochondrial ribosomal protein S34 | 0.305962574 | 3.30.161 || MTRF1L | 3.30 | mitochondrial translational release factor 1 like | 0.512985038 | 3.30.164 || MUM1 | 3.30 | melanoma associated antigen (mutated) 1 | 0.846361478 | 3.30.161 || MYBL2 | 3.30 | MYB proto-oncogene like 2 | 0.321355477 | 3.30.161 || NADSYN1 | 3.30 | NAD synthetase 1 | 0.276552096 | — || NANOG | 3.30 | Nanog homeobox | 0.969002288 | 3.30.161 || NBEA | 3.30 | neurobeachin | 0.319732489 | 3.30.161 || NDUFAF7 | 3.30 | NADH:ubiquinone oxidoreductase complex assembly factor 7 | 0.275815248 | 3.30.161 || NLGN4X | 3.30 | neuroligin 4, X-linked | 0.228910945 | 3.30.161 || NLN | 3.30 | neurolysin | 0.526426523 | 3.30.161 || NME6 | 3.30 | NME/NM23 nucleoside diphosphate kinase 6 | 0.620866214 | 3.30.161 || NMT1 | 3.30 | N-myristoyltransferase 1 | 0.344492238 | 3.30.164 || NOP10 | 3.30 | NOP10 ribonucleoprotein | 0.23502896 | 3.30.163 || NOP2 | 3.30 | NOP2 nucleolar protein | 0.274619566 | — || NOTCH2NL | 3.30 | notch 2 N-terminal like | 0.316218069 | 3.30.161 || NOVA2 | 3.30 | neuro-oncological ventral antigen 2 | 0.332706539 | 3.30.161 || NPEPL1 | 3.30 | aminopeptidase-like 1 | 0.505830032 | 3.30.164 || NPRL2 | 3.30 | NPR2-like, GATOR1 complex subunit | 0.259521118 | 3.30.162 || NPTN-IT1 | 3.30 | NPTN intronic transcript 1 | 0.645011649 | 3.30.163 || NRIP1 | 3.30 | nuclear receptor interacting protein 1 | 0.540479072 | 3.30.164 || NUB1 | 3.30 | negative regulator of ubiquitin-like proteins 1 | 0.223485752 | — || NUBPL | 3.30 | nucleotide binding protein like | 0.35114588 | 3.30.161 || NUDT2 | 3.30 | nudix hydrolase 2 | 0.242382319 | — || NUMBL | 3.30 | numb homolog (*Drosophila*)-like | 0.452337826 | 3.30.164 || NUP58 | 3.30 | nucleoporin 58 kDa | 0.707272837 | 3.30.161 || NUP93 | 3.30 | nucleoporin 93 kDa | 0.260078771 | — || NUTM2B-AS1 | 3.30 | NUTM2B antisense RNA 1 | 0.618545548 | 3.30.161 || NXPE3 | 3.30 | neurexophilin and PC-esterase domain family member 3 | 0.655944585 | 3.30.162 || OGFR | 3.30 | opioid growth factor receptor | 0.223730018 | 3.30.161 || ORAI2 | 3.30 | ORAI calcium TABLE 3B-continued The genes within the significant gene clusters, listed in Table 3A. (3966 Genes Listed by: Gene Symbol | Gen 2 Module | Gene Description | RowVariance | Gen 3 Module ||)

release-activated calcium modulator 2 | 0.611215362 | 3.30.161 || ORMDL2 | 3.30 | ORMDL sphingolipid biosynthesis regulator 2 | 0.383004896 | 3.30.161 || OTUD6B | 3.30 | OTU domain containing 6B | 0.408954059 | 3.30.161 || PABPN1 | 3.30 | poly(A) binding protein, nuclear 1 | 0.433609034 | 3.30.161 || PAK1 | 3.30 | p21 protein (Cdc42/Rac)-activated kinase 1 | 0.255512807 | 3.30.161 || PALM2 | 3.30 | paralemmin 2 | 0.624064675 | 3.30.164 || PAXIP1-AS1 | 3.30 | PAXIP1 antisense RNA 1 (head to head) | 0.381161759 | 3.30.161 || PCBD2 | 3.30 | pterin-4 alpha-carbinolamine dehydratase 2 | 0.53520521 | — || PCBP1-AS1 | 3.30 | PCBP1 antisense RNA 1 | 0.451561689 | 3.30.161 || PDCD7 | 3.30 | programmed cell death 7 | 0.365597024 | 3.30.161 || PDCL | 3.30 | phosducin like | 0.248924835 | 3.30.161 || PDE4DIP | 3.30 | phosphodiesterase 4D interacting protein | 1.238864848 | — || PECR | 3.30 | peroxisomal trans-2-enoyl-CoA reductase | 0.677321678 | 3.30.161 || PGF | 3.30 | placental growth factor | 0.389492364 | 3.30.161 || PHF19 | 3.30 | PHD finger protein 19 | 0.223424043 | 3.30.161 || PHF20L1 | 3.30 | PHD finger protein 20-like 1 | 0.420513453 | — || PIEZO2 | 3.30 | piezo type mechanosensitive ion channel component 2 | 1.544273829 | — || POLD4 | 3.30 | polymerase (DNA) delta 4, accessory subunit | 0.3957221 | 3.30.161 || POLR1B | 3.30 | polymerase (RNA) I subunit B | 0.796356992 | 3.30.161 || POLRMT | 3.30 | polymerase (RNA) mitochondrial | 0.310785506 | 3.30.161 || PPA2 | 3.30 | pyrophosphatase (inorganic) 2 | 0.687462604 | 3.30.161 || PPHLN1 | 3.30 | periphilin 1 | 0.254201029 | 3.30.163 || PPP2R5D | 3.30 | protein phosphatase 2 regulatory subunit B', delta | 0.296598581 | 3.30.161 || PPP5C | 3.30 | protein phosphatase 5 catalytic subunit | 0.27648773 | 3.30.161 || PRR11 | 3.30 | proline rich 11 | 0.387011318 | 3.30.161 || PTHLH | 3.30 | parathyroid hormone-like hormone | 0.237342811 | — || RAB2B | 3.30 | RAB2B, member RAS oncogene family | 0.217029099 | 3.30.161 || RABEP1 | 3.30 | rabaptin, RAB GTPase binding effector protein 1 | 0.247033339 | 3.30.163 || RABGAP1 | 3.30 | RAB GTPase activating protein 1 | 0.283328283 | 3.30.161 || RAD1 | 3.30 | RAD1 checkpoint DNA exonuclease | 0.550238703 | 3.30.161 || RANGRF | 3.30 | RAN guanine nucleotide release factor | 0.36937128 | — || RAPH1 | 3.30 | Ras association (RalGDS/AF-6) and pleckstrin homology domains 1 | 0.246647221 | 3.30.164 || RBBP5 | 3.30 | retinoblastoma binding protein 5 | 0.383802185 | 3.30.161 || RBM26-AS1 | 3.30 | RBM26 antisense RNA 1 | 0.33348482 | — || RDH5 | 3.30 | retinol dehydrogenase 5 | 1.348755651 | 3.30.161 || REL | 3.30 | v-rel avian reticuloendotheliosis viral oncogene homolog | 0.585549063 | — || RFX3 | 3.30 | regulatory factor X3 | 0.398367876 | 3.30.161 || RIT1 | 3.30 | Ras-like without CAAX 1 | 0.708957957 | 3.30.162 || RNGTT | 3.30 | RNA guanylyltransferase and 5'-phosphatase | 0.345966138 | 3.30.161 || RP2 | 3.30 | retinitis pigmentosa 2 (X-linked recessive) | 0.328088093 | — || RPRD2 | 3.30 | regulation of nuclear pre-mRNA domain containing 2 | 0.355487833 | 3.30.164 || RPS19BP1 | 3.30 | ribosomal protein S19 binding protein 1 | 0.232584469 | — || RRAGD | 3.30 | Ras related GTP binding D | 0.370224662 | 3.30.161 || RSPRY1 | 3.30 | ring finger and SPRY domain containing 1 | 0.303005833 | — || SAMD4B | 3.30 | sterile alpha motif domain containing 4B | 0.530246528 | 3.30.161 || SCAF4 | 3.30 | SR-related CTD-associated factor 4 | 1.133357927 | 3.30.161 || SCO1 | 3.30 | SCO1 cytochrome c oxidase assembly protein | 0.408620694 | 3.30.163 || SDHAF1 | 3.30 | succinate dehydrogenase complex assembly factor 1 | 0.341757346 | — || SEC14L1P1 | 3.30 | SEC14 like 1 pseudogene 1 | 0.755378479 | 3.30.161 || SEC22A | 3.30 | SEC22 homolog A, vesicle trafficking protein | 0.390611834 | 3.30.164 || SELK | 3.30 | selenoprotein K | 0.26075525 | — || SERPING1 | 3.30 | serpin peptidase inhibitor, clade G (C1 inhibitor), member 1 | 0.333217799 | 3.30.161 || SEZ6L2 | 3.30 | seizure related 6 homolog (mouse)-like 2 | 0.372348623 | 3.30.164 || SGK494 | 3.30 | uncharacterized serine/threonine-protein kinase SgK494 | 0.664146991 | 3.30.161 || SHISA4 | 3.30 | shisa family member 4 | 1.07176908 | — || SLC26A6 | 3.30 | solute carrier family 26 member 6 | 0.467606888 | 3.30.161 || SLC35B4 | 3.30 | solute carrier family 35 member B4 | 0.224178696 | 3.30.161 || SLC35D1 | 3.30 | solute carrier family 35 member D1 | 0.355639249 | 3.30.162 || SLC35E1 | 3.30 | solute carrier family 35 member E1 | 0.297085088 | 3.30.161 || SMIM12 | 3.30 | small integral membrane protein 12 | 0.232600441 | — || SMIM8 | 3.30 | small integral membrane protein 8 | 0.286061502 | 3.30.161 || SMO | 3.30 | smoothened, frizzled class receptor | 0.627909031 | 3.30.163 || SNRNP200 | 3.30 | small nuclear ribonucleoprotein U5 subunit 200 | 0.738522656 | 3.30.161 || SNRNP25 | 3.30 | small nuclear ribonucleoprotein U11/U12 subunit 25 | 0.558607689 | 3.30.161 || SNX1 | 3.30 | sorting nexin 1 | 0.334783242 | — || SORBS1 | 3.30 | sorbin and SH3 domain containing 1 | 0.297206207 | 3.30.161 || SPRY4-IT1 | 3.30 | SPRY4 intronic transcript 1 | 0.272385534 | 3.30.162 || SREBF2 | 3.30 | sterol regulatory element binding transcription factor 2 | 0.231625924 | 3.30.161 || SRFBP1 | 3.30 | serum response factor binding protein 1 | 0.98837139 | 3.30.161 || SRGAP1 | 3.30 | SLIT-ROBO Rho GTPase activating protein 1 | 0.690167007 | 3.30.161 || SSBP3-AS1 | 3.30 | SSBP3 antisense RNA 1 | 0.373058087 | 3.30.161 || SSNA1 | 3.30 | Sjogren syndrome nuclear autoantigen 1 | 0.228474379 | 3.30.163 || STARD10 | 3.30 | StAR related lipid transfer domain containing 10 | 0.3466871 | 3.30.161 || STIP1 | 3.30 | stress induced phosphoprotein 1 | 0.301017828 | — || STRN | 3.30 | striatin | 0.741047152 | 3.30.161 || STX16 | 3.30 | syntaxin 16 | 0.412854668 | 3.30.161 || STXBP5 | 3.30 | syntaxin binding protein 5 | 1.089528566 | 3.30.164 || SUSD1 | 3.30 | sushi domain containing 1 | 0.485327403 | 3.30.161 || SYMPK | 3.30 | symplekin | 0.323207194 | — || TBC1D32 | 3.30 | TBC1 domain family member 32 | 0.324652475 | 3.30.164 || TBC1D5 | 3.30 | TBC1 domain family member 5 | 0.404257669 | — || TCAF1 | 3.30 | TRPM8 channel-associated factor 1 | 0.347099512 | 3.30.161 || TCP11L2 | 3.30 | t-complex 11, testis-specific-like 2 | 0.363127472 | — || TCTN2 | 3.30 | tectonic family member 2 | 0.439404652 | 3.30.161 || TFAM | 3.30 | transcription factor A, mitochondrial | 0.665120986 | — || THUMPD3-AS1 | 3.30 | THUMPD3 antisense RNA 1 | 0.244344561 | 3.30.161 || TM9SF1 | 3.30 | transmembrane 9 superfamily member 1 | 0.330628147 | 3.30.161 || TMED1 | 3.30 | transmembrane p24 trafficking protein 1 | 0.320024357 | — || TMEM160 | 3.30 | transmembrane protein 160 | 0.38000783 | — || TMEM209 | 3.30 | transmembrane protein 209 | 0.46025373 | 3.30.163 || TMEM260 | 3.30 | transmembrane protein 260 | 0.320205953 | — || TMEM67 | 3.30 | transmembrane protein 67 | 0.677453744 | 3.30.164 || TMPRSS6 | 3.30 | transmembrane protease, serine 6 | 0.399668197 | 3.30.161 || TNFRSF10D | 3.30 | tumor necrosis factor receptor superfamily member 10d | 0.339928148 | — || TOLLIP | 3.30 | toll interacting protein | 0.358870057 | 3.30.161 || TOPORS | 3.30 | topoisomerase I binding, arginine/serine-rich, E3 ubiquitin protein ligase | 0.367545283 | 3.30.161 || TOR1B | 3.30 | torsin family 1 member B | 0.293724707 | 3.30.161 || TRA2A | 3.30 | transformer 2 alpha homolog (*Drosophila*) | 0.704028796 | 3.30.163 || TRIM38 | 3.30 | tripartite motif containing 38 | 0.229195649 | 3.30.161 || TRIM66 | 3.30 | tripartite motif containing 66 | 0.875678341 | — || TRMT10B | 3.30 | tRNA TABLE 3B-continued The genes within the significant gene clusters, listed in Table 3A. (3966 Genes Listed by: Gene Symbol | Gen 2 Module | Gene Description | RowVariance | Gen 3 Module ||)

methyltransferase 10B | 0.260649423 | 3.30.162 || TSC22D2 | 3.30 | TSC22 domain family member 2 | 0.422337416 | — || TSEN2 | 3.30 | tRNA splicing endonuclease subunit 2 | 0.40337825 | 3.30.161 || TSR1 | 3.30 | TSR1, 20S rRNA accumulation, homolog (*S. cerevisiae*) | 0.231857811 | 3.30.161 || TTC32 | 3.30 | tetratricopeptide repeat domain 32 | 0.363074357 | 3.30.161 || TTC5 | 3.30 | tetratricopeptide repeat domain 5 | 0.310589861 | 3.30.162 || TXNDC17 | 3.30 | thioredoxin domain containing 17 | 0.220925814 | 3.30.163 || UACA | 3.30 | uveal autoantigen with coiled-coil domains and ankyrin repeats | 0.246988249 | 3.30.161 || UBAC1 | 3.30 | UBA domain containing 1 | 0.214671317 | 3.30.161 || UBE2G1 | 3.30 | ubiquitin conjugating enzyme E2G 1 | 0.291900447 | — || UBE2S | 3.30 | ubiquitin conjugating enzyme E2S | 0.268642983 | 3.30.161 || UBE3D | 3.30 | ubiquitin protein ligase E3D | 0.606740871 | 3.30.162 || UBN2 | 3.30 | ubinuclein 2 | 0.436643149 | 3.30.164 || UBXN2A | 3.30 | UBX domain protein 2A | 0.332342825 | 3.30.161 || UCKL1 | 3.30 | uridine-cytidine kinase 1-like 1 | 0.301351666 | 3.30.162 || USP34 | 3.30 | ubiquitin specific peptidase 34 | 0.440042036 | 3.30.161 || VAMP2 | 3.30 | vesicle associated membrane protein 2 | 0.389730645 | 3.30.164 || VGLL4 | 3.30 | vestigial like family member 4 | 0.273340825 | 3.30.164 || VHL | 3.30 | von Hippel-Lindau tumor suppressor | 0.599904226 | 3.30.162 || VTI1A | 3.30 | vesicle transport through interaction with t-SNAREs 1A | 0.477960914 | 3.30.161 || WASF1 | 3.30 | WAS protein family member 1 | 0.455656022 | 3.30.164 || WDPCP | 3.30 | WD repeat containing planar cell polarity effector | 0.521484164 | 3.30.161 || WDR92 | 3.30 | WD repeat domain 92 | 0.604784359 | 3.30.161 || WSB1 | 3.30 | WD repeat and SOCS box containing 1 | 0.347045553 | — || WTAP | 3.30 | Wilms tumor 1 associated protein | 0.324388067 | 3.30.161 || WWP1 | 3.30 | WW domain containing E3 ubiquitin protein ligase 1 | 0.267222347 | 3.30.161 || ZC3HAV1L | 3.30 | zinc finger CCCH-type containing, antiviral 1 like | 0.955106743 | — || ZDHHC16 | 3.30 | zinc finger DHHC-type containing 16 | 0.257332465 | 3.30.162 || ZGPAT | 3.30 | zinc finger CCCH-type and G-patch domain containing | 0.35496962 | 3.30.161 || ZNF107 | 3.30 | zinc finger protein 107 | 0.48019711 | — || ZNF136 | 3.30 | zinc finger protein 136 | 0.741766055 | 3.30.161 || ZNF160 | 3.30 | zinc finger protein 160 | 0.472219291 | 3.30.161 || ZNF185 | 3.30 | zinc finger protein 185 (LIM domain) | 0.243878375 | 3.30.161 || ZNF230 | 3.30 | zinc finger protein 230 | 0.531498798 | 3.30.162 || ZNF275 | 3.30 | zinc finger protein 275 | 0.381879871 | 3.30.161 || ZNF281 | 3.30 | zinc finger protein 281 | 0.303494188 | — || ZNF3 | 3.30 | zinc finger protein 3 | 0.907549536 | — || ZNF333 | 3.30 | zinc finger protein 333 | 1.010036815 | 3.30.161 || ZNF37A | 3.30 | zinc finger protein 37A | 0.341349617 | 3.30.161 || ZNF37BP | 3.30 | zinc finger protein 37B, pseudogene | 1.791939962 | 3.30.161 || ZNF431 | 3.30 | zinc finger protein 431 | 2.274358104 | 3.30.161 || ZNF451 | 3.30 | zinc finger protein 451 | 0.287704099 | 3.30.161 || ZNF486 | 3.30 | zinc finger protein 486 | 0.235414336 | — || ZNF514 | 3.30 | zinc finger protein 514 | 0.975589962 | 3.30.161 || ZNF518A | 3.30 | zinc finger protein 518A | 0.505753968 | 3.30.161 || ZNF528 | 3.30 | zinc finger protein 528 | 0.364951731 | 3.30.161 || ZNF550 | 3.30 | zinc finger protein 550 | 0.275532844 | — || ZNF551 | 3.30 | zinc finger protein 551 | 1.023046204 | 3.30.161 || ZNF562 | 3.30 | zinc finger protein 562 | 0.389253803 | — || ZNF585A | 3.30 | zinc finger protein 585A | 0.437874075 | 3.30.161 || ZNF587 | 3.30 | zinc finger protein 587 | 0.216364592 | 3.30.161 || ZNF587B | 3.30 | zinc finger protein 587B | 0.259307402 | 3.30.161 || ZNF669 | 3.30 | zinc finger protein 669 | 0.390451114 | 3.30.163 || ZNF706 | 3.30 | zinc finger protein 706 | 0.29526667 | 3.30.161 || ZNF721 | 3.30 | zinc finger protein 721 | 0.299909179 | 3.30.161 || ZNF75A | 3.30 | zinc finger protein 75a | 0.228062974 | 3.30.162 || ZNF785 | 3.30 | zinc finger protein 785 | 2.268123854 | 3.30.164 || ZNF787 | 3.30 | zinc finger protein 787 | 0.292078686 | 3.30.161 || ZNF850 | 3.30 | zinc finger protein 850 | 0.279345017 | 3.30.162 || ZNRF1 | 3.30 | zinc and ring finger 1, E3 ubiquitin protein ligase | 0.269880812 | — || AAAS | 3.30.161 | aladin WD repeat nucleoporin | 0.352373522 | 3.30.161 || ACO2 | 3.30.161 | aconitase 2 | 0.295624058 | 3.30.161 || ADAM15 | 3.30.161 | ADAM metallopeptidase domain 15 | 0.346230317 | 3.30.161 || ADAM33 | 3.30.161 | ADAM metallopeptidase domain 33 | 0.254840952 | 3.30.161 || ADAT1 | 3.30.161 | adenosine deaminase, tRNA-specific 1 | 0.52589383 | 3.30.161 || AGBL5 | 3.30.161 | ATP/GTP binding protein-like 5 | 0.350600851 | 3.30.161 || ALDH1B1 | 3.30.161 | aldehyde dehydrogenase 1 family member B1 | 0.307312348 | 3.30.161 || ALMS1 | 3.30.161 | ALMS1, centrosome and basal body associated protein | 0.317654559 | 3.30.161 || ALPK1 | 3.30.161 | alpha kinase 1 | 0.335151621 | 3.30.161 || ANKLE2 | 3.30.161 | ankyrin repeat and LEM domain containing 2 | 0.456517817 | 3.30.161 || AP1AR | 3.30.161 | adaptor related protein complex 1 associated regulatory protein | 0.673226766 | 3.30.161 || APOPT1 | 3.30.161 | apoptogenic 1, mitochondrial | 0.268376405 | 3.30.161 || ARID2 | 3.30.161 | AT-rich interaction domain 2 | 0.330695084 | 3.30.161 || ASXL1 | 3.30.161 | additional sex combs like 1, transcriptional regulator | 0.715793671 | 3.30.161 || ATAD3B | 3.30.161 | ATPase family, AAA domain containing 3B | 0.271465067 | 3.30.161 || ATF4 | 3.30.161 | activating transcription factor 4 | 0.216035027 | 3.30.161 || ATP8B1 | 3.30.161 | ATPase phospholipid transporting 8B1 | 0.43453393 | 3.30.161 || AZI2 | 3.30.161 | 5-azacytidine induced 2 | 0.364985673 | 3.30.161 || BCL2L1 | 3.30.161 | BCL2 like 1 | 0.47724347 | 3.30.161 || BLOC1S3 | 3.30.161 | biogenesis of lysosomal organelles complex 1 subunit 3 | 0.239303652 | 3.30.161 || BMP7 | 3.30.161 | bone morphogenetic protein 7 | 0.245166177 | 3.30.161 || BPTF | 3.30.161 | bromodomain PHD finger transcription factor | 0.305189338 | 3.30.161 || C19orf60 | 3.30.161 | chromosome 19 open reading frame 60 | 0.247303532 | 3.30.161 || C2orf68 | 3.30.161 | chromosome 2 open reading frame 68 | 1.19619938 | 3.30.161 || C9orf64 | 3.30.161 | chromosome 9 open reading frame 64 | 0.343659592 | 3.30.161 || CASP10 | 3.30.161 | caspase 10 | 0.592607805 | 3.30.161 || CCDC152 | 3.30.161 | coiled-coil domain containing 152 | 0.294292919 | 3.30.161 || CDK13 | 3.30.161 | cyclin-dependent kinase 13 | 0.576340437 | 3.30.161 || CDK2AP2 | 3.30.161 | cyclin-dependent kinase 2 associated protein 2 | 0.430001629 | 3.30.161 || CENPBD1 | 3.30.161 | CENPB DNA-binding domain containing 1 | 0.374199987 | 3.30.161 || CNPY3 | 3.30.161 | canopy FGF signaling regulator 3 | 0.274351945 | 3.30.161 || CNTLN | 3.30.161 | centlein | 1.530856311 | 3.30.161 || CRYBB2P1 | 3.30.161 | crystallin beta B2 pseudogene 1 | 0.261306653 | 3.30.161 || CYC1 | 3.30.161 | cytochrome c1 | 0.223575465 | 3.30.161 || DAPP1 | 3.30.161 | dual adaptor of phosphotyrosine and 3-phosphoinositides | 0.35628854 | 3.30.161 || DBT | 3.30.161 | dihydrolipoamide branched chain transacylase E2 | 0.310379857 | 3.30.161 || DDB2 | 3.30.161 | damage specific DNA binding protein 2 | 0.241096702 | 3.30.161 || DHFRL1 | 3.30.161 | dihydrofolate reductase like 1 | 0.243966395 | 3.30.161 || DHPS | 3.30.161 | deoxyhypusine synthase | 0.253298759 | 3.30.161 || DIP2A | 3.30.161 | disco interacting protein 2 homolog A | 0.622451462 | 3.30.161 || DLGAP4 |

TABLE 3B-continued

The genes within the significant gene clusters, listed in Table 3A. (3966 Genes Listed by: Gene Symbol | Gen 2 Module | Gene Description | RowVariance | Gen 3 Module ||)

3.30.161 | discs large homolog associated protein 4 | 0.512951009 | 3.30.161 || DNAJC27 | 3.30.161 | DnaJ heat shock protein family (Hsp40) member C27 | 0.310844827 | 3.30.161 || EPHB4 | 3.30.161 | EPH receptor B4 | 0.526923635 | 3.30.161 || EXOSC2 | 3.30.161 | exosome component 2 | 0.285655288 | 3.30.161 || FAM161B | 3.30.161 | family with sequence similarity 161 member B | 0.351430932 | 3.30.161 || FAM185A | 3.30.161 | family with sequence similarity 185 member A | 0.409938388 | 3.30.161 || FAM50A | 3.30.161 | family with sequence similarity 50 member A | 0.275008177 | 3.30.161 || FAM63A | 3.30.161 | family with sequence similarity 63 member A | 0.309692891 | 3.30.161 || FARSA | 3.30.161 | phenylalanyl-tRNA synthetase alpha subunit | 0.243472131 | 3.30.161 || FBXW12 | 3.30.161 | F-box and WD repeat domain containing 12 | 0.215501759 | 3.30.161 || FCF1 | 3.30.161 | FCF1 rRNA-processing protein | 1.564275516 | 3.30.161 || FLJ35934 | 3.30.161 | FLJ35934 | 1.465558321 | 3.30.161 || FOXC2 | 3.30.161 | forkhead box C2 | 0.494783451 | 3.30.161 || FTX | 3.30.161 | FTX transcript, XIST regulator (non-protein coding) | 0.367138006 | 3.30.161 || GDAP2 | 3.30.161 | ganglioside induced differentiation associated protein 2 | 0.245697891 | 3.30.161 || GLUD2 | 3.30.161 | glutamate dehydrogenase 2 | 0.515300288 | 3.30.161 || GPR180 | 3.30.161 | G protein-coupled receptor 180 | 0.700540683 | 3.30.161 || GRSF1 | 3.30.161 | G-rich RNA sequence binding factor 1 | 0.2286843 | 3.30.161 || GUCD1 | 3.30.161 | guanylyl cyclase domain containing 1 | 0.236375233 | 3.30.161 || HACD4 | 3.30.161 | 3-hydroxyacyl-CoA dehydratase 4 | 0.219712177 | 3.30.161 || HSCB | 3.30.161 | HscB mitochondrial iron-sulfur cluster co-chaperone | 0.401953843 | 3.30.161 || ISG20L2 | 3.30.161 | interferon stimulated exonuclease gene 20 kDa like 2 | 0.577257953 | 3.30.161 || KANSL1L | 3.30.161 | KAT8 regulatory NSL complex subunit 1 like | 0.58843994 | 3.30.161 || KATNB1 | 3.30.161 | katanin p80 (WD repeat containing) subunit B 1 | 0.282564914 | 3.30.161 || KLF8 | 3.30.161 | Kruppel-like factor 8 | 0.94019415 | 3.30.161 || KXD1 | 3.30.161 | KxDL motif containing 1 | 0.255973442 | 3.30.161 || LARS | 3.30.161 | leucyl-tRNA synthetase | 0.269634877 | 3.30.161 || LIME1 | 3.30.161 | Lck interacting transmembrane adaptor 1 | 0.219325616 | 3.30.161 || LMAN2 | 3.30.161 | lectin, mannose binding 2 | 0.27351954 | 3.30.161 || LOC388692 | 3.30.161 | uncharacterized LOC388692 | 0.247042414 | 3.30.161 || LSM4 | 3.30.161 | LSM4 homolog, U6 small nuclear RNA and mRNA degradation associated | 0.295416034 | 3.30.161 || MCM5 | 3.30.161 | minichromosome maintenance complex component 5 | 0.311663026 | 3.30.161 || MED1 | 3.30.161 | mediator complex subunit 1 | 0.437689844 | 3.30.161 || MED10 | 3.30.161 | mediator complex subunit 10 | 0.318993623 | 3.30.161 || MED25 | 3.30.161 | mediator complex subunit 25 | 0.283174309 | 3.30.161 || MFNG | 3.30.161 | MFNG O-fucosylpeptide 3-beta-N-acetylglucosaminyltransferase | 0.281534973 | 3.30.161 || MIB1 | 3.30.161 | mindbomb E3 ubiquitin protein ligase 1 | 0.36953511 | 3.30.161 || MRPS25 | 3.30.161 | mitochondrial ribosomal protein S25 | 0.346073909 | 3.30.161 || MRPS34 | 3.30.161 | mitochondrial ribosomal protein S34 | 0.305962574 | 3.30.161 || MUM1 | 3.30.161 | melanoma associated antigen (mutated) 1 | 0.846361478 | 3.30.161 || MYBL2 | 3.30.161 | MYB proto-oncogene like 2 | 0.321355477 | 3.30.161 || NANOG | 3.30.161 | Nanog homeobox | 0.969002288 | 3.30.161 || NBEA | 3.30.161 | neurobeachin | 0.319732489 | 3.30.161 || NDUFAF7 | 3.30.161 | NADH:ubiquinone oxidoreductase complex assembly factor 7 | 0.275815248 | 3.30.161 || NLGN4X | 3.30.161 | neuroligin 4, X-linked | 0.228910945 | 3.30.161 || NLN | 3.30.161 | neurolysin | 0.526426523 | 3.30.161 || NME6 | 3.30.161 | NME/NM23 nucleoside diphosphate kinase 6 | 0.620866214 | 3.30.161 || NOTCH2NL | 3.30.161 | notch 2 N-terminal like | 0.316218069 | 3.30.161 || NOVA2 | 3.30.161 | neuro-oncological ventral antigen 2 | 0.332706539 | 3.30.161 || NUBPL | 3.30.161 | nucleotide binding protein like | 0.35114588 | 3.30.161 || NUP58 | 3.30.161 | nucleoporin 58 kDa | 0.707272837 | 3.30.161 || NUTM2B-AS1 | 3.30.161 | NUTM2B antisense RNA 1 | 0.618545548 | 3.30.161 || OGFR | 3.30.161 | opioid growth factor receptor | 0.223730018 | 3.30.161 || ORAI2 | 3.30.161 | ORAI calcium release-activated calcium modulator 2 | 0.611215362 | 3.30.161 || ORMDL2 | 3.30.161 | ORMDL sphingolipid biosynthesis regulator 2 | 0.383004896 | 3.30.161 || OTUD6B | 3.30.161 | OTU domain containing 6B | 0.408954059 | 3.30.161 || PABPN1 | 3.30.161 | poly(A) binding protein, nuclear 1 | 0.433609034 | 3.30.161 || PAK1 | 3.30.161 | p21 protein (Cdc42/Rac)-activated kinase 1 | 0.255512807 | 3.30.161 || PAXIP1-AS1 | 3.30.161 | PAXIP1 antisense RNA 1 (head to head) | 0.381161759 | 3.30.161 || PCBP1-AS1 | 3.30.161 | PCBP1 antisense RNA 1 | 0.451561689 | 3.30.161 || PDCD7 | 3.30.161 | programmed cell death 7 | 0.365597024 | 3.30.161 || PDCL | 3.30.161 | phosducin like | 0.248924835 | 3.30.161 || PECR | 3.30.161 | peroxisomal trans-2-enoyl-CoA reductase | 0.677321678 | 3.30.161 || PGF | 3.30.161 | placental growth factor | 0.389492364 | 3.30.161 || PHF19 | 3.30.161 | PHD finger protein 19 | 0.223424043 | 3.30.161 || POLD4 | 3.30.161 | polymerase (DNA) delta 4, accessory subunit | 0.3957221 | 3.30.161 || POLR1B | 3.30.161 | polymerase (RNA) I subunit B | 0.796356992 | 3.30.161 || POLRMT | 3.30.161 | polymerase (RNA) mitochondrial | 0.310785506 | 3.30.161 || PPA2 | 3.30.161 | pyrophosphatase (inorganic) 2 | 0.687462604 | 3.30.161 || PPP2R5D | 3.30.161 | protein phosphatase 2 regulatory subunit B', delta | 0.296598581 | 3.30.161 || PPP5C | 3.30.161 | protein phosphatase 5 catalytic subunit | 0.27648773 | 3.30.161 || PRR11 | 3.30.161 | proline rich 11 | 0.387011318 | 3.30.161 || RAB2B | 3.30.161 | RAB2B, member RAS oncogene family | 0.217029099 | 3.30.161 || RABGAP1 | 3.30.161 | RAB GTPase activating protein 1 | 0.283328283 | 3.30.161 || RAD1 | 3.30.161 | RAD1 checkpoint DNA exonuclease | 0.550238703 | 3.30.161 || RBBP5 | 3.30.161 | retinoblastoma binding protein 5 | 0.383802185 | 3.30.161 || RDH5 | 3.30.161 | retinol dehydrogenase 5 | 1.348755651 | 3.30.161 || RFX3 | 3.30.161 | regulatory factor X3 | 0.398367876 | 3.30.161 || RNGTT | 3.30.161 | RNA guanylyltransferase and 5'-phosphatase | 0.345966138 | 3.30.161 || RRAGD | 3.30.161 | Ras related GTP binding D | 0.370224662 | 3.30.161 || SAMD4B | 3.30.161 | sterile alpha motif domain containing 4B | 0.530246528 | 3.30.161 || SCAF4 | 3.30.161 | SR-related CTD-associated factor 4 | 1.133357927 | 3.30.161 || SEC14L1P1 | 3.30.161 | SEC14 like 1 pseudogene 1 | 0.755378479 | 3.30.161 || SERPING1 | 3.30.161 | serpin peptidase inhibitor, clade G (C1 inhibitor), member 1 | 0.333217799 | 3.30.161 || SGK494 | 3.30.161 | uncharacterized serine/threonine-protein kinase SgK494 | 0.664146991 | 3.30.161 || SLC26A6 | 3.30.161 | solute carrier family 26 member 6 | 0.467606888 | 3.30.161 || SLC35B4 | 3.30.161 | solute carrier family 35 member B4 | 0.224178696 | 3.30.161 || SLC35E1 | 3.30.161 | solute carrier family 35 member E1 | 0.297085088 | 3.30.161 || SMIM8 | 3.30.161 | small integral membrane protein 8 | 0.286061502 | 3.30.161 || SNRNP200 | 3.30.161 | small nuclear ribonucleoprotein U5 subunit 200 | 0.738522656 | 3.30.161 || SNRNP25 | 3.30.161 | small nuclear ribonucleoprotein U11/U12 subunit 25 | 0.558607689 | 3.30.161 || SORBS1 | 3.30.161 | sorbin and SH3 domain containing 1 | 0.297206207 | 3.30.161 ||

TABLE 3B-continued

The genes within the significant gene clusters, listed in Table 3A. (3966 Genes Listed by: Gene Symbol | Gen 2 Module | Gene Description | RowVariance | Gen 3 Module ||)

SREBF2 | 3.30.161 | sterol regulatory element binding transcription factor 2 | 0.231625924 | 3.30.161 || SRFBP1 | 3.30.161 | serum response factor binding protein 1 | 0.98837139 | 3.30.161 || SRGAP1 | 3.30.161 | SLIT-ROBO Rho GTPase activating protein 1 | 0.690167007 | 3.30.161 || SSBP3-AS1 | 3.30.161 | SSBP3 antisense RNA 1 | 0.373058087 | 3.30.161 || STARD10 | 3.30.161 | StAR related lipid transfer domain containing 10 | 0.3466871 | 3.30.161 || STRN | 3.30.161 | striatin | 0.741047152 | 3.30.161 || STX16 | 3.30.161 | syntaxin 16 | 0.412854668 | 3.30.161 || SUSD1 | 3.30.161 | sushi domain containing 1 | 0.485327403 | 3.30.161 || TCAF1 | 3.30.161 | TRPM8 channel-associated factor 1 | 0.347099512 | 3.30.161 || TCTN2 | 3.30.161 | tectonic family member 2 | 0.439404652 | 3.30.161 || THUMPD3-AS1 | 3.30.161 | THUMPD3 antisense RNA 1 | 0.244344561 | 3.30.161 || TM9SF1 | 3.30.161 | transmembrane 9 superfamily member 1 | 0.330628147 | 3.30.161 || TMPRSS6 | 3.30.161 | transmembrane protease, serine 6 | 0.399668197 | 3.30.161 || TOLLIP | 3.30.161 | toll interacting protein | 0.358870057 | 3.30.161 || TOPORS | 3.30.161 | topoisomerase I binding, arginine/serine-rich, E3 ubiquitin protein ligase | 0.367545283 | 3.30.161 || TOR1B | 3.30.161 | torsin family 1 member B | 0.293724707 | 3.30.161 || TRIM38 | 3.30.161 | tripartite motif containing 38 | 0.229195649 | 3.30.161 || TSEN2 | 3.30.161 | tRNA splicing endonuclease subunit 2 | 0.40337825 | 3.30.161 || TSR1 | 3.30.161 | TSR1, 20S rRNA accumulation, homolog (*S. cerevisiae*) | 0.231857811 | 3.30.161 || TTC32 | 3.30.161 | tetratricopeptide repeat domain 32 | 0.363074357 | 3.30.161 || UACA | 3.30.161 | uveal autoantigen with coiled-coil domains and ankyrin repeats | 0.246988249 | 3.30.161 || UBAC1 | 3.30.161 | UBA domain containing 1 | 0.214671317 | 3.30.161 || UBE2S | 3.30.161 | ubiquitin conjugating enzyme E2S | 0.268642983 | 3.30.161 || UBXN2A | 3.30.161 | UBX domain protein 2A | 0.332342825 | 3.30.161 || USP34 | 3.30.161 | ubiquitin specific peptidase 34 | 0.440042036 | 3.30.161 || VTI1A | 3.30.161 | vesicle transport through interaction with t-SNAREs 1A | 0.477960914 | 3.30.161 || WDPCP | 3.30.161 | WD repeat containing planar cell polarity effector | 0.521484164 | 3.30.161 || WDR92 | 3.30.161 | WD repeat domain 92 | 0.604784359 | 3.30.161 || WTAP | 3.30.161 | Wilms tumor 1 associated protein | 0.324388067 | 3.30.161 || WWP1 | 3.30.161 | WW domain containing E3 ubiquitin protein ligase 1 | 0.267222347 | 3.30.161 || ZGPAT | 3.30.161 | zinc finger CCCH-type and G-patch domain containing | 0.35496962 | 3.30.161 || ZNF136 | 3.30.161 | zinc finger protein 136 | 0.741766055 | 3.30.161 || ZNF160 | 3.30.161 | zinc finger protein 160 | 0.472219291 | 3.30.161 || ZNF185 | 3.30.161 | zinc finger protein 185 (LIM domain) | 0.243878375 | 3.30.161 || ZNF275 | 3.30.161 | zinc finger protein 275 | 0.381879871 | 3.30.161 || ZNF333 | 3.30.161 | zinc finger protein 333 | 1.010036815 | 3.30.161 || ZNF37A | 3.30.161 | zinc finger protein 37A | 0.341349617 | 3.30.161 || ZNF37BP | 3.30.161 | zinc finger protein 37B, pseudogene | 1.791939962 | 3.30.161 || ZNF431 | 3.30.161 | zinc finger protein 431 | 2.274358104 | 3.30.161 || ZNF451 | 3.30.161 | zinc finger protein 451 | 0.287704099 | 3.30.161 || ZNF514 | 3.30.161 | zinc finger protein 514 | 0.975589962 | 3.30.161 || ZNF518A | 3.30.161 | zinc finger protein 518A | 0.505753968 | 3.30.161 || ZNF528 | 3.30.161 | zinc finger protein 528 | 0.364951731 | 3.30.161 || ZNF551 | 3.30.161 | zinc finger protein 551 | 1.023046204 | 3.30.161 || ZNF585A | 3.30.161 | zinc finger protein 585A | 0.437874075 | 3.30.161 || ZNF587 | 3.30.161 | zinc finger protein 587 | 0.216364592 | 3.30.161 || ZNF587B | 3.30.161 | zinc finger protein 587B | 0.259307402 | 3.30.161 || ZNF706 | 3.30.161 | zinc finger protein 706 | 0.29526667 | 3.30.161 || ZNF721 | 3.30.161 | zinc finger protein 721 | 0.299909179 | 3.30.161 || ZNF787 | 3.30.161 | zinc finger protein 787 | 0.292078686 | 3.30.161 || AGA | 3.30.162 | aspartylglucosaminidase | 0.233971109 | 3.30.162 || BMS1P5 | 3.30.162 | BMS1, ribosome biogenesis factor pseudogene 5 | 0.681368074 | 3.30.162 || CEP152 | 3.30.162 | centrosomal protein 152 kDa | 0.260393368 | 3.30.162 || CEP89 | 3.30.162 | centrosomal protein 89 kDa | 0.746193621 | 3.30.162 || CXorf21 | 3.30.162 | chromosome X open reading frame 21 | 0.331323197 | 3.30.162 || ETHE1 | 3.30.162 | ethylmalonic encephalopathy 1 | 0.447625879 | 3.30.162 || GTF2H3 | 3.30.162 | general transcription factor IIH subunit 3 | 0.466118302 | 3.30.162 || HOMER3 | 3.30.162 | homer scaffolding protein 3 | 0.432097501 | 3.30.162 || LOC100506282 | 3.30.162 | uncharacterized LOC100506282 | 0.967848883 | 3.30.162 || MFSD4B | 3.30.162 | major facilitator superfamily domain containing 4B | 0.426375024 | 3.30.162 || NPRL2 | 3.30.162 | NPR2-like, GATOR1 complex subunit | 0.259521118 | 3.30.162 || NXPE3 | 3.30.162 | neurexophilin and PC-esterase domain family member 3 | 0.655944585 | 3.30.162 || RIT1 | 3.30.162 | Ras-like without CAAX 1 | 0.708957957 | 3.30.162 || SLC35D1 | 3.30.162 | solute carrier family 35 member D1 | 0.355639249 | 3.30.162 || SPRY4-IT1 | 3.30.162 | SPRY4 intronic transcript 1 | 0.272385534 | 3.30.162 || TRMT10B | 3.30.162 | tRNA methyltransferase 10B | 0.260649423 | 3.30.162 || TTC5 | 3.30.162 | tetratricopeptide repeat domain 5 | 0.310589861 | 3.30.162 || UBE3D | 3.30.162 | ubiquitin protein ligase E3D | 0.606740871 | 3.30.162 || UCKL1 | 3.30.162 | uridine-cytidine kinase 1-like 1 | 0.301351666 | 3.30.162 || VHL | 3.30.162 | von Hippel-Lindau tumor suppressor | 0.599904226 | 3.30.162 || ZDHHC16 | 3.30.162 | zinc finger DHHC-type containing 16 | 0.257332465 | 3.30.162 || ZNF230 | 3.30.162 | zinc finger protein 230 | 0.531498798 | 3.30.162 || ZNF75A | 3.30.162 | zinc finger protein 75a | 0.228062974 | 3.30.162 || ZNF850 | 3.30.162 | zinc finger protein 850 | 0.279345017 | 3.30.162 || AAK1 | 3.30.163 | AP2 associated kinase 1 | 0.358812961 | 3.30.163 || ABCF2 | 3.30.163 | ATP binding cassette subfamily F member 2 | 0.22823075 | 3.30.163 || BSG | 3.30.163 | basigin (Ok blood group) | 0.316299297 | 3.30.163 || CCM2 | 3.30.163 | CCM2 scaffolding protein | 0.317281828 | 3.30.163 || CCZ1B | 3.30.163 | CCZ1 homolog B, vacuolar protein trafficking and biogenesis associated | 0.349017772 | 3.30.163 || CRIPT | 3.30.163 | CXXC repeat containing interactor of PDZ3 domain | 0.421443808 | 3.30.163 || EBLN3 | 3.30.163 | endogenous Bornavirus-like nucleoprotein 3 | 0.259890806 | 3.30.163 || GPATCH2L | 3.30.163 | G-patch domain containing 2 like | 1.960179904 | 3.30.163 || H6PD | 3.30.163 | hexose-6-phosphate dehydrogenase (glucose 1-dehydrogenase) | 0.420292436 | 3.30.163 || NOP10 | 3.30.163 | NOP10 ribonucleoprotein | 0.23502896 | 3.30.163 || NPTN-IT1 | 3.30.163 | NPTN intronic transcript 1 | 0.645011649 | 3.30.163 || PPHLN1 | 3.30.163 | periphilin 1 | 0.254201029 | 3.30.163 || RABEP1 | 3.30.163 | rabaptin, RAB GTPase binding effector protein 1 | 0.247033339 | 3.30.163 || SCO1 | 3.30.163 | SCO1 cytochrome c oxidase assembly protein | 0.408620694 | 3.30.163 || SMO | 3.30.163 | smoothened, frizzled class receptor | 0.627909031 | 3.30.163 || SSNA1 | 3.30.163 | Sjogren syndrome nuclear autoantigen 1 | 0.228474379 | 3.30.163 || TMEM209 | 3.30.163 | transmembrane protein 209 | 0.46025373 | 3.30.163 || TRA2A | 3.30.163 | transformer 2 alpha homolog (*Drosophila*) | 0.704028796 | 3.30.163 || TXNDC17 | 3.30.163 | thioredoxin domain containing 17 | 0.220925814 | 3.30.163 || ZNF669 | 3.30.163 | zinc finger protein 669 | 0.390451114 | 3.30.163 || AASS | 3.30.164 | aminoadipate-semialdehyde synthase |

TABLE 3B-continued

The genes within the significant gene clusters, listed in Table 3A. (3966 Genes Listed by: Gene Symbol | Gen 2 Module | Gene Description | RowVariance | Gen 3 Module ||)

1.282105419 | 3.30.164 || ARIH2 | 3.30.164 | ariadne RBR E3 ubiquitin protein ligase 2 | 0.368630654 | 3.30.164 || BORCS6 | 3.30.164 | BLOC-1 related complex subunit 6 | 0.253484607 | 3.30.164 || C12orf43 | 3.30.164 | chromosome 12 open reading frame 43 | 0.606791983 | 3.30.164 || C20orf194 | 3.30.164 | chromosome 20 open reading frame 194 | 0.496257029 | 3.30.164 || ELAVL3 | 3.30.164 | ELAV like neuron-specific RNA binding protein 3 | 0.538596786 | 3.30.164 || FBXL14 | 3.30.164 | F-box and leucine-rich repeat protein 14 | 0.24496978 | 3.30.164 || HOXC9 | 3.30.164 | homeobox C9 | 0.439238775 | 3.30.164 || MAPRE3 | 3.30.164 | microtubule associated protein RP/EB family member 3 | 0.357711959 | 3.30.164 || MBIP | 3.30.164 | MAP3K12 binding inhibitory protein 1 | 0.707044418 | 3.30.164 || MTRF1L | 3.30.164 | mitochondrial translational release factor 1 like | 0.512985038 | 3.30.164 || NMT1 | 3.30.164 | N-myristoyltransferase 1 | 0.344492238 | 3.30.164 || NPEPL1 | 3.30.164 | aminopeptidase-like 1 | 0.505830032 | 3.30.164 || NRIP1 | 3.30.164 | nuclear receptor interacting protein 1 | 0.540479072 | 3.30.164 || NUMBL | 3.30.164 | numb homolog (*Drosophila*)-like | 0.452337826 | 3.30.164 || PALM2 | 3.30.164 | paralemmin 2 | 0.624064675 | 3.30.164 || RAPH1 | 3.30.164 | Ras association (RalGDS/AF-6) and pleckstrin homology domains 1 | 0.246647221 | 3.30.164 || RPRD2 | 3.30.164 | regulation of nuclear pre-mRNA domain containing 2 | 0.355487833 | 3.30.164 || SEC22A | 3.30.164 | SEC22 homolog A, vesicle trafficking protein | 0.390611834 | 3.30.164 || SEZ6L2 | 3.30.164 | seizure related 6 homolog (mouse)-like 2 | 0.372348623 | 3.30.164 || STXBP5 | 3.30.164 | syntaxin binding protein 5 | 1.089528566 | 3.30.164 || TBC1D32 | 3.30.164 | TBC1 domain family member 32 | 0.324652475 | 3.30.164 || TMEM67 | 3.30.164 | transmembrane protein 67 | 0.677453744 | 3.30.164 || UBN2 | 3.30.164 | ubinuclein 2 | 0.436643149 | 3.30.164 || VAMP2 | 3.30.164 | vesicle associated membrane protein 2 | 0.389730645 | 3.30.164 || VGLL4 | 3.30.164 | vestigial like family member 4 | 0.273340825 | 3.30.164 || WASF1 | 3.30.164 | WAS protein family member 1 | 0.455656022 | 3.30.164 || ZNF785 | 3.30.164 | zinc finger protein 785 | 2.268123854 | 3.30.164 || ADAMTS17 | 3.31 | ADAM metallopeptidase with thrombospondin type 1 motif 17 | 0.399201568 | — || AHDC1 | 3.31 | AT-hook DNA binding motif containing 1 | 0.501331107 | — || ARMC5 | 3.31 | armadillo repeat containing 5 | 0.428724173 | — || ATHL1 | 3.31 | ATH1, acid trehalase-like 1 (yeast) | 0.249640217 | — || DGCR14 | 3.31 | DiGeorge syndrome critical region gene 14 | 0.279565174 | — || EML2 | 3.31 | echinoderm microtubule associated protein like 2 | 0.429898141 | — || FMN2 | 3.31 | formin 2 | 0.475511702 | — || GLIS3 | 3.31 | GLIS family zinc finger 3 | 1.01236834 | — || GLTSCR2 | 3.31 | glioma tumor suppressor candidate region gene 2 | 0.494146367 | — || HMCN2 | 3.31 | hemicentin 2 | 0.248366682 | — || IRF4 | 3.31 | interferon regulatory factor 4 | 0.584033475 | — || JSRP1 | 3.31 | junctional sarcoplasmic reticulum protein 1 | 0.693162624 | — || LIMD2 | 3.31 | LIM domain containing 2 | 0.223954551 | — || LRRC16B | 3.31 | leucine rich repeat containing 16B | 0.350578075 | — || MCPH1 | 3.31 | microcephalin 1 | 0.244538247 | — || MYBL1 | 3.31 | MYB proto-oncogene like 1 | 0.576729686 | — || NBAT1 | 3.31 | neuroblastoma associated transcript 1 | 0.508058663 | — || PAX5 | 3.31 | paired box 5 | 0.62551336 | — || PDE3B | 3.31 | phosphodiesterase 3B | 0.385717865 | — || PDE7B | 3.31 | phosphodiesterase 7B | 0.88226372 | — || PLCD3 | 3.31 | phospholipase C delta 3 | 0.470611566 | — || PRKD2 | 3.31 | protein kinase D2 | 1.164808234 | — || REXO1 | 3.31 | REX1, RNA exonuclease 1 homolog | 0.592885734 | — || SAMD5 | 3.31 | sterile alpha motif domain containing 5 | 0.931112195 | — || SLC4A9 | 3.31 | solute carrier family 4 member 9 | 0.372045141 | — || SPATA6L | 3.31 | spermatogenesis associated 6 like | 0.331836242 | — || TBC1D10C | 3.31 | TBC1 domain family member 10C | 0.350887391 | — || TBXA2R | 3.31 | thromboxane A2 receptor | 0.409684751 | — || TCF15 | 3.31 | transcription factor 15 (basic helix-loop-helix) | 0.330400545 | — || TRO | 3.31 | trophinin | 0.297771396 | — || ZXDB | 3.31 | zinc finger, X-linked, duplicated B | 0.217360817 | — || AK2 | 3.33 | adenylate kinase 2 | 0.327779045 | 3.33.178 || AMFR | 3.33 | autocrine motility factor receptor, E3 ubiquitin protein ligase | 3.041255337 | 3.33.178 || AP1G2 | 3.33 | adaptor related protein complex 1 gamma 2 subunit | 0.267688081 | — || ATAD2 | 3.33 | ATPase family, AAA domain containing 2 | 0.245118807 | — || ATF7IP2 | 3.33 | activating transcription factor 7 interacting protein 2 | 0.225243445 | — || ATOX1 | 3.33 | antioxidant 1 copper chaperone | 0.22425753 | 3.33.178 || ATP6V1E1 | 3.33 | ATPase H+ transporting V1 subunit E1 | 0.238647016 | 3.33.178 || ATXN7 | 3.33 | ataxin 7 | 0.351234243 | — || AURKAIP1 | 3.33 | aurora kinase A interacting protein 1 | 0.224613317 | 3.33.178 || BCAP31 | 3.33 | B-cell receptor-associated protein 31 | 0.276306527 | — || C11orf80 | 3.33 | chromosome 11 open reading frame 80 | 0.684775027 | 3.33.178 || CA5BP1 | 3.33 | carbonic anhydrase VB pseudogene 1 | 0.711806365 | 3.33.178 || CARF | 3.33 | calcium responsive transcription factor | 0.439071516 | — || CCDC28B | 3.33 | coiled-coil domain containing 28B | 0.338314322 | 3.33.178 || CLPP | 3.33 | caseinolytic mitochondrial matrix peptidase proteolytic subunit | 0.275667193 | 3.33.178 || CYLD | 3.33 | CYLD lysine 63 deubiquitinase | 0.566163172 | — || DCAF8 | 3.33 | DDB1 and CUL4 associated factor 8 | 0.530852721 | 3.33.178 || DNAJA1 | 3.33 | DnaJ heat shock protein family (Hsp40) member A1 | 0.268873868 | 3.33.178 || ECSIT | 3.33 | ECSIT signalling integrator | 0.352705202 | 3.33.178 || FAM118B | 3.33 | family with sequence similarity 118 member B | 0.238839634 | 3.33.178 || FAM214A | 3.33 | family with sequence similarity 214 member A | 0.302710804 | — || FAM21C | 3.33 | family with sequence similarity 21 member C | 0.27369566 | — || FBXL18 | 3.33 | F-box and leucine-rich repeat protein 18 | 0.232762532 | — || FBXO22 | 3.33 | F-box protein 22 | 1.788767882 | 3.33.178 || GATAD1 | 3.33 | GATA zinc finger domain containing 1 | 0.356910926 | — || GLIPR2 | 3.33 | GLI pathogenesis-related 2 | 0.665857308 | — || GPR155 | 3.33 | G protein-coupled receptor 155 | 1.604927816 | 3.33.178 || GSTK1 | 3.33 | glutathione S-transferase kappa 1 | 0.220726129 | — || GUSB | 3.33 | glucuronidase, beta | 0.280321806 | — || HAGH | 3.33 | hydroxyacylglutathione hydrolase | 0.256994681 | 3.33.178 || HELLS | 3.33 | helicase, lymphoid-specific | 0.263937318 | — || HN1 | 3.33 | hematological and neurological expressed 1 | 0.354875566 | 3.33.178 || HSPH1 | 3.33 | heat shock protein family H (Hsp110) member 1 | 0.234026353 | 3.33.178 || ILF3-AS1 | 3.33 | ILF3 antisense RNA 1 (head to head) | 0.307890642 | — || KCNE3 | 3.33 | potassium voltage-gated channel subfamily E regulatory subunit 3 | 0.271632127 | — || LPIN1 | 3.33 | lipin 1 | 0.326521724 | — || LRPAP1 | 3.33 | LDL receptor related protein associated protein 1 | 0.233469226 | — || MAP3K8 | 3.33 | mitogen-activated protein kinase kinase kinase 8 | 1.107677445 | 3.33.178 || MCM8 | 3.33 | minichromosome maintenance 8 homologous recombination repair factor | 0.540601513 | — || MIEN1 | 3.33 | migration and invasion enhancer 1 | 0.239734321 | 3.33.178 || MSRB1 | 3.33 | methionine sulfoxide reductase B1 | 0.415707406 | 3.33.178 || N4BP2 | 3.33 | NEDD4 binding protein 2 | 0.729558853 | — || NCBP1 | 3.33 | nuclear cap binding protein subunit 1 | 0.222253372 | 3.33.178 ||

TABLE 3B-continued

The genes within the significant gene clusters, listed in Table 3A. (3966 Genes Listed by: Gene Symbol | Gen 2 Module | Gene Description | RowVariance | Gen 3 Module ||)

NUPR1 | 3.33 | nuclear protein 1, transcriptional regulator | 0.445955944 | — || PLXNC1 | 3.33 | plexin C1 | 0.656119334 | 3.33.178 || POLR2J4 | 3.33 | polymerase (RNA) II subunit J4, pseudogene | 0.896981432 | 3.33.178 || PRPF38B | 3.33 | pre-mRNA processing factor 38B | 1.067536004 | 3.33.178 || PUDP | 3.33 | pseudouridine 5'-phosphatase | 0.227580038 | — || RAP1GDS1 | 3.33 | Rap1 GTPase-GDP dissociation stimulator 1 | 0.232134376 | 3.33.178 || RBBP6 | 3.33 | retinoblastoma binding protein 6 | 0.247349278 | — || RGS10 | 3.33 | regulator of G-protein signaling 10 | 0.218425273 | 3.33.178 || RHNO1 | 3.33 | RAD9-HUS1-RAD1 interacting nuclear orphan 1 | 0.743633056 | 3.33.178 || RNF213 | 3.33 | ring finger protein 213 | 0.678545516 | 3.33.178 || SCLT1 | 3.33 | sodium channel and clathrin linker 1 | 0.265780406 | — || SMYD2 | 3.33 | SET and MYND domain containing 2 | 0.242059162 | 3.33.178 || SYTL3 | 3.33 | synaptotagmin like 3 | 2.021400017 | 3.33.178 || SZRD1 | 3.33 | SUZ RNA binding domain containing 1 | 0.220013406 | — || TALDO1 | 3.33 | transaldolase 1 | 0.304590832 | — || TEFM | 3.33 | transcription elongation factor, mitochondrial | 0.957503241 | 3.33.178 || THBD | 3.33 | thrombomodulin | 0.701206969 | 3.33.178 || TKT | 3.33 | transketolase | 0.402606279 | — || TMEM11 | 3.33 | transmembrane protein 11 | 0.2704814 | 3.33.178 || TMEM140 | 3.33 | transmembrane protein 140 | 0.631231263 | — || TMEM141 | 3.33 | transmembrane protein 141 | 0.251271929 | — || TP53RK | 3.33 | TP53 regulating kinase | 0.340157462 | 3.33.178 || TRAPPC10 | 3.33 | trafficking protein particle complex 10 | 1.066633667 | 3.33.178 || TUSC2 | 3.33 | tumor suppressor candidate 2 | 0.283715013 | 3.33.178 || UNK | 3.33 | unkempt family zinc finger | 0.596736094 | 3.33.178 || UVSSA | 3.33 | UV stimulated scaffold protein A | 0.672393502 | 3.33.178 || VASH1 | 3.33 | vasohibin 1 | 1.785854403 | 3.33.178 || ZCCHC7 | 3.33 | zinc finger CCHC-type containing 7 | 0.638314648 | 3.33.178 || ZMAT3 | 3.33 | zinc finger matrin-type 3 | 0.354623939 | — || ZNF224 | 3.33 | zinc finger protein 224 | 0.87763591 | 3.33.178 || ZNF568 | 3.33 | zinc finger protein 568 | 0.236065721 | — || ZXDC | 3.33 | ZXD family zinc finger C | 0.86392643 | 3.33.178 || AK2 | 3.33.178 | adenylate kinase 2 | 0.327779045 | 3.33.178 || AMFR | 3.33.178 | autocrine motility factor receptor, E3 ubiquitin protein ligase | 3.041255337 | 3.33.178 || ATOX1 | 3.33.178 | antioxidant 1 copper chaperone | 0.22425753 | 3.33.178 || ATP6V1E1 | 3.33.178 | ATPase H+ transporting V1 subunit E1 | 0.238647016 | 3.33.178 || AURKAIP1 | 3.33.178 | aurora kinase A interacting protein 1 | 0.224613317 | 3.33.178 || C11orf80 | 3.33.178 | chromosome 11 open reading frame 80 | 0.684775027 | 3.33.178 || CA5BP1 | 3.33.178 | carbonic anhydrase VB pseudogene 1 | 0.711806365 | 3.33.178 || CCDC28B | 3.33.178 | coiled-coil domain containing 28B | 0.338314322 | 3.33.178 || CLPP | 3.33.178 | caseinolytic mitochondrial matrix peptidase proteolytic subunit | 0.275667193 | 3.33.178 || DCAF8 | 3.33.178 | DDB1 and CUL4 associated factor 8 | 0.530852721 | 3.33.178 || DNAJA1 | 3.33.178 | DnaJ heat shock protein family (Hsp40) member A1 | 0.268873868 | 3.33.178 || ECSIT | 3.33.178 | ECSIT signalling integrator | 0.352705202 | 3.33.178 || FAM118B | 3.33.178 | family with sequence similarity 118 member B | 0.238839634 | 3.33.178 || FBXO22 | 3.33.178 | F-box protein 22 | 1.788767882 | 3.33.178 || GPR155 | 3.33.178 | G protein-coupled receptor 155 | 1.604927816 | 3.33.178 || HAGH | 3.33.178 | hydroxyacylglutathione hydrolase | 0.256994681 | 3.33.178 || HN1 | 3.33.178 | hematological and neurological expressed 1 | 0.354875566 | 3.33.178 || HSPH1 | 3.33.178 | heat shock protein family H (Hsp110) member 1 | 0.234026353 | 3.33.178 || MAP3K8 | 3.33.178 | mitogen-activated protein kinase kinase kinase 8 | 1.107677445 | 3.33.178 || MIEN1 | 3.33.178 | migration and invasion enhancer 1 | 0.239734321 | 3.33.178 || MSRB1 | 3.33.178 | methionine sulfoxide reductase B1 | 0.415707406 | 3.33.178 || NCBP1 | 3.33.178 | nuclear cap binding protein subunit 1 | 0.222253372 | 3.33.178 || PLXNC1 | 3.33.178 | plexin C1 | 0.656119334 | 3.33.178 || POLR2J4 | 3.33.178 | polymerase (RNA) II subunit J4, pseudogene | 0.896981432 | 3.33.178 || PRPF38B | 3.33.178 | pre-mRNA processing factor 38B | 1.067536004 | 3.33.178 || RAP1GDS1 | 3.33.178 | Rap1 GTPase-GDP dissociation stimulator 1 | 0.232134376 | 3.33.178 || RGS10 | 3.33.178 | regulator of G-protein signaling 10 | 0.218425273 | 3.33.178 || RHNO1 | 3.33.178 | RAD9-HUS1-RAD1 interacting nuclear orphan 1 | 0.743633056 | 3.33.178 || RNF213 | 3.33.178 | ring finger protein 213 | 0.678545516 | 3.33.178 || SMYD2 | 3.33.178 | SET and MYND domain containing 2 | 0.242059162 | 3.33.178 || SYTL3 | 3.33.178 | synaptotagmin like 3 | 2.021400017 | 3.33.178 || TEFM | 3.33.178 | transcription elongation factor, mitochondrial | 0.957503241 | 3.33.178 || THBD | 3.33.178 | thrombomodulin | 0.701206969 | 3.33.178 || TMEM11 | 3.33.178 | transmembrane protein 11 | 0.2704814 | 3.33.178 || TP53RK | 3.33.178 | TP53 regulating kinase | 0.340157462 | 3.33.178 || TRAPPC10 | 3.33.178 | trafficking protein particle complex 10 | 1.066633667 | 3.33.178 || TUSC2 | 3.33.178 | tumor suppressor candidate 2 | 0.283715013 | 3.33.178 || UNK | 3.33.178 | unkempt family zinc finger | 0.596736094 | 3.33.178 || UVSSA | 3.33.178 | UV stimulated scaffold protein A | 0.672393502 | 3.33.178 || VASH1 | 3.33.178 | vasohibin 1 | 1.785854403 | 3.33.178 || ZCCHC7 | 3.33.178 | zinc finger CCHC-type containing 7 | 0.638314648 | 3.33.178 || ZNF224 | 3.33.178 | zinc finger protein 224 | 0.87763591 | 3.33.178 || ZXDC | 3.33.178 | ZXD family zinc finger C | 0.86392643 | 3.33.178 || ABHD18 | 3.34 | abhydrolase domain containing 18 | 0.347263669 | 3.34.183 || ACAP1 | 3.34 | ArfGAP with coiled-coil, ankyrin repeat and PH domains 1 | 0.797943451 | 3.34.181 || ACSL5 | 3.34 | acyl-CoA synthetase long-chain family member 5 | 0.518299994 | 3.34.183 || ADAP2 | 3.34 | ArfGAP with dual PH domains 2 | 0.706325016 | 3.34.183 || AGO2 | 3.34 | argonaute 2, RISC catalytic component | 0.494685271 | 3.34.183 || AKAP7 | 3.34 | A-kinase anchoring protein 7 | 0.308544402 | 3.34.181 || ALDH16A1 | 3.34 | aldehyde dehydrogenase 16 family member A1 | 0.358801572 | 3.34.181 || ANKRD13D | 3.34 | ankyrin repeat domain 13 family member D | 0.496209116 | 3.34.183 || AOAH | 3.34 | acyloxyacyl hydrolase | 0.788599525 | 3.34.182 || APOL3 | 3.34 | apolipoprotein L3 | 0.444787301 | 3.34.181 || AQP3 | 3.34 | aquaporin 3 (Gill blood group) | 0.669230649 | 3.34.181 || ARL10 | 3.34 | ADP ribosylation factor like GTPase 10 | 0.274793381 | 3.34.181 || ARMC6 | 3.34 | armadillo repeat containing 6 | 0.292418867 | 3.34.181 || ARMCX3 | 3.34 | armadillo repeat containing, X-linked 3 | 0.344611292 | 3.34.181 || ARNTL | 3.34 | aryl hydrocarbon receptor nuclear translocator like | 0.261599179 | 3.34.182 || ATF3 | 3.34 | activating transcription factor 3 | 3.058885398 | 3.34.181 || B3GAT3 | 3.34 | beta-1,3-glucuronyltransferase 3 | 0.362118456 | 3.34.181 || BMP8B | 3.34 | bone morphogenetic protein 8b | 0.401399873 | 3.34.183 || BTN3A3 | 3.34 | butyrophilin subfamily 3 member A3 | 0.359570298 | 3.34.181 || C12orf66 | 3.34 | chromosome 12 open reading frame 66 | 1.186714159 | 3.34.181 || C14orf28 | 3.34 | chromosome 14 open reading frame 28 | 0.351876729 | 3.34.181 || C1QTNF7 | 3.34 | C1q and tumor necrosis factor related protein 7 | 2.282375332 | 3.34.181 || C5orf56 | 3.34 | chromosome 5 open reading frame 56 | 0.401852251 | 3.34.183 || C7orf73 | 3.34 | chromosome 7

TABLE 3B-continued

The genes within the significant gene clusters, listed in Table 3A. (3966 Genes Listed by: Gene Symbol | Gen 2 Module | Gene Description | RowVariance | Gen 3 Module ||)

open reading frame 73 | 0.253127871 | 3.34.182 || CALM3 | 3.34 | calmodulin 3 (phosphorylase kinase, delta) | 0.505532715 | 3.34.181 || CAMKK2 | 3.34 | calcium/calmodulin-dependent protein kinase kinase 2 | 0.522766945 | 3.34.182 || CASD1 | 3.34 | CAS1 domain containing 1 | 0.997233305 | 3.34.181 || CBFA2T2 | 3.34 | core-binding factor, runt domain, alpha subunit 2; translocated to, 2 | 0.686453527 | 3.34.181 || CBX5 | 3.34 | chromobox 5 | 0.943629254 | 3.34.183 || CCNL1 | 3.34 | cyclin L1 | 0.718233035 | 3.34.181 || CD180 | 3.34 | CD180 molecule | 0.577642978 | 3.34.182 || CDKN1A | 3.34 | cyclin-dependent kinase inhibitor 1A | 0.293563749 | 3.34.181 || CEP85L | 3.34 | centrosomal protein 85 kDa-like | 0.426902691 | 3.34.181 || CFLAR | 3.34 | CASP8 and FADD like apoptosis regulator | 1.01380616 | 3.34.183 || CHMP2B | 3.34 | charged multivesicular body protein 2B | 0.226092619 | 3.34.181 || CNNM3 | 3.34 | cyclin and CBS domain divalent metal cation transport mediator 3 | 0.561866781 | 3.34.181 || CRAMP1 | 3.34 | cramped chromatin regulator homolog 1 | 0.279416937 | 3.34.183 || CSPG4 | 3.34 | chondroitin sulfate proteoglycan 4 | 0.541725567 | 3.34.182 || CTSZ | 3.34 | cathepsin Z | 1.961412647 | 3.34.181 || CUEDC1 | 3.34 | CUE domain containing 1 | 0.249274597 | 3.34.181 || CXADR | 3.34 | coxsackie virus and adenovirus receptor | 1.789764956 | 3.34.183 || CXXC5 | 3.34 | CXXC finger protein 5 | 0.47215513 | 3.34.181 || DIS3L2 | 3.34 | DIS3 like 3'-5' exoribonuclease 2 | 0.960816554 | 3.34.181 || DLEU2 | 3.34 | deleted in lymphocytic leukemia 2 (non-protein coding) | 1.814822257 | 3.34.183 || DNAJB14 | 3.34 | DnaJ heat shock protein family (Hsp40) member B14 | 0.355043803 | 3.34.181 || DTWD1 | 3.34 | DTW domain containing 1 | 0.617079271 | 3.34.181 || EFHC1 | 3.34 | EF-hand domain (C-terminal) containing 1 | 0.400427115 | 3.34.181 || EGFR | 3.34 | epidermal growth factor receptor | 2.045949226 | 3.34.181 || EIF1AX | 3.34 | eukaryotic translation initiation factor 1A, X-linked | 0.416610933 | 3.34.182 || ENPP7 | 3.34 | ectonucleotide pyrophosphatase/phosphodiesterase 7 | 0.278869659 | 3.34.181 || ERCC6L2 | 3.34 | excision repair cross-complementation group 6 like 2 | 0.285980254 | 3.34.181 || ETV1 | 3.34 | ETS variant 1 | 0.912856796 | 3.34.181 || FAM3A | 3.34 | family with sequence similarity 3 member A | 0.326794539 | 3.34.181 || FAM58A | 3.34 | family with sequence similarity 58 member A | 0.295626083 | 3.34.181 || FAM63B | 3.34 | family with sequence similarity 63 member B | 0.728481399 | 3.34.181 || FBXO21 | 3.34 | F-box protein 21 | 0.506755406 | 3.34.181 || FGD4 | 3.34 | FYVE, RhoGEF and PH domain containing 4 | 0.484661461 | 3.34.181 || FNIP2 | 3.34 | folliculin interacting protein 2 | 0.471294846 | 3.34.181 || FRMD3 | 3.34 | FERM domain containing 3 | 1.477940515 | 3.34.181 || FUBP3 | 3.34 | far upstream element (FUSE) binding protein 3 | 0.241847541 | 3.34.182 || FXR2 | 3.34 | FMR1 autosomal homolog 2 | 0.231085202 | 3.34.181 || GALK2 | 3.34 | galactokinase 2 | 0.343011992 | 3.34.181 || GAPLINC | 3.34 | gastric adenocarcinoma associated, positive CD44 regulator, long intergenic non-coding RNA | 0.443804638 | 3.34.182 || GAS7 | 3.34 | growth arrest specific 7 | 0.543059417 | 3.34.182 || GEMIN2 | 3.34 | gem nuclear organelle associated protein 2 | 0.919606402 | 3.34.181 || GINM1 | 3.34 | glycoprotein integral membrane 1 | 0.222152336 | 3.34.181 || GOSR1 | 3.34 | golgi SNAP receptor complex member 1 | 0.293067756 | 3.34.181 || GOSR2 | 3.34 | golgi SNAP receptor complex member 2 | 0.316869064 | 3.34.181 || GPR137 | 3.34 | G protein-coupled receptor 137 | 0.366510951 | 3.34.181 || GSE1 | 3.34 | Gse1 coiled-coil protein | 0.856456124 | 3.34.182 || GSS | 3.34 | glutathione synthetase | 0.3066072 | 3.34.181 || HCFC2 | 3.34 | host cell factor C2 | 0.503475927 | 3.34.181 || HERC5 | 3.34 | HECT and RLD domain containing E3 ubiquitin protein ligase 5 | 0.538314901 | 3.34.181 || HMGXB3 | 3.34 | HMG-box containing 3 | 0.472704277 | 3.34.181 || HSD11B1 | 3.34 | hydroxysteroid (11-beta) dehydrogenase 1 | 0.37414609 | 3.34.183 || IFT74 | 3.34 | intraflagellar transport 74 | 0.768727706 | 3.34.181 || IL18 | 3.34 | interleukin 18 | 0.717477945 | 3.34.181 || IL34 | 3.34 | interleukin 34 | 0.311738031 | 3.34.181 || ING3 | 3.34 | inhibitor of growth family member 3 | 0.217453446 | 3.34.181 || IPP | 3.34 | intracisternal A particle-promoted polypeptide | 0.375329701 | 3.34.181 || IRF2BP2 | 3.34 | interferon regulatory factor 2 binding protein 2 | 0.349979352 | 3.34.182 || ITPRIPL2 | 3.34 | inositol 1,4,5-trisphosphate receptor interacting protein-like 2 | 0.321902861 | 3.34.181 || KCNAB1 | 3.34 | potassium voltage-gated channel subfamily A member regulatory beta subunit 1 | 2.163453915 | 3.34.181 || KDSR | 3.34 | 3-ketodihydrosphingosine reductase | 0.255843924 | 3.34.181 || KIAA0040 | 3.34 | KIAA0040 | 0.299569126 | 3.34.183 || KIAA1715 | 3.34 | KIAA1715 | 0.554843041 | 3.34.181 || KIAA2026 | 3.34 | KIAA2026 | 0.340138639 | 3.34.181 || KLF6 | 3.34 | Kruppel-like factor 6 | 0.335741053 | 3.34.181 || KMT2E | 3.34 | lysine methyltransferase 2E | 0.391708808 | 3.34.181 || KMT5B | 3.34 | lysine methyltransferase 5B | 0.320865943 | 3.34.181 || L1TD1 | 3.34 | LINE-1 type transposase domain containing 1 | 0.295829028 | 3.34.183 || LATS2 | 3.34 | large tumor suppressor kinase 2 | 0.416031539 | 3.34.182 || LGALS2 | 3.34 | lectin, galactoside-binding, soluble, 2 | 0.899211275 | 3.34.183 || LIN52 | 3.34 | lin-52 DREAM MuvB core complex component | 0.27931529 | 3.34.181 || LITAF | 3.34 | lipopolysaccharide-induced TNF factor | 0.369216561 | 3.34.183 || LMLN | 3.34 | leishmanolysin like peptidase | 0.257046037 | 3.34.181 || LOC101927204 | 3.34 | uncharacterized LOC101927204 | 0.772510645 | 3.34.181 || LOC102724094 | 3.34 | uncharacterized LOC102724094 | 0.548308199 | 3.34.181 || LRRC46 | 3.34 | leucine rich repeat containing 46 | 0.451347236 | 3.34.182 || LY96 | 3.34 | lymphocyte antigen 96 | 0.314354256 | 3.34.182 || LYAR | 3.34 | Ly1 antibody reactive | 0.220128558 | 3.34.183 || MAGI3 | 3.34 | membrane associated guanylate kinase, WW and PDZ domain containing 3 | 0.277852189 | 3.34.181 || MAML2 | 3.34 | mastermind like transcriptional coactivator 2 | 0.226580944 | 3.34.181 || MANF | 3.34 | mesencephalic astrocyte derived neurotrophic factor | 0.307536561 | 3.34.182 || MBD4 | 3.34 | methyl-CpG binding domain 4 DNA glycosylase | 0.249626556 | 3.34.183 || MBNL3 | 3.34 | muscleblind like splicing regulator 3 | 0.264231685 | 3.34.181 || MCL1 | 3.34 | myeloid cell leukemia 1 | 0.289826855 | 3.34.181 || MCOLN1 | 3.34 | mucolipin 1 | 0.352743785 | 3.34.181 || MDGA1 | 3.34 | MAM domain containing glycosylphosphatidylinositol anchor 1 | 0.272317702 | 3.34.182 || MDM4 | 3.34 | MDM4, p53 regulator | 0.260834197 | 3.34.181 || MFSD12 | 3.34 | major facilitator superfamily domain containing 12 | 0.611241382 | 3.34.181 || MPHOSPH8 | 3.34 | M-phase phosphoprotein 8 | 0.453451819 | 3.34.182 || MPHOSPH9 | 3.34 | M-phase phosphoprotein 9 | 0.789933229 | 3.34.183 || MSANTD2 | 3.34 | Myb/SANT DNA binding domain containing 2 | 0.713568311 | 3.34.181 || MTAP | 3.34 | methylthioadenosine phosphorylase | 0.720927807 | 3.34.182 || MTHFR | 3.34 | methylenetetrahydrofolate reductase (NAD(P)H) | 0.714030773 | 3.34.183 || MTPAP | 3.34 | mitochondrial poly(A) polymerase | 0.375695773 | 3.34.181 || MUC5AC | 3.34 | mucin 5AC, oligomeric mucus/gel-forming | 1.13884726 | 3.34.181 || MYCBP2 | 3.34 | MYC binding protein 2, E3 ubiquitin protein ligase | 0.458305109 | 3.34.181 || MYDGF | 3.34 | myeloid-derived growth factor |

TABLE 3B-continued

The genes within the significant gene clusters, listed in Table 3A. (3966 Genes Listed by: Gene Symbol | Gen 2 Module | Gene Description | RowVariance | Gen 3 Module ||)

0.324808966 | 3.34.182 || MYLIP | 3.34 | myosin regulatory light chain interacting protein | 0.285629863 | 3.34.181 || NAGK | 3.34 | N-acetylglucosamine kinase | 0.362682316 | 3.34.181 || NBEAL1 | 3.34 | neurobeachin like 1 | 1.746272399 | 3.34.182 || NFIL3 | 3.34 | nuclear factor, interleukin 3 regulated | 0.387157537 | 3.34.183 || NPHP3 | 3.34 | nephronophthisis 3 (adolescent) | 1.109658891 | 3.34.181 || NR1D2 | 3.34 | nuclear receptor subfamily 1 group D member 2 | 2.339118073 | 3.34.182 || NSD1 | 3.34 | nuclear receptor binding SET domain protein 1 | 0.484225394 | 3.34.183 || ODF3B | 3.34 | outer dense fiber of sperm tails 3B | 0.571785467 | 3.34.181 || OGG1 | 3.34 | 8-oxoguanine DNA glycosylase | 0.730181493 | 3.34.181 || ORC2 | 3.34 | origin recognition complex subunit 2 | 0.252480341 | 3.34.183 || OTUD6B-AS1 | 3.34 | OTUD6B antisense RNA 1 (head to head) | 0.34976707 | 3.34.181 || PCSK6 | 3.34 | proprotein convertase subtilisin/kexin type 6 | 3.160999748 | 3.34.183 || PCYOX1 | 3.34 | prenylcysteine oxidase 1 | 0.329734083 | 3.34.181 || PDPR | 3.34 | pyruvate dehydrogenase phosphatase regulatory subunit | 0.830063041 | 3.34.182 || PER2 | 3.34 | period circadian clock 2 | 0.972020801 | 3.34.182 || PER3 | 3.34 | period circadian clock 3 | 0.903397282 | 3.34.182 || PHAX | 3.34 | phosphorylated adaptor for RNA export | 0.2443868 | 3.34.181 || PIAS2 | 3.34 | protein inhibitor of activated STAT 2 | 0.485873938 | 3.34.181 || PIM3 | 3.34 | Pim-3 proto-oncogene, serine/threonine kinase | 0.3316686 | 3.34.183 || PLEKHM3 | 3.34 | pleckstrin homology domain containing M3 | 0.436968042 | 3.34.181 || PM20D2 | 3.34 | peptidase M20 domain containing 2 | 0.779598912 | 3.34.181 || PNISR | 3.34 | PNN-interacting serine/arginine-rich protein | 0.767471395 | 3.34.181 || POSTN | 3.34 | periostin, osteoblast specific factor | 1.771653828 | 3.34.183 || POU6F1 | 3.34 | POU class 6 homeobox 1 | 0.344882068 | 3.34.181 || PPP1R15A | 3.34 | protein phosphatase 1 regulatory subunit 15A | 0.777418995 | 3.34.181 || PPP1R3E | 3.34 | protein phosphatase 1 regulatory subunit 3E | 0.854250805 | 3.34.181 || PPTC7 | 3.34 | PTC7 protein phosphatase homolog | 0.287690259 | 3.34.182 || PRKCI | 3.34 | protein kinase C iota | 0.341965274 | 3.34.181 || PRX | 3.34 | periaxin | 0.244877377 | 3.34.181 || PSD3 | 3.34 | pleckstrin and Sec7 domain containing 3 | 0.985521347 | 3.34.181 || PTER | 3.34 | phosphotriesterase related | 0.685036329 | 3.34.181 || RAB3GAP1 | 3.34 | RAB3 GTPase activating protein catalytic subunit 1 | 0.24367303 | 3.34.181 || RAB5C | 3.34 | RAB5C, member RAS oncogene family | 0.708900601 | 3.34.181 || RAD51-AS1 | 3.34 | RAD51 antisense RNA 1 (head to head) | 1.117574449 | 3.34.181 || RASAL2 | 3.34 | RAS protein activator like 2 | 0.276634505 | 3.34.181 || RB1 | 3.34 | retinoblastoma 1 | 0.221328701 | 3.34.181 || RBCK1 | 3.34 | RANBP2-type and C3HC4-type zinc finger containing 1 | 0.229269756 | 3.34.181 || RBM12B | 3.34 | RNA binding motif protein 12B | 0.523219204 | 3.34.183 || RBM25 | 3.34 | RNA binding motif protein 25 | 0.338114959 | 3.34.181 || RBM26 | 3.34 | RNA binding motif protein 26 | 0.368093556 | 3.34.181 || RBM41 | 3.34 | RNA binding motif protein 41 | 0.867318437 | 3.34.181 || RBM6 | 3.34 | RNA binding motif protein 6 | 0.897328782 | 3.34.183 || RCBTB1 | 3.34 | RCC1 and BTB domain containing protein 1 | 0.249974114 | 3.34.181 || RNF170 | 3.34 | ring finger protein 170 | 0.290631795 | 3.34.181 || RPL32P3 | 3.34 | ribosomal protein L32 pseudogene 3 | 0.988371146 | 3.34.181 || RPP25 | 3.34 | ribonuclease P/MRP 25 kDa subunit | 1.144822637 | 3.34.181 || RSBN1 | 3.34 | round spermatid basic protein 1 | 0.275367056 | 3.34.181 || RSF1 | 3.34 | remodeling and spacing factor 1 | 0.513250167 | 3.34.181 || RUFY2 | 3.34 RUN and FYVE domain containing 2 | 1.033520713 | 3.34.181 || RUFY3 | 3.34 | RUN and FYVE domain containing 3 | 1.145867001 | 3.34.181 || SCN9A | 3.34 | sodium voltage-gated channel alpha subunit 9 | 0.414266817 | 3.34.183 || SCYL3 | 3.34 | SCY1 like pseudokinase 3 | 1.898146295 | 3.34.181 || SDCBP2-AS1 | 3.34 | SDCBP2 antisense RNA 1 | 1.762024139 | 3.34.183 || SEL1L3 | 3.34 | SEL1L family member 3 | 2.154903827 | 3.34.181 || SELT | 3.34 | selenoprotein T | 0.426260752 | 3.34.181 || SESN3 | 3.34 | sestrin 3 | 0.597934441 | 3.34.181 || SETD6 | 3.34 | SET domain containing 6 | 1.813748347 | 3.34.181 || SHPRH | 3.34 | SNF2 histone linker PHD RING helicase | 0.23418674 | 3.34.181 || SLC2A13 | 3.34 | solute carrier family 2 member 13 | 0.533238603 | 3.34.181 || SMAD5 | 3.34 | SMAD family member 5 | 0.525501557 | 3.34.181 || SNAPC3 | 3.34 | small nuclear RNA activating complex polypeptide 3 | 0.319022756 | 3.34.183 || SNX24 | 3.34 | sorting nexin 24 | 0.447892012 | 3.34.183 || SON | 3.34 | SON DNA binding protein | 0.215952043 | 3.34.181 || SPDYE2 | 3.34 | speedy/RINGO cell cycle regulator family member E2 | 0.514703859 | 3.34.183 || SPINT2 | 3.34 | serine peptidase inhibitor, Kunitz type, 2 | 0.680207775 | 3.34.181 || SPRED3 | 3.34 | sprouty related, EVH1 domain containing 3 | 0.414830031 | 3.34.182 || STK26 | 3.34 | serine/threonine protein kinase 26 | 0.242031481 | 3.34.181 || STX17 | 3.34 | syntaxin 17 | 0.224097066 | 3.34.181 || TACC1 | 3.34 | transforming acidic coiled-coil containing protein 1 | 0.434972724 | 3.34.181 || TEF | 3.34 | thyrotrophic embryonic factor | 1.331753518 | 3.34.182 || THUMPD1 | 3.34 | THUMP domain containing 1 | 0.260783091 | 3.34.181 || TLR5 | 3.34 | toll like receptor 5 | 0.292363259 | 3.34.183 || TMEM181 | 3.34 | transmembrane protein 181 | 0.303971929 | 3.34.181 || TMUB2 | 3.34 | transmembrane and ubiquitin-like domain containing 2 | 0.32135527 | 3.34.183 || TNPO1 | 3.34 | transportin 1 | 0.408402369 | 3.34.181 || TNPO3 | 3.34 | transportin 3 | 0.218360117 | 3.34.181 || TNRC6B | 3.34 | trinucleotide repeat containing 6B | 0.453926376 | 3.34.181 || TOB2 | 3.34 | transducer of ERBB2, 2 | 0.449271682 | 3.34.182 || TOMM40 | 3.34 | translocase of outer mitochondrial membrane 40 | 0.432087442 | 3.34.181 || TOR3A | 3.34 | torsin family 3 member A | 0.431391398 | 3.34.181 || TPMT | 3.34 | thiopurine S-methyltransferase | 0.3476196 | 3.34.181 || TRABD | 3.34 | TraB domain containing | 0.490335244 | 3.34.181 || TRIM23 | 3.34 | tripartite motif containing 23 | 0.669486913 | 3.34.181 || TRIO | 3.34 | trio Rho guanine nucleotide exchange factor | 0.432140335 | 3.34.183 || TSPAN31 | 3.34 | tetraspanin 31 | 0.283605503 | 3.34.181 || TTF1 | 3.34 | transcription termination factor, RNA polymerase I | 0.550104915 | 3.34.181 || TXNRD2 | 3.34 | thioredoxin reductase 2 | 0.526032852 | 3.34.181 || UBA5 | 3.34 | ubiquitin like modifier activating enzyme 5 | 0.216705036 | 3.34.182 || UBE2H | 3.34 | ubiquitin conjugating enzyme E2H | 0.256359853 | 3.34.182 || UBXN7 | 3.34 | UBX domain protein 7 | 1.053709113 | 3.34.182 || VCPKMT | 3.34 | valosin containing protein lysine methyltransferase | 0.226876516 | 3.34.182 || VOPP1 | 3.34 | vesicular, overexpressed in cancer, prosurvival protein 1 | 0.310501971 | 3.34.181 || WIPF2 | 3.34 | WAS/WASL interacting protein family member 2 | 0.254998218 | 3.34.181 || WWC3 | 3.34 | WWC family member 3 | 0.294881978 | 3.34.182 || ZADH2 | 3.34 | zinc binding alcohol dehydrogenase domain containing 2 | 0.228537977 | 3.34.183 || ZBTB21 | 3.34 | zinc finger and BTB domain containing 21 | 0.870634529 | 3.34.182 || ZBTB41 | 3.34 | zinc finger and BTB domain containing 41 | 0.489728574 | 3.34.181 || ZMAT1 | 3.34 | zinc finger matrin-type 1 | 0.791358786 | 3.34.181 || ZNF397 | 3.34 | zinc finger protein 397 | 1.410398387 | 3.34.181 || ZNF420 |

TABLE 3B-continued

| The genes within the significant gene clusters, listed in Table 3A. (3966 Genes Listed by: Gene Symbol ❘ Gen 2 Module ❘ Gene Description ❘ RowVariance ❘ Gen 3 Module ‖) |
| --- |
| 3.34 ❘ zinc finger protein 420 ❘ 0.531606442 ❘ 3.34.181 ‖ ZNF493 ❘ 3.34 ❘ zinc finger protein 493 ❘ 1.478163813 ❘ 3.34.181 ‖ ZNF548 ❘ 3.34 ❘ zinc finger protein 548 ❘ 0.473137177 ❘ 3.34.181 ‖ ZNF565 ❘ 3.34 ❘ zinc finger protein 565 ❘ 0.404727635 ❘ 3.34.181 ‖ ZNF566 ❘ 3.34 ❘ zinc finger protein 566 ❘ 0.55922715 ❘ 3.34.181 ‖ ZNF573 ❘ 3.34 ❘ zinc finger protein 573 ❘ 1.58382204 ❘ 3.34.181 ‖ ZNF814 ❘ 3.34 ❘ zinc finger protein 814 ❘ 1.889444811 ❘ 3.34.181 ‖ ACOX1 ❘ 3.35.184 ❘ acyl-CoA oxidase 1, palmitoyl ❘ 0.467937072 ❘ 3.35.184 ‖ ANKRD17 ❘ 3.35.184 ❘ ankyrin repeat domain 17 ❘ 0.215145854 ❘ 3.35.184 ‖ ATMIN ❘ 3.35.184 ❘ ATM interactor ❘ 0.309745304 ❘ 3.35.184 ‖ BBS7 ❘ 3.35.184 ❘ Bardet-Biedl syndrome 7 ❘ 1.007546576 ❘ 3.35.184 ‖ C11orf54 ❘ 3.35.184 ❘ chromosome 11 open reading frame 54 ❘ 0.276428138 ❘ 3.35.184 ‖ CDK8 ❘ 3.35.184 ❘ cyclin-dependent kinase 8 ❘ 0.321384373 ❘ 3.35.184 ‖ CENPBD1P1 ❘ 3.35.184 ❘ CENPB DNA-binding domains containing 1 pseudogene 1 ❘ 0.637831024 ❘ 3.35.184 ‖ EPC2 ❘ 3.35.184 ❘ enhancer of polycomb homolog 2 ❘ 0.261908455 ❘ 3.35.184 ‖ FAM73A ❘ 3.35.184 ❘ family with sequence similarity 73 member A ❘ 0.293431031 ❘ 3.35.184 ‖ FGF14-AS2 ❘ 3.35.184 ❘ FGF14 antisense RNA 2 ❘ 0.488365792 ❘ 3.35.184 ‖ FLVCR1 ❘ 3.35.184 ❘ feline leukemia virus subgroup C cellular receptor 1 ❘ 0.517406166 ❘ 3.35.184 ‖ GUCY1A2 ❘ 3.35.184 ❘ guanylate cyclase 1, soluble, alpha 2 ❘ 4.978071272 ❘ 3.35.184 ‖ LRIG2 ❘ 3.35.184 ❘ leucine-rich repeats and immunoglobulin-like domains 2 ❘ 0.348012871 ❘ 3.35.184 ‖ NACC2 ❘ 3.35.184 ❘ NACC family member 2 ❘ 0.452874329 ❘ 3.35.184 ‖ NEK4 ❘ 3.35.184 ❘ NIMA related kinase 4 ❘ 0.258849738 ❘ 3.35.184 ‖ NIPSNAP3A ❘ 3.35.184 ❘ nipsnap homolog 3A (*C. elegans*) ❘ 0.595808532 ❘ 3.35.184 ‖ PAQR3 ❘ 3.35.184 ❘ progestin and adipoQ receptor family member III ❘ 0.219424326 ❘ 3.35.184 ‖ RBM48 ❘ 3.35.184 ❘ RNA binding motif protein 48 ❘ 0.434774992 ❘ 3.35.184 ‖ SLFN5 ❘ 3.35.184 ❘ schlafen family member 5 ❘ 0.466848118 ❘ 3.35.184 ‖ TMEM55A ❘ 3.35.184 ❘ transmembrane protein 55A ❘ 0.410382637 ❘ 3.35.184 ‖ TUBE1 ❘ 3.35.184 ❘ tubulin epsilon 1 ❘ 0.699948186 ❘ 3.35.184 ‖ WDR43 ❘ 3.35.184 ❘ WD repeat domain 43 ❘ 0.314939307 ❘ 3.35.184 ‖ XPNPEP3 ❘ 3.35.184 ❘ X-prolyl aminopeptidase 3, mitochondrial ❘ 0.385966784 ❘ 3.35.184 ‖ ZNF25 ❘ 3.35.184 ❘ zinc finger protein 25 ❘ 0.288185512 ❘ 3.35.184 ‖ ZNF770 ❘ 3.35.184 ❘ zinc finger protein 770 ❘ 0.359009093 ❘ 3.35.184 ‖ ADRBK2 ❘ 3.44 ❘ adrenergic, beta, receptor kinase 2 ❘ 0.779712165 ❘ — ‖ B4GALT2 ❘ 3.44 ❘ UDP-Gal:betaGlcNAc beta 1,4-galactosyltransferase, polypeptide 2 ❘ 0.307548356 ❘ — ‖ BNIP3L ❘ 3.44 ❘ BCL2/adenovirus E1B 19 kDa interacting protein 3-like ❘ 0.274315627 ❘ — ‖ C9orf3 ❘ 3.44 ❘ chromosome 9 open reading frame 3 ❘ 0.238713228 ❘ — ‖ CNPY2 ❘ 3.44 ❘ canopy FGF signaling regulator 2 ❘ 0.222055667 ❘ — ‖ DIRAS1 ❘ 3.44 ❘ DIRAS family GTP binding RAS like 1 ❘ 0.22355553 ❘ — ‖ FAM107B ❘ 3.44 ❘ family with sequence similarity 107 member B ❘ 0.261914467 ❘ — ‖ GOLM1 ❘ 3.44 ❘ golgi membrane protein 1 ❘ 1.866380879 ❘ — ‖ KDELR3 ❘ 3.44 ❘ KDEL endoplasmic reticulum protein retention receptor 3 ❘ 0.613356719 ❘ — ‖ LTBP1 ❘ 3.44 ❘ latent transforming growth factor beta binding protein 1 ❘ 0.341844814 ❘ — ‖ MAGED1 ❘ 3.44 ❘ MAGE family member D1 ❘ 0.450803272 ❘ — ‖ MAP3K1 ❘ 3.44 ❘ mitogen-activated protein kinase kinase kinase 1, E3 ubiquitin protein ligase ❘ 0.220210865 ❘ — ‖ MLF1 ❘ 3.44 ❘ myeloid leukemia factor 1 ❘ 0.818667797 ❘ — ‖ MRC1 ❘ 3.44 ❘ mannose receptor, C type 1 ❘ 0.27381441 ❘ — ‖ NDUFA4L2 ❘ 3.44 ❘ NADH dehydrogenase (ubiquinone) 1 alpha subcomplex, 4-like 2 ❘ 2.386762336 ❘ — ‖ NPTX2 ❘ 3.44 ❘ neuronal pentraxin II ❘ 2.959906407 ❘ — ‖ NUCB2 ❘ 3.44 ❘ nucleobindin 2 ❘ 0.320303426 ❘ — ‖ PDE3A ❘ 3.44 ❘ phosphodiesterase 3A ❘ 1.109327326 ❘ — ‖ PRAF2 ❘ 3.44 ❘ PRA1 domain family member 2 ❘ 0.247056102 ❘ — ‖ PTS ❘ 3.44 ❘ 6-pyruvoyltetrahydropterin synthase ❘ 0.27585133 ❘ — ‖ PXYLP1 ❘ 3.44 ❘ 2-phosphoxylose phosphatase 1 ❘ 0.561769434 ❘ — ‖ RABAC1 ❘ 3.44 ❘ Rab acceptor 1 (prenylated) ❘ 0.224482181 ❘ — ‖ RCN3 ❘ 3.44 ❘ reticulocalbin 3 ❘ 0.545215855 ❘ — ‖ SHMT2 ❘ 3.44 ❘ serine hydroxymethyltransferase 2 ❘ 0.258627156 ❘ — ‖ SMOC2 ❘ 3.44 ❘ SPARC related modular calcium binding 2 ❘ 0.758082061 ❘ — ‖ SNAP29 ❘ 3.44 ❘ synaptosome associated protein 29 kDa ❘ 0.524855101 ❘ — ‖ TCTN3 ❘ 3.44 ❘ tectonic family member 3 ❘ 0.214553148 ❘ — ‖ TMED3 ❘ 3.44 ❘ transmembrane p24 trafficking protein 3 ❘ 0.342471233 ❘ — ‖ TMEM170B ❘ 3.44 ❘ transmembrane protein 170B ❘ 1.361576158 ❘ — ‖ VKORC1 ❘ 3.44 ❘ vitamin K epoxide reductase complex subunit 1 ❘ 0.518118866 ❘ — ‖ AFAP1 ❘ 3.45 ❘ actin filament associated protein 1 ❘ 0.239106171 ❘ — ‖ AKR1B1 ❘ 3.45 ❘ aldo-keto reductase family 1, member B1 (aldose reductase) ❘ 0.338264927 ❘ — ‖ APOC1 ❘ 3.45 ❘ apolipoprotein C-I ❘ 1.577894627 ❘ — ‖ ATP5S ❘ 3.45 ❘ ATP synthase, H+ transporting, mitochondrial Fo complex subunit s (factor B) ❘ 0.277658806 ❘ — ‖ BAZ1A ❘ 3.45 ❘ bromodomain adjacent to zinc finger domain 1A ❘ 0.292369598 ❘ — ‖ BCL11A ❘ 3.45 ❘ B-cell CLL/lymphoma 11A ❘ 0.87469962 ❘ — ‖ C21orf2 ❘ 3.45 ❘ chromosome 21 open reading frame 2 ❘ 0.345826639 ❘ — ‖ CCDC102B ❘ 3.45 ❘ coiled-coil domain containing 102B ❘ 2.804011819 ❘ — ‖ CCNE2 ❘ 3.45 ❘ cyclin E2 ❘ 0.306377397 ❘ — ‖ CLPTM1 ❘ 3.45 ❘ cleft lip and palate associated transmembrane protein 1 ❘ 0.622622157 ❘ — ‖ CREB3L1 ❘ 3.45 ❘ cAMP responsive element binding protein 3-like 1 ❘ 0.486568446 ❘ — ‖ DPP7 ❘ 3.45 ❘ dipeptidyl peptidase 7 ❘ 0.263313768 ❘ — ‖ GATA6 ❘ 3.45 ❘ GATA binding protein 6 ❘ 0.620084904 ❘ — ‖ GBA2 ❘ 3.45 ❘ glucosidase, beta (bile acid) 2 ❘ 0.223333178 ❘ — ‖ GMPPA ❘ 3.45 ❘ GDP-mannose pyrophosphorylase A ❘ 0.663005049 ❘ — ‖ HM13 ❘ 3.45 ❘ histocompatibility (minor) 13 ❘ 0.344611217 ❘ — ‖ KRIT1 ❘ 3.45 ❘ KRIT1, ankyrin repeat containing ❘ 0.627055949 ❘ — ‖ LAYN ❘ 3.45 ❘ layilin ❘ 0.277894939 ❘ — ‖ MTSS1L ❘ 3.45 ❘ metastasis suppressor 1-like ❘ 0.310872987 ❘ — ‖ NAGLU ❘ 3.45 ❘ N-acetylglucosaminidase, alpha ❘ 0.257961073 ❘ — ‖ NIP7 ❘ 3.45 ❘ NIP7, nucleolar pre-rRNA processing protein ❘ 0.981361551 ❘ — ‖ PDIA6 ❘ 3.45 ❘ protein disulfide isomerase family A member 6 ❘ 0.235972168 ❘ — ‖ PEG10 ❘ 3.45 ❘ paternally expressed 10 ❘ 0.374344447 ❘ — ‖ PYHIN1 ❘ 3.45 ❘ pyrin and HIN domain family member 1 ❘ 0.680809494 ❘ — ‖ RAB27A ❘ 3.45 ❘ RAB27A, member RAS oncogene family ❘ 0.225251538 ❘ — ‖ SECISBP2 ❘ 3.45 ❘ SECIS binding protein 2 ❘ 0.301027343 ❘ — ‖ STRBP ❘ 3.45 ❘ spermatid perinuclear RNA binding protein ❘ 0.610263558 ❘ — ‖ TMED9 ❘ 3.45 ❘ transmembrane p24 trafficking protein 9 ❘ 0.21865046 ❘ — ‖ TNFRSF10A ❘ 3.45 ❘ tumor necrosis factor receptor superfamily member 10a ❘ 0.505708166 ❘ — ‖ TRAK2 ❘ 3.45 ❘ trafficking protein, kinesin binding 2 ❘ 0.423216901 ❘ — ‖ ZC3H12C ❘ 3.45 ❘ zinc finger CCCH-type containing 12C ❘ 0.364815283 ❘ |

Example 3: Unsupervised Clustering of Genes to Distinguish SLE Patients with Active Disease, but without Fibromyalgia, and SLE Patients without Active Disease, but with Fibromyalgia SLE patients often have a pain amplification syndrome, known as fibromyalgia. It can be difficult to determine clinically whether an SLE patient's symptoms are related to active SLE or co-existent fibromyalgia. Gene expression analysis was used delineate these two conditions. RNAseq data (SLE/fibromyalgia RNAseq dataset) was obtained from 10 patients with active SLE but no evidence of fibromyalgia, and 10 patients with SLE who did not have active disease but very symptomatic fibromyalgia. Standard analysis could not distinguish between SLE and fibromyalgia. CodeR-BP co-expression analysis was applied to the data and numerous informative gene modules were identified. Genes were annotated using the publicly available R bioMart package. Gene not mapped to any known proteins and genes having expression rows with an average standard deviation of zero were removed. Averaged gene expression rows were sorted by absolute value of descending row variance and the top 5,000 row variance (Lupus/Fibromyalgia-top5k rowVar) genes were selected for further analysis. This initial approach was useful for obtaining high quality data for gene clustering and subsequent analysis, reducing noise, and improving speed of computer systems. The Lupus/Fibromyalgia-top5k rowVar genes were clustered based on Gene Co-Expression Network (GCN) generation and multi-scale module formation. Planar filtered network (PFN) generated requiring a correlation false discovery rate (FDR)<0.2, and ensuing multi-scale gene modules were generated using the public R MEGENA package. Minimum module size was 20 genes. A formal tree object was created to establish module lineage and assign module lineage names. Gene modules were assigned "lineage" names based on their multi-scale dependency from the root module. 22 modules with MEs significantly correlated (p<0.2) to cohort (type 1 or type 2 patients) were identified. These 22 significant gene clusters were subsequently overlapped with various gene function signature lists selected from AMPEL LuGENE, Endotype.32, Endotype.kidney, and BIG-C, Gene Ontology (GO), and BRETIGEA brain cell type lists. The modules were annotated according to the top overlapping functional category where there were a minimum of 3 overlapping genes with the significance of those overlaps meeting Fisher's p value less than 0.2. For figure generation, where there was at least one significant AMPEL signature overlap the module received that annotation, along with the top significant GO annotation. Where there were no significant AMPEL signature overlaps the module in figures was annotated with the top two significant GO annotations.

Figure 13:
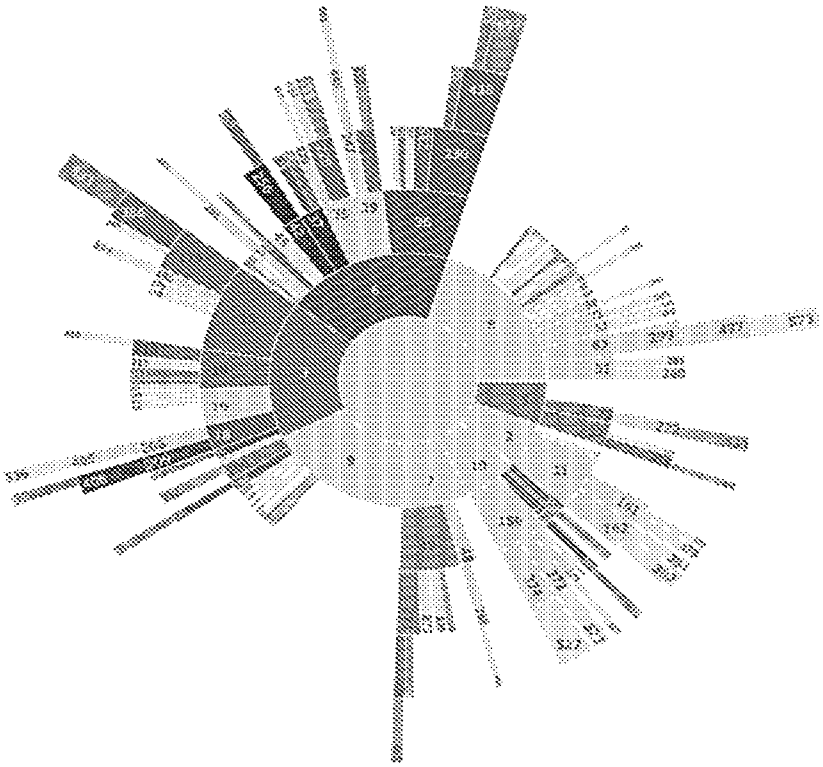
FIGS. 13A-13C: Sunburst diagrams showing lupus fibromyalgia-top5K rowVar gene modules' eigengene (ME) significant correlations (p<0.2) to presence of active disease (13A), SLEDAI score (13B), Fibromyalgia score (13C).
Figure 13B:
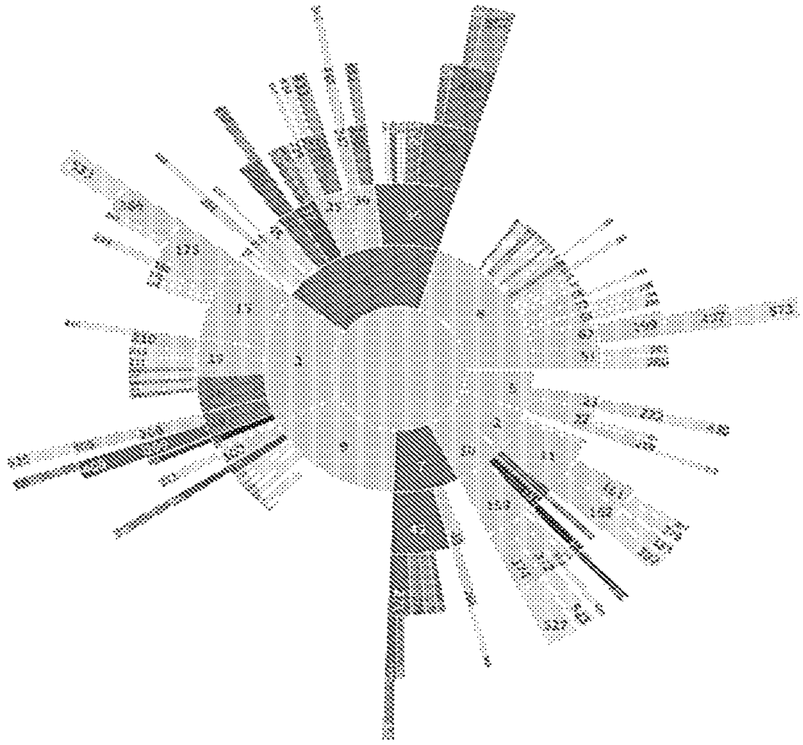
Figure 13C:
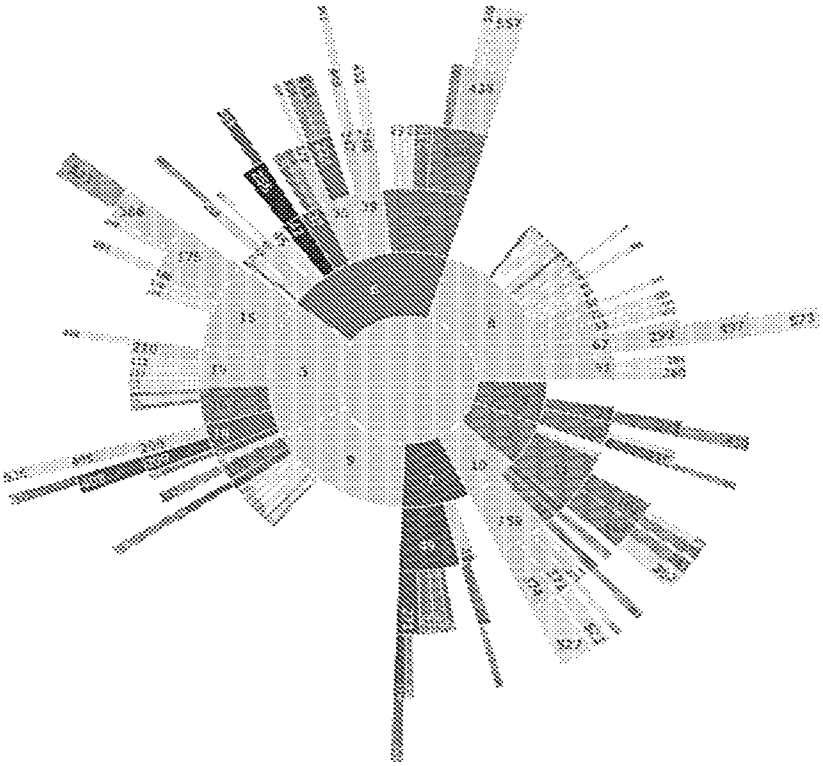

FIGS. 13A-C show Lupus/Fibromyalgia-top5k rowVar gene module sunbursts colored by ME significant correlations (p<0.2) to presence of active disease (13A), SLEDAI score (13B), Fibromyalgia score (13C). Sunburst diagrams showing module size and descendance were generated using the publicly available R package plotly.

Figure 14:
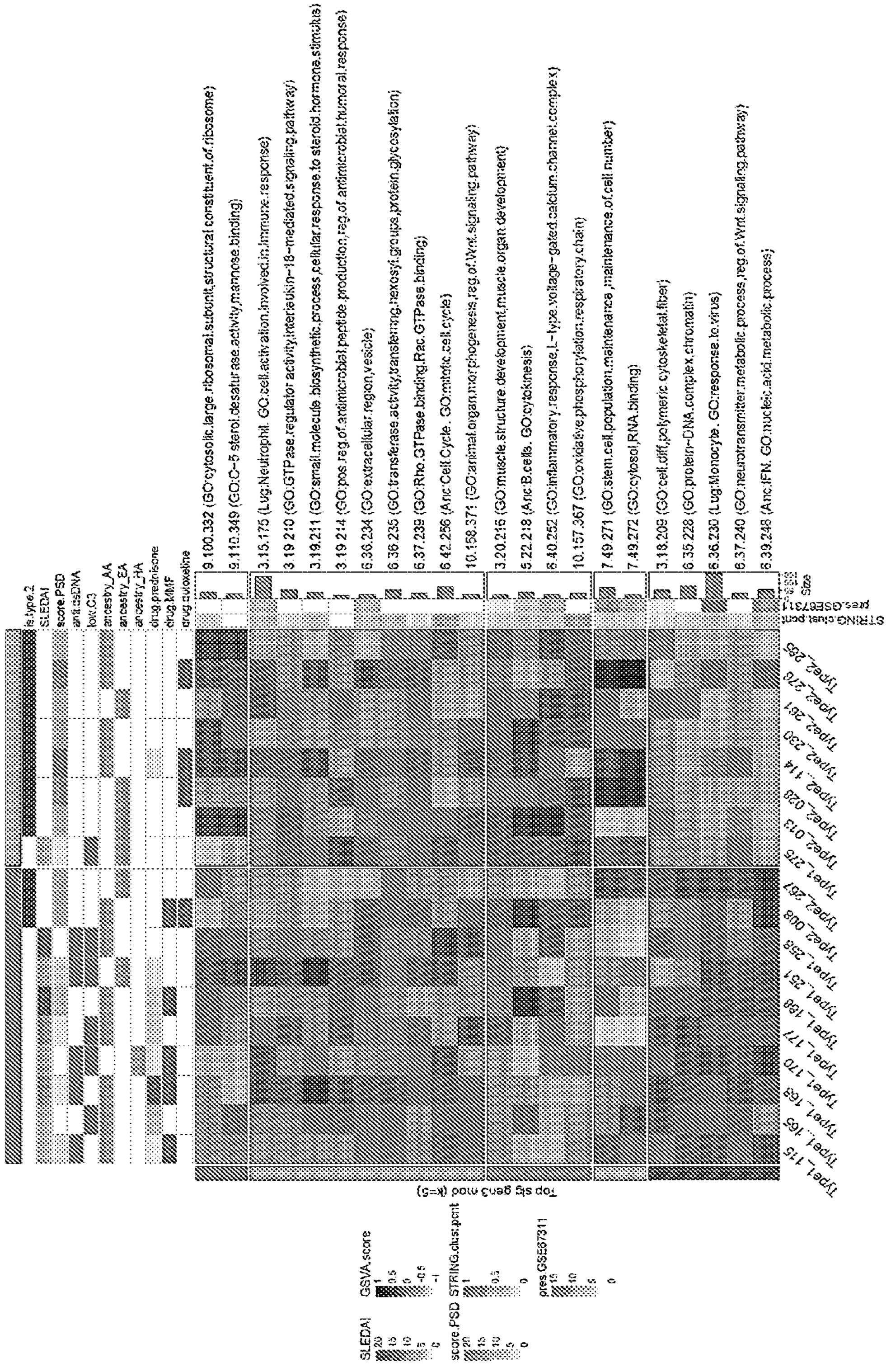
FIG. 14: Lupus/Fibromyalgia top5k rowVar genes patient gene expression first principal component (module eigengene, ME) sig (p<0.2) correlations to the top 22 Type1/Type2 cohort gene modules.
Figures 1, 14:
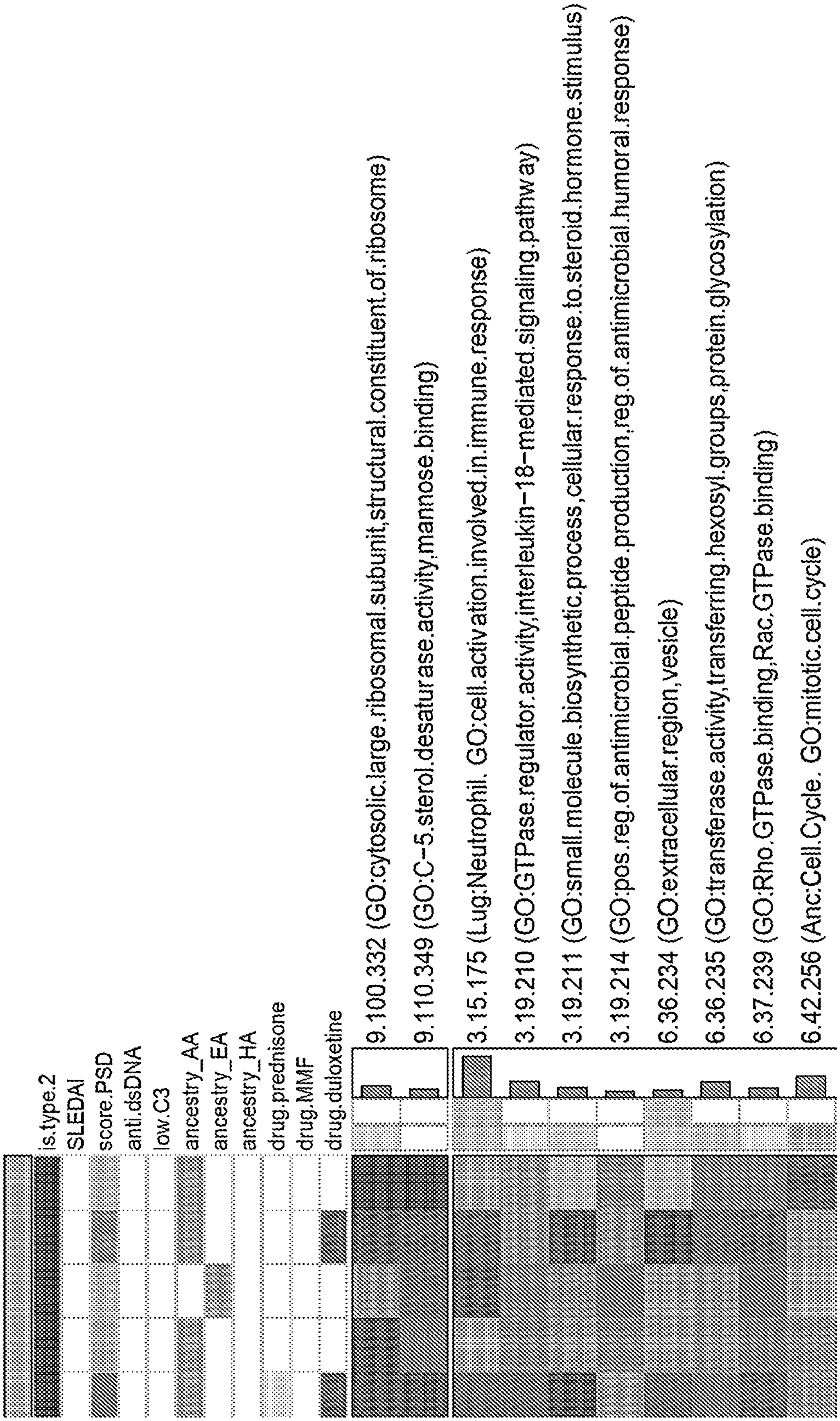
Figures 2, 14:
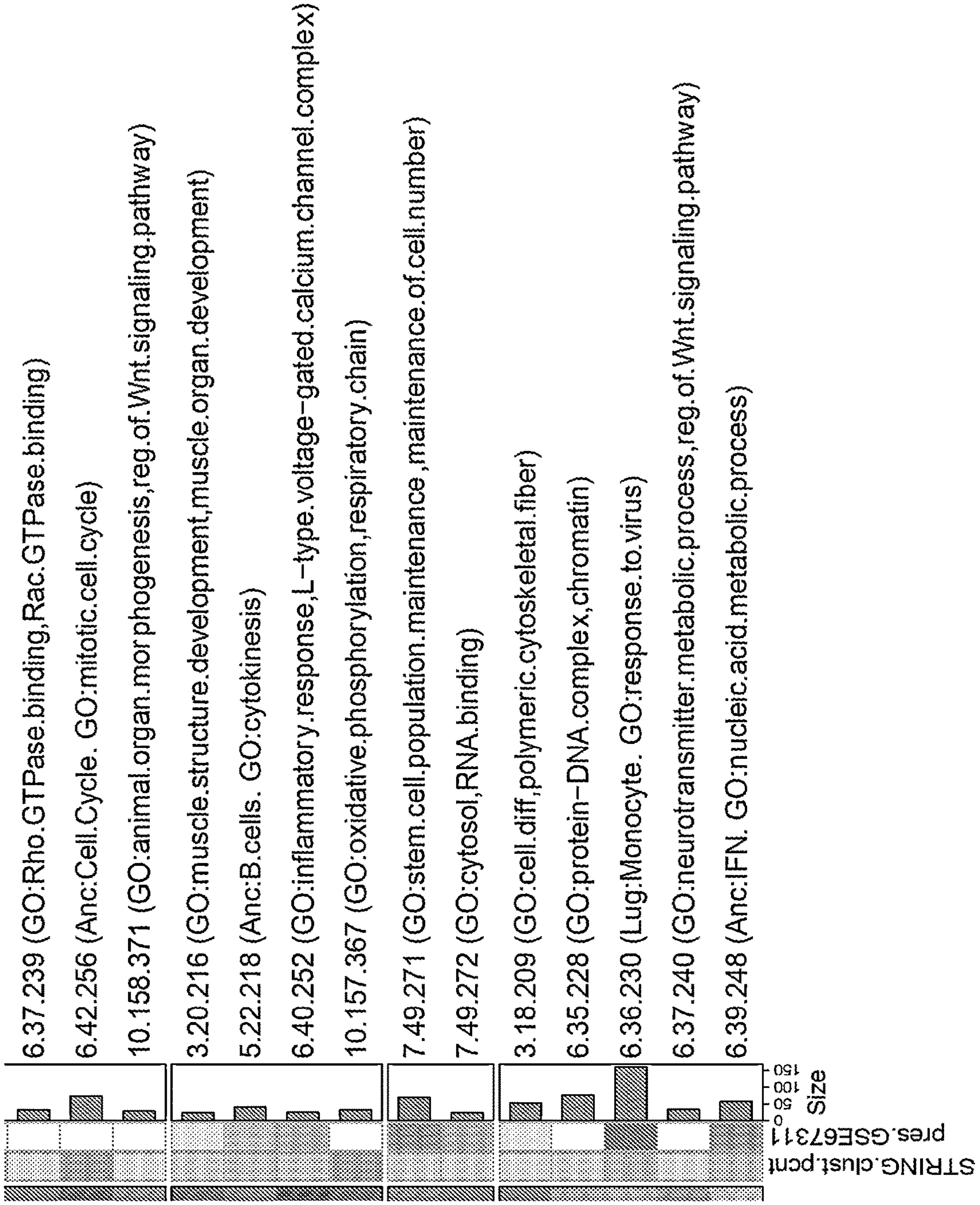
Figures 3, 14:
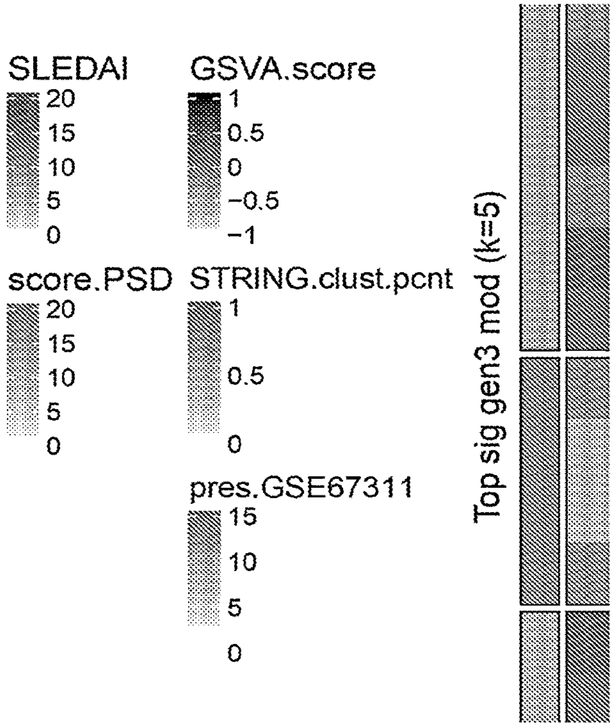
Figures 4, 14:
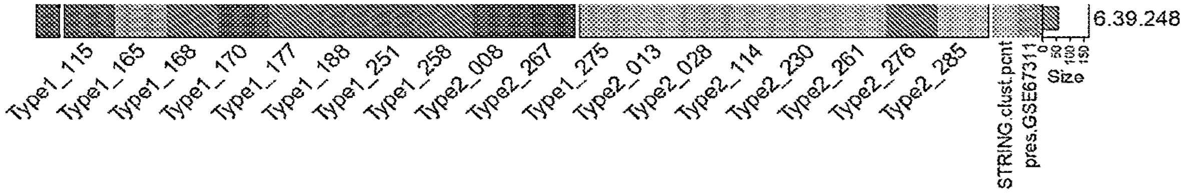

FIG. 14 shows Lupus/Fibromyalgia top5k rowVar genes patient gene expression first principal component (module eigengene, ME) sig (p<0.2) correlations to the top 22 Type1/Type cohort gene modules. Row annotations include ME correlations to SLEDAI, fibromyalgia, C3 depletion, ancestral background (AA African ancestry, EA European American ancestry, HA Hispanic ancestry, and yes/no usage of the immunotherapeutics Prednisone, CellCept, Benlysta, and Cymbalta. Gene modules were labeled by lineage, module size (number of genes, in parenthesis), and top significant functional annotations (gene symbol overlaps >=3, Fisher's p.val<0.2). Mean Expression of modules separates active SLE (Type 1; with active disease and without fibromyalgia) from SLE with Fibromyalgia (Type 2: without active disease and with fibromyalgia) by k=2 clustering of samples, with misclustering of only one type 1 patient and two type 2 patients.

Table 4A, lists the significant gene clusters (e.g. significantly correlated modules to anti.dsDNA) shown in FIG. 14, size (e.g. number of genes within the modules) of the clusters, functional characterization groups (e.g. categories) from LuGENE, AMPEL Ancestry, AMPEL Tissue, BIG-C and GO that overlaps with the clusters and respective p values, and functional annotation of the clusters. Table 4B lists the genes in the significant gene clusters of Table 4A.

TABLE 4A

The significant gene clusters as shown in FIG. 14.

| lineage | mod.size | annot.luGENE | annot.luGENE.overlaps | annot.ancestry | annot.ancestry.overlaps | annot.tissue | annot.tissue.overlaps |
|---|---|---|---|---|---|---|---|
| 10.157.367 | 32 | | | | | | |
| 10.158.371 | 28 | | | | | | |
| 3.15.175 | 140 | Neutrophil | 6 | | | | |
| 3.18.209 | 53 | | | | | | |
| 3.19.210 | 55 | | | | | | |
| 3.19.211 | 35 | | | | | | |
| 3.19.214 | 21 | | | | | | |
| 3.20.216 | 24 | | | | | | |
| 5.22.218 | 41 | | | B cells | 3 | | |
| 6.35.228 | 77 | | | | | | |
| 6.36.230 | 160 | Monocyte | 4 | | | | |
| 6.36.234 | 25 | | | | | | |
| 6.36.235 | 54 | | | | | | |
| 6.37.239 | 32 | | | | | | |
| 6.37.240 | 33 | | | | | | |
| 6.39.248 | 57 | | | IFN | 10 | | |
| 6.40.252 | 25 | | | | | | |
| 6.42.256 | 73 | | | Cell Cycle | 7 | | |
| 7.49.271 | 70 | | | | | | |
| 7.49.272 | 24 | | | | | | |
| 9.100.332 | 39 | | | | | | |
| 9.110.349 | 29 | | | | | | |

TABLE 4A-continued

The significant gene clusters as shown in FIG. 14.

| lineage | annot.BIG.C | annot.BIG.C.overlaps | annot.GO.1 | annot.GO.1.coverage |
|---|---|---|---|---|
| 10.157.367 | Mitochondria-Oxidative-Phosphorylation | 13 | oxidative phosphorylation | 0.481 |
| 10.158.371 | | | animal organ morphogenesis | 0.231 |
| 3.15.175 | | | cell activation involved in immune response | 0.281 |
| 3.18.209 | Cytoskeleton | 4 | cell differentiation | 0.444 |
| 3.19.210 | | | GTPase regulator activity | 0.085 |
| 3.19.211 | Glycolysis-Gluconeogenesis-and-Pentose-Phosphate-Pathways | 4 | small molecule biosynthetic process | 0.214 |
| 3.19.214 | | | positive regulation of antimicrobial peptide production | 0.056 |
| 3.20.216 | | | muscle structure development | 0.286 |
| 5.22.218 | | | cytokinesis | 0.075 |
| 6.35.228 | | | protein-DNA complex | 0.1 |
| 6.36.230 | | | response to virus | 0.148 |
| 6.36.234 | Secreted-and-ECM | 3 | extracellular region | 0.583 |
| 6.36.235 | Mitochondria-Oxidative-Phosphorylation | 3 | transferase activity, transferring hexosyl groups | 0.07 |
| 6.37.239 | Unknown | 3 | Rho GTPase binding | 0.143 |
| 6.37.240 | | | neurotransmitter metabolic process | 0.107 |
| 6.39.248 | | | nucleic acid metabolic process | 0.431 |
| 6.40.252 | | | inflammatory response | 0.286 |
| 6.42.256 | | | mitotic cell cycle | 0.453 |
| 7.49.271 | | | stem cell population maintenance | 0.065 |
| 7.49.272 | mRNA-Processing | 3 | cytosol | 0.667 |
| 9.100.332 | | | cytosolic large ribosomal subunit | 0.091 |
| 9.110.349 | | | C-5 sterol desaturase activity | 0.037 |

| lineage | annot.GO.2 | annot.GO.2.coverage | annot.figures |
|---|---|---|---|
| 10.157.367 | respiratory chain | 0.407 | GO: oxidative.phosphorylation, respiratory.chain |
| 10.158.371 | regulation of Wnt signaling pathway | 0.115 | GO: animal.organ.morphogenesis, reg.of.Wnt.signaling.pathway |
| 3.15.175 | myeloid cell activation involved in immune response | 0.258 | Lug: Neutrophil. GO: cell.activation.involved.in.immune.response |
| 3.18.209 | polymeric cytoskeletal fiber | 0.156 | GO: cell.diff, polymeric.cytoskeletal.fiber |
| 3.19.210 | interleukin-18-mediated signaling pathway | 0.043 | GO: GTPase.regulator.activity, interleukin-18-mediated.signaling.pathway |
| 3.19.211 | cellular response to steroid hormone stimulus | 0.143 | GO: small.molecule.biosynthetic.process, cellular.response.to.steroid.hormone.stimulus |
| 3.19.214 | regulation of antimicrobial humoral response | 0.056 | GO: pos.reg.of.antimicrobial.peptide.production, reg.of.antimicrobial.humoral.response |
| 3.20.216 | muscle organ development | 0.238 | GO: muscle.structure.development, muscle.organ.development |

TABLE 4A-continued

| The significant gene clusters as shown in FIG. 14. | | | |
|---|---|---|---|
| 5.22.218 | epithelial tube branchingi nvolved in lung morphogenesis | 0.05 | Anc: B.cells. GO: cytokinesis |
| 6.35.228 | chromatin | 0.1 | GO: protein-DNA.complex, chromatin |
| 6.36.230 | defense response to virus | 0.134 | Lug: Monocyte. GO: response.to.virus |
| 6.36.234 | vesicle | 0.542 | GO: extracellular.region, vesicle |
| 6.36.235 | protein glycosylation | 0.07 | GO: transferase.activity, transferring.hexosyl.groups, protein.glycosylation |
| 6.37.239 | Rac GTPase binding | 0.107 | GO: Rho.GTPase.binding, Rac.GTPase.binding |
| 6.37.240 | regulation of Wnt signaling pathway | 0.107 | GO: neurotransmitter.metabolic.process, reg.of.Wnt.signaling.pathway |
| 6.39.248 | viral process | 0.196 | Anc: IFN. GO: nucleic.acid.metabolic.process |
| 6.40.252 | L-type voltage-gated calcium channel complex | 0.095 | GO: inflammatory.response, L-type.voltage-gated.calcium.channel.complex |
| 6.42.256 | cell cycle process | 0.453 | Anc: Cell.Cycle. GO: mitotic.cell.cycle |
| 7.49.271 | maintenance of cell number | 0.065 | GO: stem.cell.population.maintenance, maintenance.of.cell.number |
| 7.49.272 | RNA binding | 0.333 | GO: cytosol, RNA.binding |
| 9.100.332 | structural constituent of ribosome | 0.091 | GO: cytosolic.large.ribosomal.subunit, structural.constituent.of.ribosome |
| 9.110.349 | mannose binding | 0.037 | GO: C-5.sterol.desaturase.activity, mannose.binding |

TABLE 4B

The genes within the significant gene clusters, listed in Table 4A. (1127 Genes Listed by: Gene Symbol | Module | Hugo GENE Nomenclature Committee (HGNC) Gene Description [HGNC ID] | Chromosome Number | Row Variance) ||)

APOA1-AS | 10.157.367 | APOA1 antisense RNA [40079] | 11 | 0.261729465 || BLM | 10.157.367 | BLM RecQ like helicase [1058] | 15 | 0.2527249 || BNIP3P1 | 10.157.367 | BCL2 interacting protein 3 pseudogene 1 [19922] | 14 | 0.200006491 || DGKH | 10.157.367 | diacylglycerol kinase eta [2854] | 13 | 0.202089805 || FN1 | 10.157.367 | fibronectin 1 [3778] | 2 | 0.749457501 || HSD17B7P2 | 10.157.367 | hydroxysteroid 17-beta dehydrogenase 7 pseudogene 2 [28120] | 10 | 0.233053649 || LINC02745 | 10.157.367 | long intergenic non-protein coding RNA 2745 [54263] | 11 | 0.261786126 || MEX3B | 10.157.367 | mex-3 RNA binding family member B [25297] | 15 | 0.203786465 || MT-ATP6 | 10.157.367 | mitochondrially encoded ATP synthase membrane subunit 6 [7414] | MT | 0.474643081 || MT-ATP8 | 10.157.367 | mitochondrially encoded ATP synthase membrane subunit 8 [7415] | MT | 0.54945114 || MT-CO1 | 10.157.367 | mitochondrially encoded cytochrome c oxidase I [7419] | MT | 0.32978585 || MT-CO2 | 10.157.367 | mitochondrially encoded cytochrome c oxidase II [7421] | MT | 0.362709565 || MT-CO3 | 10.157.367 | mitochondrially encoded cytochrome c oxidase III [7422] | MT | 0.347557653 || MT-CYB | 10.157.367 | mitochondrially encoded cytochrome b [7427] | MT | 0.458301604 || MT-ND1 | 10.157.367 | mitochondrially encoded NADH:ubiquinone oxidoreductase core subunit 1 [7455] | MT | 0.491885996 || MT-ND2 | 10.157.367 | mitochondrially encoded NADH:ubiquinone oxidoreductase core subunit 2 [7456] | MT | 0.53507275 || MT-ND3 | 10.157.367 | mitochondrially encoded NADH:ubiquinone oxidoreductase core subunit 3 [7458] | MT | 0.484944055 || MT-ND4 | 10.157.367 | mitochondrially encoded NADH:ubiquinone oxidoreductase core subunit 4 [7459] | MT | 0.473023851 || MT-ND4L | 10.157.367 | mitochondrially encoded NADH:ubiquinone oxidoreductase core subunit 4L [7460] | MT | 0.652316345 || MT-ND5 | 10.157.367 | mitochondrially encoded NADH:ubiquinone oxidoreductase core subunit 5 [7461] | MT | 0.403157297 || MT-ND6 | 10.157.367 | mitochondrially encoded NADH:ubiquinone oxidoreductase core subunit 6 [7462] | MT | 0.332037951 || MT-TE | 10.157.367 | mitochondrially encoded tRNA-Glu (GAA/G) [7479] | MT | 0.27594952 || MTMR9LP | 10.157.367 | myotubularin related protein 9 like, pseudogene [27920] | 1 | 0.265598489 || NETO2 | 10.157.367 | neuropilin and tolloid like 2 [14644] | 16 | 0.249460946 || NPAP1L | 10.157.367 | nuclear pore associated protein 1 like [53980] | 16 | 0.192842212 || PELATON | 10.157.367 | plaque enriched lncRNA in atherosclerotic and inflammatory bowel macrophage regulation [50328] | 20 | 0.22136332 || RTN4RL1 | 10.157.367 | reticulon 4 receptor like 1 [21329] | 17 | 0.199618943 || SLC22A23 | 10.157.367 | solute carrier family 22 member 23 [21106] | 6 | 0.349422866 || SLC39A4 | 10.157.367 | solute carrier family 39 member 4 [17129] | 8 | 0.207082747 || SNPH | 10.157.367 | syntaphilin [15931] | 20 | 0.255741969 || SPOCD1 | 10.157.367 | SPOC domain containing 1 [26338] | 1 | 1.521369047 || VIPR2 | 10.157.367 | vasoactive intestinal peptide receptor 2 [12695] | 7 | 0.30376832 || ALPK2 | 10.158.371 | alpha TABLE 4B-continued The genes within the significant gene clusters, listed in Table 4A. (1127 Genes Listed by: Gene Symbol | Module | Hugo GENE Nomenclature Committee (HGNC) Gene Description [HGNC ID] | Chromosome Number | Row Variance) ||)

kinase 2 [20565] | 18 | 0.62566016 || BHLHE40-AS1 | 10.158.371 | BHLHE40 antisense RNA 1 [44471] | 3 | 0.199450514 || CCDC167 | 10.158.371 | coiled-coil domain containing 167 [21239] | 6 | 0.244875536 || CD70 | 10.158.371 | CD70 molecule [11937] | 19 | 0.358798698 || CRMP1 | 10.158.371 | collapsin response mediator protein 1 [2365] | 4 | 0.461816296 || DACT1 | 10.158.371 | dishevelled binding antagonist of beta catenin 1 [17748] | 14 | 0.690108888 || DNAH6 | 10.158.371 | dynein axonemal heavy chain 6 [2951] | 2 | 0.209959805 || EDARADD | 10.158.371 | EDAR associated death domain [14341] | 1 | 0.305191804 || EGLN3 | 10.158.371 | egl-9 family hypoxia inducible factor 3 [14661] | 14 | 0.208423506 || FDXR | 10.158.371 | ferredoxin reductase [3642] | 17 | 0.237711326 || HEBP2 | 10.158.371 | heme binding protein 2 [15716] | 6 | 0.308569102 || HSPG2 | 10.158.371 | heparan sulfate proteoglycan 2 [5273] | 1 | 0.263394345 || IKZF2 | 10.158.371 | IKAROS family zinc finger 2 [13177] | 2 | 0.238576333 || LINC01871 | 10.158.371 | long intergenic non-protein coding RNA 1871 [52690] | 2 | 0.412536822 || LINC01934 | 10.158.371 | long intergenic non-protein coding RNA 1934 [52757] | 2 | 0.505216937 || MAP6 | 10.158.371 | microtubule associated protein 6 [6868] | 11 | 0.354314931 || MIR34AHG | 10.158.371 | MIR34A host gene [51913] | 1 | 0.692102411 || NFASC | 10.158.371 | neurofascin [29866] | 1 | 0.532400593 || NPDC1 | 10.158.371 | neural proliferation, differentiation and control 1 [7899] | 9 | 0.478930921 || NUGGC | 10.158.371 | nuclear GTPase, germinal center associated [33550] | 8 | 0.740186915 || PHLDA1 | 10.158.371 | pleckstrin homology like domain family A member 1 [8933] | 12 | 0.251664432 || PLEKHA5 | 10.158.371 | pleckstrin homology domain containing A5 [30036] | 12 | 0.350949814 || PTK7 | 10.158.371 | protein tyrosine kinase 7 (inactive) [9618] | 6 | 0.20048699 || SH3RF2 | 10.158.371 | SH3 domain containing ring finger 2 [26299] | 5 | 0.647972167 || SLC24A4 | 10.158.371 | solute carrier family 24 member 4 [10978] | 14 | 0.308825739 || SLC40A1 | 10.158.371 | solute carrier family 40 member 1 [10909] | 2 | 0.316976197 || TMEM18 | 10.158.371 | transmembrane protein 18 [25257] | 2 | 0.365791343 || TTC9 | 10.158.371 | tetratricopeptide repeat domain 9 [20267] | 14 | 0.255157146 || ABCA13 | 3.15.175 | ATP binding cassette subfamily A member 13 [14638] | 7 | 1.949803467 || ACOX1 | 3.15.175 | acyl-CoA oxidase 1 [119] | 17 | 0.214742926 || ACVRL1 | 3.15.175 | activin A receptor like type 1 [175] | 12 | 0.231756931 || ADCY6 | 3.15.175 | adenylate cyclase 6 [237] | 12 | 0.247167428 || AFF2 | 3.15.175 | AF4/FMR2 family member 2 [3776] | X | 0.267934414 || ANLN | 3.15.175 | anillin actin binding protein [14082] | 7 | 0.41560359 || ANO5 | 3.15.175 | anoctamin 5 [27337] | 11 | 0.2377969 || ANTXRL | 3.15.175 | ANTXR like [27277] | 10 | 0.280307341 || ARG1 | 3.15.175 | arginase 1 [663] | 6 | 0.80271313 || ARNT2 | 3.15.175 | aryl hydrocarbon receptor nuclear translocator 2 [16876] | 15 | 0.218439172 || ASGR2 | 3.15.175 | asialoglycoprotein receptor 2 [743] | 17 | 0.324538818 || ASPG | 3.15.175 | asparaginase [20123] | 14 | 0.234876218 || ATOH8 | 3.15.175 | atonal bHLH transcription factor 8 [24126] | 2 | 0.709648486 || ATP2C2 | 3.15.175 | ATPase secretory pathway Ca2+ transporting 2 [29103] | 16 | 0.412897973 || ATP8B4 | 3.15.175 | ATPase phospholipid transporting 8B4 (putative) [13536] | 15 | 0.386137845 || AZU1 | 3.15.175 | azurocidin 1 [913] | 19 | 2.181689008 || BAHCC1 | 3.15.175 | BAH domain and coiled-coil containing 1 [29279] | 17 | 0.270198566 || BEX1 | 3.15.175 | brain expressed X-linked 1 [1036] | X | 0.29241416 || BPI | 3.15.175 | bactericidal permeability increasing protein [1095] | 20 | 2.287641596 || CABP1 | 3.15.175 | calcium binding protein 1 [1384] | 12 | 0.215040244 || CACNA1H | 3.15.175 | calcium voltage-gated channel subunit alpha1 H [1395] | 16 | 0.331682973 || CAMP | 3.15.175 | cathelicidin antimicrobial peptide [1472] | 3 | 3.732215332 || CCND1 | 3.15.175 | cyclin D1 [1582] | 11 | 0.218848045 || CD163L1 | 3.15.175 | CD163 molecule like 1 [30375] | 12 | 0.375002955 || CHIT1 | 3.15.175 | chitinase 1 [1936] | 1 | 1.387557791 || CITED4 | 3.15.175 | Cbp/p300 interacting transactivator with Glu/Asp rich carboxy-terminal domain 4 [18696] | 1 | 0.53779215 || CLDN18 | 3.15.175 | claudin 18 [2039] | 3 | 1.002499809 || CLTCL1 | 3.15.175 | clathrin heavy chain like 1 [2093] | 22 | 0.439095307 || COL17A1 | 3.15.175 | collagen type XVII alpha 1 chain [2194] | 10 | 1.145468935 || COL4A1 | 3.15.175 | collagen type IV alpha 1 chain [2202] | 13 | 0.301394451 || COPDA1 | 3.15.175 | chronic obstructive pulmonary disease associated lncRNA 1 [53171] | 14 | 1.155463391 || CRISP2 | 3.15.175 | cysteine rich secretory protein 2 [12024] | 6 | 0.626376301 || CRISP3 | 3.15.175 | cysteine rich secretory protein 3 [16904] | 6 | 3.32862636 || CSGALNACT2 | 3.15.175 | chondroitin sulfate N-acetylgalactosaminyltransferase 2 [24292] | 10 | 0.196127822 || CSHL1 | 3.15.175 | chorionic somatomammotropin hormone like 1 [2442] | 17 | 0.254070282 || CTSG | 3.15.175 | cathepsin G [2532] | 14 | 2.434312453 || DDN-AS1| 3.15.175 | DDN and PRKAG1 antisense RNA 1 [53464] | 12 | 0.231291953 || DEFA1 | 3.15.175 | defensin alpha 1 [2761] | 8 | 6.02885698 || DEFA1B | 3.15.175 | defensin alpha 1B [33596] | 8 | 6.020733119 || DEFA3 | 3.15.175 | defensin alpha 3 [2762] | 8 | 6.060081949 || DEFA4 | 3.15.175 | defensin alpha 4 [2763] | 8 | 3.286274628 || DEFA8P | 3.15.175 | defensin alpha 8, pseudogene [31799] | 8 | 0.502341929 || DIP2C | 3.15.175 | disco interacting protein 2 homolog C [29150] | 10 | 0.237581706 || DOC2B | 3.15.175 | double C2 domain beta [2986] | 17 | 0.895900742 || DRC1 | 3.15.175 | dynein regulatory complex subunit 1 [24245] | 2 | 0.477110908 || DUOXA1 | 3.15.175 | dual oxidase maturation factor 1 [26507] | 15 | 0.222017738 || ELANE | 3.15.175 | elastase, neutrophil expressed [3309] | 19 | 2.83743961 || ENO2 | 3.15.175 | enolase 2 [3353] | 12 | 0.211392449 || ERG | 3.15.175 | ETS transcription factor ERG [3446] | 21 | 0.789595522 || FBN1 | 3.15.175 | fibrillin 1 [3603] | 15 | 0.307525909 || FCRL3 | 3.15.175 | Fc receptor like 3 [18506] | 1 | 0.512370572 || FGD4 | 3.15.175 | FYVE, RhoGEF and PH domain containing 4 [19125] | 12 | 0.341188761 || FKBP9 | 3.15.175 | FKBP prolyl isomerase 9 [3725] | 7 | 0.333011746 || FOXC1 | 3.15.175 | forkhead box C1 [3800] | 6 | 0.343490025 || GATA3 | 3.15.175 | GATA binding protein 3 [4172] | 10 | 0.260338459 || GLOD5 | 3.15.175 | glyoxalase domain containing 5 [33358] | X | 0.366791338 || GRK1 | 3.15.175 | G protein-coupled receptor kinase 1 [10013] | 13 | 0.21652433 || GUCY2C | 3.15.175 | guanylate cyclase 2C [4688] | 12 | 0.418695295 || H1-0 | 3.15.175 | H1.0 linker histone [4714] | 22 | 0.785887146 || HLA-DPB1 | 3.15.175 | major histocompatibility complex, class II, DP beta TABLE 4B-continued The genes within the significant gene clusters, listed in Table 4A. (1127 Genes Listed by: Gene Symbol | Module | Hugo GENE Nomenclature Committee (HGNC) Gene Description [HGNC ID] | Chromosome Number | Row Variance) ||)

1 [4940] | 6 | 0.400616809 || HMGN3-AS1 | 3.15.175 | HMGN3 antisense RNA 1 [48984] | 6 | 0.22182561 || HTRA3 | 3.15.175 | HtrA serine peptidase 3 [30406] | 4 | 1.279383652 || IL18R1 | 3.15.175 | interleukin 18 receptor 1 [5988] | 2 | 0.580414371 || INHBA | 3.15.175 | inhibin subunit beta A [6066] | 7 | 0.472910979 || IRF4 | 3.15.175 | interferon regulatory factor 4 [6119] | 6 | 0.273290762 || JDP2 | 3.15.175 | Jun dimerization protein 2 [17546] | 14 | 0.395452255 || JPH3 | 3.15.175 | junctophilin 3 [14203] | 16 | 0.196598142 || KCNE1B | 3.15.175 | potassium voltage-gated channel subfamily E regulatory subunit 1B [52280] | 21 | 0.338191339 || KLHL8 | 3.15.175 | kelch like family member 8 [18644] | 4 | 0.219613484 || LCN2 | 3.15.175 | lipocalin 2 [6526] | 9 | 4.429700359 || LINC00671 | 3.15.175 | long intergenic non-protein coding RNA 671 [44339] | 17 | 0.547241153 || LINC01529 | 3.15.175 | long intergenic non-protein coding RNA 1529 [51268] | 19 | 0.28449384 || LINC01579 | 3.15.175 | long intergenic non-protein coding RNA 1579 [27519] | 15 | 0.741679367 || LINC02009 | 3.15.175 | long intergenic non-protein coding RNA 2009 [52845] | 3 | 2.571876215 || LRRC2 | 3.15.175 | leucine rich repeat containing 2 [14676] | 3 | 0.222335049 || LTF | 3.15.175 | lactotransferrin [6720] | 3 | 5.356296816 || MCEMP1 | 3.15.175 | mast cell expressed membrane protein 1 [27291] | 19 | 0.396882101 || METTL7B | 3.15.175 | methyltransferase like 7B [28276] | 12 | 0.386773446 || MGST1 | 3.15.175 | microsomal glutathione S-transferase 1 [7061] | 12 | 0.19381817 || MIR223HG | 3.15.175 | MIR223 host gene [54520] | X | 0.434236839 || MMP8 | 3.15.175 | matrix metallopeptidase 8 [7175] | 11 | 4.297062153 || MPO | 3.15.175 | myeloperoxidase [7218] | 17 | 1.812866741 || MS4A3 | 3.15.175 | membrane spanning 4-domains A3 [7317] | 11 | 1.456577717 || NLRC4 | 3.15.175 | NLR family CARD domain containing 4 [16412] | 2 | 0.214984717 || NTRK1 | 3.15.175 | neurotrophic receptor tyrosine kinase 1 [8031] | 1 | 0.284500207 || NXF3 | 3.15.175 | nuclear RNA export factor 3 [8073] | X | 0.365785424 || OLFM4 | 3.15.175 | olfactomedin 4 [17190] | 13 | 3.551682823 || OLR1 | 3.15.175 | oxidized low density lipoprotein receptor 1 [8133] | 12 | 1.685099579 || OR6N1 | 3.15.175 | olfactory receptor family 6 subfamily N member 1 [15034] | 1 | 0.333893435 || ORM1 | 3.15.175 | orosomucoid 1 [8498] | 9 | 0.917913406 || ORM2 | 3.15.175 | orosomucoid 2 [8499] | 9 | 0.316655223 || PARP4P2 | 3.15.175 | poly(ADP-ribose) polymerase family member 4 pseudogene 2 [37760] | 13 | 0.203443319 || PASK | 3.15.175 | PAS domain containing serine/threonine kinase [17270] | 2 | 0.321654544 || PCOLCE2 | 3.15.175 | procollagen C-endopeptidase enhancer 2 [8739] | 3 | 0.444993305 || PCSK9 | 3.15.175 | proprotein convertase subtilisin/kexin type 9 [20001] | 1 | 0.338971895 || PDE3A | 3.15.175 | phosphodiesterase 3A [8778] | 12 | 0.324403802 || PGLYRP1 | 3.15.175 | peptidoglycan recognition protein 1 [8904] | 19 | 1.37540449 || PGM5 | 3.15.175 | phosphoglucomutase 5 [8908] | 9 | 0.352919635 || PHC1P1 | 3.15.175 | polyhomeotic homolog 1 pseudogene 1 [34502] | 12 | 0.205306824 || PLA2G2D | 3.15.175 | phospholipase A2 group IID [9033] | 1 | 0.304184834 || PLBD1 | 3.15.175 | phospholipase B domain containing 1 [26215] | 12 | 0.313549619 || PRRT4 | 3.15.175 | proline rich transmembrane protein 4 [37280] | 7 | 1.456430276 || PRTN3 | 3.15.175 | proteinase 3 [9495] | 19 | 2.09866507 || PXYLP1 | 3.15.175 | 2-phosphoxylose phosphatase 1 [26303] | 3 | 0.207173298 || RAB44 | 3.15.175 | RAB44, member RAS oncogene family [21068] | 6 | 0.211604532 || RNASE3 | 3.15.175 | ribonuclease A family member 3 [10046] | 14 | 1.086529053 || RNF144B | 3.15.175 | ring finger protein 144B [21578] | 6 | 0.270154628 || RNU6-1176P | 3.15.175 | RNA, U6 small nuclear 1176, pseudogene [48139] | 1 | 0.229033329 || RPL10P19 | 3.15.175 | ribosomal protein L10 pseudogene 19 [52350] | 8 | 0.252468664 || RTN4R | 3.15.175 | reticulon 4 receptor [18601] | 22 | 0.293286614 || S1PR1 | 3.15.175 | sphingosine-1-phosphate receptor 1 [3165] | 1 | 0.248382272 || SAMSN1 | 3.15.175 | SAM domain, SH3 domain and nuclear localization signals 1 [10528] | 21 | 0.261843442 || SEMA3C | 3.15.175 | semaphorin 3C [10725] | 7 | 0.430616292 || SEMA4C | 3.15.175 | semaphorin 4C [10731] | 2 | 0.216768036 || SERPINB10 | 3.15.175 | serpin family B member 10 [8942] | 18 | 1.083219397 || SLAMF1 | 3.15.175 | signaling lymphocytic activation molecule family member 1 [10903] | 1 | 0.193367619 || SLC5A9 | 3.15.175 | solute carrier family 5 member 9 [22146] | 1 | 0.235399574 || SORCS2 | 3.15.175 | sortilin related VPS10 domain containing receptor 2 [16698] | 4 | 0.336072785 || ST14 | 3.15.175 | ST14 transmembrane serine protease matriptase [11344] | 11 | 0.540976999 || STOM | 3.15.175 | stomatin [3383] | 9 | 0.225942026 || STOX2 | 3.15.175 | storkhead box 2 [25450] | 4 | 0.658794954 || TCN1 | 3.15.175 | transcobalamin 1 [11652] | 11 | 1.779278216 || TCTEX1D1 | 3.15.175 | Tctex1 domain containing 1 [26882] | 1 | 0.428020312 || TEKT2 | 3.15.175 | tektin 2 [11725] | 1 | 0.238958678 || TFF3 | 3.15.175 | trefoil factor 3 [11757] | 21 | 0.443869955 || THAP7-AS1 | 3.15.175 | THAP7 antisense RNA 1 [41013] | 22 | 0.357196119 || TMEM252-DT | 3.15.175 | TMEM252 divergent transcript [54377] | 9 | 0.295532519 || TMEM52B | 3.15.175 | transmembrane protein 52B [26438] | 12 | 0.249424729 || TRAV8-4 | 3.15.175 | T cell receptor alpha variable 8-4 [12149] | 14 | 0.313639831 || TRBV7-4 | 3.15.175 | T cell receptor beta variable 7-4 [12238] | 7 | 0.192877586 || TRNP1 | 3.15.175 | TMF1 regulated nuclear protein 1 [34348] | 1 | 0.382095317 || TRPM2 | 3.15.175 | transient receptor potential cation channel subfamily M member 2 [12339] | 21 | 0.305147315 || TSKS | 3.15.175 | testis specific serine kinase substrate [30719] | 19 | 0.435682152 || TSPAN7 | 3.15.175 | tetraspanin 7 [11854] | X | 0.42507701 || TUBA5P | 3.15.175 | tubulin alpha 5, pseudogene [54799] | 1 | 0.25001043 || TUSC8 | 3.15.175 | tumor suppressor candidate 8 [49111] | 13 | 0.315571137 || TXNL4B | 3.15.175 | thioredoxin like 4B [26041] | 16 | 0.826279004 || VEGFA | 3.15.175 | vascular endothelial growth factor A [12680] | 6 | 0.271157146 || XKR7 | 3.15.175 | XK related 7 [23062] | 20 | 0.269042149 || ZC3H12D | 3.15.175 | zinc finger CCCH-type containing 12D [21175] | 6 | 0.254952762 || ADAMTSL4-AS1 | 3.18.209 | ADAMTSL4 antisense RNA 1 [32041] | 1 | 0.498597084 || ADAMTSL4-AS2 | 3.18.209 | ADAMTSL4 antisense RNA 2 [40895] | 1 | 0.769186842 || ALDH1A2 | 3.18.209 | aldehyde dehydrogenase 1 family member A2 [15472] | 15 | 0.649791759 || ANK3-DT | 3.18.209 | ANK3 divergent transcript [54102] | 10 | 0.212167801 || ARHGAP22 | 3.18.209 | Rho GTPase activating protein 22 [30320] | 10 | 0.32517591 || BNIPL | 3.18.209 | BCL2

TABLE 4B-continued

The genes within the significant gene clusters, listed in Table 4A. (1127 Genes Listed by: Gene Symbol | Module | Hugo GENE Nomenclature Committee (HGNC) Gene Description [HGNC ID] | Chromosome Number | Row Variance) ||)

interacting protein like [16976] | 1 | 0.218646934 || BTN1A1 | 3.18.209 | butyrophilin subfamily 1 member A1 [1135] | 6 | 0.316808346 || CA12 | 3.18.209 | carbonic anhydrase 12 [1371] | 15 | 0.347394647 || CAPN13 | 3.18.209 | calpain 13 [16663] | 2 | 0.379810692 || CNIH2 | 3.18.209 | cornichon family AMPA receptor auxiliary protein 2 [28744] | 11 | 0.194677624 || CNTF | 3.18.209 | ciliary neurotrophic factor [2169] | 11 | 0.195516836 || CSF1 | 3.18.209 | colony stimulating factor 1 [2432] | 1 | 0.237190276 || DNAH17 | 3.18.209 | dynein axonemal heavy chain 17 [2946] | 17 | 0.38817531 || ENAH | 3.18.209 | ENAH actin regulator [18271] | 1 | 0.249285147 || FAAHP1 | 3.18.209 | fatty acid amide hydrolase pseudogene 1 [50679] | 1 | 0.339731185 || FAR2 | 3.18.209 | fatty acyl-CoA reductase 2 [25531] | 12 | 0.271583502 || FGGY | 3.18.209 | FGGY carbohydrate kinase domain containing [25610] | 1 | 0.23600642 || GLI1 | 3.18.209 | GLI family zinc finger 1 [4317] | 12 | 0.366125689 || GRM2 | 3.18.209 | glutamate metabotropic receptor 2 [4594] | 3 | 0.221311405 || H4C6 | 3.18.209 | H4 clustered histone 6 [4783] | 6 | 0.216346115 || HCG27 | 3.18.209 | HLA complex group 27 [27366] | 6 | 0.334749528 || IFITM3P2 | 3.18.209 | IFITM3 pseudogene 2 [54539] | 12 | 1.877448714 || IGHD3-10 | 3.18.209 | immunoglobulin heavy diversity 3-10 [5495] | 14 | 0.235072947 || KCTD15 | 3.18.209 | potassium channel tetramerization domain containing 15 [23297] | 19 | 0.219875585 || KLK1 | 3.18.209 | kallikrein 1 [6357] | 19 | 0.61159451 || KRT7 | 3.18.209 | keratin 7 [6445] | 12 | 0.261016383 || KRT74 | 3.18.209 | keratin 74 [28929] | 12 | 0.223807226 || LINC01093 | 3.18.209 | long intergenic non-protein coding RNA 1093 [49218] | 4 | 0.418320287 || LINC01791 | 3.18.209 | long intergenic non-protein coding RNA 1791 [52581] | 19 | 0.35312663 || LINC02656 | 3.18.209 | long intergenic non-protein coding RNA 2656 [54142] | 10 | 0.247082307 || MDM2 | 3.18.209 | MDM2 proto-oncogene [6973] | 12 | 0.196186937 || MIR24-2 | 3.18.209 | microRNA 24-2 [31608] | 19 | 0.320069777 || MIR3648-2 | 3.18.209 | microRNA 3648-2 [50843] | 21 | 0.261340759 || MY06 | 3.18.209 | myosin VI [7605] | 6 | 0.229367878 || NANOS3 | 3.18.209 | nanos C2HC-type zinc finger 3 [22048] | 19 | 0.199982458 || NEFL | 3.18.209 | neurofilament light [7739] | 8 | 0.57819922 || PCP4L1 | 3.18.209 | Purkinje cell protein 4 like 1 [20448] | 1 | 0.257711621 || PLXNA4 | 3.18.209 | plexin A4 [9102] | 7 | 0.782935274 || PRSS16 | 3.18.209 | serine protease 16 [9480] | 6 | 0.295347342 || RBM47 | 3.18.209 | RNA binding motif protein 47 [30358] | 4 | 0.197917198 || RPS3AP18 | 3.18.209 | RPS3A pseudogene 18 [35893] | 4 | 0.195137815 || SEMA3B | 3.18.209 | semaphorin 3B [10724] | 3 | 0.335771172 || SLC52A3 | 3.18.209 | solute carrier family 52 member 3 [16187] | 20 | 0.193580148 || SMPDL3B | 3.18.209 | sphingomyelin phosphodiesterase acid like 3B [21416] | 1 | 0.284539507 || SPACA6 | 3.18.209 | sperm acrosome associated 6 [27113] | 19 | 0.313977254 || TAFA1 | 3.18.209 | TAFA chemokine like family member 1 [21587] | 3 | 0.228016041 || TEK | 3.18.209 | TEK receptor tyrosine kinase [11724] | 9 | 0.437582366 || TMEM119 | 3.18.209 | transmembrane protein 119 [27884] | 12 | 1.229728093 || TMEM221 | 3.18.209 | transmembrane protein 221 [21943] | 19 | 0.213446597 || TUBA1C | 3.18.209 | tubulin alpha 1c [20768] | 12 | 0.268287088 || TULP2 | 3.18.209 | TUB like protein 2 [12424] | 19 | 0.215791333 || WNT1 | 3.18.209 | Wnt family member 1 [12774] | 12 | 0.264033266 || ZDHHC19 | 3.18.209 | zinc finger DHHC-type palmitoyltransferase 19 [20713] | 3 | 0.598926152 || ADIG | 3.19.210 | adipogenin [28606] | 20 | 0.375549148 || ARHGAP24 | 3.19.210 | Rho GTPase activating protein 24 [25361] | 4 | 0.330365942 || ARMC12 | 3.19.210 | armadillo repeat containing 12 [21099] | 6 | 0.388160273 || BSND | 3.19.210 | barttin CLCNK type accessory subunit beta [16512] | 1 | 0.387925506 || CASKIN1 | 3.19.210 | CASK interacting protein 1 [20879] | 16 | 0.273226407 || CCDC181 | 3.19.210 | coiled-coil domain containing 181 [28051] | 1 | 0.198534058 || CCNA1 | 3.19.210 | cyclin A1 [1577] | 13 | 0.837711805 || COL9A2 | 3.19.210 | collagen type IX alpha 2 chain [2218] | 1 | 0.819416632 || CPLX1 | 3.19.210 | complexin 1 [2309] | 4 | 0.284412758 || CYP2S1 | 3.19.210 | cytochrome P450 family 2 subfamily S member 1 [15654] | 19 | 0.265056218 || DAAM2 | 3.19.210 | dishevelled associated activator of morphogenesis 2 [18143] | 6 | 2.568877722 || EPCAM-DT | 3.19.210 | EPCAM divergent transcript [52639] | 2 | 0.823091071 || FAM24B | 3.19.210 | family with sequence similarity 24 member B [23475] | 10 | 0.361099035 || FLT1P1 | 3.19.210 | FLT1 pseudogene 1 [44609] | 3 | 0.750626828 || FSD1 | 3.19.210 | fibronectin type III and SPRY domain containing 1 [13745] | 19 | 0.311243254 || GSTT2 | 3.19.210 | glutathione S-transferase theta 2 (gene/pseudogene) [4642] | 22 | 0.284499228 || GSTT2B | 3.19.210 | glutathione S-transferase theta 2B [33437] | 22 | 0.373292778 || GUCY2D | 3.19.210 | guanylate cyclase 2D, retinal [4689] | 17 | 0.449922072 || HCG14 | 3.19.210 | HLA complex group 14 [18323] | 6 | 0.275297037 || HGD | 3.19.210 | homogentisate 1,2-dioxygenase [4892] | 3 | 0.192005757 || IL18RAP | 3.19.210 | interleukin 18 receptor accessory protein [5989] | 2 | 0.57872753 || IL1R2 | 3.19.210 | interleukin 1 receptor type 2 [5994] | 2 | 1.564546297 || ITGAD | 3.19.210 | integrin subunit alpha D [6146] | 16 | 0.380564957 || LAMB3 | 3.19.210 | laminin subunit beta 3 [6490] | 1 | 0.265486227 || MAMSTR | 3.19.210 | MEF2 activating motif and SAP domain containing transcriptional regulator [26689] | 19 | 0.235235691 || MED6P1 | 3.19.210 | mediator complex subunit 6 pseudogene 1 [45164] | 10 | 0.267120527 || NIPAL2 | 3.19.210 | NIPA like domain containing 2 [25854] | 8 | 0.761215573 || NT5DC4 | 3.19.210 | 5'-nucleotidase domain containing 4 [27678] | 2 | 0.24572225 || OLAH | 3.19.210 | oleoyl-ACP hydrolase [25625] | 10 | 1.089751506 || PDGFB | 3.19.210 | platelet derived growth factor subunit B [8800] | 22 | 0.44743659 || PTGFRN | 3.19.210 | prostaglandin F2 receptor inhibitor [9601] | 1 | 0.207709575 || PTPDC1 | 3.19.210 | protein tyrosine phosphatase domain containing 1 [30184] | 9 | 0.212118548 || PTPN3 | 3.19.210 | protein tyrosine phosphatase non-receptor type 3 [9655] | 9 | 0.210206736 || RN7SL251P | 3.19.210 | RNA, 7SL, cytoplasmic 251, pseudogene [46267] | 2 | 0.217141822 || SCRG1 | 3.19.210 | stimulator of chondrogenesis 1 [17036] | 4 | 0.557849541 || SETD9 | 3.19.210 | SET domain containing 9 [28508] | 5 | 0.348948138 || SH3BP4 | 3.19.210 | SH3 domain binding protein 4 [10826] | 2 | 0.214899159 || SLC1A3 | 3.19.210 | solute carrier family 1 member 3 [10941] | 5 | 0.257670688 || SRGAP1 | 3.19.210 | SLIT-ROBO Rho GTPase activating protein 1 [17382] | 12 | 0.387373215 ||

TABLE 4B-continued

| The genes within the significant gene clusters, listed in Table 4A. (1127 Genes Listed by: Gene Symbol ǀ Module ǀ Hugo GENE Nomenclature Committee (HGNC) Gene Description [HGNC ID] ǀ Chromosome Number ǀ Row Variance) ǀǀ) |
|---|
| ST6GALNAC3 ǀ 3.19.210 ǀ ST6 N-acetylgalactosaminide alpha-2,6-sialyltransferase 3 [19343] ǀ 1 ǀ 0.322684367 ǀǀ STK19B ǀ 3.19.210 ǀ serine/threonine kinase 19B (pseudogene) [21668] ǀ 6 ǀ 0.194892707 ǀǀ TAC3 ǀ 3.19.210 ǀ tachykinin precursor 3 [11521] ǀ 12 ǀ 0.200305555 ǀǀ TBC1D8 ǀ 3.19.210 ǀ TBC1 domain family member 8 [17791] ǀ 2 ǀ 0.198085751 ǀǀ TMIGD3 ǀ 3.19.210 ǀ transmembrane and immunoglobulin domain containing 3 [51375] ǀ 1 ǀ 0.431544394 ǀǀ TPST1 ǀ 3.19.210 ǀ tyrosylprotein sulfotransferase 1 [12020] ǀ 7 ǀ 1.172045609 ǀǀ TRAJ3 ǀ 3.19.210 ǀ T cell receptor alpha joining 3 [12059] ǀ 14 ǀ 0.285689486 ǀǀ TRAV2 ǀ 3.19.210 ǀ T cell receptor alpha variable 2 [12116] ǀ 14 ǀ 0.206872299 ǀǀ TRAV8-1 ǀ 3.19.210 ǀ T cell receptor alpha variable 8-1 [12146] ǀ 14 ǀ 0.501099006 ǀǀ TRBV10-1 ǀ 3.19.210 ǀ T cell receptor beta variable 10-1 [12177] ǀ 7 ǀ 0.229389662 ǀǀ TSHZ2 ǀ 3.19.210 ǀ teashirt zinc finger homeobox 2 [13010] ǀ 20 ǀ 0.384265605 ǀǀ VCX ǀ 3.19.210 ǀ variable charge X-linked [12667] ǀ X ǀ 0.234404795 ǀǀ VCX3A ǀ 3.19.210 ǀ variable charge X-linked 3A [18159] ǀ X ǀ 0.32746452 ǀǀ VCX3B ǀ 3.19.210 ǀ variable charge X-linked 3B [31838] ǀ X ǀ 0.372263482 ǀǀ VSIG4 ǀ 3.19.210 ǀ V-set and immunoglobulin domain containing 4 [17032] ǀ X ǀ 0.915220718 ǀǀ ZNF667 ǀ 3.19.210 ǀ zinc finger protein 667 [28854] ǀ 19 ǀ 0.277352387 ǀǀ A4GALT ǀ 3.19.211 ǀ alpha 1,4-galactosyltransferase (P blood group) [18149] ǀ 22 ǀ 0.491952916 ǀǀ ADAMTS2 ǀ 3.19.211 ǀ ADAM metallopeptidase with thrombospondin type 1 motif 2 [218] ǀ 5 ǀ 3.295258199 ǀǀ ALDH1A1 ǀ 3.19.211 ǀ aldehyde dehydrogenase 1 family member A1 [402] ǀ 9 ǀ 0.247050333 ǀǀ ALDH2 ǀ 3.19.211 ǀ aldehyde dehydrogenase 2 family member [404] ǀ 12 ǀ 0.253408173 ǀǀ ALOX15B ǀ 3.19.211 ǀ arachidonate 15-lipoxygenase type B [434] ǀ 17 ǀ 2.491960444 ǀǀ ASB2 ǀ 3.19.211 ǀ ankyrin repeat and SOCS box containing 2 [16012] ǀ 14 ǀ 0.269448936 ǀǀ BCAT1 ǀ 3.19.211 ǀ branched chain amino acid transaminase 1 [976] ǀ 12 ǀ 0.228670978 ǀǀ CD163 ǀ 3.19.211 ǀ CD163 molecule [1631] ǀ 12 ǀ 0.94004824 ǀǀ CPM ǀ 3.19.211 ǀ carboxypeptidase M [2311] ǀ 12 ǀ 0.514551432 ǀǀ DDIT4 ǀ 3.19.211 ǀ DNA damage inducible transcript 4 [24944] ǀ 10 ǀ 0.991607316 ǀǀ ENPP3 ǀ 3.19.211 ǀ ectonucleotide pyrophosphatase/phosphodiesterase 3 [3358] ǀ 6 ǀ 0.193664294 ǀǀ FHDC1 ǀ 3.19.211 ǀ FH2 domain containing 1 [29363] ǀ 4 ǀ 0.333491532 ǀǀ FHL2 ǀ 3.19.211 ǀ four and a half LIM domains 2 [3703] ǀ 2 ǀ 0.211121448 ǀǀ GLDN ǀ 3.19.211 ǀ gliomedin [29514] ǀ 15 ǀ 0.552947263 ǀǀ IQGAP3 ǀ 3.19.211 ǀ IQ motif containing GTPase activating protein 3 [20669] ǀ 1 ǀ 0.480958456 ǀǀ KLF9 ǀ 3.19.211 ǀ Kruppel like factor 9 [1123] ǀ 9 ǀ 0.480404726 ǀǀ LINC00482 ǀ 3.19.211 ǀ long intergenic non-protein coding RNA 482 [26816] ǀ 17 ǀ 0.56455715 ǀǀ LINC01127 ǀ 3.19.211 ǀ long intergenic non-protein coding RNA 1127 [49292] ǀ 2 ǀ 0.484275183 ǀǀ LINC01736 ǀ 3.19.211 ǀ long intergenic non-protein coding RNA 1736 [52524] ǀ 1 ǀ 0.278607593 ǀǀ LINC02087 ǀ 3.19.211 ǀ long intergenic non-protein coding RNA 2087 [52938] ǀ 17 ǀ 0.251322959 ǀǀ LRMDA ǀ 3.19.211 ǀ leucine rich melanocyte differentiation associated [23405] ǀ 10 ǀ 0.264254212 ǀǀ LYZ ǀ 3.19.211 ǀ lysozyme [6740] ǀ 12 ǀ 0.251575699 ǀǀ MARCHF1 ǀ 3.19.211 ǀ membrane associated ring-CH-type finger 1 [26077] ǀ 4 ǀ 0.197429879 ǀǀ MARVELD1 ǀ 3.19.211 ǀ MARVEL domain containing 1 [28674] ǀ 10 ǀ 0.42115698 ǀǀ MIR181A1HG ǀ 3.19.211 ǀ MIR181A1 host gene [48659] ǀ 1 ǀ 0.513077625 ǀǀ MS4A6A ǀ 3.19.211 ǀ membrane spanning 4-domains A6A [13375] ǀ 11 ǀ 0.282247454 ǀǀ MY010 ǀ 3.19.211 ǀ myosin X [7593] ǀ 5 ǀ 0.275167325 ǀǀ NBPF2P ǀ 3.19.211 ǀ NBPF member 2, pseudogene [31987] ǀ 1 ǀ 0.197461688 ǀǀ PER1 ǀ 3.19.211 ǀ period circadian regulator 1 [8845] ǀ 17 ǀ 0.882501466 ǀǀ SAP30 ǀ 3.19.211 ǀ Sin3A associated protein 30 [10532] ǀ 4 ǀ 0.652480523 ǀǀ SH3PXD2B ǀ 3.19.211 ǀ SH3 and PX domains 2B [29242] ǀ 5 ǀ 0.809753441 ǀǀ SIGLEC16 ǀ 3.19.211 ǀ sialic acid binding Ig like lectin 16 [24851] ǀ 19 ǀ 0.335176412 ǀǀ SPTLC2 ǀ 3.19.211 ǀ serine palmitoyltransferase long chain base subunit 2 [11278] ǀ 14 ǀ 0.229877559 ǀǀ TRGJP ǀ 3.19.211 ǀ T cell receptor gamma joining P [12279] ǀ 7 ǀ 0.200096724 ǀǀ VCAN ǀ 3.19.211 ǀ versican [2464] ǀ 5 ǀ 0.383408657 ǀǀ ABCC11 ǀ 3.19.214 ǀ ATP binding cassette subfamily C member 11 [14639] ǀ 16 ǀ 0.361172017 ǀǀ CDH22 ǀ 3.19.214 ǀ cadherin 22 [13251] ǀ 20 ǀ 0.224452542 ǀǀ CEACAM22P ǀ 3.19.214 ǀ CEA cell adhesion molecule 22, pseudogene [38029] ǀ 19 ǀ 0.446461315 ǀǀ COL6A5 ǀ 3.19.214 ǀ collagen type VI alpha 5 chain [26674] ǀ 3 ǀ 0.205456512 ǀǀ DNM1 ǀ 3.19.214 ǀ dynamin 1 [2972] ǀ 9 ǀ 0.319784201 ǀǀ ELAPOR1 ǀ 3.19.214 ǀ endosome-lysosome associated apoptosis and autophagy regulator 1 [29618] ǀ 1 ǀ 1.095051024 ǀǀ F12 ǀ 3.19.214 ǀ coagulation factor XII [3530] ǀ 5 ǀ 0.195853016 ǀǀ GGT8P ǀ 3.19.214 ǀ gamma-glutamyltransferase 8 pseudogene [33438] ǀ 2 ǀ 0.22670833 ǀǀ GSTM2 ǀ 3.19.214 ǀ glutathione S-transferase mu 2 [4634] ǀ 1 ǀ 0.815782322 ǀǀ IQCD ǀ 3.19.214 ǀ IQ motif containing D [25168] ǀ 12 ǀ 0.291413296 ǀǀ KLRC1 ǀ 3.19.214 ǀ killer cell lectin like receptor C1 [6374] ǀ 12 ǀ 0.633409664 ǀǀ LINC01629 ǀ 3.19.214 ǀ long intergenic non-protein coding RNA 1629 [52260] ǀ 14 ǀ 0.857597284 ǀǀ LINC02288 ǀ 3.19.214 ǀ long intergenic non-protein coding RNA 2288 [27505] ǀ 14 ǀ 0.302419386 ǀǀ LMX1B ǀ 3.19.214 ǀ LIM homeobox transcription factor 1 beta [6654] ǀ 9 ǀ 0.214243895 ǀǀ NYAP1 ǀ 3.19.214 ǀ neuronal tyrosine phosphorylated phosphoinositide-3-kinase adaptor 1 [22009] ǀ 7 ǀ 0.279288328 ǀǀ OR7E66P ǀ 3.19.214 ǀ olfactory receptor family 7 subfamily E member 66 pseudogene [8442] ǀ 3 ǀ 0.199460104 ǀǀ PGC ǀ 3.19.214 ǀ progastricsin [8890] ǀ 6 ǀ 0.256435589 ǀǀ PRRT1B ǀ 3.19.214 ǀ proline rich transmembrane protein 1B [53642] ǀ 9 ǀ 0.356204901 ǀǀ PSCA ǀ 3.19.214 ǀ prostate stem cell antigen [9500] ǀ 8 ǀ 0.200797905 ǀǀ SCN2B ǀ 3.19.214 ǀ sodium voltage-gated channel beta subunit 2 [10589] ǀ 11 ǀ 0.268219836 ǀǀ TRBD1 ǀ 3.19.214 ǀ T cell receptor beta diversity 1 [12158] ǀ 7 ǀ 0.195701374 ǀǀ AMPD2 ǀ 3.20.216 ǀ adenosine monophosphate deaminase 2 [469] ǀ 1 ǀ 0.221608386 ǀǀ ANXA2P2 ǀ 3.20.216 ǀ annexin A2 pseudogene 2 [539] ǀ 9 ǀ 0.226094066 ǀǀ ATP1A4 ǀ 3.20.216 ǀ ATPase Na+/K+ transporting subunit alpha 4 [14073] ǀ 1 ǀ 0.706927663 ǀǀ ATP2B2 ǀ 3.20.216 ǀ ATPase plasma membrane Ca2+ transporting 2 [815] ǀ 3 ǀ 0.213271481 ǀǀ C1QA ǀ 3.20.216 ǀ complement C1q A chain [1241] ǀ 1 ǀ 1.05495733 ǀǀ CASQ1 ǀ 3.20.216 ǀ calsequestrin 1 [1512] ǀ 1 ǀ 0.324434806 ǀǀ CNN3 ǀ 3.20.216 ǀ calponin 3 [2157] ǀ 1 ǀ 0.480876689 ǀǀ E2F2 ǀ 3.20.216 ǀ E2F transcription factor 2 [3114] ǀ 1 ǀ 0.227143978 ǀǀ EPS8L1 ǀ 3.20.216 ǀ EPS8 like 1 [21295] ǀ 19 ǀ 0.247839187 ǀǀ EVC ǀ 3.20.216 ǀ EvC ciliary complex subunit 1 [3497] ǀ 4 ǀ 0.281961561 ǀǀ GOLGA6L9 ǀ 3.20.216 ǀ golgin A6 family like 9 [37229] ǀ 15 ǀ 0.195732801 ǀǀ GSTA6P ǀ 3.20.216 ǀ glutathione S- |

TABLE 4B-continued

The genes within the significant gene clusters, listed in Table 4A. (1127 Genes Listed by: Gene Symbol | Module | Hugo GENE Nomenclature Committee (HGNC) Gene Description [HGNC ID] | Chromosome Number | Row Variance) ||)

transferase alpha 6, pseudogene [4630] | 6 | 0.309384595 || KIR3DX1 | 3.20.216 | killer cell immunoglobulin like receptor, three Ig domains X1 (pseudogene) [25043] | 19 | 0.215158425 || KRT5 | 3.20.216 | keratin 5 [6442] | 12 | 0.339298636 || LGALS1 | 3.20.216 | galectin 1 [6561] | 22 | 0.344899724 || MDS2 | 3.20.216 | myelodysplastic syndrome 2 translocation associated [29633] | 1 | 0.34209574 || NOG | 3.20.216 | noggin [7866] | 17 | 0.790412867 || NT5E | 3.20.216 | 5'-nucleotidase ecto [8021] | 6 | 0.65741595 || PARP11-AS1 | 3.20.216 | PARP11 antisense RNA 1 [40103] | 12 | 0.530049442 || PATL2 | 3.20.216 | PAT1 homolog 2 [33630] | 15 | 0.296429142 || SLC22A17 | 3.20.216 | solute carrier family 22 member 17 [23095] | 14 | 0.59941877 || SOX8 | 3.20.216 | SRY-box transcription factor 8 [11203] | 16 | 0.405416714 || SPEG | 3.20.216 | striated muscle enriched protein kinase [16901] | 2 | 0.298251987 || TSPAN6 | 3.20.216 | tetraspanin 6 [11858] | X | 0.191579507 || BCL11A | 5.22.218 | BAF chromatin remodeling complex subunit BCL11A [13221] | 2 | 0.347761634 || BLNK | 5.22.218 | B cell linker [14211] | 10 | 0.448890192 || CD40 | 5.22.218 | CD40 molecule [11919] | 20 | 0.374783431 || CELSR1 | 5.22.218 | cadherin EGF LAG seven-pass G-type receptor 1 [1850] | 22 | 0.685302559 || CENPV | 5.22.218 | centromere protein V [29920] | 17 | 0.234605007 || CEP55 | 5.22.218 | centrosomal protein 55 [1161] | 10 | 0.339355777 || COBLL1 | 5.22.218 | cordon-bleu WH2 repeat protein like 1 [23571] | 2 | 0.515125404 || COLCA1 | 5.22.218 | colorectal cancer associated 1 [33789] | 11 | 0.227228703 || CR2 | 5.22.218 | complement C3d receptor 2 [2336] | 1 | 0.879483603 || DCLK2 | 5.22.218 | doublecortin like kinase 2 [19002] | 4 | 0.345643102 || DNMT3L | 5.22.218 | DNA methyltransferase 3 like [2980] | 21 | 0.62576454 || E2F5 | 5.22.218 | E2F transcription factor 5 [3119] | 8 | 0.266685005 || EPB41L2 | 5.22.218 | erythrocyte membrane protein band 4.1 like 2 [3379] | 6 | 0.198773579 || FCMR | 5.22.218 | Fc fragment of IgM receptor [14315] | 1 | 0.215576187 || FCRL2 | 5.22.218 | Fc receptor like 2 [14875] | 1 | 0.959563597 || H3C13 | 5.22.218 | H3 clustered histone 13 [25311] | 1 | 0.234208814 || HLA-DOA | 5.22.218 | major histocompatibility complex, class II, DO alpha [4936] | 6 | 0.671265409 || HRK | 5.22.218 | harakiri, BCL2 interacting protein [5185] | 12 | 0.834628456 || KCNH8 | 5.22.218 | potassium voltage-gated channel subfamily H member 8 [18864] | 3 | 0.375278453 || LARGE2 | 5.22.218 | LARGE xylosyl- and glucuronyltransferase 2 [16522] | 11 | 0.78527598 || LINC00926 | 5.22.218 | long intergenic non-protein coding RNA 926 [27514] | 15 | 1.609914288 || LINC01342 | 5.22.218 | long intergenic non-protein coding RNA 1342 [50551] | 1 | 0.92939897 || LINC01413 | 5.22.218 | long intergenic non-protein coding RNA 1413 [50705] | 15 | 0.252961886 || LINC01907 | 5.22.218 | long intergenic non-protein coding RNA 1907 [52726] | 2 | 0.21198543 || MICAL3 | 5.22.218 | microtubule associated monooxygenase, calponin and LIM domain containing 3 [24694] | 22 | 0.2433002 || MIR4538 | 5.22.218 | microRNA 4538 [41664] | 14 | 0.60701744 || MIR5195 | 5.22.218 | microRNA 5195 [43526] | 14 | 0.291289101 || NUSAP1 | 5.22.218 | nucleolar and spindle associated protein 1 [18538] | 15 | 0.236394408 || PAX5 | 5.22.218 | paired box 5 [8619] | 9 | 1.260980358 || PCDH9 | 5.22.218 | protocadherin 9 [8661] | 13 | 0.334106337 || PKIG | 5.22.218 | cAMP-dependent protein kinase inhibitor gamma [9019] | 20 | 0.295482159 || PRAMENP | 5.22.218 | PRAME N-terminal like, pseudogene [34302] | 22 | 0.366827974 || RPS2P17 | 5.22.218 | ribosomal protein S2 pseudogene 17 [35764] | 2 | 0.212933519 || SCGB3A1 | 5.22.218 | secretoglobin family 3A member 1 [18384] | 5 | 1.371411692 || SLC44A5 | 5.22.218 | solute carrier family 44 member 5 [28524] | 1 | 0.203809505 || SPRY1 | 5.22.218 | sprouty RTK signaling antagonist 1 [11269] | 4 | 0.273196801 || STRBP | 5.22.218 | spermatid perinuclear RNA binding protein [16462] | 9 | 0.336815489 || SYNPO | 5.22.218 | synaptopodin [30672] | 5 | 0.63686154 || TLCD2 | 5.22.218 | TLC domain containing 2 [33522] | 17 | 0.223265214 || TNFRSF13C | 5.22.218 | TNF receptor superfamily member 13C [17755] | 22 | 1.226719071 || VWA7 | 5.22.218 | von Willebrand factor A domain containing 7 [13939] | 6 | 0.215455188 || ADAMTSL4 | 6.35.228 | ADAMTS like 4 [19706] | 1 | 0.268471797 || ADCY4 | 6.35.228 | adenylate cyclase 4 [235] | 14 | 0.364343738 || AIM2 | 6.35.228 | absent in melanoma 2 [357] | 1 | 0.609756419 || ANKRD20A5P | 6.35.228 | ankyrin repeat domain 20 family member A5, pseudogene [33833] | 18 | 0.30109966 || APOBEC3A | 6.35.228 | apolipoprotein B mRNA editing enzyme catalytic subunit 3A [17343] | 22 | 0.350724053 || C17orf97 | 6.35.228 | chromosome 17 open reading frame 97 [33800] | 17 | 0.303242441 || CASP1 | 6.35.228 | caspase 1 [1499] | 11 | 0.300245509 || CD300LD | 6.35.228 | CD300 molecule like family member d [16848] | 17 | 0.45377454 || CDHR1 | 6.35.228 | cadherin related family member 1 [14550] | 10 | 0.479784077 || CFAP58-DT | 6.35.228 | CFAP58 divergent transcript [45243] | 10 | 0.443170974 || CFAP99 | 6.35.228 | cilia and flagella associated protein 99 [51180] | 4 | 0.249776346 || CIB3 | 6.35.228 | calcium and integrin binding family member 3 [24580] | 19 | 0.514517722 || CIR1 | 6.35.228 | corepressor interacting with RBPJ, CIR1 [24217] | 2 | 0.194578448 || CRHR2 | 6.35.228 | corticotropin releasing hormone receptor 2 [2358] | 7 | 0.239972233 || DDAH2 | 6.35.228 | dimethylarginine dimethylaminohydrolase 2 [2716] | 6 | 0.246550569 || ESCO2 | 6.35.228 | establishment of sister chromatid cohesion N-acetyltransferase 2 [27230] | 8 | 0.27112119 || FAM174B | 6.35.228 | family with sequence similarity 174 member B [34339] | 15 | 0.352645229 || FCGR2B | 6.35.228 | Fc fragment of IgG receptor IIb [3618] | 1 | 0.301757356 || FCGR2C | 6.35.228 | Fc fragment of IgG receptor IIc (gene/pseudogene) [15626] | 1 | 0.276406895 || FCRLB | 6.35.228 | Fc receptor like B [26431] | 1 | 0.239702019 || FGFR4 | 6.35.228 | fibroblast growth factor receptor 4 [3691] | 5 | 0.225113663 || GPRASP2 | 6.35.228 | G protein-coupled receptor associated sorting protein 2 [25169] | X | 0.235258607 || GRASLND | 6.35.228 | glycosaminoglycan regulatory associated long non-coding RNA [30963] | 2 | 0.251757877 || GSG1L | 6.35.228 | GSG1 like [28283] | 16 | 0.453139684 || H1-12P | 6.35.228 | H1.12 linker histone, cluster member pseudogene [19163] | 6 | 0.30945726 || H2AC18 | 6.35.228 | H2A clustered histone 18 [4736] | 1 | 0.303343422 || H2AC19 | 6.35.228 | H2A clustered histone 19 [29668] | 1 | 0.302225631 || H2BC18 | 6.35.228 | H2B clustered histone 18 [24700] | 1 | 0.341476029 || H2BC6 | 6.35.228 | H2B clustered histone 6 [4753] | 6 | 0.918601632 || H4C4 |

TABLE 4B-continued

The genes within the significant gene clusters, listed in Table 4A. (1127 Genes Listed by: Gene Symbol | Module | Hugo GENE Nomenclature Committee (HGNC) Gene Description [HGNC ID] | Chromosome Number | Row Variance) ||)

6.35.228 | H4 clustered histone 4 [4782] | 6 | 0.613026665 || H4C8 | 6.35.228 | H4 clustered histone 8 [4788] | 6 | 0.604744118 || HCG18 | 6.35.228 | HLA complex group 18 [31337] | 6 | 0.268159837 || HSPA7 | 6.35.228 | heat shock protein family A (Hsp70) member 7 (pseudogene) [5240] | 1 | 0.333870173 || IL27 | 6.35.228 | interleukin 27 [19157] | 16 | 0.276658353 || JUP | 6.35.228 | junction plakoglobin [6207] | 17 | 1.441104381 || KCND1 | 6.35.228 | potassium voltage-gated channel subfamily D member 1 [6237] | X | 0.279690482 || KCNK7 | 6.35.228 | potassium two pore domain channel subfamily K member 7 [6282] | 11 | 0.206215509 || LGALSL | 6.35.228 | galectin like [25012] | 2 | 0.363010876 || LINC00173 | 6.35.228 | long intergenic non-protein coding RNA 173 [33791] | 12 | 0.430523646 || LINC02212 | 6.35.228 | long intergenic non-protein coding RNA 2212 [53079] | 5 | 0.614903795 || LINC02213 | 6.35.228 | long intergenic non-protein coding RNA 2213 [53080] | 5 | 0.382086467 || LLCFC1 | 6.35.228 | LLLL and CFNLAS motif containing 1 [21750] | 7 | 0.431567685 || LRRC77P | 6.35.228 | leucine rich repeat containing 77, pseudogene [50536] | 3 | 0.304272298 || MAP1LC3B2 | 6.35.228 | microtubule associated protein 1 light chain 3 beta 2 [34390] | 12 | 0.454292797 || MYBPC3 | 6.35.228 | myosin binding protein C3 [7551] | 11 | 0.229452524 || NOVA1 | 6.35.228 | NOVA alternative splicing regulator 1 [7886] | 14 | 0.231117223 || NOXRED1 | 6.35.228 | NADP dependent oxidoreductase domain containing 1 [20487] | 14 | 0.194850655 || NTNG2 | 6.35.228 | netrin G2 [14288] | 9 | 0.902037564 || OR52K1 | 6.35.228 | olfactory receptor family 52 subfamily K member 1 [15222] | 11 | 0.319145737 || OVOL1 | 6.35.228 | ovo like transcriptional repressor 1 [8525] | 11 | 0.325157365 || PAQR6 | 6.35.228 | progestin and adipoQ receptor family member 6 [30132] | 1 | 0.469446502 || PDE9A | 6.35.228 | phosphodiesterase 9A [8795] | 21 | 0.689817966 || PDIA2 | 6.35.228 | protein disulfide isomerase family A member 2 [14180] | 16 | 0.211273665 || PI4KAP1 | 6.35.228 | phosphatidylinositol 4-kinase alpha pseudogene 1 [33576] | 22 | 0.236819448 || PMP22 | 6.35.228 | peripheral myelin protein 22 [9118] | 17 | 0.334090477 || PPL | 6.35.228 | periplakin [9273] | 16 | 0.697501616 || PRRG4 | 6.35.228 | proline rich and Gla domain 4 [30799] | 11 | 0.216198967 || PSTK | 6.35.228 | phosphoseryl-tRNA kinase [28578] | 10 | 0.211837638 || RGL3 | 6.35.228 | ral guanine nucleotide dissociation stimulator like 3 [30282] | 19 | 0.552500498 || RNF112 | 6.35.228 | ring finger protein 112 [12968] | 17 | 0.22652736 || SCART1 | 6.35.228 | scavenger receptor family member expressed on T cells 1 [32411] | 10 | 0.458140987 || SLC16A8 | 6.35.228 | solute carrier family 16 member 8 [16270] | 22 | 0.337784288 || SLC35F3 | 6.35.228 | solute carrier family 35 member F3 [23616] | 1 | 0.344525339 || SMCHD1 | 6.35.228 | structural maintenance of chromosomes flexible hinge domain containing 1 [29090] | 18 | 0.262814871 || SP110 | 6.35.228 | SP110 nuclear body protein [5401] | 2 | 0.375701361 || SPATC1 | 6.35.228 | spermatogenesis and centriole associated 1 [30510] | 8 | 0.695935211 || TACR2 | 6.35.228 | tachykinin receptor 2 [11527] | 10 | 0.429099015 || TMEM132D | 6.35.228 | transmembrane protein 132D [29411] | 12 | 0.192946779 || TMEM191B | 6.35.228 | transmembrane protein 191B [33600] | 22 | 0.486686271 || TMEM191C | 6.35.228 | transmembrane protein 191C [33601] | 22 | 0.261257133 || TMEM200B | 6.35.228 | transmembrane protein 200B [33785] | 1 | 0.199316752 || TMEM244 | 6.35.228 | transmembrane protein 244 [21571] | 6 | 0.260649996 || TPBGL | 6.35.228 | trophoblast glycoprotein like [44159] | 11 | 0.248817439 || TRAV16 | 6.35.228 | T cell receptor alpha variable 16 [12112] | 14 | 0.271238945 || TRIM25 | 6.35.228 | tripartite motif containing 25 [12932] | 17 | 0.280123205 || VSIG10L | 6.35.228 | V-set and immunoglobulin domain containing 10 like [27111] | 19 | 0.240866074 || ZNF396 | 6.35.228 | zinc finger protein 396 [18824] | 18 | 0.574864152 || ACO1 | 6.36.230 | aconitase 1 [117] | 9 | 0.90855768 || ACOT9 | 6.36.230 | acyl-CoA thioesterase 9 [17152] | X | 0.321617031 || AGRN | 6.36.230 | agrin [329] | 1 | 1.040920761 || ALS2CL | 6.36.230 | ALS2 C-terminal like [20605] | 3 | 0.237907209 || ANTXRLP1 | 6.36.230 | ANTXR like pseudogene 1 [45004] | 10 | 0.25362146 || ANXA10 | 6.36.230 | annexin A10 [534] | 4 | 0.401601351 || APOBEC3B-AS1 | 6.36.230 | APOBEC3B antisense RNA 1 [43836] | 22 | 0.827677569 || AXL | 6.36.230 | AXL receptor tyrosine kinase [905] | 19 | 0.752927004 || BTN2A3P | 6.36.230 | butyrophilin subfamily 2 member A3, pseudogene [13229] | 6 | 0.226008437 || C1orf127 | 6.36.230 | chromosome 1 open reading frame 127 [26730] | 1 | 0.248334614 || CA8 | 6.36.230 | carbonic anhydrase 8 [1382] | 8 | 0.210534049 || CACNA1I | 6.36.230 | calcium voltage-gated channel subunit alpha1 I [1396] | 22 | 0.323219596 || CACNA2D2 | 6.36.230 | calcium voltage-gated channel auxiliary subunit alpha2delta 2 [1400] | 3 | 0.559952795 || CAMK2N1 | 6.36.230 | calcium/calmodulin dependent protein kinase II inhibitor 1 [24190] | 1 | 0.221856974 || CCDC194 | 6.36.230 | coiled-coil domain containing 194 [53438] | 19 | 1.116822796 || CCL8 | 6.36.230 | C-C motif chemokine ligand 8 [10635] | 17 | 0.444107165 || CCR12P | 6.36.230 | C—C motif chemokine receptor 12, pseudogene [39812] | 13 | 0.557370553 || CCR5AS | 6.36.230 | CCR5 antisense RNA [54398] | 3 | 0.637433752 || CCRL2 | 6.36.230 | C—C motif chemokine receptor like 2 [1612] | 3 | 0.315577397 || CETP | 6.36.230 | cholesteryl ester transfer protein [1869] | 16 | 0.39784003 || CHMP5 | 6.36.230 | charged multivesicular body protein 5 [26942] | 9 | 0.447055019 || CHRNB2 | 6.36.230 | cholinergic receptor nicotinic beta 2 subunit [1962] | 1 | 0.336319628 || CMPK2 | 6.36.230 | cytidine/uridine monophosphate kinase 2 [27015] | 2 | 3.024979032 || CMTR1 | 6.36.230 | cap methyltransferase 1 [21077] | 6 | 0.281452412 || COL5A1 | 6.36.230 | collagen type V alpha 1 chain [2209] | 9 | 0.343008662 || CSPG4P11 | 6.36.230 | chondroitin sulfate proteoglycan 4 pseudogene 11 [48363] | 15 | 0.208611839 || CYP21A1P | 6.36.230 | cytochrome P450 family 21 subfamily A member 1, pseudogene [2599] | 6 | 0.222874811 || DDX58 | 6.36.230 | DExD/H-box helicase 58 [19102] | 9 | 0.760340689 || DDX60 | 6.36.230 | DExD/H-box helicase 60 [25942] | 4 | 1.661610056 || DDX60L | 6.36.230 | DExD/H-box 60 like [26429] | 4 | 0.803026285 || DLG5 | 6.36.230 | discs large MAGUK scaffold protein 5 [2904] | 10 | 0.206479677 || DNAJA1 | 6.36.230 | DnaJ heat shock protein family (Hsp40) member A1 [5229] | 9 | 0.194658491 || DOCK4 | 6.36.230 | dedicator of cytokinesis 4 [19192] | 7 | 0.334214721 || DTX3L | 6.36.230 | deltex E3 ubiquitin ligase 3L [30323] | 3 | 0.414061274 ||

TABLE 4B-continued

The genes within the significant gene clusters, listed in Table 4A. (1127 Genes Listed by: Gene Symbol | Module | Hugo GENE Nomenclature Committee (HGNC) Gene Description [HGNC ID] | Chromosome Number | Row Variance) ||)

EBF4 | 6.36.230 | EBF family member 4 [29278] | 20 | 0.427293266 || EDAR | 6.36.230 | ectodysplasin A receptor [2895] | 2 | 0.303487264 || EIF2AK2 | 6.36.230 | eukaryotic translation initiation factor 2 alpha kinase 2 [9437] | 2 | 1.393622294 || EMP1 | 6.36.230 | epithelial membrane protein 1 [3333] | 12 | 0.32067645 || EPB41L5 | 6.36.230 | erythrocyte membrane protein band 4.1 like 5 [19819] | 2 | 0.591963329 || EPSTI1 | 6.36.230 | epithelial stromal interaction 1 [16465] | 13 | 2.589333906 || FAM131B | 6.36.230 | family with sequence similarity 131 member B [22202] | 7 | 0.252242604 || FAM230E | 6.36.230 | family with sequence similarity 230 member E [52450] | 22 | 0.257589003 || FAM247A | 6.36.230 | family with sequence similarity 247 member A [54926] | 22 | 0.902237458 || FAM247B | 6.36.230 | family with sequence similarity 247 member B [54927] | 22 | 0.845861304 || FEZ1 | 6.36.230 | fasciculation and elongation protein zeta 1 [3659] | 11 | 0.547616473 || FKBP10 | 6.36.230 | FKBP prolyl isomerase 10 [18169] | 17 | 0.257799981 || FRG1HP | 6.36.230 | FSHD region gene 1 family member H, pseudogene [51767] | 9 | 0.231441838 || FRG1KP | 6.36.230 | FSHD region gene 1 family member K, pseudogene [51769] | 9 | 0.20537641 || FRMD3 | 6.36.230 | FERM domain containing 3 [24125] | 9 | 0.294895789 || GDF7 | 6.36.230 | growth differentiation factor 7 [4222] | 2 | 0.339361995 || GNB4 | 6.36.230 | G protein subunit beta 4 [20731] | 3 | 0.209440189 || GPD2 | 6.36.230 | glycerol-3-phosphate dehydrogenase 2 [4456] | 2 | 0.222567972 || GPM6A | 6.36.230 | glycoprotein M6A [4460] | 4 | 0.255474259 || GRAMD1B | 6.36.230 | GRAM domain containing 1B [29214] | 11 | 0.309422209 || HCG9 | 6.36.230 | HLA complex group 9 [21243] | 6 | 0.32398752 || HERC5 | 6.36.230 | HECT and RLD domain containing E3 ubiquitin protein ligase 5 [24368] | 4 | 2.995367846 || HERC6 | 6.36.230 | HECT and RLD domain containing E3 ubiquitin protein ligase family member 6 [26072] | 4 | 1.169656851 || HES4 | 6.36.230 | hes family bHLH transcription factor 4 [24149] | 1 | 2.020503811 || HESX1 | 6.36.230 | HESX homeobox 1 [4877] | 3 | 0.84552775 || HEY2 | 6.36.230 | hes related family bHLH transcription factor with YRPW motif 2 [4881] | 6 | 0.230510476 || HIC1 | 6.36.230 | HIC ZBTB transcriptional repressor 1 [4909] | 17 | 0.267771619 || HLA-F-AS1 | 6.36.230 | HLA-F antisense RNA 1 [26645] | 6 | 0.320725832 || HLA-G | 6.36.230 | major histocompatibility complex, class I, G [4964] | 6 | 0.708306757 || IFI16 | 6.36.230 | interferon gamma inducible protein 16 [5395] | 1 | 0.464101976 || IFI27 | 6.36.230 | interferon alpha inducible protein 27 [5397] | 14 | 10.54360419 || IFI44 | 6.36.230 | interferon induced protein 44 [16938] | 1 | 4.030557556 || IFI44L | 6.36.230 | interferon induced protein 44 like [17817] | 1 | 6.65455388 || IFI6 | 6.36.230 | interferon alpha inducible protein 6 [4054] | 1 | 3.123271561 || IFIH1 | 6.36.230 | interferon induced with helicase C domain 1 [18873] | 2 | 0.952383607 || IFIT5 | 6.36.230 | interferon induced protein with tetratricopeptide repeats 5 [13328] | 10 | 1.078841308 || IGHV3-64D | 6.36.230 | immunoglobulin heavy variable 3-64D [49603] | 14 | 0.851935178 || IGHV5-10-1 | 6.36.230 | immunoglobulin heavy variable 5-10-1 [5661] | 14 | 1.273144766 || IL17RE | 6.36.230 | interleukin 17 receptor E [18439] | 3 | 0.330546983 || ISG15 | 6.36.230 | ISG15 ubiquitin like modifier [4053] | 1 | 4.234704942 || ITGA9-AS1 | 6.36.230 | ITGA9 antisense RNA 1 [49668] | 3 | 0.295210978 || JPH4 | 6.36.230 | junctophilin 4 [20156] | 14 | 0.214069776 || KANK3 | 6.36.230 | KN motif and ankyrin repeat domains 3 [24796] | 19 | 0.280665942 || KIAA1841 | 6.36.230 | KIAA1841 [29387] | 2 | 0.246164866 || KIAA1958 | 6.36.230 | KIAA1958 [23427] | 9 | 0.487696594 || KLHDC7B | 6.36.230 | kelch domain containing 7B [25145] | 22 | 1.702898587 || LAMP3 | 6.36.230 | lysosomal associated membrane protein 3 [14582] | 3 | 1.220656522 || LGALS3BP | 6.36.230 | galectin 3 binding protein [6564] | 17 | 1.411500538 || LHFPL2 | 6.36.230 | LHFPL tetraspan subfamily member 2 [6588] | 5 | 0.320875768 || LINC00243 | 6.36.230 | long intergenic non-protein coding RNA 243 [30956] | 6 | 0.298015894 || LINC00487 | 6.36.230 | long intergenic non-protein coding RNA 487 [42947] | 2 | 1.912762565 || LINC00638 | 6.36.230 | long intergenic non-protein coding RNA 638 [28325] | 14 | 0.416690146 || LINC02068 | 6.36.230 | long intergenic non-protein coding RNA 2068 [52914] | 3 | 0.274806253 || LINC02574 | 6.36.230 | long intergenic non-protein coding RNA 2574 [53746] | 1 | 0.41419558 || LINC02785 | 6.36.230 | long intergenic non-protein coding RNA 2785 [54305] | 1 | 0.352342123 || LIPA | 6.36.230 | lipase A, lysosomal acid type [6617] | 10 | 0.281581021 || LPAL2 | 6.36.230 | lipoprotein(a) like 2, pseudogene [21210] | 6 | 0.246871223 || LTK | 6.36.230 | leukocyte receptor tyrosine kinase [6721] | 15 | 0.68905563 || LY6E | 6.36.230 | lymphocyte antigen 6 family member E [6727] | 8 | 2.949758688 || MILR1 | 6.36.230 | mast cell immunoglobulin like receptor 1 [27570] | 17 | 0.250498008 || MIR4477A | 6.36.230 | microRNA 4477a [41859] | 9 | 0.217435401 || MIR4477B | 6.36.230 | microRNA 4477b [41898] | 9 | 0.282563762 || MT1DP | 6.36.230 | metallothionein 1D, pseudogene [7396] | 16 | 0.267522231 || MX1 | 6.36.230 | MX dynamin like GTPase 1 [7532] | 21 | 2.801157351 || NKD1 | 6.36.230 | NKD inhibitor of WNT signaling pathway 1 [17045] | 16 | 0.307409235 || NR3C2 | 6.36.230 | nuclear receptor subfamily 3 group C member 2 [7979] | 4 | 0.197610807 || NRIR | 6.36.230 | negative regulator of interferon response [51269] | 2 | 2.125976014 || OAS1 6.36.230 | 2'-5'-oligoadenylate synthetase 1 [8086] | 12 | 2.240070609 || OR52K2 | 6.36.230 | olfactory receptor family 52 subfamily K member 2 [15223] | 11 | 0.264929757 || OTOF | 6.36.230 | otoferlin [8515] | 2 | 11.15122376 || P3H3 | 6.36.230 | prolyl 3-hydroxylase 3 [19318] | 12 | 0.22487299 || PARP12 | 6.36.230 | poly(ADP-ribose) polymerase family member 12 [21919] | 7 | 0.885652048 || PARP14 | 6.36.230 | poly(ADP-ribose) polymerase family member 14 [29232] | 3 | 0.696981339 || PARP9 | 6.36.230 | poly(ADP-ribose) polymerase family member 9 [24118] | 3 | 0.796424677 || PGAP1 | 6.36.230 | post-GPI attachment to proteins inositol deacylase 1 [25712] | 2 | 0.255094114 || PHF11 | 6.36.230 | PHD finger protein 11 [17024] | 13 | 0.376056477 || PIMREG | 6.36.230 | PICALM interacting mitotic regulator [25483] | 17 | 0.233347976 || PLSCR1 | 6.36.230 | phospholipid scramblase 1 [9092] | 3 | 1.32770107 || PLSCR2 | 6.36.230 | phospholipid scramblase 2 [16494] | 3 | 0.343387893 || PMEL | 6.36.230 | premelanosome protein [10880] | 12 | 0.216236281 || PNPT1 | 6.36.230 | polyribonucleotide nucleotidyltransferase 1 [23166] | 2 | 0.493873613 || PPP1R27 | 6.36.230 |

TABLE 4B-continued

The genes within the significant gene clusters, listed in Table 4A. (1127 Genes Listed by: Gene Symbol | Module | Hugo GENE Nomenclature Committee (HGNC) Gene Description [HGNC ID] | Chromosome Number | Row Variance) ||)

protein phosphatase 1 regulatory subunit 27 [16813] | 17 | 0.204093793 || PRAL | 6.36.230 | p53 regulation associated lncRNA [52646] | 17 | 0.514894996 || PRR5L | 6.36.230 | proline rich 5 like [25878] | 11 | 0.273377487 || RASGRF2 | 6.36.230 | Ras protein specific guanine nucleotide releasing factor 2 [9876] | 5 | 0.263677635 || REC8 | 6.36.230 | REC8 meiotic recombination protein [16879] | 14 | 0.423802128 || RHAG | 6.36.230 | Rh associated glycoprotein [10006] | 6 | 0.88433306 || RNF213 | 6.36.230 | ring finger protein 213 [14539] | 17 | 0.323041803 || RNF213-AS1 | 6.36.230 | RNF213 antisense RNA 1 [54402] | 17 | 0.632629285 || RPS2P7 | 6.36.230 | ribosomal protein S2 pseudogene 7 [15838] | 20 | 0.314242178 || RSAD2 | 6.36.230 | radical S-adenosyl methionine domain containing 2 [30908] | 2 | 6.333921026 || RSPH9 | 6.36.230 | radial spoke head component 9 [21057] | 6 | 0.853283556 || RUFY4 | 6.36.230 | RUN and FYVE domain containing 4 [24804] | 2 | 0.803950745 || S100A7 | 6.36.230 | S100 calcium binding protein A7 [10497] | 1 | 0.339510122 || SAMD4A | 6.36.230 | sterile alpha motif domain containing 4A [23023] | 14 | 0.24586476 || SAMD9 | 6.36.230 | sterile alpha motif domain containing 9 [1348] | 7 | 0.745507841 || SAMD9L | 6.36.230 | sterile alpha motif domain containing 9 like [1349] | 7 | 0.988684894 || SCARB2 | 6.36.230 | scavenger receptor class B member 2 [1665] | 4 | 0.216439617 || SIGLEC1 | 6.36.230 | sialic acid binding Ig like lectin 1 [11127] | 20 | 5.957492936 || SLC26A5 | 6.36.230 | solute carrier family 26 member 5 [9359] | 7 | 0.554268459 || SLC8A3 | 6.36.230 | solute carrier family 8 member A3 [11070] | 14 | 0.290592472 || SLITRK5 | 6.36.230 | SLIT and NTRK like family member 5 [20295] | 13 | 0.276400242 || SMTNL1 | 6.36.230 | smoothelin like 1 [32394] | 11 | 2.183697047 || SP100 | 6.36.230 | SP100 nuclear antigen [11206] | 2 | 0.311273447 || SPATS2L | 6.36.230 | spermatogenesis associated serine rich 2 like [24574] | 2 | 2.634953952 || SPON1 | 6.36.230 | spondin 1 [11252] | 11 | 0.391285817 || STAT2 | 6.36.230 | signal transducer and activator of transcription 2 [11363] | 12 | 0.480979322 || SYNDIG1L | 6.36.230 | synapse differentiation inducing 1 like [32388] | 14 | 0.254792177 || TDRD7 | 6.36.230 | tudor domain containing 7 [30831] | 9 | 0.440956048 || TIMM10 | 6.36.230 | translocase of inner mitochondrial membrane 10 [11814] | 11 | 1.308599007 || TMEM123 | 6.36.230 | transmembrane protein 123 [30138] | 11 | 0.459980207 || TRAJ25 | 6.36.230 | T cell receptor alpha joining 25 (non-functional) [12054] | 14 | 0.273762148 || TRIM5 | 6.36.230 | tripartite motif containing 5 [16276] | 11 | 0.451333898 || TSPAN15 | 6.36.230 | tetraspanin 15 [23298] | 10 | 0.427460426 || TSPOAP1 | 6.36.230 | TSPO associated protein 1 [16831] | 17 | 0.316371413 || TUBA8 | 6.36.230 | tubulin alpha 8 [12410] | 22 | 0.979755197 || UNC93B4 | 6.36.230 | unc-93 homolog B4 (pseudogene) [13484] | 4 | 0.204885446 || USP13 | 6.36.230 | ubiquitin specific peptidase 13 [12611] | 3 | 0.193957652 || USP18 | 6.36.230 | ubiquitin specific peptidase 18 [12616] | 22 | 3.685167371 || USP41 | 6.36.230 | ubiquitin specific peptidase 41 [20070] | 22 | 2.530479306 || VSIG1 | 6.36.230 | V-set and immunoglobulin domain containing 1 [28675] | X | 0.203195596 || XAF1 | 6.36.230 | XIAP associated factor 1 [30932] | 17 | 1.793261727 || ZCCHC2 | 6.36.230 | zinc finger CCHC-type containing 2 [22916] | 18 | 0.949790079 || ZNF600 | 6.36.230 | zinc finger protein 600 [30951] | 19 | 0.261321329 || ZNF684 | 6.36.230 | zinc finger protein 684 [28418] | 1 | 0.519925297 || ZNF835 | 6.36.230 | zinc finger protein 835 [34332] | 19 | 0.274809327 || AK5 | 6.36.234 | adenylate kinase 5 [365] | 1 | 0.322202648 || BLVRA | 6.36.234 | biliverdin reductase A [1062] | 7 | 0.34468082 || C3AR1 | 6.36.234 | complement C3a receptor 1 [1319] | 12 | 0.697158525 || CD300E | 6.36.234 | CD300e molecule [28874] | 17 | 0.278403912 || CTSL | 6.36.234 | cathepsin L [2537] | 9 | 0.474090728 || CYP46A1 | 6.36.234 | cytochrome P450 family 46 subfamily A member 1 [2641] | 14 | 0.224161243 || EPHB2 | 6.36.234 | EPH receptor B2 [3393] | 1 | 0.909118576 || FAM170B-AS1 | 6.36.234 | FAM170B antisense RNA 1 [45006] | 10 | 0.226266357 || FBLN2 | 6.36.234 | fibulin 2 [3601] | 3 | 0.315576855 || HID1 | 6.36.234 | HID1 domain containing [15736] | 17 | 0.293582897 || KRT72 | 6.36.234 | keratin 72 [28932] | 12 | 2.075736559 || KRT73 | 6.36.234 | keratin 73 [28928] | 12 | 1.415874512 || KRT73-AS1 | 6.36.234 | KRT73 antisense RNA 1 [49607] | 12 | 1.273863194 || LAP3 | 6.36.234 | leucine aminopeptidase 3 [18449] | 4 | 0.658033422 || LDLRAD3 | 6.36.234 | low density lipoprotein receptor class A domain containing 3 [27046] | 11 | 0.234334121 || LILRB4 | 6.36.234 | leukocyte immunoglobulin like receptor B4 [6608] | 19 | 0.269968343 || LINC01307 | 6.36.234 | long intergenic non-protein coding RNA 1307 [50494] | 1 | 0.202364018 || LINC01504 | 6.36.234 | long intergenic non-protein coding RNA 1504 [51185] | 9 | 0.201075588 || MIR503HG | 6.36.234 | MIR503 host gene [28258] | X | 0.230311785 || MS4A4A | 6.36.234 | membrane spanning 4-domains A4A [13371] | 11 | 0.790949296 || MYOF | 6.36.234 | myoferlin [3656] | 10 | 0.470637112 || NID1 | 6.36.234 | nidogen 1 [7821] | 1 | 0.358318137 || RARRES2 | 6.36.234 | retinoic acid receptor responder 2 [9868] | 7 | 0.199809404 || SSC4D | 6.36.234 | scavenger receptor cysteine rich family member with 4 domains [14461] | 7 | 0.247905259 || TCN2 | 6.36.234 | transcobalamin 2 [11653] | 22 | 0.843794884 || ACBD7 | 6.36.235 | acyl-CoA binding domain containing 7 [17715] | 10 | 0.223339861 || ADAMTS10 | 6.36.235 | ADAM metallopeptidase with thrombospondin type 1 motif 10 [13201] | 19 | 0.317352825 || CACNA1A | 6.36.235 | calcium voltage-gated channel subunit alpha1 A [1388] | 19 | 0.49545927 || CAPN5 | 6.36.235 | calpain 5 [1482] | 11 | 0.463506112 || CHN1 | 6.36.235 | chimerin 1 [1943] | 2 | 0.224930456 || DNAJC15 | 6.36.235 | DnaJ heat shock protein family (Hsp40) member C15 [20325] | 13 | 0.194055064 || ENTPD1-AS1 | 6.36.235 | ENTPD1 antisense RNA 1 [45203] | 10 | 0.205703886 || EPHB3 | 6.36.235 | EPH receptor B3 [3394] | 3 | 0.192359997 || ERFE | 6.36.235 | erythroferrone [26727] | 2 | 0.666727592 || FAM178B | 6.36.235 | family with sequence similarity 178 member B [28036] | 2 | 0.211238564 || FBXO39 | 6.36.235 | F-box protein 39 [28565] | 17 | 1.34750468 || FITM1 | 6.36.235 | fat storage inducing transmembrane protein 1 [33714] | 14 | 0.278908897 || FLT4 | 6.36.235 | fms related receptor tyrosine kinase 4 [3767] | 5 | 1.186642084 || FOLR3 | 6.36.235 | folate receptor gamma [3795] | 11 | 1.31748135 || FUT2 | 6.36.235 | fucosyltransferase 2 [4013] | 19 | 0.236509375 || GALNT12 | 6.36.235 | polypeptide N-acetylgalactosaminyltransferase 12 [19877] | 9 |

TABLE 4B-continued

The genes within the significant gene clusters, listed in Table 4A. (1127 Genes Listed by: Gene Symbol | Module | Hugo GENE Nomenclature Committee (HGNC) Gene Description [HGNC ID] | Chromosome Number | Row Variance) ||)

0.251920129 || IFITM3P4 | 6.36.235 | IFITM3 pseudogene 4 [54542] | 7 | 0.797636958 || IGHE | 6.36.235 | immunoglobulin heavy constant epsilon [5522] | 14 | 0.638555537 | IL15 | 6.36.235 | interleukin 15 [5977] | 4 | 0.314421988 || ISLR2 | 6.36.235 | immunoglobulin superfamily containing leucine rich repeat 2 [29286] | 15 | 0.217100442 || ISM1 | 6.36.235 | isthmin 1 [16213] | 20 | 0.317258831 || ITGA10 | 6.36.235 | integrin subunit alpha 10 [6135] | 1 | 0.2313648 || ITGA7 | 6.36.235 | integrin subunit alpha 7 [6143] | 12 | 0.23389651 || KIT | 6.36.235 | KIT proto-oncogene, receptor tyrosine kinase [6342] | 4 | 0.259431743 || LINC01344 | 6.36.235 | long intergenic non-protein coding RNA 1344 [50554] | 1 | 0.204143274 || LINC01918 | 6.36.235 | long intergenic non-protein coding RNA 1918 [52737] | 2 | 0.268891499 || LINC02446 | 6.36.235 | long intergenic non-protein coding RNA 2446 [53378] | 12 | 1.015961898 || LINC02754 | 6.36.235 | long intergenic non-protein coding RNA 2754 [54274] | 11 | 0.371415009 || LRP12 | 6.36.235 | LDL receptor related protein 12 [31708] | 8 | 0.191701957 || LRRC36 | 6.36.235 | leucine rich repeat containing 36 [25615] | 16 | 0.221115164 || LRRC71 | 6.36.235 | leucine rich repeat containing 71 [26556] | 1 | 0.208086881 || LSP1P4 | 6.36.235 | LSP1 pseudogene 4 [53915] | 2 | 0.236160847 || LY6E-DT | 6.36.235 | LY6E divergent transcript [53728] | 8 | 1.136892379 || MAFA | 6.36.235 | MAF bZIP transcription factor A [23145] | 8 | 0.378153313 || MID2 | 6.36.235 | midline 2 [7096] | X | 0.231175405 || MTHFD1L | 6.36.235 | methylenetetrahydrofolate dehydrogenase (NADP+ dependent) 1 like [21055] | 6 | 0.201910464 || ODF3B | 6.36.235 | outer dense fiber of sperm tails 3B [34388] | 22 | 0.6001168 || OSBPL6 | 6.36.235 | oxysterol binding protein like 6 [16388] | 2 | 0.421119823 || PPFIBP1 | 6.36.235 | PPFIA binding protein 1 [9249] | 12 | 0.303987283 || PPM1K-DT | 6.36.235 | PPM1K divergent transcript [54093] | 4 | 0.969977106 || RETREG1 | 6.36.235 | reticulophagy regulator 1 [25964] | 5 | 0.199559987 || RGPD2 | 6.36.235 | RANBP2 like and GRIP domain containing 2 [32415] | 2 | 0.381611289 || SCO2 | 6.36.235 | synthesis of cytochrome C oxidase 2 [10604] | 22 | 0.666687099 || SLC7A8 | 6.36.235 | solute carrier family 7 member 8 [11066] | 14 | 0.5725867 || SLPI | 6.36.235 | secretory leukocyte peptidase inhibitor [11092] | 20 | 0.845601927 || TEKT1 | 6.36.235 | tektin 1 [15534] | 17 | 0.335262479 || TRBV6-2 | 6.36.235 | T cell receptor beta variable 6-2 [12227] | 7 | 0.435341422 || TRBV7-1 | 6.36.235 | T cell receptor beta variable 7-1 (non-functional) [12235] | 7 | 0.197711588 || TYMP | 6.36.235 | thymidine phosphorylase [3148] | 22 | 0.429975382 || ULBP2 | 6.36.235 | UL16 binding protein 2 [14894] | 6 | 0.206036715 || UNC93B3 | 6.36.235 | unc-93 homolog B3 (pseudogene) [13483] | 3 | 0.341749643 || UNC93B5 | 6.36.235 | unc-93 homolog B5 (pseudogene) [34051] | 11 | 0.341748548 || UNC93B7 | 6.36.235 | unc-93 homolog B7 (pseudogene) [44036] | 4 | 0.30122451 || ZNF514 | 6.36.235 | zinc finger protein 514 [25894] | 2 | 0.200002822 || ACSM3 | 6.37.239 | acyl-CoA synthetase medium chain family member 3 [10522] | 16 | 0.195035517 || ANKRD35 | 6.37.239 | ankyrin repeat domain 35 [26323] | 1 | 0.342718586 || DBH | 6.37.239 | dopamine beta-hydroxylase [2689] | 9 | 0.373962555 || DEPDC1 | 6.37.239 | DEP domain containing 1 [22949] | 1 | 0.275505948 || ESPNP | 6.37.239 | espin pseudogene [23285] | 1 | 0.380034543 || FAM225A | 6.37.239 | family with sequence similarity 225 member A [27855] | 9 | 0.664607195 || FAM225B | 6.37.239 | family with sequence similarity 225 member B [21865] | 9 | 0.579357668 || FMNL2 | 6.37.239 | formin like 2 [18267] | 2 | 0.234331857 || FOXRED2 | 6.37.239 | FAD dependent oxidoreductase domain containing 2 [26264] | 22 | 0.201603769 || GSDMC | 6.37.239 | gasdermin C [7151] | 8 | 0.215377787 || LINC01238 | 6.37.239 | long intergenic non-protein coding RNA 1238 [49795] | 2 | 0.27192661 || LINC02287 | 6.37.239 | long intergenic non-protein coding RNA 2287 [53204] | 14 | 0.285294022 || LMO7 | 6.37.239 | LIM domain 7 [6646] | 13 | 0.410766339 || NPTXR | 6.37.239 | neuronal pentraxin receptor [7954] | 22 | 0.273202225 || PLEKHB1 | 6.37.239 | pleckstrin homology domain containing B1 [19079] | 11 | 0.221339925 || PNMT | 6.37.239 | phenylethanolamine N-methyltransferase [9160] | 17 | 0.26099279 || RETN | 6.37.239 | resistin [20389] | 19 | 2.0446486 || RNASE2 | 6.37.239 | ribonuclease A family member 2 [10045] | 14 | 0.898738246 || ROBO3 | 6.37.239 | roundabout guidance receptor 3 [13433] | 11 | 0.350185519 || SLC16A11 | 6.37.239 | solute carrier family 16 member 11 [23093] | 17 | 0.263378806 || SLC45A3 | 6.37.239 | solute carrier family 45 member 3 [8642] | 1 | 0.552345171 || SRGAP2 | 6.37.239 | SLIT-ROBO Rho GTPase activating protein 2 [19751] | 1 0.269317011 || SRGAP2B | 6.37.239 | SLIT-ROBO Rho GTPase activating protein 2B [35237] | 1 | 0.261301605 || SRGAP2C | 6.37.239 | SLIT-ROBO Rho GTPase activating protein 2C [30584] | 1 | 0.246873493 || TAF11L2 | 6.37.239 | TATA-box binding protein associated factor 11 like 2 [53845] | 5 | 0.228681474 || TARM1 | 6.37.239 | T cell-interacting, activating receptor on myeloid cells 1 [37250] | 19 | 1.037481676 || TLE2 | 6.37.239 | TLE family member 2, transcriptional corepressor [11838] | 19 | 0.285223272 || TRAJ20 | 6.37.239 | T cell receptor alpha joining 20 [12049] | 14 | 0.19823945 || TRAJ32 | 6.37.239 | T cell receptor alpha joining 32 [12062] | 14 | 0.194741634 || UCKL1-AS1 | 6.37.239 | UCKL1 antisense RNA 1 [31967] | 20 | 0.735472237 || WNT7A | 6.37.239 | Wnt family member 7A [12786] | 3 | 0.397738705 || ZNF595 | 6.37.239 | zinc finger protein 595 [27196] | 4 | 0.326055995 || ASPH | 6.37.240 | aspartate beta-hydroxylase [757] | 8 | 0.365927482 || C1QTNF7 | 6.37.240 | C1q and TNF related 7 [14342] | 4 | 0.245767444 || C1QTNF7-AS1 | 6.37.240 | C1QTNF7 antisense RNA 1 [40683] | 4 | 0.557112742 || CC2D2A | 6.37.240 | coiled-coil and C2 domain containing 2A [29253] | 4 | 0.261613419 || CCDC162P | 6.37.240 | coiled-coil domain containing 162, pseudogene [21565] | 6 | 0.23849214 || CSAG2 | 6.37.240 | CSAG family member 2 [16847] | X | 0.22514824 || CSAG3 | 6.37.240 | CSAG family member 3 [26237] | X | 0.241384443 || CYP1A1 | 6.37.240 | cytochrome P450 family 1 subfamily A member 1 [2595] | 15 | 0.246742636 || DISC1 | 6.37.240 | DISC1 scaffold protein [2888] | 1 | 0.279173115 || EXT1 | 6.37.240 | exostosin glycosyltransferase 1 [3512] | 8 | 0.275637224 || FCER1A | 6.37.240 | Fc fragment of IgE receptor Ia [3609] | 1 | 1.213906511 || GRB10 | 6.37.240 | growth factor receptor bound protein 10 [4564] | 7 | 1.177641815 || LGALSL-DT | 6.37.240 | LGALSL divergent transcript [53951] | 2 | 0.42888353 || LHFPL3-AS2 | 6.37.240 | LHFPL3 antisense TABLE 4B-continued The genes within the significant gene clusters, listed in Table 4A. (1127 Genes Listed by: Gene Symbol | Module | Hugo GENE Nomenclature Committee (HGNC) Gene Description [HGNC ID] | Chromosome Number | Row Variance) ||)

RNA 2 [44106] | 7 | 0.201728937 || LINC00398 | 6.37.240 | long intergenic non-protein coding RNA 398 [42727] | 13 | 0.306230068 || LINC02042 | 6.37.240 | long intergenic non-protein coding RNA 2042 [52882] | 3 | 0.194232358 || LINC02458 | 6.37.240 | long intergenic non-protein coding RNA 2458 [53394] | 12 | 0.348048812 || LINC02568 | 6.37.240 | long intergenic non-protein coding RNA 2568 [51430] | 15 | 0.250013643 || MAOA | 6.37.240 | monoamine oxidase A [6833] | X | 0.372519006 || MROCKI | 6.37.240 | MARCKS cis regulating lncRNA promoter of cytokines and inflammation [50323] | 6 | 0.243708028 || OLFML2A | 6.37.240 | olfactomedin like 2A [27270] | 9 | 0.226827349 || OR52B4 | 6.37.240 | olfactory receptor family 52 subfamily B member 4 [15209] | 11 | 0.199272508 || PODXL2 | 6.37.240 | podocalyxin like 2 [17936] | 3 | 0.193434297 || PTGDR2 | 6.37.240 | prostaglandin D2 receptor 2 [4502] | 11 | 0.775640901 || RNF175 | 6.37.240 | ring finger protein 175 [27735] | 4 | 0.485407745 || SEPTIN9-DT | 6.37.240 | SEPTIN9 divergent transcript [52818] | 17 | 0.36978394 || SLC12A1 | 6.37.240 | solute carrier family 12 member 1 [10910] | 15 | 5.151688237 || SLC4A3 | 6.37.240 | solute carrier family 4 member 3 [11029] | 2 | 0.420528225 || SRGAP2D | 6.37.240 | SLIT-ROBO Rho GTPase activating protein 2D (pseudogene) [43932] | 1 | 0.199742844 || TLR2 6.37.240 | toll like receptor 2 [11848] | 4 | 0.440078676 || UPB1 | 6.37.240 | beta-ureidopropionase 1 [16297] | 22 | 0.422369002 || WARS1 | 6.37.240 | tryptophanyl-tRNA synthetase 1 [12729] | 14 | 0.308066739 || ZNF727 | 6.37.240 | zinc finger protein 727 [22785] | 7 | 0.199739235 || AANAT | 6.39.248 | aralkylamine N-acetyltransferase [19] | 17 | 0.216682269 || ABCB1 | 6.39.248 | ATP binding cassette subfamily B member 1 [40] | 7 | 0.34699187 || ANKRD22 | 6.39.248 | ankyrin repeat domain 22 [28321] | 10 | 0.800706931 || BATF2 | 6.39.248 | basic leucine zipper ATF-like transcription factor 2 [25163] | 11 | 1.453937786 || BST2 | 6.39.248 | bone marrow stromal cell antigen 2 [1119] | 19 | 0.582785094 || COLQ | 6.39.248 | collagen like tail subunit of asymmetric acetylcholinesterase [2226] | 3 | 0.28547444 || DHX58 | 6.39.248 | DExH-box helicase 58 [29517] | 17 | 0.913774089 || DRAP1 | 6.39.248 | DR1 associated protein 1 [3019] | 11 | 0.255539528 || DUX4L37 | 6.39.248 | double homeobox 4 like 37 (pseudogene) [51775] | 20 | 0.36416134 || DUX4L50 | 6.39.248 | double homeobox 4 like 50 (pseudogene) [51788] | 9 | 0.320865224 || EPOP | 6.39.248 | elongin BC and polycomb repressive complex 2 associated protein [34493] | 17 | 0.229493944 || ETV7 | 6.39.248 | ETS variant transcription factor 7 [18160] | 6 | 2.046407232 || FBXO6 | 6.39.248 | F-box protein 6 [13585] | 1 | 0.481202128 || FZD8 | 6.39.248 | frizzled class receptor 8 [4046] | 10 | 0.239316604 || HELZ2 | 6.39.248 | helicase with zinc finger 2 [30021] | 20 | 0.788651275 || HSH2D | 6.39.248 | hematopoietic SH2 domain containing [24920] | 19 | 0.323425031 || IFI35 | 6.39.248 | interferon induced protein 35 [5399] | 17 | 0.923554273 || IRF7 | 6.39.248 | interferon regulatory factor 7 [6122] | 11 | 1.300473752 || ISG20 | 6.39.248 | interferon stimulated exonuclease gene 20 [6130] | 15 | 0.242732269 || KIAA0895L | 6.39.248 | KIAA0895 like [34408] | 16 | 0.263517108 || KLHDC7B-DT | 6.39.248 | KLHDC7B divergent transcript [53791] | 22 | 0.906465559 || KPTN | 6.39.248 | kaptin, actin binding protein [6404] | 19 | 0.32397457 || LGALS9 | 6.39.248 | galectin 9 [6570] | 17 | 0.560157519 || LGALS9DP | 6.39.248 | galectin 9D, pseudogene [49896] | 17 | 0.466392533 || LINC01531 | 6.39.248 | long intergenic non-protein coding RNA 1531 [51270] | 19 | 0.477124507 || LINC01671 | 6.39.248 | long intergenic non-protein coding RNA 1671 [52459] | 21 | 0.251607242 || MDK | 6.39.248 | midkine [6972] | 11 | 0.238203965 || MOV10 | 6.39.248 | Mov10 RISC complex RNA helicase [7200] | 1 | 0.477921613 || MT2A | 6.39.248 | metallothionein 2A [7406] | 16 | 1.420422062 || MT2P1 | 6.39.248 | metallothionein 2 pseudogene 1 [7407] | 4 | 0.274606909 || MYBL1 | 6.39.248 | MYB proto-oncogene like 1 [7547] | 8 | 0.249535497 || NAGK | 6.39.248 | N-acetylglucosamine kinase [17174] | 2 | 0.227907622 || NAPA | 6.39.248 | NSF attachment protein alpha [7641] | 19 | 0.246853745 || NEURL3 | 6.39.248 | neuralized E3 ubiquitin protein ligase 3 [25162] | 2 | 0.536715009 || OASL | 6.39.248 | 2'-5'-oligoadenylate synthetase like [8090] | 12 | 2.118852155 || PARP10 | 6.39.248 | poly(ADP-ribose) polymerase family member 10 [25895] | 8 | 0.439404323 || PML | 6.39.248 | PML nuclear body scaffold [9113] | 15 | 0.477673549 || PSMB9 | 6.39.248 | proteasome 20S subunit beta 9 [9546] | 6 | 0.226403444 || PXT1 | 6.39.248 | peroxisomal testis enriched protein 1 [18312] | 6 | 0.281532969 || RAB40A | 6.39.248 | RAB40A, member RAS oncogene family [18283] | X | 0.214657512 || RBCK1 | 6.39.248 | RANBP2-type and C3HC4-type zinc finger containing 1 [15864] | 20 | 0.191740347 || RMI2 | 6.39.248 | RecQ mediated genome instability 2 [28349] | 16 | 0.989177043 || RORC | 6.39.248 | RAR related orphan receptor C [10260] | 1 | 0.732939038 || RTP4 | 6.39.248 | receptor transporter protein 4 [23992] | 3 | 1.323868483 || SHISA5 | 6.39.248 | shisa family member 5 [30376] | 3 | 0.454760562 || SLC4A10 | 6.39.248 | solute carrier family 4 member 10 [13811] | 2 | 0.527677671 || SSTR3 | 6.39.248 | somatostatin receptor 3 [11332] | 22 | 0.303642004 || SYT3 | 6.39.248 | synaptotagmin 3 [11511] | 19 | 0.252079502 || TOR1B | 6.39.248 | torsin family 1 member B [11995] | 9 | 0.553016926 || TRGV9 | 6.39.248 | T cell receptor gamma variable 9 [12295] | 7 | 0.372767639 || TRIM69 | 6.39.248 | tripartite motif containing 69 [17857] | 15 | 0.283062013 || TTC21A | 6.39.248 | tetratricopeptide repeat domain 21A [30761] | 3 | 0.504384187 || UBE2L6 | 6.39.248 | ubiquitin conjugating enzyme E2 L6 [12490] | 11 | 0.616565381 || UBE2Q2P2 | 6.39.248 | ubiquitin conjugating enzyme E2 Q2 pseudogene 2 [37440] | 15 | 0.350262462 || UNC93B1 | 6.39.248 | unc-93 homolog B1, TLR signaling regulator [13481] | 11 | 0.318933576 || UNC93B8 | 6.39.248 | unc-93 homolog B8 (pseudogene) [44037] | 4 | 0.395723654 || ZNF496 | 6.39.248 | zinc finger protein 496 [23713] | 1 | 0.379134451 || ADAMTS7P1 | 6.40.252 | ADAMTS7 pseudogene 1 [49407] | 15 | 0.279878737 || ADGRE4P | 6.40.252 | adhesion G protein-coupled receptor E4, pseudogene [19240] | 19 | 0.698757455 || ALOX15 | 6.40.252 | arachidonate 15-lipoxygenase [433] | 17 | 1.575391049 || CACNG6 | 6.40.252 | calcium voltage-gated channel auxiliary subunit gamma 6 [13625] | 19 | 0.502103666 || CACNG8 | 6.40.252 | calcium voltage-gated channel auxiliary subunit gamma 8 [13628] | 19 | 0.478246745 || CLC | 6.40.252 | Charcot-Leyden crystal galectin [2014] | 19 | 0.617333924 || COL11A2 | 6.40.252 | collagen type XI alpha 2 chain TABLE 4B-continued The genes within the significant gene clusters, listed in Table 4A. (1127 Genes Listed by: Gene Symbol | Module | Hugo GENE Nomenclature Committee (HGNC) Gene Description [HGNC ID] | Chromosome Number | Row Variance) ||)

[2187] | 6 | 0.27095882 || COL26A1 | 6.40.252 | collagen type XXVI alpha 1 chain [18038] | 7 | 0.425887249 || DNASE1L3 | 6.40.252 | deoxyribonuclease 1 like 3 [2959] | 3 | 0.304938107 || ENPP7P8 | 6.40.252 | ectonucleotide pyrophosphatase/phosphodiesterase 7 pseudogene 8 [48691] | 11 | 0.260887153 || EPHA2 | 6.40.252 | EPH receptor A2 [3386] | 1 | 0.197791833 || HRH4 | 6.40.252 | histamine receptor H4 [17383] | 18 | 0.453437938 || IL34 | 6.40.252 | interleukin 34 [28529] | 16 | 0.20647022 || IL5RA | 6.40.252 | interleukin 5 receptor subunit alpha [6017] | 3 | 0.672030576 || LINC01226 | 6.40.252 | long intergenic non-protein coding RNA 1226 [49678] | 1 | 0.268704398 || PRSS33 | 6.40.252 | serine protease 33 [30405] | 16 | 1.120393232 || PTMS | 6.40.252 | parathymosin [9629] | 12 | 0.28440514 || RHOXF1P1 | 6.40.252 | Rhox homeobox family member 1 pseudogene 1 [51580] | X | 0.260181147 || RPL35AP26 | 6.40.252 | ribosomal protein L35a pseudogene 26 [36465] | 11 | 0.200397213 || SIGLEC8 | 6.40.252 | sialic acid binding Ig like lectin 8 [10877] | 19 | 0.639668259 || SLC29A1 | 6.40.252 | solute carrier family 29 member 1 (Augustine blood group) [11003] | 6 | 0.224149491 || SLC4A9 | 6.40.252 | solute carrier family 4 member 9 [11035] | 5 | 0.260457556 || SMPD3 | 6.40.252 | sphingomyelin phosphodiesterase 3 [14240] | 16 | 0.344914553 || SPNS3 | 6.40.252 | sphingolipid transporter 3 (putative) [28433] | 17 | 0.221511096 || TFEC | 6.40.252 | transcription factor EC [11754] | 7 | 0.347474283 || ADAM23 | 6.42.256 | ADAM metallopeptidase domain 23 [202] | 2 | 0.601216431 || ASPM | 6.42.256 | assembly factor for spindle microtubules [19048] | 1 | 0.430903181 || ATP5MGP1 | 6.42.256 | ATP synthase membrane subunit g pseudogene 1 [13214] | 11 | 0.247159033 || BIRC5 | 6.42.256 | baculoviral IAP repeat containing 5 [593] | 17 | 0.481015061 || BMP8B | 6.42.256 | bone morphogenetic protein 8b [1075] | 1 | 0.21720825 || BUB1 | 6.42.256 | BUB1 mitotic checkpoint serine/threonine kinase [1148] | 2 | 0.432478314 || C1DP5 | 6.42.256 | C1D nuclear receptor corepressor pseudogene 5 [51613] | 11 | 0.255927984 || CCNA2 | 6.42.256 | cyclin A2 [1578] | 4 | 0.418396298 || CCNB2 | 6.42.256 | cyclin B2 [1580] | 15 | 0.202164975 || CD38 | 6.42.256 | CD38 molecule [1667] | 4 | 0.201426739 || CDC20 | 6.42.256 | cell division cycle 20 [1723] | 1 | 0.81073008 || CDC25A | 6.42.256 | cell division cycle 25A [1725] | 3 | 0.35380974 || CDC45 | 6.42.256 | cell division cycle 45 [1739] | 22 | 0.353879651 || CDCA3 | 6.42.256 | cell division cycle associated 3 [14624] | 12 | 0.204725917 || CDK1 | 6.42.256 | cyclin dependent kinase 1 [1722] | 10 | 0.25976005 || CDKN3 | 6.42.256 | cyclin dependent kinase inhibitor 3 [1791] | 14 | 0.230564775 || CDT1 | 6.42.256 | chromatin licensing and DNA replication factor 1 [24576] | 16 | 0.324554961 || CIT | 6.42.256 | citron rho-interacting serine/threonine kinase [1985] | 12 | 0.352522952 || CNGB1 | 6.42.256 | cyclic nucleotide gated channel subunit beta 1 [2151] | 16 | 0.431001278 || CPAMD8 | 6.42.256 | C3 and PZP like alpha-2-macroglobulin domain containing 8 [23228] | 19 | 0.497408191 || DLGAP5 | 6.42.256 | DLG associated protein 5 [16864] | 14 | 0.292678073 || DNM1P31 | 6.42.256 | dynamin 1 pseudogene 31 [35178] | 15 | 0.250497007 || EPN2 | 6.42.256 | epsin 2 [18639] | 17 | 0.322165287 || ESPL1 | 6.42.256 | extra spindle pole bodies like 1, separase [16856] | 12 | 0.308847473 || FIGNL2 | 6.42.256 | fidgetin like 2 [13287] | 12 | 0.216007353 || FPGT-TNNI3K | 6.42.256 | FPGT-TNNI3K readthrough [42952] | 1 | 0.199298049 || GRAPL | 6.42.256 | GRB2 related adaptor protein like [37240] | 17 | 0.312247016 || GSDME | 6.42.256 | gasdermin E [2810] | 7 | 0.23790114 || GTSE1 | 6.42.256 | G2 and S-phase expressed 1 [13698] | 22 | 0.327194403 || HJURP | 6.42.256 | Holliday junction recognition protein [25444] | 2 | 0.268197348 || HMGB3 | 6.42.256 | high mobility group box 3 [5004] | X | 0.232346237 || HMMR | 6.42.256 | hyaluronan mediated motility receptor [5012] | 5 | 0.227753654 || ICA1 | 6.42.256 | islet cell autoantigen 1 [5343] | 7 | 0.226919215 || IGHV1-3 | 6.42.256 | immunoglobulin heavy variable 1-3 [5552] | 14 | 1.288804186 || INAVA | 6.42.256 | innate immunity activator [25599] | 1 | 0.366563795 || INSL6 | 6.42.256 | insulin like 6 [6089] | 9 | 0.228968942 || KIF11 | 6.42.256 | kinesin family member 11 [6388] | 10 | 0.204793947 || KIF18B | 6.42.256 | kinesin family member 18B [27102] | 17 | 0.407382162 || KIF4A | 6.42.256 | kinesin family member 4A [13339] | X | 0.232531926 || KIFC1 | 6.42.256 | kinesin family member C1 [6389] | 6 | 0.279239537 || KLHL33 | 6.42.256 | kelch like family member 33 [31952] | 14 | 0.303291131 || LINC00475 | 6.42.256 | long intergenic non-protein coding RNA 475 [23569] | 9 | 0.215543723 || LINC00683 | 6.42.256 | long intergenic non-protein coding RNA 683 [44467] | 18 | 0.27797949 || LINC02610 | 6.42.256 | long intergenic non-protein coding RNA 2610 [27177] | 2 | 0.331123542 || MCM10 | 6.42.256 | minichromosome maintenance 10 replication initiation factor [18043] | 10 | 0.325218502 || MIXL1 | 6.42.256 | Mix paired-like homeobox [13363] | 1 | 0.253507895 || MKI67 | 6.42.256 | marker of proliferation Ki-67 [7107] | 10 | 0.818370802 || MTCL1 | 6.42.256 | microtubule crosslinking factor 1 [29121] | 18 | 0.210131785 || MTND4P24 | 6.42.256 | MT-ND4 pseudogene 24 [42220] | X | 0.915475437 || MYRFL | 6.42.256 | myelin regulatory factor like [26316] | 12 | 0.200170987 || NCAPG | 6.42.256 | non-SMC condensin I complex subunit G [24304] | 4 | 0.366359253 || NCAPH | 6.42.256 | non-SMC condensin I complex subunit H [1112] | 2 | 0.321088797 || NDC80 | 6.42.256 | NDC80 kinetochore complex component [16909] | 18 | 0.254215616 || NUF2 | 6.42.256 | NUF2 component of NDC80 kinetochore complex [14621] | 1 | 0.282494857 || OR13A1 | 6.42.256 | olfactory receptor family 13 subfamily A member 1 [14772] | 10 | 0.336905131 || PACSIN1 | 6.42.256 | protein kinase C and casein kinase substrate in neurons 1 [8570] | 6 | 0.344211707 || PDGFC | 6.42.256 | platelet derived growth factor C [8801] | 4 | 0.288144692 || PKMYT1 | 6.42.256 | protein kinase, membrane associated tyrosine/threonine 1 [29650] | 16 | 0.401757272 || RFPL4A | 6.42.256 | ret finger protein like 4A [16449] | 19 | 0.467878374 || RNA5SP315 | 6.42.256 | RNA, 5S ribosomal pseudogene 315 [43215] | 10 | 0.253064875 || SKA1 | 6.42.256 | spindle and kinetochore associated complex subunit 1 [28109] | 18 | 0.195201008 || SLC7A11 | 6.42.256 | solute carrier family 7 member 11 [11059] | 4 | 0.220458758 || SLC9C1 | 6.42.256 | solute carrier family 9 member C1 [31401] | 3 | 0.198347487 || SNHG5 | 6.42.256 | small nucleolar RNA host gene 5 [21026] | 6 | 0.324239417 || TEDDM1 | 6.42.256 | transmembrane epididymal protein 1 [30233] | 1 | 0.225871566 || TOP2A | 6.42.256 | DNA topoisomerase II alpha [11989] | 17 | 0.371974329 ||

TABLE 4B-continued

| The genes within the significant gene clusters, listed in Table 4A. (1127 Genes Listed by: Gene Symbol ǀ Module ǀ Hugo GENE Nomenclature Committee (HGNC) Gene Description [HGNC ID] ǀ Chromosome Number ǀ Row Variance) ǀǀ) |
| --- |
| TPX2 ǀ 6.42.256 ǀ TPX2 microtubule nucleation factor [1249] ǀ 20 ǀ 0.397033017 ǀǀ TROAP ǀ 6.42.256 ǀ trophinin associated protein [12327] ǀ 12 ǀ 0.311835888 ǀǀ TSPAN3 ǀ 6.42.256 ǀ tetraspanin 3 [17752] ǀ 15 ǀ 0.220115775 ǀǀ TWIST2 ǀ 6.42.256 ǀ twist family bHLH transcription factor 2 [20670] ǀ 2 ǀ 0.303107915 ǀǀ VPS33B-DT ǀ 6.42.256 ǀ VPS33B divergent transcript [51413] ǀ 15 ǀ 0.199583463 ǀǀ WBP1LP2 ǀ 6.42.256 ǀ WBP1L pseudogene 2 [43949] ǀ 7 ǀ 0.213383273 ǀǀ ZC2HC1C ǀ 6.42.256 ǀ zinc finger C2HC-type containing 1C [20354] ǀ 14 ǀ 0.263807661 ǀǀ A2ML1-AS1 ǀ 7.49.271 ǀ A2ML1 antisense RNA 1 [41022] ǀ 12 ǀ 2.12318117 ǀǀ ADIPOR1 ǀ 7.49.271 ǀ adiponectin receptor 1 [24040] ǀ 1 ǀ 1.030334244 ǀǀ AHSP ǀ 7.49.271 ǀ alpha hemoglobin stabilizing protein [18075] ǀ 16 ǀ 2.181005389 ǀǀ AQP1 ǀ 7.49.271 ǀ aquaporin 1 (Colton blood group) [633] ǀ 7 ǀ 0.662113564 ǀǀ BBOF1 ǀ 7.49.271 ǀ basal body orientation factor 1 [19855] ǀ 14 ǀ 0.414637096 ǀǀ BCAM ǀ 7.49.271 ǀ basal cell adhesion molecule (Lutheran blood group) [6722] ǀ 19 ǀ 1.244309301 ǀǀ BEND3P1 ǀ 7.49.271 ǀ BEN domain containing 3 pseudogene 1 [45014] ǀ 10 ǀ 0.274969058 ǀǀ BLVRB ǀ 7.49.271 ǀ biliverdin reductase B [1063] ǀ 19 ǀ 0.41608986 ǀǀ BNIP3L ǀ 7.49.271 ǀ BCL2 interacting protein 3 like [1085] ǀ 8 ǀ 0.647713469 ǀǀ C1orf116 ǀ 7.49.271 ǀ chromosome 1 open reading frame 116 [28667] ǀ 1 ǀ 0.281852693 ǀǀ C1orf198 ǀ 7.49.271 ǀ chromosome 1 open reading frame 198 [25900] ǀ 1 ǀ 0.217341841 ǀǀ CA2 ǀ 7.49.271 ǀ carbonic anhydrase 2 [1373] ǀ 8 ǀ 0.437048337 ǀǀ CHPT1 ǀ 7.49.271 ǀ choline phosphotransferase 1 [17852] ǀ 12 ǀ 0.572034931 ǀǀ CPNE7 ǀ 7.49.271 ǀ copine 7 [2320] ǀ 16 ǀ 0.445973054 ǀǀ CRB3 ǀ 7.49.271 ǀ crumbs cell polarity complex component 3 [20237] ǀ 19 ǀ 0.242925589 ǀǀ DMTN ǀ 7.49.271 ǀ dematin actin binding protein [3382] ǀ 8 ǀ 1.090800207 ǀǀ EIF1B ǀ 7.49.271 ǀ eukaryotic translation initiation factor 1B [30792] ǀ 3 ǀ 0.240985483 ǀǀ EMC3 ǀ 7.49.271 ǀ ER membrane protein complex subunit 3 [23999] ǀ 3 ǀ 0.341961143 ǀǀ EPHA1 ǀ 7.49.271 ǀ EPH receptor A1 [3385] ǀ 7 ǀ 0.22462714 ǀǀ FAM210B ǀ 7.49.271 ǀ family with sequence similarity 210 member B [16102] ǀ 20 ǀ 1.363838672 ǀǀ FAXDC2 ǀ 7.49.271 ǀ fatty acid hydroxylase domain containing 2 [1334] ǀ 5 ǀ 0.78693266 ǀǀ FBXO7 ǀ 7.49.271 ǀ F-box protein 7 [13586] ǀ 22 ǀ 0.873251771 ǀǀ FUNDC2P1 ǀ 7.49.271 ǀ FUN14 domain containing 2 pseudogene 1 [17253] ǀ 5 ǀ 0.297773231 ǀǀ GFUS ǀ 7.49.271 ǀ GDP-L-fucose synthase [12390] ǀ 8 ǀ 0.565931003 ǀǀ HAGH ǀ 7.49.271 ǀ hydroxyacylglutathione hydrolase [4805] ǀ 16 ǀ 0.416388884 ǀǀ HBB ǀ 7.49.271 ǀ hemoglobin subunit beta [4827] ǀ 11 ǀ 1.926792104 ǀǀ HPS1 ǀ 7.49.271 ǀ HPS1 biogenesis of lysosomal organelles complex 3 subunit 1 [5163] ǀ 10 ǀ 0.23662815 ǀǀ IGF2BP2 ǀ 7.49.271 ǀ insulin like growth factor 2 mRNA binding protein 2 [28867] ǀ 3 ǀ 0.880588413 ǀǀ ISCA1P1 ǀ 7.49.271 ǀ iron-sulfur cluster assembly 1 pseudogene 1 [33263] ǀ 5 ǀ 0.425499558 ǀǀ KCNMA1 ǀ 7.49.271 ǀ potassium calcium-activated channel subfamily M alpha 1 [6284] ǀ 10 ǀ 0.838273734 ǀǀ KDM7A-DT ǀ 7.49.271 ǀ KDM7A divergent transcript [48959] ǀ 7 ǀ 0.449711845 ǀǀ KEL ǀ 7.49.271 ǀ Kell metallo-endopeptidase (Kell blood group) [6308] ǀ 7 ǀ 0.531165877 ǀǀ KLC3 ǀ 7.49.271 ǀ kinesin light chain 3 [20717] ǀ 19 ǀ 1.140737604 ǀǀ KLHDC8A ǀ 7.49.271 ǀ kelch domain containing 8A [25573] ǀ 1 ǀ 0.302016044 ǀǀ LEFTY1 ǀ 7.49.271 ǀ left-right determination factor 1 [6552] ǀ 1 ǀ 0.230315474 ǀǀ LINC01036 ǀ 7.49.271 ǀ long intergenic non-protein coding RNA 1036 [49024] ǀ 1 ǀ 1.029041967 ǀǀ LOXHD1 ǀ 7.49.271 ǀ lipoxygenase homology domains 1 [26521] ǀ 18 ǀ 0.445717822 ǀǀ LRRC75A ǀ 7.49.271 ǀ leucine rich repeat containing 75A [32403] ǀ 17 ǀ 0.200399095 ǀǀ MFSD2B ǀ 7.49.271 ǀ major facilitator superfamily domain containing 2B [37207] ǀ 2 ǀ 0.705908235 ǀǀ MPP1 ǀ 7.49.271 ǀ membrane palmitoylated protein 1 [7219] ǀ X ǀ 0.476216456 ǀǀ NCOA4 ǀ 7.49.271 ǀ nuclear receptor coactivator 4 [7671] ǀ 10 ǀ 0.221480792 ǀǀ PAGE2 ǀ 7.49.271 ǀ PAGE family member 2 [31804] ǀ X ǀ 0.37367835 ǀǀ PAGE2B ǀ 7.49.271 ǀ PAGE family member 2B [31805] ǀ X ǀ 0.552124697 ǀǀ PBX1 ǀ 7.49.271 ǀ PBX homeobox 1 [8632] ǀ 1 ǀ 0.522202523 ǀǀ PINK1 ǀ 7.49.271 ǀ PTEN induced kinase 1 [14581] ǀ 1 ǀ 0.258845806 ǀǀ POU5F1 ǀ 7.49.271 ǀ POU class 5 homeobox 1 [9221] ǀ 6 ǀ 0.312072731 ǀǀ PPM1A ǀ 7.49.271 ǀ protein phosphatase, Mg2+/Mn2+ dependent 1A [9275] ǀ 14 ǀ 0.389457034 ǀǀ RAB3IL1 ǀ 7.49.271 ǀ RAB3A interacting protein like 1 [9780] ǀ 11 ǀ 0.584995655 ǀǀ RGS10 ǀ 7.49.271 ǀ regulator of G protein signaling 10 [9992] ǀ 10 ǀ 0.328526647 ǀǀ RNF10 ǀ 7.49.271 ǀ ring finger protein 10 [10055] ǀ 12 ǀ 0.532085932 ǀǀ SFRP2 ǀ 7.49.271 ǀ secreted frizzled related protein 2 [10777] ǀ 4 ǀ 0.754614353 ǀǀ SGIP1 ǀ 7.49.271 ǀ SH3GL interacting endocytic adaptor 1 [25412] ǀ 1 ǀ 0.69697643 ǀǀ SHISA7 ǀ 7.49.271 ǀ shisa family member 7 [35409] ǀ 19 ǀ 0.517513771 ǀǀ SLC25A37 ǀ 7.49.271 ǀ solute carrier family 25 member 37 [29786] ǀ 8 ǀ 0.458782075 ǀǀ SLC25A39 ǀ 7.49.271 ǀ solute carrier family 25 member 39 [24279] ǀ 17 ǀ 1.359458081 ǀǀ SLC6A19 ǀ 7.49.271 ǀ solute carrier family 6 member 19 [27960] ǀ 5 ǀ 0.400096613 ǀǀ SLC6A8 ǀ 7.49.271 ǀ solute carrier family 6 member 8 [11055] ǀ X ǀ 1.087069436 ǀǀ SNX3 ǀ 7.49.271 ǀ sorting nexin 3 [11174] ǀ 6 ǀ 0.203673236 ǀǀ TAL1 ǀ 7.49.271 ǀ TAL bHLH transcription factor 1, erythroid differentiation factor [11556] ǀ 1 ǀ 0.848113712 ǀǀ TMEM121B ǀ 7.49.271 ǀ transmembrane protein 121B [1844] ǀ 22 ǀ 0.295114749 ǀǀ TMEM63B ǀ 7.49.271 ǀ transmembrane protein 63B [17735] ǀ 6 ǀ 0.212391705 ǀǀ TPGS2 ǀ 7.49.271 ǀ tubulin polyglutamylase complex subunit 2 [24561] ǀ 18 ǀ 0.415880149 ǀǀ TRAJ39 ǀ 7.49.271 ǀ T cell receptor alpha joining 39 [12069] ǀ 14 ǀ 0.248940552 ǀǀ TRIM10 ǀ 7.49.271 ǀ tripartite motif containing 10 [10072] ǀ 6 ǀ 0.894007414 ǀǀ UBB ǀ 7.49.271 ǀ ubiquitin B [12463] ǀ 17 ǀ 0.804945801 ǀǀ UBBP1 ǀ 7.49.271 ǀ ubiquitin B pseudogene 1 [12464] ǀ 2 ǀ 0.383367805 ǀǀ UBBP4 ǀ 7.49.271 ǀ ubiquitin B pseudogene 4 [12467] ǀ 17 ǀ 0.771836699 ǀǀ YBX1 ǀ 7.49.271 ǀ Y-box binding protein 1 [8014] ǀ 1 ǀ 0.215475194 ǀǀ YBX1P1 ǀ 7.49.271 ǀ Y-box binding protein 1 pseudogene 1 [8015] ǀ 14 ǀ 0.22068152 ǀǀ YBX1P10 ǀ 7.49.271 ǀ Y-box binding protein 1 pseudogene 10 [42432] ǀ 9 ǀ 0.209173083 ǀǀ ALDH6A1 ǀ 7.49.272 ǀ aldehyde dehydrogenase 6 family member A1 [7179] ǀ 14 ǀ 0.207582453 ǀǀ ANK1 ǀ 7.49.272 ǀ ankyrin 1 [492] ǀ 8 ǀ 1.117339036 ǀǀ ANKRD9 ǀ 7.49.272 ǀ ankyrin repeat domain 9 [20096] ǀ 14 ǀ 0.670775701 ǀǀ ARHGEF12 ǀ 7.49.272 ǀ Rho guanine nucleotide exchange factor 12 [14193] ǀ 11 ǀ 0.424193984 ǀǀ DCAF12 ǀ 7.49.272 ǀ DDB1 and CUL4 associated factor 12 [19911] ǀ 9 ǀ 0.803806854 ǀǀ DNAJC6 ǀ 7.49.272 ǀ DnaJ heat shock protein family (Hsp40) member C6 [15469] ǀ 1 ǀ 0.32342718 ǀǀ EPPK1 ǀ 7.49.272 ǀ epiplakin 1 [15577] ǀ 8 ǀ 0.514033262 ǀǀ FBXO9 ǀ 7.49.272 ǀ F- |

TABLE 4B-continued

The genes within the significant gene clusters, listed in Table 4A. (1127 Genes Listed by: Gene Symbol | Module | Hugo GENE Nomenclature Committee (HGNC) Gene Description [HGNC ID] | Chromosome Number | Row Variance) ||)

box protein 9 [13588] | 6 | 0.321617025 || GMPR | 7.49.272 | guanosine monophosphate reductase [4376] | 6 | 0.996833356 || GSPT1 | 7.49.272 | G1 to S phase transition 1 [4621] | 16 | 0.755995296 || HBD | 7.49.272 | hemoglobin subunit delta [4829] | 11 | 0.938900253 || ISCA1P6 | 7.49.272 | iron-sulfur cluster assembly 1 pseudogene 6 [38027] | 2 | 0.262902662 || LINC01781 | 7.49.272 | long intergenic non-protein coding RNA 1781 [52571] | 1 | 0.367384487 || LTBP2 | 7.49.272 | latent transforming growth factor beta binding protein 2 [6715] | 14 | 0.334856584 || MKRN1 | 7.49.272 | makorin ring finger protein 1 [7112] | 7 | 0.634052172 || NUDT4 | 7.49.272 | nudix hydrolase 4 [8051] | 12 | 0.221198333 || NUDT4B | 7.49.272 | nudix hydrolase 4B [18012] | 1 | 0.432011489 || NUDT4P2 | 7.49.272 | nudix hydrolase 4 pseudogene 2 [18013] | 1 | 0.445307424 || OSBP2 | 7.49.272 | oxysterol binding protein 2 [8504] | 22 | 0.955425102 || RANBP10 | 7.49.272 | RAN binding protein 10 [29285] | 16 | 0.314350913 || RBM38 | 7.49.272 | RNA binding motif protein 38 [15818] | 20 | 0.687193644 || SOX6 | 7.49.272 | SRY-box transcription factor 6 [16421] | 11 | 0.268036765 || STRADBP1 | 7.49.272 | STE20-related kinase adaptor beta pseudogene 1 [22478] | 7 | 0.535297874 || TRIM58 | 7.49.272 | tripartite motif containing 58 [24150] | 1 | 1.575244625 || AQP7 | 9.100.332 | aquaporin 7 [640] | 9 | 0.237241947 || ARHGAP28 | 9.100.332 | Rho GTPase activating protein 28 [25509] | 18 | 0.27668972 || CBX3P2 | 9.100.332 | chromobox 3 pseudogene 2 [42874] | 18 | 0.231008198 || CCDC59 | 9.100.332 | coiled-coil domain containing 59 [25005] | 12 | 0.191934298 || DMRTC1B | 9.100.332 | DMRT like family C1B [31686] | X | 0.202694651 || EID2 | 9.100.332 | EP300 interacting inhibitor of differentiation 2 [28292] | 19 | 0.263889385 || GRPEL2 | 9.100.332 | GrpE like 2, mitochondrial [21060] | 5 | 0.295214654 || GUCY1A2 | 9.100.332 | guanylate cyclase 1 soluble subunit alpha 2 [4684] | 11 | 0.247659701 || HLA-DPA3 | 9.100.332 | major histocompatibility complex, class II, DP alpha 3 (pseudogene) [19393] | 6 | 0.276867891 || HLF | 9.100.332 | HLF transcription factor, PAR bZIP family member [4977] | 17 | 0.341672115 || LINC01284 | 9.100.332 | long intergenic non-protein coding RNA 1284 [50342] | X | 0.301435442 || LINC01424 | 9.100.332 | long intergenic non-protein coding RNA 1424 [40558] | 21 | 0.210465155 || LINC01765 | 9.100.332 | long intergenic non-protein coding RNA 1765 [52555] | 1 | 0.404016253 || LINC02298 | 9.100.332 | long intergenic non-protein coding RNA 2298 [53216] | 14 | 0.19647663 || LINC02884 | 9.100.332 | long intergenic non-protein coding RNA 2884 [54808] | 1 | 0.198374863 || NCK1-DT | 9.100.332 | NCK1 divergent transcript [49645] | 3 | 0.22884271 || PFDN4 | 9.100.332 | prefoldin subunit 4 [8868] | 20 | 0.243635026 || RARRES2P2 | 9.100.332 | retinoic acid receptor responder 2 pseudogene 2 [48701] | 10 | 0.312593978 || RARRES2P4 | 9.100.332 | retinoic acid receptor responder 2 pseudogene 4 [48703] | 4 | 0.204048442 || RASGRF2-AS1 | 9.100.332 | RASGRF2 antisense RNA 1 [40499] | 5 | 0.319041566 || RET | 9.100.332 | ret proto-oncogene [9967] | 10 | 0.202083525 || RFPL3S | 9.100.332 | RFPL3 antisense [9981] | 22 | 0.211020681 || RLN3 | 9.100.332 | relaxin 3 [17135] | 19 | 0.255110937 || RPL21P11 | 9.100.332 | ribosomal protein L21 pseudogene 11 [19800] | 14 | 0.22294619 || RPL26P19 | 9.100.332 | ribosomal protein L26 pseudogene 19 [36393] | 5 | 0.213951178 || RPL26P6 | 9.100.332 | ribosomal protein L26 pseudogene 6 [34023] | 10 | 0.206462471 || RPL31 | 9.100.332 | ribosomal protein L31 [10334] | 2 | 0.197987394 || RPL31P12 | 9.100.332 | ribosomal protein L31 pseudogene 12 [35546] | 1 | 0.283006768 || RPL34 | 9.100.332 | ribosomal protein L34 [10340] | 4 | 0.217295411 || RPL7P19 | 9.100.332 | ribosomal protein L7 pseudogene 19 [36268] | 5 | 0.20592564 || RPS18P9 | 9.100.332 | ribosomal protein S18 pseudogene 9 [36483] | 6 | 0.19358743 || RPS24P8 | 9.100.332 | ribosomal protein S24 pseudogene 8 [37016] | 3 | 0.324924804 || RPS3AP25 | 9.100.332 | RPS3A pseudogene 25 [36801] | 7 | 0.292899598 || RPS8P10 | 9.100.332 | ribosomal protein S8 pseudogene 10 [35628] | 15 | 0.221650989 || SNRPE | 9.100.332 | small nuclear ribonucleoprotein polypeptide E [11161] | 1 | 0.206637228 || TMEM132A | 9.100.332 | transmembrane protein 132A [31092] | 11 | 0.191994855 || TPT1P4 | 9.100.332 | tumor protein, translationally-controlled 1 pseudogene 4 [49298] | 6 | 0.215599037 || UQCRB | 9.100.332 | ubiquinol-cytochrome c reductase binding protein [12582] | 8 | 0.265478003 || ZNF785 | 9.100.332 | zinc finger protein 785 [26496] | 16 | 0.422494968 || ANKRD12 | 9.110.349 | ankyrin repeat domain 12 [29135] | 18 | 0.23921232 || C12orf29 | 9.110.349 | chromosome 12 open reading frame 29 [25322] | 12 | 0.434978233 || CD207 | 9.110.349 | CD207 molecule [17935] | 2 | 0.234114101 || CFAP54 | 9.110.349 | cilia and flagella associated protein 54 [26456] | 12 | 0.357168653 || CPNE4 | 9.110.349 | copine 4 [2317] | 3 | 0.220620462 || EXD2 | 9.110.349 | exonuclease 3'-5' domain containing 2 [20217] | 14 | 0.191742825 || HLTF | 9.110.349 | helicase like transcription factor [11099] | 3 | 0.203203055 || IGIP | 9.110.349 | IgA inducing protein [33847] | 5 | 0.315424065 || ITPR1-DT | 9.110.349 | ITPR1 divergent transcript [44470] | 3 | 0.272252746 || KBTBD8 | 9.110.349 | kelch repeat and BTB domain containing 8 [30691] | 3 | 0.371983316 || LINC00402 | 9.110.349 | long intergenic non-protein coding RNA 402 [42732] | 13 | 0.269195063 || LINC00698 | 9.110.349 | long intergenic non-protein coding RNA 698 [27720] | 3 | 0.234442582 || LINC02575 | 9.110.349 | long intergenic non-protein coding RNA 2575 [53747] | 21 | 0.223011805 || LRRC3 | 9.110.349 | leucine rich repeat containing 3 [14965] | 21 | 0.247212423 || LVRN | 9.110.349 | laeverin [26904] | 5 | 0.230177094 || MYCT1 | 9.110.349 | MYC target 1 [23172] | 6 | 0.207094686 || NAP1L3 | 9.110.349 | nucleosome assembly protein 1 like 3 [7639] | X | 0.353957204 || PRELID3B | 9.110.349 | PRELI domain containing 3B [15892] | 20 | 0.308472291 || PTPN13 | 9.110.349 | protein tyrosine phosphatase non-receptor type 13 [9646] | 4 | 0.382298131 || RLN2 | 9.110.349 | relaxin 2 [10027] | 9 | 0.34058002 || SC5D | 9.110.349 | sterol-C5-desaturase [10547] | 11 | 0.480866713 || SMIM10L2A | 9.110.349 | small integral membrane protein 10 like 2A [34499] | X | 0.472158246 || SPAG8 | 9.110.349 | sperm associated antigen 8 [14105] | 9 | 0.259512162 || UFL1 | 9.110.349 | UFM1 specific ligase 1 [23039] | 6 | 0.209006134 || UGT8 | 9.110.349 | UDP glycosyltransferase 8 [12555] | 4 | 0.337784013 || UTP15 | 9.110.349 |

TABLE 4B-continued

| The genes within the significant gene clusters, listed in Table 4A. (1127 Genes Listed by: Gene Symbol \| Module \| Hugo GENE Nomenclature Committee (HGNC) Gene Description [HGNC ID] \| Chromosome Number \| Row Variance) \|\|) |
|---|
| UTP15 small subunit processome component [25758] \| 5 \| 0.274107733 \|\| XIRP1 \| 9.110.349 \| xin actin binding repeat containing 1 [14301] \| 3 \| 0.231299442 \|\| ZNF404 \| 9.110.349 \| zinc finger protein 404 [19417] \| 19 \| 0.204613129 \|\| ZNF471 \| 9.110.349 \| zinc finger protein 471 [23226] \| 19 \| 0.389219293 \|\| |

Figure 15A:
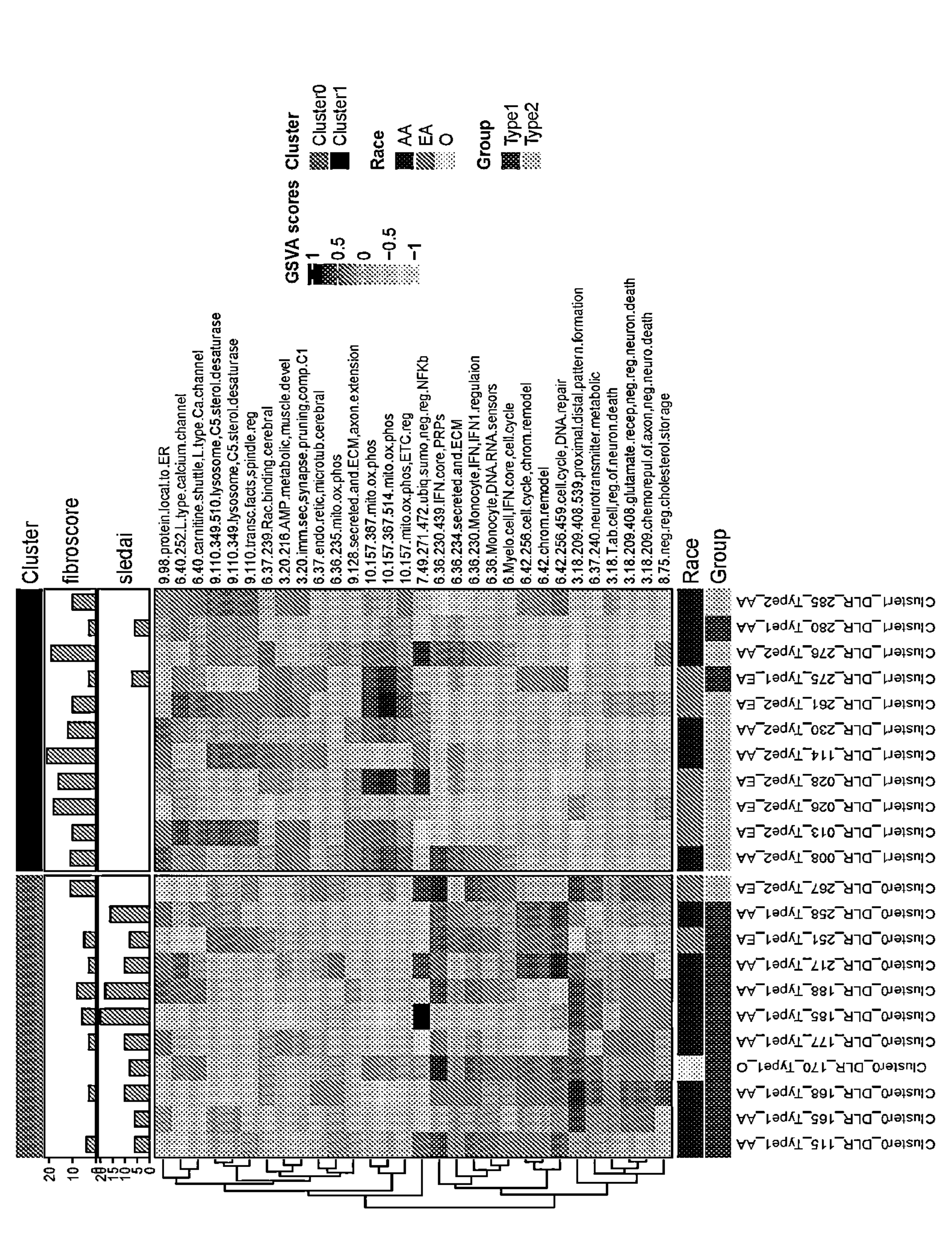
FIG. 15A: Gene Set Variation Analysis (GSVA) performed using genes within the 30 significant gene clusters (obtained from clustering Lupus/Fibromyalgia-top5k rowVar genes).
Figure 15B:
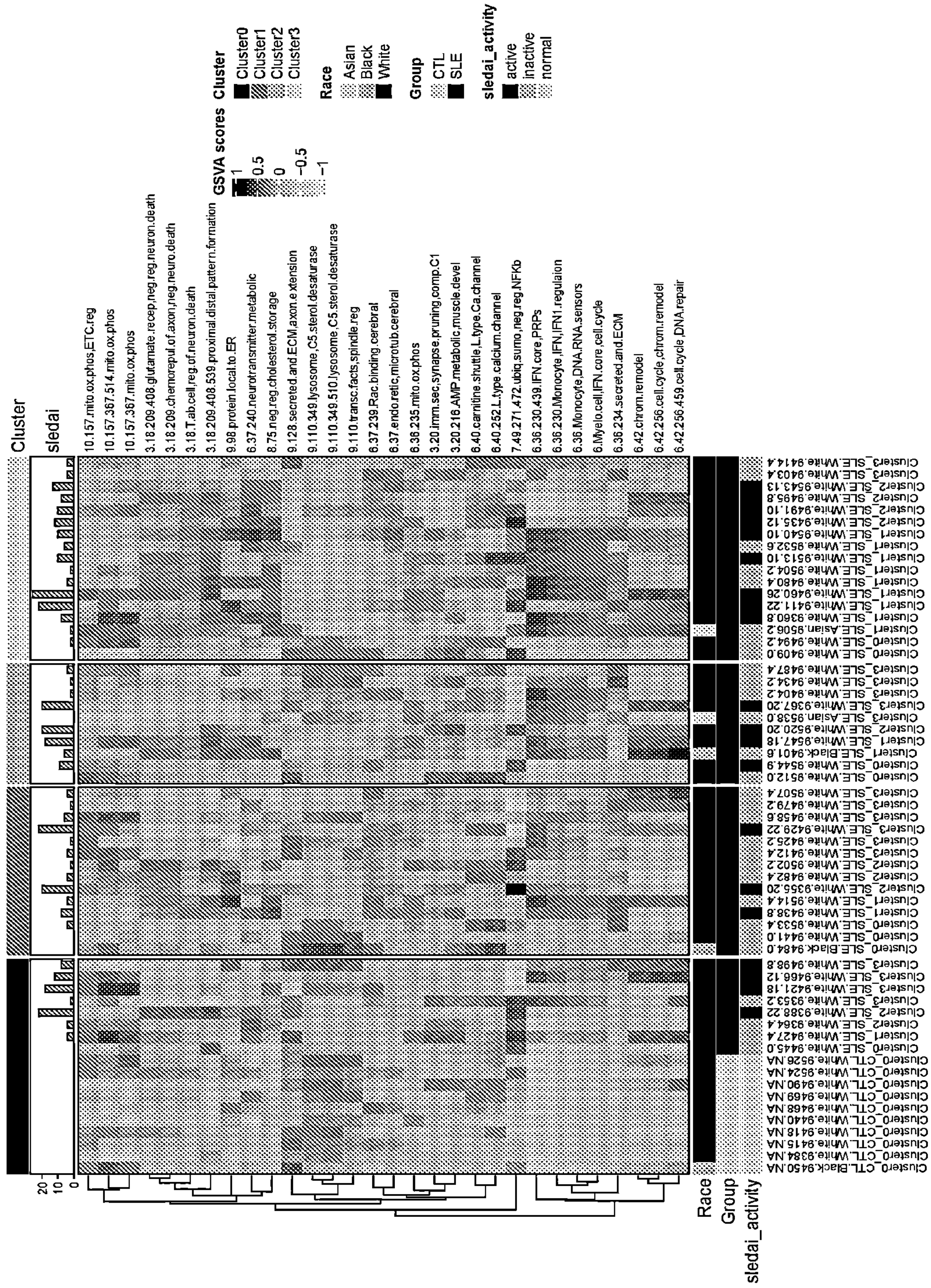
FIG. 15B: GSVA performed using genes within the 30 significant gene clusters (obtained from clustering Lupus/Fibromyalgia—top5k rowVar genes) on GSE49454 (Chaussabel) blood data set.

FIGS. 15A-15B. Gene set variation analysis (GSVA) for enrichment of the genes of the significant gene clusters was analyzed. K-means clustering of k=2 separated patients active SLE from SLE with fibromyalgia, with misplacement of only two type 1 patients and one type 2 patient (FIG. 15A).

GSVA was performed for enrichment of genes of the significant gene clusters in GSE49454 (Chaussabel) blood microarray dataset. K-means clustering of k=4 separated healthy samples from active SLE (SLEDAI >6), with misplacement of only one active SLE patient (FIG. 15B). The significant gene clusters obtained from the SLE/fibromyalgia RNAseq dataset, was able to classify the patients of the GSE49454 microarray dataset.

Example 4: Utility of Baseline Transcriptomic Analysis of Rheumatoid Arthritis Synovium as an Indicator for Long-Term Clinical Outcomes As a means to begin to sub-set patients with early RA, a microarray-based strategy was applied to evaluate the synovial transcriptome in fine-needle tissue biopsy samples from DMARD-naïve RA patients relative to those with established RA. These molecular signatures were correlated with clinical outcomes collected from these individuals periodically during a 15-year longitudinal follow-up post-DMARD intervention.

Materials & Methods

Study design: The study was approved by the Biomedical Research Ethics Board of the University of Manitoba, and the Band Councils of the individual study communities in Manitoba. All the participants were members of the First Nations communities of Manitoba and were recruited into our study protocol from our early RA (ERA) clinic between 2000-2005. All patients were enrolled before initiation of a first DMARD. After the biopsy, patients were treated according to current guidelines for early RA. Clinical data was acquired every 3 months and captured in a custom database. These individuals were followed longitudinally for a minimum of 15 years and their clinical outcomes were recorded. However, no attempt was made to guide their DMARD therapy, which was solely based on clinical indications. Baseline synovial biopsies from DMARD-naïve RA patients were obtained using a minimally invasive closed needle biopsy technique (Parker-Pearson method). All the biopsies were performed on clinically inflamed knee joints. Samples were obtained from multiple areas in each biopsied joint, and all samples were adequate for transcriptomic and immunohistopathological analysis. Two individuals had bilateral biopsies of their affected knees. As controls, synovial tissues from advanced RA (n=6) patients that were collected from anonymous donors during joint replacement surgery was used. RA diagnosis was made based on fulfilling the 2010 ACR/EULAR classification criteria, as determined by a rheumatologist (HEG/CH).

Sample collection, storage, and serology: Venous blood was collected into SST™ serum separation tubes (BD Biosciences) and processed as per the manufacturer's instructions. Screening for high-sensitivity C-reactive protein (hs-CRP), erythrocyte sedimentation rate (ESR), and rheumatoid factor (RF) was performed at a clinical and/or research laboratory at a single tertiary care hospital (Health Sciences Centre, Winnipeg, Manitoba, Canada).

Assessment of clinical parameters: Analysis of clinical outcomes were undertaken using all the available clinical data for each study participant. Because of the asynchronous nature of clinical visits and duration of follow up, area under the curve (AUC), normalized to duration of follow up was used to estimate the burden of specific disease manifestations such as functional disability (HAQ) and treatment resistant disease (number of DMARDs).

Immunohistology: H&E (hematoxylin & eosin) staining was carried out on paraffin-embedded tissues. Total cell counts were determined through light microscopy image analysis. Immunohistological analysis and quantification of the same synovial samples was undertaken of OCT-embedded tissue blocks for differentially expressed genes (DEGs) identified in the transcriptomic analysis.

RNA Isolation, and microarray: Tissue homogenization, and total RNA isolation (RNeasy RNA isolation kit, Qiagen Inc) was carried out on fresh synovial biopsy samples as per manufacturer's instructions. To minimize variability, at least 2 individual samples were collected from different locations of each joint being used for this purpose. In the case of synovial tissues obtained from patients with late-stage RA (n=6) at the time of joint arthroplasty, representative samples from each synovial tissue were used to generate total RNA, which was then processed in an identical manner to the needle biopsy samples. 10 ug of high-quality RNA (28/18S ratio >1) was extracted from these synovial biopsy samples. RNA quality was determined on Agilent Bioanalyzer using the Agilent RNA 6000 Nano kit and quantified on a Nanodrop ND-1000 spectrophotometer. Total RNA with a A260/280 >2.0 and an RNA integrity number (RIN)>8.0 was used for assessing synovial transcriptome. Total RNA was converted to complementary RNA (cRNA) and hybridized to Affymetrix HU133plus2 chips that had 54,675 probe sets corresponding to the entire human genome. Hybridized chips were scanned using an Affymetrix Genechip Scanner 3000.

Data analysis & statistics: Data from the microarray chips was normalized and analyzed using the MAS 5.0 algorithm, then imported into Array Assist software (Stratagene) and analyzed using Significance Analysis of Microarray (SAM) analysis (Stanford, California) (7). Mann-Whitney U test, Chi-square test, Pearson correlation and Spearman rank correlation analyses were used as and when required. Graphpad Prism (v9.1) was used for graphical representation of the results. R packages or Ingenuity Pathway Analysis were used to perform functional network analysis as explained below.

Weighted Gene Co-expression Network Analysis (WGCNA) and Multi-scale Embedded Gene Co-expression Network Analysis (MEGENA): WGCNA algorithm was used to construct co-expressed gene network modules that were assessed further for their functional significance (8). Raw microarray data files underwent background correction and GCRMA normalization resulting in $log_2$ intensity values compiled into an expression set object (e-set). The e-set was then restricted to the top 5000 probes with the highest variance among the DMARD-naïve samples. A scale-free topology matrix (TOM) was calculated to encode the network strength between probes with a soft thresholding power of 30. TOM distances were used to cluster probes into WGCNA modules. Resulting co-expression networks were trimmed using dynamic tree cutting and the deepSplit function in R. Partitioning around medoids (PAM) was also utilized to assign outliers to the nearest cluster. The resulting network was formed with a minimum module size of 100, cut height of 1, and merge height of 0.2. Modules were given random color assignments and expression profiles summarized by a module eigengene (ME). Final membership of probes representing the same gene were decided based on strongest within-module correlation to the ME value. For each module, ME values were correlated by Pearson correlation to the clinical data including cohort (MMP-high group=1, MMP-low group=0), ESR, CRP, age, sex, swollen joints, disease duration, tender joints, and total affected joints. Significance was determined using an adjusted p-value≤0.2. MEGENA is a multi-scale co-expression gene clustering algorithm, which was used to create additional gene expression networks by applying it on the normalized and filtered gene modules from WGCNA. Multi-scale clustering structures were identified using planar filtered networks and resultant gene co-expression modules were also correlated to clinical metadata as described for WGCNA (9).

Functional annotation of gene expression networks: Co-expression modules were annotated according to the top overlapping functional category with the most significant p-value and a minimum of 4 overlapping genes. In the absence of significant overlaps, “unknown” was the assigned annotation. Functional enrichment within the gene co-expression modules and relative significance with clinical outcomes was calculated using gene ontology (GO), transcriptomic signatures derive from published literature and functional aggregation tools, namely Immune/Inflammation-Scope (I-Scope), Tissue-Scope (T-Scope) and Biologically Informed Gene Clustering (BIG-C) (10-14). I-Scope categorizes gene transcripts into one of a possible 28 hematopoietic cell categories based on matching transcripts known to mark various types of immune/inflammatory cells. T-Scope is an additional aggregation tool to characterize cell types found in specific tissues. BIG-C classifies genes into 53 different groups based on their most probable biological function and/or cellular or subcellular localization. Odds ratios and overlap p-values were calculated using Fisher’s Exact test in R using the fisher.test function. Statistical significance was obtained using an adjusted p-value≤0.2.

Results

Study population: In total, 15 DMARD-naïve ERA patients were enrolled in this longitudinal study and underwent baseline synovial biopsy of an affected knee joint using the Parker-Pearson technique, prior to initiation of their first DMARD. Two of these study participants in whom both knees were affected underwent bilateral synovial biopsy. Table 5 summarizes the clinical characteristics of the subjects at baseline. Of this study population, 12/15 (80%) were female, median age was 44 years, and median disease duration was 6 months. Although anti-CCP antibody levels were not available, 10/15 (67%) were seropositive for RF (median=181 IU, range 0-1140). Median (range) swollen and tender joint counts (66/68 joints assessed) were 7 (2-28) and 6 (2-35), and 11/15 (73%) had elevated CRP and/or ESR. The calculated median DAS-CRP score was 5.1 for the group, indicating that most of the study subjects had active inflammatory arthritis.

TABLE 5

Baseline characteristics of DMARD-naïve RA patients: All values are reported as mean (SD).

| | DMARD-naïve early RA (n = 15) |
|---|---|
| Age, years, mean (SD) | 48.8 (13.5) |
| Female, n (%) | 14 (82%) |
| hs-CRP, mg/L, mean (SD) | 39.5 (33) |
| DAS-CRP, mean (SD) | 5.3 (1.3) |
| RF titer, IU/mL, mean (SD) | 334.2 (421.3) |
| ESR, mean (SD) | 49.1 (27.6) |
| Swollen Joint, median | 19 (2.8) |
| Tender Joints, median | 20 (11.3) |
| TJC, median | 13.2 (9.1) |
| Disease duration, months, mean (SD) | 20.9 (25.9) |

RA = Rheumatoid Arthritis,
RF = rheumatoid factor,
BMI = Body mass index,
DAS = disease activity score,
hs-CRP = high sensitivity C-reactive protein,
ESR = erythrocyte sedimentation rate and
TJC = total joint count.

Transcriptomic analysis of synovial biopsies reveals unique MMP signature: Affymetrix microarray was used to characterize the transcriptome in each synovial tissue. The datasets generated were normalized using the Robust Multichip Average (RMA) technique and analyzed using Stanford Analysis of Microarray (SAM) software to identify transcripts which exhibited significant variability within the transcriptomes.

Figure 16A:
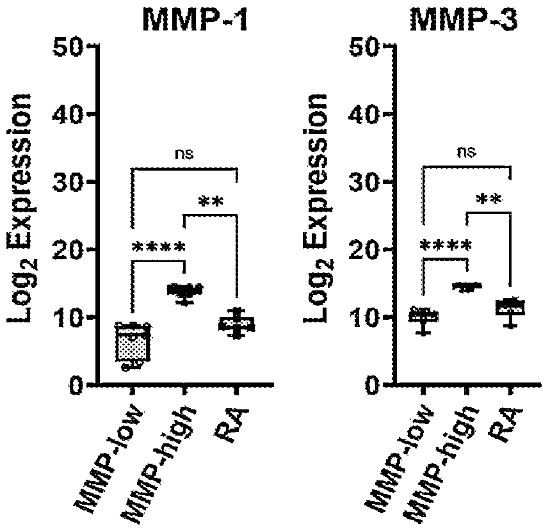
FIGS. 16A-16C: Analysis of synovial gene expression in DMARD-naïve RA patients.
Figure 16B:
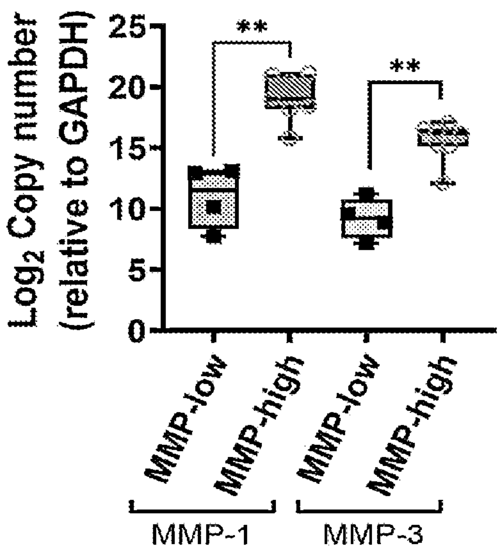
Figure 16C:
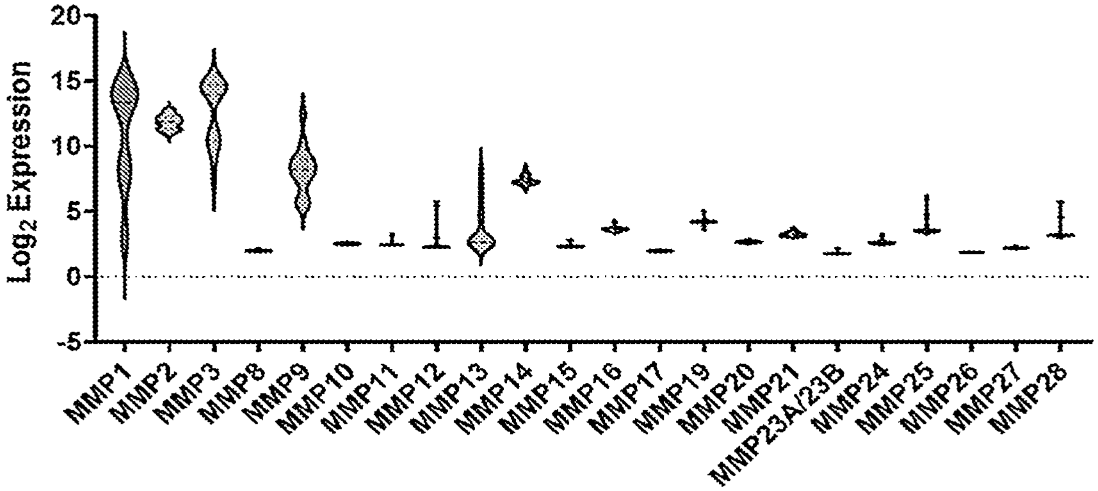

After adjustment for a false discovery rate of <10%, a total of 20 mRNA transcripts (corresponding to 17 unique genes) were either significantly up- or down-regulated in the synovial biopsy samples from DMARD-naïve EIA patients compared to samples from advanced RA patients (Table 6). Of these, MMP-1, MMP-3, CD82, VCAM1 and CHES1 (fold change=76.87, 19.41, 1.73, 2.65 and 5.83 respectively; Table 6) were the most significantly up-regulated genes. Because MMP-1 and MMP-3 are produced abundantly by the synovial lining layer and are known to play a key role in the progressive joint damage that occurs in RA (15, 16), we focused on these two molecules as potential biomarkers for classifying the early inflamed synovium (FIGS. 16A-16C). A dichotomous distribution in the transcript levels of both MMP-1 and MMP-3 in the 17 EIA synovial tissue samples (including two individuals who had bilateral synovial biopsy samples) was noted. As such, 10/17 synovial tissues (60%) exhibited high transcript levels of both MMP-1 and MMP-3, and 7/17 (40%) exhibited low transcript levels, the latter being comparable to the levels detected in the advanced RA samples (FIG. 16A). The MMP-1 and MMP-3 expression levels were confirmed using qPCR (FIG. 16B) and showed that there was a very strong correlation between MMP-1 and MMP-3 mRNA levels in the DMARD-naïve RA patients (r=0.8897, P=0.001). Moreover, in analyzing the microarray datasets, it was shown that this dichotomous distribution was unique to MMP-1 and MMP-3 as it was not demonstrable with any other MMP or TIMP transcripts, except for MMP-13, where similar trends were observed (FIG. 16C and Table 7). Importantly, in the two individuals who had bilateral synovial samples obtained from both their affected knees joints, there was concordance in the MMP-1 and MMP-3 transcript levels between the two knee joints of the same individual, with one patient exhibiting bilateral high levels, and the other bilateral low levels. This suggests that the MMP-1 and MMP-3 transcript levels were reflective of the individual's pathologic process and not simply related to local factors in each joint. Based on these findings, each DMARD-naïve patient was categorized as being either an MMP-high or MMP-low mRNA expressor in their inflamed synovial tissue.

TABLE 6

Table showing differential expression of gene transcripts between ERA and RA patients. Data was analyzed by Student t test and corrected for false-discovery rate.

| Gene ID | Gene Name | Fold Change | q-value(%) |
|---|---|---|---|
| MMP3 | NM_002422 | 19.41 | 0.00 |
| MMP1 | NM_002421 | 76.87 | 0.00 |
| CD82 | NM_002231 | 1.73 | 0.00 |
| VCAM1 | NM_001078 | 2.65 | 0.00 |
| CHES1 | AA860806 | 5.83 | 0.00 |
| | BF513121 | 3.22 | 0.00 |
| | BF439063 | 6.01 | 0.00 |
| T1A-2 | AW590196 | 8.48 | 6.81 |
| FOXC1 | AU145890 | 2.27 | 6.81 |
| SELE | NM_000450 | 258.37 | 6.81 |
| GABRA4 | AF238869 | 125.11 | 6.81 |
| ZNRF1 | AL136903 | 1.64 | 6.81 |

TABLE 7

Table showing the mRNA abundance of MMPs and TIMPs in MMP-high and MMP-low groups. Data is represented as log2-normalized values and was analyzed by independent samples T test.

| | MMP-high (n = 10) | MMP-low (n = 7) | p-value |
|---|---|---|---|
| MMP1 | 13.06 | 7.58 | <0.000001 |
| MMP2 | 12.24 | 11.97 | NS |
| MMP3 | 13.94 | 10.26 | <0.000001 |
| MMP8 | 5.81 | 5.23 | NS |
| MMP9 | 9.42 | 9.24 | NS |
| MMP10 | 3.82 | 3.98 | NS |
| MMP11 | 6.74 | 6.41 | NS |
| MMP12 | 6.23 | 5.42 | NS |
| MMP13 | 6.33 | 3.55 | 0.006 |
| MMP14 | 9.24 | 8.99 | NS |
| MMP15 | 3.31 | 2.79 | NS |
| MMP16 | 5.83 | 6.11 | NS |
| MMP17 | 4.10 | 4.26 | NS |
| MMP19 | 8.54 | 8.71 | NS |
| MMP20 | 3.01 | 2.45 | NS |
| MMP21 | 3.53 | 3.28 | NS |
| MMP24 | 5.46 | 5.63 | NS |
| MMP25 | 6.81 | 7.00 | NS |
| MMP26 | 5.84 | 5.62 | NS |

TABLE 7-continued

Table showing the mRNA abundance of MMPs and TIMPs in MMP-high and MMP-low groups. Data is represented as log2-normalized values and was analyzed by independent samples T test.

| | MMP-high (n = 10) | MMP-low (n = 7) | p-value |
|---|---|---|---|
| MMP27 | 6.07 | 5.78 | NS |
| MMP28 | 5.75 | 5.91 | NS |
| | | | NS |
| TIMP1 | 13.24 | 12.69 | NS |
| TIMP2 | 12.26 | 12.29 | NS |
| TIMP3 | 12.17 | 12.09 | NS |
| TIMP4 | 7.23 | 8.87 | NS |

Figure 17A:
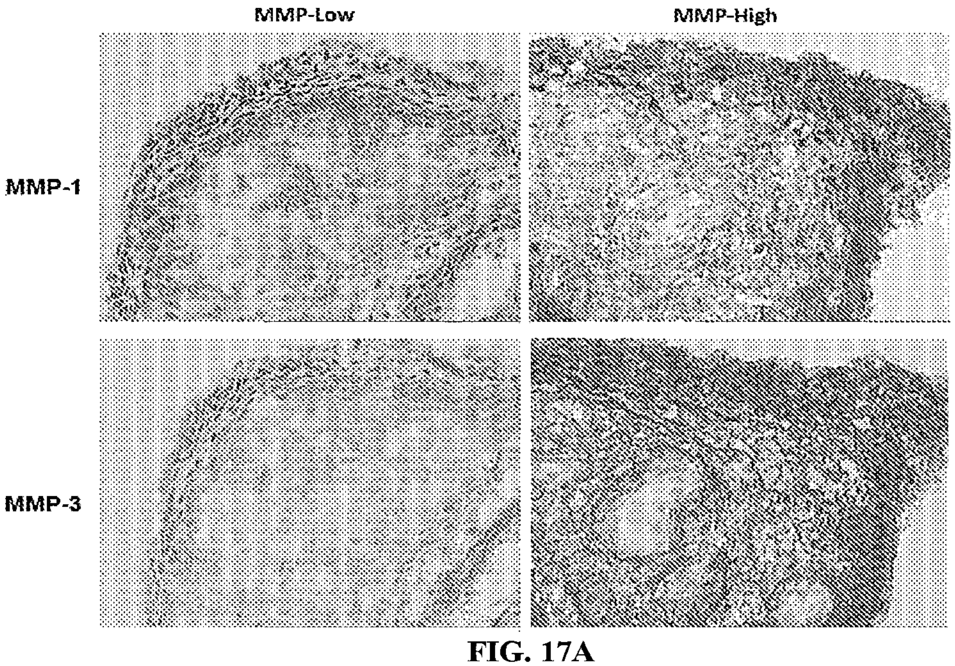
FIGS. 17A-17G: Analysis of MMP-1 and MMP-3 protein expression in the synovium of DMARD-naïve RA patients.
Figure 17B:
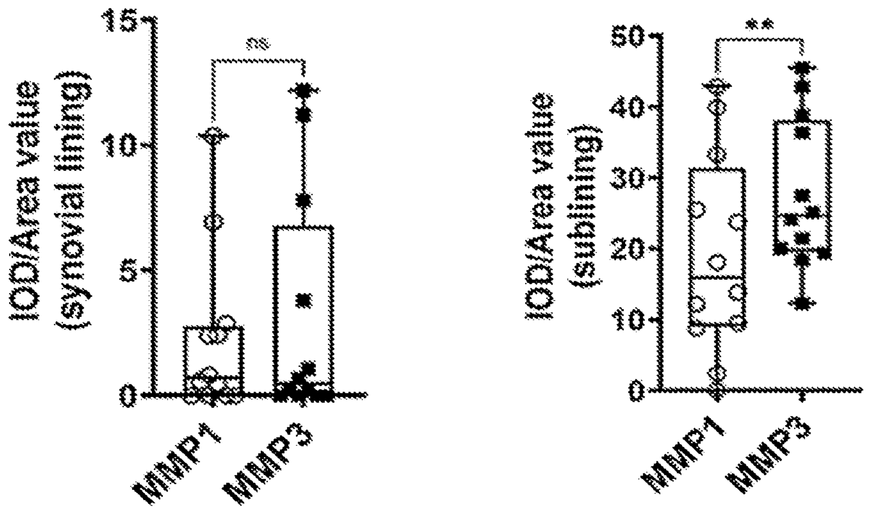
Figure 17C:
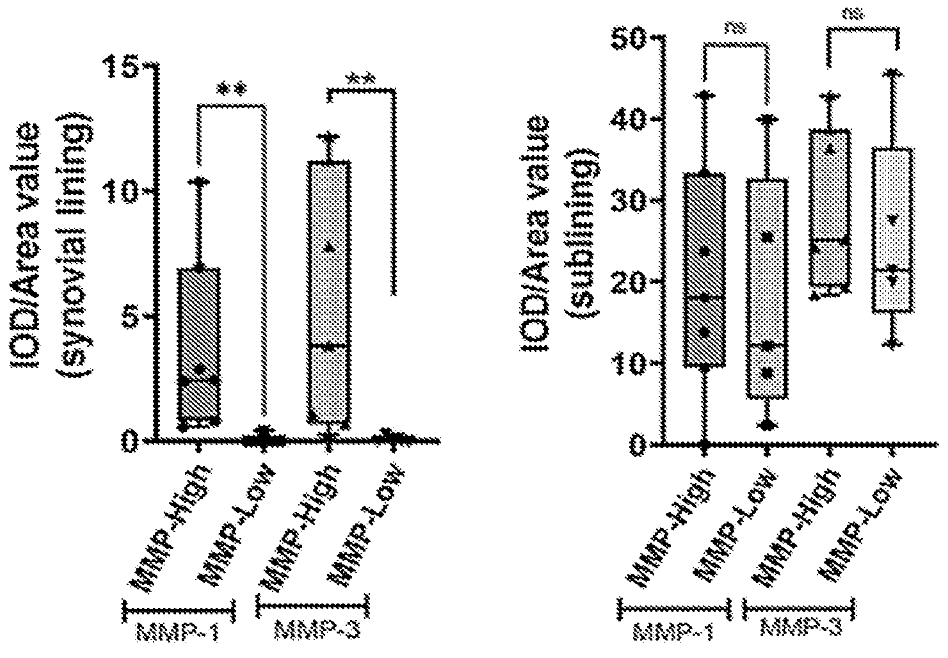
Figure 17D:
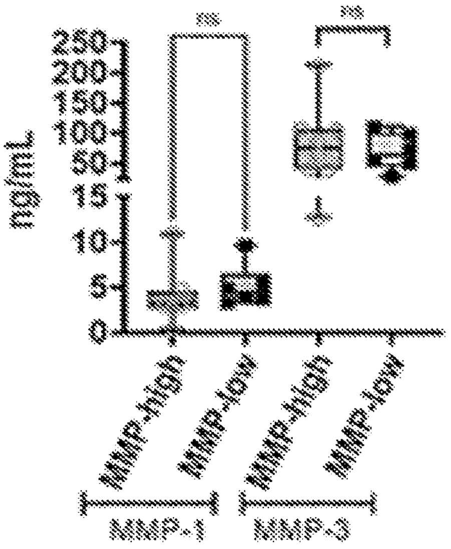
Figure 17E:
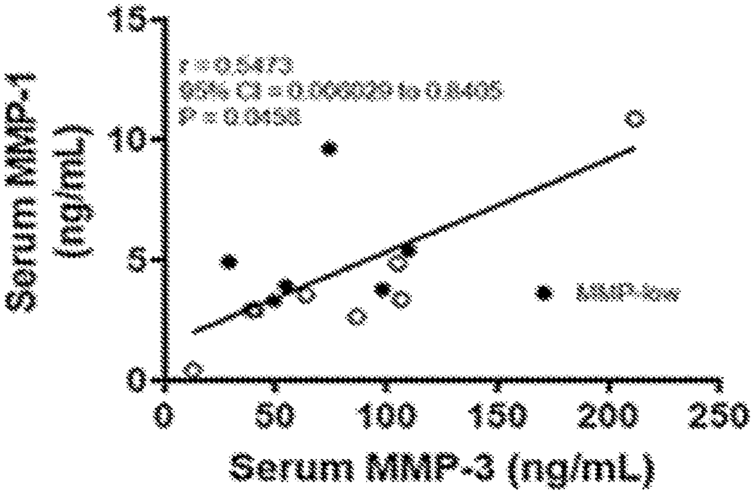
Figure 17F:
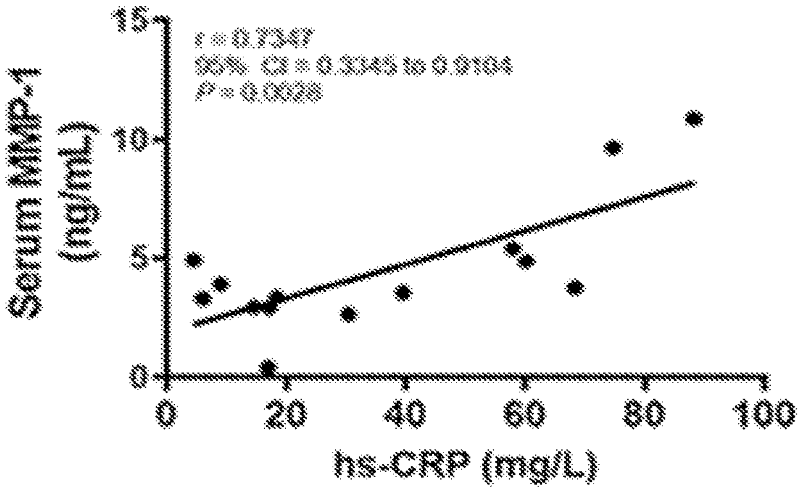
Figure 17G:
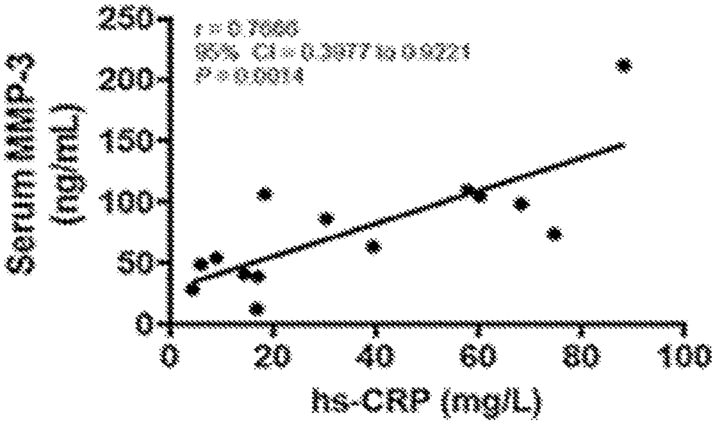

MMP-1 and MMP-3 protein expression in EIA synovium, but not in the circulation, is concordant with synovial mRNA transcript levels: It was then determined whether the grouping of the EIA samples based on MMP-1/MMP-3 synovial mRNA transcript levels was reflected in the expression of the corresponding proteins, both locally in the synovial tissue using IHC (FIG. 17A), and systemically in the circulation using ELISA. As shown in FIGS. 17B and 17C, there were dramatic differences in the expression of both MMP-1 and MMP-3 protein in the synovium between the MMP-high and MMP-low mRNA groups. Compared to the MMP-low group, the MMP-high group exhibited higher intensity of IHC staining for MMP-1 and MMP-3 in the synovial lining layer and in the sub-lining areas (FIG. 17C). Although much of the staining appeared to be extracellular, we were able to demonstrate intense intracellular staining for these proteins in the synovial lining cells (FIG. 17A). In contrast to levels observed in the synovial biopsy samples, circulating MMP-1 and MMP-3 levels did not show similar dichotomy (FIG. 17D-E), although the levels of these two proteins were highly concordant in the serum (r=0.5473, P=0.0478), and correlated with the degree of inflammation as indicated by CRP levels (FIG. 17F-G).

Figure 18A:
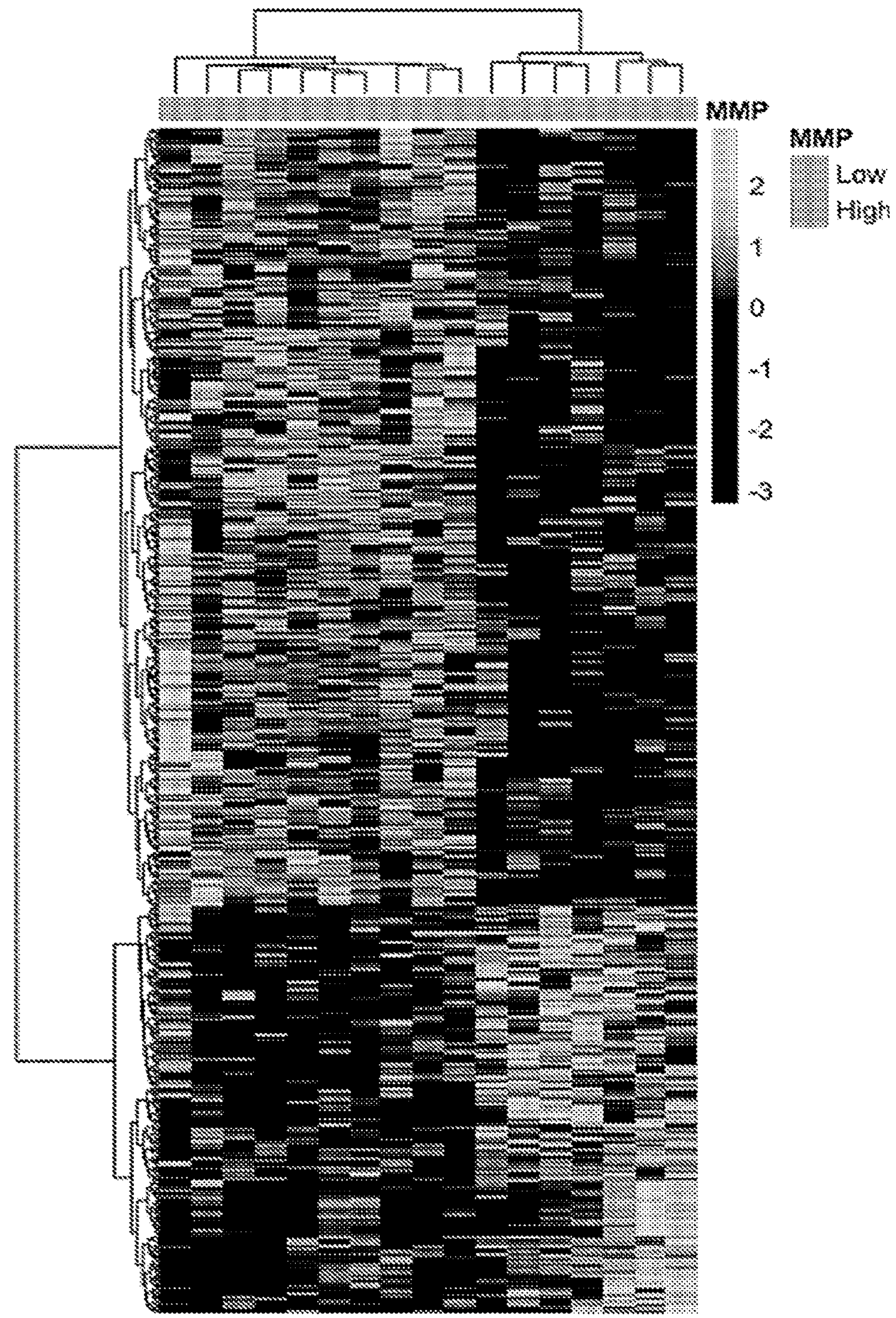
FIGS. 18A-18E.

Delineation of a synovial transcriptomic signature based on the MMP-1/MMP-3 grouping: Unsupervised hierarchical clustering algorithm was applied to identify the spectrum of differentially expressed genes (DEGs) within the microarray dataset between MMP-high and MMP-low groups (FIG. 18A). Analysis revealed the presence of 2 distinct clusters based on the gene expression profile. While 622 genes were found to be increased in MMP-high subjects, expression of 325 genes was high in the MMP-low group.

Figure 18B:
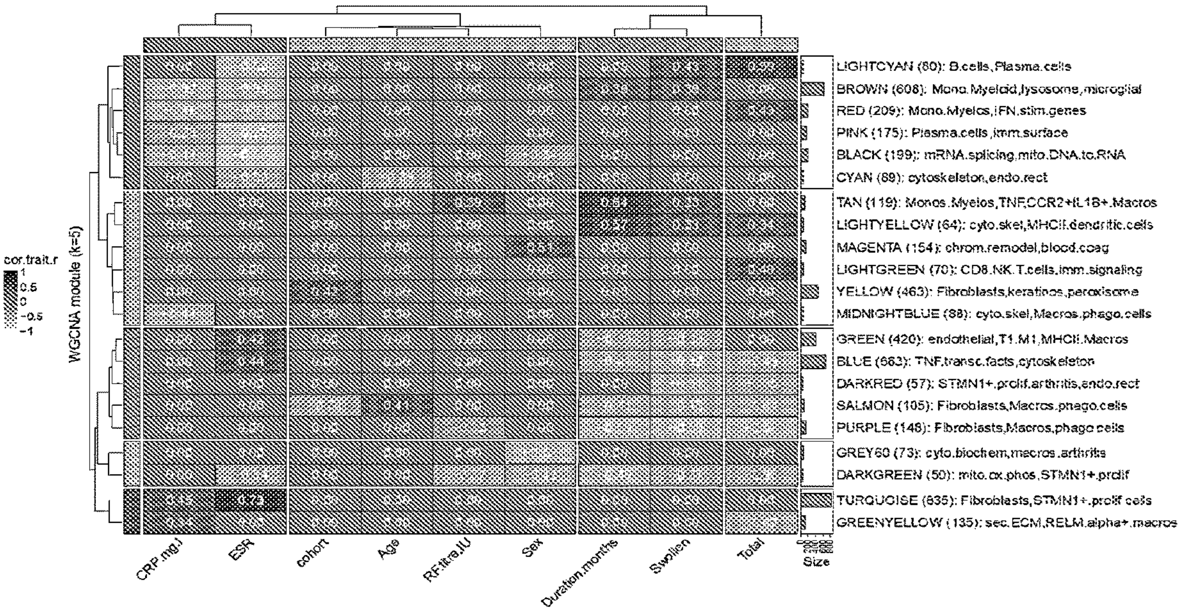
Figure 18C:
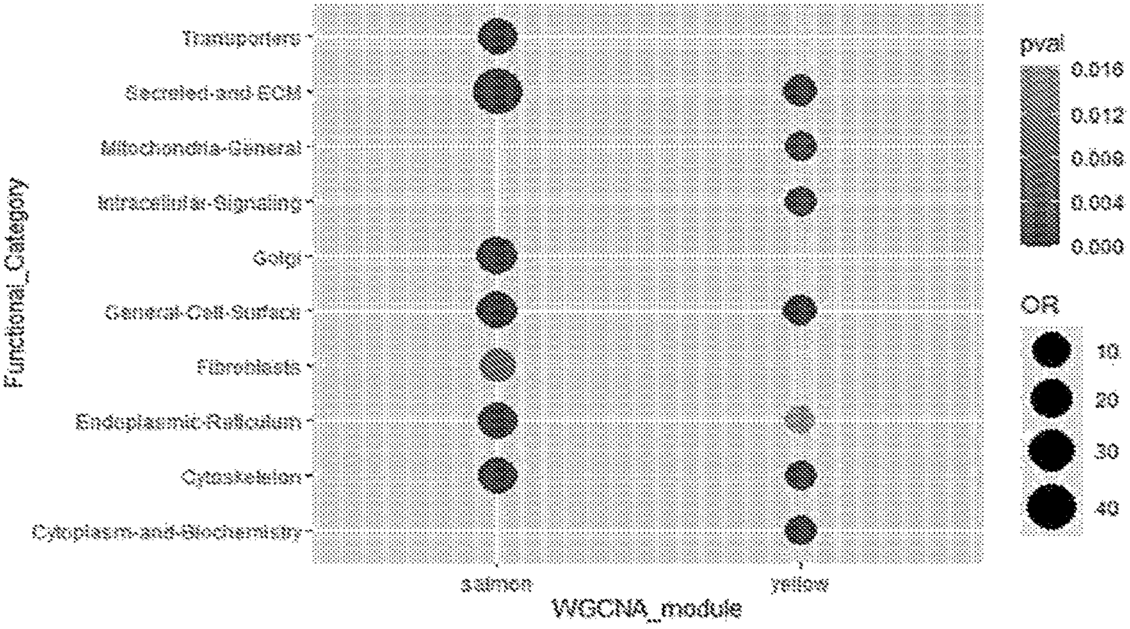
Figure 18D:
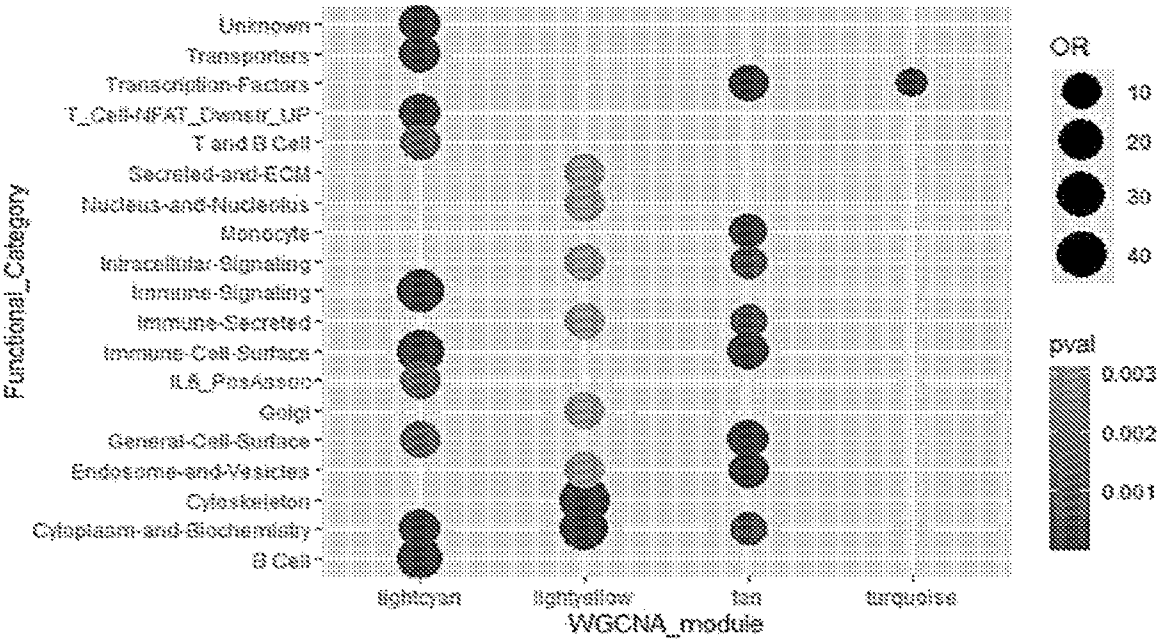

WGCNA and MEGENA analysis was applied to the transcriptomic data to explore gene co-expression modules and determine biological processes that drive their differential expression in DMARD-naïve subjects (FIG. 18B-D). WGCNA analysis yielded 23 co-expressed gene modules (each module was assigned a color), 21 of which correlated with at least one clinical outcome (FIG. 18B). Of these, salmon and yellow were the only modules that showed association with the MMP-status of the cohort (r=−0.34 and r=0.42, respectively). Therefore, these modules were selected for further analysis. As shown in FIG. 18C, subsequent assessment of the yellow module for functional relevance revealed an enrichment for genes involved in metabolic functions (Mitochondria, Cytoplasm and Biochemistry) and was associated with MMP-high group. On the other hand, the salmon module was enriched for fibroblast and stromal signatures (Cytoskeleton, Secreted and ECM) and associated with the MMP-low group (FIG. 18C). We also interrogated gene expression signature in the lightcyan, lightyellow, tan and turquoise modules owing to their correlation with total affected joints, swollen joints, disease duration, ESR and CRP. These modules were enriched for B cell, T cell, and IL-6 gene signatures (FIG. 18C). MEGENA was applied to further dissect complex co-regulatory gene networks and explore their interaction with clinical outcomes in DMARD-naïve patients (FIG. 18D). A majority of these modules correlated positively with MMP-status of the patient, followed by ESR and CRP. Most importantly, parent modules were found to be enriched for inflammatory and phagocytic macrophage-associated gene signatures, including those involved in TNF signaling. An enrichment of the fibroblast transcriptomic signature in module 2.10 and related modules, was observed.

Figure 18E:
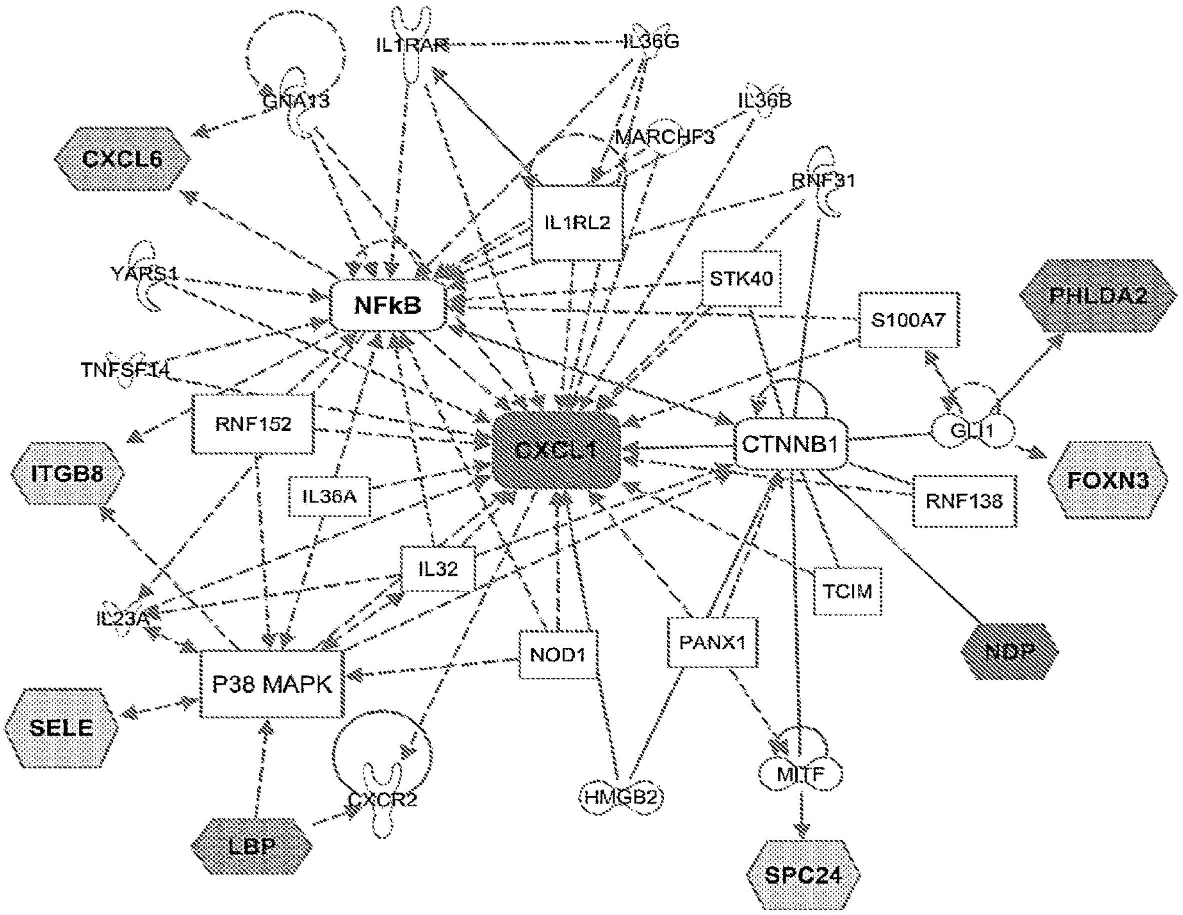

IPA bioinformatics tool was then applied to identify common transcriptional hubs that were primarily responsible for differential expression of certain genes in MMP-high patients. Analysis of curated functional networks revealed direct and indirect relationships with multiple cell-signaling molecules that were centrally connected to NF-kB, β-catenin (CTNNB1) and p38MAPK, and converge leading to increased CXCL1 expression (FIG. 18E). Most of these molecules were acute-phase proteins involved in IL-17A signaling in autoimmune diseases such as psoriasis and arthritis (14.3% overlap; P=0.0000266).

Figure 19A:
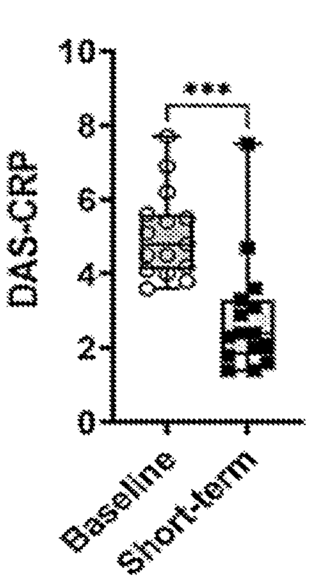
FIGS. 19A-19D: Analysis of short-term clinical outcomes in DMARD-naïve RA patients.
Figure 19:
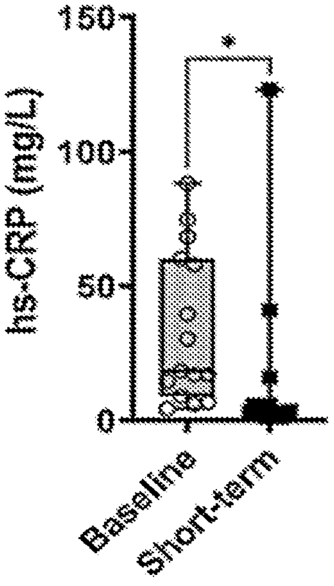
Figure 19C:
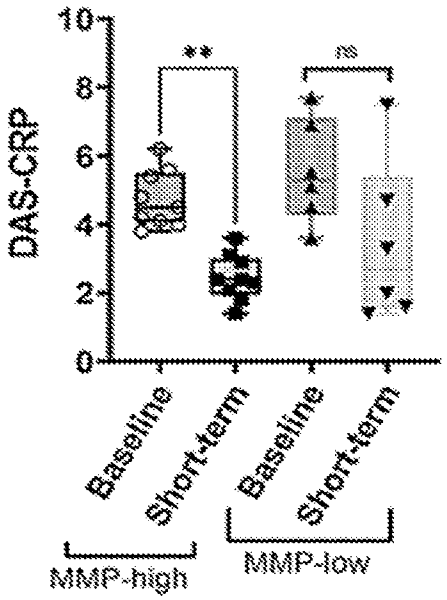
Figure 19D:
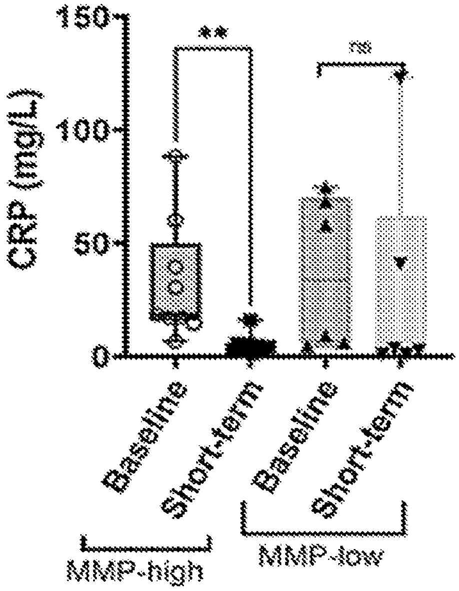
Figure 20A:
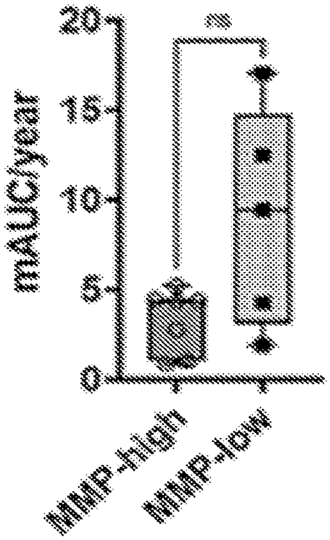
FIGS. 20A-20B: Analysis of long-term clinical outcomes in DMARD-naïve RA patients.
Figure 20B:
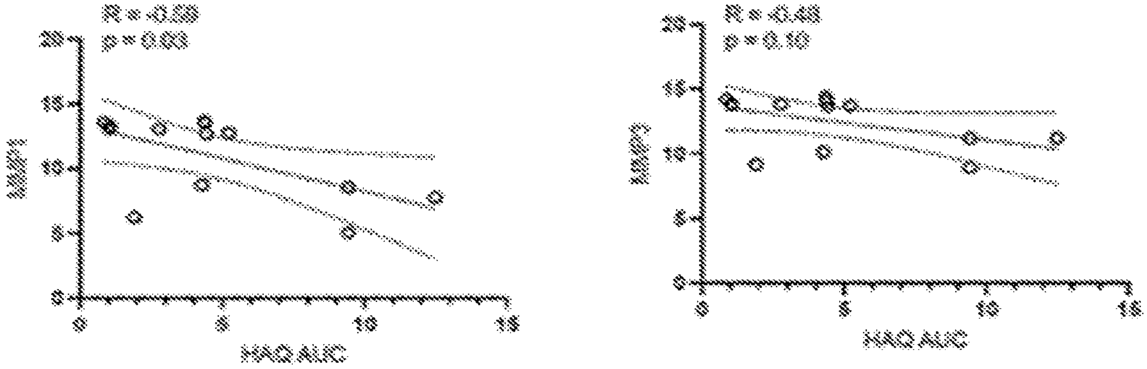

High baseline MMP1 and MMP3 mRNA levels in the inflamed synovium are associated with better long-term outcomes: Given the distinct baseline synovial transcriptomic signatures identified in the cohort of individuals with early, untreated inflammatory arthritis, it was then determined whether there were differences in the longitudinal clinical outcomes, when categorized based on MMP dichotomy. Patients enrolled in the study were followed for a median of 12.3 years (#clinical visit=24 IQR 16). Clinical assessment (swollen and tender joints), functional scores (mHAQ) and medications were recorded at each clinical assessment. Baseline clinical features were similar between MMP-high and MMP-low groups (Table 8). At short-term follow-up interval of 31 months, DMARD-naïve RA patients displayed a significant reduction in their CRP levels and DAS-CRP scores relative to the levels at their baseline visit (FIGS. 19A & B). Interestingly, reduced DAS-CRP was highly prominent in the MMP-high group compared to the MMP-low patients (FIGS. 19C & D). To determine the burden of long-term functional disability, we next assessed mHAQ scores across all longitudinal visits, normalized to follow-up duration (mHAQ AUC/year). Longitudinal mHAQ scores showed an increasing trend in MMP low patients compared to MMP high (FIG. 20A; 9.5 vs 4.4, P=0.20). Similar trends were observed in swollen joint counts and number of DMARDs, a surrogate for treatment resistant disease (Table 9), based on the MMP status at arthritis onset. Importantly, baseline MMP-1, and to a lesser extent MMP3, mRNA levels showed an inverse correlation with long-term mHAQ AUC scores (FIG. 20B). We also observed that the median length of follow up was longer for MMP-low patients (177 months) compared to MMP-high (74 months), though the number of annual visits were similar between the groups (MMP-high vs MMP-low; 2.03 vs 1.96 per year). Together, these data suggest that the MMP-high group appeared to accrue less long-term disability compared to the MMP-low group.

TABLE 8

Table showing baseline clinical features between MMP-high and MMP-low ERA patients. Data is represented as median (range) and analyzed by independent samples T test.

| | MMP-high (n = 9) | MMP-low (n = 6) | P value |
|---|---|---|---|
| age (yrs) | 43 (29-64) | 56 (30-74) | 0.15 |
| duration (mo) | 7 (1-84) | 6 (6-12) | 0.86 |
| RF titre (IU) | 255 (0-1010) | 154 (0-1440) | 0.96 |
| swollen | 6 (2-20) | 12 (3-280 | 0.39 |
| tender | 6 (2-15) | 12 (5-35) | 0.15 |
| total active | 9 (3-20) | 15 (5-35) | 0.11 |
| ESR | 51 (20-95) | 34 (14-49) | 0.23 |
| CRP | 18 (7-88) | 34 (6-75) | 0.78 |

TABLE 9

Long-term clinical outcomes in MMP-high and MMP-low DMARD-naïve early RA patients.

| MMP Status | Follow-up time (months) | No. of visits (total) | mean HAQ | HAQ AUC/yr | Mean # Swollen joints | Mean # Swollen joints/yr | # medications/yr |
|---|---|---|---|---|---|---|---|
| MMP-High | | | | | | | |
| ERA 133 | 195 | 29 | 0.32 | 2.78 | 0.8 | 10.76 | 0.12 |
| ERA 123 | 60 | 11 | 0.16 | 1.03 | 1.36 | 10.2 | 0.2 |
| ERA 135 | 50 | 8 | 0.39 | 4.44 | 0.75 | 8.13 | 0.25 |
| ERA 115 | 183 | 31 | 0.52 | 4.37 | 1.5 | 0.69 | 0.31 |
| ERA 95 | 182 | 30 | 0.08 | 0.86 | 1.39 | 14.97 | 0.2 |
| ERA 82 | 74 | 17 | 0.49 | 5.22 | 7.38 | 79.58 | 0.67 |
| ERA 144 | 26 | 5 | 0.29 | 4.38 | 1.5 | 17 | 0 |
| Median | 74 | 2.03 | 0.32 | 4.37 | 1.39 | 10.76 | 0.20 |
| MMP-Low | | | | | | | |
| ERA 116 | 198 | 25 | 0.39 | 4.28 | 1 | 7.62 | 0.18 |
| ERA 110 | 178 | 29 | 1.09 | 12.49 | 2.83 | 27.47 | 0.33 |
| ERA 3 | 117 | 34 | 0.29 | 1.9 | 5.52 | 28.43 | 0.5 |

TABLE 9-continued

Long-term clinical outcomes in MMP-high and MMP-low DMARD-naïve early RA patients.

| MMP Status | Follow-up time (months) | No. of visits (total) | mean HAQ | HAQ AUC/yr | Mean # Swollen joints | Mean # Swollen joints/yr | # medications/yr |
|---|---|---|---|---|---|---|---|
| ERA 143 | 177 | 23 | 0.81 | 9.43 | 3.15 | 29 | 0.29 |
| ERA 25 | 74 | 14 | 1.29 | 17.05 | 5.15 | 69.17 | 0.83 |
| Median | 177 | 1.96 | 0.81 | 9.43 | 3.15 | 28.43 | 0.33 |

HAQ = health assessment questionnaire; AUC = area under the curve.

Discussion

Presented are the results of a broad transcriptomic analysis of baseline synovial tissue samples that were obtained using closed needle biopsy from DMARD-naïve patients with inflammatory arthritis, most of whom were diagnosed with seropositive early RA (ERA). We defined the transcriptomic signature that was predictive of long-term clinical outcomes in these patients who all received standard care of treatment.

The synovium is the primary target organ for the chronic immuno-inflammatory process that characterizes RA, and other chronic arthropathies (17). It is also well established that both the systemic and synovial responses to a wide array of available DMARD/biologic therapies is heterogeneous, and notoriously difficult to predict based on clinical parameters and circulating biomarkers such as autoantibody profiles and CRP. This challenge is further complicated by the unpredictable loss of therapeutic efficacy to currently available RA drugs, necessitating empiric trials of alternative therapies in the hope of recapturing control of the disease. Because of this, there has been a longstanding interest in identifying predictive synovial biomarkers early in the disease process that could help classify the inflammatory lesions based on pathotypes which could, in turn, potentially inform difficult clinical decisions (18, 19). Much progress has been made in this area, particularly recently, where large international consortia have provided intriguing new data based on state-of-the-art analyses of the synovial biopsies (3, 18, 20). Yet, despite the availability of sizable cohorts of RA patients who have undergone synovial biopsy in research settings, a key gap is the lack of data regarding the long-term outcomes of these biopsied RA patients in routine clinical settings where individuals typically cycle through several agents, alone or in combination. The data presented in the current study are an attempt to address this gap by providing longitudinal outcome data in a cohort of RA patients who underwent baseline synovial biopsy and were then followed for up to fifteen years under routine clinical care.

Overall, here it is shown that the transcriptional signature of the synovium of DMARD-naïve patients with active RA was heterogenous, and this heterogeneity was primarily defined by dichotomous expression of MMP-1 and MMP-3 genes, both at the gene and protein level. Characterization of molecular pathways underlying divergent synovial MMP1/MMP3 expression suggests the presence of distinct types of synovitis, one of which is regulated by NF-κB and β-catenin. Importantly, RA patients with high MMP1/MMP3 expression exhibited a significant reduction in their disease activity, and inflammation at a short-term follow-up point and improved quality of life (QoL) when assessed after 15 years of DMARD therapy. In contrast, short and long-term treatment response in MMP-low cohort was reminiscent of outcomes observed in treatment resistant individuals. Taken together, data presented here suggests a strong association between baseline MMP-status of the synovium and response to DMARD treatment, thereby underscoring the diagnostic value of synovial transcriptome at the pre-DMARD stage as a predictor of response to RA therapy.

To determine the potential clinical utility of the baseline synovial MMP grouping, the clinical outcomes of the cohort was evaluated over an extended longitudinal timeframe. We defined relatively short-term outcomes after an average of ~ two years, and long-term outcomes after more than one decade. No attempt was made to guide the subsequent DMARD/biologic therapy these individuals received, and they were treated using standard of care. As such, there was serial visits for each member of the cohort, with documentation of joint counts and HAQ scores. Unfortunately, there was no systematic documentation of the radiographic damage accrued, either in the biopsied joint(s) or in standardized radiographs of hand and feet, as is the case with structured clinical trials. Since no one visit could be regarded as an endpoint, an area under the curve (AUC) analysis as a method to quantify longitudinal outcomes, was performed. Despite these shortcomings, we were able to clearly delineate two major synovial subsets based on the levels of MMP-1 and MMP-3 mRNA and protein expression, both of which paralleled each other. These two MMPs are known to play a key role in the pathogenesis and destructiveness of inflammatory arthritis (15, 22, 23). Importantly, at baseline, the two groups were clinically indistinguishable suggesting that there may be potential clinical utility to assessing their synovial expression. As such, it is important to point out that the circulating levels of the MMPs did not correlate with their synovial expression levels. Using this approach, we unexpectedly demonstrated that the group with the highest baseline synovial expression levels of MMP-1/MMP-3 appeared to accrue less functional disability over time than the group with substantially lower levels, the latter being comparable to the levels we demonstrated in synovial samples obtained from RA patients at the time of joint arthroplasty. This finding seems to be counter intuitive considering the role these molecules play in the destruction of cartilage and connective tissue in the synovial compartment (23). One potential explanation for this unexpected finding is that the individuals with a high MMP-1/MMP-3 baseline signature are more responsive to DMARD therapy. This may be analogous to observations made in the context of malignancies where highly proliferative, activated neoplasms respond better to chemotherapy than do those that are more indolent (24).

Evidence suggests synovial phenotypes can range from a myeloid pattern to a lymphoid or a fibroid phenotype defined primarily by the cell-types infiltrating into the synovium [1, 10, 12]. Gene expression analysis or immunohistological staining did not show any evidence of either myeloid lymphoid or pauci-immune phenotypes prior to DMARD therapy. A homogenous infiltration of macrophages (CD68), fibroblasts (CD55) and lymphocytes (CD3 and CD20) in the synovium, was observed. This may be due to a low sample size, use of a different methodology for identifying gene expression or a different patient population. The co-expression analysis identified an enrichment of metabolic, and inflammatory genes in the MMP-high subtype, most of which are involved in active intracellular signaling. Most of these pathways, including those targeted by DMARDs regulate the expression of molecules that are involved in the NF-kB pathway (25). In contrast, MMP-low samples showed a predominance of fibroblast genes that are involved in ECM and cytoskeletal reorganization. IPA curated analysis of genes enriched in MMP-high group identified NF-kB complex, and β-catenin as the two major transcriptional nodes. In patients with early inflammatory arthritis, NF-kB activation in the synovium facilitates proliferation of synovial fibroblasts, modulates tissue-specific immune responses, and perpetuates chronic inflammation by promoting secretion of pro-inflammatory mediators including MMP1 and MMP-3 in the synovium (25-28).

In conclusion, it is demonstrated that MMP-centered synovial heterogeneity in DMARD-naïve RA patients, which could reliably predict short-term and long-term response to treatment irrespective of the DMARD being administered. This may be a valuable metric for clinicians to identify individuals who could have homogenous response to specific treatments and allow them to provide the right treatment to right patient, a step towards precision medicine in RA.

Figure 21A:
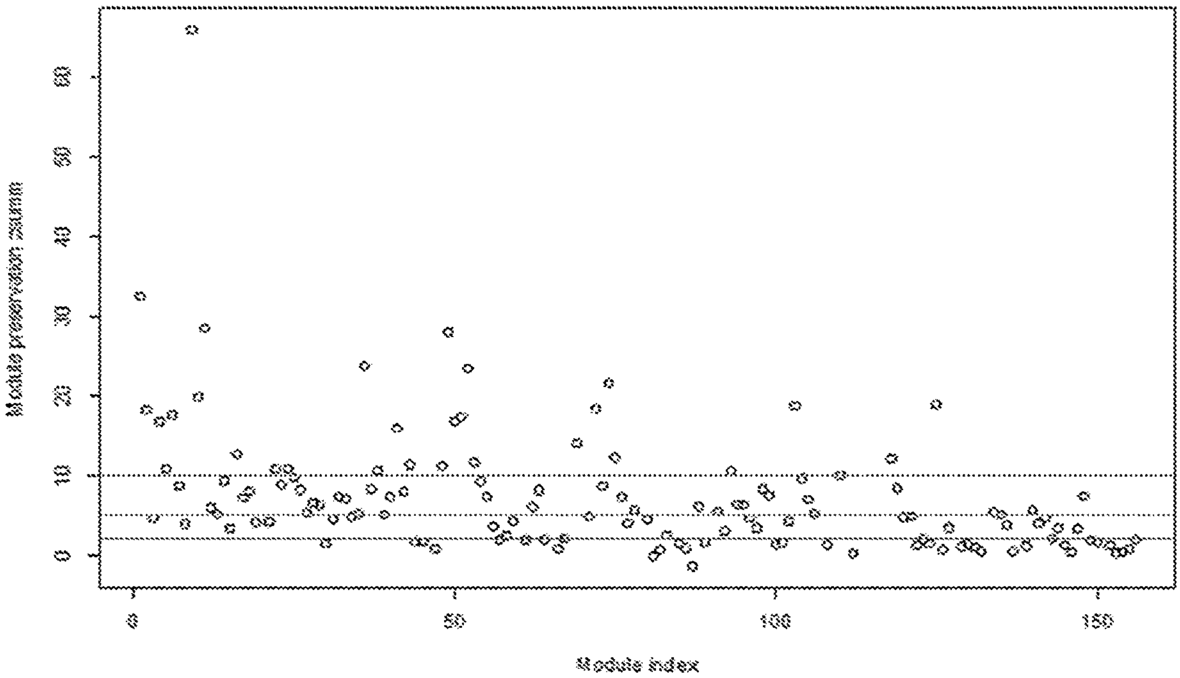
FIGS. 21A-21B: Module preservation z.summary statistics.
Figure 21B:
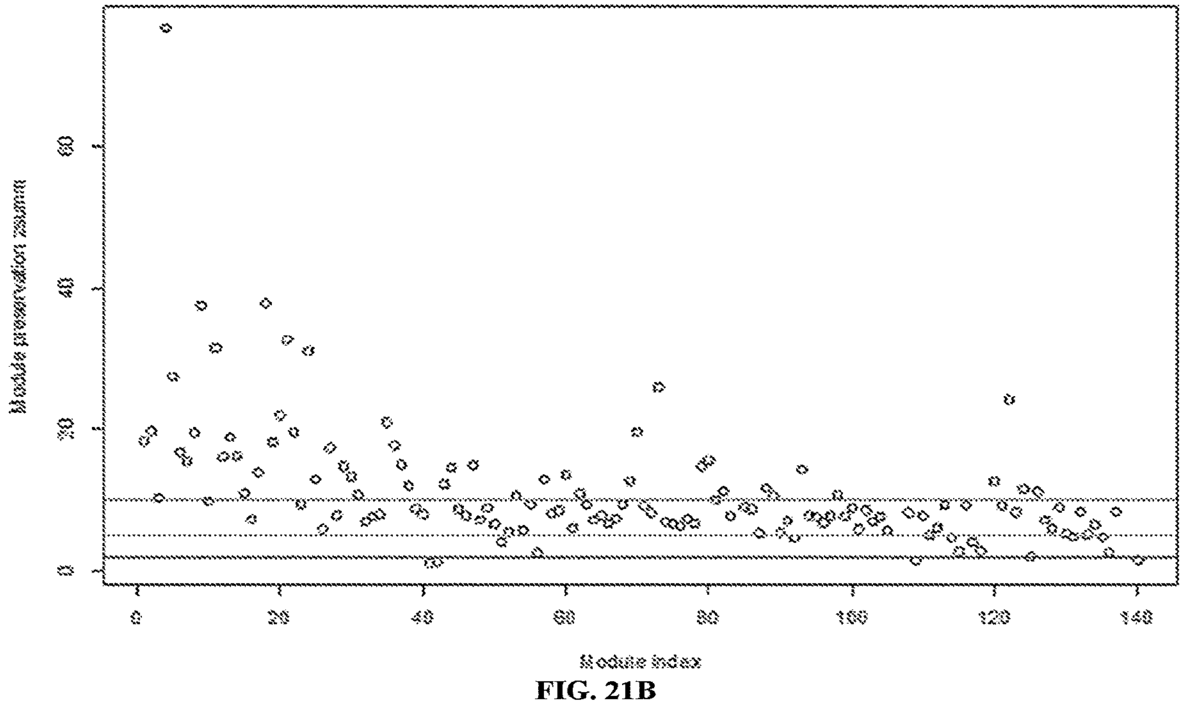

Example 5: Unsupervised Gene Clustering with and without Selected Top 5,000 Row Variance (Top5k rowVar) Genes As an important filtration step at the CodeR-BP pipeline, only the top 5,000 row variance (top5k rowVar) genes were retained for downstream analysis. Use of top5k rowVar genes reduces dimensionality of data, reduces expensive co-expression calculation time, reduces expensive computation time, and importantly preserves gene modules of biological importance. The ILLUMINATE 1 (GSE88884) data set which includes 813 SLE patients and 10 healthy controls, a set which is well known for its heterogeneity and inherent challenges to conventional analytics, was analyzed. After basic quality control measures and annotation requirements, 12,534 genes were submitted to the CodeR-BP pipeline, with this set defined as the baseline output and hereafter labeled as "ILLUM-1 All". As performance benchmark, module preservations was calculated between ILLUM-1 All and the top5k outputs, utilizing an algorithm within the WGCNA package which generates a z.summ composite score of 20 metrics. Module preservation is a careful measurement of the overall intactness of a module of genes from a reference study posited against a test set, ergo preserved. A z.summ score of >=2 is considered to be minimally preserved, >=5 being moderately preserved, and z.summ>=10 being well preserved. Not all gene modules in ILLUM-1 all were able to be compared to the top5k set due to its inordinate gene input size (12,534 vs 5,000) and the differing number of module generations, but it was able to be determined that amongst the calculable (generation 2 through 5) 135 ILLUM-1 all modules, 99 (73%) were at least minimally preserved in the top5k (FIG. 21A). Conversely, 130/134 (97%) of calculable modules in the top5k were at least minimally preserved in the ILLUM-1 all set, with many being well preserved (FIG. 21B).

Figure 22A:
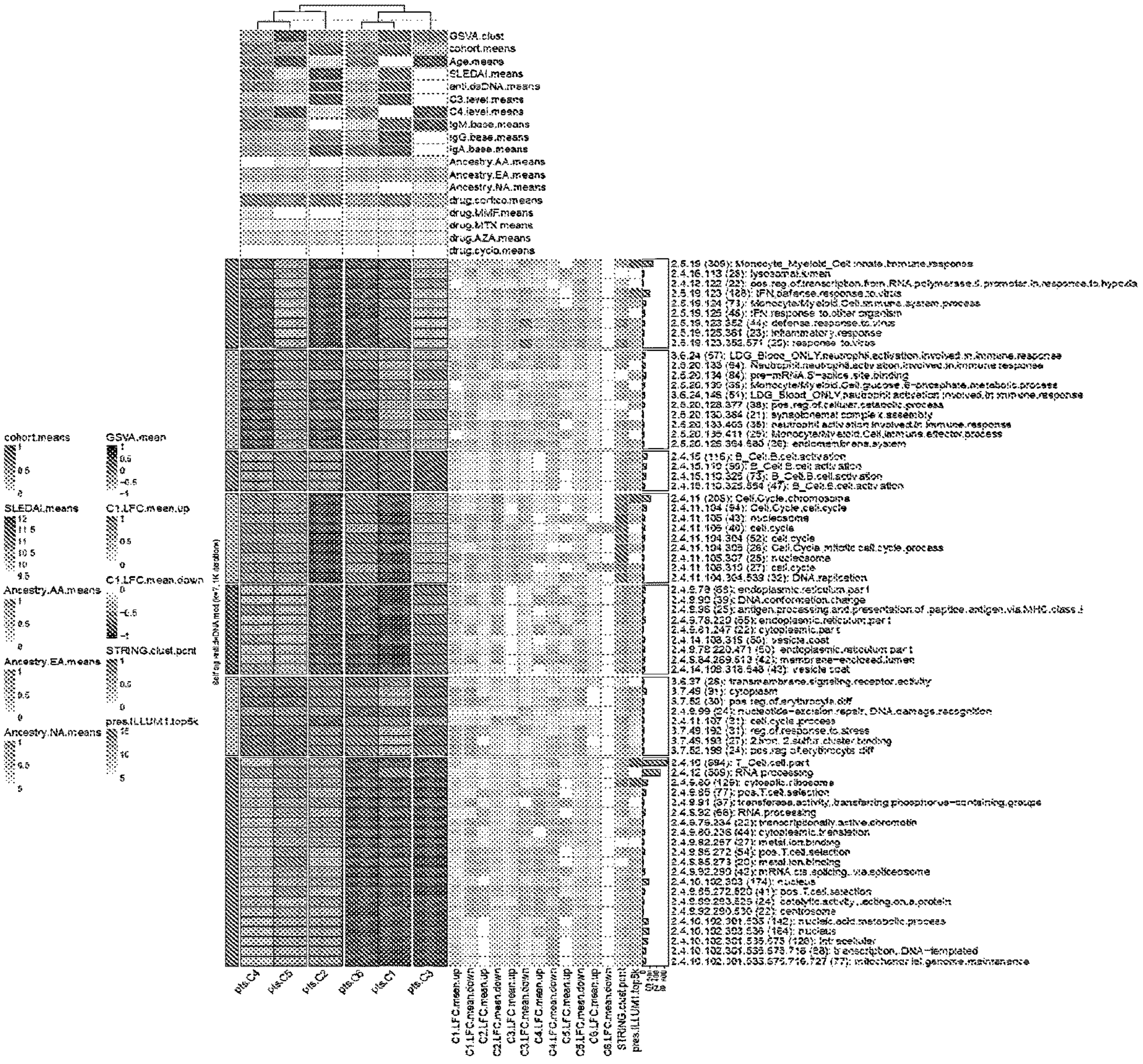
FIGS. 22A-22B: Mean GSVA scores per patient cluster. Self GSVA was performed on the ILLUM-1 all genes 70 modules significantly correlated to anti.dsDNA, clustered into k=6 patient clusters using optimal 1K passes (FIG. 22A). Self GSVA was performed on the ILLUM-1 top5k genes 57 modules significantly correlated to anti.dsDNA, clustered into k=6 patient clusters using optimal 1K passes (FIG. 22B). For both FIGS. 22A and 22B, means per patient cluster were calculated for sample traits (top annotations). Modules are functionally annotated if a minimum of four gene symbols significantly overlapped (Fisher's p.val<0.2) with various signature lists including LuGENE, AMPEL ancestry, or GO. Limma was performed on each patient cluster vs the others and their mean up and down LFCs included in the row annotations, as well as percentage of a module's PPI STRING.db connectedness, and degree of module preservation in the ILLUM-1 top5k generation 2-5 modules. A similar figure was prepared but conversely for the ILLUM-1 top5k vs. ILLUM-1 all
Figure 22B:
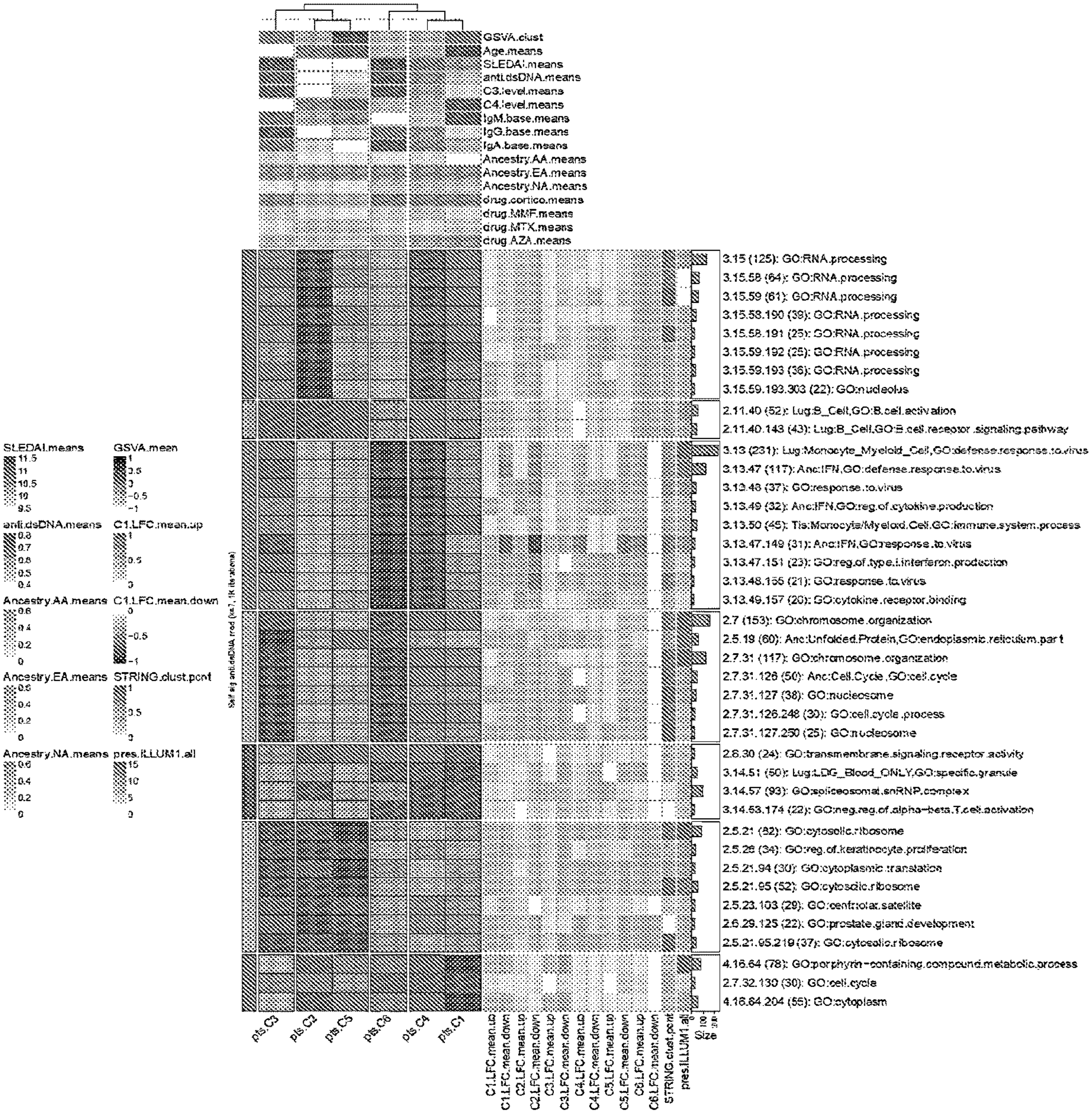

By sheer virtue of the large ILLUM-1 all set vs. the winnowed top5k set it was numerically expected the larger set would have fewer preserved modules in the smaller set. However, greater concern was that modules from the larger set which might be of biological importance would somehow be lost after top5k rowVar filtration requirement. ILLUM-1 at large only contains 10 controls vs. 813 patients, thus a conventional cohort metric of healthy controls vs. SLE patients would be statistically inappropriate given the paucity of balance and matching between the two groups. In order to compare modules of biological importance rather than all modules, samples were segregated based on the presence of elevated auto-antibodies to double stranded DNA (anti.dsDNA), a classical metric associated with SLE. Given this in the ILLUM-1 All set, 70 modules were identified whose first principal components of averaged gene expression, known as the module eigengenes (MEs) were significantly correlated ($p<0.01$) to the elevated anti.dsDNA no/yes designation. Whereas, 57 modules were identified in top5k set whose MEs were significantly correlated ($p<0.01$) to anti.dsDNA. For each, these significant modules were used as signatures for GSVA analysis, an algorithm which involves a ranking system based on gene expression to score the relative importance of each given module. An idealized/iterative k-means clustering algorithm was applied to identify six unique clusters of patients and visualized the mean GSVA scores of these clusters for ILLUM-1 all vs. the top5k (FIGS. 22A and B).

Figure 23A:
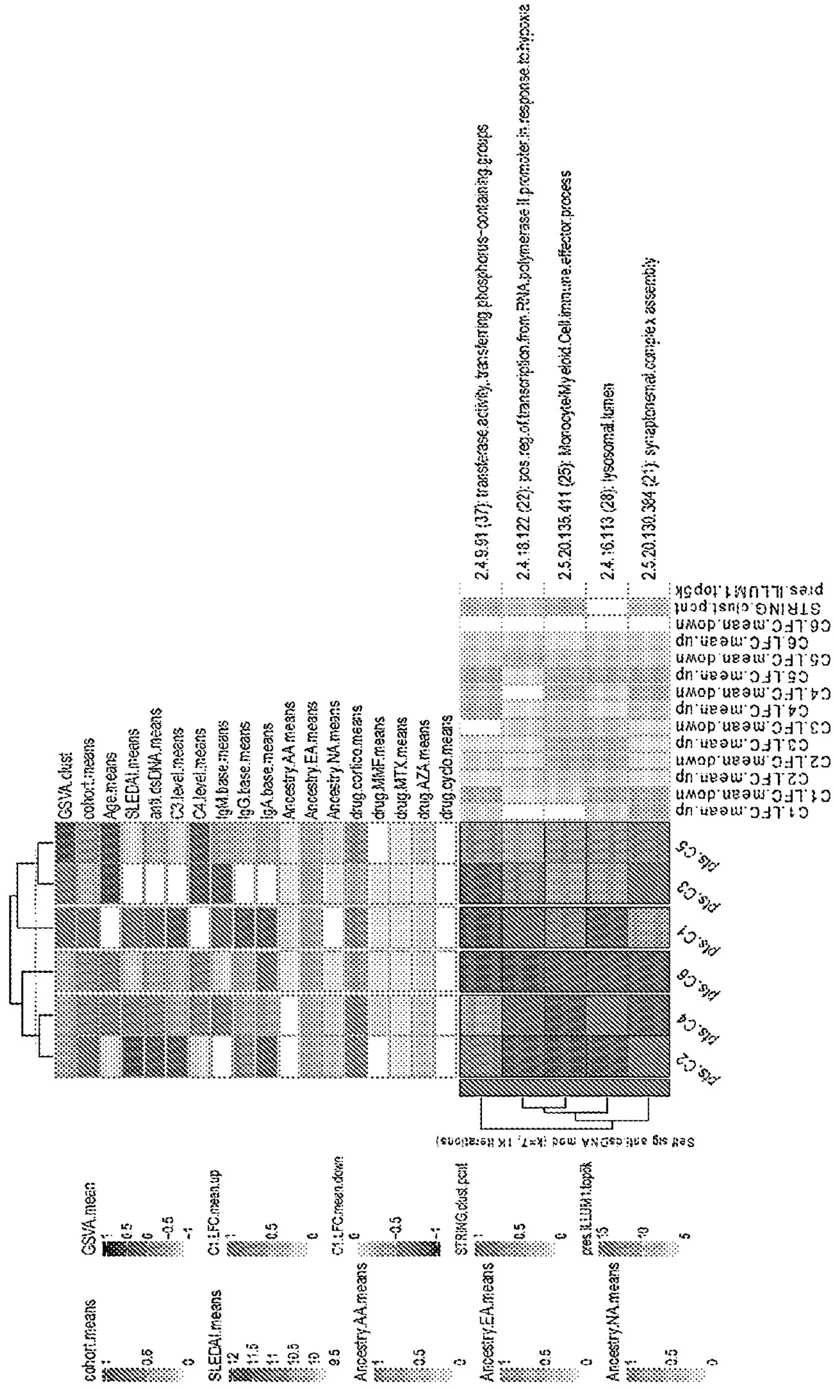
FIG. 23A: ILLUM-1 all genes, 5/34 calculable significant anti.dsDNA modules not preserved amongst the 57 the ILLUM-1 top5k sig anti.dsDNA modules.

The functional/biological annotations of the 70 ILLUM-1 all significantly correlated anti.dsDNA modules were compared to those of the 57 top5k anti.dsDNA modules, and it was found that they were remarkably similar. Statistically, only 5/34 (15%) of the calculable ILLUM-all sig anti.dsDNA modules weren't preserved in the top5k sig anti.dsDNA modules (FIG. 23A). These 5 were functionally annotated as involving transferase, transcription regulation, the lysosomal lumen, and possibly the synaptonemal complex assembly. These are higher-order cellular functions, and given their small module sizes (the largest being only 37 genes) it was concluded that these non-preserved modules were of no great consequence to the regulatory network underpinnings of SLE. One ILLUM-1 All module, M.2.5.20.135.411 was annotated as monocyte/myeloid cells. These are of interest from immunological perspective, but it was found these immune cell types represented in other modules that passed preservation.

Figure 23B:
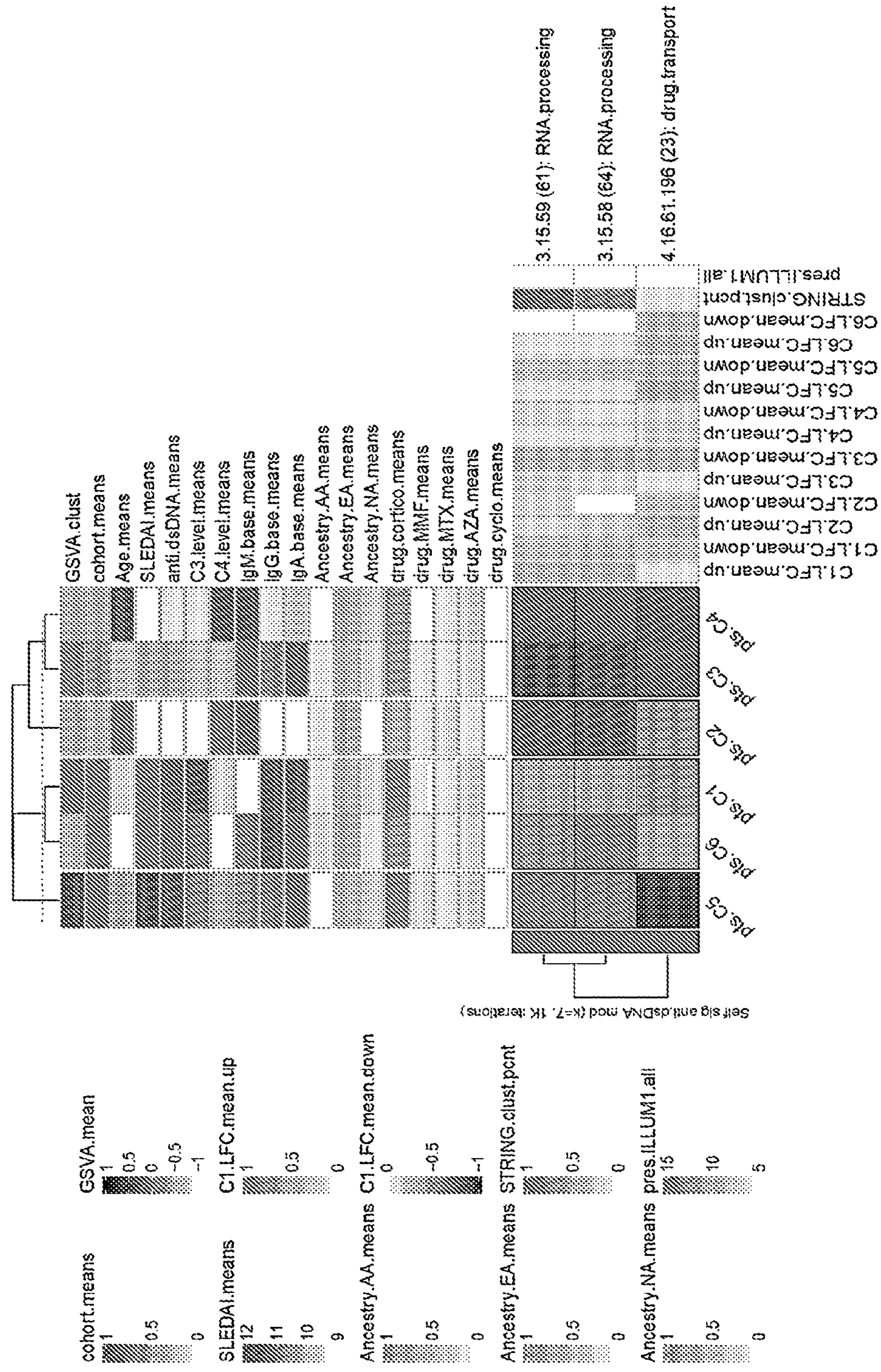
FIG. 23B: ILLUM-1 top5k genes, 3/48 calculable significant anti.dsDNA modules not preserved amongst the 70 the ILLUM-1 all sig anti.dsDNA modules.

Conversely, only 3/48 of the top5k sig calculable anti.dsDNA mods weren't preserved amongst the ILLUM-1 all mods (FIG. 23B). This was very interesting, given that at the global level 97% of all calculable top5 modules were preserved in the ILLUM-1 all set. Closer inspection of these non-preserved top5k modules included 2/3 annotating as RNA processing. Further, they contained densely intraconnected and highly down-regulated SNORD genes (FIG. 9), which have been shown in the literature to have strong connections to the SLE pathology. This is a good example of where top5k filtering and reduction of dimensionality and noise can reveal important regulatory networks which couldn't have been identified by inputting all genes from a set into our CodeR-BP coexpression pipeline.

It can be concluded from this analysis that using the top5k row var genes reduces expensive computation time, further simplifies dimensionality reduction, safely preserves modules of biological importance, and in at least one embodiment, can reveal important modules of regulatory networks otherwise lost when not performing input filtering. Accordingly, it should be appreciated that several benefits may be realized through the selection and use of top5k rowVar filtration techniques, including but not limited to a significant reduction in dimensionality that significantly reduces the computational resources needed to train machine learning models, while still being characterized with high module preservation, and reduction in noise that, in at least one embodiment, resulted in the identification of additional functional annotations that were not otherwise detected using the full ILLUM-1 baseline (e.g., family of down-regulated snoRNA (SNORD) genes which involved in SLE).

Example 6: Molecular Endotypes of Type 1 and Type 2 SLE

To characterize the molecular landscape of patients with Type 1 and Type 2 systemic lupus erythematosus (SLE) by analyzing gene expression profiles from peripheral blood.

Full transcriptomic RNA sequencing was carried out on whole blood samples from 18 subjects with SLE selected by manifestations of Type 1 and Type 2 SLE as determined by SLE Disease Activity Index (SLEDAI) and Polysymptomatic Distress (PSD) score, respectively. The top 5,000 row variance genes were analyzed by a suite of gene expression technologies, including Multiscale Embedded Gene Co-expression Network Analysis (MEGENA) to generate gene coexpression modules which were functionally annotated and correlated to various demographic traits, clinical features and laboratory assays.

Stable k-means clustering of gene coexpression modules effectively segregated Type 1 from Type 2 SLE. Expression of specific gene coexpression modules correlated with individual features of Type 1 and 2 SLE and also effectively segregated samples from Type 1 from Type 2 SLE patients. Unique Type 1 SLE enrichments included IFN, neutrophils, monocytes, IL-1, TNF, T cells, cell cycle, and neurotransmitter pathways, whereas unique Type 2 SLE enrichments included B cells, plasma cells, Ig chains, metabolic pathways and neuromuscular pathways. Enrichment of the IFN signature was not observed in Type 2 SLE. Gene expression patterns of some Type 2 SLE patients were identified amongst gene expression profiles reported in the literature for inactive SLE and idiopathic fibromyalgia (FM) patients and also identified subsets of patients with active SLE with a greater frequency of severe fatigue.

A suite of orthogonal gene coexpression technologies successfully identified unique transcriptional patterns that segregate Type 1 SLE from Type 2 SLE, and further identified Type 2 molecular features in patients with inactive SLE or FM and with active SLE with severe fatigue.

Systemic lupus erythematosus (SLE) is a prototypic autoimmune disease characterized by diverse clinical manifestations that vary in severity and intensity over time (1). Although deposition of immune complexes and the actions of type 1 interferon can account for at least some manifestations of SLE, many of the symptoms that bother patients the most, including fatigue and widespread pain, have an uncertain relationship to inflammation and immunologic disturbance. Despite their frequency and impact on patients with SLE, these symptoms are not included in criteria for disease classification and are not represented in most measures of disease activity (2).

A new conceptual framework for assessing SLE, that includes pain and fatigue, has been proposed (3). In this model, Type 1 features, such as nephritis, arthritis and cutaneous SLE, are typically inflammatory in origin and can be associated with specific autoantibodies (e.g., anti-DNA and nephritis). In contrast, Type 2 manifestations include widespread pain, fatigue, depression, sleep disturbance and other neuropsychological findings such as "brain fog." Because of the high frequency of these symptoms in SLE compared to the normal population (4) it has further been posited that Type 2 features are intrinsic features of SLE and related to underlying pathogenesis, even if they might not track with inflammation. It is important to emphasize that signs and symptoms of SLE vary with time and treatment in individual patients and those presenting with Type 1 SLE may evolve into Type 2 and vice versa and those with Type 2 may have persistent or intermittent symptoms (3)

Here, we have used a molecular approach to distinguish Type 1 and Type 2 SLE, testing the hypothesis that the two subsets or phases of SLE might arise from distinct pathogenetic disturbances that can be revealed by analysis of gene expression profiles in peripheral blood cells. For this purpose, we used a "bookend" approach and characterized patients with isolated Type 1 and Type 2 SLE. As the data presented herein indicate, patients with Type 1 and Type 2 SLE can be distinguished by analysis of peripheral blood cell gene expression, with the pathways identified providing insights into the mechanisms of these manifestations and potentially pointing to new treatment targets.

Materials & Methods

Patient Population: All patients were enrolled in the Duke SLE Registry (DLR) and were adults (>18 years old) who met 1997 ACR or 2012 SLICC criteria for SLE (5, 6). All patients signed informed consent to participate in the registry and provided informed consent for collection of the RNA samples (Duke Health IRB Pro00008875). This was a cross-sectional analysis on a selected subset of 18 patients (Duke Health IRB Pro00094645) using a "bookend" approach that specifically identified patients who had predominant Type 1 or Type 2 disease at the time of analysis. For each patient, data included 106 clinical and molecular attributes (Table 10), notably including SLEDAI, PSD score, anti-dsDNA, complement C3 assays, usage of immunosuppressive agents; and the use of duloxetine was also recorded. To be included in the Type 1 SLE group, patients had a clinical SLEDAI >4, active nephritis, SLEDAI ≥6, or Type 1 Physician Global Assessment (PGA) ≥1 and inactive Type 2 SLE (defined as a defined as a Polysymptomatic Distress Scale (PSD)≤6 and Type 2 PGA≤0.25). Type 2 SLE group had active Type 2 SLE symptoms (defined as FSS ≥11 and Type 2 PGA ≥1) and inactive Type 1 SLE (defined as SLEDAI =0 and Type 1 PGA≤0.5).

Data Collection: At the time blood was obtained for gene expression analysis, patients completed the PSD, which includes two subscales: the widespread pain index (WPI) and symptom severity score (SSS) (7-10). The total PSD score ranges from 0-31. In addition to patient-reported measures, patients' treating rheumatologists completed disease activity measures, including the SLEDAI, PGA for Type 1 activity, and a PGA for Type 2 activity (2,11,12); rheumatologists scored the severity of Type 1 and Type 2 SLE activity separately on scales from 0 (no activity) to 3 (severe activity). (Table 11 and 12).

Gene expression data and gene filtering: Whole blood was collected in PAXgene Blood RNA tubes. After removal of ribosomal RNA and globin transcripts with the Ribo-Zero Globin Removal kit (Illumina), stranded libraries were prepared with the TruSeq Library prep kit (Illumina) and hybridized to a flow cell for sequencing with the Illumina HiSeq platform. The top 5,000 row variances (top5k rowVar) genes determined using standard deviation between samples were retained for further analysis. Data were analyzed for differentially expressed genes (DEGs), for subset clustering by Principal Component Analysis (PCA) and for co-expressed genes using Multiscale Embedded Gene Co-expression Network Analysis (MEGENA) (13) as described in detailed materials & methods. Gene expression data from FM patients was obtained from GSE67311 (14) and analyzed as described in the detailed materials & methods. Gene expression data from inactive SLE (SLEDAI<6) patients was obtained from GSE45291 (15) and GSE49454 (16). Gene expression data from active SLE patients was obtained from GSE88884 (Illuminate 2) Raw data files have been deposited in NCBI accession PRJNA858861.

Detailed Materials & Methods

Figures 25A, 25B:
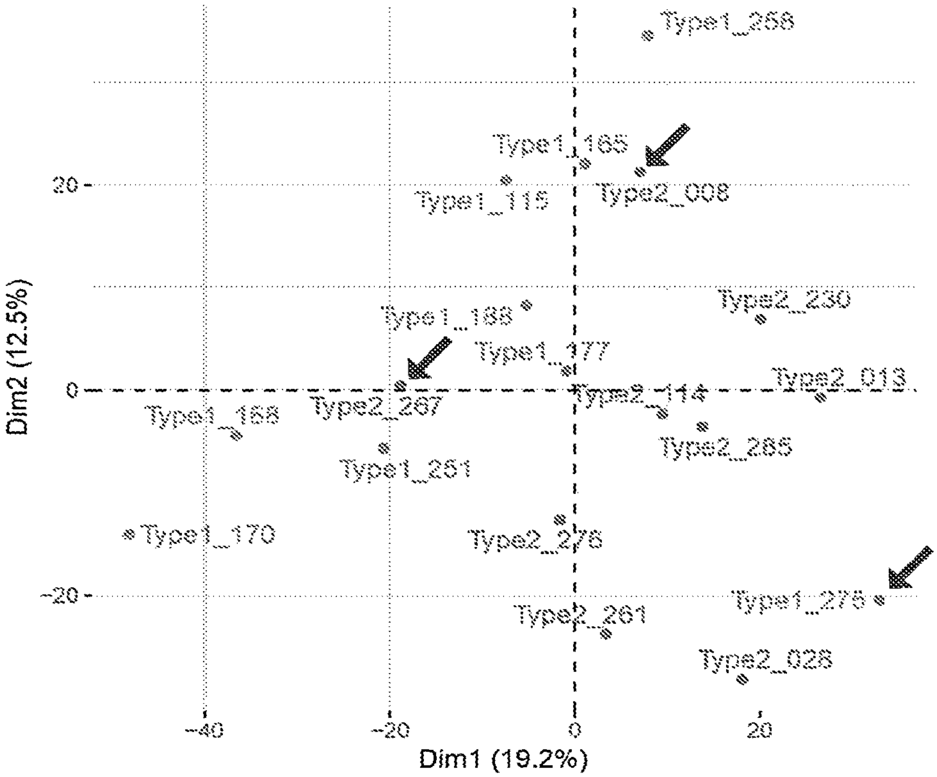
FIGS. 25A-C: Patient heterogeneity and gene expression dimensionality reduction using principal component (PC) analysis of variance. Table of study participants and explained variance of first 4 PCs totaling to 66.3% (FIG. 25A). Biplot of PC2:PC1 of top 5k rowVar gene normalized expressions. Sample points colored by patient type. Arrows indicate PCA outliers (FIG. 25B). Top 20 patient clinical/molecular attributes correlating to each of the top 4 PCs. Cells indicate r^2 correlation values and range from −0.2 to +0.2. Trait rows clustered by k=6 Euclidean distances (FIG. 25C).

Patient Population: All patients were adults (>18 years old) who met 1997 ACR or 2012 SLICC criteria for SLE (37, 38). These patients were enrolled in the Duke Lupus Registry (DLR), a prospective registry of adult patients with SLE who receive rheumatology care from six treating rheumatologists in the outpatient clinics of Duke University Medical Center. All patients signed informed consent to participate in the registry; all patients in this analysis provided informed consent to collect RNA samples at clinic visits (Duke Health IRB Pro00008875). This was a cross-sectional analysis on a selected subset of 22 patients (Duke Health IRB Pro00094645), 4 of which were removed from as statistical outliers. On average, patients had been diagnosed with SLE for 15.8 years (SD: 7.3) and 55% had a history of lupus nephritis. Most patients were female, 17 females, with one male. Three ancestral backgrounds were represented including 11 of African ancestry (AA), 6 of European ancestry (EA), and one patient of Hispanic ancestry (HA), and the mean patient age was 41 (FIG. 25A). Samples were accompanied by 106 clinical and molecular attributes (supplementary table) notably including SLEDAI, polysymptomatic distress score (PSD), anti.dsDNA and complement C3 assays, and yes/no usage of the immunotherapeutics prednisone, mycophenolate mofetil (MMF/CellCept), and duloxetine (Cymbalta).

Data Collection: At routine visits in the DLR Clinic, patients completed the Polysymptomatic Distress Scale (PSD), that includes two subscales: the widespread pain index (WPI) and symptom severity score (SSS) (39-42). For the WPI, patients report the number of areas out of 19 where they have experienced pain in the previous month. For the SSS, patients report the presence and severity of fatigue, cognitive symptoms, and waking unrefreshed over the past month, as well as whether they had experienced a headache, pain or cramps in the lower abdomen, or depression in the last 6 months. The SSS ranges from 0 to 12 and the total is added to the WPI for a total PSD score of 0-31.

In addition to patient-reported measures, patients' treating rheumatologists completed disease activity measures, including the SLE Disease Activity Index (SLEDAI), Physician's Global Assessment of Disease Activity (PGA) for Type 1 activity, and a PGA for Type 2 activity (38, 43, 44) or the PGAs, rheumatologists scored the severity of Type 1 & 2 SLE activity separately on scales from 0 (no activity) to 3 (severe activity). Medications, vital signs, and laboratory measures at each visit were also documented. All data was stored in a secure REDCap database.

Patient Stratification: SLE patients were divided into distinct clinical groups based on physician- and patient-reported assessments of Type 1 & Type 2 SLE activity. Type 1 SLE activity was measured by clinical SLEDAI (scored without laboratory measures), full SLEDAI (scored with laboratory measures), presence of active lupus nephritis, and Type 1 PGA. Type 2 SLE activity was measured by Type 2 PGA and patient-reported PSD scores. Patients were divided into classifications of Minimal, Type 1, Type 2, and Mixed based on the extent of their Type 1 & 2 SLE activity (Table 11). For this study, 9 patients were identified who had Type 1 and 9 patients with Type 2.

Gene expression data and gene filtering: Whole blood was collected in PAXgene Blood RNA tubes. After removal of ribosomal RNA and globin transcripts with the Ribo-Zero Globin Removal kit (Illumina), stranded libraries were prepared with the TruSeq Library prep kit (Illumina) and hybridized to a flow cell for sequencing with the Illumina HiSeq platform. Raw RNAseq output counts were VST normalized using the R DESeq2 package (45). Genes were further annotated using the R biomaRt (46) library and those without mappings to known proteins were discarded. Duplicate gene symbols were removed using the collapseRows function in the R WGCNA package (47). The top 5,000 row variance (top5k rowVar) genes determined using standard deviation between samples were retained for further analysis.

Differentially Expressed Gene (DEG) analysis: The R limma package (48) was used to perform DEG analysis between cohort (type.1.SLE vs type.2.SLE) and calculate empirically Bayesian corrected log fold changes (LFCs). P-values were adjusted for multiple comparisons using Benjamini-Hodgkin adjustment.

Principal component analysis (PCA) & mixed model patient clustering: Sample attributes including subjective clinical ascertainments and objective laboratory assay results were encoded as discrete binary values (no-0 or yes=1) or retained as continuous numerical values. The core R prcomp function and PCAtools package (49) was used to conduct exploratory PCA on the top5k rowVar genes. The first four PCs were correlated to the sample attributes using R Im linear regression and the top 20 traits contributing to PC variance visualized using R ComplexHeatmap (50).

Multiscale Embedded Gene Co-expression Network Analysis (MEGENA): The MEGENA (51) R package was used to generate a gene coexpression network by inputting the top5k rowVar genes. MEGENA multi-scale clustering analysis (MCA) formed lineages of gene modules followed by identification of densely intraconnected hub genes using multi-scale hub analysis (MHA). Modules were assigned "lineage" names based on their multiscale pedigree from the root MEGENA module. The prcomp package was utilized to perform singular value decomposition and calculate MEGENA module eigengenes (MEs), equivalent to the first principal component calculated amongst the variance of a given MEGENA module. MEGENA MEs were correlated to the numerically encoded sample traits.

Coexpressed gene module annotation: Module gene symbols were overlapped with a number of annotation tools (52), as well as the publicly available Gene Ontology (GO) signatures (53). Annotations of MEGENA modules were considered significant if there were at least 3 overlapping gene symbols between the module gene symbols and annotation signature gene symbols, and the Fisher's p value statistic of the overlap was p<0.2. Where there were multiple overlaps, the most significant overlap was assigned. For selection of a given GO annotation, all GO annotations significant by p<0.2 per the GO enrichment algorithm were ranked in order of decreasing module coverage.

Coexpression gene network PFN visualization: The MEGENA planar filtered coexpression network (PFN) of the top5k rowVar genes was imported into Cytoscape along with gene node annotations including functional enrichments, hub node identification, and all generation/scale levels a gene was inherited into. The resulting figure included hub node labels sized according to their scaled degree of intramodular connectedness. The PFN gene nebula was subsequently colored and annotated based on additional relevant information.

Sample trait intracorrelations: Correlation of sample traits to the MEs of all relevant MEGENA modules identified 23 significant ($p<0.05$) correlations. These top 40 sample trait correlations (sig trait corrs) were used as inputs to the R corrplot package (54) to generate a top 40 sample traits intra-correlated correlogram.

Coexpression module preservation in GSE67311 Fibromyalgia: Gene expression data from fibromyalgia patients was obtained from the Gene Expression Omnibus (GEO) study GSE67311 (55). This study originally included 70 fibromyalgia patients and 70 matched controls. The raw files from the Affymetrix® Human Gene 1.1 ST Peg arrays were RMA normalized using the R affycoretools package (56). COMBAT batch correction was applied using the R SVA package (57) followed by normalization to commonly known house-keeping (HK) genes. The normalized top5k rowVar genes from fibromyalgia patients were submitted to MEGENA for formation and annotation of gene coexpression modules. We calculated module preservations between the SLE type 1/2 and GSE67311 fibromyalgia patients MEGENA modules utilizing an algorithm that generates z.summ composite scores of 20 preservation metrics (47).

Coexpression module correlation and enrichment plots: Sunburst correlation plots were generated using the R plotly (58) package to illustrate MEGENA significant ($p<0.05$) ME correlations to demographics and clinical features. These were followed by significant ME correlations to patient type (type. 1.SLE or type.2.SLE), full (anti.dsDNA validated) SLEDAI and PSD score. Enrichment sunbursts were generated by statistically overlapping the gene symbols within a given MEGENA module with the various enrichment lists previously mentioned. An overlap was significant if there were at least 4 gene symbols overlapping with an enrichment signature and the Fisher's p.val of that overlap was $<0.2$.

A heatmap was generated using ComplexHeatmap visualizing the top 40 sample trait correlations to the 23 MEGENA modules that were significantly ($p<0.2$) correlated to cohort (type.1.SLE=0 and type.2.SLE=1). Module gene symbols were used to programmatically query the STRING database (59) and calculate the percentage of genes within a given module predicted to have known protein-protein interactions (PPI) ranging from 0 to 100%.

MEGENA module eigenegene (ME) correlations to patient gene expression: The MEs of the 23 significant modules were correlated to mean gene expression of a given module per patient and visualized using Complex heatmap. Columns of patients were clustered using idealized k-means clustering. Rows were annotated in a manner similar to the trait correlations heatmap and again included STRING PPI intraconnectedness and module preservation with GSE67311.fibromyalgia patient samples.

Gene Set Variation Analysis (GSVA): The GSVA (60) (V1.25.0) R software package was used as a non-parametric, unsupervised method for estimating the variation of pre-defined gene sets over all MEGENA module log 2 gene expression values. Input genes were employed only if the interquartile range (IQR) of their expression across the samples was greater than 0. Enrichment scores (GSVA scores) were calculated non-parametrically using a Kolmogorov Smirnoff (KS)-like random walk statistic. The enrichment scores (ES) were the largest positive and negative random walk deviations from zero, respectively, for a particular sample amongst the module gene set. The GSVA scores were used an input for unsupervised stable k-means clustering, and two different disease phenotypes or clusters were identified. GSVA was performed using the 23 significant gen3 MEGENA modules as gene signatures.

Differential Gene Co-Expression Analysis (DGCA): The R DGCA (61) software package was utilized to identify differentially expressed gene pairs between type. 1.SLE & type.2.SLE patients. Significant DGCA pairs were queried against the CellTalk (62) repository of 3,398 human ligands and receptors. The plotly package was utilized to generate sunbursts of the totaled DGCA intermodular pairs between the top unique interconnected gen3 modules and the modules labeled with their top functional annotation. Cytoscape was used to visualize the intramodular and intermodular connections/edges found between various interconnected gen3 MEGENA modules.

Patient Age Adjustment Analysis. Type 1 SLE patients 168 and 251, and type 2 SLE patients 028 and 230 were removed from the data set leaving 7 patients from each cohort with balanced age distributions. Gene expression of the 14 patients were submitted to MEGENA analysis forming new modules and the top 40 type 2 SLE ME module correlations visualized as a complex heat map. GSVA was performed on the top5k rowVar gene expressions using the top 40 age-balanced modules as signatures.

The top5k rowVar gene expressions of the original 18 patients were adjusted using linear modeling with age as a covariant. These were submitted to MEGENA analysis forming new modules and the top 40 type 2 SLE ME module correlations visualized as a complex heat map. GSVA was performed on the top5k rowVar gene expressions using the top 40 age-adjusted modules as signatures.

Inactive SLE Data Sets Analysis. The top 5,000 row variance genes from inactive lupus studies ($SLEDAI<6$) GSE45291 and GSE49454 were used submitted to GSVA analysis and the GSVA enrichment scores visualized in the manner previously described. Mean GSVA enrichment scores and patient traits per patient cluster were calculated. The mean scores per patient cluster underwent cosine similarity tests using the R lsa package (28) against the two type 1/2 SLE mean GSVA patient clusters. visualized as complex heatmaps. Column annotations included patient traits from their respective studies along with cosine similarity scores ranging from −1 to +1.

Active SLE Data Set Analysis. The top 5,000 row variance genes from active lupus study GSE88884 (Illuminate-2) were used submitted to GSVA analysis and the GSVA enrichment scores visualized in the manner previously described. Mean GSVA enrichment scores and patient traits per patient cluster were calculated. The mean scores per patient cluster underwent cosine similarity tests to the Type 1/2 SLE GSVA means reference clusters and visualized in a manner similar to the inactive SLE GSVA means heatmaps. The differences between the proportions of mild and severe pain and fatigue groups in each k-means cluster were tested using the R stat package proportion test. The distribution of mild and severe fatigue and pain groups in each cluster were visualized using bar plots. Patient clusters marked as (*) exhibited a significant difference between the frequency of severe and mild fatigue or pain, respectively.

Aggregation of Type 1/2 SLE, Inactive SLE, Active SLE, and Classic FM GSVA Means Clusters. The GSVA mean enrichment scores from the four studies were aggregated into a single matrix, clustered using idealized k-means, and visualized using a complex heatmap. Column annotations included SLEDAI (where available), and cosine similarity to the Type 1/2 SLE reference clusters. Row annotations included module correlation to Type 2 SLE, “fatigue”, and “tired”. Bar plots were generated indicating the percent of patients in the inactive SLE, active SLE, and classic FM patients that significantly resembled Type 1 or Type 2 SLE per cosine similarity.

Results

Patients: Patients had been diagnosed with SLE for a mean of 15.8 years (SD: 7.3) and 55% had a history of SLE nephritis. Seventeen patients were female and one was male; the mean patient age was 41 (FIG. 25A).

Figure 25C:
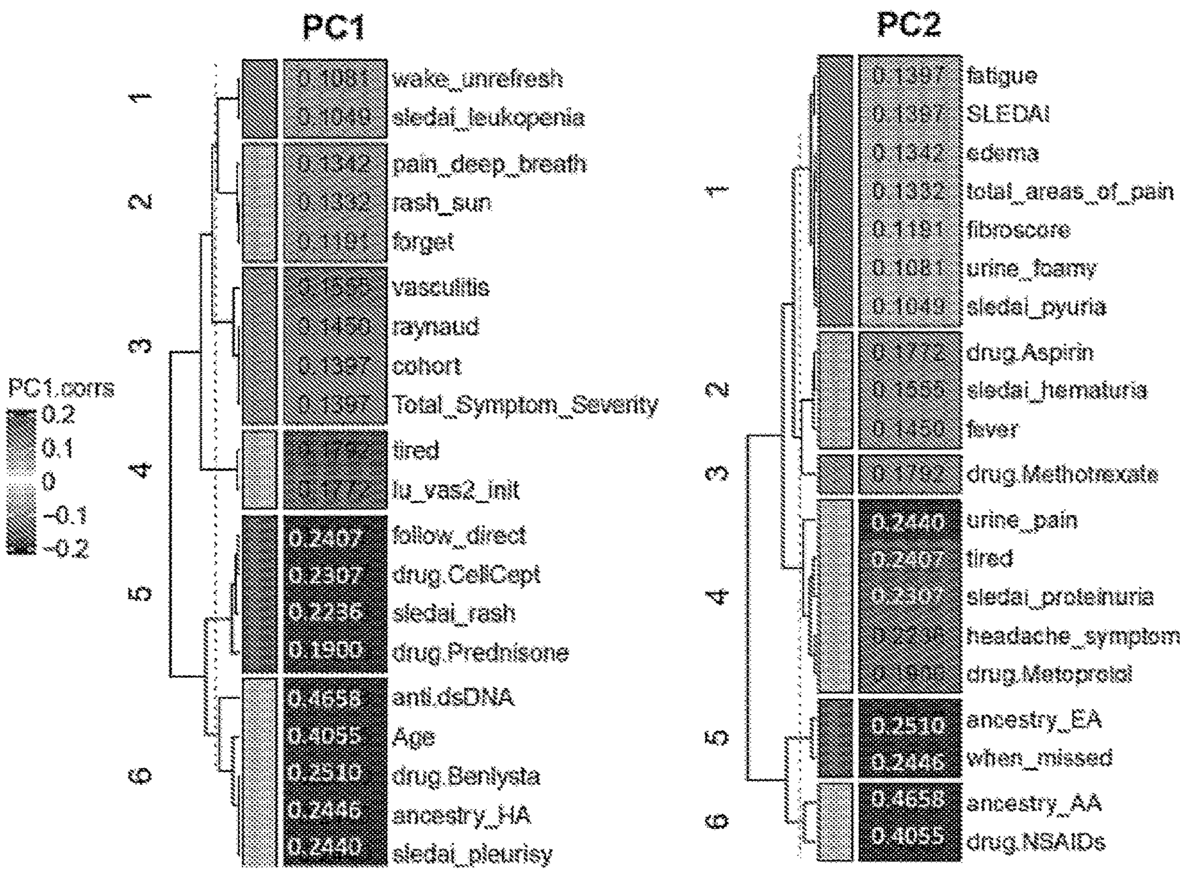
Figure 25C:
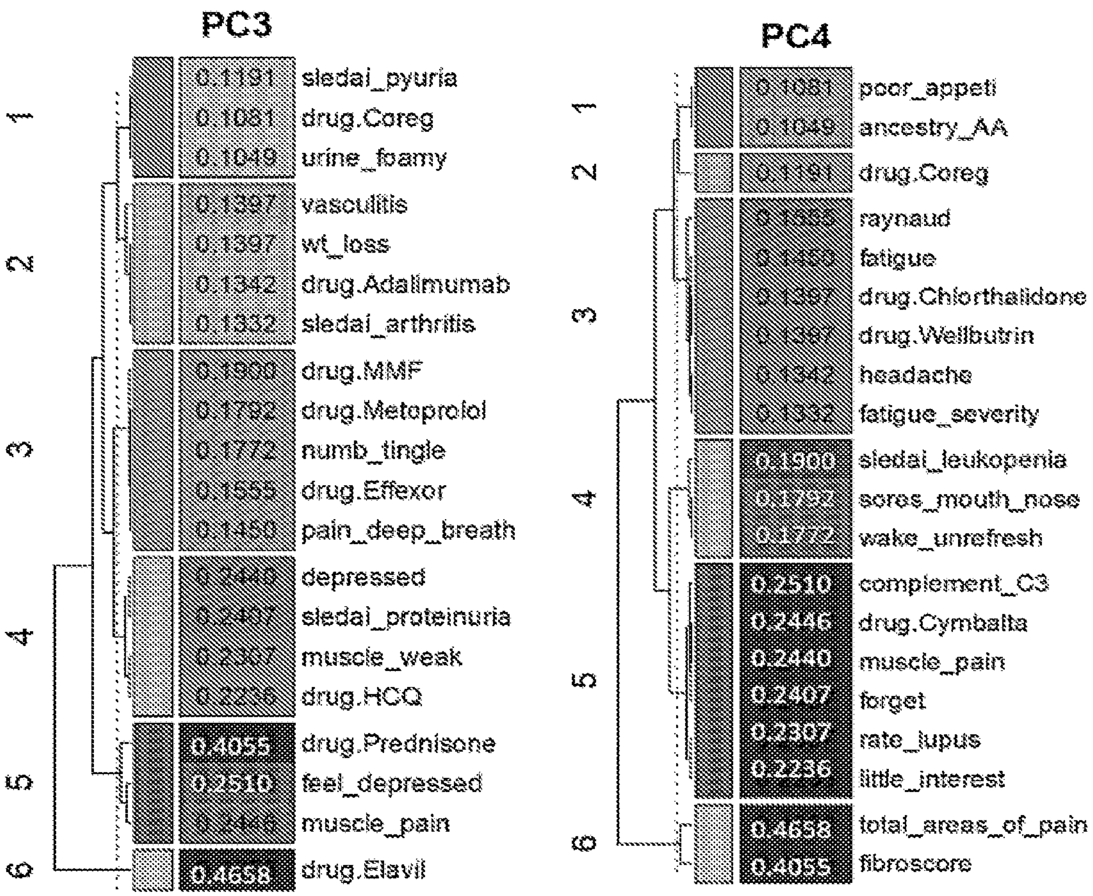

PCA Groups Type 1 and Type 2 SLE Patients: Initially, we determined that differential gene expression analysis generated only one significant DEG, likely because of the high variance patterns within the two sample sets rather than between them. Therefore, additional analytic approaches were applied to the top5k row Var genes encoding known proteins. PCA generally separated samples from Type 1 and Type 2 SLE, although 3 outliers were clearly noted (patient IDs Type1_275, Type2_008, and Type2_267 (arrows, FIG. 25B). To obtain a preliminary idea of the clinical features segregating with the samples in PCA space, the first four principal component (PC) vectors were correlated to the 106 recorded sample traits and the top 20 positive or negative correlations per PC visualized (FIG. 25C). Of note, PC1 highly correlated to anti-dsDNA, age, and Hispanic ancestry, PC2 to NSAID usage and African ancestry, PC3 to prednisone and amitriptyline usage, and PC4 to PSD score and total areas of pain. These results suggest that Type 1 and Type 2 SLE are largely but not completely separable based on gene expression variance, and that specific clinical characteristics segregate with gene expression variance patterns.

Figure 26A:
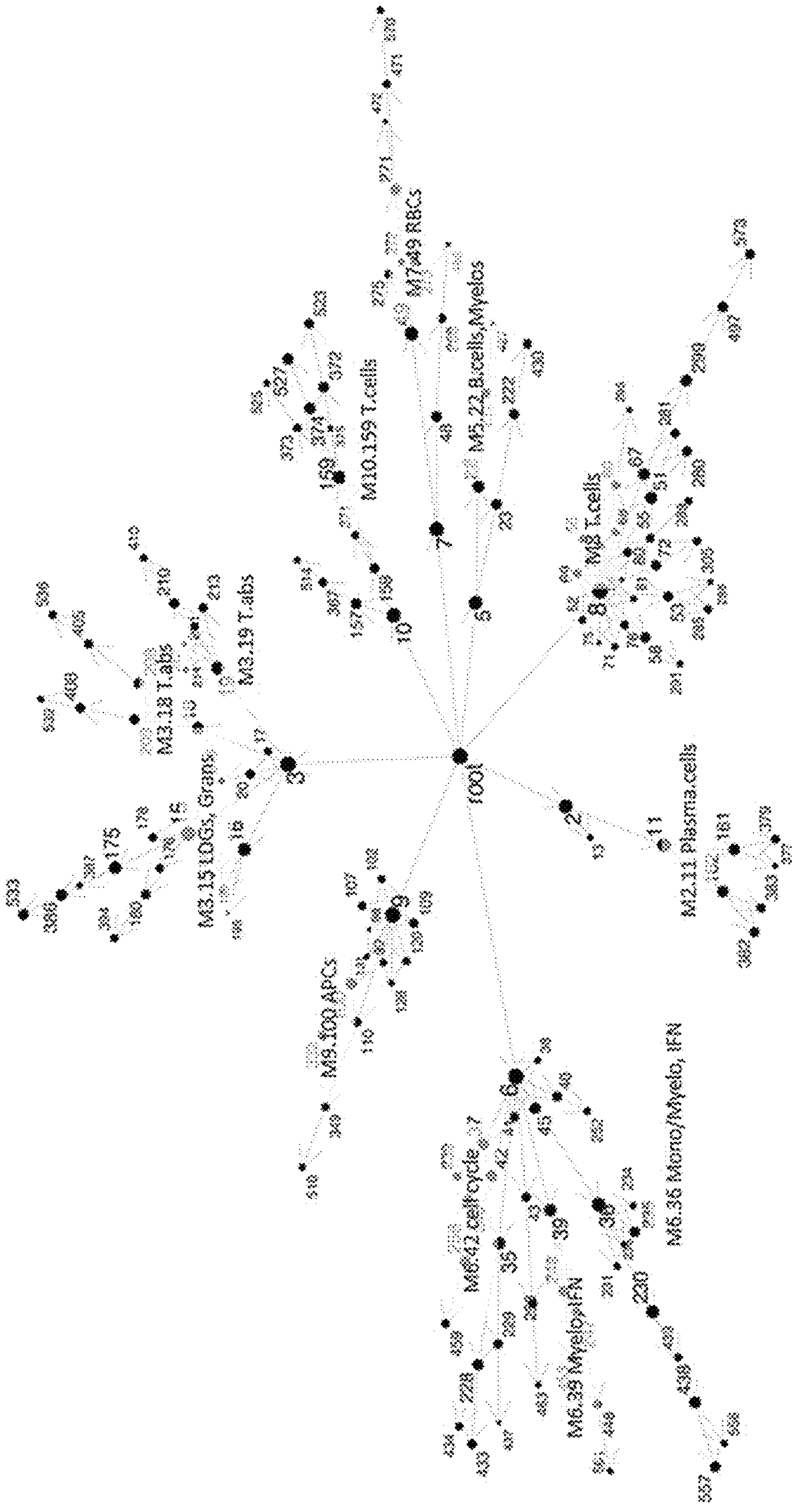
FIGS. 26A-B: MEGENA coexpression module hierarchy visualizations. The top 5,000 row variance genes mapping to known proteins amongst the original 58,381 genes were used to generate modules containing genes that were significantly intracorrelated by gene expression. The modules were iteratively clustered from the initial founder root modules and the lineages depicted as module nodes connected by straight interconnecting lines indicating module descendance (FIG. 26A). Modules are functionally annotated by statistically overlapping their gene symbols with lists of unique cell type or biological pathway gene markers. Functional designation required a minimum overlap of >=3 gene symbols and the overlap Fisher's exact test (p<0.2) to discard overlaps that occurred due to random chance alone. The architecture of module lineage is shown in (FIG. 26B) with modules pseudocolored by root clade descendance to depict their linear relationships.
Figure 26B:
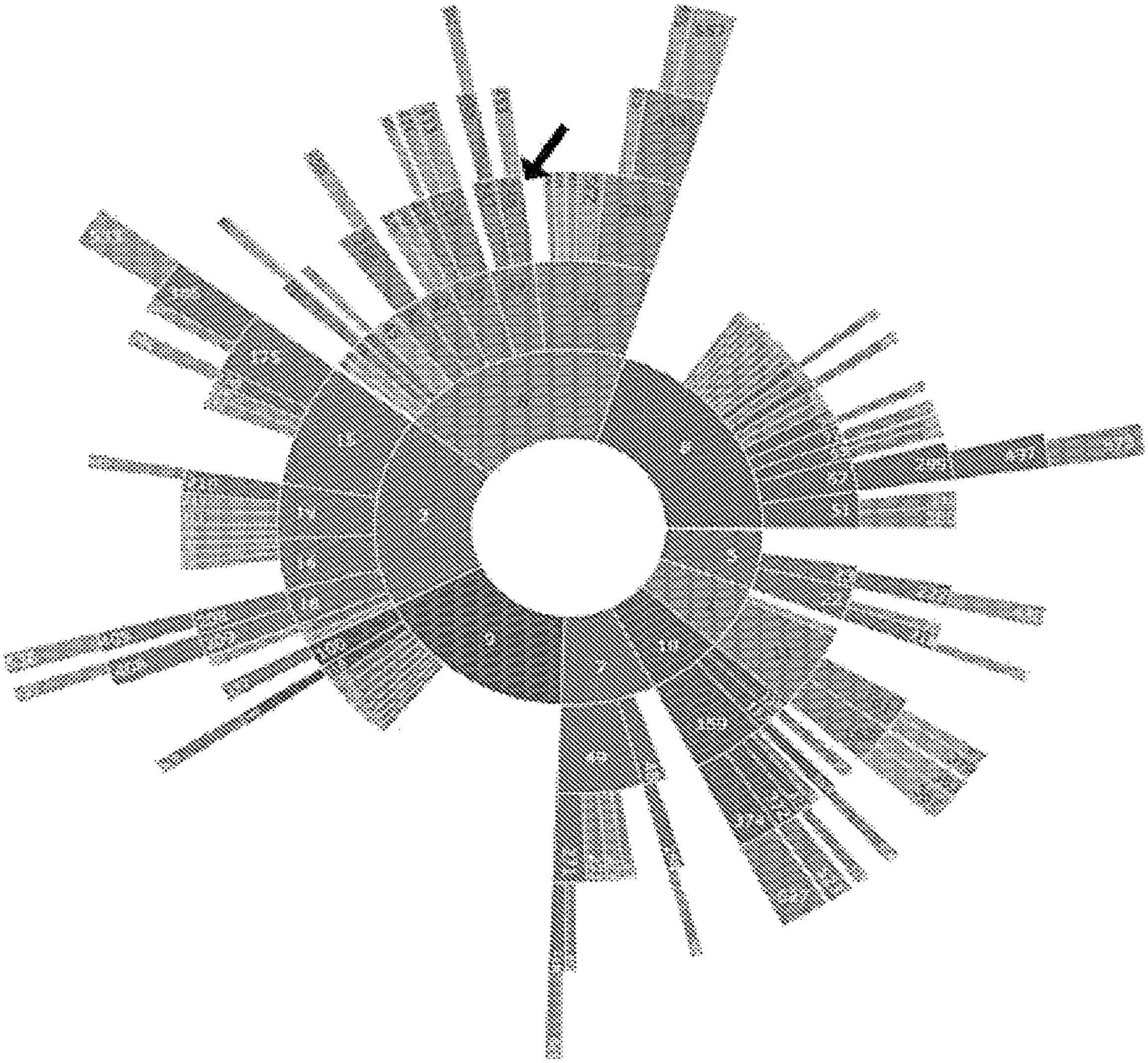

Gene Co-expression Analysis Identifies Distinct Type 1 and Type 2 Gene Modules: Gene Co-expression analysis was next employed to delineate transcriptomic differences between type 1 and type 2 SLE in greater detail. MEGENA, an analytic technique not previously employed with samples from SLE patients, was employed to generate co-expression modules from the top5k row Var genes of the SLE samples (FIG. 26A). The functional nature of co-expression modules was identified by examining genes in each module for overlap with gene modules identifying specific cells or functions (FIG. 26A).

Figure 27:
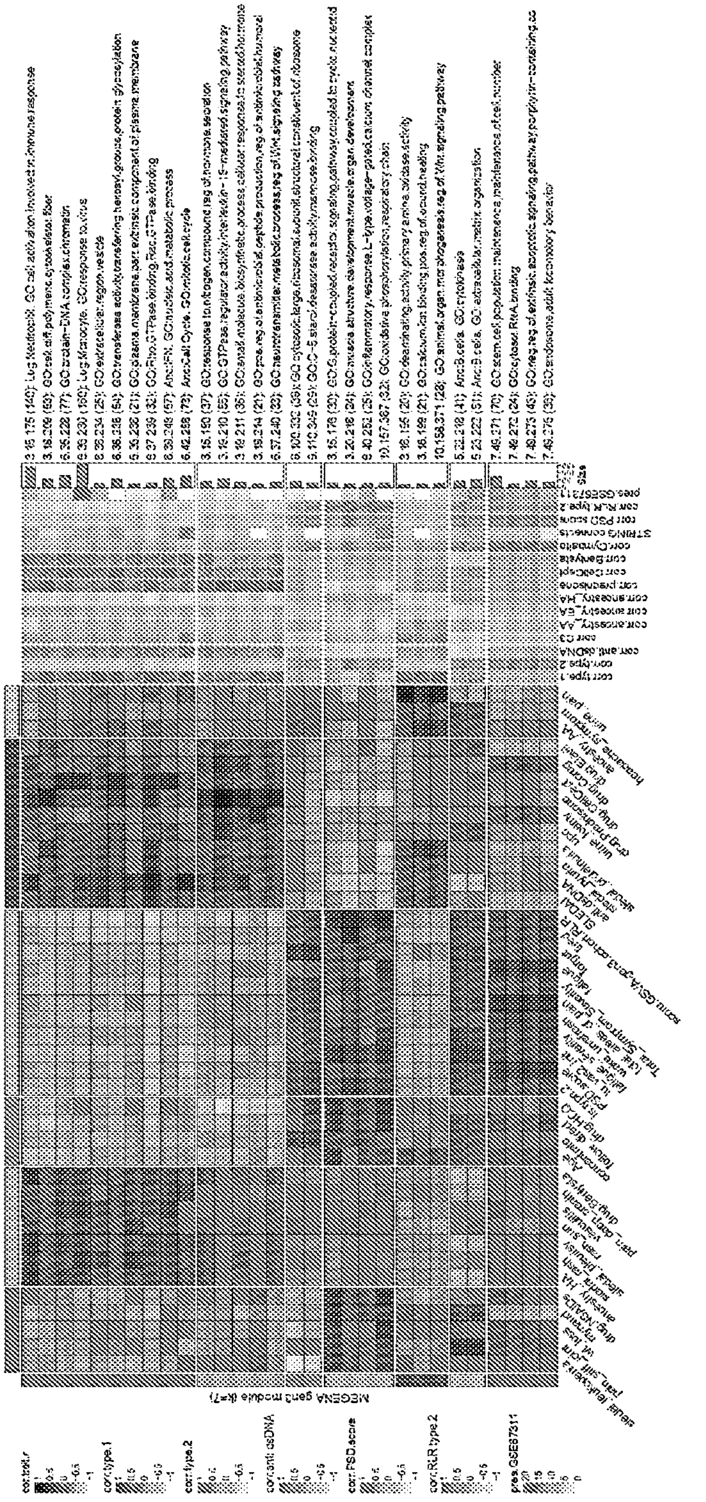
FIG. 27: Gene co-expression module correlation to clinical & demographic features. Numerically encoded sample/patient traits were correlated to the first principal components (equivalent to the module eigengene ME) of all gen3 MEGENA modules followed by selection of the top 30 significant (p<0.2) correlations. The top 30 sample trait correlations were identified by descending ranking order of absolute values of the summed correlations per each of the top 30 modules. Row annotations include sample traits that may not have been included in the top 30 filtering but are of interest. These include ME correlations to SLEDAI, PSD score, ancestral background, usage of the immunotherapeutics prednisone, MMF (mycophenolate mofetil), belimumab, and duloxetine (Cymbalta). Also shown is percentage of a given module's genes participation in predicted protein-protein interactions per the STRING, and the degree of module preservation in the fibromyalgia reference study GSE67311.
Figures 2, 27:
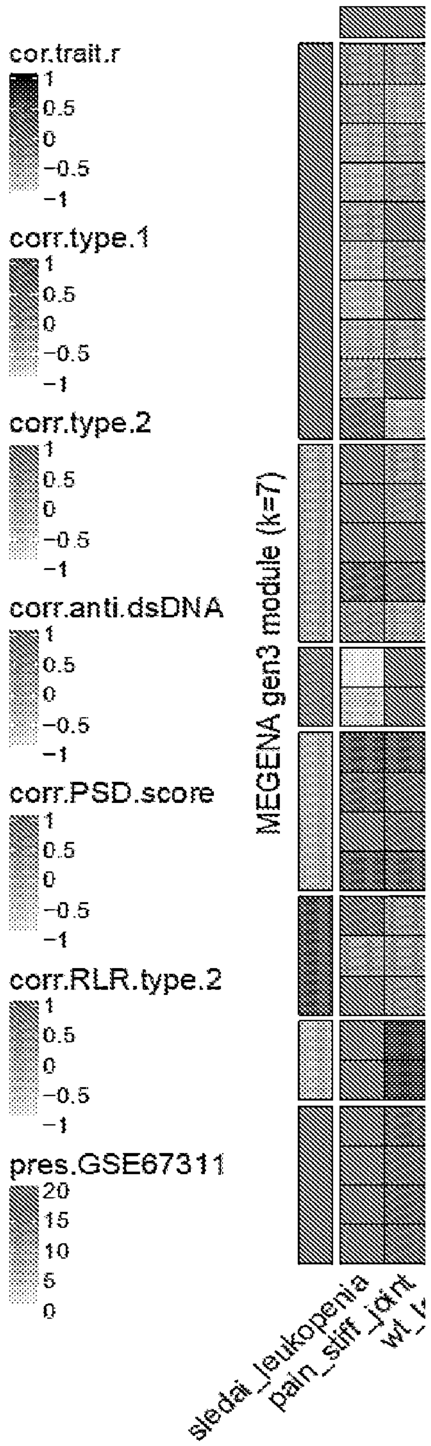
Figures 3, 27:
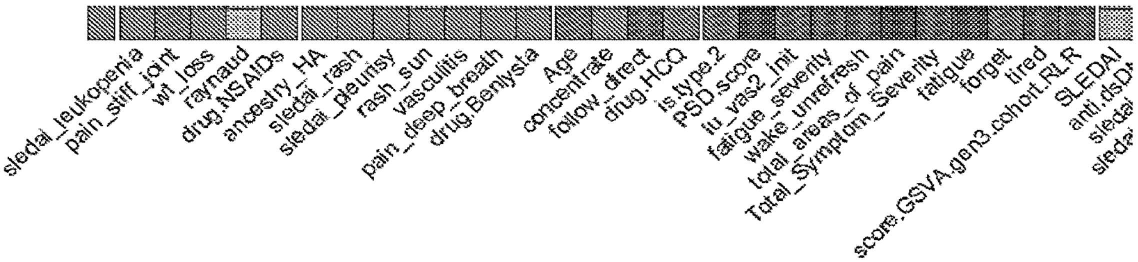
Figures 4, 27:
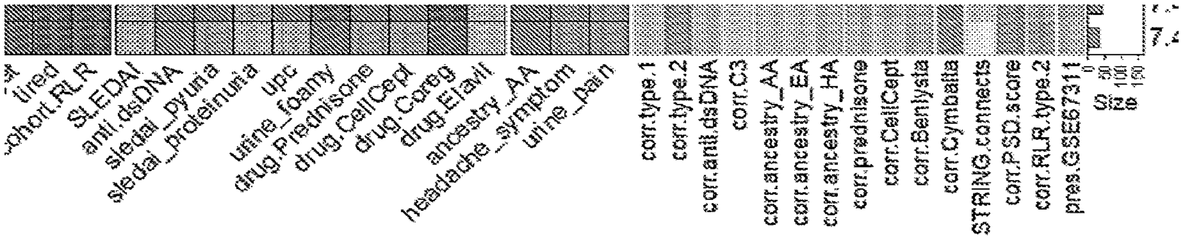
Figure 28A:
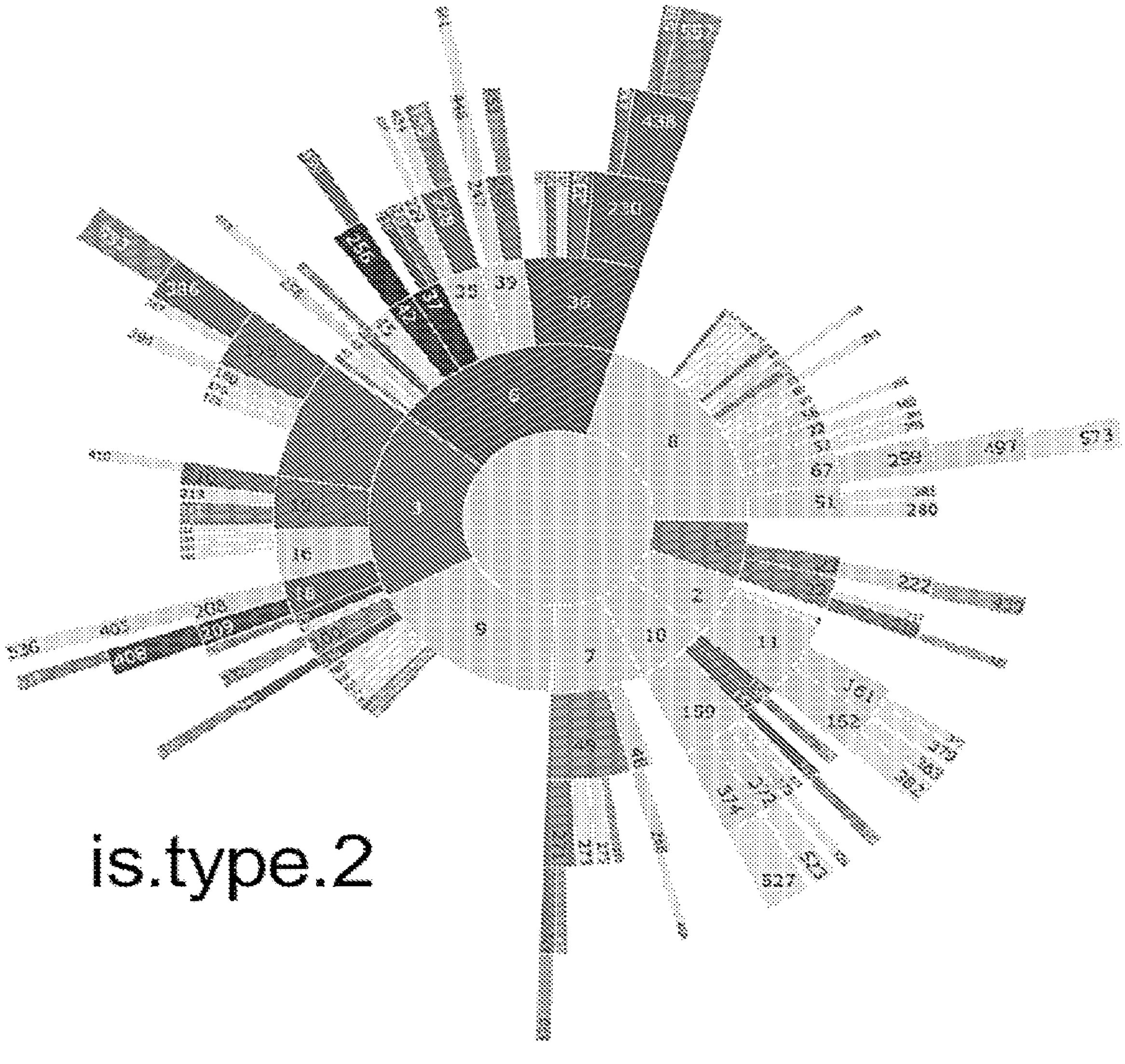
FIGS. 28A-I: Correlations of MEGENA module expression and various clinical and demographic features. The module eigengene (ME, equivalent to the first principal component) for each module was calculated and Pearson correlations to MEs calculated for multiple demographic and clinical features with correlations ranging from −1 to +1 (FIGS. 28A-F). Functional identity of the modules was carried out by matching module genes with various cell type or biological pathway markers (FIGS. 28G-I) as performed for FIG. 1. Is.type.2 (FIG. 28A); SLEDAI (FIG. 28B); PSD (FIG. 28C); African ancestry (AA) (FIG. 28D); European ancestry (EA) (FIG. 28E); and Hispanic ancestry (HA) (FIG. 28F); Significant LuGENE enrichment (FIG. 28G); Significant Ancestry enrichment (FIG. 28H); and Significant tissues enrichment (FIG. 28I).
Figure 28B:
Figure 28C:
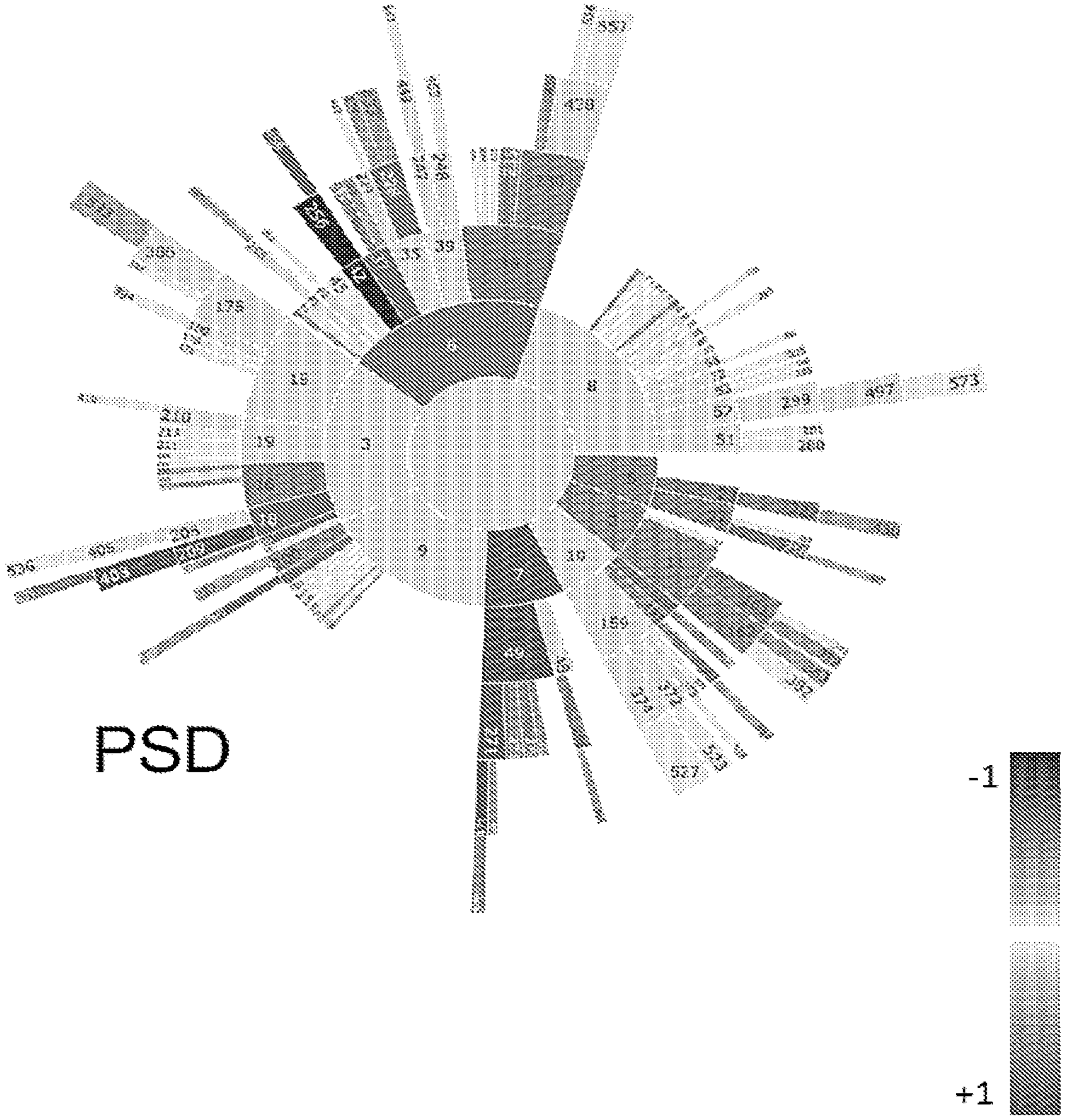
Figure 28D:
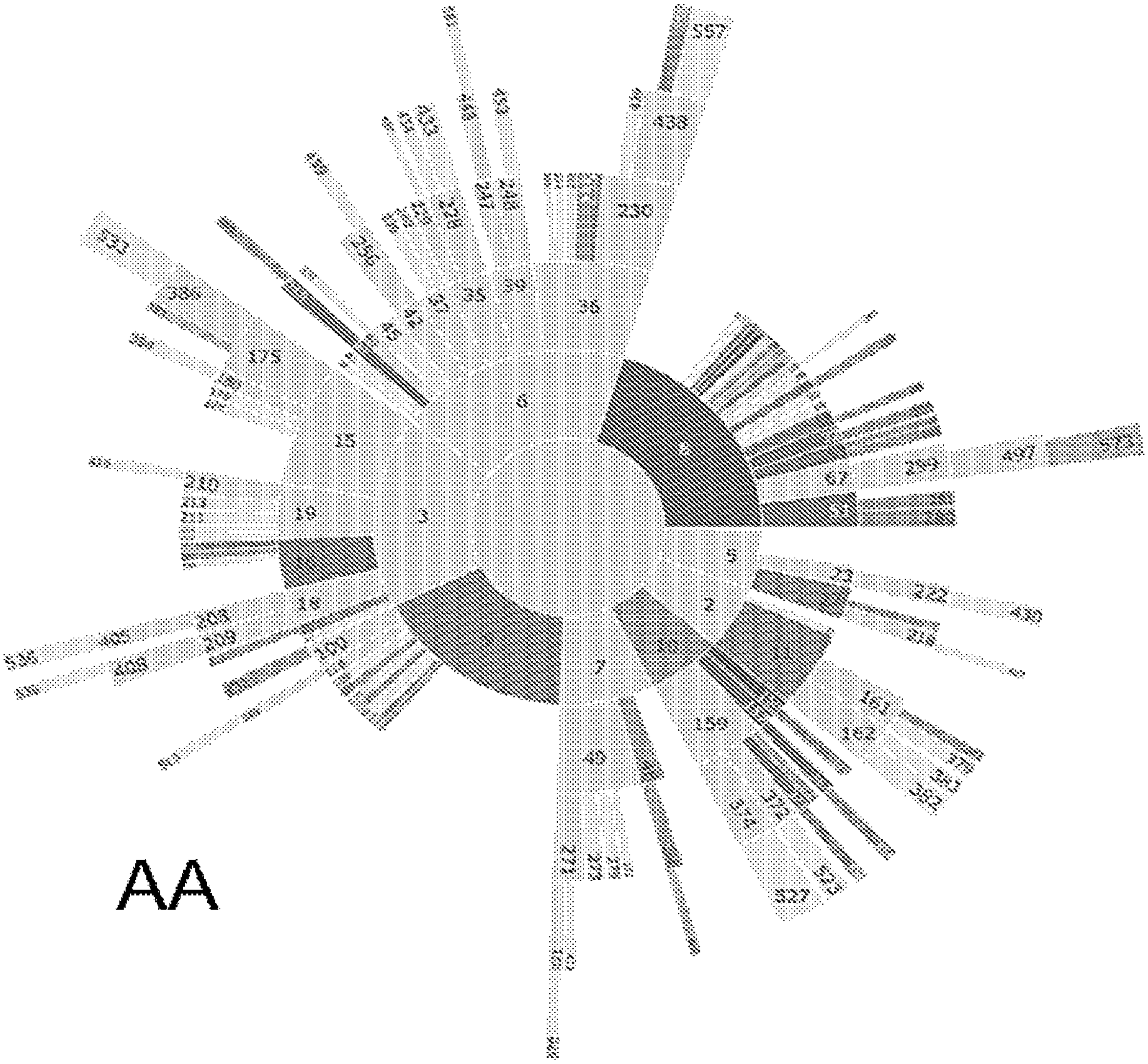
Figure 28E:
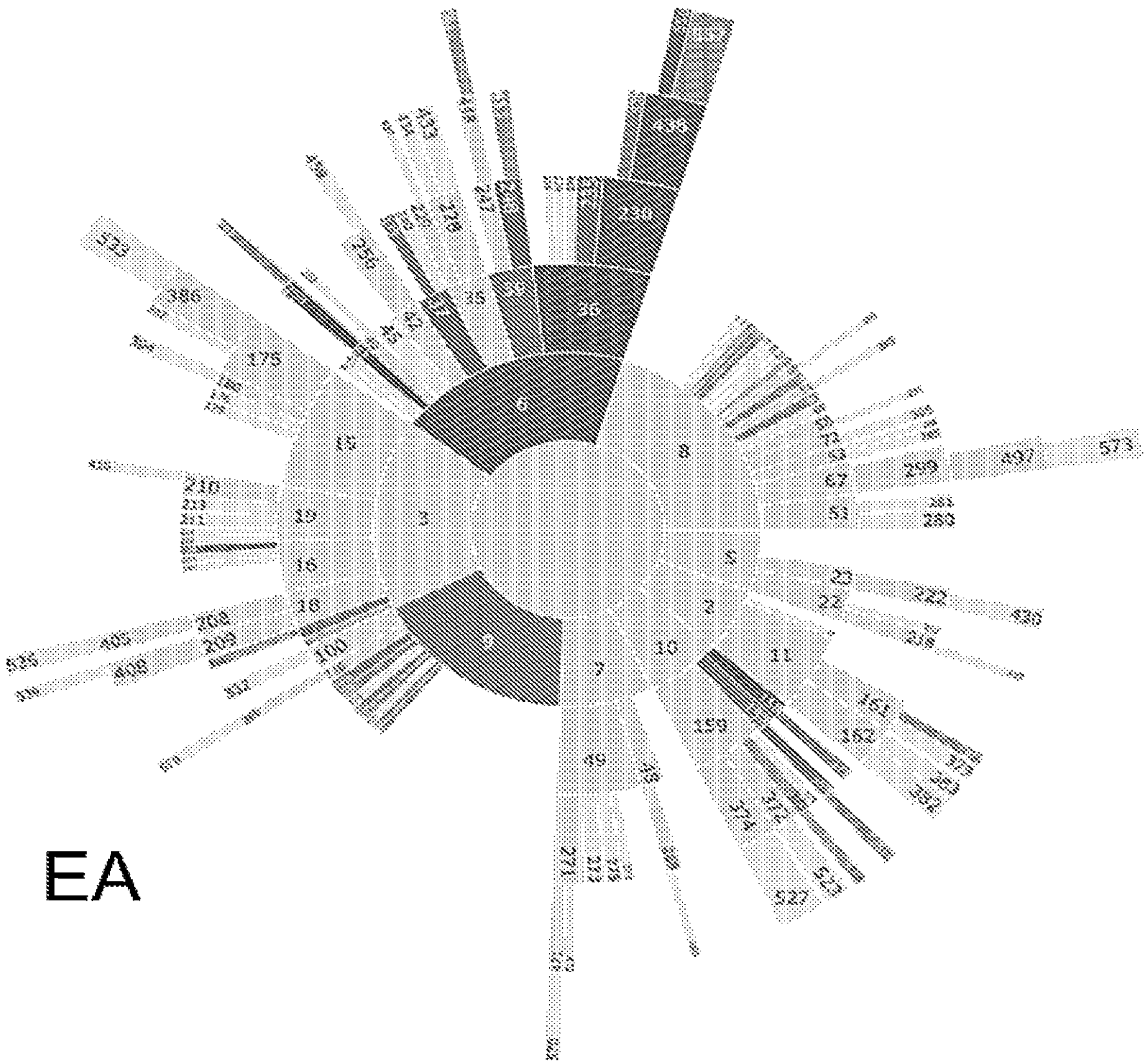
Figure 28F:
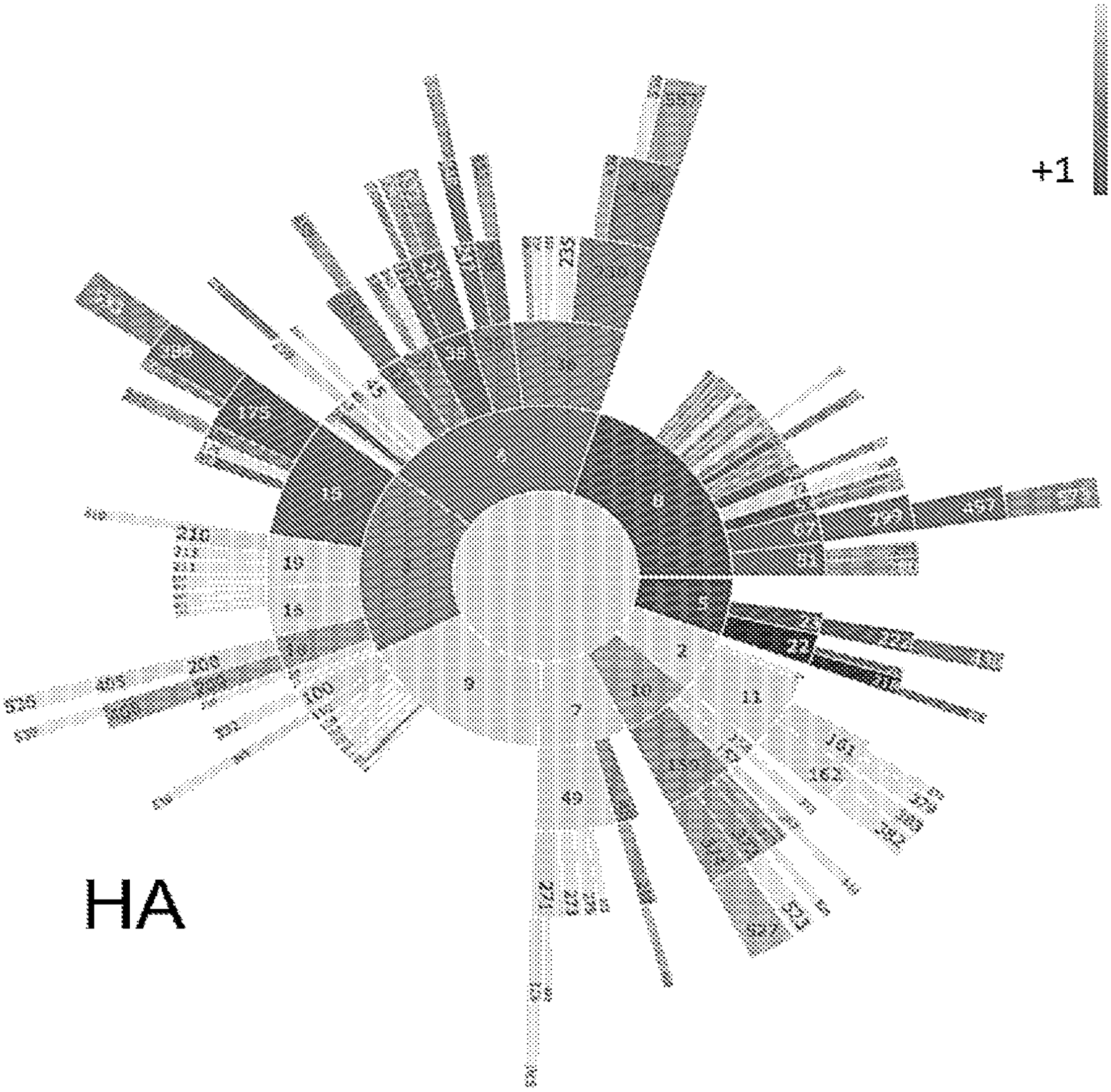
Figure 28G:
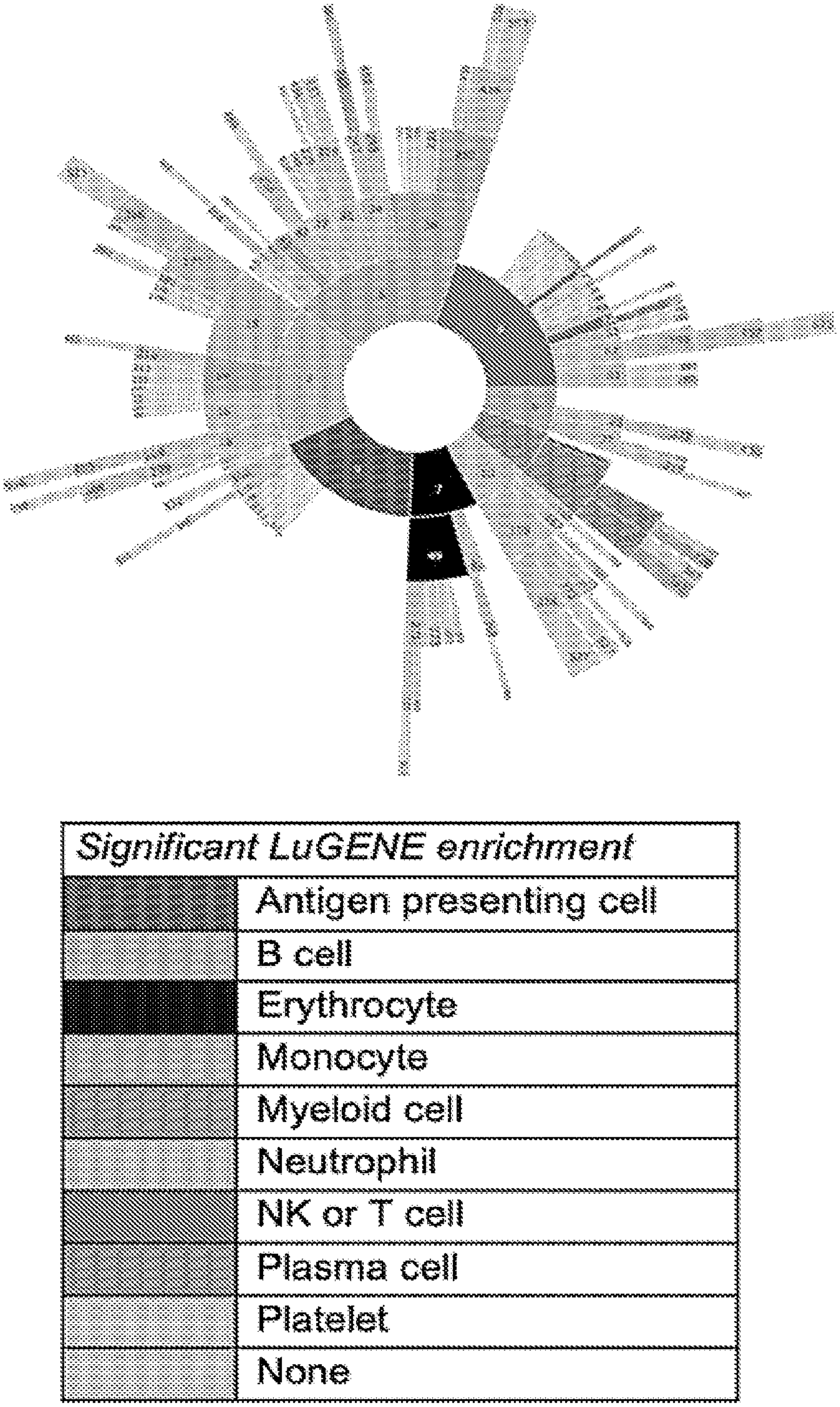
Figure 28H:
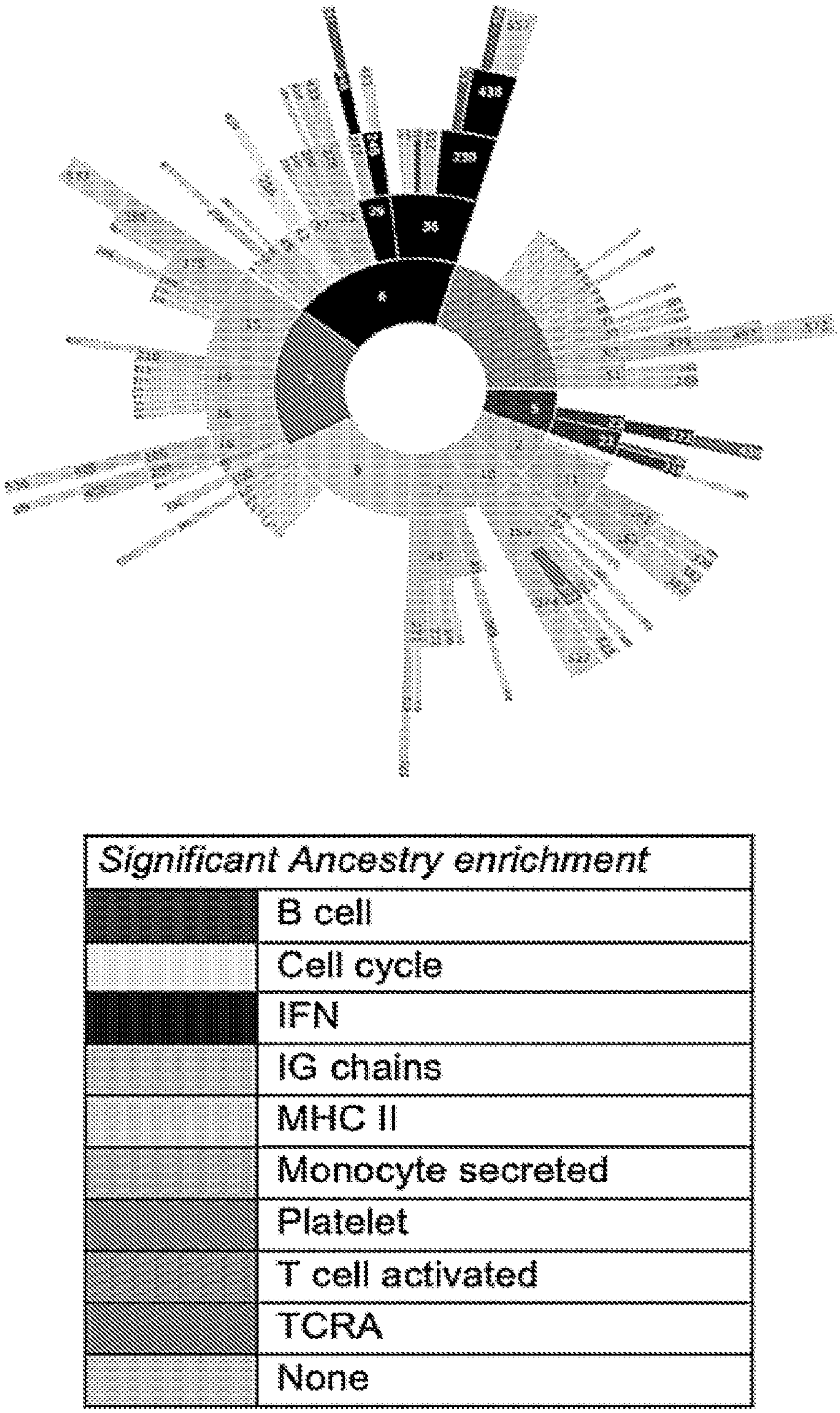
Figure 28I:
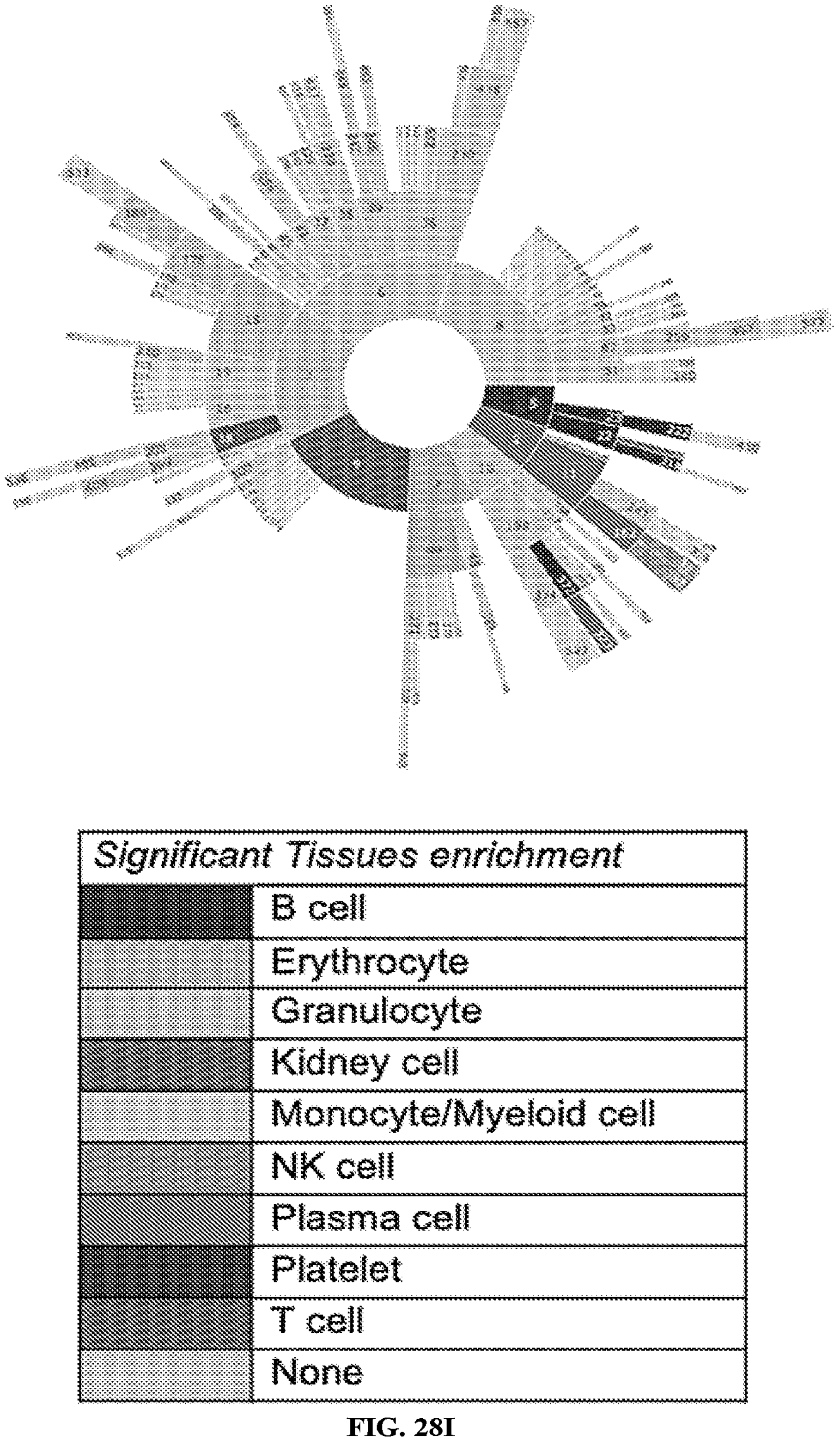
Figure 29A:
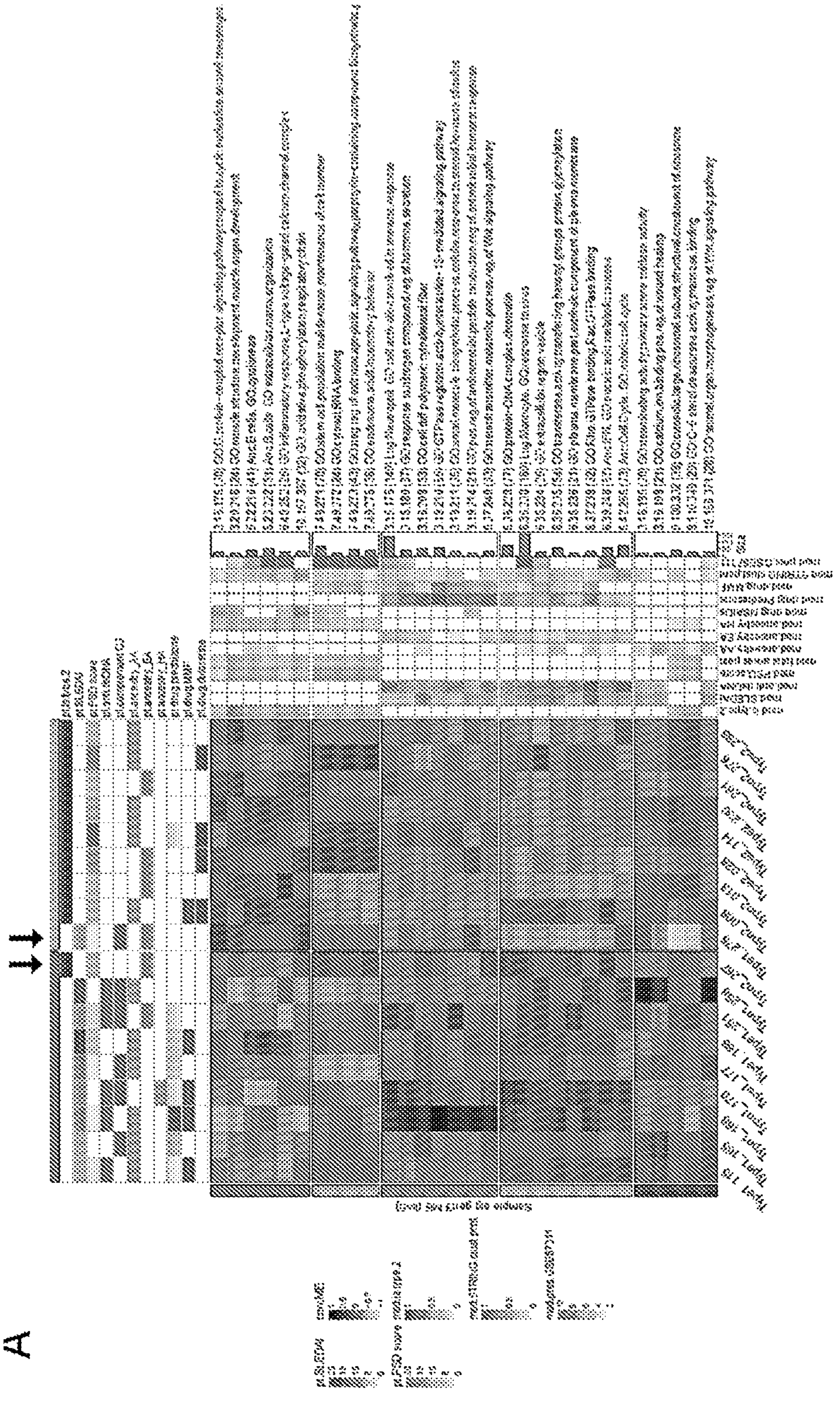
FIGS. 29A-B: Type 1 SLE & Type 2 SLE Gen3 module eigengene (ME) correlations. The top 30 significant type 1/2 SLE gen3 cohort MEs per patients were clustered into optimal k=2 patient clusters. Patients type1 275 and type2 267 (arrows) correspond to outliers identified during PCA analysis in FIG. 25 (FIG. 29A). Data from FIG. 29A was plotted as a means of the patients in each cluster (FIG. 29B).
Figures 1, 29A:
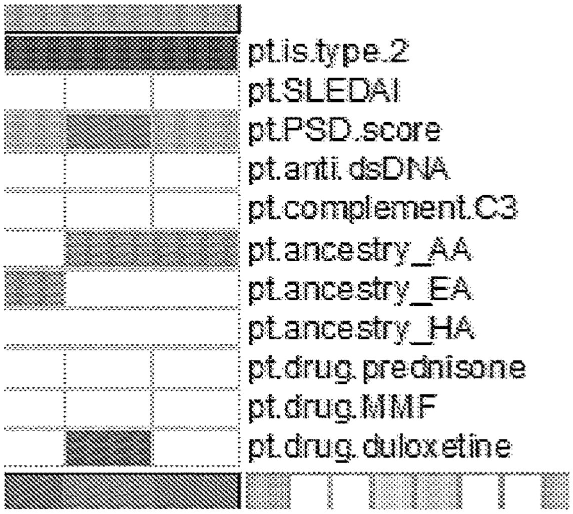
Figures 2, 29A:
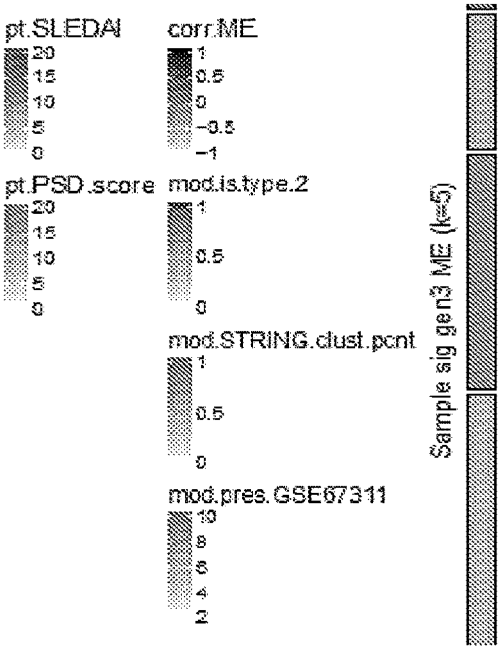
Figures 3, 29A:
Figures 4, 29A:
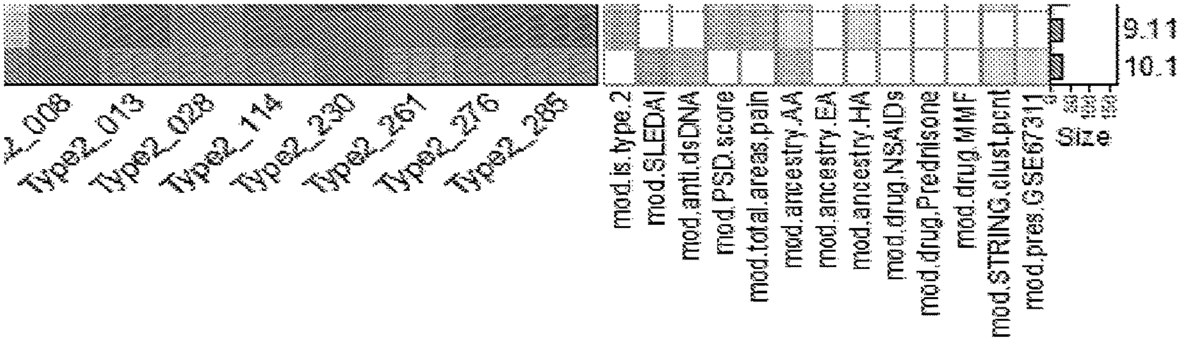
Figure 29B:
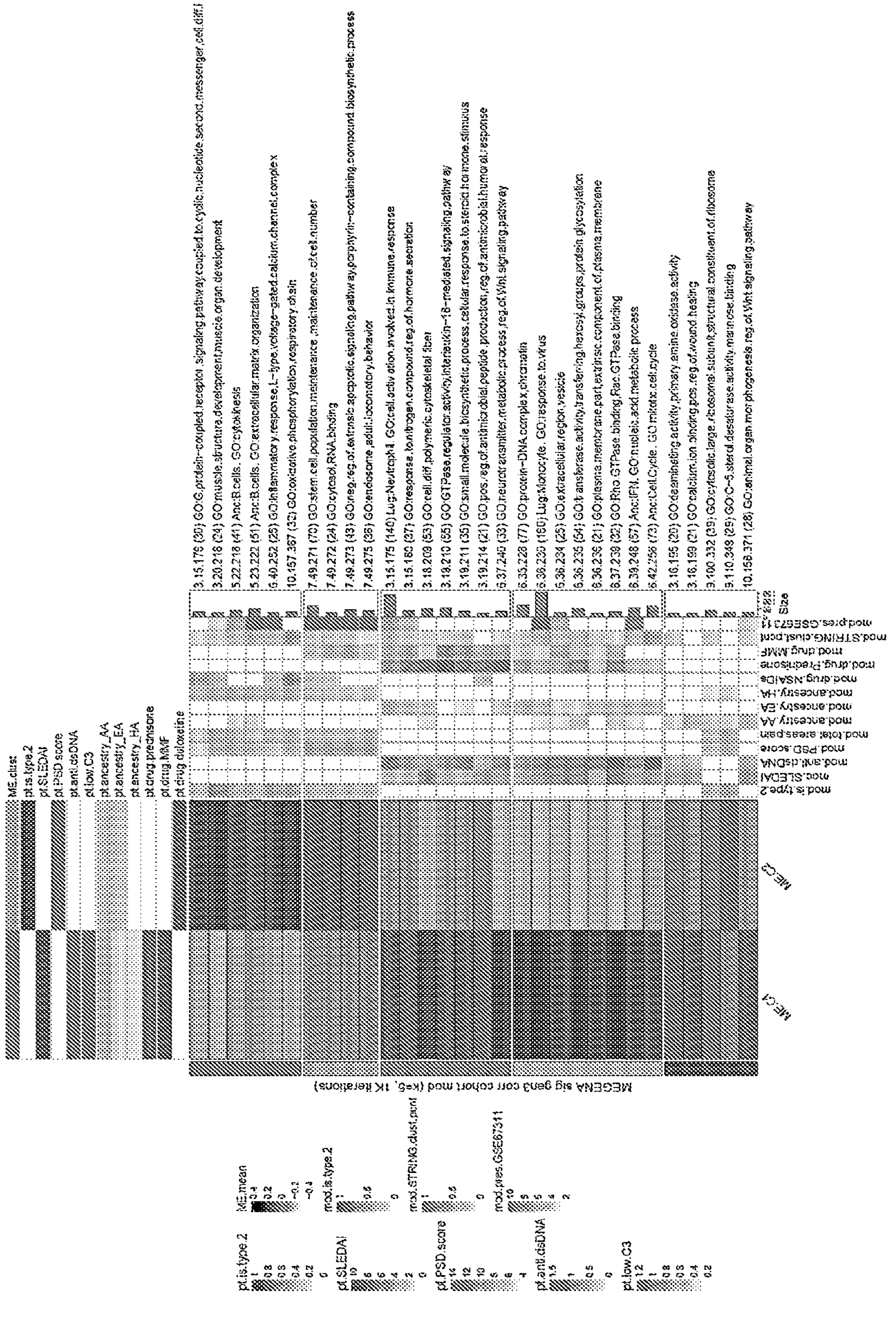
Figure 29C:
FIGS. 29C-D: Type 1 SLE & Type 2 SLE Gen2.4 module eigengene (ME) correlations. The top 30 significant type 1/2 SLE gen3 cohort MEs per patients were clustered into optimal k=2 patient clusters (FIG. 29C). Data from FIG. 29C was plotted as a means of the patients in each cluster (FIG. 29D)
Figure 29D:
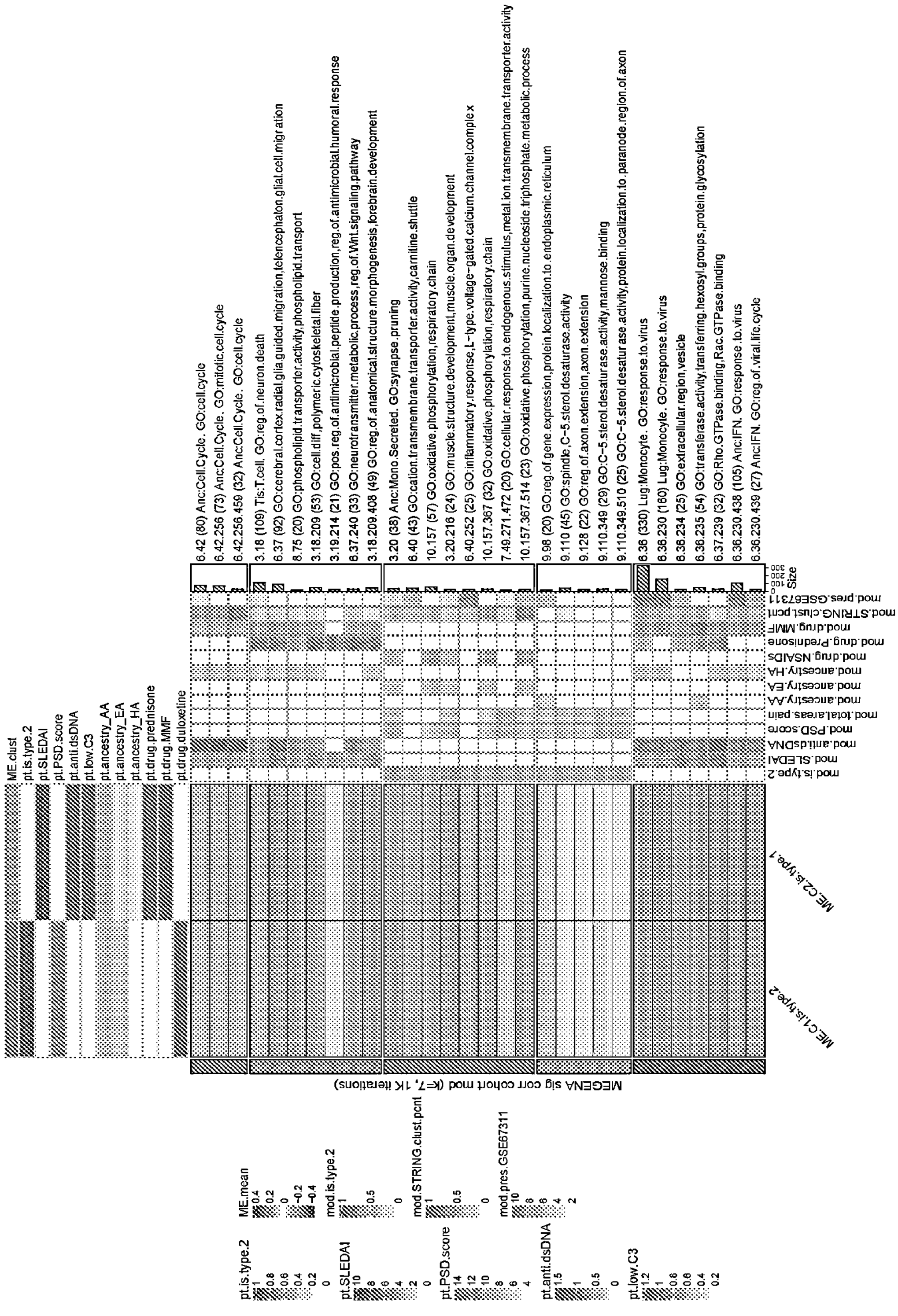
Figure 30A:
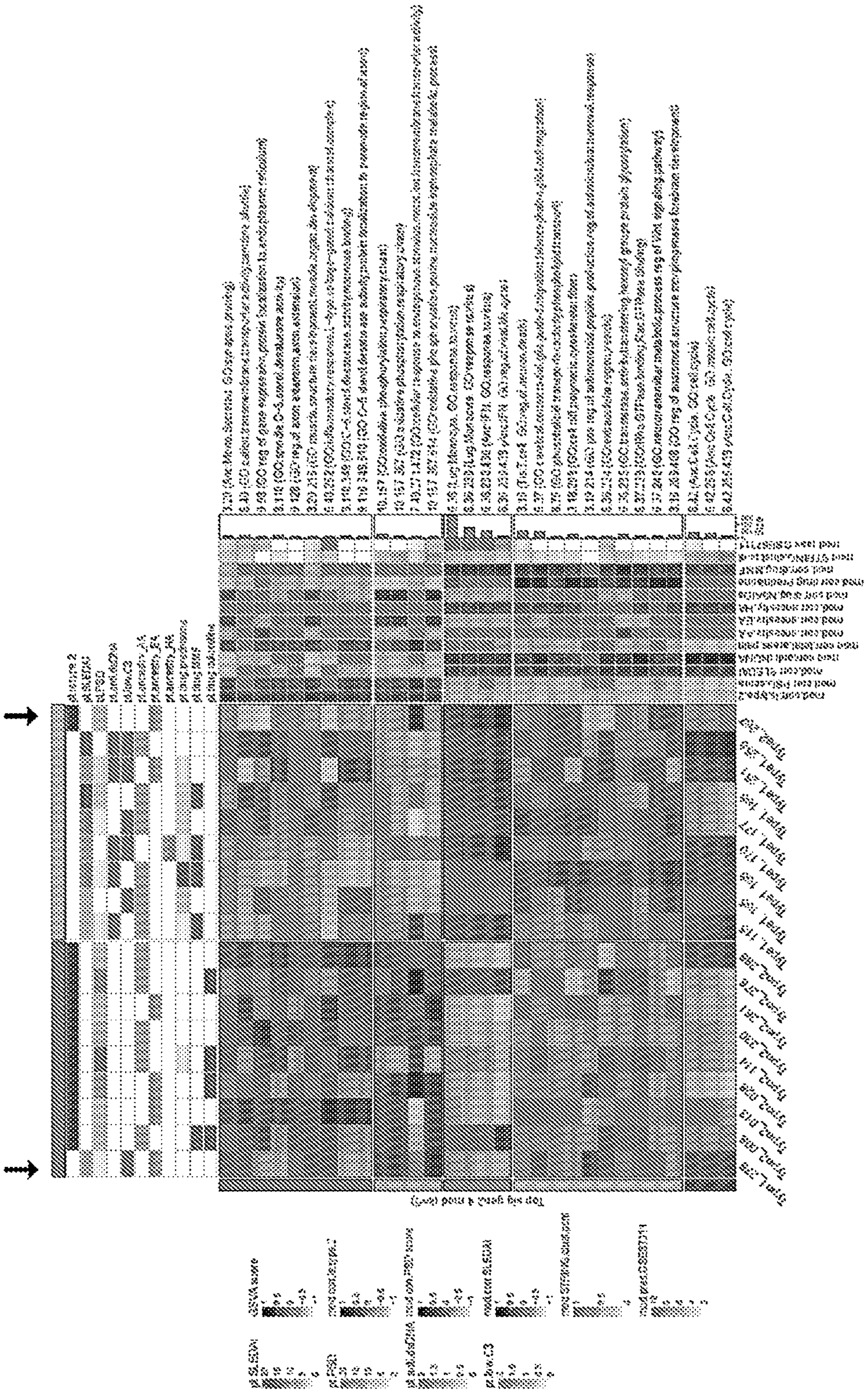
FIGS. 30A-B: Gene Set Variation Analysis (GSVA) using MEGENA modules as input gene sets effectively separates subjects with Type 1 and Type 2 SLE. Heatmaps indicate GSVA enrichment scores per patient for each module. Patient column annotations include patient type (type. 1.SLE white, type.2.SLE dark), SLEDAI score (with lab), PSD score, anti.dsDNA (binary), low C3 (binary), ancestral background (AA, EA, HA), prednisone dosage, and usage of MMF or duloxetine (binary). Columns of sample traits were clustered using optimized k-means clustering of 1K iterations on k=2. Module rows were clustered in a similar manner on k=5 and are annotated with only positive correlations to sample traits and range from 0 to +1. Gen3 module gene symbols were used to programmatically query the STRING database and calculate the percentage of genes within a given module predicted to have known protein-protein interactions (PPI) ranging from 0 to 100% ("STRING.clust.pont"), along with zsummary module preservation against the GSE67311 fibromyalgia test data set ("pres.GSE67311"). Patients type1 275 and type2 267 (arrows) correspond to outliers identified during PCA analysis in FIG. 25 (FIG. 30A). Data from FIG. 30A was plotted as a mean of the patients in each cluster (FIG. 30B).
Figures 1, 30A:
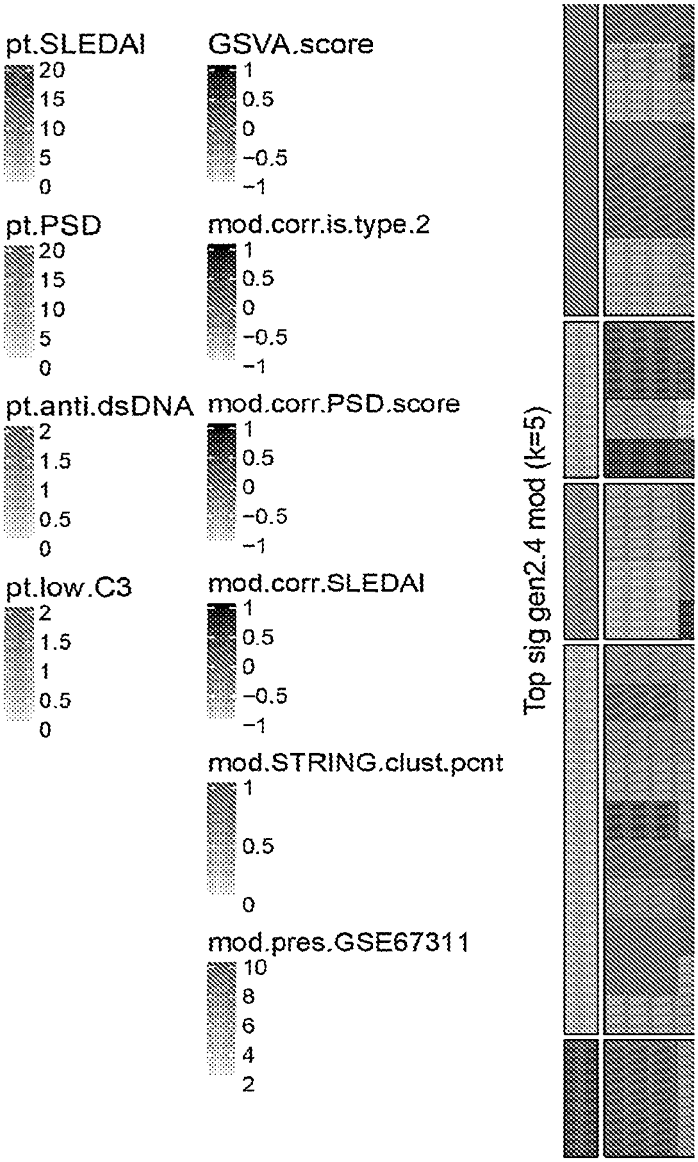
Figures 3, 30A:
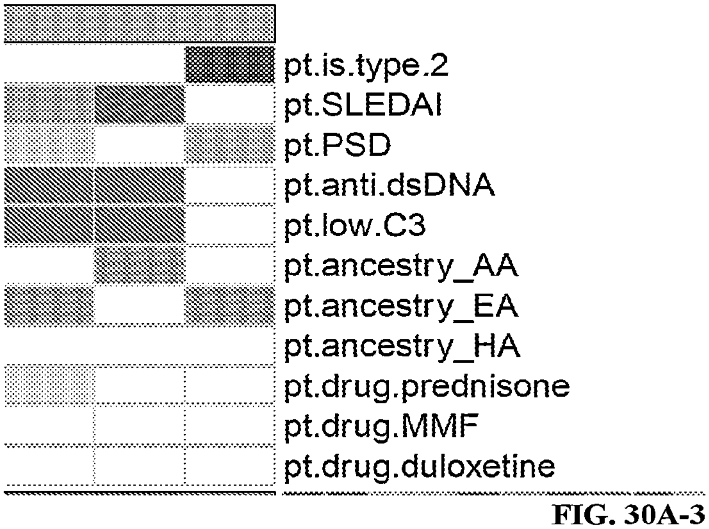
Figures 4, 30A:
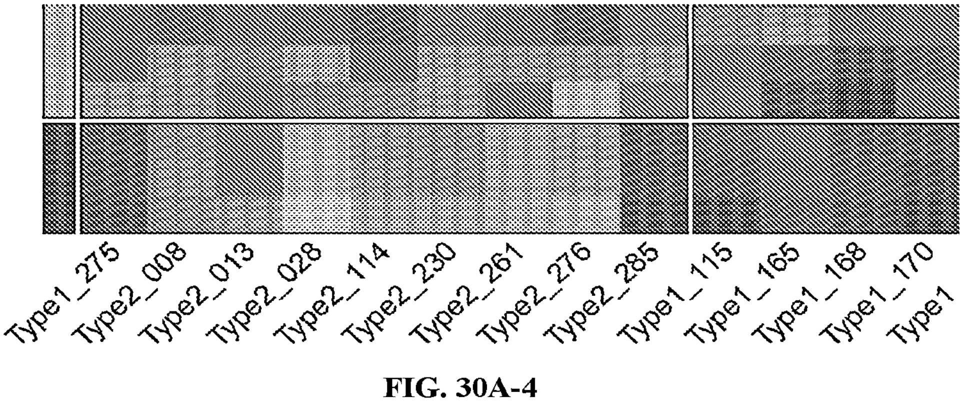
Figures 5, 30A:
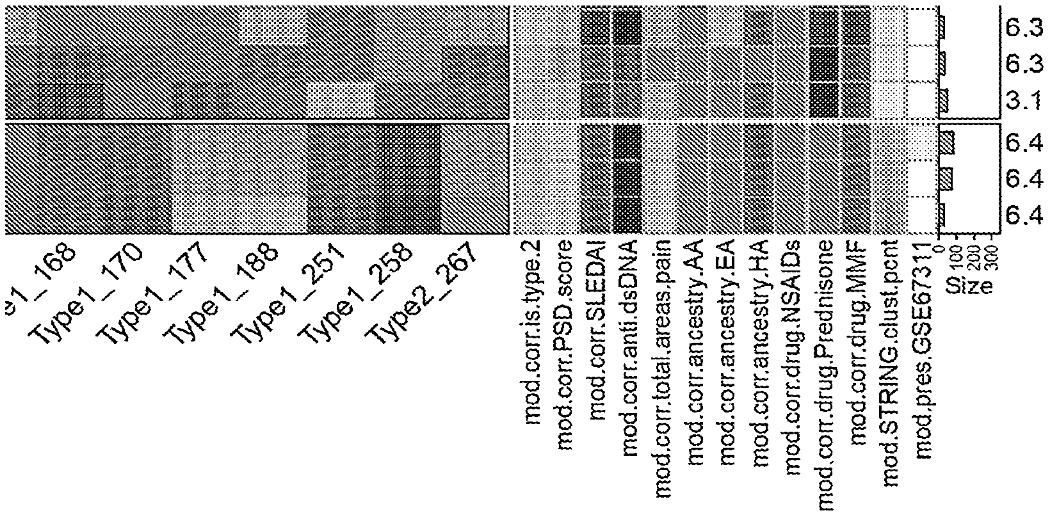
Figure 30B:
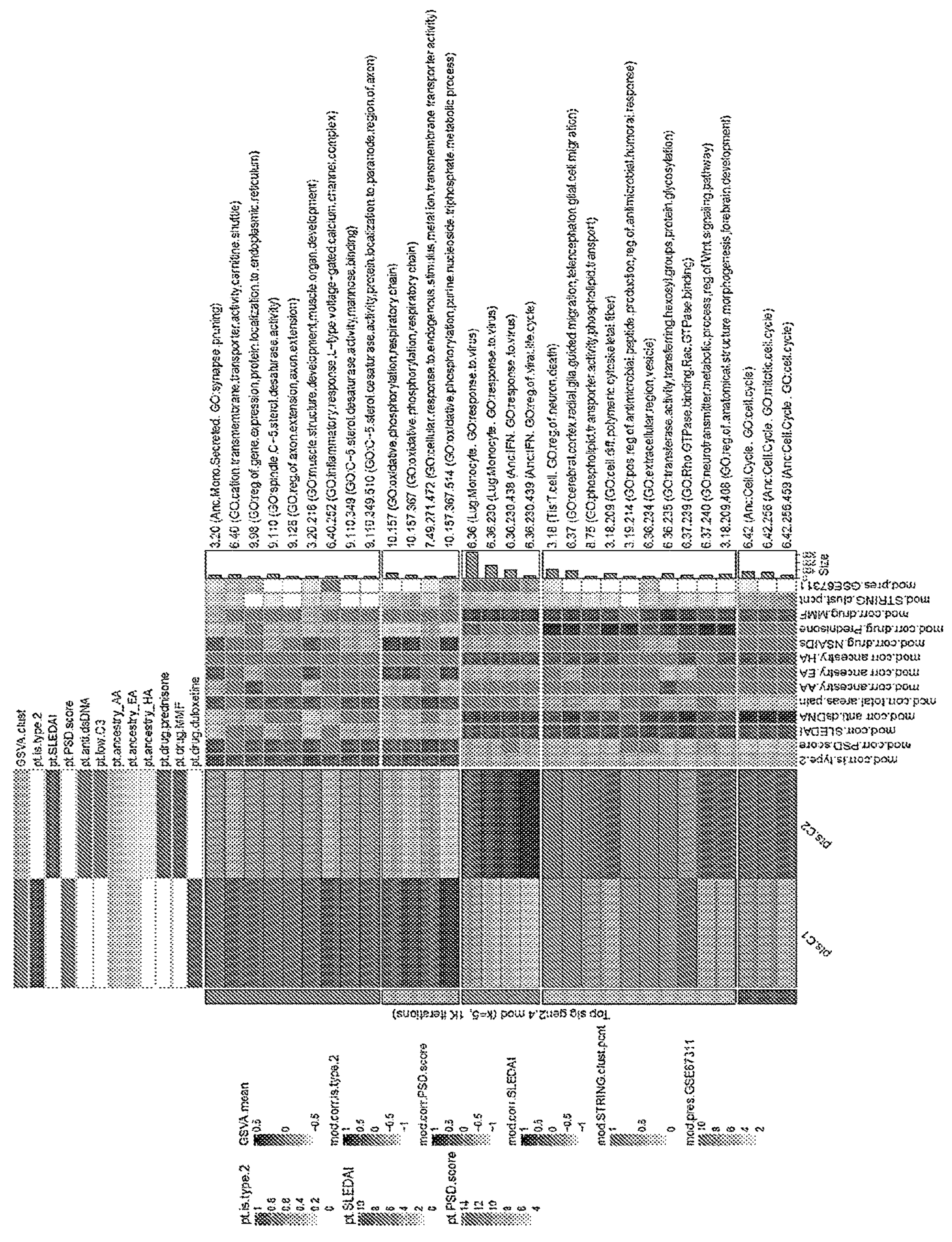

Gene Co-expression Module Correlation to Clinical & Demographic Features: To determine the correlation of co-expression modules with clinical features, the module eigengene (ME) of each module was calculated, and correlated to the 106 recorded clinical and demographic traits and the top 30 positive or negative ME correlations identified (FIG. 27 & Table 10). Genes within the top 30 gen2.4 modules, and functional annotation of the modules are presented in Tables 17-1 to 17-30. Genes within the top 30 gen3 modules, and functional annotation of the modules are presented in Tables 24-1 to 24-30. Stable k-means clustering revealed groupings of clinical traits and correlated molecular functions. PSD score and Type 2 SLE patients were found in the second column (from left) cluster along with total areas of pain, waking up unrefreshed, forgetfulness, fatigue, and lack of concentration. SLEDAI was found in the fourth column (from left) cluster along with anti-dsDNA, pyuria, proteinuria, and prednisone usage.

Because there was a numeric but not significant disparity in age between the groups (Type 1, 36.9+/−10.8 Type 2, 46.0+/−8.7, p=0.07), we carried out two additional analyses to confirm that age was not contributing to the results. First, we eliminated the two youngest patients from the Type 1 group and the two oldest from the Type 2 group and repeated the analysis, resulting in a very similar separation of clinical features. Secondly, we used the entire group of patients and carried out the same analysis after covariant adjustment for age, again with similar results. These results are all consistent with the conclusion that expression of co-expression modules is uniquely correlated with specific features of Type 1 and Type 2 SLE independent of age.

Associations between MEs of specific co-expression modules and clinical features are shown in FIG. 28. Unique patterns of co-expression module MEs and Type 1 and Type 2 SLE, respectively, can clearly be seen. Moreover, unique and opposing co-expression module ME correlations with SLEDAI and PSD scores were found. Notably, MEs of co-expression modules identifying the interferon signature and monocytes were highly positively correlated to SLEDAI and negatively correlated to PSD score. Conversely, the MEs of the erythrocyte modules were negatively correlated to SLEDAI and positively to PSD score. Similarly, the MEs of the B cell and plasma cell modules were correlated to PSD scores. Finally, patient ancestry also was correlated with specific co-expression module MEs.

Figure 39:
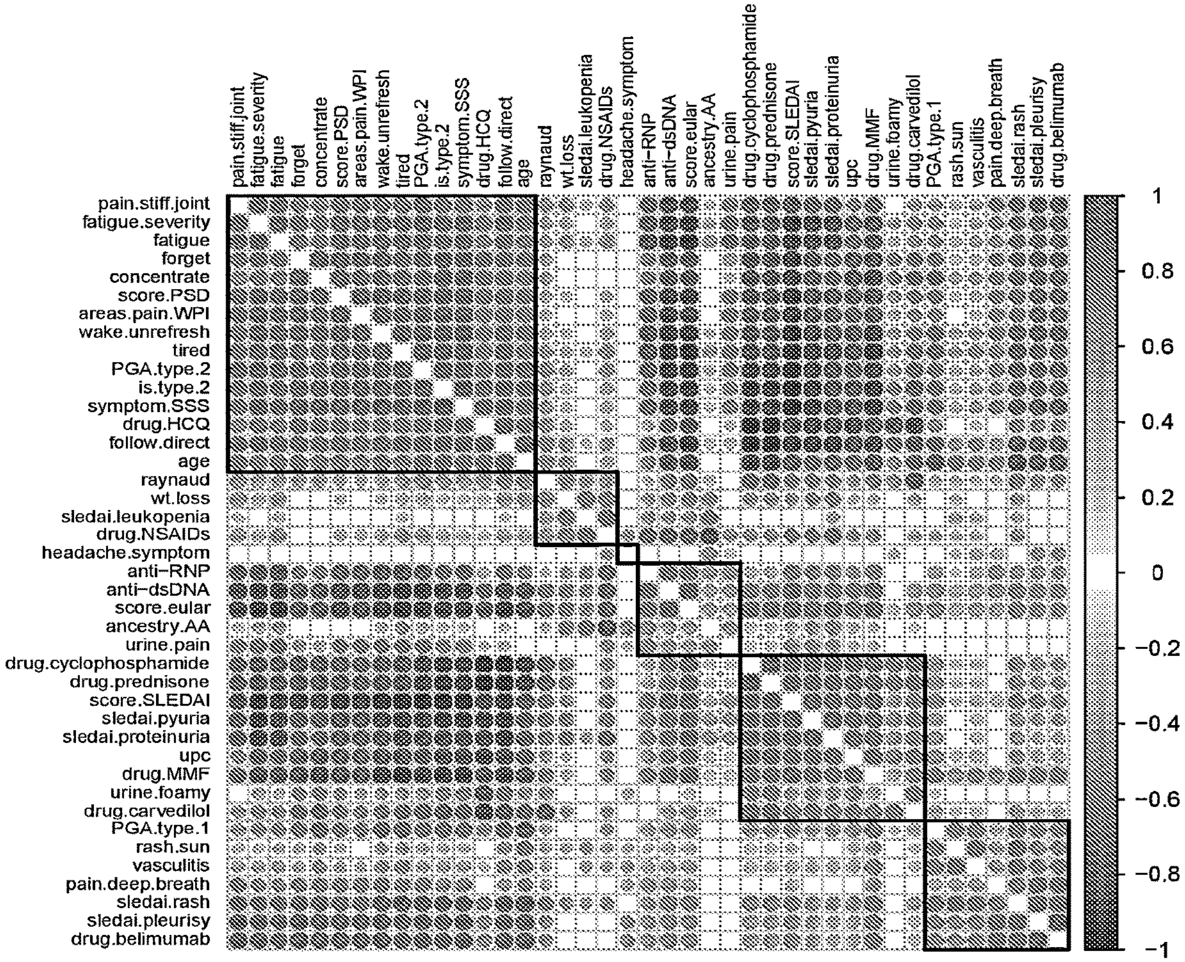
FIG. 39: Plot of significant ($p<0.05$) correlations of expression of the top 40 cohort module MEs to clinical and molecular attributes. Red arrows indicate the clinical scores PSD, PGA.type.1, PGA.type2, SLEDAI, and is.type.2 cohort. Red indicates a positive correlation and blue indicates a negative one.
Figure 40:
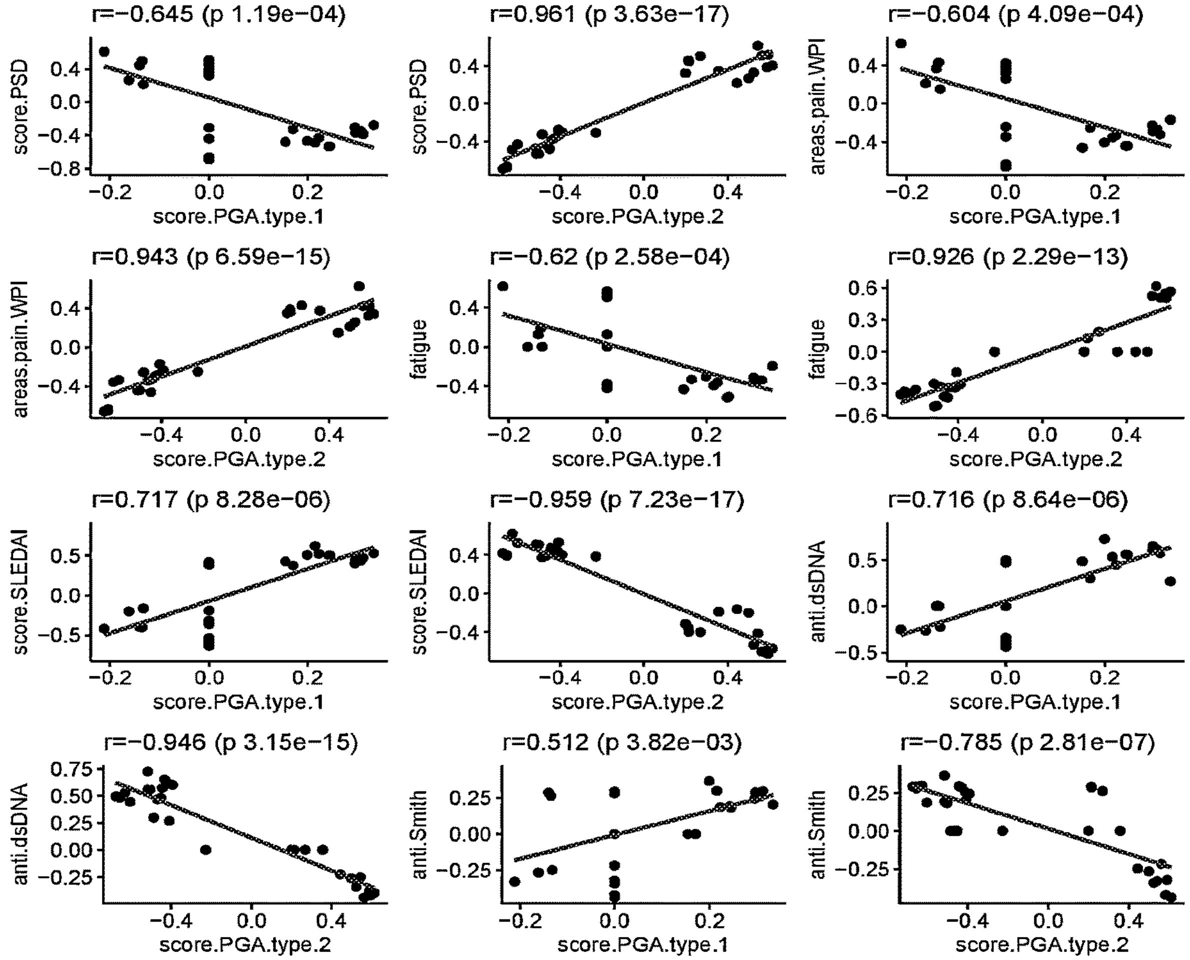
FIG. 40: Correlations of the top 40 genes expression MEs with specific clinical features. The MEs of the top 40 gene expression modules were correlated with various clinical features and the correlation coefficients of the associations plotted on a two-dimensional matrix.

Co-expression Modules Distinguish Type 1 and Type 2 SLE: Stable K-means clustering of co-expression module MEs was also used to determine whether Type 1 and Type 2 SLE patient samples could be distinguished. Effective separation of Type 1 and Type 2 SLE patients was achieved, with only two outliers (Type1_275 and Type2_267) noted (FIG. 29). Unique patterns of co-expression module MEs and Type 1 and Type 2 SLE, respectively, can clearly be seen. Moreover, unique and opposing co-expression module ME correlations with SLEDAI and PSD scores or PGA Type 2 were found. Notably, MEs of co-expression modules identifying the interferon signature and monocytes were highly positively correlated to SLEDAI and negatively correlated to PSD score. Conversely, the MEs of the axon extension, muscle structure development and B cell modules were negatively correlated to SLEDAI and positively to PSD score. Finally, patient ancestry also was correlated with specific co-expression module MEs. The detailed correlations between the coefficients of specific gene module expression and clinical traits are shown in FIG. 39 and FIG. 40 and confirm the largely mutually exclusive relationship between co-expression module expression and Type 1 or Type 2 features.

To confirm this finding in an orthogonal manner, we used Gene Set Variation Analysis (GSVA) followed by stable k-means clustering of GSVA scores. This approach also effectively distinguished Type 1 and Type 2 SLE patients (FIG. 30).

Figure 31A:
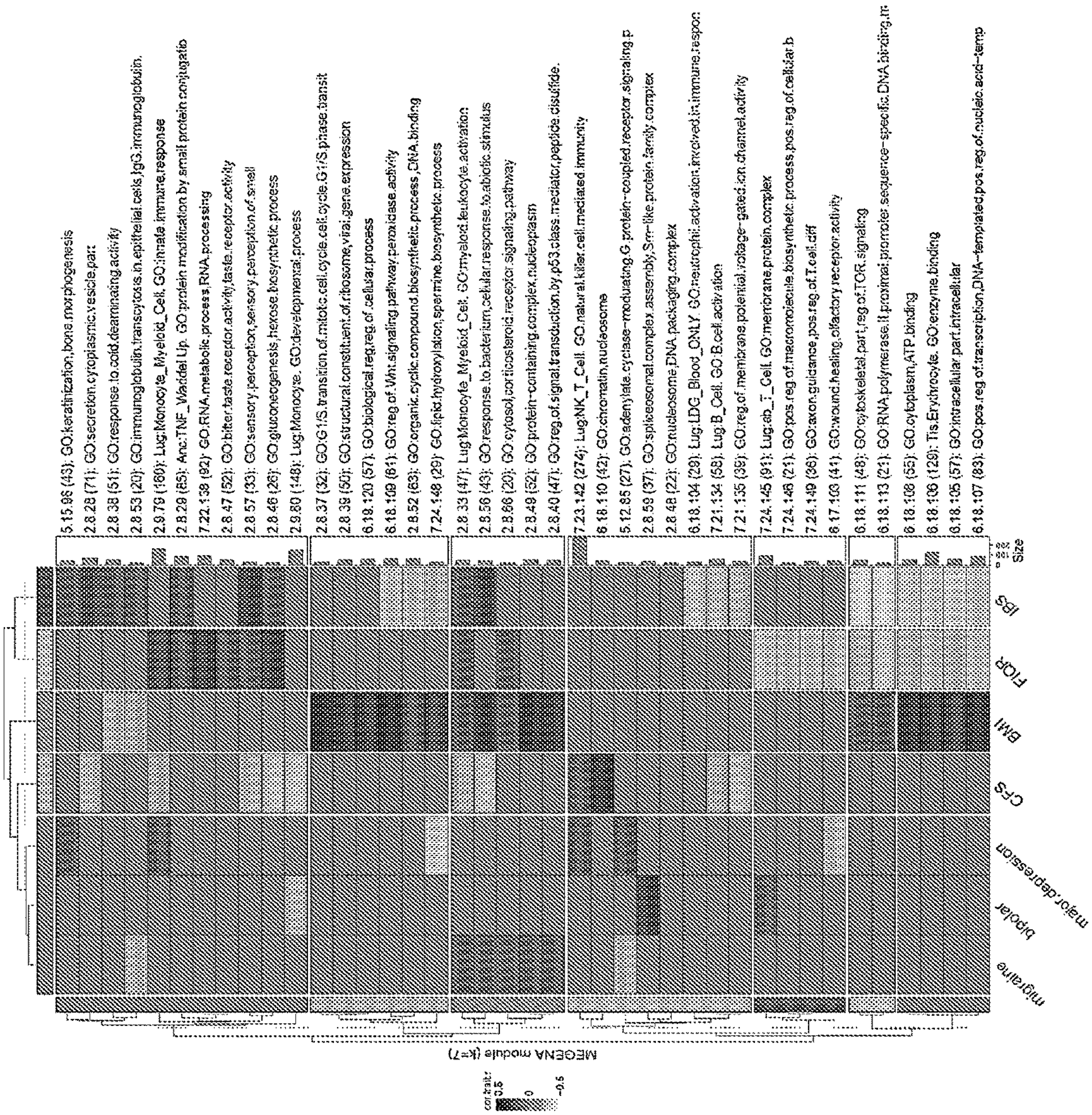
FIGS. 31A-B: Type 1/2 SLE MEGENA gen3 module preservation amongst the gen3 GSE67311 fibromyalgia (FM) MEGENA modules. Heatmap of the top 40 gen3 MEs significantly ($p<0.2$) correlated to the seven available patient traits in GSE67311 (FIG. 31A). Module preservation composite zsummary (z.summ) statistics calculated using the gen3 type 1/2 SLE modules as reference tested against the gen3 GSE67311 FM modules. Modules are considered minimally preserved with a z.summ>2, moderately preserved at z.summ>5, and well preserved at z.summ>10 (FIG. 31B).
Figure 31B:
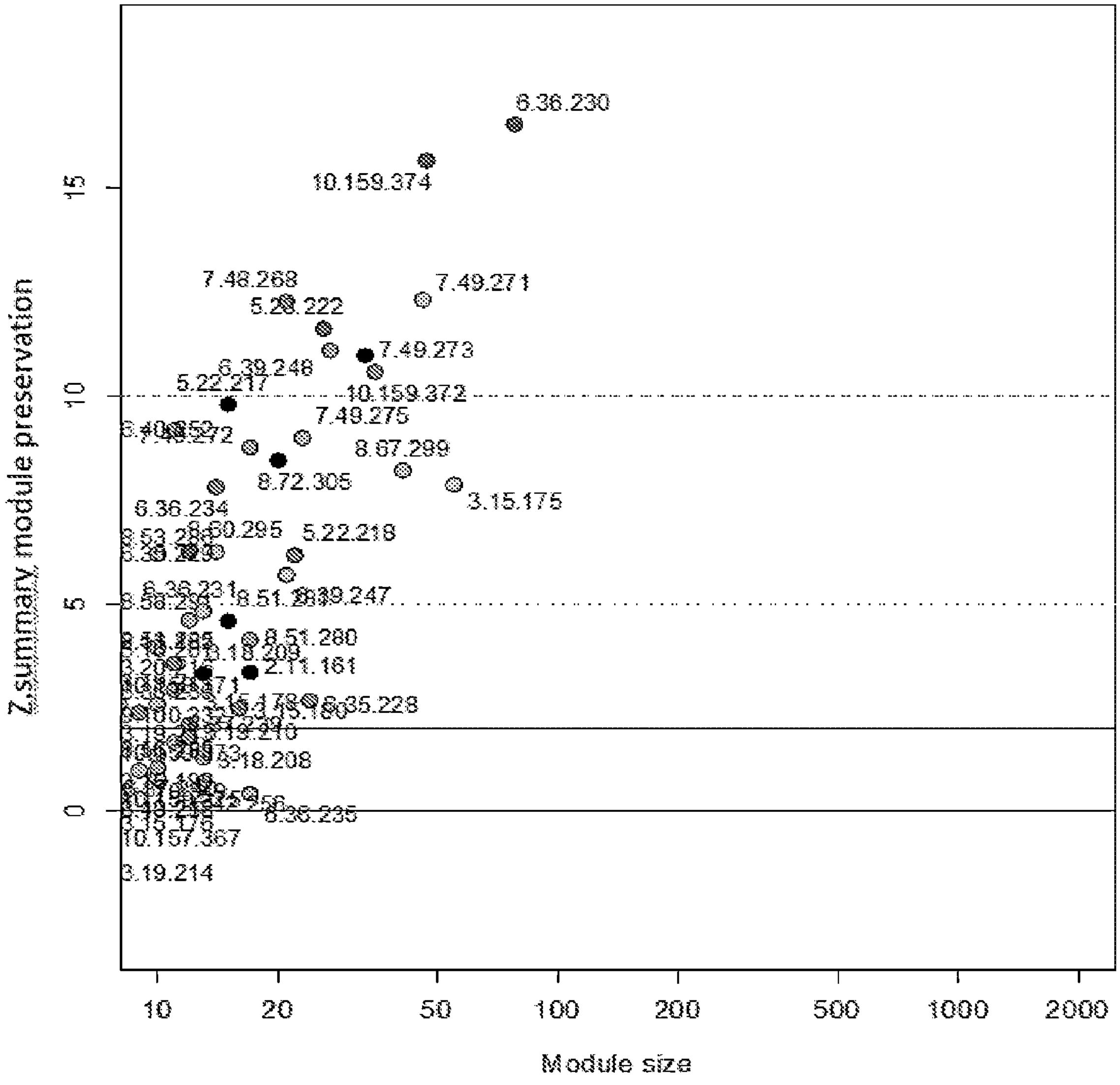

Co-expression Module Preservation Between Type 1 and Type 2 SLE and FM Samples: Next, we sought to determine the relationship between the co-expression modules used to distinguish Type 1 and Type 2 SLE and those generated from a dataset of idiopathic FM (GSE67311). MEGENA was employed to generate co-expression modules from the 70 FM patient samples in this dataset, and the MEs of the top 40 modules correlating to the seven clinical traits (bipolar disorder, BMI, CFS, FIQR, IBS, migraine, major depression) were visualized (FIG. 31A). Module preservation was then carried out between the Type 1 and Type 2 SLE co-expression modules and those generated from GSE67311 FM samples. Using a composite z summary score (FIG. 31B), 40 of the 157 Type 1 and Type 2 SLE modules were preserved (z score >2), 29 were moderately preserved (z score >5), and 21 were well preserved (z score >10) among the FM co-expression modules. Functional annotations of top preserved modules showed immune/inflammatory cells, including monocytes, T cells, neutrophils, B cells and plasma cells, functional activities, including IL-1, cytokines, MHC binding and IFN, and also glial cell migration and axon guidance (Table 13).

GSVA Further Distinguishes Type 1 and Type 2 SLE Patients and Identifies a Subset of Fibromyalgia (FM): We next assessed in greater detail 1) the molecular features that could distinguish Type 1 & 2 SLE and 2) the relationship between SLE gene expression abnormalities and those in FM. For this purpose, we used stable k-means clustering of GSVA scores to generate five distinct groups of co-expression modules that strongly correlated in opposing directions to patients with Type 1 SLE vs Type 2 SLE symptoms (FIG. 30). The green (second from top), blue (third from top), and light blue (fourth from top) GSVA module clusters are significantly positively correlated to Type 1 SLE activity, SLEDAI, and anti-dsDNA. The Type 1 SLE blue cluster modules were associated with monocytes and IFN. Notably, all were highly preserved in the GSE67311 FM dataset. The Type 1 SLE light blue cluster contained three modules related to cell cycle, whereas the Type 1 SLE green GSVA cluster included T cell pathways, antimicrobial peptide production, vesicle activity, phospholipid transport, transferase, GTPase binding, cell differentiation, cytoskeletal fiber activity and Wnt signaling. The green module also included Type 1 neurological pathway annotations for glial cell migration, neurotransmitter metabolism, and regulation of neuron death. We also found that most modules in the three Type 1 SLE clusters significantly positively correlated to Hispanic ancestry and MMF usage, and the green Type 1 SLE cluster significantly correlated to prednisone usage.

The red (top) and purple (bottom) GSVA module MEs significantly positively correlated to patients with active Type 2 SLE symptoms as well as PSD score and total areas of pain. The Type 2 SLE red cluster included oxidative phosphorylation (ox-phos) and metal ion transmembrane transport, whereas the Type 2 SLE purple module included monocyte secretion, additional cation transmembrane transport, voltage-gated calcium channel complexes, inflammatory response components, sterol desaturase activity, the carnitine shuttle, and muscle structure development. Of note, the purple module also contained neurological pathways, including synapse pruning, regulation of axon extension, and accompanying protein localization to the axonal paranode region.

Amongst the GSVA green Type 1 SLE modules, vesicle activity and neuronal death regulation were moderately preserved in FM. Modules associated with Type 2 SLE were well preserved in FM, including those associated with cation transport/carnitine shuttle as well as the calcium channel module. The Type 2 SLE associated monocyte secretion/synapse pruning and muscle structure development modules were moderately preserved in the FM test study. Together, these findings suggest that specific co-expression modules for both Type 1 and Type 2 SLE are also expressed by unique subsets of FM patients.

Figure 32A:
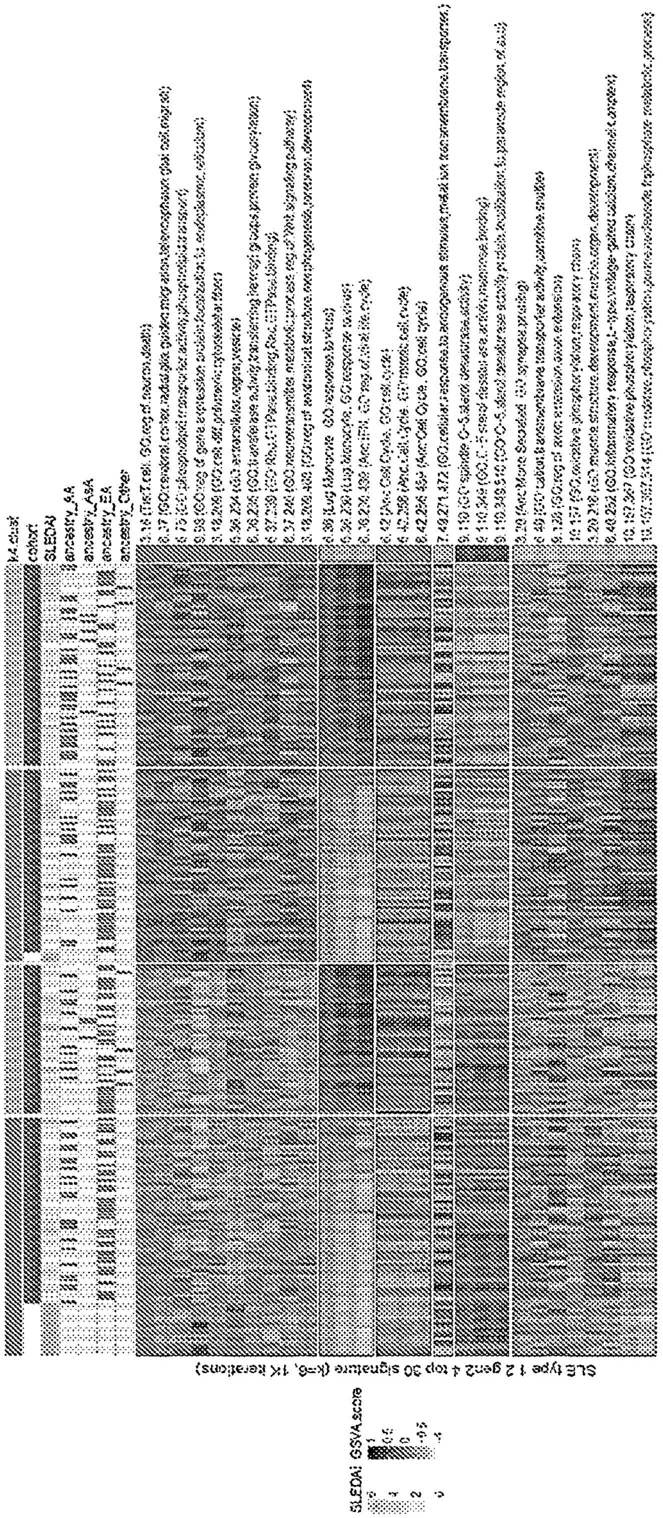
FIGS. 32A-B: GSE45291 inactive SLE (SLEDAI<6) patients GSVA using Type 1/2 SLE self top 30 modules. The top5k rowVar genes from GSE45291 were submitted to GSVA analysis using the top 30 significant ($p<0.2$) Type 1/2 SLE gen2.4 modules as GSVA signatures. Column annotations include cohort (healthy or SLE), SLEDAI score, and ancestral background (AA African ancestry, AsA Asian ancestry, EA European ancestry, and other). Columns were optimally clustered (1k iterations) into k=4 patient clusters and rows optimally clustered into k=6 groups of modules (FIG. 32A). GSVA enrichment score row means and sample traits were calculated per the four patient clusters. Column annotations include cosine similarity to the Type 1 SLE & Type 2 SLE patient clusters (FIG. 32B).
Figure 32B:
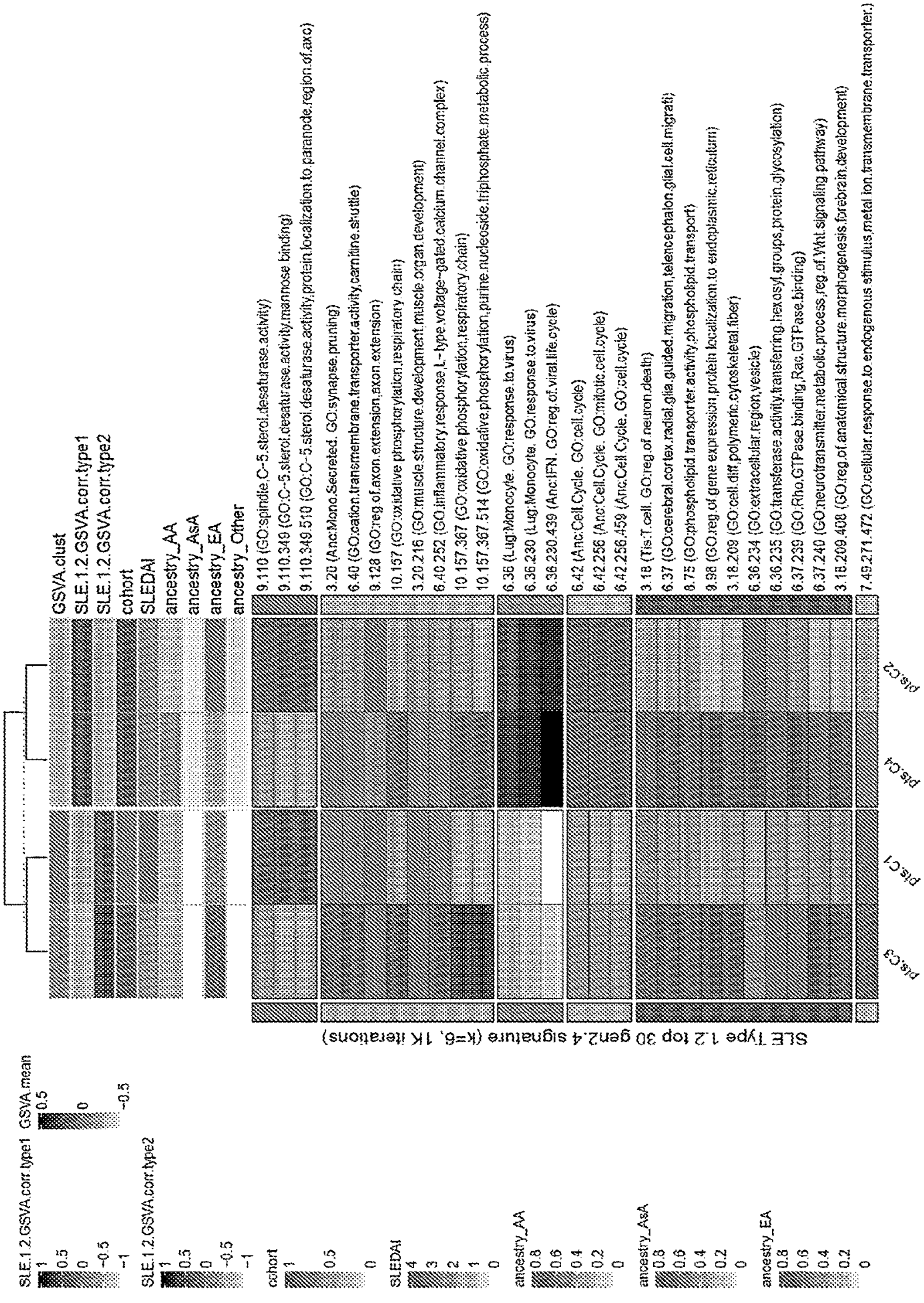

We identified two patient clusters in GSE67311 FM that had high negative or positive cosine similarity to Type 1 & 2 SLE GSVA patients (FIG. 32). To explore the nature of these FM subsets in greater detail, we examined them for enrichment of immune and inflammatory cells and processes using GSVA and gene sets known to identify these cells and pathways. Stable k-means clustering effectively identified subsets of FM patients that were Type 1- and Type 2-like; we further demonstrated through cosine association that the Type 1 SLE-like FM patients were also enriched for inhibitory macrophages, monocytes, neutrophils, as well as the interferon, TNF and IL-1 pathways. In contrast, Type 2 SLE-like FM samples were enriched for B cells, plasma cells, and Ig chains.

Protein-protein Interaction (PPI) Analysis Identifies Biologic Function of Co-expression Modules: To provide insight into the biologic functions of genes within co-expression modules, we assessed genes within the top 40 MEGENA modules for PPIs using the STRING database (17). We found that 34 of the top 40 co-expression modules contained genes that were intraconnected by known PPIs, with 25 exhibiting 10-50% and 5 having >50% PPI intraconnectedness (Table 14). This finding confirms that the co-expression modules have captured known molecular pathways in an unsupervised manner. Type 1 SLE PPI intraconnected modules included cell cycle, T cells/regulation of neuronal death, extracellular region/vesicles, and most highly IFN and monocytes. Type 2 SLE PPI intraconnected modules included monocyte secretion/synapse pruning, cation transport, muscle structure development, and the inflammatory response/voltage gated calcium channel complexes.

Figure 33A:
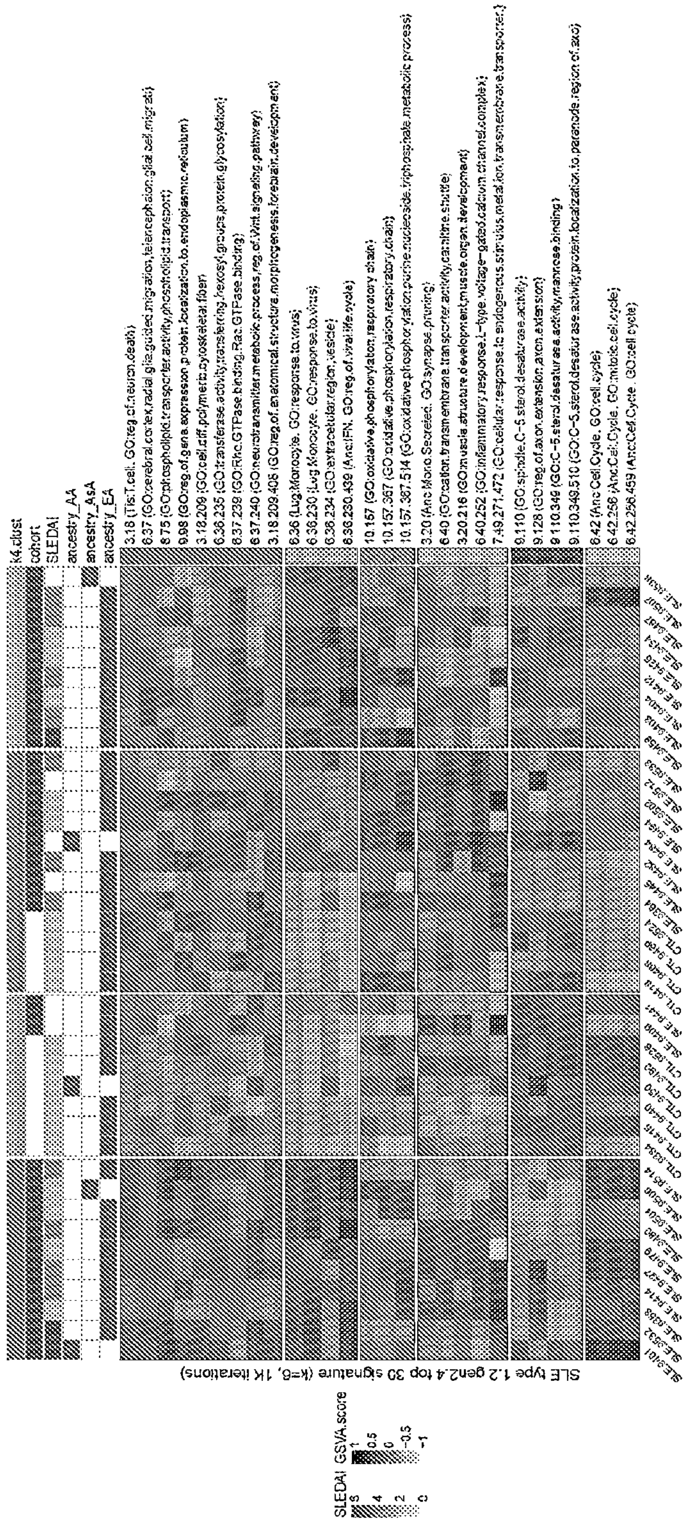
FIGS. 33A-B: GSE49454 inactive SLE (SLEDAI<6) patients GSVA using Type 1/2 SLE self top 30 modules. The top5k rowVar genes from GSE49454 were submitted to GSVA analysis using the top 30 significant ($p<0.2$) Type 1/2 SLE gen2.4 modules as GSVA signatures. Column annotations include cohort (healthy or SLE), SLEDAI score, and ancestral background (AA African ancestry, AsA Asian ancestry, and EA European ancestry). Columns were optimally clustered (1k iterations) into k=4 patient clusters and rows optimally clustered into k=6 groups of modules (FIG. 33A). GSVA enrichment score row means and sample traits were calculated per the four patient clusters. Column annotations include cosine similarity to the Type 1 SLE & Type 2 SLE GSVA patient clusters (FIG. 33B).
Figure 33B:
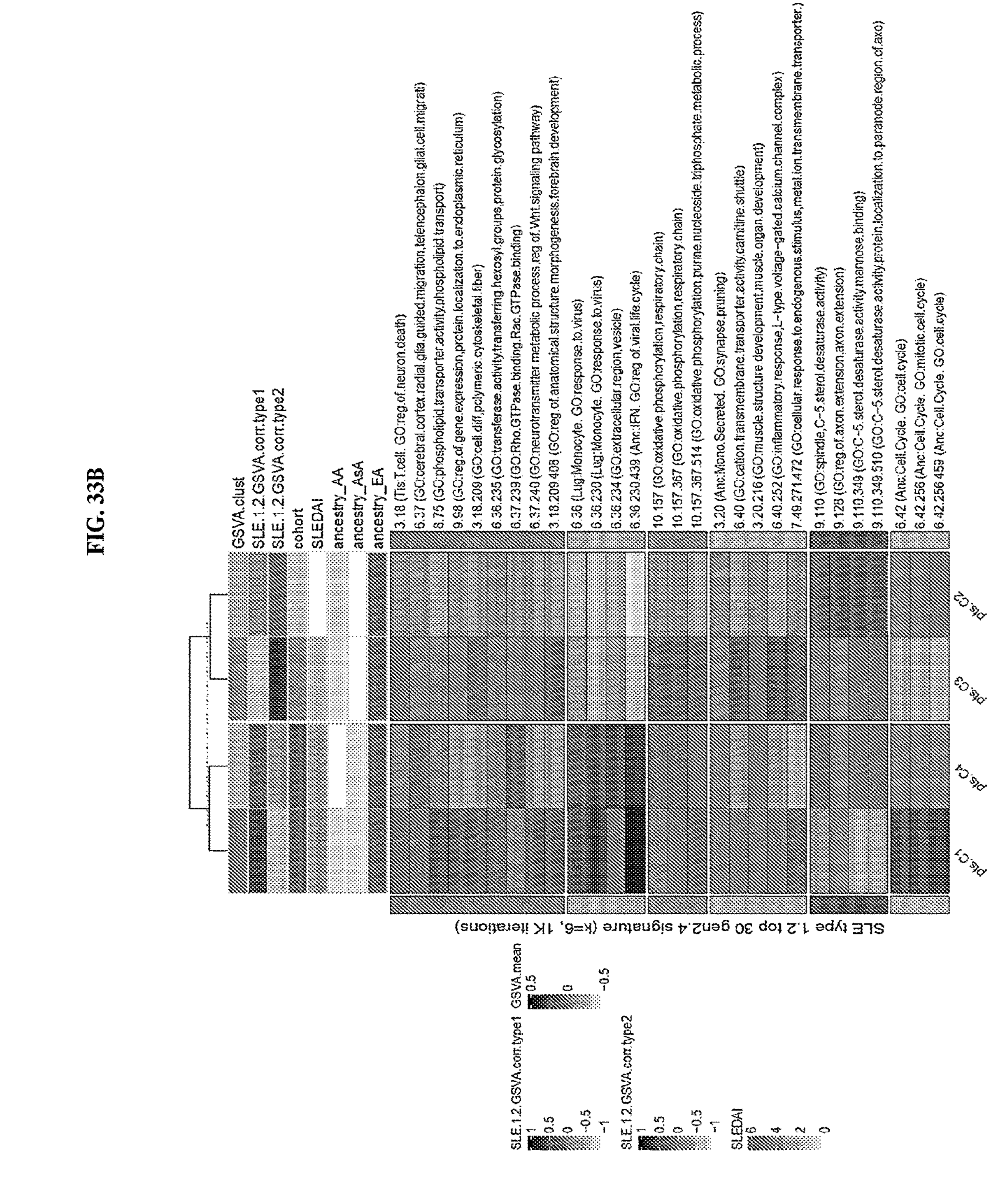

Type 1 and 2 SLE Modules Identify a Subset of Inactive SLE Patients: We next determined whether patients with the Type 2 SLE signature could be found in other datasets of patients (GSE45291 and GSE49454) with inactive SLE (SLEDAI<6). Stable k-means clustering based on GSVA scores using the Type 1 and Type 2 SLE co-expression clusters formed four distinct groups within each study (FIGS. 32 & 33). Amongst these inactive SLE patient groups, we identified two groups from each that had positive correlations to Type 2 SLE co-expression clusters. The four inactive patient groups were visualized together with the Type 2 SLE patient group (FIG. 34). Stable k-means clustering generated two meta clusters where the Type 2 SLE patients (red arrow) were most similar to inactive SLE patients in GSE4529 cluster 2 and GSE49454 cluster 2. Further, the module gene expressions they exhibited in common and showed positive correlations to Type 2 SLE included cation transport, muscle structure development, monocyte secretion, synapse pruning, ox-phos, voltage-gated calcium channel complexes, cation transport, axonal paranode protein localization, axon extension, and sterol desaturase activity.

Figure 41A:
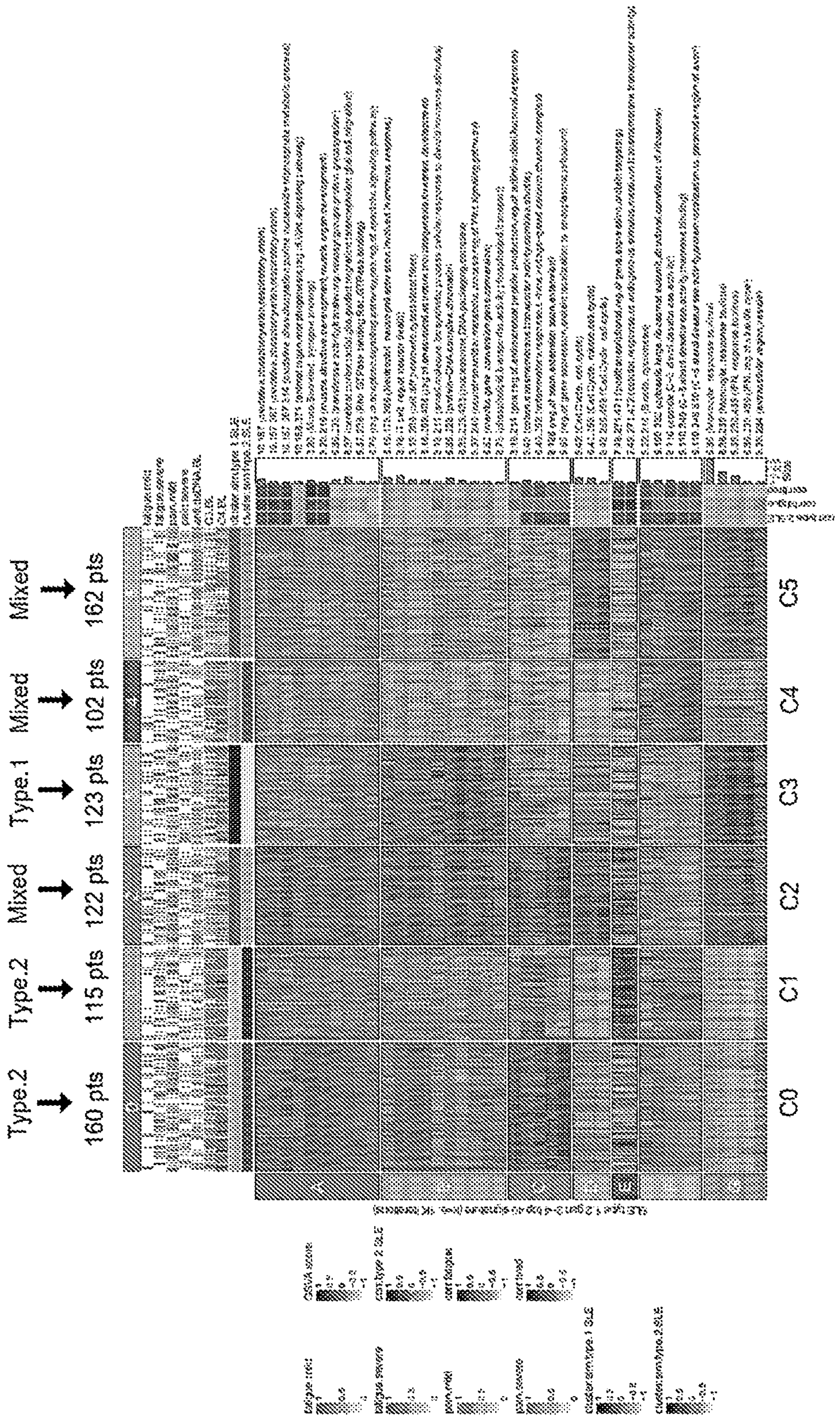
FIGS. 41A-C: Analysis of patients with active SLE (GSE88884) identifies patient groups with severe fatigue. GSVA was carried out on GSE88884 (ILLUM-2) using the top 40 type 1/2 SLE cohort modules as signatures. Stable k-means clustering of GSVA enrichment scores formed 6 patient clusters and 6 module clusters. Column annotations include mild or severe fatigue (mild 1-3, severe 8-10) using the Brief Fatigue Inventory, mild or severe pain scored using the Brief Pain Inventory (mild 1-4, severe 7-10), anti-dsDNA, C3 and C4 at baseline (low −1, normal 0, high +1), and mean cluster cosine similarity to the Type 1 SLE & Type 2 SLE patient clusters. ILLUM-2 patient cluster 3 was most similar by cosine similarity to type 1 SLE signatures, and clusters 0 & 1 were most similar to type 2 SLE signatures. Clusters 2, 4, and 5 were mixed (type.2.SLE cosine similarities-0.34, +0.36, and −0.23, respectively). Row annotations indicate modules that were significantly correlated to type 1/2 SLE, fatigue, and tired (FIG. 41A). Proportion test analysis significantly ($p<0.05$) identifies ILLUM-2 patient groups with fatigue by the Brief Fatigue Inventory (mild 1-3, severe 8-10) (FIG. 41B) and those with pain scored using the Brief Pain Inventory (mild 1-4, severe 7-10) (FIG. 41C). Patient clusters marked as (*) exhibit a significant difference between the frequency of severe and mild fatigue or pain, respectively.
Figure 41B:
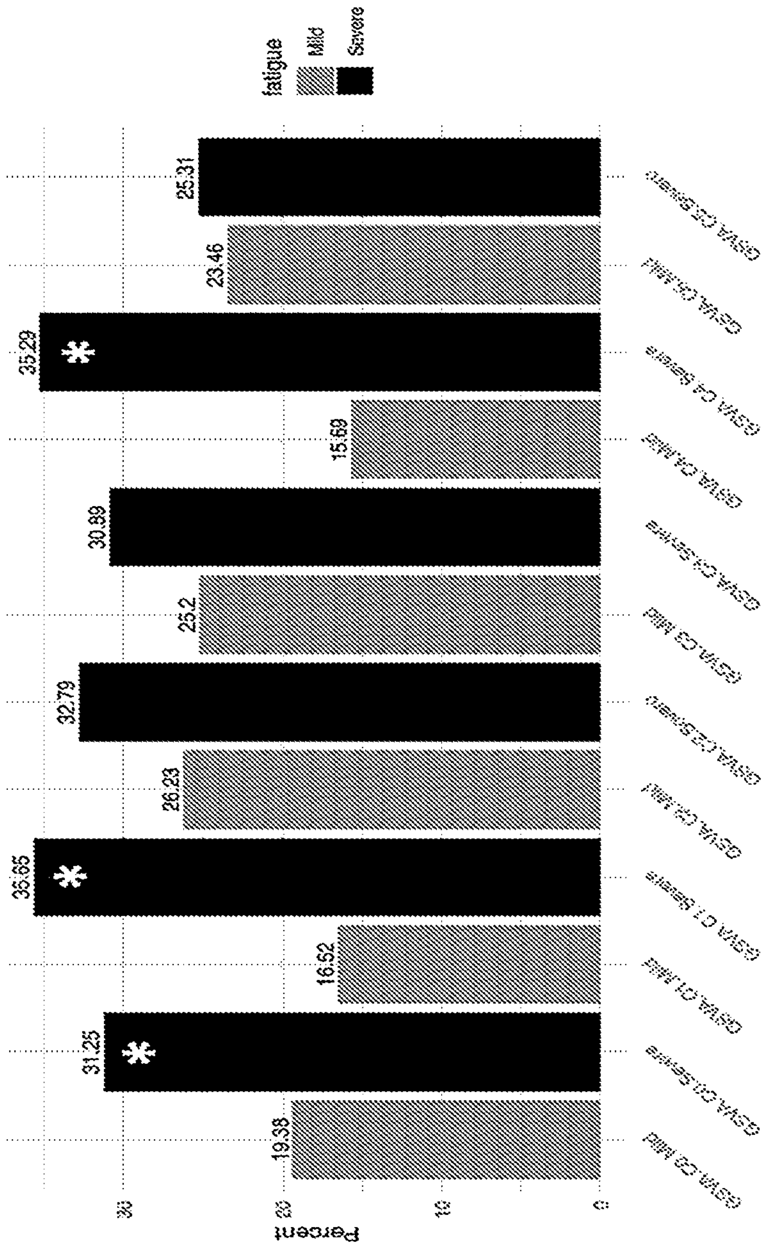
Figure 41C:
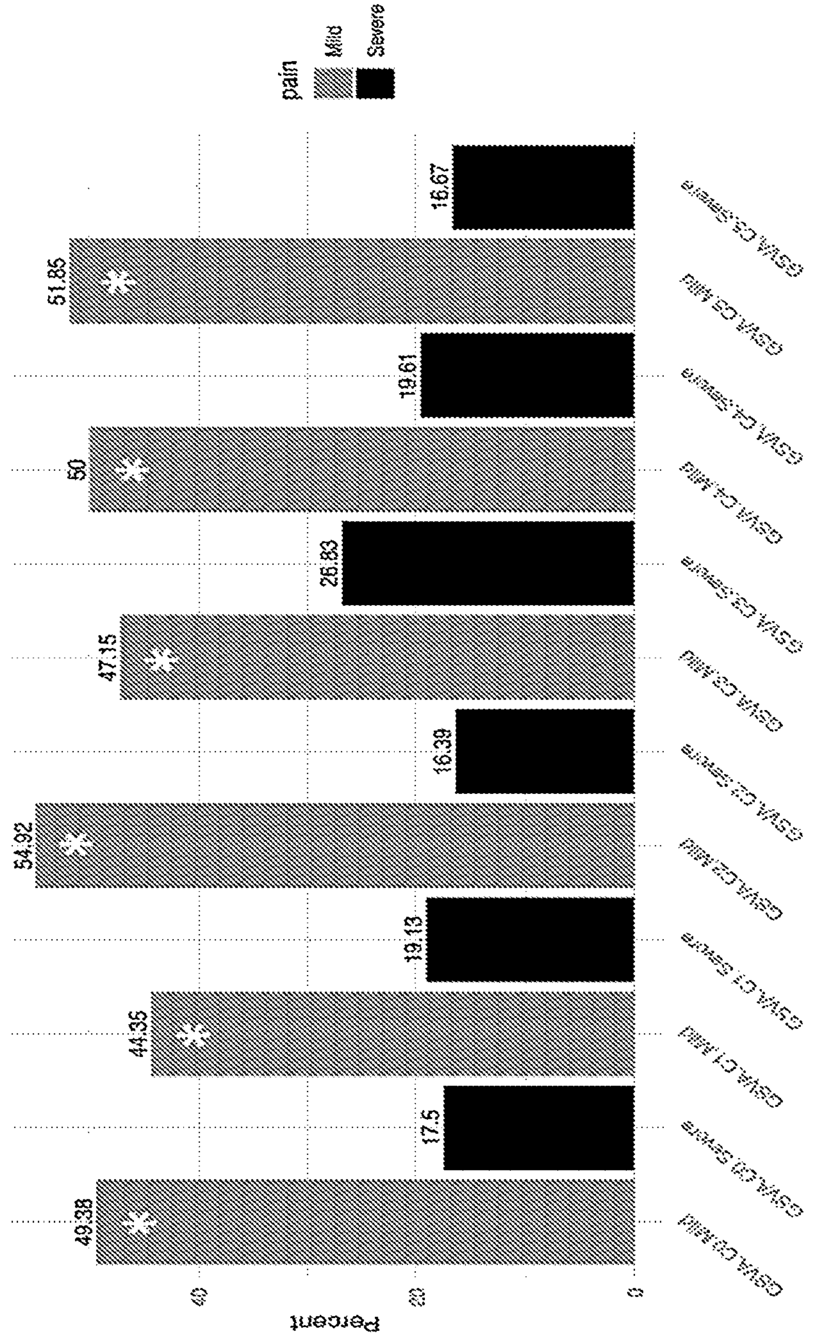

SLE Subsets Identified by Type 2 SLE Gene Modules Have Severe Fatigue More Frequently: Finally, we sought to determine whether subsets of SLE patients identified by enrichment of Type 2 SLE modules have a greater frequency of severe fatigue. We employed GSE88884 (Illuminate 2) for this analysis even though this dataset set was limited to patients with active disease (SLEDAI of 6 or more) because fatigue and pain were measured, albeit using different metrics (Brief Fatigue Inventory and Brief Pain Inventory). As can be seen in FIG. 41, using k-means clustering based on enrichment of the 40 SLE Type 1 and 2 co-expression modules and GSVA, GSE88884 samples were separated into 6 subsets, 2 with similarity to Type 2 SLE, 1 with similarity to Type 1 SLE, and 3 with mixed features. When these subsets were interrogated for the frequency of severe fatigue, the two Type 2-like subsets were significantly enriched for patients with severe fatigue along with one of the mixed subsets. Further analysis of this mixed subset indicated minimal or no enrichment of the horizontal module cluster G containing monocyte and interferon signatures. It is notable that all subsets contained significantly more patients with mild pain with no differences between the subsets.

Figure 37A:
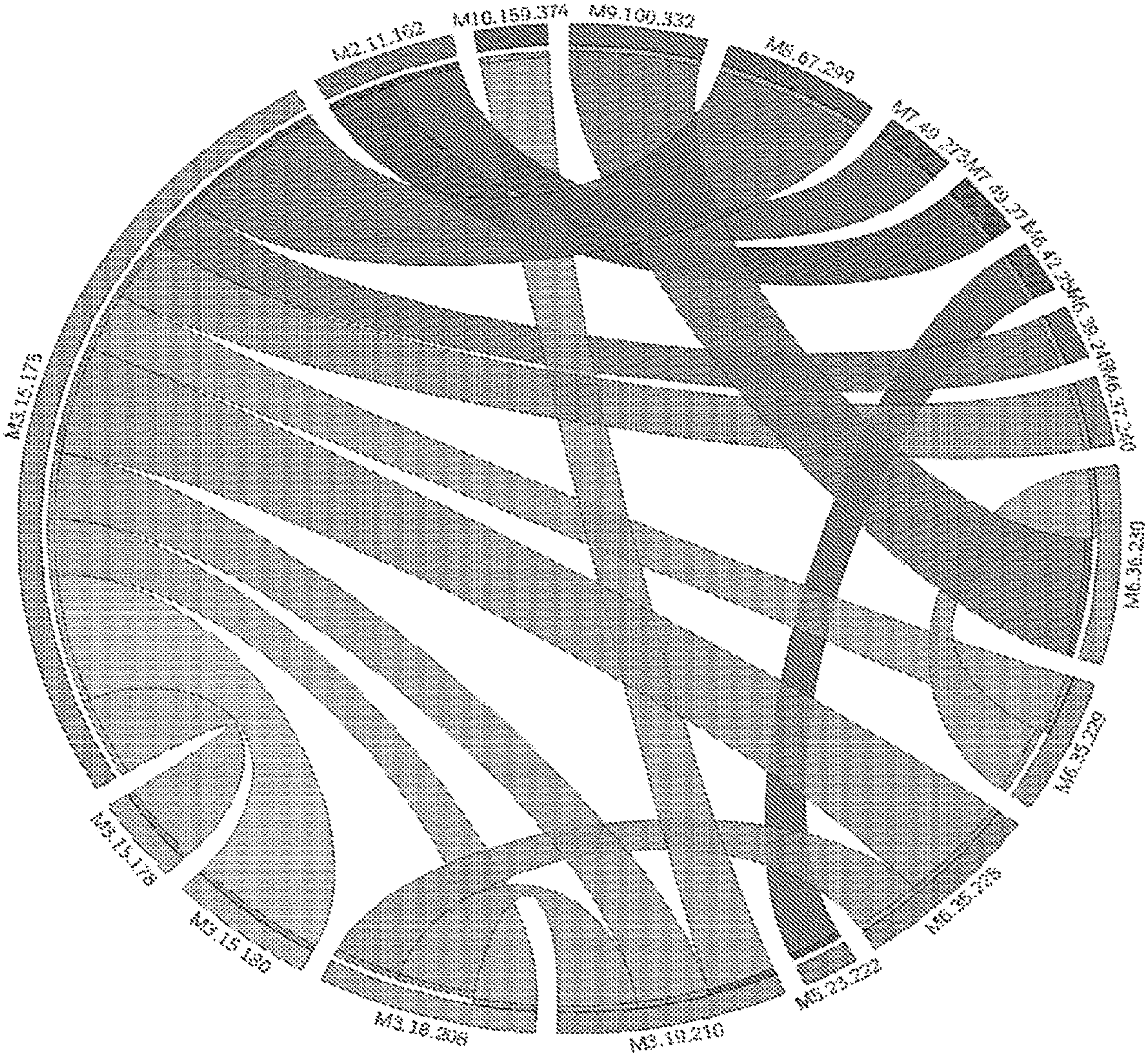
FIGS. 37A-B: Differentially expressed gene pairs distinguish Type 1 & Type 2 SLE patients. Top type 1 SLE and type 2 SLE DGCA intermodular pair totals visualized using circosplots to illustrate the degree of intermodular pair totals between gen3 module largely unique to each condition. Type 1 SLE gene pairs (FIG. 37A) and Type 2 SLE gene pairs (FIG. 37B). Bolded modules were involved in the highest numbers of totaled module pairings.
Figure 37B:
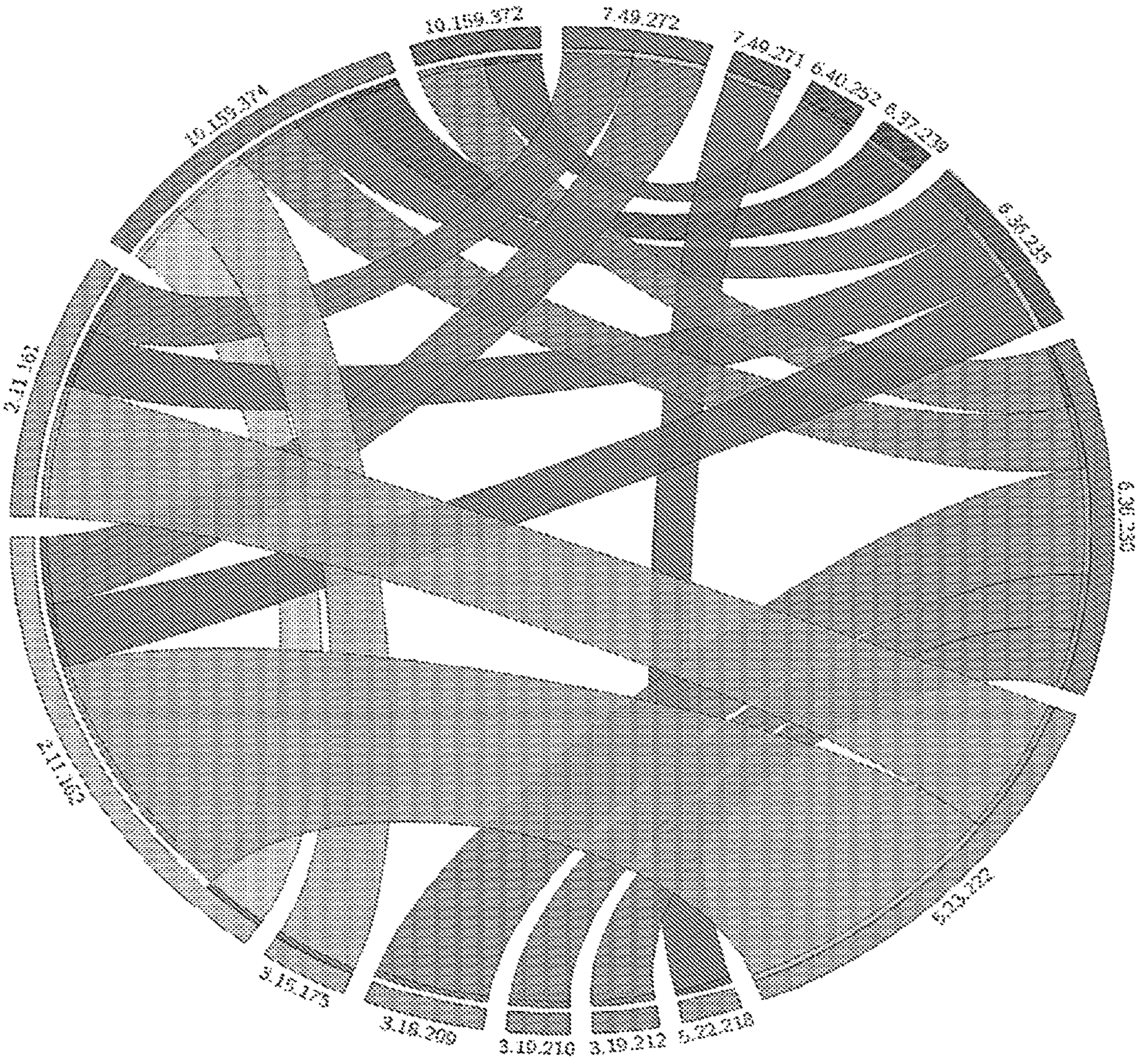

DEG Pairs Distinguish Type 1 and Type 2 SLE Samples: Finally, we employed Differential Gene Coexpression Analysis (DGCA) (18) as a complementary method to distinguish patients with active Type 1 or Type 2 SLE symptoms in greater detail. Here, DGCA was used to detect intermodular pairs of genes as a way to delineate potential differences between the molecular communication inherent in Type 1 and Type 2 SLE pathology. As seen in FIGS. 37A-B and Tables 15 & 16, top unique intermodular connections distinguished Type 1 SLE from Type 2 SLE patients. Type 1 SLE patients were remarkable for neutrophil involvement/cell activation immune response and monocytes, and Type 2 SLE patients largely for B cell and plasma cell interactions.

Figure 35:
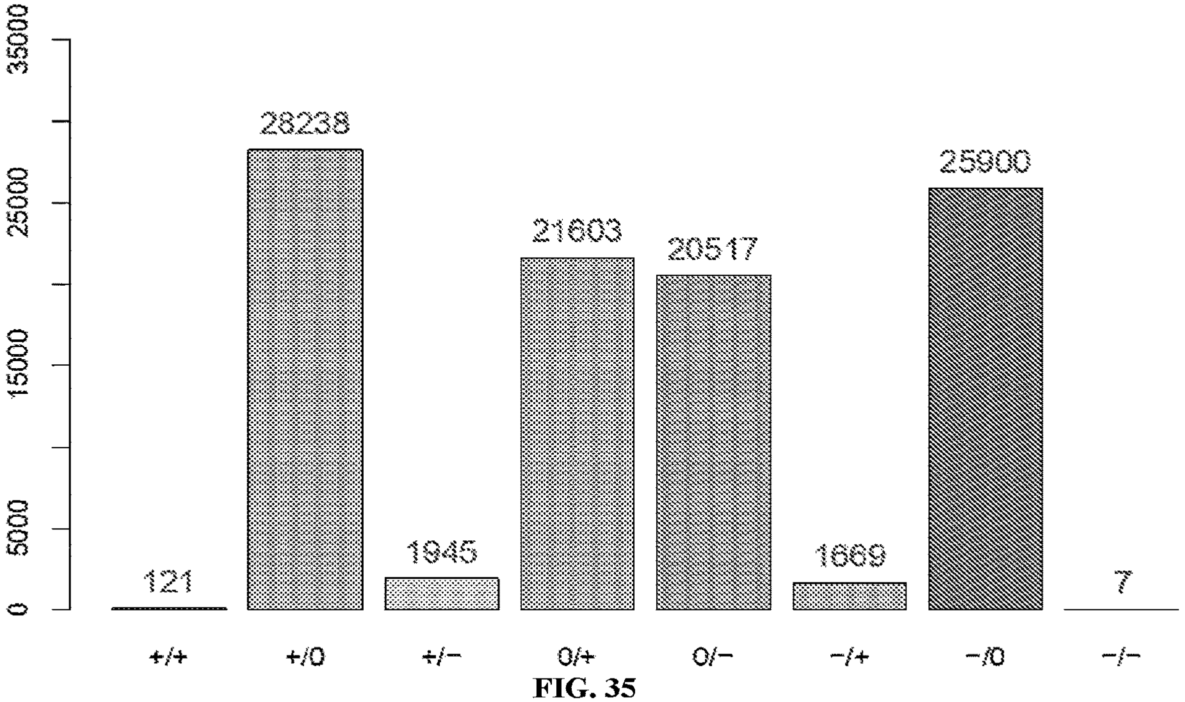
FIG. 35: Global class pair totals amongst the top 100,000 significant DGCA pairs confirmed four classtypes of interest were in greatest abundance and analytic fidelity was largely retained.

The top 5,000 row variances genes were submitted to the DGCA package using cohort (Type 1/2 SLE) as the condition comparator. DGCA forms a list of every gene pair and correlates the difference in gene expression between the pair amongst type 1 and type 2 SLE patients. This is measured as the Z score difference between the two with an associated p value of significance and includes the correlation of the pair to either type. Only the top 100,000 significant pairs were retained (p.val<0.05). Genes were further annotated by which MEGENA gen3 module they were found in, if any. A pair was considered intramodular if both members of the gene pair were found in the same gen3 module, and intermodular if the pair members were found in different modules. Intramodular pairs were later discarded as there's greater biological interest in intermodular pairs which suggest molecular interactions between discrete regulatory pathways. (Table 18). DGCA assigns a class type indicating which correlation direction the pair exhibited (type 1/type 2). Only the −/0, +/0, 0/−, and 0/+ class types were later retained for further analysis where classes −/0 and +/0 indicate pairs unique to type 1 SLE, and 0/− and 0/+ pairs are unique to type 2 SLE (Table 19). Global class pair totals amongst the top 100,000 significant DGCA pairs were briefly inspected which confirmed the four class types of interest were in greatest abundance and analytic fidelity was largely retained (FIG. 35).

Figure 36A:
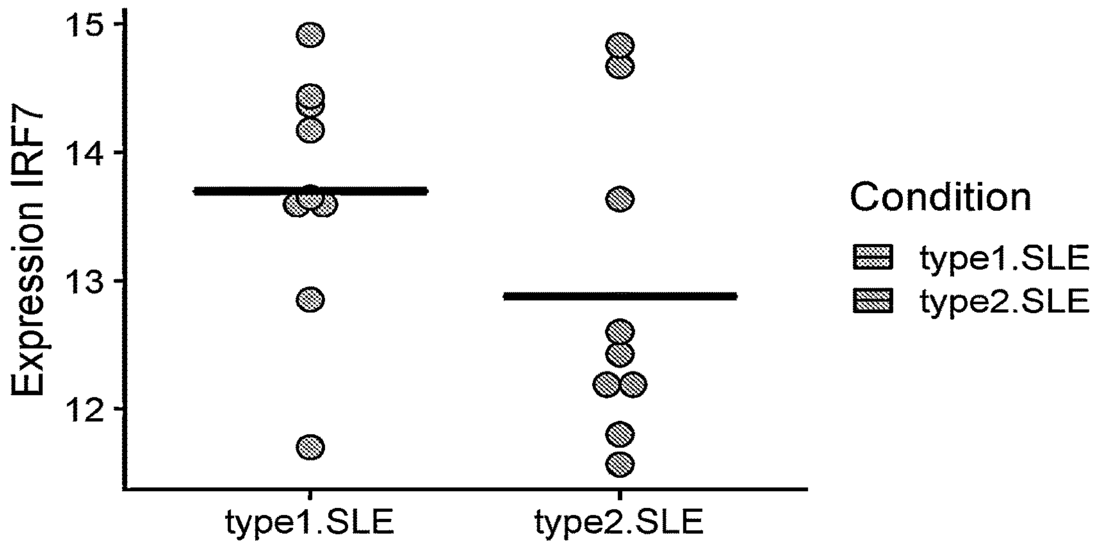
FIGS. 36A-C: DGCA gene intermodular pair correlation example. The genes IRF7 (interferon regulatory factor 7 found in MEGENA module 6.39.248) and HLA-G (major histocompatibility complex, class I, G found in module 6.36.230) were selected to illustrate a DGCA pair correlation which is DGCA at its most granular level. This intermodular gene pair was also selected for illustration as the pair is highly correlated to type1.SLE. Further, the pair is part of the interferon gene signature (IGS) which at large was found to highly segregate type 1 inflammatory SLE from type 2 painful SLE patients. Expression of IRF7 in type 1 SLE vs. type 2 SLE patients (FIG. 36A) and the same for HLA-G (FIG. 36B). Correlation of gene expression of the pair in type 1 SLE vs type 2 SLE (FIG. 36C) is markedly different and resulted in classification of this pair as +/0 (positive gene pair correlation in type. 1.SLE, no pair correlation in type.2.SLE).
Figure 36B:
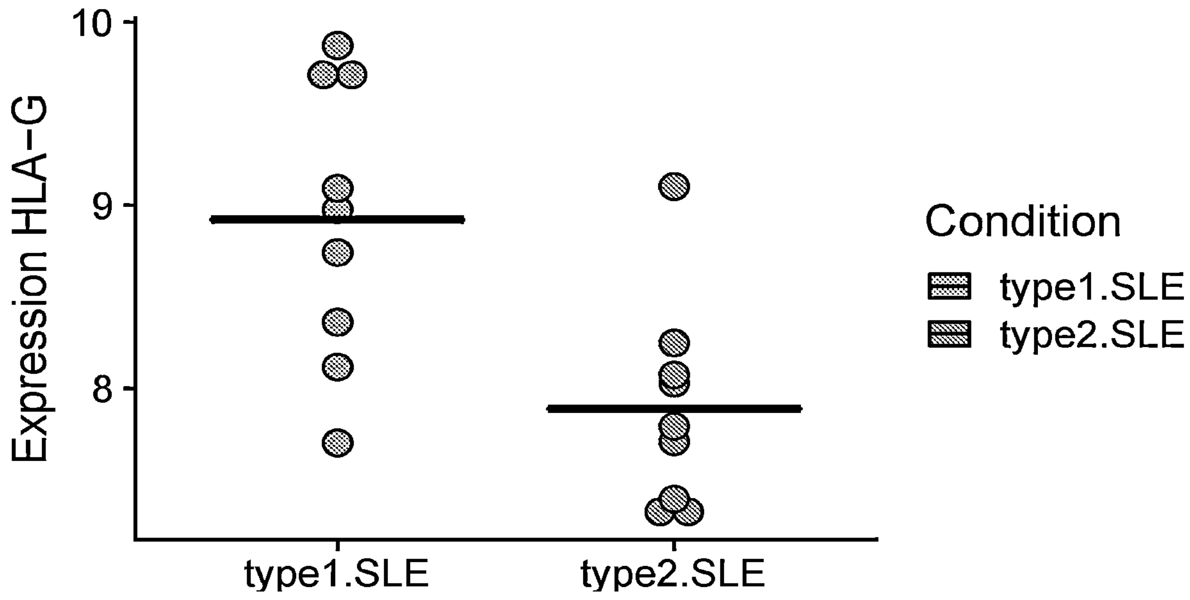
Figure 36C:
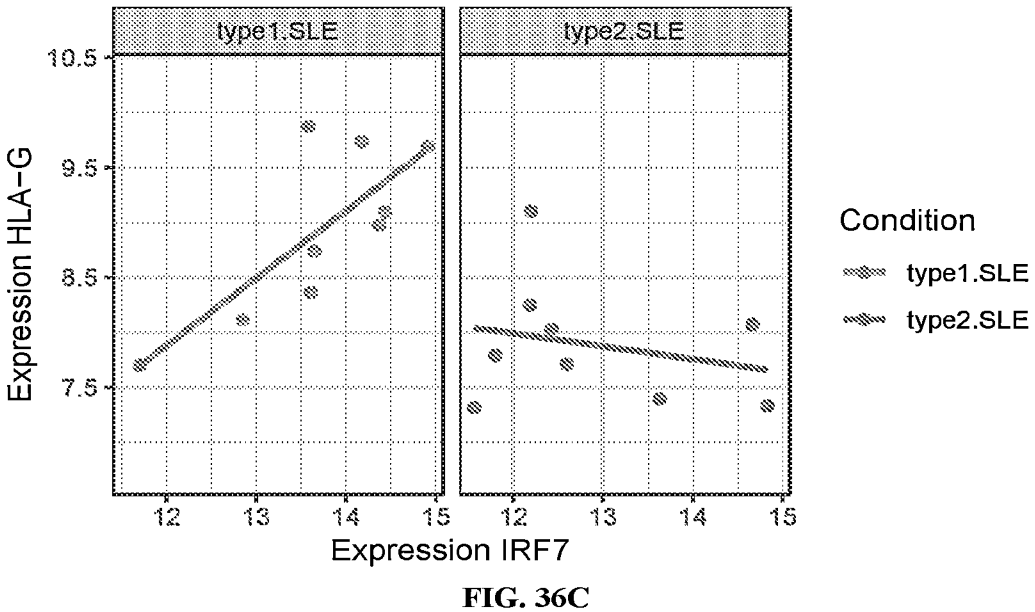
Figure 38:
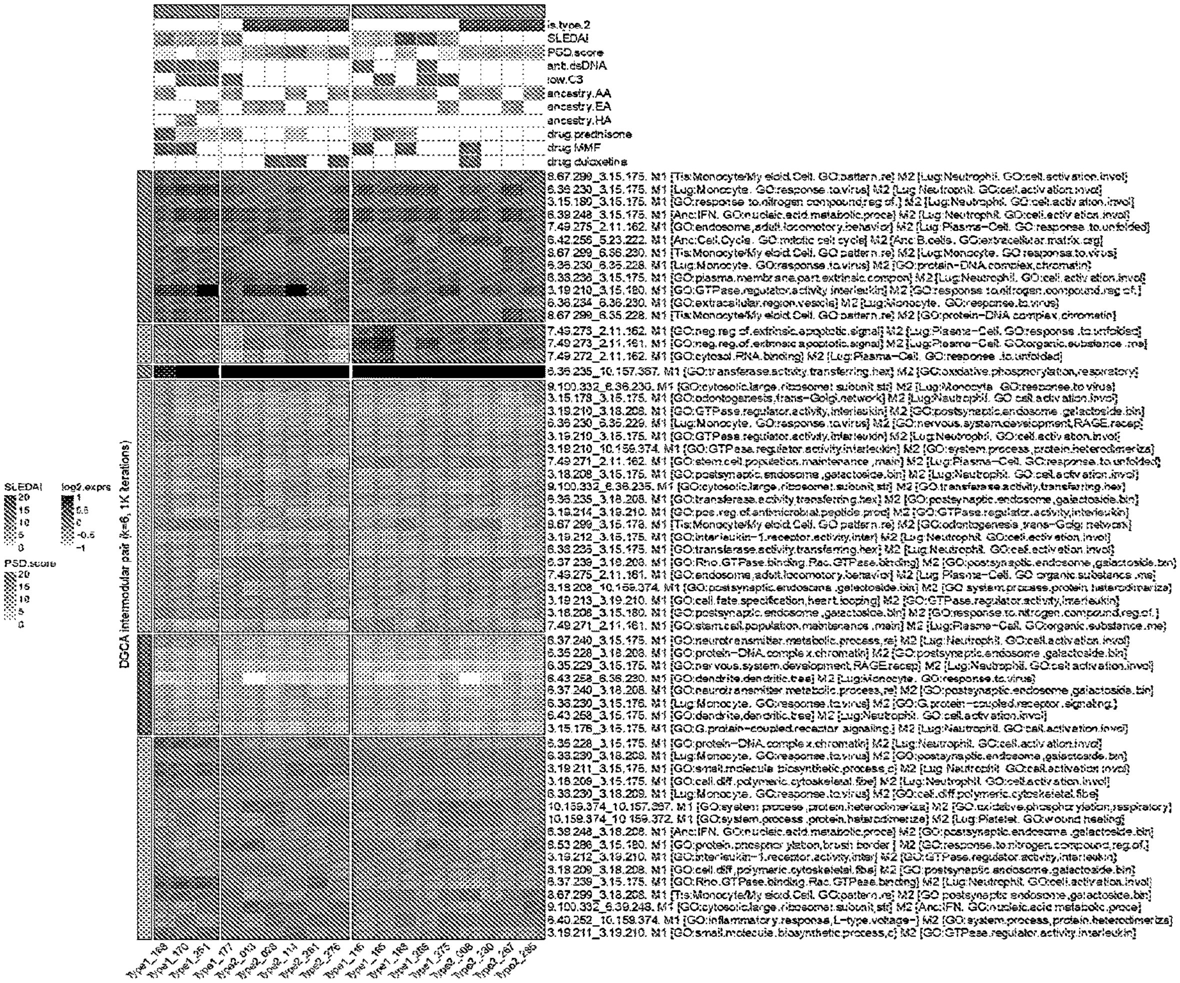
FIG. 38: Patient clustering using totaled DGCA pairings largely segregates type 1 inflammatory SLE from type 2 painful SLE. Gene expression within top intermodular+/0 DGCA pairs (pairs positively correlated to type 1 SLE) was calculated per patient and subjected to idealized k means clustering forming 3 patient clusters. Only one type 1 SLE patient and two type 2 SLE patients were miscategorized. Interestingly through this approach we found four patients in the green patient cluster whose gene expressions are markedly different than the other patients. The primary utility of DGCA analysis is to help elucidate implied molecular interactions between distinct gene modules. However, this orthogonal approach also helps validate the idealized k means clustering performed on both module eigengene (ME) per patient and GSVA enrichment score clustering per patient.

As shown in FIGS. 36A-C, DGCA gene intermodular pair correlation example. The genes IRF7 (interferon regulatory factor 7 found in MEGENA module 6.39.248) and HLA-G (major histocompatibility complex, class I, G found in module 6.36.230) were selected to illustrate a DGCA pair correlation which is DGCA at its most granular level. This intermodular gene pair was also selected for illustration as the pair is highly correlated to type1.SLE. Further, the pair is part of the interferon gene signature (IGS) which at large was found to highly segregate type 1 inflammatory SLE from type 2 painful SLE patients. Expression of IRF7 in type 1 SLE vs. type 2 SLE patients (FIG. 36A) and the same for HLA-G (FIG. 36B). Correlation of gene expression of the pair in type 1 SLE vs type 2 SLE (FIG. 36C) is markedly different and resulted in classification of this pair as +/0 (positive gene pair correlation in type. 1.SLE, no pair correlation in type.2.SLE). Top DGCA type 1 inflammatory SLE intramodular pair totals per gen3 module (Table 20). Intermodular gene pairs were totaled per gen3 MEGENA module pairing along with the class type totals. These were sorted in descending order of type1.ttls and the top 17 gen3 intermodular pairings selected for further visualization and discussion. Amongst others, interesting pairings included upregulated IFN activity in type 1 SLE which was markedly lower in type 2 SLE. Extensive neutrophil and plasma cell pairs were also seen upregulated in type 1 SLE but not type 2, further reinforcing the observation of distinct regulatory pathways segregating type 1 inflammatory SLE from type 2 non-inflammatory SLE. Top DGCA type 2 non-inflammatory SLE intramodular pair totals per gen3 module (Table 21). Intermodular pairs were totaled as they were for type 1 SLE, but sorted by descending type2.ttls. Largely unique to type 2 noninflammatory SLE are upregulated interactions between B cells and plasma cells and downregulated interactions of plasma cells with RNA binding and transferase functions. Certain monocyte interactions were uniquely downregulated in type 2 SLE including interactions with IL-1. Platelet interactions with L-type voltage-gated calcium channel complexes were also uniquely downregulated in type 2 SLE. This point was discussed as it hearkens to disordered neuromuscular junction activity seen in idiopathic fibromyalgia patients described in the literature. Like the largely unique type 1 SLE DGCA pair totals, these type 2 SLE pair totals further discriminate type 1 from type 2 SLE using this novel DGCA approach integrated with gen3 MEGENA modules. FIGS. 37A and B, and Table 22 and 23, show differentially expressed gene pairs distinguish Type 1 & Type 2 SLE patients. Top type 1 SLE and type 2 SLE DGCA intermodular pair totals visualized using circos plots to illustrate the degree of intermodular pair totals between gen3 module largely unique to each condition. Type 1 SLE gene pairs (FIG. 37A, Table 22) and Type 2 SLE gene pairs (FIG. 37B, Table 23). Bolded modules were involved in the highest numbers of totaled module pairings. Patient clustering using totaled DGCA pairings largely segregates type 1 inflammatory SLE from type 2 painful SLE (FIG. 38). Gene expression within top intermodular +/0 DGCA pairs (pairs positively correlated to type 1 SLE) was calculated per patient and subjected to idealized k means clustering forming 3 patient clusters. Only one type 1 SLE patient and two type 2 SLE patients were miscategorized. Interestingly through this approach we found four patients in the green patient cluster whose gene expressions are markedly different than the other patients. The primary utility of DGCA analysis is to help elucidate implied molecular interactions between distinct gene modules. However, this orthogonal approach also helps validate the idealized k means clustering performed on both module eigengene (ME) per patient and GSVA enrichment score clustering per patient.

Figure 42:
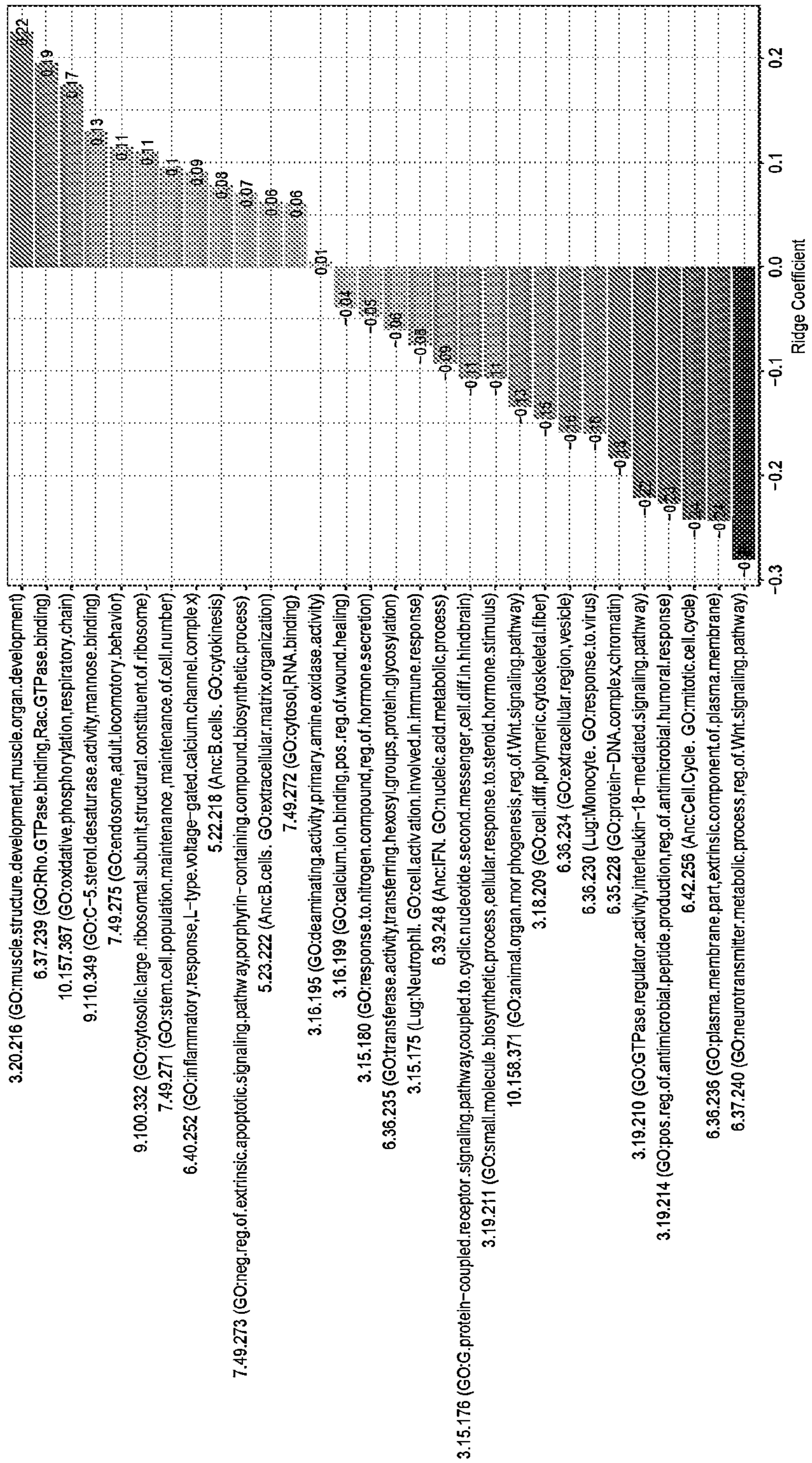
FIG. 42: Molecular-based GSVA module scoring coefficients prioritizes modules. GSVA gen3 module enrichment values were submitted to logistic regression to generate module coefficients. These were subsequently adjusted using either lasso and or ridge regression penalization. Final module coefficients were visualized using a waterfall plot sorted in descending order of positive to negative module coefficients.
Figure 43:
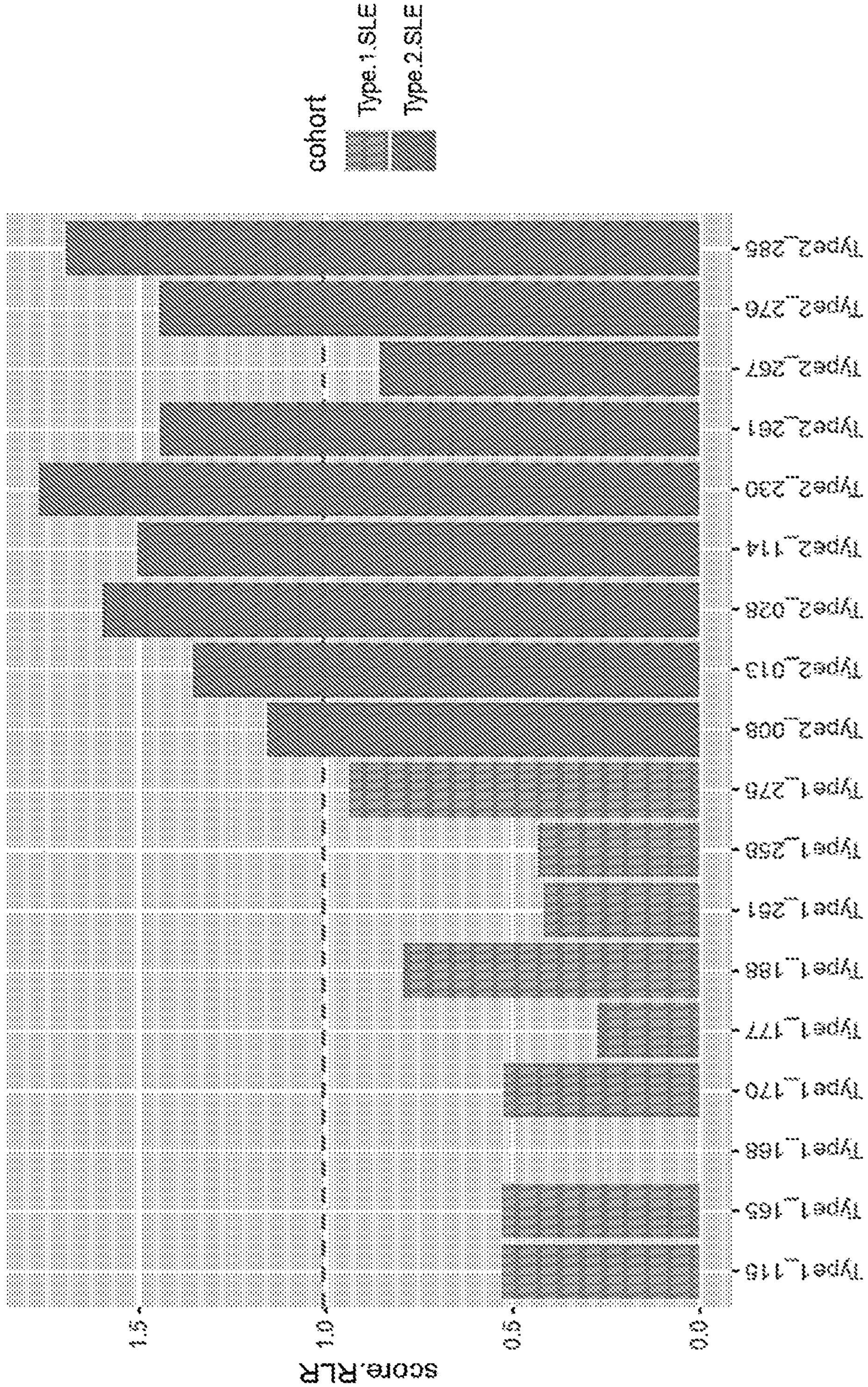
FIG. 43: Ridge-penalized logistic regression (RLR) patient scoring suggests targeted SLE type 1 and type 2 classification and therapeutics. Original GSVA enrichment values per patient were multiplied by the RLR coefficients. These were summed per patient and added to the absolute value of the smallest sum making all patient scores positive values. An RLR threshold of >1 was used to classify patients as either type 1 SLE or type 2 SLE (dashed line).
Figure 44A:
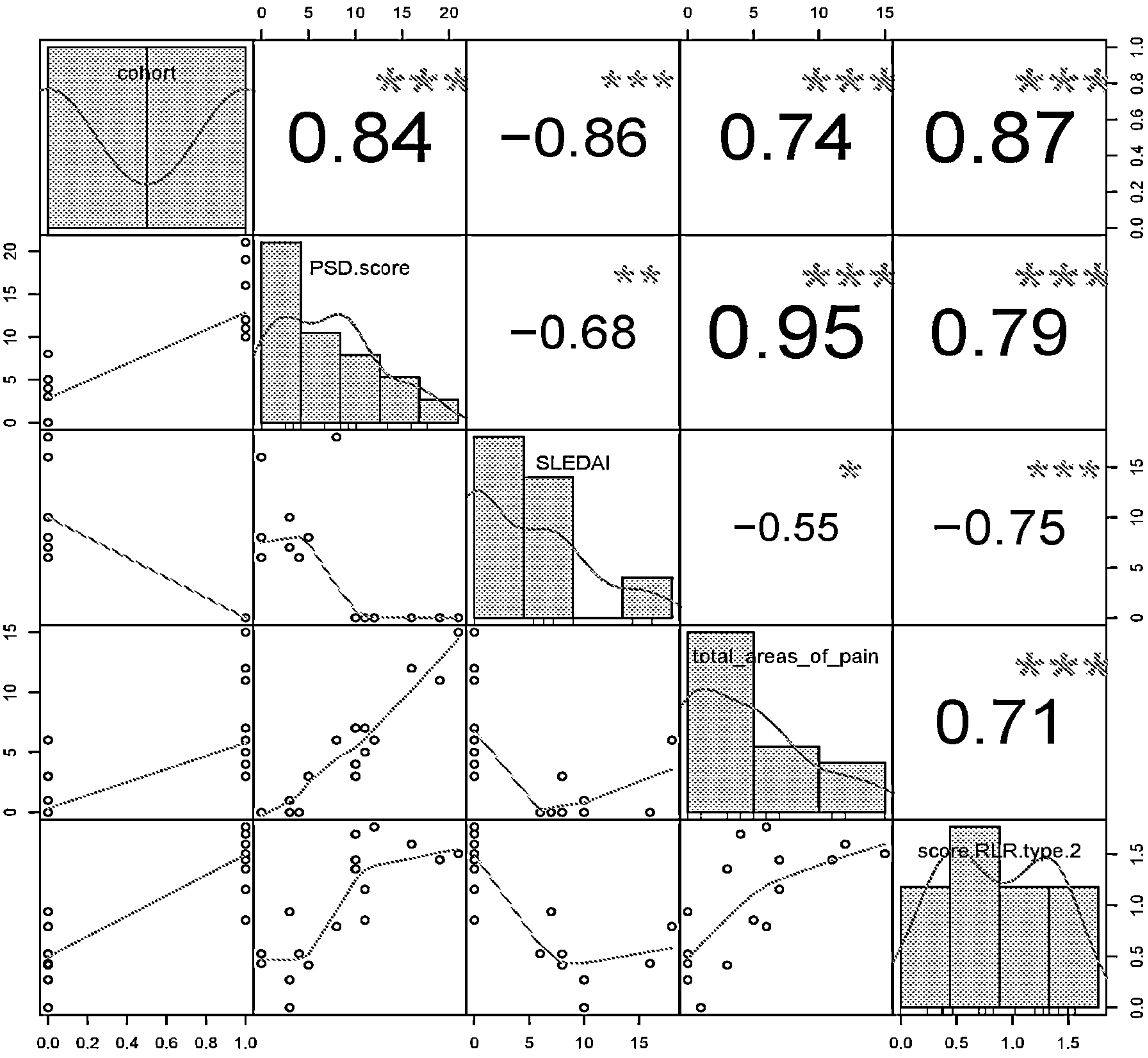
FIGS. 44A-C: RLR patient scoring highly correlates to clinical findings.
Figure 44B:
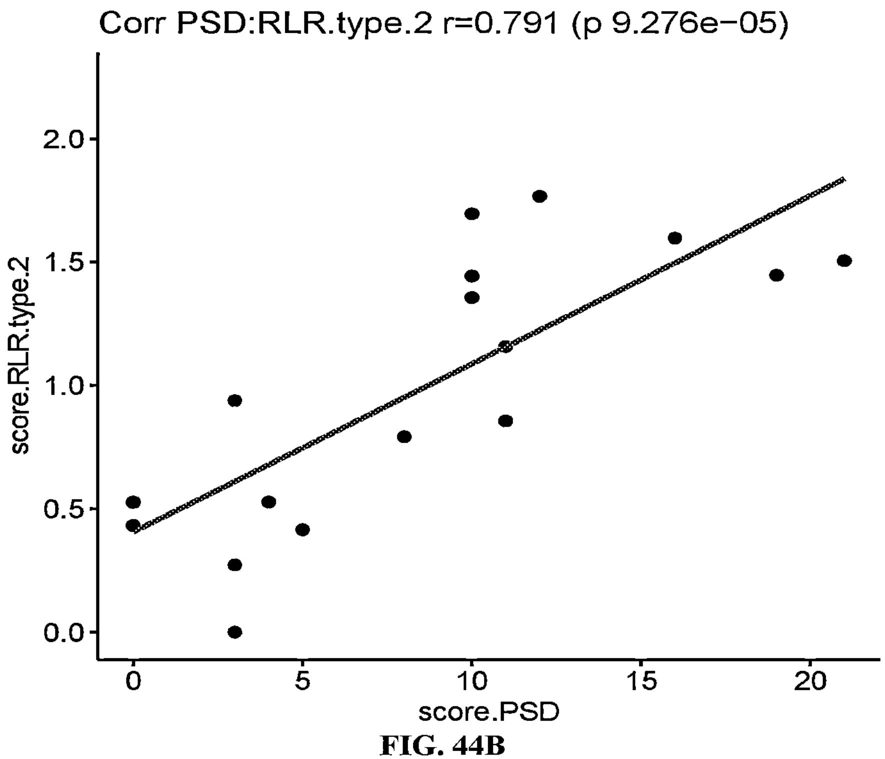
Figure 44C:
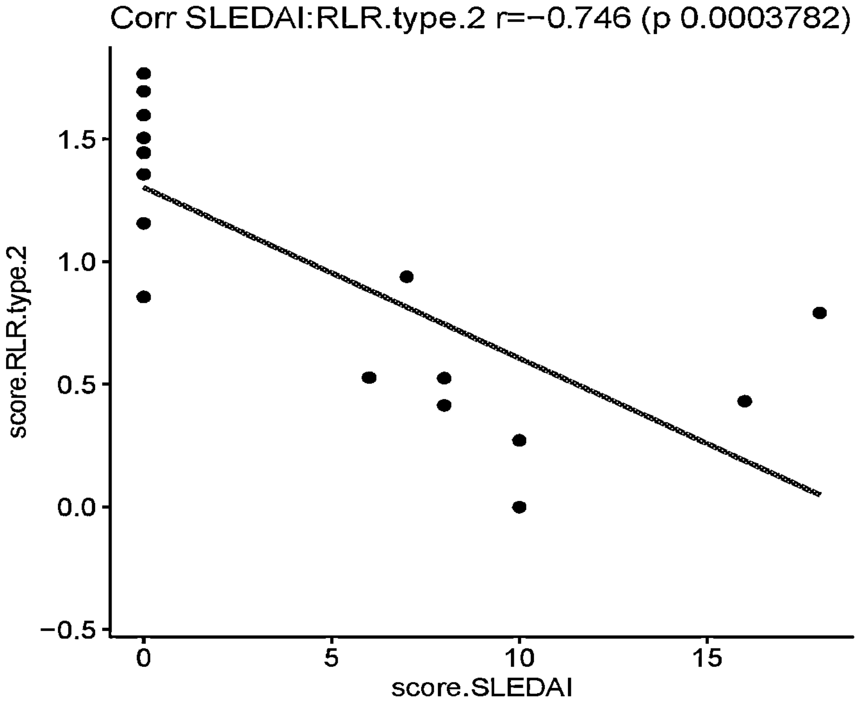

Lupus Disease Risk score: GSVA of the 30 gene modules (Tables 24-1 to 24-30) was run independently on the samples of the dataset set of Table 11. The GSVA scores in each sample were binarized, where GSVA scores >0 became 1, and GSVA scores <0 became 0. Logistic regression with ridge penalty was then run, with the 30 binarized GSVA scores in each sample serving as features. Coefficients were calculated for each iteration and final coefficients were obtained by taking the average of all iterations. FIG. 42 shows the resulting coefficients for classification of lupus disease state of the patient after the ridge regression model was run for the iterations. To calculate lupus disease risk score in each sample, the coefficient for each feature from the logistic regression model is multiplied by the binarized GSVA score for that feature and all categories are summed to generate a final score. As can be seen from FIG. 43, and Table 25A, type 1 and type 2 patients can be separated based on lupus disease risk score. Table 25A shows along with clinical and demographic features such as ancestral background, SLEDAI, and PSD scores, RLR (lupus disease score determined based on Ridge-penalized logistic regression) based patient classification as type 1 lupus or type 2 lupus can help guide a patient's therapeutic approach. Findings of this study suggest anti-inflammatory agents are ineffective agents for type 2 lupus as these pathways were only minimally enriched within type 2 lupus patients. Table 25B shows examples of therapies for type-1 and type-2 lupus patients.

Discussion

In this pilot study using a bookend approach, we tested the hypothesis that patients with SLE with high levels of Type 1 or Type 2 symptomatology can be distinguished on the basis of transcriptomic analysis of peripheral blood cells. While the number of patients in this study was limited, the data nevertheless support three important conclusions concerning Type 1 and Type 2 SLE activity. First, patients with active Type 1 or Type 2 SLE have quite distinct gene expression profiles, with perturbations of specific molecular pathways. Co-expression gene modules derived from Type 1 and 2 SLE patients highly correlate with specific features of Type 1 and 2 SLE Secondly, patients with active Type 1 or Type 2 SLE have quite distinct gene expression profiles, with perturbations of specific molecular pathways. Thirdly, the Type 1 and Type 2 SLE-related gene expression profiles can identify unique subsets of FM patients. Fourthly, the gene expression profiles of Type 2 SLE can be detected in unrelated datasets comprised of patients with inactive SLE. Finally, the Type 2 SLE gene co-expression modules identify subsets of patients with active SLE with a greater frequency of severe fatigue.

Previous studies of peripheral blood cells have primarily addressed the relationship of changes in gene expression to inflammatory disease activity as measured by instruments such as the SLEDAI (19). These studies have thus focused largely on Type 1 disease. This raises the question of whether the differences in gene expression profiles merely are indicative of differences in disease activity. A number of studies have assessed gene expression changes related to changes in disease activity measured by SLEDAI. Although changes have been identified in different studies (63), no consensus pattern of gene expression has been determined (64) Moreover, in this study, the Type 2 gene expression profile was seen in only a small fraction of inactive patients in two datasets and also in a subset of SLE patients with active disease. Therefore, it is unlikely that the Type 2 gene expression profile merely reflects changes in SLEDAI score. In this regard, association of the interferon gene signature with Type 1 SLE is notable. In general, the interferon signature is associated with the diagnosis of SLE, but may not change significantly over time in longitudinal studies of adult patients (20, 21). In contrast, studies of children with SLE have demonstrated changes in the interferon signature with disease activity in individual patients (22, 23). Of note, recent studies have revealed a significant association between the interferon signature and the presence of specific autoantibodies, especially those to RNA binding nuclear proteins, including anti-RNP, anti-Sm and anti-SSA (24). Notably, administration of type 1 interferon as a therapeutic can cause symptoms consistent with Type 2 SLE activity, including fatigue and achiness (25). In the current study, an association was found between the interferon gene signature and Type 1 but not Type 2 SLE activity. These results clearly establish an association between the interferon signature and Type 1 SLE, consistent with the role of both interferon and autoantibodies in the inflammatory features of SLE (26).

Beyond the interferon gene signature, expression of other specific gene modules was shown to be useful in distinguishing Type 1 and Type 2 SLE activity. These findings were validated using a number of orthogonal analytic techniques, including module eigengene correlations, GSVA enrichment scores, and analysis of DGCA intermodular pairings. Unique Type 1 SLE gene module enrichments included monocytes, neutrophils, T cells, interferon, IL-1, TNF, cell cycle and Wnt signaling, all characteristic of the inflammatory nature of this form of SLE. DGCA more specifically implicated Type 1 SLE interactions between monocytes and neutrophils and a host of other neutrophil interactions, notably including IL-1 and IFN. DGCA also showed that cell cycle was paired with the generation of superoxide and hydrogen peroxide as part of the neutrophil innate immune response, steroid precursor generation for manufacture of many molecules including immune signals, and T cell and Fc receptor activity. These features are all typical of the inflammatory nature of Type 1 SLE symptoms as previously reported for active SLE in general (1).

In contrast to findings with Type 1 SLE, expression of a number of other gene modules characterized active Type 2 SLE symptoms. Notably, Type 2 SLE was characterized by enrichments of B cells, plasma cells, and Ig chains, all features of active SLE, but also found in persons of African ancestry with or without SLE (20). In this study, African ancestry was associated with a plasma cell signature; however, it is unlikely that ancestry played the only role in the association of Type 2 SLE and the plasma cell signature since comparable numbers of SLE patients of African ancestry were found in the groups with Type 1 (n=6) and Type 2 (n=6) SLE (20). It is of interest that recent work has suggested that the immunoglobulin fraction of serum from FM patients can transfer features of FM to mice, including increased pain sensitivity (27). The elevated plasma cell signature in patients with Type 2 SLE may therefore relate to the role of antibodies in modulating pain in SLE.

We also found a number of neural features that distinguished Type 1 and Type 2 SLE activity. Unique Type 1 SLE module enrichments included those annotated as regulation of neuronal cell death, cerebral cortex microglial cell migration, and neurotransmitter metabolism. DGCA more specifically suggested Type 1 SLE intermodular connections between neutrophils and neurotransmitter metabolism, postsynaptic endosomes, and nervous system development. It was initially surprising in this study of peripheral blood that one module was annotated as microglia rather than monocytes/macrophages. Although these cell types share no common progenitor, they are both members of the mononuclear phagocyte system and share functional features which could lead to overlaps in cell type annotations. Additional studies will be necessary to determine whether enrichment of this module reflects microglial or general monocyte/macrophage enrichment in Type 1 SLE, but this enrichment is consistent with previous studies on the contribution of mononuclear phagocyte activity to inflammatory features of SLE (28-30).

It is also of interest that Type 1 SLE activity was associated with a neutrophil signature. Previous studies have clearly delineated a role of neutrophil subpopulations in active SLE (31, 32) and, notably, in this study, this association was only found in patients with active Type 1 and not Type 2 SLE. In addition, steroid usage was positively correlated to neutrophils, monocytes, IL-1, and the Fc-receptor in Type 1, but these features were all negatively correlated to Type 2 SLE. This finding implies that neutrophils may contribute to the features of Type 1 but not Type 2 SLE, although steroid administration is a possible contributor (21,22,33).

Type 2 SLE was also notable for neuromuscular and metabolism enrichments, sufficiently distinct to be detected in peripheral blood. These findings include muscle structure development, oxidative phosphorylation, cation transport, the carnitine shuttle (concentrated in skeletal and cardiac muscle), and L-type voltage gated calcium channel complexes (which are associated with skeletal, smooth, and cardiac muscle). Mitochondrial dysfunction and homeostatic imbalance have been investigated in FM as potentially modulating neuropathic pain through links with energy metabolism (33) including mitochondrial abnormalities in carnitine fatty acid metabolism (34). It has been suggested that there is a connection between reactive oxygen species (ROS) and neuropathic pain and that mitochondria could be a therapeutic target in FM and may also be involved in sensitivity to painful stimuli in Type 2 SLE (35, 36).

Besides identifying gene expression modules that discriminate Type 1 from Type 2 SLE, we identified patient clusters derived from two studies of inactive SLE patients that shared some transcriptional patterns with those we found with Type 2 SLE. Only a small fraction of inactive SLE patients were enriched for the Type 2 gene signature (20.1-34.6%). Because we did not have information on Type 2 symptoms in these patients, we went on to analyze patients from a clinical trial (GSE88884, Illuminate 2) because fatigue and pain were recorded, even though all of these patients manifested active disease (SLEDAI >=6). It is notable that an increased frequency of severe fatigue was found in the subsets with Type 2 gene expression features and even in a subset with mixed molecular features but diminished Type 1 monocyte and interferon gene expression. It was surprising that no difference in the frequency of severe pain was noted in the subsets, but this could relate to differences in the information collected by the WPI versus the Brief Pain Inventory. Two patient subsets were most similar to the reference Type 2 SLE cluster, whereas two others grouped separately from the Type 2 SLE reference. Notably, none of the inactive SLE clusters showed the cell cycle, monocyte or IFN enrichments seen in Type 1 SLE. Whether these patients had symptoms of Type 2 SLE is not known because of the lack of this clinical information; it is intriguing, however, that a subset of inactive SLE patients from completely different datasets had molecular features of Type 2 SLE.

Our study is the first attempt to assess differences in gene expression in patients who have been selected to have primarily Type 1 SLE or Type 2 SLE at the time of analysis, a so-called bookend approach. All patients with current Type 2 SLE activity have had active Type 1 SLE in the past, as Type 1 activity is required to meet criteria for SLE (5, 6). It is, therefore, interesting to speculate that Type 1 and Type 2 symptoms may vary in individual SLE patients and gene expression profiling may be useful to delineate or possibly even predict the transition. It is also possible that Type 1 and 2 symptoms may co-exist in some patients as fatigue, for example, is present in as many as 90% of all SLE patients, and that gene expression profiling might be useful in dissecting the molecular endotype of each set of manifestations.

Our study also indicates a relationship between transcriptional patterns in Type 2 SLE and a subset of FM patients, including enrichments of B cells, plasma cells, and IgG chains. Since many factors can lead to central sensitization, a key postulated mechanism for FM, it is not surprising that there is heterogeneity in the transcriptional profiles. The observation of common features in a subset of FM is, therefore, notable and suggests that despite diversity of causative factors for central sensitization, common transcriptional changes can occur whether FM occurs by itself or in the context of an inflammatory disease.

It is also of interest that a second subset of FM had a gene expression profile similar to that of Type 1 SLE. Notably, this subset had additional gene expression features of inflammation, including enrichments of monocytes, inhibitory macrophages, neutrophils, as well as interferon, TNF and IL-1 pathways. Unfortunately, detailed clinical evaluations of these patients are not available to determine whether they did indeed have underlying inflammatory disease. Despite this uncertainty, the data suggest that gene expression profiling can distinguish subsets of FM, one of which is molecularly similar to Type 2 SLE, and a second with more inflammatory features typical of Type 1 SLE.

We did not have detailed clinical information about subjects with FM or inactive SLE. Despite this, the results are provocative and merit confirmation in larger datasets.

In summary, our study utilized a number of orthogonal bioinformatics approaches to distinguish Type 1 from Type 2 SLE based on unique transcriptional patterns. Additionally, we identified a subset of Type 2 SLE-like patients in datasets of FM and inactive SLE, suggesting molecular similarities of these entities. Moreover, we could identify a subset of patients with active SLE who expressed the Type 2 gene expression profile and exhibited an increased frequency of severe fatigue. Finally, we found that a subset of FM patients showed molecular features of Type 1 SLE with upregulation of many inflammatory genes; these finding suggest the possibility of inflammatory components in some patients with idiopathic FM.

TABLE 10

SLE Type ½ sample attributes.

Listed by: pt.ID | cohort | PSD.score | SLEDAI | anti.dsDNA | complement_C3 | Age | ancestry_AA | ancestry_EA | ancestry_HA | is_female | lu_vas1_init | lu_vas2_init | sledai_arthritis | sledai_rash | sledai_ulcers | sledai_pleurisy | sledai_leukopenia | sledai_hematuria | sledai_pyuria | sledai_proteinuria | fatigue_severity | cognitive | wake_unrefresh | headache_symptom | cramps | depression | total_areas_of_pain | Total_Symptom_Severity | totalpain | month_flare | muscle_weak | muscle_pain | swell_joints | pain_stiff_joint | rash_malar | rash_sun | vasculitis | rash_oth | wt_loss | fatigue | fever | swollen_glands | alopecia | dry_eye_mouth | sores_mouth_nose | raynaud | short_breath | pain_deep_breath | forget | feel_depressed | anxiety | headache | stroke | numb_tingle | belly_pain | edema | hypertension | upc | urine_foamy | urine_pain | rate_lupus | er_visit | little_interest | depressed | sleep_trouble | tired | poor_appeti | disappoint | concentrate | slow_fidget | understand | follow_direct | miss_dose | when_missed | percent_med | drug.HCQ | drug.Prednisone | drug.Cytoxan | drug.CellCept | drug.MMF | drug.Azathioprine | drug.Methotrexate | drug.Benlysta | drug.Adalimumab | drug.NSAIDs | drug.Leflunomide | drug.ACE | drug.ARB | drug.Aspirin | drug.Amlodipine | drug.HCTZ | drug.Lasix | drug.Metoprolol | drug.Coreg | drug.Chlorthalidone |

TABLE 10-continued

SLE Type ½ sample attributes.

drug.Gabapentin | drug.Lyrica | drug.Flexeril | drug.Elavil | drug.Cymbalta | drug.Effexor |
drug.Milnacipran | drug.Wellbutrin | drug.Tramadol.

Type1__115 | 0 | 4 | 6 | 2 | 0 | 49 | 1 | 0 | 0 | 1 | 0.5 | 0 | 4 | 0 | 0 | 0 | 0 | 0 | 0 | 0 | 2 | 1 | 1 | 1 | 1 | 1 | 0 |
4 | 2 | 2 | 1 | 2 | 2 | 2 | 1 | 0 | 0 | 0 | 1 | 2 | 2 | 0 | 2 | 2 | 1 | 0 | 1 | 1 | 1 | 1 | 1 | 0 | 0 | 0 | 0 | 0 | 1 | 0 | 0 |
0
| 4 | 0 | 1 | 1 | 2 | 2 | 1 | 0 | 0 | 0 | 2 | 3 | 0 | 0 | 100 | 400 | 4 | 1 | 2 | 1 | 1 | 1 | 1 | 1 | 1 | 1 | 1 | 1 | 0 | 1 |
1
| 1 | 2 | 1 | 1 | 2 | 1 | 1 | 1 | 1 | 1 | 1 | 1 | 1; Type1__165 | 0 | 0 | 6 | 0 | 2 | 32 | 1 | 0 | 0 | 1 | 2 | 0 | 0 | 0 | 0
| 0 | 0 | 0 | 0 | 4 | 0 | 0 | 0 | 1 | 1 | 1 | 0 | 0 | 1 | 1 0 | 0 | 1 | 0 | 0 | 0 | 0 | 0 | 0 | 0 | 0 | 0 | 0 | 1 | 0 | 0 |
0 | 0 | 0 | 0 | 0 | 0 | 0 | 0 | 0 | 0 | 0 | 0 | 0 | 4 | 0 | 0 | 0 | 0 | 0 | 0 | 0 | 0 | 0 | 3 | 2 | 0 | 5 | 95 | 200 | 15 | 2
|
1 | 1 | 1 | 1 | 1 | 1 | 1 | 1 | 1 | 1 | 0 | 1 | 1 | 2 | 1 | 1 | 1 | 1 | 1 | 1 | 1 | 1 | 1 | 1 | 1 | 1; Type1__168 | 0 | 3 |
10 | 2 | 0 | 30 | 1 | 0 | 0 | 1 | 0 | 0 | 0 | 0 | 0 | 0 | 0 | 0 | 4 | 4 | 1 | 0 | 1 | 1 | 2 | 1 | 1 | 2 | 3 | 0 | 0 | 0 | 1 |
1 |
0 | 0 | 0 | 0 | 0 | 1 | 1 | 0 | 0 | 1 | 0 | 0 | 1 | 0 | 0 | 0 | 0 | 0 | 0 | 0 | 0 | 0 | 0 | 1 | 1 | 0 | 3 | 0 | 1 | 0 | 2 | 1 |
3
| 0 | 0 | 0 | 2 | 2 | 0 | 5 | 80 | 0 | 40 | 1 | 2 | 1 | 1 | 1 | 1 | 1 | 1 | 1 | 1 | 1 | 0 | 2 | 1 | 1 | 1 | 2 | 1 | 1 | 1 | 1
| 2
| 1 | 1 | 1 | 1 | 1; Type1__170 | 0 | 0 | 8 | 2 | 2 | 27 | 0 | 0 | 1 | 1 | 1.5 | 0 | 0 | 2 | 0 | 2 | 0 | 0 | 0 | 0 | 0 | 0 |
0 | 0 | 1 | 1 | 0 | 0 | 1 | 1 | 0 | 1 | 0 | 0 | 1 | 2 | 3 | 0 | 0 | 0 | 0 | 0 | 0 | 0 | 0 | 0 | 0 | 2 | 0 | 0 | 0 | 0 | 0 | 0 |
0
| 0 | 0 | 0 | 0 | 0 | 1 | 0 | 0 | 0 | 0 | 0 | 0 | 0 | 0 | 0 | 2 | 2 | 2 | 3 | 90 | 400 | 5 | 1 | 2 | 1 | 1 | 1 | 2 | 1 | 2 | 1
|
2 | 1 | 0 | 1 | 1 | 1 | 1 | 1 | 1 | 1 | 1 | 1 | 1 | 1 | 1 | 1 | 1 | 1; Type1__177 | 0 | 3 | 10 | 0 | 2 | 30 | 1 | 0 | 0 | 1
| 1 | 0.25 | 0 | 0 | 0 | 0 | 0 | 4 | 0 | 4 | 1 | 1 | 1 | 1 | 2 | 2 | 0 | 3 | 4 | 0 | 1 | 1 | 1 | 1 | 0 | 0 | 1 | 0 | 0 | 0 | 0
|
0 | 0 | 1 | 0 | 1 | 0 | 0 | 1 | 0 | 1 | 1 | 0 | 0 | 1 | 1 | 1 | 0 | 0 | 0 | 2 | 0 | 1 | 1 | 1 | 1 | 1 | 1 | 1 | 1 | 2 | 2 | 1 |
5
| 80 | 400 | 10 | 1 | 1 | 2 | 1 | 1 | 1 | 1 | 1 | 1 | 1 | 2 | 0 | 1 | 1 | 2 | 1 | 1 | 1 | 1 | 1 | 1 | 2 | 1 | 1 | 1 | 1 | 1;
Type1__188 | 0 | 8 | 18 | 0 | 0 | 38 | 1 | 0 | 0 | 1 | 2 | 1.5 | 4 | 2 | 0 | 0 | 0 | 4 | 4 | 4 | 2 | 0 | 0 | 1 | 2 | 2 | 6
|
2 | 4 | 2 | 3 | 3 | 3 | 3 | 3 | 3 | 3 | 3 | 0 | 2 | 1 | 1 | 0 | 0 | 1 | 0 | 0 | 0 | 2 | 2 | 2 | 1 | 0 | 1 | 1 | 2 | 1 | 0 | 0 |
0
| 8 | 1 | 0 | 2 | 2 | 1 | 0 | 0 | 0 | 0 | 3 | 3 | 0 | 1 | 80 | 400 | 10 | 1 | 2 | 1 | 1 | 1 | 1 | 1 | 1 | 1 | 1 | 2 | 81 | 1
|
1 | 1 | 2 | 1 | 1 | 1 | 2 | 1 | 2 | 1 | 2 | 1 | 1 | 1; Type1__251 | 0 | 5 | 8 | 2 | 2 | 27 | 0 | 1 | 0 | 0 | 1.5 | 0 | 0 |
2 | 2 | 0 | 0 | 0 | 0 | 0 | 2 | 0 | 0 | 1 | 2 | 1 | 3 | 2 | 3 | 3 | 0 | 1 | 2 | 2 | 3 | 3 | 0 | 3 | 0 | 1 | 0 | 0 | 3 | 2 | 1 |
0
| 0 | 0 | 0 | 0 | 0 | 2 | 0 | 0 | 2 | 0 | 0 | 0 | 0 | 0 | 8 | 0 | 0 | 0 | 0 | 1 | 0 | 0 | 0 | 0 | 3 | 3 | 0 | 6 | 100 | 400 |
5
| 1 | 1 | 1 | 2 | 1 | 1 | 1 | 1 | 1 | 1 | 1 | 0 | 1 | 1 | 1 | 1 | 1 | 1 | 1 | 1 | 2 | 1 | 1 | 1 | 1 | 1 | 1; Type1__258 | 0
|
0 | 16 | 2 | 2 | 58 | 1 | 0 | 0 | 1 | 0 | 0 | 0 | 0 | 0 | 0 | 0 | 4 | 4 | 4 | 0 | 0 | 0 | 1 | 2 | 1 0 | 0 | 3 | 0 | 0 | 0 | 1
|
0 | 0 | 0 | 0 | 0 | 0 | 0 | 0 | 0 | 0 | 1 | 0 | 0 | 1 | 0 | 0 | 0 | 0 | 1 | 0 | 0 | 1 | 1 | 0 | 0 | 0 | 1 | 0 | 0 | 0 | 0 | 0 |
0
| 0 | 0 | 0 | 0 | 3 | 3 | 1 | 3 | 85 | 400 | 0 | 1 | 1 | 1 | 1 | 1 | 1 | 1 | 1 | 1 | 1 | 1 | 0 | 1 | 1 | 1 | 1 | 1 | 1 | 1 | 1
|
1 | 1 | 1 | 1 | 1 | 1 | 2; Type1__275 | 0 | 3 | 7 | 0 | 2 | 41 | 0 | 1 | 0 | 1 | 1 | 1 | 4 | 0 | 0 | 0 | 1 | 0 | 0 | 0 | 2 |
0 | 1 | 1 | 1 | 1 | 0 | 3 | 2 | 1 | 0 | 0 | 2 | 2 | 0 | 0 | 0 | 0 | 1 | 2 | 0 | 0 | 0 | 0 | 0 | 2 | 0 | 0 | 0 | 0 | 1 | 0 | 0 |
0
| 0 | 0 | 0 | 0 | 0 | 0 | 3 | 0 | 0 | 0 | 2 | 2 | 0 | 0 | 0 | 0 | 2 | 3 | 0 | 6 | 100 | 350 | 0 | 1 | 1 | 1 | 1 | 1 | 1 | 1 |
2
| 1 | 1 | 1 | 0 | 1 | 1 | 1 | 1 | 1 | 1 | 1 | 1 | 1 | 1 | 1 | 1 | 1 | 1 | 1; Type2__008 | 1 | 11 | 0 | 0 | 0 | 47 | 1 | 0 |
0 | 1 | 0.5 | 1.5 | 0 | 0 | 0 | 0 | 0 | 0 | 0 | 0 | 2 | 1 | 1 | 1 | 1 | 1 | 7 | 4 | 1 | 1 | 3 | 2 | 2 | 3 | 2 | 1 | 1 | 0 | 1 |
2
| 1 | 1 | 2 | 2 | 0 | 3 | 2 | 1 | 1 | 1 | 0 | 1 | 2 | 2 | 0 | 2 | 0 | 1 | 0 | 0 | 7 | 0 | 0 | 1 | 0 | 1 | 1 | 0 | 0 | 1 | 2 | 3
|
0 | 0 | 100 | 400 | 0 | 1 | 2 | 1 | 1 | 1 | 1 | 1 | 1 | 1 | 1 | 2 | 0 | 1 | 1 | 1 | 2 | 1 | 1 | 2 | 1 | 2 | 1 | 2 | 1 | 1 | 1
|
1; Type2__013 | 1 | 10 | 0 | 0 | 0 | 43 | 0 | 1 | 0 | 1 | 0.5 | 1 | 0 | 0 | 0 | 0 | 0 | 0 | 0 | 0 | 2 | 3 | 2 | 1 | 1 | 1 |
3 | 7 | 2 | 0 | 0 | 0 | 0 | 1 | 1 | 1 | 0 | 1 | 0 | 1 | 0 | 0 | 0 | 0 | 0 | 2 | 1 | 0 | 2 | 0 | 0 | 0 | 0 | 0 | 1 | 0 | 0 | 0 |
0 | 0
| 0 | 1 | 0 | 0 | 0 | 2 | 3 | 0 | 0 | 2 | 0 | 3 | 3 | 0 | 0 | 100 | 400 | 0 | 1 | 1 | 1 | 1 | 1 | 1 | 2 | 1 | 2 | 1 | 1 | 0 |
1
| 1 | 1 | 1 | 1 | 1 | 1 | 1 | 1 | 2 | 1 | 1 | 1 | 1 | 1; Type2__028 | 1 | 16 | 0 | 0 | 0 | 62 | 0 | 1 | 0 | 1 | 0.2 | 1.5 |
0 | 0 | 0 | 0 | 0 | 0 | 0 | 0 | 2 | 0 | 2 | 0 | 1 | 1 | 12 | 4 | 1 | 3 | 3 | 3 | 1 | 3 | 1 | 0 | 1 | 0 | 1 | 2 | 0 | 0 | 0 | 1
|
1 | 0 | 1 | 0 | 1 | 0 | 0 | 1 | 0 | 0 | 0 | 1 | 0 | 0 | 1 | 0 | 10 | 0 | 0 | 0 | 0 | 2 | 0 | 0 | 0 | 0 | 2 | 3 | 0 | 6 | 90 |
400 | 0 | 1 | 1 | 1 | 1 | 2 | 1 | 1 | 2 | 1 | 1 | 1 | 81 | 1 | 1 | 1 | 1 | 1 | 1 | 2 | 1 | 1 | 1 | 2 | 1 | 1 | 1 | 2;
Type2__114 | 1 | 21 | 0 | 0 | 0 | 47 | 1 | 0 | 0 | 1 | 0 | 1.5 | 0 | 0 | 0 | 0 | 0 | 0 | 0 | 0 | 2 | 1 | 3 | 1 | 2 | 2 | 15
| 6 | 4 | 0 | 0 | 3 | 0 | 1 | 0 | 0 | 0 | 0 | 0 | 2 | 0 | 0 | 0 | 3 | 2 | 0 | 0 | 0 | 2 | 1 | 1 | 1 | 0 | 0 | 0 | 1 | 1 | 0 | 0
|
0 | 3 | 0 | 2 | 1 | 3 | 3 | 3 | 0 | 1 | 0 | 3 | 3 | 0 | 0 | 100 | 400 | 5 | 1 | 1 | 1 | 1 | 1 | 1 | 1 | 1 | 1 | 1 | 1 | 0 | 1
|
1 | 1 | 1 | 1 | 1 | 2 | 1 | 1 | 1 | 2 | 1 | 1 | 1 | 1; Type2__230 | 1 | 12 | 0 | 0 | 0 | 55 | 1 | 0 | 0 | 1 | 0 | 2.5 | 0 |
0 | 0 | 0 | 0 | 0 | 0 | 0 | 2 | 2 | 2 | 1 | 2 | 2 | 6 | 6 | 4 | 0 | 1 | 1 | 1 | 3 | 0 | 0 | 0 | 0 | 0 | 1 | 0 | 0 | 0 | 3 | 0 |
1
| 0 | 0 | 3 | 3 | 3 | 3 | 0 | 1 | 1 | 1 | 1 | 0 | 0 | 0 | 5 | 1 | 1 | 2 | 3 | 2 | 3 | 3 | 3 | 0 | 3 | 3 | 2 | 2 | 50 | 400 | 0
|
1 | 1 | 1 | 1 | 1 | 1 | 1 | 2 | 1 | 2 | 1 | 0 | 2 | 2 | 1 | 1 | 1 | 1 | 1 | 2 | 1 | 1 | 1 | 1 | 2 | 1 | 1; Type2__261 | 1 |

TABLE 10-continued

SLE Type ½ sample attributes.

10 | 0 | 0 | 0 | 46 | 0 | 1 | 0 | 1 | 0.5 | 2 | 0 | 0 | 0 | 0 | 0 | 0 | 0 | 0 | 1 | 1 | 1 | 1 | 2 | 2 | 7 | 3 | 4 | 1 | 0 | 1
|
2 | 2 | 1 | 2 | 0 | 1 | 0 | 2 | 0 | 0 | 0 | 1 | 1 | 0 | 1 | 0 | 1 | 1 | 2 | 1 | 0 | 1 | 1 | 0 | 0 | 0 | 0 | 0 | 4 | 0 | 0 | 1 |
2
| 3 | 0 | 0 | 1 | 2 | 3 | 3 | 0 | 6 | 96 | 400 | 0 | 1 | 1 | 1 | 1 | 1 | 1 | 1 | 2 | 1 | 1 | 1 | 325 | 1 | 1 | 1 | 1 | 1 | 1
|
1 | 1 | 2 | 1 | 1 | 1 | 1 | 1 | 1; Type2__267 | 1 | 11 | 0 | 0 | 0 | 37 | 0 | 1 | 0 | 1 | 0 | 1.5 | 0 | 0 | 0 | 0 | 0 | 0 |
0 | 0 | 2 | 2 | 2 | 1 | 2 | 2 | 5 | 6 | 4 | 0 | 2 | 2 | 0 | 0 | 0 | 1 | 1 | 0 | 0 | 1 | 0 | 0 | 0 | 1 | 1 | 1 | 0 | 0 | 1 | 2 |
2
| 1 | 0 | 1 | 2 | 1 | 0 | 0 | 0 | 0 | 2 | 0 | 1 | 3 | 2 | 2 | 0 | 1 | 1 | 0 | 3 | 3 | 1 | 3 | 78 | 400 | 0 | 1 | 1 | 1 | 1 | 1
|
1 | 1 | 1 | 1 | 1 | 1 | 81 | 1 | 1 | 1 | 1 | 1 | 1 | 1 | 1 | 1 | 1 | 1 | 2 | 1 | 1 | 1; Type2__276 | 1 | 19 | 0 | 0 | 0 |
44 | 1 | 0 | 0 | 1 | 0.5 | 2 | 0 | 0 | 0 | 0 | 0 | 0 | 0 | 0 | 3 | 2 | 3 | 1 | 2 | 2 | 11 | 8 | 4 | 1 | 0 | 2 | 2 | 2 | 1 | 0
|
1 | 0 | 0 | 3 | 0 | 0 | 0 | 1 | 0 | 0 | 0 | 0 | 3 | 1 | 1 | 2 | 0 | 2 | 1 | 0 | 0 | 0 | 0 | 0 | 6 | 0 | 2 | 1 | 2 | 3 | 1 | 0 |
2
| 0 | 2 | 3 | 0 | 6 | 90 | 400 | 0 | 1 | 1 | 1 | 1 | 1 | 1 | 1 | 1 | 2 | 1 | 2 | 0 | 1 | 1 | 1 | 1 | 2 | 2 | 1 | 1 | 1 | 1 | 2
|
1 | 1 | 2 | 1; Type2__285 | 1 | 10 | 0 | 0 | 0 | 33 | 1 | 0 | 0 | 1 | 0 | 1 | 0 | 0 | 0 | 0 | 0 | 0 | 0 | 0 | 2 | 2 | 2 | 1
| 2 | 1 | 4 | 6 | 3 | 1 | 1 | 1 | 0 | 0 | 0 | 0 | 0 | 0 | 0 | 2 | 0 | 0 | 0 | 0 | 0 | 0 | 1 | 1 | 2 | 0 | 3 | 1 | 0 | 0 | 1 | 0
|
0 | 0 | 0 | 0 | 3 | 0 | 0 | 0 | 2 | 3 | 3 | 0 | 1 | 1 | 3 | 3 | 1 | 5 | 90 | 400 | 0 | 1 | 1 | 1 | 1 | 1 | 1 | 1 | 1 | 1 | 1
| 0 | 1 | 1 | 1 | 1 | 1 | 1 | 1 | 1 | 1 | 1 | 1 | 1 | 1 | 1 | 1;

TABLE 11

Classification of patients based on the extent of Type 1 & 2 SLE activity.

| | Overall N = 18 | Type 1 N = 9 | Type 2 N = 9 |
|---|---|---|---|
| Demographics | | | |
| Mean age (SD) | 41.4 (10.6) | 36.9 (10.8) | 46.0 (8.7) |
| % Female | 17 (94%) | 8 (89%) | 9 (100%) |
| African American | 11 (61%) | 6 (67%) | 5 (56%) |
| Ethnicity Hispanic | 1 (6%) | 1 (11%) | 0 (0%) |
| Mean length of disease; mean yrs (SD) | 16.4 (4.9) | 15.0 (4.8) | 17.9 (4.9) |
| % Historical renal disease | 9 (50%) | 7 (78%) | 2 (22%) |
| 1997 ACR Criteria; n (% yes) | 16 (89%) | 8 (89%) | 8 (89%) |
| 2011 SLICC Criteria; n (% yes) | 18 (100%) | 9 (100%) | 9 (100%) |
| 2019 ACR/EULAR Criteria; n (% yes) | 18 (100%) | 9 (100%) | 9 (100%) |
| 2019 ACR/EULAR Total Score; Median (IQR) | 33 (17-38) | 38 (37-40) | 18 (16-33) |
| Current Medications | | | |
| HCQ; n(%) | 17 (94%) | 8 (89%) | 9 (100%) |
| DMARD (MTX, Aza, MMF); n (%) | 8 (44%) | 6 (67%) | 2 (22%) |
| Prednisone > 5 mg; n (%) | 4 (22%) | 4 (44%) | 0 (0%) |
| Benlysta, Rituxan, Cytoxan; n (%) | 2 (11%) | 2 (22%) | 0 (0%) |
| Current Activity | | | |
| Type 1 PGA; mean (%) | 0.7 (0.7) | 1.2 (0.7) | 0.2 (0.3) |
| SLEDAI; mean (%) | 4.5 (5.1) | 9.0 (3.1) | 0 (0) |
| Type 2 PGA; mean (%) | 1.0 (0.8) | 0.3 (0.6) | 1.6 (0.5) |
| 2016 PSD; mean (%) | 9.8 (7.0) | 4.2 (3.4) | 15.4 (4.6) |
| Fatigue (mod-severe); n(%) | 12 (67%) | 4 (44%) | 8 (89%) |
| Depression yes; n (%) (n = 16) | 7 (44%) | 2 (25%) | 5 (63%) |

TABLE 12

Classification of patients based on the extent of Type 1 & 2 SLE activity.

| | Type 1 SLE Activity | Type 2 SLE Activity |
|---|---|---|
| Minimal | Clinical SLEDAI <4, SLEDAI <6, no active nephritis and Type 1 PGA ≤0.5 | FSS ≤4 and Type 2 PGA <1 |
| Mixed (Type 1-2) | Clinical SLEDAI ≥4, active nephritis, SLEDAI ≥6, or Type 1 PGA ≥1 | FSS ≥8 or Type 2 PGA ≥1 |

TABLE 12-continued

| Classification of patients based on the extent of Type 1 & 2 SLE activity. | | |
|---|---|---|
| | Type 1 SLE Activity | Type 2 SLE Activity |
| Type 1 | Clinical SLEDAI ≥4, active nephritis, SLEDAI ≥6, or Type 1 PGA ≥1 | FSS ≤6 and Type 2 PGA ≤0.25 |
| Type 2 | SLEDAI = 0 and Type 1 PGA ≤0.5 | FSS ≥11 and Type 2 PGA ≥1 |

TABLE 13

SLE Type 1/2 MEGENA module preservation in GSE67311 FM

| mod.name | mod.annot | Zsummary.pres | module Size |
|---|---|---|---|
| 7.49 | GO: oxidative.phosphorylation, respiratory.chain | 28.63 | 161 |
| 10.159 | GO: adaptive.immune.response, MHC.protein.binding | 22.33 | 105 |
| 6.36 | Lug: Platelet. GO: blood.coagulation | 22.19 | 155 |
| 7.48 | Lug: Plasma-Cell. GO: carbohydrate.derivative.biosynthetic.process | 16.09 | 29 |
| 7.49.271 | Lug: Nk-cell. GO: axon.guidance | 15.33 | 46 |
| 6.36.230 | Lug: Neutrophil. GO: cell.activation.involved.in.immune.response | 15.24 | 78 |
| 8.72 | GO: cytokine.receptor.activity, cytokine.binding | 14.63 | 27 |
| 5.23 | GO: histone.demethylase.activity, histone.demethylation | 14.26 | 34 |
| 10.159.374 | Tis: T.cell. GO: reg.of.neuron.death | 13.74 | 47 |
| 6.36.230.438 | Lug: Monocyte. GO: interleukin-1.receptor.activity | 13.19 | 42 |
| 5.22 | Anc: Mono.Secreted. GO: synapse.pruning | 12.06 | 59 |
| 7.49.273 | Anc: B.cells. GO: B.cell.activation | 11.97 | 33 |
| 5.23.222 | Anc: B.cells. GO: transcription.regulator.activity | 11.47 | 26 |
| 7.49.275 | GO: protein-DNA.complex, nucleosome | 11.39 | 23 |
| 10.159.372 | Lug: Monocyte. GO: response.to.virus | 11.06 | 35 |
| 6.39 | GO: cerebral.cortex.radial.glia.guided.migration, telencephalon.glial.cell.migration | 10.84 | 62 |
| 7.48.268 | GO: protein.kinase.regulator.activity, kinase.regulator.activity | 10.83 | 21 |
| 10.159.372.523 | Anc: IFN. GO: response.to.stress | 10.79 | 24 |
| 3.15 | GO: cation.transmembrane.transporter.activity, carnitine.shuttle | 10.49 | 138 |
| 7.49.272 | GO: blastocyst.development, organelle.localization.by.membrane.tethering | 10.34 | 17 |
| 10.159.374.527 | Anc: Cell.Cycle. GO: cell.cycle | 10.18 | 35 |
| 8.51 | GO: dendrite, pos.reg.of.synaptic.transmission | 9.87 | 58 |
| 6.40.252 | Lug: Myeloid-Cell. GO: divalent.metal.ion.transport | 9.71 | 11 |
| 6.39.248 | GO: cofactor.catabolic.process, hydrogen.peroxide.catabolic.process | 9.06 | 27 |
| 8.60 | Lug: Erythrocyte. GO: erythrocyte.diff | 9 | 20 |
| 3.17 | GO: neutrophil.chemotaxis, neutrophil.migration | 8.95 | 17 |
| 8.58 | GO: meiotic.gene.conversion, gene.conversion | 8.78 | 23 |
| 8.53 | GO: leukocyte.degranulation, Fc.receptor.signaling.pathway | 8.31 | 25 |
| 5.22.217 | GO: superoxide-generating.NADPH.oxidase.activity, NADPH.oxidase.complex | 7.99 | 15 |
| 8.72.305 | GO: transcription.factor.complex, cation.channel.activity | 7.97 | 20 |
| 8.67 | GO: extracellular.exosome, extracellular.vesicle | 7.92 | 51 |
| 6.36.230.439 | Lug: NK-or-T-cell. GO: collagen.metabolic.process | 7.77 | 17 |
| 8.67.299 | GO: dephosphorylation, immunoglobulin.production.involved.in.immunoglobulin.mediated.immune.response | 7.16 | 41 |
| 6.36.231 | GO: pattern.recognition.receptor.signaling.pathway, specific.granule | 6.78 | 13 |
| 3.15.175 | GO: neutrophil.degranulation, neutrophil.activation.involved.in.immune.response | 6.74 | 55 |
| 6.39.247 | GO: response.to.growth.factor, cellular.anion.homeostasis | 6.61 | 21 |
| 8.53.286 | GO: proteasome.regulatory.particle, proteasome.regulatory.particle, lid.subcomplex | 6.61 | 12 |
| 5.22.218 | Lug: NK-or-T-cell. GO: extrinsic.component.of.cytoplasmic.side.of.plasma.membrane | 6.53 | 22 |
| 5.23.222.430 | GO: phospholipid.transporter.activity, phospholipid.transport | 6.39 | 14 |
| 3.19 | GO: reg.of.apoptotic.signaling.pathway, pos.reg.of.apoptotic.signaling.pathway | 6.18 | 50 |
| 8.60.295 | GO: anterior/posterior.pattern.specification, corticotropin.hormone.secreting.cell.diff | 6.11 | 14 |
| 6.40 | GO: protein.depalmitoylation, N,-dimethylaniline.monooxygenase.activity | 6.05 | 19 |

TABLE 13-continued

| SLE Type 1/2 MEGENA module preservation in GSE67311 FM | | | |
|---|---|---|---|
| mod.name | mod.annot | Zsummary.pres | module Size |
| 2.11 | GO: leukotriene.catabolic.process, leukotriene.B4.catabolic.process | 6 | 51 |
| 6.36.234 | GO: cerebral.cortex.cell.migration, telencephalon.cell.migration | 5.92 | 14 |
| 7.49.271.471 | GO: RNA.binding, ribonucleoprotein.complex | 5.9 | 14 |
| 6.35.229 | GO: endopeptidase.activity, peptidase.activity, acting.on.L-amino.acid.peptides | 5.75 | 10 |
| 8.68 | GO: receptor.complex, growth.factor.binding | 5.45 | 18 |
| 6.39.248.453 | GO: microtubule.cytoskeleton, sulfur.amino.acid.metabolic.process | 5.16 | 13 |
| 8.80 | GO: spindle, C-5.sterol.desaturase.activity | 5.1 | 17 |
| 8.53.285 | GO: glucagon.receptor.activity, melatonin.receptor.activity | 5 | 10 |
| 6.45 | GO: reg.of.axon.extension, axon.extension | 4.86 | 27 |
| 6.35 | GO: catalytic.activity, acting.on.DNA, DNA.translocase.activity | 4.8 | 35 |
| 8.51.281 | GO: reg.of.gene.expression, protein.localization.to.endoplasmic.reticulum | 4.66 | 15 |
| 3.15.180 | GO: spliceosomal.tri-snRNP.complex.assembly, formation.of.quadruple.SL/U4/U5/U6.snRNP | 4.58 | 16 |
| 2.11.161 | GO: oxidative.phosphorylation, respiratory.chain | 4.53 | 17 |
| 6.41 | GO: animal.organ.morphogenesis, reg.of.Wnt.signaling.pathway | 4.48 | 13 |
| 8.51.280 | Lug: Platelet. GO: wound healing | 4.34 | 17 |
| 3.15.175.386 | GO: neg.reg.of.growth, fertilization | 4.19 | 21 |
| 6.39.247.448 | GO: system.process, protein.heterodimerization.activity | 4.09 | 10 |
| 3.20 | GO: olfactory.receptor.activity, detection.of.chemical.stimulus.involved.in.sensory.perception.of.smell | 3.95 | 16 |
| 7.48.268.468 | Lug: Plasma-Cell. GO: organic.substance.metabolic.process | 3.93 | 6 |
| 10.158 | Lug: Plasma-Cell. GO: response.to.unfolded.protein | 3.91 | 20 |
| 8.58.291 | Lug: Neutrophil. GO: cell.activation.involved.in.immune.response | 3.89 | 12 |
| 8.56 | GO: G.protein-coupled.receptor.signaling.pathway, coupled.to.cyclic.nucleotide.second.messenger, cell.diff.in.hindbrain | 3.73 | 11 |
| 3.18 | GO: odontogenesis, trans-Golgi.network | 3.57 | 28 |
| 8.55 | GO: response.to.nitrogen.compound, reg.of.hormone.secretion | 3.54 | 13 |
| 2.11.162 | GO: deaminating.activity, primary.amine.oxidase.activity | 3.54 | 11 |
| 3.20.216 | GO: calcium.ion.binding, pos.reg.of.wound.healing | 3.43 | 11 |
| 10.158.371 | GO: virus.receptor.activity, hijacked.molecular.function | 3.36 | 8 |
| 2.13 | GO: postsynaptic.endosome, galactoside.binding | 3.31 | 10 |
| 8.67.299.497 | GO: cell.diff, polymeric.cytoskeletal.fiber | 3.16 | 16 |
| 6.36.230.438.556 | GO: GTPase.regulator.activity, interleukin-18-mediated.signaling.pathway | 3.1 | 10 |
| 8.66 | GO: small.molecule.biosynthetic.process, cellular.response.to.steroid.hormone.stimulus | 3.04 | 10 |
| 5.22.218.427 | GO: interleukin-1.receptor.activity, interleukin-1-mediated.signaling.pathway | 2.94 | 10 |
| 7.49.271.472 | GO: cell.fate.specification, heart.looping | 2.91 | 6 |
| 9.100 | GO: pos.reg.of.antimicrobial.peptide.production, reg.of.antimicrobial.humoral.response | 2.81 | 21 |
| 8.69 | GO: muscle.structure.development, muscle.organ.development | 2.74 | 15 |
| 6.42 | Lug: B-Cell. GO: immune response-activating.cell.surface.receptor.signaling.pathway | 2.72 | 19 |
| 8.76 | Anc: B.cells. GO: cytokinesis | 2.66 | 14 |
| 3.19.211 | Anc: B.cells. GO: extracellular.matrix.organization | 2.51 | 10 |
| 8.81 | GO: protein-DNA.complex, chromatin | 2.41 | 11 |
| 6.36.230.438.557 | GO: nervous.system.development, RAGE.receptor.binding | 2.39 | 12 |
| 8.71 | Lug: Monocyte. GO: response.to.virus | 2.24 | 11 |
| 6.37.239 | Anc: IFN. GO: protein.homodimerization.activity | 2.23 | 11 |
| 6.35.228 | GO: extracellular.region, vesicle | 2.13 | 24 |
| 8.55.289 | GO: transferase.activity, transferring.hexosyl.groups, protein.glycosylation | 2.12 | 7 |
| 3.18.209 | GO: plasma.membrane.part, extrinsic.component.of.plasma membrane | 2.1 | 13 |
| 6.36.236 | GO: Rho.GTPase.binding, Rac.GTPase.binding | 2.08 | 9 |
| 3.19.210 | GO: neurotransmitter.metabolic.process, reg.of.Wnt.signaling.pathway | 2.07 | 12 |
| 6.35.229.437 | GO: pos.reg.of.viral.life.cycle, pos.reg.of. viral.process | 2.01 | 3 |

TABLE 14

SLE Type 1/2 MEGENA module STRING statistics.

Listed by: mod.name | mod.annot | pcnt.PPI.intraconnected | mod.size | corr.type2 | corr.SLEDAI | corr.PSD | number_of_nodes | number_of_edges | average_node_degree | p_value
6.42.256.459 | Anc: Cell.Cycle. GO: cell.cycle | 70.6% | 32 | −0.5448 | 0.3917 | −0.6619 | 30 | 194 | 12.93 | 0; 10.157.367.514 | GO: oxidative.phosphorylation, purine.nucleoside.triphosphate.metabolic.process | 65.0% | 23 | 0.513 | −0.5733 | 0.4006 | 20 | 78 | 7.8 | 0; 6.42.256 | Anc: Cell.Cycle. GO: mitotic.cell.cycle | 57.8% | 73 | −0.5919 | 0.4174 | −0.6903 | 60 | 498 | 16.6 | 0; 10.157.367 | GO: oxidative.phosphorylation, respiratory.chain | 57.7% | 32 | 0.5149 | −0.5866 | 0.3844 | 24 | 79 | 6.58 | 0; 6.42 | Anc: Cell.Cycle. GO: cell.cycle | 57.3% | 80 | −0.5739 | 0.3981 | −0.6778 | 65 | 521 | 16.03 | 0; 6.36 | Lug: Monocyte. GO: response.to.virus | 45.5% | 330 | −0.4474 | 0.447 | −0.3717 | 256 | 760 | 5.94 | 0; 6.36.230.438 | Anc: IFN. GO: response.to.virus | 40.8% | 105 | −0.4013 | 0.3998 | 0 | 81 | 251 | 6.2 | 0; 6.36.230 | Lug: Monocyte. GO: response.to.virus | 39.4% | 160 | −0.4321 | 0.4362 | −0.3456 | 126 | 465 | 7.38 | 0; 10.157 | GO: oxidative.phosphorylation, respiratory.chain | 38.5% | 57 | 0.4416 | −0.5346 | 0.3285 | 36 | 81 | 4.5 | 0; 6.36.235 | GO: transferase.activity, transferring.hexosyl.groups, protein.glycosylation | 38.5% | 54 | −0.523 | 0.508 | −0.4702 | 39 | 11 | 0.56 | 0.00025; 6.36.230.439 | Anc: IFN. GO: reg.of.viral.life.cycle | 31.6% | 27 | −0.4734 | 0.4735 | −0.3872 | 23 | 24 | 2.09 | 0; 3.20 | Anc: Mono. Secreted. GO: synapse.pruning | 31.0% | 38 | 0.5605 | −0.6045 | 0.5063 | 29 | 7 | 0.48 | 0.0024; 6.36.234 | GO: extracellular.region, vesicle | 30.0% | 25 | −0.4665 | 0.5289 | 0 | 20 | 4 | 0.4 | 0.0034; 6.40 | GO: cation.transmembrane.transporter.activity, carnitine.shuttle | 28.7% | 43 | 0.4326 | 0 | 0 | 29 | 8 | 0.55 | 0.000079; 6.40.252 | GO: inflammatory.response, L-type.voltage-gated.calcium.channel.complex | 28.1% | 25 | 0.4767 | 0 | 0 | 19 | 5 | 0.53 | 0.00011; 7.49.271.472 | GO: cellular.response.to.endogenous.stimulus, metal.ion.transmembrane.transporter.activity | 23.5% | 20 | 0.4631 | −0.4173 | 0.6095 | 17 | 2 | 0.24 | 0.0581; 6.37 | GO: cerebral.cortex.radial.glia.guided.migration, telencephalon.glial.cell.migration | 23.1% | 92 | −0.5786 | 0.5231 | −0.4318 | 60 | 22 | 0.73 | 0.0000249; 3.18 | Tis: T.cell. GO: reg.of.neuron.death | 22.4% | 109 | −0.4121 | 0.3929 | −0.4392 | 76 | 20 | 0.53 | 0.0833; 3.20.216 | GO: muscle.structure.development, muscle.organ.development | 20.0% | 24 | 0.6103 | −0.6323 | 0.5124 | 20 | 2 | 0.2 | 0.2141; 6.37.240 | GO: neurotransmitter.metabolic.process, reg.of.Wnt.signaling.pathway | 19.0% | 33 | −0.4776 | 0.373 | −0.3266 | 21 | 2 | 0.19 | 0.2795; 6.37.239 | GO: Rho.GTPase.binding, Rac.GTPase.binding | 17.4% | 32 | −0.6226 | 0.6181 | −0.4897 | 23 | 2 | 0.17 | 0.0996; 3.18.209 | GO: cell.diff, polymeric.cytoskeletal.fiber | 15.0% | 53 | −0.5183 | 0.5029 | −0.5311 | 40 | 9 | 0.45 | 0.213; 8.75 | GO: phospholipid.transporter.activity, phospholipid.transport | 13.3% | 20 | −0.4442 | 0.4263 | −0.479 | 15 | 1 | 0.13 | 0.414; 9.110 | GO: spindle, C-5.sterol.desaturase.activity | 11.4% | 45 | 0.4903 | −0.3981 | 0.4448 | 35 | 2 | 0.11 | 0.4617; 3.18.209.408 | GO: reg.of.anatomical.structure.morphogenesis, forebrain.development | 10.8% | 49 | −0.5219 | 0.5038 | −0.5324 | 37 | 8 | 0.43 | 0.0749; 9.98 | GO: reg.of.gene.expression, protein.localization.to.endoplasmic reticulum | 0.0% | 20 | 0.4328 | 0 | 0.3472 | 10 | 0 | 0 | 1; 9.128 | GO: reg.of.axon.extension, axon.extension | 0.0% | 22 | 0.4165 | 0 | 0.3229 | 12 | 0 | 0 | 1; 3.19.214 | GO: pos.reg.of.antimicrobial.peptide.production, reg.of.antimicrobial.humoral.response | 0.0% | 21 | −0.41 | 0.3839 | 0 | 14 | 0 | 0 | 1; 9.110.349 | GO: C-5.sterol.desaturase.activity, mannose.binding | 0.0% | 29 | 0.5126 | −0.4017 | 0.4991 | 24 | 0 | 0 | 1; 9.110.349.510 | GO: C-5.sterol.desaturase.activity, protein.localization.to.paranode.region.of.axon | 0.0% | 25 | 0.474 | −0.3596 | 0.4562 | 21 | 0 | 0 | 1;

TABLE 15

Top DGCA intermodular pairs unique to Type 1.
Listed by: patientsmod1 | mod2 | mod1.annot | mod2.annot | −/0 | +/0 | 0/− | 0/+ | type1.ttls | type2.ttls 3.19.210 | 10.159.374 | GO: GTPase.regulator.activity, interleukin-18-mediated.signaling.pathway | GO: system.process, protein.heterodimerization.activity | 144 | 179 | 45 | 18 | 323 | 63; 7.49.273 | 2.11.162 | GO: neg.reg.of.extrinsic.apoptotic.signaling.pathway, porphyrin-containing.compound.biosynthetic.process | Lug: Plasma-Cell. GO: response.to.unfolded.protein | 28 | 302 | 69 | 42 | 330 | 111; 7.49.271 | 2.11.162 | GO: stem.cell.population.maintenance, maintenance.of.cell.number | Lug: Plasma-Cell. GO: response.to.unfolded.protein | 28 | 283 | 96 | 12 | 311 | 108; 8.67.299 | 3.15.175 | Tis: Monocyte/Myeloid.Cell. GO: pattern.recognition.receptor.signaling.pathway | Lug: Neutrophil. GO: cell.activation.involved.in.immune.response | 131 | 575 | 28 | 14 | 706 | 42; 3.15.180 | 3.15.175 | GO: response.to.nitrogen.compound, reg.of.hormone.secretion | Lug: Neutrophil. GO: cell.activation.involved.in.immune.response | 187 | 470 | 15 | 13 | 657 | 28; 6.35.228 | 3.15.175 | GO: protein-DNA.complex, chromatin | Lug: Neutrophil. GO: cell.activation.involved.in.immune.response | 236 | 320 | 36 | 48 | 556 | 84; 3.15.178 | 3.15.175 | GO: odontogenesis, trans-Golgi.network | Lug: Neutrophil. GO: cell.activation.involved.in.immune.response | 226 | 188 | 4 | 13 | 414 | 17; 3.19.210 | 3.15.175 | GO: GTPase.regulator.activity, interleukin-18-mediated.signaling.pathway | Lug: Neutrophil. GO: cell.activation.involved.in.immune.response | 142 | 198 | 47 | 38 | 340 | 85; 6.37.240 | 3.15.175 | GO: neurotransmitter.metabolic.process, reg.of.Wnt.signaling.pathway | Lug: Neutrophil. GO: cell.activation.involved.in.immune.response | 85 | 254 | 8 | 11 | 339 | 19; 6.35.229 | 3.15.175 | GO: nervous.system.development, RAGE.receptor.binding | Lug: Neutrophil. GO: cell.activation.involved.in.immune.response | 121 | 183 | 3 | 6 | 304 | 9; 3.18.208 | 3.15.175 |

TABLE 15-continued

| Top DGCA intermodular pairs unique to Type 1. Listed by: patientsmod1 ∣ mod2 ∣ mod1.annot ∣ mod2.annot ∣ −/0 ∣ +/0 ∣ 0/− ∣ 0/+ ∣ type1.ttls ∣ type2.ttls |
|---|
| GO: postsynaptic.endosome, galactoside.binding ∣ Lug: Neutrophil. GO: cell.activation.involved.in.immune.response ∣ 162 ∣ 137 ∣ 37 ∣ 25 ∣ 299 ∣ 62; 6.39.248 ∣ 3.15.175 ∣ Anc: IFN. GO: nucleic.acid.metabolic.process ∣ Lug: Neutrophil. GO: cell.activation.involved.in.immune.response ∣ 24 ∣ 237 ∣ 53 ∣ 19 ∣ 261 ∣ 72; 3.19.210 ∣ 3.18.208 ∣ GO: GTPase.regulator.activity, interleukin-18-mediated.signaling.pathway ∣ GO: postsynaptic.endosome, galactoside.binding ∣ 182 ∣ 184 ∣ 17 ∣ 23 ∣ 366 ∣ 40; 6.35.228 ∣ 3.18.208 ∣ GO: protein-DNA.complex, chromatin ∣ GO: postsynaptic.endosome, galactoside.binding ∣ 138 ∣ 181 ∣ 23 ∣ 13 ∣ 319 ∣ 36; 6.42.256 ∣ 5.23.222 ∣ Anc: Cell.Cycle. GO: mitotic.cell.cycle ∣ Anc: B.cells. GO: extracellular.matrix.organization ∣ 180 ∣ 75 ∣ 17 ∣ 52 ∣ 255 ∣ 69; 6.36.230 ∣ 6.35.229 ∣ Lug: Monocyte. GO: response.to.virus ∣ GO: nervous.system.development, RAGE.receptor.binding ∣ 141 ∣ 213 ∣ 6 ∣ 7 ∣ 354 ∣ 13; 9.100.332 ∣ 6.36.230 ∣ GO: cytosolic.large.ribosomal.subunit, structural.constituent.of.ribosome ∣ Lug: Monocyte. GO: response.to.virus ∣ 103 ∣ 509 ∣ 47 ∣ 23 ∣ 612 ∣ 70; |

TABLE 16

| Top DGCA intermodular pairs unique to Type 2 patients. Listed by: mod1 ∣ mod2 ∣ mod1.annot ∣ mod2.annot ∣ −/0 ∣ +/0 ∣ 0/− ∣ 0/+ ∣ type1.ttls ∣ type2.ttls |
|---|
| 6.36.230 ∣ 10.159.372 ∣ Lug: Monocyte. GO: response.to.virus ∣ Lug: Platelet. GO: wound.healing ∣ 10 ∣ 20 ∣ 91 ∣ 58 ∣ 30 ∣ 149; 6.40.252 ∣ 10.159.372 ∣ GO: inflammatory.response, L-type.voltage-gated.calcium.channel.complex ∣ Lug: Platelet. GO: wound.healing ∣ 37 ∣ 58 ∣ 104 ∣ 24 ∣ 95 ∣ 128; 3.15.175 ∣ 10.159.374 ∣ Lug: Neutrophil. GO: cell.activation.involved.in.immune.response ∣ GO: system.process, protein.heterodimerization.activity ∣ 45 ∣ 27 ∣ 71 ∣ 117 ∣ 72 ∣ 188; 6.36.230 ∣ 10.159.374 ∣ Lug: Monocyte. GO: response.to.virus ∣ GO: system.process, protein.heterodimerization.activity ∣ 28 ∣ 24 ∣ 41 ∣ 114 ∣ 52 ∣ 155; 2.11.162 ∣ 10.159.374 ∣ Lug: Plasma-Cell. GO: response.to.unfolded.protein ∣ GO: system.process, protein.heterodimerization.activity ∣ 7 ∣ 14 ∣ 134 ∣ 12 ∣ 21 ∣ 146; 6.37.239 ∣ 10.159.374 ∣ GO: Rho.GTPase.binding, Rac.GTPase.binding ∣ GO: system.process, protein.heterodimerization.activity ∣ 7 ∣ 12 ∣ 83 ∣ 45 ∣ 19 ∣ 128; 6.36.235 ∣ 10.159.374 ∣ GO: transferase.activity, transferring.hexosyl.groups, protein.glycosylation ∣ GO: system.process, protein.heterodimerization.activity ∣ 31 ∣ 20 ∣ 66 ∣ 56 ∣ 51 ∣ 122; 5.23.222 ∣ 2.11.161 ∣ Anc: B.cells. GO: extracellular.matrix.organization ∣ Lug: Plasma-Cell. GO: organic.substance.metabolic.process ∣ 99 ∣ 6 ∣ 13 ∣ 316 ∣ 105 ∣ 329; 7.49.272 ∣ 2.11.161 ∣ GO: cytosol, RNA.binding ∣ Lug: Plasma-Cell. GO: organic.substance.metabolic.process ∣ 6 ∣ 42 ∣ 128 ∣ 28 ∣ 48 ∣ 156; 6.36.235 ∣ 2.11.161 ∣ GO: transferase.activity, transferring.hexosyl.groups, protein.glycosylation ∣ Lug: Plasma-Cell. GO: organic.substance.metabolic.process ∣ 9 ∣ 32 ∣ 84 ∣ 59 ∣ 41 ∣ 143; 5.23.222 ∣ 2.11.162 ∣ Anc: B.cells. GO: extracellular.matrix.organization ∣ Lug: Plasma-Cell. GO: response.to.unfolded.protein ∣ 37 ∣ 12 ∣ 63 ∣ 564 ∣ 49 ∣ 627; 7.49.272 ∣ 2.11.162 ∣ GO: cytosol, RNA.binding ∣ Lug: Plasma-Cell. GO: response.to.unfolded.protein ∣ 19 ∣ 110 ∣ 135 ∣ 29 ∣ 129 ∣ 164; 6.36.235 ∣ 2.11.162 ∣ GO: transferase.activity, transferring.hexosyl.groups, protein.glycosylation ∣ Lug: Plasma-Cell. GO: response.to.unfolded.protein ∣ 9 ∣ 43 ∣ 104 ∣ 53 ∣ 52 ∣ 157; 6.36.230 ∣ 3.18.209 ∣ Lug: Monocyte. GO: response.to.virus ∣ GO: cell.diff, polymeric.cytoskeletal.fiber ∣ 128 ∣ 61 ∣ 213 ∣ 46 ∣ 189 ∣ 259; 6.36.230 ∣ 3.19.210 ∣ Lug: Monocyte. GO: response.to.virus GO: GTPase.regulator.activity, interleukin-18-mediated.signaling.pathway ∣ 20 ∣ 9 ∣ 62 ∣ 73 ∣ 29 ∣ 135; 6.36.230 ∣ 3.19.212 ∣ Lug: Monocyte. GO: response.to.virus ∣ GO: interleukin-1.receptor.activity, interleukin-1-mediated.signaling.pathway ∣ 16 ∣ 9 ∣ 100 ∣ 42 ∣ 25 ∣ 142; 7.49.271 ∣ 5.22.218 ∣ GO: stem.cell.population.maintenance, maintenance.of.cell.number ∣ Anc: B.cells. GO: cytokinesis ∣ 5 ∣ 38 ∣ 102 ∣ 25 ∣ 43 ∣ 127; |

TABLE 17

| The top 30 gen 2 to 4 modules | | |
|---|---|---|
| Size | Funntional annotation | genes |
| Table 17-1: Module - 10.157 | | |
| 57 | GO: oxidative.phosphorylation, respiratory.chain | DDX11L9, MT-ATP6, DDX11L1, MT-ND4, MT-ND2, MT-ND4L, DDX11L2, MT-ATP8, MT-CO3, MT-CYB, MT-ND5, MT-CO2, DDX11L16, MT-ND3, DDX11L17, MT-ND1, DDX11L5, FN1, CFAP45, MT-ND6, LMNA, VIPR2, MIR23AHG, DDX11L10, IQCN, TUBB6, SPOCD1, SLC22A23, APOA1-AS, HSD17B7P2, ZSWIM4, PKNOX2, BLM, SCN5A, MTMR9LP, SNPH, MT-TE, MEX3B, LINC00658, OR7E94P, MT-CO1, |

TABLE 17-continued

The top 30 gen 2 to 4 modules

| Size | Funntional annotation | genes |
|---|---|---|
| | | DDX11L8, SLC39A4, DGKH, LINC02745, MIR23A, NPAP1L, GHRLOS, FBX05, NETO2, ATP1B1, BNIP3P1, RTN4RL1, PELATON, ELF3, NOL3, CHD1L |
| | Table 17-2: Module - 10.157.367 | |
| 32 | GO: oxidative.phosphorylation, respiratory.chain | MT-ATP6, MT-ND4, MT-ND2, MT-ND4L, MT-ATP8, MT-CO3, MT-CYB, MT-ND5, MT-CO2, MT-ND3, MT-ND1, FN1, MT-ND6, VIPR2, SPOCD1, SLC22A23, APOA1-AS, HSD17B7P2, BLM, MTMR9LP, SNPH, MT-TE, MEX3B, MT-CO1, SLC39A4, DGKH, LINC02745, NPAP1L, NETO2, BNIP3P1, RTN4RL1, PELATON |
| | Table 17-3: Module - 10.157.367.514 | |
| 23 | GO: oxidative.phosphorylation, purine.nucleoside.triphosphate.metabolic.process | MT-ATP6, MT-ND4, MT-ND2, MT-ND4L, MT-ATP8, MT-CO3, MT-CYB, MT-ND5, MT-CO2, MT-ND3, MT-ND1, MT-ND6, VIPR2, SPOCD1, BLM, MTMR9LP, SNPH, MT-TE, MT-CO1, SLC39A4, DGKH, RTN4RL1, PELATON |
| | Table 17-4: Module - 3.18 | |
| 109 | Tis: T.cell.<br>GO: reg.of.neuron.death | BMS1P15, SSH2, HCG27, LGALS9B, ADAMTSL4-AS2, ADAMTSL4-AS1, NEDD9, FAR2, ZNF615, DNAH17, BTN1A1, TUBA1C, BMS1P16, BMS1P11, GLI1, BMS1P9, FAAHP1, OR52B3P, VNN1, LINC02656, SLC31A2, LINC01093, CNRIP1, ZDHHC19, IFITM3P2, TMEM119, MIR24-2, SEMA3B, ZNF718, BEAN1, TRAV13-2, ALDH1A2, PROKR2, RBM47, BNIPL, CSF1, AVP, SALL2, FRGCA, MRPL19, EPHB1, NEFL, LGALS9C, CDRT15, IL6R-AS1, CAPN13, TMEM221, KRT7, ENAH, PCP4L1, MCPH1-AS1, OR11H2, CD164L2, SMPDL3B, LINC02421, KIF27, BSPRY, PTOV1-AS1, TEK, SPACA6, IGHD3-10, KLK1, TRAV20, KCTD15, CELSR3, CCL4L2, LINC01791, MYO6, KRT74, CLEC40, TPTEP2, CALML6, PRSS16, IDI2-AS1, PPM1F-AS1, BTNL3, PMFBP1, GGTLC2, CASC2, GRM2, BMS1P10, LINC01882, PLXNA4, MIR3648-2, EFR3B, WNT1, PICK1, MDM2, NUPR1, CNIH2, KCNJ3, CFAP43, TULP2, SLC52A3, FGGY, RPS3AP18, FBXO24, RTEL1, ANK3-DT, CA12, OR51R1P, H4C6, TAFA1, BOK, NANOS3, ARHGAP22, NSG1, SLC25A18, CNTF |
| | Table 17-5: Module - 3.18.209 | |
| 53 | GO: cell.diff, polymeric.cytoskeletal.fiber | HCG27, ADAMTSL4-AS2, ADAMTSL4-AS1, FAR2, DNAH17, BTN1A1, TUBA1C, GLI1, FAAHP1, LINC02656, LINC01093, ZDHHC19, IFITM3P2, TMEM119, MIR24-2, SEMA3B, ALDH1A2, RBM47, BNIPL, CSF1, NEFL, CAPN13, TMEM221, KRT7, ENAH, PCP4L1, SMPDL3B, TEK, SPACA6, IGHD3-10, KLK1, KCTD15, LINC01791, MYO6, KRT74, PRSS16, GRM2, PLXNA4, MIR3648-2, WNT1, MDM2, CNIH2, TULP2, SLC52A3, FGGY, RPS3AP18, ANK3-DT, CA12, H4C6, TAFA1, NANOS3, ARHGAP22, CNTF |
| | Table 17-6: Module - 3.18.209.408 | |
| 49 | GO: reg.of.anatomical.structure.morphogenesis, forebrain.development | HCG27, ADAMTSL4-AS2, ADAMTSL4-AS1, FAR2, DNAH17, BTN1A1, TUBA1C, GLI1, FAAHP1, LINC02656, LINC01093, ZDHHC19, IFITM3P2, TMEM119, MIR24-2, SEMA3B, ALDH1A2, RBM47, BNIPL, CSF1, NEFL, CAPN13, TMEM221, PCP4L1, SMPDL3B, TEK, SPACA6, KLK1, KCTD15, LINC01791, MYO6, KRT74, PRSS16, GRM2, PLXNA4, MIR3648-2, WNT1, MDM2, CNIH2, TULP2, SLC52A3, FGGY, RPS3AP18, ANK3-DT, CA12, TAFA1, NANOS3, ARHGAP22, CNTF |
| | Table 17-7: Module - 3.19.214 | |
| 21 | GO: pos.reg.of.antimicrobial.peptide.production, reg.of.antimicrobial.humoral.response | IQCD, LMX1B, ABCC11, CEACAM22P, LINC01629, LINC02288, SCN2B, NYAP1, KLRC1, GSTM2, OR7E66P, ELAPOR1, GGT8P, DNM1, PRRT1B, CDH22, COL6A5, PGC, TRBD1, F12, PSCA |
| | Table 17-8: Module - 3.20 | |
| 38 | Anc: Mono.Secreted.<br>GO: synapse.pruning | C1QB, NOG, MPP2, C1QC, SLC22A17, SPEG, CNN3, CIQA, LGALS1, GOLGA6L9, TRBV28, NT5E, C14orf132, LDHD, KIR3DX1, GSTA6P, PATL2, KRT5, |

TABLE 17-continued

| Size | Funntional annotation | genes |
|---|---|---|
| | The top 30 gen 2 to 4 modules | |
| | | PPP4R1-AS1, ATP1A4, AMPD2, LINC01293, PCBP3, EVC, SOX8, RP1L1, UNC119B, MCF2L, ANXA2P2, MDS2, ATP2B2, EPS8L1, CALD1, ZNF812P, CASQ1, PARP11-AS1, TSPAN6, E2F2 |
| | Table 17-9: Module - 3.20.216 | |
| 24 | GO: muscle.structure.development, muscle.organ.development | NOG, SLC22A17, SPEG, CNN3, C1QA, LGALS1, GOLGA6L9, NT5E, KIR3DX1, GSTA6P, PATL2, KRT5, ATP1A4, AMPD2, EVC, SOX8, ANXA2P2, MDS2, ATP2B2, EPS8L1, CASQ1, PARP11-AS1, TSPAN6, E2F2 |
| | Table 17-10: Module - 6.36 | |
| 330 | Lug: Monocyte. GO: response.to.virus | IFI44L, SPATS2L, RSAD2, IFI44, DDX60, EIF2AK2, USP18, DDX58, CMPK2, HERC5, IFIT5, IFIH1, IFI6, EPSTI1, MX1, PLSCR1, PNPT1, FAM247A, ISG15, ZCCHC2, IFI27, SAMD9L, SMTNL1, STAT1, CHMP5, STAT2, GBP1, HERC6, PARP9, PHF11, SIGLEC1, OAS1, USP41, LY6E, MIR4477B, SAMD9, MTCO1P53, CCDC194, FAM230D, PARP12, IFI16, RSPH9, DDX60L, TUBA8, EPB41L5, TMEM123, ACO1, CETP, GBP1P1, KRT72, HES4, ODF3B, TRIM5, TYMP, FAM230H, PARP14, HESX1, APOL6, KLHDC7B, EPHB2, LY6E-DT, LIPA, FBXO39, KIAA1958, ACOT9, LAMP3, NRIR, LGALS3BP, SCO2, UNC93B3, FRG1HP, KRT73, IFITM3P4, UNC93B5, XAF1, NEXN, LINC00487, TIMM10, ZNF684, EDAR, TENT5A, TDRD7, LINC02785, LAP3, DOCK4, PLSCR2, MIR4477A, DTX3L, CCL3L1, CHRNB2, KANK3, CMTR1, TSPOAP1, GPRC5C, UTS2B, GBP4, PPM1K-DT, IL2RB, CCR5AS, NCR3, ATF3, NOS2P2, RGL1, GRAMD1B, RHAG, GPD2, FEZ1, CCRL2, UNC93B7, FAM230A, NKD1, IGHV5-10-1, OR52K2, ITGA10, LTK, PRR5L, C8orf31, CLEC2B, FAM230E, FCN1, ENTPD1-AS1, HIC1, OTOF, PTGFR, SEZ6L, OSBPL6, FLT4, GBP5, GALM, CCL2, FAM131B, DNM1P47, MS4A4A, CCR12P, ANTXRLP1, APOBEC3B-AS1, SPON1, HLA-G, CD274, FITM1, CACNA2D2, CAPN5, PITPNM3, CD300C, ADPRH, RASGRF2, TBPL2, LINC02574, TSPAN15, GDF7, LDLRAD3, LPAL2, KRT73-AS1, AXL, LRRC71, GPRC5D-AS1, HLA-F-AS1, PDCD1LG2, TRBV6-2, LINC02446, TCN2, C3AR1, ISM1, TMEM255A, SLFN5, ITGA9-AS1, LINC00638, CACNA1I, LILRB4, CD14, KIT, MYCL, SNTG2, CCL8, BLVRA, PIMREG, CACNA1A, IGHE, COL5A1, MT1DP, SLC7A8, ZNF600, CD300E, CHN1, LINC02754, SLPI, NECTIN2, PLB1, SSC4D, MTCO1P40, PLPP2, EMP1, NID1, LINC01163, GPM6A, H3C6, EBF4, ACBD7, IGHV3-64D, ERFE, LINC00243, FAM3D, SLC26A5, LRRC36, LINC02068, FBLN2, HCG9, CTSL, NOS2P3, FOLR3, RTN1, COLGALT2, TEKT1, HID1, KCNH7, PID1, TDRG1, SLC8A3, FUT2, MID2, RGPD2, NCAPG2, ULBP2, GNG5, IL15, CMKLR1, OCLNP1, GRIK4, LINC01918, RUFY4, MYOF, KCNJ2, CCL20, CRIP2, TPSD1, FAM66D, S100A7, LINC01344, HEY2, SCGB1C2, FAM178B, SCARB2, ISLR2, CYP21A1P, P3H3, KIAA1841, FAM247B, AGRN, SP100, RNF213, FAM230B, REC8, FRG1KP, ANXA10, GNB4, MILR1, KYNU, FRMD3, DNAJA1, PGAP1, SAMD4A, PRAL, CDH24, GBP3, ADAMTS10, DLG5, LMO2, SDS, UNC93B4, LHFPL2, VSIG1, FAM209A, GALNT12, PPFIBP1, LINC01484, SAMD15, MTHFD1L, PMEL, ZNF514, SLITRK5, AK5, LINC01504, EPHB3, DNAJC15, REELD1, NR3C2, NR2F1-AS1, ALS2CL, MIR503HG, IL17RE, KCNC3, MAFA, CYP46A1, RARRES2, FKBP10, FAM170B-AS1, USP13, BTN2A3P, TRAJ25, RPS2P7, JPH4, LRP12, LINC01307, PPP1R27, RNF213-AS1, CHCHD2P8, CAMK2N1, SLC7A10, GLIS3, PTRH1, C1orf127, MYG1-AS1, H4C12, HCAR1, CMTM8, TRBV7-1, ZNF835, ITGA7, CSPG4P11, MMP17, LSP1P4, CA8, EGR3, CYP4F12, DPYS, ZNF208, CPB1, SYNDIG1L, RETREG1, MPPED1 |
| | Table 17-11: Module - 6.36.230 | |
| 160 | Lug: Monocyte. GO: response.to.virus | IFI44L, SPATS2L, RSAD2, IFI44, DDX60, EIF2AK2, USP18, DDX58, CMPK2, HERC5, IFIT5, IFIH1, IFI6, EPSTI1, MX1, PLSCR1, PNPT1, FAM247A, ISG15, |

TABLE 17-continued

The top 30 gen 2 to 4 modules

| Size | Funntional annotation | genes |
|---|---|---|
| | | ZCCHC2, IFI27, SAMD9L, SMTNL1, CHMP5, STAT2, HERC6, PARP9, PHF11, SIGLEC1, OAS1, USP41, LY6E, MIR4477B, SAMD9, CCDC194, PARP12, IFI16, RSPH9, DDX60L, TUBA8, EPB41L5, TMEM123, ACO1, CETP, HES4, TRIM5, PARP14, HESX1, KLHDC7B, LIPA, KIAA1958, ACOT9, LAMP3, NRIR, LGALS3BP, FRG1HP, XAF1, LINC00487, TIMM10, ZNF684, EDAR, TDRD7, LINC02785, DOCK4, PLSCR2, MIR4477A, DTX3L, CHRNB2, KANK3, CMTR1, TSPOAP1, CCR5AS, GRAMD1B, RHAG, GPD2, FEZ1, CCRL2, NKD1, IGHV5-10-1, OR52K2, LTK, PRR5L, FAM230E, HIC1, OTOF, FAM131B, CCR12P, ANTXRLP1, APOBEC3B-AS1, SPON1, HLA-G, CACNA2D2, RASGRF2, LINC02574, TSPAN15, GDF7, LPAL2, AXL, HLA-F-AS1, ITGA9-AS1, LINC00638, CACNA1I, CCL8, PIMREG, COL5A1, MTIDP, ZNF600, EMP1, GPM6A, EBF4, IGHV3-64D, LINC00243, SLC26A5, LINC02068, HCG9, SLC8A3, RUFY4, S100A7, HEY2, SCARB2, CYP21A1P, P3H3, KIAA1841, FAM247B, AGRN, SP100, RNF213, REC8, FRG1KP, ANXA10, GNB4, MILR1, FRMD3, DNAJA1, PGAP1, SAMD4A, PRAL, DLG5, UNC93B4, LHFPL2, VSIG1, PMEL, SLITRK5, NR3C2, ALS2CL, IL17RE, FKBP10, USP13, BTN2A3P, TRAJ25, RPS2P7, JPH4, PPPIR27, RNF213-AS1, CAMK2N1, C1orf127, ZNF835, CSPG4P11, CA8, SYNDIG1L |
| | Table 17-12: Module - 6.36.230.438 | |
| 105 | Anc: IFN.<br>GO: response.to.virus | IFI44L, RSAD2, IFI44, DDX60, EIF2AK2, DDX58, CMPK2, HERC5, IFIT5, IFIH1, IFI6, EPSTI1, MX1, PLSCR1, PNPT1, ISG15, ZCCHC2, IFI27, SAMD9L, SMTNL1, CHMP5, PARP9, PHF11, SIGLEC1, MIR4477B, SAMD9, CCDC194, IFI16, RSPH9, DDX60L, EPB41L5, TMEM123, ACO1, PARP14, HESX1, LIPA, KIAA1958, ACOT9, NRIR, XAF1, LINC00487, TIMM10, ZNF684, TDRD7, LINC02785, DOCK4, PLSCR2, MIR4477A, DTX3L, CHRNB2, KANK3, TSPOAP1, CCR5AS, RHAG, GPD2, CCRL2, NKD1, IGHV5-10-1, OR52K2, LTK, PRR5L, HIC1, FAM131B, ANTXRLP1, APOBEC3B-AS1, LINC02574, TSPAN15, LPAL2, AXL, HLA-F-AS1, CACNA1I, PIMREG, COL5A1, ZNF600, EBF4, LINC00243, LINC02068, HCG9, S100A7, HEY2, SCARB2, CYP21A1P, KIAA1841, AGRN, SP100, FRG1KP, ANXA10, GNB4, MILR1, FRMD3, DNAJA1, PGAP1, PRAL, DLG5, UNC93B4, LHFPL2, VSIG1, PMEL, FKBP10, BTN2A3P, TRAJ25, RPS2P7, CAMK2N1, CSPG4P11, SYNDIG1L |
| | Table 17-13: Module - 6.36.230.439 | |
| 27 | Anc: IFN.<br>GO: reg.of.viral.life.cycle | SPATS2L, USP18, FAM247A, STAT2, HERC6, OAS1, USP41, LY6E, PARP12, TUBA8, CETP, HES4, TRIM5, LAMP3, LGALS3BP, CMTR1, GRAMD1B, FAM230E, CCL8, GPM6A, P3H3, FAM247B, RNF213, REC8, SAMD4A, JPH4, RNF213-AS1 |
| | Table 17-14: Module - 6.36.234 | |
| 25 | GO: extracellular.region, vesicle | KRT72, EPHB2, KRT73, LAP3, MS4A4A, LDLRAD3, KRT73-AS1, TCN2, C3AR1, LILRB4, BLVRA, CD300E, SSC4D, NID1, FBLN2, CTSL, HID1, MYOF, AK5, LINC01504, MIR503HG, CYP46A1, RARRES2, FAM170B-AS1, LINC01307 |
| | Table 17-15: Module - 6.36.235 | |
| 54 | GO: transferase.activity, transferring.hexosyl.groups, protein.glycosylation | ODF3B, TYMP, LY6E-DT, FBX039, SCO2, UNC93B3, IFITM3P4, UNC93B5, PPMIK-DT, UNC93B7, ITGA10, ENTPD1-AS1, OSBPL6, FLT4, FITM1, CAPN5, LRRC71, TRBV6-2, LINC02446, ISM1, KIT, CACNA1A, IGHE, SLC7A8, CHN1, LINC02754, SLPI, ACBD7, ERFE, LRRC36, FOLR3, TEKT1, FUT2, MID2, RGPD2, ULBP2, IL15, LINC01918, LINC01344, FAM178B, ISLR2, ADAMTS10, GALNT12, PPFIBP1, MTHFD1L, ZNF514, EPHB3, DNAJC15, MAFA, LRP12, TRBV7-1, ITGA7, LSP1P4, RETREG1 |

TABLE 17-continued

| The top 30 gen 2 to 4 modules | | |
|---|---|---|
| Size | Funntional annotation | genes |
| Table 17-16: Module - 6.37 | | |
| 92 | GO: cerebral.cortex.radial.glia.guided.migration, telencephalon.glial.cell.migration | SRGAP2B, FAM225A, CSAG3, SRGAP2C, SRGAP2, RNF175, FCER1A, RNASE2, ANKRD35, WNT7A, FAM225B, ROBO3, TLR2, ZFP57, RETN, PTGDR2, LINC02458, SLC12A1, ZNF595, TARM1, KRT8P26, DBH, DISC1, TAF11L2, MAOA, TLE2, UPB1, IL4, CC2D2A, OLFML2A, KCNG1, C1QTNF7-AS1, MYOM2, DEPDC1, LINC01238, LINC02761, DBNDD1, UCKL1-AS1, LINC00884, LGALSL-DT, DPYSL4, SLC45A3, SLC4A3, ACTBP8, LMO7, CNR1, SRGAP2D, CCDC162P, C3orf20, LINC02568, WARS1, ESPNP, H2AC13, LINC02520, TRAJ20, TRAV14DV4, SEPTIN9-DT, GRB10, NPTXR, GSDMC, ZNF727, SLC16A11, ASPH, MT1E, CPA5, C1QTNF7, CCDC144B, CDK2AP2P2, C5orf64, CSAG2, ACSM3, MOG, OR52B4, FMNL2, EXT1, MROCKI, LINC02042, PLEKHB1, NPM2, LINC00398, SPTBN5, CYP1A1, LINC02287, BRD7P5, SPC24, EFNA3, PNMT, FOXRED2, PODXL2, TRAJ32, LHFPL3-AS2, MIR150 |
| Table 17-17: Module - 6.37.239 | | |
| 32 | GO: Rho.GTPase.binding, Rac.GTPase.binding | SRGAP2B, FAM225A, SRGAP2C, SRGAP2, RNASE2, ANKRD35, WNT7A, FAM225B, ROBO3, RETN, ZNF595, TARM1, DBH, TAF11L2, TLE2, DEPDC1, LINC01238, UCKL1-AS1, SLC45A3, LMO7, ESPNP, TRAJ20, NPTXR, GSDMC, SLC16A11, ACSM3, FMNL2, PLEKHB1, LINC02287, PNMT, FOXRED2, TRAJ32 |
| Table 17-18: Module - 6.37.240 | | |
| 33 | GO: neurotransmitter.metabolic.process, reg.of.Wnt.signaling.pathway | CSAG3, RNF175, FCER1A, TLR2, PTGDR2, LINC02458, SLC12A1, DISC1, MAOA, UPB1, CC2D2A, OLFML2A, C1QTNF7-AS1, LGALSL-DT, SLC4A3, SRGAP2D, CCDC162P, LINC02568, WARS1, SEPTIN9-DT, GRB10, ZNF727, ASPH, C1QTNF7, CSAG2, OR52B4, EXT1, MROCKI, LINC02042, LINC00398, CYP1A1, PODXL2, LHFPL3-AS2 |
| Table 17-19: Module - 6.40 | | |
| 43 | GO: cation.transmembrane.transporter.activity, carnitine.shuttle | KRT17P2, KRT17P1, CPT1A, ADGRE4P, PRSS33, SIGLEC8, ALOX15, NME4, HRH4, CACNG6, SLC45A2, FAM138B, COL26A1, CACNG8, IL5RA, CLC, DNASE1L3, PTMS, WARS1P1, RHOXF1P1, COL11A2, SLC4A9, COLEC12, KRT17P6, PDK4, SMPD3, IL34, CNTN4-AS1, LINC01226, SLC25A20, ADAMTS7P1, ARHGEF35-AS1, SPNS3, EPHA2, ANOS1, ENPP7P8, RPL35AP26, SLC29A1, KRT2, TFEC, LINC01300, HPN, PTPRF |
| Table 17-20: Module - 6.40.252 | | |
| 25 | GO: inflammatory.response, L-type.voltage-gated.calcium.channel.complex | ADGRE4P, PRSS33, SIGLEC8, ALOX15, HRH4, CACNG6, COL26A1, CACNG8, IL5RA, CLC, DNASE1L3, PTMS, RHOXF1P1, COL11A2, SLC4A9, SMPD3, IL34, LINC01226, ADAMTS7P1, SPNS3, EPHA2, ENPP7P8, RPL35AP26, SLC29A1, TFEC |
| Table 17-21: Module - 6.42 | | |
| 80 | Anc: Cell.Cycle. GO: cell.cycle | EPN2, MKI67, CCNA2, TPX2, BUB1, BIRC5, TOP2A, GTSE1, CDC20, CIT, PKMYT1, ESPL1, KCNH3, ASPM, ADAM23, HJURP, KIF18B, KIFC1, TROAP, NCAPG, MIXL1, CDK1, CDC25A, CDC45, CDKN3, ZC2HC1C, INAVA, OR13A1, HMGB3, IGHV1-3, NUF2, KIF4A, POLR2J3, DLGAP5, STIL, CBLN2, MCM10, RNA5SP315, HMMR, GRAPL, NCAPH, CDT1, ATP5MGP1, CPAMD8, RFPL4A, ICA1, COPS5P2, LINC00683, CNGB1, TWIST2, FIGNL2, C1DP5, CDCA3, PACSIN1, MTND4P24, KLHL33, FPGT-TNNI3K, CCNB2, KIF11, INSL6, NDC80, VPS33B-DT, LINC00475, DNM1P31, TSPAN3, HTR1E, SLC7A11, SLC9C1, CD38, GSDME, SKA1, HAUS6P1, TEDDM1, MYRFL, MTCL1, WBP1LP2, BMP8B, PDGFC, SNHG5, LINC02610 |

TABLE 17-continued

| Size | Funntional annotation | genes |
|---|---|---|
| | The top 30 gen 2 to 4 modules | |
| | Table 17-22: Module - 6.42.256 | |
| 73 | Anc: Cell.Cycle. GO: mitotic.cell.cycle | EPN2, MKI67, CCNA2, TPX2, BUB1, BIRC5, TOP2A, GTSE1, CDC20, CIT, PKMYT1, ESPL1, ASPM, ADAM23, HJURP, KIF18B, KIFC1, TROAP, NCAPG, MIXL1, CDK1, CDC25A, CDC45, CDKN3, ZC2HC1C, INAVA, OR13A1, HMGB3, IGHV1-3, NUF2, KIF4A, DLGAP5, MCM10, RNA5SP315, HMMR, GRAPL, NCAPH, CDT1, ATP5MGP1, CPAMD8, RFPL4A, ICA1, LINC00683, CNGB1, TWIST2, FIGNL2, C1DP5, CDCA3, PACSIN1, MTND4P24, KLHL33, FPGT-TNNI3K, CCNB2, KIF11, INSL6, NDC80, VPS33B-DT, LINC00475, DNM1P31, TSPAN3, SLC7A11, SLC9C1, CD38, GSDME, SKA1, TEDDM1, MYRFL, MTCL1, WBP1LP2, BMP8B, PDGFC, SNHG5, LINC02610 |
| | Table 17-23: Module - 6.42.256.459 | |
| 32 | Anc: Cell.Cycle. GO: cell.cycle | MKI67, CCNA2, TPX2, BUB1, TOP2A, GTSE1, CDC20, CIT, HJURP, KIF18B, KIFC1, NCAPG, MIXL1, CDK1, CDC45, CDKN3, NUF2, MCM10, CDT1, CNGB1, TWIST2, FIGNL2, CDCA3, PACSIN1, MIND4P24, CCNB2, INSL6, TSPAN3, CD38, SKA1, TEDDM1, MYRFL |
| | Table 17-24: Module - 7.49.271.472 | |
| 20 | GO: cellular.response.to.endogenous.stimulus, metal.ion.transmembrane.transporter.activity | HBB, FAM210B, ADIPOR1, PBX1, EMC3, FBXO7, PPM1A, PAGE2B, LINC01036, SLC25A37, PAGE2, RGS10, SLC6A19, KCNMA1, TPGS2, BBOF1, FUNDC2P1, C1orf198, BEND3P1, LEFTY1 |
| | Table 17-25: Module - 8.75 | |
| 20 | GO: phospholipid.transporter.activity, phospholipid.transport | TUFT1, KIAA0319, ABCA1, CORIN, ABCG1, VASH1, NFXL1, STARD10, NMRAL2P, RPA2, COL9A3, LINC00222, LINC01305, LINC01644, TMEM273, SYT17, SLC3A2, NEO1, PTPN5, DNM1P34 |
| | Table 17-26: Module - 9.110 | |
| 45 | GO: spindle, C-5.sterol.desaturase.activity | SC5D, KBTBD8, PRELID3B, CCDC82, C12orf29, PRKAR2A-AS1, UGT8, IGIP, SRP9, RLN2, CFAP54, UFL1, LRRC3, NAPIL3, NCAM2, UTP15, RLN1, CFAP100, CENPE, ZNF404, PTPN13, SMIM10L2A, CD207, LRFN2, ANKRD12, KLRA1P, LINC00698, TMEM158, LVRN, ZNF471, LINC02575, ZNF204P, RIN1, CHEK2P2, HLTF, ALKAL2, MYCT1, SPAG8, EXD2, LINC00402, XIRP1, GK4P, CPNE4, ITPR1-DT, UNC5A |
| | Table 17-27: Module - 9.110.349 | |
| 29 | GO: C-5.sterol.desaturase.activity, mannose.binding | SC5D, KBTBD8, PRELID3B, C12orf29, UGT8, IGIP, RLN2, CFAP54, UFL1, LRRC3, NAPIL3, UTP15, ZNF404, PTPN13, SMIM10L2A, CD207, ANKRD12, LINC00698, LVRN, ZNF471, LINC02575, HLTF, MYCT1, SPAG8, EXD2, LINC00402, XIRP1, CPNE4, ITPR1-DT |
| | Table 17-28: Module - 9.110.349.510 | |
| 25 | GO: C-5.sterol.desaturase.activity, protein.localization.to.paranode.region.of.axon | SC5D, KBTBD8, PRELID3B, C12orf29, UGT8, IGIP, RLN2, UFL1, LRRC3, NAPIL3, UTP15, ZNF404, PTPN13, SMIM10L2A, ANKRD12, LINC00698, LVRN, LINC02575, HLTF, MYCT1, SPAG8, EXD2, XIRP1, CPNE4, ITPR1-DT |
| | Table 17-29: Module - 9.128 | |
| 22 | GO: reg.of.axon.extension, axon.extension | RASIP1, IL9RP1, SEC61G-DT, MAP1B, PLIN1, ZNF436-AS1, KRT18, OLFM1, SEMA3F, IRAG1-AS1, CALCB, GRM7, HOXC4, FGF17, ARHGAP5-AS1, LINC02280, LINC02666, RN7SKP1, ZNF165, CFAP299, LINC02356, DNM1P33 |
| | Table 17-30: Module - 9.98 | |
| 20 | GO: reg.of.gene.expression, protein.localization.to.endoplasmic.reticulum | RPS26P6, RPS26P8, RPS26P58, ANK2, RPS26, RPS26P13, CHST6, LINC02175, EBF3, RPS26P2, OR52P2P, PERM1, RGMA, CFAP46, CREB3L3, RPS26P39, DAB1, TINCR, ZMYND15, LINC02141 |

TABLE 18

| DGCA gene pairs | | | | | | | | |
|---|---|---|---|---|---|---|---|---|
| Genel | Gene2 | zScoreDiff | pValDiff_adj | Classes | Gene1.gen3.mod | Gene2.gen3.mod | pair.cor.type1 | pair.cor.type2 |
| IGHV3-15 | ALDH6A1 | 5.56141657 | 0.00266931 | −/+ | 2.11.162 | 7.49.272 | −0.7622773 | 0.97618278 |
| TPBGL | ICA1 | −5.3043561 | 0.00376905 | +/− | 6.35.228 | 6.42.256 | 0.8816868 | −0.9327547 |
| ENKUR | PTGFRN | −5.2108492 | 0.00467862 | +/− | 10.159.374 | 3.19.210 | 0.94222127 | −0.8485643 |
| IGKV1OR2-6 | B3GNT3 | 5.17013025 | 0.00467862 | −/+ | 2.11.161 | 10.159.375 | −0.9013685 | 0.90613845 |
| PRAL | TPTEP2 | −5.0852437 | 0.00468527 | +/0 | 6.36.230 | 3.18.208 | 0.97970551 | −0.5688288 |
| ANKRD20A5P | NCK1-DT | 5.07501268 | 0.00468527 | 0/+ | 6.35.228 | 9.100.332 | −0.609454 | 0.97677552 |
| DGKH | PICK1 | −5.0428198 | 0.00468527 | +/− | 10.157.367 | 3.18.208 | 0.93335852 | −0.8418905 |
| SAPCD2 | CFAP54 | −5.025981 | 0.00468527 | +/− | 3.19.213 | 9.110.349 | 0.88067176 | −0.9092187 |
| GRB10 | LOXL4 | 4.98120194 | 0.00468527 | −/+ | 6.37.240 | 3.15.180 | −0.9181 | 0.86149202 |
| LINC02458 | MLF1 | −4.9780645 | 0.00468527 | +/− | 6.37.240 | 3.19.212 | 0.94324855 | −0.8031305 |
| GSTM2 | ASB9 | −4.9766806 | 0.00468527 | +/− | 3.19.214 | 10.159.374 | 0.9048706 | −0.8797865 |
| BAMBI | RPL35AP26 | 4.96350868 | 0.00468527 | −/+ | 7.48.268 | 6.40.252 | −0.8892872 | 0.8951329 |
| METTL7B | FBXO24 | −4.9343394 | 0.00468527 | +/− | 3.15.175 | 3.18.208 | 0.88761009 | −0.8933542 |
| SETD9 | ZNF337 | −4.93247 | 0.00468527 | +/0 | 3.19.210 | 8.51.280 | 0.98128415 | −0.4751474 |
| SRGN | EGLN3 | −4.9131025 | 0.00468527 | +/− | 8.58.291 | 10.158.371 | 0.78487603 | −0.9445483 |
| SEPTIN9-DT | AK5 | 4.91258796 | 0.00468527 | −/+ | 6.37.240 | 6.36.234 | −0.8243912 | 0.93100921 |
| VCX3A | XIRP1 | 4.89903468 | 0.00468527 | 0/+ | 3.19.210 | 9.110.349 | −0.1798296 | 1 |
| IGHV1-3 | SLAMF8 | −4.8947311 | 0.00468527 | +/− | 6.42.256 | 10.159.375 | 0.91136463 | −0.8592453 |
| TRAJ3 | TMEM244 | −4.8743964 | 0.00468527 | +/− | 3.19.210 | 6.35.228 | 0.96087462 | −0.694733 |
| CC2D2A | MLF1 | 4.86784844 | 0.00468527 | −/+ | 6.37.240 | 3.19.212 | −0.9574947 | 0.7141278 |

TABLE 19

| DGCA class type | | |
|---|---|---|
| Class | Type 1 Pair | Type 2 Pair |
| −/− | Down | Down |
| **−/0** | **Down** | **No change** |
| 0/0 | No change | No change |
| **+/0** | **Up** | **No change** |

TABLE 19-continued

| DGCA class type | | |
|---|---|---|
| Class | Type 1 Pair | Type 2 Pair |
| −/+ | Down | Up |
| +/− | Up | Down |
| **0/−** | **No change** | **Down** |
| **0/+** | **No change** | **Up** |
| +/+ | Up | Up |

TABLE 20

Top DGCA type 1 inflammatory SLE intramodular pair totals per gen3 module.

| mod1 | mod2 | mod1.annot |
|---|---|---|
| 3.19.210 | 10.159.374 | GO: GTPase.regulator.activity, interleukin-18-mediated.signaling.pathway |
| 7.49.273 | 2.11.162 | GO: neg.reg.of.extrinsic.apoptotic.signaling.pathway, porphyrin-containing.compound.biosynthetic.process |
| 7.49.271 | 2.11.162 | GO: stem.cell.population.maintenance, maintenance.of.cell.number |
| 8.67.299 | 3.15.175 | Tis: Monocyte/Myeloid.Cell. GO: pattern.recognition.receptor.signaling.pathway |
| 3.15.180 | 3.15.175 | GO: response.to.nitrogen.compound, reg.of.hormone.secretion |
| 6.35.228 | 3.15.175 | GO: protein-DNA.complex, chromatin |
| 3.15.178 | 3.15.175 | GO: odontogenesis, trans-Golgi.network |
| 3.19.210 | 3.15.175 | GO: GTPase.regulator.activity, interleukin-18-mediated.signaling.pathway |
| 6.37.240 | 3.15.175 | GO: neurotransmitter.metabolic.process, reg.of.Wnt.signaling.pathway |
| 6.35.229 | 3.15.175 | GO: nervous.system.development, RAGE.receptor.binding |
| 3.18.208 | 3.15.175 | GO: postsynaptic.endosome, galactoside.binding |
| 6.39.248 | 3.15.175 | Anc: IFN. GO: nucleic.acid.metabolic.process |
| 3.19.210 | 3.18.208 | GO: GTPase.regulator.activity, interleukin-18-mediated.signaling.pathway |
| 6.35.228 | 3.18.208 | GO: protein-DNA.complex, chromatin |
| 6.42.256 | 5.23.222 | Anc: Cell.Cycle.GO: mitotic.cell.cycle |
| 6.36.230 | 6.35.229 | Lug: Monocyte. GO: response.to.virus |
| 9.100.332 | 6.36.230 | GO: cytosolic.large.ribosomal.subunit, structural.constituent.of.ribosome |

| mod1 | mod2 | mod2.annot | −/0 | +/0 | 0/− | 0/+ | type1.ttls | type2.ttls |
|---|---|---|---|---|---|---|---|---|
| 3.19.210 | 10.159.374 | GO: system.process, protein.heterodimerization.activity | **144** | **179** | 45 | 18 | **323** | 63 |
| 7.49.273 | 2.11.162 | Lug: Plasma-Cell. GO: response.to.unfolded.protein | **28** | **302** | 69 | 42 | **330** | 111 |
| 7.49.271 | 2.11.162 | Lug: Plasma-Cell. GO: response.to.unfolded.protein | **28** | **283** | 96 | 12 | **311** | 108 |

TABLE 20-continued

Top DGCA type 1 inflammatory SLE intramodular pair totals per gen3 module.

| | | | | | | | | |
|---|---|---|---|---|---|---|---|---|
| 8.67.299 | 3.15.175 | Lug: Neutrophil. GO: cell.activation.involved.in.immune.response | **131** | **575** | 28 | 14 | **706** | 42 |
| 3.15.180 | 3.15.175 | Lug: Neutrophil. GO: cell.activation.involved.in.immune.response | **187** | **470** | 15 | 13 | **657** | 28 |
| 6.35.228 | 3.15.175 | Lug: Neutrophil. GO: cell.activation.involved.in.immune.response | **236** | **230** | 36 | 48 | **556** | 84 |
| 3.15.178 | 3.15.175 | Lug: Neutrophil. GO: cell.activation.involved.in.immune.response | **226** | **188** | 4 | 13 | **414** | 17 |
| 3.19.210 | 3.15.175 | Lug: Neutrophil. GO: cell.activation.involved.in.immune.response | **142** | **198** | 47 | 38 | **340** | 85 |
| 6.37.240 | 3.15.175 | Lug: Neutrophil. GO: cell.activation.involved.in.immune.response | **85** | **254** | 8 | 11 | **339** | 19 |
| 6.35.229 | 3.15.175 | Lug: Neutrophil. GO: cell.activation.involved.in.immune.response | **121** | **183** | 3 | 6 | **304** | 9 |
| 3.18.208 | 3.15.175 | Lug: Neutrophil. GO: cell.activation.involved.in.immune.response | **162** | **137** | 37 | 25 | **299** | 62 |
| 6.39.248 | 3.15.175 | Lug: Neutrophil. GO: cell.activation.involved.in.immune.response | **24** | **237** | 53 | 19 | **261** | 72 |
| 3.19.210 | 3.18.208 | GO: postsynaptic.endosome, galactoside.binding | **182** | **184** | 17 | 23 | **366** | 40 |
| 6.35.228 | 3.18.208 | GO: postsynaptic.endosome, galactoside.binding | **138** | **181** | 23 | 13 | **319** | 36 |
| 6.42.256 | 5.23.222 | Anc: B.cells. GO: extracellular.matrix.organization | **180** | **75** | 17 | 52 | **255** | 69 |
| 6.36.230 | 6.35.229 | GO: nervous.system.development, RAGE.receptor.binding | **141** | **213** | 6 | 7 | **354** | 13 |
| 9.100.332 | 6.36.230 | Lug: Monocyte. GO: response.to.virus | **103** | **509** | 47 | 23 | **612** | 70 |

TABLE 21

Top DGCA type 2 non-inflammatory SLE intramodular pair totals per gen3 module.

| mod1 | mod2 | mod1.annot | |
|---|---|---|---|
| 6.36.230 | 10.159.372 | Lug: Monocyte. GO: response.to.virus | Lug: Platelet. mod2.annot |
| 6.40.252 | 10.159.372 | GO: inflammatory.response, L-type.voltage-gated.calcium.channel.complex | Lug: Platelet. GO: wound.healing |
| 3.15.175 | 10.159.374 | Lug: Neutrophil. GO: cell.activation.involved.in.immune.response | GO: system.process, protein.heterodimerization.activity |
| 6.36.230 | 10.159.374 | Lug: Monocyte. GO: response.to.virus | GO: system.process, protein.heterodimerization.activity |
| 2.11.162 | 10.159.374 | Lug: Plasma-Cell. GO: response.to.unfolded.protein | GO: system.process, protein.heterodimerization.activity |
| 6.37.239 | 10.159.374 | GO: Rho.GTPase.binding, Rac.GTPase.binding | GO: system.process, protein.heterodimerization.activity |
| 6.36.235 | 10.159.374 | GO: transferase.activity, transferring.hexosyl.groups, protein.glycosylation | GO: system.process, protein.heterodimerization.activity |
| 5.23.222 | 2.11.161 | Anc: B.cells. GO: extracellular.matrix.organization | Lug: Plasma-Cell. GO: organic.substance.metabolic.process |
| 7.49.272 | 2.11.161 | GO: cytosol, RNA.binding | Lug: Plasma-Cell. GO: organic.substance.metabolic.process |
| 6.36.235 | 2.11.161 | GO: transferase.activity, transferring.hexosyl.groups, protein.glycosylation | Lug: Plasma-Cell. GO: organic.substance.metabolic.process |
| 5.23.222 | 2.11.162 | Anc: B.cells. GO: extracellular.matrix.organization | Lug: Plasma-Cell. GO: response.to.unfolded.protein |
| 7.49.272 | 2.11.162 | GO: cytosol, RNA.binding | Lug: Plasma-Cell. GO: response.to.unfolded.protein |
| 6.36.235 | 2.11.162 | GO: transferase.activity, transferring.hexosyl.groups, protein.glycosylation | Lug: Plasma-Cell. GO: response.to.unfolded.protein |
| 6.36.230 | 3.18.209 | Lug: Monocyte. GO: response.to.virus | GO: cell.diff, polymeric.cytoskeletal.fiber |
| 6.36.230 | 3.19.210 | Lug: Monocyte. GO: response.to.virus | GO: GTPase.regulator.activity, interleukin-18-mediated.signaling.pathway |
| 6.36.230 | 3.19.212 | Lug: Monocyte. GO: response.to.virus | GO: interleukin-1.receptor.activity, interleukin-1-mediated.signaling.pathway |
| 7.49.271 | 5.22.218 | GO: stem.cell.population.maintenance, maintenance.of.cell.number | Anc: B.cells. GO: cytokinesis |

TABLE 21-continued

Top DGCA type 2 non-inflammatory SLE intramodular pair totals per gen3 module.

| mod1 | mod2 | −/0 | +/0 | 0/− | 0/+ | type1.ttls | type2.ttls |
|---|---|---|---|---|---|---|---|
| 6.36.230 | 10.159.372 | 10 | 20 | **91** | **58** | 30 | **149** |
| 6.40.252 | 10.159.372 | 37 | 58 | **104** | **24** | 95 | **128** |
| 3.15.175 | 10.159.374 | 45 | 27 | **71** | **117** | 72 | **188** |
| 6.36.230 | 10.159.374 | 28 | 24 | **41** | **114** | 52 | **155** |
| 2.11.162 | 10.159.374 | 7 | 14 | **134** | **12** | 21 | **146** |
| 6.37.239 | 10.159.374 | 7 | 12 | **83** | **45** | 19 | **128** |
| 6.36.235 | 10.159.374 | 31 | 20 | **66** | **56** | 51 | **122** |
| 5.23.222 | 2.11.161 | 99 | 6 | **13** | **316** | 105 | **329** |
| 7.49.272 | 2.11.161 | 6 | 42 | **128** | **28** | 48 | **156** |
| 6.36.235 | 2.11.161 | 9 | 32 | **84** | **59** | 41 | **143** |
| 5.23.222 | 2.11.162 | 37 | 12 | **63** | **564** | 49 | **627** |
| 7.49.272 | 2.11.162 | 19 | 110 | **135** | **29** | 129 | **164** |
| 6.36.235 | 2.11.162 | 9 | 43 | **104** | **53** | 52 | **157** |
| 6.36.230 | 3.18.209 | 128 | 61 | **213** | **46** | 189 | **259** |
| 6.36.230 | 3.19.210 | 20 | 9 | **62** | **73** | 29 | **135** |
| 6.36.230 | 3.19.212 | 16 | 9 | **100** | **42** | 25 | **142** |
| 7.49.271 | 5.22.218 | 5 | 38 | **102** | **25** | 43 | **127** |

TABLE 22

Top unique Type 1 SLE DGCA module pair members

| lineage | enrichment |
|---|---|
| 10.159.374 | GO: system.process, protein.heterodimerization.activity |
| 2.11.162 | Lug: Plasma-Cell. GO: response.to.unfolded.protein |
| **3.15.175** | **Lug: Neutrophil. GO: cell.activation.involved.in.immune.response** |
| 3.15.178 | GO: odontogenesis, trans-Golgi.network |
| 3.15.180 | GO: response.to.nitrogen.compound, reg.of.hormone.secretion |
| 3.18.208 | GO: postsynaptic.endosome, galactoside.binding |
| 3.19.210 | GO: GTPase.regulator.activity, interleukin-18-mediated.signaling.pathway |
| 5.23.222 | Anc: B.cells. GO: extracellular.matrix.organization |
| 6.35.228 | GO: protein-DNA.complex, chromatin |
| 6.35.229 | GO: nervous.system.development, RAGE.receptor.binding |
| 6.36.230 | Lug: Monocyte. GO: response.to.virus |
| 6.37.240 | GO: neurotransmitter.metabolic.process, reg.of.Wnt.signaling.pathway |
| 6.39.248 | Anc: IFN. GO: nucleic.acid.metabolic.process |
| 6.42.256 | Anc: Cell.Cycle. GO: mitotic.cell.cycle |
| 7.49.271 | GO: stem.cell.population.maintenance, maintenance.of.cell.number |
| 7.49.273 | GO: neg.reg.of.extrinsic.apoptotic.signaling.pathway, porphyrin |
| 8.67.299 | Tis: Monocyte/Myeloid.Cell. GO: pattern.recognition.receptor.signaling.pathway |
| 9.100.332 | GO: cytosolic.large.ribosomal.subunit, structural.constituent.of.ribosome |

TABLE 23

Top unique Type 2 SLE DGCA module pair members

| lineage | enrichment |
|---|---|
| 10.159.372 | Lug: Platelet. GO: wound healing |
| 10.159.374 | GO: system.process, protein.heterodimerization.activity |
| **2.11.161** | **Lug: Plasma-Cell. GO: organic.substance.metabolic.process** |
| **2.11.162** | **Lug: Plasma-Cell. GO: response.to.unfolded.protein** |
| 3.15.175 | Lug: Neutrophil. GO: cell.activation.involved.in.immune.response |
| 3.18.209 | GO: cell.diff, polymeric.cytoskeletal.fiber |
| 3.19.210 | GO: GTPase.regulator.activity, interleukin-18-mediated.signaling.pathway |
| 3.19.212 | GO: interleukin-1.receptor.activity, interleukin-1-mediated.signaling.pathway |
| 5.22.218 | Anc: B.cells. GO: cytokinesis |
| **5.23.222** | **Anc: B.cells. GO: extracellular.matrix.organization** |
| 6.36.230 | Lug: Monocyte. GO: response.to.virus |
| 6.36.235 | GO: transferase.activity, transferring.hexosyl.groups, protein.glycosylation |

TABLE 23-continued

| Top unique Type 2 SLE DGCA module pair members | |
|---|---|
| lineage | enrichment |
| 6.37.239 | GO: Rho.GTPase.binding, Rac.GTPase.binding |
| 6.40.252 | GO: inflammatory.response, L-type.voltage-gated.calcium.channel.complex |
| 7.49.271 | GO: stem.cell.population.maintenance, maintenance.of.cell.number |
| 7.49.272 | GO: cytosol, RNA.binding |

TABLE 24

| Top 30 gen 3 Modules | | |
|---|---|---|
| Size | Functional Annotation | Genes |
| Table 24-1. Module: 10.158.371; Co-efficient: −0.133951009074388 | | |
| 28 | GO: animal.organ.morphogenesis, reg.of.Wnt.signaling.pathway | LINC01934, CCDC167, ALPK2, CRMP1, SLC24A4, SLC40A1, MAP6, NUGGC, EDARADD, NPDC1, SH3RF2, MIR34AHG, TMEM18, NFASC, HEBP2, CD70, PLEKHA5, DACT1, DNAH6, TTC9, IKZF2, PHLDA1, BHLHE40-AS1, HSPG2, LINC01871, FDXR, PTK7, EGLN3 |
| Table 24-2. Module: 3.15.175; Co-efficient: −0.0756131114231847 | | |
| 140 | Lug: Neutrophil.GO: cell.activation.involved.in.immune.response | DEFA1, DEFA3, LTF, DEFA1B, DEFA4, LCN2, CAMP, BPI, MMP8, LINC02009, OLR1, ELANE, CRISP3, AZU1, PDE3A, LINC01579, LINC00671, ERG, TCN1, JDP2, ABCA13, ATP8B4, FGD4, ORM1, ENO2, PCOLCE2, TRAV8-4, IL18R1, DRC1, CHIT1, TXNL4B, MS4A3, OLFM4, CLTCL1, HTRA3, ASGR2, S1PR1, CITED4, CLDN18, SERPINB10, DOC2B, PGLYRP1, TUSC8, STOX2, CRISP2, VEGFA, CACNA1H, PRTN3, PLA2G2D, FCRL3, GUCY2C, PLBD1, CTSG, FKBP9, GATA3, MPO, MIR223HG, METTL7B, PRRT4, RNF144B, COL17A1, RNASE3, PCSK9, ARG1, PASK, ADCY6, NTRK1, HLA-DPB1, AFF2, H1-0, RTN4R, INHBA, ZC3H12D, TMEM252-DT, TMEM52B, THAP7-AS1, ATP2C2, IRF4, KCNE1B, GLOD5, DUOXA1, SEMA3C, LINC01529, TFF3, TRNP1, CCND1, COL4A1, SORCS2, BEX1, ATOH8, SLC5A9, TSPAN7, ASPG, CD163L1, RPL10P19, ST14, CSHL1, ANTXRL, TEKT2, PGM5, CABP1, COPDA1, KLHL8, TSKS, FBN1, TRPM2, ANO5, BAHCC1, HMGN3-AS1, ORM2, FOXC1, PHC1P1, OR6N1, CSGALNACT2, DEFA8P, SLAMF1, PXYLP1, MCEMP1, PARP4P2, MGST1, NLRC4, TUBA5P, NXF3, STOM, SEMA4C, SAMSN1, XKR7, TRBV7-4, RNU6-1176P, ACOX1, RAB44, ANLN, GRK1, JPH3, DIP2C, DDN-AS1, TCTEX1D1, ACVRL1, LRRC2, ARNT2 |
| Table 24-3. Module: 3.15.176; Co-efficient: −0.106958448196497 | | |
| 30 | GO: G.protein-coupled.receptor.signaling.pathway, coupled.to.cyclic.nucleotide.second.messenger, cell.diff.in.hindbrain | TRIM51BP, HDC, GRM3, GATA2, FKBP9P1, PRRG3, MTDHP1, WFDC5, KNDC1, LPAR3, TRIM51EP, LINC02474, RPS23P9, NRN1, MSANTD3-TMEFF1, MS4A2, ZNF273, LINC00958, MUC12, HIPK1-AS1, PTX4, SIGLEC10, AKAP12, CILP2, OGDHL, PRSS1, CA10, CTSD, ERI1, FBLIM1 |
| Table 24-4. Module: 3.15.180; Co-efficient: −0.0474535632578916 | | |
| 37 | GO: response.to.nitrogen.compound, reg.of.hormone.secretion | KCNE1, ZBTB16, FKBP5, PFKFB2, FLT3, ECHDC3, CCND3, RELL1, SMAP2, MTARC1, KCNB1, TSC22D3, IRAK3, ENHO, IRS2, P2RY10, URAD, LOXL4, PPARG, UACA, SYT15, ITGA11, MY07A, LAMB2, DUSP5, PLGLB1, TRAV19, MYB, ERLIN1, TRAV39, NEK11, GAS2L3, H2AC12, SERPINB2, AKR7L, RASAL1, HSPB1 |
| Table 24-5. Module: 3.16.199; Co-efficient: −0.0392356634714267 | | |
| 21 | GO: calcium.ion.binding.pos.reg.of.wound.healing | SEMA3G, SPSB1, HSF4, TMIGD2, IGHV1-69-2, MSC-AS1, KIF26A, MMRN1, GTSF1L, JSRP1, ASAP3, CD93, IFNLR1, MIR3142HG, PVT1, RPS23P3, USP46, THBD, SMOC2, TMEM44, CASTOR1 |
| Table 24-6. Module: 3.18.209; Co-efficient: −0.145992002307631 | | |
| 53 | GO: cell.diff, polymeric.cytoskeletal.fiber | HCG27, ADAMTSL4-AS2, ADAMTSL4-AS1, FAR2, DNAH17, BTN1A1, TUBA1C, GLI1, FAAHP1, LINC02656, LINC01093, ZDHHC19, IFITM3P2, TMEM119, MIR24-2, SEMA3B, ALDH1A2, RBM47, BNIPL, CSF1, NEFL, CAPN13, TMEM221, KRT7, ENAH, PCP4L1, SMPDL3B, TEK, SPACA6, IGHD3-10, KLK1, KCTD15, LINC01791, MY06, KRT74, PRSS16, GRM2, PLXNA4, MIR3648-2, WNT1, MDM2, CNIH2, TULP2, SLC52A3, FGGY, RPS3AP18, ANK3-DT, CA12, H4C6, TAFA1, NANOS3, ARHGAP22, CNTF |

TABLE 24-continued

Top 30 gen 3 Modules

| Size | Functional Annotation | Genes |
|---|---|---|
| | | Table 24-7. Module: 3.19.210; Co-efficient: −0.221413124916465 |
| 55 | GO: GTPase.regulator.activity, interleukin-18-mediated.signaling.pathway | VCX3B, DAAM2, IL1R2, ADIG, GSTT2B, PDGFB, TMIGD3, TRAV8-1, TPST1, EPCAM-DT, OLAH, SCRG1, ARHGAP24, SETD9, VCX3A, GUCY2D, SLC1A3, COL9A2, ARMC12, VSIG4, VCX, NIPAL2, SRGAP1, CCNA1, ST6 GALNAC3, BSND, TBC1D8, GSTT2, FSD1, MAMSTR, TRAJ3, LAMB3, NT5DC4, ITGAD, FLT1P1, IL18RAP, PTPN3, MED6P1, ZNF667, CPLX1, SH3BP4, CASKIN1, HCG14, TAC3, FAM24B, HGD, TRBV10-1, TSHZ2, TRAV2, RN7SL251P, PTPDC1, CCDC181, PTGFRN, STK19B, CYP2S1 |
| | | Table 24-8. Module: 3.19.211; Co-efficient: −0.107148351487244 |
| 35 | GO: small.moleculebiosynthetic.process, cellular.response.to.steroid.hormone.stimulus | ALOX15B, ADAMTS2, PER1, CPM, SAP30, GLDN, CD163, MARVELD1, KLF9, DDIT4, SIGLEC16, LINC00482, SH3PXD2B, VCAN, FHDC1, MIR181A1HG, MYO10, LINC01127, A4GALT, MS4A6A, IQGAP3, ALDH2, LINC01736, LRMDA, FHL2, LYZ, TRGJP, SPTLC2, ENPP3, ASB2, MARCHF1, BCAT1, ALDH1A1, NBPF2P, LINC02087 |
| | | Table 24-9. Module: 3.19.214; Co-efficient: −0.226789428580797 |
| 21 | GO: pos.reg.of.antimicrobial.peptide.production, reg.of.antimicrobial.humoral.response | IQCD, LMX1B, ABCC11, CEACAM22P, LINC01629, LINC02288, SCN2B, NYAP1, KLRC1, GSTM2, OR7E66P, ELAPOR1, GGT8P, DNM1, PRRT1B, CDH22, COL6A5, PGC, TRBD1, F12, PSCA |
| | | Table 24-10. Module: 6.35.228; Co-efficient: −0.183261186934737 |
| 77 | GO: protein-DNA.complex, chromatin | H2AC18, SP110, TMEM191B, CASP1, NTNG2, LINC02213, ADCY4, H2BC6, CIB3, AIM2, LINC02212, TRIM25, APOBEC3A, H2BC18, H4C4, ADAMTSL4, CFAP58-DT, H4C8, ZNF396, ANKRD20A5P, MAP1LC3B2, PDE9A, FCGR2B, SCART1, GSG1L, OR52K1, PPL, SMCHD1, TRAV16, JUP, FAM174B, H1-12P, SPATC1, RGL3, PAQR6, LGALSL, TMEM191C, LINC00173, LLCFC1, PI4KAP1, CDHR1, HSPA7, KCND1, VSIG10L, SLC16A8, OVOL1, ESCO2, C17orf97, HCG18, TACR2, SLC35F3, GRASLND, GPRASP2, CRHR2, TMEM244, CD300LD, TPBGL, NOVA1, LRRC77P, FCRLB, PMP22, H2AC19, CIR1, DDAH2, IL27, PSTK, NOXRED1, MYBPC3, PRRG4, KCNK7, TMEM132D, TMEM200B, CFAP99, FCGR2C, PDIA2, FGFR4, RNF112 |
| | | Table 24-11. Module: 6.36.230; Co-efficient: −0.159696860764768 |
| 160 | Lug: Monocyte. GO: response.to.virus | IFI44L, SPATS2L, RSAD2, IFI44, DDX60, EIF2AK2, USP18, DDX58, CMPK2, HERC5, IFIT5, IFIH1, IFI6, EPSTI1, MX1, PLSCR1, PNPT1, FAM247A, ISG15, ZCCHC2, IFI27, SAMD9L, SMTNL1, CHMP5, STAT2, HERC6, PARP9, PHF11, SIGLEC1, OAS1, USP41, LY6E, MIR4477B, SAMD9, CCDC194, PARP12, IFI16, RSPH9, DDX60L, TUBA8, EPB41L5, TMEM123, ACO1, CETP, HES4, TRIM5, PARP14, HESX1, KLHDC7B, LIPA, KIAA1958, ACOT9, LAMP3, NRIR, LGALS3BP, FRG1HP, XAF1, LINC00487, TIMM10, ZNF684, EDAR, TDRD7, LINC02785, DOCK4, PLSCR2, MIR4477A, DTX3L, CHRNB2, KANK3, CMTR1, TSPOAP1, CCR5AS, GRAMD1B, RHAG, GPD2, FEZ1, CCRL2, NKD1, IGHV5-10-1, OR52K2, LTK, PRR5L, FAM230E, HIC1, OTOF, FAM131B, CCR12P, ANTXRLP1, APOBEC3B-AS1, SPON1, HLA-G, CACNA2D2, RASGRF2, LINC02574, TSPAN15, GDF7, LPAL2, AXL, HLA-F-AS1, ITGA9-AS1, LINC00638, CACNA1I, CCL8, PIMREG, COL5A1, MT1DP, ZNF600, EMP1, GPM6A, EBF4, IGHV3-64D, LINC00243, SLC26A5, LINC02068, HCG9, SLC8A3, RUFY4, S100A7, HEY2, SCARB2, CYP21A1P, P3H3, KIAA1841, FAM247B, AGRN, SP100, RNF213, REC8, FRG1KP, ANXA10, GNB4, MILR1, FRMD3, DNAJA1, PGAP1, SAMD4A, PRAL, DLG5, UNC93B4, LHFPL2, VSIG1, PMEL, SLITRK5, NR3C2, ALS2CL, IL17RE, FKBP10, USP13, BTN2A3P, TRAJ25, RPS2P7, JPH4, PPPIR27, RNF213-AS1, CAMK2N1, C1orf127, ZNF835, CSPG4P11, CA8, SYNDIG1L |
| | | Table 24-12. Module: 6.36.234; Co-efficient: −0.158660927804175 |
| 25 | GO: extracellular.region, vesicle | KRT72, EPHB2, KRT73, LAP3, MS4A4A, LDLRAD3, KRT73-AS1, TCN2, C3AR1, LILRB4, BLVRA, CD300E, SSC4D, NID1, FBLN2, CTSL, HID1, MYOF, AK5, LINC01504, MIR503HG, CYP46A1, RARRES2, FAM170B-AS1, LINC01307 |
| | | Table 24-13. Module: 6.36.235; Co-efficient: −0.0604892816322406 |
| 54 | GO: transferase.activity, transferring.hexosyl.groups, protein.glycosylation | ODF3B, TYMP, LY6E-DT, FBXO39, SCO2, UNC93B3, IFITM3P4, UNC93B5, PPM1K-DT, UNC93B7, ITGA10, ENTPD1-AS1, OSBPL6, FLT4, FITM1, CAPN5, LRRC71, TRBV6-2, |

TABLE 24-continued

Top 30 gen 3 Modules

| Size | Functional Annotation | Genes |
| --- | --- | --- |
| | | LINC02446, ISM1, KIT, CACNA1A, IGHE, SLC7A8, CHN1, LINC02754, SLPI, ACBD7, ERFE, LRRC36, FOLR3, TEKT1, FUT2, MID2, RGPD2, ULBP2, IL15, LINC01918, LINC01344, FAM178B, ISLR2, ADAMTS10, GALNT12, PPFIBP1, MTHFD1L, ZNF514, EPHB3, DNAJC15, MAFA, LRP12, TRBV7-1, ITGA7, LSP1P4, RETREG1 |
| Table 24-14. Module: 6.36.236; Co-efficient: −0.243515855578611 | | |
| 21 | GO: plasma.membrane.part, extrinsic.component.of.plasma.membrane | NEXN, TENT5A, GPRC5C, UTS2B, IL2RB, NCR3, RGL1, FCN1, PTGFR, CD300C, ADPRH, GPRC5D-AS1, TMEM255A, CD14, PLPP2, LINC01163, GNG5, GRIK4, KYNU, CDH24, ZNF208 |
| Table 24-15. Module: 6.37.240; Co-efficient: −0.280804872626724 | | |
| 33 | GO: neurotransmitter.metabolic.process, reg.of.Wnt.signaling.pathway | CSAG3, RNF175, FCER1A, TLR2, PTGDR2, LINC02458, SLC12A1, DISC1, MAOA, UPB1, CC2D2A, OLFML2A, C1QTNF7-AS1, LGALSL-DT, SLC4A3, SRGAP2D, CCDC162P, LINC02568, WARS1, SEPTIN9-DT, GRB10, ZNF727, ASPH, C1QTNF7, CSAG2, OR52B4, EXT1, MROCKI, LINC02042, LINC00398, CYP1A1, PODXL2, LHFPL3-AS2 |
| Table 24-16. Module: 6.39.248; Co-efficient: −0.0923673604266681 | | |
| 57 | Anc: IFN. GO: nucleic.acid.metabolic.process | BATF2, IRF7, IFI35, LGALS9, OASL, DHX58, UBE2L6, HELZ2, PML, RTP4, SHISA5, KLHDC7B-DT, MT2A, RMI2, KPTN, ETV7, PARP10, BST2, UNC93B8, DRAP1, UNC93B1, DUX4L50, TTC21A, HSH2D, DUX4L37, TRIM69, TOR1B, MOV10, SSTR3, COLQ, ABCB1, UBE2Q2P2, TRGV9, SLC4A10, ANKRD22, LGALS9DP, RORC, LINC01531, NEURL3, SYT3, PXT1, MYBL1, FBX06, ISG20, RBCK1, NAPA, PSMB9, NAGK, MDK, ZNF496, KIAA0895L, MT2P1, FZD8, AANAT, EPOP, LINC01671, RAB40A |
| Table 24-17. Module: 6.42.256; Co-efficient: −0.242579870980789 | | |
| 73 | Anc: Cell.Cycle. GO: mitotic.cell.cycle | EPN2, MKI67, CCNA2, TPX2, BUB1, BIRC5, TOP2A, GTSE1, CDC20, CIT, PKMYT1, ESPL1, ASPM, ADAM23, HJURP, KIF18B, KIFC1, TROAP, NCAPG, MIXL1, CDK1, CDC25A, CDC45, CDKN3, ZC2HC1C, INAVA, OR13A1, HMGB3, IGHV1-3, NUF2, KIF4A, DLGAP5, MCM10, RNA5SP315, HMMR, GRAPL, NCAPH, CDT1, ATP5MGP1, CPAMD8, RFPL4A, ICA1, LINC00683, CNGB1, TWIST2, FIGNL2, C1DP5, CDCA3, PACSIN1, MTND4P24, KLHL33, FPGT-TNNI3K, CCNB2, KIF11, INSL6, NDC80, VPS33B-DT, LINC00475, DNM1P31, TSPAN3, SLC7A11, SLC9C1, CD38, GSDME, SKA1, TEDDM1, MYRFL, MTCL1, WBP1LP2, BMP8B, PDGFC, SNHG5, LINC02610 |
| Table 24-18. Module: 10.157.367; Co-efficient: 0.174415577799991 | | |
| 32 | GO: oxidative.phosphorylation, respiratory.chain | MT-ATP6, MT-ND4, MT-ND2, MT-ND4L, MT-ATP8, MT-CO3, MT-CYB, MT-ND5, MT-CO2, MT-ND3, MT-ND1, FN1, MT-ND6, VIPR2, SPOCD1, SLC22A23, APOA1-AS, HSD17B7P2, BLM, MTMR9LP, SNPH, MT-TE, MEX3B, MT-CO1, SLC39A4, DGKH, LINC02745, NPAP1L, NETO2, BNIP3P1, RTN4RL1, PELATON |
| Table 24-19. Module: 3.16.195; Co-efficient: 0.00513577153174272 | | |
| 20 | GO: deaminating.activity, primary.amine.oxidase.activity | AOC3, RFX8, CADM1, EHF, GPR25, ACE, PTPRN, LRIG3, GPC2, SDC2, LINC00426, LINC00511, MROH9, CCL25, GLB1L3, AOC2, CCR7, RYR1, MOGAT1, BTNL10 |
| Table 24-20. Module: 3.20.216; Co-efficient: 0.224880190812446 | | |
| 24 | GO: muscle.structure.development, muscle.organ.development | NOG, SLC22A17, SPEG, CNN3, C1QA, LGALS1, GOLGA6L9, NT5E, KIR3DX1, GSTA6P, PATL2, KRT5, ATP1A4, AMPD2, EVC, SOX8, ANXA2P2, MDS2, ATP2B2, EPS8L1, CASQ1, PARP11-AS1, TSPAN6, E2F2 |
| Table 24-21. Module: 5.22.218; Co-efficient: 0.0781638769261978 | | |
| 41 | Anc: B.cells. GO: cytokinesis | PAX5, LINC00926, LARGE2, HLA-DOA, BLNK, SYNPO, TNFRSF13C, FCRL2, CD40, BCL11A, LINC01342, STRBP, KCNH8, DNMT3L, CR2, COBLL1, CEP55, MIR4538, MIR5195, CELSR1, PRAMENP, SCGB3A1, FCMR, LINC01907, PCDH9, HRK, PKIG, LINC01413, DCLK2, H3C13, COLCA1, VWA7, E2F5, NUSAP1, SLC44A5, MICAL3, SPRY1, EPB41L2, RPS2P17, CENPV, TLCD2 |

TABLE 24-continued

Top 30 gen 3 Modules

| Size | Functional Annotation | Genes |
|---|---|---|
| | | Table 24-22. Module: 5.23.222; Co-efficient: 0.0615017498720204 |
| 51 | Anc: B.cells. GO: extracellular.matrix.organization | NIBAN3, FCRL1, SNX22, AFF3, TCL1A, FCER2, CD79B, CORO2B, IGHM, COL19A1, SNX29P1, MIR4539, VPREB3, PMEPA1, ABCB4, SPIB, FADS3, SCN4A, BACH2, MMP11, CD200, STAP1, MYBPC2, NXPH4, KHDRBS2, MIR4537, AUTS2, TLE1, AEBP1, LIX1-AS1, TBC1D16, CNR2, HS3ST1, HLA-DQA2, DNAH11, AK8, HIP1R, RAB30, NEIL1, BTLA, PLD4, SLCO4C1, CIITA, LAMC1, LAMB4, FAM81A, COL9A1, DLGAP3, GPS2P1, LRRK2-DT, CNTNAP2 |
| | | Table 24-23. Module: 6.37.239; Co-efficient: 0.194993831717576 |
| 32 | GO: Rho.GTPase.binding, Rac.GTPase.binding | SRGAP2B, FAM225A, SRGAP2C, SRGAP2, RNASE2, ANKRD35, WNT7A, FAM225B, ROBO3, RETN, ZNF595, TARM1, DBH, TAF11L2, TLE2, DEPDC1, LINC01238, UCKL1-AS1, SLC45A3, LMO7, ESPNP, TRAJ20, NPTXR, GSDMC, SLC16A11, ACSM3, FMNL2, PLEKHB1, LINC02287, PNMT, FOXRED2, TRAJ32 |
| | | Table 24-24. Module: 6.40.252; Co-efficient: 0.0904358506476921 |
| 25 | GO: inflammatory.response, L-type.voltage-gated.calcium.channel.complex | ADGRE4P, PRSS33, SIGLEC8, ALOX15, HRH4, CACNG6, COL26A1, CACNG8, IL5RA, CLC, DNASE1L3, PTMS, RHOXF1P1, COL11A2, SLC4A9, SMPD3, IL34, LINC01226, ADAMTS7P1, SPNS3, EPHA2, ENPP7P8, RPL35AP26, SLC29A1, TFEC |
| | | Table 24-25. Module: 7.49.271; Co-efficient: 0.0957605969965719 |
| 70 | GO: stem.cell.population.maintenance, maintenance.of.cell.number | YBX1P1, UBB, SLC25A39, YBX1, HBB, RNF10, FAM210B, DMTN, IGF2BP2, SLC6A8, UBBP4, ADIPOR1, MFSD2B, A2ML1-AS1, MPP1, FAXDC2, BNIP3L, PBX1, HPS1, AHSP, CHPT1, ISCA1P1, HAGH, GFUS, TAL1, SFRP2, EIF1B, RAB3IL1, KLC3, SHISA7, EMC3, FBXO7, PPM1A, BCAM, TRIM10, PAGE2B, YBX1P10, LINC01036, SGIP1, CA2, SLC25A37, AQP1, KEL, PAGE2, RGS10, PINK1, EPHA1, CPNE7, SNX3, SLC6A19, KDM7A-DT, KCNMA1, LOXHD1, UBBP1, BLVRB, TMEM63B, TPGS2, BBOF1, FUNDC2P1, LRRC75A, C1orf116, KLHDC8A, C1orf198, POU5F1, BEND3P1, NCOA4, LEFTY1, TMEM121B, TRAJ39, CRB3 |
| | | Table 24-26. Module: 7.49.272; Co-efficient: 0.0604669553599939 |
| 24 | GO: cytosol, RNA.binding | NUDT4P2, TRIM58, DCAF12, ANK1, MKRN1, NUDT4B, OSBP2, GMPR, GSPT1, DNAJC6, STRADBP1, RANBP10, RBM38, HBD, LTBP2, LINC01781, EPPK1, ARHGEF12, NUDT4, SOX6, FBX09, ANKRD9, ISCA1P6, ALDH6A1 |
| | | Table 24-27. Module: 7.49.273; Co-efficient: 0.0701333886058961 |
| 43 | GO: neg.reg.of.extrinsic.apoptotic.signaling.pathway, porphyrin-containing.compound.biosynthetic.process | TNS1, SLC4A1, SELENBP1, EPB42, NFIX, BCL2L1, GLRX5, ALAS2, SPTB, FECH, TENT5C, YBX3, SIAH2, SLC6A9, KRT1, TGM2, MARCHF8, STRADB, LGALS3, KLF1, CTNNAL1, SLC14A1, GLRX5P1, MT1L, RAP1GAP, MTDHP3, MKRN9P, TSPAN5, CREG1, ZNF429, CYBRD1, GSTA7P, SRRD, OR2W3, YBX3P1, TFDP1, MICAL2, CA3-AS1, FKBP1B, ARHGEF37, IGHV3-35, PAQR9, CMBL |
| | | Table 24-28. Module: 7.49.275; Co-efficient: 0.114633742529131 |
| 36 | GO: endosome, adult.locomotory.behavior | TMOD1, MXI1, SNCA, SLC6A10P, LINC00570, PLVAP, HEMGN, ABCC13, ALDH5A1, ISCA1, FAM83A, ABCA7, TLCD4, RNF11, NEDD4L, PLEK2, BAIAP3, PRPH2, CYP4F25P, CTSE, S1PR3, DNAJA4, CYP4F60P, CA15P1, FAM104A, CLN8, TTC25, GID4, MEIS3P1, C9orf78, EZR-AS1, RBP5, GASK1B, FZD5, MYCBPAP, ZDHHC2 |
| | | Table 24-29. Module: 9.100.332; Co-efficient: 0.109978945008615 |
| 39 | GO: cytosolic.large.ribosomal.subunit, structural.constituent.of.ribosome | RPL26P19, RPL34, ZNF785, UQCRB, RPS24P8, RARRES2P2, RPS8P10, SNRPE, PFDN4, RPL26P6, RPL31, TPT1P4, RPS3AP25, RASGRF2-AS1, NCK1-DT, LINC01284, EID2, RPL21P11, ARHGAP28, LINC01765, GRPEL2, RPL31P12, CBX3P2, LINC01424, AQP7, HLF, RLN3, HLA-DPA3, CCDC59, RARRES2P4, RPS18P9, RFPL3S, LINC02298, DMRTC1B, RET, LINC02884, TMEM132A, GUCY1A2, RPL7P19 |

TABLE 24-continued

| Top 30 gen 3 Modules | | |
|---|---|---|
| Size | Functional Annotation | Genes |
| Table 24-30. Module: 9.110.349; Co-efficient: 0.129325965025752 | | |
| 29 | GO: C-5.sterol.desaturase.activity, mannose.binding | SC5D, KBTBD8, PRELID3B, C12orf29, UGT8, IGIP, RLN2, CFAP54, UFL1, LRRC3, NAP1L3, UTP15, ZNF404, PTPN13, SMIM10L2A, CD207, ANKRD12, LINC00698, LVRN, ZNF471, LINC02575, HLTF, MYCT1, SPAG8, EXD2, LINC00402, XIRP1, CPNE4, ITPR1-DT |

TABLE 25A

Clinical and demographic features such as ancestral background, SLEDAI, and PSD scores, and RLR patient classification as type 1 SLE or type 2 SLE patients

| pt.ID | cohort | PSD.score | SLEDAI | anti.dsDNA | C3 | ttl_areas_pain | cog_dysfx | wake_unrefresh | score.RLR | RLR.classif |
|---|---|---|---|---|---|---|---|---|---|---|
| Type1_115 | Type.1.SLE | 4 | 6 | 2 | 0 | 0 | 1 | 1 | 0.527 | RLR.type.1 |
| Type1_165 | Type.1.SLE | 0 | 6 | 0 | 2 | 0 | 0 | 0 | 0.528 | RLR.type.1 |
| Type1_168 | Type.1.SLE | 3 | 10 | 2 | 0 | 1 | 0 | 1 | 0.000 | RLR.type.1 |
| Type1_170 | Type.1.SLE | 0 | 8 | 2 | 2 | 0 | 0 | 0 | 0.525 | RLR.type.1 |
| Type1_177 | Type.1.SLE | 3 | 10 | 0 | 2 | 0 | 1 | 1 | 0.271 | RLR.type.1 |
| Type1_188 | Type.1.SLE | 8 | 18 | 0 | 0 | 6 | 0 | 0 | 0.792 | RLR.type.1 |
| Type1_251 | Type.1.SLE | 5 | 8 | 2 | 2 | 3 | 0 | 0 | 0.415 | RLR.type.1 |
| Type1_258 | Type.1.SLE | 0 | 16 | 2 | 2 | 0 | 0 | 0 | 0.431 | RLR.type.1 |
| Type1_275 | Type.1.SLE | 3 | 7 | 0 | 2 | 0 | 0 | 1 | 0.938 | RLR.type.1 |
| Type2_008 | Type.2.SLE | 11 | 0 | 0 | 0 | 7 | 1 | 1 | 1.157 | RLR.type.2 |
| Type2_013 | Type.2.SLE | 10 | 0 | 0 | 0 | 3 | 3 | 2 | 1.356 | RLR.type.2 |
| Type2_028 | Type.2.SLE | 16 | 0 | 0 | 0 | 12 | 0 | 2 | 1.598 | RLR.type.2 |
| Type2_114 | Type.2.SLE | 21 | 0 | 0 | 0 | 15 | 1 | 3 | 1.505 | RLR.type.2 |
| Type2_230 | Type.2.SLE | 12 | 0 | 0 | 0 | 6 | 2 | 2 | 1.767 | RLR.type.2 |
| Type2_261 | Type.2.SLE | 10 | 0 | 0 | 0 | 7 | 1 | 1 | 1.444 | RLR.type.2 |
| **Type2_267** | Type.2.SLE | 11 | 0 | 0 | 0 | 5 | 2 | 2 | **0.856** | **RLR.type.1** |
| Type2_276 | Type.2.SLE | 19 | 0 | 0 | 0 | 11 | 2 | 3 | 1.447 | RLR.type.2 |
| Type2_285 | Type.2.SLE | 10 | 0 | 0 | 0 | 4 | 2 | 2 | 1.696 | RLR.type.2 |

TABLE 25B

| Therapies of Type-1 and Type-2 lupus |
|---|
| SLE TYPE 1 THERAPIES |
| SOC DRUGS |
| Prednisone |
| Hydroxychloroquine |
| NSAIDS |
| OFF LABEL DRUGS |
| Methotrexate (MTX) |
| Cyclophosphamide (CTX) |
| Mycophenolate mofetil (MMF) |
| Azathioprine (AZA) |
| FDA APPROVED BIOLOGICS |
| Belimumab |
| Anifrolumab |

TABLE 25B-continued

| Therapies of Type-1 and Type-2 lupus |
|---|
| Voclosporin |
| SLE TYPE 2 THERAPIES |
| OFF LABEL DRUGS |
| Duloxetine |
| Gabapentin |
| Milnacipran |
| Pregabalin |
| OTHER THERAPIES |
| Physical therapy |
| Occupational therapy |
| Counseling |
| Mindfulness |

TABLE 25B-continued

| Therapies of Type-1 and Type-2 lupus |
| --- |
| Alcohol intake reduction |
| Sleep hygiene |
| Keto eating plan |

REFERENCES

1. Ferretti C, Cava A la. Overview of the Pathogenesis of Systemic Lupus Erythematosus. In: Systemic Lupus Erythematosus. Elsevier; 2016:55-62.
2. Rogers J L, Eudy A M, Criscione-Schreiber L G, Pisetsky D S, Sun K, Doss J, et al. A novel approach to addressing fibromyalgia symptomatology in SLE. In: Abstracts. Lupus Foundation of America; 2019: A77.1-A77.
3. Rogers J L, Eudy A M, Pisetsky D, Criscione-Schreiber L G, Sun K, Doss J, et al. Using Clinical Characteristics and Patient-Reported Outcome Measures to Categorize Systemic Lupus Erythematosus Subtypes. *Arthritis Care & Research* 2021; 73:386-393.
4. Barraclough M, McKie S, Parker B, Jackson A, Pemberton P, Elliott R, et al. Altered cognitive function in systemic lupus erythematosus and associations with inflammation and functional and structural brain changes. *Annals of the Rheumatic Diseases* 2019; 78:934. Available at: ard.bmj.com/content/78/7/934.abstract.
5. Hochberg M C. Updating the American college of rheumatology revised criteria for the classification of systemic lupus erythematosus. *Arthritis & Rheumatism* 1997; 40:1725-1725.
6. Petri M, Orbai A-M, Alarcón G S, Gordon C, Merrill J T, Fortin P R, et al. Derivation and validation of the Systemic Lupus International Collaborating Clinics classification criteria for systemic lupus erythematosus. Arthritis & Rheumatism 2012; 64:2677-2686.
7. Wolfe F, Clauw D J, Fitzcharles M-A, Goldenberg D L, Häuser W, Katz R L, et al. 2016 Revisions to the 2010/2011 fibromyalgia diagnostic criteria. *Seminars in Arthritis and Rheumatism* 2016; 46:319-329.
8. Wolfe F, Clauw D J, Fitzcharles M A, Goldenberg D L, Häuser W, Katz R S, et al. Fibromyalgia Criteria and Severity Scales for Clinical and Epidemiological Studies: A Modification of the ACR Preliminary Diagnostic Criteria for Fibromyalgia. *The Journal of Rheumatology* 2011; 38:1113-1122.
9. Wolfe F, Clauw D J, Fitzcharles M-A, Goldenberg D L, Katz R S, Mease P, et al. The American College of Rheumatology Preliminary Diagnostic Criteria for Fibromyalgia and Measurement of Symptom Severity. *Arthritis Care & Research* 2010; 62:600-610.
10. Wolfe F, Walitt B T, Rasker J J, Katz R S, Häuser W. The Use of Polysymptomatic Distress Categories in the Evaluation of Fibromyalgia (FM) and FM Severity. *The Journal of Rheumatology* 2015; 42:1494-1501.
11. Gladman D D, Ibañez D, Urowitz M B. Systemic lupus erythematosus disease activity index 2000. *J Rheumatol* 2002; 29:288-91.
12. Petri M, Hellmann D, Hochberg M. Validity and reliability of lupus activity measures in the routine clinic setting. *J Rheumatol* 1992; 19:53-9.
13. Song W-M, Zhang B. Multiscale Embedded Gene Co-expression Network Analysis. *PLOS Computational Biology* 2015; 11:e1004574.
14. Jones K D, Gelbart T, Whisenant T C, Waalen J, Mondala T S, Iklé D N, et al. Genome-wide expression profiling in the peripheral blood of patients with fibromyalgia. *Clin Exp Rheumatol* 2016; 34: S89-98.
15. Petri M, Fu W, Ranger A, Allaire N, Cullen P, Magder L S, et al. Association between changes in gene signatures expression and disease activity among patients with systemic lupus erythematosus. *BMC Med Genomics* 2019; 12:4.
16. Chiche L, Jourde-Chiche N, Whalen E, Presnell S, Gersuk V, Dang K, et al. Modular transcriptional repertoire analyses of adults with systemic lupus erythematosus reveal distinct type I and type II interferon signatures. *Arthritis Rheumatol* 2014; 66:1583-95.
17. Szklarczyk D, Franceschini A, Wyder S, Forslund K, Heller D, Huerta-Cepas J, et al. STRING v10: protein-protein interaction networks, integrated over the tree of life. *Nucleic Acids Research* 2015; 43:D447-D452.
18. Mckenzie A T, Katsyv I, Song W-M, Wang M, Zhang B. DGCA: A comprehensive R package for Differential Gene Correlation Analysis. *BMC Systems Biology* 2016; 10:106.
19. Feng X, Wu H, Grossman J M, Hanvivadhanakul P, FitzGerald J D, Park G S, et al. Association of increased interferon-inducible gene expression with disease activity and lupus nephritis in patients with systemic lupus erythematosus. *Arthritis & Rheumatism* 2006; 54:2951-2962.
20. Catalina M D, Bachali P, Yeo A E, Geraci N S, Petri M A, Grammer A C, et al. Patient ancestry significantly contributes to molecular heterogeneity of systemic lupus erythematosus. *JCI Insight* 2020; 5.
21. Baechler E C, Batliwalla F M, Karypis G, Gaffney P M, Ortmann W A, Espe K J, et al. Interferon-inducible gene expression signature in peripheral blood cells of patients with severe lupus. *Proceedings of the National Academy of Sciences* 2003; 100:2610-2615.
22. Tesser A, Carvalho L M de, Sandrin-Garcia P, Pin A, Pastore S, Taddio A, et al. Higher interferon score and normal complement levels may identify a distinct clinical subset in children with systemic lupus erythematosus. *Arthritis Research & Therapy* 2020; 22:91.
23. Postal M, Sinicato N A, Peliçari K O, Marini R, Costallat L T L, Appenzeller S. Clinical and serological manifestations associated with interferon-a levels in childhood-onset systemic lupus erythematosus. *Clinics* 2012; 67:157-162.
24. Hubbard E L, Pisetsky D S, Lipsky P E. Anti-RNP antibodies are associated with the interferon gene signature but not decreased complement levels in SLE. *Annals of the Rheumatic Diseases* 2022; 81:632. Available at: ard.bmj.com/content/81/5/632.abstract.
25. Russell A, Hepgul N, Nikkheslat N, Borsini A, Zajkowska Z, Moll N, et al. Persistent fatigue induced by interferon-alpha: a novel, inflammation-based, proxy model of chronic fatigue syndrome. *Psychoneuroendocrinology* 2019; 100:276-285.
26. Gupta S, Tatouli I P, Rosen L B, Hasni S, Alevizos I, Manna Z G, et al. Distinct Functions of Autoantibodies Against Interferon in Systemic Lupus Erythematosus: A Comprehensive Analysis of Anticytokine Autoantibodies in Common Rheumatic Diseases. *Arthritis & Rheumatology* 2016; 68:1677-1687.
27. Goebel A, Krock E, Gentry C, Israel M R, Jurczak A, Urbina C M, et al. Passive transfer of fibromyalgia symptoms from patients to mice. *Journal of Clinical Investigation* 2021; 131.

28. Ma C, Xia Y, Yang Q, Zhao Y. The contribution of macrophages to systemic lupus erythematosus. *Clinical Immunology* 2019; 207:1-9.
29. Katsiari C G, Liossis S-N C, Sfikakis P P. The Pathophysiologic Role of Monocytes and Macrophages in Systemic Lupus Erythematosus: A Reappraisal. *Seminars in Arthritis and Rheumatism* 2010; 39:491-503.
30. Bennett L, Palucka A K, Arce E, Cantrell V, Borvak J, Banchereau J, et al. Interferon and Granulopoiesis Signatures in Systemic Lupus Erythematosus Blood. *Journal of Experimental Medicine* 2003; 197:711-723.
31. Denny M F, Yalavarthi S, Zhao W, Thacker S G, Anderson M, Sandy A R, et al. A Distinct Subset of Proinflammatory Neutrophils Isolated from Patients with Systemic Lupus Erythematosus Induces Vascular Damage and Synthesizes Type I IFNs. *The Journal of Immunology* 2010; 184:3284-3297.
32. Caielli S, Athale S, Domic B, Murat E, Chandra M, Banchereau R, et al. Oxidized mitochondrial nucleoids released by neutrophils drive type I interferon production in human lupus. *Journal of Experimental Medicine* 2016; 213:697-713.
33. Tilburg M A L van, Parisien M, Boles R G, Drury G L, Smith-Voudouris J, Verma V, et al. A genetic polymorphism that is associated with mitochondrial energy metabolism increases risk of fibromyalgia. *Pain* 2020; 161:2860-2871.
34. Bax K, Isackson P J, Moore M, Ambrus J L. Carnitine Palmitoyl Transferase Deficiency in a University Immunology Practice. *Current Rheumatology Reports* 2020; 22:8.
35. Meeus M, Nijs J, Hermans L, Goubert D, Calders P. The role of mitochondrial dysfunctions due to oxidative and nitrosative stress in the chronic pain or chronic fatigue syndromes and fibromyalgia patients: peripheral and central mechanisms as therapeutic targets? *Expert Opinion on Therapeutic Targets* 2013; 17:1081-1089.
36. Wu Y, Chen M, Jiang J. Mitochondrial dysfunction in neurodegenerative diseases and drug targets via apoptotic signaling. *Mitochondrion* 2019; 49:35-45.
37. Hochberg M C. Updating the American college of rheumatology revised criteria for the classification of systemic lupus erythematosus. *Arthritis & Rheumatism* 1997; 40:1725-1725.
38. Petri M, Hellmann D, Hochberg M. Validity and reliability of lupus activity measures in the routine clinic setting. *J Rheumatol* 1992; 19:53-9.
39. Wolfe F, Walitt B T, Rasker J J, Katz R S, Häuser W. The Use of Polysymptomatic Distress Categories in the Evaluation of Fibromyalgia (F M) and F M Severity. *The Journal of Rheumatology* 2015; 42:1494-1501.
40. Wolfe F, Clauw D J, Fitzcharles M A, Goldenberg D L, Häuser W, Katz R S, et al. Fibromyalgia Criteria and Severity Scales for Clinical and Epidemiological Studies: A Modification of the ACR Preliminary Diagnostic Criteria for Fibromyalgia. *The Journal of Rheumatology* 2011; 38:1113-1122.
41. Wolfe F, Clauw D J, Fitzcharles M-A, Goldenberg D L, Häuser W, Katz R L, et al. 2016 Revisions to the 2010/2011 fibromyalgia diagnostic criteria. *Seminars in Arthritis and Rheumatism* 2016; 46:319-329.
42. Wolfe F, Clauw D J, Fitzcharles M-A, Goldenberg D L, Katz R S, Mease P, et al. The American College of Rheumatology Preliminary Diagnostic Criteria for Fibromyalgia and Measurement of Symptom Severity. *Arthritis Care & Research* 2010; 62:600-610.
43. Gladman D D, Ibañez D, Urowitz M B. Systemic lupus erythematosus disease activity index 2000. *J Rheumatol* 2002; 29:288-91.
44. Rogers J L, Eudy A M, Criscione-Schreiber L G, Pisetsky D S, Sun K, Doss J, et al. A novel approach to addressing fibromyalgia symptomatology in SLE. In: *Abstracts. Lupus Foundation of America;* 2019: A77.1-A77.
45. Love M I, Huber W, Anders S. Moderated estimation of fold change and dispersion for RNA-seq data with DESeq2. Genome Biology 2014; 15:550.
46. Durinck S, Moreau Y, Kasprzyk A, Davis S, Moor B de, Brazma A, et al. BioMart and Bioconductor: a powerful link between biological databases and microarray data analysis. *Bioinformatics* 2005; 21:3439-3440.
47. Langfelder P, Horvath S. WGCNA: an R package for weighted correlation network analysis. *BMC Bioinformatics* 2008; 9:559.
48. Ritchie M E, Phipson B, Wu D, Hu Y, Law C W, Shi W, et al. limma powers differential expression analyses for RNA-sequencing and microarray studies. *Nucleic Acids Research* 2015; 43:e47-e47.
49. Blighe K, Lun A. R package "PCAtools": Everything Principal Components Analysis. R package version 2.2.0. *github.com/kevinblighe/PCAtools* 2020.
50. Gu Z, Eils R, Schlesner M. Complex heatmaps reveal patterns and correlations in multidimensional genomic data. *Bioinformatics* 2016; 32:2847-2849.
51. Song W-M, Zhang B. Multiscale Embedded Gene Co-expression Network Analysis. *PLOS Computational Biology* 2015; 11:e1004574.
52. Catalina M D, Bachali P, Yeo A E, Geraci N S, Petri M A, Grammer A C, et al. Patient ancestry significantly contributes to molecular heterogeneity of systemic lupus erythematosus. *JCI Insight* 2020; 5.
53. Carbon S, Douglass E, Good B M, Unni D R, Harris N L, Mungall C J, et al. The Gene Ontology resource: enriching a Gold mine. *Nucleic Acids Research* 2021; 49:D325-D334.
54. Wei T, Simko V. R package "corrplot": Visualization of a Correlation Matrix. Version 0.92. *github.com/taiyun/corrplot* 2021.
55. Jones K D, Gelbart T, Whisenant T C, Waalen J, Mondala T S, Ikle D N, et al. Genome-wide expression profiling in the peripheral blood of patients with fibromyalgia. *Clin Exp Rheumatol* 2016; 34:S89-98.
56. MacDonald J. R package "affycoretools": Functions useful for those doing repetitive analyses with Affymetrix GeneChips. *R package version* 1680 2020.
57. Leek J T, Johnson W E, Parker H S, Jaffe A E, Storey J D. The sva package for removing batch effects and other unwanted variation in high-throughput experiments. *Bioinformatics* 2012; 28:882-883.
58. Plotly Technologies Inc. Plotly collaborative data science. *plot.ly* 2015.
59. Szklarczyk D, Franceschini A, Wyder S, Forslund K, Heller D, Huerta-Cepas J, et al. STRING v10: protein-protein interaction networks, integrated over the tree of life. *Nucleic Acids Research* 2015; 43:D447-D452.
60. Hänzelmann S, Castelo R, Guinney J. GSVA: gene set variation analysis for microarray and RNA-Seq data. *BMC Bioinformatics* 2013; 14:7.
61. Mckenzie A T, Katsyv I, Song W-M, Wang M, Zhang B. DGCA: A comprehensive R package for Differential Gene Correlation Analysis. *BMC Systems Biology* 2016; 10:106.

62. Shao X, Liao J, Li C, Lu X, Cheng J, Fan X. CellTalkDB: a manually curated database of ligand-receptor interactions in humans and mice. *Briefings in Bioinformatics* 2021; 22.

63. Labonte A C, Kegerreis B, Geraci N S, Bachali P, Madamanchi S, Robl R, et al. Identification of alterations in macrophage activation associated with disease activity in systemic lupus erythematosus. *PLOS One* 2018; 13:e0208132.

64. Kegerreis B, Catalina M D, Bachali P, Geraci N S, Labonte A C, Zeng C, et al. Machine learning approaches to predict lupus disease activity from gene expression data. *Sci Rep* 2019; 9:9617.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

The invention claimed is:

1. A method for classifying and treating a type 1 lupus disease state or type 2 lupus disease state of a subject, the method comprising:

(a) obtaining a subject data set comprising or derived from gene expression measurements data of at least 21 genes from a biological sample obtained or derived from the subject, wherein the at least 21 genes are each selected from at least 21 different gene sets, and wherein the different genes sets are selected from:

a first gene set comprising: DDX11L9, MT-ATP6, DDX11L1, MT-ND4, MT-ND2, MT-ND4L, DDX11L2, MT-ATP8, MT-CO3, MT-CYB, MT-ND5, MT-CO2, DDX11L16, MT-ND3, DDX11L17, MT-ND1, DDX11L5, FN1, CFAP45, MT-ND6, LMNA, VIPR2, MIR23AHG, DDX11L10, IQCN, TUBB6, SPOCD1, SLC22A23, APOA1-AS, HSD17B7P2, ZSWIM4, PKNOX2, BLM, SCN5A, MTMR9LP, SNPH, MT-TE, MEX3B, LINC00658, OR7E94P, MT-CO1, DDX11L8, SLC39A4, DGKH, LINC02745, MIR23A, NPAPIL, GHRLOS, FBXO5, NETO2, ATP1B1, BNIP3P1, RTN4RL1, PELATON, ELF3, NOL3, and CHD1L;

a second gene set comprising: MT-ATP6, MT-ND4, MT-ND2, MT-ND4L, MT-ATP8, MT-CO3, MT-CYB, MT-ND5, MT-CO2, MT-ND3, MT-ND1, FN1, MT-ND6, VIPR2, SPOCD1, SLC22A23, APOA1-AS, HSD17B7P2, BLM, MTMR9LP, SNPH, MT-TE, MEX3B, MT-CO1, SLC39A4, DGKH, LINC02745, NPAPIL, NETO2, BNIP3P1, RTN4RL1, and PELATON;

a third gene set comprising: MT-ATP6, MT-ND4, MT-ND2, MT-ND4L, MT-ATP8, MT-CO3, MT-CYB, MT-ND5, MT-CO2, MT-ND3, MT-ND1, MT-ND6, VIPR2, SPOCD1, BLM, MTMR9LP, SNPH, MT-TE, MT-CO1, SLC39A4, DGKH, RTN4RL1, and PELATON;

a fourth gene set comprising: BMS1P15, SSH2, HCG27, LGALS9B, ADAMTSL4-AS2, ADAMTSL4-AS1, NEDD9, FAR2, ZNF615, DNAH17, BTN1A1, TUBA1C, BMS1P16, BMS1P11, GLI1, BMS1P9, FAAHP1, OR52B3P, VNN1, L0INC02656, SLC31A2, LINC01093, CNRIP1, ZDHHC19, IFITM3P2, TMEM119, MIR24-2, SEMA3B, ZNF718, BEAN1, TRAV13-2, ALDH1A2, PROKR2, RBM47, BNIPL, CSF1, AVP, SALL2, FRGCA, MRPL19, EPHB1, NEFL, LGALS9C, CDRT15, IL6R-AS1, CAPN13, TMEM221, KRT7, ENAH, PCP4L1, MCPH1-AS1, OR11H2, CD164L2, SMPDL3B, LINC02421, KIF27, BSPRY, PTOV1-AS1, TEK, SPACA6, IGHD3-10, KLK1, TRAV20, KCTD15, CELSR3, CCL4L2, LINC01791, MY06, KRT74, CLEC40, TPTEP2, CALML6, PRSS16, IDI2-AS1, PPM1F-AS1, BTNL3, PMFBP1, GGTLC2, CASC2, GRM2, BMS1P10, LINC01882, PLXNA4, MIR3648-2, EFR3B, WNT1, PICK1, MDM2, NUPR1, CNIH2, KCNJ3, CFAP43, TULP2, SLC52A3, FGGY, RPS3AP18, FBXO24, RTEL1, ANK3-DT, CA12, OR51RIP, H4C6, TAFA1, BOK, NANOS3, ARHGAP22, NSG1, SLC25A18, and CNTF;

a fifth gene set comprising: HCG27, ADAMTSL4-AS2, ADAMTSL4-AS1, FAR2, DNAH17, BTN1A1, TUBA1C, GLI1, FAAHP1, LINC02656, LINC01093, ZDHHC19, IFITM3P2, TMEM119, MIR24-2, SEMA3B, ALDH1A2, RBM47, BNIPL, CSF1, NEFL, CAPN13, TMEM221, KRT7, ENAH, PCP4L1, SMPDL3B, TEK, SPACA6, IGHD3-10, KLK1, KCTD15, LINC01791, MYO6, KRT74, PRSS16, GRM2, PLXNA4, MIR3648-2, WNT1, MDM2, CNIH2, TULP2, SLC52A3, FGGY, RPS3AP18, ANK3-DT, CA12, H4C6, TAFA1, NANOS3, ARHGAP22, and CNTF;

a sixth gene set comprising: HCG27, ADAMTSL4-AS2, ADAMTSL4-AS1, FAR2, DNAH17, BTN1A1, TUBA1C, GLI1, FAAHP1, LINC02656, LINC01093, ZDHHC19, IFITM3P2, TMEM119, MIR24-2, SEMA3B, ALDH1A2, RBM47, BNIPL, CSF1, NEFL, CAPN13, TMEM221, PCP4L1, SMPDL3B, TEK, SPACA6, KLK1, KCTD15, LINC01791, MY06, KRT74, PRSS16, GRM2, PLXNA4, MIR3648-2, WNT1, MDM2, CNIH2, TULP2, SLC52A3, FGGY, RPS3AP18, ANK3-DT, CA12, TAFA1, NANOS3, ARHGAP22, and CNTF;

a seventh gene set comprising: IQCD, LMX1B, ABCC11, CEACAM22P, LINC01629, LINC02288, SCN2B, NYAP1, KLRC1, GSTM2, OR7E66P, ELAPOR1, GGT8P, DNM1, PRRT1B, CDH22, COL6A5, PGC, TRBD1, F12, and PSCA;

an eighth gene set comprising: C1QB, NOG, MPP2, C1QC, SLC22A17, SPEG, CNN3, C1QA, LGALS1, GOLGA6L9, TRBV28, NT5E, C14orf132, LDHD, KIR3DX1, GSTA6P, PATL2, KRT5, PPP4R1-AS1, ATP1A4, AMPD2, LINC01293, PCBP3, EVC, SOX8, RP1L1, UNC119B, MCF2L, ANXA2P2, MDS2, ATP2B2, EPS8L1, CALD1, ZNF812P, CASQ1, PARP11-AS1, TSPAN6, and E2F2;

a ninth gene set comprising: NOG, SLC22A17, SPEG, CNN3, C1QA, LGALS1, GOLGA6L9, NT5E, KIR3DX1, GSTA6P, PATL2, KRT5, ATP1A4, AMPD2, EVC, SOX8, ANXA2P2, MDS2, ATP2B2, EPS8L1, CASQ1, PARP11-AS1, TSPAN6, and E2F2;

a tenth gene set comprising: IFI44L, SPATS2L, RSAD2, IFI44, DDX60, EIF2AK2, USP18, DDX58, CMPK2, HERC5, IFIT5, IFIH1, IFI6, EPSTI1, MX1, PLSCR1, PNPT1, FAM247A, ISG15, ZCCHC2, IFI27, SAMD9L, SMTNL1, STAT1, CHMP5, STAT2, GBP1, HERC6, PARP9, PHF11, SIGLEC1, OAS1, USP41, LY6E, MIR4477B, SAMD9, MTCO1P53, CCDC194, FAM230D, PARP12, IFI16, RSPH9, DDX60L, TUBA8, EPB41L5, TMEM123, ACO1, CETP, GBP1P1, KRT72, HES4, ODF3B, TRIM5, TYMP, FAM230H, PARP14, HESX1, APOL6, KLHDC7B, EPHB2, LY6E-DT, LIPA, FBX039, KIAA1958, ACOT9, LAMP3, NRIR, LGALS3BP, SCO2, UNC93B3, FRG1HP, KRT73, IFITM3P4, UNC93B5, XAF1, NEXN, LINC00487, TIMM10, ZNF684, EDAR, TENT5A, TDRD7, LINC02785, LAP3, DOCK4, PLSCR2, MIR4477A, DTX3L, CCL3L1, CHRNB2, KANK3, CMTR1, TSPOAP1, GPRC5C, UTS2B, GBP4, PPMIK-DT, IL2RB, CCR5AS, NCR3, ATF3, NOS2P2, RGL1, GRAMD1B, RHAG, GPD2, FEZ1, CCRL2, UNC93B7, FAM230A, NKD1, IGHV5-10-1, OR52K2, ITGA10, LTK, PRR5L, C8orf31, CLEC2B, FAM230E, FCN1, ENTPD1-AS1, HIC1, OTOF, PTGFR, SEZ6L, OSBPL6, FLT4, GBP5, GALM, CCL2, FAM131B, DNM1P47, MS4A4A, CCR12P, ANTXRLP1, APOBEC3B-AS1, SPON1, HLA-G, CD274, FITM1, CACNA2D2, CAPN5, PITPNM3, CD300C, ADPRH, RASGRF2, TBPL2, LINC02574, TSPAN15, GDF7, LDLRAD3, LPAL2, KRT73-AS1, AXL, LRRC71, GPRC5D-AS1, HLA-F-AS1, PDCD1LG2, TRBV6-2, LINC02446, TCN2, C3AR1, ISM1, TMEM255A, SLFN5, ITGA9-AS1, LINC00638, CACNA1I, LILRB4, CD14, KIT, MYCL, SNTG2, CCL8, BLVRA, PIMREG, CACNA1A, IGHE, COL5A1, MT1DP, SLC7A8, ZNF600, CD300E, CHN1, LINC02754, SLPI, NECTIN2, PLB1, SSC4D, MTCO1P40, PLPP2, EMP1, NID1, LINC01163, GPM6A, H3C6, EBF4, ACBD7, IGHV3-64D, ERFE, LINC00243, FAM3D, SLC26A5, LRRC36, LINC02068, FBLN2, HCG9, CTSL, NOS2P3, FOLR3, RTN1, COLGALT2, TEKT1, HID1, KCNH7, PID1, TDRG1, SLC8A3, FUT2, MID2, RGPD2, NCAPG2, ULBP2, GNG5, IL15, CMKLR1, OCLNP1, GRIK4, LINC01918, RUFY4, MYOF, KCNJ2, CCL20, CRIP2, TPSD1, FAM66D, S100A7, LINC01344, HEY2, SCGB1C2, FAM178B, SCARB2, ISLR2, CYP21A1P, P3H3, KIAA1841, FAM247B, AGRN, SP100, RNF213, FAM230B, REC8, FRG1KP, ANXA10, GNB4, MILR1, KYNU, FRMD3, DNAJA1, PGAP1, SAMD4A, PRAL, CDH24, GBP3, ADAMTS10, DLG5, LMO2, SDS, UNC93B4, LHFPL2, VSIG1, FAM209A, GALNT12, PPFIBP1, LINC01484, SAMD15, MTHFD1L, PMEL, ZNF514, SLITRK5, AK5, LINC01504, EPHB3, DNAJC15, REELD1, NR3C2, NR2F1-AS1, ALS2CL, MIR503HG, IL17RE, KCNC3, MAFA, CYP46A1, RARRES2, FKBP10, FAM170B-AS1, USP13, BTN2A3P, TRAJ25, RPS2P7, JPH4, LRP12, LINC01307, PPP1R27, RNF213-AS1, CHCHD2P8, CAMK2N1, SLC7A10, GLIS3, PTRH1, Clorf127, MYG1-AS1, H4C12, HCAR1, CMTM8, TRBV7-1, ZNF835, ITGA7, CSPG4P11, MMP17, LSP1P4, CA8, EGR3, CYP4F12, DPYS, ZNF208, CPB1, SYNDIG1L, RETREG1, and MPPED1;

an eleventh gene set comprising: IFI44L, SPATS2L, RSAD2, IFI44, DDX60, EIF2AK2, USP18, DDX58, CMPK2, HERC5, IFIT5, IFIH1, IFI6, EPSTI1, MX1, PLSCR1, PNPT1, FAM247A, ISG15, ZCCHC2, IFI27, SAMD9L, SMTNL1, CHMP5, STAT2, HERC6, PARP9, PHF11, SIGLEC1, OAS1, USP41, LY6E, MIR4477B, SAMD9, CCDC194, PARP12, IFI16, RSPH9, DDX60L, TUBA8, EPB41L5, TMEM123, ACO1, CETP, HES4, TRIM5, PARP14, HESX1, KLHDC7B, LIPA, KIAA1958, ACOT9, LAMP3, NRIR, LGALS3BP, FRG1HP, XAF1, LINC00487, TIMM10, ZNF684, EDAR, TDRD7, LINC02785, DOCK4, PLSCR2, MIR4477A, DTX3L, CHRNB2, KANK3, CMTR1, TSPOAP1, CCR5AS, GRAMD1B, RHAG, GPD2, FEZ1, CCRL2, NKD1, IGHV5-10-1, OR52K2, LTK, PRR5L, FAM230E, HIC1, OTOF, FAM131B, CCR12P, ANTXRLP1, APOBEC3B-AS1, SPON1, HLA-G, CACNA2D2, RASGRF2, LINC02574, TSPAN15, GDF7, LPAL2, AXL, HLA-F-AS1, ITGA9-AS1, LINC00638, CACNA1I, CCL8, PIMREG, COL5A1, MT1DP, ZNF600, EMP1, GPM6A, EBF4, IGHV3-64D, LINC00243, SLC26A5, LINC02068, HCG9, SLC8A3, RUFY4, S100A7, HEY2, SCARB2, CYP21A1P, P3H3, KIAA1841, FAM247B, AGRN, SP100, RNF213, REC8, FRG1KP, ANXA10, GNB4, MILR1, FRMD3, DNAJA1, PGAP1, SAMD4A, PRAL, DLG5, UNC93B4, LHFPL2, VSIG1, PMEL, SLITRK5, NR3C2, ALS2CL, IL17RE, FKBP10, USP13, BTN2A3P, TRAJ25, RPS2P7, JPH4, PPP1R27, RNF213-AS1, CAMK2N1, Clorf127, ZNF835, CSPG4P11, CA8, and SYNDIG1L;

a twelfth gene set comprising: IFI44L, RSAD2, IFI44, DDX60, EIF2AK2, DDX58, CMPK2, HERC5, IFIT5, IFIH1, IFI6, EPST1, MX1, PLSCR1, PNPT1, ISG15, ZCCHC2, IFI27, SAMD9L, SMTNL1, CHMP5, PARP9, PHF11, SIGLEC1, MIR4477B, SAMD9, CCDC194, IFI16, RSPH9, DDX60L, EPB41L5, TMEM123, ACO1, PARP14, HESX1, LIPA, KIAA1958, ACOT9, NRIR, XAF1, LINC00487, TIMM10, ZNF684, TDRD7, LINC02785, DOCK4, PLSCR2, MIR4477A, DTX3L, CHRNB2, KANK3, TSPOAP1, CCR5AS, RHAG, GPD2, CCRL2, NKD1, IGHV5-10-1, OR52K2, LTK, PRR5L, HIC1, FAM131B, ANTXRLP1, APOBEC3B-AS1, LINC02574, TSPAN15, LPAL2, AXL, HLA-F-AS1, CACNA1I, PIMREG, COL5A1, ZNF600, EBF4, LINC00243, LINC02068, HCG9, S100A7, HEY2, SCARB2, CYP21A1P, KIAA1841, AGRN, SP100, FRG1KP, ANXA10, GNB4, MILR1, FRMD3, DNAJA1, PGAP1, PRAL, DLG5, UNC93B4, LHFPL2, VSIG1, PMEL, FKBP10, BTN2A3P, TRAJ25, RPS2P7, CAMK2N1, CSPG4P11, and SYNDIG1L;

a thirteenth gene set comprising: SPATS2L, USP18, FAM247A, STAT2, HERC6, OAS1, USP41, LY6E, PARP12, TUBA8, CETP, HES4, TRIM5, LAMP3, LGALS3BP, CMTR1, GRAMD1B, FAM230E, CCL8, GPM6A, P3H3, FAM247B, RNF213, REC8, SAMD4A, JPH4, and RNF213-AS1;

a fourteenth gene set comprising: KRT72, EPHB2, KRT73, LAP3, MS4A4A, LDLRAD3, KRT73-AS1, TCN2, C3AR1, LILRB4, BLVRA, CD300E, SSC4D, NID1, FBLN2, CTSL, HID1, MYOF, AK5, LINC01504, MIR503HG, CYP46A1, RARRES2, FAM170B-AS1, and LINC01307;

a fifteenth gene set comprising: ODF3B, TYMP, LY6E-DT, FBX039, SCO2, UNC93B3, IFITM3P4, UNC93B5, PPMIK-DT, UNC93B7, ITGA10, ENTPD1-AS1, OSBPL6, FLT4, FITM1, CAPN5, LRRC71, TRBV6-2, LINC02446, ISM1, KIT, CACNA1A, IGHE, SLC7A8, CHN1, LINC02754, SLPI, ACBD7, ERFE, LRRC36, FOLR3, TEKT1, FUT2, MID2, RGPD2, ULBP2, IL15, LINC01918, LINC01344, FAM178B, ISLR2, ADAMTS10, GALNT12, PPFIBP1, MTHFD1L, ZNF514, EPHB3, DNAJC15, MAFA, LRP12, TRBV7-1, ITGA7, LSP1P4, and RETREG1;

a sixteenth gene set comprising: SRGAP2B, FAM225A, CSAG3, SRGAP2C, SRGAP2, RNF175, FCER1A, RNASE2, ANKRD35, WNT7A, FAM225B, ROBO3, TLR2, ZFP57, RETN, PTGDR2, LINC02458, SLC12A1, ZNF595, TARM1, KRT8P26, DBH, DISC1, TAF11L2, MAOA, TLE2, UPB1, IL4, CC2D2A, OLFML2A, KCNG1, C1QTNF7-AS1, MYOM2, DEPDC1, LINC01238, LINC02761, DBNDD1, UCKL1-AS1, LINC00884, LGALSL-DT, DPYSL4, SLC45A3, SLC4A3, ACTBP8, LMO7, CNR1, SRGAP2D, CCDC162P, C3orf20, LINC02568, WARS1, ESPNP, H2AC13, LINC02520, TRAJ20, TRAV14DV4, SEPTIN9-DT, GRB10, NPTXR, GSDMC, ZNF727, SLC16A11, ASPH, MTIE, CPA5, C1QTNF7, CCDC144B, CDK2AP2P2, C5orf64, CSAG2, ACSM3, MOG, OR52B4, FMNL2, EXT1, MROCK1, LINC02042, PLEKHB1, NPM2, LINC00398, SPTBN5, CYP1A1, LINC02287, BRD7P5, SPC24, EFNA3, PNMT, FOXRED2, PODXL2, TRAJ32, LHFPL3-AS2, and MIR150;

a seventeenth gene set comprising: SRGAP2B, FAM225A, SRGAP2C, SRGAP2, RNASE2, ANKRD35, WNT7A, FAM225B, ROBO3, RETN, ZNF595, TARM1, DBH, TAF11L2, TLE2, DEPDC1, LINC01238, UCKL1-AS1, SLC45A3, LM07, ESPNP, TRAJ20, NPTXR, GSDMC, SLC16A11, ACSM3, FMNL2, PLEKHB1, LINC02287, PNMT, FOXRED2, and TRAJ32;

an eighteenth gene set comprising: CSAG3, RNF175, FCER1A, TLR2, PTGDR2, LINC02458, SLC12A1, DISC1, MAOA, UPB1, CC2D2A, OLFML2A, C1QTNF7-AS1, LGALSL-DT, SLC4A3, SRGAP2D, CCDC162P, LINC02568, WARS1, SEPTIN9-DT, GRB10, ZNF727, ASPH, C1QTNF7, CSAG2, OR52B4, EXT1, MROCK1, LINC02042, LINC00398, CYP1A1, PODXL2, and LHFPL3-AS2;

a nineteenth gene set comprising: KRT17P2, KRT17P1, CPT1A, ADGRE4P, PRSS33, SIGLEC8, ALOX15, NME4, HRH4, CACNG6, SLC45A2, FAM138B, COL26A1, CACNG8, IL5RA, CLC, DNASE1L3, PTMS, WARS1P1, RHOXF1P1, COL11A2, SLC4A9, COLEC12, KRT17P6, PDK4, SMPD3, IL34, CNTN4-AS1, LINC01226, SLC25A20, ADAMTS7P1, ARHGEF35-AS1, SPNS3, EPHA2, ANOS1, ENPP7P8, RPL35AP26, SLC29A1, KRT2, TFEC, LINC01300, HPN, and PTPRF;

a twentieth gene set comprising: ADGRE4P, PRSS33, SIGLEC8, ALOX15, HRH4, CACNG6, COL26A1, CACNG8, IL5RA, CLC, DNASE1L3, PTMS, RHOXF1P1, COL11A2, SLC4A9, SMPD3, IL34, LINC01226, ADAMTS7P1, SPNS3, EPHA2, ENPP7P8, RPL35AP26, SLC29A1, and TFEC;

a twenty-first gene set comprising: EPN2, MKI67, CCNA2, TPX2, BUB1, BIRC5, TOP2A, GTSE1, CDC20, CIT, PKMYT1, ESPL1, KCNH3, ASPM, ADAM23, HJURP, KIF18B, KIFC1, TROAP, NCAPG, MIXL1, CDK1, CDC25A, CDC45, CDKN3, ZC2HC1C, INAVA, OR13A1, HMGB3, IGHV1-3, NUF2, KIF4A, POLR2J3, DLGAP5, STIL, CBLN2, MCM10, RNA5SP315, HMMR, GRAPL, NCAPH, CDT1, ATP5MGP1, CPAMD8, RFPL4A, ICA1, COPS5P2, LINC00683, CNGB1, TWIST2, FIGNL2, CIDP5, CDCA3, PACSIN1, MTND4P24, KLHL33, FPGT-TNNI3K, CCNB2, KIF11, INSL6, NDC80, VPS33B-DT, LINC00475, DNM1P31, TSPAN3, HTR1E, SLC7A11, SLC9C1, CD38, GSDME, SKA1, HAUS6P1, TEDDM1, MYRFL, MTCL1, WBP1LP2, BMP8B, PDGFC, SNHG5, and LINC02610;

a twenty-second gene set comprising: MKI67, CCNA2, TPX2, BUB1, TOP2A, GTSE1, CDC20, CIT, HJURP, KIF18B, KIFC1, NCAPG, MIXL1, CDK1, CDC45, CDKN3, NUF2, MCM10, CDT1, CNGB1, TWIST2, FIGNL2, CDCA3, PACSIN1, MTND4P24, CCNB2, INSL6, TSPAN3, CD38, SKA1, TEDDM1, and MYRFL;

a twenty-third gene set comprising: HBB, FAM210B, ADIPOR1, PBX1, EMC3, FBX07, PPMIA, PAGE2B, LINC01036, SLC25A37, PAGE2, RGS10, SLC6A19, KCNMA1, TPGS2, BBOF1, FUNDC2P1, Clorf198, BEND3P1, and LEFTY1;

a twenty-fourth gene set comprising: TUFT1, KIAA0319, ABCA1, CORIN, ABCG1, VASH1, NFXL1, STARD10, NMRAL2P, RPA2, COL9A3, LINC00222, LINC01305, LINC01644, TMEM273, SYT17, SLC3A2, NEO1, PTPN5, and DNM1P34;

a twenty-fifth gene set comprising: SC5D, KBTBD8, PRELID3B, CCDC82, C12orf29, PRKAR2A-AS1, UGT8, IGIP, SRP9, RLN2, CFAP54, UFL1, LRRC3, NAP1L3, NCAM2, UTP15, RLN1, CFAP100, CENPE, ZNF404, PTPN13, SMIM10L2A, CD207, LRFN2, ANKRD12, KLRA1P, LINC00698, TMEM158, LVRN, ZNF471, LINC02575, ZNF204P, RIN1, CHEK2P2, HLTF, ALKAL2, MYCT1, SPAG8, EXD2, LINC00402, XIRP1, GK4P, CPNE4, ITPR1-DT, and UNC5A;

a twenty-sixth gene set comprising: SC5D, KBTBD8, PRELID3B, C12orf29, UGT8, IGIP, RLN2, CFAP54, UFL1, LRRC3, NAP1L3, UTP15, ZNF404, PTPN13, SMIM10L2A, CD207, ANKRD12, LINC00698, LVRN, ZNF471, LINC02575, HLTF, MYCT1, SPAG8, EXD2, LINC00402, XIRP1, CPNE4, and ITPR1-DT;

a twenty-seventh gene set comprising: SC5D, KBTBD8, PRELID3B, C12orf29, UGT8, IGIP, RLN2, UFL1, LRRC3, NAP1L3, UTP15, ZNF404, PTPN13, SMIM10L2A, ANKRD12, LINC00698, LVRN, LINC02575, HLTF, MYCT1, SPAG8, EXD2, XIRP1, CPNE4, and ITPR1-DT;

a twenty-eighth gene set comprising: RASIP1, IL9RP1, SEC61G-DT, MAP1B, PLIN1, ZNF436-AS1, KRT18, OLFM1, SEMA3F, IRAG1-AS1, CALCB, GRM7, HOXC4, FGF17, ARHGAP5-AS1, LINC02280, LINC02666, RN7SKP1, ZNF165, CFAP299, LINC02356, and DNM1P33;

a twenty-nineth gene set comprising: RPS26P6, RPS26P8, RPS26P58, ANK2, RPS26, RPS26P13, CHST6, LINC02175, EBF3, RPS26P2, OR52P2P, PERM1, RGMA, CFAP46, CREB3L3, RPS26P39, DAB1, TINCR, ZMYND15, and LINC02141; and a thirtieth gene set comprising: RPS26P6, RPS26P8, RPS26P58, ANK2, RPS26, RPS26P13, CHST6, LINC02175, EBF3, RPS26P2, OR52P2P, PERM1, CFAP46, CREB3L3, RPS26P39, DAB1, TINCR, ZMYND15, and LINC02141;

(b) classifying the subject as having the type 1 lupus disease state or the type 2 lupus disease state of the subject using a machine-learning model to process gene expression levels of at least a subset of the at least 21 gene sets in the gene expression measurements data; and (c) administering a treatment to the subject, wherein the treatment comprises Prednisone, Hydroxychloroquine, Methotrexate (MTX), Cyclophosphamide (CTX), Mycophenolate mofetil (MMF), Azathioprine (AZA), Belimumab, Anifrolumab, or Voclosporin when the subject is classified as having the type 1 lupus disease state, or wherein the treatment comprises Duloxetine, Gabapentin, Milnacipran, or Pregabalin when the subject is classified as having the type 2 lupus disease state.

2. The method of claim 1, wherein the subject data set comprises or is derived from the gene expression measurements data of at least 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 450, 500, 550, 600, 650, 700, 750, 850, 900, 950, 1000, 1050, 1100, 1150, 1200, 1250, 1300, 1350, 1400, 1450, 1500, 1550, 1600, 1700, 1800, 1900, 2000, or all, genes, selected from the genes listed in the first to the thirtieth gene sets, from the biological sample from the subject.

3. The method of claim 1, wherein the subject data set comprises or is derived from the gene expression measurements data of the at least 21 genes selected from the genes listed in each of the first to the thirtieth gene sets, from the biological sample from the subject, wherein a number of genes selected from different gene sets may be different or the same.

4. The method of claim 1, wherein the subject data set comprises or is derived from the gene expression measurements data of an effective number of genes selected from the genes listed in each of the gene sets selected from the group consisting of: the first to the thirtieth gene sets, from the biological sample from the subject, wherein number of genes selected from different gene sets may be different or the same.

5. The method of claim 1, wherein the subject data set comprises or is derived from the gene expression measurements data of all genes listed in each of the gene sets.

6. The method of claim 1, wherein the subject data set comprises at least 21 module eigengenes corresponding to the at least 21 gene sets, wherein the obtaining in (a) further comprises calculating, for each of the at least 21 module eigengenes, a first principal component based on a variance of gene expression values of genes in the corresponding gene set, and wherein the classifying in (b) further comprises using the machine-learning model to process gene expression levels of at least a subset of the at least 21 module eigengenes.

7. The method of claim 1, wherein the subject data set comprises one or more GSVA scores of the subject, wherein the obtaining in (a) further comprises generating the one or more GSVA scores based on the at least 21 gene sets, wherein for each gene set, at least one GSVA score of the subject is generated based on enrichment of expression of the genes selected from the gene set in the biological sample, and wherein the classifying in (b) further comprises using the machine-learning model to process the one or more GSVA scores.

8. The method of claim 1, wherein the classifying in (b) further comprises electronically outputting a report indicating the type 1 lupus disease state or the type 2 disease state of the subject.

9. The method of claim 1, wherein the machine-learning model: (i) is trained using linear regression, logistic regression, Ridge regression, Lasso regression, elastic net (EN) regression, support vector machine (SVM), gradient boosted machine (GBM), k nearest neighbors (kNN), generalized linear model (GLM), naive Bayes (NB) classifier, neural network, Random Forest (RF), deep learning algorithm, linear discriminant analysis (LDA), decision tree learning (DTREE), adaptive boosting (ADB), Classification and Regression Tree (CART), hierarchical clustering, or any combination thereof; or (ii) has a receiver operating characteristic (ROC) curve with an Area-Under-Curve (AUC) of at least 0.85.

10. The method of claim 1, wherein the classifying in (b) further comprises using the machine-learning model to generate a lupus disease risk score of the subject based on the subject data set, and wherein the classifying in (b) is based on the lupus disease risk score.

11. The method of claim 1, wherein the classifying in (b) comprises an accuracy of at least 85%, a sensitivity of at least 85%, a specificity of at least 85%, a positive predictive value of at least 85%, a negative predictive value of at least 85%, or any combination thereof.

12. The method of claim 1, wherein the subject: (i) is at elevated risk of having lupus; (ii) is suspected of having lupus; (iii) is asymptomatic for lupus; (iv) has lupus; (v) is at elevated risk of having, is suspected of having, is asymptomatic for, and/or has inactive lupus; or (vi) is at elevated risk of having, is suspected of having, is asymptomatic for, and/or has fibromyalgia.

13. The method of claim 10, wherein the lupus disease risk score of the subject is generated based on one or more GSVA scores of the subject.

14. The method of claim 6, wherein the subject data set comprises gene set variation analysis (GSVA) data, gene set enrichment analysis (GSEA) data, weighted gene co-expression network analysis (WGCNA) data, differential expression analysis data, Z-score data, log 2 expression analysis data, or any combination thereof, of the at least 21 module eigengenes.

15. The method of claim 1, wherein the gene expression measurements data comprises at least 25 genes from a biological sample obtained or derived from the subject, wherein the at least 25 genes are each selected from at least 25 different gene sets, and wherein the at least 25 different gene sets are selected from the first to the thirtieth gene sets.

16. The method of claim 15, wherein the gene expression measurements data comprises at least 30 genes from a biological sample obtained or derived from the subject, wherein the at least 30 genes are each selected from at least 30 different gene sets, and wherein the at least 30 different gene sets are selected from the first to the thirtieth gene sets.

* * * * *